United States Patent
Ruppel et al.

(10) Patent No.: US 12,351,579 B2
(45) Date of Patent: *Jul. 8, 2025

(54) COMPOUNDS AND USES THEREOF

(71) Applicant: FOGHORN THERAPEUTICS INC., Cambridge, MA (US)

(72) Inventors: Sabine K. Ruppel, Cambridge, MA (US); Zhaoxia Yang, Belmont, MA (US); Jason T. Lowe, East Bridgewater, MA (US); Johannes H. Voigt, Cambridge, MA (US); Matthew Netherton, Cambridge, MA (US)

(73) Assignee: FOGHORN THERAPEUTICS INC., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/216,392

(22) Filed: Jun. 29, 2023

(65) Prior Publication Data

US 2023/0416246 A1    Dec. 28, 2023

Related U.S. Application Data

(63) Continuation of application No. 17/425,153, filed as application No. PCT/US2020/015746 on Jan. 29, 2020.

(60) Provisional application No. 62/881,195, filed on Jul. 31, 2019, provisional application No. 62/798,374, filed on Jan. 29, 2019.

(51) Int. Cl.
| | |
|---|---|
| *C07D 471/04* | (2006.01) |
| *A61P 35/00* | (2006.01) |
| *C07D 401/14* | (2006.01) |
| *C07D 471/10* | (2006.01) |
| *C07D 487/04* | (2006.01) |
| *C07D 487/10* | (2006.01) |
| *C07D 498/10* | (2006.01) |
| *C07D 519/00* | (2006.01) |

(52) U.S. Cl.
CPC .......... *C07D 471/04* (2013.01); *A61P 35/00* (2018.01); *C07D 401/14* (2013.01); *C07D 471/10* (2013.01); *C07D 487/04* (2013.01); *C07D 487/10* (2013.01); *C07D 498/10* (2013.01); *C07D 519/00* (2013.01)

(58) Field of Classification Search
CPC .................................................. C07D 471/04
USPC ..................................................... 514/210.16
See application file for complete search history.

(56) References Cited

U.S. PATENT DOCUMENTS

| | | | |
|---|---|---|---|
| 5,858,358 A | 1/1999 | June et al. | |
| 5,883,223 A | 3/1999 | Gray | |
| 6,352,694 B1 | 3/2002 | June et al. | |
| 6,534,055 B1 | 3/2003 | June et al. | |
| 6,692,964 B1 | 2/2004 | June et al. | |
| 6,797,514 B2 | 9/2004 | Berenson et al. | |
| 6,867,041 B2 | 3/2005 | Berenson et al. | |
| 6,887,466 B2 | 5/2005 | June et al. | |
| 6,905,680 B2 | 6/2005 | June et al. | |
| 6,905,681 B1 | 6/2005 | June et al. | |
| 6,905,874 B2 | 6/2005 | Berenson et al. | |
| 7,056,883 B2 | 6/2006 | Ito et al. | |
| 7,067,318 B2 | 6/2006 | June et al. | |
| 7,144,575 B2 | 12/2006 | June et al. | |
| 7,172,869 B2 | 2/2007 | June et al. | |
| 7,175,843 B2 | 2/2007 | June et al. | |
| 7,205,103 B2 | 4/2007 | Emerson | |
| 7,232,566 B2 | 6/2007 | June et al. | |
| 9,271,978 B2 | 3/2016 | Liu et al. | |
| 9,410,943 B2 | 8/2016 | Kadoch et al. | |
| 9,750,816 B2 | 9/2017 | Bradner et al. | |
| 9,821,068 B2 | 11/2017 | Bradner et al. | |
| 10,105,420 B2 | 10/2018 | Kadoch et al. | |
| 10,239,888 B2 | 3/2019 | Bradner et al. | |
| 10,464,925 B2 | 11/2019 | Bradner et al. | |
| 10,646,575 B2 | 5/2020 | Phillips et al. | |
| 10,660,968 B2 | 5/2020 | Phillips et al. | |
| 10,669,253 B2 | 6/2020 | Bradner et al. | |
| 10,849,982 B2 | 12/2020 | Phillips et al. | |
| 10,905,768 B1 | 2/2021 | Phillips et al. | |
| 11,059,801 B2 | 7/2021 | Bradner et al. | |
| 11,185,592 B2 | 11/2021 | Phillips et al. | |
| 11,306,105 B2 | 4/2022 | Bradner et al. | |
| 11,414,416 B1 * | 8/2022 | Ruppel | C07D 401/14 |
| 11,485,743 B2 | 11/2022 | Mainolfi et al. | |
| 11,524,949 B2 | 12/2022 | Phillips et al. | |
| 11,560,381 B1 * | 1/2023 | Ruppel | C07D 401/14 |
| 11,583,586 B2 | 2/2023 | Bradner et al. | |
| 11,691,972 B2 | 7/2023 | Nasveschuk et al. | |
| 11,773,085 B2 | 10/2023 | Zhou et al. | |
| 2005/0079512 A1 | 4/2005 | Emerson et al. | |
| 2006/0121005 A1 | 6/2006 | Berenson et al. | |

(Continued)

FOREIGN PATENT DOCUMENTS

| | | |
|---|---|---|
| CN | 108690020 A | 10/2018 |
| WO | WO-2012/003281 A2 | 1/2012 |

(Continued)

OTHER PUBLICATIONS

U.S. Appl. No. 18/216,280, Ruppel et al.
U.S. Appl. No. 18/216,362, Ruppel et al.
U.S. Appl. No. 18/216,441, Ruppel et al.
U.S. Appl. No. 18/223,443, Gu et al.
U.S. Appl. No. 18/454,594, Bocker et al.

(Continued)

*Primary Examiner* — Niloofar Rahmani

(74) *Attorney, Agent, or Firm* — Clark & Elbing LLP

(57) ABSTRACT

The present invention relates to compositions and methods for the treatment of BAF-related disorders, such as cancers and viral infections.

18 Claims, 14 Drawing Sheets

Specification includes a Sequence Listing.

(56) References Cited

U.S. PATENT DOCUMENTS

| | | |
|---|---|---|
| 2011/0061116 A1 | 3/2011 | Haldar et al. |
| 2016/0058872 A1 | 3/2016 | Crew et al. |
| 2016/0176916 A1 | 6/2016 | Bradner et al. |
| 2017/0014491 A1 | 1/2017 | Kadoch et al. |
| 2017/0050968 A1 | 2/2017 | Bennett et al. |
| 2017/0158709 A1 | 6/2017 | Boloor |
| 2018/0044335 A1 | 2/2018 | Martin et al. |
| 2018/0085465 A1 | 3/2018 | Bradner et al. |
| 2018/0134684 A1 | 5/2018 | Bradner et al. |
| 2018/0187614 A1 | 7/2018 | Dudar |
| 2018/0213422 A1 | 7/2018 | Kazmi et al. |
| 2018/0215766 A1 | 8/2018 | Bair et al. |
| 2018/0215866 A1 | 8/2018 | Zhao et al. |
| 2018/0327419 A1 | 11/2018 | Bradner et al. |
| 2019/0071415 A1 | 3/2019 | Bradner et al. |
| 2019/0076539 A1 | 3/2019 | Phillips et al. |
| 2019/0247509 A1 | 8/2019 | Buckley et al. |
| 2020/0140456 A1 | 5/2020 | Phillips et al. |
| 2020/0206344 A1 | 7/2020 | Kadoch et al. |
| 2021/0009568 A1 | 1/2021 | Zhou et al. |
| 2021/0116454 A1 | 4/2021 | Anton et al. |
| 2021/0198256 A1 | 7/2021 | Nasveschuk et al. |
| 2021/0230190 A1 | 7/2021 | Ruppel et al. |
| 2022/0016083 A1 | 1/2022 | Centore et al. |
| 2022/0079940 A1 | 3/2022 | Centore et al. |
| 2022/0098190 A1 | 3/2022 | Ruppel et al. |
| 2022/0098194 A1 | 3/2022 | Nasveschuk et al. |
| 2022/0119378 A1 | 4/2022 | Anthony et al. |
| 2022/0289711 A1 | 9/2022 | Ruppel et al. |
| 2023/0060334 A1 | 3/2023 | Nasveschuk et al. |
| 2023/0065463 A1 | 3/2023 | Ruppel et al. |
| 2023/0066136 A1* | 3/2023 | Ruppel .............. C07D 401/14 |
| 2023/0072053 A1 | 3/2023 | Ruppel et al. |
| 2023/0077730 A1 | 3/2023 | Ruppel et al. |
| 2023/0079819 A1 | 3/2023 | Vaswani et al. |
| 2023/0121497 A1 | 4/2023 | Vaswani et al. |
| 2023/0138480 A1 | 5/2023 | Anthony et al. |
| 2023/0142883 A1* | 5/2023 | Ruppel .............. C07D 471/04 |
| | | 544/362 |
| 2023/0331722 A1 | 10/2023 | Ruppel et al. |
| 2024/0002382 A1 | 1/2024 | Ruppel et al. |
| 2024/0067642 A1 | 2/2024 | Ruppel et al. |
| 2024/0101550 A1 | 3/2024 | Vaswani et al. |

FOREIGN PATENT DOCUMENTS

| | | |
|---|---|---|
| WO | WO-2013/106643 A2 | 7/2013 |
| WO | WO-2016/105518 A1 | 6/2016 |
| WO | WO-2016/139361 A1 | 9/2016 |
| WO | WO-2017/007612 A1 | 1/2017 |
| WO | WO-2017/024317 A2 | 2/2017 |
| WO | WO-2017/197036 A1 | 11/2017 |
| WO | WO-2017/197046 A1 | 11/2017 |
| WO | WO-2017/197051 A1 | 11/2017 |
| WO | WO-2017/197055 A1 | 11/2017 |
| WO | WO-2017/197056 A1 | 11/2017 |
| WO | WO-2017/223452 A1 | 12/2017 |
| WO | WO-2018/064589 A1 | 4/2018 |
| WO | WO-2018/177297 A1 | 10/2018 |
| WO | WO-2019/099868 A2 | 5/2019 |
| WO | WO-2019/165229 A1 | 8/2019 |
| WO | WO-2020/010227 A1 | 1/2020 |
| WO | WO-2020/051235 A1 | 3/2020 |
| WO | WO-2020/132561 A1 | 6/2020 |
| WO | WO-2020/160192 A1 | 8/2020 |
| WO | WO-2020/160193 A2 | 8/2020 |
| WO | WO-2020/160196 A1 | 8/2020 |
| WO | WO-2020/160198 A1 | 8/2020 |
| WO | WO-2020/264177 A1 | 12/2020 |
| WO | WO-2021/022163 A2 | 2/2021 |
| WO | WO-2021/055295 A1 | 3/2021 |
| WO | WO-2021/155100 A1 | 8/2021 |
| WO | WO-2021/178920 A1 | 9/2021 |
| WO | WO-2023/039208 A1 | 3/2023 |
| WO | WO-2023/109892 A1 | 6/2023 |

OTHER PUBLICATIONS

U.S. Appl. No. 18/456,301, Ruppel et al.
U.S. Appl. No. 62/798,374, Ruppel et al.
U.S. Appl. No. 62/881,195, Ruppel et al.
U.S. Appl. No. 62/985,774, Nasveschuk et al.
U.S. Appl. No. 63/061,659, Nasveschuk et al.
Brien et al., "Targeted degradation of BRD9 reverses oncogenic gene expression in synovial sarcoma," eLife. 7:e41305 (Nov. 15, 2018) (26 pages).
Communication Pursuant to Rule 164(1) for European Patent Application 19746772.3, dated Oct. 7, 2021 (13 pages).
Crawford et al., "Inhibition of bromodomain-containing protein 9 for the prevention of epigenetically-defined drug resistance," Bioorg Med Chem Lett. 27(15):3534-41(2017).
Decision Denying Institution of Post-Grant Review of U.S. Pat. No. 11,414,416 dated Sep. 12, 2023 (4 Pages).
Del Gaudio et al., "BRD9 binds cell type-specific chromatin regions regulating leukemic cell survival via STAT5 inhibition," Cell Death Dis. 10(5):338 (Apr. 2019) doi: 10.1038/s41419-019-1570-9 (14 pages).
Extended European Search Report for European Application No. 19746772.3, dated Feb. 7, 2022 (15 pages).
Extended European Search Report for European Application No. 20748462.7, dated Jan. 2, 2023 (10 pages).
Hay et al., "Design and synthesis of potent and selective inhibitors of BRD7 and BRD9 bromodomains," Med. Chem. Commun. 6:1381-86 (2015).
Hohmann et al., "Sensitivity and engineered resistance of myeloid leukemia cells to BRD9 inhibition," Nat Chem Biol. 12(9):672-679 (Sep. 2016) (12 pages).
International Search Report and Written Opinion for International Patent Application No. PCT/US2019/015733, dated Jul. 1, 2019 (17 pages).
International Search Report and Written Opinion for PCT/US2020/015746, mailed May 18, 2020 (11 pages).
K. Luby-Phelps, "Cytoarchitecture and Physical Properties of Cytoplasm: Volume Viscosity, Diffusion, Intracellular Surface Area," Int Rev Cytol. 192:189-221 (2000).
Kadoch et al., "Mammalian SWI/SNF chromatin remodeling complexes and cancer: Mechanistic insights gained from human genomics," Sci Adv. 1(5):e1500447 (2015) (17 pages).
Kadoch et al., "Proteomic and bioinformatic analysis of mammalian SWI/SNF complexes identifies extensive roles in human malignancy," Nat Genet. 45(6):592-601 (2013) (11 pages).
Kadoch et al., "Reversible Disruption of mSWI/SNF (BAF) Complexes by the SS18-SSX Oncogenic Fusion in Synovial Sarcoma," Cell. 153(1):71-85 (2013).
Martin et al., "Structure-Based Design of an in Vivo Active Selective BRD9 Inhibitor," J Med Chem. 59(10):4462-75 (2016).
McBride et al., "Disruption of mammalian SWI/SNF and polycomb complexes in human sarcomas: mechanisms and therapeutic opportunities," J Pathol. 244(5): 638-649 (Apr. 2018).
Michel et al., "Abstract PR15: BRD9 defines a novel mammalian SWI/SNF (BAF) complex configuration which supports proliferation in AML," Clin Cancer Res. 23(24_Suppl) Abstract PR15 (2017) (4 pages).
Nasir, M.S. et al., "Fluorescence Polarization: An analytical tool for Immunoassay and Drug Discovery," Comb. Chem High Throughput Screen. 2(4):177-190 (Aug. 1999).
Pan et al., "A major chromatin regulator determines resistance of tumor cells to T cell-mediated killing," Science. 359(6377):770-75 (2018) (11 pages).
Petition for Post Grant Review of U.S. Pat. No. 11,414,416 filed May 1, 2023 (133 Pages).
Picaud et al., "9H-purine scaffold reveals induced-fit pocket plasticity of the BRD9 bromodomain," J Med Chem. 58(6):2718-36 (2015).

(56) References Cited

OTHER PUBLICATIONS

Remillard et al., "Degradation of the BAF Complex Factor BRD9 by Heterobifunctional Ligands," Angew Chem Int Ed Engl. 56(21):5738-43 (2017) (7 pages).
Sender et al., "Revised Estimates for the No. of Human and Bacteria Cells in the Body," PLoS Biol. 14(8):e1002533 (Aug. 19, 2016) (14 pages).
Supporting Information for Remillard et al., "Degradation of the BAF Complex Factor BRD9 by Heterobifunctional Ligands," Angew Chem Int Ed Engl. 56(21):5738-43 (2017) (43 pages).
Teuscher et al., "A Versatile Method to Determine the Cellular Bioavailability of Small-Molecule Inhibitors," J Med Chem. 60(1):157-169 (2017).
Theodoulou et al., "Discovery of I-BRD9, a Selective Cell Active Chemical Probe for Bromodomain Containing Protein 9 Inhibition," J Med Chem. 59(4):1425-39 (2015).
Vangamudi et al., "The SMARCA2/4 ATPase Domain Surpasses the Bromodomain as a Drug Target in SWI/SNF-Mutant Cancers: Insights from cDNA Rescue and PFI-3 Inhibitor Studies," Cancer Res. 75(18):3865-78 (2015).
Wang et al., "NMR Fragment Screening Hit Induces Plasticity of BRD7/9 Bromodomains," Chembiochem. 17(15):1456-63 (2016).
Z.X. Wang, "An exact mathematical expression for describing competitive binding of two different ligands to a protein molecule," FEBS Lett. 360(2):111-114 (Feb. 1995).
Zoppi et al., "Iterative Design and Optimization of Initially Inactive Proteolysis Targeting Chimeras (PROTACs) Identify VZ185 as a Potent, Fast, and Selective von Hippel-Lindau (VHL) Based Dual Degrader Probe of BRD9 and BRD7," J Med Chem. 62(2):699-726 (Jan. 2019).
U.S. Appl. No. 18/281,022, Vaswani et al.
U.S. Appl. No. 18/282,279, Huang, Liyue.
U.S. Appl. No. 18/373,518, Vaswani et al.
Tsherniak et al. "Defining a Cancer Dependency Map," Cell. 170(3):564-576 (Jul. 2017) (40 pages).
Munoz et al. "CRISPR Screens Provide a Comprehensive Assessment of Cancer Vulnerabilities but Generate False-Positive Hits for Highly Amplified Genomic Regions," Cancer Discov. 6(8):900-13 (Aug. 2016) (14 pages).
Declaration of Christopher G. Nasveschuk, Ph.D. Under 37 C.F.R. §1.68 and §42.53(a), dated Oct. 19, 2023 (24 pages).
Declaration of Kevin T. Sprott, Ph.D., Under 37 C.F.R. §1.68 and §42.53(a), dated Oct. 19, 2023 (74 pages).
Declaration of Stevan W. Djuric, Ph.D. Under 37 C.F.R. §1.68 and §42.53(a), dated Oct. 19, 2023 (202 pages).
Petition for Post Grant Review of U.S. Pat. No. 11,560,381 filed Oct. 23, 2023 (163 Pages).
Decision Denying Institution of Post-Grant Review of U.S. Pat. No. 11,560,381, dated Jan. 23, 2024 (4 Pages).

* cited by examiner

RD

HCT116

Calu6

COMPOUNDS AND USES THEREOF

CROSS-REFERENCE TO RELATED APPLICATIONS

The present application is a continuation application of U.S. patent application Ser. No. 17/425,153, filed Jul. 22, 2021, which is a 371 national phase entry of PCT App. No. PCT/US2020/015746, filed Jan. 29, 2020, which claims priority to U.S. Provisional App. No. 62/881,195, filed Jul. 31, 2019, and to U.S. Provisional App. No. 62/798,374, filed Jan. 29, 2019, each of which is incorporated by reference in its entirety.

SEQUENCE LISTING

The instant application contains a Sequence Listing which has been submitted electronically in XML format and is hereby incorporated by reference in its entirety. Said XML copy, created on Jun. 30, 2023, is named "51121-027009_Sequence_Listing_6_30_23" and is 456,817 bytes in size.

BACKGROUND

Disorders can be affected by the BAF complex. BRD9 is a component of the BAF complex. The present invention relates to useful compositions and methods for the treatment of BAF complex-related disorders, such as cancer and infection.

SUMMARY

Bromodomain-containing protein 9 (BRD9) is a protein encoded by the BRD9 gene on chromosome 5. BRD9 is a component of the BAF (BRG1- or BRM-associated factors) complex, a SWI/SNF ATPase chromatin remodeling complex, and belongs to family IV of the bromodomain-containing proteins. BRD9 is present in several SWI/SNF ATPase chromatin remodeling complexes and is upregulated in multiple cancer cell lines. Accordingly, agents that reduce the levels and/or activity of BRD9 may provide new methods for the treatment of disease and disorders, such as cancer and infection. The inventors have found that depleting BRD9 in cells results in the depletion of the SS18-SSX fusion protein in those cells. The SS18-SSX fusion protein has been detected in more than 95% of synovial sarcoma tumors and is often the only cytogenetic abnormality in synovial sarcoma. Additionally, evidence suggests that the BAF complex is involved in cellular antiviral activities. Thus, agents that degrade BRD9 (e.g., compounds) are useful in the treatment of disorders (e.g., cancers or infections) related to BAF, BRD9, and/or SS18-SSX.

The present disclosure features compounds and methods useful for treating BAF-related disorders (e.g., cancer or infection).

In an aspect, the disclosure features a compound having the structure of Formula I:

A-L-B      Formula I, where
A is a BRD9 binding moiety;
B is a degradation moiety; and
L has the structure of Formula II:

$A^1-(E^1)-(F_1)-(C^3)_m-(E^3)_n-(F^2)_{o1}-(F^3)_{o2}-(E^2)_p-A^2$,     Formula II where
$A^1$ is a bond between the linker and A;
$A^2$ is a bond between B and the linker;
each of m, n, o1, o2, and p is, independently, 0 or 1;
each of $E^1$ and $E^2$ is, independently, O, S, NRN, optionally substituted $C_{1-10}$ alkylene, optionally substituted $C_{2-10}$ alkenylene, optionally substituted $C_{2-10}$ alkynylene, optionally substituted $C_2$-$C_{10}$ polyethylene glycol, or optionally substituted $C_{1-10}$ heteroalkylene;
$E^3$ is optionally substituted $C_1$-$C_6$ alkylene, optionally substituted $C_1$-$C_6$ heteroalkylene, O, S, or NRN;
each $R^N$ is, independently, H, optionally substituted $C_{1-4}$ alkyl, optionally substituted $C_{2-4}$ alkenyl, optionally substituted $C_{2-4}$ alkynyl, optionally substituted $C_{2-6}$ heterocyclyl, optionally substituted $C_{6-12}$ aryl, or optionally substituted $C_{1-7}$ heteroalkyl;
$C_3$ is carbonyl, thiocarbonyl, sulphonyl, or phosphoryl; and
each of $F_1$, $F_2$, and $F_3$ is, independently, optionally substituted $C_3$-$C_{10}$ carbocyclylene, optionally substituted $C_{2-10}$ heterocyclylene, optionally substituted $C_6$-$C_{10}$ arylene, or optionally substituted $C_2$-$C_9$ heteroarylene, or a pharmaceutically acceptable salt thereof.

In some embodiments, the linker has the structure of Formula IIa:

$A^1-(E^1)-(F^1)-(C^3)_m-(E^2)_p-A^2$,     Formula IIa

In some embodiments, the linker has the structure of Formula IIb:

$A^1-(E^1)-(F^1)-(E^2)_p-A^2$,     Formula IIb

In some embodiments, the linker has the structure of Formula IIc:

$A^1-(E^1)-(F^1)-A^2$,     Formula IIc

In some embodiments, the linker has the structure of Formula IId:

$A^1-(E^1)-(F^1)-(C^3)_m-(F^2)_{o1}-A^2$,     Formula IId

In some embodiments, the linker has the structure of Formula IIe:

$A^1-(E^1)-(F^1)-(E^3)_n-(F^2)_{o1}-(E^2)_p-A^2$,     Formula IIe

In some embodiments, the linker has the structure of Formula IIf:

$A^1-(E^1)-(F^1)-(C_3)_m-(E^3)_n-(F^2)_{o1}-(E^2)_p-A^2$,     Formula IIf

In some embodiments, the linker has the structure of Formula IIg:

$A^1-(E^1)-(F^1)-(E^3)_n-(F^2)_{o1}-A$,     Formula IIg

In some embodiments, each of $E^1$ and $E^2$ is, independently, $NR^N$, optionally substituted $C_{1-10}$ alkylene, optionally substituted $C_2$-$C_{10}$ polyethylene glycolene, or optionally substituted $C_{1-10}$ heteroalkylene.

In some embodiments, $E^3$ is optionally substituted $C_1$-$C_6$ alkylene, O, S, or $NR^N$;

In some embodiments, $E^3$ is optionally substituted $C_1$-$C_6$ alkylene. In some embodiments, $E^3$ is optionally substituted $C_1$-$C_3$ alkylene. In some embodiments, $E^3$ is O, S, or $NR^N$.

In some embodiments, $E^3$ is $C_1$-$C_6$ alkylene. In some embodiments, $E^3$ is $C_1$-$C_3$ alkylene. In some embodiments, $E^3$ is O.

In some embodiments, $E^3$ is

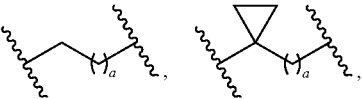

-continued
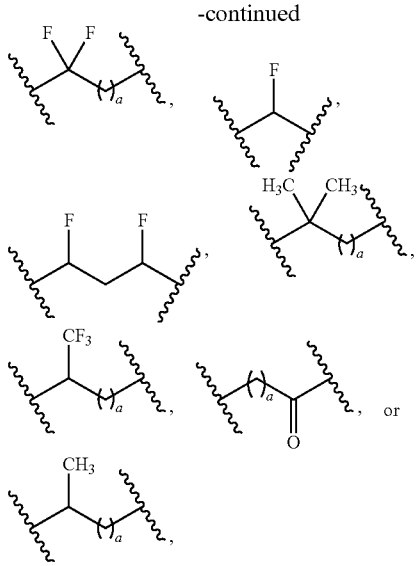
where a is 0, 1, 2, 3, 4, or 5.
In some embodiments, $E^3$ is
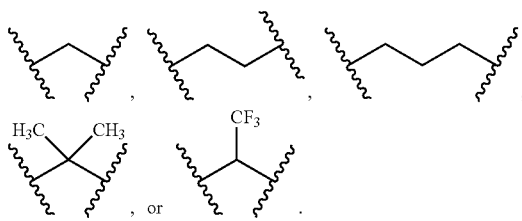
, or .
In some embodiments, each $R^N$ is, independently, H or optionally substituted $C_{1-4}$ alkyl.
In some embodiments, each $R^N$ is, independently, H or methyl.
In some embodiments, $E^1$ is
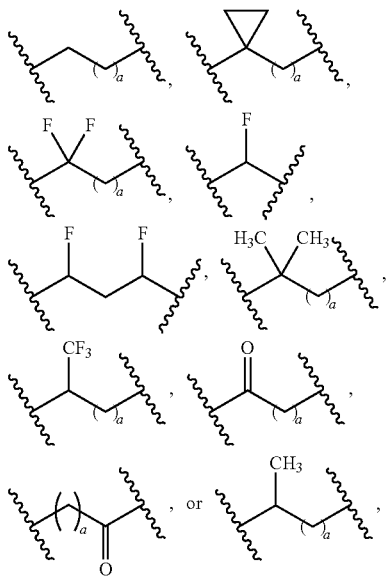
where a is 0, 1, 2, 3, 4, or 5.
In some embodiments, $E^1$ is
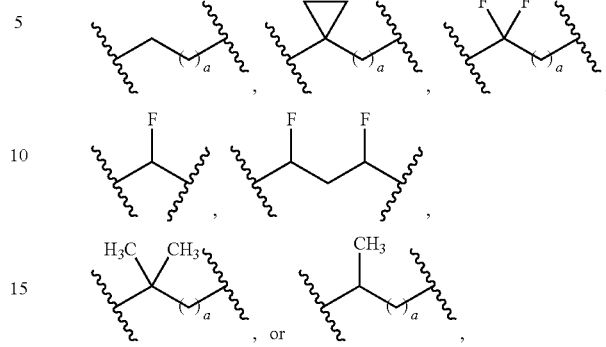
where a is 0, 1, 2, 3, 4, or 5.
In some embodiments, $E^1$ is
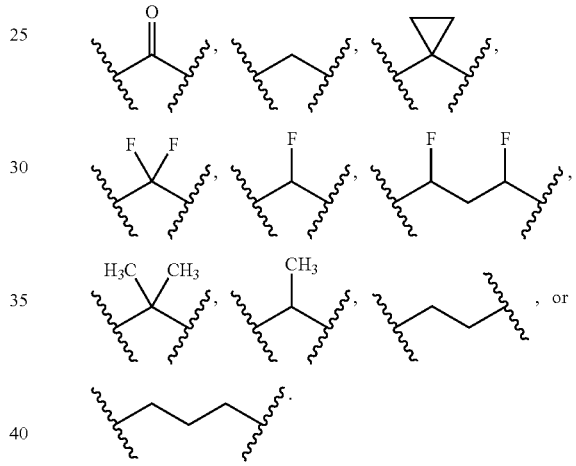
In some embodiments, $E^1$ is
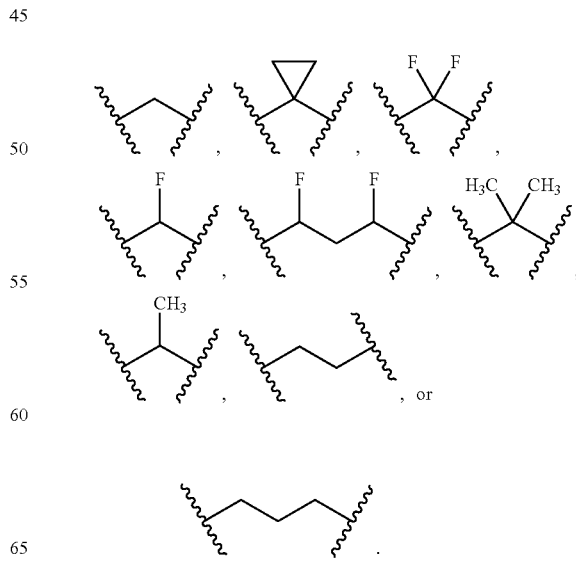

In some embodiments, $E^1$ is

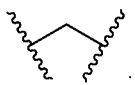

In some embodiments, $E^1$ is

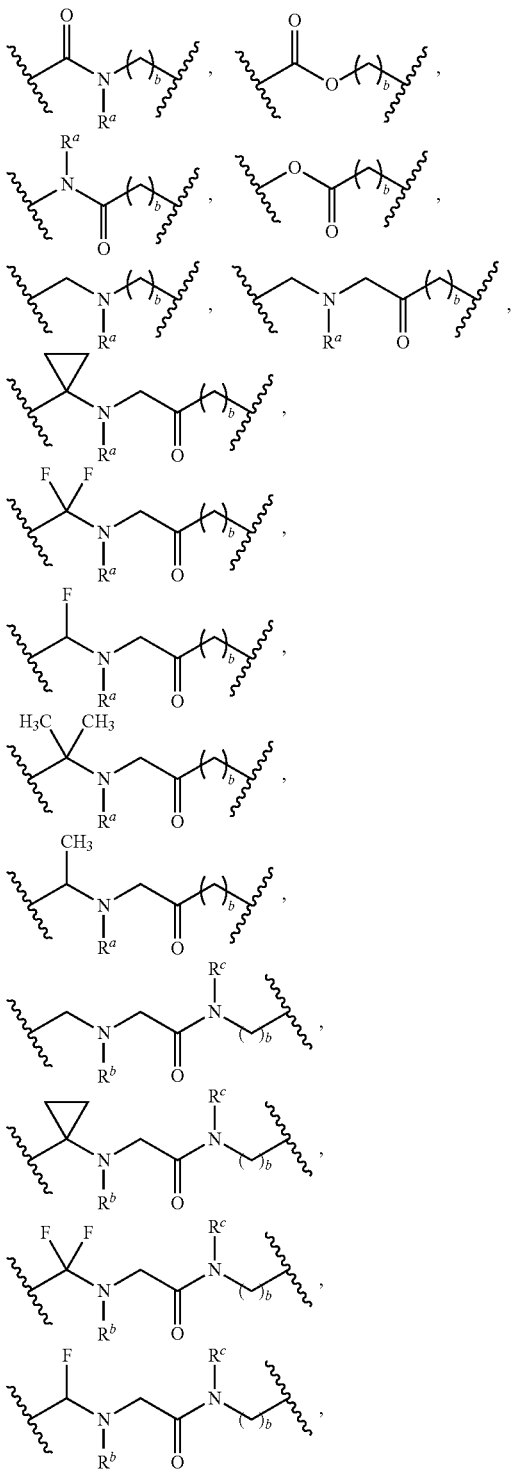

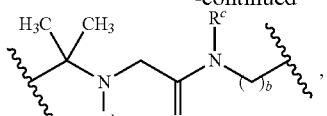

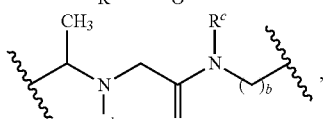

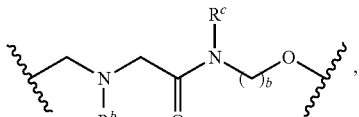

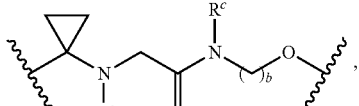

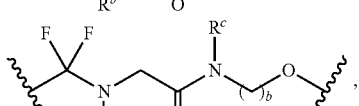

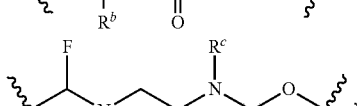

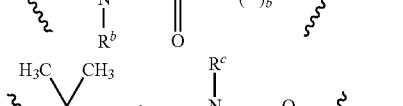, or

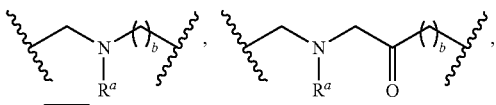

where b is 0, 1, 2, 3, 4, 5, or 6;

$R^a$ is H, optionally substituted $C_1$-$C_6$ alkyl, optionally substituted $C_1$-$C_6$ heteroalkyl, or optionally substituted $C_3$-$C_6$ carbocyclyl;

$R^b$ is H, optionally substituted $C_1$-$C_6$ alkyl, optionally substituted $C_1$-$C_6$ heteroalkyl, or optionally substituted $C_3$-$C_6$ carbocyclyl; and $R^c$ is H, optionally substituted $C_1$-$C_6$ alkyl, optionally substituted $C_1$-$C_6$ heteroalkyl, or optionally substituted $C_3$-$C_6$ carbocyclyl.

In some embodiments, $E^1$ is

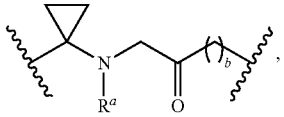

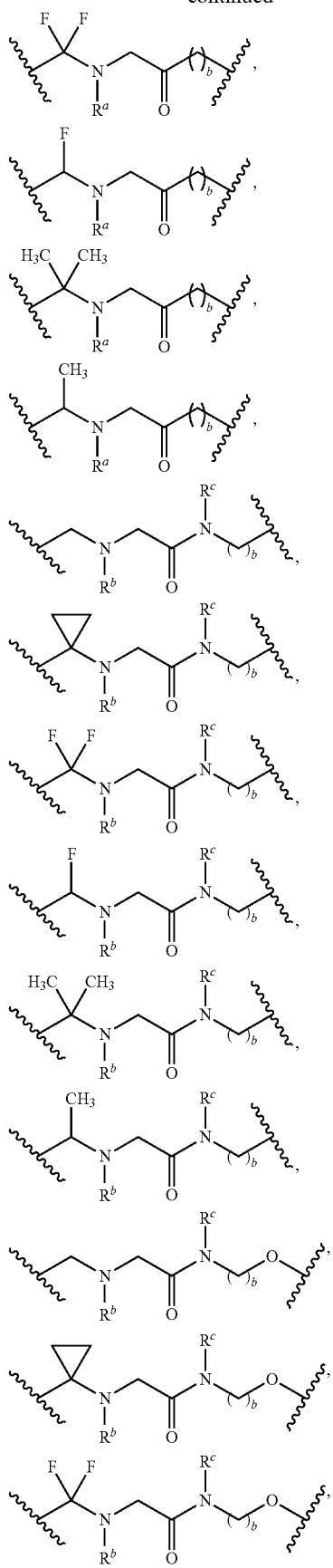

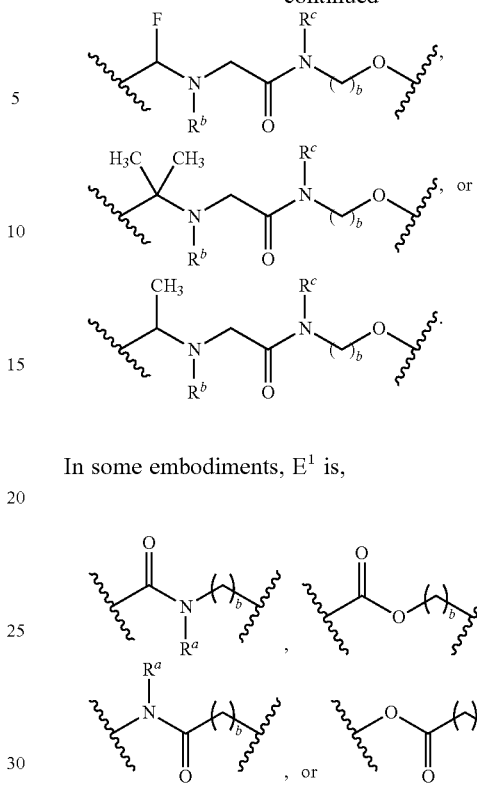

In some embodiments, $E^1$ is,

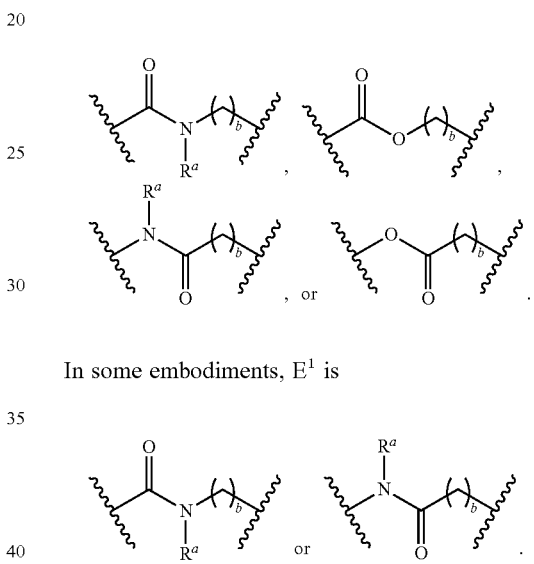

In some embodiments, $E^1$ is

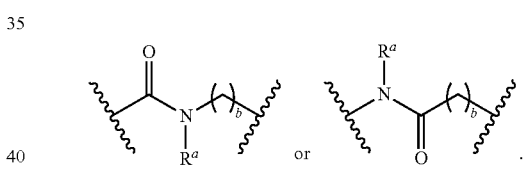

In some embodiments, $R^a$ is H or optionally substituted $C_1$-$C_6$ alkyl. In some embodiments, $R^b$ is H or optionally substituted $C_1$-$C_6$ alkyl. In some embodiments, $R^c$ is H or optionally substituted $C_1$-$C_6$ alkyl.

In some embodiments, $R^a$ is H or methyl. In some embodiments, $R^b$ is H or methyl. In some embodiments, $R^c$ is H or methyl.

In some embodiments, b is 0, 1, 2, or 3. In some embodiments, b is 0. In some embodiments, b is 1. In some embodiments, b is 2. In some embodiments, b is 3.

In some embodiments, $E^1$ is

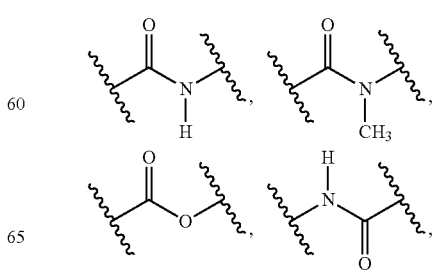

-continued
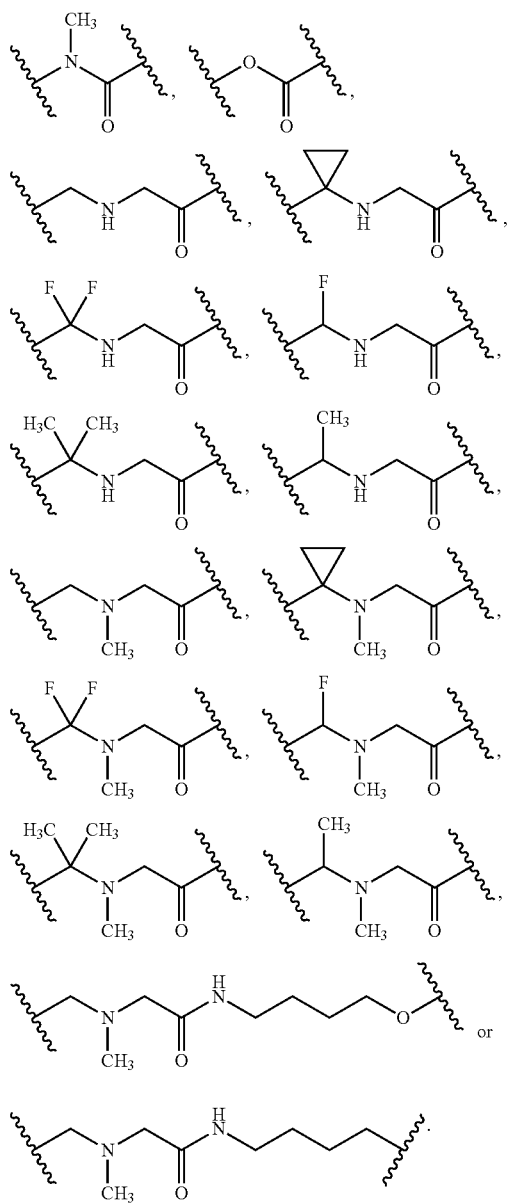
In some embodiments, $E^1$ is
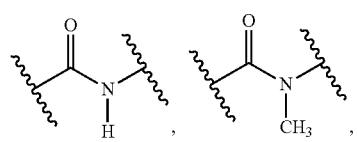
In some embodiments, $E^1$ is
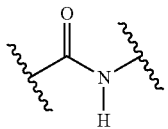
In some embodiments, $E^1$ is
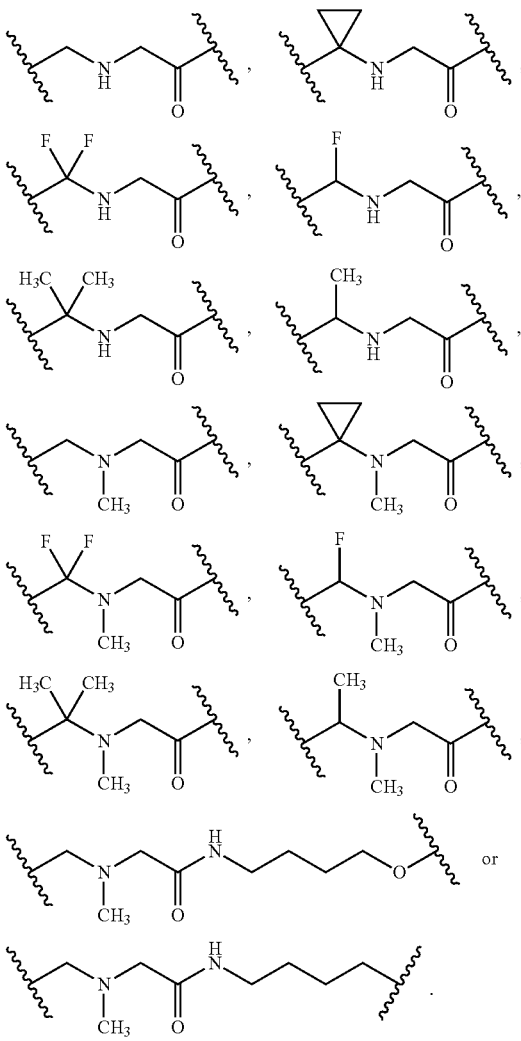
In some embodiments, $E^1$ is
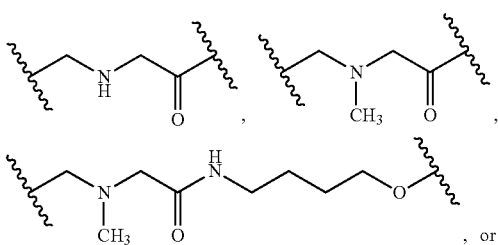
, or -continued

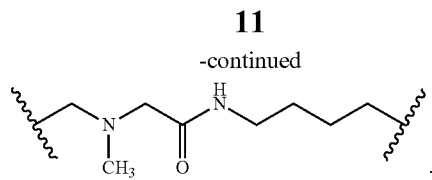

In some embodiments, $E^1$ is

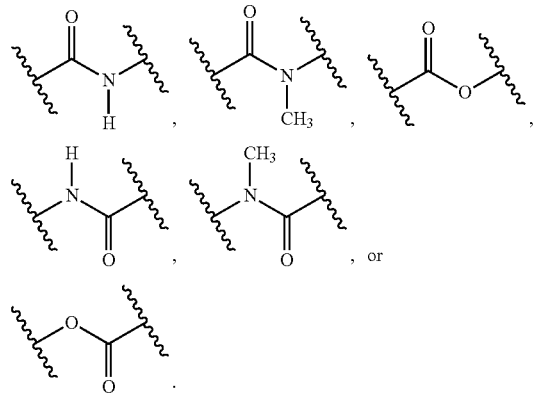

In some embodiments, $E^2$ is O, $NR^N$,

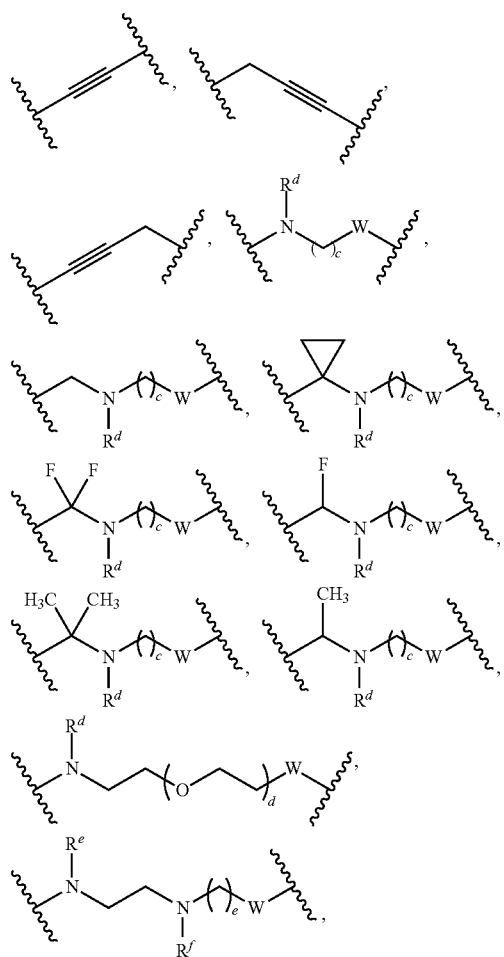

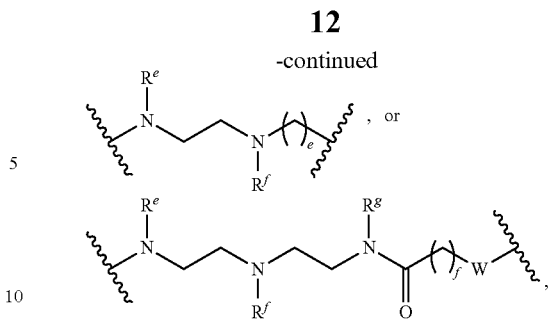

wherein
c is 0, 1, 2, 3, 4, 5, 6, 7, or 8;
d is 0, 1, 2, or 3;
e is 0, 1, 2, 3, 4, 5, or 6;
f is 0, 1, 2, 3, or 4;
$R^d$ is H, optionally substituted $C_1$-$C_6$ alkyl, optionally substituted $C_1$-$C_6$ heteroalkyl, or optionally substituted $C_3$-$C_6$ carbocyclyl;
$R^e$ is H, optionally substituted $C_1$-$C_6$ alkyl, optionally substituted $C_1$-$C_6$ heteroalkyl, or optionally substituted $C_3$-$C_6$ carbocyclyl;
$R^f$ is H, optionally substituted $C_1$-$C_6$ alkyl, optionally substituted $C_1$-$C_6$ heteroalkyl, or optionally substituted $C_3$-$C_6$ carbocyclyl;
$R^g$ is H, optionally substituted $C_1$-$C_6$ alkyl, optionally substituted $C_1$-$C_6$ heteroalkyl, or optionally substituted $C_3$-$C_6$ carbocyclyl; and
W is O or $NR^W$, wherein $R^w$ is H or optionally substituted $C_1$-$C_6$ alkyl.
In some embodiments, $E^2$ is O, $NR^W$,

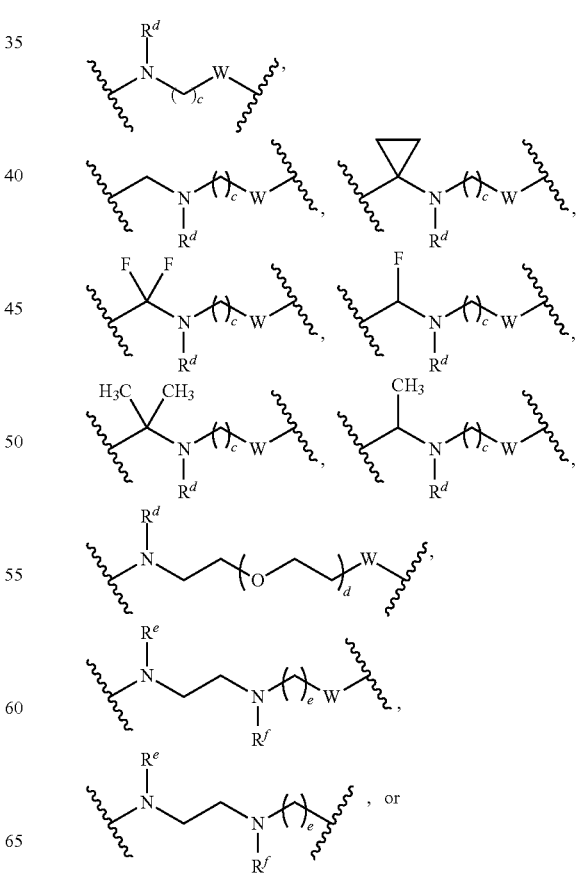

-continued

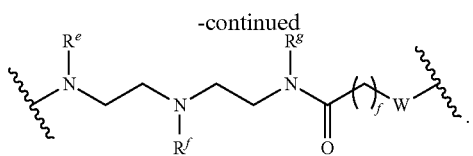

In some embodiments, $R^d$ is H or optionally substituted $C_1$-$C_6$ alkyl. In some embodiments, $R^e$ is H or optionally substituted $C_1$-$C_6$ alkyl. In some embodiments, R' is H or optionally substituted $C_1$-$C_6$ alkyl. In some embodiments, $R^g$ is H or optionally substituted $C_1$-$C_6$ alkyl. In some embodiments, $R^w$ is H or optionally substituted $C_1$-$C_6$ alkyl.

In some embodiments, $R^d$ is H or methyl. In some embodiments, $R^e$ is H or methyl. In some embodiments, $R^f$ is H or methyl. In some embodiments, $R^g$ is H or methyl. In some embodiments, $R^w$ is H or methyl.

In some embodiments, $E^2$ is

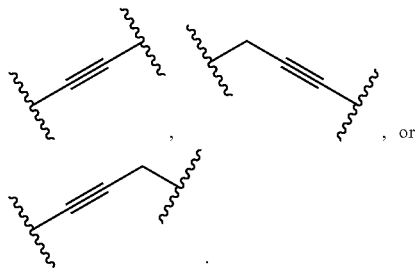

In some embodiments, $E^2$ is O,

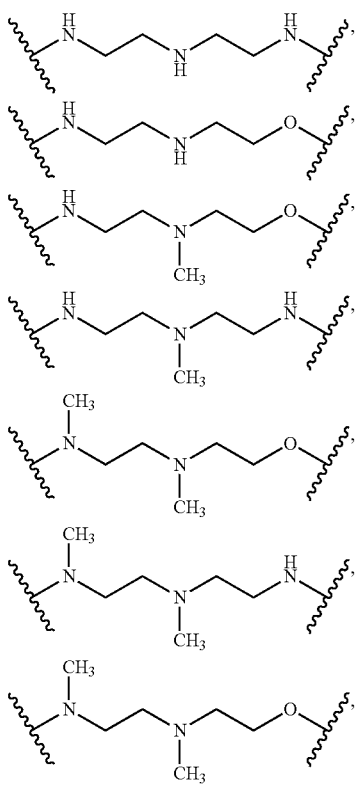

-continued

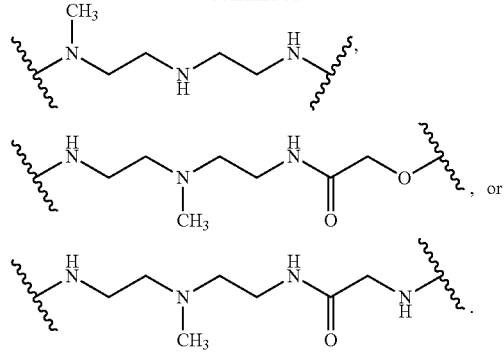

In some embodiments, each of $F^1$, $F^2$, or $F^3$ is, independently, optionally substituted $C_3$-$C_{10}$ carbocyclylene.

In some embodiments, the $C_3$-$C_{10}$ carbocyclylene is monocyclic. In some embodiments, the $C_3$-$C_{10}$ carbocyclylene is polycyclic.

In some embodiments, the $C_3$-$C_{10}$ carbocyclylene is bicyclic.

In some embodiments, the $C_3$-$C_{10}$ carbocyclylene is bridged. In some embodiments, the $C_3$-$C_{10}$ carbocyclylene is fused. In some embodiments, the $C_3$-$C_{10}$ carbocyclylene is spirocyclic.

In some embodiments, the $C_3$-$C_{10}$ carbocyclylene is

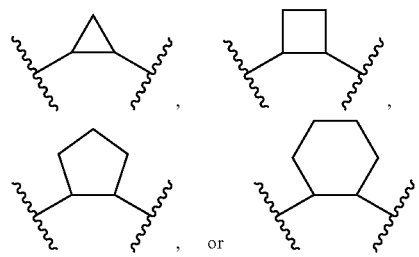

In some embodiments, $F^2$ is

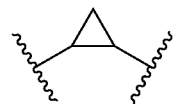

In some embodiments, the $C_3$-$C_{10}$ carbocyclylene is

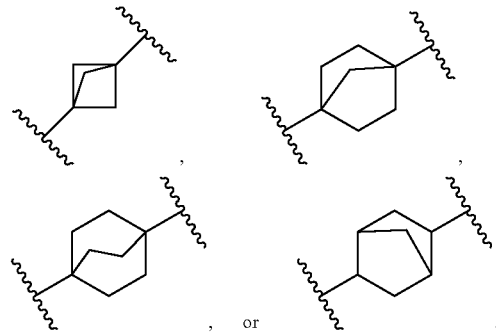

In some embodiments, F¹ is

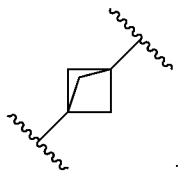 [SMILES: *C12CC(*)(C1)C2]

In some embodiments, each of $F^1$, $F^2$, or $F^3$ is, independently, optionally substituted $C_2$-$C_9$ heterocyclylene.

In some embodiments, the $C_2$-$C_9$ heterocyclylene is monocyclic. In some embodiments, the $C_2$-$C_9$ heterocyclylene is polycyclic.

In some embodiments, the $C_2$-$C_9$ heterocyclylene is bicyclic.

In some embodiments, the $C_2$-$C_9$ heterocyclylene is bridged. In some embodiments, the $C_2$-$C_g$ heterocyclylene is fused. In some embodiments, the $C_2$-$C_9$ heterocyclylene is spirocyclic.

In some embodiments, the $C_2$-$C_9$ heterocyclylene includes a quaternary amine.

In some embodiments, the $C_2$-$C_9$ heterocyclylene is

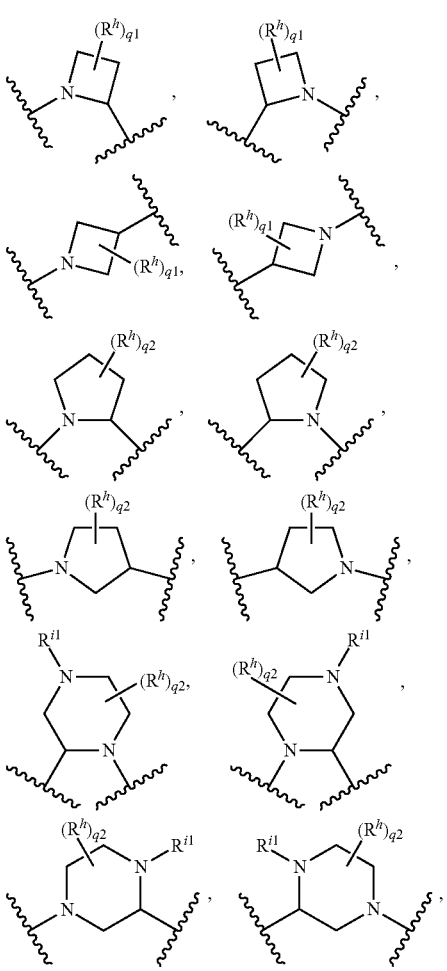

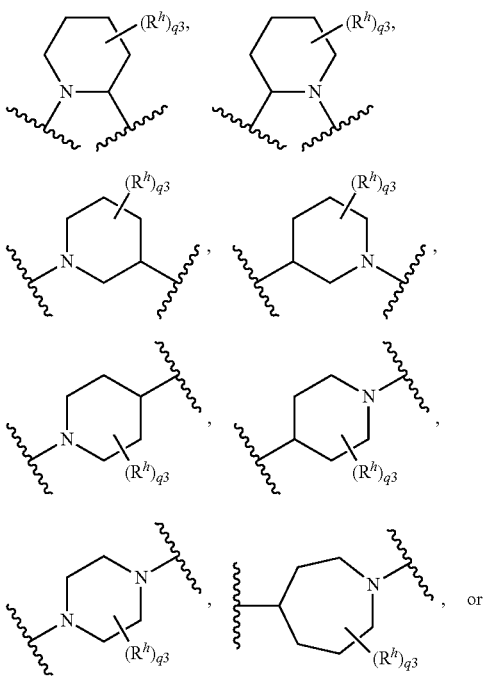

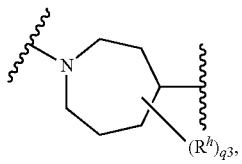

where:
q1 is 0, 1, 2, 3, or 4;
q2 is 0, 1, 2, 3, 4, 5, or 6;
q3 is 0, 1, 2, 3, 4, 5, 6, 7, or 8;
each $R^h$ is, independently, 2H, halogen, optionally substituted $C_1$-$C_6$ alkyl, $OR^{i2}$, or $NR^{i3}R^{i4}$; or two $R^h$ groups, together with the carbon atom to which each is attached, combine to form optionally substituted $C_3$-$C_{10}$ carbocyclyl or optionally substituted $C_2$-$C_9$ heterocyclyl; or two $R^h$ groups, together with the carbon atoms to which each is attached, combine to form optionally substituted $C_3$-$C_{10}$ carbocyclyl or optionally substituted $C_2$-$C_9$ heterocyclyl;
$R^{i1}$ is H or optionally substituted $C_1$-$C_6$ alkyl;
$R^{i2}$ is H, optionally substituted $C_1$-$C_6$ alkyl, optionally substituted $C_1$-$C_6$ heteroalkyl, or optionally substituted $C_3$-$C_6$ carbocyclyl;
$R^{i3}$ is H or optionally substituted $C_1$-$C_6$ alkyl; and
$R^{i4}$ is H or optionally substituted $C_1$-$C_6$ alkyl.

In some embodiments, each $R^h$ is, independently, halogen, optionally substituted $C_1$-$C_6$ alkyl, $OR^{i2}$, or $NR^{i3}R^{i4}$. In some embodiments, $R^{i1}$ is H or optionally substituted $C_1$-$C_6$ alkyl. In some embodiments, $R^{i2}$ is H or optionally substituted $C_1$-$C_6$ alkyl. In some embodiments, $R^{i3}$ is H or optionally substituted $C_1$-$C_6$ alkyl. In some embodiments, $R^{i4}$ is H or optionally substituted $C_1$-$C_6$ alkyl.

In some embodiments, the $C_2$-$C_9$ heterocyclylene is

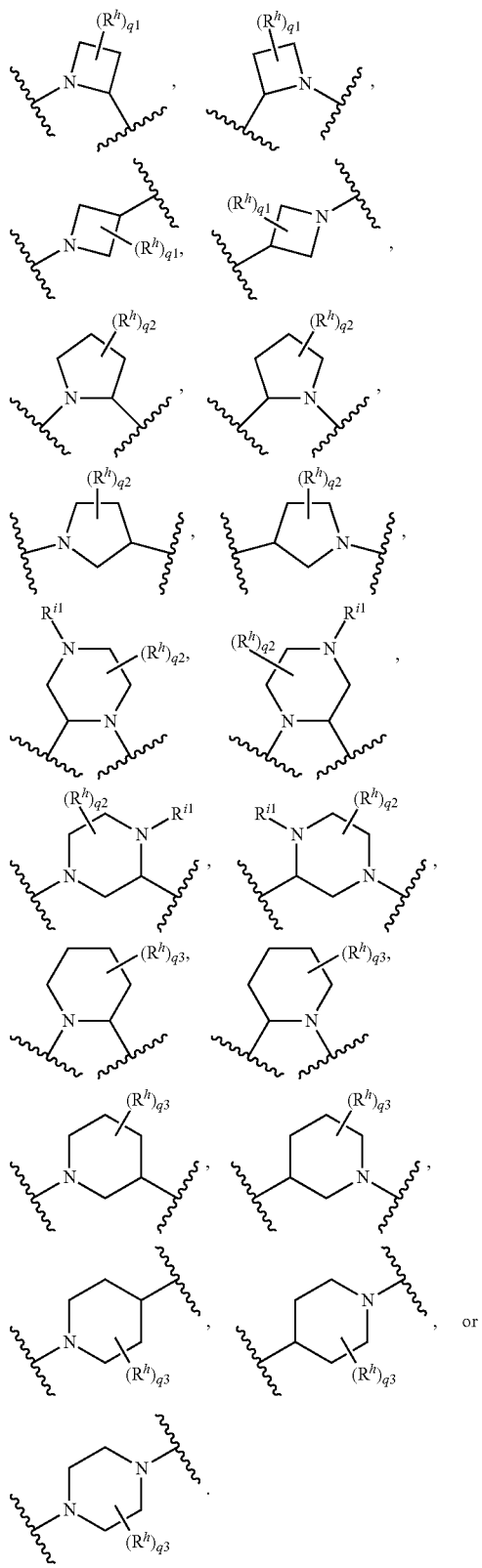

In some embodiments, each $R^h$ is, independently, halogen, optionally substituted $C_1$-$C_6$ alkyl, $OR^{i2}$, or $NR^{i3}R^{i4}$. In some embodiments, each $R^h$ is, independently, halogen, optionally substituted $C_1$-$C_6$ alkyl, or $NR^{i3}R^{i4}$.

In some embodiments, each $R^h$ is, independently, 2H, halogen, cyano, optionally substituted $C_1$-$C_6$ alkyl, $OR^{i2}$, or $NR^{i3}R^{i4}$. In some embodiments, two $R^h$ groups, together with the carbon atom to which each is attached, combine to form optionally substituted $C_3$-$C_{10}$ carbocyclyl or optionally substituted $C_2$-$C_9$ heterocyclyl. In some embodiments, two $R^h$ groups, together with the carbon atoms to which each is attached, combine to form optionally substituted $C_3$-$C_{10}$ carbocyclyl or optionally substituted $C_2$-$C_9$ heterocyclyl.

In some embodiments, each $R^h$ is, independently, 2H, F, methyl,

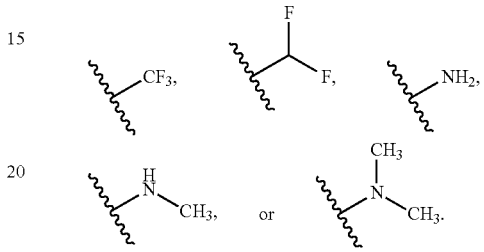

In some embodiments, each $R^h$ is, independently, F, methyl, or $NR^{i3}R^{i4}$.

In some embodiments, q1 is 0, 1, or 2. In some embodiments, q1 is 0. In some embodiments, q1 is 1. In some embodiments, q1 is 2.

In some embodiments, q2 is 0, 1, or 2. In some embodiments, q2 is 0. In some embodiments, q2 is 1. In some embodiments, q2 is 2.

In some embodiments, q3 is 0, 1, or 2. In some embodiments, q3 is 0. In some embodiments, q3 is 1. In some embodiments, q3 is 2.

In some embodiments, the $C_2$-$C_9$ heterocyclylene is

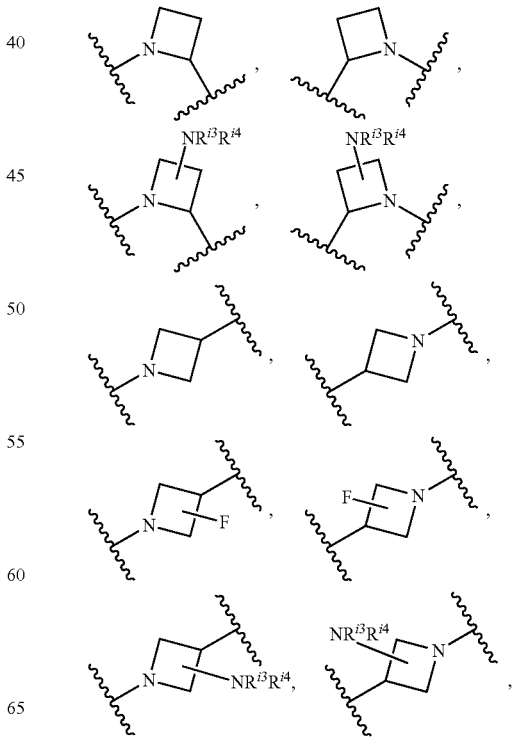

-continued
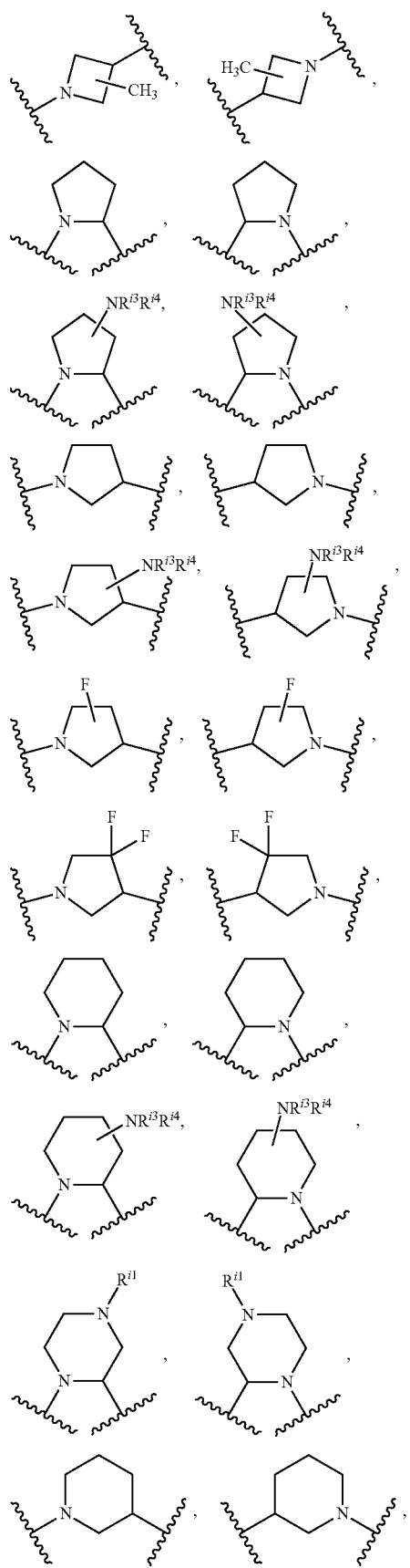
-continued
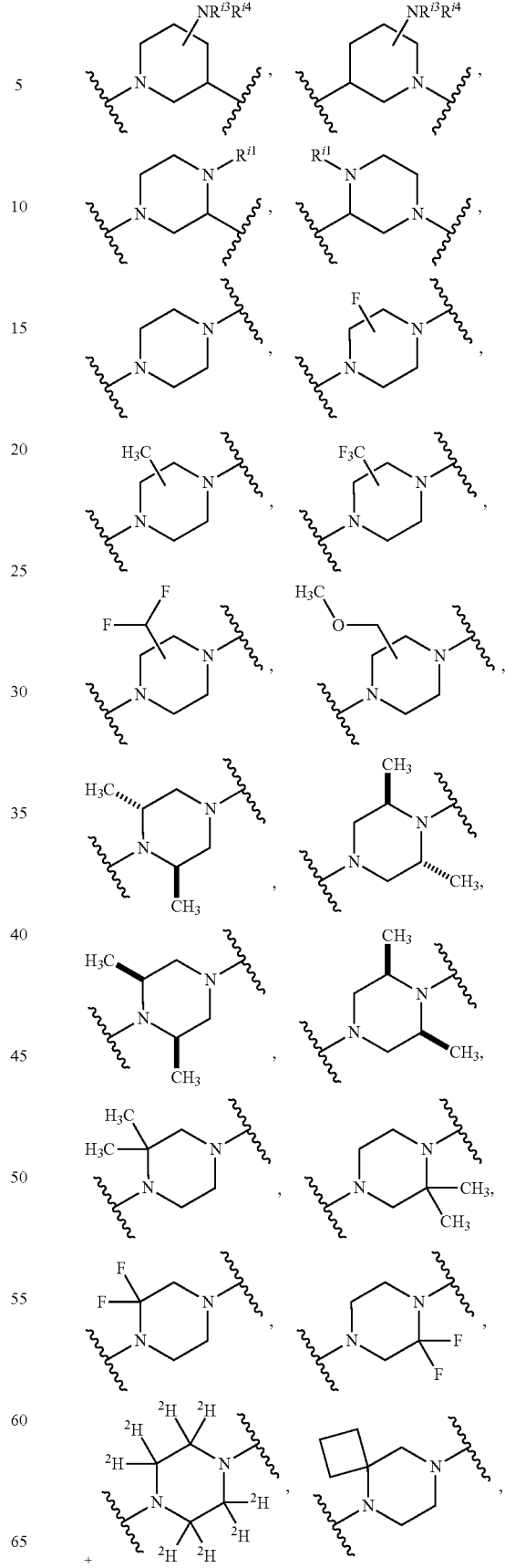

21
-continued
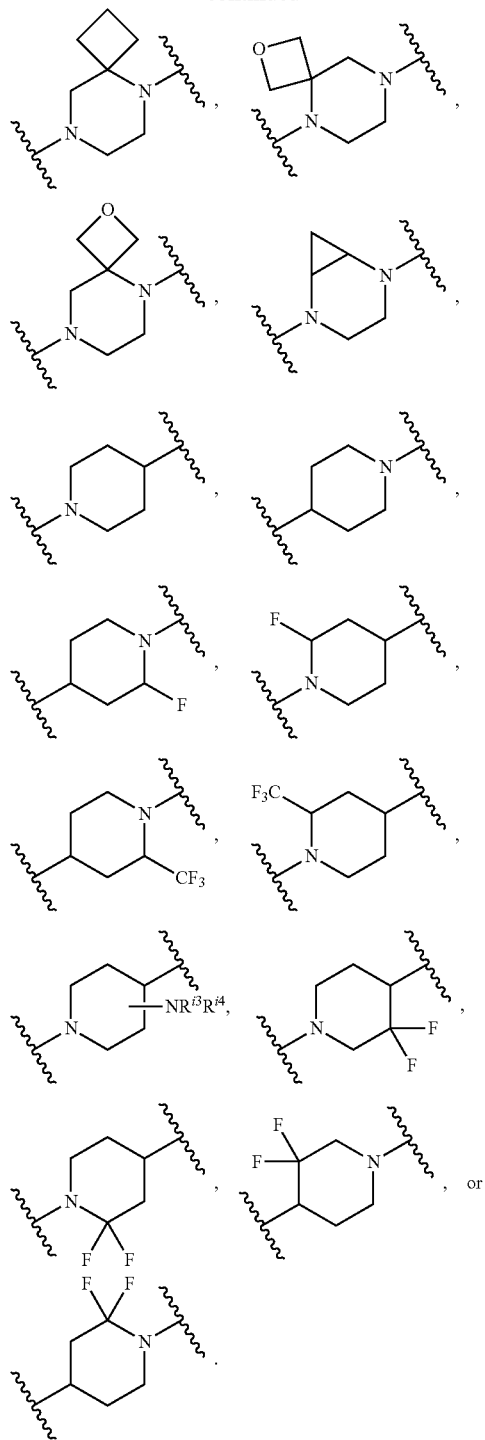
In some embodiments, the $C_2$-$C_9$ heterocyclylene is
22
-continued
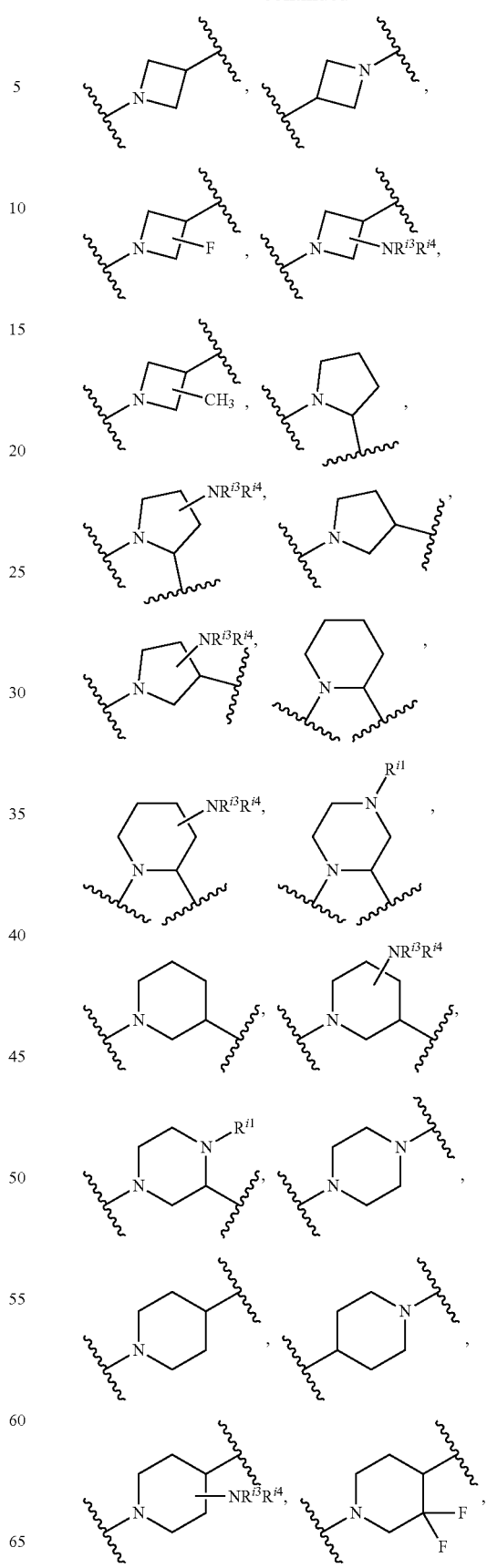

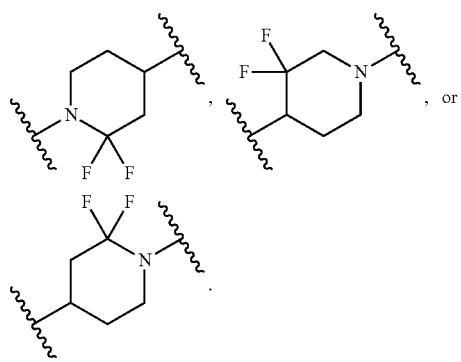
In some embodiments, the $C_2$-$C_9$ heterocyclylene is
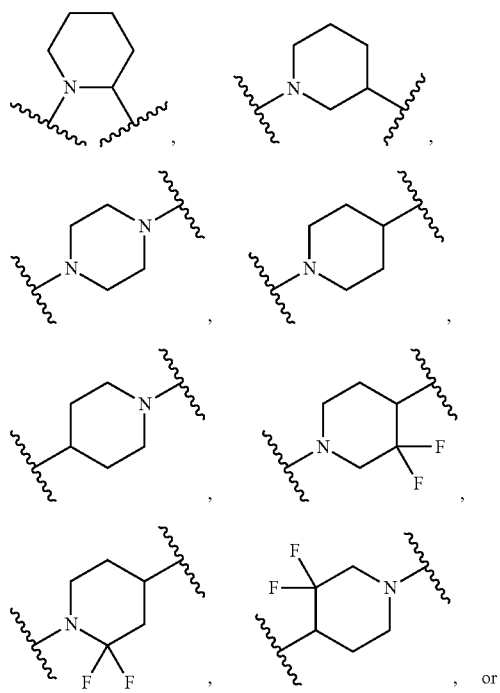
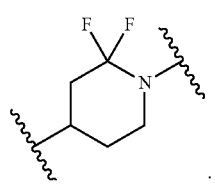
In some embodiments, the $C_2$-$C_9$ heterocyclylene is
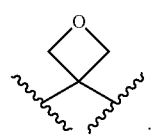 [SMILES: *C1(*)COC1]
In some embodiments, $F^1$ is
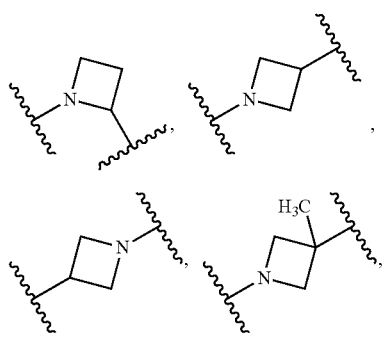
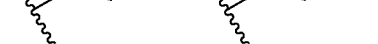
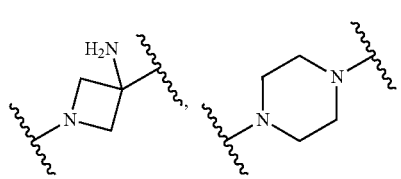
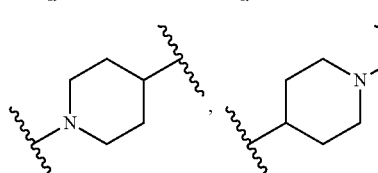
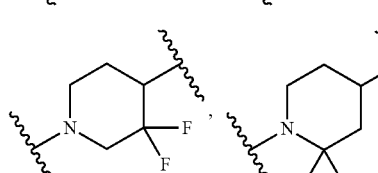
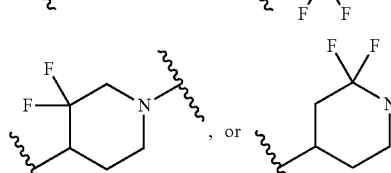
In some embodiments, $F^1$ is
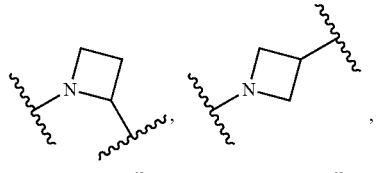
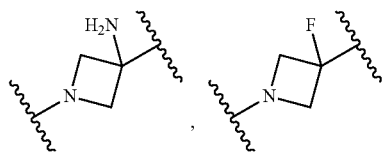

-continued
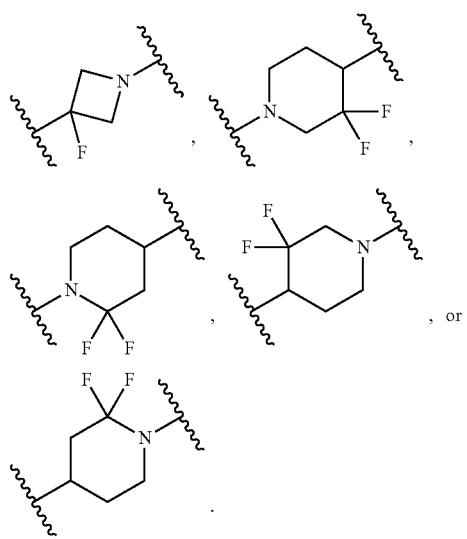
In some embodiments, F¹ is
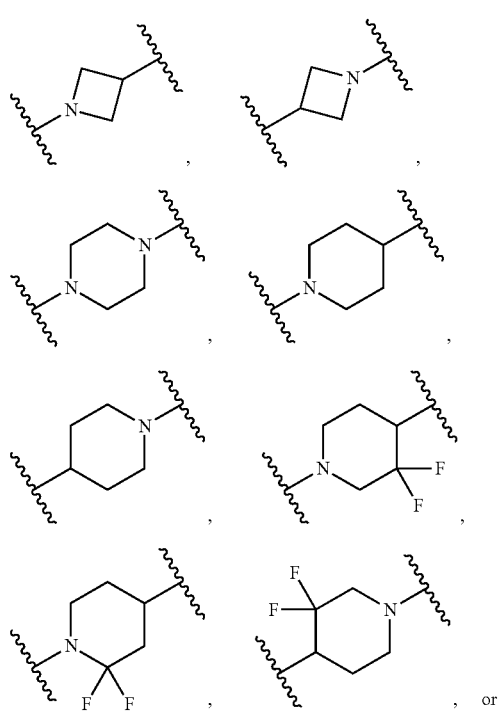
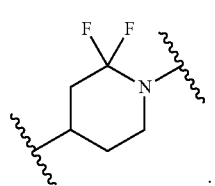
In some embodiments, F² is
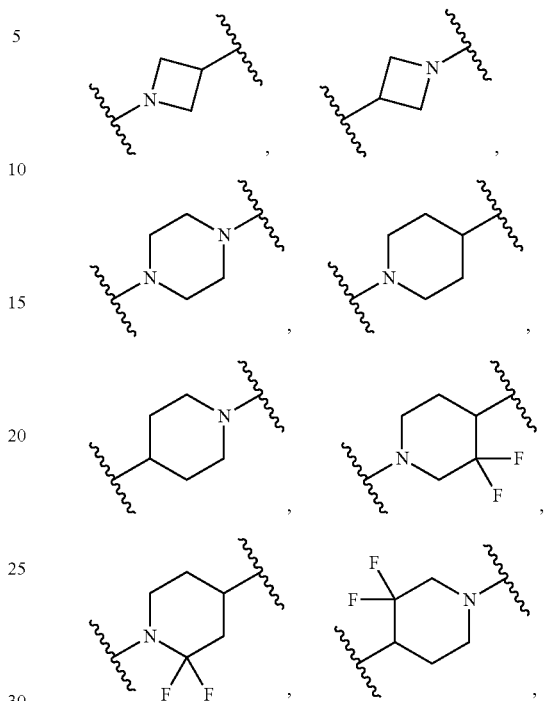
In some embodiments, F² is
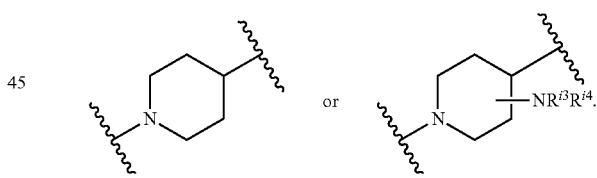
In some embodiments, F³ is
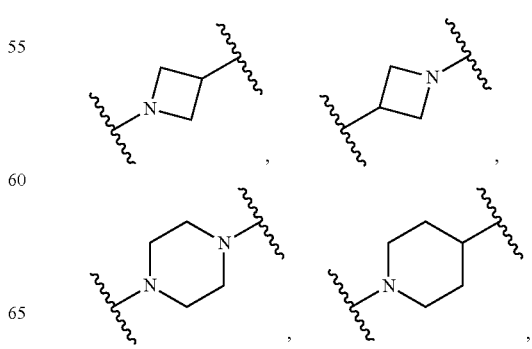

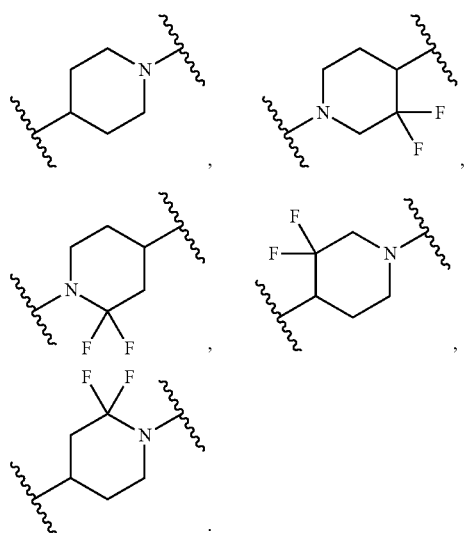
In some embodiments, F³ is
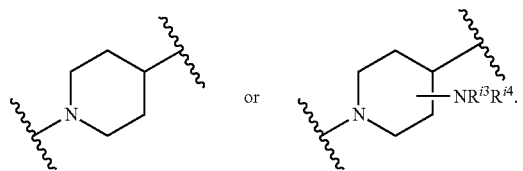
In some embodiments, R$^{i1}$ is H or methyl. In some embodiments, R$^{i2}$ is H or methyl. In some embodiments, R$^{i3}$ is H or methyl. In some embodiments, R$^{i4}$ is H or methyl.
In some embodiments, the C$_2$-C$_9$ heterocyclylene is
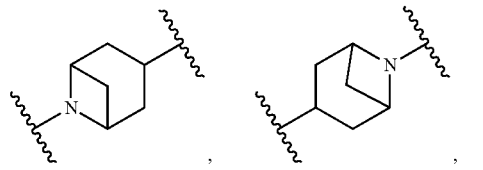
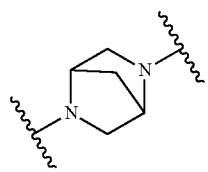
In some embodiments, the C$_2$-C$_9$ heterocyclylene is
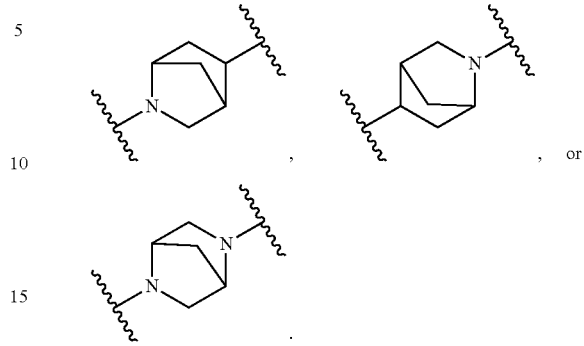
In some embodiments, the C$_2$-C$_9$ heterocyclylene is
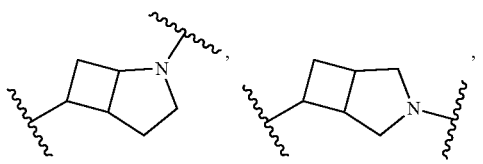
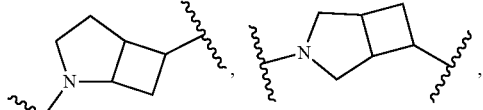
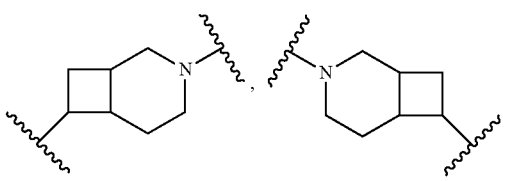
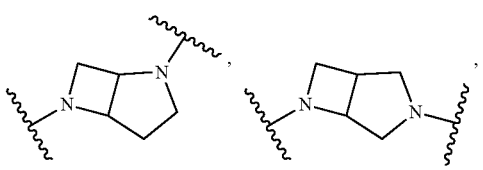
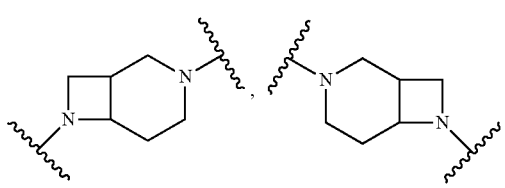
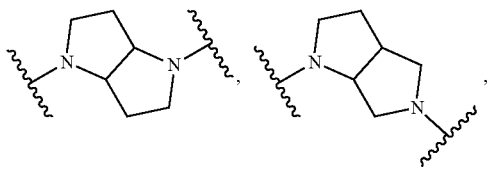

-continued
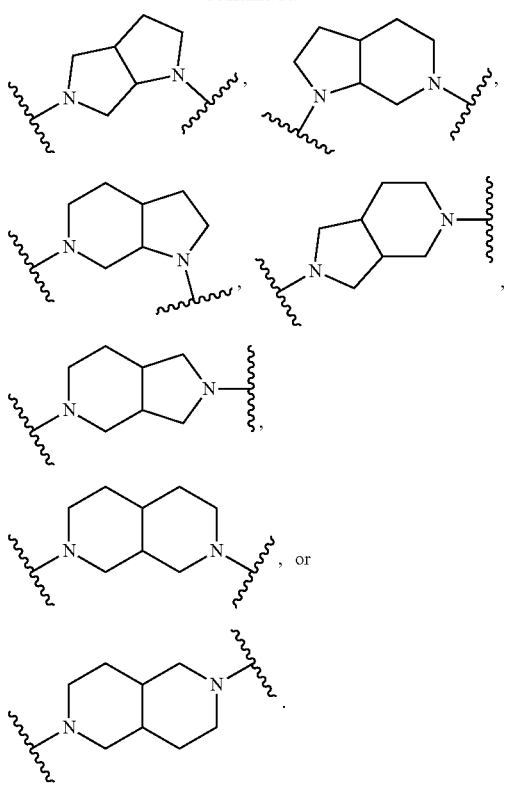
In some embodiments, the $C_2$-$C_9$ heterocyclylene is
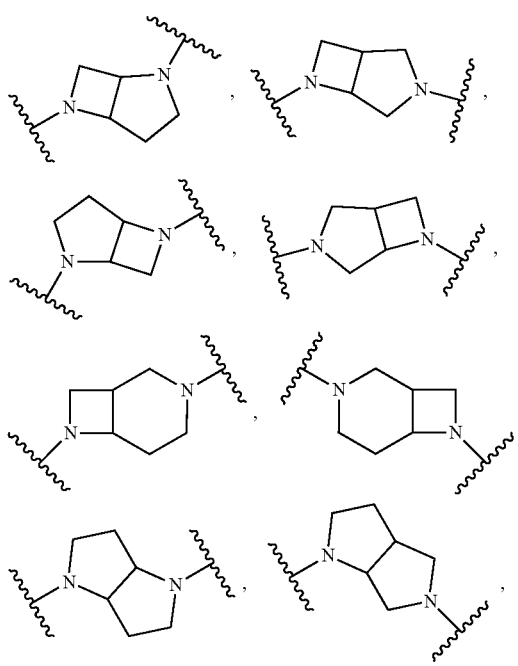
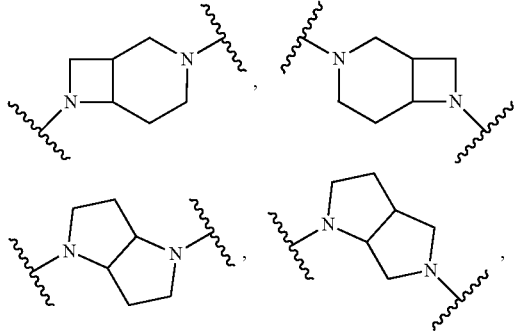
-continued
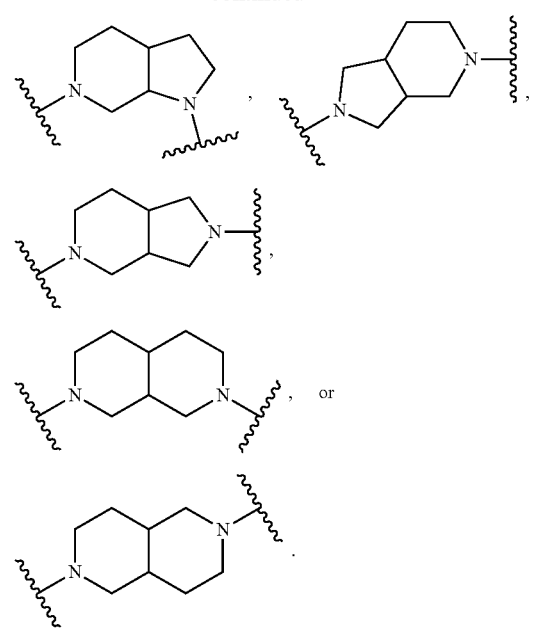
In some embodiments, the $C_2$-$C_9$ heterocyclylene is
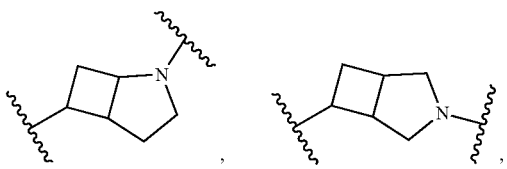
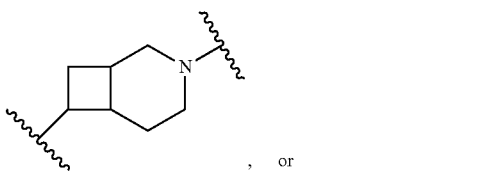
In some embodiments, $F^1$ is
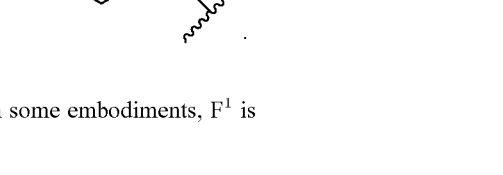
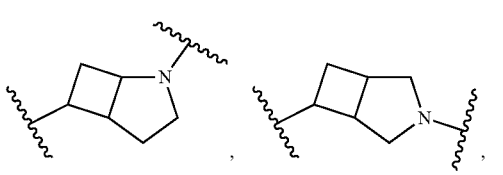

-continued

In some embodiments, F¹ is

In some embodiments, F¹ is

, or

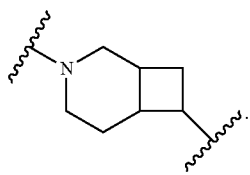
In some embodiments, $F^2$ is
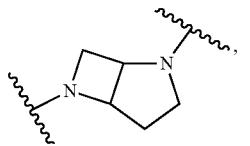
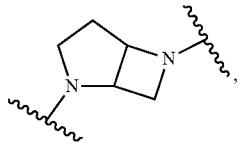
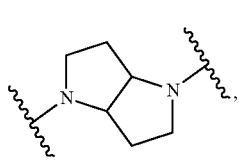
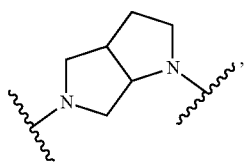
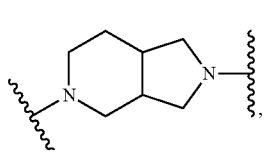
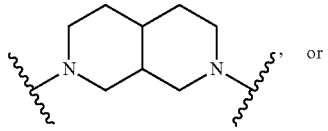, or
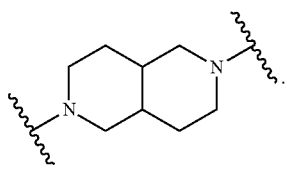.
In some embodiments, the $C_2$-$C_9$ heterocyclyl is
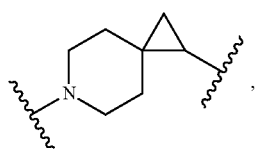 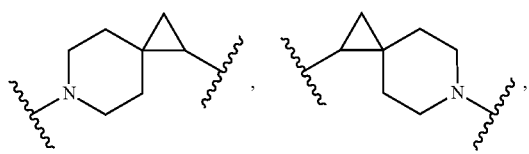
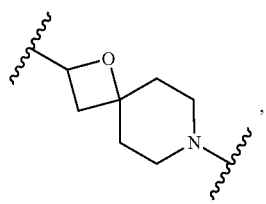
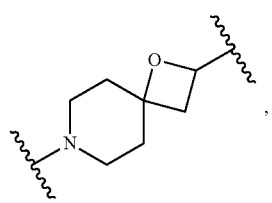
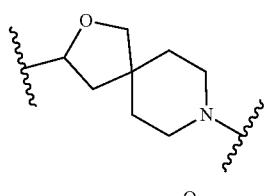
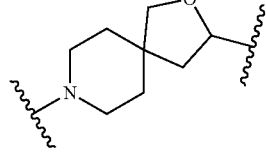
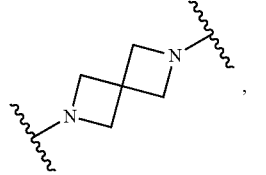
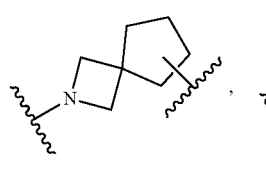
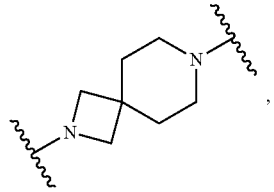
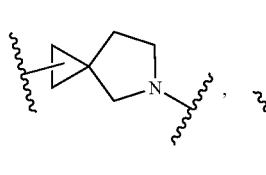
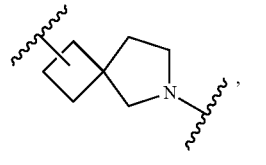 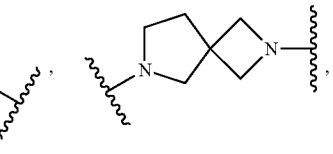

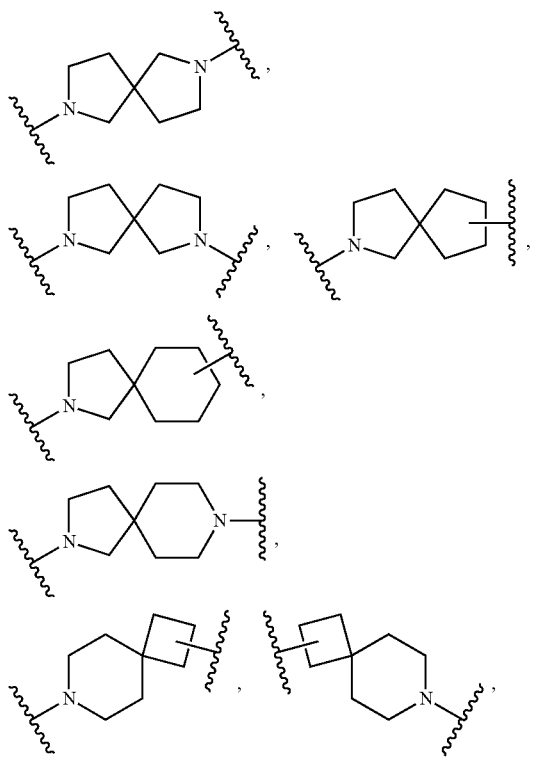
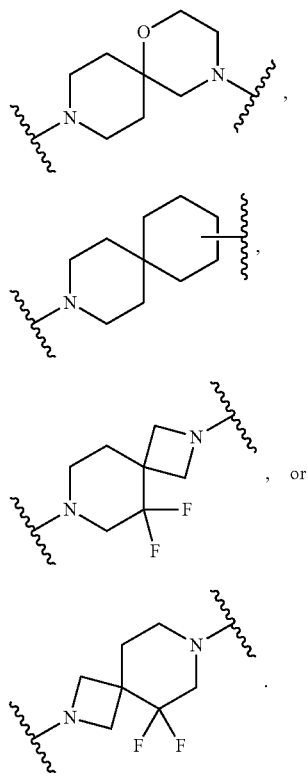
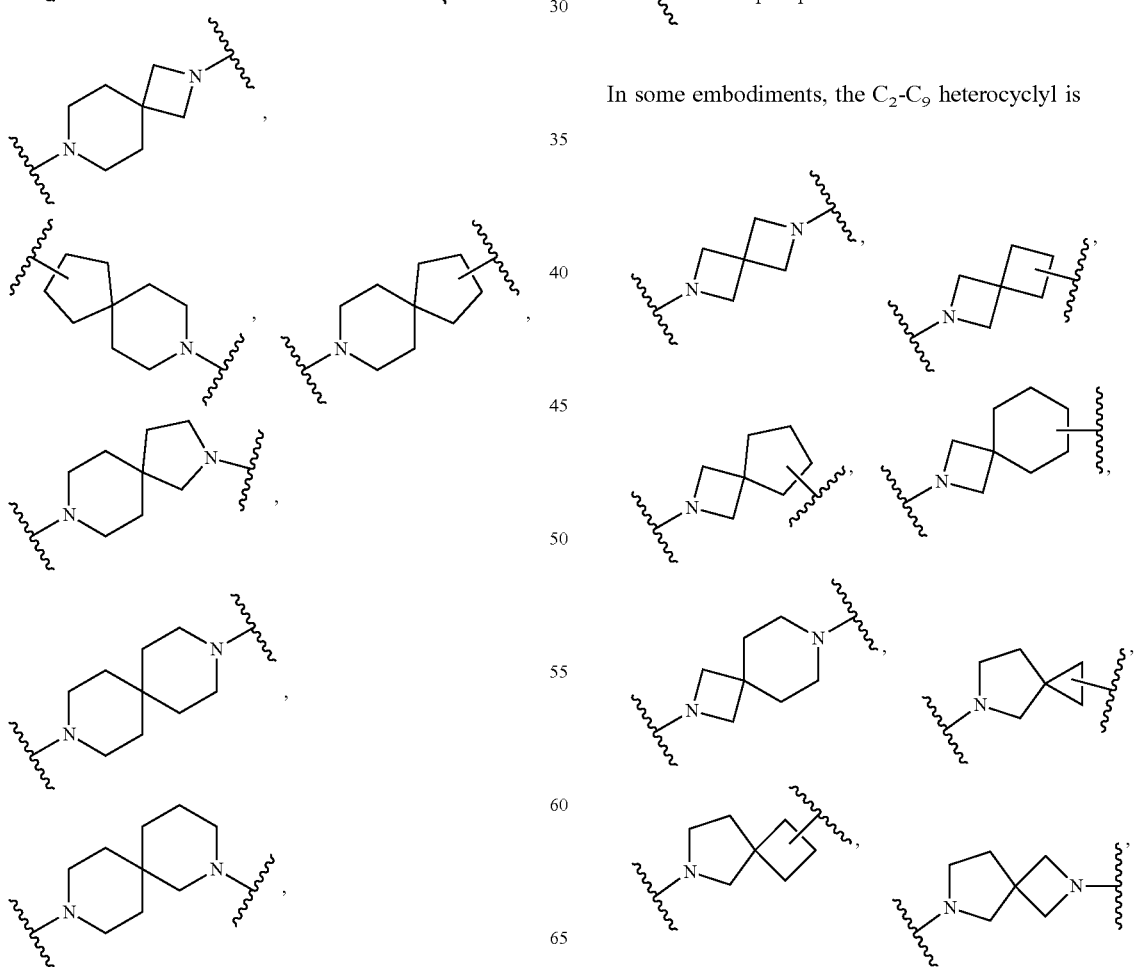
In some embodiments, the $C_2$-$C_9$ heterocyclyl is -continued
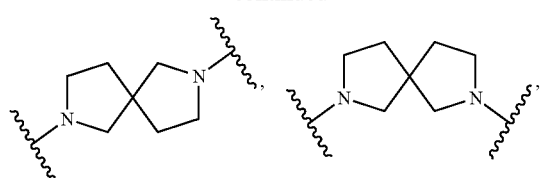
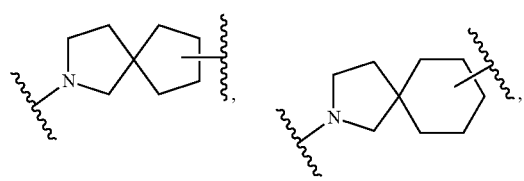
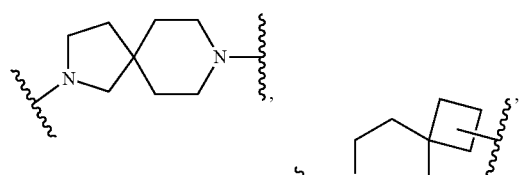
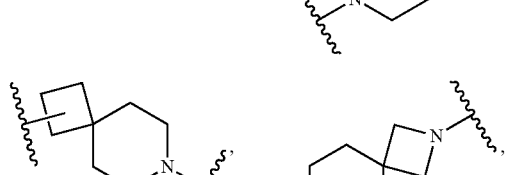
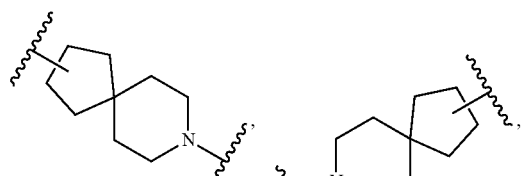
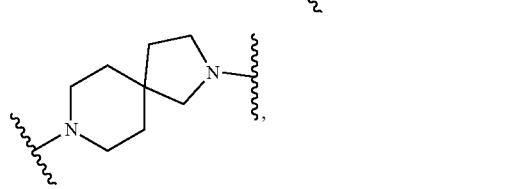
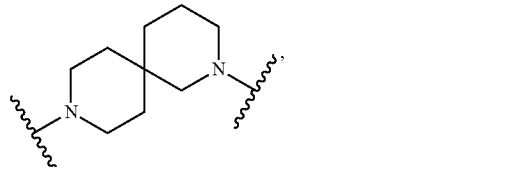
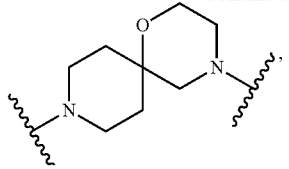
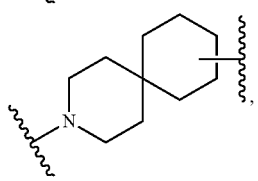
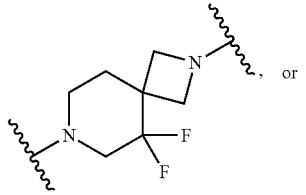, or
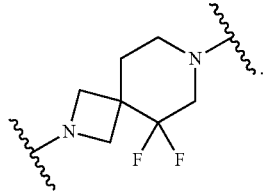 [SMILES: *N1CCC2(CN(*)C2)C(F)(F)C1].
In some embodiments, the $C_2$-$C_9$ heterocyclyl is
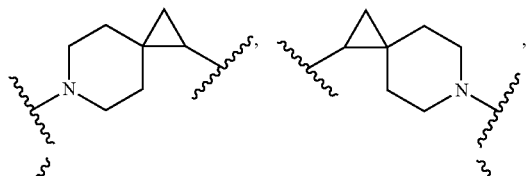
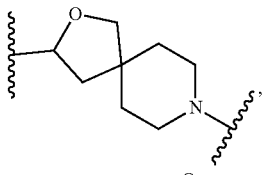
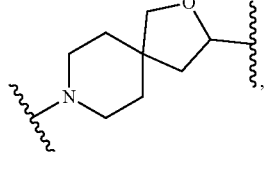
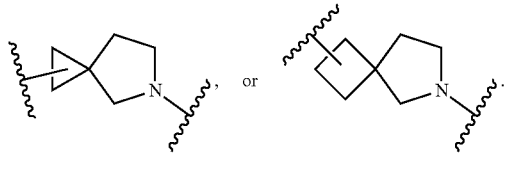

In some embodiments, the $C_2$-$C_9$ heterocyclyl is
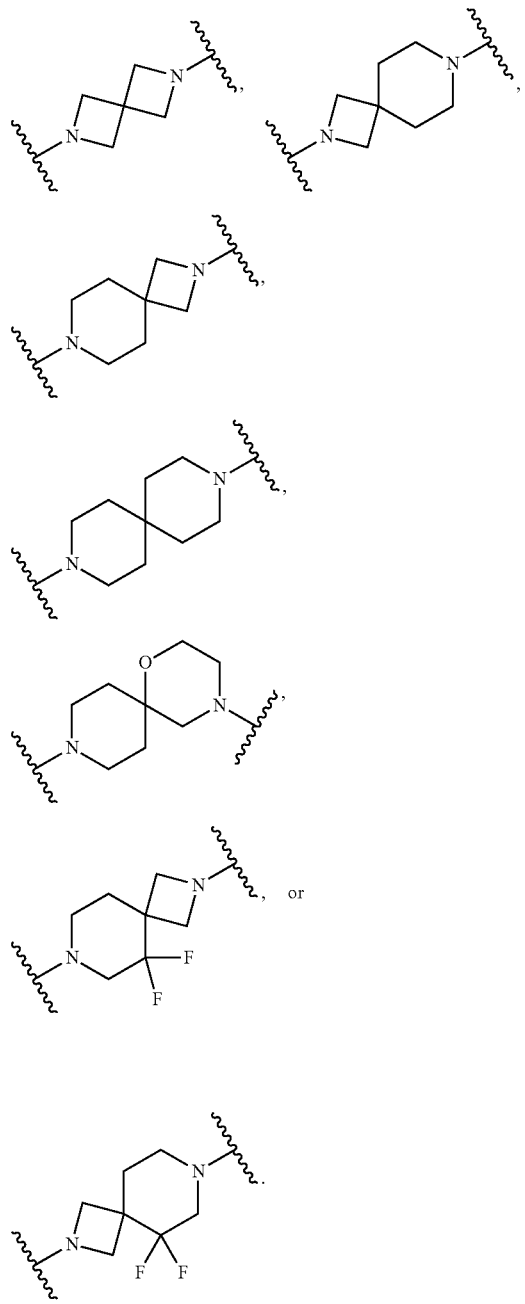
, or
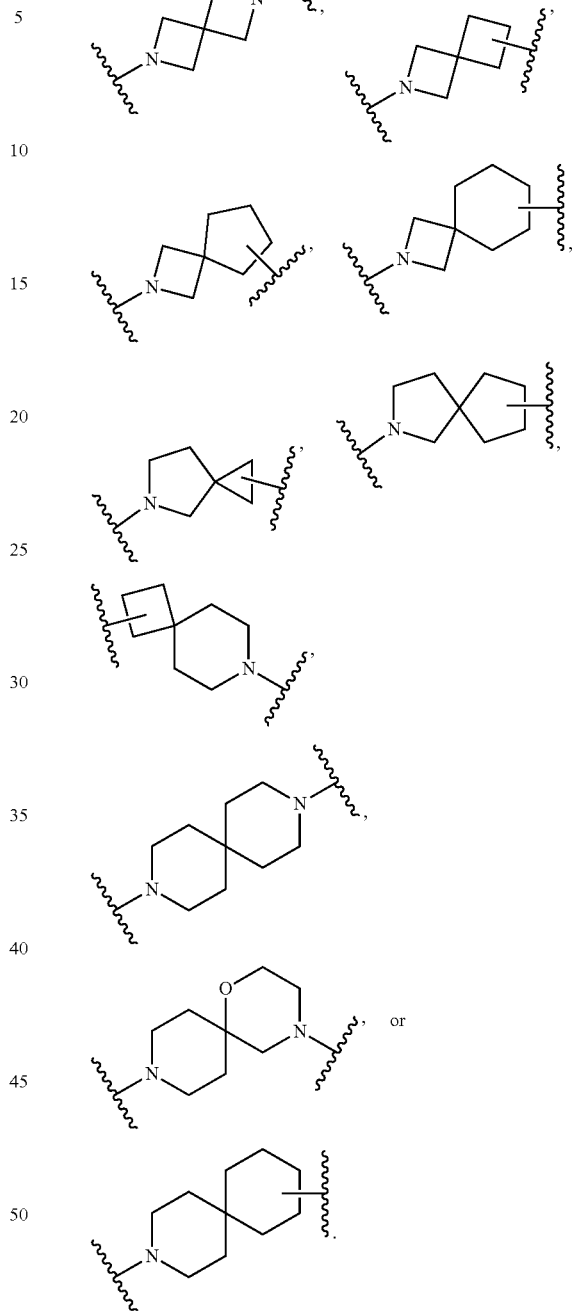
.
In some embodiments, $F^1$ is
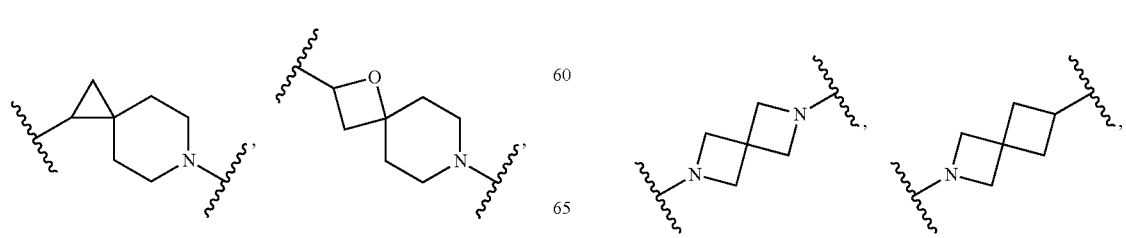

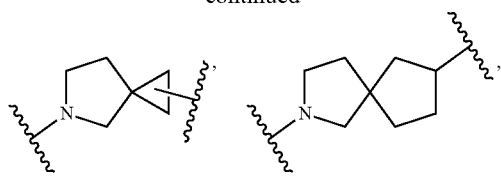
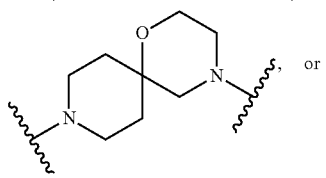
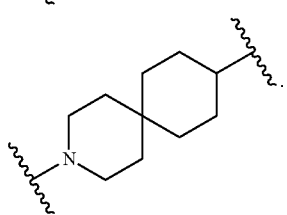
In some embodiments, F¹ is
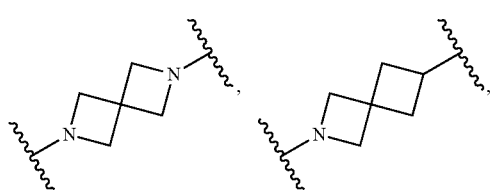
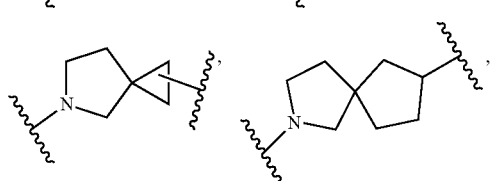
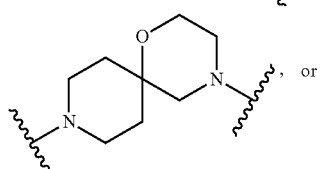
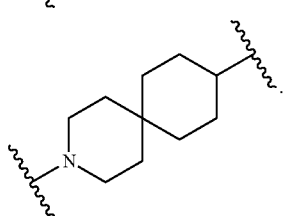
In some embodiments, F¹ is
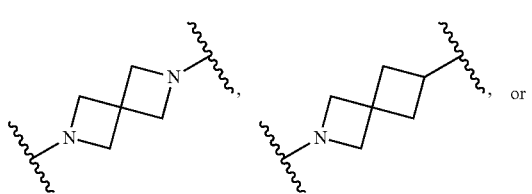
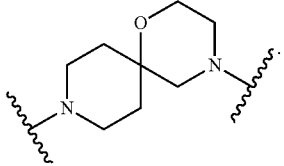
In some embodiments, F¹ is
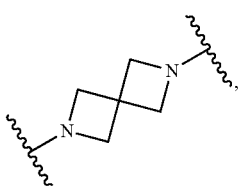
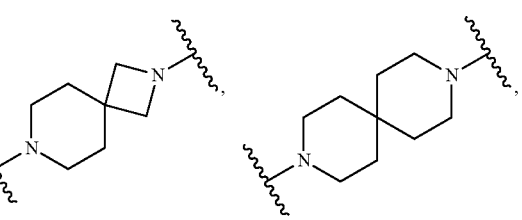
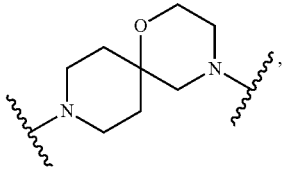
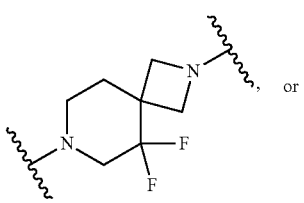
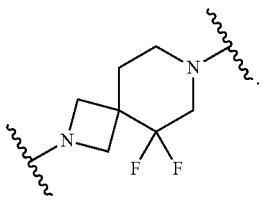
In some embodiments, F² is
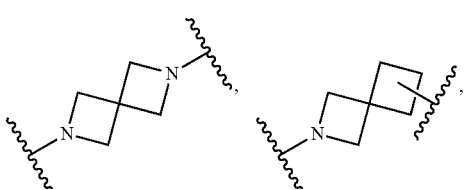

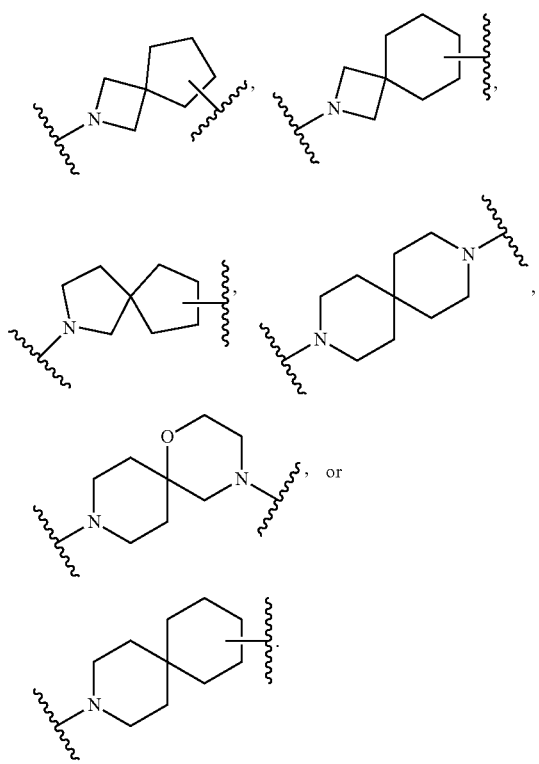
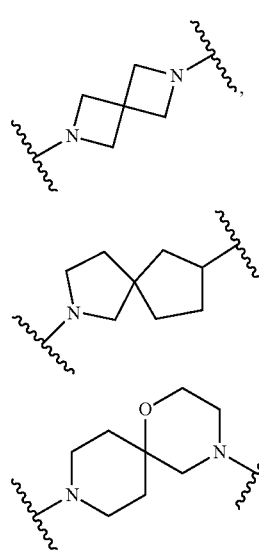
In some embodiments, F² is
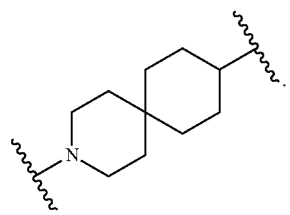
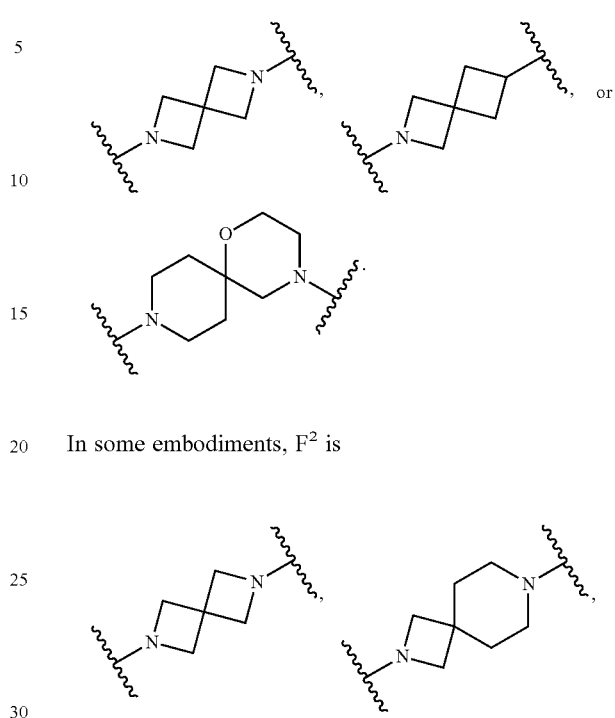
In some embodiments, F² is
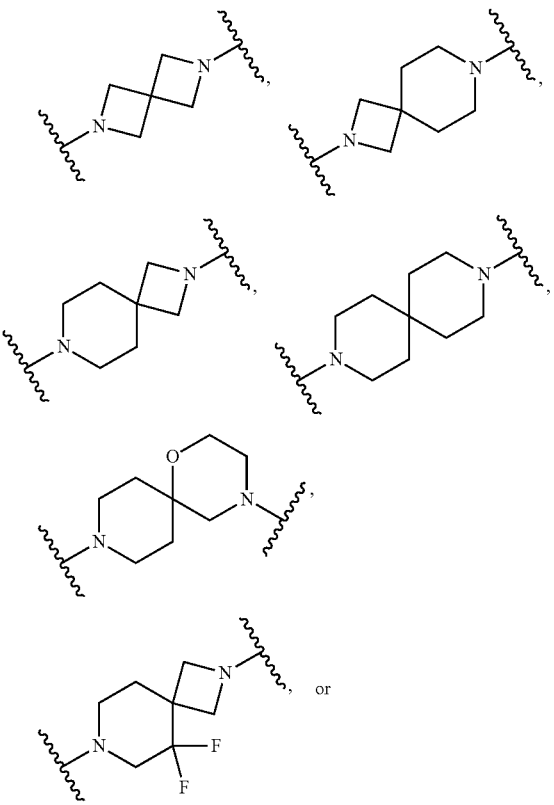
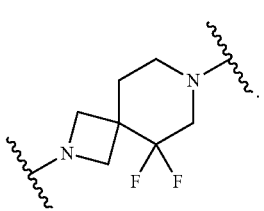

In some embodiments, $F^3$ is
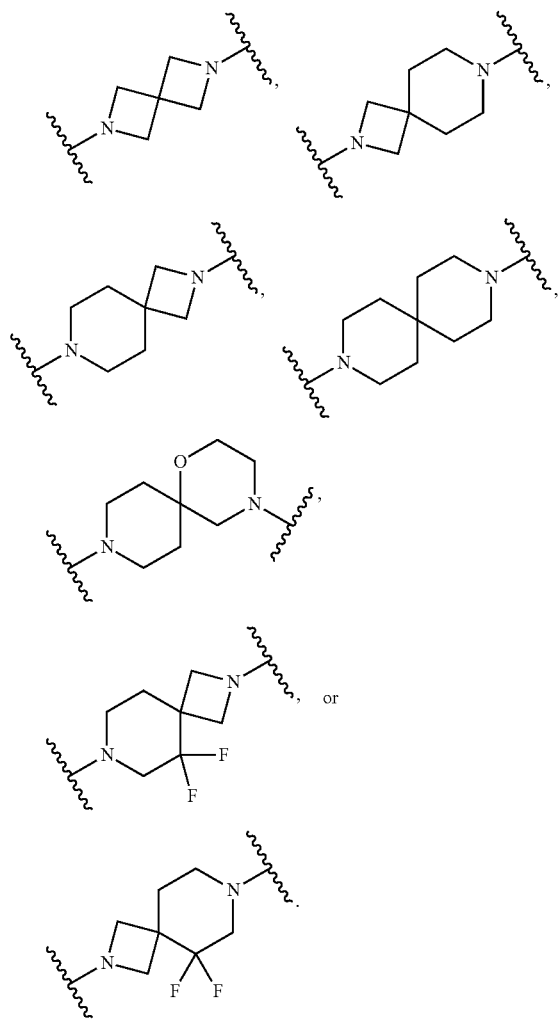
In some embodiments, each of $F^1$, $F^2$, or $F^3$ is, independently, optionally substituted $C_6$-$C_{10}$ arylene.
In some embodiments, the $C_6$-$C_{10}$ arylene is
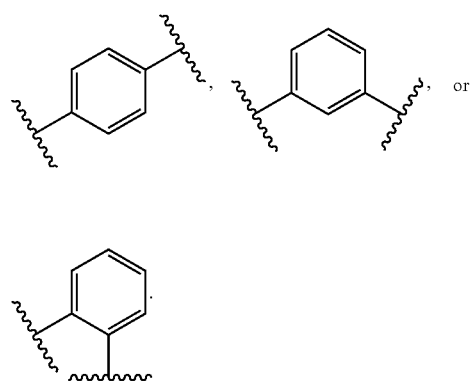 [SMILES: *c1ccc(*)cc1 ; *c1cccc(*)c1 ; *c1ccccc1*]
In some embodiments, each of $F^1$, $F^2$, or $F^3$ is, independently, optionally substituted $C_2$-$C_9$ heteroarylene.
In some embodiments, the $C_2$-$C_9$ heteroarylene is
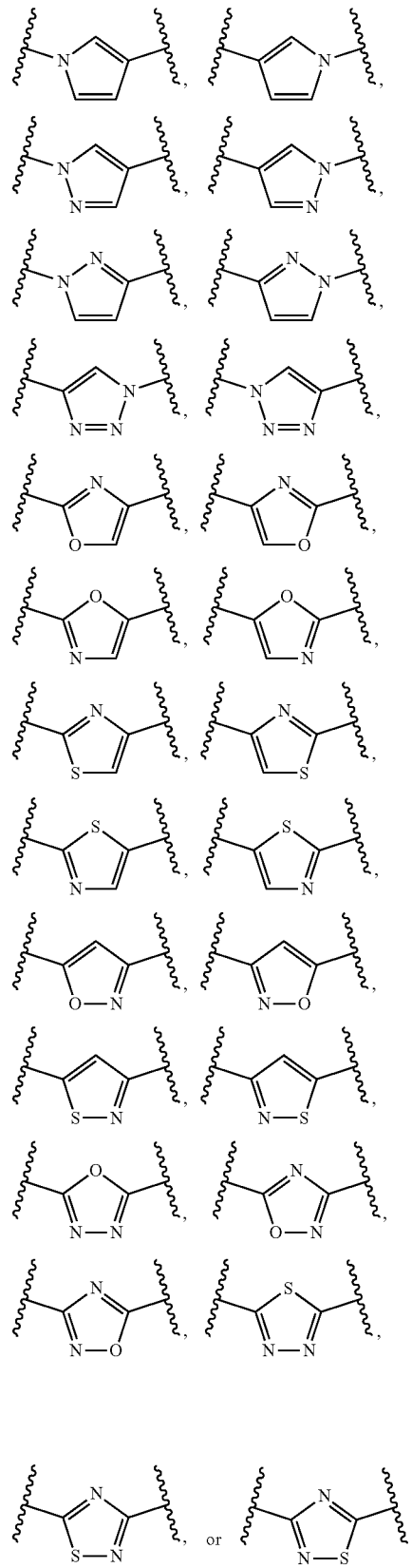

In some embodiments, F² is
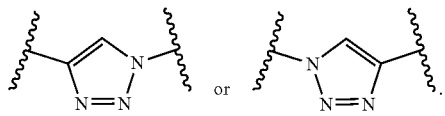 [SMILES: *c1cn(*)nn1 ; *c1cn(*)nn1] or 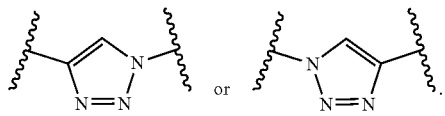 [SMILES: *c1cn(*)nn1 ; *c1cn(*)nn1].
In some embodiments, F² is
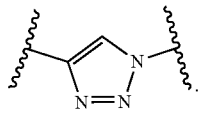 [SMILES: *c1cn(*)nn1].
In some embodiments, C³ is
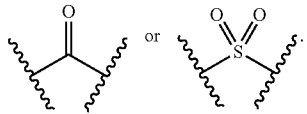.
In some embodiments, C³ is
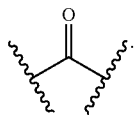 [SMILES: *C(*)=O].
In some embodiments, m is 1. In some embodiments, p is 1.
In some embodiments, the linker has the structure of
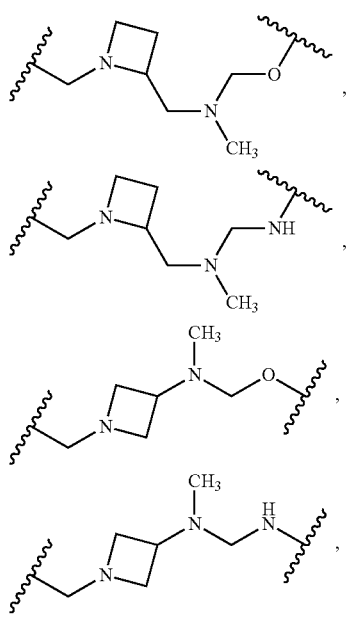
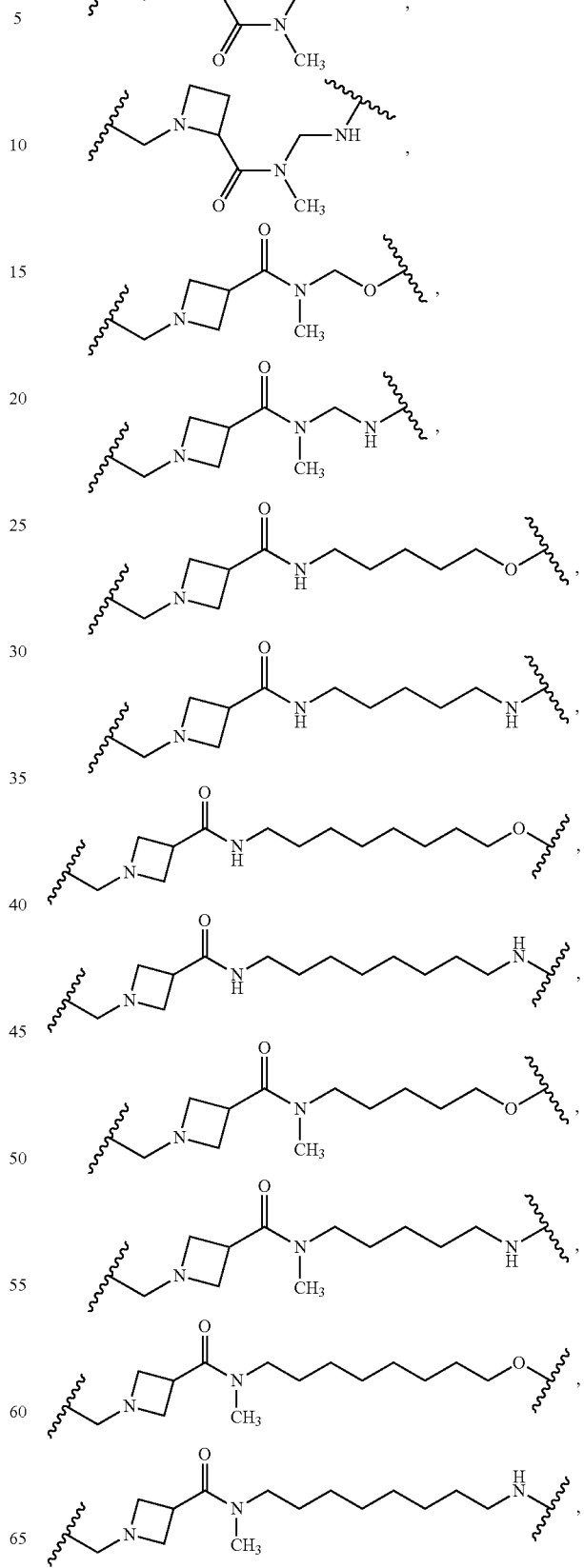

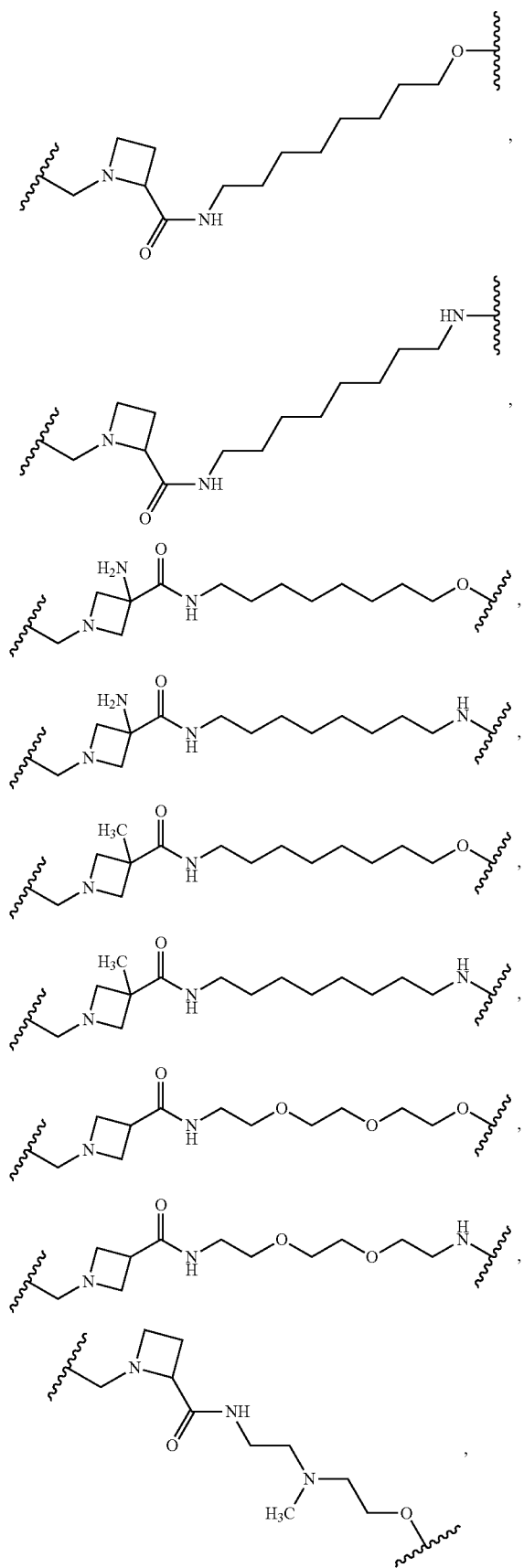
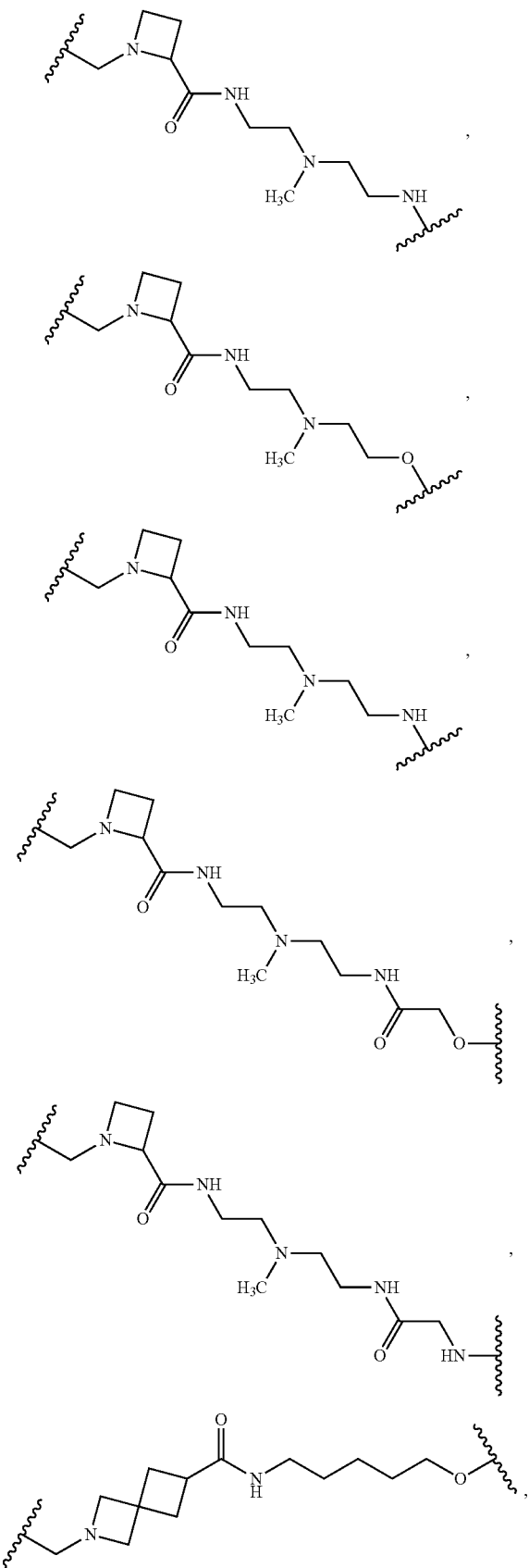

51
-continued
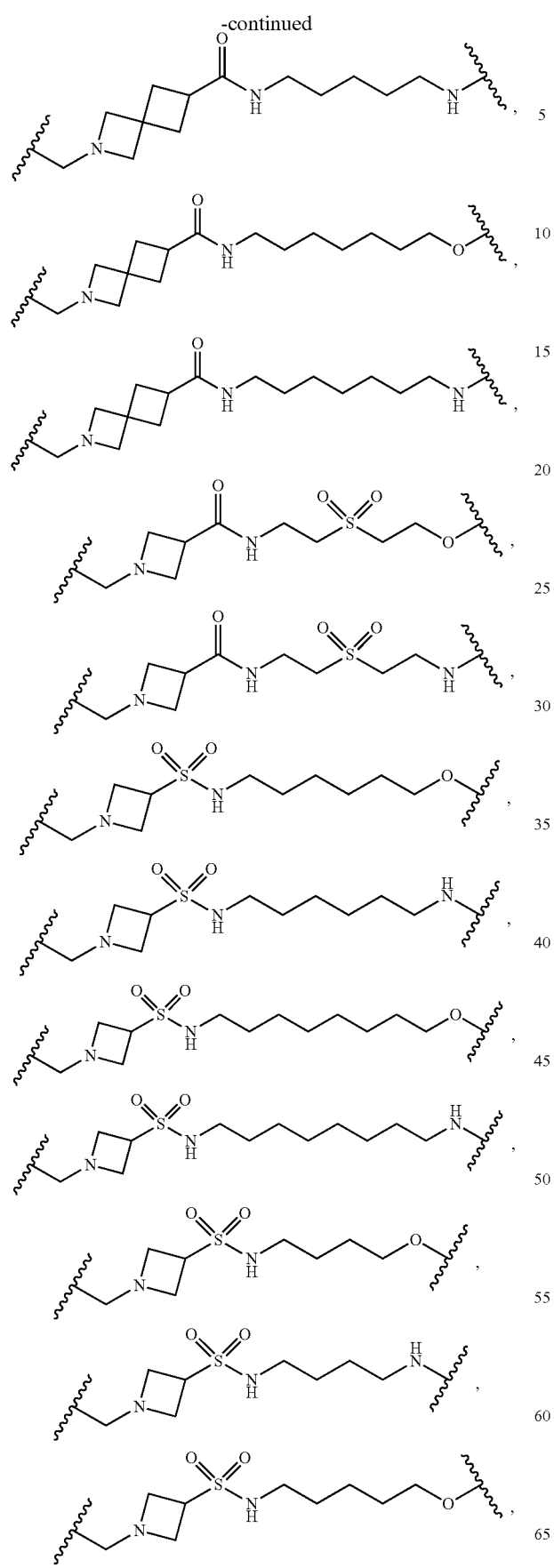
52
-continued
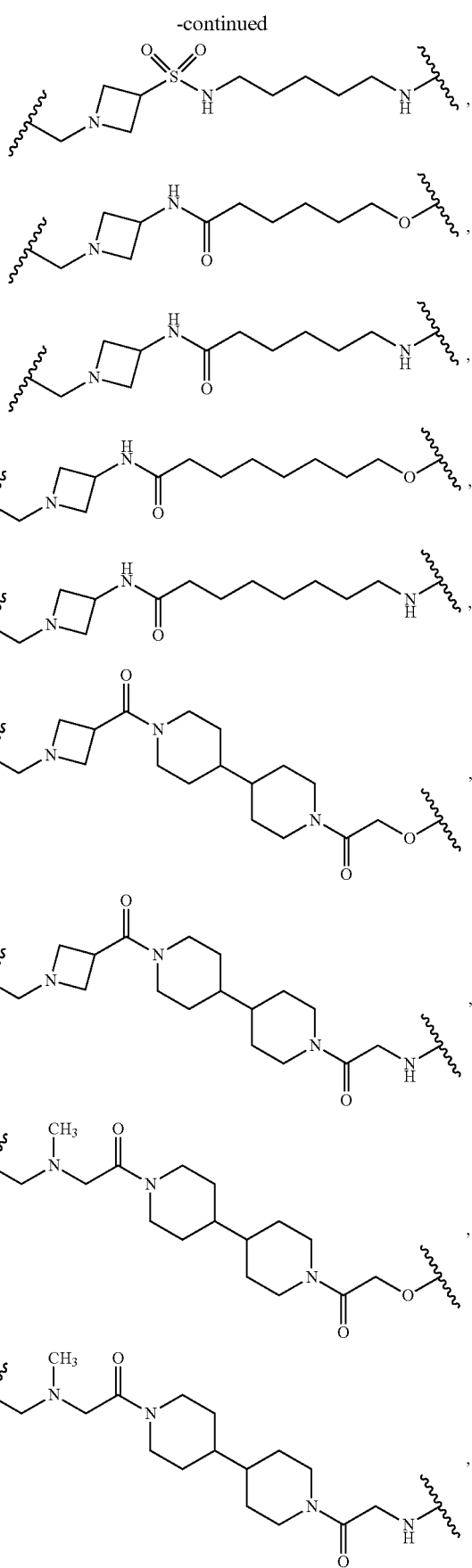

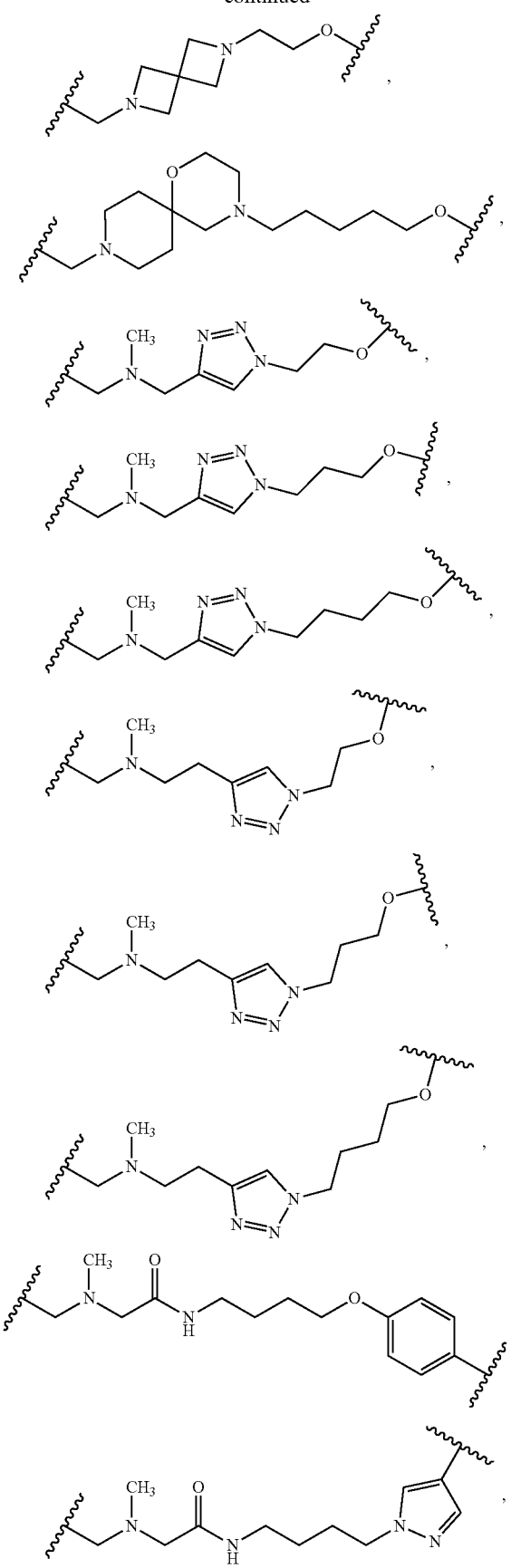
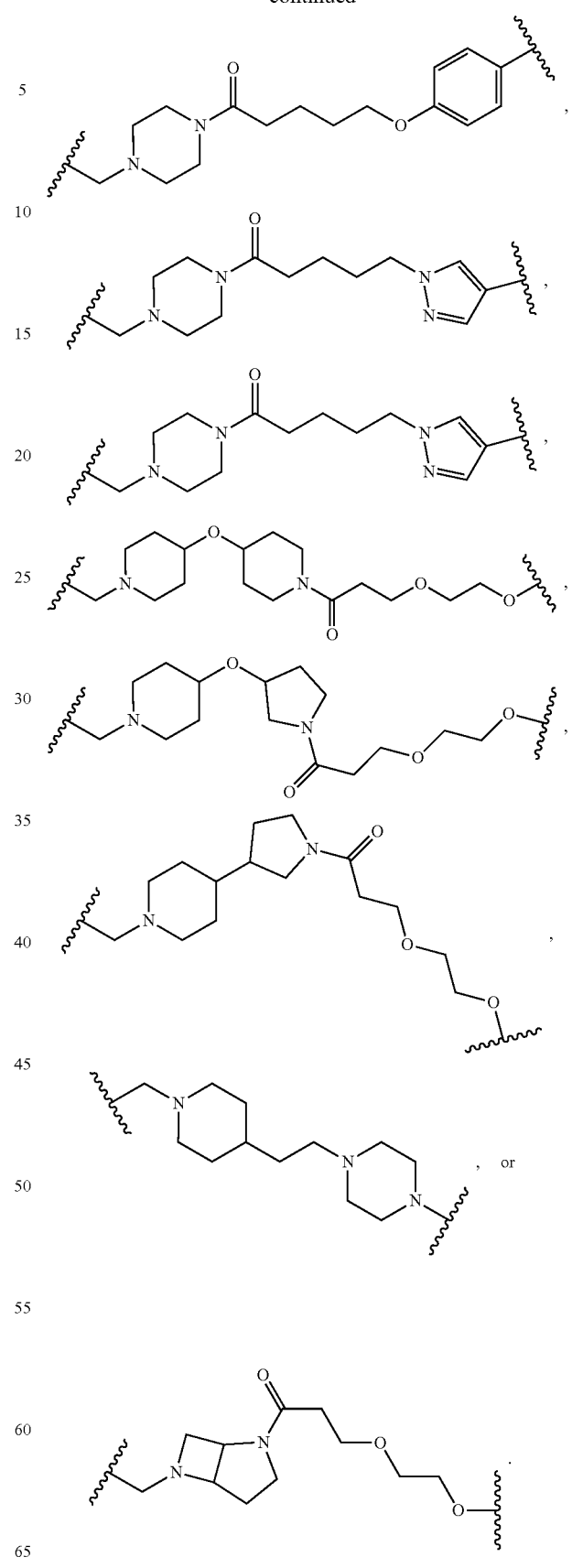

In some embodiments, the linker has the structure of
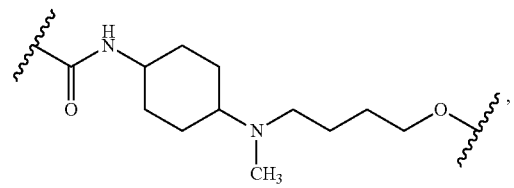
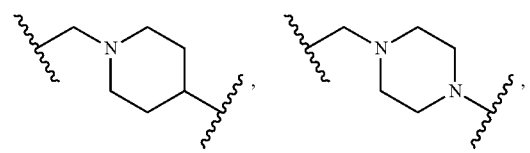
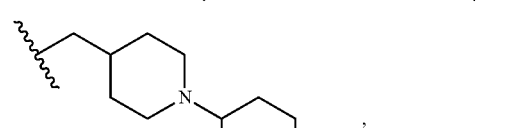

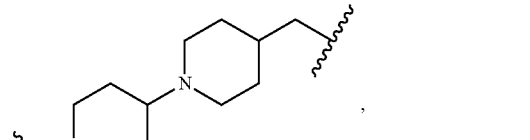
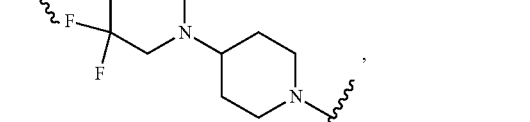
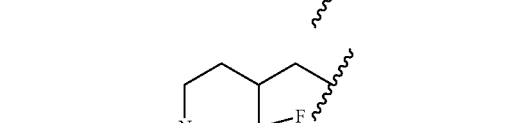
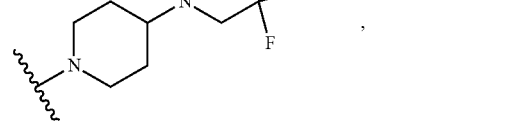
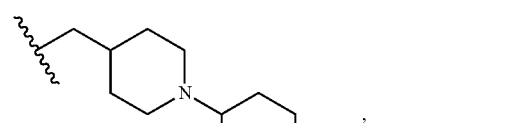
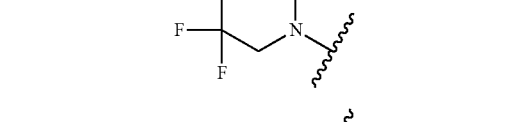
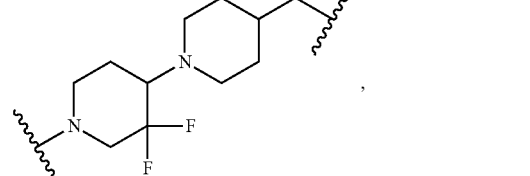
-continued
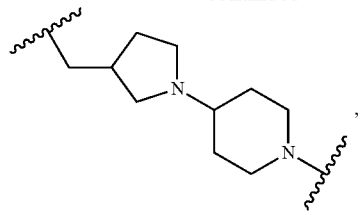
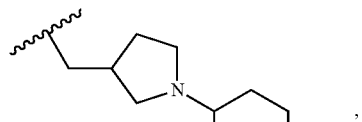
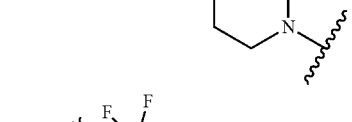
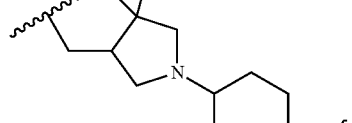
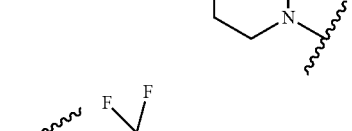
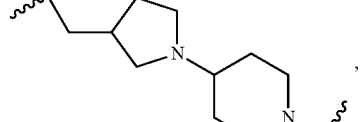
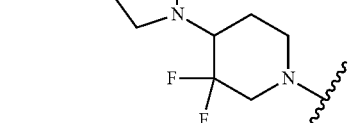
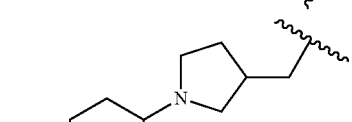
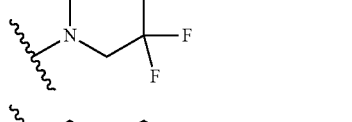
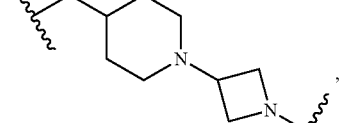
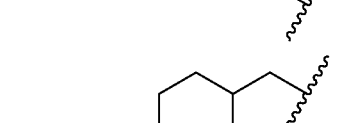
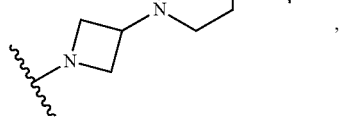

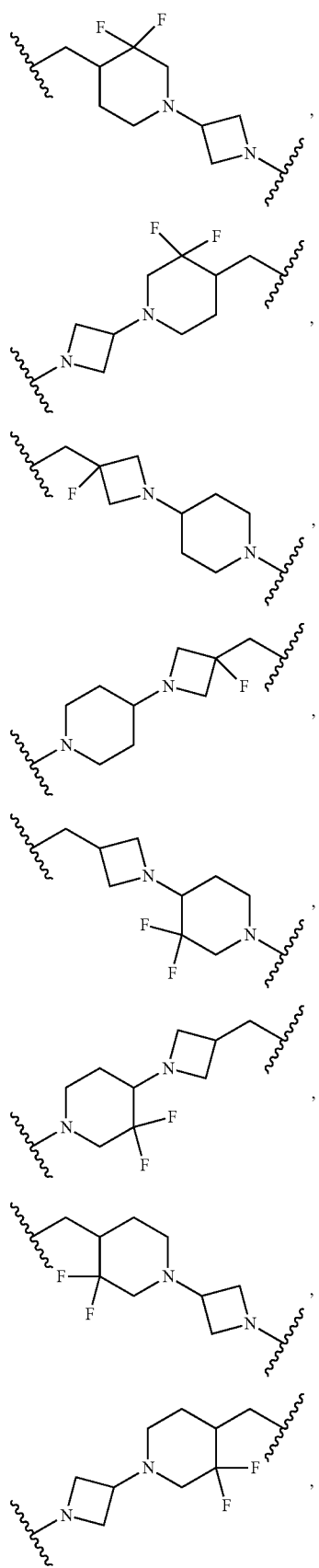
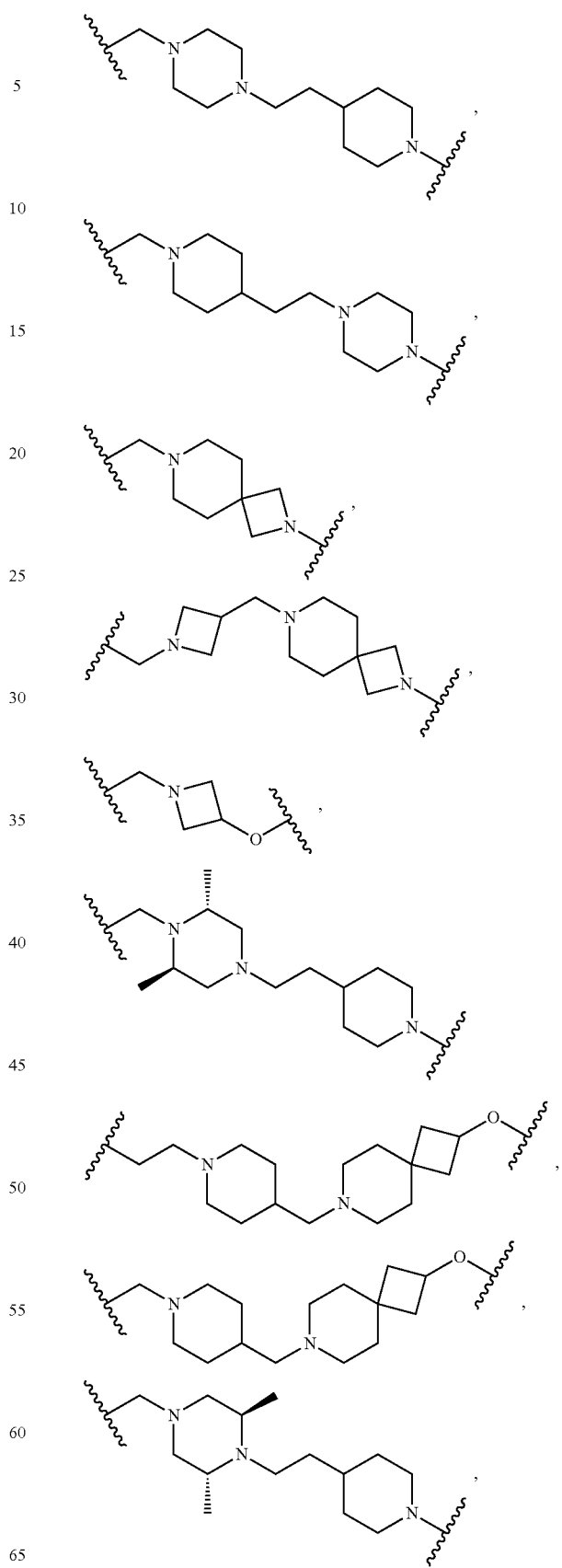

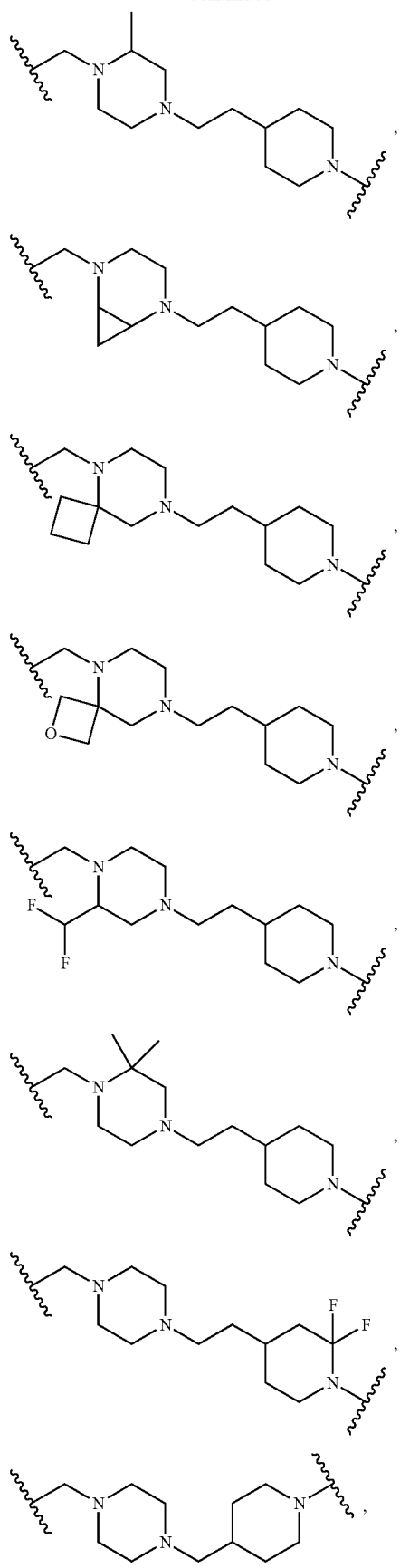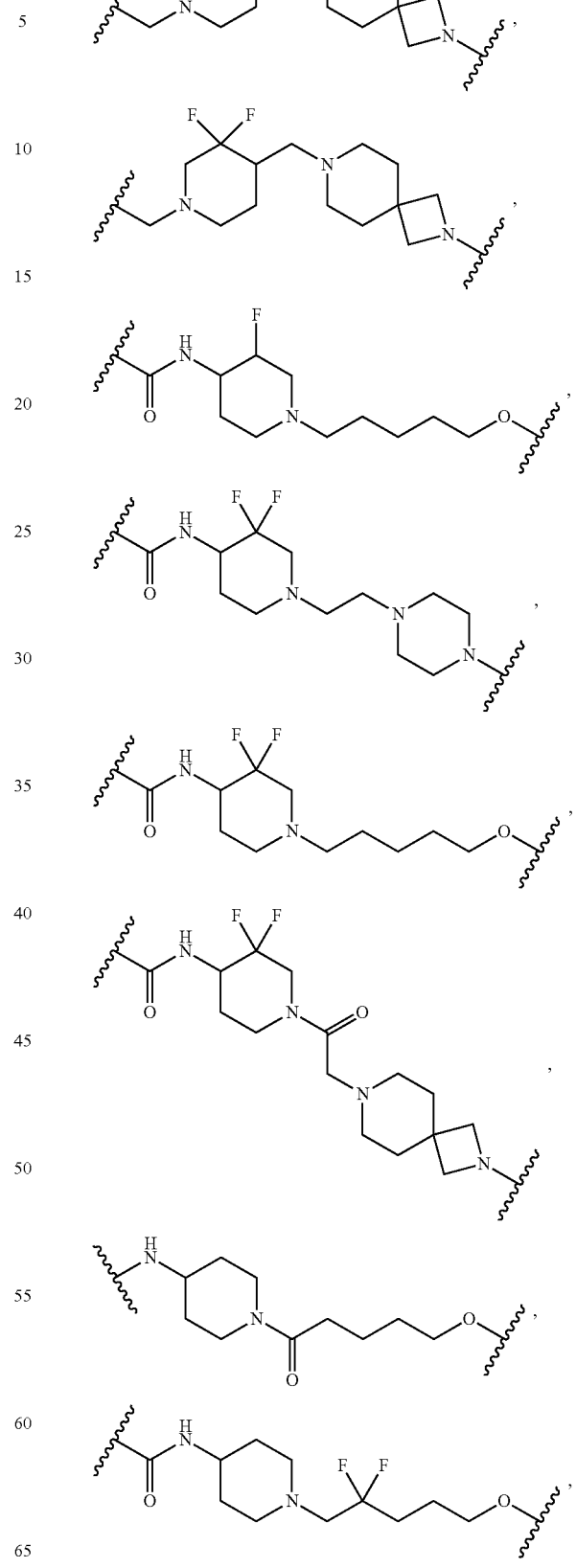

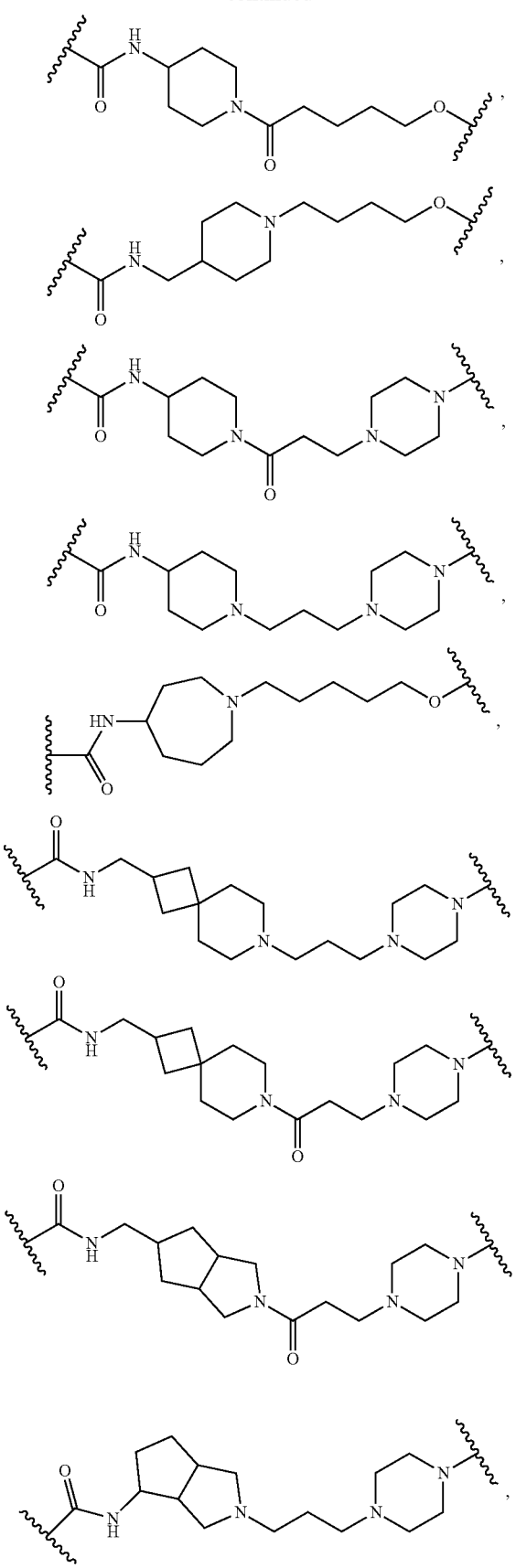
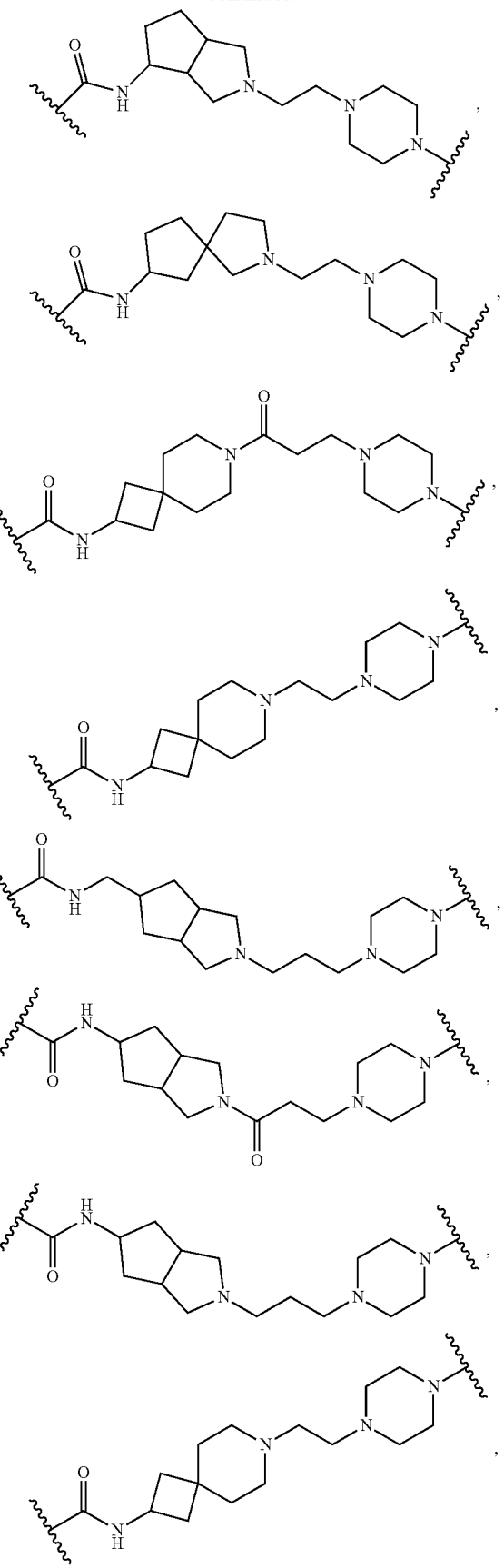

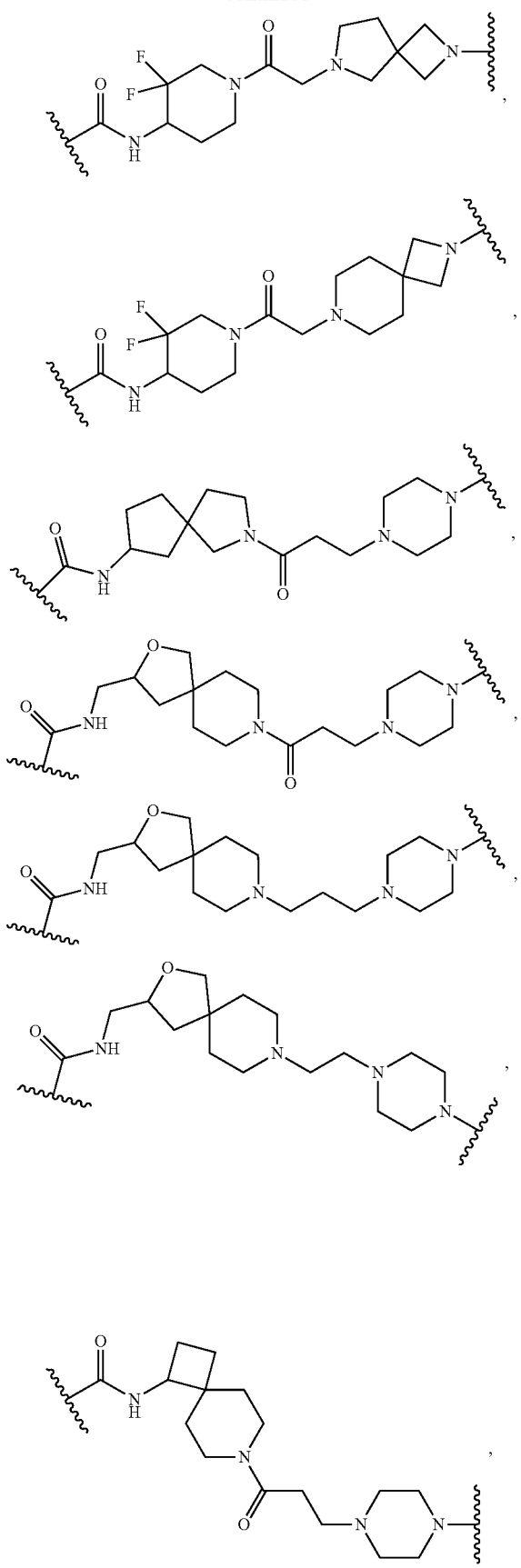
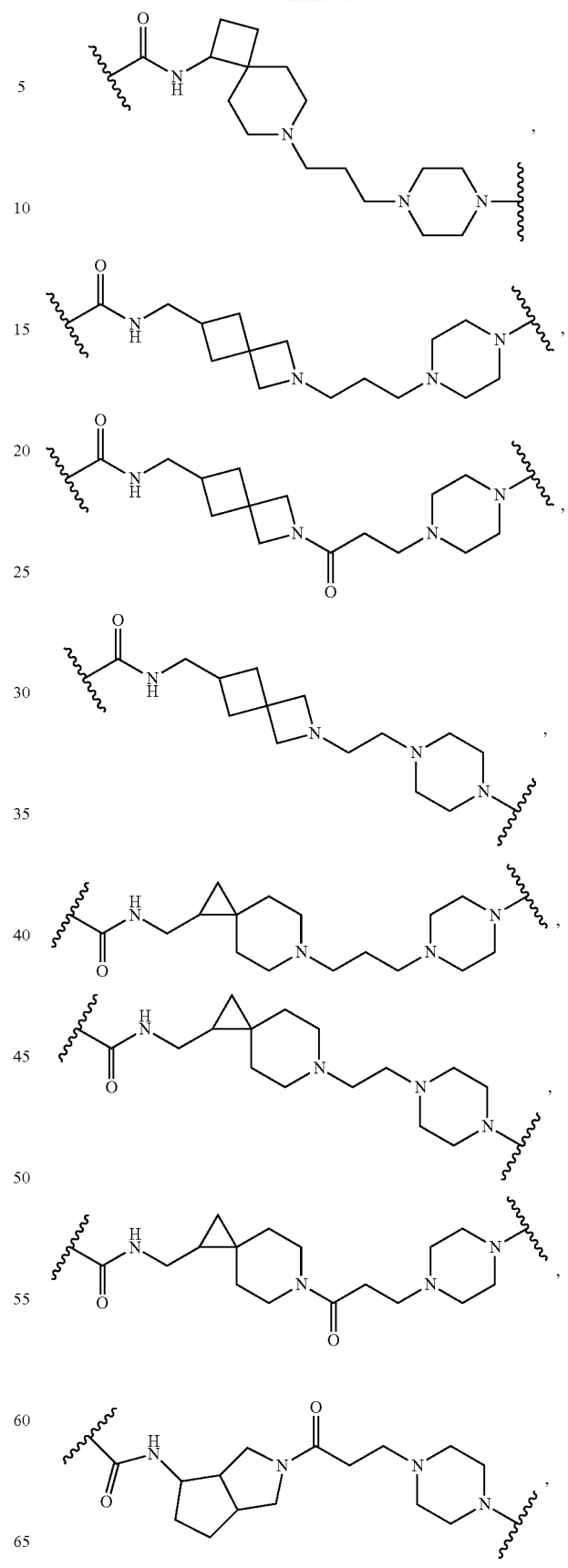

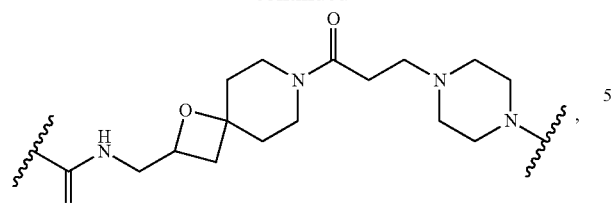
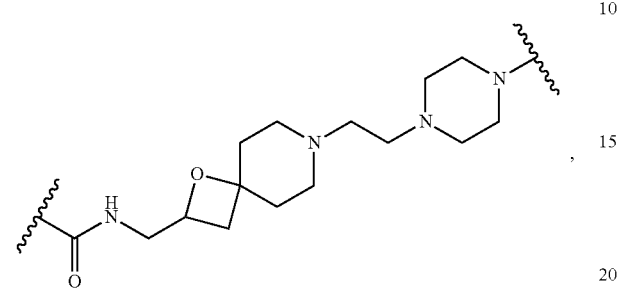
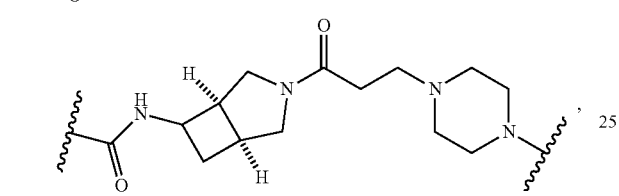
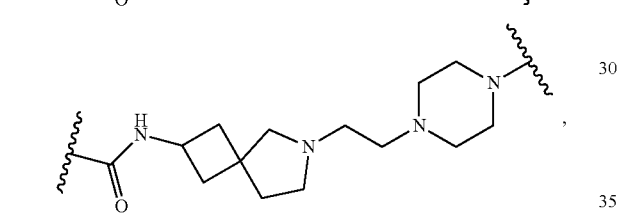
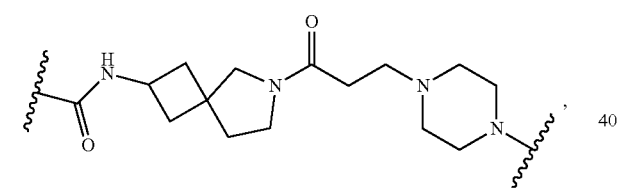
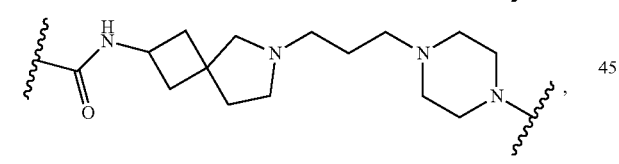
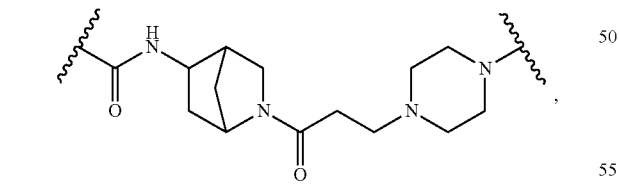
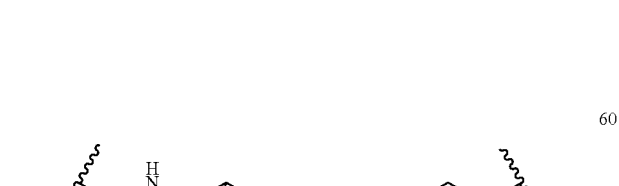
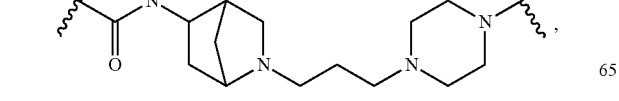
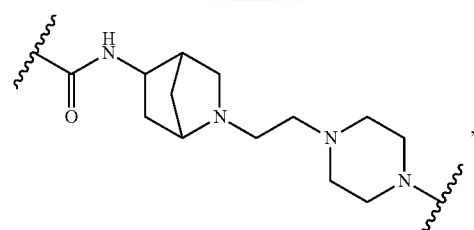
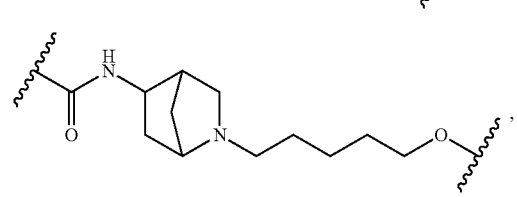
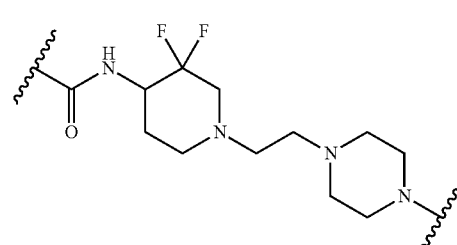
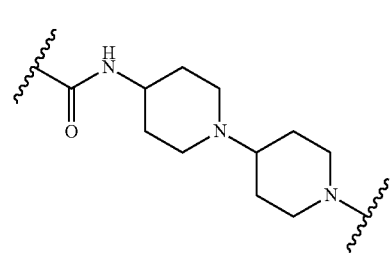
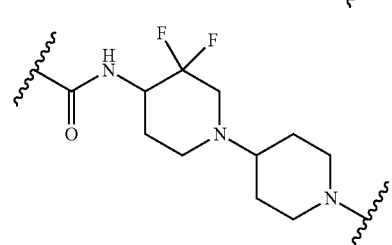
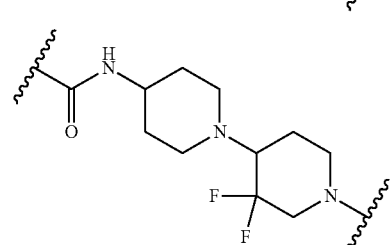
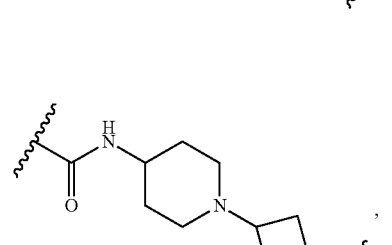

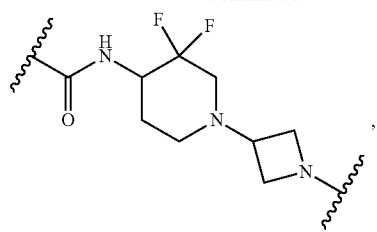
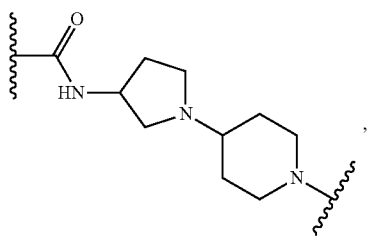
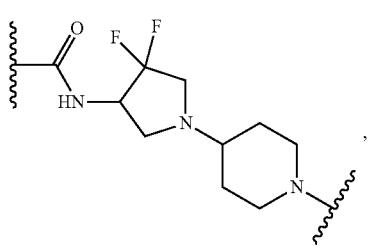
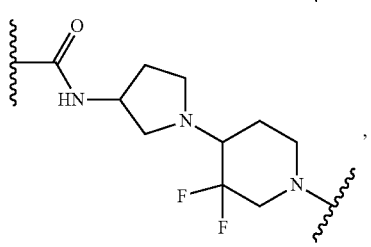
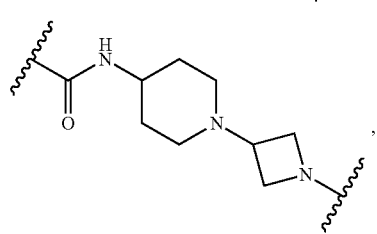
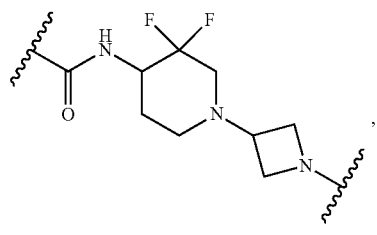
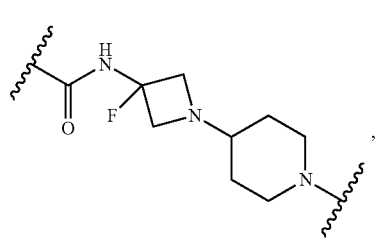
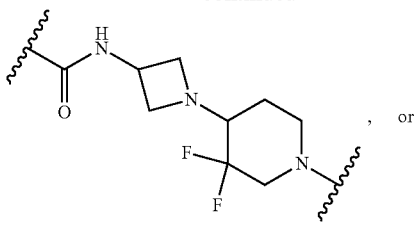
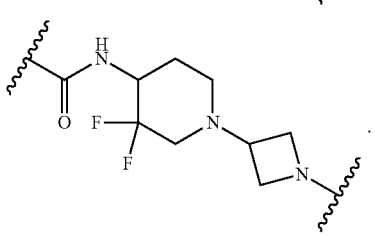
In some embodiments, the linker has the structure of:
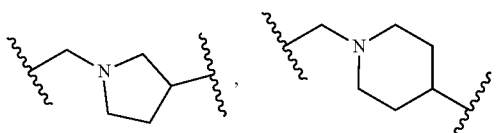
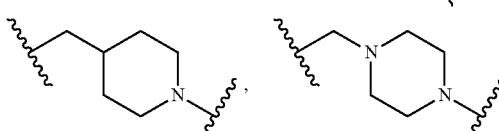
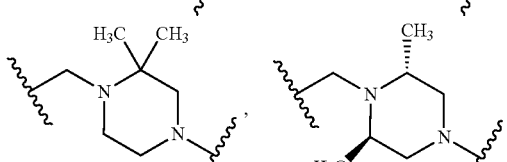
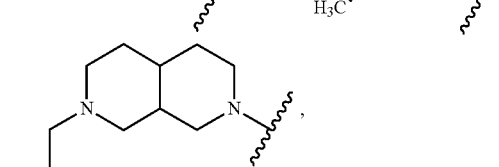
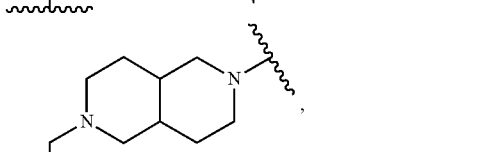
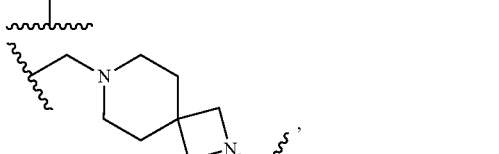
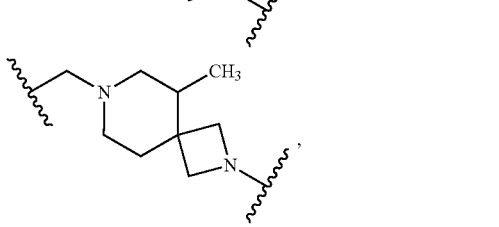

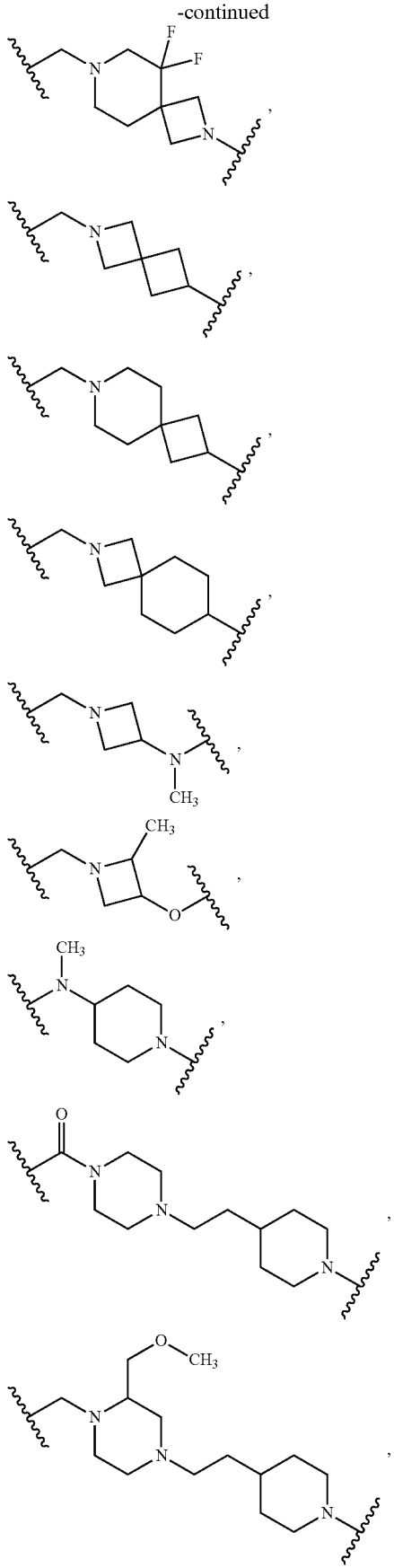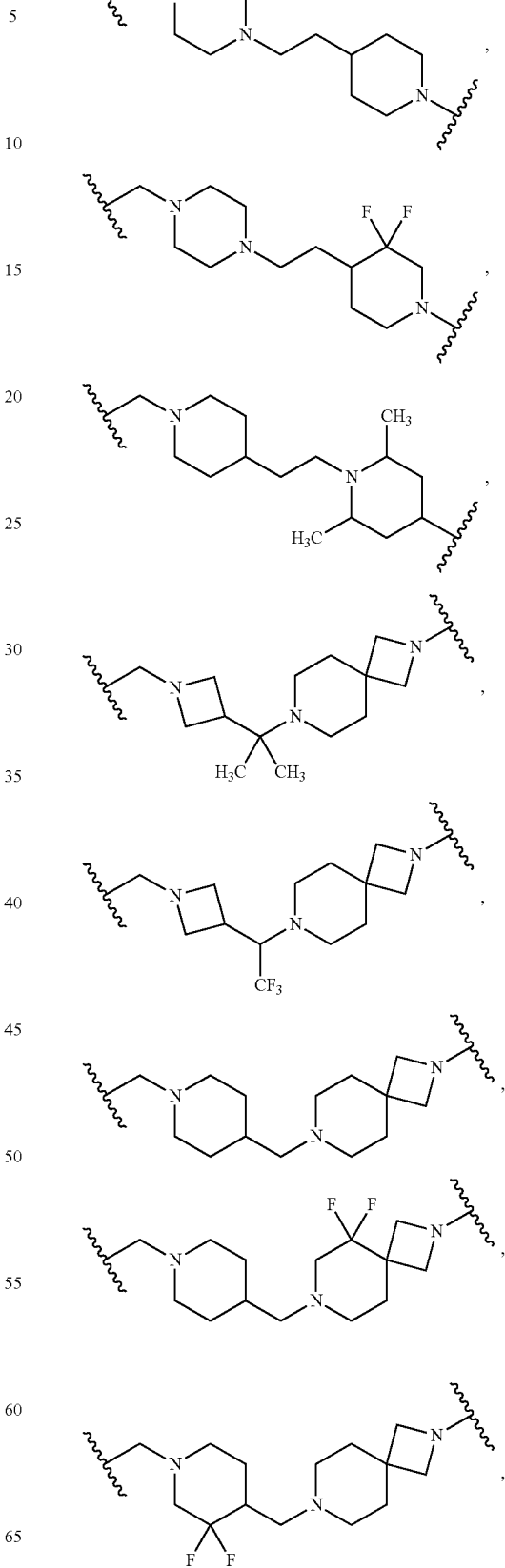

-continued

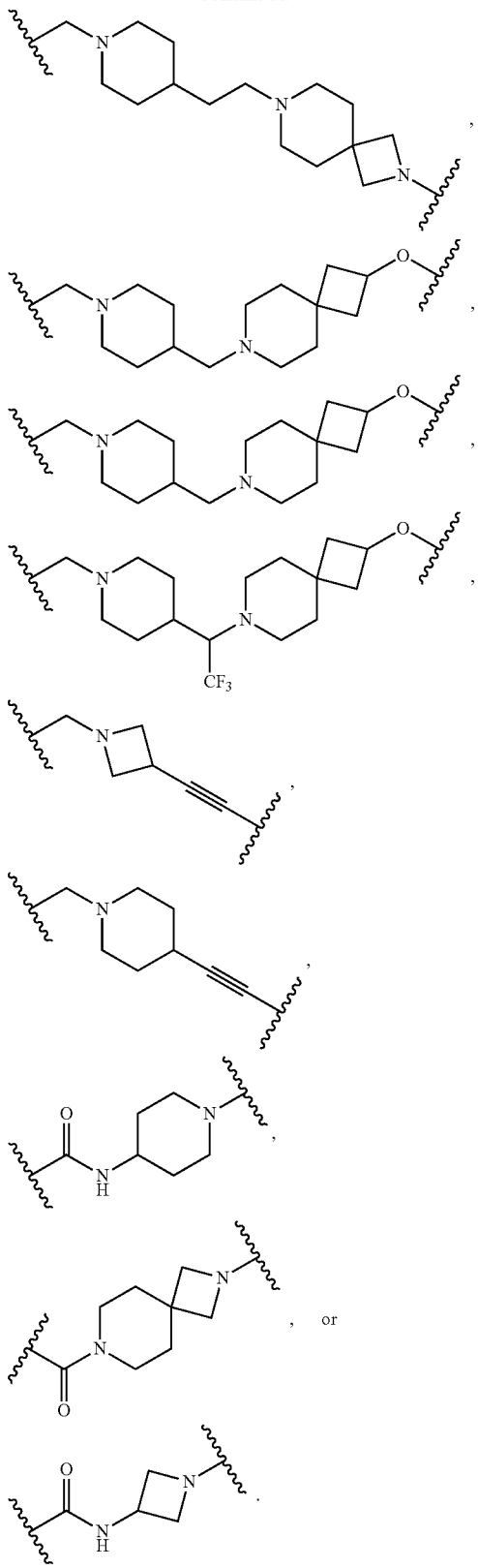

In some embodiments, the linker is absent.
In some embodiments, the linker is optionally substituted $C_3$-$C_{10}$ carbocyclylene, optionally substituted $C_{2-10}$ hetero-cyclylene, optionally substituted $C_6$-$C_{10}$ arylene, or optionally substituted $C_2$-$C_9$ heteroarylene.

In some embodiments, the linker is optionally substituted $C_3$-$C_{10}$ carbocyclylene or optionally substituted $C_{2-10}$ heterocyclylene. In some embodiments, the linker is optionally substituted $C_6$-$C_{10}$ arylene or optionally substituted $C_2$-$C_9$ heteroarylene.

In some embodiments, the linker is optionally substituted $C_{2-10}$ heterocyclylene.

In some embodiments, the $C_2$-$C_9$ heterocyclylene is monocyclic. In some embodiments, the $C_2$-Cg heterocyclylene is polycyclic.

In some embodiments, the $C_2$-$C_9$ heterocyclylene is bicyclic.

In some embodiments, the $C_2$-$C_9$ heterocyclylene is bridged. In some embodiments, the $C_2$-Cg heterocyclylene is fused. In some embodiments, the $C_2$-$C_9$ heterocyclylene is spirocyclic.

In some embodiments, the linker has the structure of

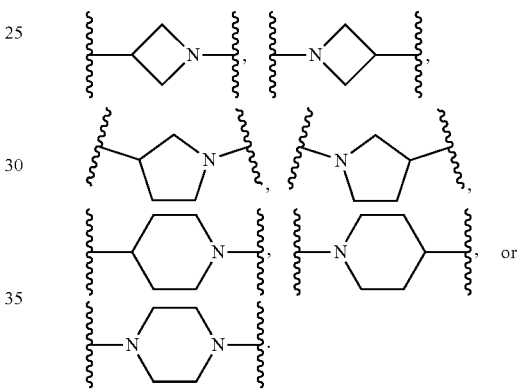

, or

In some embodiments, the linker has the structure of

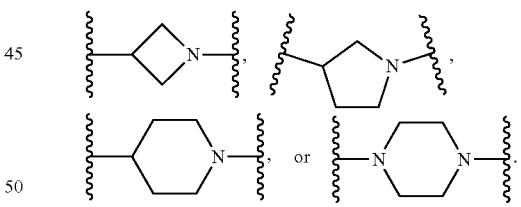

In some embodiments, the degradation moiety is a ubiquitin ligase binding moiety.

In some embodiments, the ubiquitin ligase binding moiety comprises Cereblon ligands, IAP (Inhibitors of Apoptosis) ligands, mouse double minute 2 homolog (MDM2), or von Hippel-Lindau (VHL) ligands, or derivatives or analogs thereof.

In some embodiments, the degradation moiety is a ubiquitin ligase binding moiety.

In some embodiments, the ubiquitin ligase binding moiety comprises Cereblon ligands, IAP (Inhibitors of Apoptosis) ligands, mouse double minute 2 homolog (MDM2), or von Hippel-Lindau (VHL) ligands, or derivatives or analogs thereof.

In some embodiments, the degradation moiety includes the structure of Formula Y:

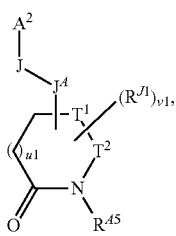

Formula Y where
A² is a bond between the degradation moiety and the linker;
v1 is 0, 1, 2, 3, 4, or 5;
u1 is 1, 2, or 3;
T¹ is a bond or

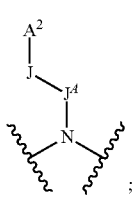

;

T² is

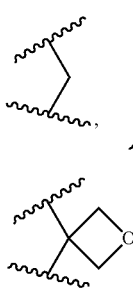

$R^{5A}$ is H, optionally substituted $C_1$-$C_6$ alkyl, or optionally substituted $C_1$-$C_6$ heteroalkyl;
each $R^{J1}$ is, independently, halogen, optionally substituted $C_1$-$C_6$ alkyl, or optionally substituted $C_1$-$C_6$ heteroalkyl;
$J^A$ is absent, O, optionally substituted amino, optionally substituted $C_1$-$C_6$ alkyl, or optionally substituted $C_1$-$C_6$ heteroalkyl; and
J is absent, optionally substituted $C_3$-$C_{10}$ carbocyclylene, optionally substituted $C_6$-$C_{10}$ arylene, optionally substituted $C_2$-$C_9$ heterocyclylene, or optionally substituted $C_2$-$C_9$ heteroarylene, or a pharmaceutically acceptable salt thereof.

In some embodiments, T² is

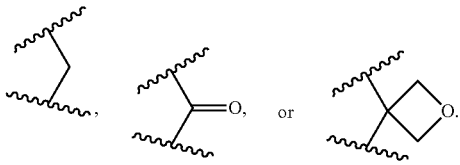

In some embodiments, T² is

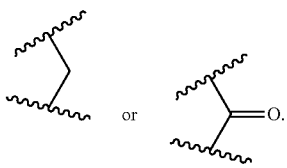

In some embodiments, T² is

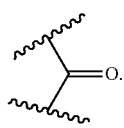

In some embodiments, T² is

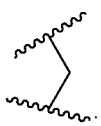 [SMILES: *C*]

In some embodiments, the structure of Formula Y has the structure of Formula Y1:

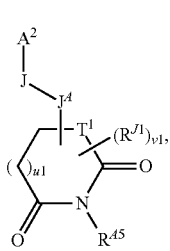

Formula Y1 or a pharmaceutically acceptable salt thereof.

In some embodiments, T¹ is a bond. In some embodiments, T¹ is

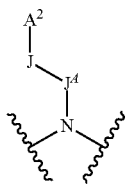

In some embodiments, the structure of Formula Y has the structure of Formula Y2:

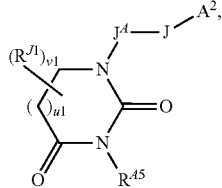

Formula Y2 or a pharmaceutically acceptable salt thereof.

In some embodiments, the structure of Formula Y has the structure of Formula Z:

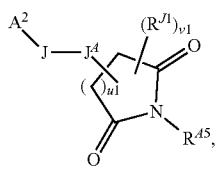

Formula Z or a pharmaceutically acceptable salt thereof.

In some embodiments, u1 is 1. In some embodiments, u1 is 2. In some embodiments u1 is 3.

In some embodiments, the structure of Formula Z has the structure of Formula AA0:

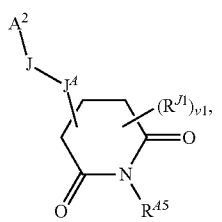

Formula AA0 or a pharmaceutically acceptable salt thereof.

In some embodiments, the structure of Formula Z has the structure of Formula AB:

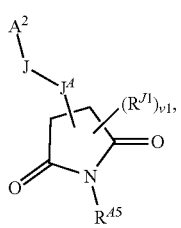

Formula AB or a pharmaceutically acceptable salt thereof.

In some embodiments, the structure of Formula Z has the structure of Formula AC:

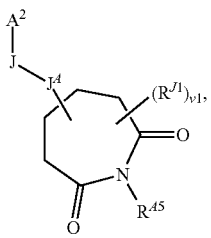

Formula AC or a pharmaceutically acceptable salt thereof.

In some embodiments, $J^A$ is absent. In some embodiments, $J^A$ is optionally substituted $C_1$-$C_6$ alkyl. In some embodiments, $J^A$ is optionally substituted $C_1$-$C_6$ heteroalkyl. In some embodiments, $J^A$ is O or optionally substituted amino.

In some embodiments, $J^A$ is

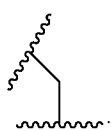

In some embodiments, the structure of Formula AA0 has the structure of Formula AA0:

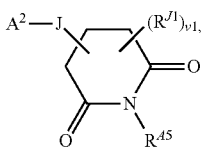

Formula AA or a pharmaceutically acceptable salt thereof.

In some embodiments, v1 is 0, 1, 2, or 3. In some embodiments, v1 is 0. In some embodiments, v1 is 1. In some embodiments, v1 is 2. In some embodiments, v1 is 3.

In some embodiments, the structure of Formula AA has the structure of Formula AA1:

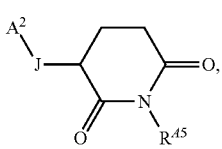

Formula AA1 or a pharmaceutically acceptable salt thereof.

In some embodiments, the structure of Formula AB has the structure of Formula AB1:

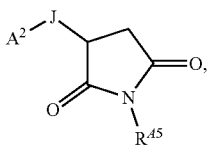

Formula AB1 or a pharmaceutically acceptable salt thereof.

In some embodiments, the structure of Formula AC has the structure of Formula AC1:

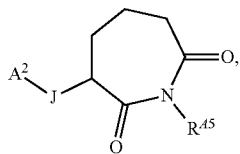

Formula AC1 or a pharmaceutically acceptable salt thereof.

In some embodiments, J is absent. In some embodiments, J is optionally substituted $C_3$-$C_{10}$ carbocyclylene or optionally substituted $C_6$-$C_{10}$ arylene. In some embodiments, J is optionally substituted $C_2$-$C_9$ heterocyclylene or optionally substituted $C_2$-$C_9$ heteroarylene.

In some embodiments, J is optionally substituted heterocyclylene. In some embodiments, J is optionally substituted $C_6$-$C_{10}$ arylene.

In some embodiments, J is

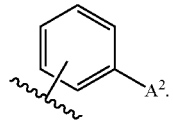

In some embodiments, the structure of Formula AA has the structure of Formula AA2:

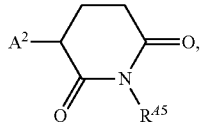

Formula AA2 or a pharmaceutically acceptable salt thereof.

In some embodiments, the structure of Formula AA has the structure of Formula AA3:

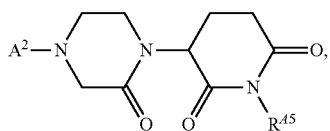

Formula AA3 or a pharmaceutically acceptable salt thereof.

In some embodiments, the structure of Formula AA has the structure of Formula AA4:

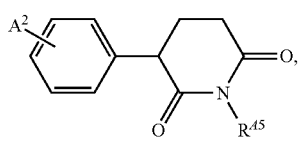

Formula AA4 or a pharmaceutically acceptable salt thereof.

In some embodiments, $R^{A5}$ is H or optionally substituted $C_1$-$C_6$ alkyl. In some embodiments, $R^{A5}$ is optionally substituted $C_1$-$C_6$ heteroalkyl.

In some embodiments, $R^{A5}$ is H or methyl. In some embodiments, $R^{A5}$ is H. In some embodiments, $R^{A5}$ is methyl. In some embodiments, $R^{A5}$ is

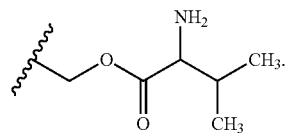

In some embodiments, the structure of Formula AA has the structure of Formula A:

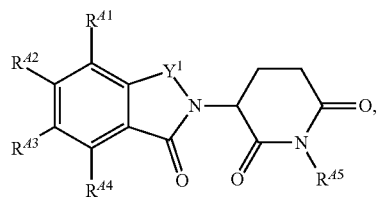

Formula A where

Y1 is

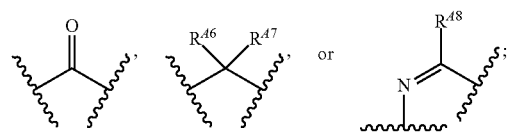

$R^{A5}$ is H, optionally substituted $C_1$-$C_6$ alkyl, or optionally substituted $C_1$-$C_6$ heteroalkyl;

$R^{A6}$ is H or optionally substituted $C_1$-$C_6$ alkyl; and $R^{A7}$ is H or optionally substituted $C_1$-$C_6$ alkyl; or $R^{A6}$ and $R^{A7}$, together with the carbon atom to which each is bound, combine to form optionally substituted $C_3$-$C_6$ carbocyclyl or optionally substituted $C_2$-$C_8$ heterocyclyl; or $R^{A6}$ and $R^{A7}$, together with the carbon atom to which each is bound, combine to form optionally substituted $C_3$-$C_6$ carbocyclyl or optionally substituted $C_2$-$C_5$ heterocyclyl;

$R^{A8}$ is H, optionally substituted $C_1$-$C_6$ alkyl, or optionally substituted $C_1$-$C_6$ heteroalkyl;

each of $R^{A1}$, $R^{A2}$, $R^{A3}$, and $R^{A4}$ is, independently, H, $A^2$, halogen, optionally substituted $C_1$-$C_6$ alkyl, optionally substituted $C_1$-$C_6$ heteroalkyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_2$-$C_9$ heteroaryl, optionally substituted $C_2$-$C_6$ alkenyl, optionally substituted $C_2$-$C_6$ heteroalkenyl, optionally substituted-O—$C_3$-$C_6$ carbocyclyl, hydroxyl, thiol, or optionally substituted amino; or $R^{A1}$ and $R^{A2}$, $R^{A2}$ and $R^{A3}$, and/or $R^{A3}$ and $R^{A4}$, together with the carbon atoms to which each is attached, combine to form

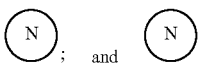

is optionally substituted $C_6$-$C_{10}$ aryl, optionally substituted $C_3$-$C_{10}$ carbocyclyl, optionally substituted $C_2$-$C_9$ heteroaryl, or $C_2$-$C_9$ heterocyclyl, any of which is optionally substituted with $A^2$, where one of $R^{41}$, $R^{42}$, $R^{43}$, and $R^{44}$ is $A^2$, or

is substituted with $A^2$, or a pharmaceutically acceptable salt thereof.

In some embodiments, each of $R^{41}$, $R^{42}$, $R^{43}$, and $R^{44}$ is, independently, H, $A^2$, halogen, optionally substituted $C_1$-$C_6$ alkyl, optionally substituted $C_1$-$C_5$ heteroalkyl, optionally substituted $C_3$-$C_{10}$ carbocyclyl, optionally substituted $C_2$-$C_8$ heterocyclyl, optionally substituted $C_6$-$C_{10}$ aryl, optionally substituted $C_2$-$C_9$ heteroaryl, optionally substituted $C_2$-$C_6$ alkenyl, optionally substituted $C_2$-$C_6$ heteroalkenyl, hydroxyl, thiol, or optionally substituted amino; or $R^{41}$ and $R^{42}$, $R^{42}$ and $R^{43}$, and/or $R^{43}$ and $R^{44}$, together with the carbon atoms to which each is attached, combine to form

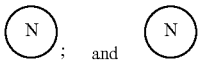

is optionally substituted $C_6$-$C_{10}$ aryl, optionally substituted $C_3$-$C_{10}$ carbocyclyl, optionally substituted $C_2$-$C_9$ heteroaryl, or $C_2$-$C_9$ heterocyclyl, any of which is optionally substituted with $A^2$, where one of $R^{41}$, $R^{42}$, $R^{43}$, and $R^{44}$ is $A^2$, or

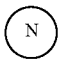

is substituted with $A^2$, or a pharmaceutically acceptable salt thereof.

In some embodiments, each of $R^{41}$, $R^{42}$, $R^{43}$, and $R^{44}$ is, H, $A^2$, halogen, optionally substituted $C_1$-$C_6$ alkyl, optionally substituted $C_1$-$C_6$ heteroalkyl, optionally substituted-O—$C_3$-$C_6$ carbocyclyl, hydroxyl, optionally substituted amino; or $R^{41}$ and $R^{42}$, $R^{42}$ and $R^{43}$, or $R^{43}$ and $R^{44}$, together with the carbon atoms to which each is attached, combine to form

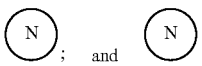

is optionally substituted $C_2$-$C_9$ heterocyclyl, which is optionally substituted with $A^2$, where one of $R^{41}$, $R^{42}$, $R^{43}$, and $R^{44}$ is $A^2$, or

is substituted with $A^2$.

In some embodiments, each of $R^{41}$, $R^{42}$, $R^{43}$, and $R^{44}$ is, independently, H, $A^2$, F,

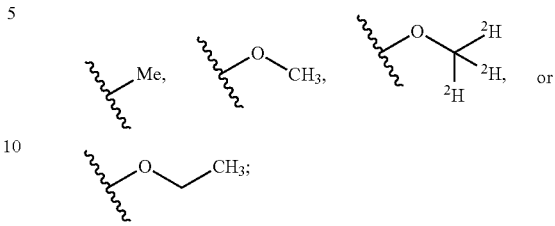

or $R^{41}$ and $R^{42}$, $R^{42}$ and $R^{43}$, or $R^{43}$ and $R^{44}$, together with the carbon atoms to which each is attached, combine to form

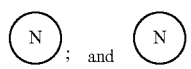

is optionally substituted $C_2$-$C_9$ heterocyclyl, which is optionally substituted with $A^2$, where one of $R^{41}$, $R^{42}$, $R^{43}$, and $R^{44}$ is $A^2$, or

is substituted with $A^2$.

In some embodiments, $R^{41}$ is $A^2$. In some embodiments, $R^{42}$ is $A^2$. In some embodiments, $R^{43}$ is $A^2$. In some embodiments, $R^{44}$ is $A^2$. In some embodiments, $R^{45}$ is $A^2$.

In some embodiments, $R^{45}$ is H or optionally substituted $C_1$-$C_6$ alkyl.

In some embodiments, $R^{45}$ is H or

In some embodiments, $R^{45}$ is H. In some embodiments, $R^{45}$ is

In some embodiments, Y1 is

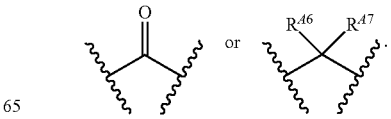

In some embodiments, Y1 is

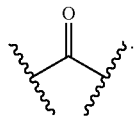 [SMILES: *C(*)=O]

In some embodiments, Y1 is

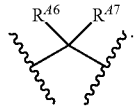

In some embodiments, each of $R^{A6}$ and $R^{A7}$ is, independently, H, F,

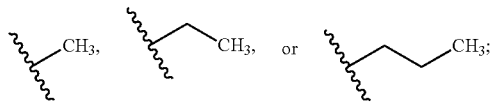

or $R^{A6}$ and $R^{A7}$, together with the carbon atom to which each is bound, combine to form

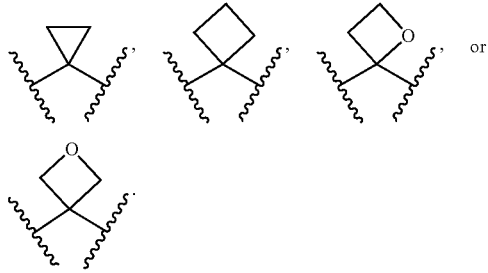

In some embodiments, $R^{A6}$ is H and $R^{A7}$ is H.

In some embodiments, Y1 is:

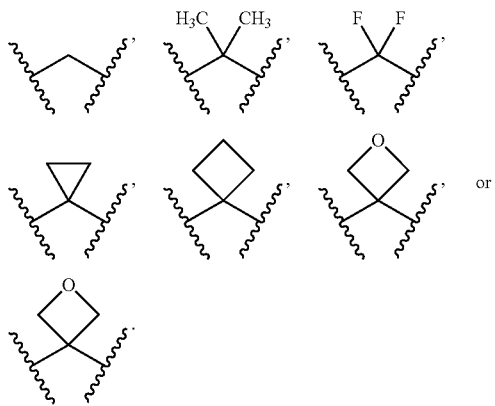

In some embodiments, Y1 is

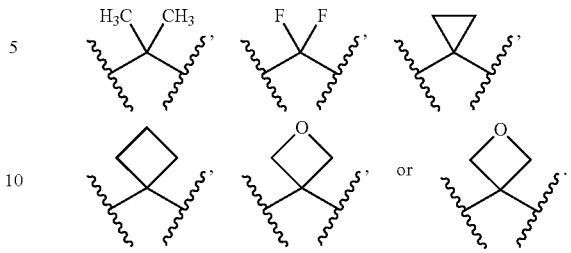

In some embodiments, Y1 is

In some embodiments, the structure of Formula A has the structure of Formula A1:

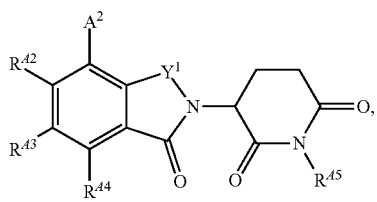

Formula A1 or a pharmaceutically acceptable salt thereof.

In some embodiments, the structure of Formula A has the structure of Formula A2:

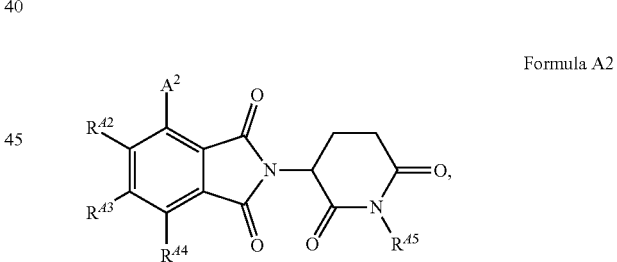

Formula A2 or a pharmaceutically acceptable salt thereof.

In some embodiments, the structure of Formula A has the structure of Formula A3:

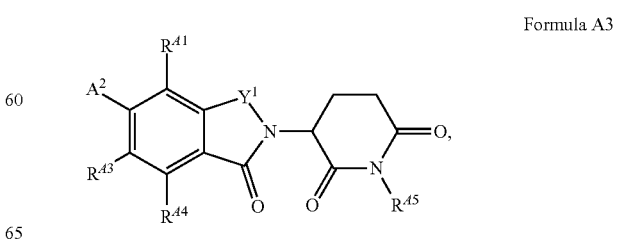

Formula A3 or a pharmaceutically acceptable salt thereof.

In some embodiments, the structure of Formula A has the structure of Formula A4:

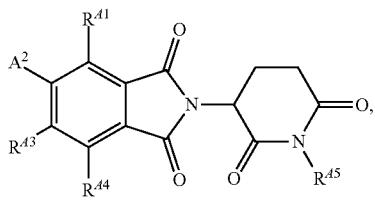

Formula A4 or a pharmaceutically acceptable salt thereof.

In some embodiments, the structure of Formula A has the structure of Formula A5:

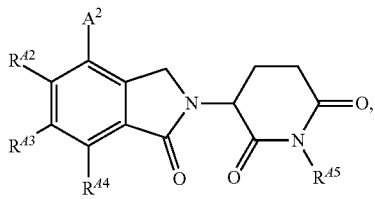

Formula A5 or a pharmaceutically acceptable salt thereof.

In some embodiments, the structure of Formula A has the structure of Formula A6:

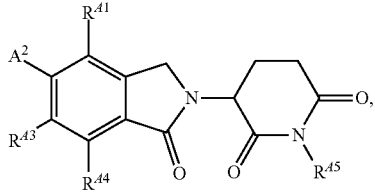

Formula A6 or a pharmaceutically acceptable salt thereof.

In some embodiments, the structure of Formula A has the structure of Formula A7:

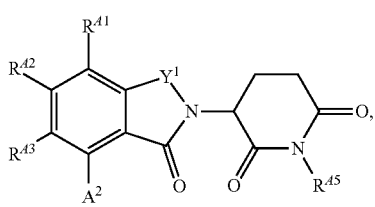

Formula A7 or a pharmaceutically acceptable salt thereof.

In some embodiments, the structure of Formula A has the structure of Formula A8:

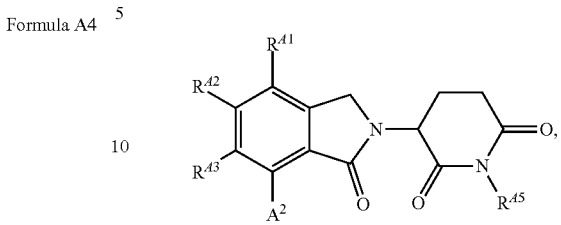

Formula A8 or a pharmaceutically acceptable salt thereof.

In some embodiments, the structure of Formula A has the structure of Formula A9:

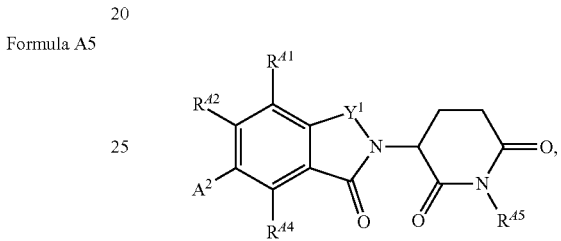

Formula A9 or a pharmaceutically acceptable salt thereof.

In some embodiments, the structure of Formula A has the structure of Formula A10:

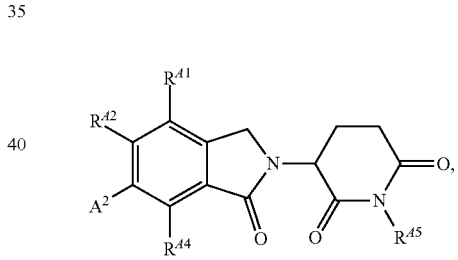

Formula A10 or a pharmaceutically acceptable salt thereof.

In some embodiments, wherein the structure of Formula A is

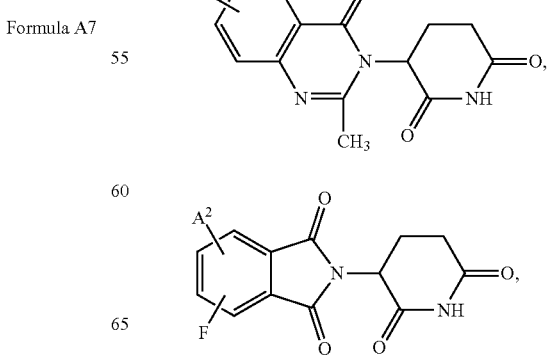

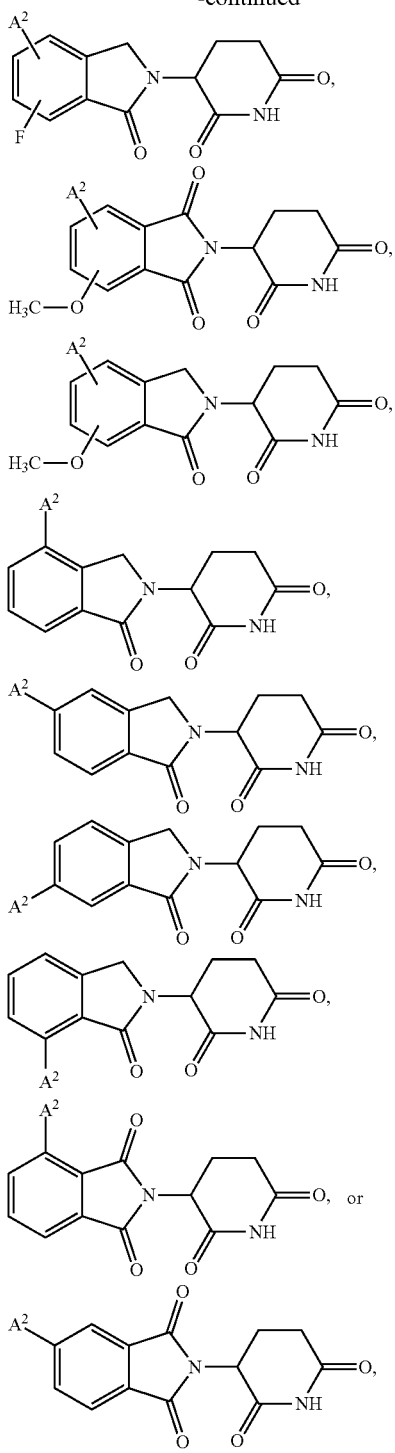
or derivative or analog thereof.
In some embodiments, the structure of Formula A is
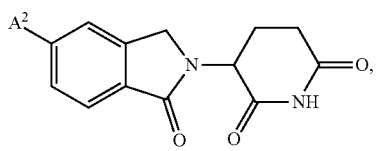
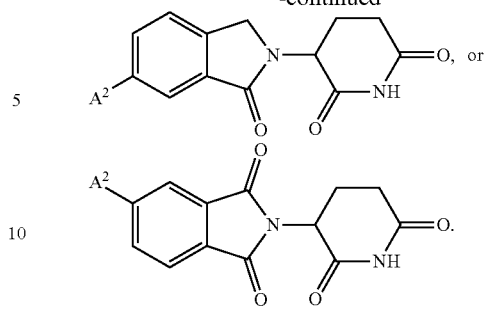
In some embodiments, the structure of Formula A is
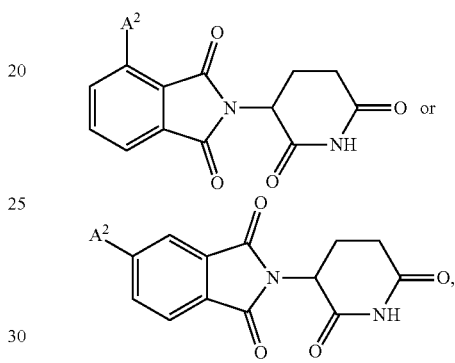
or derivative or analog thereof.
In some embodiments,
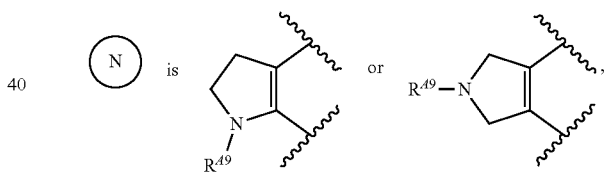
where $R^{A9}$ is H, $A^2$, optionally substituted $C_1$-$C_6$ alkyl, or optionally substituted $C_1$-$C_6$ heteroalkyl.
In some embodiments, the structure of Formula A is
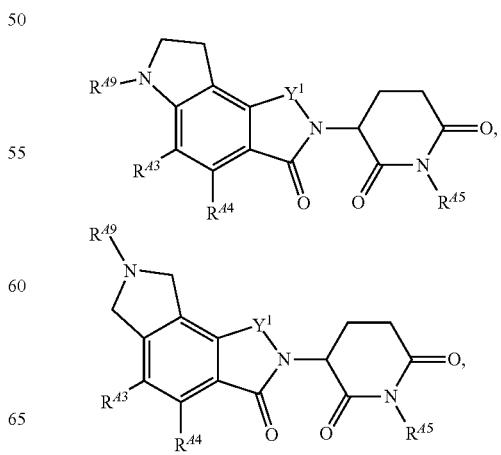

-continued

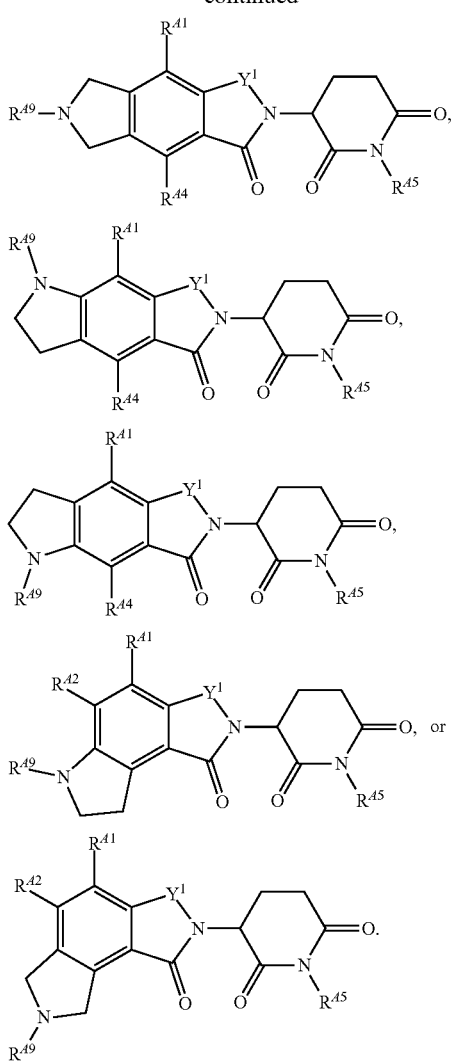

In some embodiments, $R^{A9}$ is H, $A^2$, or optionally substituted $C_1$-$C_6$ alkyl. In some embodiments, $R^{A9}$ is H, $A^2$, or methyl. In some embodiments, $R^{9A}$ is H. In some embodiments, $R^{9A}$ is methyl. In some embodiments, $R^{A9}$ is $A^2$.

In some embodiments, the structure of Formula A is

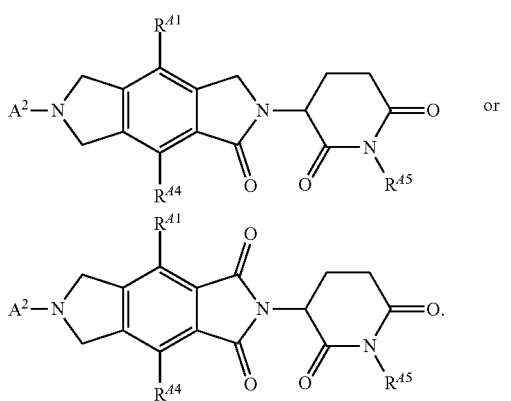

In some embodiments, the structure of Formula AA has the structure of Formula B:

Formula B

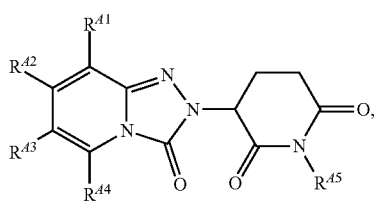

where
$R^{A5}$ is H, optionally substituted $C_1$-$C_6$ alkyl, or optionally substituted $C_1$-$C_6$ heteroalkyl;
each of $R^{A1}$, $R^{A2}$, $R^{A3}$, and $R^{A4}$ is, independently, H, $A^2$, halogen, optionally substituted $C_1$-$C_6$ alkyl, optionally substituted $C_1$-$C_6$ heteroalkyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_2$-$C_9$ heteroaryl, optionally substituted $C_2$-$C_6$ alkenyl, optionally substituted $C_2$-$C_6$ heteroalkenyl, optionally substituted-O—$C_3$-$C_6$ carbocyclyl, hydroxyl, thiol, or optionally substituted amino; or $R^{A1}$ and $R^{A2}$, $R^{A2}$ and $R^{A3}$, and/or $R^{A3}$ and
$R^{A4}$, together with the carbon atoms to which each is attached, combine to form

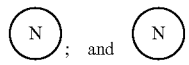 ; and 

is optionally substituted $C_6$-$C_{10}$ aryl, optionally substituted $C_3$-$C_{10}$ carbocyclyl, optionally substituted $C_2$-$C_9$ heteroaryl, or $C_2$-$C_9$ heterocyclyl, any of which is optionally substituted with $A^2$, where one of $R^{A1}$, $R^{A2}$, $R^{A3}$, and $R^{A4}$ is $A^2$, or

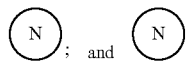

is substituted with $A^2$, or a pharmaceutically acceptable salt thereof.

In some embodiments, each of $R^{A1}$, $R^{A2}$, $R^{A3}$, and $R^{A4}$ is, H, $A^2$, halogen, optionally substituted $C_1$-$C_6$ alkyl, optionally substituted $C_1$-$C_6$ heteroalkyl, optionally substituted-O—$C_3$-$C_6$ carbocyclyl, hydroxyl, optionally substituted amino; or $R^{A1}$ and $R^{A2}$, $R^{A2}$ and $R^{A3}$, or $R^{A3}$ and $R^{A4}$, together with the carbon atoms to which each is attached, combine to form

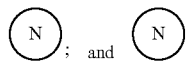 ; and 

is optionally substituted $C_2$-$C_9$ heterocyclyl, which is optionally substituted with $A^2$, where one of $R^{A1}$, $R^{A2}$, $R^{A3}$, and $R^{A4}$ is $A^2$, or

is substituted with $A^2$.

In some embodiments, each of $R^{A1}$, $R^{A2}$, $R^{A3}$, and $R^{A4}$ is, independently, H, $A^2$, F,

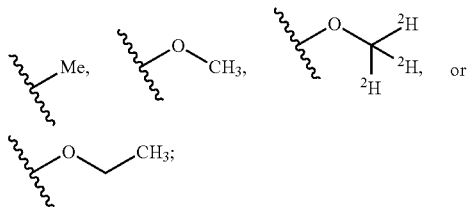 or

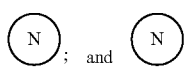

or $R^{A1}$ and $R^{A2}$, $R^{A2}$ and $R^{A3}$, or $R^{A3}$ and $R^{A4}$, together with the carbon atoms to which each is attached, combine to form

is optionally substituted $C_2$-$C_g$ heterocyclyl, which is optionally substituted with $A^2$, where one of $R^{A1}$, $R^{A2}$, $R^{A3}$, and $R^{A4}$ is $A^2$, or

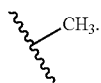

is substituted with $A^2$.

In some embodiments, $R^{A1}$ is $A^2$. In some embodiments, $R^{A2}$ is $A^2$. In some embodiments, $R^{A3}$ is $A^2$. In some embodiments, $R^{A4}$ is $A^2$. In some embodiments, $R^{A5}$ is $A^2$.

In some embodiments, $R^{A5}$ is H or optionally substituted $C_1$-$C_6$ alkyl.

In some embodiments, $R^{A5}$ is H or

In some embodiments, $R^{A5}$ is H. In some embodiments, $R^{A5}$ is

In some embodiments, the structure of Formula B has the structure of Formula B1:

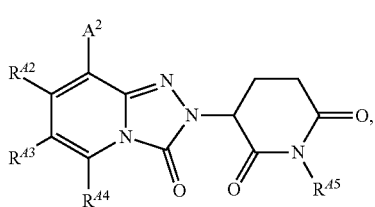

Formula B1 or a pharmaceutically acceptable salt thereof.

In some embodiments, the structure of Formula B has the structure of Formula B2:

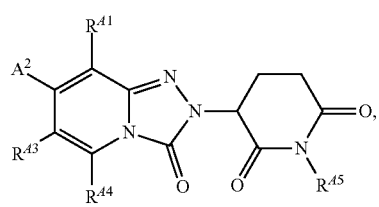

Formula B2 or a pharmaceutically acceptable salt thereof.

In some embodiments, the structure of Formula B has the structure of Formula B3:

Formula B3 or a pharmaceutically acceptable salt thereof.

In some embodiments, the structure of Formula B has the structure of Formula B4:

Formula B4 or a pharmaceutically acceptable salt thereof.

In some embodiments, the structure of Formula B is

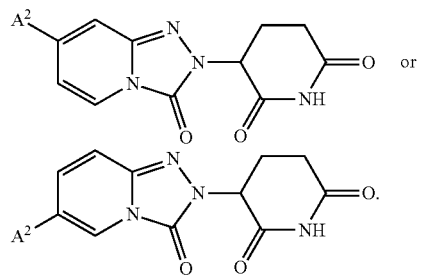

or

In some embodiments, the structure of Formula B is

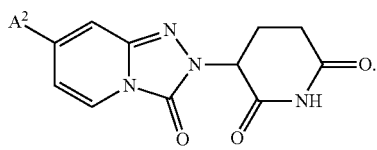

In some embodiments, the structure of Formula B is

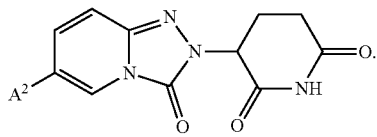

In some embodiments, the ubiquitin ligase binding moiety comprises a von Hippel-Lindau ligand.

In some embodiments, the von Hippel-Lindau ligand has the structure of

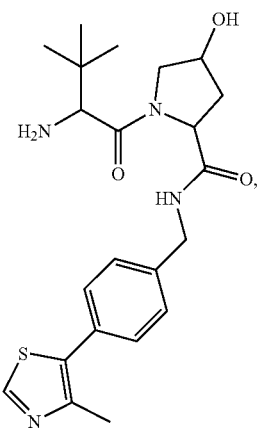 [SMILES: Cc1ncsc1-c1ccc(CNC(=O)C2CC(O)CN2C(=O)C(N)C(C)(C)C)cc1]

or derivative or analog thereof.

In some embodiments, the degradation moiety includes the structure of Formula C:

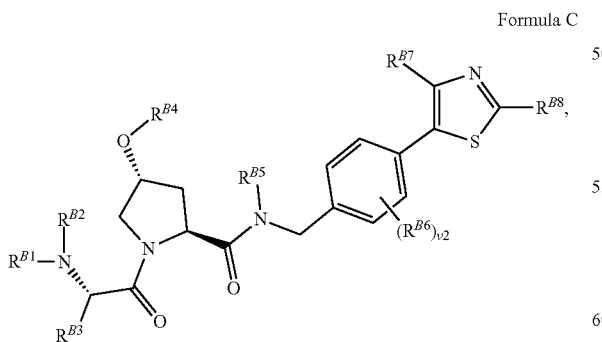

Formula C where
$R^{B1}$ is H, $A^2$, optionally substituted $C_1$-$C_6$ alkyl, or optionally substituted $C_1$-$C_6$ heteroalkyl;
$R^{B2}$ is H, optionally substituted $C_1$-$C_6$ alkyl, or optionally substituted $C_1$-$C_6$ heteroalkyl;

$R^{B3}$ is $A^2$, optionally substituted $C_1$-$C_6$ alkyl, optionally substituted $C_1$-$C_6$ heteroalkyl, optionally substituted $C_3$-$C_{10}$ carbocyclyl, optionally substituted $C_6$-$C_{10}$ aryl, optionally substituted $C_1$-$C_6$ alkyl $C_3$-$C_{10}$ carbocyclyl, or optionally substituted $C_1$-$C_6$ alkyl $C_6$-$C_{10}$ aryl;

$R^{B4}$ is H, optionally substituted $C_1$-$C_6$ alkyl, optionally substituted $C_3$-$C_{10}$ carbocyclyl, optionally substituted $C_6$-$C_{10}$ aryl, optionally substituted $C_1$-$C_6$ alkyl $C_3$-$C_{10}$ carbocyclyl, or optionally substituted $C_1$-$C_6$ alkyl $C_6$-$C_{10}$ aryl;

$R^{B5}$ is H, optionally substituted $C_1$-$C_6$ alkyl, or optionally substituted $C_1$-$C_6$ heteroalkyl;

v2 is 0, 1, 2, 3, or 4;

each $R^{B6}$ is, independently, halogen, optionally substituted $C_1$-$C_6$ alkyl, optionally substituted $C_1$-$C_6$ heteroalkyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_2$-$C_9$ heteroaryl, optionally substituted $C_2$-$C_6$ alkenyl, optionally substituted $C_2$-$C_6$ heteroalkenyl, hydroxy, thiol, or optionally substituted amino; and each of $R^{B7}$ and $R^{B8}$ is, independently, H, halogen, optionally substituted $C_1$-$C_6$ alkyl, or optionally substituted $C_6$-$C_{10}$ aryl, where one of $R^{B1}$ and $R^{B3}$ is $A^2$, or a pharmaceutically acceptable salt thereof.

In some embodiments, the structure of Formula C is

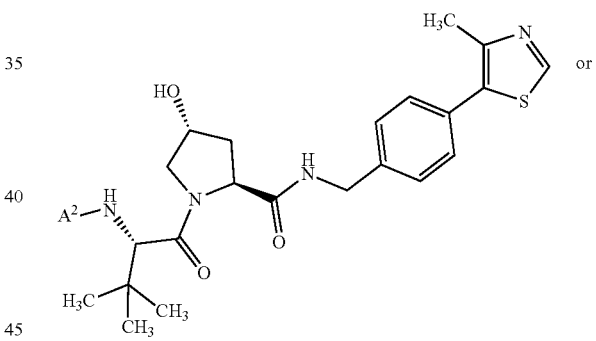

or

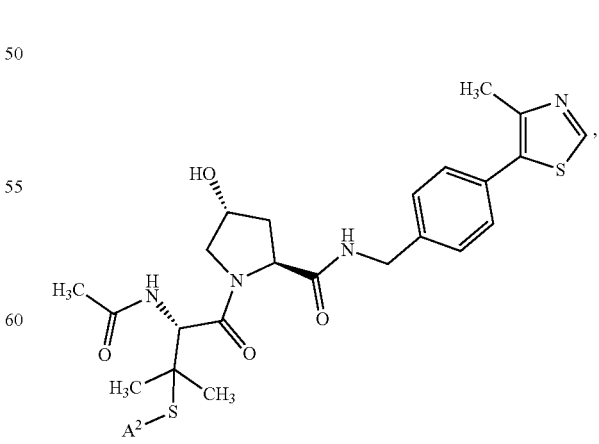

or derivative or analog thereof.

In some embodiments, the structure of Formula C is

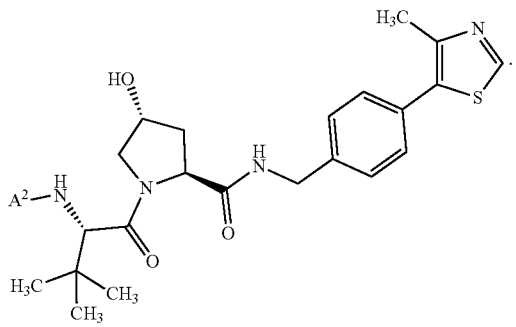

In some embodiments, the degrader moiety includes the structure of Formula D:

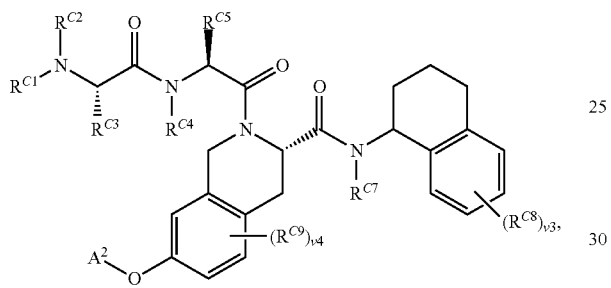

Formula D where
- $A^2$ is a bond between B and the linker;
- each of $R^{C1}$, $R^{C2}$, and $R^{C7}$ is, independently, H, optionally substituted $C_1$-$C_6$ alkyl, or optionally substituted $C_1$-$C_6$ heteroalkyl;
- $R^{C3}$ is optionally substituted $C_1$-$C_6$ alkyl, optionally substituted $C_3$-$C_{10}$ carbocyclyl, optionally substituted $C_6$-$C_{10}$ aryl, optionally substituted $C_1$-$C_6$ alkyl $C_3$-$C_{10}$ carbocyclyl, or optionally substituted $C_1$-$C_6$ alkyl $C_6$-$C_{10}$ aryl;
- $R^{C5}$ is optionally substituted $C_1$-$C_6$ alkyl, optionally substituted $C_3$-$C_{10}$ carbocyclyl, optionally substituted $C_6$-$C_{10}$ aryl, optionally substituted $C_1$-$C_6$ alkyl $C_3$-$C_{10}$ carbocyclyl, or optionally substituted $C_1$-$C_6$ alkyl $C_6$-$C_{10}$ aryl;
- v3 is 0, 1, 2, 3, or 4;
- each $R^{C8}$ is, independently, halogen, optionally substituted $C_1$-$C_6$ alkyl, optionally substituted $C_1$-$C_6$ heteroalkyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_2$-$C_9$ heteroaryl, optionally substituted $C_2$-$C_6$ alkenyl, optionally substituted $C_2$-$C_6$ heteroalkenyl, hydroxy, thiol, or optionally substituted amino;
- v4 is 0, 1, 2, 3, or 4; and
- each $R^{C9}$ is, independently, halogen, optionally substituted $C_1$-$C_6$ alkyl, optionally substituted $C_1$-$C_6$ heteroalkyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_2$-$C_9$ heteroaryl, optionally substituted $C_2$-$C_6$ alkenyl, optionally substituted $C_2$-$C_6$ heteroalkenyl, hydroxy, thiol, or optionally substituted amino, or a pharmaceutically acceptable salt thereof.

In some embodiments, the structure of Formula D is

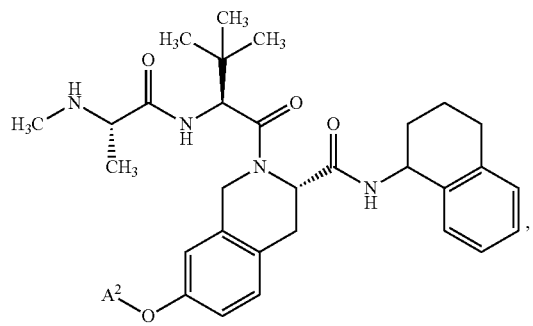

or derivative or analog thereof.

In some embodiments, the degrader moiety includes the structure of Formula E:

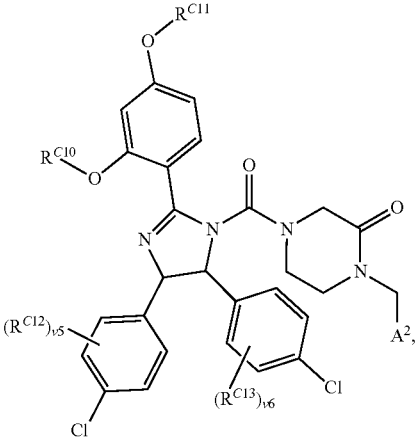

Formula E where
- $A^2$ is a bond between B and the linker;
- each of $R^{C10}$ and $R^{C11}$ is, independently, H, optionally substituted $C_1$-$C_6$ alkyl, optionally substituted $C_3$-$C_{10}$ carbocyclyl, optionally substituted $C_6$-$C_{10}$ aryl, optionally substituted $C_1$-$C_6$ alkyl $C_3$-$C_{10}$ carbocyclyl, or optionally substituted $C_1$-$C_6$ alkyl $C_6$-$C_{10}$ aryl;
- v5 is 0, 1, 2, 3, or 4;
- each $R^{C12}$ is, independently, halogen, optionally substituted $C_1$-$C_6$ alkyl, optionally substituted $C_1$-$C_6$ heteroalkyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_2$-$C_9$ heteroaryl, optionally substituted $C_2$-$C_6$ alkenyl, optionally substituted $C_2$-$C_6$ heteroalkenyl, hydroxy, thiol, or optionally substituted amino;
- v6 is 0, 1, 2, 3, or 4; and
- each $R^{21}$ is, independently, halogen, optionally substituted $C_1$-$C_6$ alkyl, optionally substituted $C_1$-$C_6$ heteroalkyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_2$-$C_9$ heteroaryl, optionally substituted $C_2$-$C_6$ alkenyl, optionally substituted $C_2$-$C_6$ heteroalkenyl, hydroxy, thiol, or optionally substituted amino, or a pharmaceutically acceptable salt thereof.

In some embodiments, the structure of Formula E is

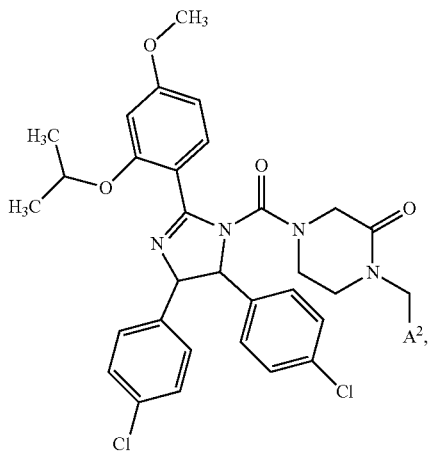

or derivative or analog thereof.

In some embodiments, the degradation moiety includes the structure of Formula FA:

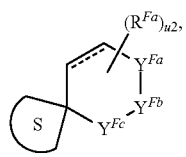

Formula FA where

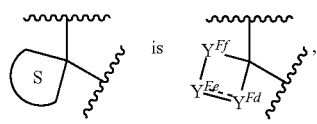

or a bicyclic moiety which is substituted with $A^2$ and substituted with one or more groups independently selected from H, $R^{FF1}$, and oxo;

==== is a single bond or a double bond;
u2 is 0, 1, 2, or 3;
$A^2$ is a bond between the degrader and the linker;
$Y^{Fa}$ is $CR^{Fb}R^{Fc}$, C=O, C=S, C=CH$_2$, SO$_2$, S(O), P(O) Oalkyl, P(O) NHalkyl, P(O)N(alkyl)$_2$, P(O)alkyl, P(O) OH, P(O)NH$_2$;
$Y^{Fb}$ is NH, NR$^{FF1}$, CH$_2$, CHR$^{FF1}$, C(R$^{FF1}$)$_2$, O, or S;
$Y^{Fc}$ is $CR^{Fd}R^{Fe}$, C=O, C=S, C=CH$_2$, SO$_2$, S(O), P(O) Oalkyl, P(O) NHalkyl, P(O)N(alkyl)$_2$, P(O)alkyl, P(O) OH, P(O)NH$_2$;
each of $R^{Fb}$, $R^{Fc}$, $R^{Fd}$, and $R^{Fe}$ is, independently, H, alkyl, aliphatic, heteroaliphatic, aryl, heteroaryl, carbocyclyl, hydroxyl, alkoxy, amino, -NHalkyl, or -Nalkyl$_2$;
or $R^{Fb}$ and $R^{Fc}$, together with the carbon atom to which each is attached, combine to form a 3-, 4-, 5-, or 6-membered spirocarbocyclylene, or a 4-, 5-, or 6-membered spiroheterocyclylene comprising 1 or 2 heteroatoms selected from N and O;
or $R^{Fd}$ and $R^{Fe}$, together with the carbon atom to which each is attached, combine to form a 3-, 4-, 5-, or 6-membered spirocarbocyclylene, or a 4-, 5-, or 6-membered spiroheterocyclylene comprising 1 or 2 heteroatoms selected from N and O; and
or $R^{Fd}$ and $R^{Fb}$, together with the carbon atoms to which each is attached, combine to form a 1, 2, 3, or 4 carbon bridged ring;
each of $Y^{Fd}$ and $Y^{Ff}$ is, independently, CH$_2$, CHR$^{FF2}$, C(R$^{FF2}$)$_2$, C(O), N, NH, NR$^{FF3}$, O, S, or S(O);
$Y^{Fe}$ is a bond or a divalent moiety attached to $Y^{Fd}$ and $Y^{Ff}$ that contains 1 to 5 contiguous carbon atoms that form a 3 to 8-membered ring,
wherein 1, 2, or 3 carbon atoms can be replaced with a nitrogen, oxygen, or sulfur atom;
wherein one of the ring atoms is substituted with $A^2$ and the others are substituted with one or more groups independently selected from H and $R^{FF1}$; and
wherein the contiguous atoms of $Y^{Fe}$ can be attached through a single or double bond;
each $R^{FF1}$ is, independently, H, alkyl, alkenyl, alkynyl, aliphatic, heteroaliphatic, carbocyclyl, halogen, hydroxyl, amino, cyano, alkoxy, aryl, heteroaryl, heterocyclyl, alkylamino, alkylhydroxyl, or haloalkyl;
each $R^{FF2}$ is, independently, alkyl, alkene, alkyne, halogen, hydroxyl, alkoxy, azide, amino, —C(O) H, —C(O)OH, —C(O) (aliphatic, including alkyl), —C(O) O (aliphatic, including alkyl), —NH (aliphatic, including alkyl), -N(aliphatic including alkyl) (aliphatic including alkyl), —NHSOzalkyl, —N(alkyl) SOzalkyl, —NHSOzaryl, —N(alkyl) SOzaryl, —NH-SOzalkenyl, —N(alkyl) SOzalkenyl, —NHSOzalkynyl, —N(alkyl) SOzalkynyl, aliphatic, heteroaliphatic, aryl, heteroaryl, hetercyclic, carbocyclic, cyano, nitro, nitroso, —SH, —Salkyl, or haloalkyl; and
$R^{FF3}$ is alkyl, alkenyl, alkynyl, —C(O) H, —C(O)OH, —C(O)alkyl, or —C(O) Oalkyl,
wherein if $Y^{Fd}$ or $Y^{Ff}$ is substituted with $A^2$, then $Y^{Fe}$ is a bond, or a pharmaceutically acceptable salt thereof.

In some embodiments, the compound of Formula FA has the structure of Formula FA1:

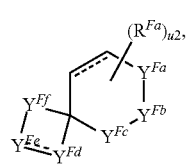

Formula FA1 or a pharmaceutically acceptable salt thereof.

In some embodiments, the degradation moiety includes the structure of Formula FB:

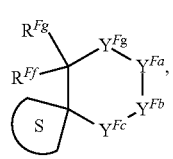

Formula FB where

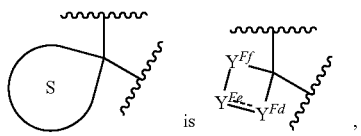 is , or a bicyclic moiety which is substituted with $A^2$ and substituted with one or more groups independently selected from H, $R^{FF1}$, and oxo;

$A^2$ is a bond between the degrader and the linker;

$Y^{Fa}$ is $CR^{Fb}R^{FC}$, C=O, C=S, C=CH$_2$, SO$_2$, S(O), P(O) Oalkyl, P(O) NHalkyl, P(O)N(alkyl)$_2$, P(O)alkyl, P(O) OH, P(O)NH$_2$;

each of $Y^{Fb}$ and $Y^{Fg}$ is, independently, NH, $NR^{FF1}$, CH$_2$, $CHR^{FF1}$, $C(R^{FF1})_2$, O, or S;

$Y^{Fc}$ is $CR^{Fd}R^{Fe}$, C=O, C=S, C=CH$_2$, SO$_2$, S(O), P(O) Oalkyl, P(O) NHalkyl, P(O)N(alkyl)$_2$, P(O)alkyl, P(O) OH, P(O)NH$_2$;

each of $R^{Fb}$, $R^{FC}$, $R^{Fd}$, $R^{Fe}$, $R^{Ff}$, and $R^{Fg}$ is, independently, H, alkyl, aliphatic, heteroaliphatic, aryl, heteroaryl, carbocyclyl, hydroxyl, alkoxy, amino, -NHalkyl, or -Nalkyl$_2$;

or $R^{Fb}$ and $R^{Fc}$, together with the carbon atom to which each is attached, combine to form a 3-, 4-, 5-, or 6-membered spirocarbocyclylene, or a 4-, 5-, or 6-membered spiroheterocyclylene comprising 1 or 2 heteroatoms selected from N and O;

or $R^{Fd}$ and $R^{Fe}$, together with the carbon atom to which each is attached, combine to form a 3-, 4-, 5-, or 6-membered spirocarbocyclylene, or a 4-, 5-, or 6-membered spiroheterocyclylene comprising 1 or 2 heteroatoms selected from N and O;

or $R^{Ff}$ and $R^{Fg}$, together with the carbon atom to which each is attached, combine to form a 3-, 4-, 5-, or 6-membered spirocarbocyclylene, or a 4-, 5-, or 6-membered spiroheterocyclylene comprising 1 or 2 heteroatoms selected from N and O;

or $R^{Fd}$ and $R^{Fb}$, together with the carbon atoms to which each is attached, combine to form a 1, 2, 3, or 4 carbon bridged ring;

or $R^{Fd}$ and $R^{Ff}$, together with the carbon atoms to which each is attached, combine to form a 1, 2, 3, or 4 carbon bridged ring;

or $R^{Fb}$ and $R^{Fg}$, together with the carbon atoms to which each is attached, combine to form a 1, 2, 3, or 4 carbon bridged ring;

each of $Y^{Fd}$ and $Y^{Ff}$ is, independently, CH$_2$, $CHR^{FF2}$, $C(R^{FF2})_2$, C(O), N, NH, $NR^{FF3}$, O, S, or S(O);

$Y^{Fe}$ is a bond or a divalent moiety attached to $Y^{Fd}$ and $Y^{Ff}$ that contains 1 to 5 contiguous carbon atoms that form a 3 to 8-membered ring,
wherein 1, 2, or 3 carbon atoms can be replaced with a nitrogen, oxygen, or sulfur atom;
wherein one of the ring atoms is substituted with $A^2$ and the others are substituted with one or more groups independently selected from H and $R^{FF1}$; and
wherein the contiguous atoms of $Y^{Fe}$ can be attached through a single or double bond;

each $R^{FF1}$ is, independently, H, alkyl, alkenyl, alkynyl, aliphatic, heteroaliphatic, carbocyclyl, halogen, hydroxyl, amino, cyano, alkoxy, aryl, heteroaryl, heterocyclyl, alkylamino, alkylhydroxyl, or haloalkyl;

each $R^{FF2}$ is, independently, alkyl, alkene, alkyne, halogen, hydroxyl, alkoxy, azide, amino, —C(O) H, —C(O)OH, —C(O) (aliphatic, including alkyl), —C(O) O (aliphatic, including alkyl), —NH (aliphatic, including alkyl), -N(aliphatic including alkyl) (aliphatic including alkyl), —NHSOzalkyl, —N(alkyl) SOzalkyl, —NHSOzaryl, —N(alkyl) SOzaryl, —NH-SOzalkenyl, —N(alkyl) SOzalkenyl, —NHSOzalkynyl, —N(alkyl) SOzalkynyl, aliphatic, heteroaliphatic, aryl, heteroaryl, hetercyclic, carbocyclic, cyano, nitro, nitroso, —SH, —Salkyl, or haloalkyl; and $R^{FF3}$ is alkyl, alkenyl, alkynyl, —C(O) H, —C(O)OH, —C(O)alkyl, or —C(O) Oalkyl, wherein if $Y^{Fd}$ or $Y^{Ff}$ is substituted with $A^2$, then $Y^{Fe}$ is a bond, or a pharmaceutically acceptable salt thereof.

In some embodiments, the compound of Formula FB has the structure of Formula FB1:

Formula FB1 or a pharmaceutically acceptable salt thereof.

In some embodiments, the degradation moiety includes the structure of Formula $F^1$:

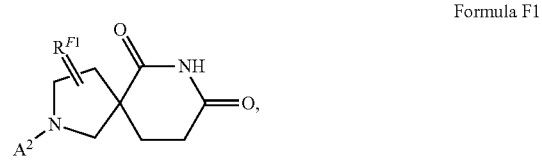

Formula F1 where $A^2$ is a bond between the degrader and the linker; and $R^{F1}$ is absent or O, or a pharmaceutically acceptable salt thereof.

In some embodiments, $R^{F1}$ is absent. In some embodiments, $R^{F1}$ is O.

In some embodiments, the structure of Formula $F^1$ is

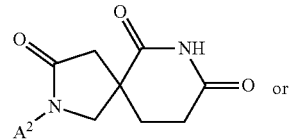 or

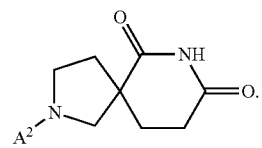

In some embodiments, the degradation moiety includes the structure Formula $F^2$:

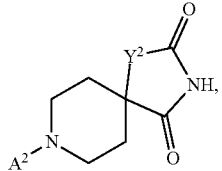

Formula F2 where $A^2$ is a bond between the degrader and the linker; and Y2 is $CH_2$ or NH, or a pharmaceutically acceptable salt thereof.

In some embodiments, Y2 is NH. In some embodiments, Y2 is $CH_2$.

In some embodiments, structure of Formula $F^2$ is

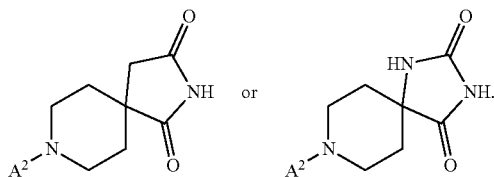

In some embodiments, the degradation moiety includes the structure Formula G:

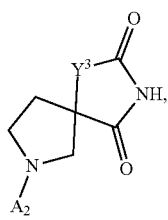

Formula G where $A^2$ is a bond between the degrader and the linker; and Y3 is $CH_2$ or NH, or a pharmaceutically acceptable salt thereof.

In some embodiments, Y3 is NH. In some embodiments, Y3 is $CH_2$.

In some embodiments, structure of Formula G is

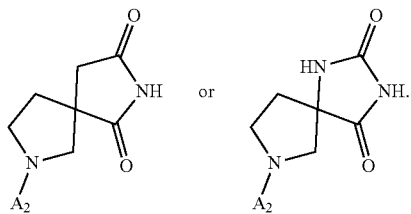

The degradation moiety may also include structures found in, e.g., WO2017/197036; WO2019/204354; WO2019/236483, WO2020/010177; and WO2020/010227, the structures of which are herein incorporated by reference.

In some embodiments, A hast the structure of Formula III:

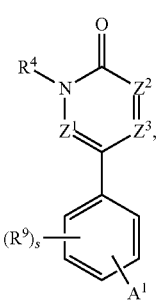

Formula III where
$R^4$ is H, optionally substituted $C_1$-$C_6$ alkyl, optionally substituted $C_2$-$C_6$ alkenyl, optionally substituted $C_1$-$C_6$ heteroalkyl, or optionally substituted $C_3$-$C_{10}$ carbocyclyl; $Z^1$ is N or $CR^5$;
$Z^2$ is N or $CR^6a$;
$Z^3$ is N or $CR^6b$;
$R^5$ is H, halogen, optionally substituted $C_1$-$C_6$ alkyl, optionally substituted $C_1$-$C_6$ heteroalkyl, optionally substituted $C_3$-$C_{10}$ carbocyclyl, or optionally substituted $C_6$-$C_{10}$ aryl;
$R^{6a}$ is H, halogen, cyano, optionally substituted $C_1$-$C_6$ alkyl, optionally substituted $C_1$-$C_6$ heteroalkyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_2$-$C_9$ heteroaryl, optionally substituted $C_2$-$C_6$ alkenyl, optionally substituted $C_2$-$C_6$ heteroalkenyl, hydroxy, thiol, or optionally substituted amino; $R^{6b}$ is H, halogen, cyano, optionally substituted $C_1$-$C_6$ alkyl, optionally substituted $C_1$-$C_6$ heteroalkyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_2$-$C_9$ heteroaryl, optionally substituted $C_2$-$C_6$ alkenyl, optionally substituted $C_2$-$C_6$ heteroalkenyl, hydroxy, thiol, or optionally substituted amino; or $R^{6a}$ and $R^{6b}$, together with the carbon atoms to which each is attached, combine to form optionally substituted $C_6$-$C_{10}$ aryl or optionally substituted $C_2$-$C_9$ heteroaryl;
s is 0, 1, 2, 3, or 4;
each $R^9$ is, independently, halogen, optionally substituted $C_1$-$C_6$ alkyl, optionally substituted $C_1$-$C_6$ heteroalkyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_2$-$C_9$ heteroaryl, optionally substituted $C_2$-$C_6$ alkenyl, optionally substituted $C_2$-$C_6$ heteroalkenyl, hydroxy, thiol, or optionally substituted amino; and
$A^1$ is a bond between A and the linker, or a pharmaceutically acceptable salt thereof.

In some embodiments, $Z^1$ is N. In some embodiments, $Z^1$ is $CR^5$.

In some embodiments, $Z^2$ is N. In some embodiments, $Z^2$ is $CR^6a$.

In some embodiments, $Z^3$ is N. In some embodiments, $Z^3$ is $CR^6b$.

In some embodiments, $Z^1$ is $CR^5$, $Z^2$ is $CR^6a$, and $Z^3$ is $CR^6b$. In some embodiments, $Z^1$ is N, $Z^2$ is $CR^{6a}$, and $Z^2$ is $CR^6b$. In some embodiments, $Z^1$ is $CR^5$, $Z^2$ is N, and $Z^3$ is $CR^6b$. In some embodiments, $Z^1$ is N, $Z^2$ is $CR^6a$, and $Z^3$ is N. In some embodiments, $Z^1$ is N, $Z^2$ is N, and $Z^3$ is $CR^6b$. In some embodiments, $Z^1$ is $CR^5$, $Z^2$ is N, and $Z^3$ is N.

In some embodiments, $R^4$ is H, optionally substituted $C_1$-$C_6$ alkyl, optionally substituted $C_1$-$C_6$ heteroalkyl, or optionally substituted $C_3$-$C_{10}$ carbocyclyl. In some embodiments, $R^4$ is H, optionally substituted $C_1$-$C_6$ alkyl, optionally substituted $C_2$-$C_6$ alkenyl, or optionally substituted $C_3$-$C_{10}$ carbocyclyl. In some embodiments, $R^4$ is H, optionally substituted $C_1$-$C_6$ alkyl, or optionally substituted $C_3$-$C_{10}$ carbocyclyl.

In some embodiments, optionally substituted $C_1$-$C_6$ alkyl is $C_1$-$C_6$ perfluoroalkyl.

In some embodiments, $R^4$ is H,

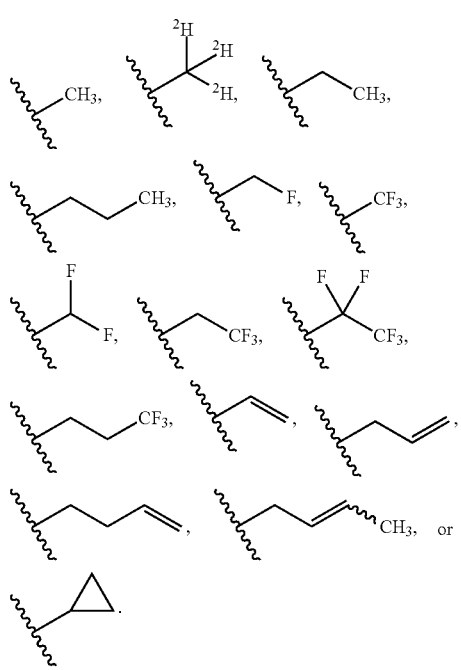

In some embodiments, $R^4$ is

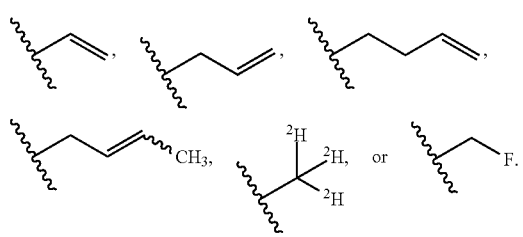

In some embodiments, $R^4$ is H,

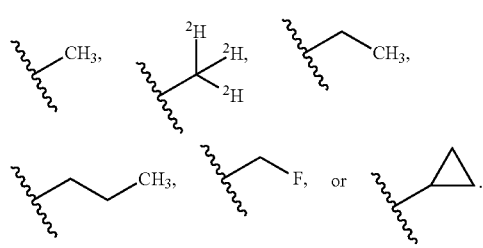

In some embodiments, $R^4$ is H,

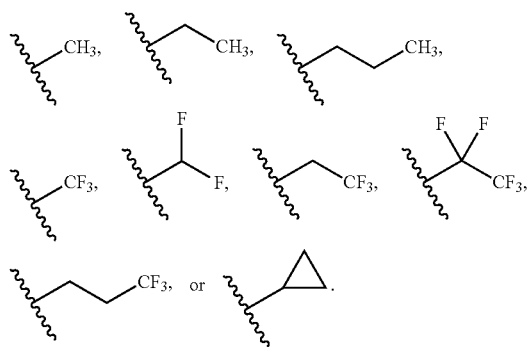

In some embodiments, $R^4$ is H,

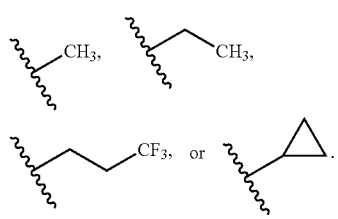

In some embodiments, $R^4$ is H or

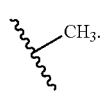

In some embodiments, $R^4$ is H. In some embodiments, $R^4$ is

In some embodiments, $R^5$ is H, optionally substituted $C_1$-$C_6$ alkyl, or optionally substituted $C_6$-$C_{10}$ aryl. In some embodiments, $R^5$ is H, optionally substituted $C_1$-$C_6$ alkyl, optionally substituted $C_1$-$C_6$ heteroalkyl, or optionally substituted $C_3$-$C_{10}$ carbocyclyl. In some embodiments, $R^5$ is H, optionally substituted $C_1$-$C_6$ alkyl, or optionally substituted $C_3$-$C_{10}$ carbocyclyl.

In some embodiments, optionally substituted $C_1$-$C_6$ alkyl is $C_1$-$C_6$ perfluoroalkyl.

In some embodiments, $R^5$ is H,

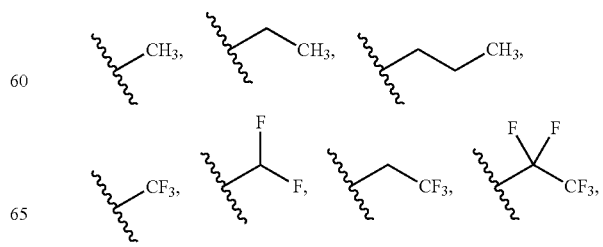

-continued

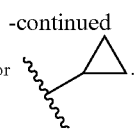

In some embodiments, $R^5$ is H,

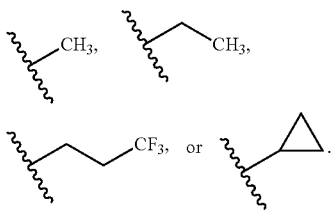

In some embodiments, $R^5$ is H or

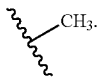

In some embodiments, $R^5$ is H. In some embodiments, $R^5$ is

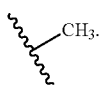

In some embodiments, $R^{6a}$ is H, halogen, optionally substituted $C_1$-$C_6$ alkyl, optionally substituted $C_1$-$C_6$ heteroalkyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_2$-$C_9$ heteroaryl, optionally substituted $C_2$-$C_6$ alkenyl, optionally substituted $C_2$-$C_6$ heteroalkenyl, hydroxy, thiol, or optionally substituted amino.

In some embodiments, $R^{6a}$ is H, halogen, cyano, optionally substituted $C_1$-$C_6$ alkyl, optionally substituted $C_1$-$C_6$ heteroalkyl, or optionally substituted $C_3$-$C_{10}$ carbocyclyl. In some embodiments, $R^{6a}$ is H, halogen, cyano, optionally substituted $C_1$-$C_6$ alkyl, or optionally substituted $C_1$-$C_6$ heteroalkyl. In some embodiments, $R^{6a}$ is H, halogen, cyano, or optionally substituted $C_1$-$C_6$ alkyl. In some embodiments, $R^{6a}$ is optionally substituted $C_1$-$C_6$ heteroalkyl.

In some embodiments, $R^{6a}$ is H, F, cyano,

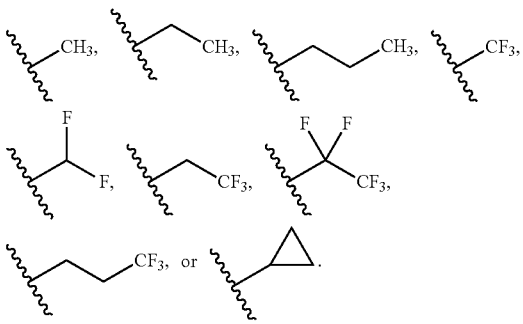

In some embodiments, $R^{6a}$ is H, F, cyano,

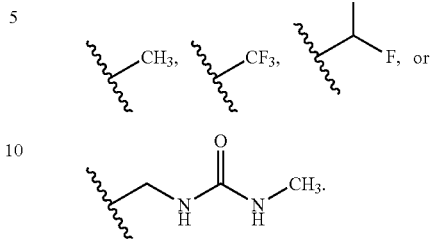

In some embodiments, $R^{6a}$ is H, F, cyano, or

In some embodiments, $R^{6a}$ is

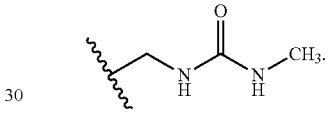

In some embodiments, $R^{6a}$ is H or

In some embodiments, $R^a$ is H. In some embodiments, $R^{6a}$ is

In some embodiments, $R^{6b}$ is H, halogen, optionally substituted $C_1$-$C_6$ alkyl, optionally substituted $C_1$-$C_6$ heteroalkyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_2$-$C_9$ heteroaryl, optionally substituted $C_2$-$C_6$ alkenyl, optionally substituted $C_2$-$C_6$ heteroalkenyl, hydroxy, thiol, or optionally substituted amino.

In some embodiments, $R^{6b}$ is H, halogen, cyano, optionally substituted $C_1$-$C_6$ alkyl, optionally substituted $C_1$-$C_6$ heteroalkyl, or optionally substituted $C_3$-$C_{10}$ carbocyclyl. In some embodiments, $R^{6b}$ is H, halogen, cyano, optionally substituted $C_1$-$C_6$ alkyl, or optionally substituted $C_1$-$C_6$ heteroalkyl. In some embodiments, $R^{6b}$ is H, halogen, cyano, or optionally substituted $C_1$-$C_6$ alkyl. In some embodiments, $R^{6b}$ is optionally substituted $C_1$-$C_6$ heteroalkyl.

In some embodiments, $R^{6b}$ is H, F, cyano,

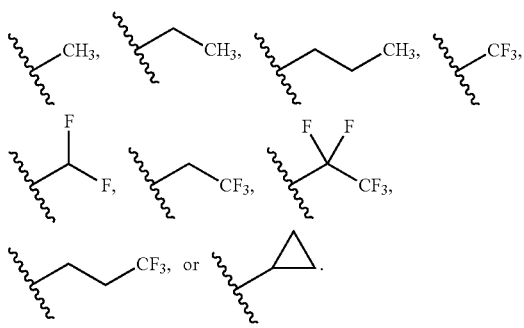

In some embodiments, $R^{6b}$ is H, F, cyano,

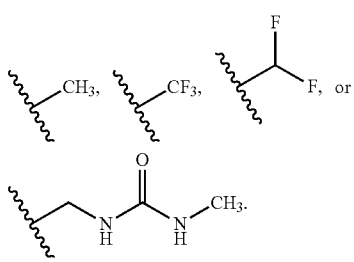

In some embodiments, $R^{6b}$ is H, F, cyano, or

In some embodiments, $R^{6b}$ is

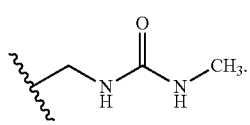

In some embodiments, $R^{6b}$ is H or

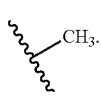

In some embodiments, $R^{6b}$ is H. In some embodiments, $R^{6b}$ is

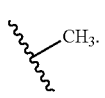

In some embodiments, $R^{6a}$ and $R^{6b}$, together with the carbon atoms to which each is attached, combine to form optionally substituted $C_6$-$C_{10}$ aryl or optionally substituted $C_2$-$C_9$ heteroaryl.

In some embodiments, s is 0, 1, or 2. In some embodiments, s is 1 or 2. In some embodiments, s is 2.

In some embodiments, each $R^9$ is, independently, halogen, optionally substituted $C_1$-$C_6$ alkyl, or optionally substituted $C_1$-$C_6$ heteroalkyl. In some embodiments, each $R^9$ is, independently, optionally substituted $C_1$-$C_6$ alkyl or optionally substituted $C_1$-$C_6$ heteroalkyl.

In some embodiments, $R^9$ is

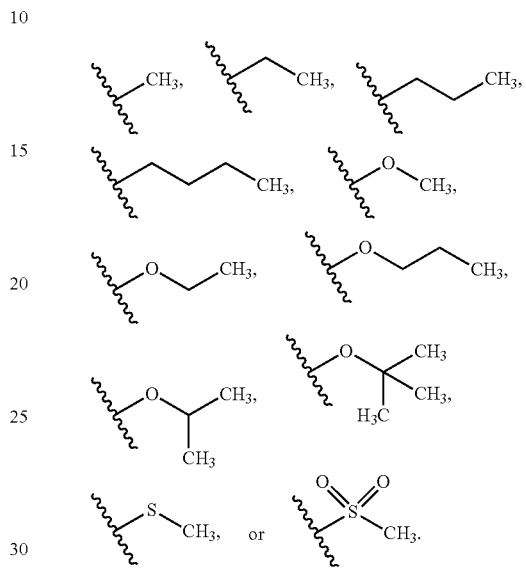

In some embodiments, each $R^9$ is, independently, halogen,

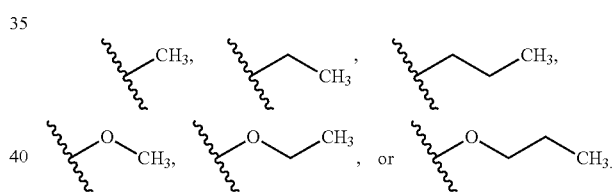

In some embodiments, each $R^9$ is, independently, F, Cl,

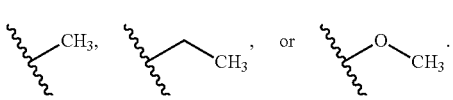

In some embodiments, the structure of Formula III has the structure of Formula IIIa:

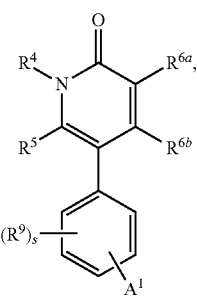

Formula IIIa or a pharmaceutically acceptable salt thereof.

In some embodiments, the structure of Formula III has the structure of Formula IIIb:

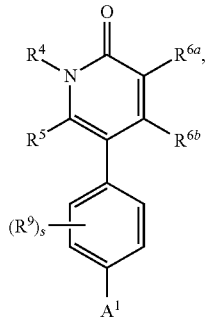

Formula IIIb or a pharmaceutically acceptable salt thereof.

In some embodiments, the structure of Formula III has the structure of Formula IIIc:

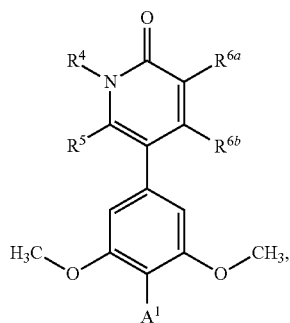

Formula IIIc or a pharmaceutically acceptable salt thereof.

In some embodiments, the structure of Formula III has the structure of Formula IIId:

Formula IIId

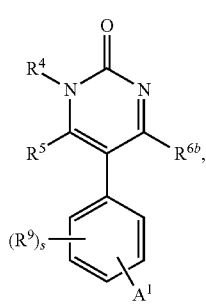

or a pharmaceutically acceptable salt thereof.

In some embodiments, the structure of Formula III has the structure of Formula IIIe:

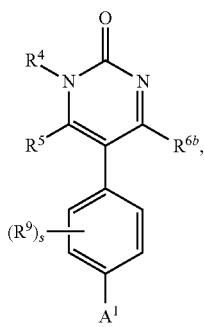

Formula IIIe or a pharmaceutically acceptable salt thereof.

In some embodiments, the structure of Formula III has the structure of Formula IIIf:

Formula IIIf

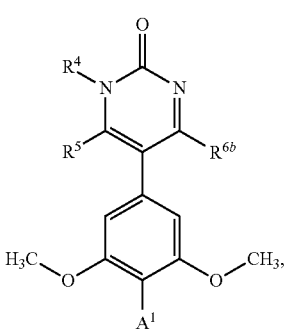

or a pharmaceutically acceptable salt thereof.

In some embodiments, the structure of Formula III has the structure of Formula IIIg:

Formula IIIg

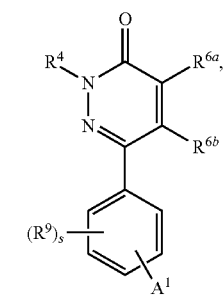

or a pharmaceutically acceptable salt thereof.

In some embodiments, the structure of Formula III has the structure of Formula IIIh:

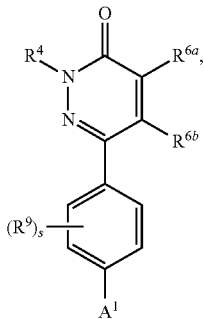

Formula IIIh or a pharmaceutically acceptable salt thereof.

In some embodiments, the structure of Formula III has the structure of Formula IIIi:

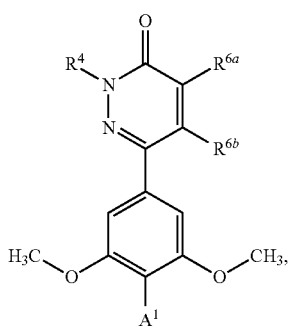

Formula IIIi or a pharmaceutically acceptable salt thereof.

In some embodiments, the structure of Formula III has the structure of Formula IV:

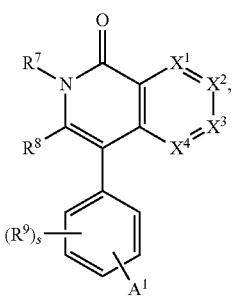

Formula IV where
R$^7$ is H, optionally substituted C$_1$-C$_6$ alkyl, optionally substituted C$_2$-C$_6$ alkenyl, optionally substituted C$_1$-C$_6$ heteroalkyl, or optionally substituted C$_3$-C$_{10}$ carbocyclyl;
R$^8$ is H, halogen, optionally substituted C$_1$-C$_6$ alkyl, optionally substituted C$_1$-C$_6$ heteroalkyl, optionally substituted C$_3$-C$_{10}$ carbocyclyl, or optionally substituted C$_6$-C$_{10}$ aryl;
s is 0, 1, 2, 3, or 4;
each R$^9$ is, independently, halogen, optionally substituted C$_1$-C$_6$ alkyl, optionally substituted C$_1$-C$_6$ heteroalkyl, optionally substituted C$_3$-C$_{10}$ carbocyclyl, optionally substituted C$_2$-C$_9$ heterocyclyl, optionally substituted C$_6$-C$_{10}$ aryl, optionally substituted C$_2$-C$_9$ heteroaryl, optionally substituted C$_2$-C$_6$ alkenyl, optionally substituted C$_2$-C$_6$ heteroalkenyl, hydroxy, thiol, or optionally substituted amino;
X$^1$ is N or CR$^{10a}$;
X$^2$ is N or fCR$^{10b}$;
X$^3$ is N or CR$^{10c}$;
X$^4$ is N or CR$^{10d}$;
each of R$^{10a}$, R$^{10b}$, R$^{10c}$, and R$^{10d}$ is, independently, H, halogen, hydroxy, optionally substituted C$_1$-C$_6$ alkyl, optionally substituted C$_1$-C$_6$ heteroalkyl, optionally substituted C$_3$-C$_{10}$ carbocyclyl, optionally substituted C$_2$-C$_9$ heterocyclyl, optionally substituted C$_6$-C$_{10}$ aryl, optionally substituted C$_2$-C$_9$ heteroaryl, optionally substituted C$_2$-C$_6$ alkenyl, optionally substituted C$_2$-C$_6$ heteroalkenyl, hydroxy, thiol, or optionally substituted amino; and
A$^1$ is a bond between A and the linker, or a pharmaceutically acceptable salt thereof.

In some embodiments, X$^1$ is N. In some embodiments, X$^1$ is CR$^{10}$a. In some embodiments, X$^2$ is N. In some embodiments, X$^2$ is CR$^{10}$b. In some embodiments, X$^3$ is N. In some embodiments, X$^3$ is CR$^{10}$c. In some embodiments, X$^4$ is N. In some embodiments, X$^1$ is CR$^{10}$d.

In some embodiments, X$^1$ is CR$^{10}$a, X$^2$ is CR$^{10}$b, X$^3$ is CR$^{10}$c, and X$^4$ is CR$^{10}$d. In some embodiments, X$^1$ is N, X$^2$ is CR$^{10}$b, X$^3$ is CR$^{10}$c, and X$^4$ is CR$^{10}$d. In some embodiments, X$^1$ is CR$^{10}$a, X$^2$ is N, X$^3$ is CR$^{10}$c, and X$^4$ is CR$^{10}$d. In some embodiments, X$^1$ is CR$^{10}$a, X$^2$ is CR$^{10}$b, X$^3$ is N, and X$^4$ is CR$^{10}$d. In some embodiments, X$^1$ is CR$^{10}$a, X$^2$ is CR$^{10}$b, X$^3$ is CR$^{10}$c, and X$^4$ is N. In some embodiments, X$^1$ is N, X$^2$ is N, X$^3$ is CR$^{10}$c, and X$^4$ is CR$^{10}$d. In some embodiments, X$^1$ is N, X$^2$ is CR$^{10}$b, X$^3$ is N, and X$^4$ is CR$^{10}$d. In some embodiments, X$^1$ is N, X$^2$ is CR$^{10}$b, X$^3$ is CR$^{10}$c, and X$^4$ is N. In some embodiments, X$^1$ is CR$^{10}$a, X$^2$ is N, X$^3$ is N, and X$^4$ is CR$^{10}$d. In some embodiments, X$^1$ is CR$^{10}$a, X$^2$ is N, X$^3$ is CR$^{10}$c, and X$^4$ is N. In some embodiments, X$^1$ is CR$^{10}$a, X$^2$ is CR$^{10}$b, X$^3$ is N, and X$^4$ is N.

In some embodiments, R$^7$ is H, optionally substituted C$_1$-C$_6$ alkyl, optionally substituted C$_1$-C$_6$ heteroalkyl, or optionally substituted C$_3$-C$_{10}$ carbocyclyl. In some embodiments, R$^7$ is H, optionally substituted C$_1$-C$_6$ alkyl, optionally substituted C$_2$-C$_6$ alkenyl, or optionally substituted C$_3$-C$_{10}$ carbocyclyl. In some embodiments, R$^7$ is H, optionally substituted C$_1$-C$_6$ alkyl, or optionally substituted C$_3$-C$_{10}$ carbocyclyl.

In some embodiments, optionally substituted C$_1$-C$_6$ alkyl is C$_1$-C$_6$ perfluoroalkyl.

In some embodiments, R$^7$ is H,

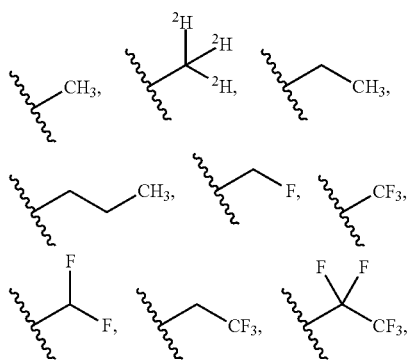

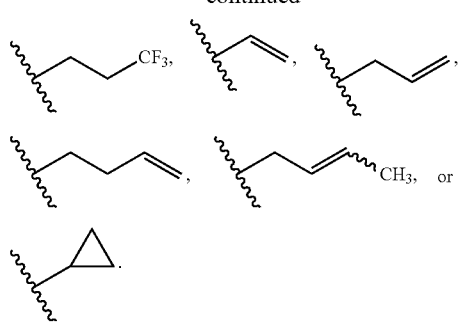

In some embodiments, $R^7$ is

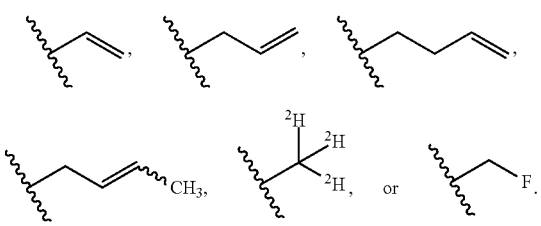

In some embodiments, $R^7$ is H,

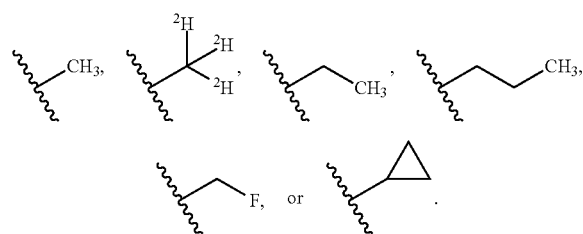

In some embodiments, $R^7$ is H,

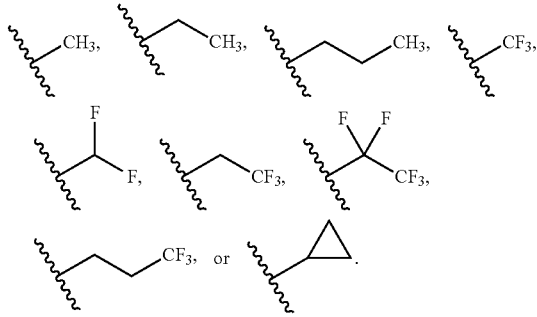

In some embodiments, $R^7$ is H,

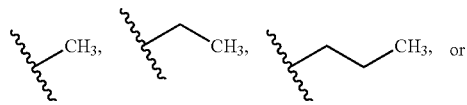

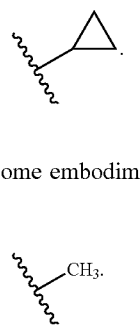

In some embodiments, $R^7$ is H or

In some embodiments, $R^7$ is H. In some embodiments, $R^7$ is

In some embodiments, $R^8$ is H, optionally substituted $C_1$-$C_6$ alkyl, or optionally substituted $C_6$-$C_{10}$ aryl. In some embodiments, $R^8$ is H, optionally substituted $C_1$-$C_6$ alkyl, optionally substituted $C_1$-$C_6$ heteroalkyl, or optionally substituted $C_3$-$C_{10}$ carbocyclyl. In some embodiments, $R^8$ is H, optionally substituted $C_1$-$C_6$ alkyl, or optionally substituted $C_3$-$C_{10}$ carbocyclyl. In some embodiments, $R^8$ is H or optionally substituted $C_1$-$C_6$ alkyl.

In some embodiments, optionally substituted $C_1$-$C_6$ alkyl is $C_1$-$C_6$ perfluoroalkyl.

In some embodiments, $R^8$ is H,

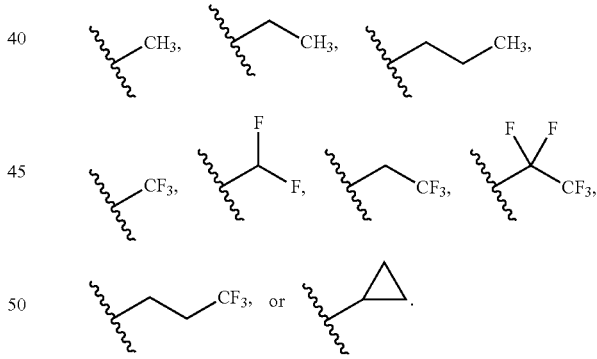

In some embodiments, $R^8$ is H,

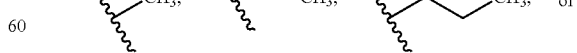

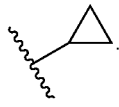

In some embodiments, $R^8$ is H or

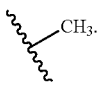

In some embodiments, $R^8$ is H. In some embodiments, $R^8$ is

In some embodiments, s is 0, 1, or 2. In some embodiments, s is 1 or 2. In some embodiments, s is 2. In some embodiments, s is 1.

In some embodiments, each $R^9$ is, independently, halogen, optionally substituted $C_1$-$C_6$ alkyl, or optionally substituted $C_1$-$C_6$ heteroalkyl. In some embodiments, each $R^9$ is, independently, optionally substituted $C_1$-$C_6$ alkyl or optionally substituted $C_1$-$C_6$ heteroalkyl.

In some embodiments, $R^9$ is

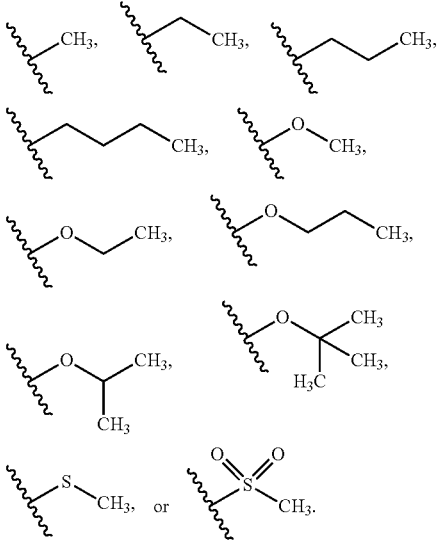

In some embodiments, each $R^9$ is, independently, halogen,

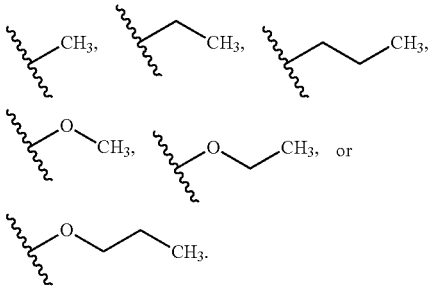

In some embodiments, each $R^9$ is, independently, F, Cl,

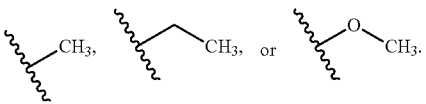

In some embodiments, $R^{10a}$ is H, halogen, cyano, optionally substituted $C_1$-$C_6$ alkyl, optionally substituted $C_1$-$C_6$ heteroalkyl, or optionally substituted $C_3$-$C_{10}$ carbocyclyl. In some embodiments, $R^{10a}$ is H, halogen, cyano, optionally substituted $C_1$-$C_6$ alkyl, or optionally substituted $C_1$-$C_6$ heteroalkyl. In some embodiments, $R^{10a}$ is H, halogen, cyano, or optionally substituted $C_1$-$C_6$ alkyl. In some embodiments, $R^{10a}$ is optionally substituted $C_1$-$C_6$ heteroalkyl.

In some embodiments, $R^{10a}$ is H, F, cyano,

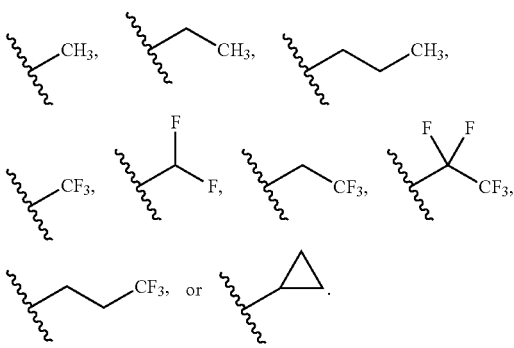

In some embodiments, $R^{10a}$ is H, F, cyano,

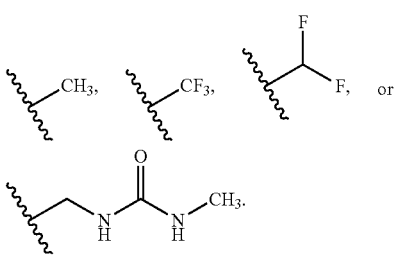

In some embodiments, $R^{10a}$ is H, F, cyano, or

In some embodiments, $R^{10a}$ is

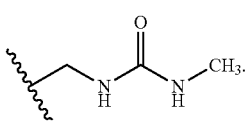 [SMILES: *CNC(=O)NC]

In some embodiments, $R^{10a}$ is H or

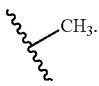

In some embodiments, $R^{10a}$ is H. In some embodiments, $R^{10a}$ is

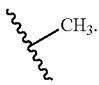

In some embodiments, $R^{10b}$ is H, halogen, cyano, optionally substituted $C_1$-$C_6$ alkyl, optionally substituted $C_1$-$C_6$ heteroalkyl, or optionally substituted $C_3$-$C_{10}$ carbocyclyl. In some embodiments, $R^{10b}$ is H, halogen, cyano, optionally substituted $C_1$-$C_6$ alkyl, or optionally substituted $C_1$-$C_6$ heteroalkyl. In some embodiments, $R^{10b}$ is H, halogen, cyano, or optionally substituted $C_1$-$C_6$ alkyl. In some embodiments, $R^{10b}$ is optionally substituted $C_1$-$C_6$ heteroalkyl.

In some embodiments, $R^{10b}$ is H, F, cyano,

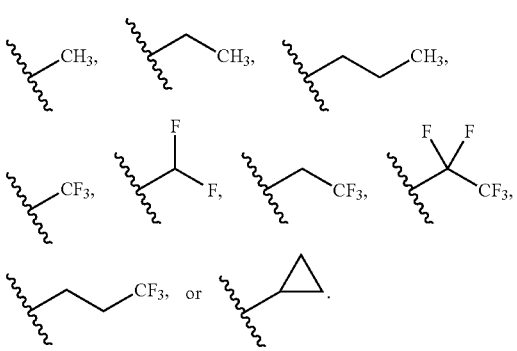

In some embodiments, $R^{10b}$ is H, F, cyano,

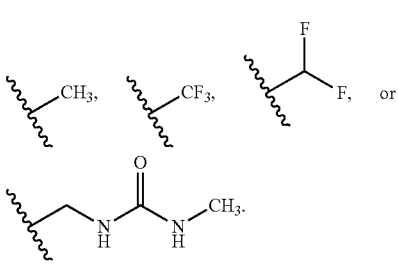

In some embodiments, $R^{10b}$ is H, F, cyano, or

In some embodiments, $R^{10b}$ is

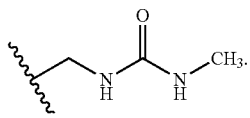 [SMILES: *CNC(=O)NC]

In some embodiments, $R^{10b}$ is H or

In some embodiments, $R^{10b}$ is H. In some embodiments, $R^{10b}$ is

In some embodiments, $R^{10c}$ is H, halogen, cyano, optionally substituted $C_1$-$C_6$ alkyl, optionally substituted $C_1$-$C_6$ heteroalkyl, or optionally substituted $C_3$-$C_{10}$ carbocyclyl. In some embodiments, $R^{10c}$ is H, halogen, cyano, optionally substituted $C_1$-$C_6$ alkyl, or optionally substituted $C_1$-$C_6$ heteroalkyl. In some embodiments, $R^{10c}$ is H, halogen, cyano, or optionally substituted $C_1$-$C_6$ alkyl. In some embodiments, $R^{10c}$ is optionally substituted $C_1$-$C_6$ heteroalkyl.

In some embodiments, $R^{10c}$ is H, F, cyano,

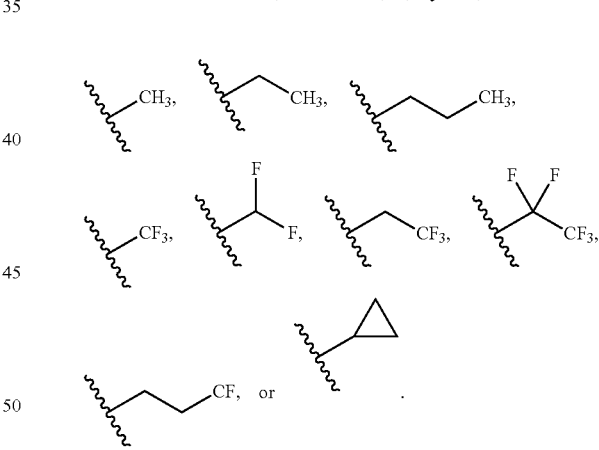

In some embodiments, $R^{10c}$ is H, F, cyano,

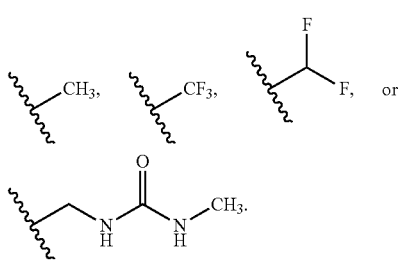

In some embodiments, $R^{10c}$ is H, F, cyano, or

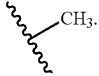

In some embodiments, $R^{10c}$ is

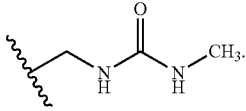 [SMILES: *CNC(=O)NC]

In some embodiments, $R^{10c}$ is H or

In some embodiments, $R^{10c}$ is H. In some embodiments, $R^{10c}$ is

In some embodiments, $R^{10d}$ is H, halogen, cyano, optionally substituted $C_1$-$C_6$ alkyl, optionally substituted $C_1$-$C_6$ heteroalkyl, or optionally substituted $C_3$-$C_{10}$ carbocyclyl. In some embodiments, $R^{10d}$ is H, halogen, cyano, optionally substituted $C_1$-$C_6$ alkyl, or optionally substituted $C_1$-$C_6$ heteroalkyl. In some embodiments, $R^{10d}$ is H, halogen, cyano, or optionally substituted $C_1$-$C_6$ alkyl. In some embodiments, $R^{10d}$ is optionally substituted $C_1$-$C_6$ heteroalkyl.

In some embodiments, $R^{10d}$ is H, F, cyano,

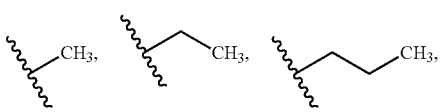

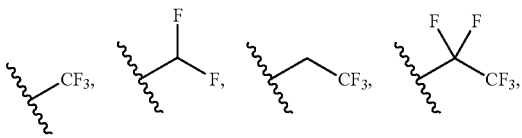

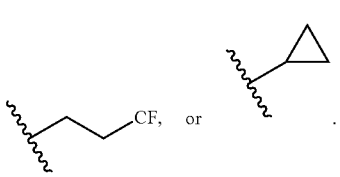

In some embodiments, $R^{10d}$ is H, F, cyano,

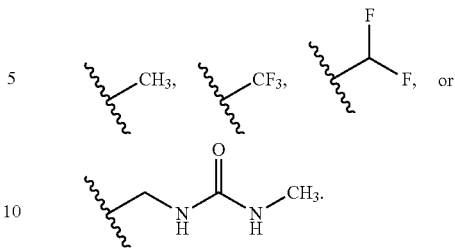

In some embodiments, $R^{10d}$ is H, F, cyano, or

In some embodiments, $R^{10d}$ is

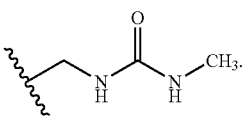 [SMILES: *CNC(=O)NC]

In some embodiments, $R^{10d}$ is H or

In some embodiments, $R^{10d}$ is H. In some embodiments, $R^{10d}$ is

In some embodiments, each of $R^{10a}$, $R^{10b}$, $R^{10c}$, and $R^{10d}$ is, independently, optionally substituted $C_1$-$C_6$ alkyl, optionally substituted $C_1$-$C_6$ heteroalkyl, or optionally substituted amino.

In some embodiments, each of $R^{10a}$, $R^{10b}$, $R^{10c}$, and $R^{10d}$ is, independently, —NH$_2$,

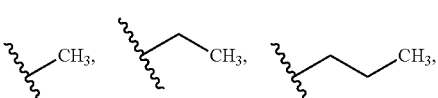

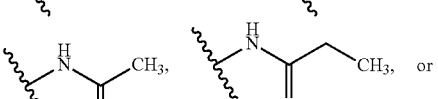

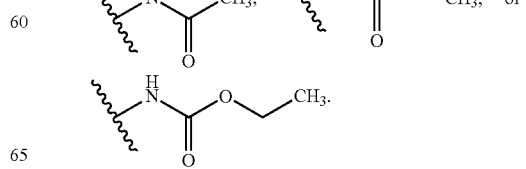

In some embodiments, A includes the structure of Formula IVa:

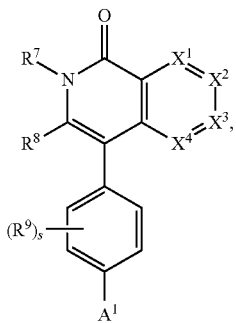

Formula IVa or a pharmaceutically acceptable salt thereof.

In some embodiments, A includes the structure of Formula IVb:

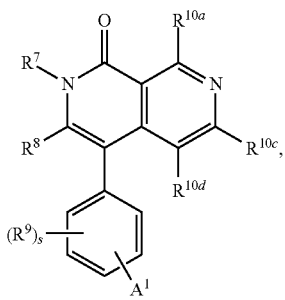

Formula IVb or a pharmaceutically acceptable salt thereof.

In some embodiments, A includes the structure of Formula IVc:

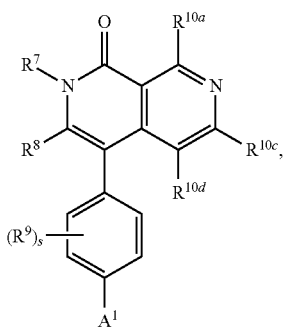

Formula IVc or a pharmaceutically acceptable salt thereof.

In some embodiments, A includes the structure of Formula IVd:

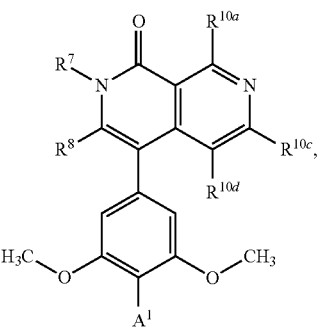

Formula IVd or a pharmaceutically acceptable salt thereof.

In some embodiments, A includes the structure of Formula IVe:

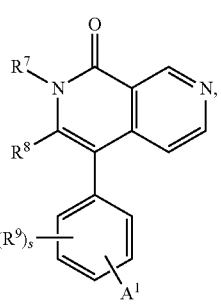

Formula IVe or a pharmaceutically acceptable salt thereof.

In some embodiments, A includes the structure of Formula IVf:

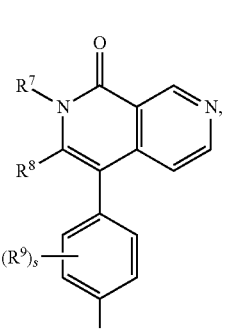

Formula IVf or a pharmaceutically acceptable salt thereof.

In some embodiments, A includes the structure of Formula IVg:

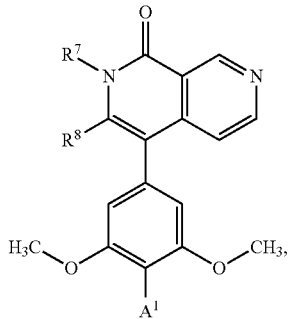

Formula IVg or a pharmaceutically acceptable salt thereof.

In some embodiments, A includes the structure of Formula IVh:

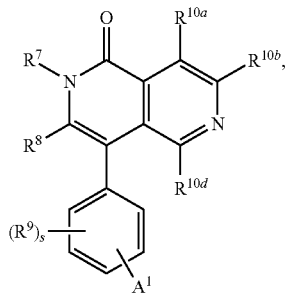

Formula IVh or a pharmaceutically acceptable salt thereof.

In some embodiments, A includes the structure of Formula IVi:

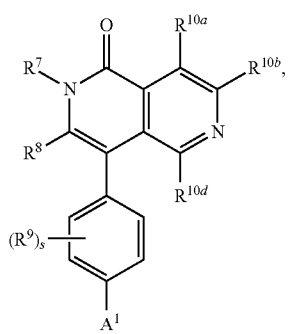

Formula IVi or a pharmaceutically acceptable salt thereof.

In some embodiments, A includes the structure of Formula IVj:

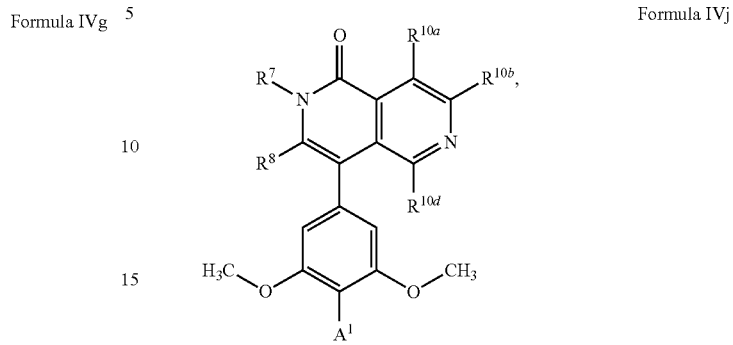

Formula IVj or a pharmaceutically acceptable salt thereof.

In some embodiments, A includes the structure of Formula IVk:

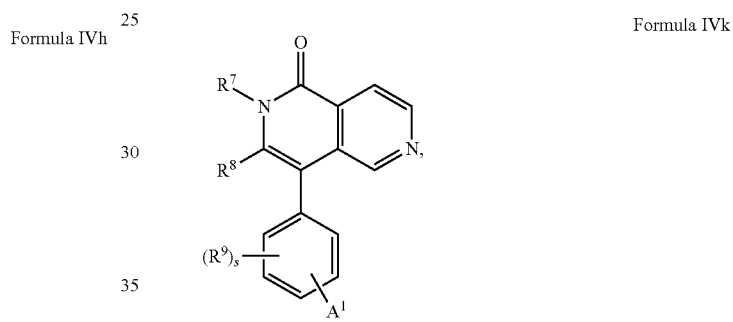

Formula IVk or a pharmaceutically acceptable salt thereof.

In some embodiments, A includes the structure of Formula IVm:

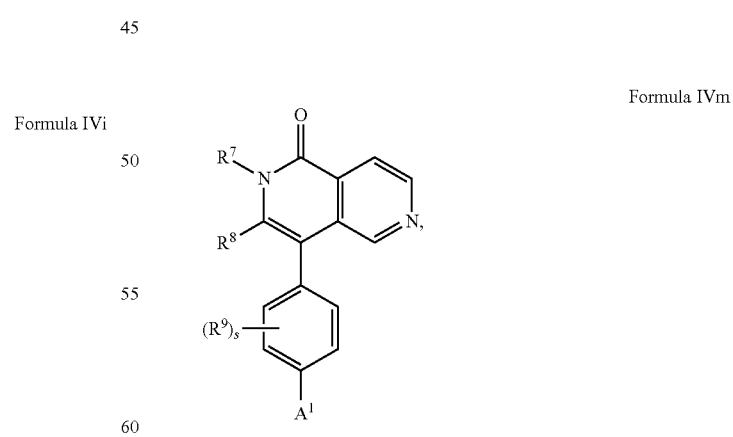

Formula IVm or a pharmaceutically acceptable salt thereof.

In some embodiments, A includes the structure of Formula IVn:

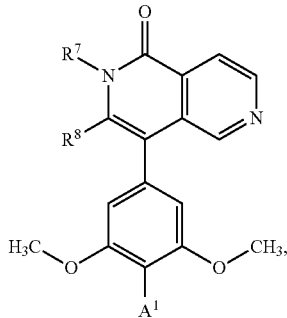

Formula IVn or a pharmaceutically acceptable salt thereof.

In some embodiments, A includes the structure of any one of

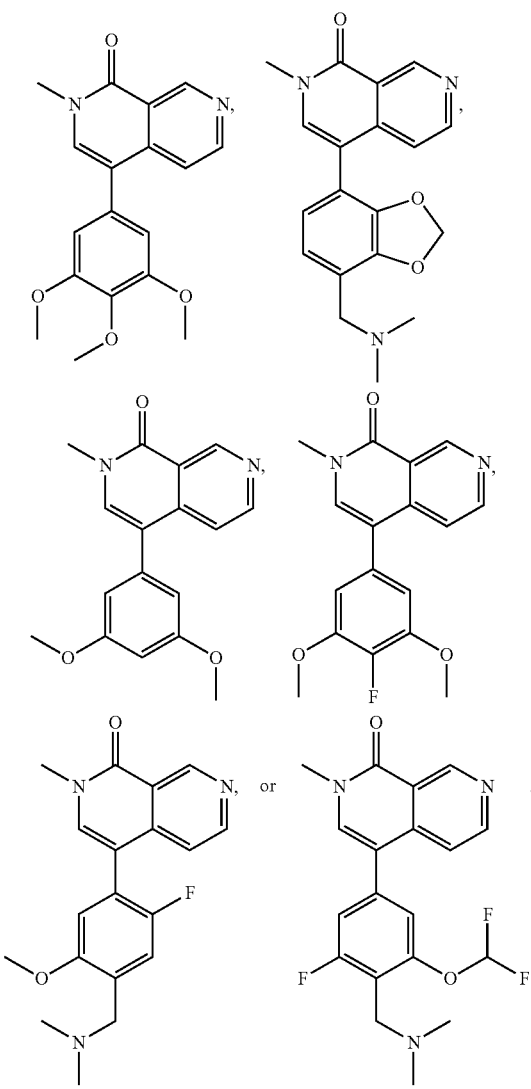

In some embodiments, A includes the structure of Formula V

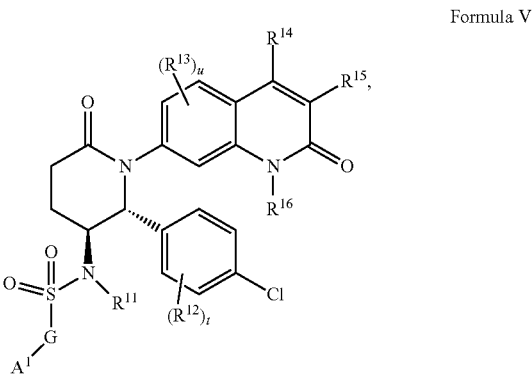

Formula V where each $R^{11}$ and $R^{16}$ is, independently, H, optionally substituted $C_1$-$C_6$ alkyl, or optionally substituted $C_1$-$C_6$ heteroalkyl;

t is 0, 1, 2, 3, or 4;

each $R^{12}$ is, independently, halogen, optionally substituted $C_1$-$C_6$ alkyl, optionally substituted $C_1$-$C_6$ heteroalkyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_2$-$C_9$ heteroaryl, optionally substituted $C_2$-$C_6$ alkenyl, optionally substituted $C_2$-$C_6$ heteroalkenyl, hydroxy, thiol, or optionally substituted amino;

u is 0, 1, 2, 3, or 4;

each $R^{13}$ is, independently, halogen, optionally substituted $C_1$-$C_6$ alkyl, optionally substituted $C_1$-$C_6$ heteroalkyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_2$-$C_9$ heteroaryl, optionally substituted $C_2$-$C_6$ alkenyl, optionally substituted $C_2$-$C_6$ heteroalkenyl, hydroxy, thiol, or optionally substituted amino;

each $R^{14}$ and $R^{15}$ is, independently, selected form the group consisting of H, halogen, optionally substituted $C_1$-$C_6$ alkyl, or optionally substituted $C_6$-$C_{10}$ aryl;

G is optionally substituted $C_1$-$C_6$ alkylene, optionally substituted $C_6$-$C_{10}$ arylene, or optionally substituted $C_3$-$C_6$ carbocyclylene; and $A^1$ is a bond between A and the linker, or a pharmaceutically acceptable salt thereof.

In some embodiments, A includes the structure of Formula VI:

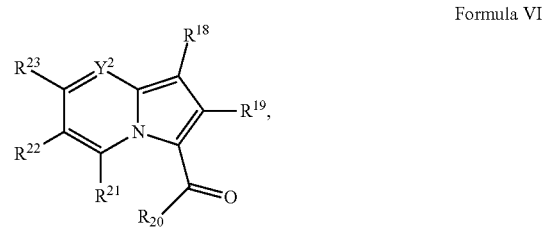

Formula VI where
Y2 is $CR^{17}$ or N;
$R^{18}$ is $A^1$, optionally substituted $C_6$-$C_{10}$ aryl or $C_2$-$C_9$ heteroaryl;
$R^{19}$ is H, halogen, optionally substituted $C_1$-$C_6$ alkyl, or optionally substituted $C_6$-$C_{10}$ aryl;
$R^{20}$ is H, optionally substituted $C_1$-$C_6$ alkyl, or optionally substituted $C_6$-$C_{10}$ aryl;
each $R^{17}$, $R^{21}$, and $R^{22}$ is, independently, H, halogen, optionally substituted $C_1$-$C_6$ alkyl, optionally substituted $C_1$-$C_6$ heteroalkyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_2$-$C_9$ heteroaryl, optionally substituted $C_2$-$C_6$ alkenyl, optionally substituted $C_2$-$C_6$ heteroalkenyl, hydroxy, thiol, or optionally substituted amino;
$R^{23}$ is H or —$NR^{24}R^{25}$; and
each of $R^{24}$ and $R^{25}$ is, independently, H, $A^1$, optionally substituted $C_1$-$C_6$ alkyl, or optionally substituted $C_1$-$C_6$ heteroalkyl, or $R^{24}$ and $R^{25}$ combine to form optionally substituted $C_2$-$C_9$ heterocyclyl,
where one of $R^{18}$, $R^{24}$, or $R^{25}$ is $A^1$, or a pharmaceutically acceptable salt thereof.

In some embodiments, A includes the structure of Formula VII:

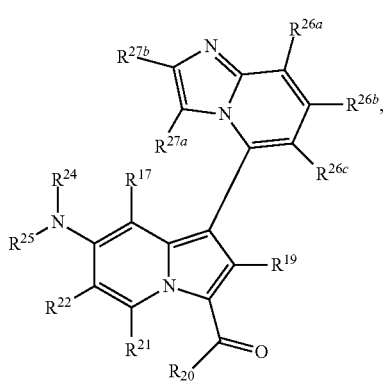

Formula VII where
each $R^{26a}$, $R^{26b}$, and $R^{26c}$ is, independently, H, $A^1$, halogen, optionally substituted $C_1$-$C_6$ alkyl, optionally substituted $C_1$-$C_6$ heteroalkyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_2$-$C_9$ heteroaryl, optionally substituted $C_2$-$C_6$ alkenyl, optionally substituted $C_2$-$C_6$ heteroalkenyl, hydroxy, thiol, or optionally substituted amino;
each $R^{27a}$ and $R^{27b}$ is, independently, H, halogen, optionally substituted $C_1$-$C_6$ alkyl, or optionally substituted $C_6$-$C_{10}$ aryl;
$R^{19}$ is H, halogen, optionally substituted $C_1$-$C_6$ alkyl, or optionally substituted $C_6$-$C_{10}$ aryl;
$R^{20}$ is H, optionally substituted $C_1$-$C_6$ alkyl, or optionally substituted $C_6$-$C_{10}$ aryl;
each $R^{17}$, $R^{21}$, and $R^{22}$ is, independently, H, halogen, optionally substituted $C_1$-$C_6$ alkyl, optionally substituted $C_1$-$C_6$ heteroalkyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_2$-$C_9$ heteroaryl, optionally substituted $C_2$-$C_6$ alkenyl, optionally substituted $C_2$-$C_6$ heteroalkenyl, hydroxy, thiol, or optionally substituted amino; and
each of $R^{24}$ and $R^{25}$ is, independently, H, $A^1$, optionally substituted $C_1$-$C_6$ alkyl, or optionally substituted $C_1$-$C_6$ heteroalkyl, or $R^{24}$ and $R^{25}$ combine to form optionally substituted $C_2$-$C_9$ heterocyclyl,
where one of $R^{26a}$, $R^{26b}$, $R^{26c}$, $R^{24}$, or $R^{25}$ is $A^1$, or a pharmaceutically acceptable salt thereof.

In some embodiments, A includes the structure of Formula VIII:

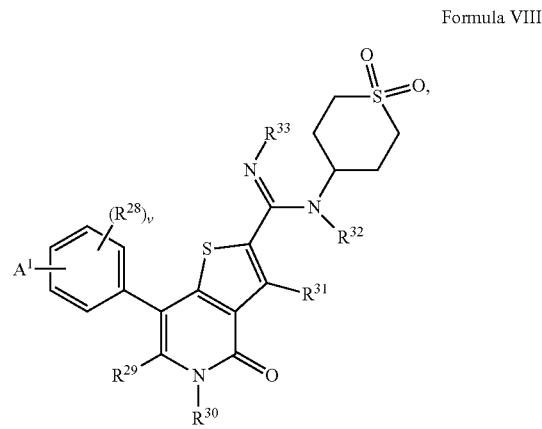

Formula VIII where
v is 0, 1, 2, 3, or 4;
each $R^{28}$ is, independently, halogen, optionally substituted $C_1$-$C_6$ alkyl, optionally substituted $C_1$-$C_6$ heteroalkyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_2$-$C_9$ heteroaryl, optionally substituted $C_2$-$C_6$ alkenyl, optionally substituted $C_2$-$C_6$ heteroalkenyl, hydroxy, thiol, or optionally substituted amino;
$R^{29}$ is H, halogen, optionally substituted $C_1$-$C_6$ alkyl, or optionally substituted $C_6$-$C_{10}$ aryl;
$R^{31}$ is H, halogen, optionally substituted $C_1$-$C_6$ alkyl, or optionally substituted $C_6$-$C_{10}$ aryl;
each $R^{30}$, $R^{32}$, and $R^{33}$ is, independently, H, optionally substituted $C_1$-$C_6$ alkyl, or optionally substituted $C_1$-$C_6$ heteroalkyl; and
$A^1$ is a bond between A and the linker, or a pharmaceutically acceptable salt thereof.

In some embodiments, A includes the structure of Formula IX:

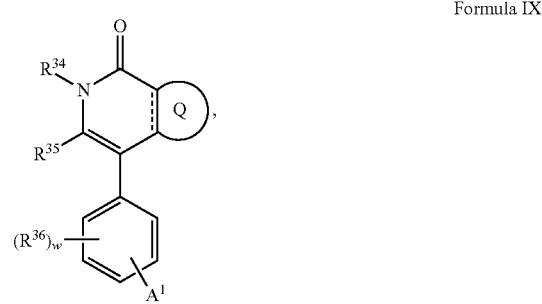

Formula IX where

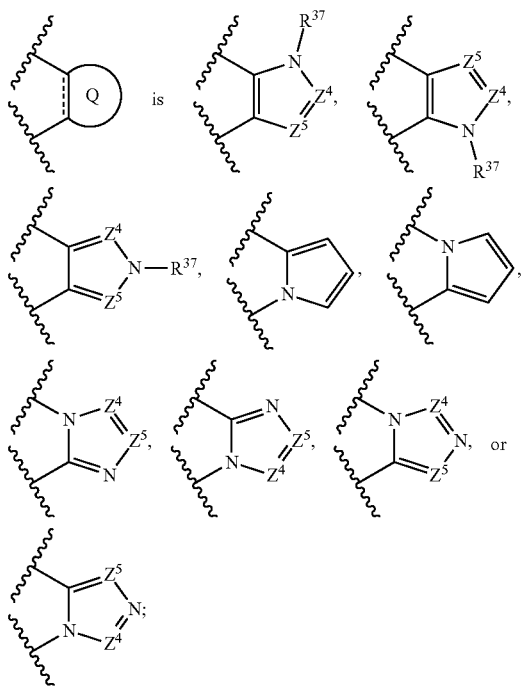

$Z^4$ is N or $CR^{38}$;

$Z^5$ is N or $CR^{39}$;

$R^{34}$ is H, optionally substituted $C_1$-$C_6$ alkyl, optionally substituted $C_2$-$C_6$ alkenyl, optionally substituted $C_1$-$C_6$ heteroalkyl, or optionally substituted $C_3$-$C_{10}$ carbocyclyl;

$R^{35}$ is H, halogen, optionally substituted $C_1$-$C_6$ alkyl, optionally substituted $C_1$-$C_6$ heteroalkyl, optionally substituted $C_3$-$C_6$ carbocyclyl, or optionally substituted $C_6$-$C_{10}$ aryl;

$R^{37}$ is H, optionally substituted $C_1$-$C_6$ alkyl, or optionally substituted $C_1$-$C_6$ heteroalkyl;

$R^{38}$ is H, halogen, optionally substituted $C_1$-$C_6$ alkyl, or optionally substituted $C_6$-$C_{10}$ aryl;

$R^{39}$ is H, halogen, optionally substituted $C_1$-$C_6$ alkyl, or optionally substituted $C_6$-$C_{10}$ aryl;

w is 0, 1, 2, 3, or 4;

each $R^{36}$ is, independently, halogen, optionally substituted $C_1$-$C_6$ alkyl, optionally substituted $C_1$-$C_6$ heteroalkyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_2$-$C_9$ heteroaryl, optionally substituted $C_2$-$C_6$ alkenyl, optionally substituted $C_2$-$C_6$ heteroalkenyl, hydroxy, thiol, or optionally substituted amino; and $A^1$ is a bond between A and the linker, or a pharmaceutically acceptable salt thereof.

In some embodiments, $Z^4$ is N. In some embodiments, $Z^4$ is $R^{38}$. In some embodiments, $Z^5$ is N. In some embodiments, $Z^5$ is $R^{39}$.

In some embodiments, $Z^4$ is N and $Z^5$ is $R^{39}$. In some embodiments, $Z^4$ is $R^{38}$ and $Z^5$ is N. In some embodiments, $Z^4$ is $R^{38}$ and $Z^5$ is $R^{39}$.

In some embodiments,

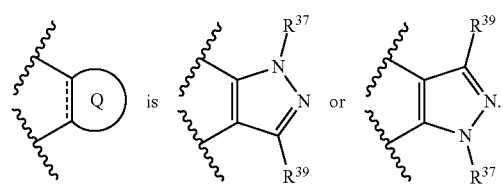

In some embodiments,

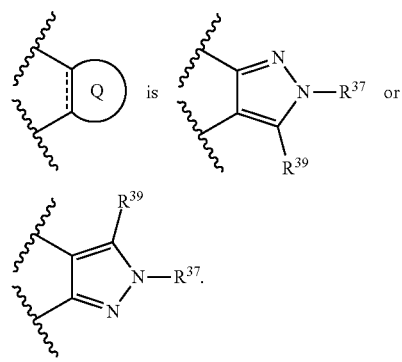

In some embodiments,

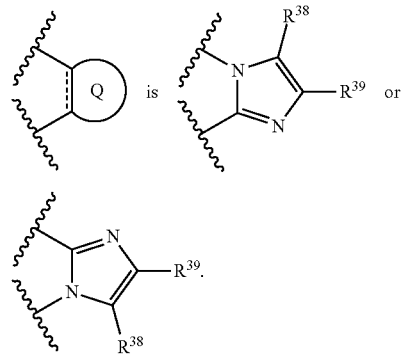

In some embodiments,

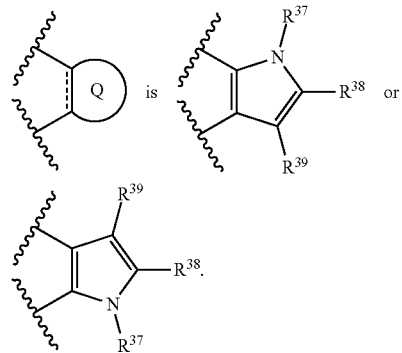

In some embodiments,

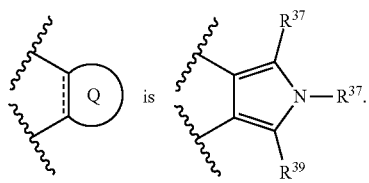

In some embodiments,

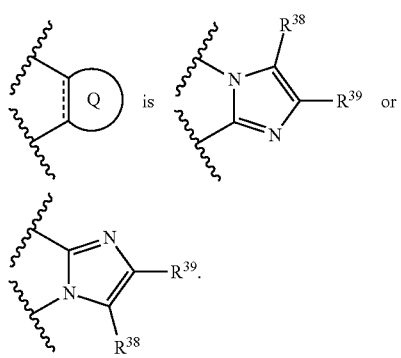

In some embodiments,

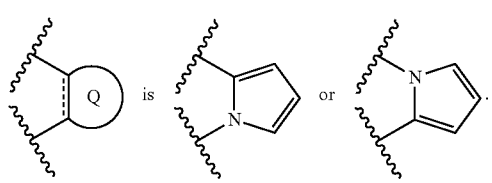

In some embodiments, $R^{37}$ is H or optionally substituted $C_1$-$C_6$ alkyl. In some embodiments, $R^{37}$ is H or

In some embodiments, $R^{38}$ is H or optionally substituted $C_1$-$C_6$ alkyl. In some embodiments, $R^{38}$ is H or

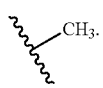

In some embodiments, $R^{39}$ is H or optionally substituted $C_1$-$C_6$ alkyl. In some embodiments, $R^{39}$ is H or

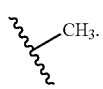

In some embodiments, $R^{34}$ is H, optionally substituted $C_1$-$C_6$ alkyl, optionally substituted $C_1$-$C_6$ heteroalkyl, or optionally substituted $C_3$-$C_{10}$ carbocyclyl. In some embodiments, $R^{34}$ is H, optionally substituted $C_1$-$C_6$ alkyl, optionally substituted $C_2$-$C_6$ alkenyl, or optionally substituted $C_3$-$C_{10}$ carbocyclyl. In some embodiments, $R^{34}$ is H, optionally substituted $C_1$-$C_6$ alkyl, or optionally substituted $C_3$-$C_{10}$ carbocyclyl.

In some embodiments, optionally substituted $C_1$-$C_6$ alkyl is $C_1$-$C_6$ perfluoroalkyl.

In some embodiments, $R^{34}$ is H.

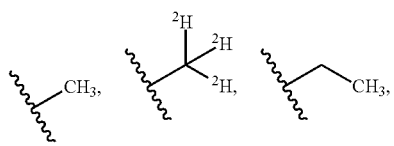

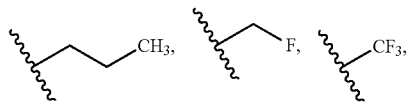

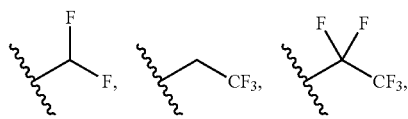

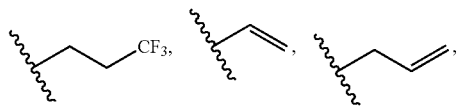

In some embodiments, $R^{34}$ is

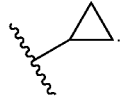

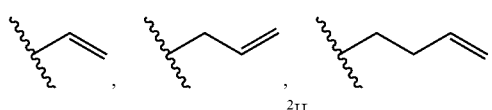

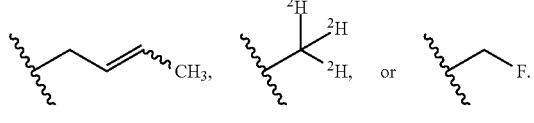

In some embodiments, $R^{34}$ is H,

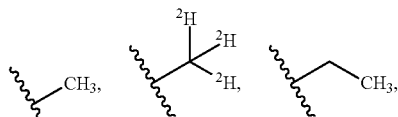

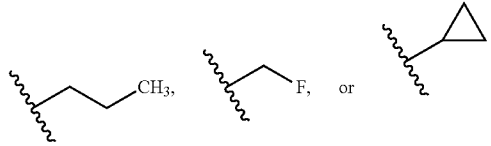

In some embodiments, $R^{34}$ is H,

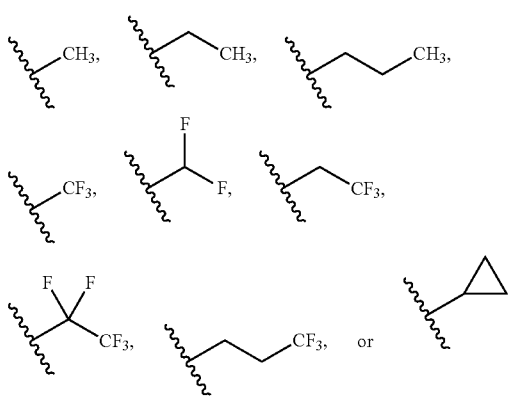

In some embodiments, $R^{34}$ is H,

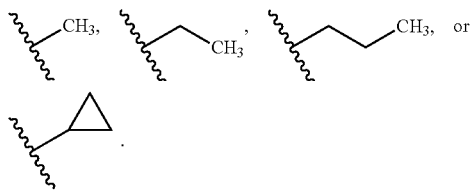

In some embodiments, $R^{34}$ is H or

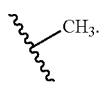

In some embodiments, $R^{34}$ is H. In some embodiments, $R^{34}$ is

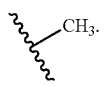

In some embodiments, $R^{35}$ is H, optionally substituted $C_1$-$C_6$ alkyl, or optionally substituted $C_6$-$C_{10}$ aryl. In some embodiments, $R^{35}$ is H, optionally substituted $C_1$-$C_6$ alkyl, optionally substituted $C_1$-$C_6$ heteroalkyl, or optionally substituted $C_3$-$C_{10}$ carbocyclyl. In some embodiments, $R^{35}$ is H, optionally substituted $C_1$-$C_6$ alkyl, or optionally substituted $C_3$-$C_{10}$ carbocyclyl. In some embodiments, $R^{35}$ is H or optionally substituted $C_1$-$C_6$ alkyl.

In some embodiments, optionally substituted $C_1$-$C_6$ alkyl is $C_1$-$C_6$ perfluoroalkyl.

In some embodiments, $R^{35}$ is H,

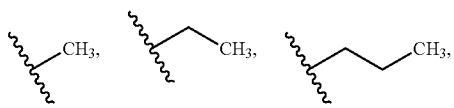

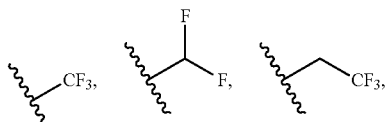

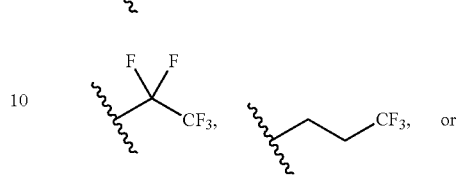

In some embodiments, $R^{35}$ is H,

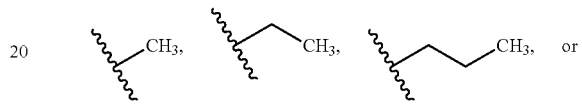

In some embodiments, $R^{35}$ is H or

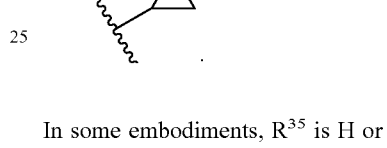

In some embodiments, $R^{35}$ is H. In some embodiments, $R^{35}$ is

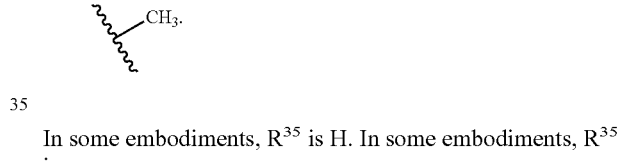

In some embodiments, w is 0, 1, or 2. In some embodiments, w is 1 or 2. In some embodiments, w is 2.

In some embodiments, each $R^{36}$ is, independently, halogen, optionally substituted $C_1$-$C_6$ alkyl, or optionally substituted $C_1$-$C_6$ heteroalkyl. In some embodiments, each $R^{36}$ is, independently, optionally substituted $C_1$-$C_6$ alkyl or optionally substituted $C_1$-$C_6$ heteroalkyl.

In some embodiments, each $R^{36}$ is, independently,

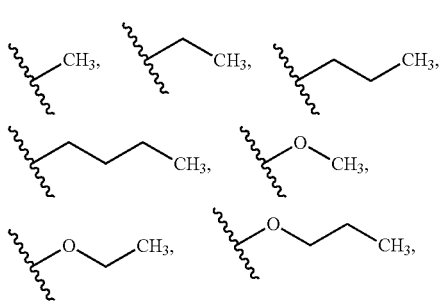

-continued

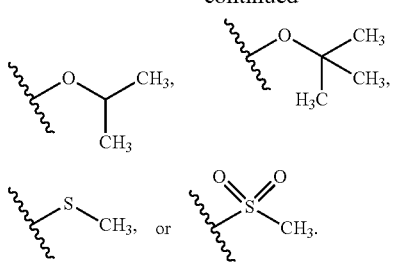

In some embodiments, each $R^{36}$ is, independently, halogen,

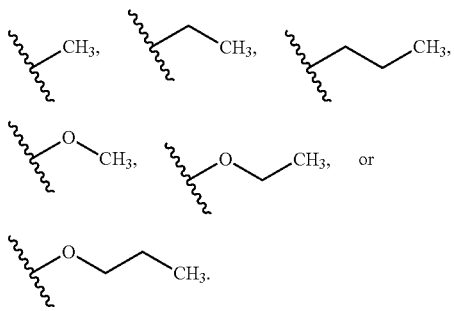

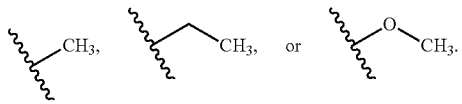

In some embodiments, each $R^{36}$ is, independently, F, Cl,

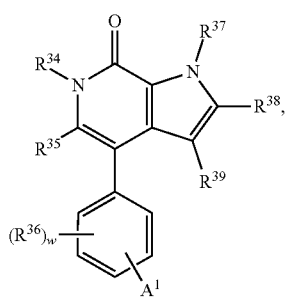

In some embodiments, the structure of Formula IX has the structure of Formula IXa:

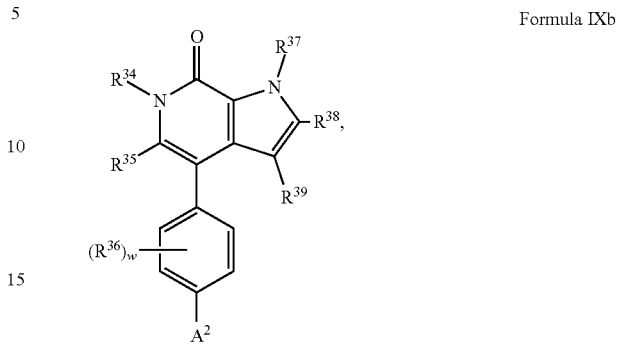

Formula IXa or a pharmaceutically acceptable salt thereof.

In some embodiments, the structure of Formula IX has the structure of Formula IXb:

Formula IXb or a pharmaceutically acceptable salt thereof.

In some embodiments, the structure of Formula IX has the structure of Formula IXc:

Formula IXc or a pharmaceutically acceptable salt thereof.

In some embodiments, the structure of Formula IX has the structure of Formula IXd:

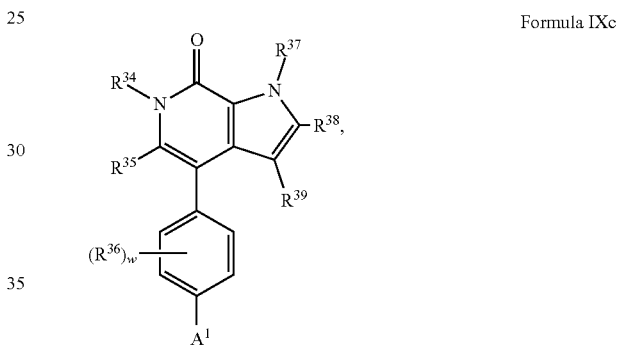

Formula IXd or a pharmaceutically acceptable salt thereof.

In some embodiments, the structure of Formula IX has the structure of Formula IXe:

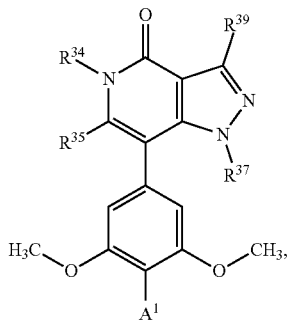

Formula IXe or a pharmaceutically acceptable salt thereof.

In some embodiments, the structure of Formula IX has the structure of Formula IXf:

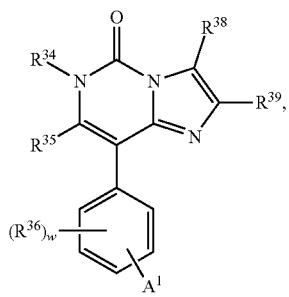

Formula IXf or a pharmaceutically acceptable salt thereof.

In some embodiments, the structure of Formula IX has the structure of Formula IXg:

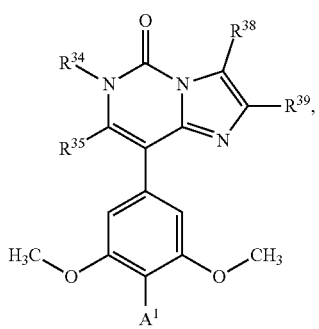

Formula IXg or a pharmaceutically acceptable salt thereof.

In some embodiments, the structure of Formula IX has the structure of Formula IXh:

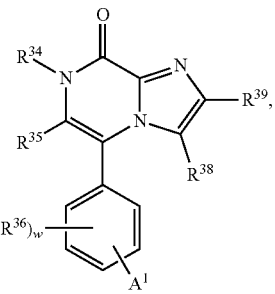

Formula IXh or a pharmaceutically acceptable salt thereof.

In some embodiments, the structure of Formula IX has the structure of Formula IXi:

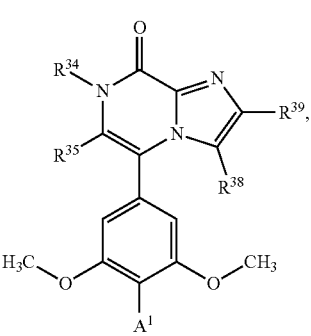

Formula IXi or a pharmaceutically acceptable salt thereof.

In some embodiments, A includes the structure of:

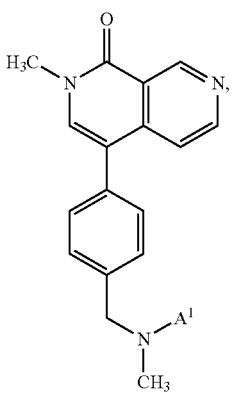

X2

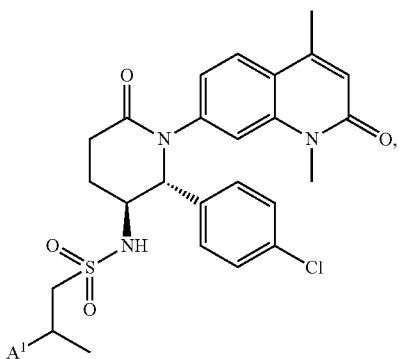

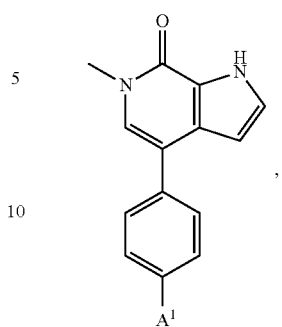

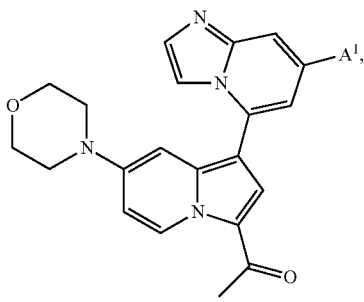

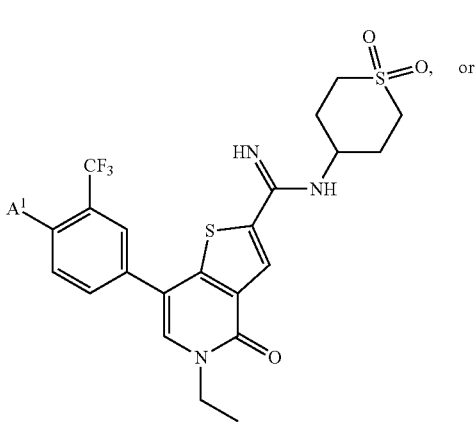

where $A^1$ is a bond between A and the linker, or derivative or analog thereof.

In some embodiments, the compound has the structure of any one of compounds D1-D177 in Table 1A, or a pharmaceutically acceptable salt thereof. In some embodiments, the compound has the structure of any one of compounds D178-D371 in Table 1B, or a pharmaceutically acceptable salt thereof. In some embodiments, the compound has the structure of any one of compounds D372-D476 in Table 1D, or a pharmaceutically acceptable salt thereof.

In some embodiments, the compound has the structure of any one of compounds D1, D3, D6, D9-D20, D23, D33, D33-D35, D37-D40, D42, D44-D47, D50-D53, D56-D60, D67, D69, D71-D73, D75, D76, D80, D81, D89, D92, D100, D108, D113, D122-D124, D128-D132, D143, D152, D157, D167, D168, D170, D171, D173, and D176 in Table 1A, or a pharmaceutically acceptable salt thereof. In some embodiments, the compound has the structure of any one of compounds D178, D180, D184-D189, D191, D194, D197-D199, D201-D208, D211, D213-D230, D235-D244, D246, D247, D250-D263, D268, D269, D271-D275, D277, D279, D280, D287-D291, D297-D299, D300-D302, D304, D306-D308, D310, D312, D313, D315, D316, D318-D333, D335-D341, D343-D349, D353, D354, D356-D363, and D366-D371 in Table 1B, or a pharmaceutically acceptable salt thereof. In some embodiments, the compound has the structure of any one of compounds D372-D379, D381, D382, D384-D388, D395-D428, D430, D431, D433, D434, D436, D438-D444, D448, D450, D453-D460, D462, D463, D465, D466, D471, and D476 in Table 1D, or a pharmaceutically acceptable salt thereof.

In an aspect, the disclosure features a compound having the structure of any one of compounds D1-D177 in Table 1A, or a pharmaceutically acceptable salt thereof.

In another aspect, the disclosure features a compound having the structure of any one of compounds D178-D371 in Table 1B, or a pharmaceutically acceptable salt thereof.

In another aspect, the disclosure features a compound having the structure of any one of compounds D372-D476 in Table 1D, or a pharmaceutically acceptable salt thereof.

In another aspect, the disclosure features a compound having the structure of any one of compounds DD1-DD10 in Table 1C, or a pharmaceutically acceptable salt thereof.

In another aspect, the disclosure features a compound having the structure of any one of compounds DD11-DD16 in Table 1E, or a pharmaceutically acceptable salt thereof.

TABLE 1A
Compounds D1-D177 of the Disclosure
| Compound No. | Structure |
| --- | --- |
| D1 | 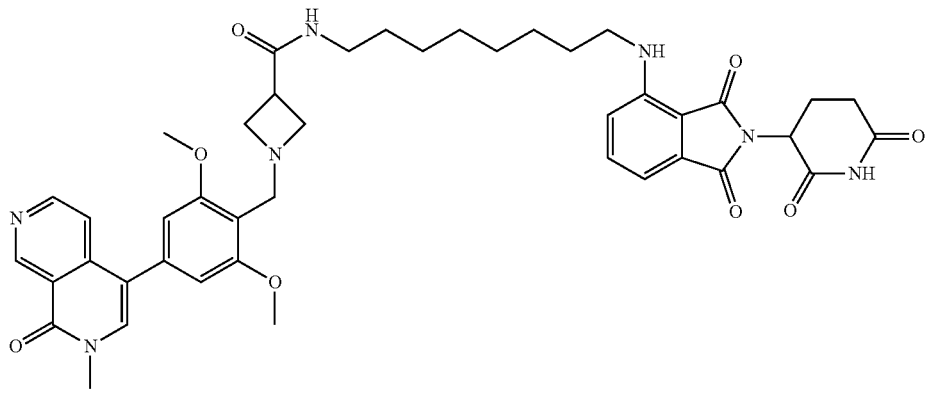 [SMILES: COc1cc(-c2cn(C)c(=O)c3cnccc23)cc(OC)c1CN1CC(C(=O)NCCCCCCCCNc2cccc3c2C(=O)N(C2CCC(=O)NC2=O)C3=O)C1] |
| D2 | 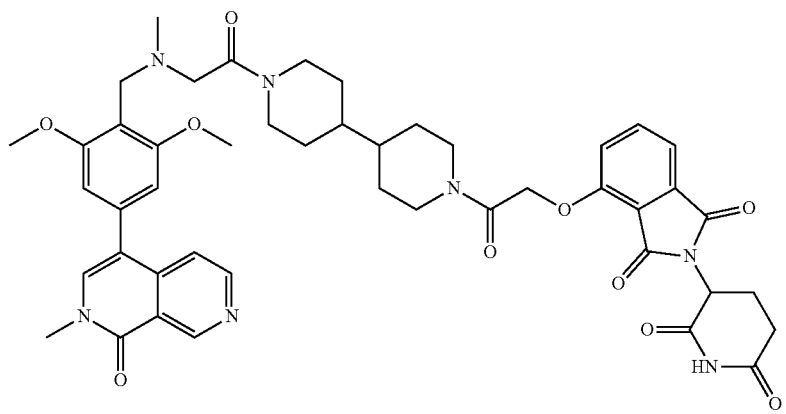 [SMILES: COc1cc(-c2cn(C)c(=O)c3cnccc23)cc(OC)c1CN(C)CC(=O)N1CCC(C2CCN(C(=O)COc3cccc4c3C(=O)N(C3CCC(=O)NC3=O)C4=O)CC2)CC1] |
| D3 | 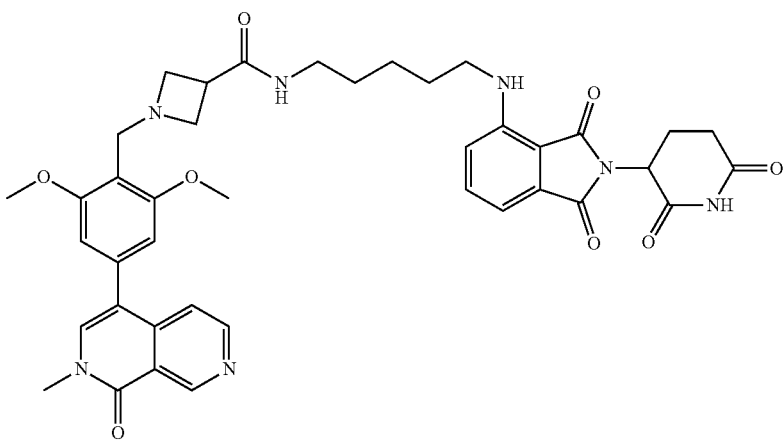 [SMILES: COc1cc(-c2cn(C)c(=O)c3cnccc23)cc(OC)c1CN1CC(C(=O)NCCCCCNc2cccc3c2C(=O)N(C2CCC(=O)NC2=O)C3=O)C1] |

TABLE 1A-continued
Compounds D1-D177 of the Disclosure
| Compound No. | Structure |
|---|---|
| D4 | 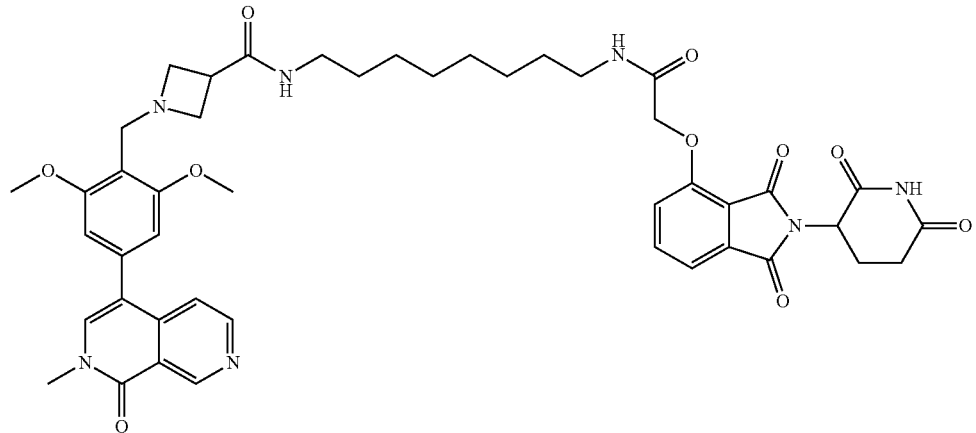 [SMILES: COc1cc(-c2cn(C)c(=O)c3cnccc23)cc(OC)c1CN1CC(C(=O)NCCCCCCCCNC(=O)COc2cccc3c2C(=O)N(C2CCC(=O)NC2=O)C3=O)C1] |
| D5 | 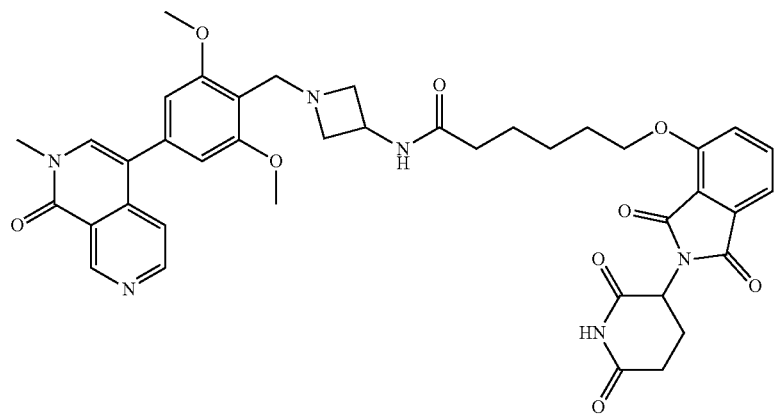 [SMILES: COc1cc(-c2cn(C)c(=O)c3cnccc23)cc(OC)c1CN1CC(NC(=O)CCCCCOc2cccc3c2C(=O)N(C2CCC(=O)NC2=O)C3=O)C1] |
| D6 | 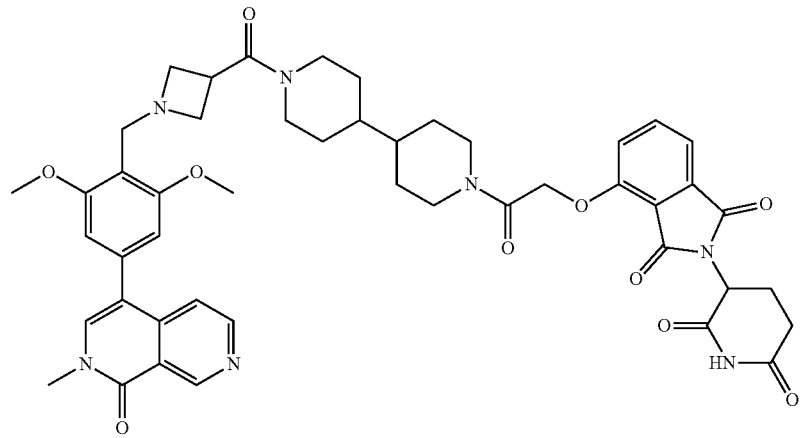 [SMILES: COc1cc(-c2cn(C)c(=O)c3cnccc23)cc(OC)c1CN1CC(C(=O)N2CCC(C3CCN(C(=O)COc4cccc5c4C(=O)N(C4CCC(=O)NC4=O)C5=O)CC3)CC2)C1] |

TABLE 1A-continued
Compounds D1-D177 of the Disclosure
| Compound No. | Structure |
|---|---|
| D7 | 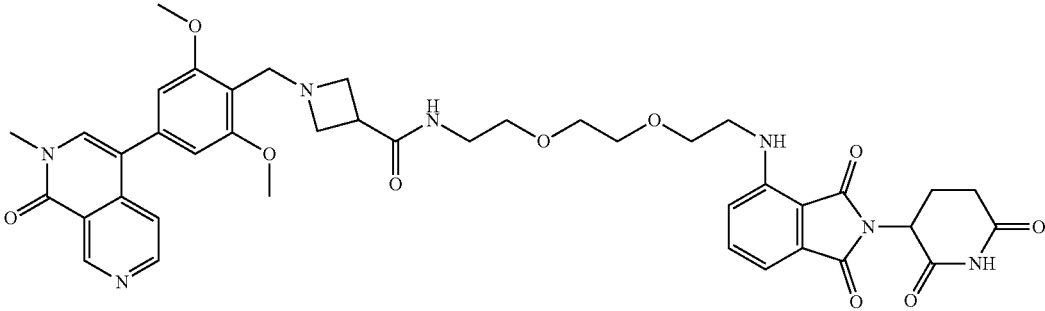 [SMILES: COc1cc(-c2cn(C)c(=O)c3cnccc23)cc(OC)c1CN1CC(C(=O)NCCOCCOCCNc2cccc3c2C(=O)N(C2CCC(=O)NC2=O)C3=O)C1] |
| D8 | 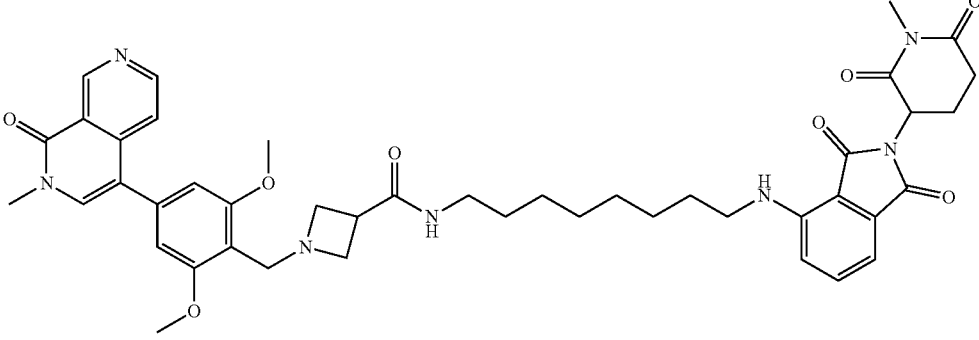 |
| D9 | 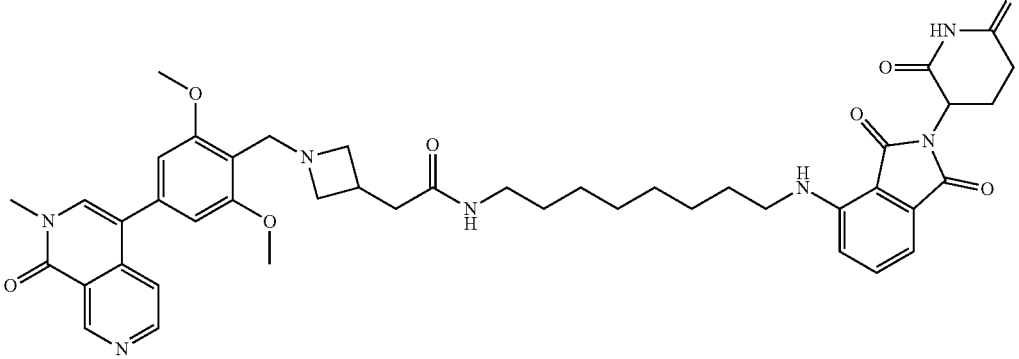 |

TABLE 1A-continued

Compounds D1-D177 of the Disclosure

| Compound No. | Structure |
|---|---|
| D10 | 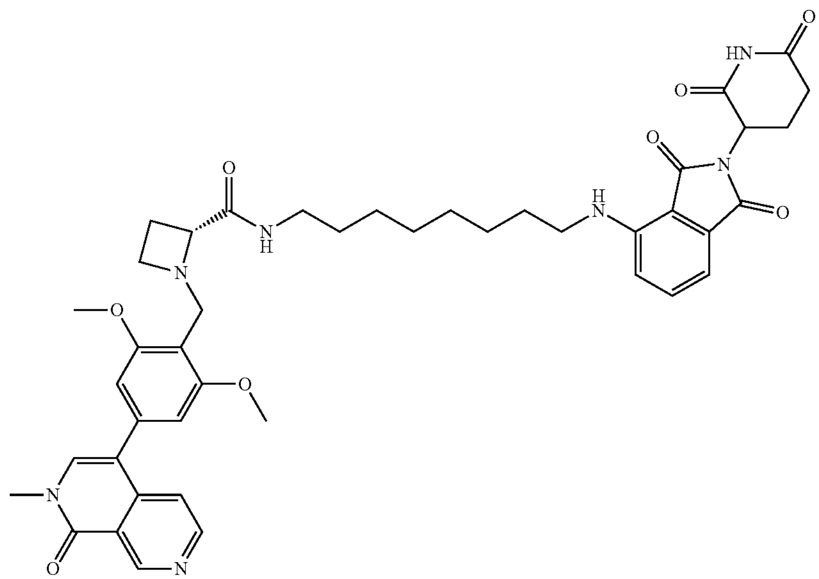 [SMILES: COc1cc(-c2cn(C)c(=O)c3cnccc23)cc(OC)c1CN1CC[C@@H]1C(=O)NCCCCCCCCNc1cccc2c1C(=O)N(C1CCC(=O)NC1=O)C2=O] |
| D11 | 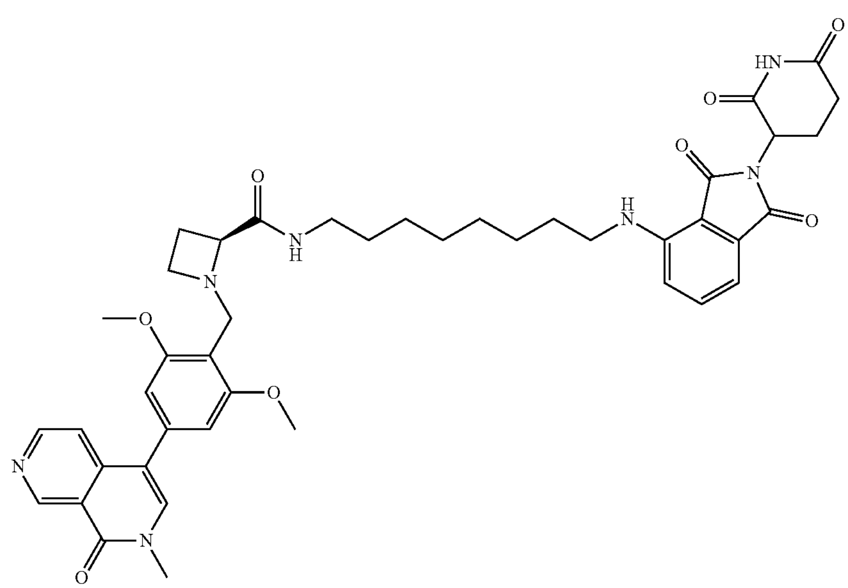 [SMILES: COc1cc(-c2cn(C)c(=O)c3cnccc23)cc(OC)c1CN1CC[C@H]1C(=O)NCCCCCCCCNc1cccc2c1C(=O)N(C1CCC(=O)NC1=O)C2=O] |

TABLE 1A-continued

Compounds D1-D177 of the Disclosure

| Compound No. | Structure |
|---|---|
| D12 | 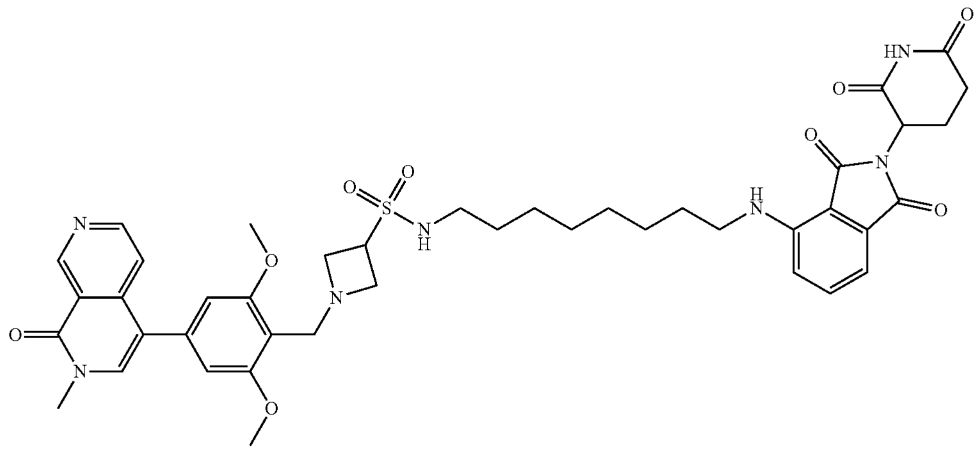 [SMILES: COc1cc(-c2cn(C)c(=O)c3cnccc23)cc(OC)c1CN1CC(S(=O)(=O)NCCCCCCCCNc2cccc3c2C(=O)N(C2CCC(=O)NC2=O)C3=O)C1] |
| D13 | 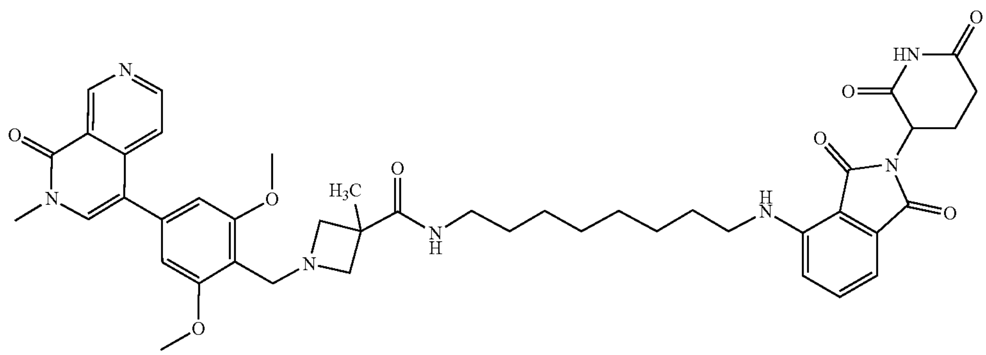 [SMILES: COc1cc(-c2cn(C)c(=O)c3cnccc23)cc(OC)c1CN1CC(C)(C(=O)NCCCCCCCCNc2cccc3c2C(=O)N(C2CCC(=O)NC2=O)C3=O)C1] |
| D14 | 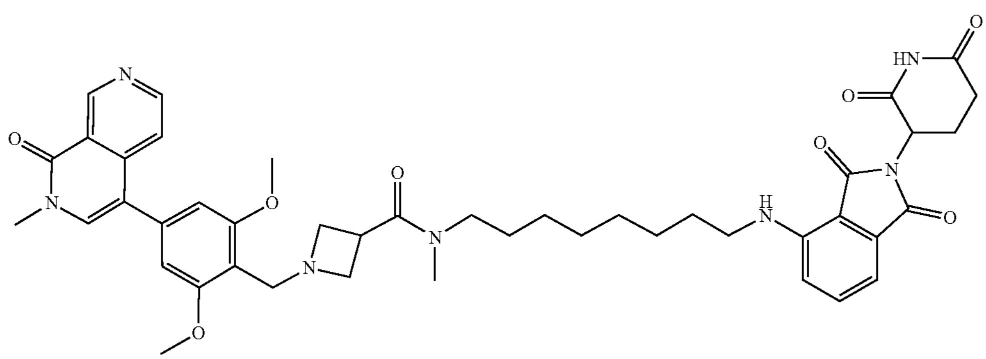 [SMILES: COc1cc(-c2cn(C)c(=O)c3cnccc23)cc(OC)c1CN1CC(C(=O)N(C)CCCCCCCCNc2cccc3c2C(=O)N(C2CCC(=O)NC2=O)C3=O)C1] |
| D15 | 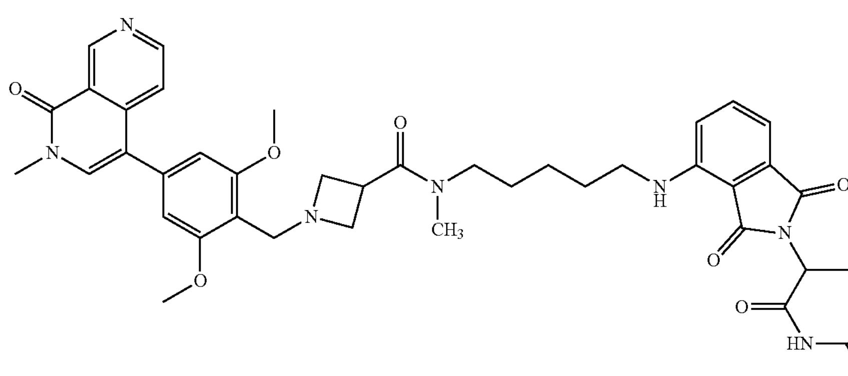 |

TABLE 1A-continued
Compounds D1-D177 of the Disclosure
| Compound No. | Structure |
|---|---|
| D16 | 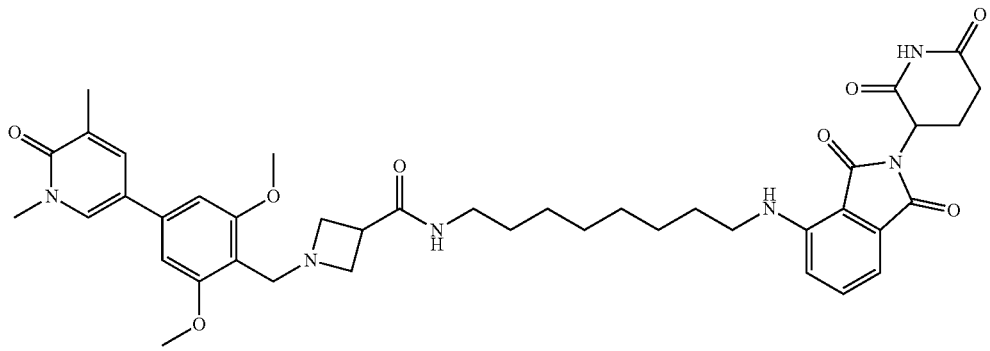 [SMILES: COc1cc(-c2cc(C)c(=O)n(C)c2)cc(OC)c1CN1CC(C(=O)NCCCCCCCCNc2cccc3c2C(=O)N(C2CCC(=O)NC2=O)C3=O)C1] |
| D17 | 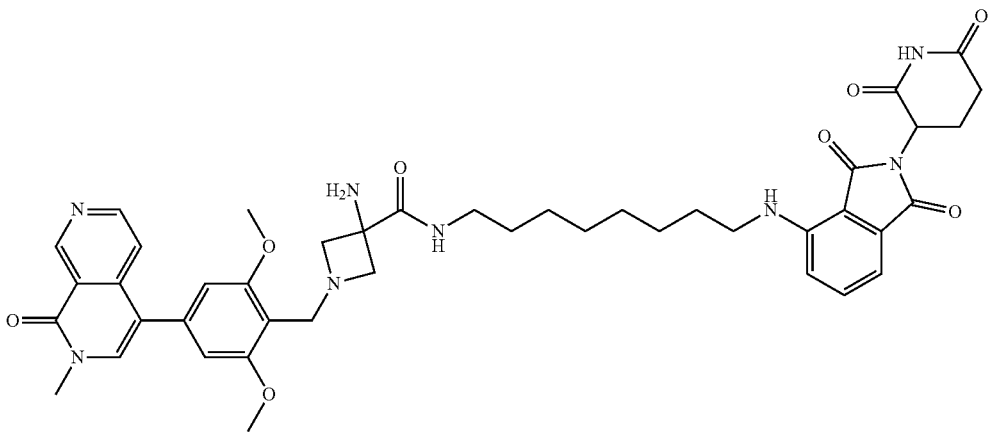 [SMILES: COc1cc(-c2cn(C)c(=O)c3cnccc23)cc(OC)c1CN1CC(N)(C(=O)NCCCCCCCCNc2cccc3c2C(=O)N(C2CCC(=O)NC2=O)C3=O)C1] |
| D18 | 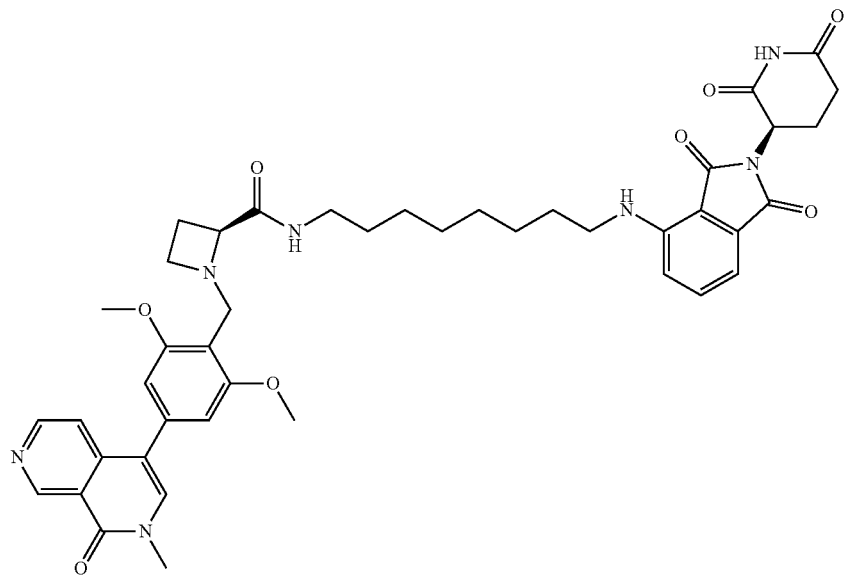 [SMILES: COc1cc(-c2cn(C)c(=O)c3cnccc23)cc(OC)c1CN1CC[C@H]1C(=O)NCCCCCCCCNc1cccc2c1C(=O)N([C@@H]1CCC(=O)NC1=O)C2=O] |

TABLE 1A-continued
Compounds D1-D177 of the Disclosure
| Compound No. | Structure |
|---|---|
| D19 | 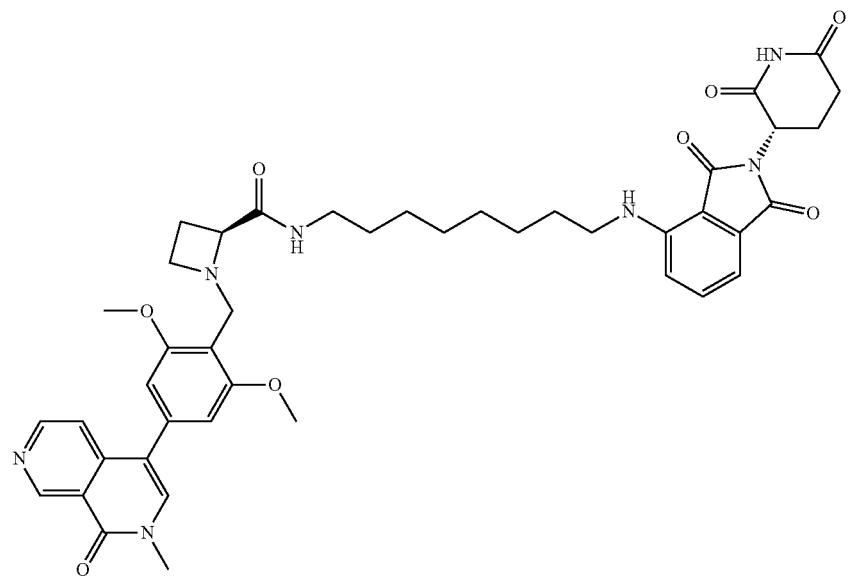 [SMILES: COc1cc(-c2cn(C)c(=O)c3cnccc23)cc(OC)c1CN1CC[C@H]1C(=O)NCCCCCCCCNc1cccc2c1C(=O)N([C@H]1CCC(=O)NC1=O)C2=O] |
| D20 | 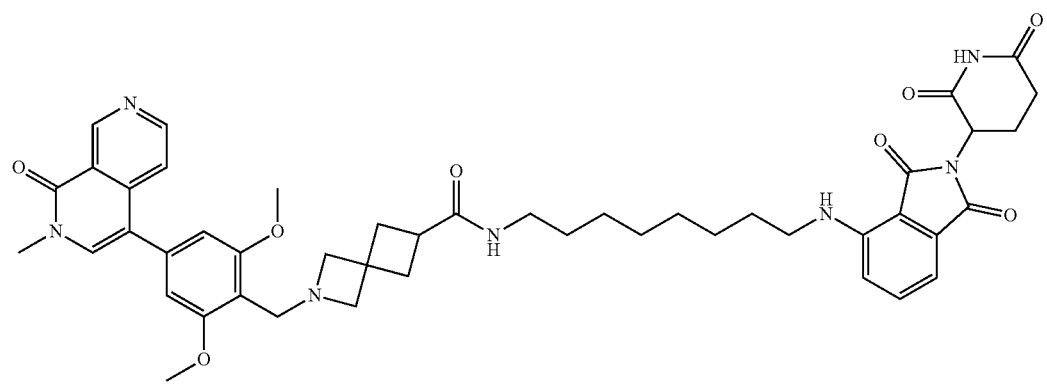 [SMILES: COc1cc(-c2cn(C)c(=O)c3cnccc23)cc(OC)c1CN1CC2(CC(C(=O)NCCCCCCCCNc3cccc4c3C(=O)N(C3CCC(=O)NC3=O)C4=O)C2)C1] |
| D21 | 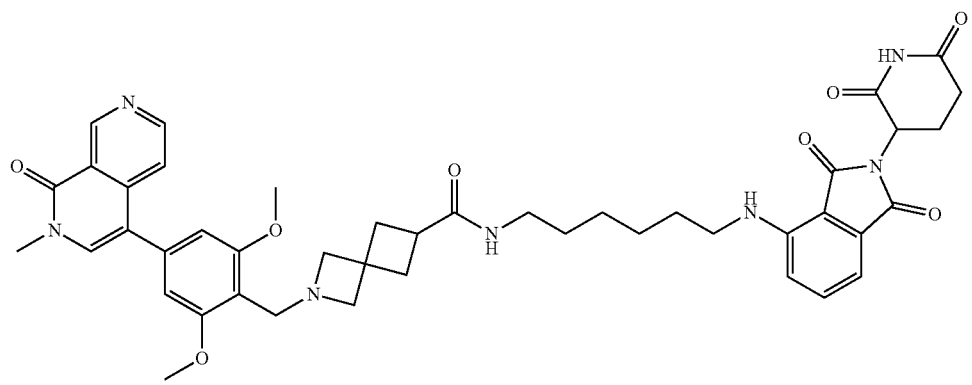 [SMILES: COc1cc(-c2cn(C)c(=O)c3cnccc23)cc(OC)c1CN1CC2(CC(C(=O)NCCCCCCNc3cccc4c3C(=O)N(C3CCC(=O)NC3=O)C4=O)C2)C1] |

TABLE 1A-continued

Compounds D1-D177 of the Disclosure

| Compound No. | Structure |
|---|---|
| D22 | 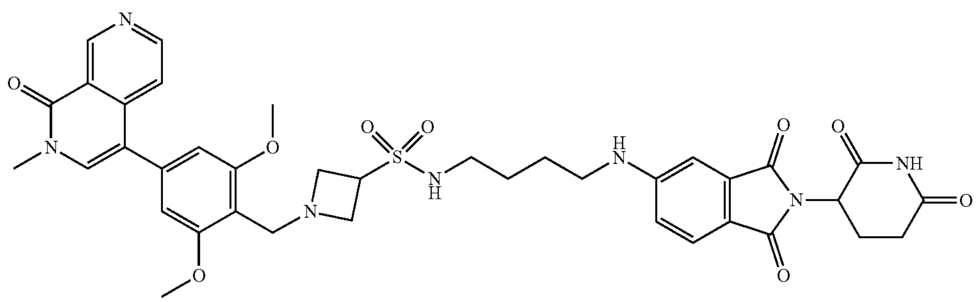 [SMILES: COc1cc(-c2cn(C)c(=O)c3cnccc23)cc(OC)c1CN1CC(S(=O)(=O)NCCCCNc2ccc3c(c2)C(=O)N(C2CCC(=O)NC2=O)C3=O)C1] |
| D23 | 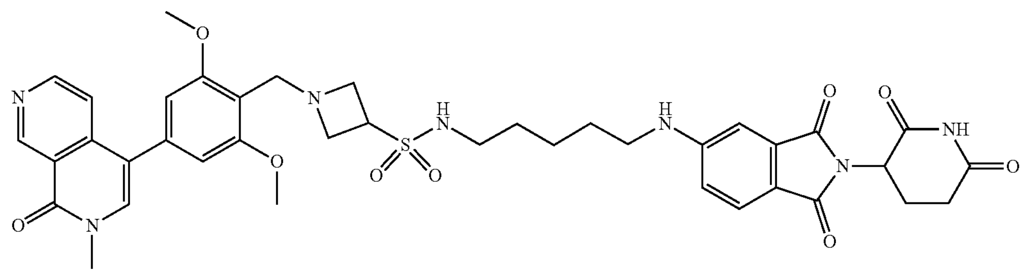 [SMILES: COc1cc(-c2cn(C)c(=O)c3cnccc23)cc(OC)c1CN1CC(S(=O)(=O)NCCCCCNc2ccc3c(c2)C(=O)N(C2CCC(=O)NC2=O)C3=O)C1] |
| D24 | 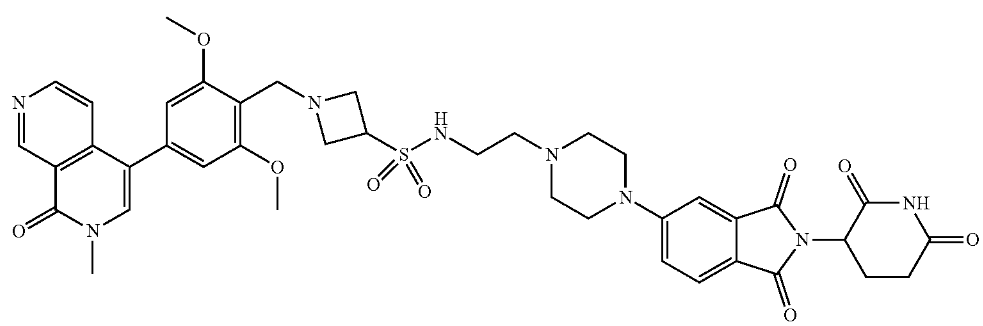 [SMILES: COc1cc(-c2cn(C)c(=O)c3cnccc23)cc(OC)c1CN1CC(S(=O)(=O)NCCN2CCN(c3ccc4c(c3)C(=O)N(C3CCC(=O)NC3=O)C4=O)CC2)C1] |
| D25 | 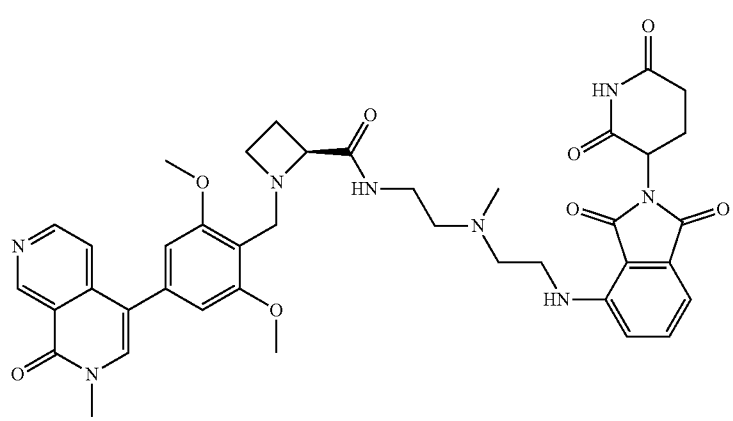 [SMILES: COc1cc(-c2cn(C)c(=O)c3cnccc23)cc(OC)c1CN1CC[C@H]1C(=O)NCCN(C)CCNc1cccc2c1C(=O)N(C1CCC(=O)NC1=O)C2=O] |

TABLE 1A-continued
Compounds D1-D177 of the Disclosure
| Compound No. | Structure |
|---|---|
| D26 | 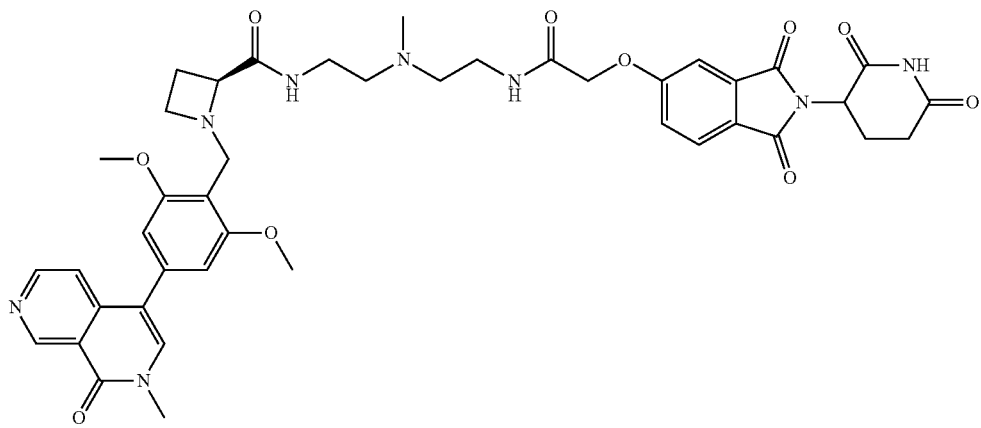 [SMILES: COc1cc(-c2cn(C)c(=O)c3cnccc23)cc(OC)c1CN1CC[C@H]1C(=O)NCCN(C)CCNC(=O)COc1ccc2c(c1)C(=O)N(C1CCC(=O)NC1=O)C2=O] |
| D27 | 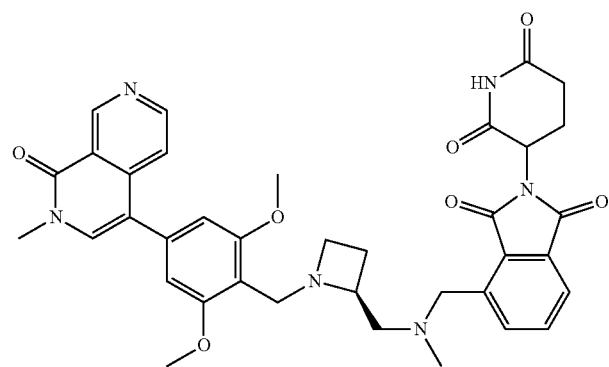 [SMILES: COc1cc(-c2cn(C)c(=O)c3cnccc23)cc(OC)c1CN1CC[C@H]1CN(C)Cc1cccc2c1C(=O)N(C1CCC(=O)NC1=O)C2=O] |
| D28 | 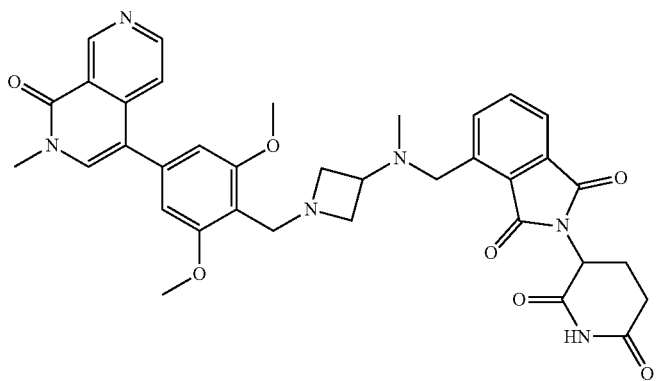 [SMILES: COc1cc(-c2cn(C)c(=O)c3cnccc23)cc(OC)c1CN1CC(N(C)Cc2cccc3c2C(=O)N(C2CCC(=O)NC2=O)C3=O)C1] |
| D29 | 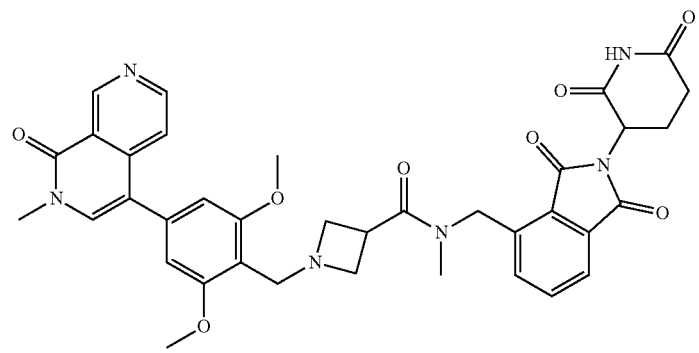 [SMILES: COc1cc(-c2cn(C)c(=O)c3cnccc23)cc(OC)c1CN1CC(C(=O)N(C)Cc2cccc3c2C(=O)N(C2CCC(=O)NC2=O)C3=O)C1] |

TABLE 1A-continued

Compounds D1-D177 of the Disclosure

| Compound No. | Structure |
|---|---|
| D30 | 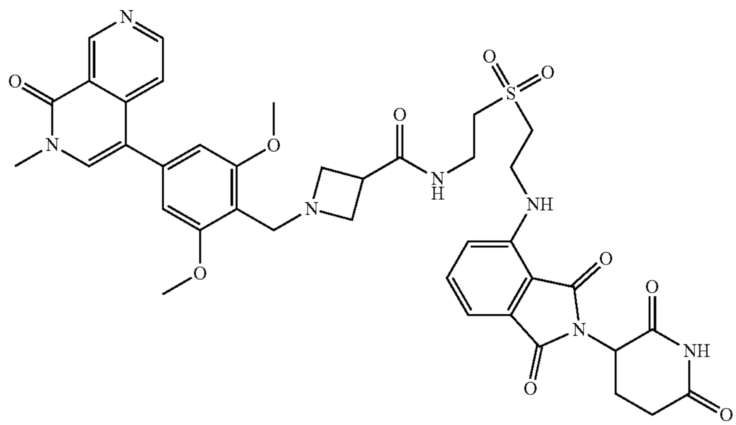 [SMILES: COc1cc(-c2cn(C)c(=O)c3cnccc23)cc(OC)c1CN1CC(C(=O)NCCS(=O)(=O)CCNc2cccc3c2C(=O)N(C2CCC(=O)NC2=O)C3=O)C1] |
| D31 | 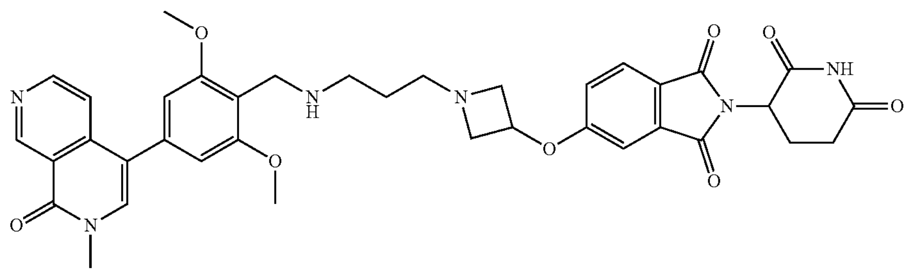 [SMILES: COc1cc(-c2cn(C)c(=O)c3cnccc23)cc(OC)c1CNCCCN1CC(Oc2ccc3c(c2)C(=O)N(C2CCC(=O)NC2=O)C3=O)C1] |
| D32 | 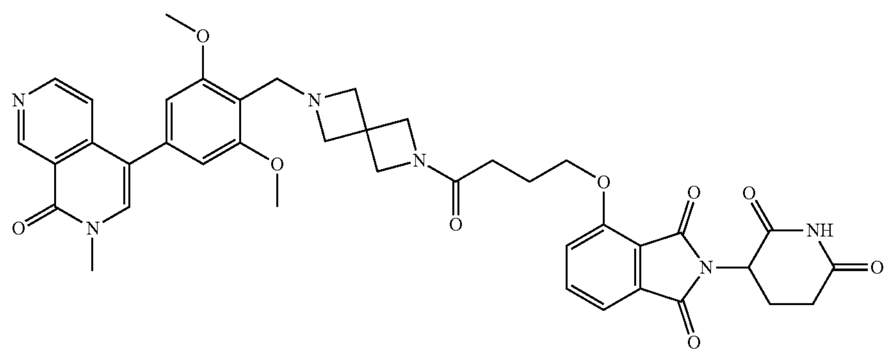 [SMILES: COc1cc(-c2cn(C)c(=O)c3cnccc23)cc(OC)c1CN1CC2(C1)CN(C(=O)CCCOc1cccc3c1C(=O)N(C1CCC(=O)NC1=O)C3=O)C2] |
| D33 | 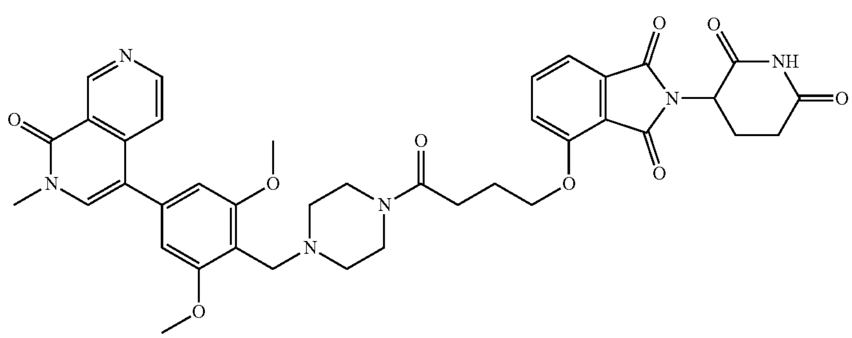 [SMILES: COc1cc(-c2cn(C)c(=O)c3cnccc23)cc(OC)c1CN1CCN(C(=O)CCCOc2cccc3c2C(=O)N(C2CCC(=O)NC2=O)C3=O)CC1] |

TABLE 1A-continued
Compounds D1-D177 of the Disclosure
| Compound No. | Structure |
| --- | --- |
| D34 | 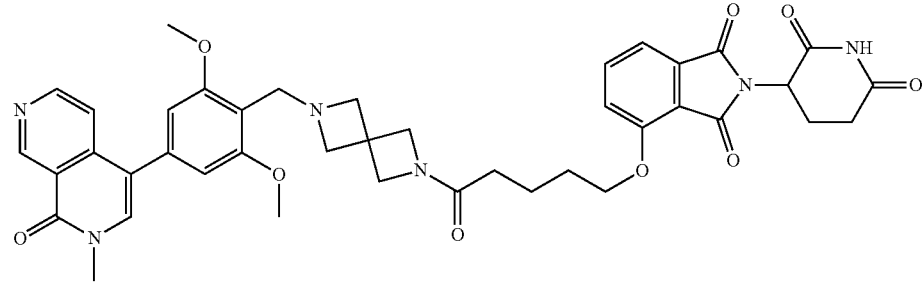 [SMILES: COc1cc(-c2cn(C)c(=O)c3cnccc23)cc(OC)c1CN1CC2(C1)CN(C(=O)CCCCOc1cccc3c1C(=O)N(C1CCC(=O)NC1=O)C3=O)C2] |
| D35 | 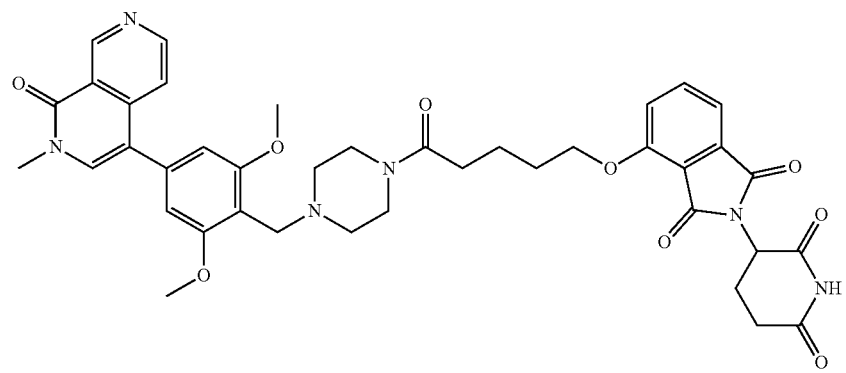 [SMILES: COc1cc(-c2cn(C)c(=O)c3cnccc23)cc(OC)c1CN1CCN(C(=O)CCCCOc2cccc3c2C(=O)N(C2CCC(=O)NC2=O)C3=O)CC1] |
| D36 | 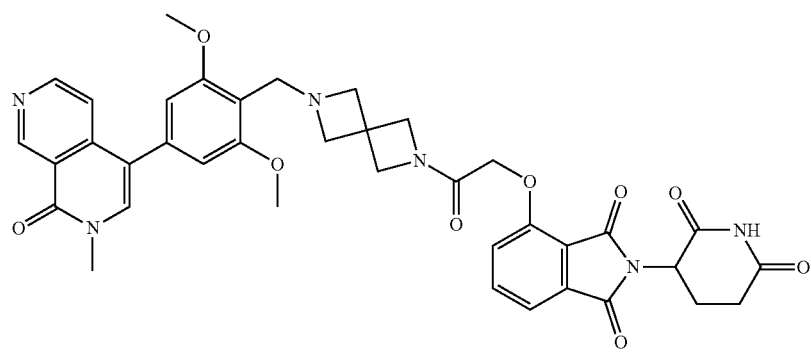 [SMILES: COc1cc(-c2cn(C)c(=O)c3cnccc23)cc(OC)c1CN1CC2(C1)CN(C(=O)COc1cccc3c1C(=O)N(C1CCC(=O)NC1=O)C3=O)C2] |
| D37 | 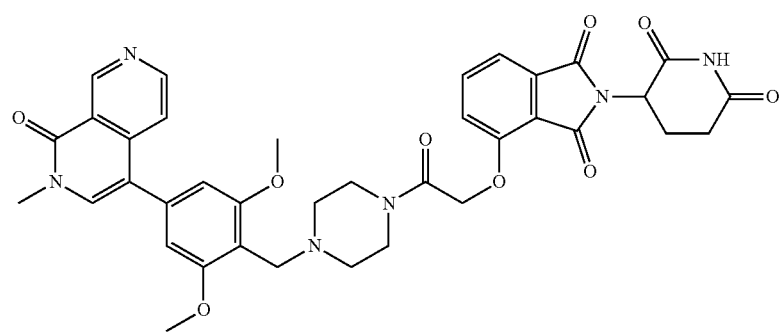 [SMILES: COc1cc(-c2cn(C)c(=O)c3cnccc23)cc(OC)c1CN1CCN(C(=O)COc2cccc3c2C(=O)N(C2CCC(=O)NC2=O)C3=O)CC1] |

TABLE 1A-continued
Compounds D1-D177 of the Disclosure
| Compound No. | Structure |
|---|---|
| D38 | 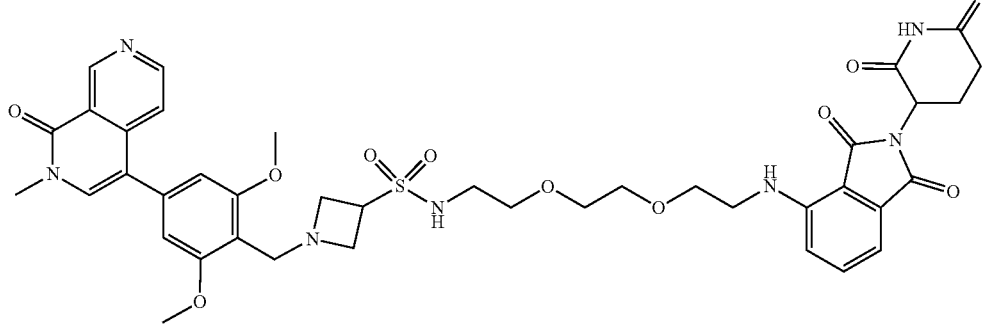 |
| D39 | 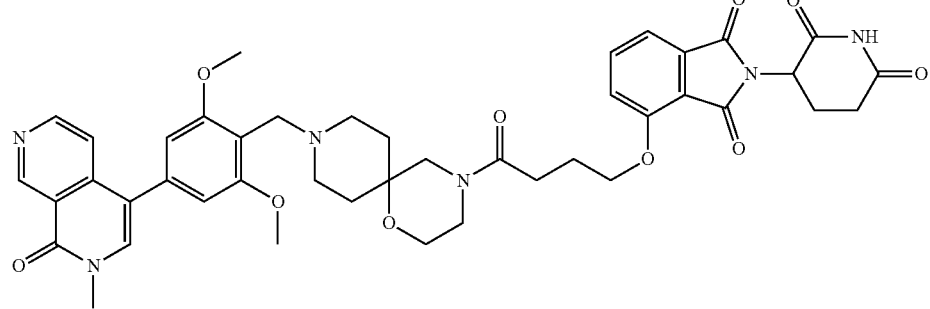 |
| D40 | 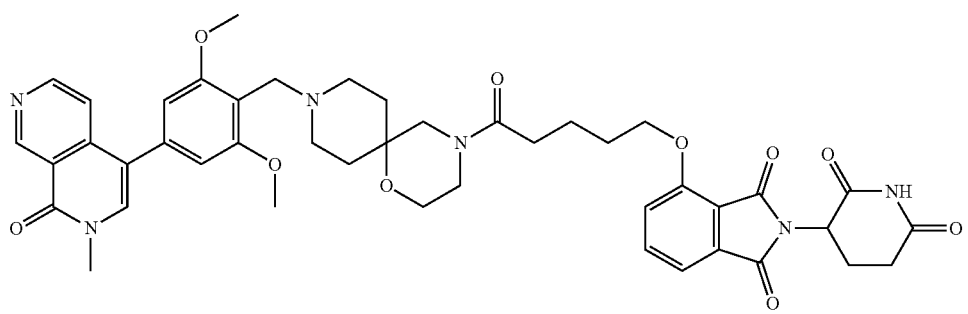 [SMILES: COc1cc(-c2cn(C)c(=O)c3cnccc23)cc(OC)c1CN1CCC2(CC1)CN(C(=O)CCCCOc1cccc3c1C(=O)N(C1CCC(=O)NC1=O)C3=O)CCO2] |
| D41 | 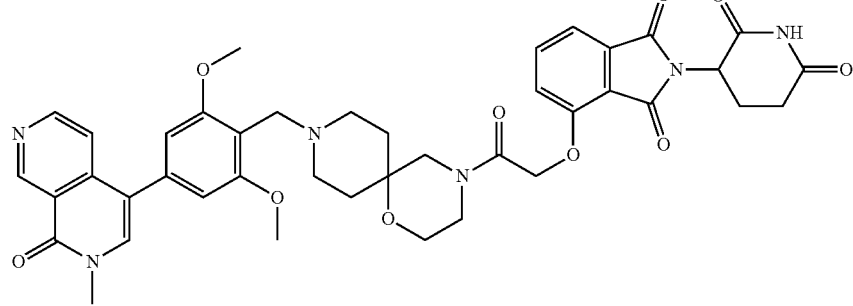 |

TABLE 1A-continued
Compounds D1-D177 of the Disclosure
| Compound No. | Structure |
| --- | --- |
| D42 | 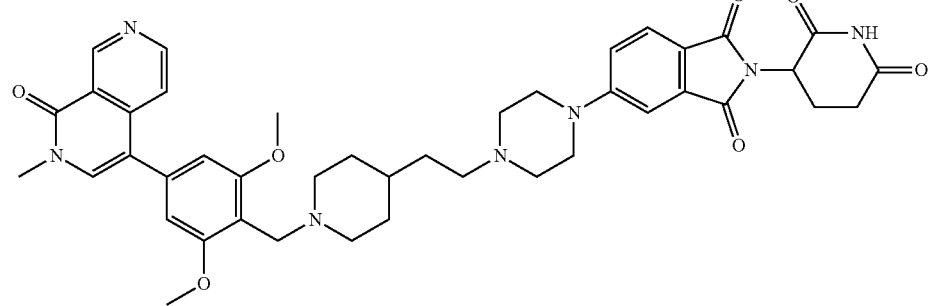 |
| D43 | 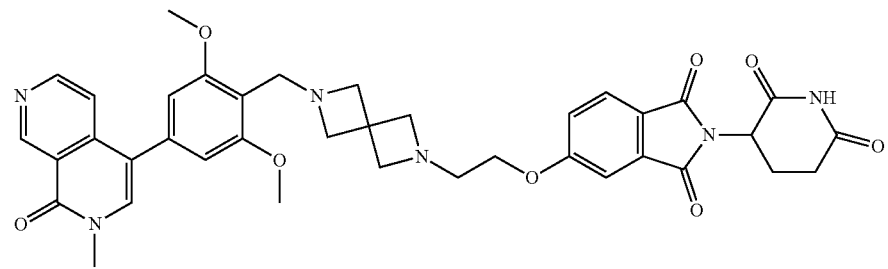 [SMILES: COc1cc(-c2cn(C)c(=O)c3cnccc23)cc(OC)c1CN1CC2(CN(CCOc3ccc4c(c3)C(=O)N(C3CCC(=O)NC3=O)C4=O)C2)C1] |
| D44 | 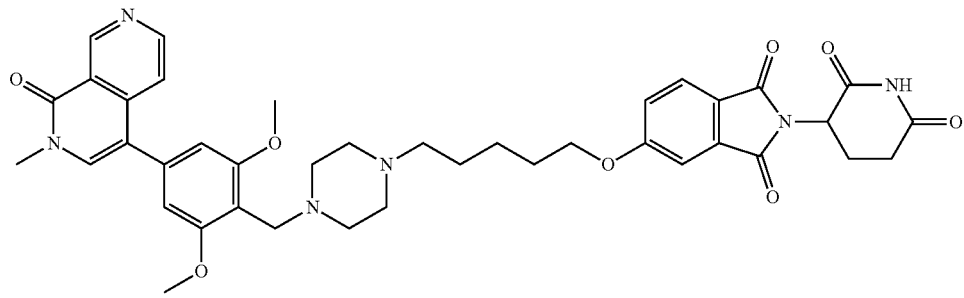 [SMILES: COc1cc(-c2cn(C)c(=O)c3cnccc23)cc(OC)c1CN1CCN(CCCCCOc2ccc3c(c2)C(=O)N(C2CCC(=O)NC2=O)C3=O)CC1] |
| D45 | 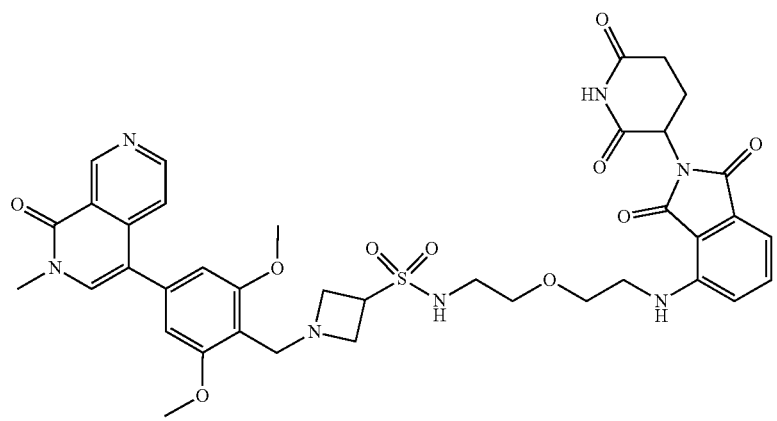 [SMILES: COc1cc(-c2cn(C)c(=O)c3cnccc23)cc(OC)c1CN1CC(S(=O)(=O)NCCOCCNc2cccc3c2C(=O)N(C2CCC(=O)NC2=O)C3=O)C1] |

TABLE 1A-continued

Compounds D1-D177 of the Disclosure

| Compound No. | Structure |
|---|---|
| D46 | 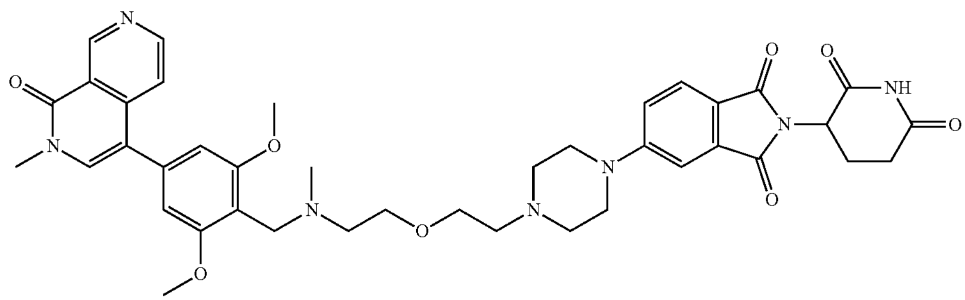 [SMILES: COc1cc(-c2cn(C)c(=O)c3cnccc23)cc(OC)c1CN(C)CCOCCN1CCN(c2ccc3c(c2)C(=O)N(C2CCC(=O)NC2=O)C3=O)CC1] |
| D47 | 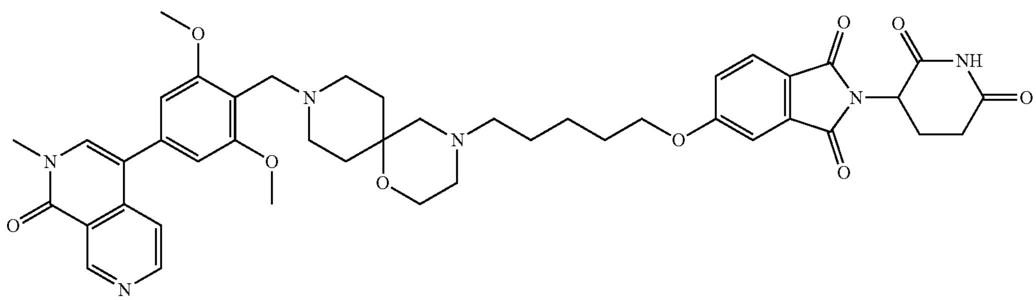 [SMILES: COc1cc(-c2cn(C)c(=O)c3cnccc23)cc(OC)c1CN1CCC2(CC1)CN(CCCCCOc1ccc3c(c1)C(=O)N(C1CCC(=O)NC1=O)C3=O)CCO2] |
| D48 | 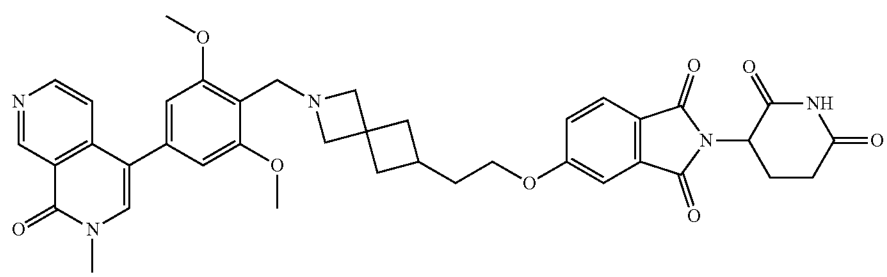 [SMILES: COc1cc(-c2cn(C)c(=O)c3cnccc23)cc(OC)c1CN1CC2(CC(CCOc3ccc4c(c3)C(=O)N(C3CCC(=O)NC3=O)C4=O)C2)C1] |
| D49 | 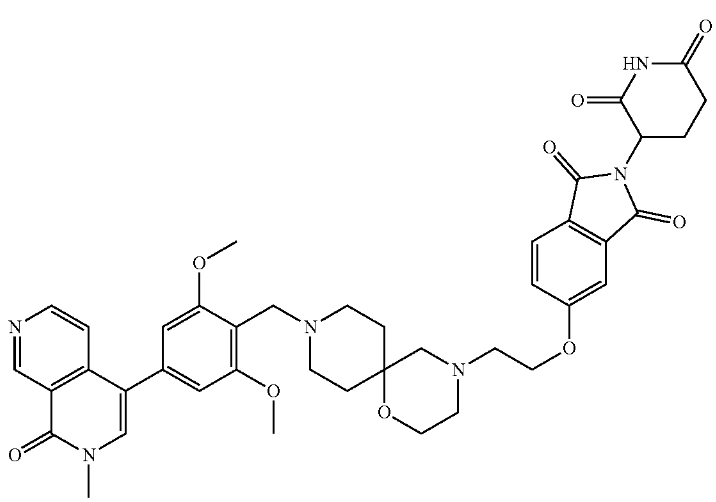 [SMILES: COc1cc(-c2cn(C)c(=O)c3cnccc23)cc(OC)c1CN1CCC2(CC1)CN(CCOc1ccc3c(c1)C(=O)N(C1CCC(=O)NC1=O)C3=O)CCO2] |

TABLE 1A-continued
Compounds D1-D177 of the Disclosure
| Compound No. | Structure |
|---|---|
| D50 | 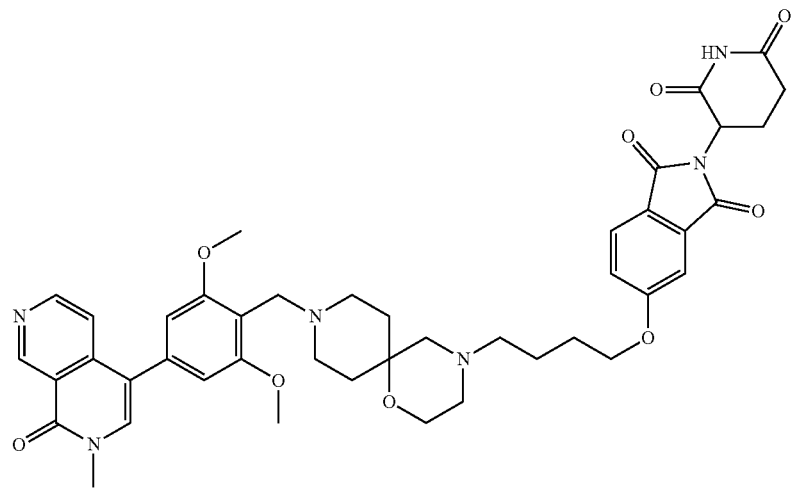 [SMILES: COc1cc(-c2cn(C)c(=O)c3cnccc23)cc(OC)c1CN1CCC2(CC1)CN(CCCCOc1ccc3c(c1)C(=O)N(C1CCC(=O)NC1=O)C3=O)CCO2] |
| D51 | 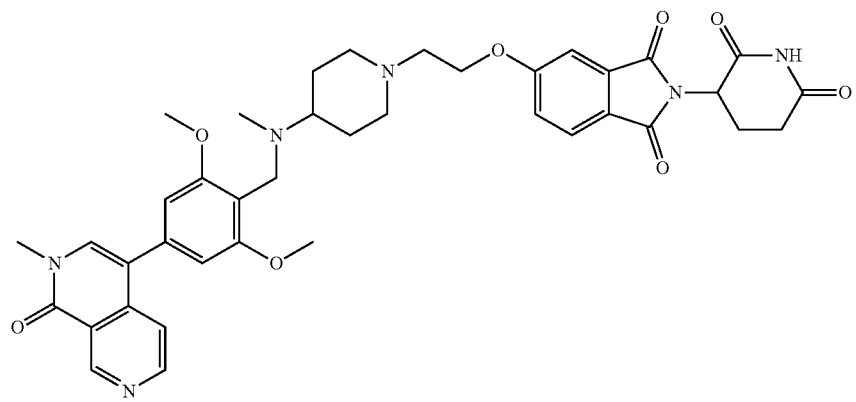 [SMILES: COc1cc(-c2cn(C)c(=O)c3cnccc23)cc(OC)c1CN(C)C1CCN(CCOc2ccc3c(c2)C(=O)N(C2CCC(=O)NC2=O)C3=O)CC1] |
| D52 | 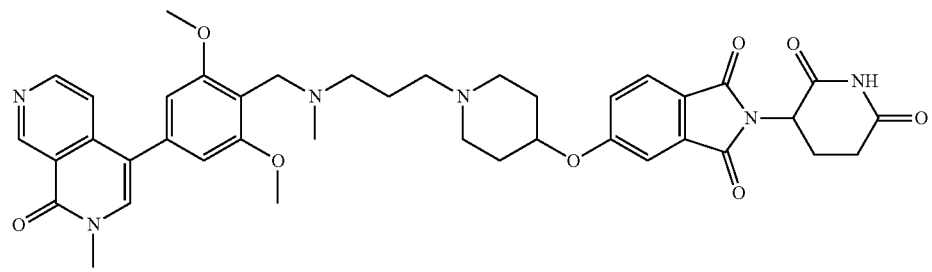 [SMILES: COc1cc(-c2cn(C)c(=O)c3cnccc23)cc(OC)c1CN(C)CCCN1CCC(Oc2ccc3c(c2)C(=O)N(C2CCC(=O)NC2=O)C3=O)CC1] |
| D53 | 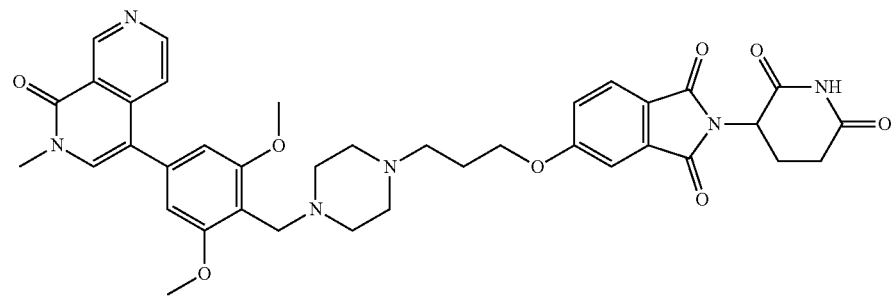 [SMILES: COc1cc(-c2cn(C)c(=O)c3cnccc23)cc(OC)c1CN1CCN(CCCOc2ccc3c(c2)C(=O)N(C2CCC(=O)NC2=O)C3=O)CC1] |

TABLE 1A-continued

Compounds D1-D177 of the Disclosure

| Compound No. | Structure |
|---|---|
| D54 | 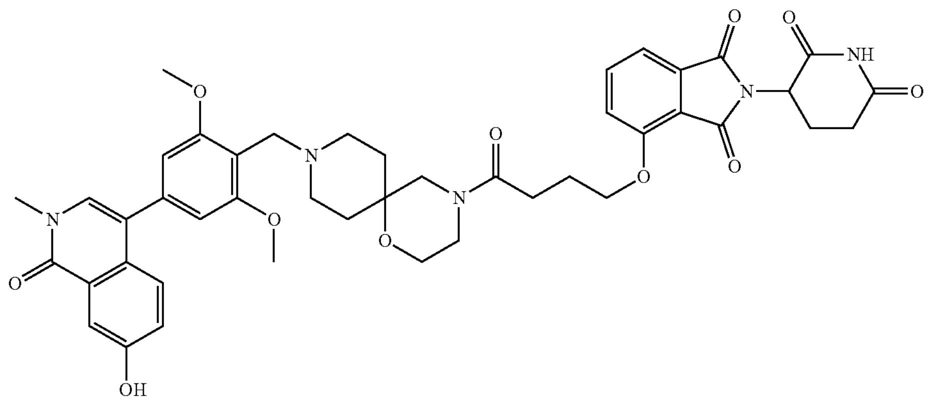 [SMILES: COc1cc(-c2cn(C)c(=O)c3cc(O)ccc23)cc(OC)c1CN1CCC2(CC1)CN(C(=O)CCCOc1cccc3c1C(=O)N(C1CCC(=O)NC1=O)C3=O)CCO2] |
| D55 | 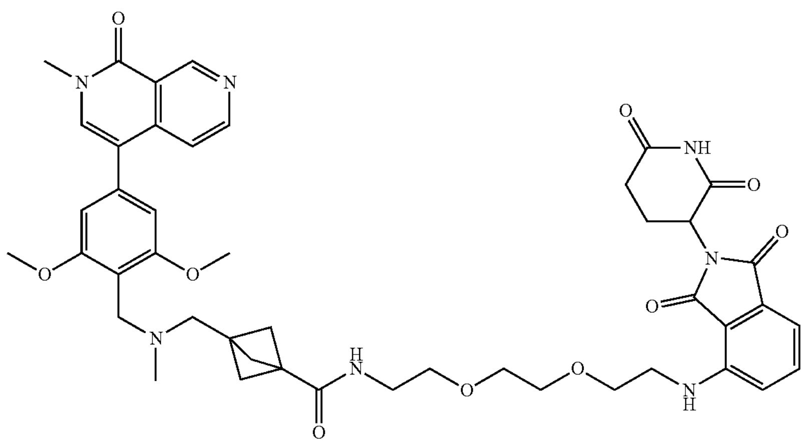 [SMILES: COc1cc(-c2cn(C)c(=O)c3cnccc23)cc(OC)c1CN(C)CC12CC(C(=O)NCCOCCOCCNc3cccc4c3C(=O)N(C3CCC(=O)NC3=O)C4=O)(C1)C2] |
| D56 | 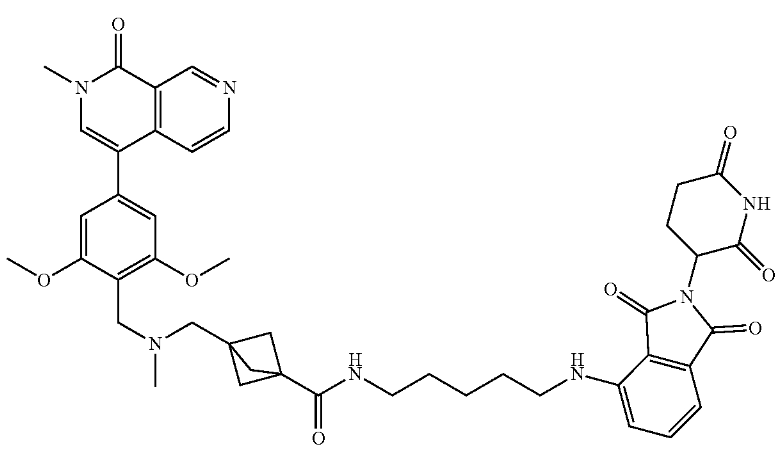 [SMILES: COc1cc(-c2cn(C)c(=O)c3cnccc23)cc(OC)c1CN(C)CC12CC(C(=O)NCCCCCNc3cccc4c3C(=O)N(C3CCC(=O)NC3=O)C4=O)(C1)C2] |

TABLE 1A-continued
Compounds D1-D177 of the Disclosure
| Compound No. | Structure |
|---|---|
| D57 | 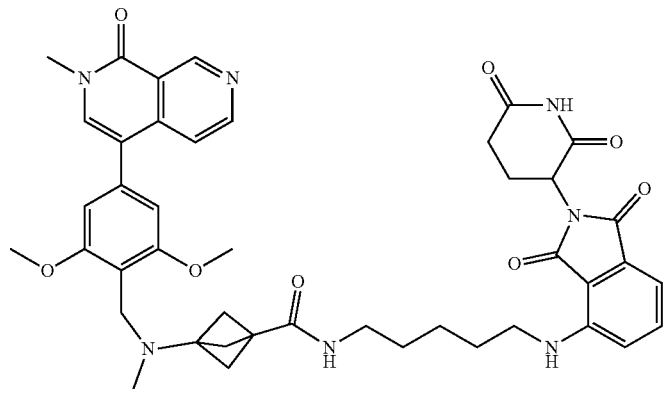 [SMILES: COc1cc(-c2cn(C)c(=O)c3cnccc23)cc(OC)c1CN(C)C12CC(C(=O)NCCCCCNc3cccc4c3C(=O)N(C3CCC(=O)NC3=O)C4=O)(C1)C2] |
| D58 | 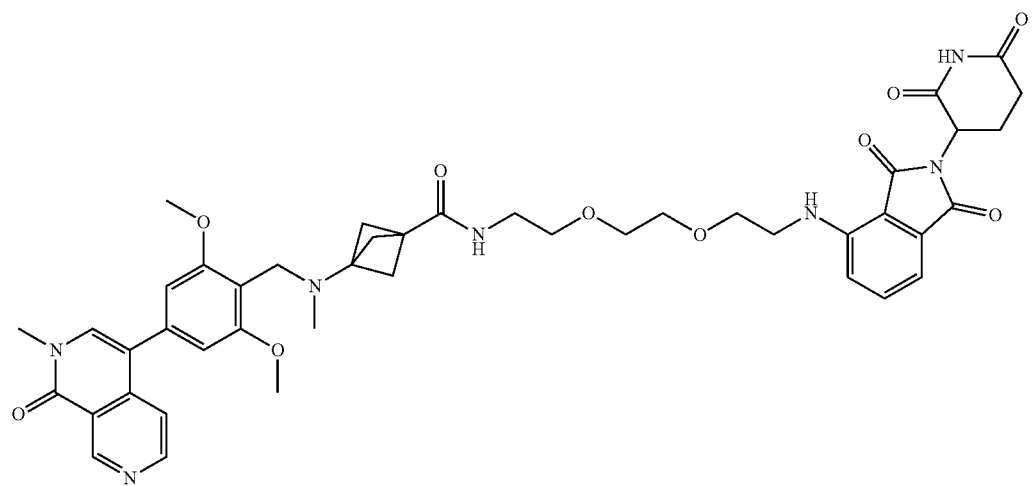 [SMILES: COc1cc(-c2cn(C)c(=O)c3cnccc23)cc(OC)c1CN(C)C12CC(C(=O)NCCOCCOCCNc3cccc4c3C(=O)N(C3CCC(=O)NC3=O)C4=O)(C1)C2] |
| D59 | 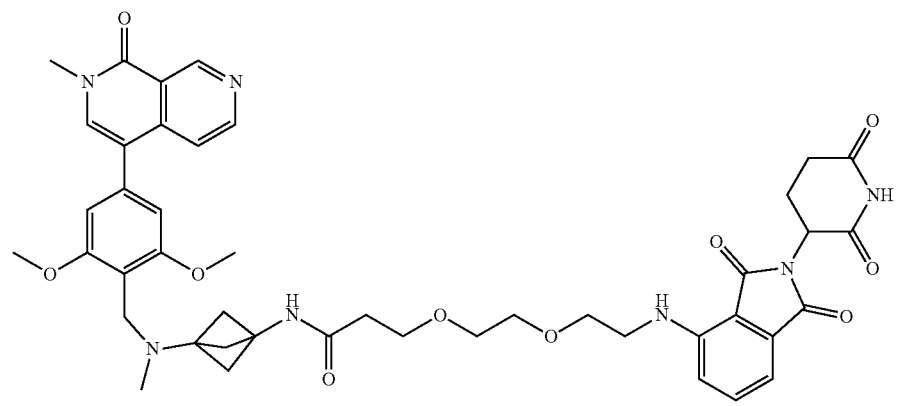 [SMILES: COc1cc(-c2cn(C)c(=O)c3cnccc23)cc(OC)c1CN(C)C12CC(NC(=O)CCOCCOCCNc3cccc4c3C(=O)N(C3CCC(=O)NC3=O)C4=O)(C1)C2] |

TABLE 1A-continued
Compounds D1-D177 of the Disclosure
| Compound No. | Structure |
|---|---|
| D60 | 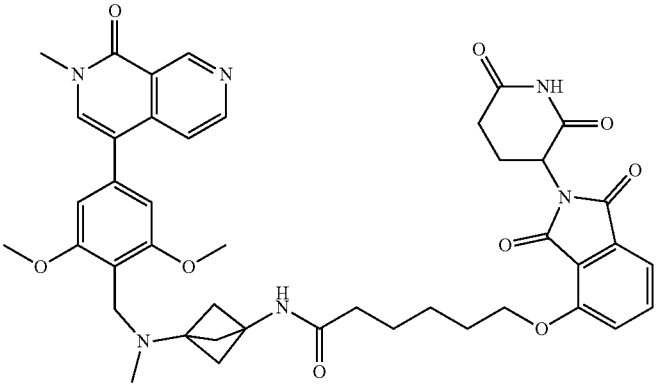 [SMILES: COc1cc(-c2cn(C)c(=O)c3cnccc23)cc(OC)c1CN(C)C12CC(NC(=O)CCCCCOc3cccc4c3C(=O)N(C3CCC(=O)NC3=O)C4=O)(C1)C2] |
| D61 | 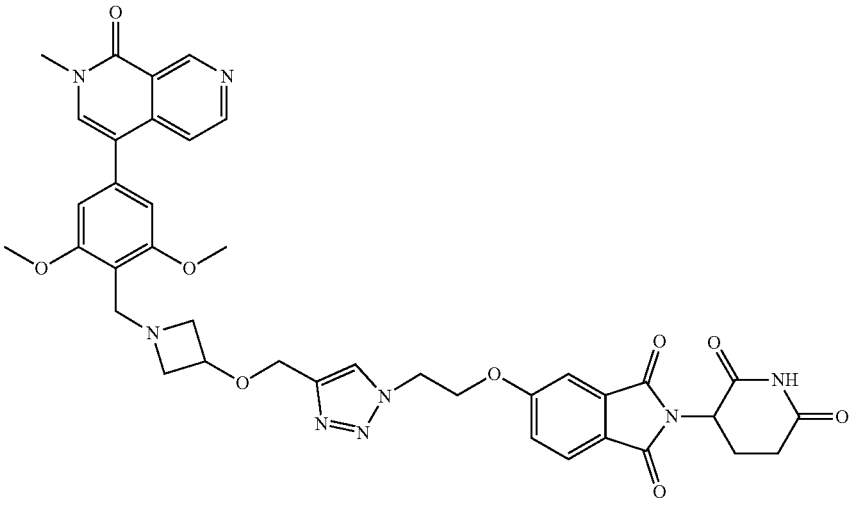 [SMILES: COc1cc(-c2cn(C)c(=O)c3cnccc23)cc(OC)c1CN1CC(OCc2cn(CCOc3ccc4c(c3)C(=O)N(C3CCC(=O)NC3=O)C4=O)nn2)C1] |
| D62 | 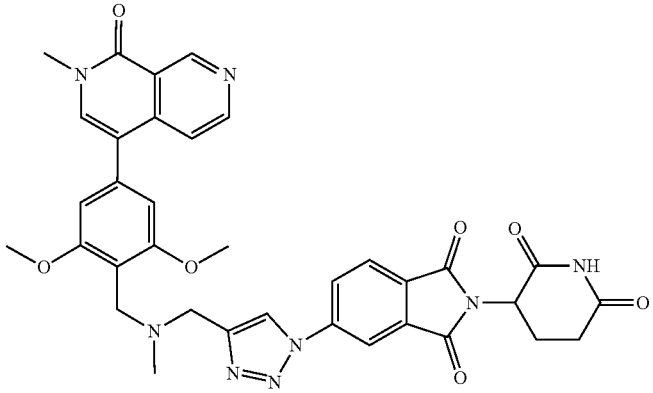 [SMILES: COc1cc(-c2cn(C)c(=O)c3cnccc23)cc(OC)c1CN(C)Cc1cn(-c2ccc3c(c2)C(=O)N(C2CCC(=O)NC2=O)C3=O)nn1] |

TABLE 1A-continued

Compounds D1-D177 of the Disclosure

| Compound No. | Structure |
|---|---|
| D63 | 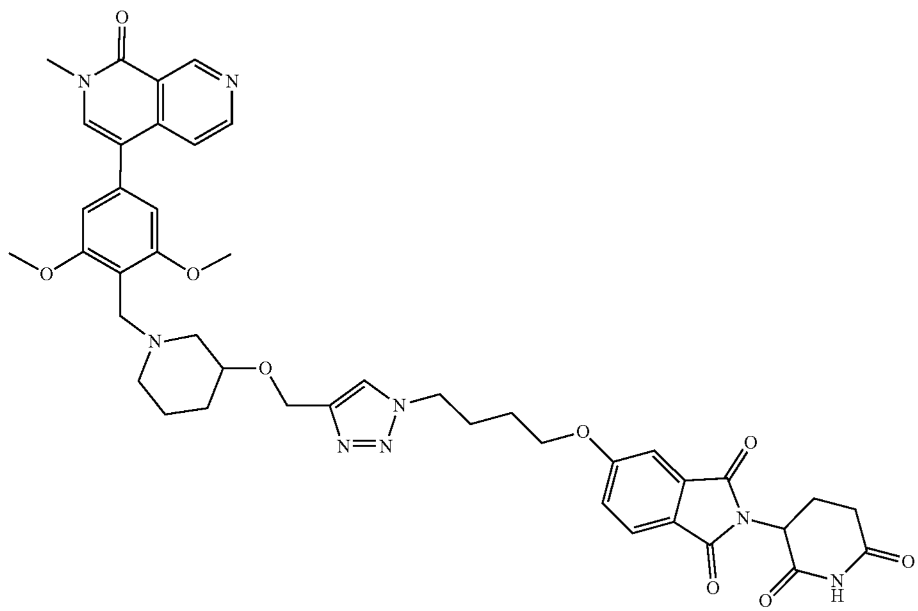 [SMILES: COc1cc(-c2cn(C)c(=O)c3cnccc23)cc(OC)c1CN1CCCC(OCc2cn(CCCCOc3ccc4c(c3)C(=O)N(C3CCC(=O)NC3=O)C4=O)nn2)C1] |
| D64 | 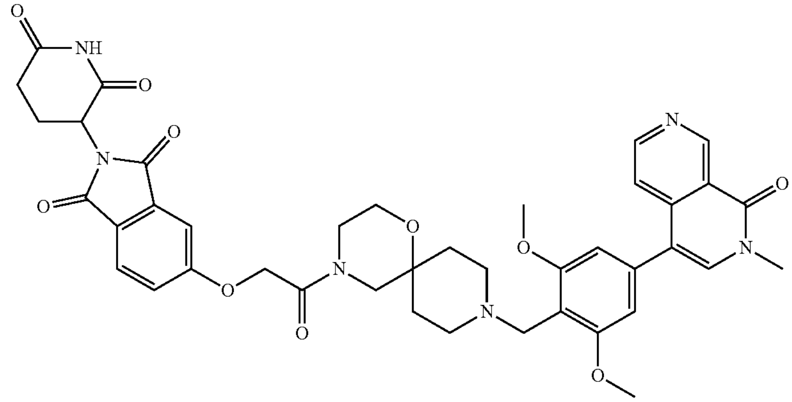 [SMILES: COc1cc(-c2cn(C)c(=O)c3cnccc23)cc(OC)c1CN1CCC2(CC1)CN(C(=O)COc1ccc3c(c1)C(=O)N(C1CCC(=O)NC1=O)C3=O)CCO2] |
| D65 | 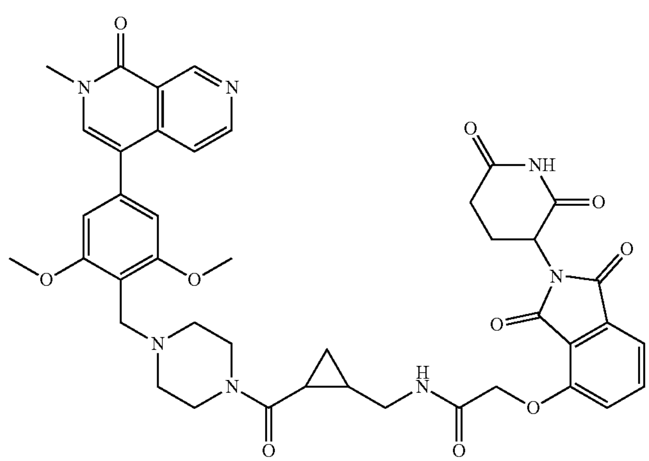 [SMILES: COc1cc(-c2cn(C)c(=O)c3cnccc23)cc(OC)c1CN1CCN(C(=O)C2CC2CNC(=O)COc2cccc3c2C(=O)N(C2CCC(=O)NC2=O)C3=O)CC1] |

TABLE 1A-continued

Compounds D1-D177 of the Disclosure

| Compound No. | Structure |
|---|---|
| D66 | 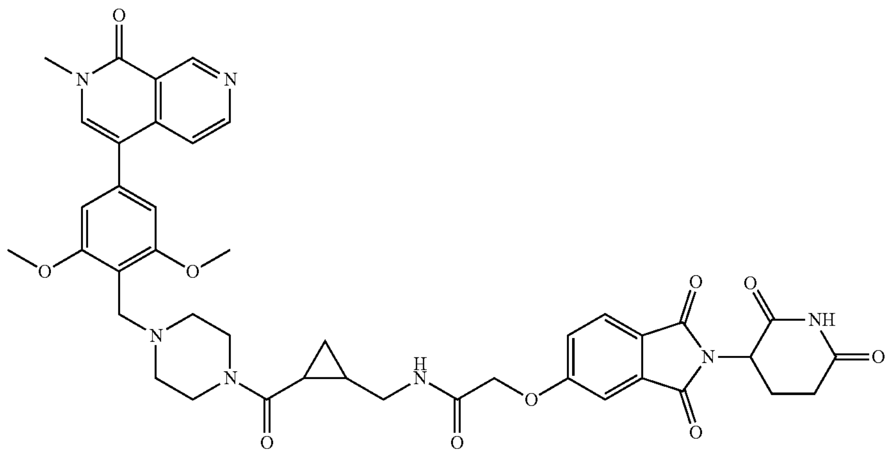 [SMILES: COc1cc(-c2cn(C)c(=O)c3cnccc23)cc(OC)c1CN1CCN(C(=O)C2CC2CNC(=O)COc2ccc3c(c2)C(=O)N(C2CCC(=O)NC2=O)C3=O)CC1] |
| D67 | 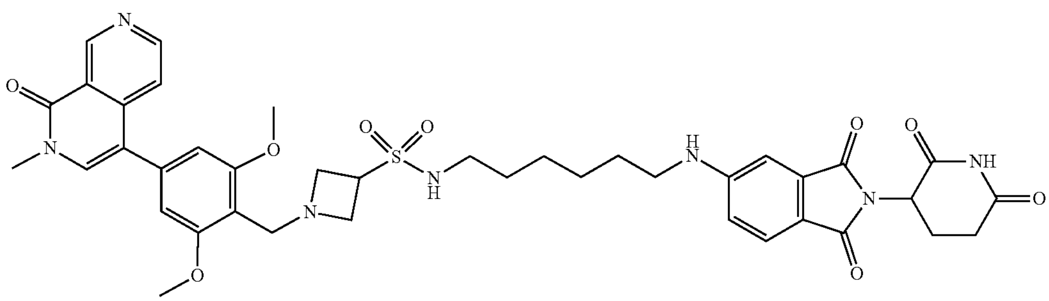 [SMILES: COc1cc(-c2cn(C)c(=O)c3cnccc23)cc(OC)c1CN1CC(S(=O)(=O)NCCCCCCNc2ccc3c(c2)C(=O)N(C2CCC(=O)NC2=O)C3=O)C1] |
| D68 | 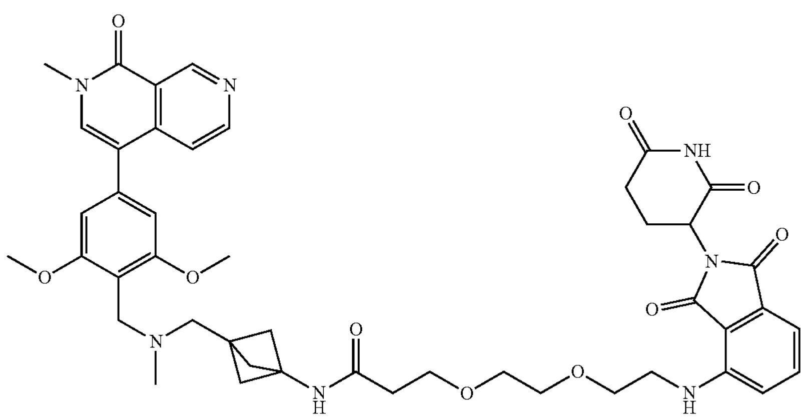 [SMILES: COc1cc(-c2cn(C)c(=O)c3cnccc23)cc(OC)c1CN(C)CC12CC(NC(=O)CCOCCOCCNc3cccc4c3C(=O)N(C3CCC(=O)NC3=O)C4=O)(C1)C2] |

TABLE 1A-continued
Compounds D1-D177 of the Disclosure
| Compound No. | Structure |
| --- | --- |
| D69 | 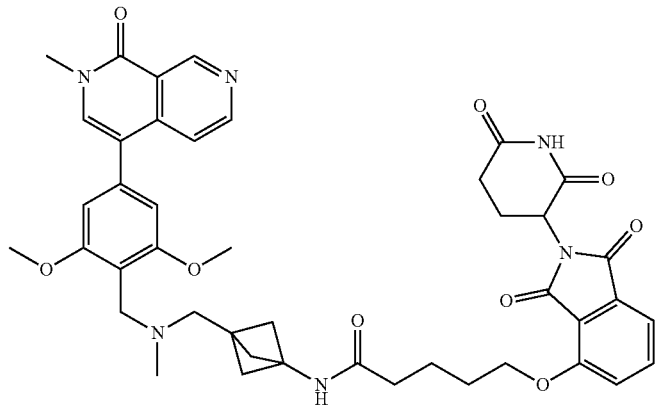 [SMILES: COc1cc(-c2cn(C)c(=O)c3cnccc23)cc(OC)c1CN(C)CC12CC(NC(=O)CCCCOc3cccc4c3C(=O)N(C3CCC(=O)NC3=O)C4=O)(C1)C2] |
| D70 | 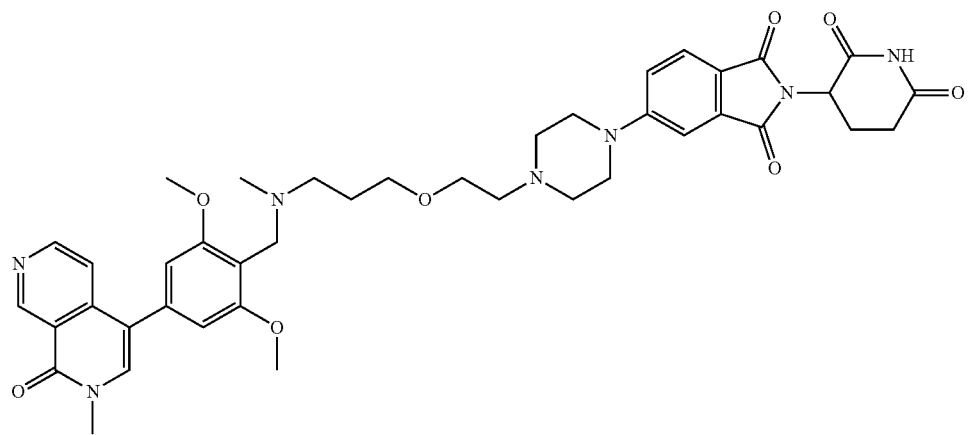 [SMILES: COc1cc(-c2cn(C)c(=O)c3cnccc23)cc(OC)c1CN(C)CCCOCCN1CCN(c2ccc3c(c2)C(=O)N(C2CCC(=O)NC2=O)C3=O)CC1] |
| D71 | 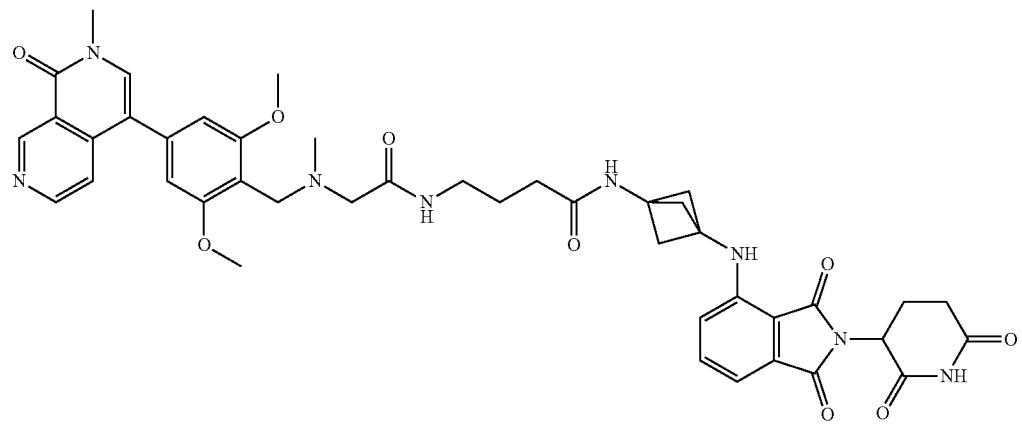 [SMILES: COc1cc(-c2cn(C)c(=O)c3cnccc23)cc(OC)c1CN(C)CC(=O)NCCCC(=O)NC12CC(Nc3cccc4c3C(=O)N(C3CCC(=O)NC3=O)C4=O)(C1)C2] |

TABLE 1A-continued
Compounds D1-D177 of the Disclosure
| Compound No. | Structure |
|---|---|
| D72 | 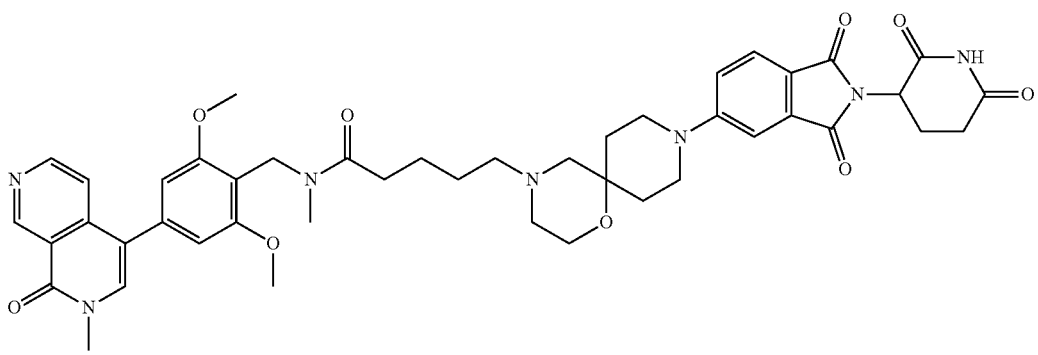 [SMILES: COc1cc(-c2cn(C)c(=O)c3cnccc23)cc(OC)c1CN(C)C(=O)CCCCN1CCOC2(CCN(c3ccc4c(c3)C(=O)N(C3CCC(=O)NC3=O)C4=O)CC2)C1] |
| D73 | 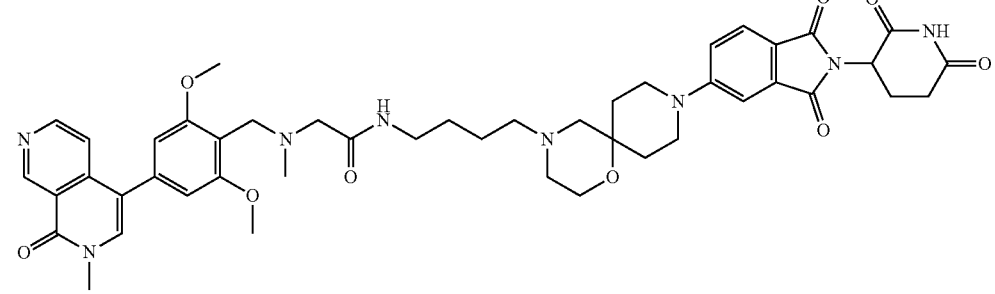 |
| D74 | 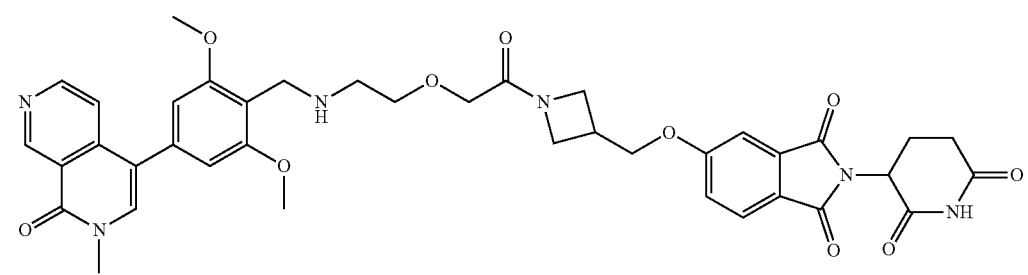 [SMILES: COc1cc(-c2cn(C)c(=O)c3cnccc23)cc(OC)c1CNCCOCC(=O)N1CC(COc2ccc3c(c2)C(=O)N(C2CCC(=O)NC2=O)C3=O)C1] |
| D75 | 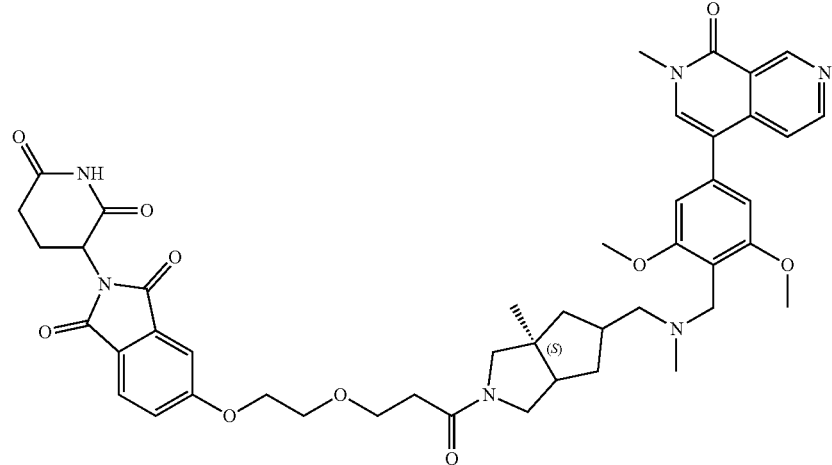 |

TABLE 1A-continued
Compounds D1-D177 of the Disclosure
| Compound No. | Structure |
|---|---|
| D76 | 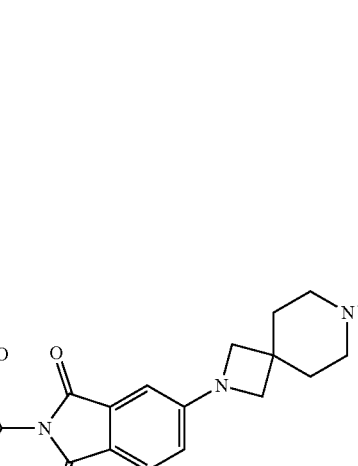 |
| D77 | 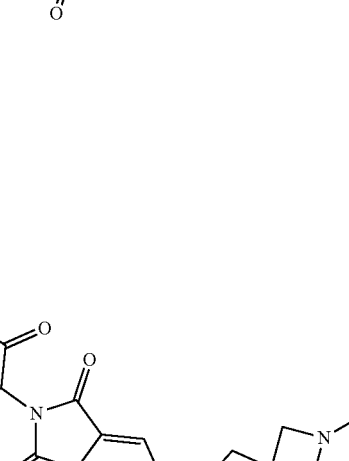 |
| D78 | 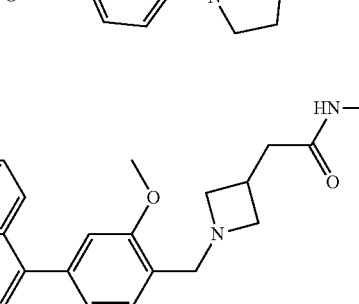 |

TABLE 1A-continued
Compounds D1-D177 of the Disclosure
| Compound No. | Structure |
| --- | --- |
| D79 | 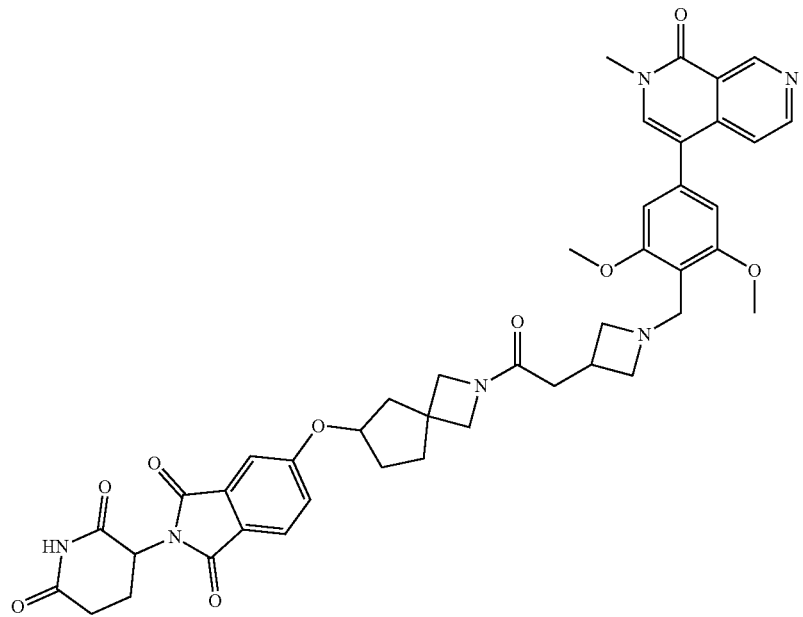 [SMILES: COc1cc(-c2cn(C)c(=O)c3cnccc23)cc(OC)c1CN1CC(CC(=O)N2CC3(CCC(Oc4ccc5c(c4)C(=O)N(C4CCC(=O)NC4=O)C5=O)C3)C2)C1] |
| D80 | 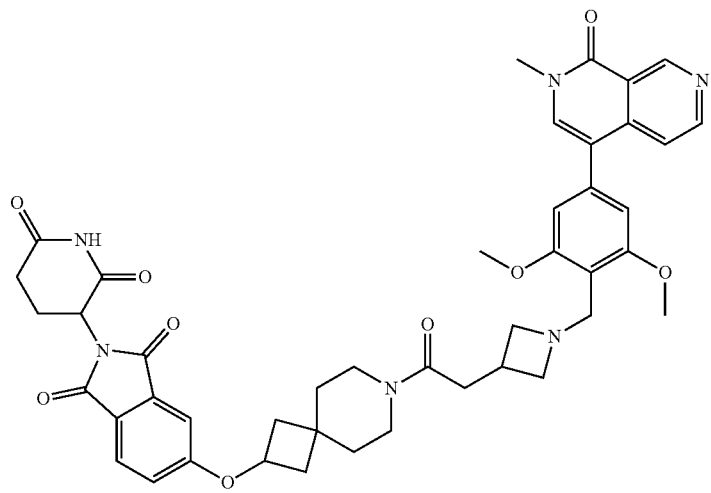 [SMILES: COc1cc(-c2cn(C)c(=O)c3cnccc23)cc(OC)c1CN1CC(CC(=O)N2CCC3(CC2)CC(Oc2ccc4c(c2)C(=O)N(C2CCC(=O)NC2=O)C4=O)C3)C1] |

TABLE 1A-continued
Compounds D1-D177 of the Disclosure
| Compound No. | Structure |
|---|---|
| D81 | 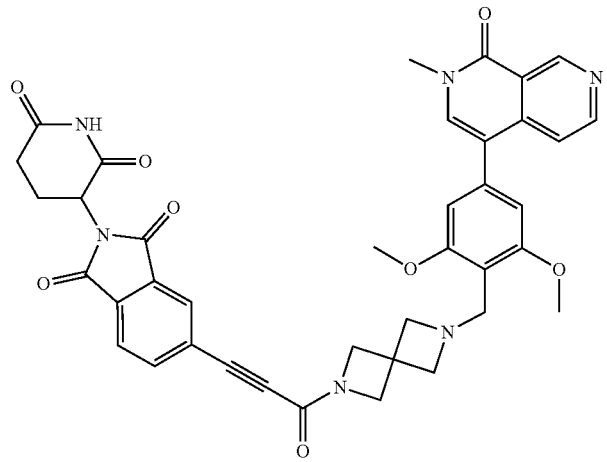 [SMILES: COc1cc(-c2cn(C)c(=O)c3cnccc23)cc(OC)c1CN1CC2(C1)CN(C(=O)C#Cc1ccc3c(c1)C(=O)N(C1CCC(=O)NC1=O)C3=O)C2] |
| D82 | 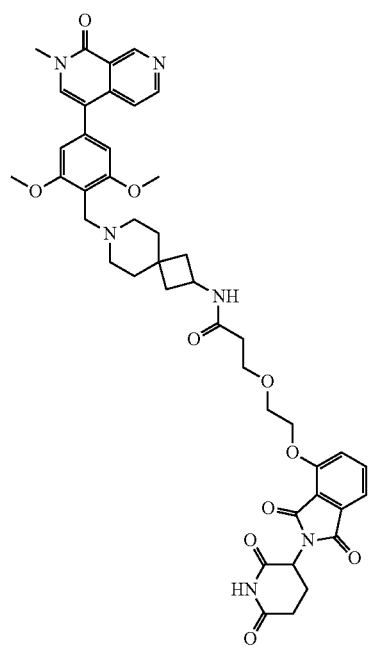 [SMILES: COc1cc(-c2cn(C)c(=O)c3cnccc23)cc(OC)c1CN1CCC2(CC1)CC(NC(=O)CCOCCOc1cccc3c1C(=O)N(C1CCC(=O)NC1=O)C3=O)C2] |
| D83 | 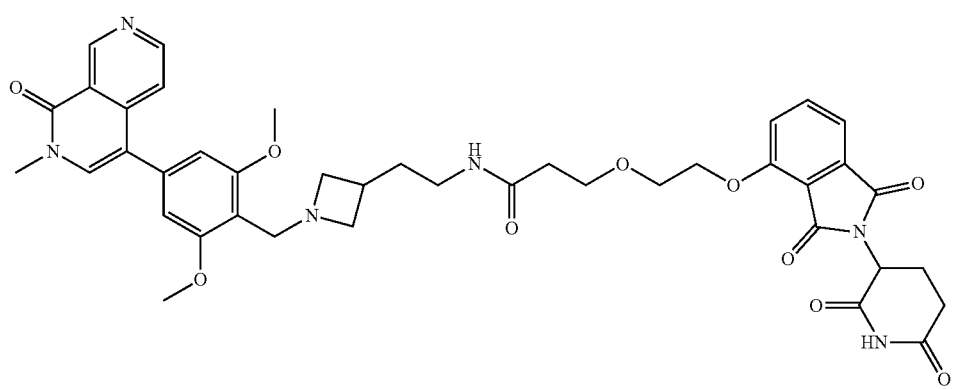 [SMILES: COc1cc(-c2cn(C)c(=O)c3cnccc23)cc(OC)c1CN1CC(CCNC(=O)CCOCCOc2cccc3c2C(=O)N(C2CCC(=O)NC2=O)C3=O)C1] |

TABLE 1A-continued
Compounds D1-D177 of the Disclosure
| Compound No. | Structure |
|---|---|
| D84 | 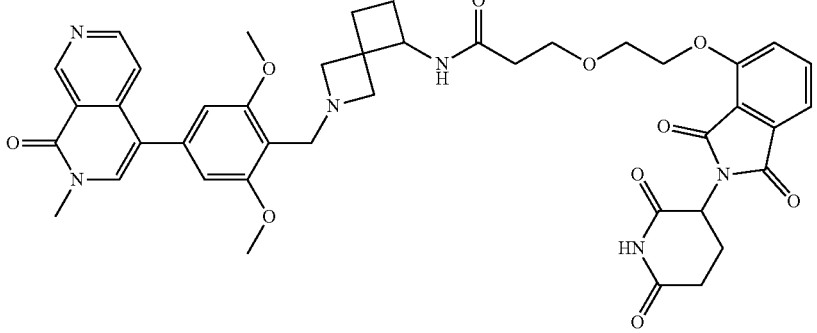 |
| D85 | 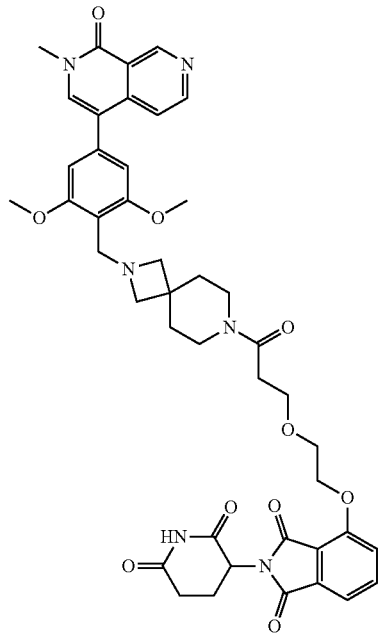 [SMILES: COc1cc(-c2cn(C)c(=O)c3cnccc23)cc(OC)c1CN1CC2(CCN(C(=O)CCOCCOc3cccc4c3C(=O)N(C3CCC(=O)NC3=O)C4=O)CC2)C1] |
| D86 | 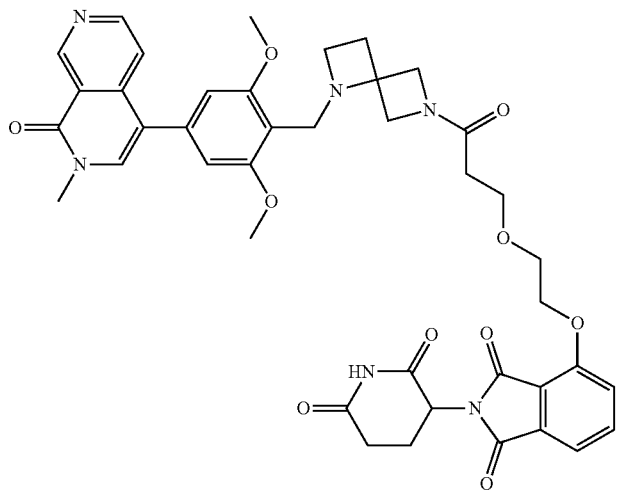 [SMILES: COc1cc(-c2cn(C)c(=O)c3cnccc23)cc(OC)c1CN1CCC12CN(C(=O)CCOCCOc1cccc3c1C(=O)N(C1CCC(=O)NC1=O)C3=O)C2] |

TABLE 1A-continued
Compounds D1-D177 of the Disclosure
| Compound No. | Structure |
|---|---|
| D87 | 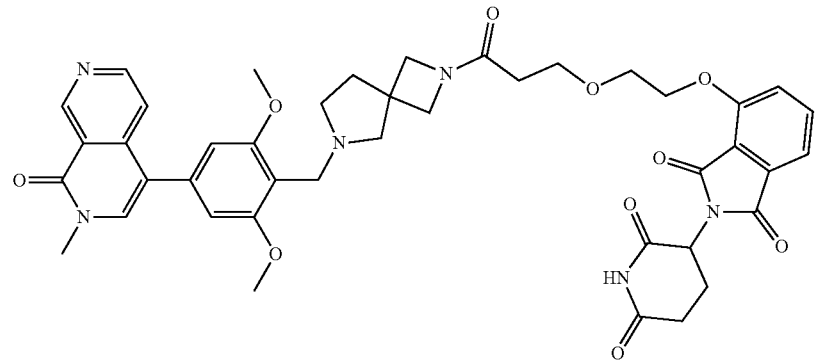 [SMILES: COc1cc(-c2cn(C)c(=O)c3cnccc23)cc(OC)c1CN1CCC2(C1)CN(C(=O)CCOCCOc1cccc3c1C(=O)N(C1CCC(=O)NC1=O)C3=O)C2] |
| D88 | 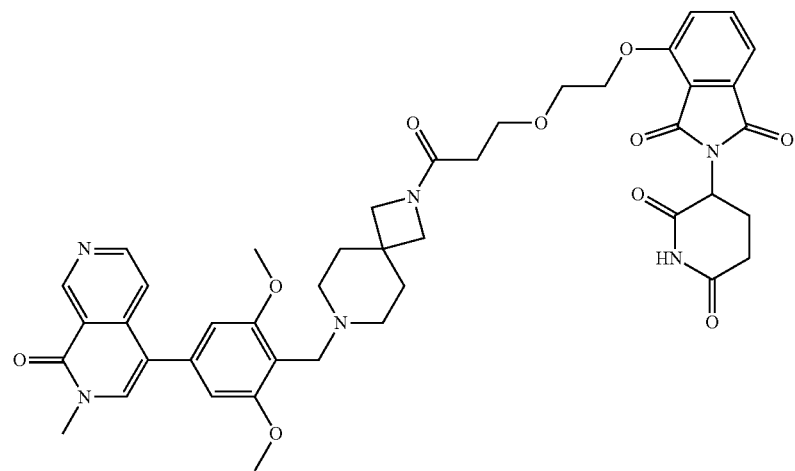 [SMILES: COc1cc(-c2cn(C)c(=O)c3cnccc23)cc(OC)c1CN1CCC2(CC1)CN(C(=O)CCOCCOc1cccc3c1C(=O)N(C1CCC(=O)NC1=O)C3=O)C2] |
| D89 | 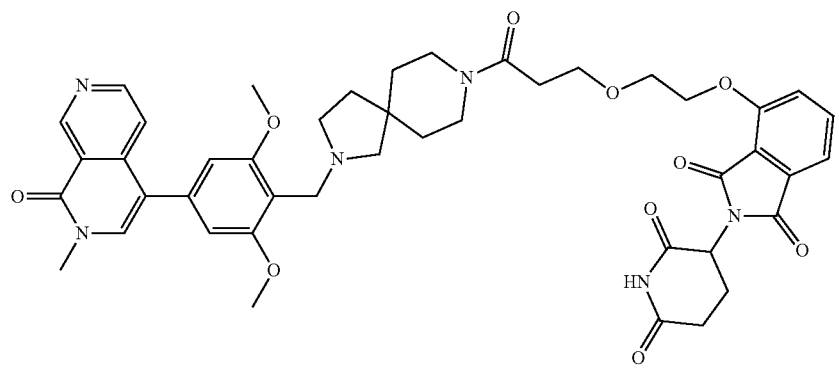 [SMILES: COc1cc(-c2cn(C)c(=O)c3cnccc23)cc(OC)c1CN1CCC2(CCN(C(=O)CCOCCOc3cccc4c3C(=O)N(C3CCC(=O)NC3=O)C4=O)CC2)C1] |

TABLE 1A-continued
Compounds D1-D177 of the Disclosure
| Compound No. | Structure |
|---|---|
| D90 | 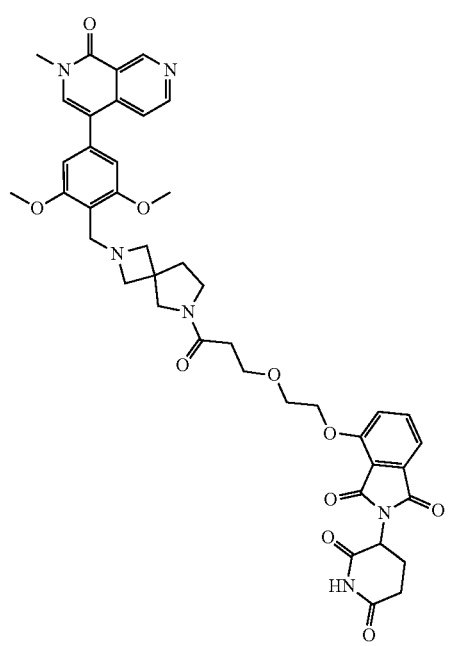 [SMILES: COc1cc(-c2cn(C)c(=O)c3cnccc23)cc(OC)c1CN1CC2(CCN(C(=O)CCOCCOc3cccc4c3C(=O)N(C3CCC(=O)NC3=O)C4=O)C2)C1] |
| D91 | 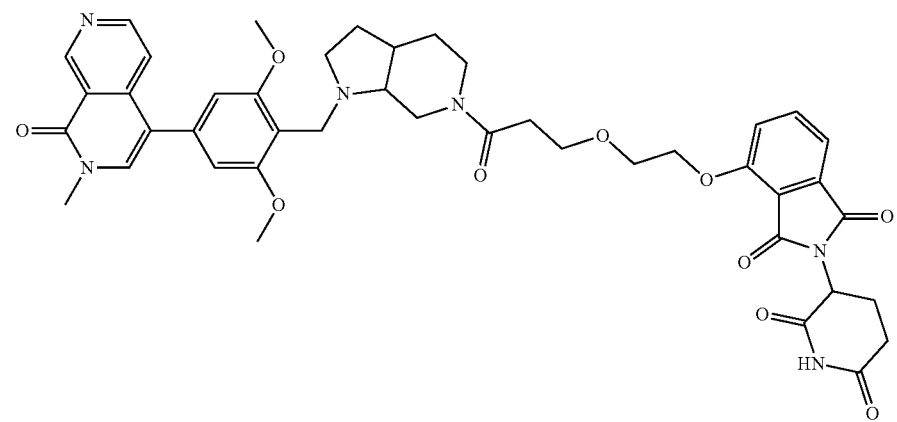 [SMILES: COc1cc(-c2cn(C)c(=O)c3cnccc23)cc(OC)c1CN1CCC2CCN(C(=O)CCOCCOc3cccc4c3C(=O)N(C3CCC(=O)NC3=O)C4=O)CC21] |
| D92 | 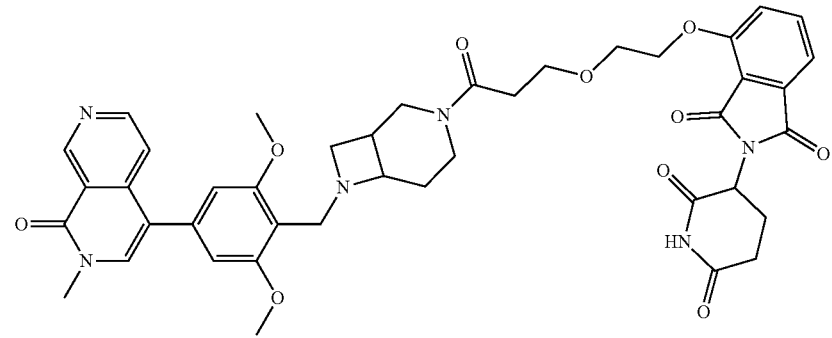 [SMILES: COc1cc(-c2cn(C)c(=O)c3cnccc23)cc(OC)c1CN1CC2CN(C(=O)CCOCCOc3cccc4c3C(=O)N(C3CCC(=O)NC3=O)C4=O)CCC21] |

195 196
TABLE 1A-continued
Compounds D1-D177 of the Disclosure
| Compound No. | Structure |
|---|---|
| D93 | 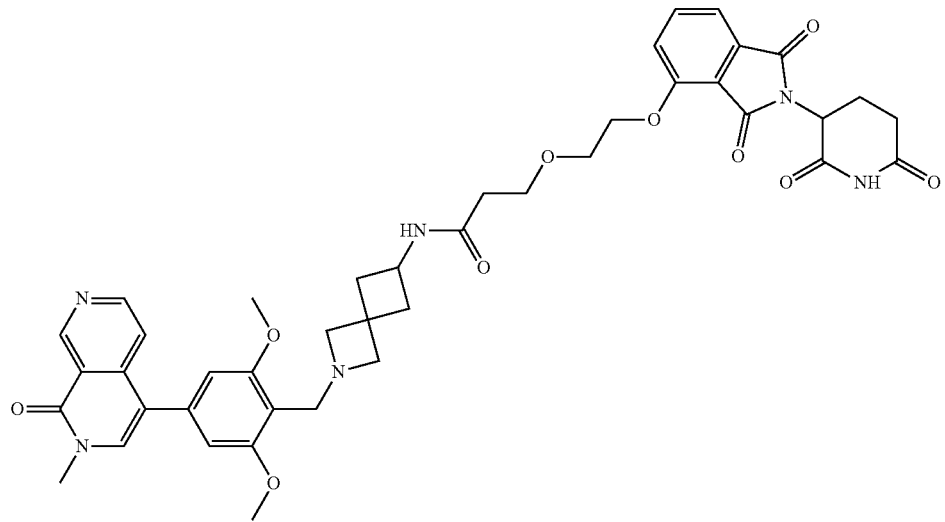 [SMILES: COc1cc(-c2cn(C)c(=O)c3cnccc23)cc(OC)c1CN1CC2(CC(NC(=O)CCOCCOc3cccc4c3C(=O)N(C3CCC(=O)NC3=O)C4=O)C2)C1] |
| D94 | 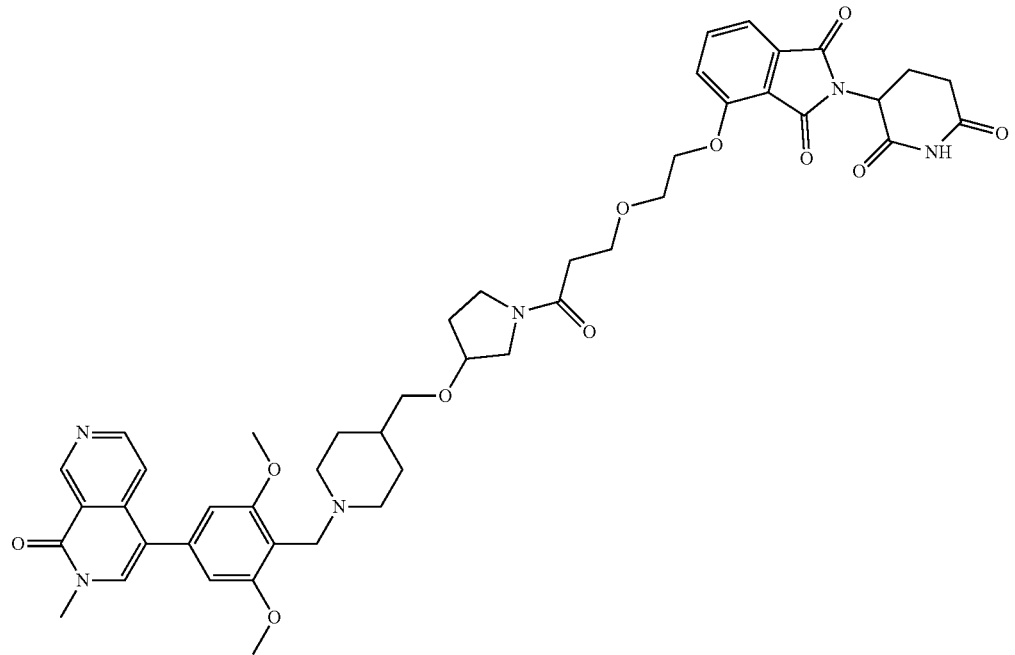 [SMILES: COc1cc(-c2cn(C)c(=O)c3cnccc23)cc(OC)c1CN1CCC(COC2CCN(C(=O)CCOCCOc3cccc4c3C(=O)N(C3CCC(=O)NC3=O)C4=O)C2)CC1] |

TABLE 1A-continued
Compounds D1-D177 of the Disclosure
| Compound No. | Structure |
|---|---|
| D95 | 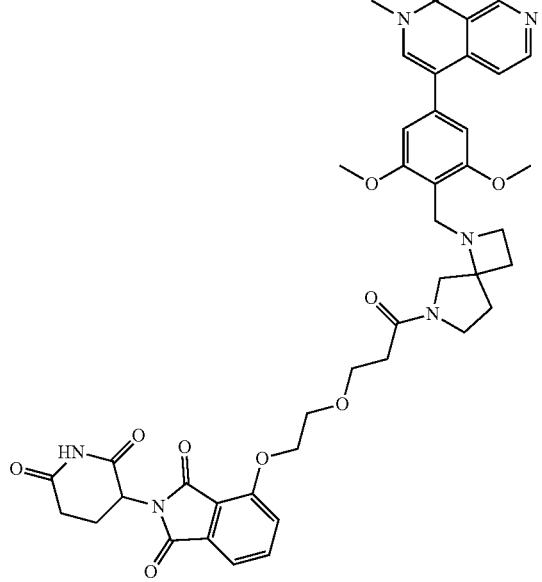 |
| D96 | 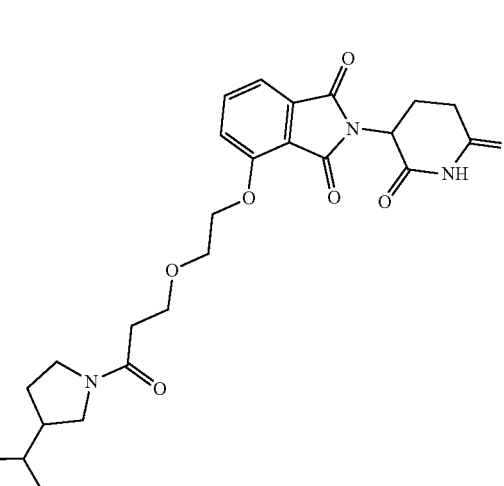 |

TABLE 1A-continued
Compounds D1-D177 of the Disclosure
| Compound No. | Structure |
|---|---|
| D97 | 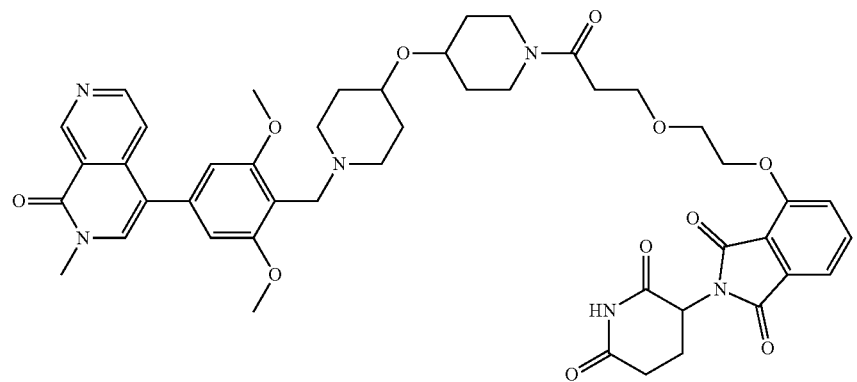 [SMILES: COc1cc(-c2cn(C)c(=O)c3cnccc23)cc(OC)c1CN1CCC(OC2CCN(C(=O)CCOCCOc3cccc4c3C(=O)N(C3CCC(=O)NC3=O)C4=O)CC2)CC1] |
| D98 | 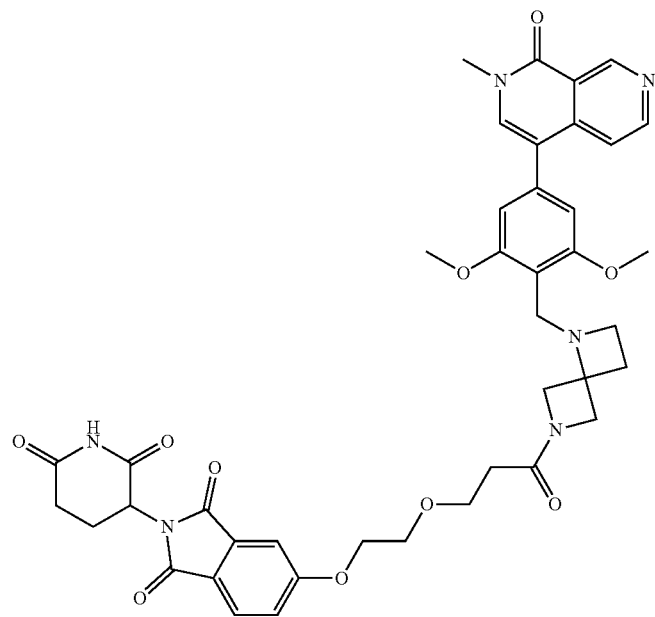 [SMILES: COc1cc(-c2cn(C)c(=O)c3cnccc23)cc(OC)c1CN1CCC12CN(C(=O)CCOCCOc1ccc3c(c1)C(=O)N(C1CCC(=O)NC1=O)C3=O)C2] |
| D99 | 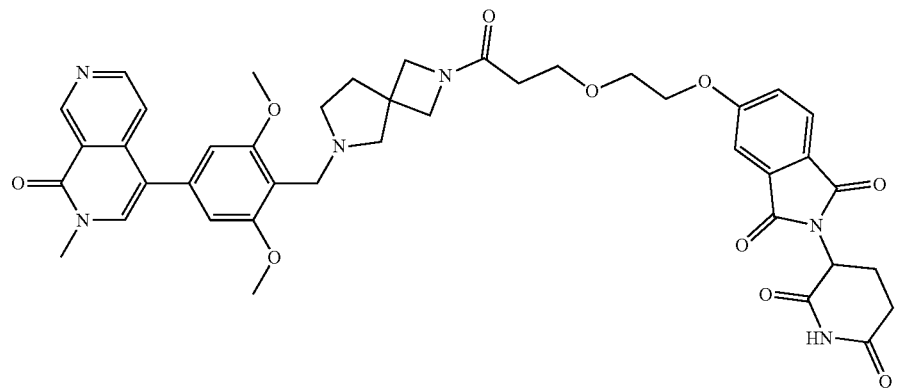 [SMILES: COc1cc(-c2cn(C)c(=O)c3cnccc23)cc(OC)c1CN1CCC2(C1)CN(C(=O)CCOCCOc1ccc3c(c1)C(=O)N(C1CCC(=O)NC1=O)C3=O)C2] |

TABLE 1A-continued
Compounds D1-D177 of the Disclosure
| Compound No. | Structure |
| --- | --- |
| D100 | 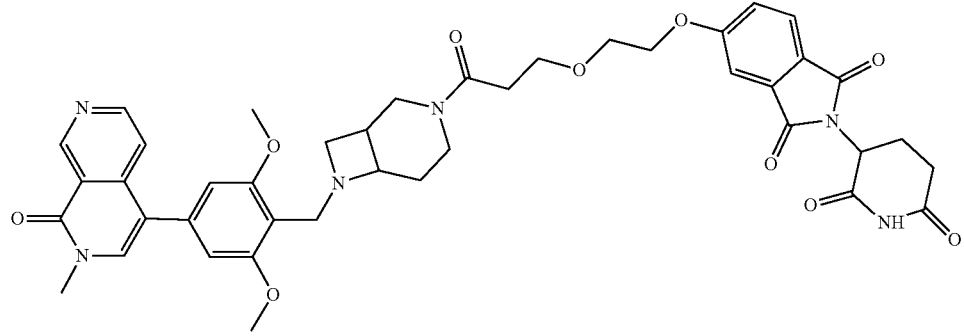 [SMILES: COc1cc(-c2cn(C)c(=O)c3cnccc23)cc(OC)c1CN1CC2CN(C(=O)CCOCCOc3ccc4c(c3)C(=O)N(C3CCC(=O)NC3=O)C4=O)CCC21] |
| D101 | 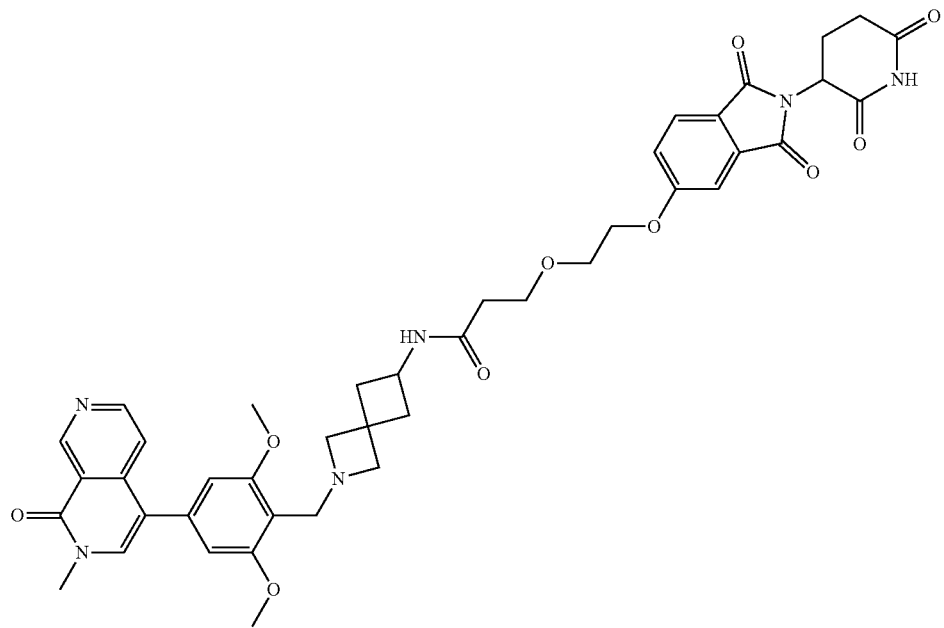 [SMILES: COc1cc(-c2cn(C)c(=O)c3cnccc23)cc(OC)c1CN1CC2(CC(NC(=O)CCOCCOc3ccc4c(c3)C(=O)N(C3CCC(=O)NC3=O)C4=O)C2)C1] |
| D102 | 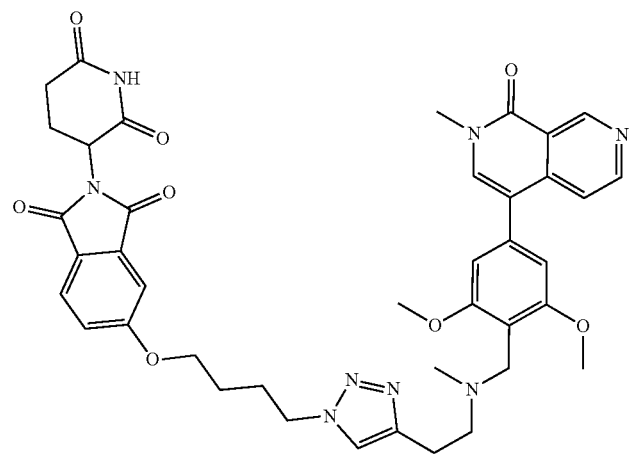 [SMILES: COc1cc(-c2cn(C)c(=O)c3cnccc23)cc(OC)c1CN(C)CCc1cn(CCCCOc2ccc3c(c2)C(=O)N(C2CCC(=O)NC2=O)C3=O)nn1] |

TABLE 1A-continued
Compounds D1-D177 of the Disclosure
| Compound No. | Structure |
|---|---|
| D103 | 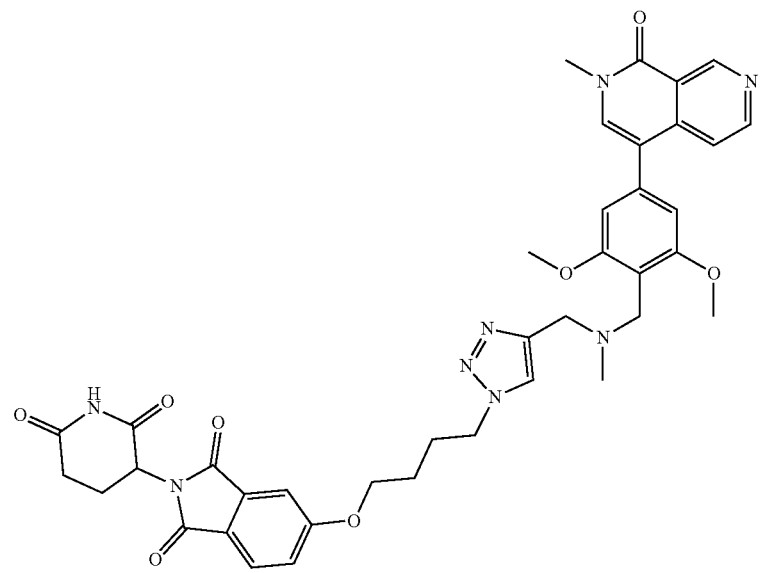 [SMILES: COc1cc(-c2cn(C)c(=O)c3cnccc23)cc(OC)c1CN(C)Cc1cn(CCCCOc2ccc3c(c2)C(=O)N(C2CCC(=O)NC2=O)C3=O)nn1] |
| D104 | 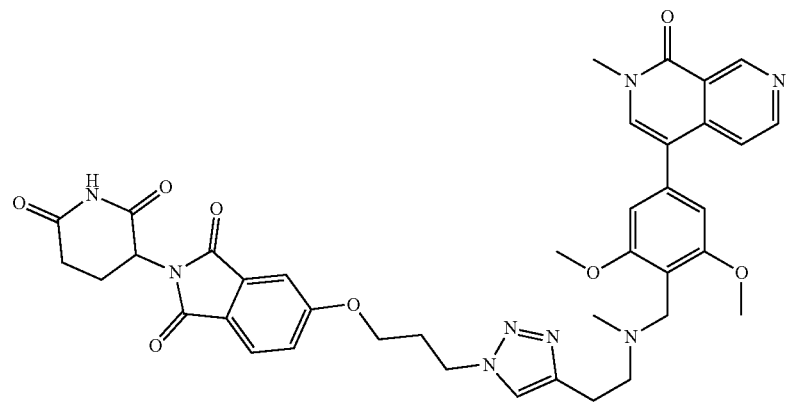 [SMILES: COc1cc(-c2cn(C)c(=O)c3cnccc23)cc(OC)c1CN(C)CCc1cn(CCCOc2ccc3c(c2)C(=O)N(C2CCC(=O)NC2=O)C3=O)nn1] |
| D105 | 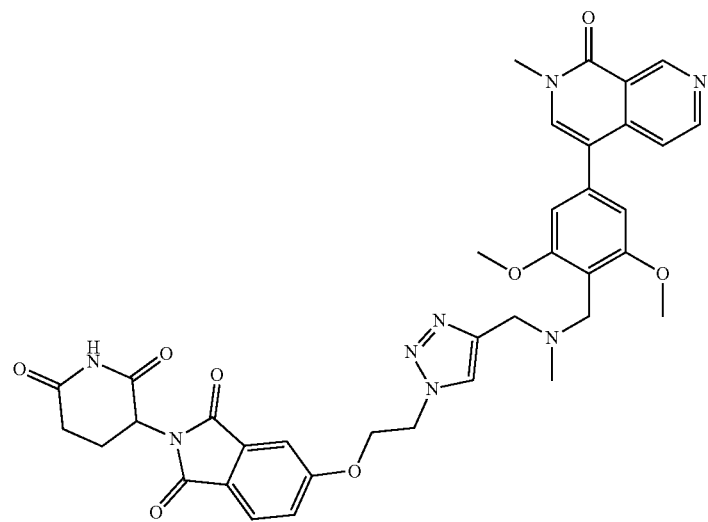 [SMILES: COc1cc(-c2cn(C)c(=O)c3cnccc23)cc(OC)c1CN(C)Cc1cn(CCOc2ccc3c(c2)C(=O)N(C2CCC(=O)NC2=O)C3=O)nn1] |

TABLE 1A-continued
Compounds D1-D177 of the Disclosure
| Compound No. | Structure |
|---|---|
| D106 | 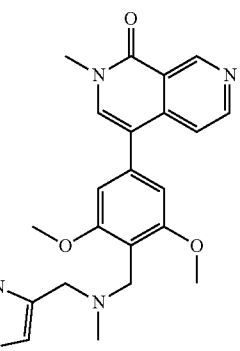 |
| D107 | 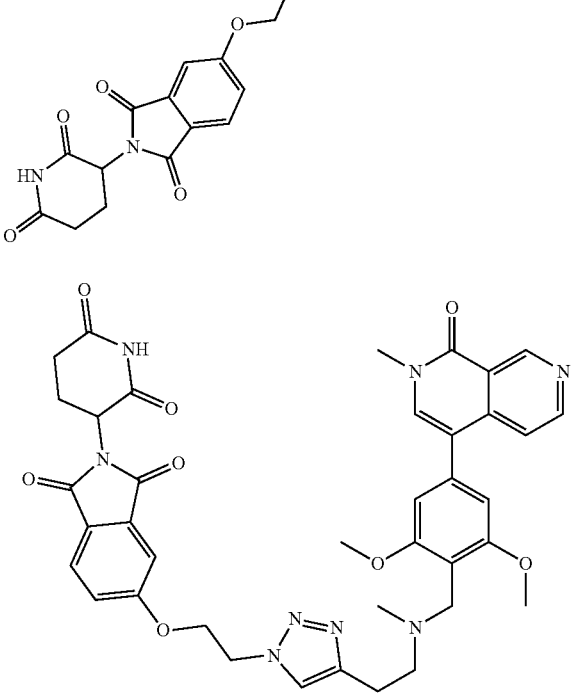 |
| D108 | 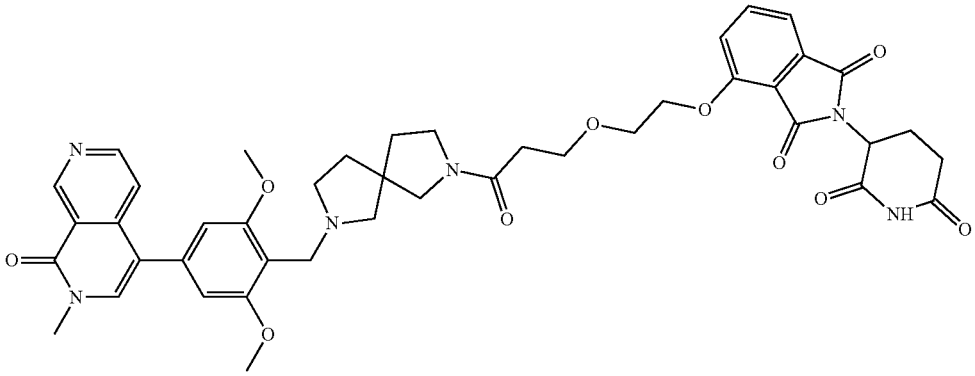 [SMILES: COc1cc(-c2cn(C)c(=O)c3cnccc23)cc(OC)c1CN1CCC2(CCN(C(=O)CCOCCOc3cccc4c3C(=O)N(C3CCC(=O)NC3=O)C4=O)C2)C1] |

TABLE 1A-continued
Compounds D1-D177 of the Disclosure
| Compound No. | Structure |
|---|---|
| D109 | 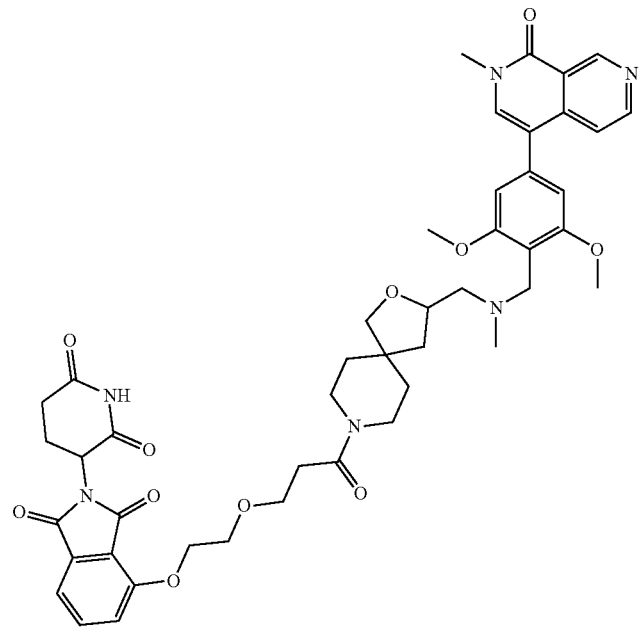 [SMILES: COc1cc(-c2cn(C)c(=O)c3cnccc23)cc(OC)c1CN(C)CC1CC2(CCN(C(=O)CCOCCOc3cccc4c3C(=O)N(C3CCC(=O)NC3=O)C4=O)CC2)CO1] |
| D110 | 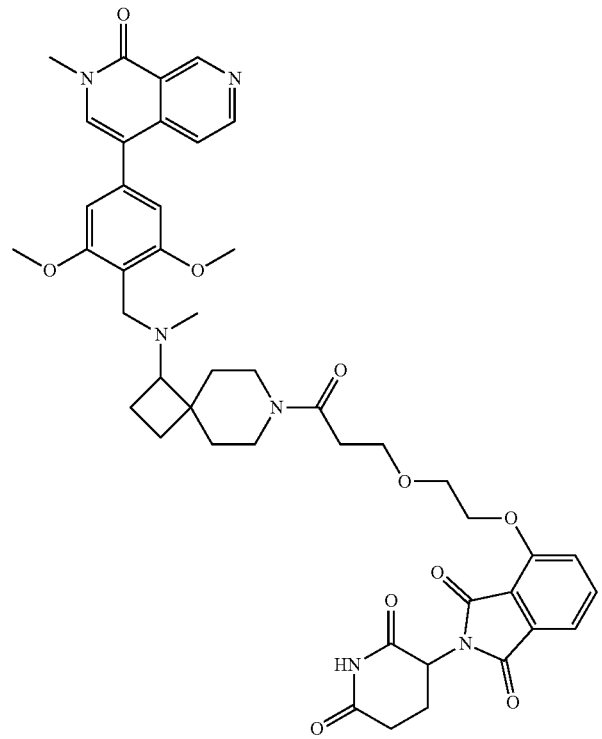 [SMILES: COc1cc(-c2cn(C)c(=O)c3cnccc23)cc(OC)c1CN(C)C1CCC12CCN(C(=O)CCOCCOc1cccc3c1C(=O)N(C1CCC(=O)NC1=O)C3=O)CC2] |

TABLE 1A-continued

Compounds D1-D177 of the Disclosure

| Compound No. | Structure |
|---|---|
| D111 | 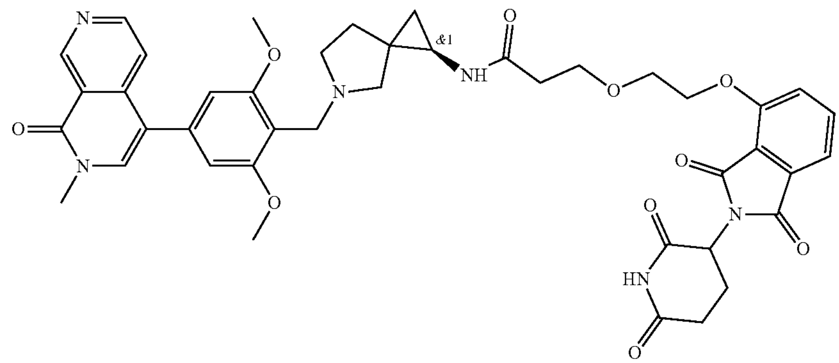 [SMILES: COc1cc(-c2cn(C)c(=O)c3cnccc23)cc(OC)c1CN1CCC2(C[C@H]2NC(=O)CCOCCOc2cccc3c2C(=O)N(C2CCC(=O)NC2=O)C3=O)C1] |
| D112 | 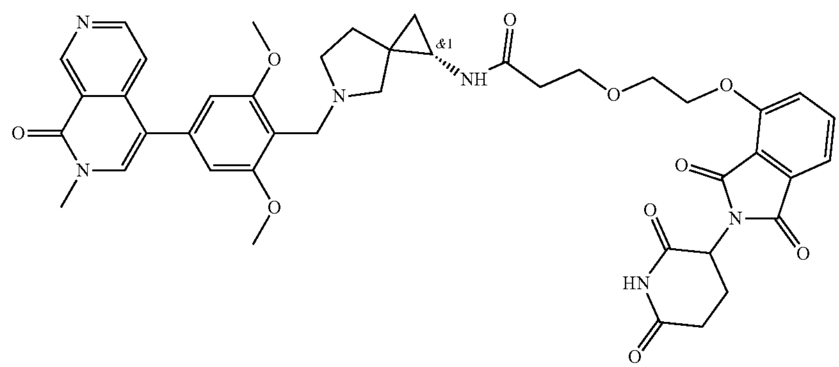 [SMILES: COc1cc(-c2cn(C)c(=O)c3cnccc23)cc(OC)c1CN1CCC2(C[C@@H]2NC(=O)CCOCCOc2cccc3c2C(=O)N(C2CCC(=O)NC2=O)C3=O)C1] |
| D113 | 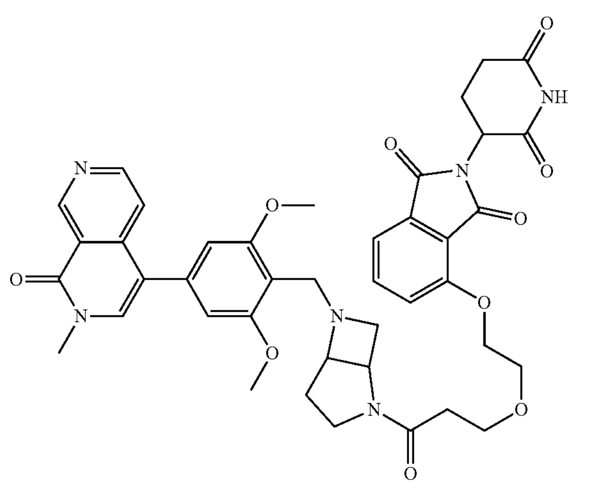 [SMILES: COc1cc(-c2cn(C)c(=O)c3cnccc23)cc(OC)c1CN1CC2C1CCN2C(=O)CCOCCOc1cccc2c1C(=O)N(C1CCC(=O)NC1=O)C2=O] |
| D114 | 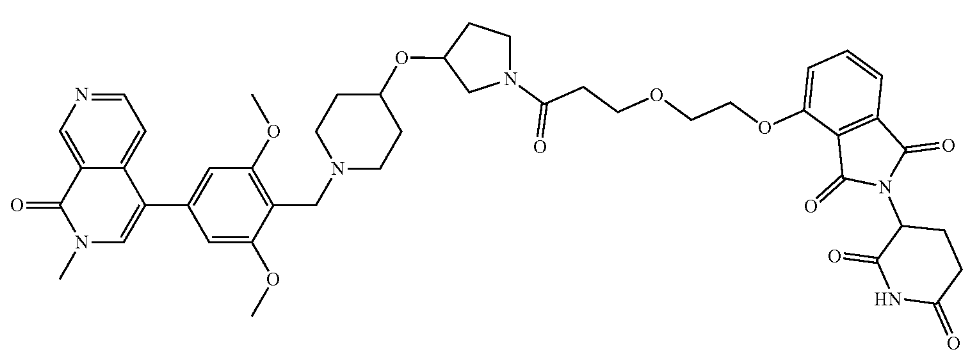 [SMILES: COc1cc(-c2cn(C)c(=O)c3cnccc23)cc(OC)c1CN1CCC(OC2CCN(C(=O)CCOCCOc3cccc4c3C(=O)N(C3CCC(=O)NC3=O)C4=O)C2)CC1] |

TABLE 1A-continued
Compounds D1-D177 of the Disclosure
| Compound No. | Structure |
|---|---|
| D115 | 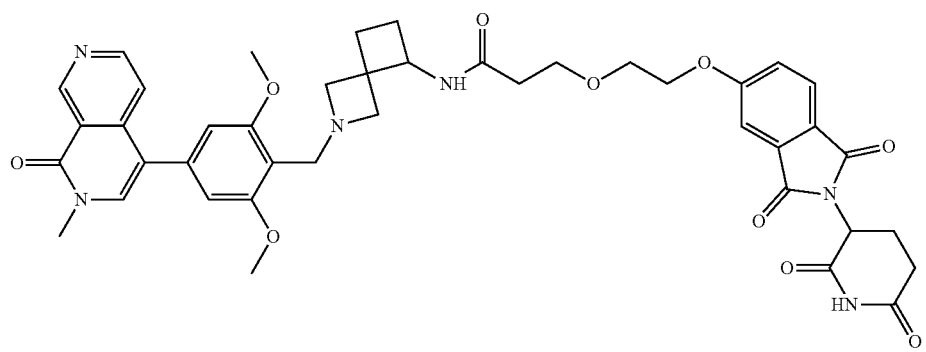 [SMILES: COc1cc(-c2cn(C)c(=O)c3cnccc23)cc(OC)c1CN1CC2(CCC2NC(=O)CCOCCOc2ccc3c(c2)C(=O)N(C2CCC(=O)NC2=O)C3=O)C1] |
| D116 | 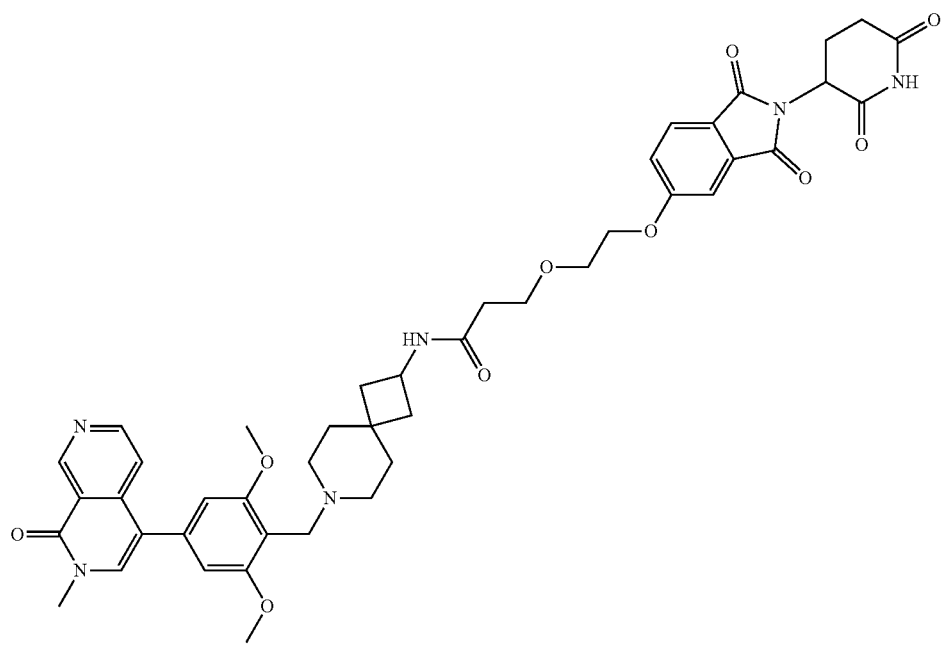 [SMILES: COc1cc(-c2cn(C)c(=O)c3cnccc23)cc(OC)c1CN1CCC2(CC1)CC(NC(=O)CCOCCOc1ccc3c(c1)C(=O)N(C1CCC(=O)NC1=O)C3=O)C2] |
| D117 | 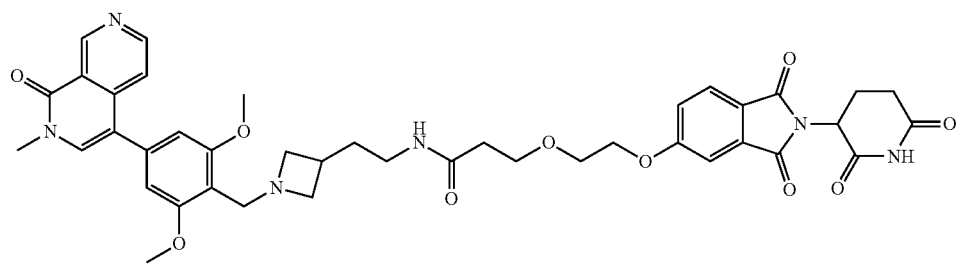 [SMILES: COc1cc(-c2cn(C)c(=O)c3cnccc23)cc(OC)c1CN1CC(CCNC(=O)CCOCCOc2ccc3c(c2)C(=O)N(C2CCC(=O)NC2=O)C3=O)C1] |

TABLE 1A-continued
Compounds D1-D177 of the Disclosure
| Compound No. | Structure |
|---|---|
| D118 | 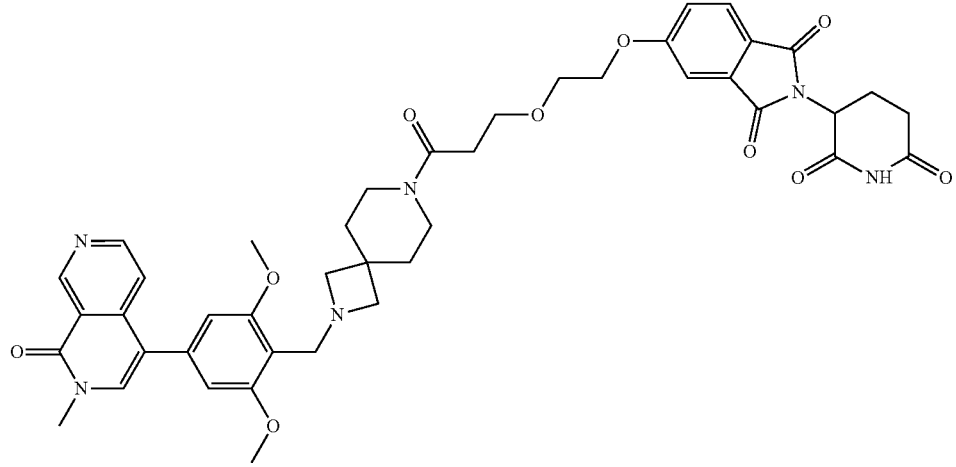 [SMILES: COc1cc(-c2cn(C)c(=O)c3cnccc23)cc(OC)c1CN1CC2(CCN(C(=O)CCOCCOc3ccc4c(c3)C(=O)N(C3CCC(=O)NC3=O)C4=O)CC2)C1] |
| D119 | 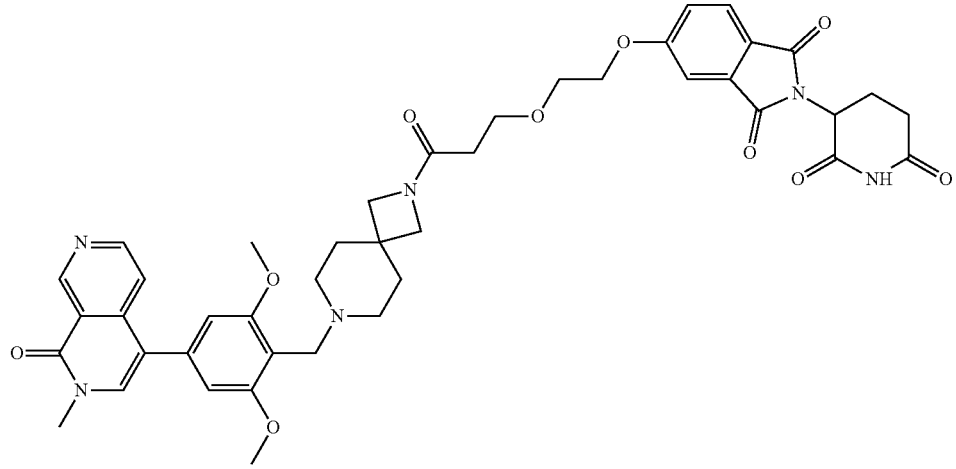 [SMILES: COc1cc(-c2cn(C)c(=O)c3cnccc23)cc(OC)c1CN1CCC2(CC1)CN(C(=O)CCOCCOc1ccc3c(c1)C(=O)N(C1CCC(=O)NC1=O)C3=O)C2] |
| D120 | 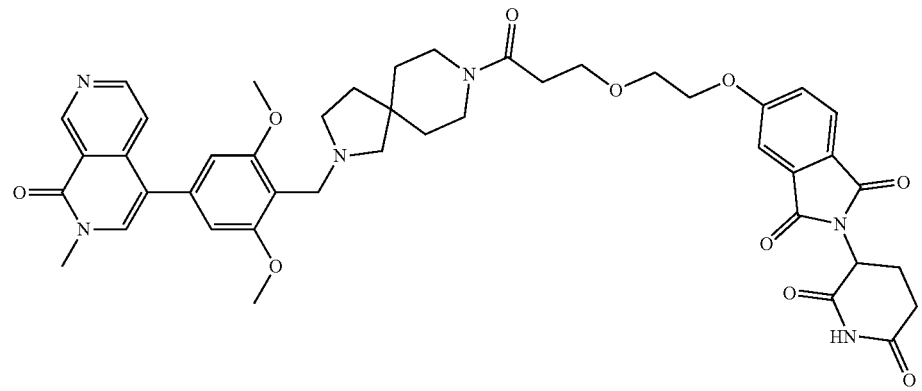 [SMILES: COc1cc(-c2cn(C)c(=O)c3cnccc23)cc(OC)c1CN1CCC2(CCN(C(=O)CCOCCOc3ccc4c(c3)C(=O)N(C3CCC(=O)NC3=O)C4=O)CC2)C1] |

TABLE 1A-continued
Compounds D1-D177 of the Disclosure
| Compound No. | Structure |
| --- | --- |
| D121 | 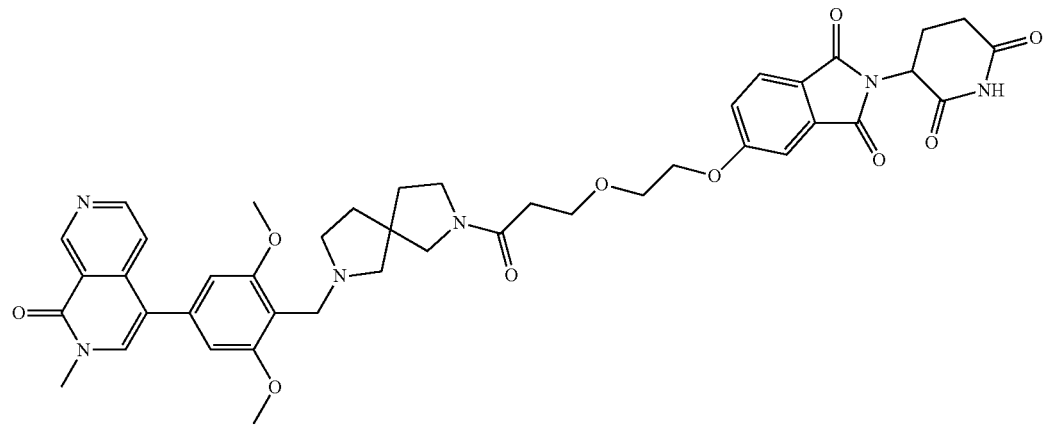 [SMILES: COc1cc(-c2cn(C)c(=O)c3cnccc23)cc(OC)c1CN1CCC2(CCN(C(=O)CCOCCOc3ccc4c(c3)C(=O)N(C3CCC(=O)NC3=O)C4=O)C2)C1] |
| D122 | 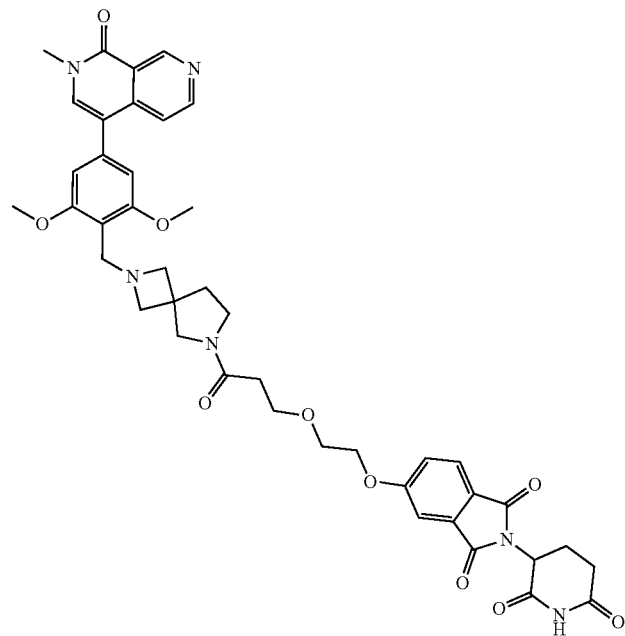 [SMILES: COc1cc(-c2cn(C)c(=O)c3cnccc23)cc(OC)c1CN1CC2(CCN(C(=O)CCOCCOc3ccc4c(c3)C(=O)N(C3CCC(=O)NC3=O)C4=O)C2)C1] |
| D123 | 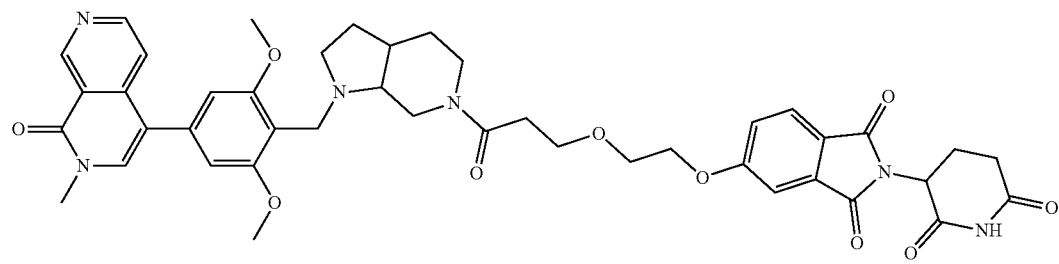 [SMILES: COc1cc(-c2cn(C)c(=O)c3cnccc23)cc(OC)c1CN1CCC2CCN(C(=O)CCOCCOc3ccc4c(c3)C(=O)N(C3CCC(=O)NC3=O)C4=O)CC21] |

TABLE 1A-continued
Compounds D1-D177 of the Disclosure
| Compound No. | Structure |
| --- | --- |
| D124 | 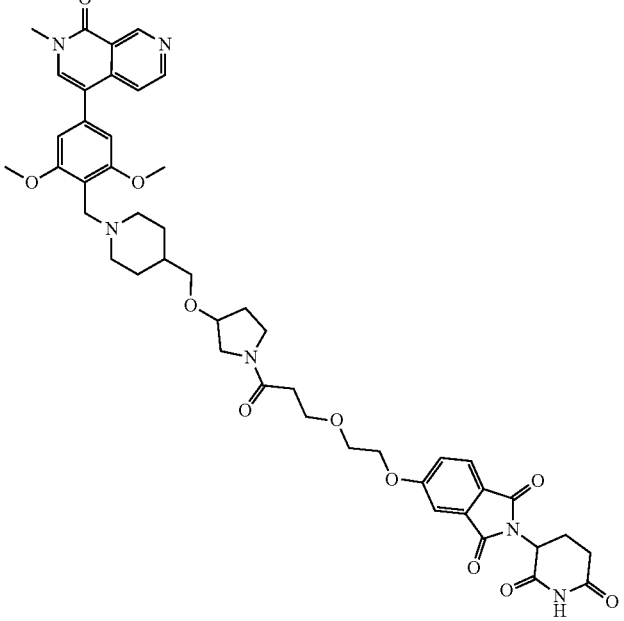 |
| D125 | 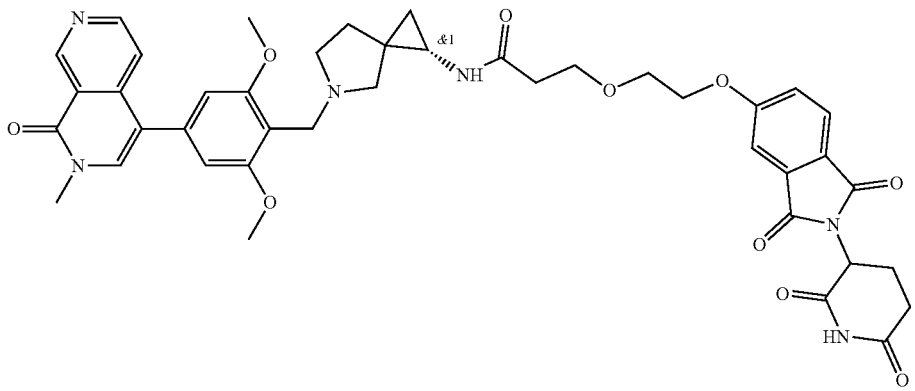 [SMILES: COc1cc(-c2cn(C)c(=O)c3cnccc23)cc(OC)c1CN1CCC2(C[C@@H]2NC(=O)CCOCCOc2ccc3c(c2)C(=O)N(C2CCC(=O)NC2=O)C3=O)C1] |
| D126 | 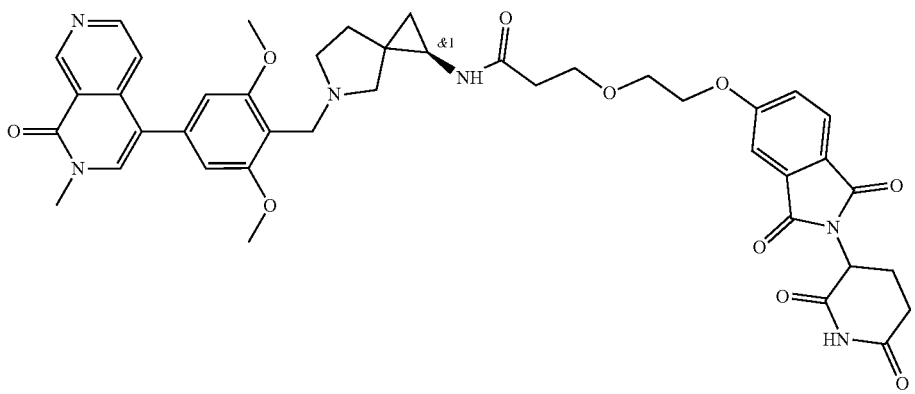 [SMILES: COc1cc(-c2cn(C)c(=O)c3cnccc23)cc(OC)c1CN1CCC2(C[C@H]2NC(=O)CCOCCOc2ccc3c(c2)C(=O)N(C2CCC(=O)NC2=O)C3=O)C1] |

TABLE 1A-continued

Compounds D1-D177 of the Disclosure

| Compound No. | Structure |
| --- | --- |
| D127 | 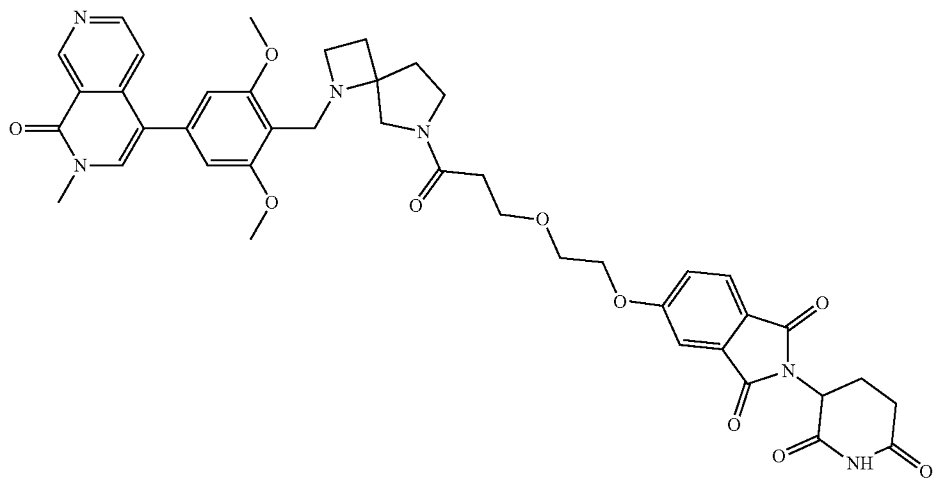 [SMILES: COc1cc(-c2cn(C)c(=O)c3cnccc23)cc(OC)c1CN1CCC12CCN(C(=O)CCOCCOc1ccc3c(c1)C(=O)N(C1CCC(=O)NC1=O)C3=O)C2] |
| D128 | 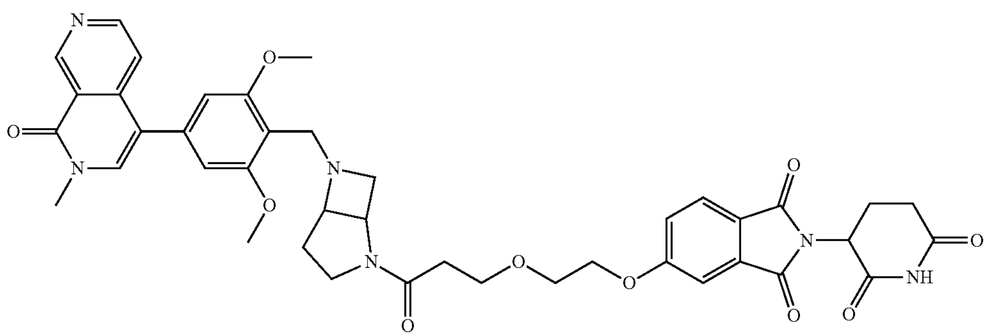 [SMILES: COc1cc(-c2cn(C)c(=O)c3cnccc23)cc(OC)c1CN1CC2C1CCN2C(=O)CCOCCOc1ccc2c(c1)C(=O)N(C1CCC(=O)NC1=O)C2=O] |
| D129 | 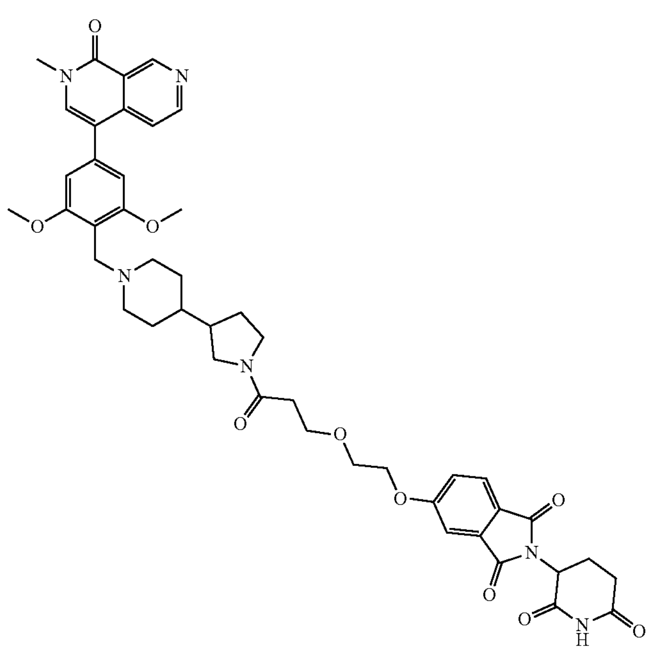 [SMILES: COc1cc(-c2cn(C)c(=O)c3cnccc23)cc(OC)c1CN1CCC(C2CCN(C(=O)CCOCCOc3ccc4c(c3)C(=O)N(C3CCC(=O)NC3=O)C4=O)C2)CC1] |

TABLE 1A-continued

Compounds D1-D177 of the Disclosure

| Compound No. | Structure |
| --- | --- |
| D130 | 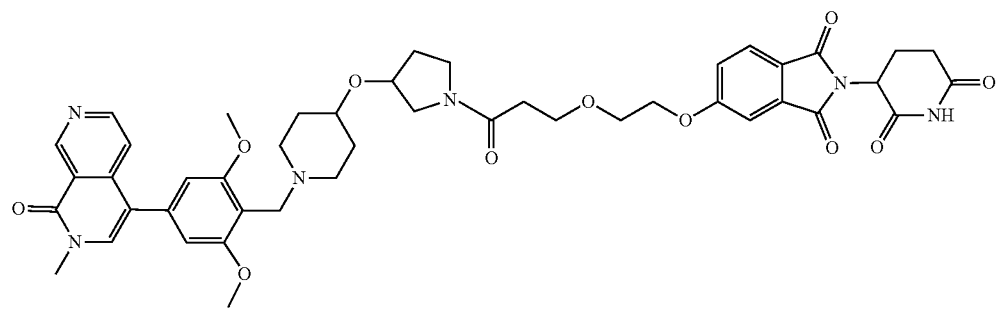 [SMILES: COc1cc(-c2cn(C)c(=O)c3cnccc23)cc(OC)c1CN1CCC(OC2CCN(CC(=O)CCOCCOc3ccc4c(c3)C(=O)N(C3CCC(=O)NC3=O)C4=O)C2)CC1] |
| D131 | 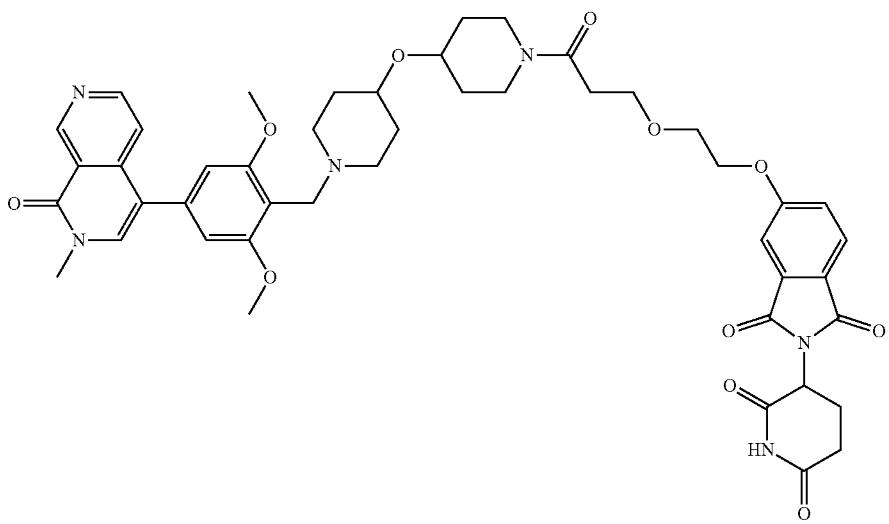 [SMILES: COc1cc(-c2cn(C)c(=O)c3cnccc23)cc(OC)c1CN1CCC(OC2CCN(C(=O)CCOCCOc3ccc4c(c3)C(=O)N(C3CCC(=O)NC3=O)C4=O)CC2)CC1] |
| D132 | 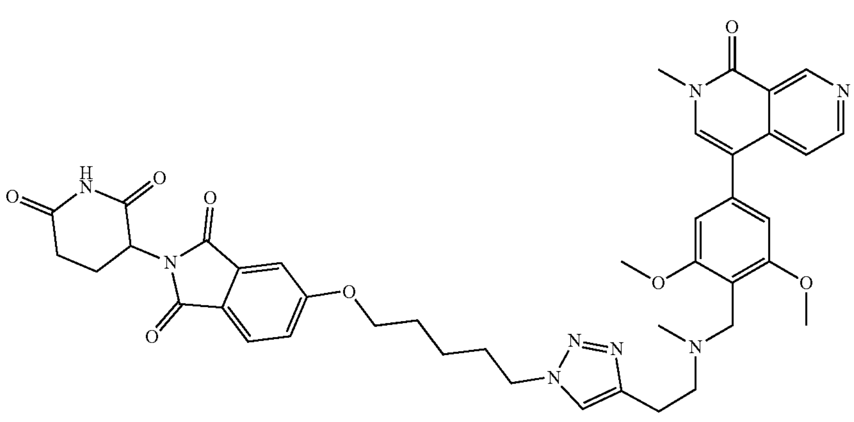 [SMILES: COc1cc(-c2cn(C)c(=O)c3cnccc23)cc(OC)c1CN(C)CCc1cn(CCCCCOc2ccc3c(c2)C(=O)N(C2CCC(=O)NC2=O)C3=O)nn1] |

TABLE 1A-continued
Compounds D1-D177 of the Disclosure
| Compound No. | Structure |
|---|---|
| D133 | 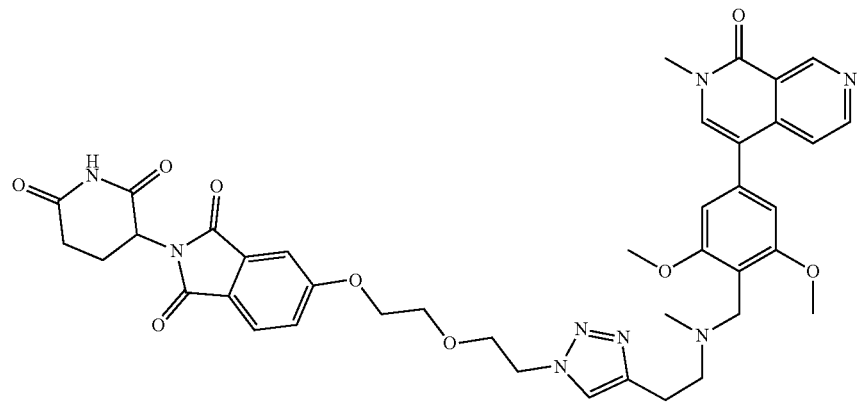 |
| D134 | 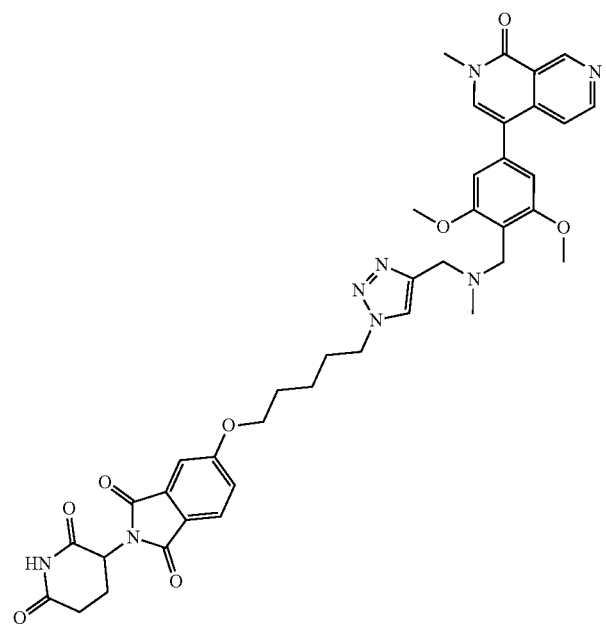 [SMILES: COc1cc(-c2cn(C)c(=O)c3cnccc23)cc(OC)c1CN(C)Cc1cn(CCCCCOc2ccc3c(c2)C(=O)N(C2CCC(=O)NC2=O)C3=O)nn1] |

TABLE 1A-continued
Compounds D1-D177 of the Disclosure
| Compound No. | Structure |
| --- | --- |
| D135 | 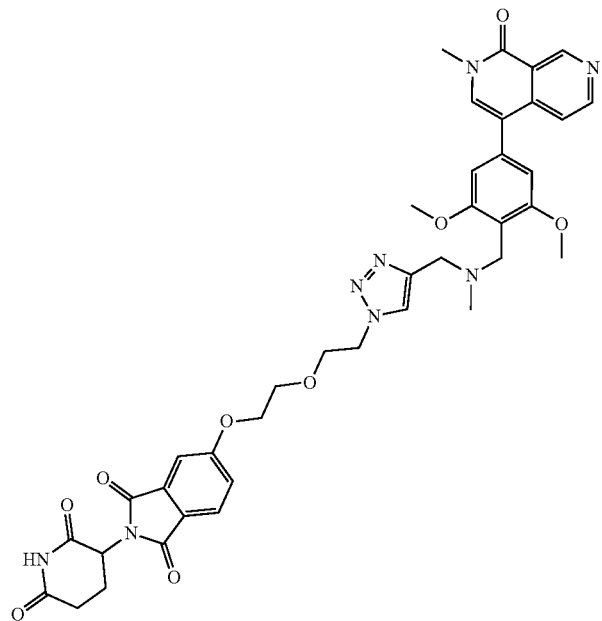 [SMILES: COc1cc(-c2cn(C)c(=O)c3cnccc23)cc(OC)c1CN(C)Cc1cn(CCOCCOc2ccc3c(c2)C(=O)N(C2CCC(=O)NC2=O)C3=O)nn1] |
| D136 | 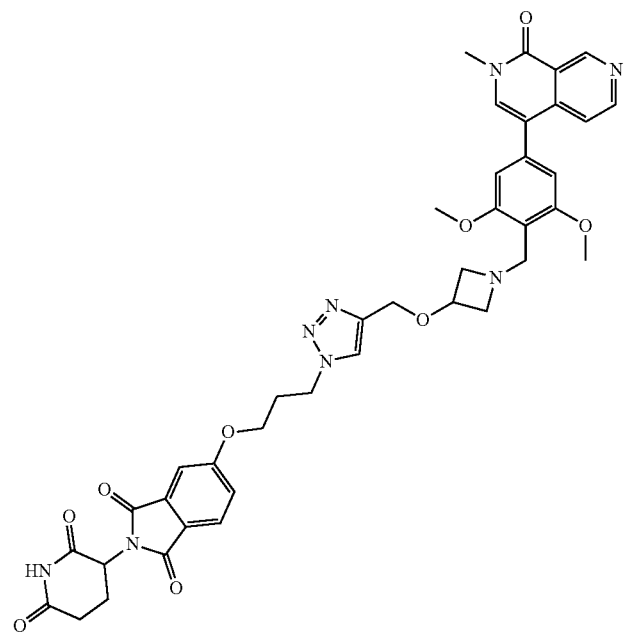 [SMILES: COc1cc(-c2cn(C)c(=O)c3cnccc23)cc(OC)c1CN1CC(OCc2cn(CCCOc3ccc4c(c3)C(=O)N(C3CCC(=O)NC3=O)C4=O)nn2)C1] |

TABLE 1A-continued
Compounds D1-D177 of the Disclosure
| Compound No. | Structure |
|---|---|
| D137 | 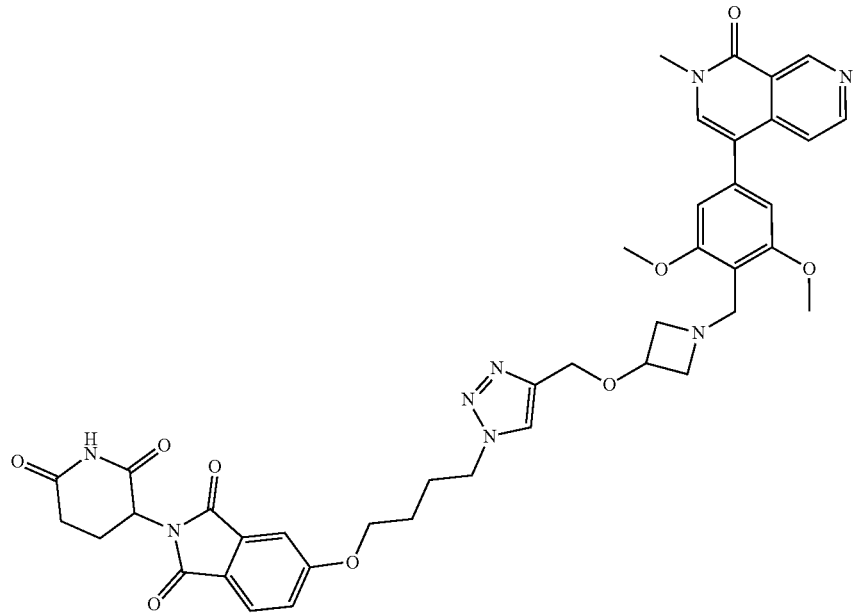 [SMILES: COc1cc(-c2cn(C)c(=O)c3cnccc23)cc(OC)c1CN1CC(OCc2cn(CCCCOc3ccc4c(c3)C(=O)N(C3CCC(=O)NC3=O)C4=O)nn2)C1] |
| D138 | 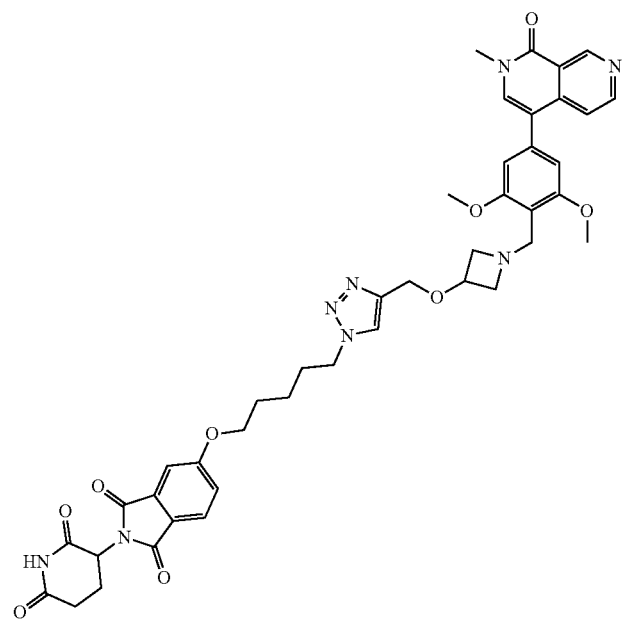 [SMILES: COc1cc(-c2cn(C)c(=O)c3cnccc23)cc(OC)c1CN1CC(OCc2cn(CCCCCOc3ccc4c(c3)C(=O)N(C3CCC(=O)NC3=O)C4=O)nn2)C1] |

TABLE 1A-continued

Compounds D1-D177 of the Disclosure

| Compound No. | Structure |
| --- | --- |
| D139 | 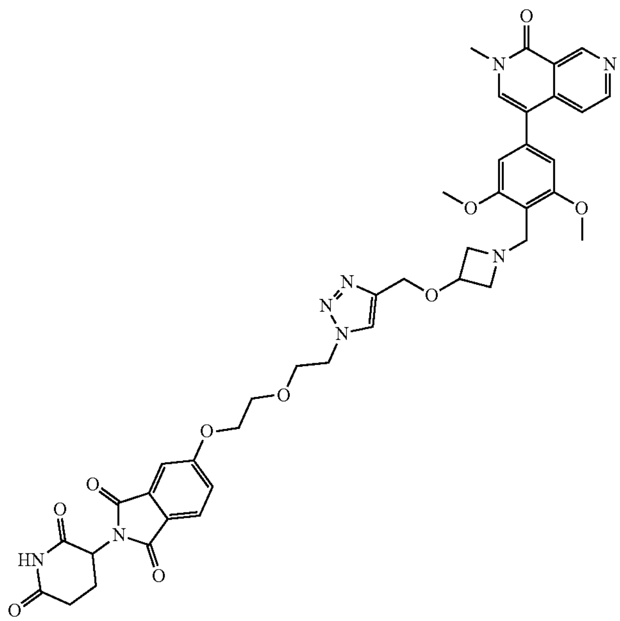 [SMILES: COc1cc(-c2cn(C)c(=O)c3cnccc23)cc(OC)c1CN1CC(OCc2cn(CCOCCOc3ccc4c(c3)C(=O)N(C3CCC(=O)NC3=O)C4=O)nn2)C1] |
| D140 | 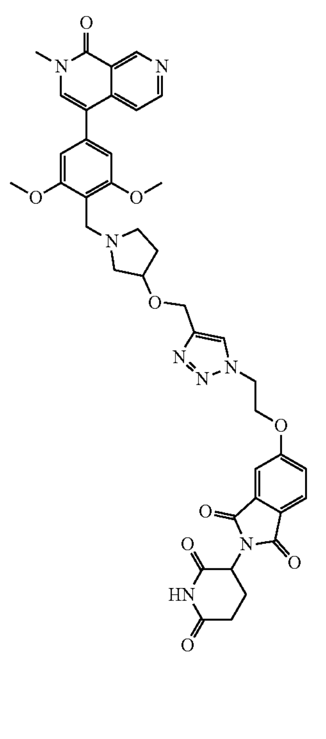 [SMILES: COc1cc(-c2cn(C)c(=O)c3cnccc23)cc(OC)c1CN1CCC(OCc2cn(CCOc3ccc4c(c3)C(=O)N(C3CCC(=O)NC3=O)C4=O)nn2)C1] |

TABLE 1A-continued

Compounds D1-D177 of the Disclosure

| Compound No. | Structure |
|---|---|
| D141 | 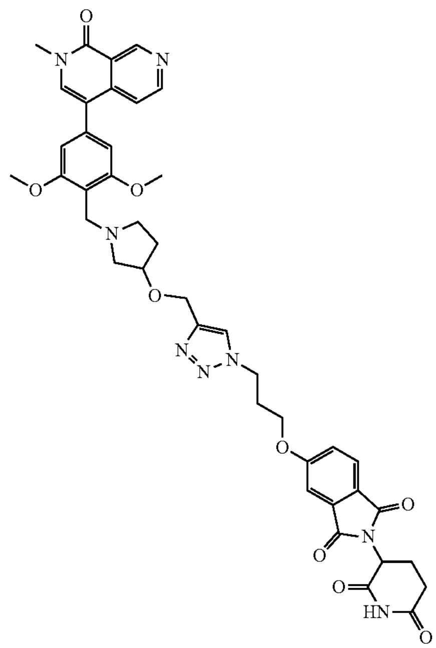 [SMILES: COc1cc(-c2cn(C)c(=O)c3cnccc23)cc(OC)c1CN1CCC(OCc2cn(CCCOc3ccc4c(c3)C(=O)N(C3CCC(=O)NC3=O)C4=O)nn2)C1] |
| D142 | 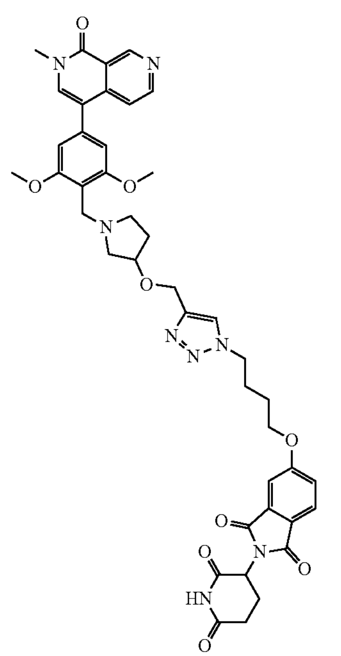 [SMILES: COc1cc(-c2cn(C)c(=O)c3cnccc23)cc(OC)c1CN1CCC(OCc2cn(CCCCOc3ccc4c(c3)C(=O)N(C3CCC(=O)NC3=O)C4=O)nn2)C1] |

TABLE 1A-continued
Compounds D1-D177 of the Disclosure
| Compound No. | Structure |
|---|---|
| D143 | 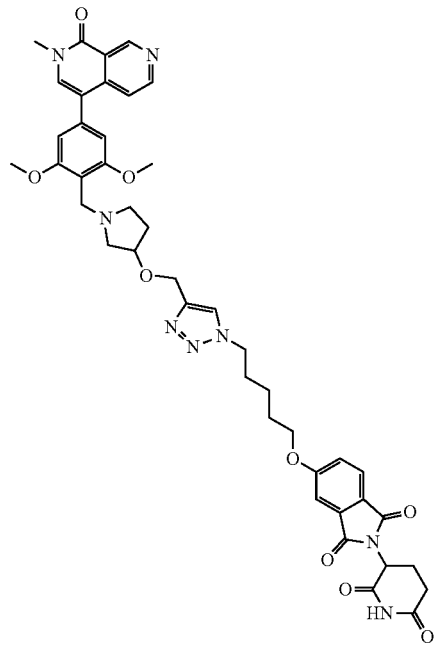 [SMILES: COc1cc(-c2cn(C)c(=O)c3cnccc23)cc(OC)c1CN1CCC(OCc2cn(CCCCCOc3ccc4c(c3)C(=O)N(C3CCC(=O)NC3=O)C4=O)nn2)C1] |
| D144 | 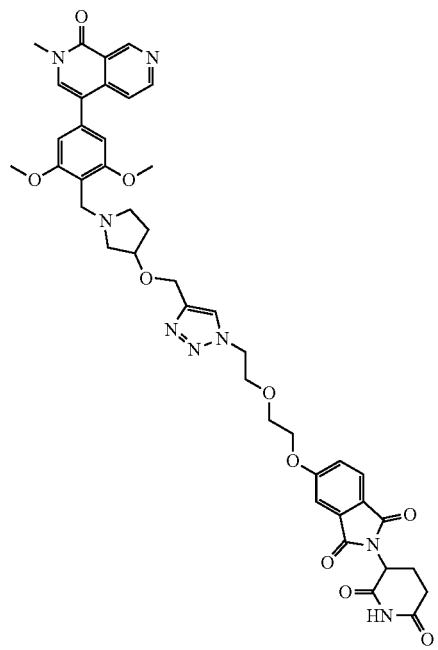 [SMILES: COc1cc(-c2cn(C)c(=O)c3cnccc23)cc(OC)c1CN1CCC(OCc2cn(CCOCCOc3ccc4c(c3)C(=O)N(C3CCC(=O)NC3=O)C4=O)nn2)C1] |

TABLE 1A-continued
Compounds D1-D177 of the Disclosure
| Compound No. | Structure |
| --- | --- |
| D145 | 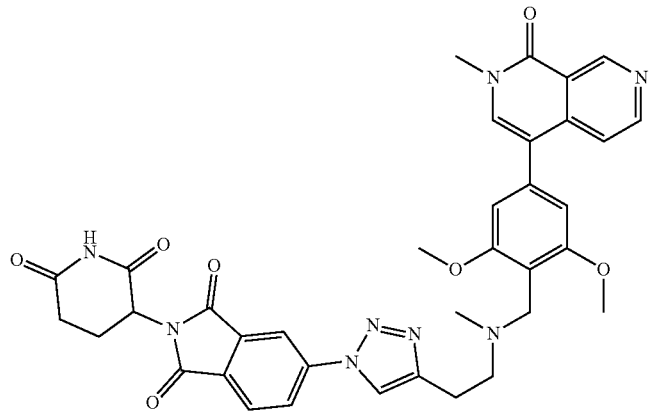 [SMILES: COc1cc(-c2cn(C)c(=O)c3cnccc23)cc(OC)c1CN(C)CCc1cn(-c2ccc3c(c2)C(=O)N(C2CCC(=O)NC2=O)C3=O)nn1] |
| D146 | 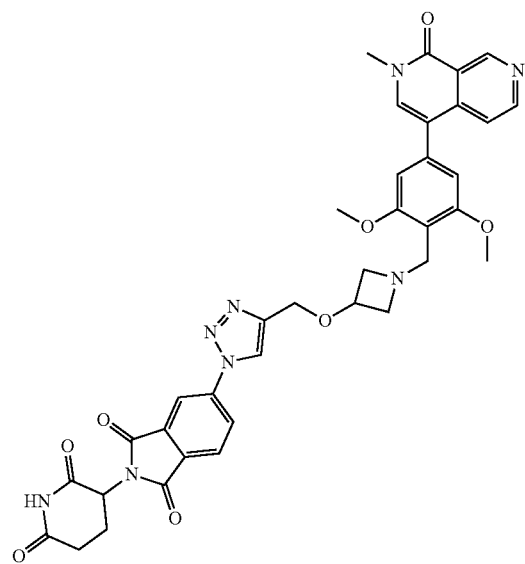 [SMILES: COc1cc(-c2cn(C)c(=O)c3cnccc23)cc(OC)c1CN1CC(OCc2cn(-c3ccc4c(c3)C(=O)N(C3CCC(=O)NC3=O)C4=O)nn2)C1] |
| D147 | 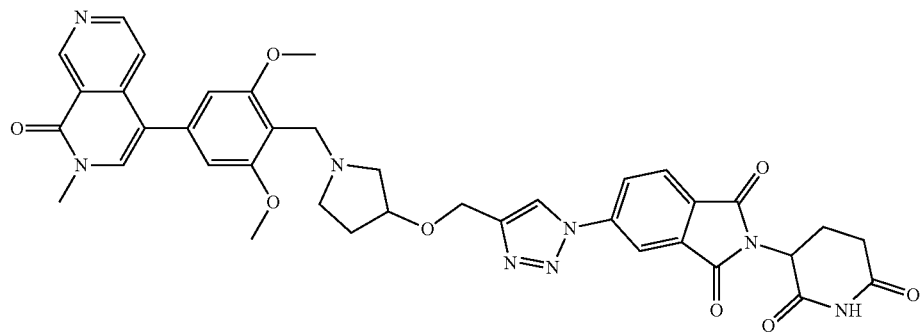 [SMILES: COc1cc(-c2cn(C)c(=O)c3cnccc23)cc(OC)c1CN1CCC(OCc2cn(-c3ccc4c(c3)C(=O)N(C3CCC(=O)NC3=O)C4=O)nn2)C1] |

TABLE 1A-continued
Compounds D1-D177 of the Disclosure
| Compound No. | Structure |
|---|---|
| D148 | 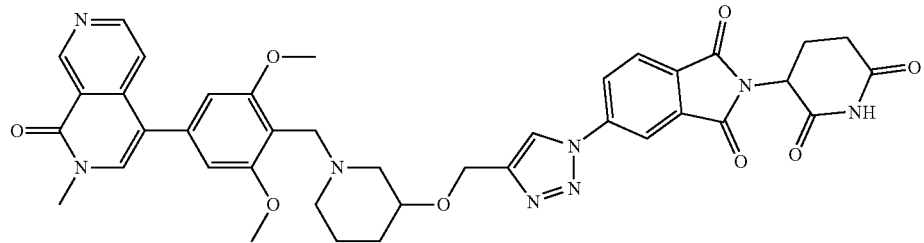 [SMILES: COc1cc(-c2cn(C)c(=O)c3cnccc23)cc(OC)c1CN1CCCC(OCc2cn(-c3ccc4c(c3)C(=O)N(C3CCC(=O)NC3=O)C4=O)nn2)C1] |
| D149 | 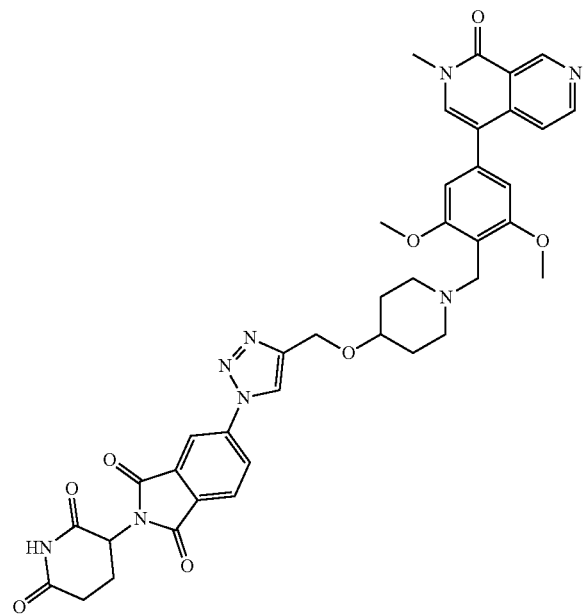 [SMILES: COc1cc(-c2cn(C)c(=O)c3cnccc23)cc(OC)c1CN1CCC(OCc2cn(-c3ccc4c(c3)C(=O)N(C3CCC(=O)NC3=O)C4=O)nn2)CC1] |
| D150 | 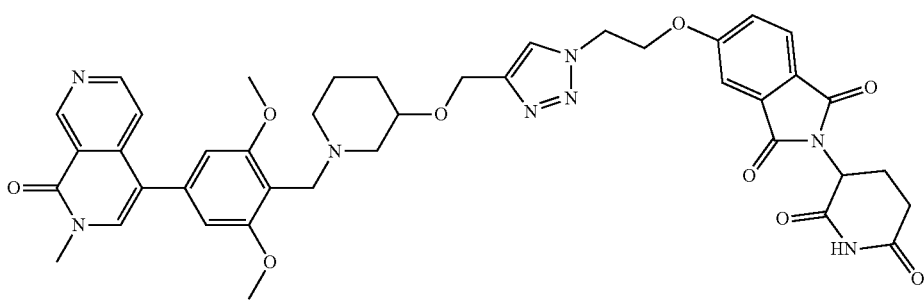 [SMILES: COc1cc(-c2cn(C)c(=O)c3cnccc23)cc(OC)c1CN1CCCC(OCc2cn(CCOc3ccc4c(c3)C(=O)N(C3CCC(=O)NC3=O)C4=O)nn2)C1] |

TABLE 1A-continued
Compounds D1-D177 of the Disclosure
| Compound No. | Structure |
|---|---|
| D151 | 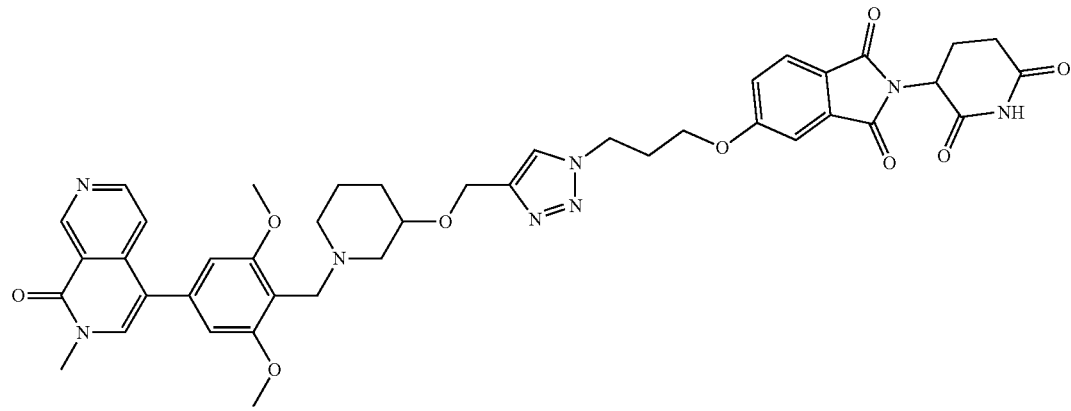 [SMILES: COc1cc(-c2cn(C)c(=O)c3cnccc23)cc(OC)c1CN1CCCC(OCc2cn(CCCOc3ccc4c(c3)C(=O)N(C3CCC(=O)NC3=O)C4=O)nn2)C1] |
| D152 | 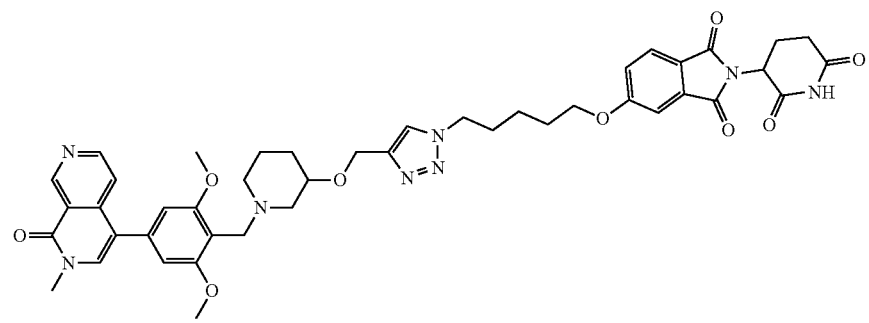 |
| D153 | 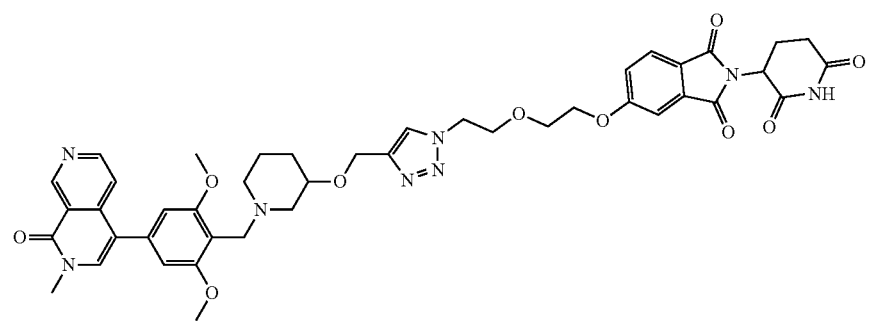 [SMILES: COc1cc(-c2cn(C)c(=O)c3cnccc23)cc(OC)c1CN1CCCC(OCc2cn(CCOCCOc3ccc4c(c3)C(=O)N(C3CCC(=O)NC3=O)C4=O)nn2)C1] |

TABLE 1A-continued

Compounds D1-D177 of the Disclosure

| Compound No. | Structure |
|---|---|
| D154 | 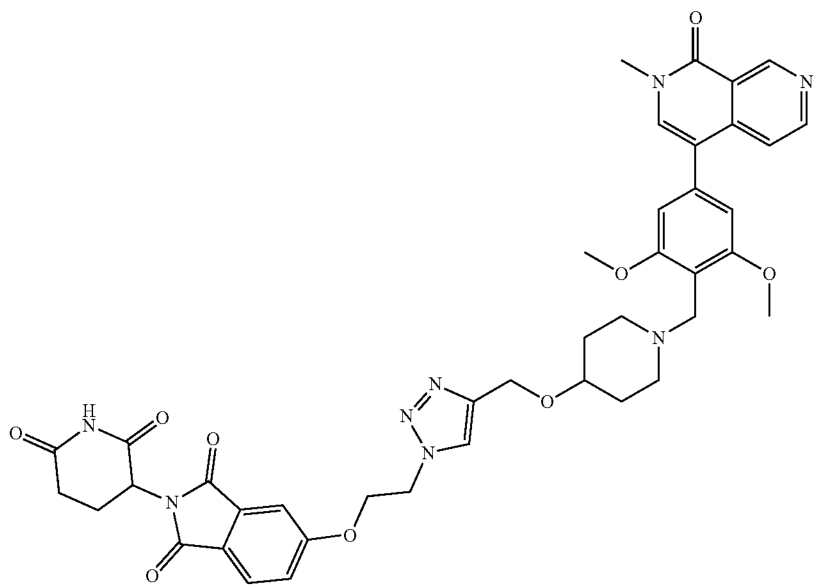 [SMILES: COc1cc(-c2cn(C)c(=O)c3cnccc23)cc(OC)c1CN1CCC(OCc2cn(CCOc3ccc4c(c3)C(=O)N(C3CCC(=O)NC3=O)C4=O)nn2)CC1] |
| D155 | 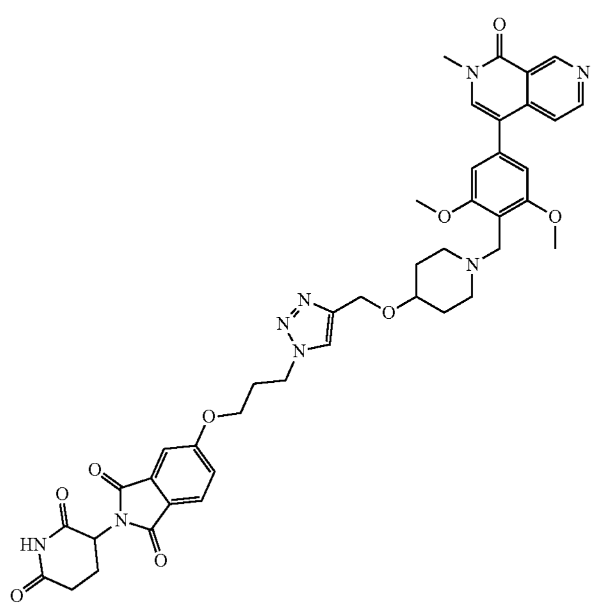 [SMILES: COc1cc(-c2cn(C)c(=O)c3cnccc23)cc(OC)c1CN1CCC(OCc2cn(CCCOc3ccc4c(c3)C(=O)N(C3CCC(=O)NC3=O)C4=O)nn2)CC1] |

TABLE 1A-continued
Compounds D1-D177 of the Disclosure
| Compound No. | Structure |
|---|---|
| D156 | 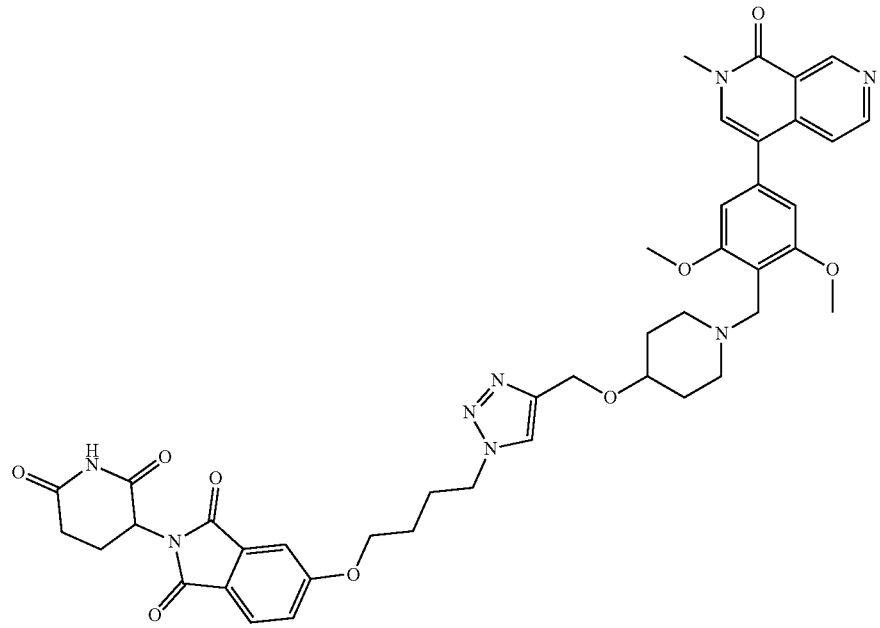 [SMILES: COc1cc(-c2cn(C)c(=O)c3cnccc23)cc(OC)c1CN1CCC(OCc2cn(CCCCOc3ccc4c(c3)C(=O)N(C3CCC(=O)NC3=O)C4=O)nn2)CC1] |
| D157 | 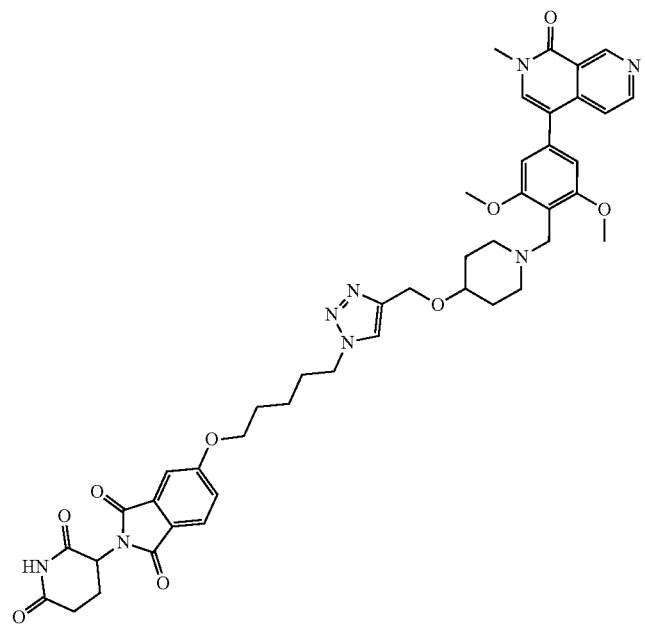 [SMILES: COc1cc(-c2cn(C)c(=O)c3cnccc23)cc(OC)c1CN1CCC(OCc2cn(CCCCCOc3ccc4c(c3)C(=O)N(C3CCC(=O)NC3=O)C4=O)nn2)CC1] |

TABLE 1A-continued
Compounds D1-D177 of the Disclosure
| Compound No. | Structure |
| --- | --- |
| D158 | 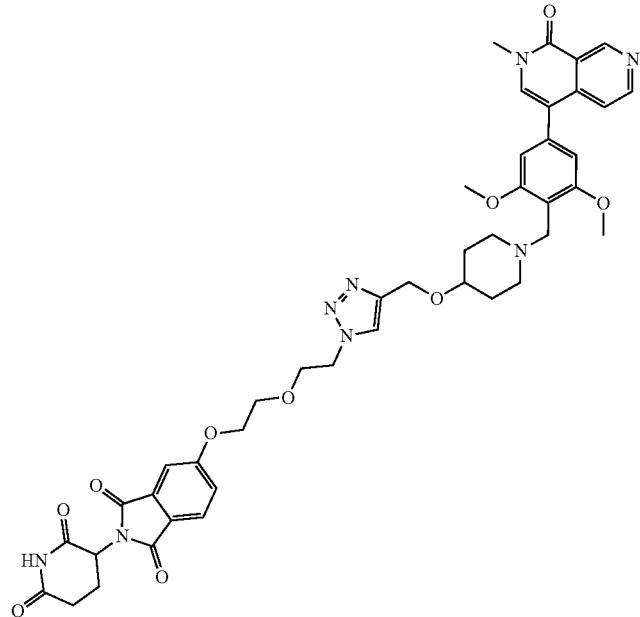 [SMILES: COc1cc(-c2cn(C)c(=O)c3cnccc23)cc(OC)c1CN1CCC(OCc2cn(CCOCCOc3ccc4c(c3)C(=O)N(C3CCC(=O)NC3=O)C4=O)nn2)CC1] |
| D159 | 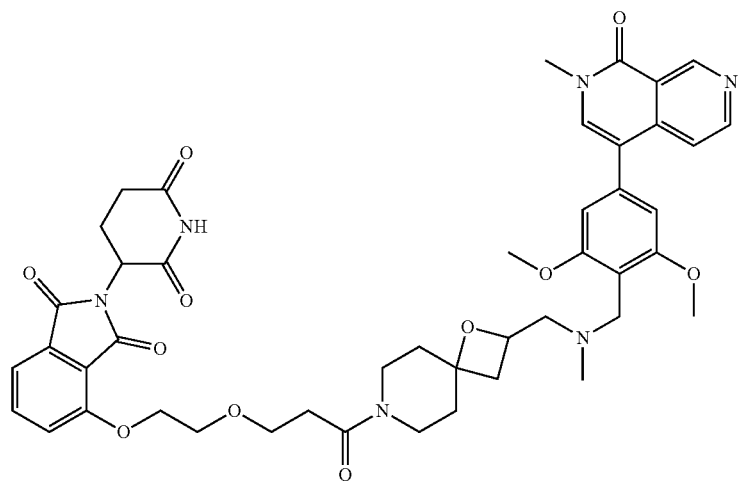 [SMILES: COc1cc(-c2cn(C)c(=O)c3cnccc23)cc(OC)c1CN(C)CC1CC2(CCN(C(=O)CCOCCOc3cccc4c3C(=O)N(C3CCC(=O)NC3=O)C4=O)CC2)O1] |

TABLE 1A-continued
Compounds D1-D177 of the Disclosure
| Compound No. | Structure |
|---|---|
| D160 | 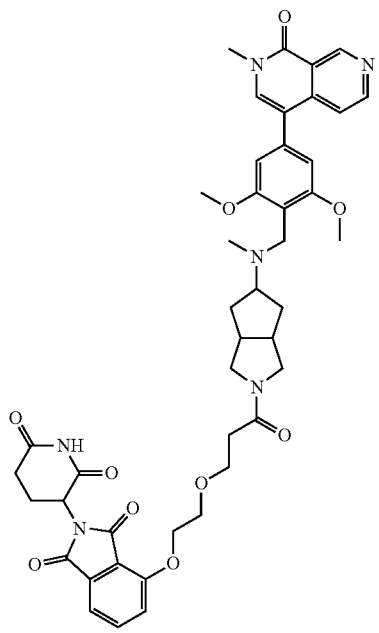 [SMILES: COc1cc(-c2cn(C)c(=O)c3cnccc23)cc(OC)c1CN(C)C1CC2CN(C(=O)CCOCCOc3cccc4c3C(=O)N(C3CCC(=O)NC3=O)C4=O)CC2C1] |
| D161 | 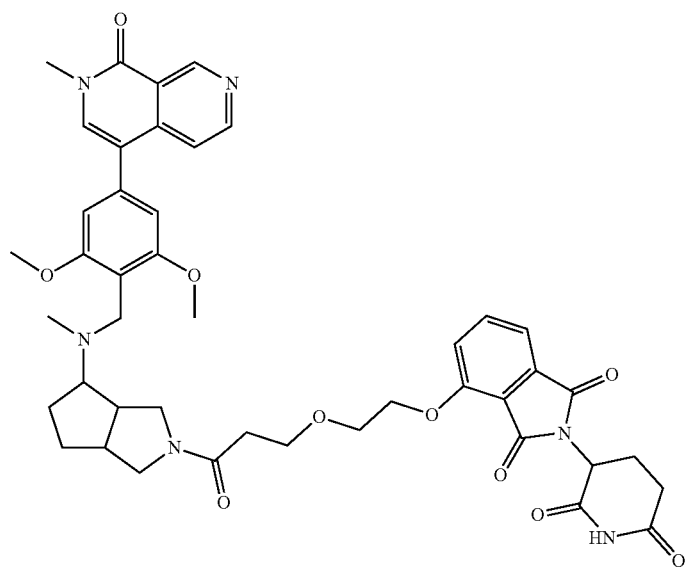 [SMILES: COc1cc(-c2cn(C)c(=O)c3cnccc23)cc(OC)c1CN(C)C1CCC2CN(C(=O)CCOCCOc3cccc4c3C(=O)N(C3CCC(=O)NC3=O)C4=O)CC21] |

TABLE 1A-continued
Compounds D1-D177 of the Disclosure
| Compound No. | Structure |
|---|---|
| D162 | 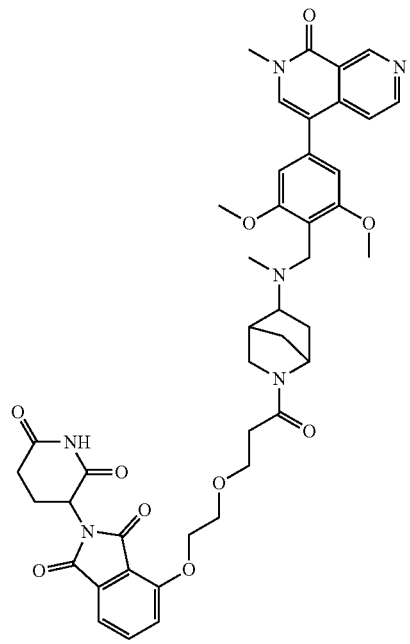 [SMILES: COc1cc(-c2cn(C)c(=O)c3cnccc23)cc(OC)c1CN(C)C1CC2CC1CN2C(=O)CCOCCOc1cccc2c1C(=O)N(C1CCC(=O)NC1=O)C2=O] |
| D163 | 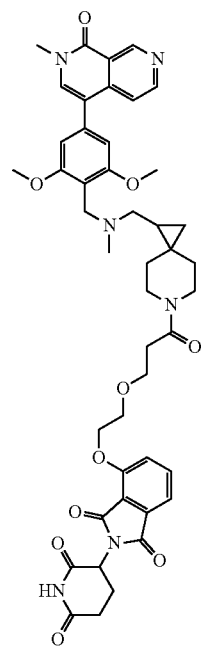 [SMILES: COc1cc(-c2cn(C)c(=O)c3cnccc23)cc(OC)c1CN(C)CC1CC12CCN(C(=O)CCOCCOc1cccc3c1C(=O)N(C1CCC(=O)NC1=O)C3=O)CC2] |

TABLE 1A-continued
Compounds D1-D177 of the Disclosure
| Compound No. | Structure |
|---|---|
| D164 | 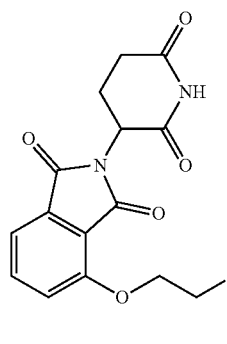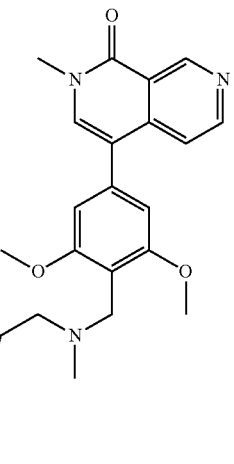 |
| D165 | 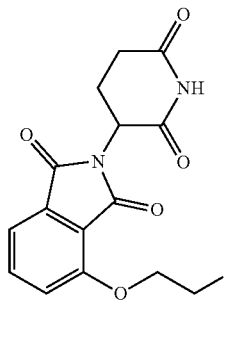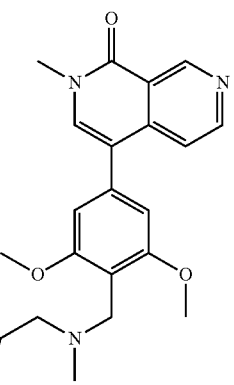 |

TABLE 1A-continued
Compounds D1-D177 of the Disclosure
| Compound No. | Structure |
|---|---|
| D166 | 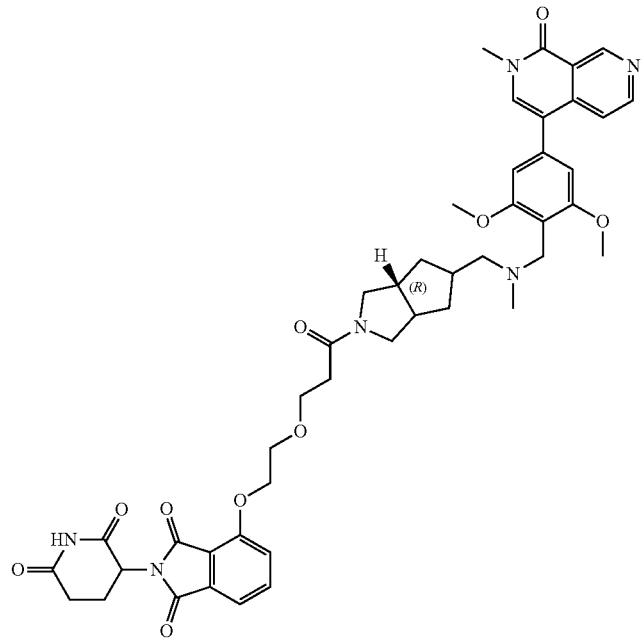 |
| D167 | 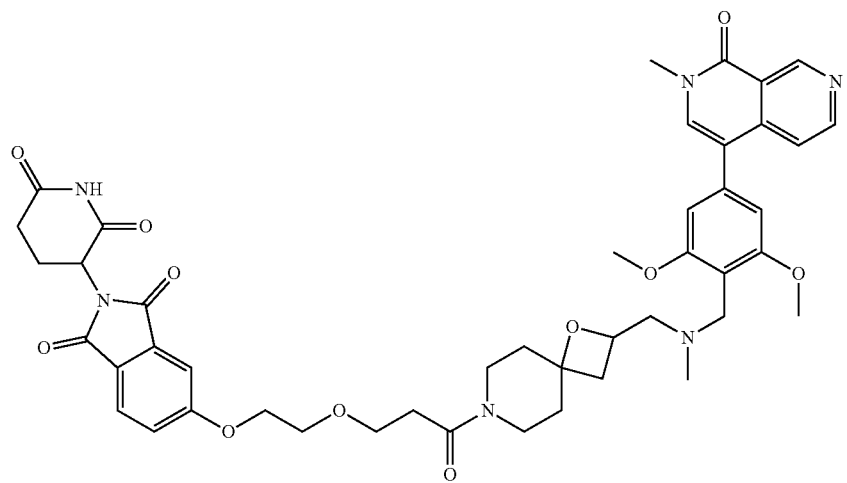 |

TABLE 1A-continued
Compounds D1-D177 of the Disclosure
| Compound No. | Structure |
| --- | --- |
| D168 | 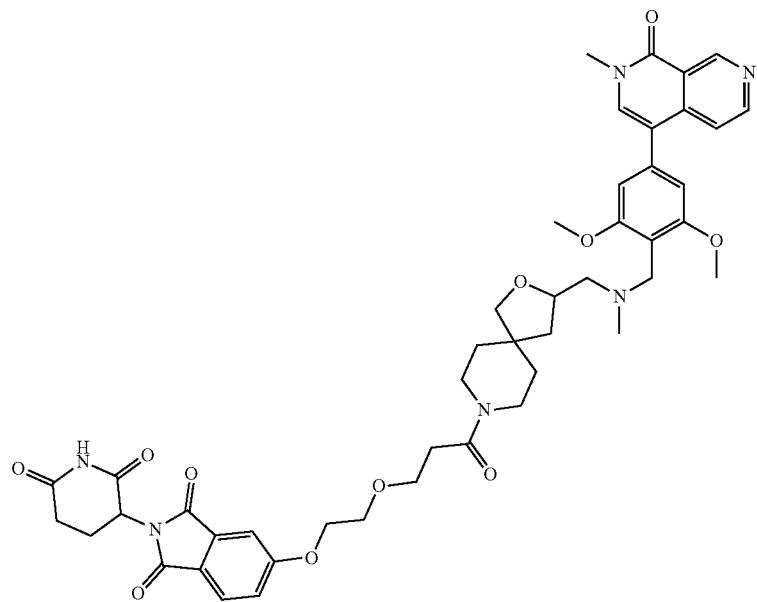 [SMILES: COc1cc(-c2cn(C)c(=O)c3cnccc23)cc(OC)c1CN(C)CC1CC2(CCN(C(=O)CCOCCOc3ccc4c(c3)C(=O)N(C3CCC(=O)NC3=O)C4=O)CC2)CO1] |
| D169 | 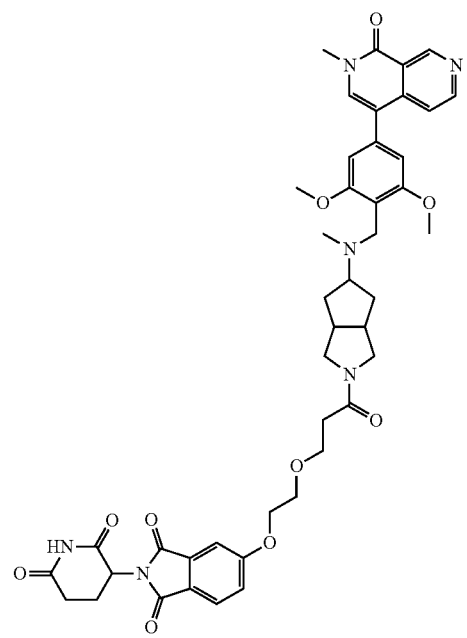 [SMILES: COc1cc(-c2cn(C)c(=O)c3cnccc23)cc(OC)c1CN(C)C1CC2CN(C(=O)CCOCCOc3ccc4c(c3)C(=O)N(C3CCC(=O)NC3=O)C4=O)CC2C1] |

TABLE 1A-continued
Compounds D1-D177 of the Disclosure
| Compound No. | Structure |
|---|---|
| D170 | 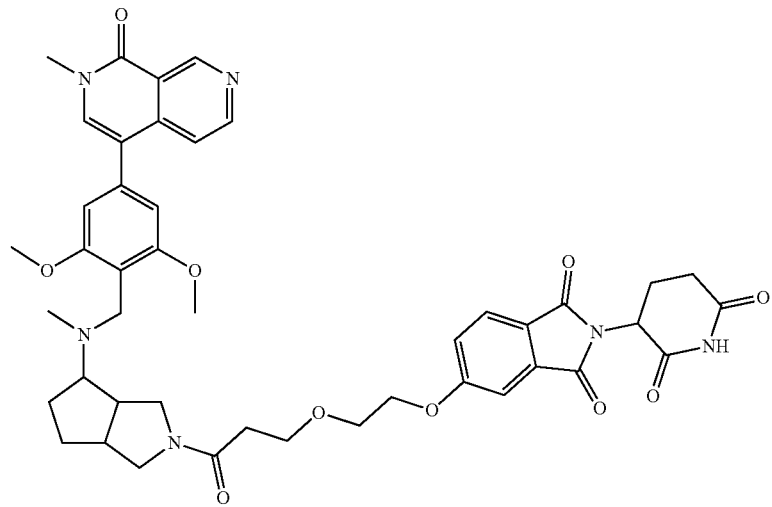 [SMILES: COc1cc(-c2cn(C)c(=O)c3cnccc23)cc(OC)c1CN(C)C1CCC2CN(C(=O)CCOCCOc3ccc4c(c3)C(=O)N(C3CCC(=O)NC3=O)C4=O)CC21] |
| D171 | 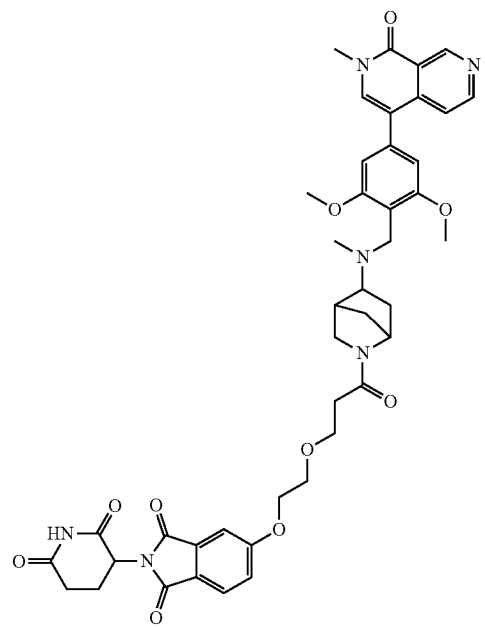 [SMILES: COc1cc(-c2cn(C)c(=O)c3cnccc23)cc(OC)c1CN(C)C1CC2CC1CN2C(=O)CCOCCOc1ccc2c(c1)C(=O)N(C1CCC(=O)NC1=O)C2=O] |

TABLE 1A-continued
Compounds D1-D177 of the Disclosure
| Compound No. | Structure |
|---|---|
| D172 | 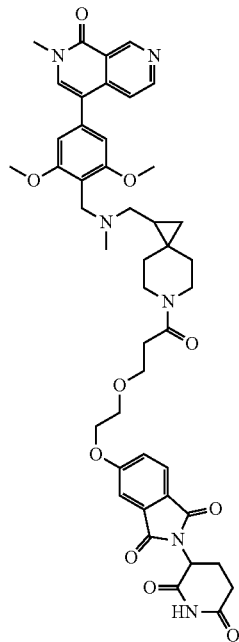 [SMILES: COc1cc(-c2cn(C)c(=O)c3cnccc23)cc(OC)c1CN(C)CC1CC12CCN(C(=O)CCOCCOc1ccc3c(c1)C(=O)N(C1CCC(=O)NC1=O)C3=O)CC2] |
| D173 | 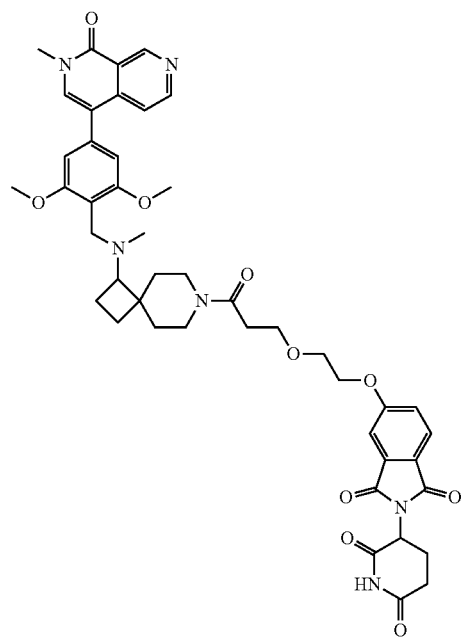 [SMILES: COc1cc(-c2cn(C)c(=O)c3cnccc23)cc(OC)c1CN(C)C1CCC12CCN(C(=O)CCOCCOc1ccc3c(c1)C(=O)N(C1CCC(=O)NC1=O)C3=O)CC2] |

TABLE 1A-continued

Compounds D1-D177 of the Disclosure

| Compound No. | Structure |
|---|---|
| D174 | 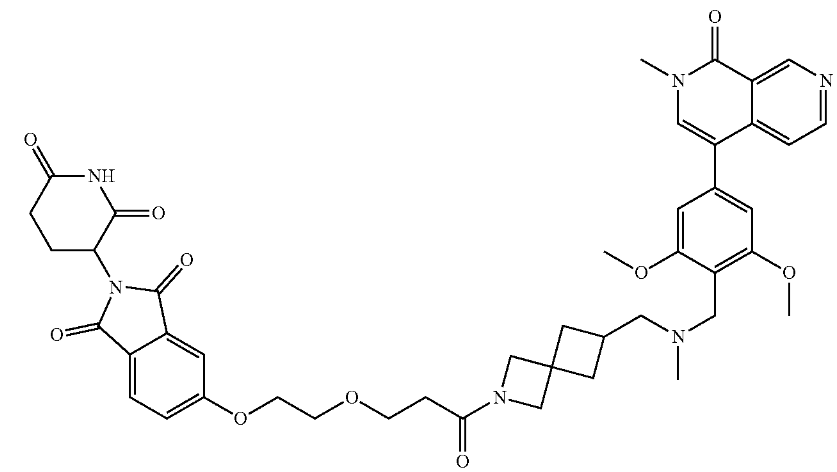 [SMILES: COc1cc(-c2cn(C)c(=O)c3cnccc23)cc(OC)c1CN(C)CC1CC2(C1)CN(C(=O)CCOCCOc1ccc3c(c1)C(=O)N(C1CCC(=O)NC1=O)C3=O)C2] |
| D175 | 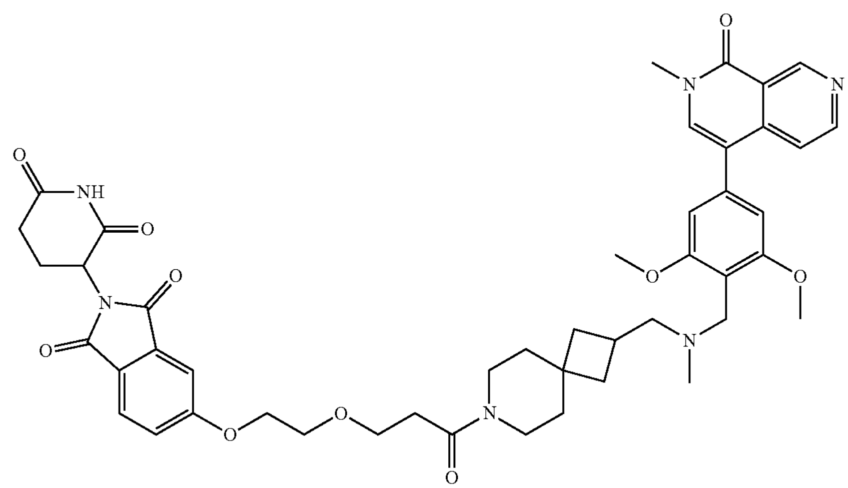 [SMILES: COc1cc(-c2cn(C)c(=O)c3cnccc23)cc(OC)c1CN(C)CC1CC2(CCN(C(=O)CCOCCOc3ccc4c(c3)C(=O)N(C3CCC(=O)NC3=O)C4=O)CC2)C1] |
| D176 | 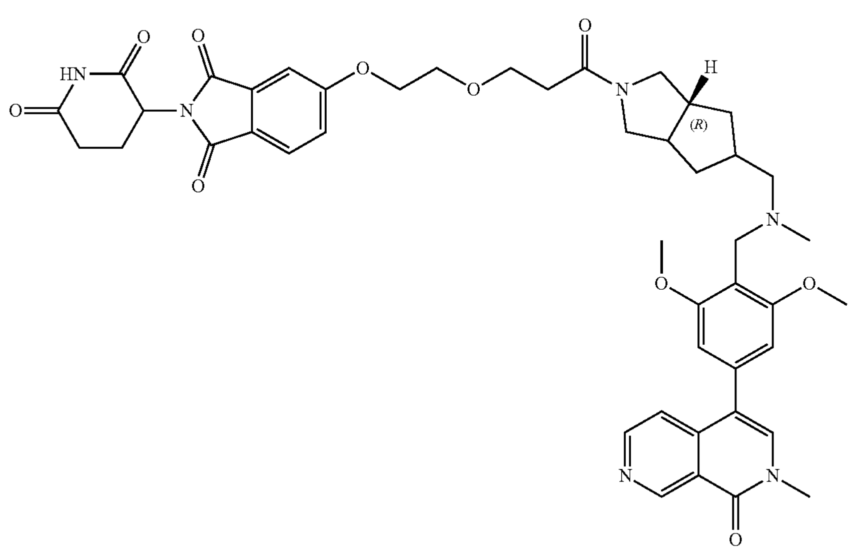 |

TABLE 1A-continued
Compounds D1-D177 of the Disclosure
| Compound No. | Structure |
| --- | --- |
| D177 | 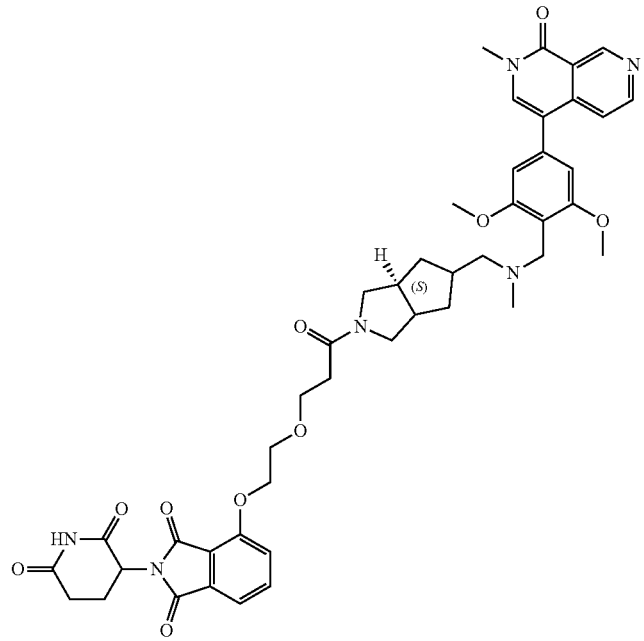 |
TABLE 1B
Compounds D178-D371 of the Disclosure
| Compound No. | Structure |
| --- | --- |
| D178 | 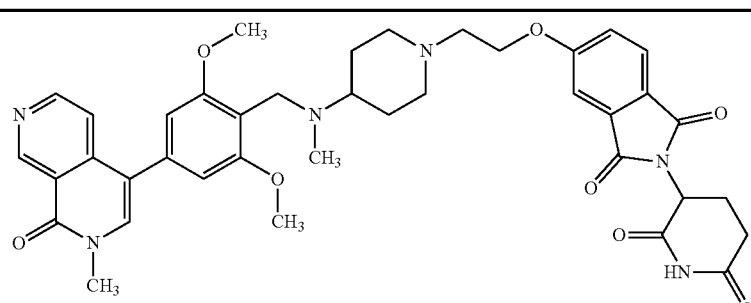 |
| D179 | 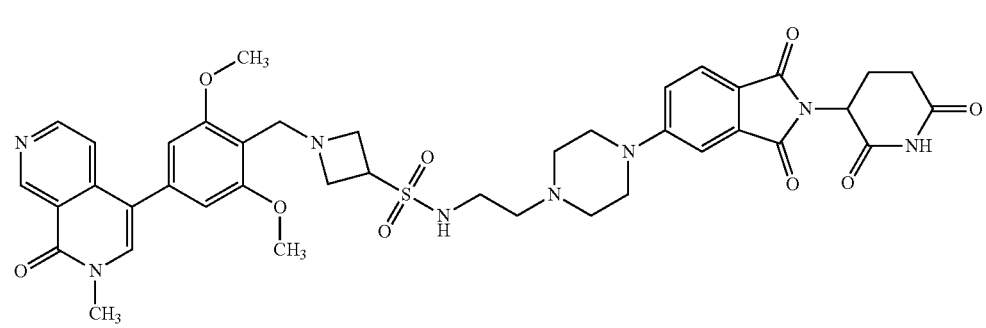 [SMILES: COc1cc(-c2cn(C)c(=O)c3cnccc23)cc(OC)c1CN1CC(S(=O)(=O)NCCN2CCN(c3ccc4c(c3)C(=O)N(C3CCC(=O)NC3=O)C4=O)CC2)C1] |

TABLE 1B-continued
Compounds D178-D371 of the Disclosure
| Compound No. | Structure |
|---|---|
| D180 | 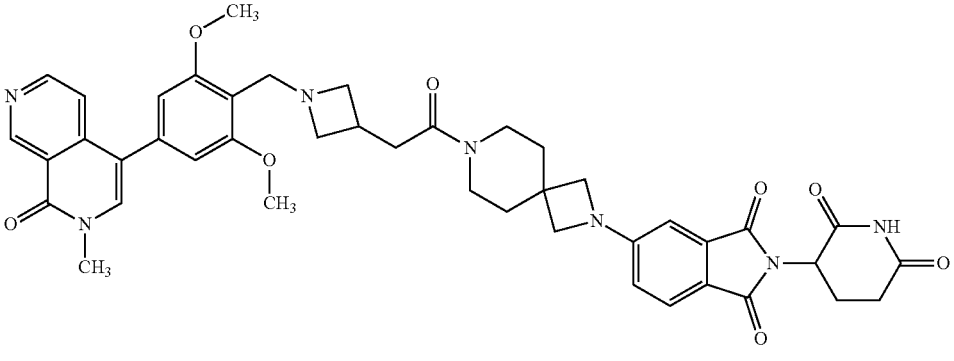 [SMILES: COc1cc(-c2cn(C)c(=O)c3cnccc23)cc(OC)c1CN1CC(CC(=O)N2CCC3(CC2)CN(c2ccc4c(c2)C(=O)N(C2CCC(=O)NC2=O)C4=O)C3)C1] |
| D181 | 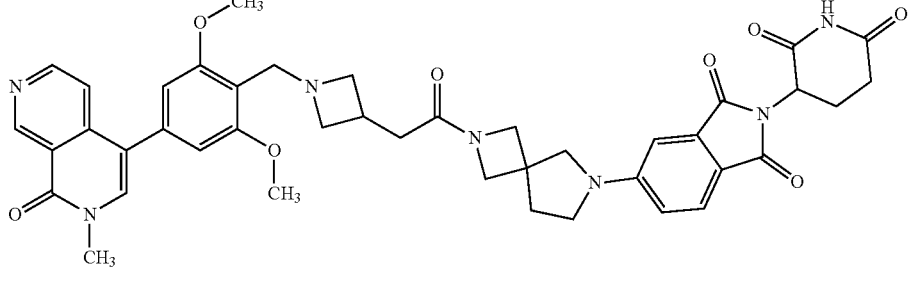 |
| D182 | 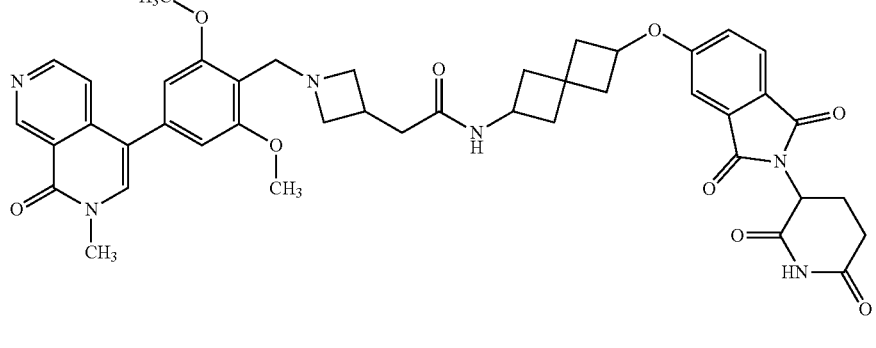 |
| D183 | 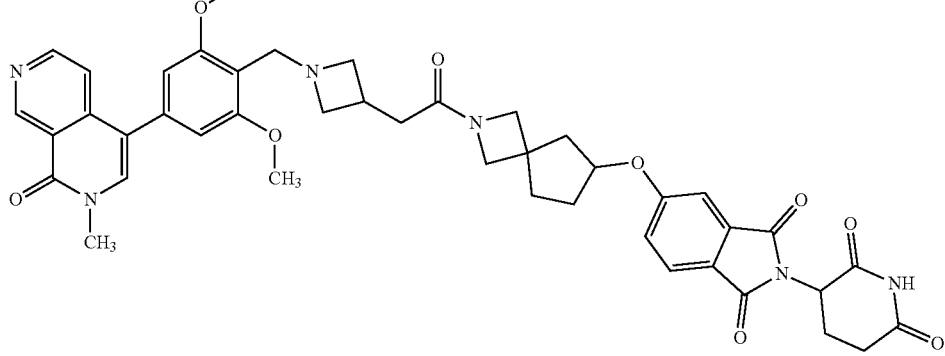 |

TABLE 1B-continued
Compounds D178-D371 of the Disclosure
| Compound No. | Structure |
| --- | --- |
| D184 | 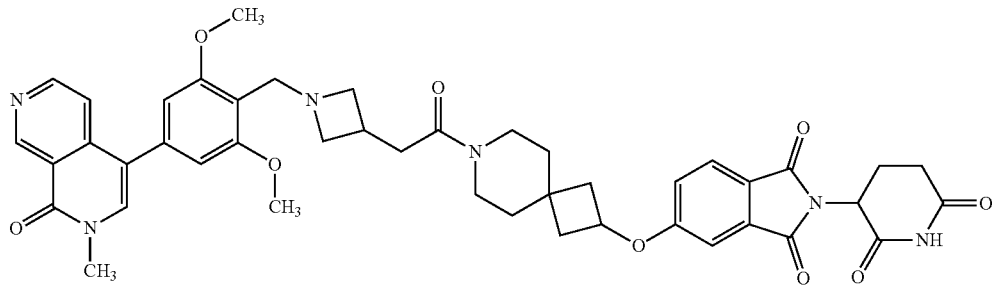 [SMILES: COc1cc(-c2cn(C)c(=O)c3cnccc23)cc(OC)c1CN1CC(CC(=O)N2CCC3(CC2)CC(Oc2ccc4c(c2)C(=O)N(C2CCC(=O)NC2=O)C4=O)C3)C1] |
| D185 | 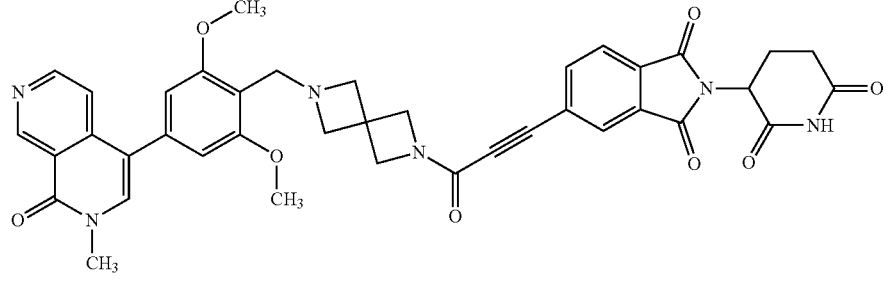 [SMILES: COc1cc(-c2cn(C)c(=O)c3cnccc23)cc(OC)c1CN1CC2(C1)CN(C(=O)C#Cc1ccc3c(c1)C(=O)N(C1CCC(=O)NC1=O)C3=O)C2] |
| D186 | 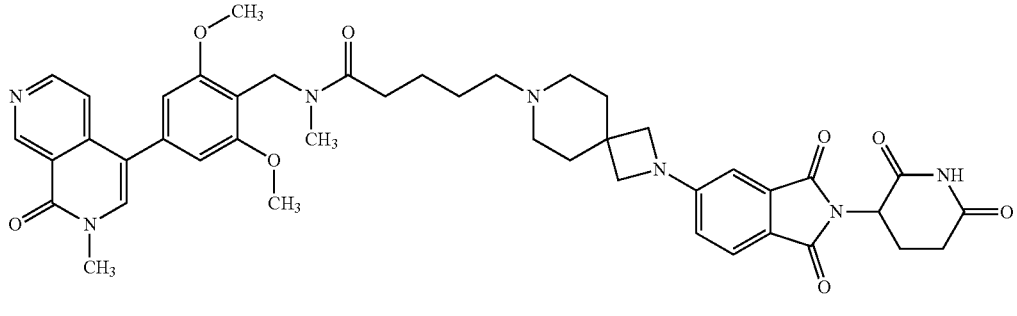 [SMILES: COc1cc(-c2cn(C)c(=O)c3cnccc23)cc(OC)c1CN(C)C(=O)CCCCN1CCC2(CC1)CN(c1ccc3c(c1)C(=O)N(C1CCC(=O)NC1=O)C3=O)C2] |
| D187 | 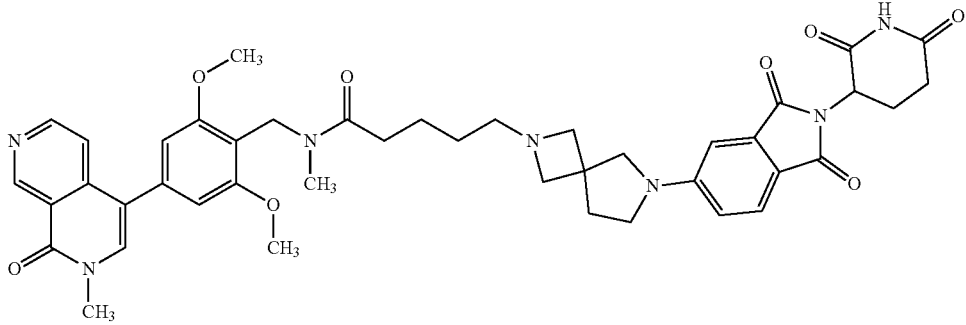 [SMILES: COc1cc(-c2cn(C)c(=O)c3cnccc23)cc(OC)c1CN(C)C(=O)CCCCN1CC2(CCN(c3ccc4c(c3)C(=O)N(C3CCC(=O)NC3=O)C4=O)C2)C1] |

TABLE 1B-continued
Compounds D178-D371 of the Disclosure
| Compound No. | Structure |
|---|---|
| D188 | 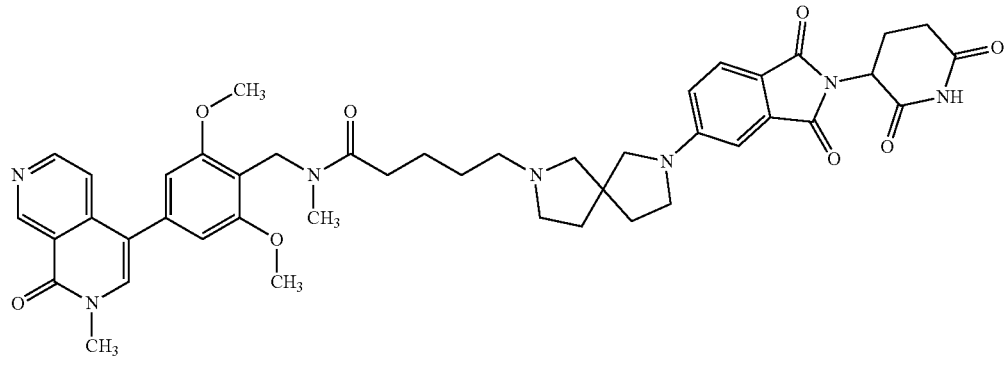 [SMILES: COc1cc(-c2cn(C)c(=O)c3cnccc23)cc(OC)c1CN(C)C(=O)CCCCN1CCC2(CCN(c3ccc4c(c3)C(=O)N(C3CCC(=O)NC3=O)C4=O)C2)C1] |
| D189 | 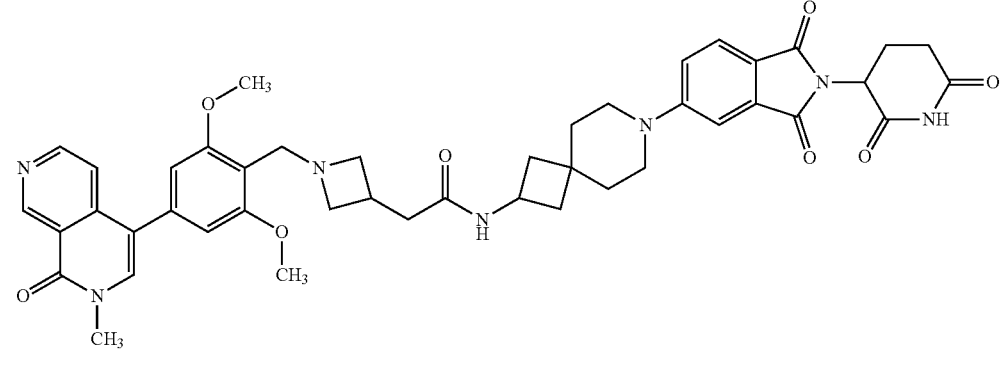 [SMILES: COc1cc(-c2cn(C)c(=O)c3cnccc23)cc(OC)c1CN1CC(CC(=O)NC2CC3(CCN(c4ccc5c(c4)C(=O)N(C4CCC(=O)NC4=O)C5=O)CC3)C2)C1] |
| D190 | 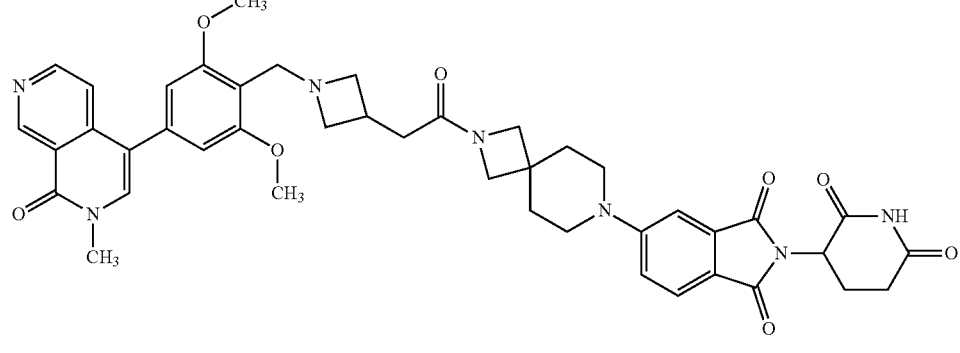 |
| D191 | 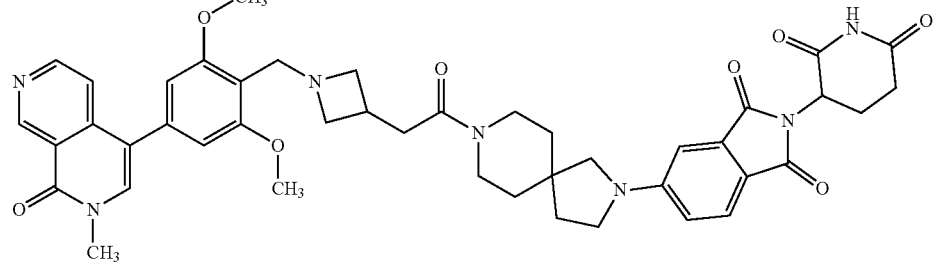 |

TABLE 1B-continued
Compounds D178-D371 of the Disclosure
| Compound No. | Structure |
|---|---|
| D192 | 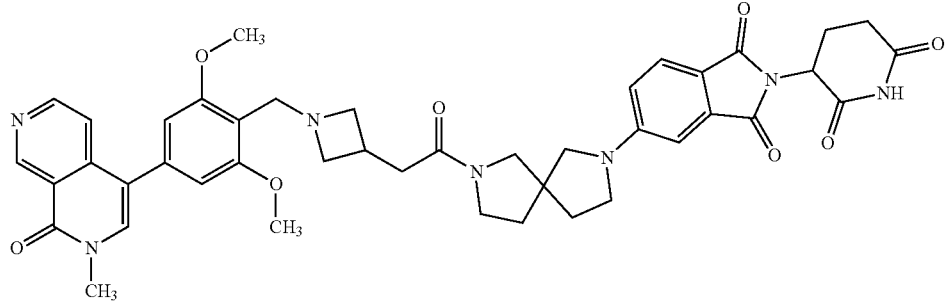 [SMILES: COc1cc(-c2cn(C)c(=O)c3cnccc23)cc(OC)c1CN1CC(CC(=O)N2CCC3(CCN(c4ccc5c(c4)C(=O)N(C4CCC(=O)NC4=O)C5=O)C3)C2)C1] |
| D193 | 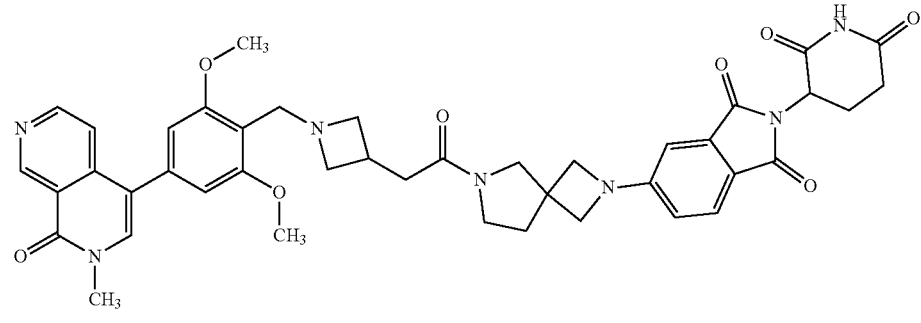 [SMILES: COc1cc(-c2cn(C)c(=O)c3cnccc23)cc(OC)c1CN1CC(CC(=O)N2CCC3(C2)CN(c2ccc4c(c2)C(=O)N(C2CCC(=O)NC2=O)C4=O)C3)C1] |
| D194 | 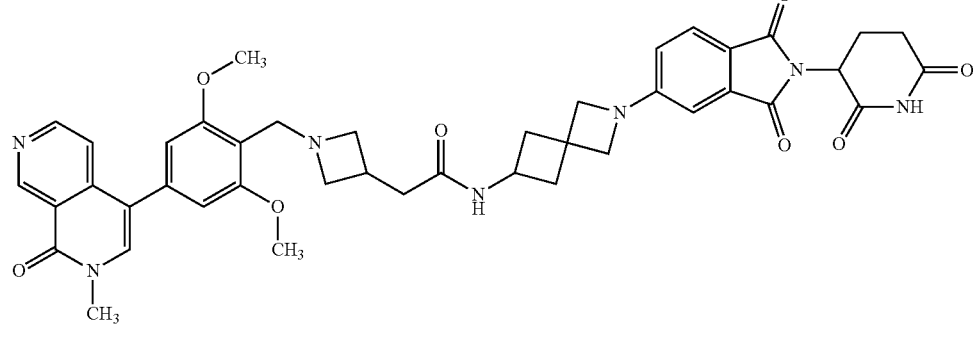 |
| D195 | 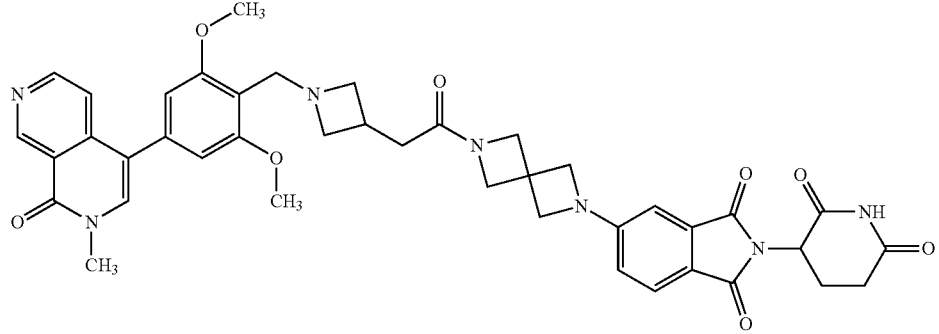 [SMILES: COc1cc(-c2cn(C)c(=O)c3cnccc23)cc(OC)c1CN1CC(CC(=O)N2CC3(C2)CN(c2ccc4c(c2)C(=O)N(C2CCC(=O)NC2=O)C4=O)C3)C1] |

TABLE 1B-continued

Compounds D178-D371 of the Disclosure

| Compound No. | Structure |
|---|---|
| D196 | 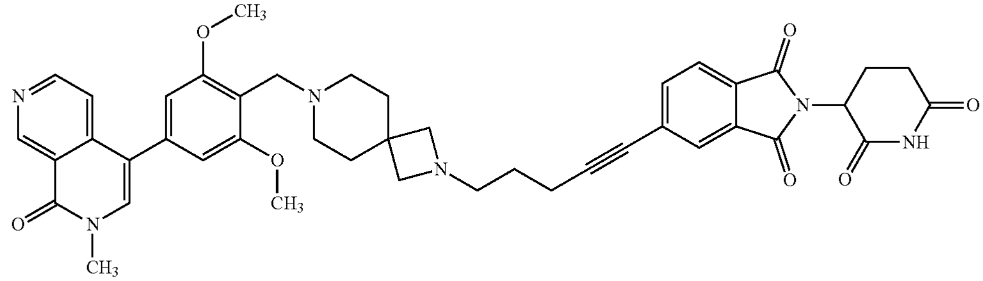 [SMILES: COc1cc(-c2cn(C)c(=O)c3cnccc23)cc(OC)c1CN1CCC2(CC1)CN(CCCC#Cc1ccc3c(c1)C(=O)N(C1CCC(=O)NC1=O)C3=O)C2] |
| D197 | 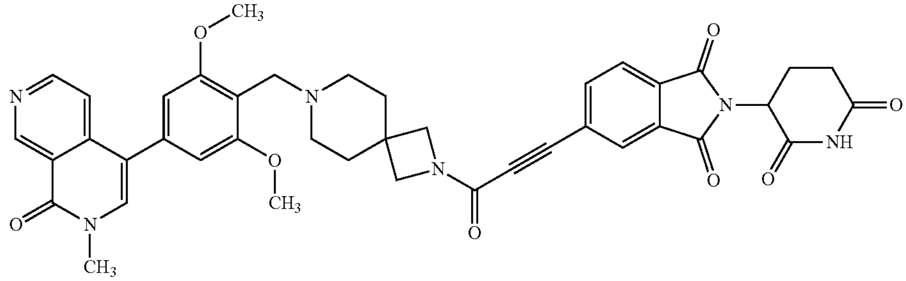 [SMILES: COc1cc(-c2cn(C)c(=O)c3cnccc23)cc(OC)c1CN1CCC2(CC1)CN(C(=O)C#Cc1ccc3c(c1)C(=O)N(C1CCC(=O)NC1=O)C3=O)C2] |
| D198 | 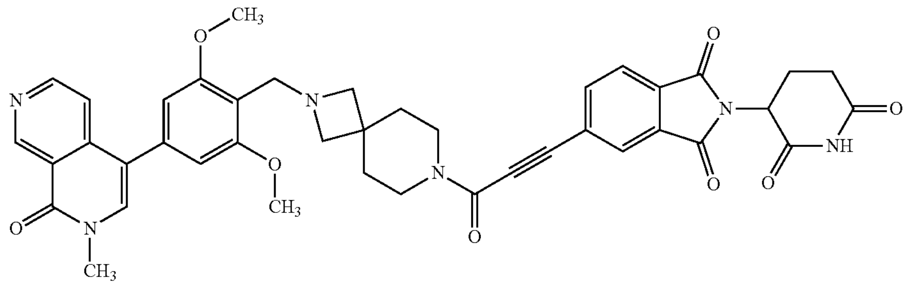 [SMILES: COc1cc(-c2cn(C)c(=O)c3cnccc23)cc(OC)c1CN1CC2(CCN(C(=O)C#Cc3ccc4c(c3)C(=O)N(C3CCC(=O)NC3=O)C4=O)CC2)C1] |
| D199 | 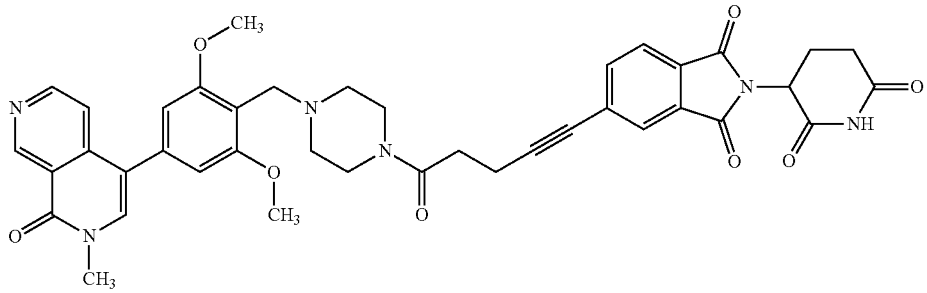 [SMILES: COc1cc(-c2cn(C)c(=O)c3cnccc23)cc(OC)c1CN1CCN(C(=O)CCC#Cc2ccc3c(c2)C(=O)N(C2CCC(=O)NC2=O)C3=O)CC1] |
| D200 | 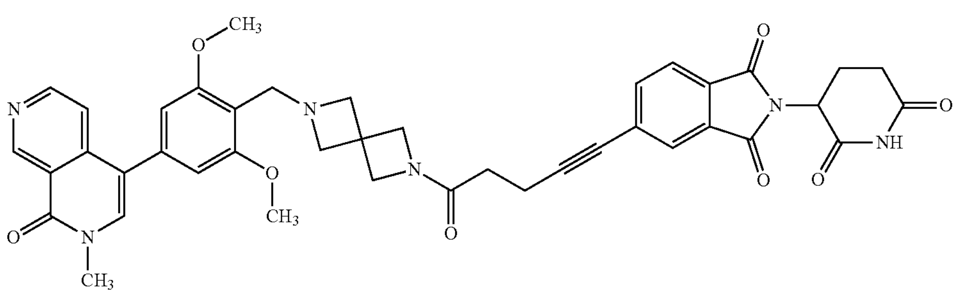 |

TABLE 1B-continued

Compounds D178-D371 of the Disclosure

| Compound No. | Structure |
|---|---|
| D201 | 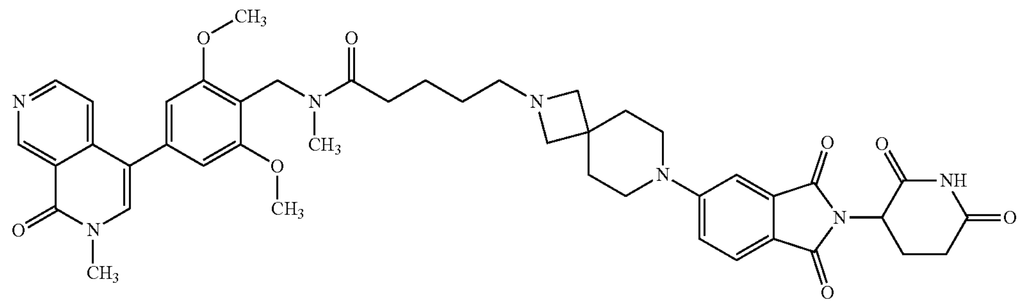 [SMILES: COc1cc(-c2cn(C)c(=O)c3cnccc23)cc(OC)c1CN(C)C(=O)CCCCN1CC2(CCN(c3ccc4c(c3)C(=O)N(C3CCC(=O)NC3=O)C4=O)CC2)C1] |
| D202 | 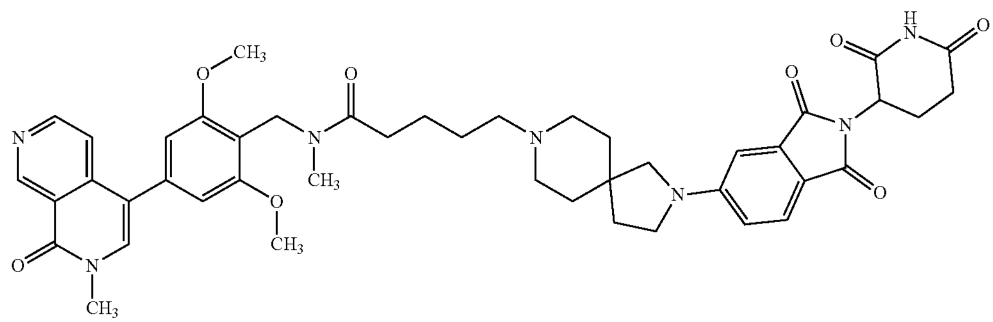 [SMILES: COc1cc(-c2cn(C)c(=O)c3cnccc23)cc(OC)c1CN(C)C(=O)CCCCN1CCC2(CC1)CCN(c1ccc3c(c1)C(=O)N(C1CCC(=O)NC1=O)C3=O)C2] |
| D203 | 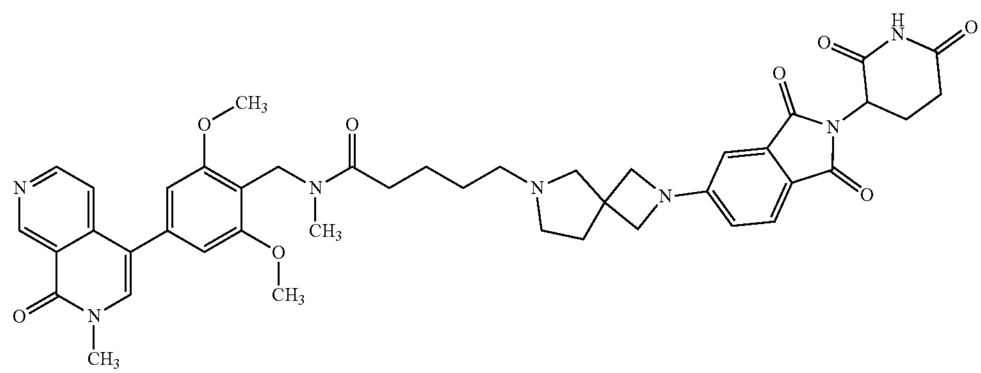 [SMILES: COc1cc(-c2cn(C)c(=O)c3cnccc23)cc(OC)c1CN(C)C(=O)CCCCN1CCC2(C1)CN(c1ccc3c(c1)C(=O)N(C1CCC(=O)NC1=O)C3=O)C2] |
| D204 | 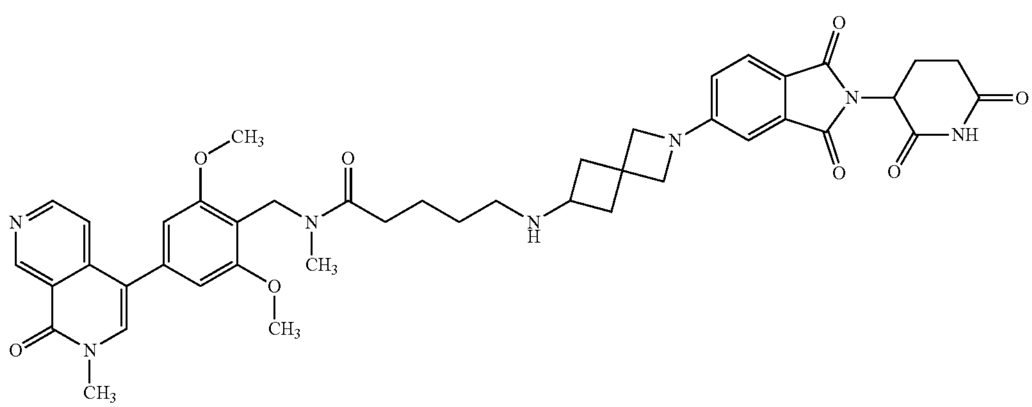 [SMILES: COc1cc(-c2cn(C)c(=O)c3cnccc23)cc(OC)c1CN(C)C(=O)CCCCNC1CC2(C1)CN(c1ccc3c(c1)C(=O)N(C1CCC(=O)NC1=O)C3=O)C2] |

TABLE 1B-continued

Compounds D178-D371 of the Disclosure

| Compound No. | Structure |
|---|---|
| D205 | 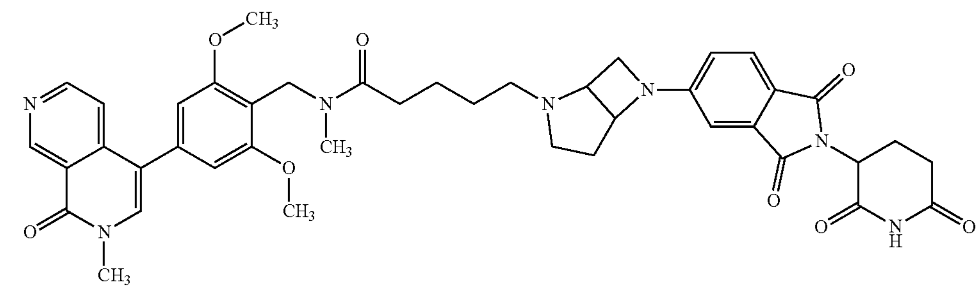 [SMILES: COc1cc(-c2cn(C)c(=O)c3cnccc23)cc(OC)c1CN(C)C(=O)CCCCN1CCC2C1CN2c1ccc2c(c1)C(=O)N(C1CCC(=O)NC1=O)C2=O] |
| D206 | 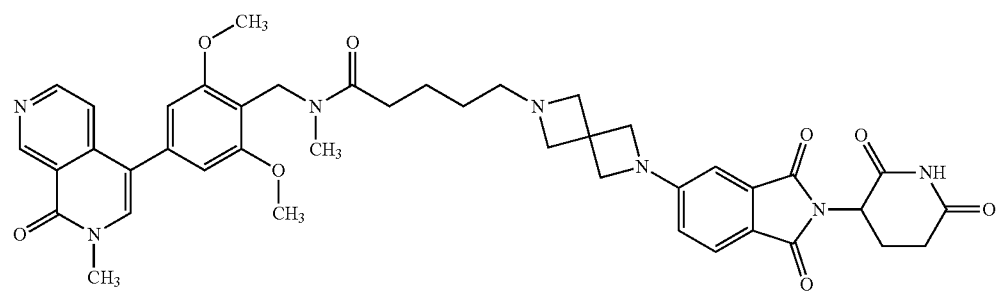 [SMILES: COc1cc(-c2cn(C)c(=O)c3cnccc23)cc(OC)c1CN(C)C(=O)CCCCN1CC2(C1)CN(c1ccc3c(c1)C(=O)N(C1CCC(=O)NC1=O)C3=O)C2] |
| D207 | 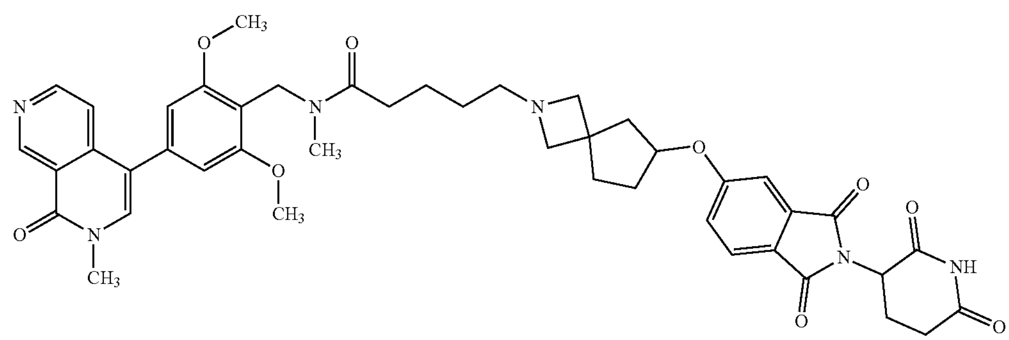 [SMILES: COc1cc(-c2cn(C)c(=O)c3cnccc23)cc(OC)c1CN(C)C(=O)CCCCN1CC2(CCC(Oc3ccc4c(c3)C(=O)N(C3CCC(=O)NC3=O)C4=O)C2)C1] |
| D208 | 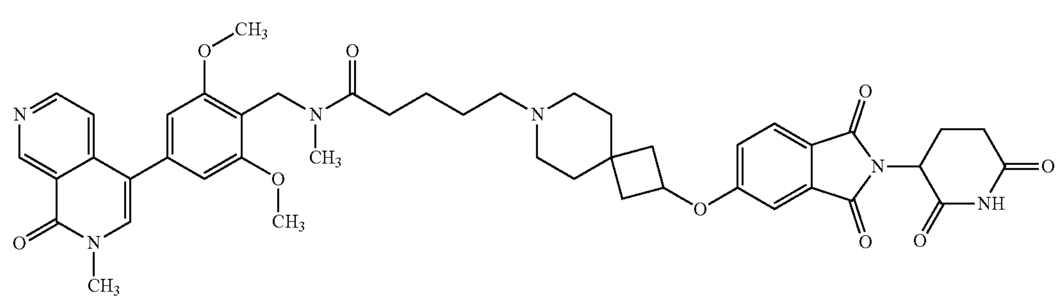 [SMILES: COc1cc(-c2cn(C)c(=O)c3cnccc23)cc(OC)c1CN(C)C(=O)CCCCN1CCC2(CC1)CC(Oc1ccc3c(c1)C(=O)N(C1CCC(=O)NC1=O)C3=O)C2] |

TABLE 1B-continued

Compounds D178-D371 of the Disclosure

| Compound No. | Structure |
| --- | --- |
| D209 | 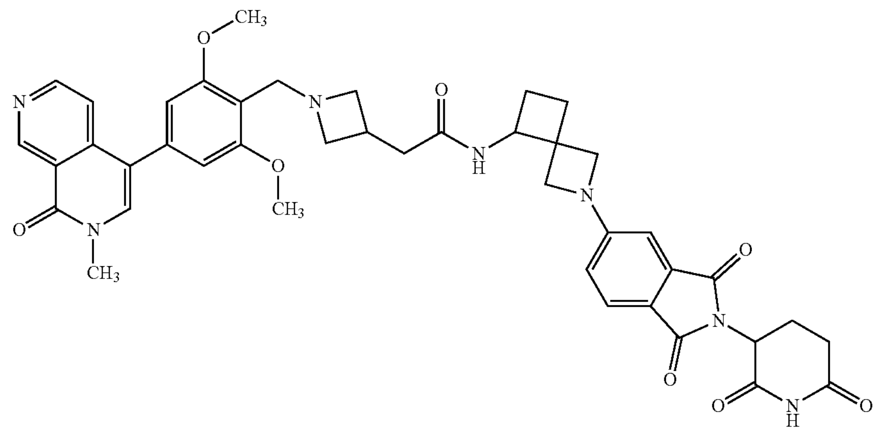 [SMILES: COc1cc(-c2cn(C)c(=O)c3cnccc23)cc(OC)c1CN1CC(CC(=O)NC2CCC23CN(c2ccc4c(c2)C(=O)N(C2CCC(=O)NC2=O)C4=O)C3)C1] |
| D210 | 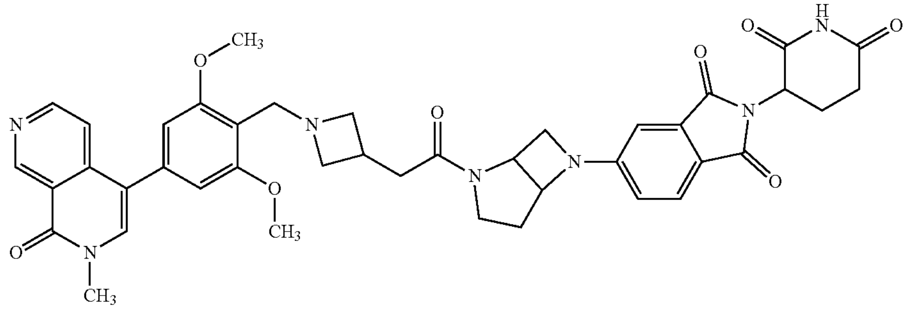 [SMILES: COc1cc(-c2cn(C)c(=O)c3cnccc23)cc(OC)c1CN1CC(CC(=O)N2CCC3C2CN3c2ccc3c(c2)C(=O)N(C2CCC(=O)NC2=O)C3=O)C1] |
| D211 | 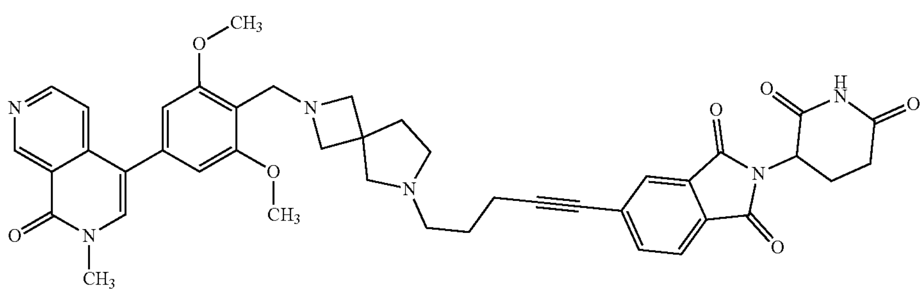 [SMILES: COc1cc(-c2cn(C)c(=O)c3cnccc23)cc(OC)c1CN1CC2(CCN(CCCC#Cc3ccc4c(c3)C(=O)N(C3CCC(=O)NC3=O)C4=O)C2)C1] |
| D212 | 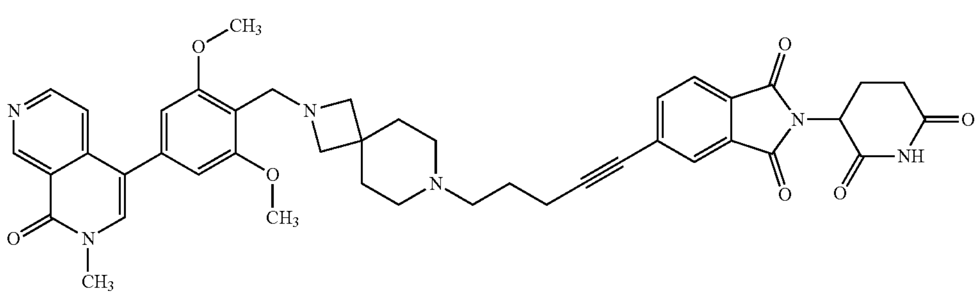 [SMILES: COc1cc(-c2cn(C)c(=O)c3cnccc23)cc(OC)c1CN1CC2(CCN(CCCC#Cc3ccc4c(c3)C(=O)N(C3CCC(=O)NC3=O)C4=O)CC2)C1] |

TABLE 1B-continued

Compounds D178-D371 of the Disclosure

| Compound No. | Structure |
| --- | --- |
| D213 | 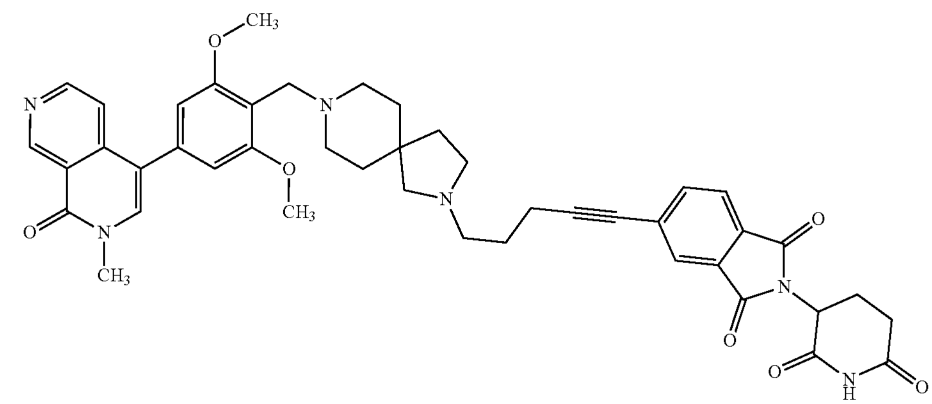 [SMILES: COc1cc(-c2cn(C)c(=O)c3cnccc23)cc(OC)c1CN1CCC2(CC1)CCN(CCCC#Cc1ccc3c(c1)C(=O)N(C1CCC(=O)NC1=O)C3=O)C2] |
| D214 | 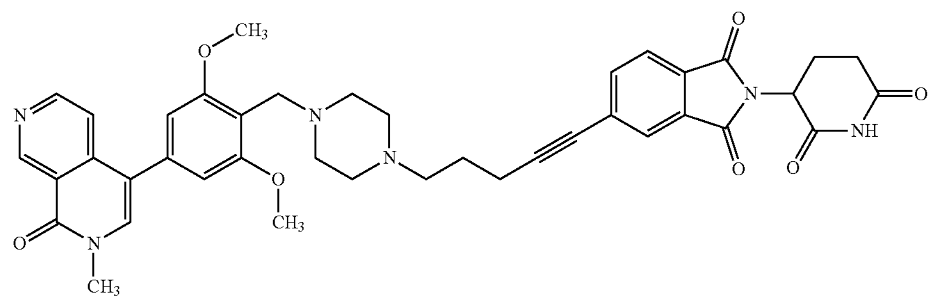 [SMILES: COc1cc(-c2cn(C)c(=O)c3cnccc23)cc(OC)c1CN1CCN(CCCC#Cc2ccc3c(c2)C(=O)N(C2CCC(=O)NC2=O)C3=O)CC1] |
| D215 | 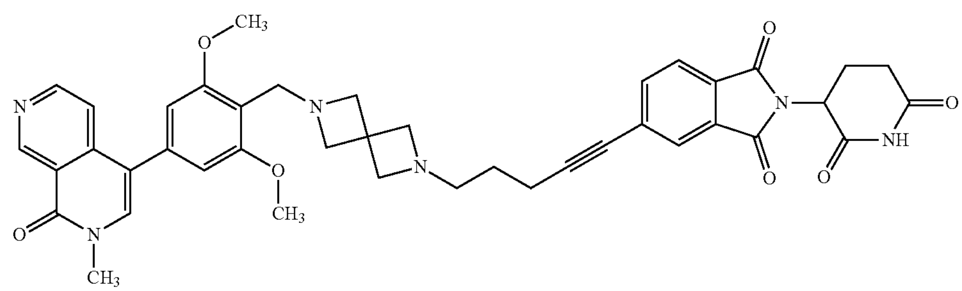 [SMILES: COc1cc(-c2cn(C)c(=O)c3cnccc23)cc(OC)c1CN1CC2(CN(CCCC#Cc3ccc4c(c3)C(=O)N(C3CCC(=O)NC3=O)C4=O)C2)C1] |
| D216 | 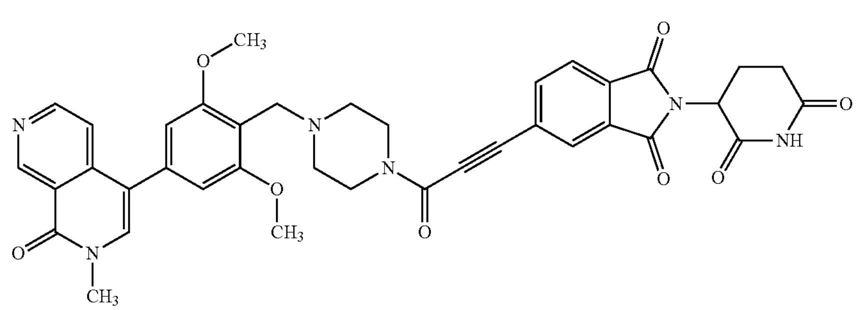 [SMILES: COc1cc(-c2cn(C)c(=O)c3cnccc23)cc(OC)c1CN1CCN(C(=O)C#Cc2ccc3c(c2)C(=O)N(C2CCC(=O)NC2=O)C3=O)CC1] |

TABLE 1B-continued
Compounds D178-D371 of the Disclosure
| Compound No. | Structure |
|---|---|
| D217 | 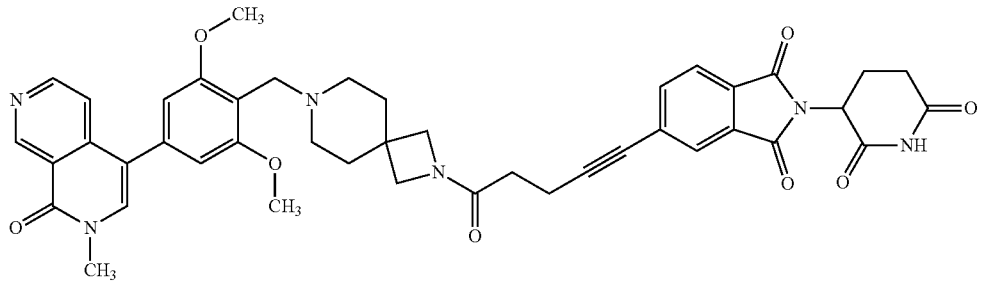 [SMILES: COc1cc(-c2cn(C)c(=O)c3cnccc23)cc(OC)c1CN1CCC2(CC1)CN(C(=O)CCC#Cc1ccc3c(c1)C(=O)N(C1CCC(=O)NC1=O)C3=O)C2] |
| D218 | 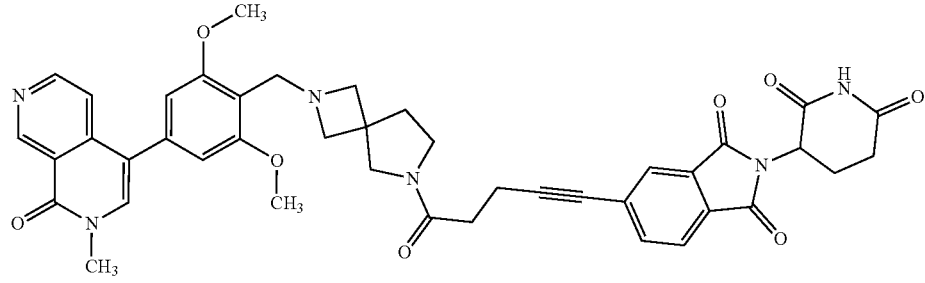 [SMILES: COc1cc(-c2cn(C)c(=O)c3cnccc23)cc(OC)c1CN1CC2(CCN(C(=O)CCC#Cc3ccc4c(c3)C(=O)N(C3CCC(=O)NC3=O)C4=O)C2)C1] |
| D219 | 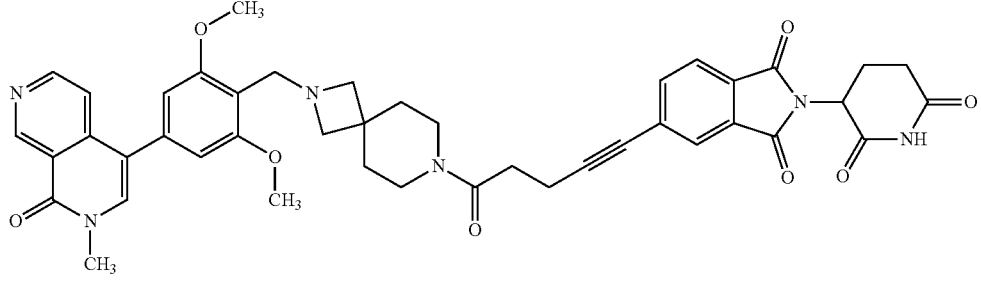 [SMILES: COc1cc(-c2cn(C)c(=O)c3cnccc23)cc(OC)c1CN1CC2(CCN(C(=O)CCC#Cc3ccc4c(c3)C(=O)N(C3CCC(=O)NC3=O)C4=O)CC2)C1] |
| D220 | 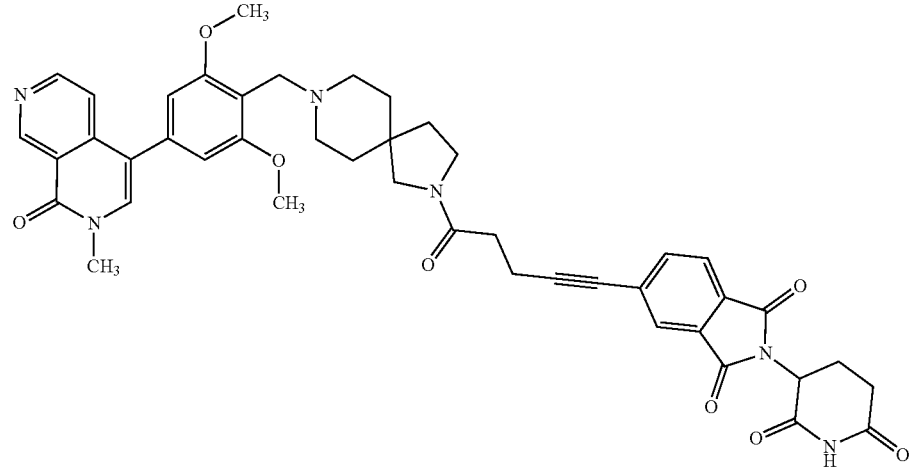 [SMILES: COc1cc(-c2cn(C)c(=O)c3cnccc23)cc(OC)c1CN1CCC2(CC1)CCN(C(=O)CCC#Cc1ccc3c(c1)C(=O)N(C1CCC(=O)NC1=O)C3=O)C2] |

TABLE 1B-continued

Compounds D178-D371 of the Disclosure

| Compound No. | Structure |
|---|---|
| D221 | 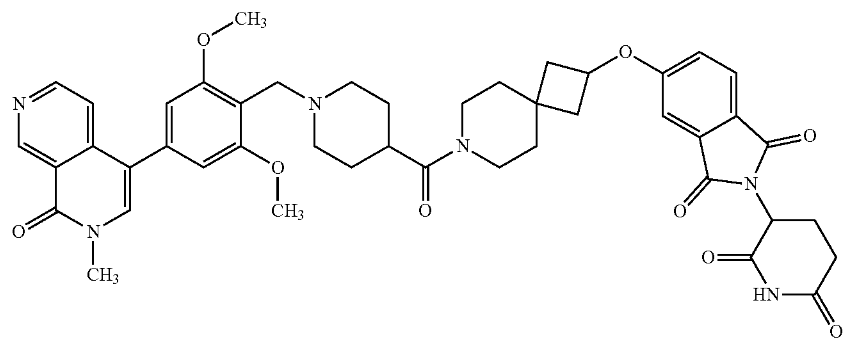 [SMILES: COc1cc(-c2cn(C)c(=O)c3cnccc23)cc(OC)c1CN1CCC(C(=O)N2CCC3(CC2)CC(Oc2ccc4c(c2)C(=O)N(C2CCC(=O)NC2=O)C4=O)C3)CC1] |
| D222 | 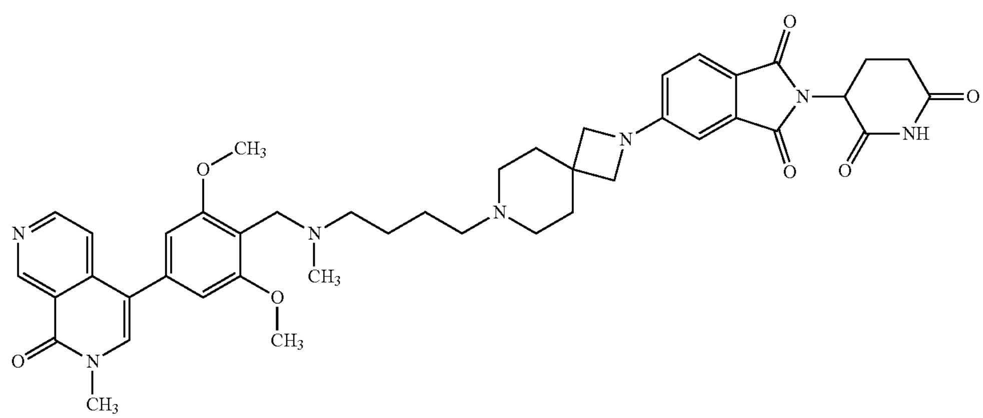 [SMILES: COc1cc(-c2cn(C)c(=O)c3cnccc23)cc(OC)c1CN(C)CCCCN1CCC2(CC1)CN(c1ccc3c(c1)C(=O)N(C1CCC(=O)NC1=O)C3=O)C2] |
| D223 | 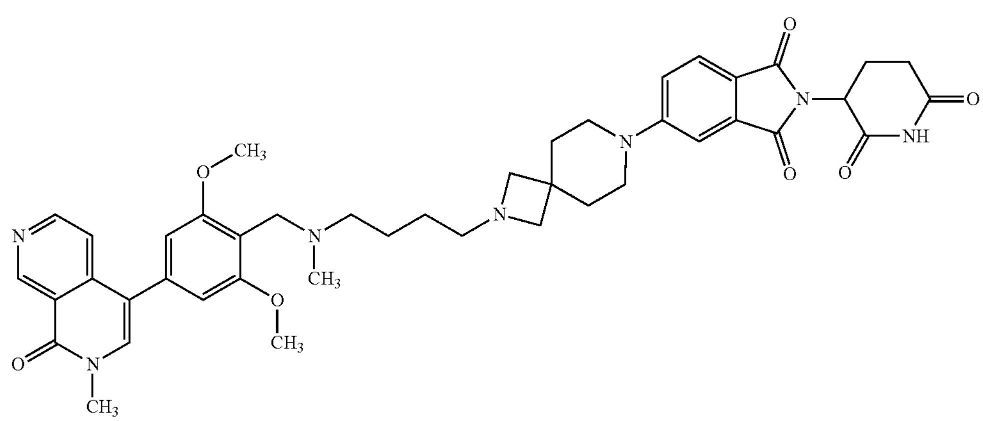 [SMILES: COc1cc(-c2cn(C)c(=O)c3cnccc23)cc(OC)c1CN(C)CCCCN1CC2(CCN(c3ccc4c(c3)C(=O)N(C3CCC(=O)NC3=O)C4=O)CC2)C1] |
| D224 | 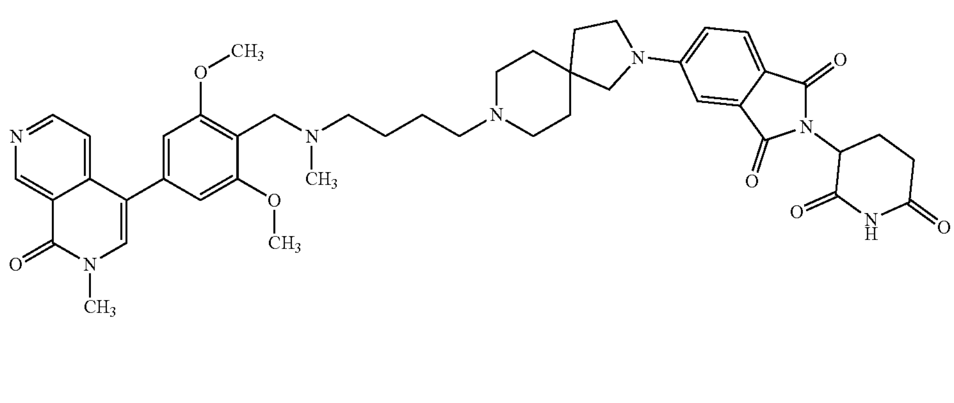 [SMILES: COc1cc(-c2cn(C)c(=O)c3cnccc23)cc(OC)c1CN(C)CCCCN1CCC2(CC1)CCN(c1ccc3c(c1)C(=O)N(C1CCC(=O)NC1=O)C3=O)C2] |

TABLE 1B-continued

Compounds D178-D371 of the Disclosure

| Compound No. | Structure |
|---|---|
| D225 | 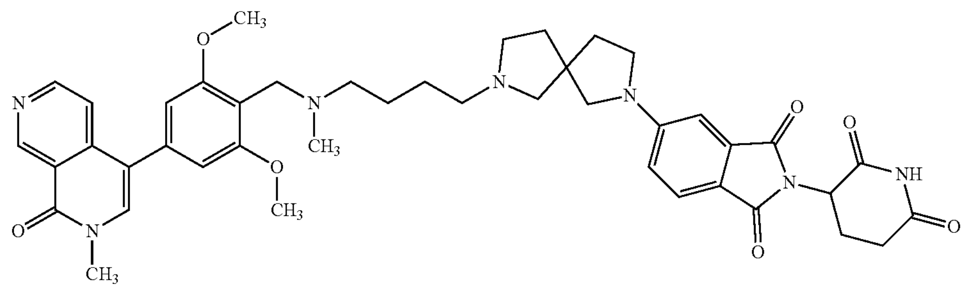 [SMILES: COc1cc(-c2cn(C)c(=O)c3cnccc23)cc(OC)c1CN(C)CCCCN1CCC2(CCN(c3ccc4c(c3)C(=O)N(C3CCC(=O)NC3=O)C4=O)C2)C1] |
| D226 | 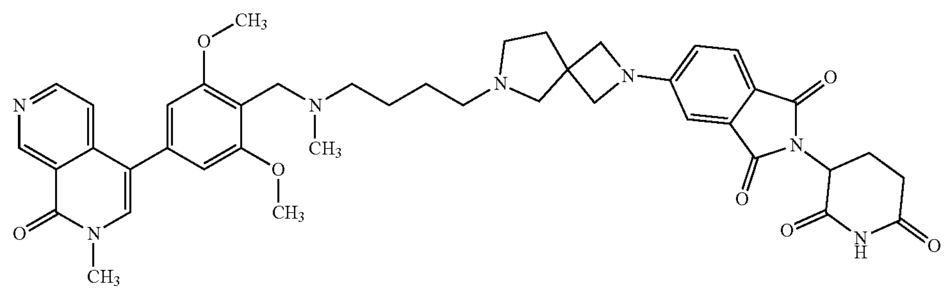 [SMILES: COc1cc(-c2cn(C)c(=O)c3cnccc23)cc(OC)c1CN(C)CCCCN1CCC2(C1)CN(c1ccc3c(c1)C(=O)N(C1CCC(=O)NC1=O)C3=O)C2] |
| D227 | 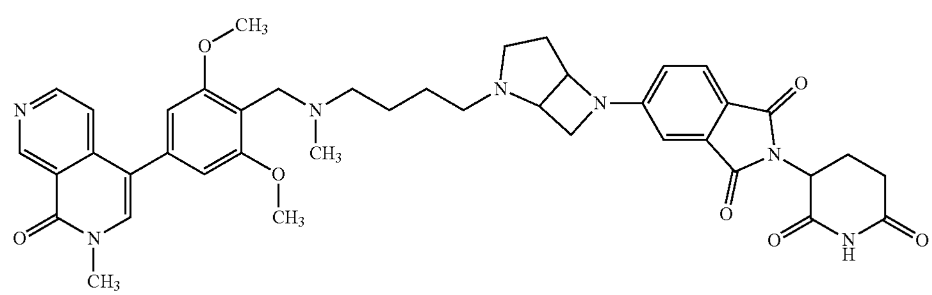 [SMILES: COc1cc(-c2cn(C)c(=O)c3cnccc23)cc(OC)c1CN(C)CCCCN1CCC2C1CN2c1ccc2c(c1)C(=O)N(C1CCC(=O)NC1=O)C2=O] |
| D228 | 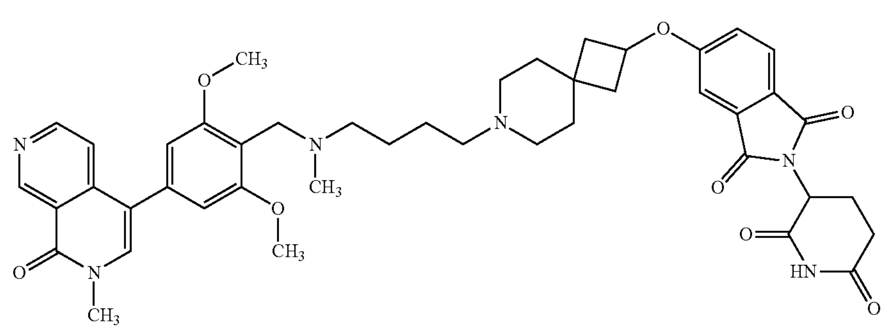 [SMILES: COc1cc(-c2cn(C)c(=O)c3cnccc23)cc(OC)c1CN(C)CCCCN1CCC2(CC1)CC(Oc1ccc3c(c1)C(=O)N(C1CCC(=O)NC1=O)C3=O)C2] |

TABLE 1B-continued

Compounds D178-D371 of the Disclosure

| Compound No. | Structure |
| --- | --- |
| D229 | 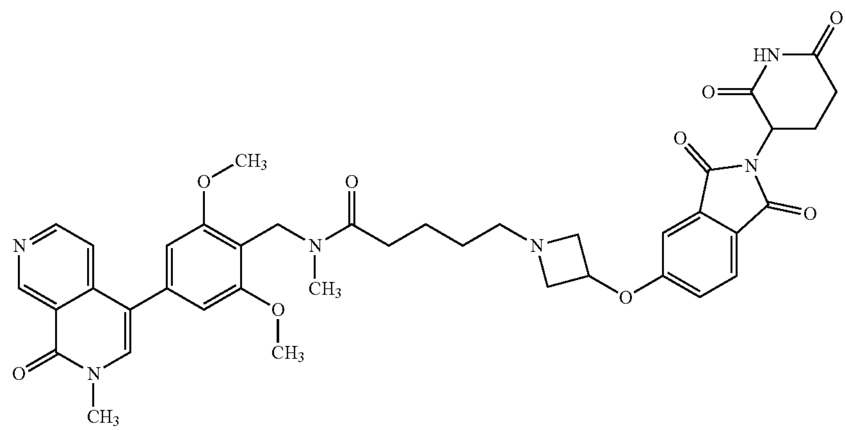 [SMILES: COc1cc(-c2cn(C)c(=O)c3cnccc23)cc(OC)c1CN(C)C(=O)CCCCN1CC(Oc2ccc3c(c2)C(=O)N(C2CCC(=O)NC2=O)C3=O)C1] |
| D230 | 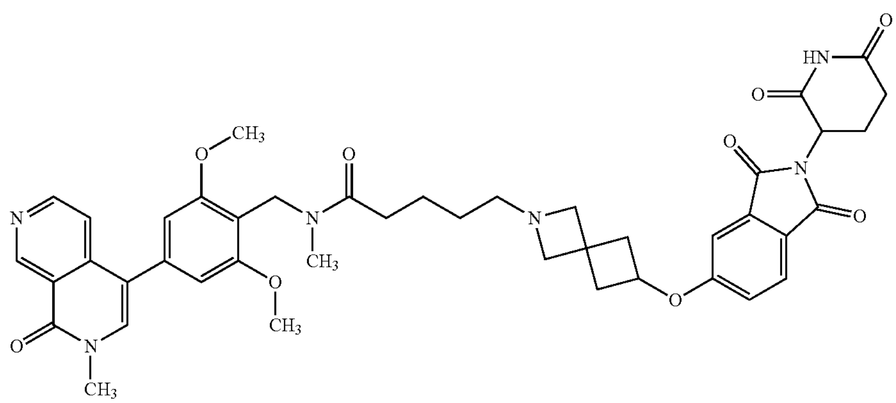 [SMILES: COc1cc(-c2cn(C)c(=O)c3cnccc23)cc(OC)c1CN(C)C(=O)CCCCN1CC2(CC(Oc3ccc4c(c3)C(=O)N(C3CCC(=O)NC3=O)C4=O)C2)C1] |
| D231 | 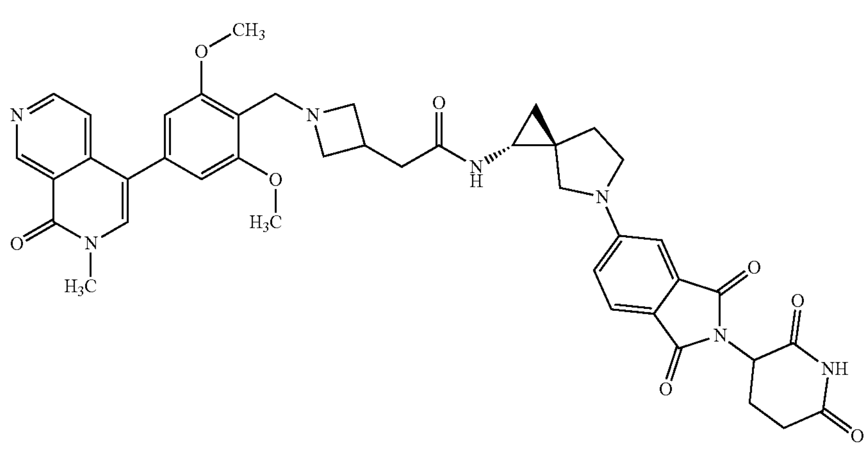 [SMILES: COc1cc(-c2cn(C)c(=O)c3cnccc23)cc(OC)c1CN1CC(CC(=O)N[C@@H]2C[C@]23CCN(c2ccc4c(c2)C(=O)N(C2CCC(=O)NC2=O)C4=O)C3)C1] |

TABLE 1B-continued

Compounds D178-D371 of the Disclosure

| Compound No. | Structure |
|---|---|
| D232 | 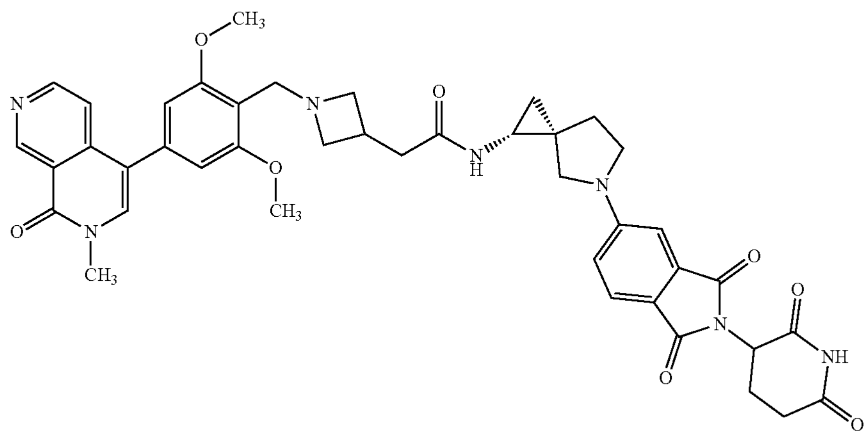 [SMILES: COc1cc(-c2cn(C)c(=O)c3cnccc23)cc(OC)c1CN1CC(CC(=O)N[C@@H]2C[C@@]23CCN(c2ccc4c(c2)C(=O)N(C2CCC(=O)NC2=O)C4=O)C3)C1] |
| D233 | 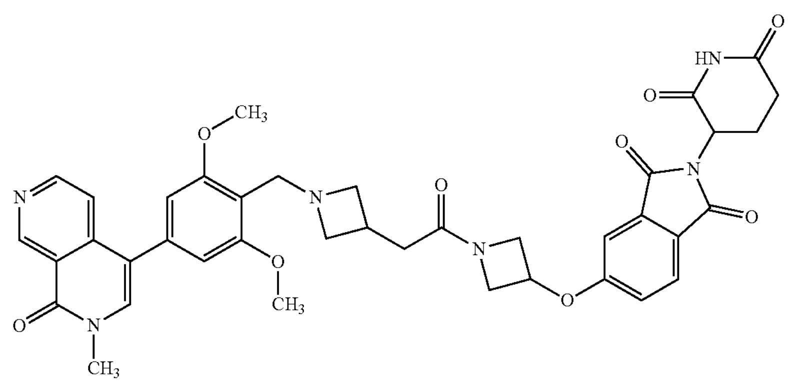 [SMILES: COc1cc(-c2cn(C)c(=O)c3cnccc23)cc(OC)c1CN1CC(CC(=O)N2CC(Oc3ccc4c(c3)C(=O)N(C3CCC(=O)NC3=O)C4=O)C2)C1] |
| D234 | 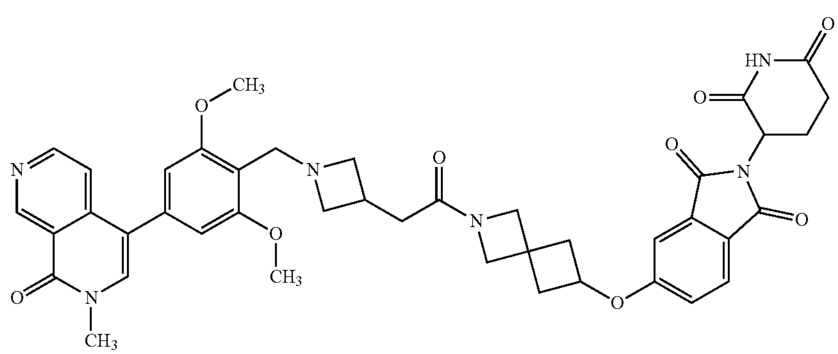 [SMILES: COc1cc(-c2cn(C)c(=O)c3cnccc23)cc(OC)c1CN1CC(CC(=O)N2CC3(CC(Oc4ccc5c(c4)C(=O)N(C4CCC(=O)NC4=O)C5=O)C3)C2)C1] |
| D235 | 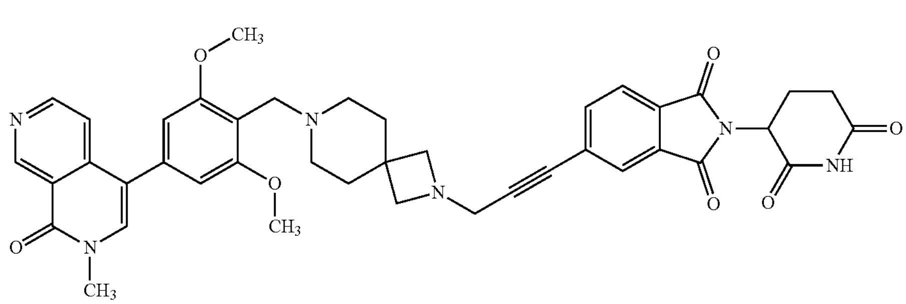 [SMILES: COc1cc(-c2cn(C)c(=O)c3cnccc23)cc(OC)c1CN1CCC2(CC1)CN(CC#Cc1ccc3c(c1)C(=O)N(C1CCC(=O)NC1=O)C3=O)C2] |

TABLE 1B-continued

Compounds D178-D371 of the Disclosure

| Compound No. | Structure |
| --- | --- |
| D236 | 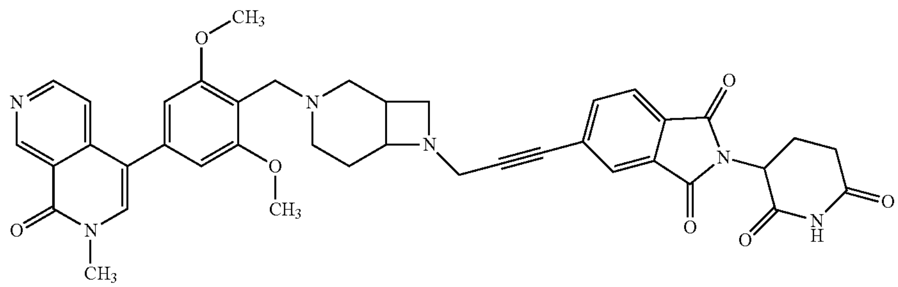 [SMILES: COc1cc(-c2cn(C)c(=O)c3cnccc23)cc(OC)c1CN1CCC2C(C1)CN2CC#Cc1ccc2c(c1)C(=O)N(C1CCC(=O)NC1=O)C2=O] |
| D237 | 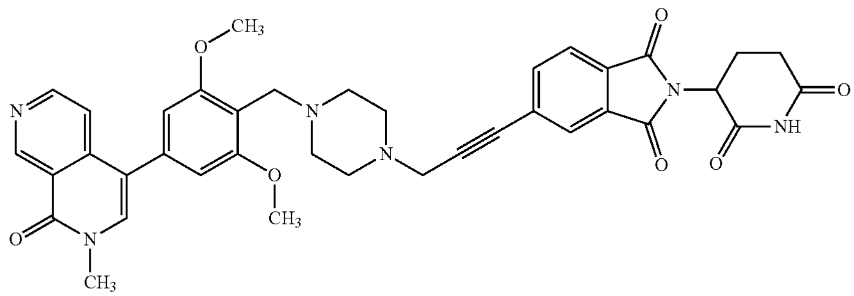 [SMILES: COc1cc(-c2cn(C)c(=O)c3cnccc23)cc(OC)c1CN1CCN(CC#Cc2ccc3c(c2)C(=O)N(C2CCC(=O)NC2=O)C3=O)CC1] |
| D238 | 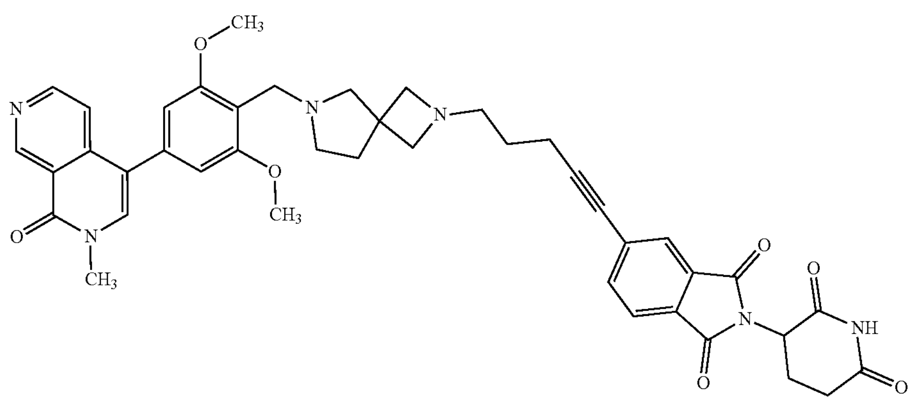 [SMILES: COc1cc(-c2cn(C)c(=O)c3cnccc23)cc(OC)c1CN1CCC2(C1)CN(CCCC#Cc1ccc3c(c1)C(=O)N(C1CCC(=O)NC1=O)C3=O)C2] |
| D239 | 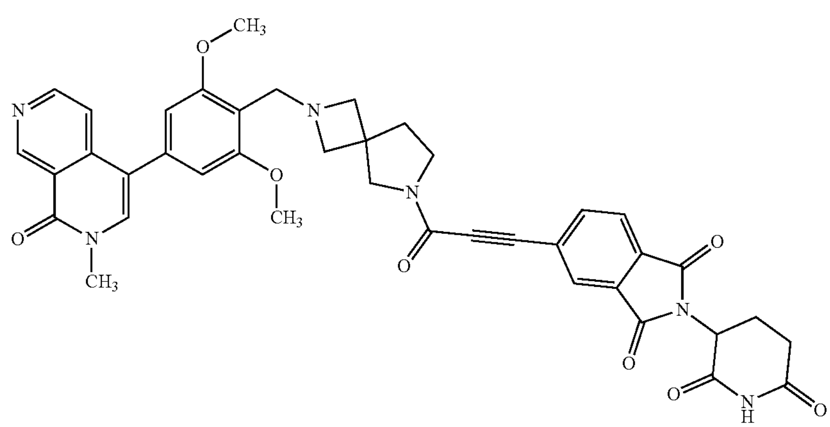 [SMILES: COc1cc(-c2cn(C)c(=O)c3cnccc23)cc(OC)c1CN1CC2(CCN(C(=O)C#Cc3ccc4c(c3)C(=O)N(C3CCC(=O)NC3=O)C4=O)C2)C1] |

TABLE 1B-continued
Compounds D178-D371 of the Disclosure
| Compound No. | Structure |
|---|---|
| D240 | 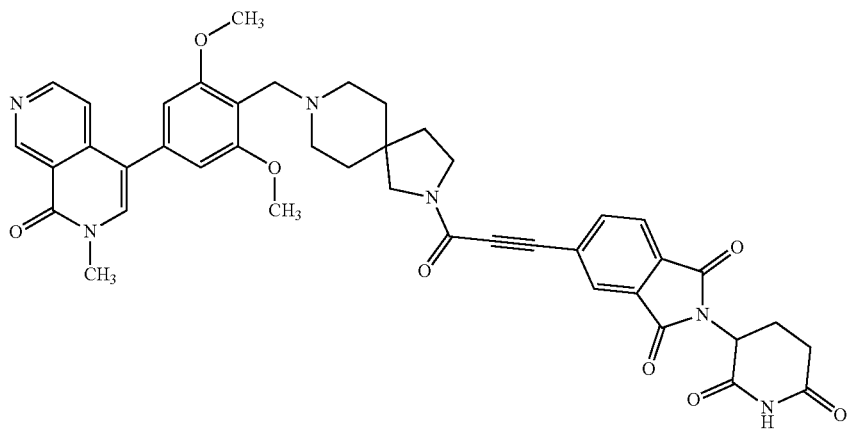 [SMILES: COc1cc(-c2cn(C)c(=O)c3cnccc23)cc(OC)c1CN1CCC2(CC1)CCN(C(=O)C#Cc1ccc3c(c1)C(=O)N(C1CCC(=O)NC1=O)C3=O)C2] |
| D241 | 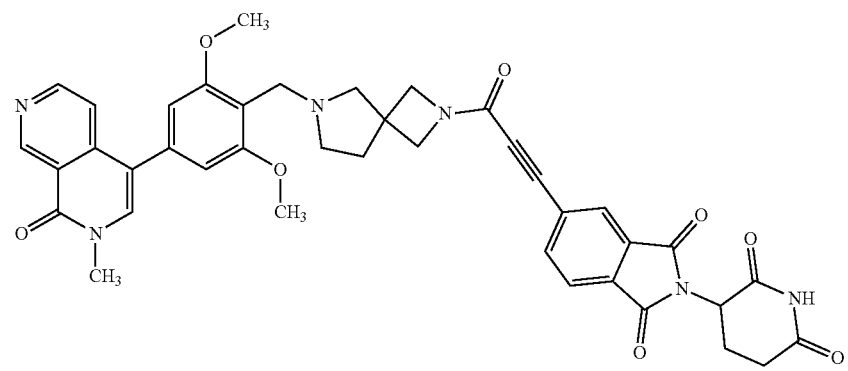 [SMILES: COc1cc(-c2cn(C)c(=O)c3cnccc23)cc(OC)c1CN1CCC2(C1)CN(C(=O)C#Cc1ccc3c(c1)C(=O)N(C1CCC(=O)NC1=O)C3=O)C2] |
| D242 | 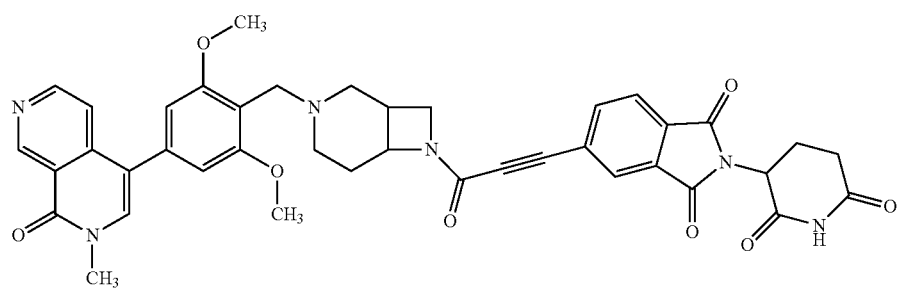 [SMILES: COc1cc(-c2cn(C)c(=O)c3cnccc23)cc(OC)c1CN1CCC2C(C1)CN2C(=O)C#Cc1ccc2c(c1)C(=O)N(C1CCC(=O)NC1=O)C2=O] |
| D243 | 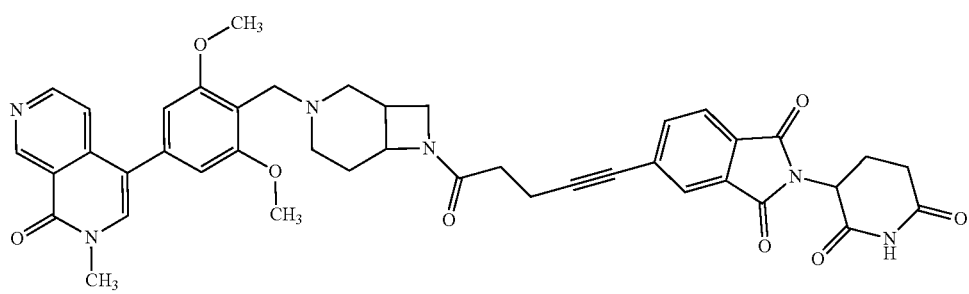 [SMILES: COc1cc(-c2cn(C)c(=O)c3cnccc23)cc(OC)c1CN1CCC2C(C1)CN2C(=O)CCC#Cc1ccc2c(c1)C(=O)N(C1CCC(=O)NC1=O)C2=O] |

TABLE 1B-continued

Compounds D178-D371 of the Disclosure

| Compound No. | Structure |
| --- | --- |
| D244 | 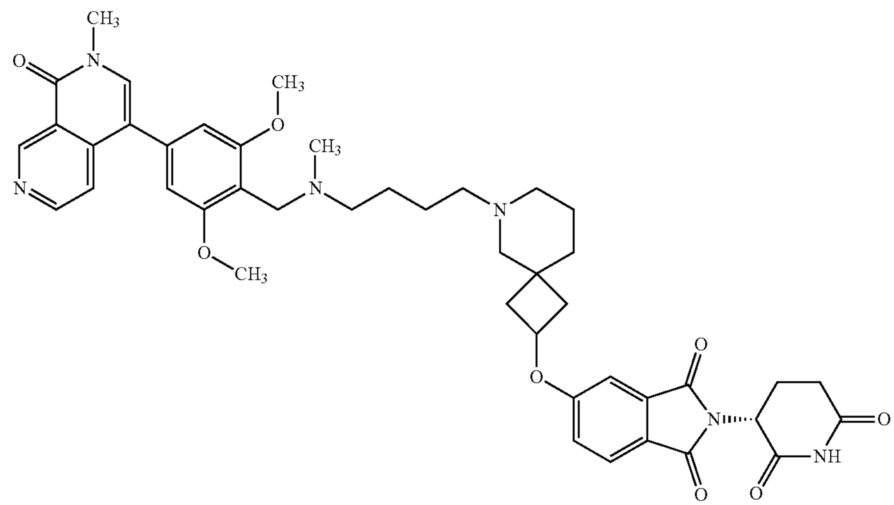 [SMILES: COc1cc(-c2cn(C)c(=O)c3cnccc23)cc(OC)c1CN(C)CCCCN1CCCC2(CC(Oc3ccc4c(c3)C(=O)N([C@@H]3CCC(=O)NC3=O)C4=O)C2)C1] |
| D245 | 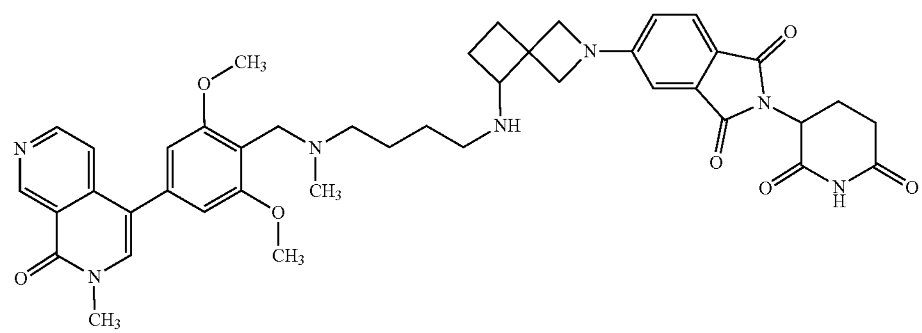 [SMILES: COc1cc(-c2cn(C)c(=O)c3cnccc23)cc(OC)c1CN(C)CCCCNC1CCC12CN(c1ccc3c(c1)C(=O)N(C1CCC(=O)NC1=O)C3=O)C2] |
| D246 | 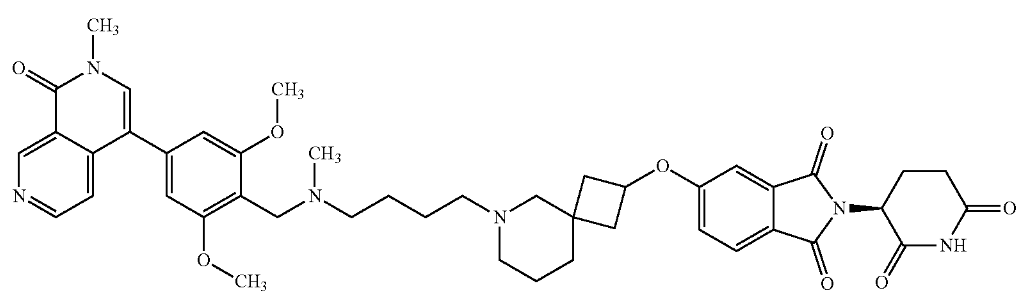 [SMILES: COc1cc(-c2cn(C)c(=O)c3cnccc23)cc(OC)c1CN(C)CCCCN1CCCC2(CC(Oc3ccc4c(c3)C(=O)N([C@H]3CCC(=O)NC3=O)C4=O)C2)C1] |
| D247 | 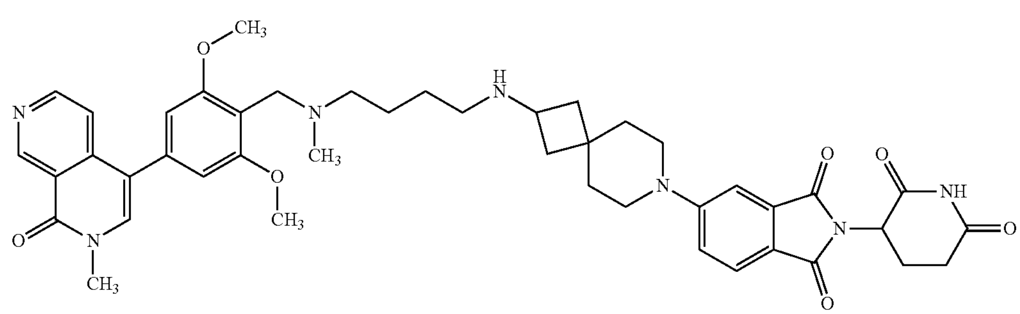 [SMILES: COc1cc(-c2cn(C)c(=O)c3cnccc23)cc(OC)c1CN(C)CCCCNC1CC2(CCN(c3ccc4c(c3)C(=O)N(C3CCC(=O)NC3=O)C4=O)CC2)C1] |

TABLE 1B-continued

Compounds D178-D371 of the Disclosure

| Compound No. | Structure |
| --- | --- |
| D248 | 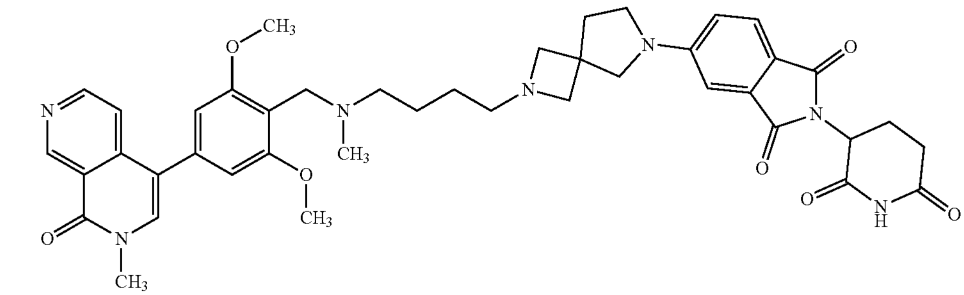 [SMILES: COc1cc(-c2cn(C)c(=O)c3cnccc23)cc(OC)c1CN(C)CCCCN1CC2(CCN(c3ccc4c(c3)C(=O)N(C3CCC(=O)NC3=O)C4=O)C2)C1] |
| D249 | 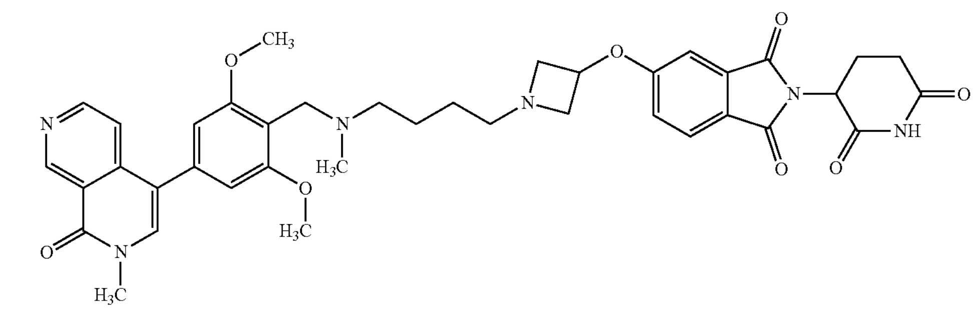 [SMILES: COc1cc(-c2cn(C)c(=O)c3cnccc23)cc(OC)c1CN(C)CCCCN1CC(Oc2ccc3c(c2)C(=O)N(C2CCC(=O)NC2=O)C3=O)C1] |
| D250 | 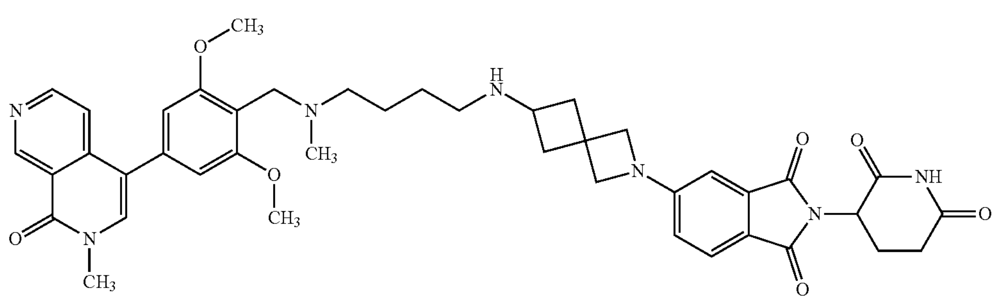 [SMILES: COc1cc(-c2cn(C)c(=O)c3cnccc23)cc(OC)c1CN(C)CCCCNC1CC2(C1)CN(c1ccc3c(c1)C(=O)N(C1CCC(=O)NC1=O)C3=O)C2] |
| D251 | 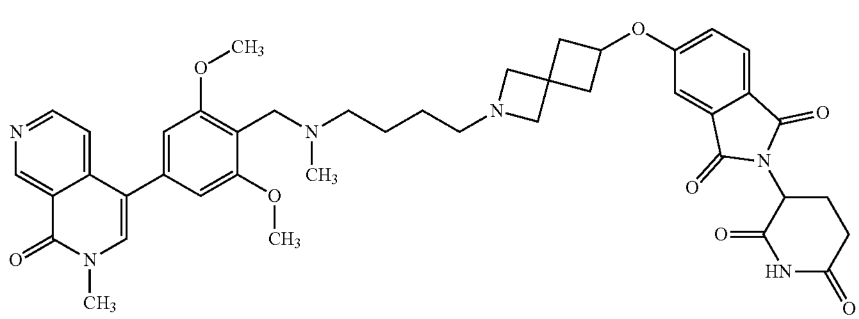 [SMILES: COc1cc(-c2cn(C)c(=O)c3cnccc23)cc(OC)c1CN(C)CCCCN1CC2(CC(Oc3ccc4c(c3)C(=O)N(C3CCC(=O)NC3=O)C4=O)C2)C1] |

TABLE 1B-continued

Compounds D178-D371 of the Disclosure

| Compound No. | Structure |
|---|---|
| D252 | 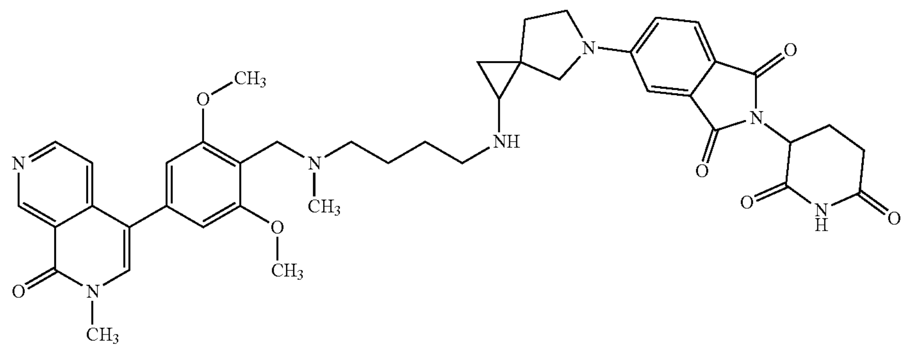 [SMILES: COc1cc(-c2cn(C)c(=O)c3cnccc23)cc(OC)c1CN(C)CCCCNC1CC12CCN(c1ccc3c(c1)C(=O)N(C1CCC(=O)NC1=O)C3=O)C2] |
| D253 | 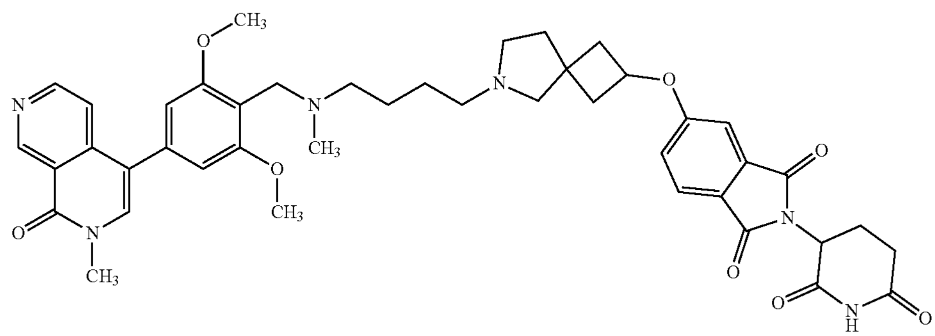 [SMILES: COc1cc(-c2cn(C)c(=O)c3cnccc23)cc(OC)c1CN(C)CCCCN1CCC2(CC(Oc3ccc4c(c3)C(=O)N(C3CCC(=O)NC3=O)C4=O)C2)C1] |
| D254 | 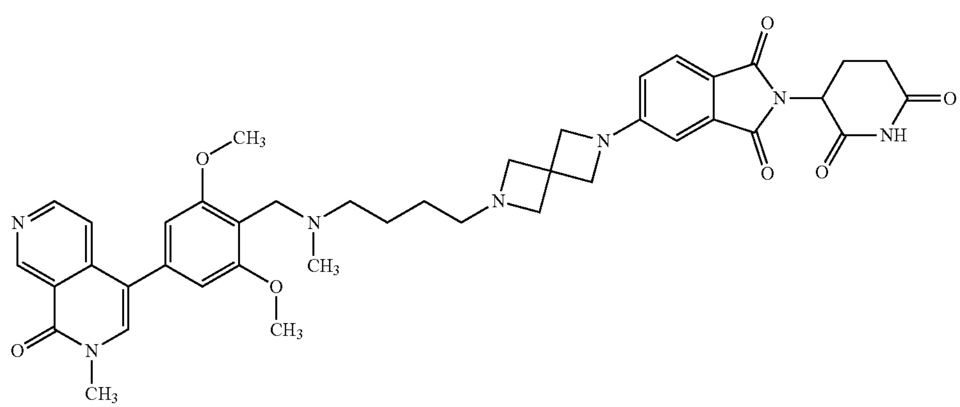 [SMILES: COc1cc(-c2cn(C)c(=O)c3cnccc23)cc(OC)c1CN(C)CCCCN1CC2(C1)CN(c1ccc3c(c1)C(=O)N(C1CCC(=O)NC1=O)C3=O)C2] |
| D255 | 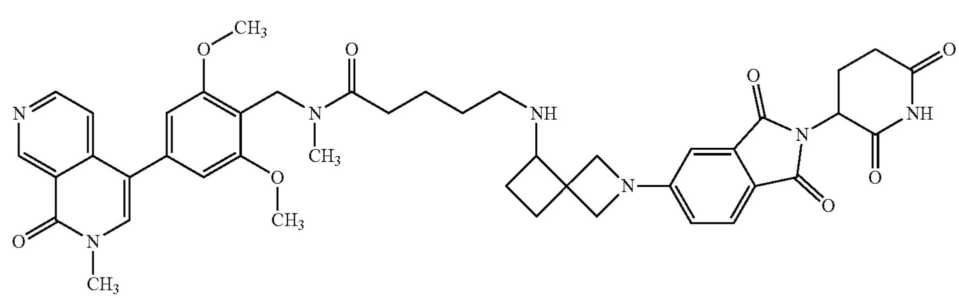 [SMILES: COc1cc(-c2cn(C)c(=O)c3cnccc23)cc(OC)c1CN(C)C(=O)CCCCNC1CCC12CN(c1ccc3c(c1)C(=O)N(C1CCC(=O)NC1=O)C3=O)C2] |

TABLE 1B-continued
Compounds D178-D371 of the Disclosure
| Compound No. | Structure |
|---|---|
| D256 | 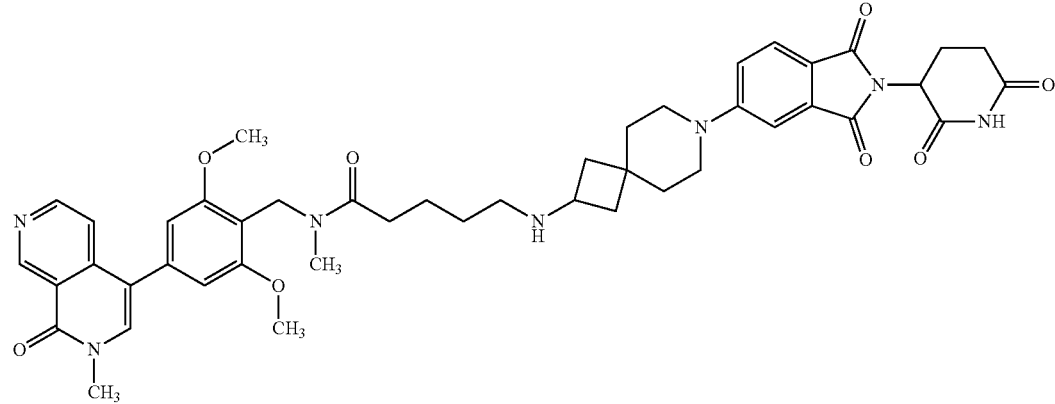 [SMILES: COc1cc(-c2cn(C)c(=O)c3cnccc23)cc(OC)c1CN(C)C(=O)CCCCNC1CC2(CCN(c3ccc4c(c3)C(=O)N(C3CCC(=O)NC3=O)C4=O)CC2)C1] |
| D257 | 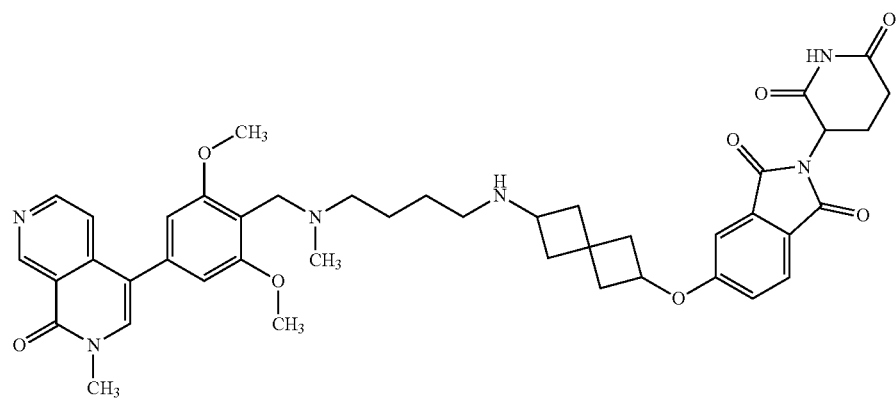 [SMILES: COc1cc(-c2cn(C)c(=O)c3cnccc23)cc(OC)c1CN(C)CCCCNC1CC2(C1)CC(Oc1ccc3c(c1)C(=O)N(C1CCC(=O)NC1=O)C3=O)C2] |
| D258 | 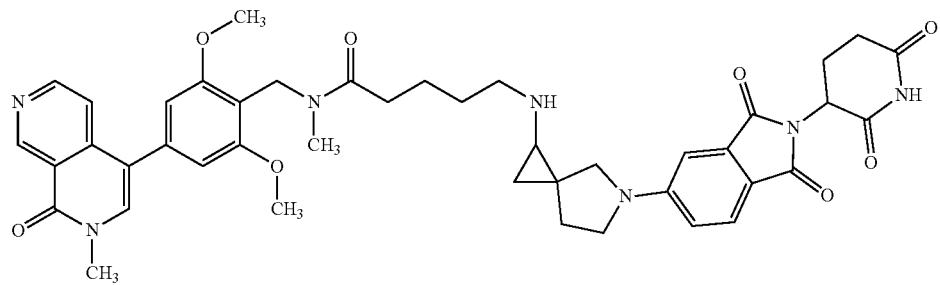 [SMILES: COc1cc(-c2cn(C)c(=O)c3cnccc23)cc(OC)c1CN(C)C(=O)CCCCNC1CC12CCN(c1ccc3c(c1)C(=O)N(C1CCC(=O)NC1=O)C3=O)C2] |

TABLE 1B-continued
Compounds D178-D371 of the Disclosure
| Compound No. | Structure |
|---|---|
| D259 | 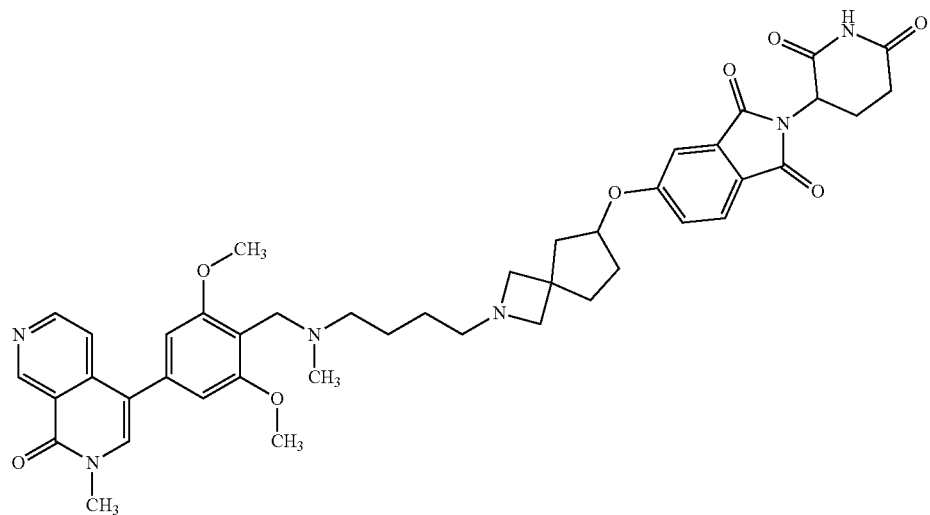 [SMILES: COc1cc(-c2cn(C)c(=O)c3cnccc23)cc(OC)c1CN(C)CCCCN1CC2(CCC(Oc3ccc4c(c3)C(=O)N(C3CCC(=O)NC3=O)C4=O)C2)C1] |
| D260 | 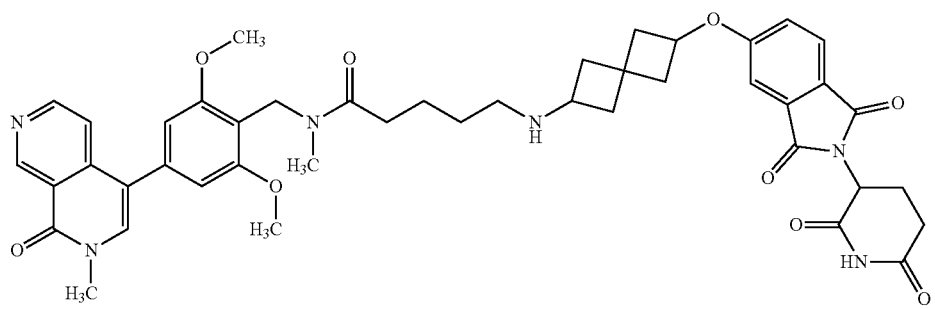 [SMILES: COc1cc(-c2cn(C)c(=O)c3cnccc23)cc(OC)c1CN(C)C(=O)CCCCNC1CC2(C1)CC(Oc1ccc3c(c1)C(=O)N(C1CCC(=O)NC1=O)C3=O)C2] |
| D261 | 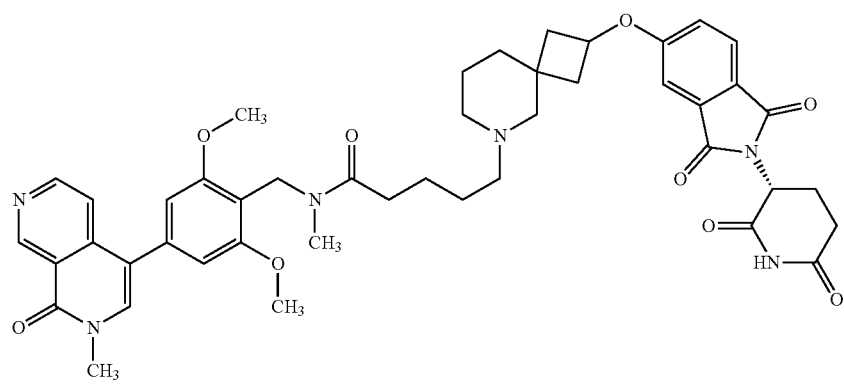 [SMILES: COc1cc(-c2cn(C)c(=O)c3cnccc23)cc(OC)c1CN(C)C(=O)CCCCN1CCCC2(CC(Oc3ccc4c(c3)C(=O)N([C@@H]3CCC(=O)NC3=O)C4=O)C2)C1] |

TABLE 1B-continued
Compounds D178-D371 of the Disclosure
| Compound No. | Structure |
|---|---|
| D262 | 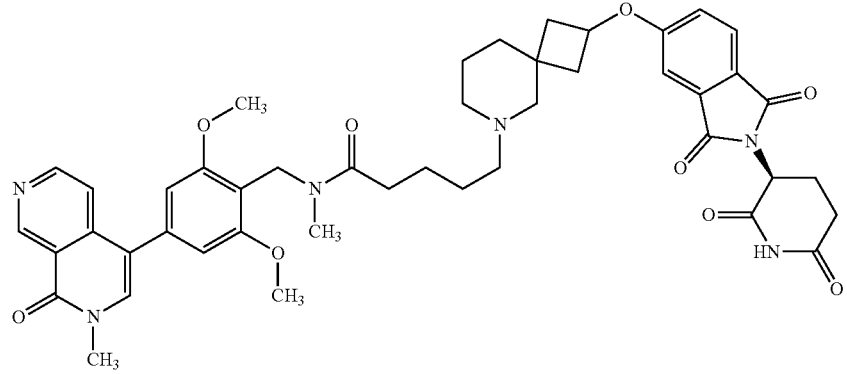 [SMILES: COc1cc(-c2cn(C)c(=O)c3cnccc23)cc(OC)c1CN(C)C(=O)CCCCN1CCCC2(CC(Oc3ccc4c(c3)C(=O)N([C@H]3CCC(=O)NC3=O)C4=O)C2)C1] |
| D263 | 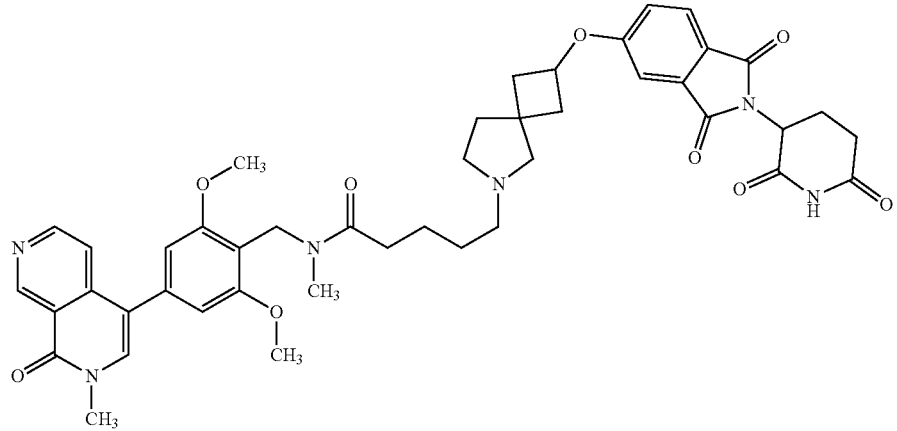 [SMILES: COc1cc(-c2cn(C)c(=O)c3cnccc23)cc(OC)c1CN(C)C(=O)CCCCN1CCC2(CC(Oc3ccc4c(c3)C(=O)N(C3CCC(=O)NC3=O)C4=O)C2)C1] |
| D264 | 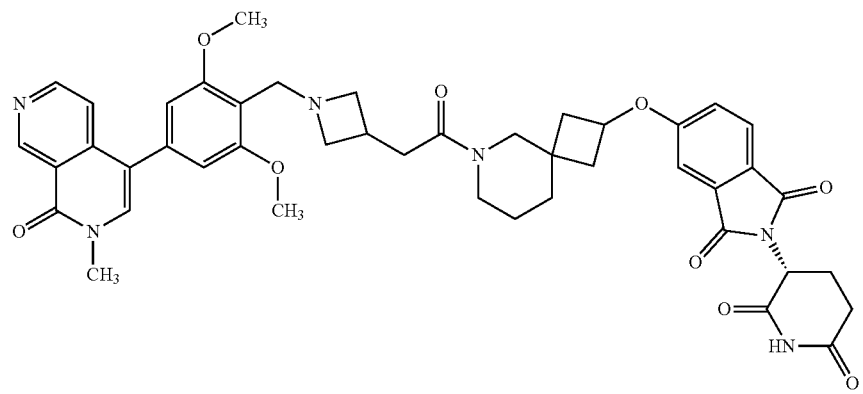 [SMILES: COc1cc(-c2cn(C)c(=O)c3cnccc23)cc(OC)c1CN1CC(CC(=O)N2CCCC3(CC(Oc4ccc5c(c4)C(=O)N([C@@H]4CCC(=O)NC4=O)C5=O)C3)C2)C1] |

TABLE 1B-continued
Compounds D178-D371 of the Disclosure
| Compound No. | Structure |
|---|---|
| D265 | 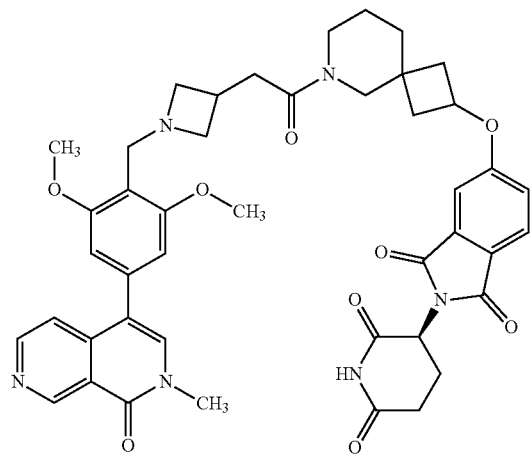 [SMILES: COc1cc(-c2cn(C)c(=O)c3cnccc23)cc(OC)c1CN1CC(CC(=O)N2CCCC3(CC(Oc4ccc5c(c4)C(=O)N([C@H]4CCC(=O)NC4=O)C5=O)C3)C2)C1] |
| D266 | 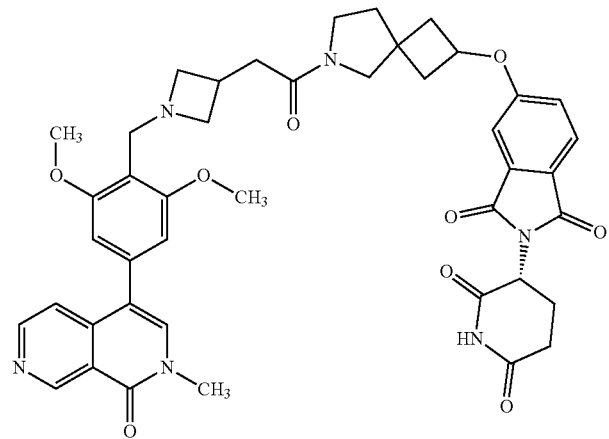 [SMILES: COc1cc(-c2cn(C)c(=O)c3cnccc23)cc(OC)c1CN1CC(CC(=O)N2CCC3(CC(Oc4ccc5c(c4)C(=O)N([C@@H]4CCC(=O)NC4=O)C5=O)C3)C2)C1] |
| D267 | 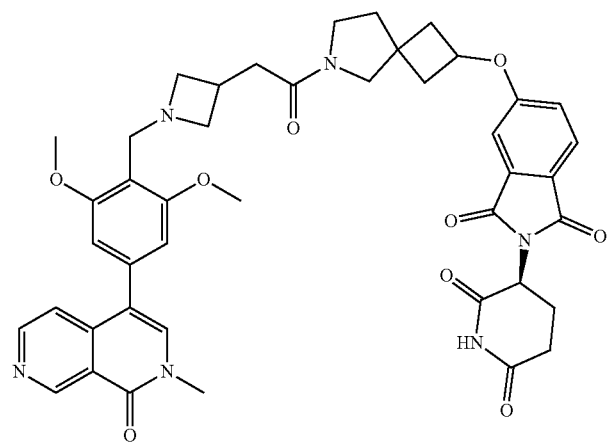 [SMILES: COc1cc(-c2cn(C)c(=O)c3cnccc23)cc(OC)c1CN1CC(CC(=O)N2CCC3(CC(Oc4ccc5c(c4)C(=O)N([C@H]4CCC(=O)NC4=O)C5=O)C3)C2)C1] |

311 312
TABLE 1B-continued
Compounds D178-D371 of the Disclosure
| Compound No. | Structure |
|---|---|
| D268 | 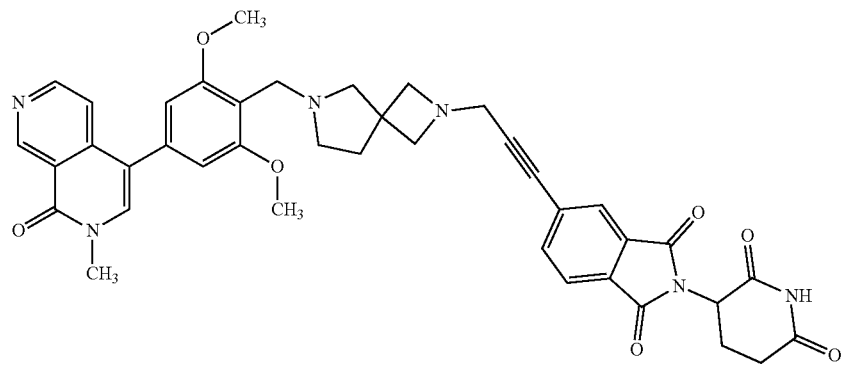 [SMILES: COc1cc(-c2cn(C)c(=O)c3cnccc23)cc(OC)c1CN1CCC2(C1)CN(CC#Cc1ccc3c(c1)C(=O)N(C1CCC(=O)NC1=O)C3=O)C2] |
| D269 | 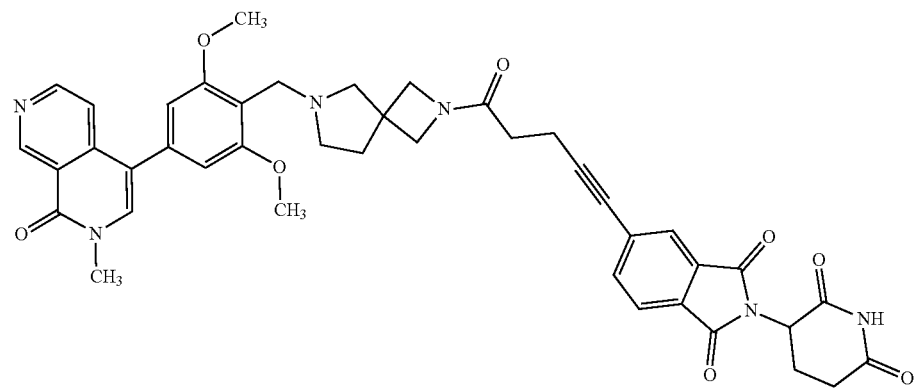 [SMILES: COc1cc(-c2cn(C)c(=O)c3cnccc23)cc(OC)c1CN1CCC2(C1)CN(C(=O)CCC#Cc1ccc3c(c1)C(=O)N(C1CCC(=O)NC1=O)C3=O)C2] |
| D270 | 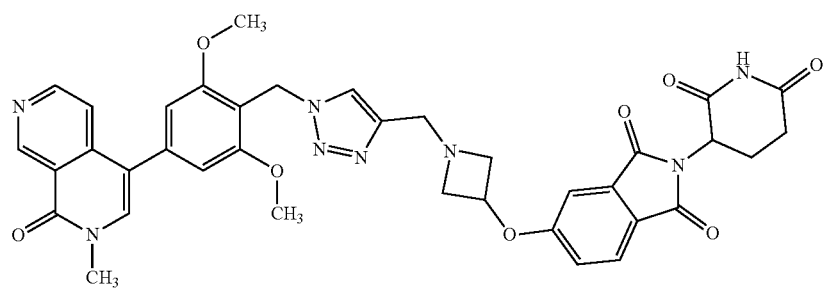 [SMILES: COc1cc(-c2cn(C)c(=O)c3cnccc23)cc(OC)c1Cn1cc(CN2CC(Oc3ccc4c(c3)C(=O)N(C3CCC(=O)NC3=O)C4=O)C2)nn1] |
| D271 | 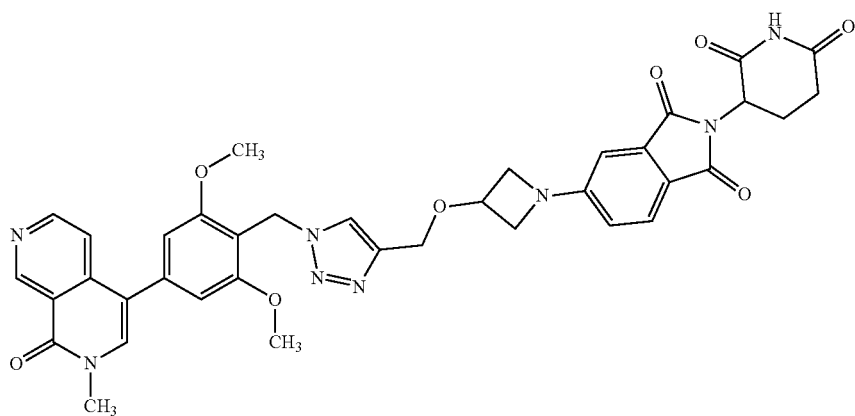 [SMILES: COc1cc(-c2cn(C)c(=O)c3cnccc23)cc(OC)c1Cn1cc(COC2CN(c3ccc4c(c3)C(=O)N(C3CCC(=O)NC3=O)C4=O)C2)nn1] |

TABLE 1B-continued
Compounds D178-D371 of the Disclosure
| Compound No. | Structure |
|---|---|
| D272 | 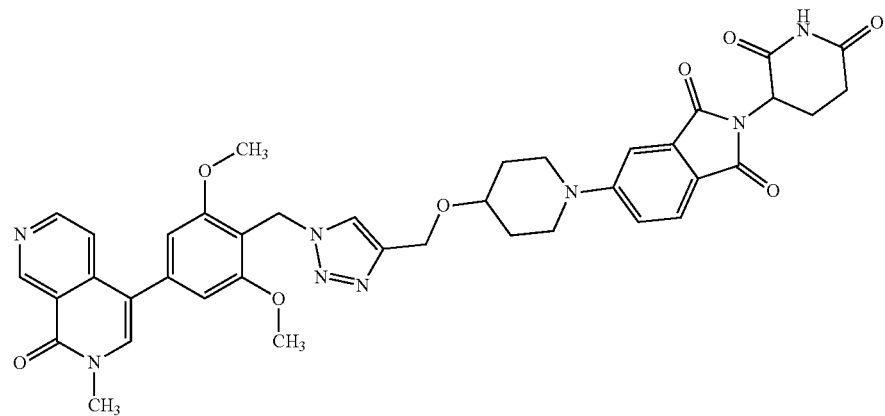 [SMILES: COc1cc(-c2cn(C)c(=O)c3cnccc23)cc(OC)c1Cn1cc(COC2CCN(c3ccc4c(c3)C(=O)N(C3CCC(=O)NC3=O)C4=O)CC2)nn1] |
| D273 | 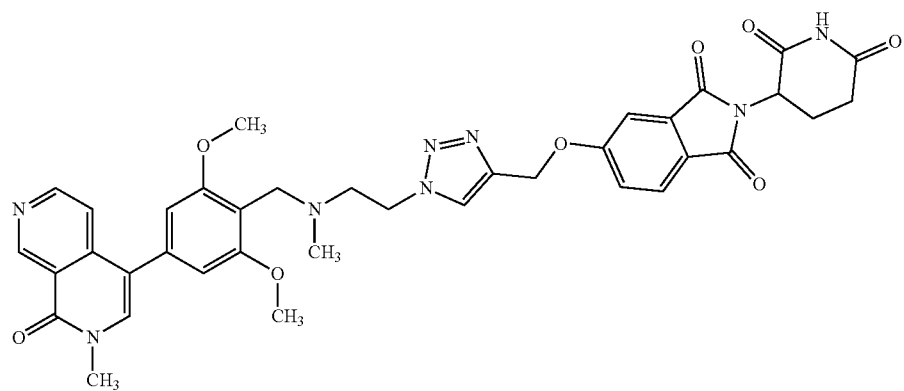 [SMILES: COc1cc(-c2cn(C)c(=O)c3cnccc23)cc(OC)c1CN(C)CCn1cc(COc2ccc3c(c2)C(=O)N(C2CCC(=O)NC2=O)C3=O)nn1] |
| D274 | 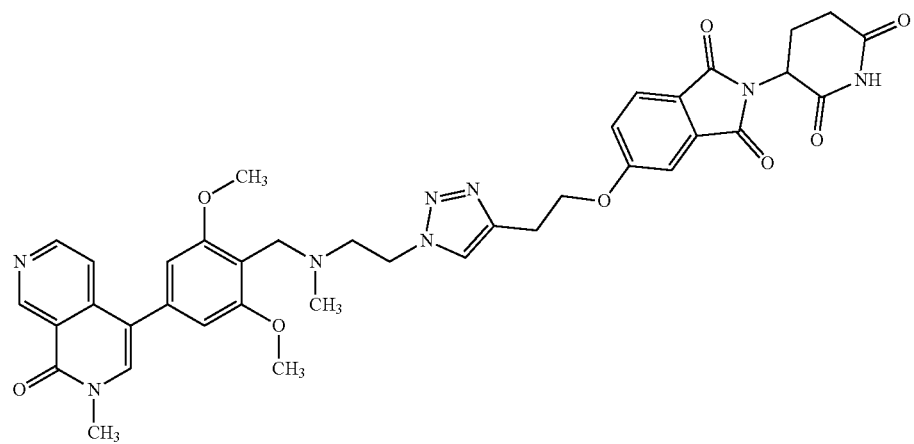 [SMILES: COc1cc(-c2cn(C)c(=O)c3cnccc23)cc(OC)c1CN(C)CCn1cc(CCOc2ccc3c(c2)C(=O)N(C2CCC(=O)NC2=O)C3=O)nn1] |

TABLE 1B-continued

Compounds D178-D371 of the Disclosure

| Compound No. | Structure |
|---|---|
| D275 | 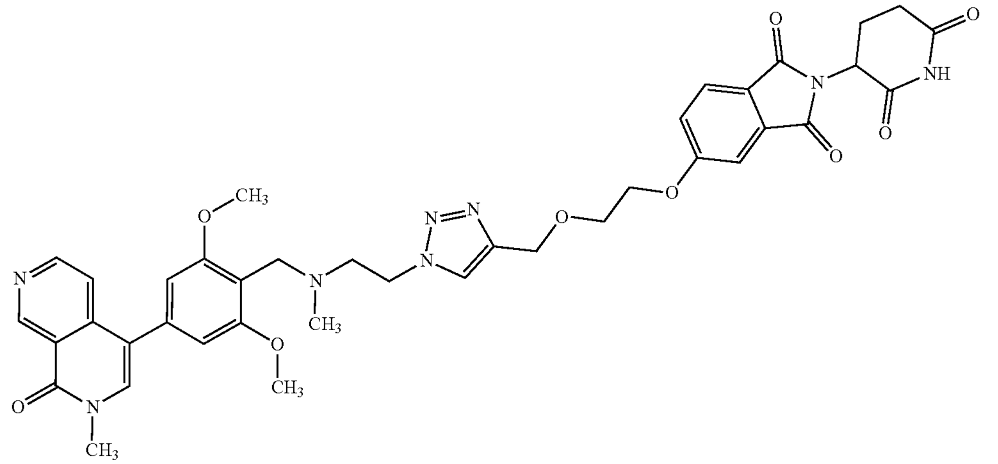 [SMILES: COc1cc(-c2cn(C)c(=O)c3cnccc23)cc(OC)c1CN(C)CCn1cc(COCCOc2ccc3c(c2)C(=O)N(C2CCC(=O)NC2=O)C3=O)nn1] |
| D276 | 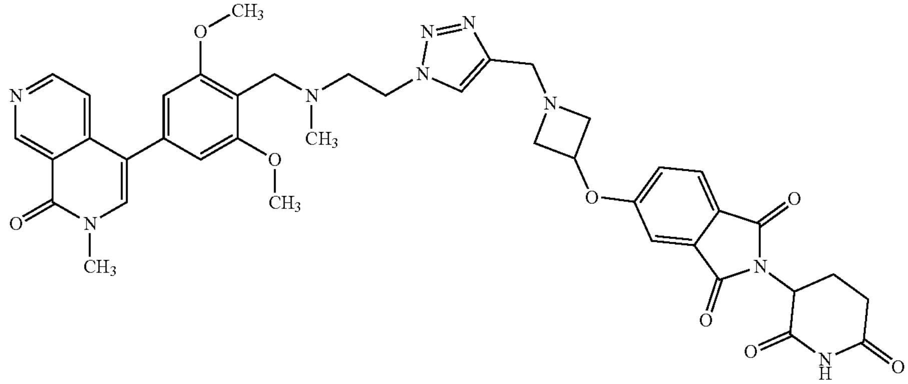 [SMILES: COc1cc(-c2cn(C)c(=O)c3cnccc23)cc(OC)c1CN(C)CCn1cc(CN2CC(Oc3ccc4c(c3)C(=O)N(C3CCC(=O)NC3=O)C4=O)C2)nn1] |
| D277 | 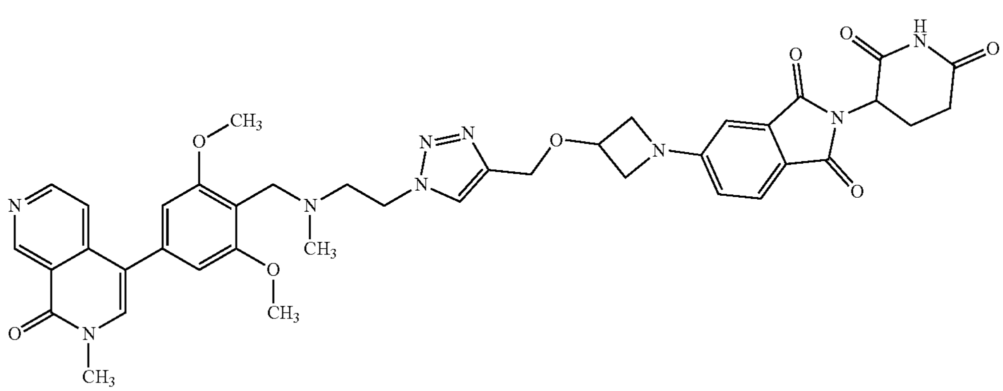 [SMILES: COc1cc(-c2cn(C)c(=O)c3cnccc23)cc(OC)c1CN(C)CCn1cc(COC2CN(c3ccc4c(c3)C(=O)N(C3CCC(=O)NC3=O)C4=O)C2)nn1] |

TABLE 1B-continued
Compounds D178-D371 of the Disclosure
| Compound No. | Structure |
|---|---|
| D278 | 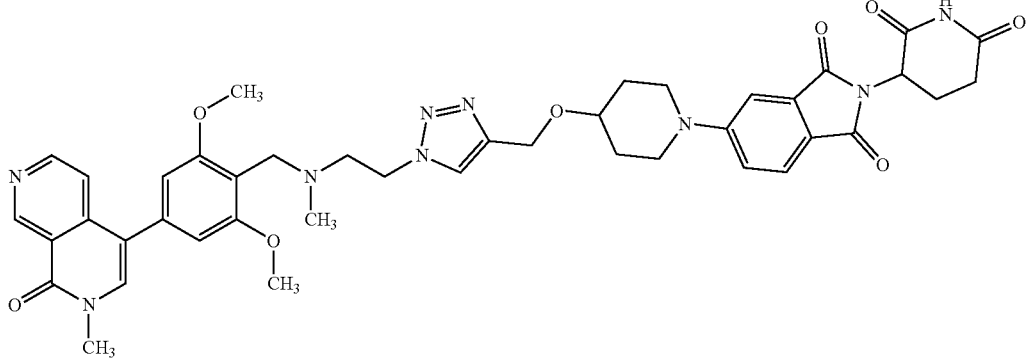 |
| D279 | 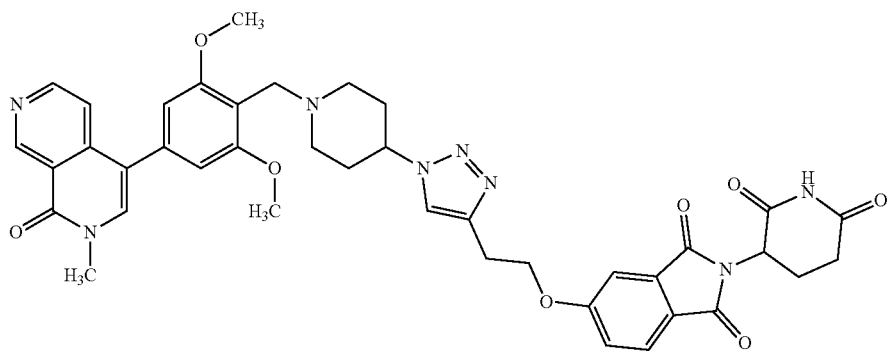 [SMILES: COc1cc(-c2cn(C)c(=O)c3cnccc23)cc(OC)c1CN1CCC(n2cc(CCOc3ccc4c(c3)C(=O)N(C3CCC(=O)NC3=O)C4=O)nn2)CC1] |
| D280 | 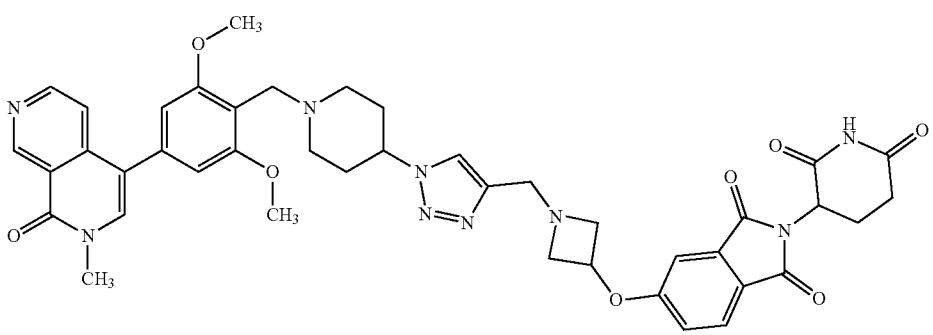 [SMILES: COc1cc(-c2cn(C)c(=O)c3cnccc23)cc(OC)c1CN1CCC(n2cc(CN3CC(Oc4ccc5c(c4)C(=O)N(C4CCC(=O)NC4=O)C5=O)C3)nn2)CC1] |
| D281 | 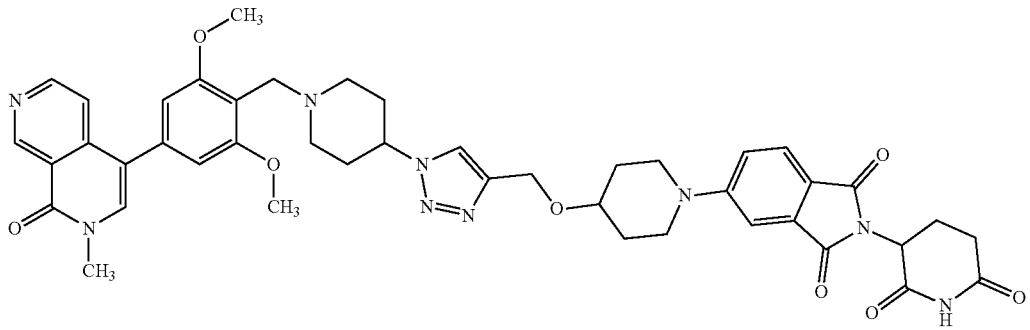 [SMILES: COc1cc(-c2cn(C)c(=O)c3cnccc23)cc(OC)c1CN1CCC(n2cc(COC3CCN(c4ccc5c(c4)C(=O)N(C4CCC(=O)NC4=O)C5=O)CC3)nn2)CC1] |

TABLE 1B-continued
Compounds D178-D371 of the Disclosure
| Compound No. | Structure |
|---|---|
| D282 | 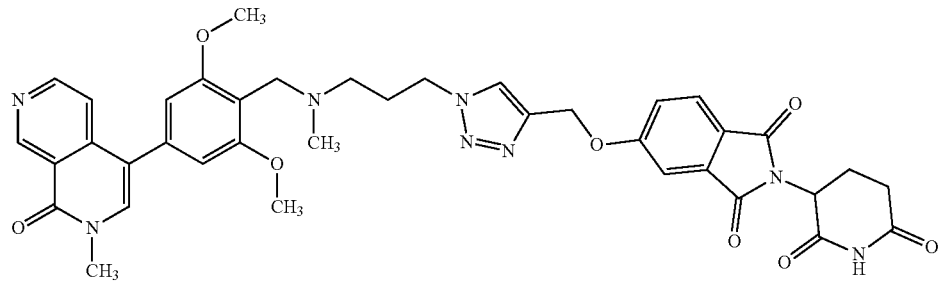 [SMILES: COc1cc(-c2cn(C)c(=O)c3cnccc23)cc(OC)c1CN(C)CCCn1cc(COc2ccc3c(c2)C(=O)N(C2CCC(=O)NC2=O)C3=O)nn1] |
| D283 | 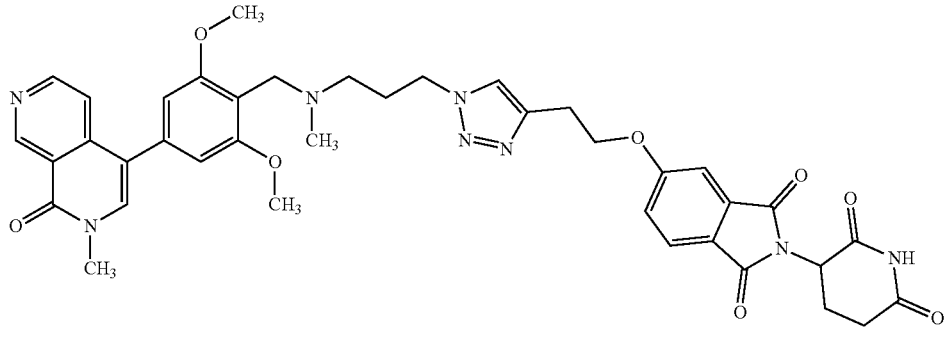 |
| D284 | 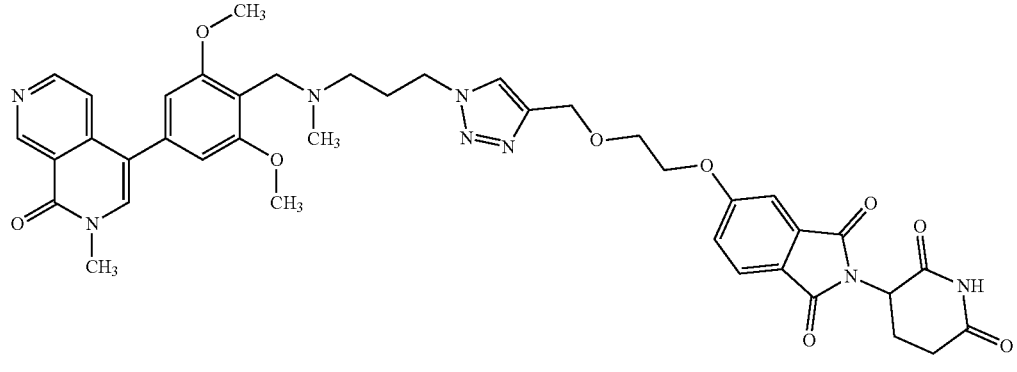 [SMILES: COc1cc(-c2cn(C)c(=O)c3cnccc23)cc(OC)c1CN(C)CCCn1cc(COCCOc2ccc3c(c2)C(=O)N(C2CCC(=O)NC2=O)C3=O)nn1] |
| D285 | 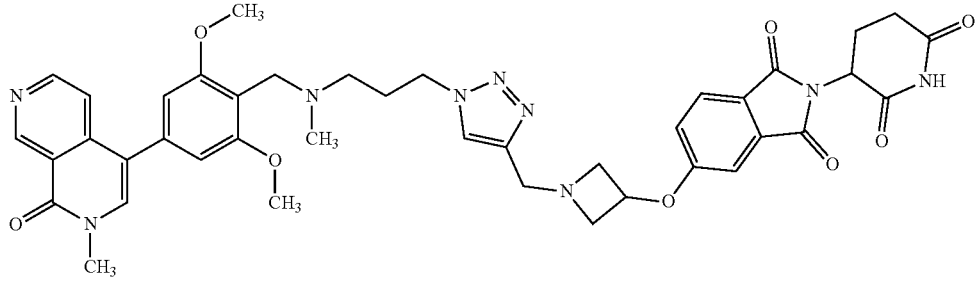 [SMILES: COc1cc(-c2cn(C)c(=O)c3cnccc23)cc(OC)c1CN(C)CCCn1cc(CN2CC(Oc3ccc4c(c3)C(=O)N(C3CCC(=O)NC3=O)C4=O)C2)nn1] |

TABLE 1B-continued
Compounds D178-D371 of the Disclosure
| Compound No. | Structure |
|---|---|
| D286 | 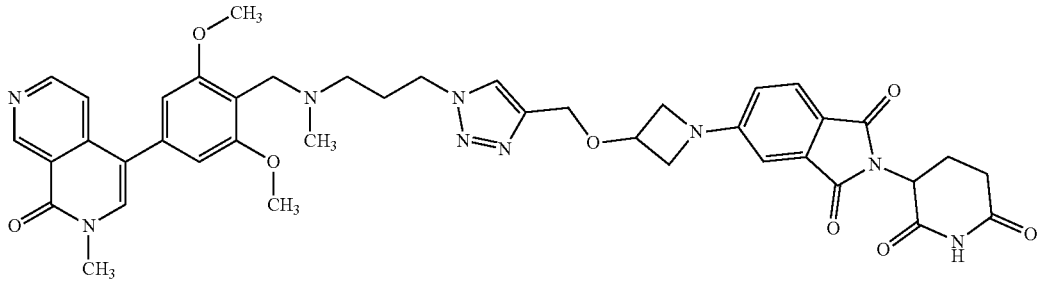 [SMILES: COc1cc(-c2cn(C)c(=O)c3cnccc23)cc(OC)c1CN(C)CCCn1cc(COC2CN(c3ccc4c(c3)C(=O)N(C3CCC(=O)NC3=O)C4=O)C2)nn1] |
| D287 | 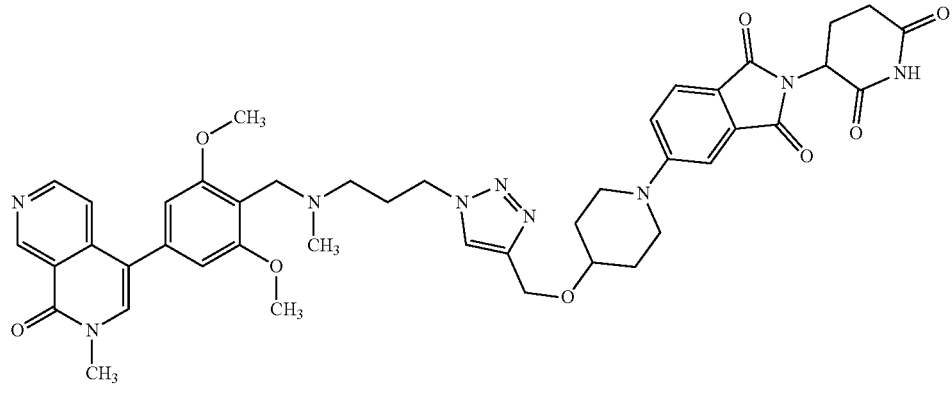 [SMILES: COc1cc(-c2cn(C)c(=O)c3cnccc23)cc(OC)c1CN(C)CCCn1cc(COC2CCN(c3ccc4c(c3)C(=O)N(C3CCC(=O)NC3=O)C4=O)CC2)nn1] |
| D288 | 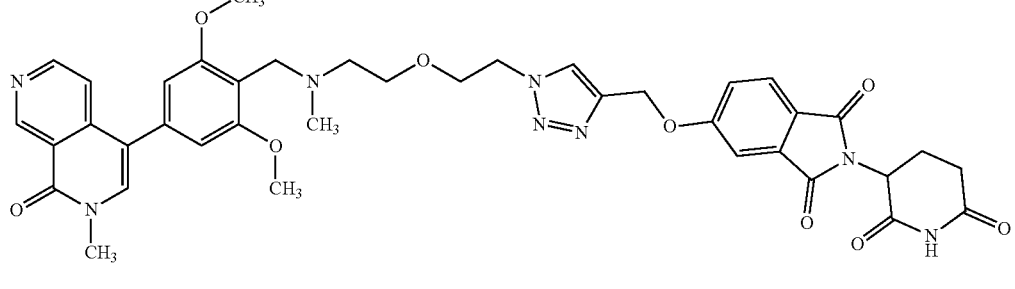 |
| D289 | 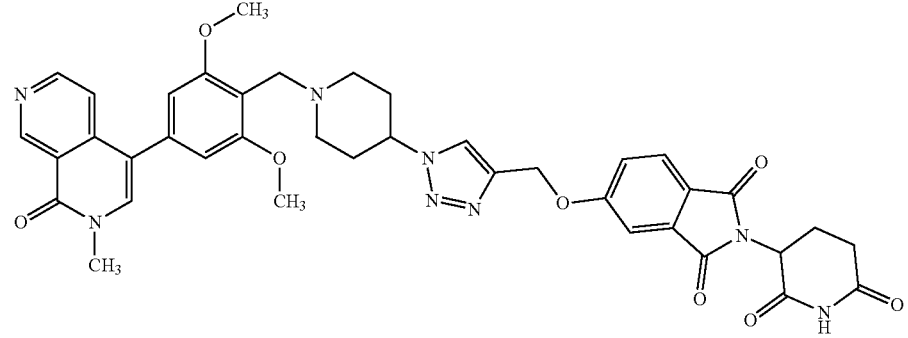 [SMILES: COc1cc(-c2cn(C)c(=O)c3cnccc23)cc(OC)c1CN1CCC(n2cc(COc3ccc4c(c3)C(=O)N(C3CCC(=O)NC3=O)C4=O)nn2)CC1] |

TABLE 1B-continued
Compounds D178-D371 of the Disclosure
| Compound No. | Structure |
|---|---|
| D290 | 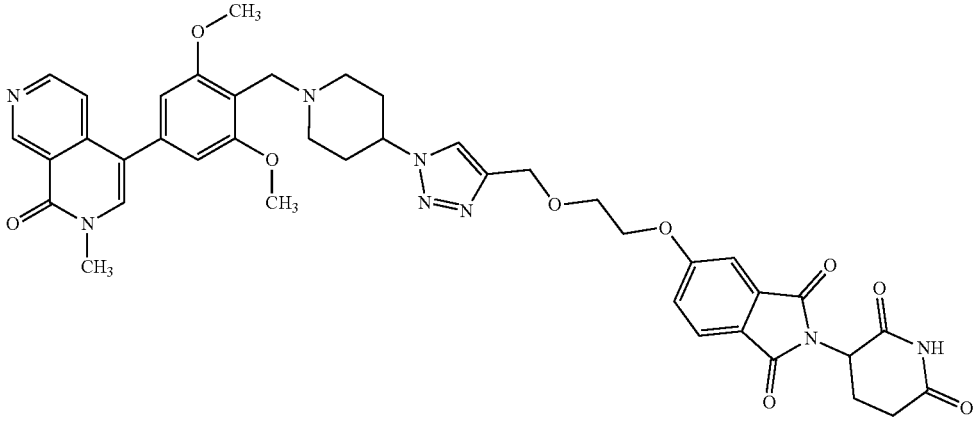 [SMILES: COc1cc(-c2cn(C)c(=O)c3cnccc23)cc(OC)c1CN1CCC(n2cc(COCCOc3ccc4c(c3)C(=O)N(C3CCC(=O)NC3=O)C4=O)nn2)CC1] |
| D291 | 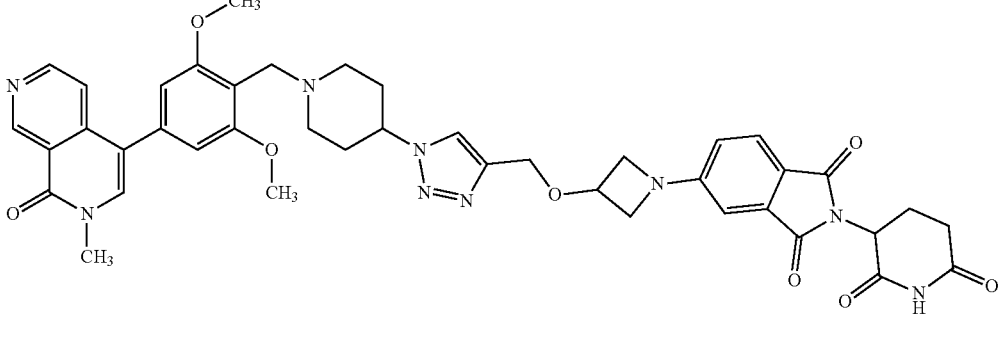 |
| D292 | 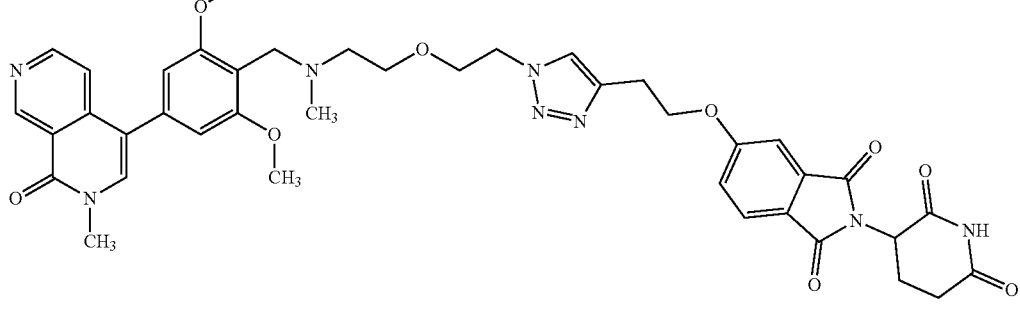 |
| D293 | 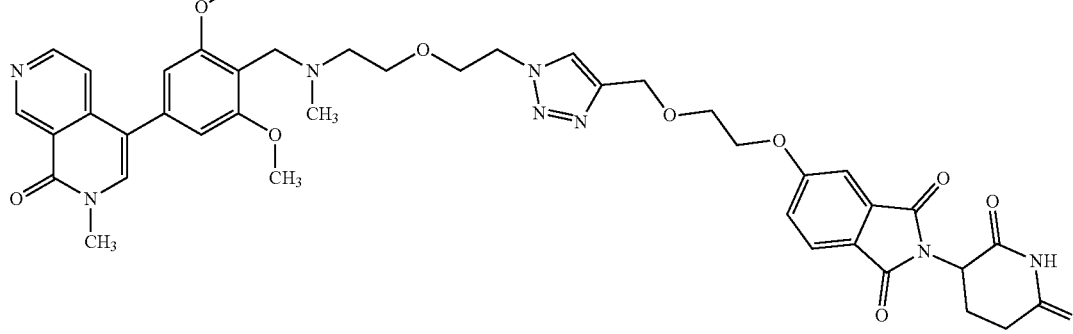 |

TABLE 1B-continued

Compounds D178-D371 of the Disclosure

| Compound No. | Structure |
|---|---|
| D294 | 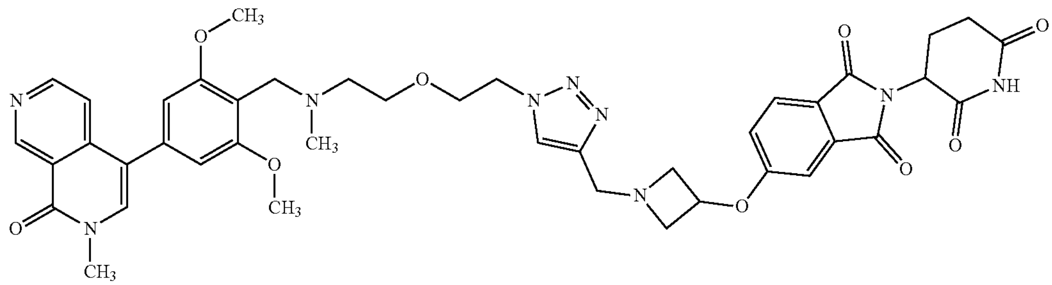 [SMILES: COc1cc(-c2cn(C)c(=O)c3cnccc23)cc(OC)c1CN(C)CCOCCn1cc(CN2CC(Oc3ccc4c(c3)C(=O)N(C3CCC(=O)NC3=O)C4=O)C2)nn1] |
| D295 | 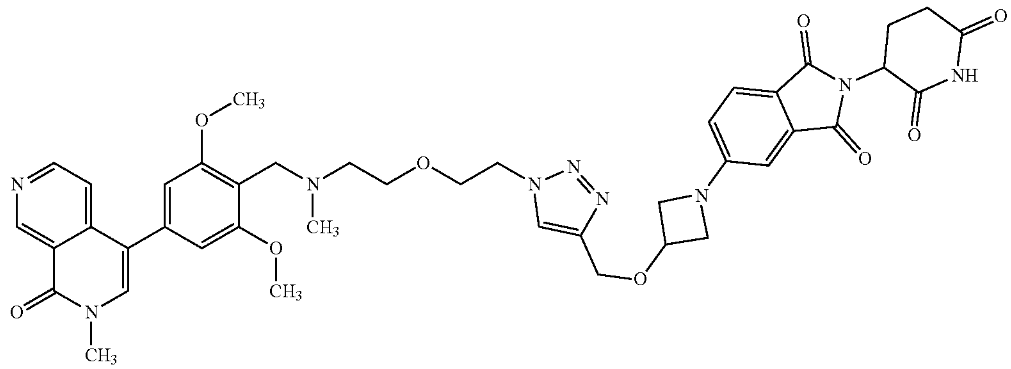 [SMILES: COc1cc(-c2cn(C)c(=O)c3cnccc23)cc(OC)c1CN(C)CCOCCn1cc(COC2CN(c3ccc4c(c3)C(=O)N(C3CCC(=O)NC3=O)C4=O)C2)nn1] |
| D296 | 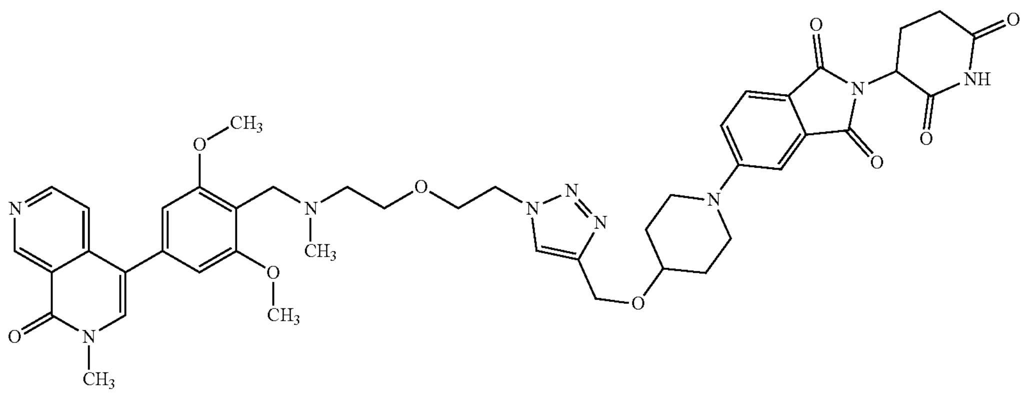 [SMILES: COc1cc(-c2cn(C)c(=O)c3cnccc23)cc(OC)c1CN(C)CCOCCn1cc(COC2CCN(c3ccc4c(c3)C(=O)N(C3CCC(=O)NC3=O)C4=O)CC2)nn1] |
| D297 | 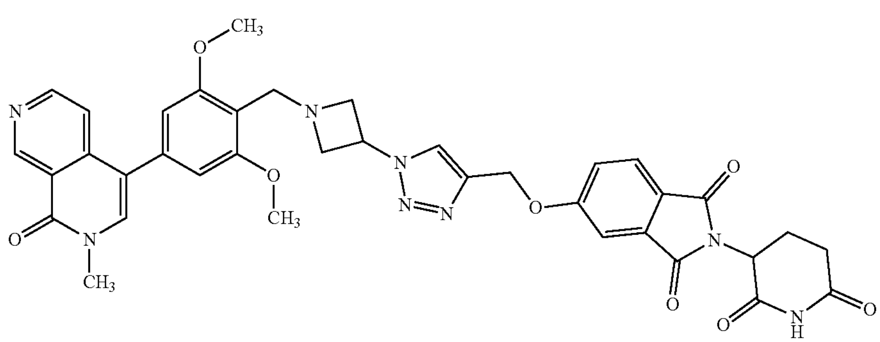 [SMILES: COc1cc(-c2cn(C)c(=O)c3cnccc23)cc(OC)c1CN1CC(n2cc(COc3ccc4c(c3)C(=O)N(C3CCC(=O)NC3=O)C4=O)nn2)C1] |

TABLE 1B-continued
Compounds D178-D371 of the Disclosure
| Compound No. | Structure |
|---|---|
| D298 | 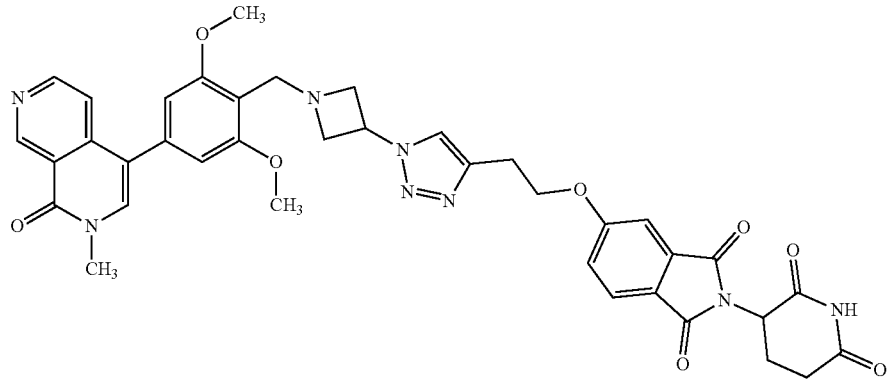 [SMILES: COc1cc(-c2cn(C)c(=O)c3cnccc23)cc(OC)c1CN1CC(n2cc(CCOc3ccc4c(c3)C(=O)N(C3CCC(=O)NC3=O)C4=O)nn2)C1] |
| D299 | 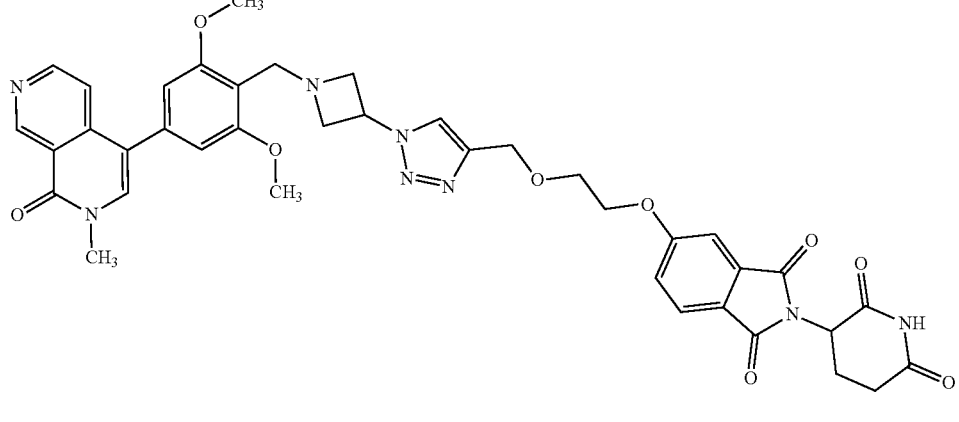 |
| D300 | 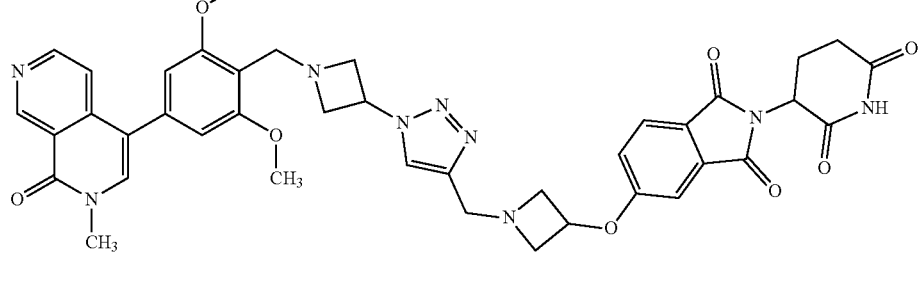 |
| D301 | 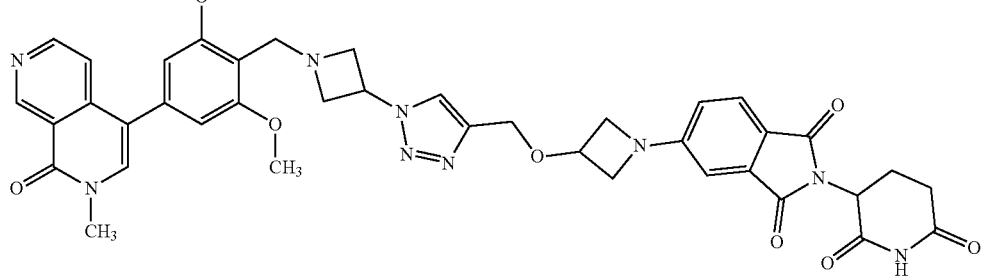 |

TABLE 1B-continued

Compounds D178-D371 of the Disclosure

| Compound No. | Structure |
|---|---|
| D302 | 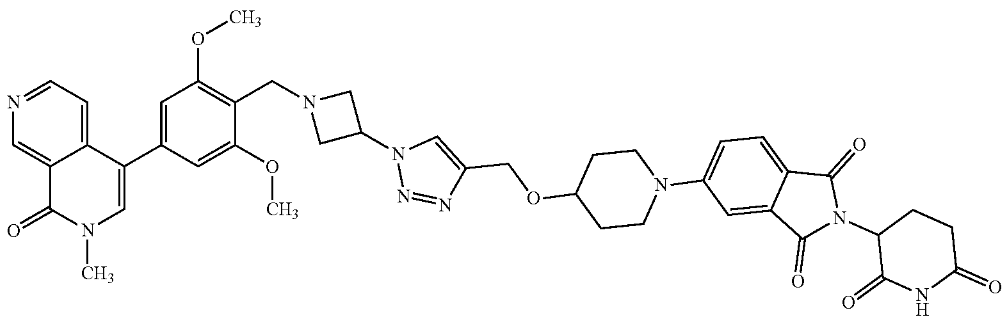 [SMILES: COc1cc(-c2cn(C)c(=O)c3cnccc23)cc(OC)c1CN1CC(n2cc(COC3CCN(c4ccc5c(c4)C(=O)N(C4CCC(=O)NC4=O)C5=O)CC3)nn2)C1] |
| D303 | 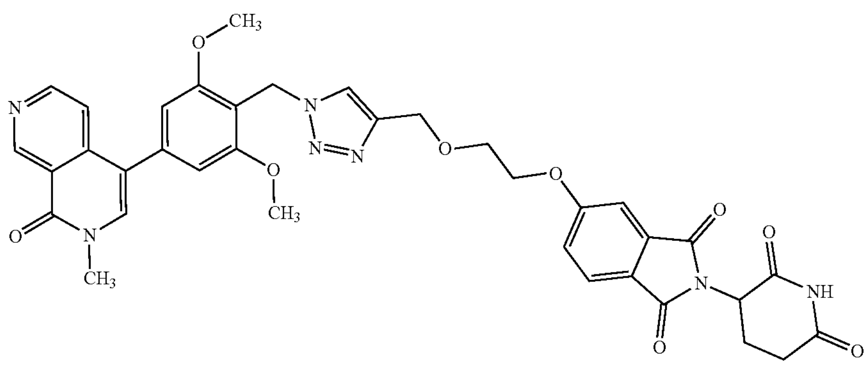 [SMILES: COc1cc(-c2cn(C)c(=O)c3cnccc23)cc(OC)c1Cn1cc(COCCOc2ccc3c(c2)C(=O)N(C2CCC(=O)NC2=O)C3=O)nn1] |
| D304 | 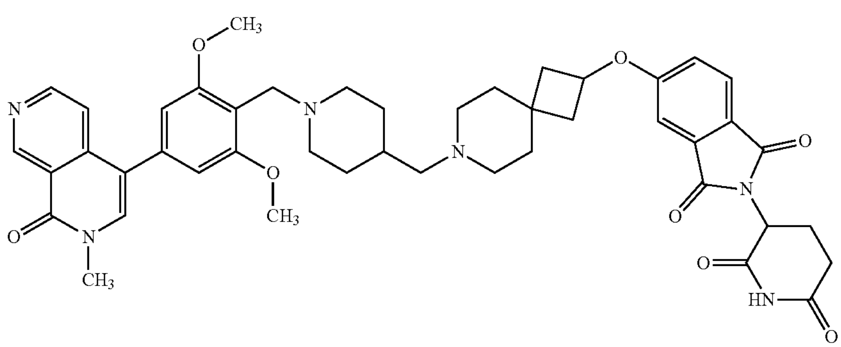 [SMILES: COc1cc(-c2cn(C)c(=O)c3cnccc23)cc(OC)c1CN1CCC(CN2CCC3(CC2)CC(Oc2ccc4c(c2)C(=O)N(C2CCC(=O)NC2=O)C4=O)C3)CC1] |
| D305 | 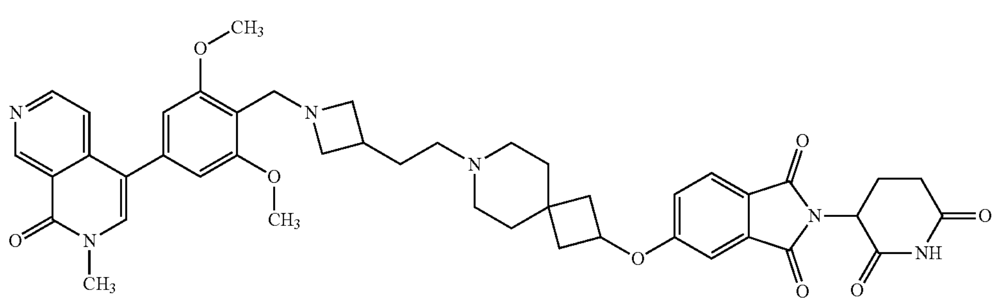 [SMILES: COc1cc(-c2cn(C)c(=O)c3cnccc23)cc(OC)c1CN1CC(CCN2CCC3(CC2)CC(Oc2ccc4c(c2)C(=O)N(C2CCC(=O)NC2=O)C4=O)C3)C1] |

TABLE 1B-continued

Compounds D178-D371 of the Disclosure

| Compound No. | Structure |
|---|---|
| D306 | 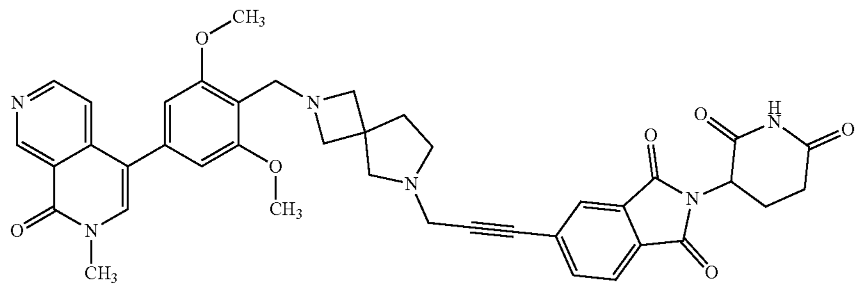 [SMILES: COc1cc(-c2cn(C)c(=O)c3cnccc23)cc(OC)c1CN1CC2(CCN(CC#Cc3ccc4c(c3)C(=O)N(C3CCC(=O)NC3=O)C4=O)C2)C1] |
| D307 | 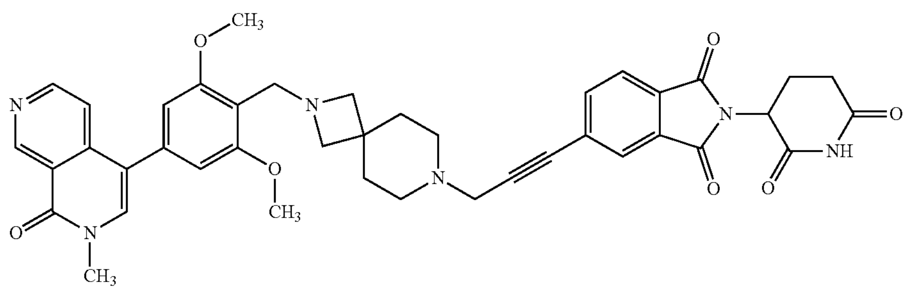 [SMILES: COc1cc(-c2cn(C)c(=O)c3cnccc23)cc(OC)c1CN1CC2(CCN(CC#Cc3ccc4c(c3)C(=O)N(C3CCC(=O)NC3=O)C4=O)CC2)C1] |
| D308 | 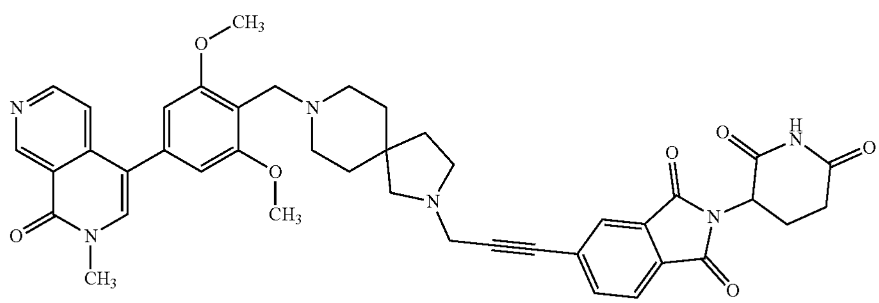 [SMILES: COc1cc(-c2cn(C)c(=O)c3cnccc23)cc(OC)c1CN1CCC2(CC1)CCN(CC#Cc1ccc3c(c1)C(=O)N(C1CCC(=O)NC1=O)C3=O)C2] |
| D309 | 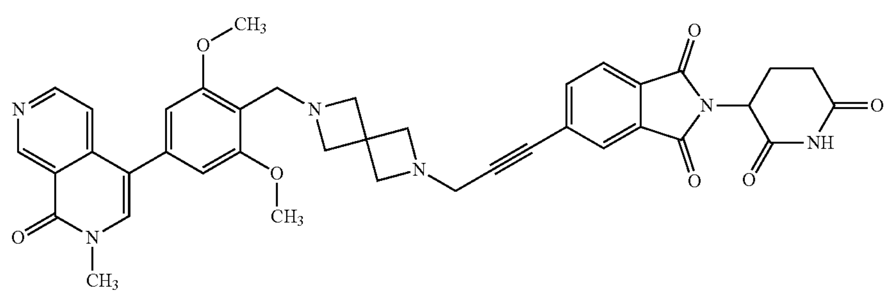 [SMILES: COc1cc(-c2cn(C)c(=O)c3cnccc23)cc(OC)c1CN1CC2(CN(CC#Cc3ccc4c(c3)C(=O)N(C3CCC(=O)NC3=O)C4=O)C2)C1] |
| D310 | 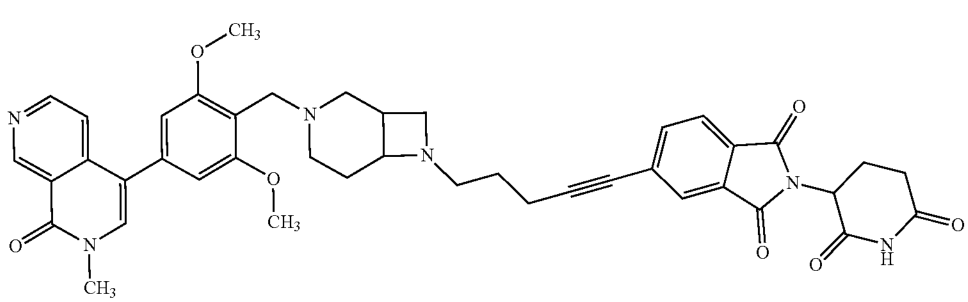 [SMILES: COc1cc(-c2cn(C)c(=O)c3cnccc23)cc(OC)c1CN1CCC2C(C1)CN2CCCC#Cc1ccc2c(c1)C(=O)N(C1CCC(=O)NC1=O)C2=O] |

TABLE 1B-continued
Compounds D178-D371 of the Disclosure
| Compound No. | Structure |
|---|---|
| D311 | 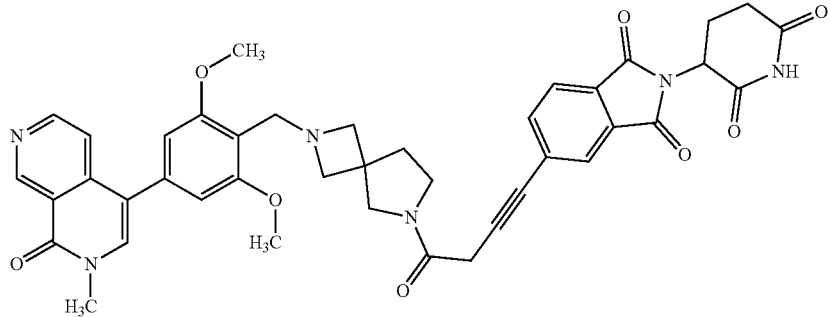 [SMILES: COc1cc(-c2cn(C)c(=O)c3cnccc23)cc(OC)c1CN1CC2(CCN(C(=O)CC#Cc3ccc4c(c3)C(=O)N(C3CCC(=O)NC3=O)C4=O)C2)C1] |
| D312 | 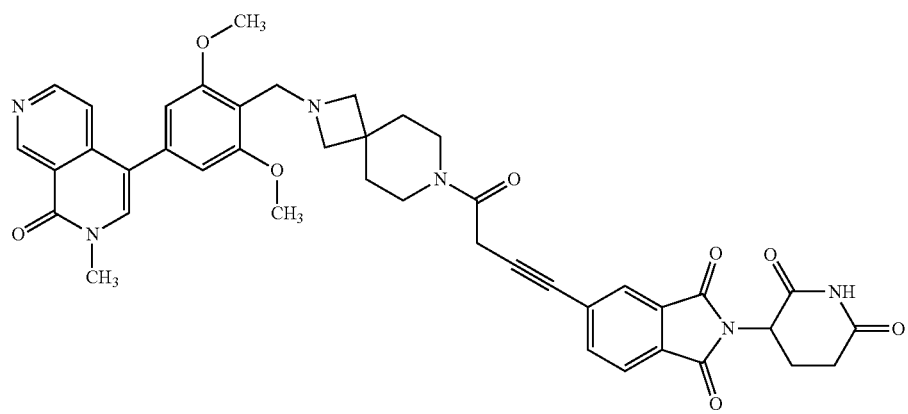 [SMILES: COc1cc(-c2cn(C)c(=O)c3cnccc23)cc(OC)c1CN1CC2(CCN(C(=O)CC#Cc3ccc4c(c3)C(=O)N(C3CCC(=O)NC3=O)C4=O)CC2)C1] |
| D313 | 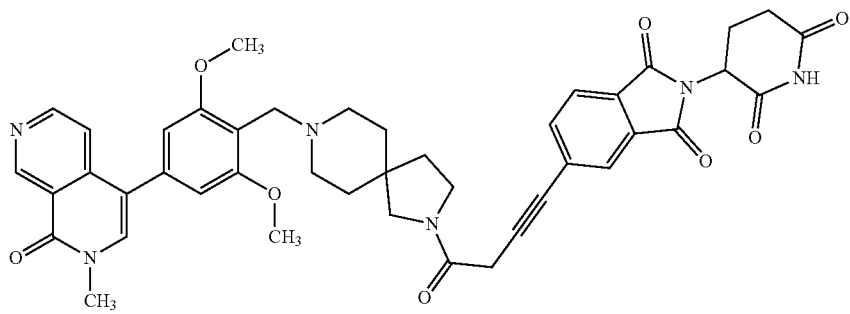 [SMILES: COc1cc(-c2cn(C)c(=O)c3cnccc23)cc(OC)c1CN1CCC2(CC1)CCN(C(=O)CC#Cc1ccc3c(c1)C(=O)N(C1CCC(=O)NC1=O)C3=O)C2] |
| D314 | 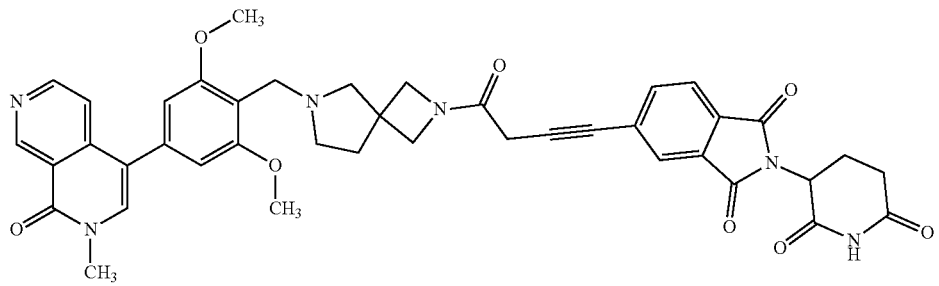 [SMILES: COc1cc(-c2cn(C)c(=O)c3cnccc23)cc(OC)c1CN1CCC2(C1)CN(C(=O)CC#Cc1ccc3c(c1)C(=O)N(C1CCC(=O)NC1=O)C3=O)C2] |

TABLE 1B-continued
Compounds D178-D371 of the Disclosure
| Compound No. | Structure |
|---|---|
| D315 | 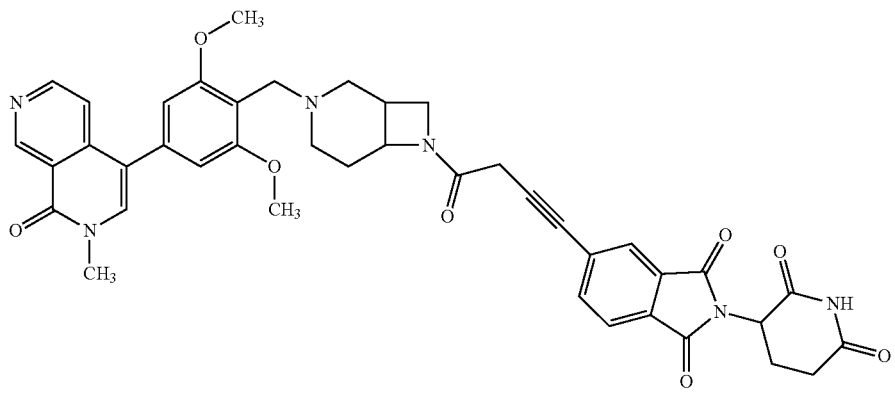 [SMILES: COc1cc(-c2cn(C)c(=O)c3cnccc23)cc(OC)c1CN1CCC2C(C1)CN2C(=O)CC#Cc1ccc2c(c1)C(=O)N(C1CCC(=O)NC1=O)C2=O] |
| D316 | 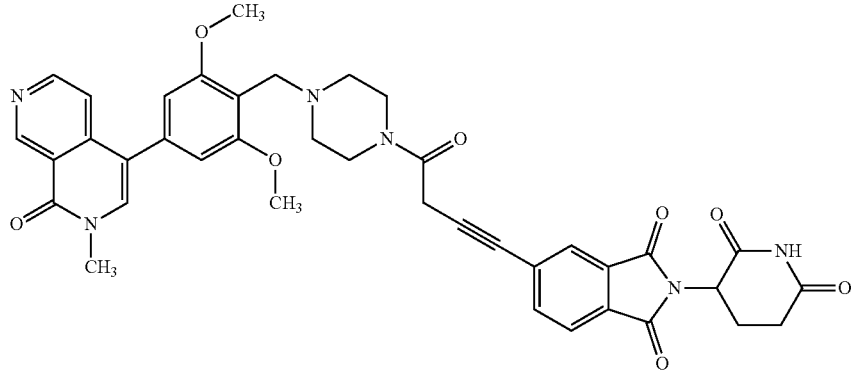 [SMILES: COc1cc(-c2cn(C)c(=O)c3cnccc23)cc(OC)c1CN1CCN(C(=O)CC#Cc2ccc3c(c2)C(=O)N(C2CCC(=O)NC2=O)C3=O)CC1] |
| D317 | 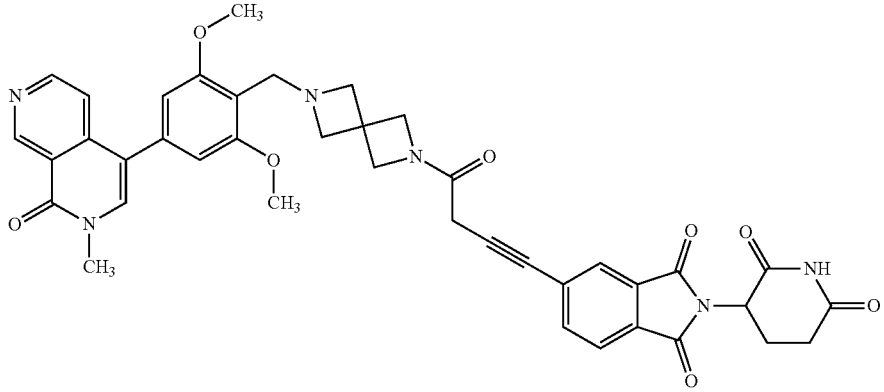 [SMILES: COc1cc(-c2cn(C)c(=O)c3cnccc23)cc(OC)c1CN1CC2(C1)CN(C(=O)CC#Cc1ccc3c(c1)C(=O)N(C1CCC(=O)NC1=O)C3=O)C2] |

TABLE 1B-continued
Compounds D178-D371 of the Disclosure
| Compound No. | Structure |
|---|---|
| D318 | 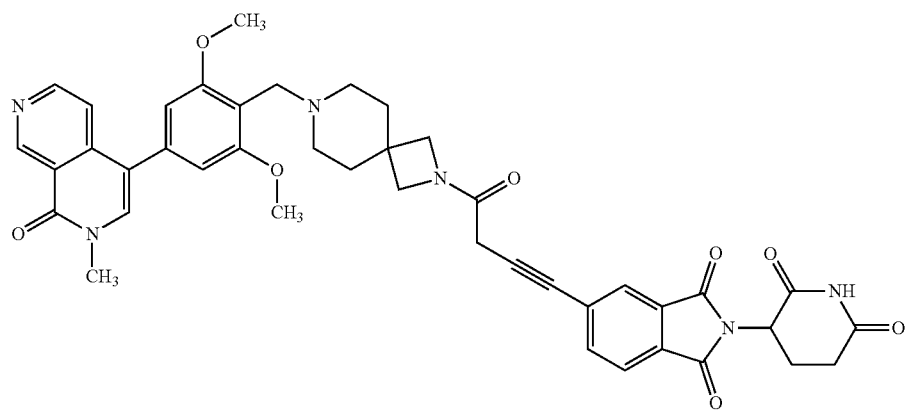 [SMILES: COc1cc(-c2cn(C)c(=O)c3cnccc23)cc(OC)c1CN1CCC2(CC1)CN(C(=O)CC#Cc1ccc3c(c1)C(=O)N(C1CCC(=O)NC1=O)C3=O)C2] |
| D319 | 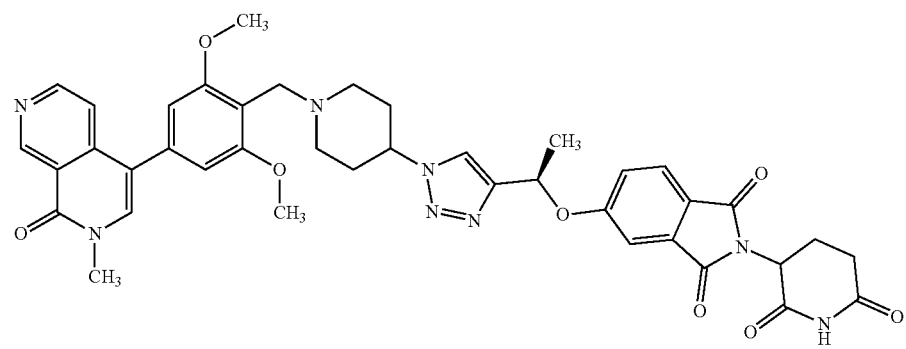 [SMILES: COc1cc(-c2cn(C)c(=O)c3cnccc23)cc(OC)c1CN1CCC(n2cc([C@@H](C)Oc3ccc4c(c3)C(=O)N(C3CCC(=O)NC3=O)C4=O)nn2)CC1] |
| D320 | 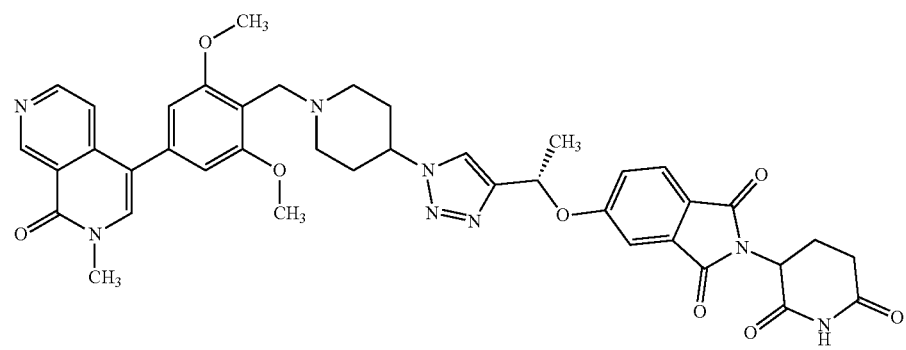 [SMILES: COc1cc(-c2cn(C)c(=O)c3cnccc23)cc(OC)c1CN1CCC(n2cc([C@H](C)Oc3ccc4c(c3)C(=O)N(C3CCC(=O)NC3=O)C4=O)nn2)CC1] |
| D321 | 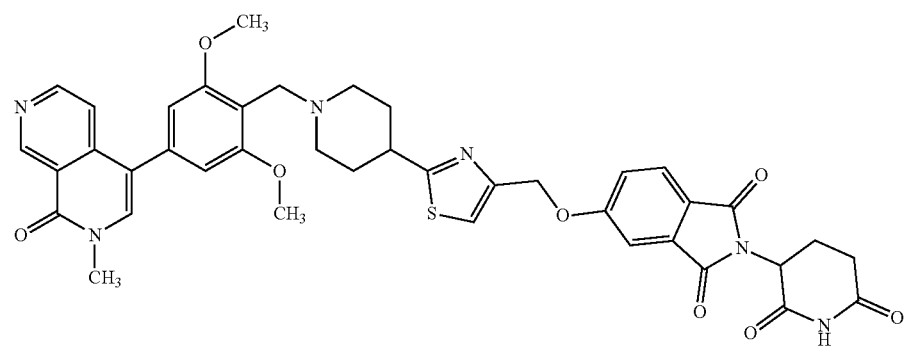 |

TABLE 1B-continued
Compounds D178-D371 of the Disclosure
| Compound No. | Structure |
| --- | --- |
| D322 | 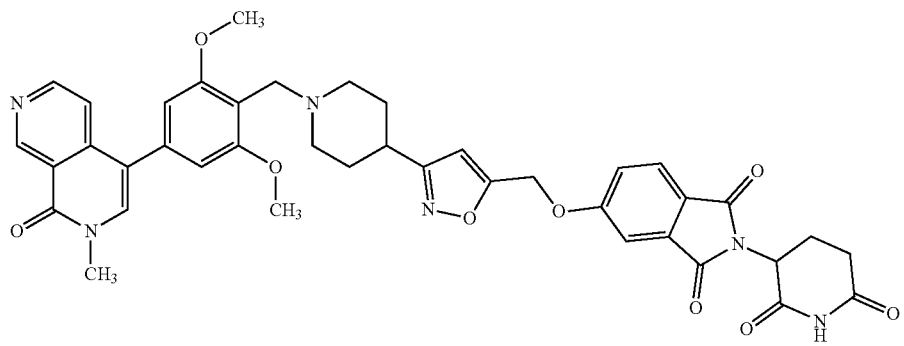 [SMILES: COc1cc(-c2cn(C)c(=O)c3cnccc23)cc(OC)c1CN1CCC(c2cc(COc3ccc4c(c3)C(=O)N(C3CCC(=O)NC3=O)C4=O)on2)CC1] |
| D323 | 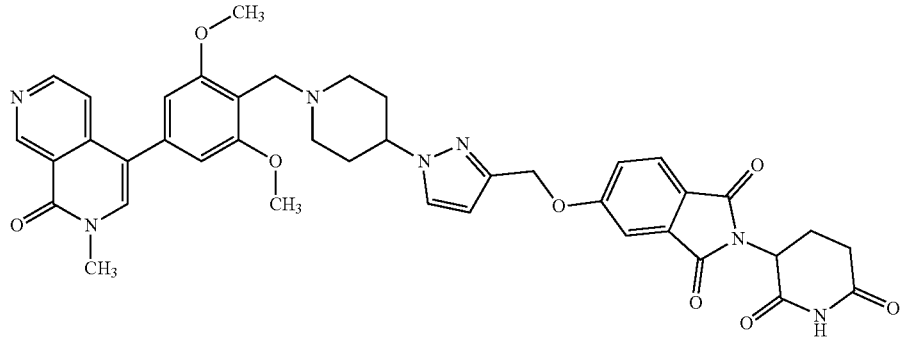 [SMILES: COc1cc(-c2cn(C)c(=O)c3cnccc23)cc(OC)c1CN1CCC(n2ccc(COc3ccc4c(c3)C(=O)N(C3CCC(=O)NC3=O)C4=O)n2)CC1] |
| D324 | 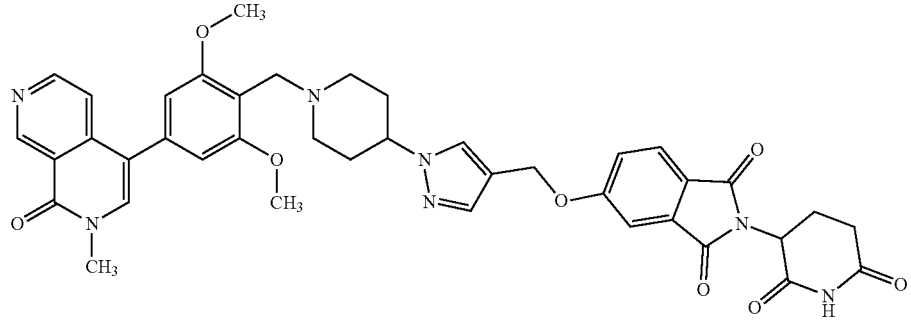 [SMILES: COc1cc(-c2cn(C)c(=O)c3cnccc23)cc(OC)c1CN1CCC(n2cc(COc3ccc4c(c3)C(=O)N(C3CCC(=O)NC3=O)C4=O)cn2)CC1] |
| D325 | 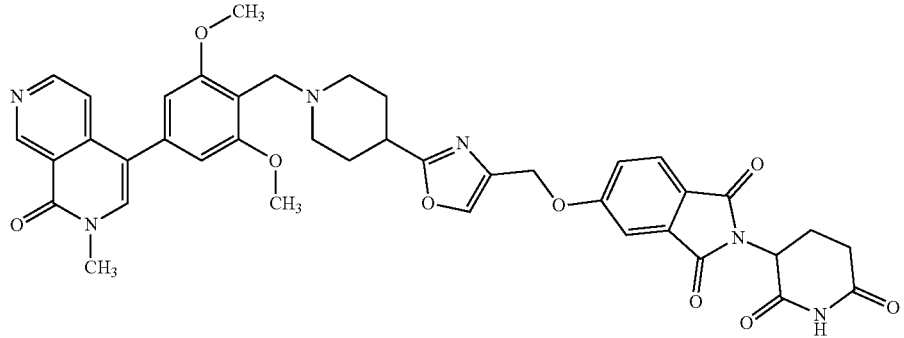 |

TABLE 1B-continued

Compounds D178-D371 of the Disclosure

| Compound No. | Structure |
| --- | --- |
| D326 | 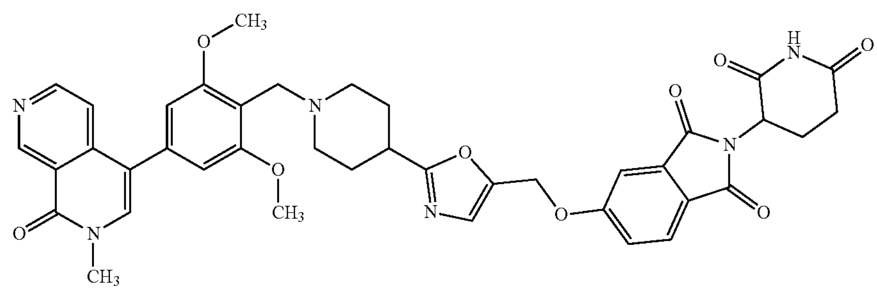 [SMILES: COc1cc(-c2cn(C)c(=O)c3cnccc23)cc(OC)c1CN1CCC(c2ncc(COc3ccc4c(c3)C(=O)N(C3CCC(=O)NC3=O)C4=O)o2)CC1] |
| D327 | 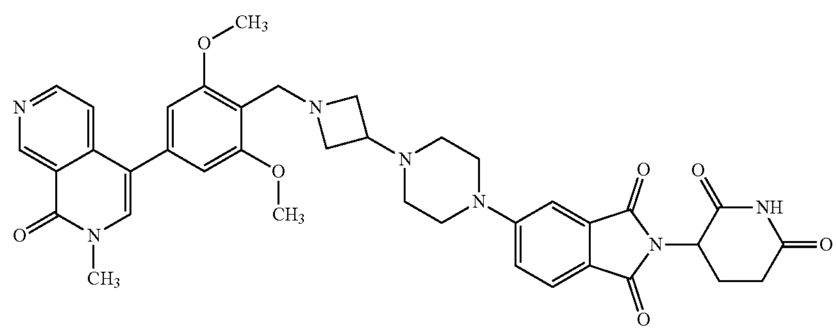 [SMILES: COc1cc(-c2cn(C)c(=O)c3cnccc23)cc(OC)c1CN1CC(N2CCN(c3ccc4c(c3)C(=O)N(C3CCC(=O)NC3=O)C4=O)CC2)C1] |
| D328 | 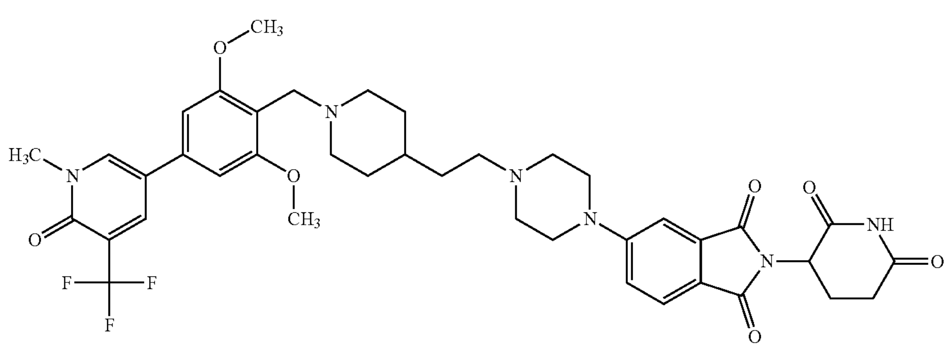 [SMILES: COc1cc(-c2cc(C(F)(F)F)c(=O)n(C)c2)cc(OC)c1CN1CCC(CCN2CCN(c3ccc4c(c3)C(=O)N(C3CCC(=O)NC3=O)C4=O)CC2)CC1] |
| D329 | 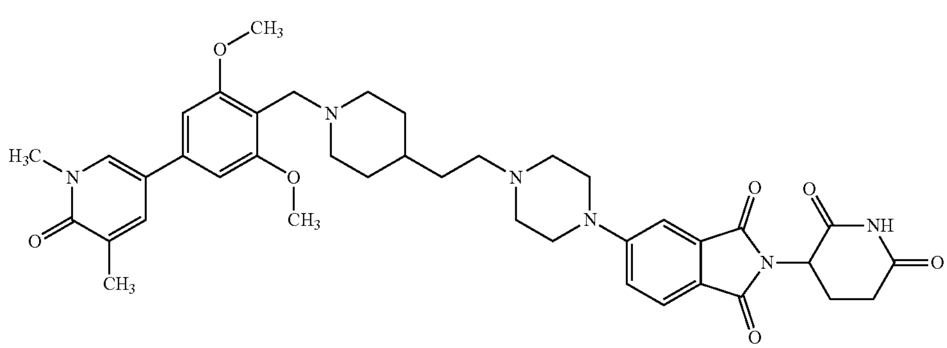 [SMILES: COc1cc(-c2cc(C)c(=O)n(C)c2)cc(OC)c1CN1CCC(CCN2CCN(c3ccc4c(c3)C(=O)N(C3CCC(=O)NC3=O)C4=O)CC2)CC1] |

TABLE 1B-continued

Compounds D178-D371 of the Disclosure

| Compound No. | Structure |
|---|---|
| D330 | 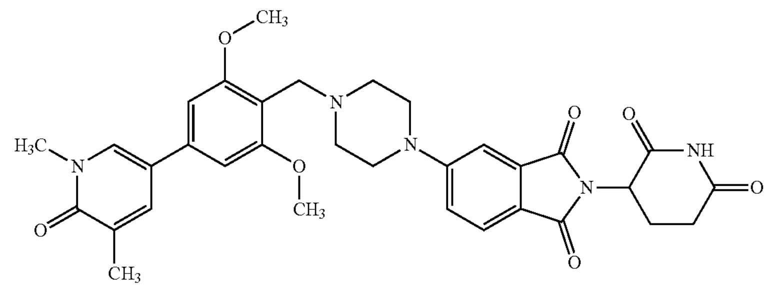 [SMILES: COc1cc(-c2cc(C)c(=O)n(C)c2)cc(OC)c1CN1CCN(c2ccc3c(c2)C(=O)N(C2CCC(=O)NC2=O)C3=O)CC1] |
| D331 | 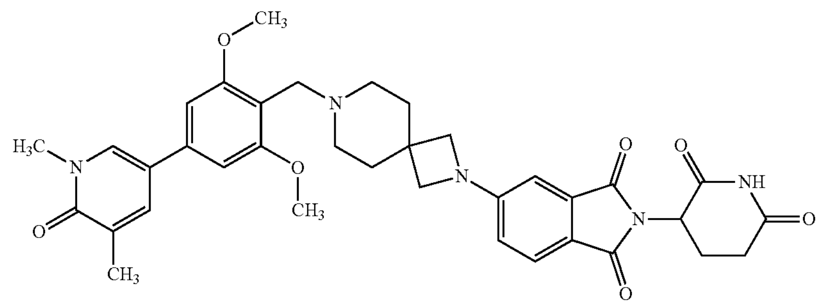 [SMILES: COc1cc(-c2cc(C)c(=O)n(C)c2)cc(OC)c1CN1CCC2(CC1)CN(c1ccc3c(c1)C(=O)N(C1CCC(=O)NC1=O)C3=O)C2] |
| D332 | 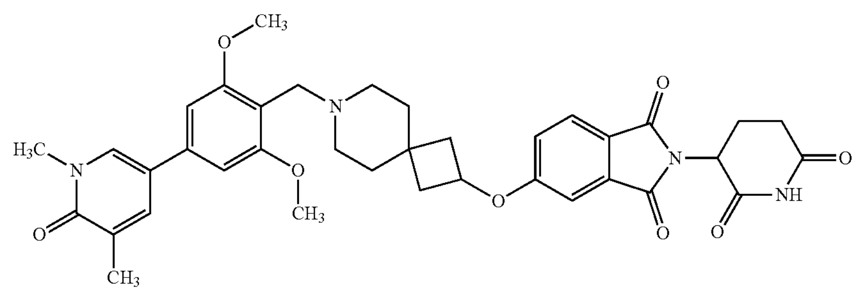 [SMILES: COc1cc(-c2cc(C)c(=O)n(C)c2)cc(OC)c1CN1CCC2(CC1)CC(Oc1ccc3c(c1)C(=O)N(C1CCC(=O)NC1=O)C3=O)C2] |
| D333 | 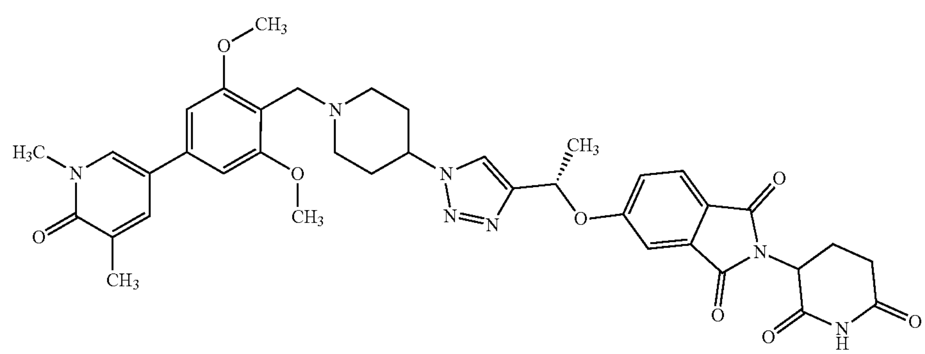 [SMILES: COc1cc(-c2cc(C)c(=O)n(C)c2)cc(OC)c1CN1CCC(n2cc([C@H](C)Oc3ccc4c(c3)C(=O)N(C3CCC(=O)NC3=O)C4=O)nn2)CC1] |
| D334 | 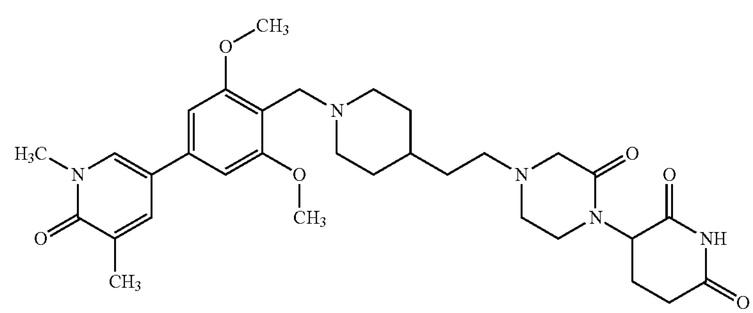 [SMILES: COc1cc(-c2cc(C)c(=O)n(C)c2)cc(OC)c1CN1CCC(CCN2CCN(C3CCC(=O)NC3=O)C(=O)C2)CC1] |

TABLE 1B-continued
Compounds D178-D371 of the Disclosure
| Compound No. | Structure |
|---|---|
| D335 | 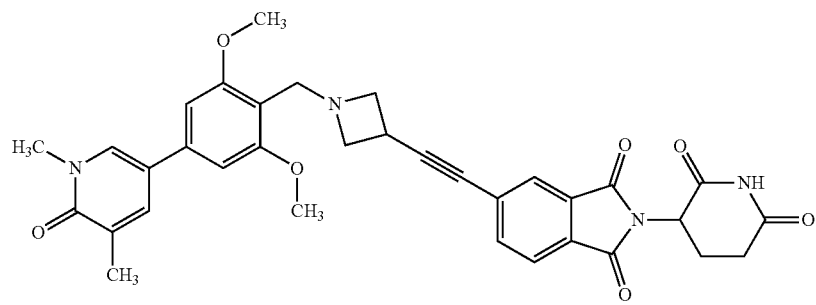 [SMILES: COc1cc(-c2cc(C)c(=O)n(C)c2)cc(OC)c1CN1CC(C#Cc2ccc3c(c2)C(=O)N(C2CCC(=O)NC2=O)C3=O)C1] |
| D336 | 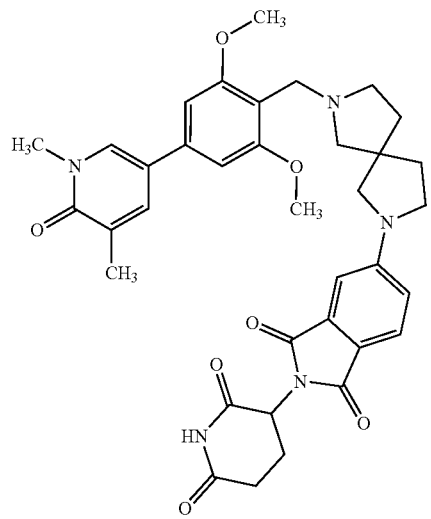 [SMILES: COc1cc(-c2cc(C)c(=O)n(C)c2)cc(OC)c1CN1CCC2(CCN(c3ccc4c(c3)C(=O)N(C3CCC(=O)NC3=O)C4=O)C2)C1] |
| D337 | 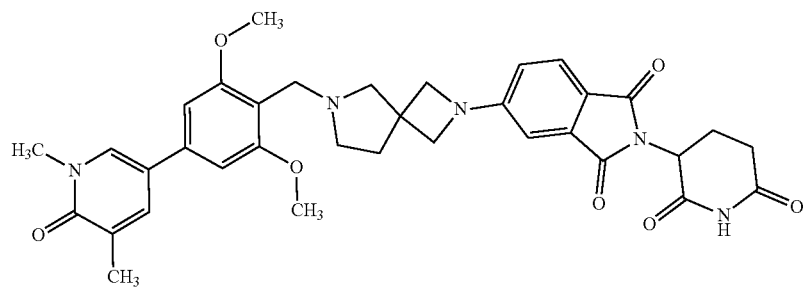 [SMILES: COc1cc(-c2cc(C)c(=O)n(C)c2)cc(OC)c1CN1CCC2(C1)CN(c1ccc3c(c1)C(=O)N(C1CCC(=O)NC1=O)C3=O)C2] |
| D338 | 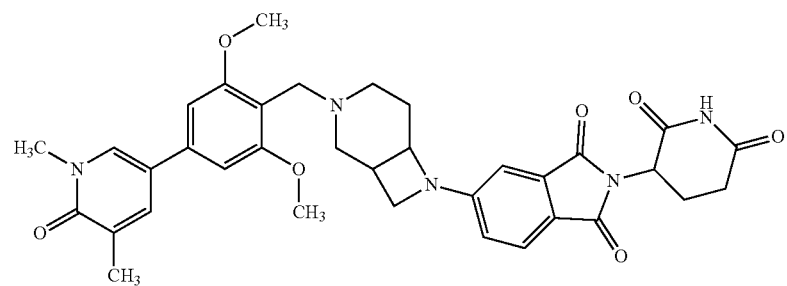 [SMILES: COc1cc(-c2cc(C)c(=O)n(C)c2)cc(OC)c1CN1CCC2C(C1)CN2c1ccc2c(c1)C(=O)N(C1CCC(=O)NC1=O)C2=O] |

TABLE 1B-continued
Compounds D178-D371 of the Disclosure
| Compound No. | Structure |
| --- | --- |
| D339 | 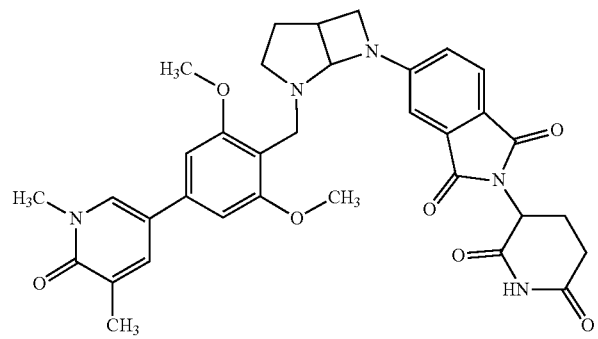 [SMILES: COc1cc(-c2cc(C)c(=O)n(C)c2)cc(OC)c1CN1CCC2CN(c3ccc4c(c3)C(=O)N(C3CCC(=O)NC3=O)C4=O)C21] |
| D340 | 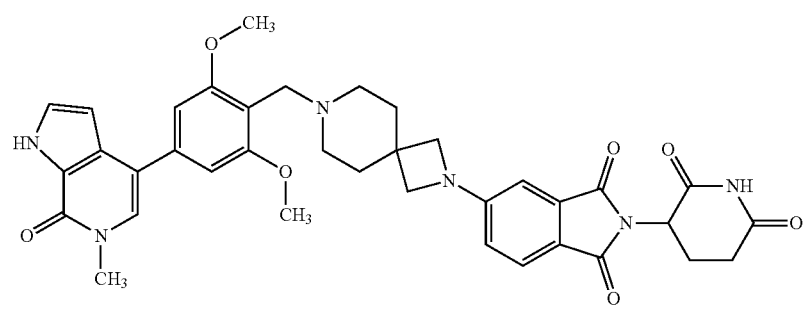 [SMILES: COc1cc(-c2cn(C)c(=O)c3[nH]ccc23)cc(OC)c1CN1CCC2(CC1)CN(c1ccc3c(c1)C(=O)N(C1CCC(=O)NC1=O)C3=O)C2] |
| D341 | 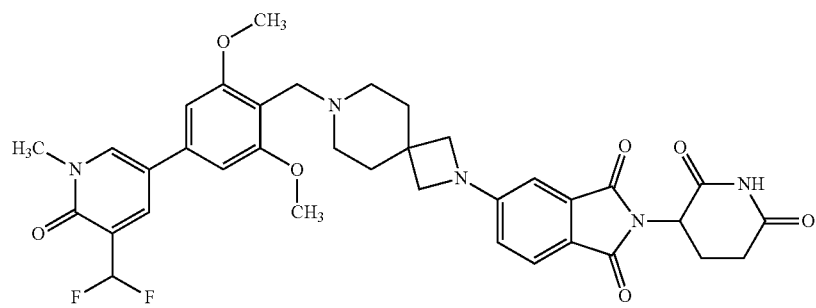 [SMILES: COc1cc(-c2cc(C(F)F)c(=O)n(C)c2)cc(OC)c1CN1CCC2(CC1)CN(c1ccc3c(c1)C(=O)N(C1CCC(=O)NC1=O)C3=O)C2] |
| D342 | 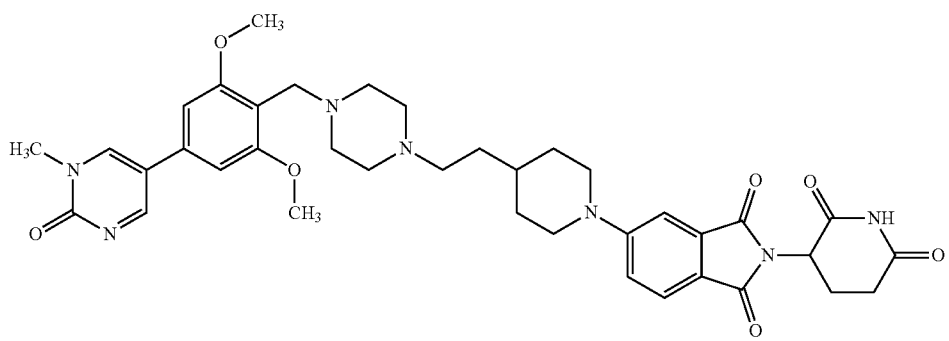 [SMILES: COc1cc(-c2cnc(=O)n(C)c2)cc(OC)c1CN1CCN(CCC2CCN(c3ccc4c(c3)C(=O)N(C3CCC(=O)NC3=O)C4=O)CC2)CC1] |

TABLE 1B-continued
Compounds D178-D371 of the Disclosure
| Compound No. | Structure |
| --- | --- |
| D343 | 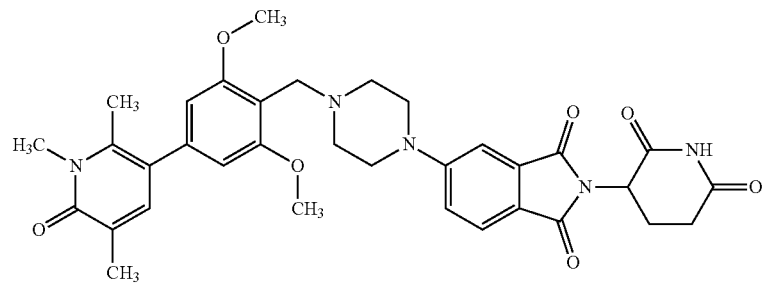 [SMILES: COc1cc(-c2cc(C)c(=O)n(C)c2C)cc(OC)c1CN1CCN(c2ccc3c(c2)C(=O)N(C2CCC(=O)NC2=O)C3=O)CC1] |
| D344 | 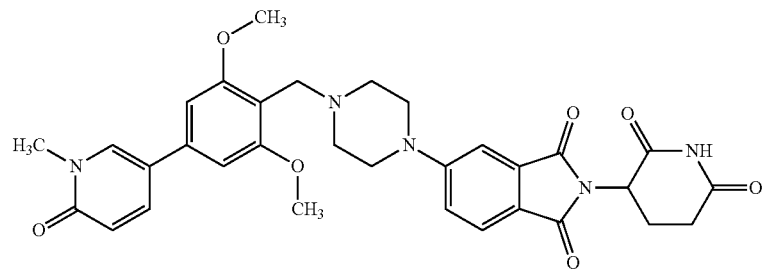 [SMILES: COc1cc(-c2ccc(=O)n(C)c2)cc(OC)c1CN1CCN(c2ccc3c(c2)C(=O)N(C2CCC(=O)NC2=O)C3=O)CC1] |
| D345 | 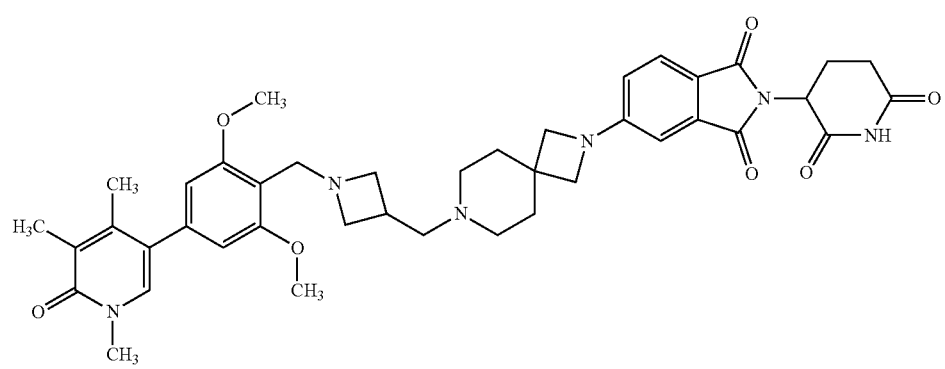 [SMILES: COc1cc(-c2cn(C)c(=O)c(C)c2C)cc(OC)c1CN1CC(CN2CCC3(CC2)CN(c2ccc4c(c2)C(=O)N(C2CCC(=O)NC2=O)C4=O)C3)C1] |
| D346 | 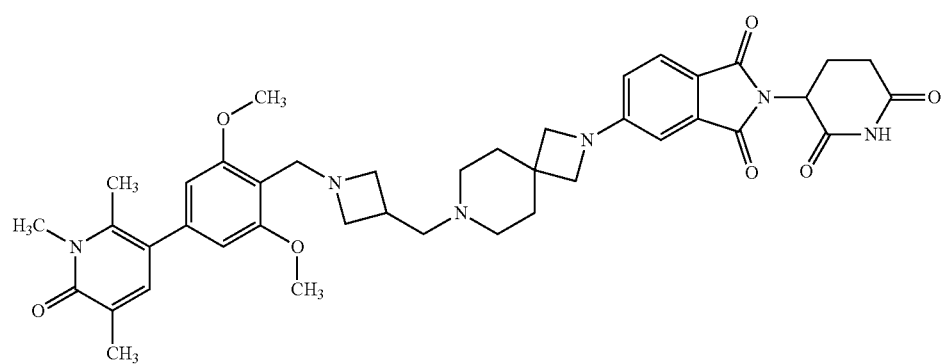 [SMILES: COc1cc(-c2cc(C)c(=O)n(C)c2C)cc(OC)c1CN1CC(CN2CCC3(CC2)CN(c2ccc4c(c2)C(=O)N(C2CCC(=O)NC2=O)C4=O)C3)C1] |

TABLE 1B-continued

Compounds D178-D371 of the Disclosure

| Compound No. | Structure |
| --- | --- |
| D347 | 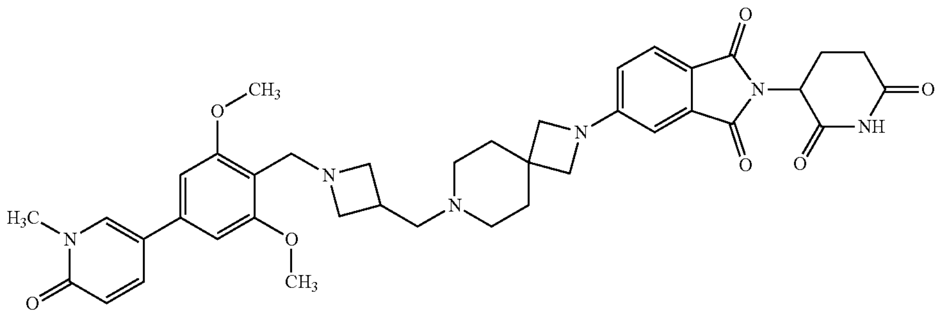 [SMILES: COc1cc(-c2ccc(=O)n(C)c2)cc(OC)c1CN1CC(CN2CCC3(CC2)CN(c2ccc4c(c2)C(=O)N(C2CCC(=O)NC2=O)C4=O)C3)C1] |
| D348 | 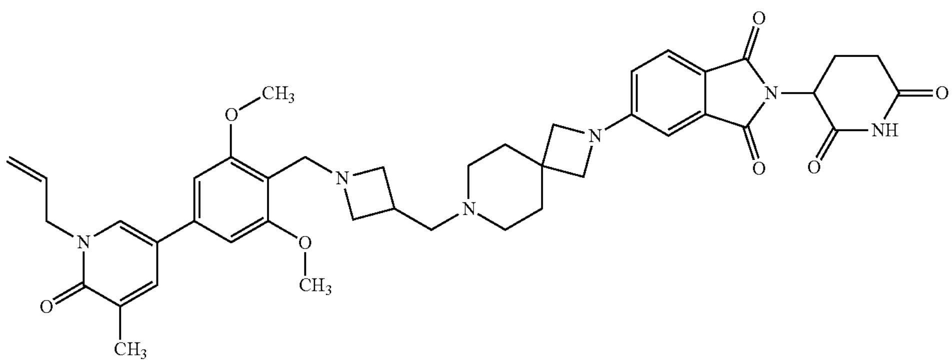 [SMILES: C=CCn1cc(-c2cc(OC)c(CN3CC(CN4CCC5(CC4)CN(c4ccc6c(c4)C(=O)N(C4CCC(=O)NC4=O)C6=O)C5)C3)c(OC)c2)cc(C)c1=O] |
| D349 | 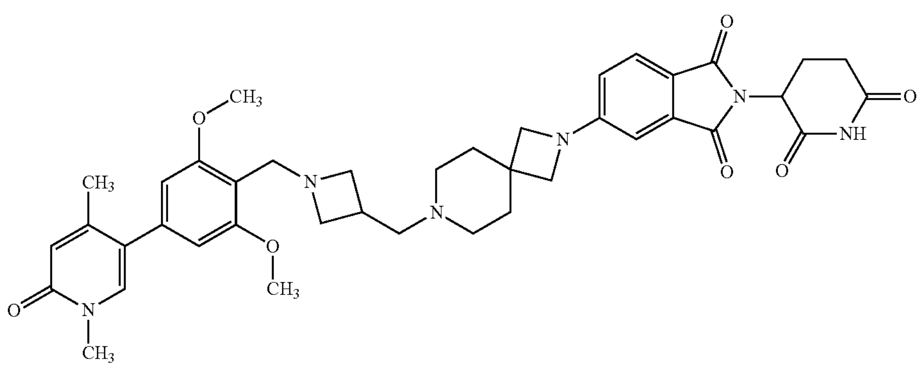 [SMILES: COc1cc(-c2cn(C)c(=O)cc2C)cc(OC)c1CN1CC(CN2CCC3(CC2)CN(c2ccc4c(c2)C(=O)N(C2CCC(=O)NC2=O)C4=O)C3)C1] |
| D350 | 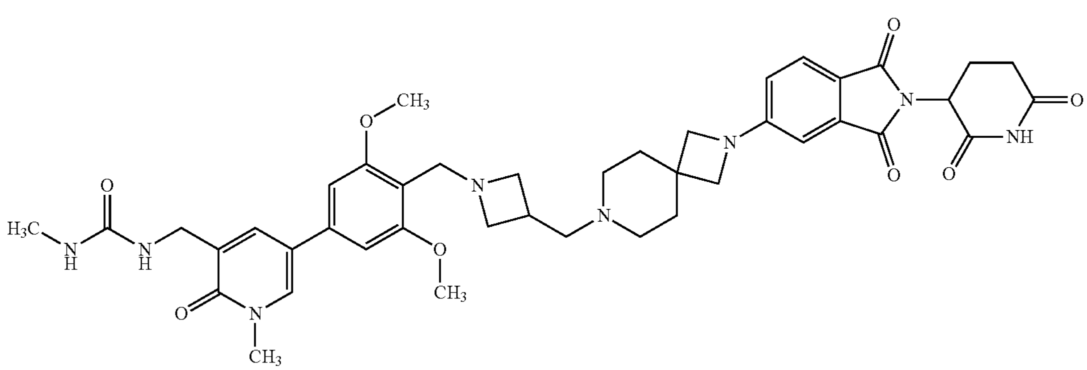 [SMILES: CNC(=O)NCc1cc(-c2cc(OC)c(CN3CC(CN4CCC5(CC4)CN(c4ccc6c(c4)C(=O)N(C4CCC(=O)NC4=O)C6=O)C5)C3)c(OC)c2)cn(C)c1=O] |

TABLE 1B-continued
Compounds D178-D371 of the Disclosure
| Compound No. | Structure |
|---|---|
| D351 | 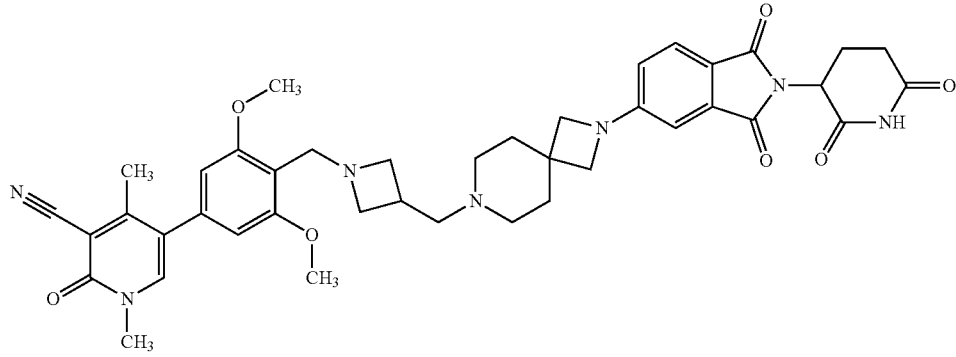 [SMILES: COc1cc(-c2cn(C)c(=O)c(C#N)c2C)cc(OC)c1CN1CC(CN2CCC3(CC2)CN(c2ccc4c(c2)C(=O)N(C2CCC(=O)NC2=O)C4=O)C3)C1] |
| D352 | 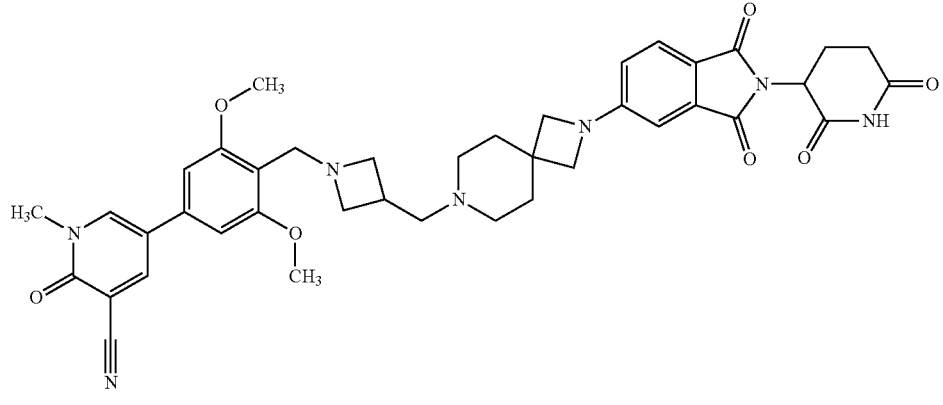 [SMILES: COc1cc(-c2cc(C#N)c(=O)n(C)c2)cc(OC)c1CN1CC(CN2CCC3(CC2)CN(c2ccc4c(c2)C(=O)N(C2CCC(=O)NC2=O)C4=O)C3)C1] |
| D353 | 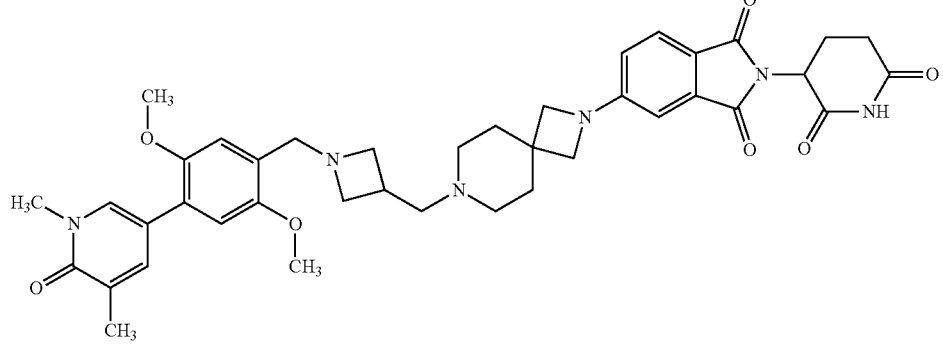 |
| D354 | 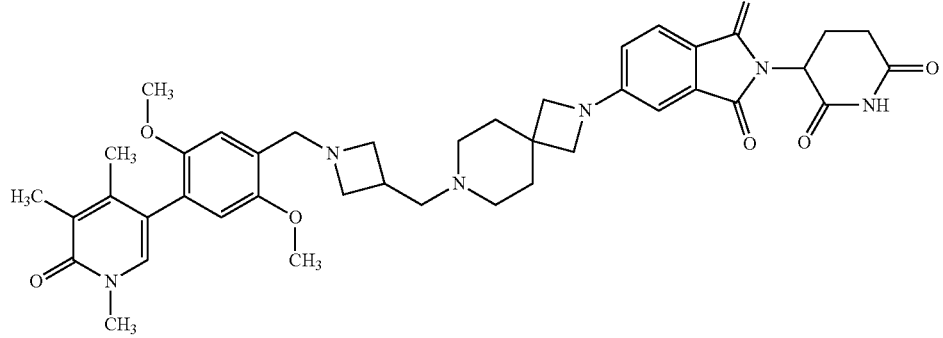 |

TABLE 1B-continued
Compounds D178-D371 of the Disclosure
| Compound No. | Structure |
|---|---|
| D355 | 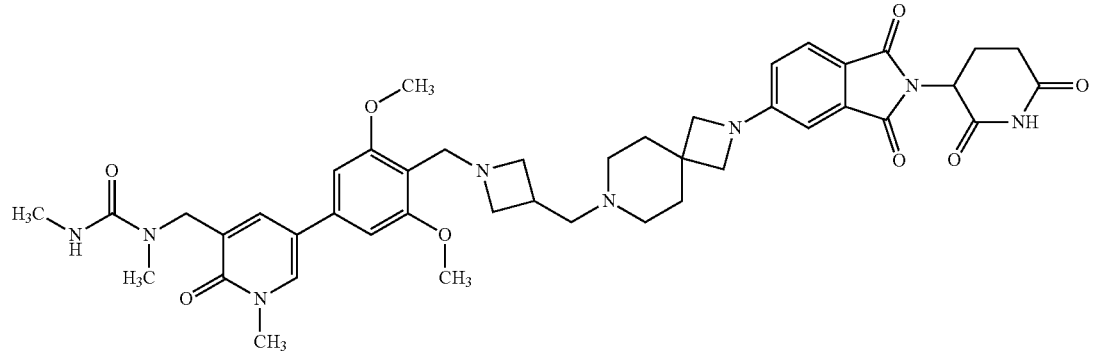 [SMILES: CNC(=O)N(C)Cc1cc(-c2cc(OC)c(CN3CC(CN4CCC5(CC4)CN(c4ccc6c(c4)C(=O)N(C4CCC(=O)NC4=O)C6=O)C5)C3)c(OC)c2)cn(C)c1=O] |
| D356 | 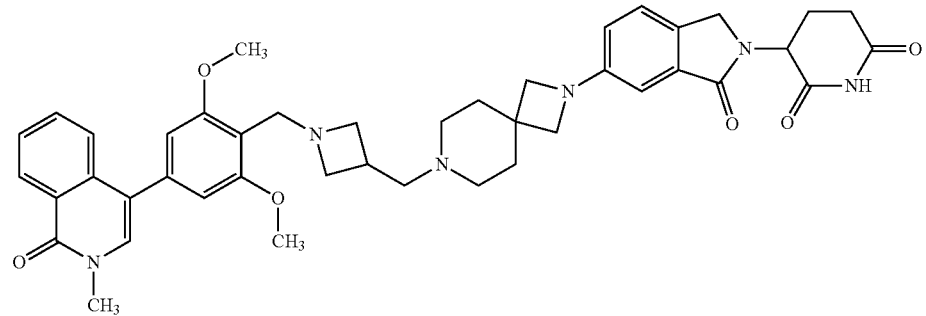 [SMILES: COc1cc(-c2cn(C)c(=O)c3ccccc23)cc(OC)c1CN1CC(CN2CCC3(CC2)CN(c2ccc4c(c2)C(=O)N(C2CCC(=O)NC2=O)C4)C3)C1] |
| D357 | 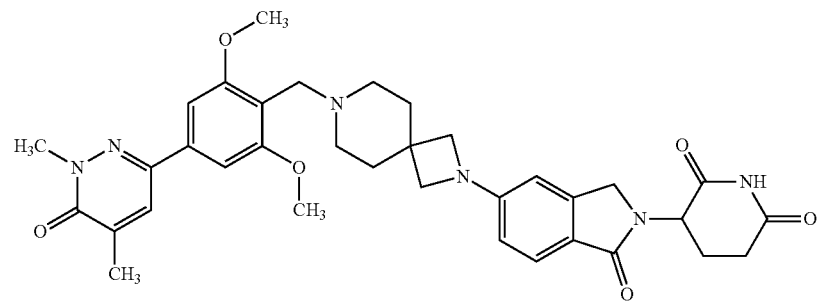 [SMILES: COc1cc(-c2cc(C)c(=O)n(C)n2)cc(OC)c1CN1CCC2(CC1)CN(c1ccc3c(c1)CN(C1CCC(=O)NC1=O)C3=O)C2] |
| D358 | 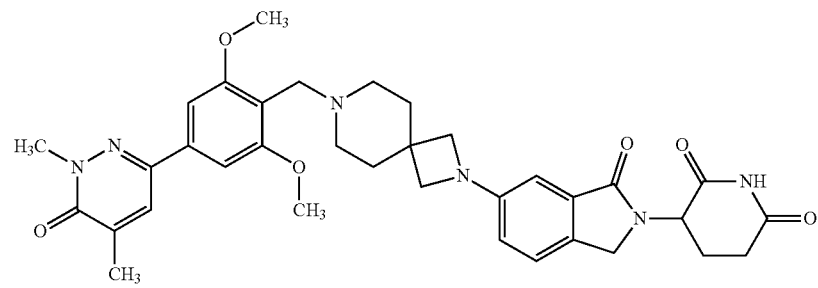 [SMILES: COc1cc(-c2cc(C)c(=O)n(C)n2)cc(OC)c1CN1CCC2(CC1)CN(c1ccc3c(c1)C(=O)N(C1CCC(=O)NC1=O)C3)C2] |

TABLE 1B-continued
Compounds D178-D371 of the Disclosure
| Compound No. | Structure |
|---|---|
| D359 | 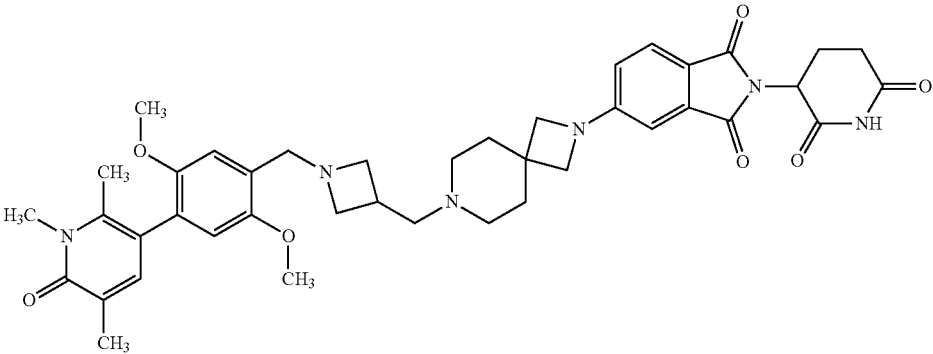 [SMILES: COc1cc(-c2cc(C)c(=O)n(C)c2C)c(OC)cc1CN1CC(CN2CCC3(CC2)CN(c2ccc4c(c2)C(=O)N(C2CCC(=O)NC2=O)C4=O)C3)C1] |
| D360 | 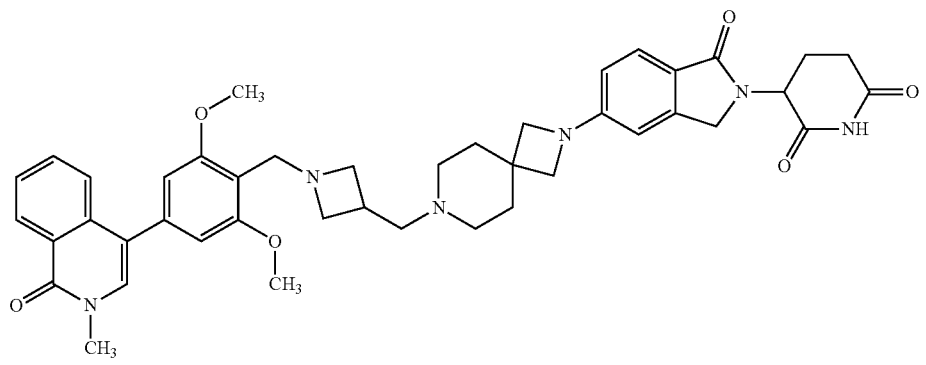 [SMILES: COc1cc(-c2cn(C)c(=O)c3ccccc23)cc(OC)c1CN1CC(CN2CCC3(CC2)CN(c2ccc4c(c2)CN(C2CCC(=O)NC2=O)C4=O)C3)C1] |
| D361 | 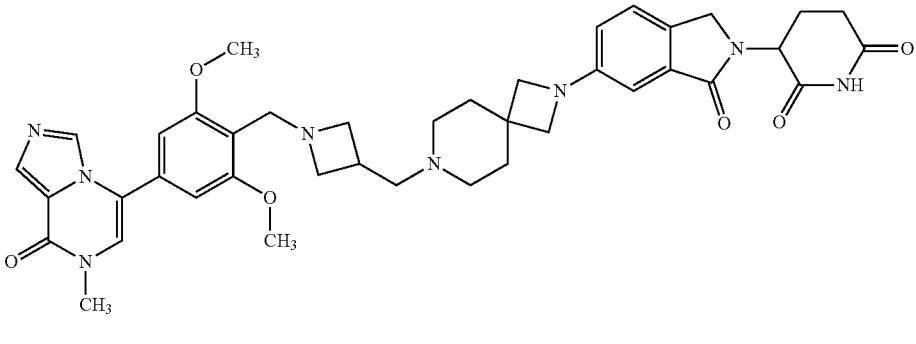 [SMILES: COc1cc(-c2cn(C)c(=O)c3cncn23)cc(OC)c1CN1CC(CN2CCC3(CC2)CN(c2ccc4c(c2)C(=O)N(C2CCC(=O)NC2=O)C4)C3)C1] |
| D362 | 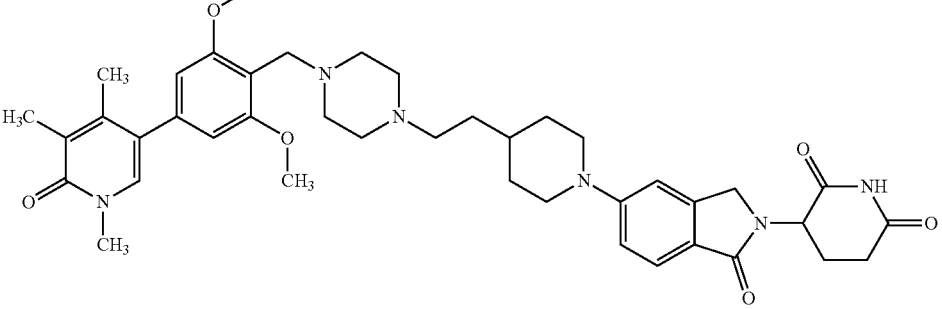 |

TABLE 1B-continued
Compounds D178-D371 of the Disclosure
| Compound No. | Structure |
|---|---|
| D363 | 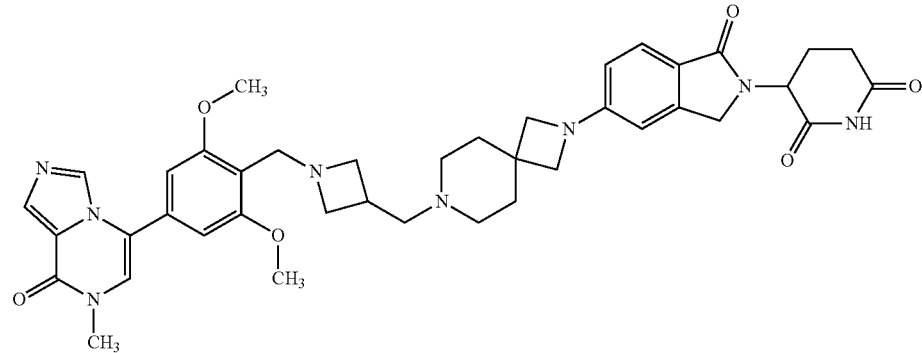 [SMILES: COc1cc(-c2cn(C)c(=O)c3cncn23)cc(OC)c1CN1CC(CN2CCC3(CC2)CN(c2ccc4c(c2)CN(C2CCC(=O)NC2=O)C4=O)C3)C1] |
| D364 | 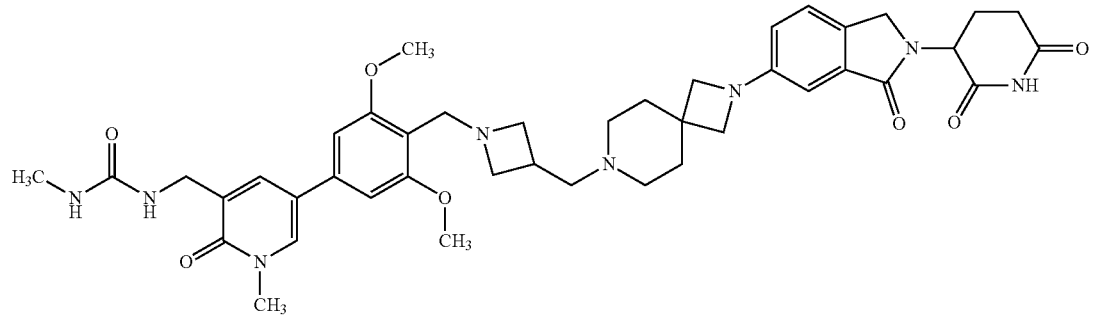 [SMILES: CNC(=O)NCc1cc(-c2cc(OC)c(CN3CC(CN4CCC5(CC4)CN(c4ccc6c(c4)C(=O)N(C4CCC(=O)NC4=O)C6)C5)C3)c(OC)c2)cn(C)c1=O] |
| D365 | 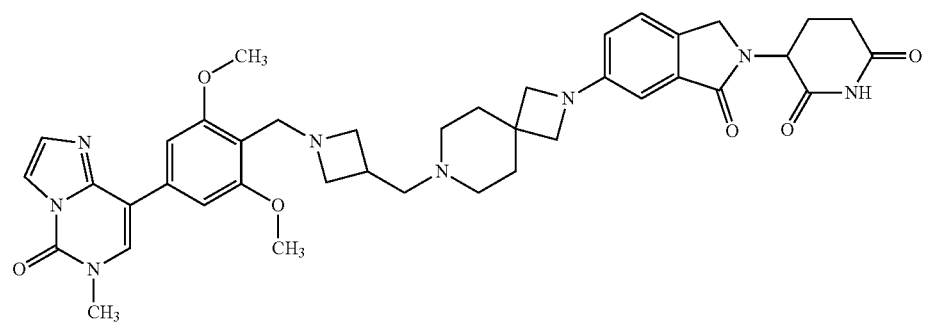 [SMILES: COc1cc(-c2cn(C)c(=O)n3ccnc23)cc(OC)c1CN1CC(CN2CCC3(CC2)CN(c2ccc4c(c2)C(=O)N(C2CCC(=O)NC2=O)C4)C3)C1] |
| D366 | 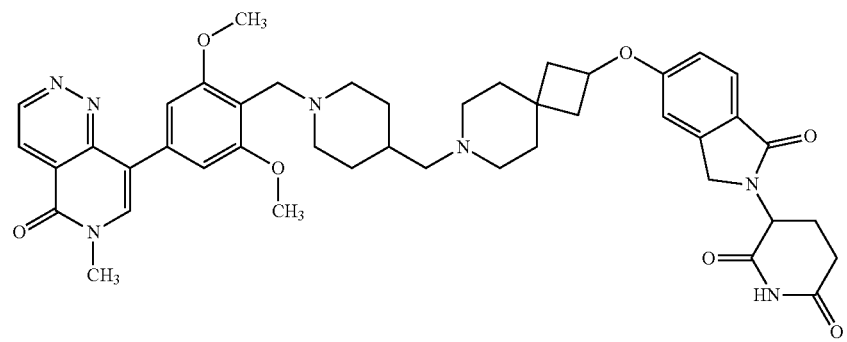 |

TABLE 1B-continued
Compounds D178-D371 of the Disclosure
| Compound No. | Structure |
|---|---|
| D367 | 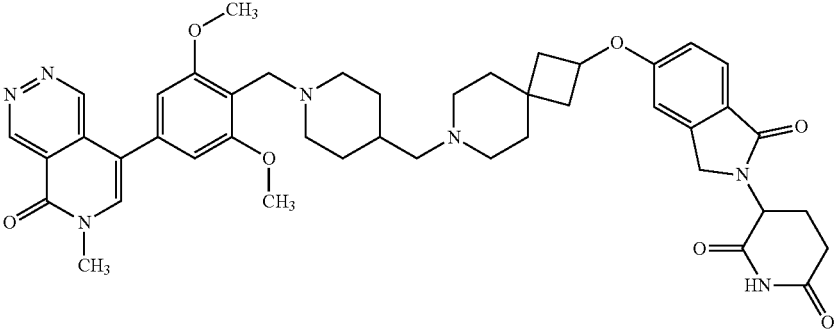 [SMILES: COc1cc(-c2cn(C)c(=O)c3ccnnc23)cc(OC)c1CN1CCC(CN2CCC3(CC2)CC(Oc2ccc4c(c2)CN(C2CCC(=O)NC2=O)C4=O)C3)CC1] |
| D368 | 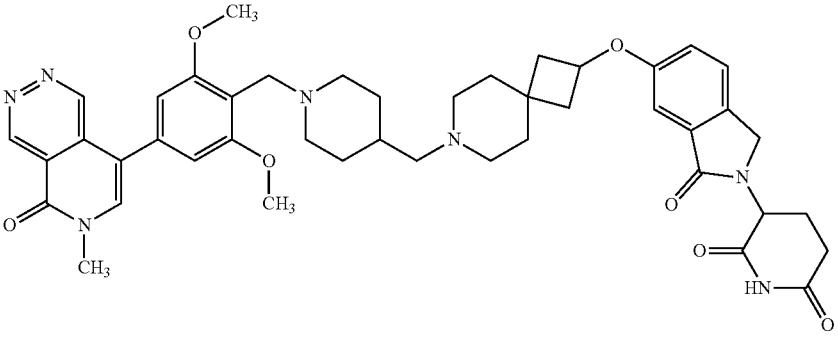 [SMILES: COc1cc(-c2cn(C)c(=O)c3cnncc23)cc(OC)c1CN1CCC(CN2CCC3(CC2)CC(Oc2ccc4c(c2)C(=O)N(C2CCC(=O)NC2=O)C4)C3)CC1] |
| D369 | 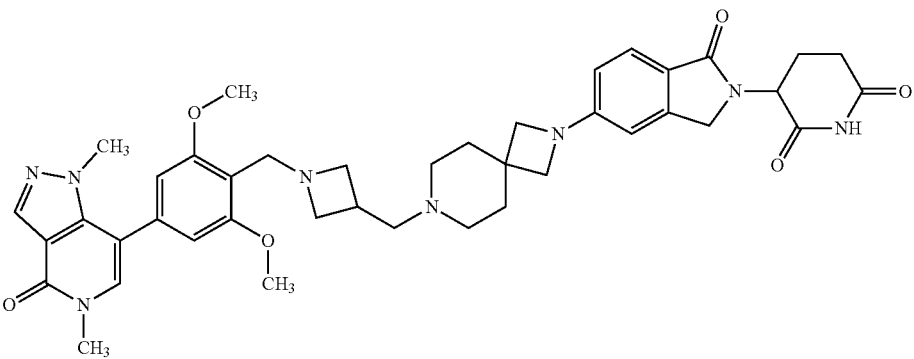 [SMILES: COc1cc(-c2cn(C)c(=O)c3cnn(C)c23)cc(OC)c1CN1CC(CN2CCC3(CC2)CN(c2ccc4c(c2)CN(C2CCC(=O)NC2=O)C4=O)C3)C1] |
| D370 | 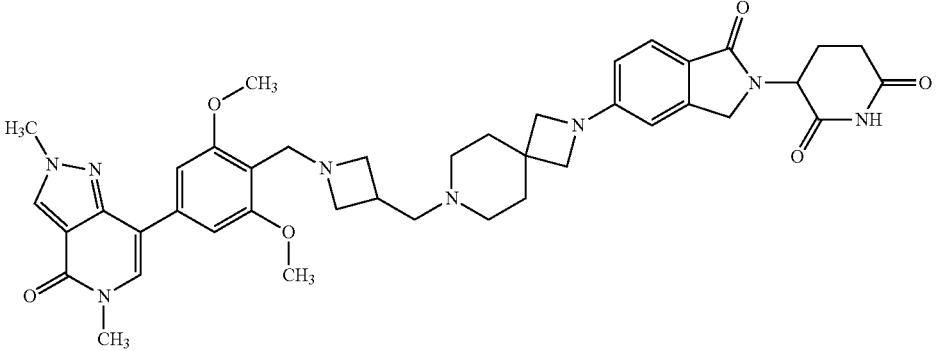 [SMILES: COc1cc(-c2cn(C)c(=O)c3cn(C)nc23)cc(OC)c1CN1CC(CN2CCC3(CC2)CN(c2ccc4c(c2)CN(C2CCC(=O)NC2=O)C4=O)C3)C1] |

TABLE 1B-continued
Compounds D178-D371 of the Disclosure
| Compound No. | Structure |
|---|---|
| D371 | 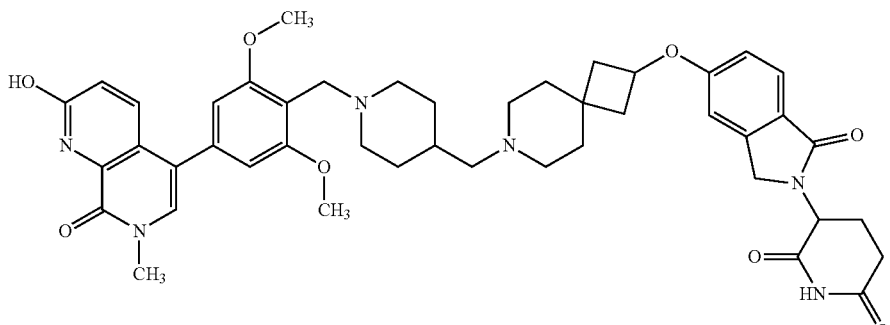 |
TABLE 1C
Compounds DD1-DD10 of the Disclosure
| Compound No. | Structure |
|---|---|
| DD1 | 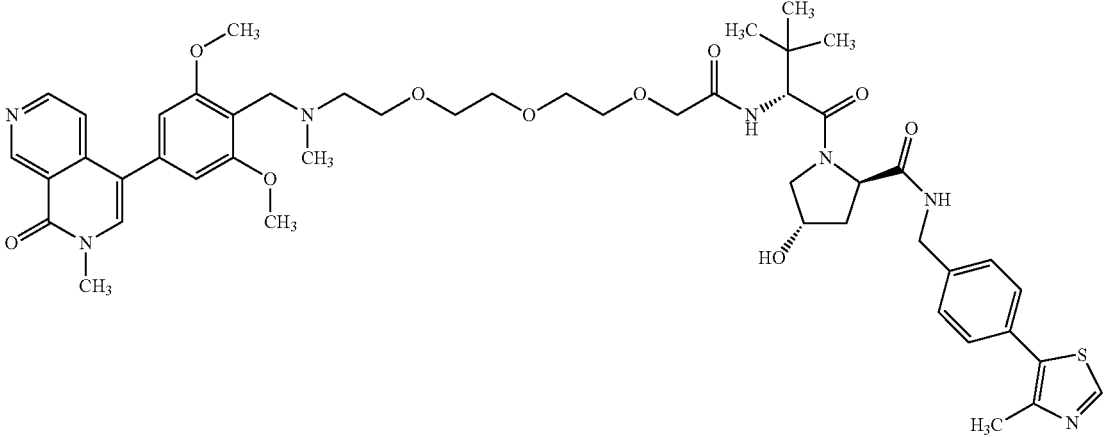 [SMILES: COc1cc(-c2cn(C)c(=O)c3cnccc23)cc(OC)c1CN(C)CCOCCOCCOCC(=O)N[C@@H](C(=O)N1C[C@@H](O)C[C@@H]1C(=O)NCc1ccc(-c2scnc2C)cc1)C(C)(C)C] |
| DD2 | 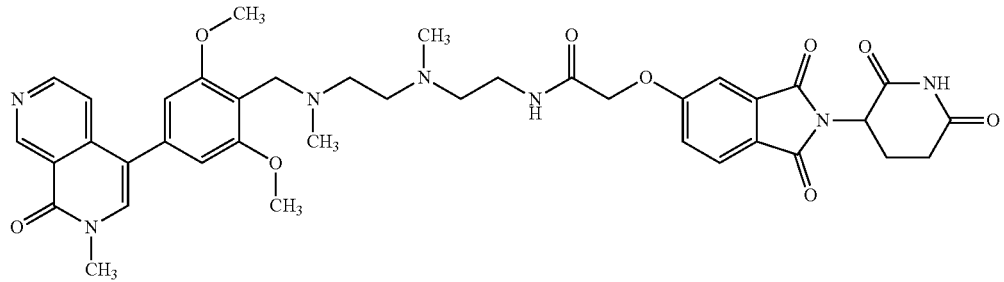 [SMILES: COc1cc(-c2cn(C)c(=O)c3cnccc23)cc(OC)c1CN(C)CCN(C)CCNC(=O)COc1ccc2c(c1)C(=O)N(C1CCC(=O)NC1=O)C2=O] |

TABLE 1C-continued
Compounds DD1-DD10 of the Disclosure
| Compound No. | Structure |
|---|---|
| DD3 | 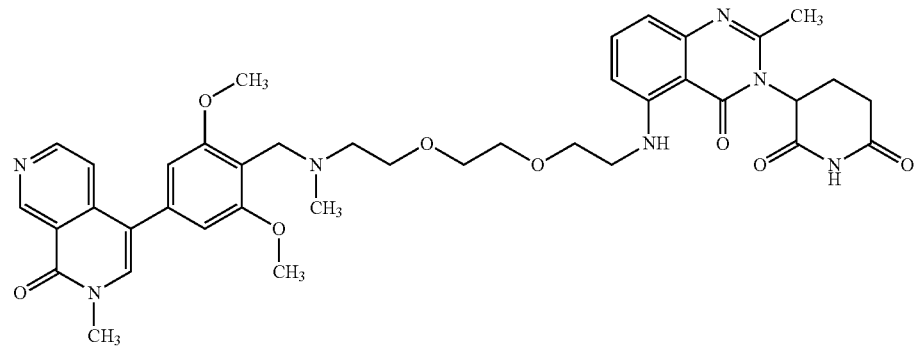 |
| DD4 | 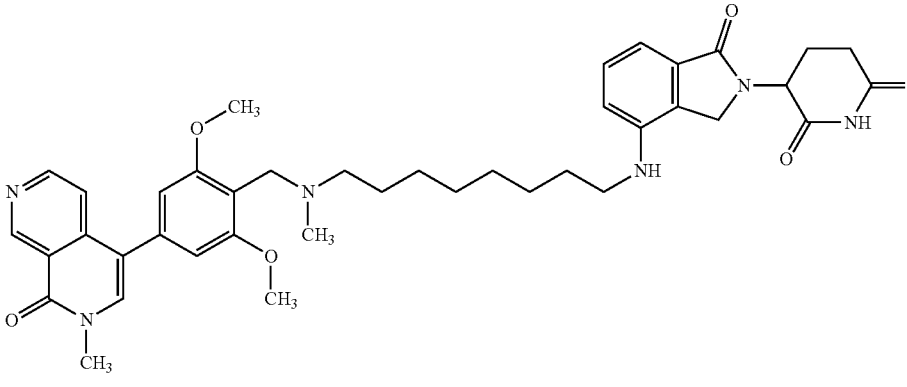 |
| DD5 | 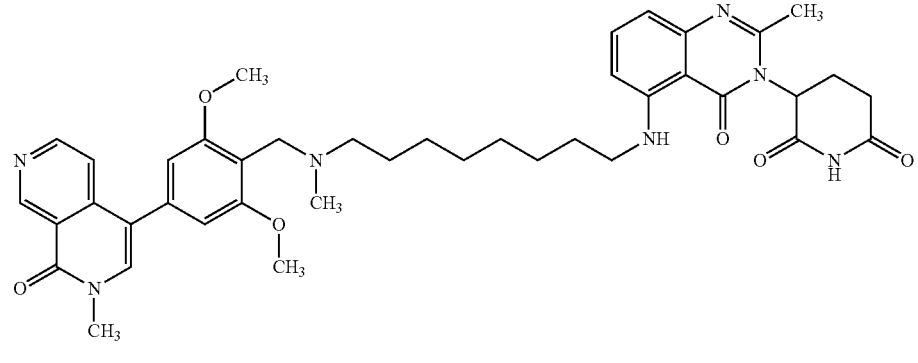 [SMILES: COc1cc(-c2cn(C)c(=O)c3cnccc23)cc(OC)c1CN(C)CCCCCCCCNc1cccc2nc(C)n(C3CCC(=O)NC3=O)c(=O)c12] |
| DD6 | 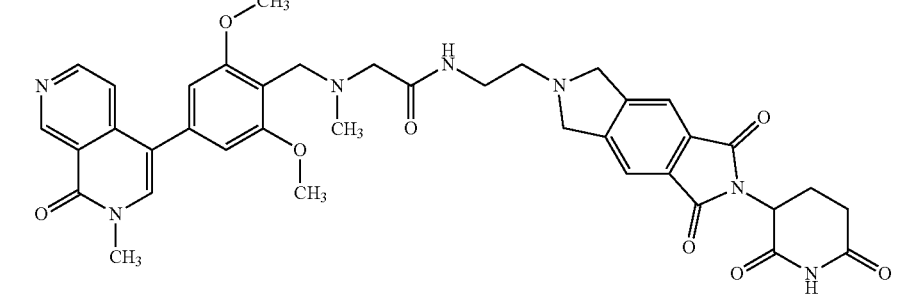 |

TABLE 1C-continued
Compounds DD1-DD10 of the Disclosure
| Compound No. | Structure |
|---|---|
| DD7 | 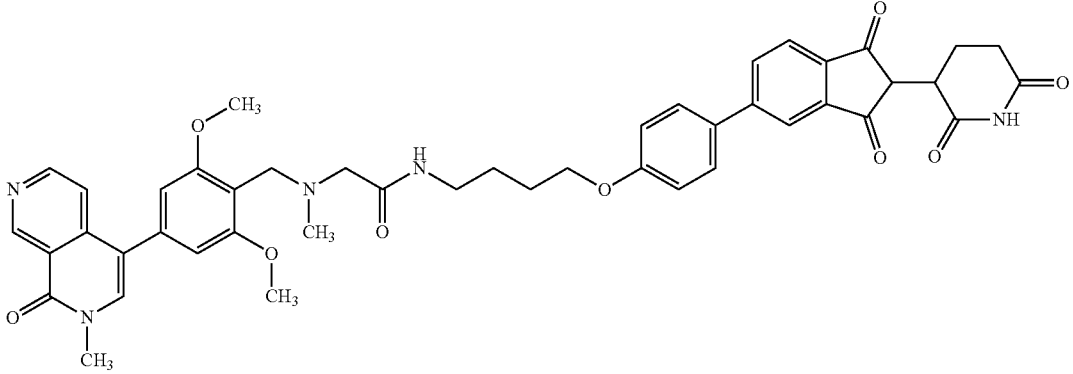 [SMILES: COc1cc(-c2cn(C)c(=O)c3cnccc23)cc(OC)c1CN(C)CC(=O)NCCCCOc1ccc(-c2ccc3c(c2)C(=O)C(C2CCC(=O)NC2=O)C3=O)cc1] |
| DD8 | 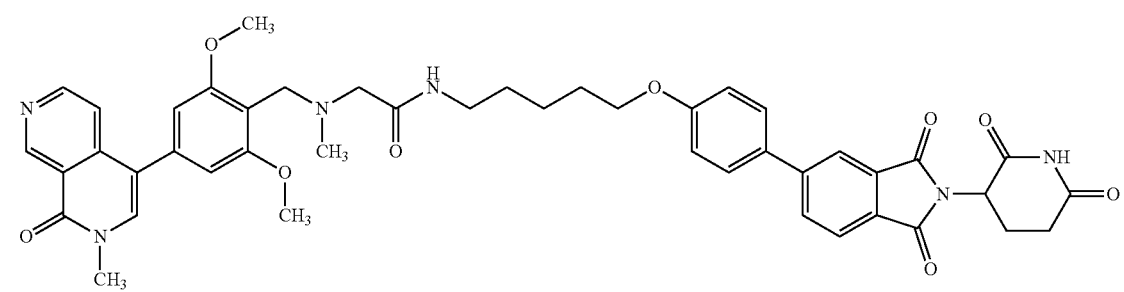 [SMILES: COc1cc(-c2cn(C)c(=O)c3cnccc23)cc(OC)c1CN(C)CC(=O)NCCCCCOc1ccc(-c2ccc3c(c2)C(=O)N(C2CCC(=O)NC2=O)C3=O)cc1] |
| DD9 | 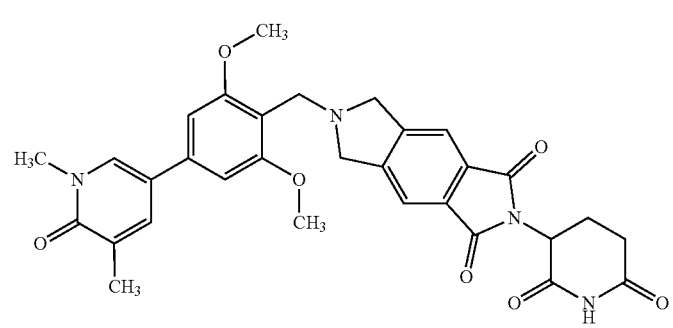 [SMILES: COc1cc(-c2cc(C)c(=O)n(C)c2)cc(OC)c1CN1Cc2cc3c(cc2C1)C(=O)N(C1CCC(=O)NC1=O)C3=O] |
| DD10 | 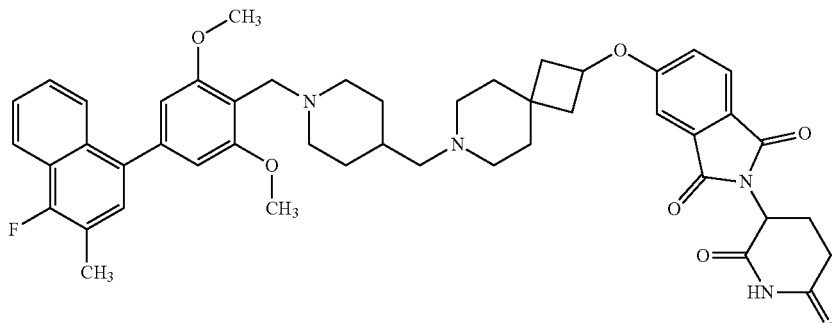 |

TABLE 1D

Compounds D372-D477 of the disclosure

| Compound No. | Structure |
|---|---|
| D372 | 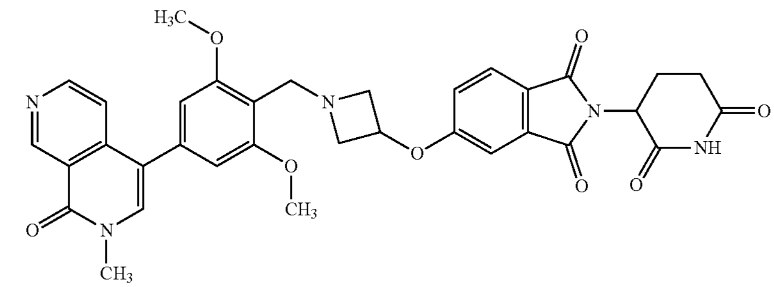 |
| D373 | 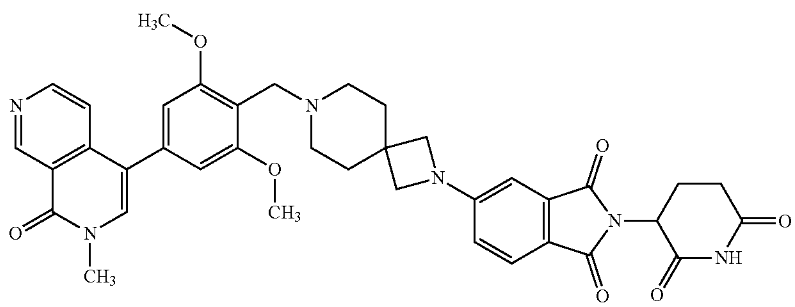 [SMILES: COc1cc(-c2cn(C)c(=O)c3cnccc23)cc(OC)c1CN1CCC2(CC1)CN(c1ccc3c(c1)C(=O)N(C1CCC(=O)NC1=O)C3=O)C2] |
| D374 | 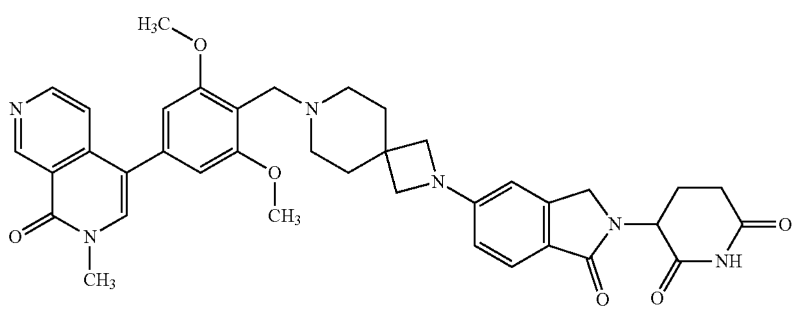 [SMILES: COc1cc(-c2cn(C)c(=O)c3cnccc23)cc(OC)c1CN1CCC2(CC1)CN(c1ccc3c(c1)CN(C1CCC(=O)NC1=O)C3=O)C2] |
| D375 | 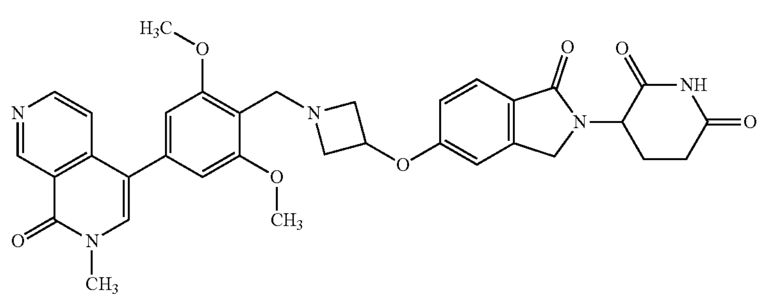 [SMILES: COc1cc(-c2cn(C)c(=O)c3cnccc23)cc(OC)c1CN1CC(Oc2ccc3c(c2)CN(C2CCC(=O)NC2=O)C3=O)C1] |
| D376 | 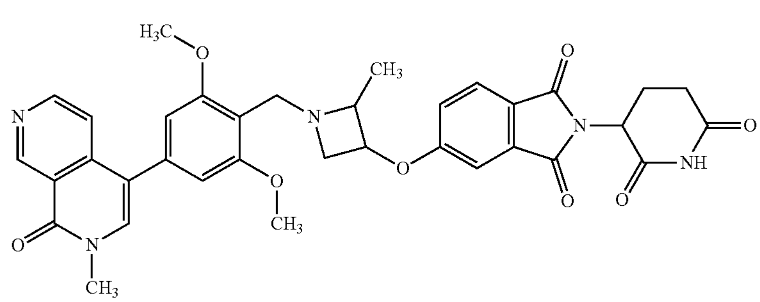 [SMILES: COc1cc(-c2cn(C)c(=O)c3cnccc23)cc(OC)c1CN1CC(Oc2ccc3c(c2)C(=O)N(C2CCC(=O)NC2=O)C3=O)C1C] |

TABLE 1D-continued

Compounds D372-D477 of the disclosure

| Compound No. | Structure |
|---|---|
| D377 | 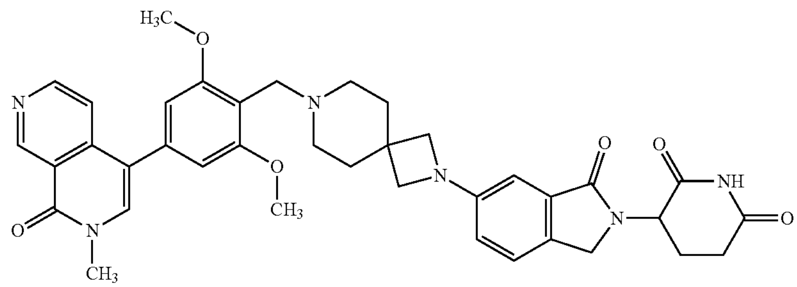 [SMILES: COc1cc(-c2cn(C)c(=O)c3cnccc23)cc(OC)c1CN1CCC2(CC1)CN(c1ccc3c(c1)C(=O)N(C1CCC(=O)NC1=O)C3)C2] |
| D378 | 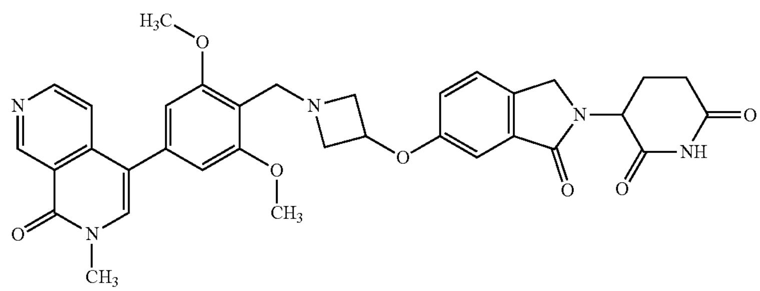 [SMILES: COc1cc(-c2cn(C)c(=O)c3cnccc23)cc(OC)c1CN1CC(Oc2ccc3c(c2)C(=O)N(C2CCC(=O)NC2=O)C3)C1] |
| D379 | 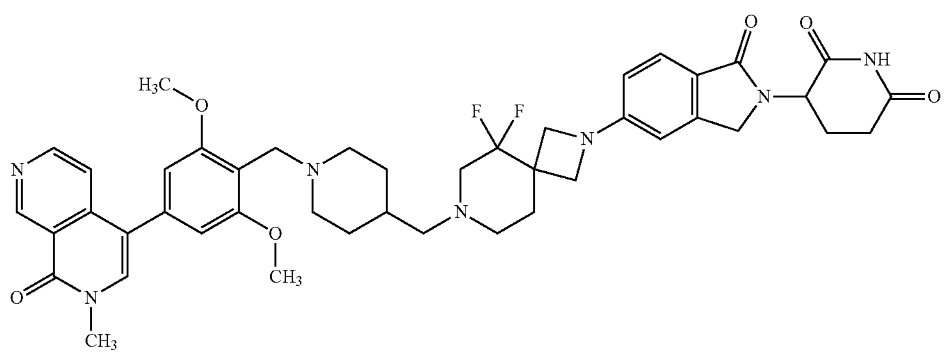 [SMILES: COc1cc(-c2cn(C)c(=O)c3cnccc23)cc(OC)c1CN1CCC(CN2CCC3(CN(c4ccc5c(c4)CN(C4CCC(=O)NC4=O)C5=O)C3)C(F)(F)C2)CC1] |
| D380 | 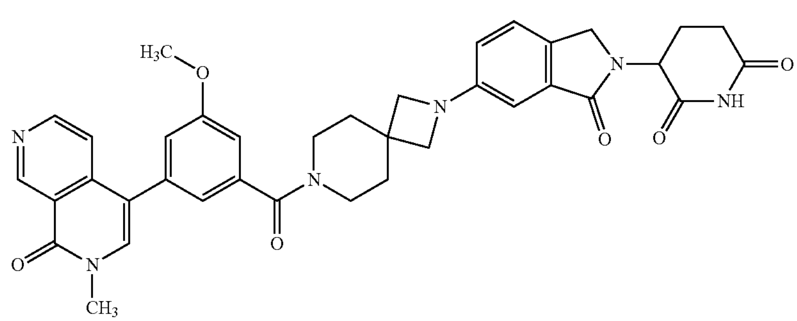 [SMILES: COc1cc(C(=O)N2CCC3(CC2)CN(c2ccc4c(c2)C(=O)N(C2CCC(=O)NC2=O)C4)C3)cc(-c2cn(C)c(=O)c3cnccc23)c1] |

TABLE 1D-continued
Compounds D372-D477 of the disclosure
| Compound No. | Structure |
|---|---|
| D381 | 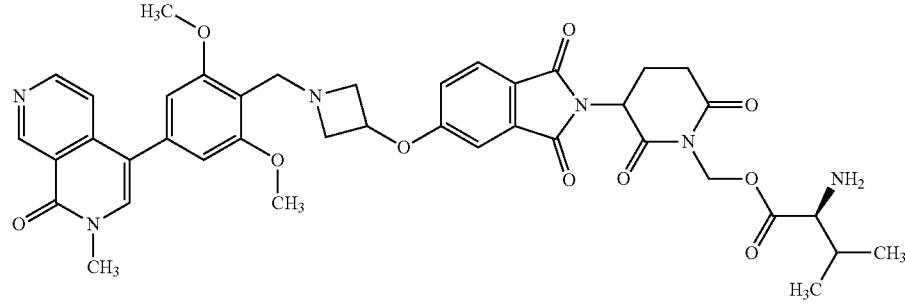 [SMILES: COc1cc(-c2cn(C)c(=O)c3cnccc23)cc(OC)c1CN1CC(Oc2ccc3c(c2)C(=O)N(C2CCC(=O)N(COC(=O)[C@@H](N)C(C)C)C2=O)C3=O)C1] |
| D382 | 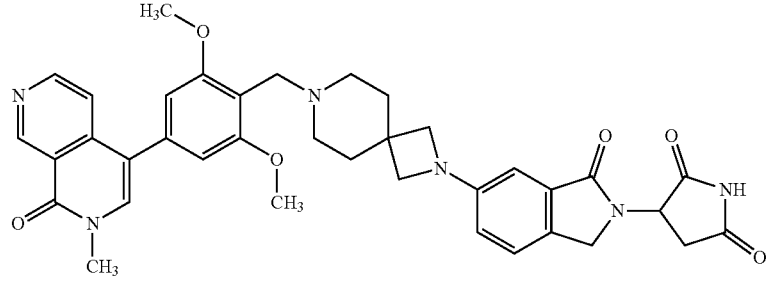 [SMILES: COc1cc(-c2cn(C)c(=O)c3cnccc23)cc(OC)c1CN1CCC2(CC1)CN(c1ccc3c(c1)C(=O)N(C1CC(=O)NC1=O)C3)C2] |
| D383 | 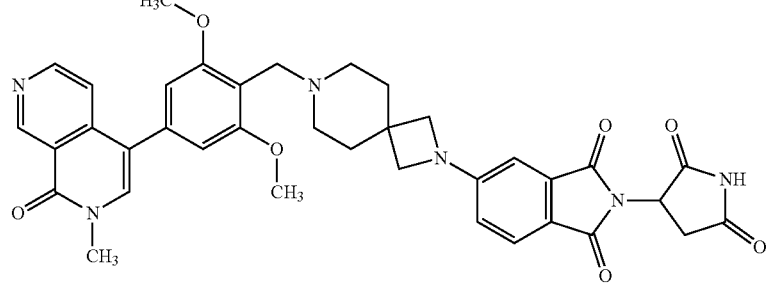 |
| D384 | 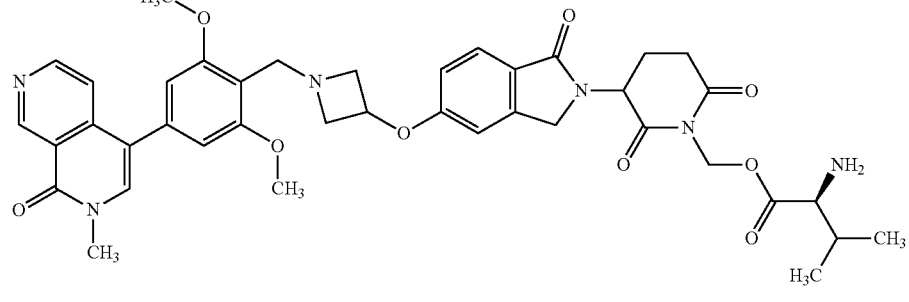 |
| D385 | 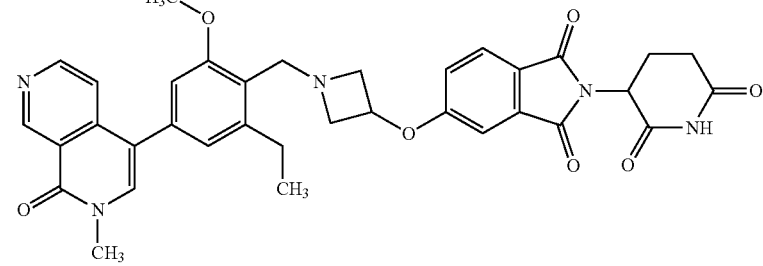 |

TABLE 1D-continued
Compounds D372-D477 of the disclosure
| Compound No. | Structure |
|---|---|
| D386 | 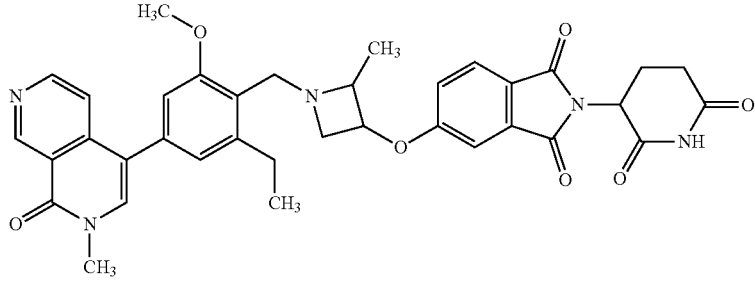 |
| D387 | 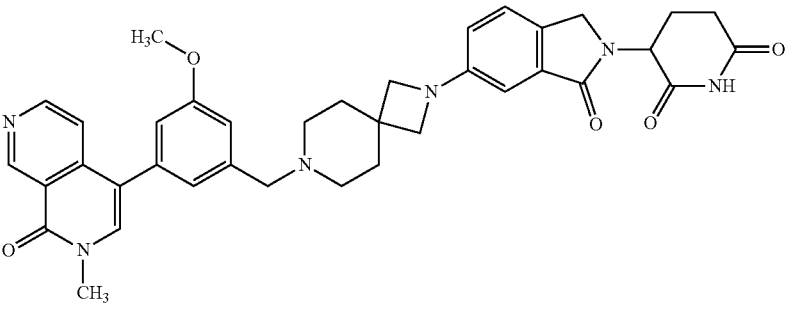 [SMILES: COc1cc(CN2CCC3(CC2)CN(c2ccc4c(c2)C(=O)N(C2CCC(=O)NC2=O)C4)C3)cc(-c2cn(C)c(=O)c3cnccc23)c1] |
| D388 | 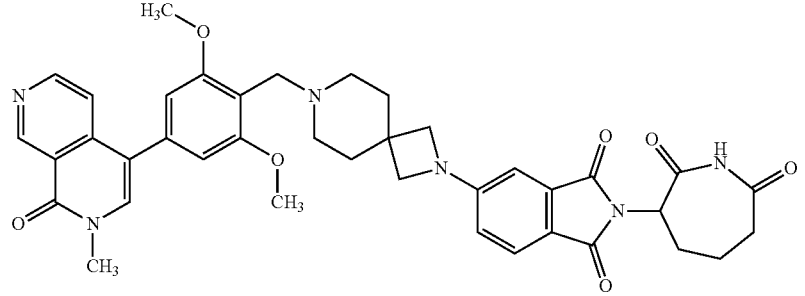 [SMILES: COc1cc(-c2cn(C)c(=O)c3cnccc23)cc(OC)c1CN1CCC2(CC1)CN(c1ccc3c(c1)C(=O)N(C1CCCC(=O)NC1=O)C3=O)C2] |
| D389 | 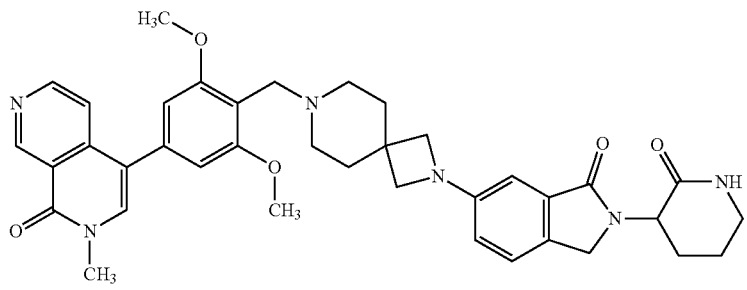 [SMILES: COc1cc(-c2cn(C)c(=O)c3cnccc23)cc(OC)c1CN1CCC2(CC1)CN(c1ccc3c(c1)C(=O)N(C1CCCNC1=O)C3)C2] |
| D390 | 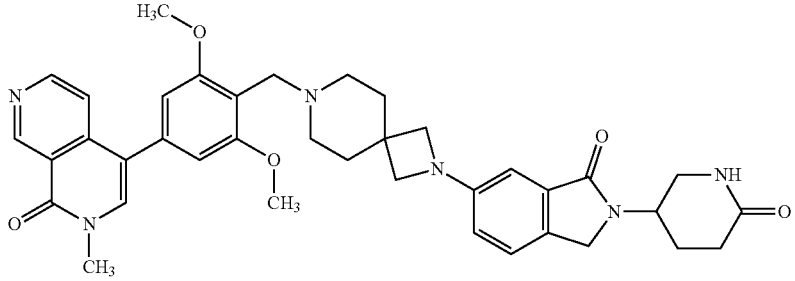 [SMILES: COc1cc(-c2cn(C)c(=O)c3cnccc23)cc(OC)c1CN1CCC2(CC1)CN(c1ccc3c(c1)C(=O)N(C1CCC(=O)NC1)C3)C2] |

TABLE 1D-continued

Compounds D372-D477 of the disclosure

| Compound No. | Structure |
|---|---|
| D391 | 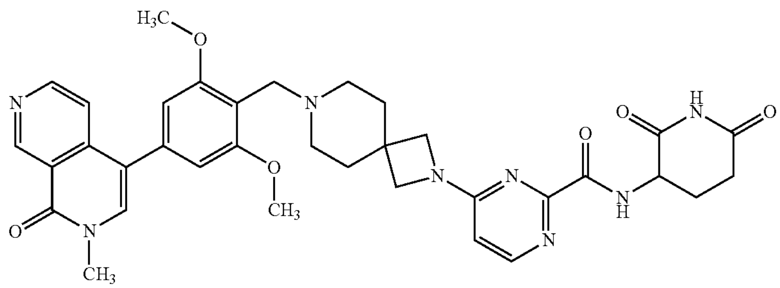 [SMILES: COc1cc(-c2cn(C)c(=O)c3cnccc23)cc(OC)c1CN1CCC2(CC1)CN(c1ccnc(C(=O)NC3CCC(=O)NC3=O)n1)C2] |
| D392 | 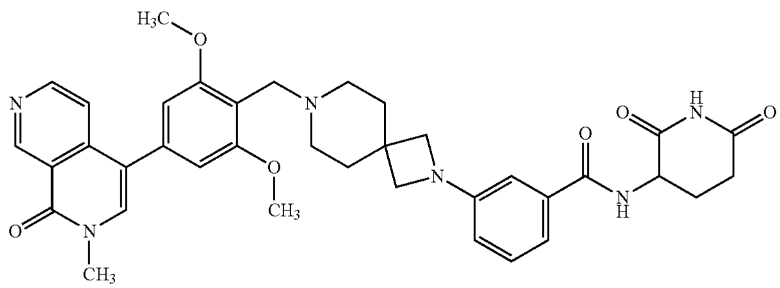 [SMILES: COc1cc(-c2cn(C)c(=O)c3cnccc23)cc(OC)c1CN1CCC2(CC1)CN(c1cccc(C(=O)NC3CCC(=O)NC3=O)c1)C2] |
| D393 | 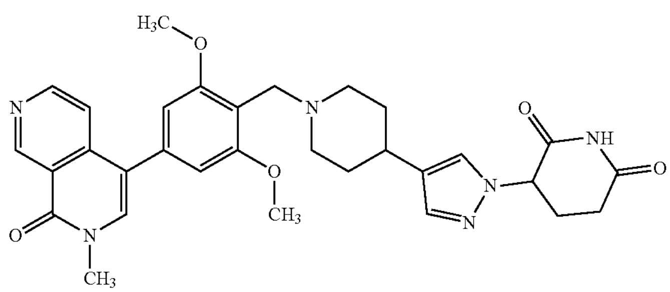 [SMILES: COc1cc(-c2cn(C)c(=O)c3cnccc23)cc(OC)c1CN1CCC(c2cnn(C3CCC(=O)NC3=O)c2)CC1] |
| D394 | 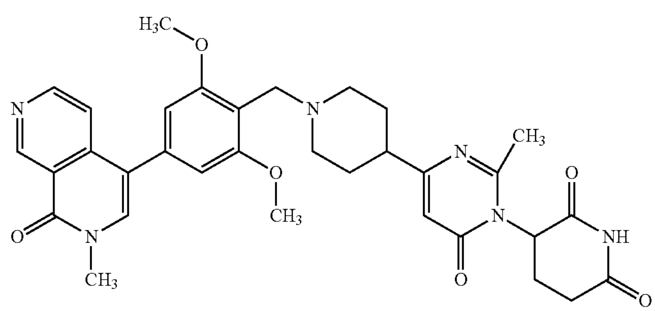 [SMILES: COc1cc(-c2cn(C)c(=O)c3cnccc23)cc(OC)c1CN1CCC(c2cc(=O)n(C3CCC(=O)NC3=O)c(C)n2)CC1] |
| D395 | 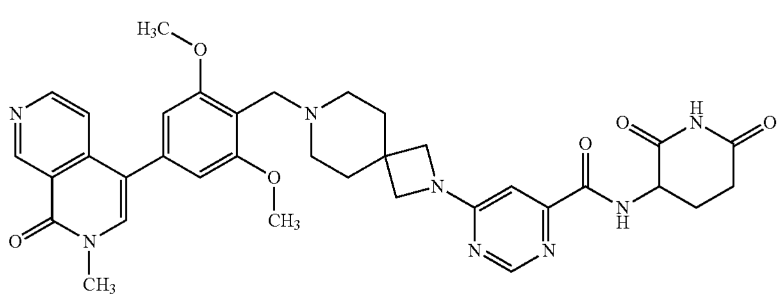 [SMILES: COc1cc(-c2cn(C)c(=O)c3cnccc23)cc(OC)c1CN1CCC2(CC1)CN(c1cc(C(=O)NC3CCC(=O)NC3=O)ncn1)C2] |

TABLE 1D-continued

Compounds D372-D477 of the disclosure

| Compound No. | Structure |
| --- | --- |
| D396 | 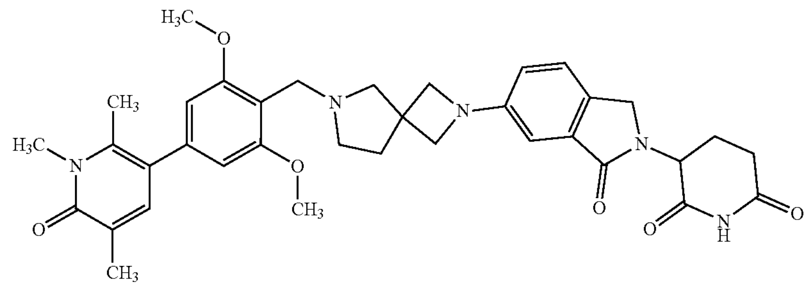 [SMILES: COc1cc(-c2cc(C)c(=O)n(C)c2C)cc(OC)c1CN1CCC2(C1)CN(c1ccc3c(c1)C(=O)N(C1CCC(=O)NC1=O)C3)C2] |
| D397 | 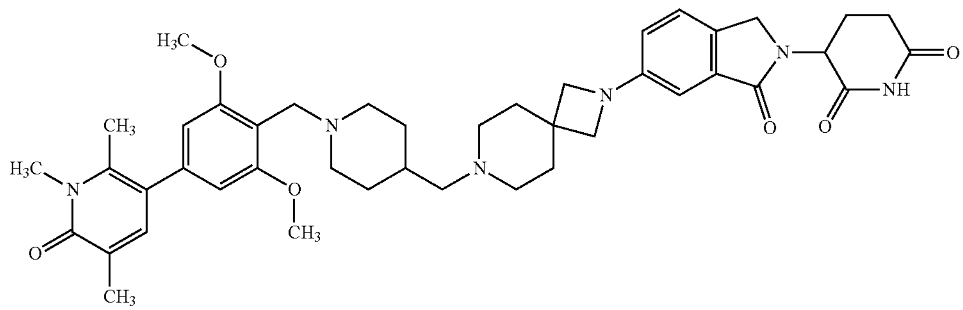 [SMILES: COc1cc(-c2cc(C)c(=O)n(C)c2C)cc(OC)c1CN1CCC(CN2CCC3(CC2)CN(c2ccc4c(c2)C(=O)N(C2CCC(=O)NC2=O)C4)C3)CC1] |
| D398 | 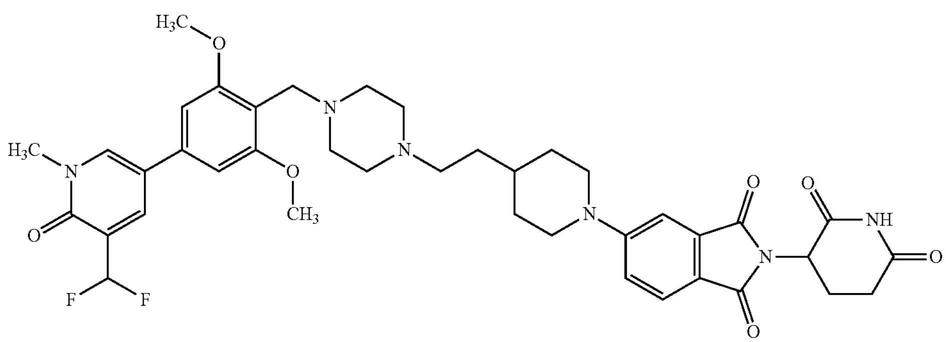 [SMILES: COc1cc(-c2cc(C(F)F)c(=O)n(C)c2)cc(OC)c1CN1CCN(CCC2CCN(c3ccc4c(c3)C(=O)N(C3CCC(=O)NC3=O)C4=O)CC2)CC1] |
| D399 | 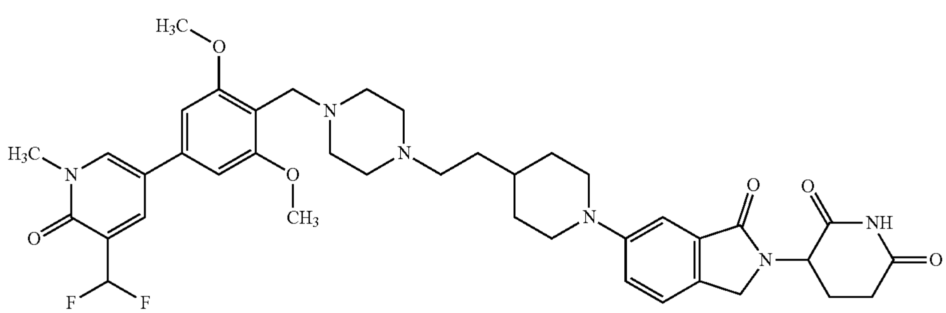 [SMILES: COc1cc(-c2cc(C(F)F)c(=O)n(C)c2)cc(OC)c1CN1CCN(CCC2CCN(c3ccc4c(c3)C(=O)N(C3CCC(=O)NC3=O)C4)CC2)CC1] |
| D400 | 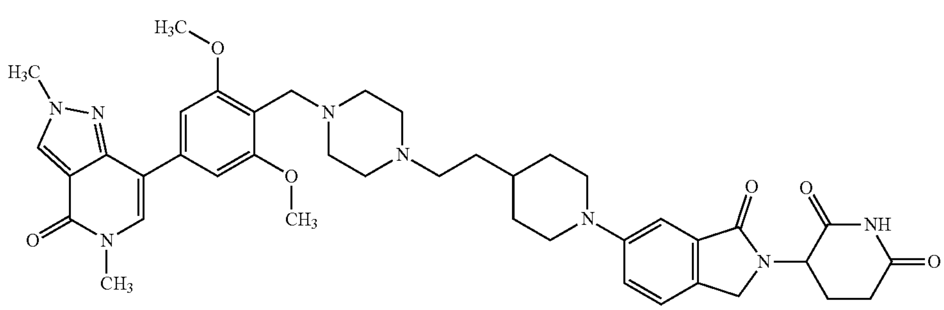 [SMILES: COc1cc(-c2cn(C)c(=O)c3cn(C)nc23)cc(OC)c1CN1CCN(CCC2CCN(c3ccc4c(c3)C(=O)N(C3CCC(=O)NC3=O)C4)CC2)CC1] |

TABLE 1D-continued
Compounds D372-D477 of the disclosure
| Compound No. | Structure |
|---|---|
| D401 | 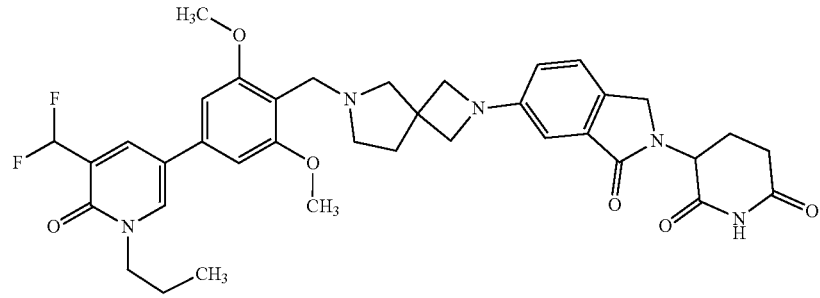 [SMILES: CCCn1cc(-c2cc(OC)c(CN3CCC4(C3)CN(c3ccc5c(c3)C(=O)N(C3CCC(=O)NC3=O)C5)C4)c(OC)c2)cc(C(F)F)c1=O] |
| D402 | 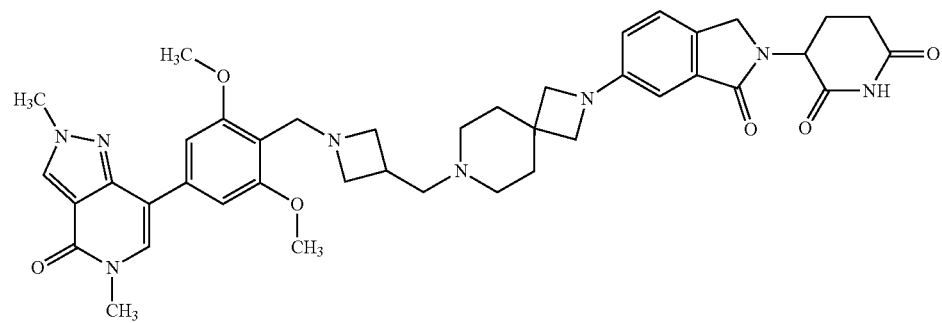 [SMILES: COc1cc(-c2cn(C)c(=O)c3cn(C)nc23)cc(OC)c1CN1CC(CN2CCC3(CC2)CN(c2ccc4c(c2)C(=O)N(C2CCC(=O)NC2=O)C4)C3)C1] |
| D403 | 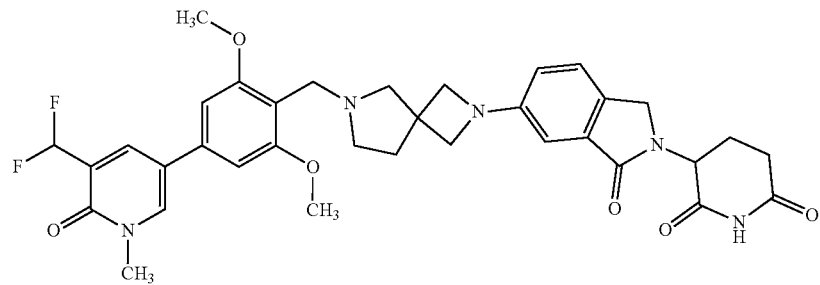 [SMILES: COc1cc(-c2cc(C(F)F)c(=O)n(C)c2)cc(OC)c1CN1CCC2(C1)CN(c1ccc3c(c1)C(=O)N(C1CCC(=O)NC1=O)C3)C2] |
| D404 | 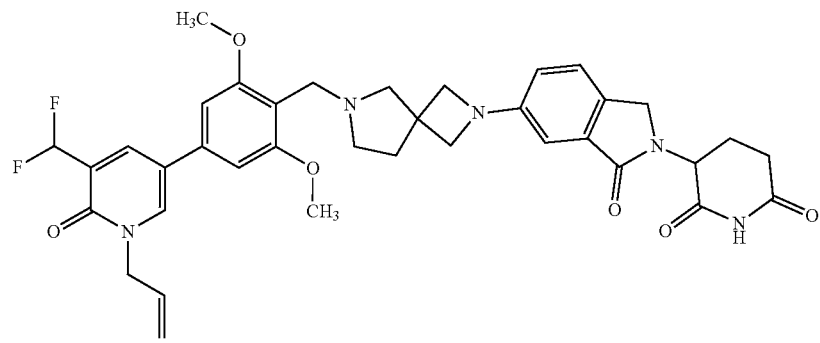 [SMILES: C=CCn1cc(-c2cc(OC)c(CN3CCC4(C3)CN(c3ccc5c(c3)C(=O)N(C3CCC(=O)NC3=O)C5)C4)c(OC)c2)cc(C(F)F)c1=O] |

TABLE 1D-continued
Compounds D372-D477 of the disclosure
| Compound No. | Structure |
|---|---|
| D405 | 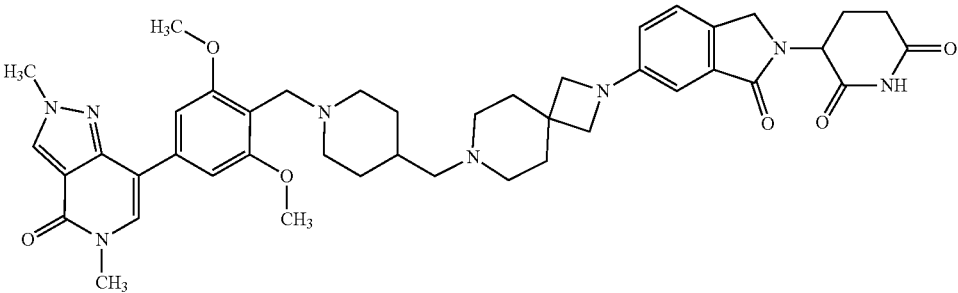 [SMILES: COc1cc(-c2cn(C)c(=O)c3cn(C)nc23)cc(OC)c1CN1CCC(CN2CCC3(CC2)CN(c2ccc4c(c2)C(=O)N(C2CCC(=O)NC2=O)C4)C3)CC1] |
| D406 | 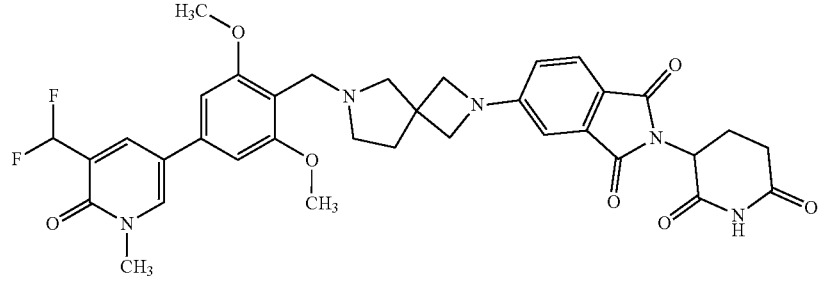 [SMILES: COc1cc(-c2cc(C(F)F)c(=O)n(C)c2)cc(OC)c1CN1CCC2(C1)CN(c1ccc3c(c1)C(=O)N(C1CCC(=O)NC1=O)C3=O)C2] |
| D407 | 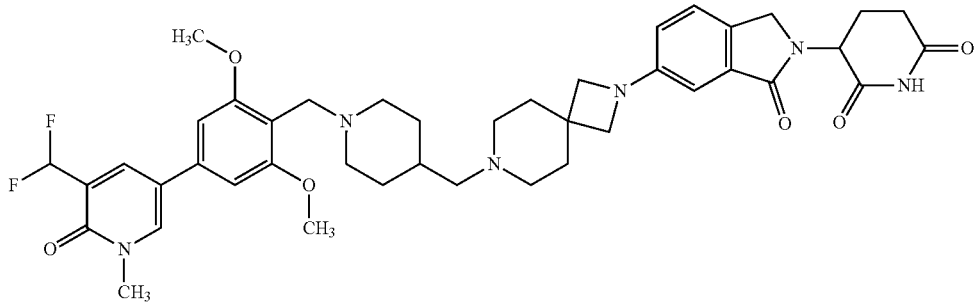 |
| D408 | 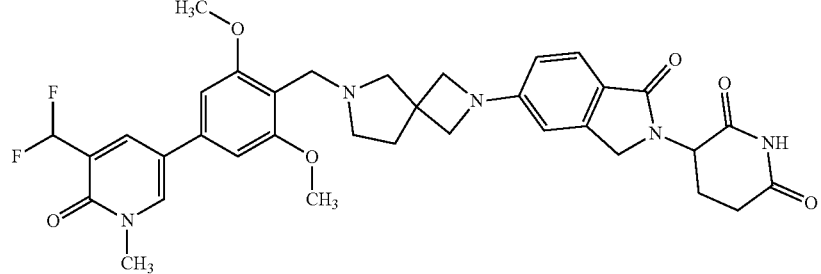 [SMILES: COc1cc(-c2cc(C(F)F)c(=O)n(C)c2)cc(OC)c1CN1CCC2(C1)CN(c1ccc3c(c1)CN(C1CCC(=O)NC1=O)C3=O)C2] |
| D409 | 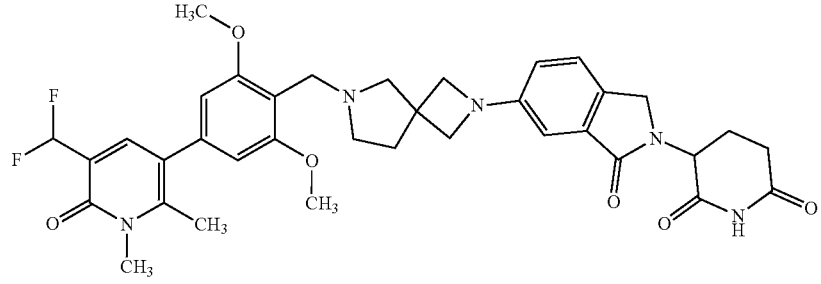 [SMILES: COc1cc(-c2cc(C(F)F)c(=O)n(C)c2C)cc(OC)c1CN1CCC2(C1)CN(c1ccc3c(c1)C(=O)N(C1CCC(=O)NC1=O)C3)C2] |

TABLE 1D-continued

Compounds D372-D477 of the disclosure

| Compound No. | Structure |
| --- | --- |
| D410 | 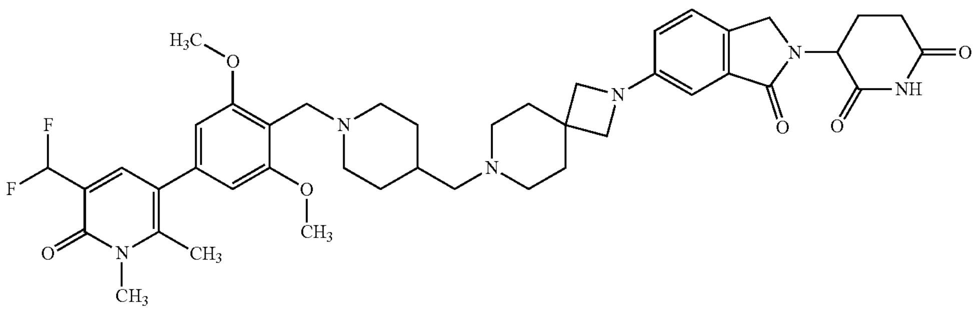 [SMILES: COc1cc(-c2cc(C(F)F)c(=O)n(C)c2C)cc(OC)c1CN1CCC(CN2CCC3(CC2)CN(c2ccc4c(c2)C(=O)N(C2CCC(=O)NC2=O)C4)C3)CC1] |
| D411 | 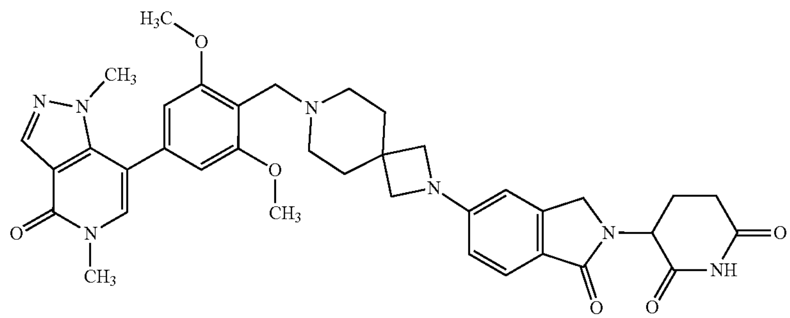 [SMILES: COc1cc(-c2cn(C)c(=O)c3cnn(C)c23)cc(OC)c1CN1CCC2(CC1)CN(c1ccc3c(c1)CN(C1CCC(=O)NC1=O)C3=O)C2] |
| D412 | 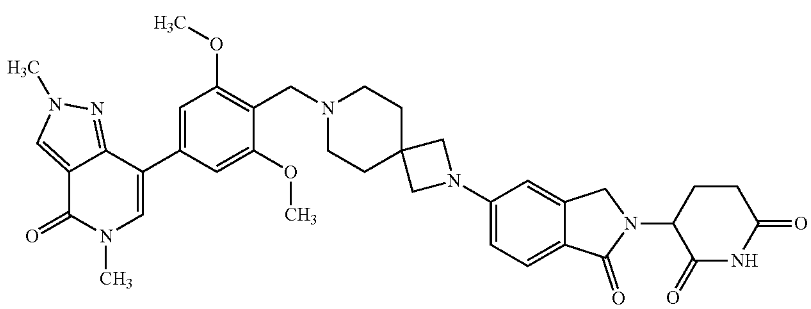 [SMILES: COc1cc(-c2cn(C)c(=O)c3cn(C)nc23)cc(OC)c1CN1CCC2(CC1)CN(c1ccc3c(c1)CN(C1CCC(=O)NC1=O)C3=O)C2] |
| D413 | 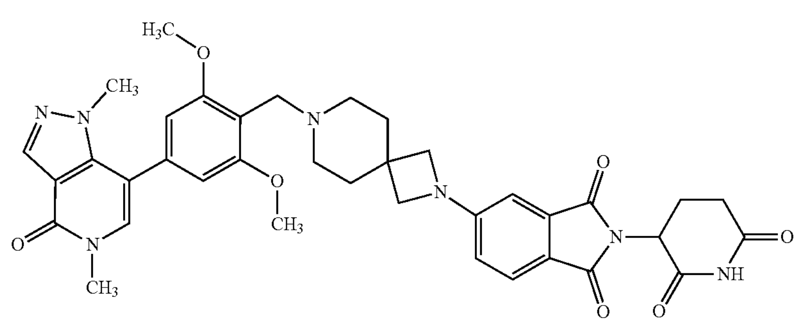 [SMILES: COc1cc(-c2cn(C)c(=O)c3cnn(C)c23)cc(OC)c1CN1CCC2(CC1)CN(c1ccc3c(c1)C(=O)N(C1CCC(=O)NC1=O)C3=O)C2] |

TABLE 1D-continued
Compounds D372-D477 of the disclosure
| Compound No. | Structure |
|---|---|
| D414 | 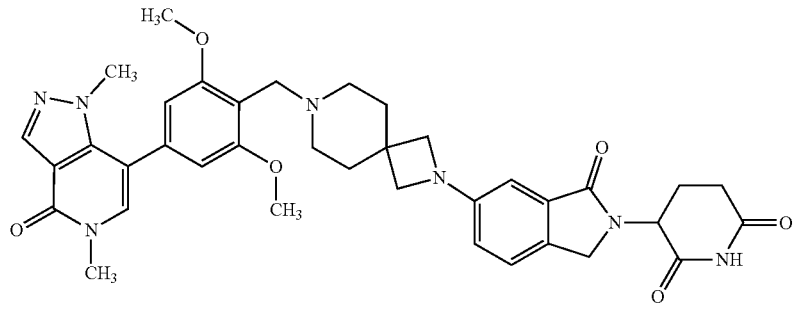 [SMILES: COc1cc(-c2cn(C)c(=O)c3cnn(C)c23)cc(OC)c1CN1CCC2(CC1)CN(c1ccc3c(c1)C(=O)N(C1CCC(=O)NC1=O)C3)C2] |
| D415 | 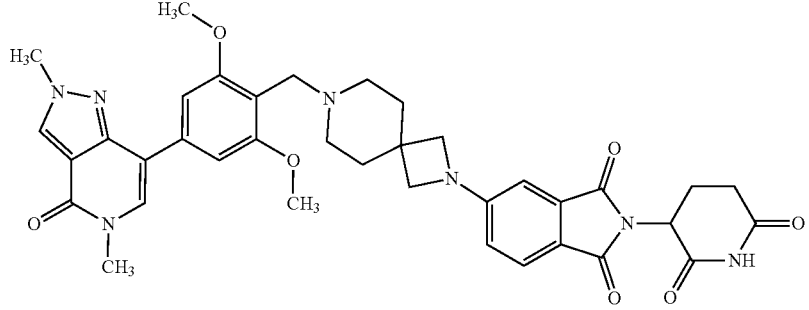 [SMILES: COc1cc(-c2cn(C)c(=O)c3cn(C)nc23)cc(OC)c1CN1CCC2(CC1)CN(c1ccc3c(c1)C(=O)N(C1CCC(=O)NC1=O)C3=O)C2] |
| D416 | 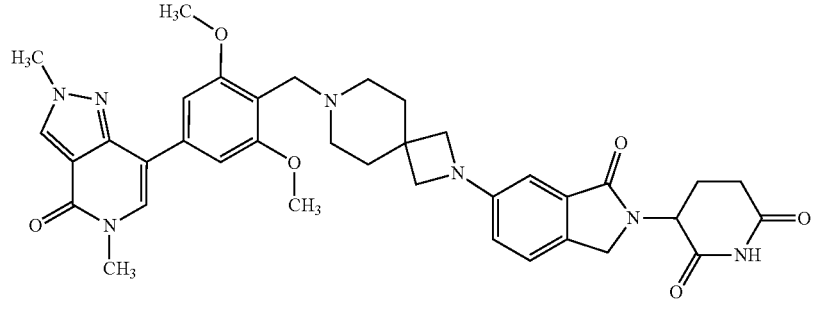 [SMILES: COc1cc(-c2cn(C)c(=O)c3cn(C)nc23)cc(OC)c1CN1CCC2(CC1)CN(c1ccc3c(c1)C(=O)N(C1CCC(=O)NC1=O)C3)C2] |
| D417 | 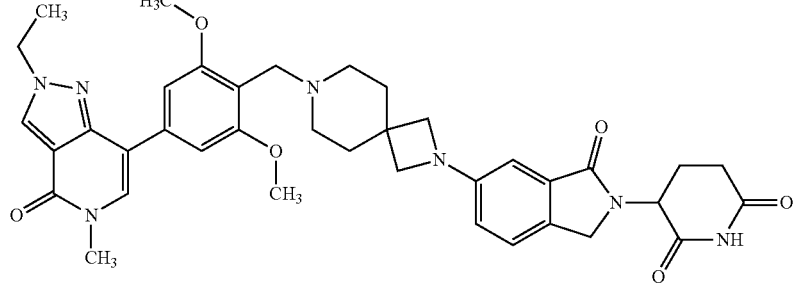 |
| D418 | 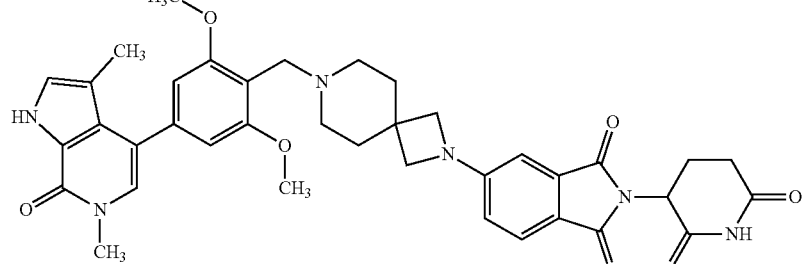 |

TABLE 1D-continued
Compounds D372-D477 of the disclosure
| Compound No. | Structure |
|---|---|
| D419 | 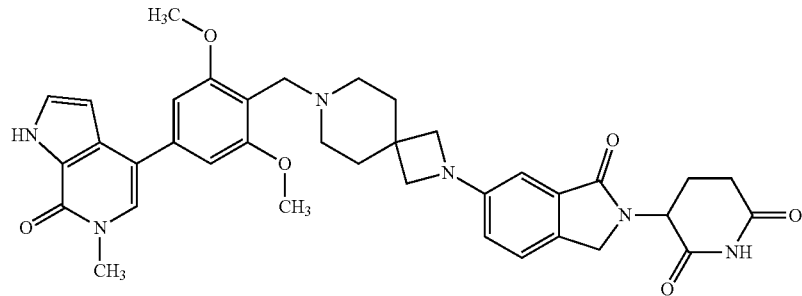 [SMILES: COc1cc(-c2cn(C)c(=O)c3[nH]ccc23)cc(OC)c1CN1CCC2(CC1)CN(c1ccc3c(c1)C(=O)N(C1CCC(=O)NC1=O)C3)C2] |
| D420 | 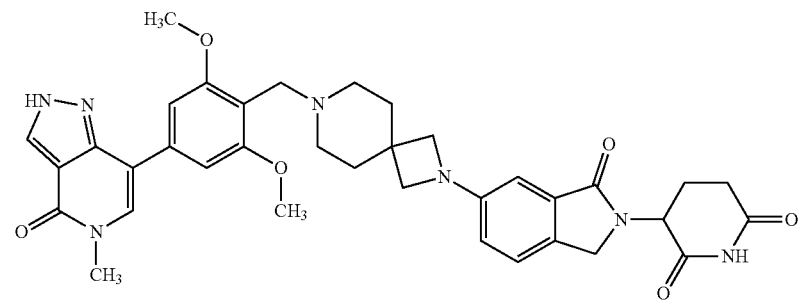 [SMILES: COc1cc(-c2cn(C)c(=O)c3c[nH]nc23)cc(OC)c1CN1CCC2(CC1)CN(c1ccc3c(c1)C(=O)N(C1CCC(=O)NC1=O)C3)C2] |
| D421 | 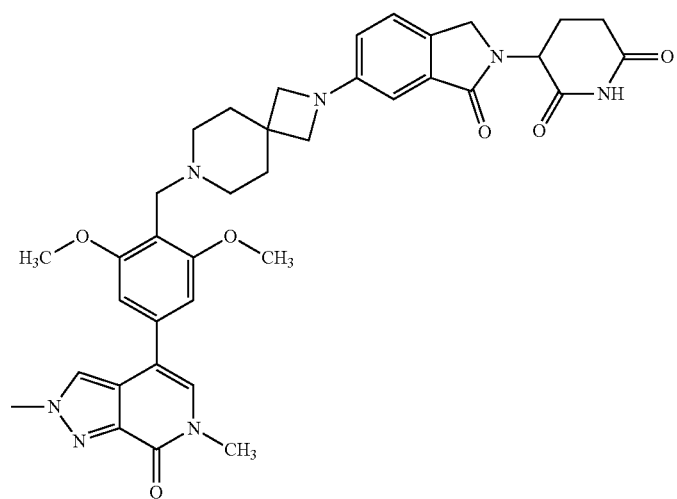 [SMILES: COc1cc(-c2cn(C)c(=O)c3nn(C)cc23)cc(OC)c1CN1CCC2(CC1)CN(c1ccc3c(c1)C(=O)N(C1CCC(=O)NC1=O)C3)C2] |

TABLE 1D-continued
Compounds D372-D477 of the disclosure
| Compound No. | Structure |
|---|---|
| D422 | 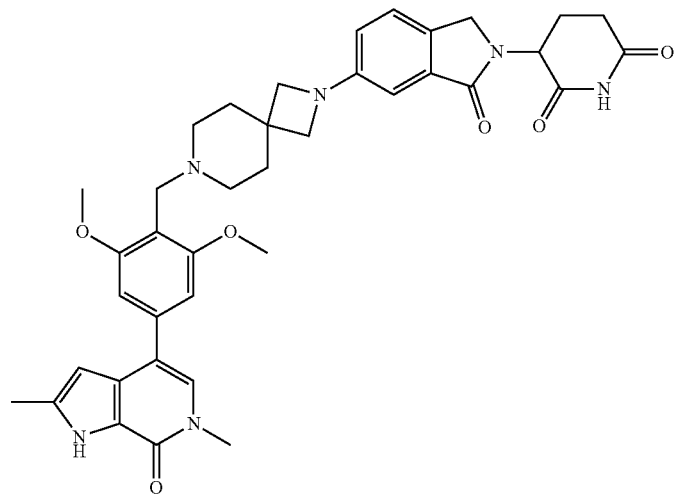 [SMILES: COc1cc(-c2cn(C)c(=O)c3[nH]c(C)cc23)cc(OC)c1CN1CCC2(CC1)CN(c1ccc3c(c1)C(=O)N(C1CCC(=O)NC1=O)C3)C2] |
| D423 | 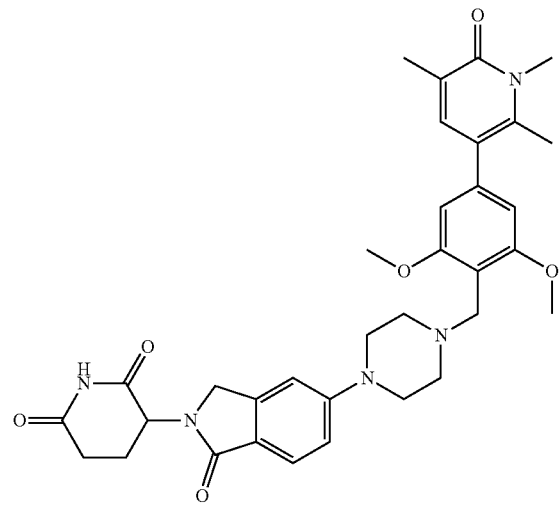 [SMILES: COc1cc(-c2cc(C)c(=O)n(C)c2C)cc(OC)c1CN1CCN(c2ccc3c(c2)CN(C2CCC(=O)NC2=O)C3=O)CC1] |

TABLE 1D-continued
Compounds D372-D477 of the disclosure
| Compound No. | Structure |
|---|---|
| D424 | 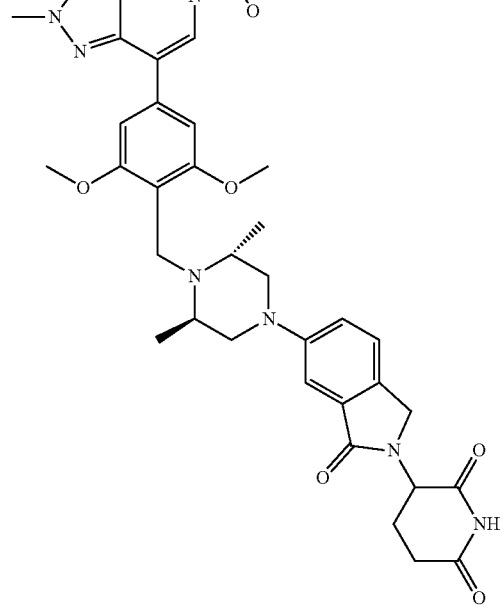 |
| D425 | 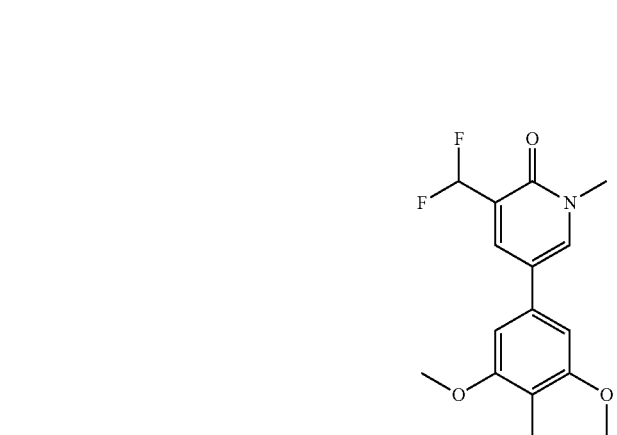 |

TABLE 1D-continued
Compounds D372-D477 of the disclosure
| Compound No. | Structure |
|---|---|
| D426 | 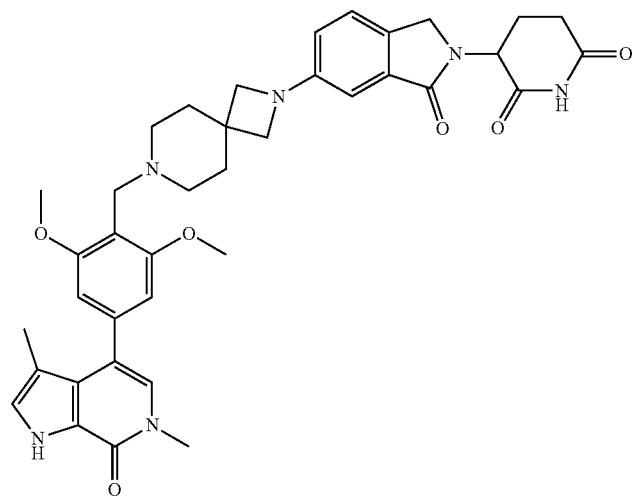 [SMILES: COc1cc(-c2cn(C)c(=O)c3[nH]cc(C)c23)cc(OC)c1CN1CCC2(CC1)CN(c1ccc3c(c1)C(=O)N(C1CCC(=O)NC1=O)C3)C2] |
| D427 | 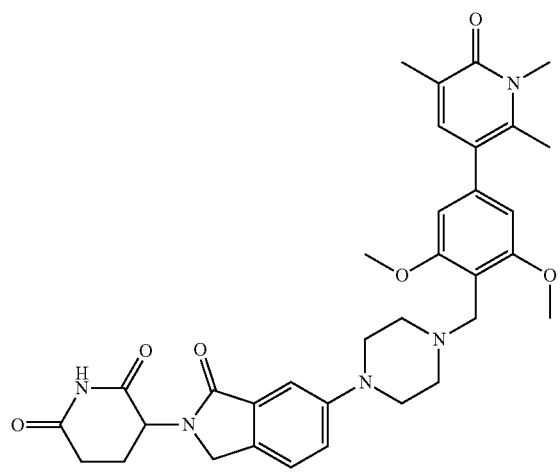 [SMILES: COc1cc(-c2cc(C)c(=O)n(C)c2C)cc(OC)c1CN1CCN(c2ccc3c(c2)C(=O)N(C2CCC(=O)NC2=O)C3)CC1] |
| D428 | 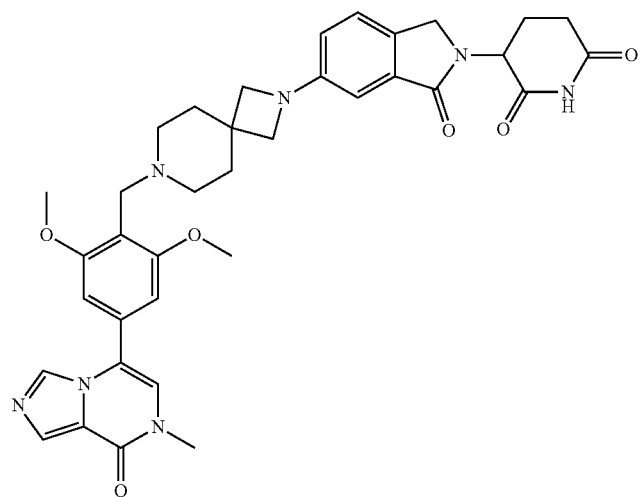 [SMILES: COc1cc(-c2cn(C)c(=O)c3cncn23)cc(OC)c1CN1CCC2(CC1)CN(c1ccc3c(c1)C(=O)N(C1CCC(=O)NC1=O)C3)C2] |

TABLE 1D-continued

Compounds D372-D477 of the disclosure

| Compound No. | Structure |
|---|---|
| D429 | 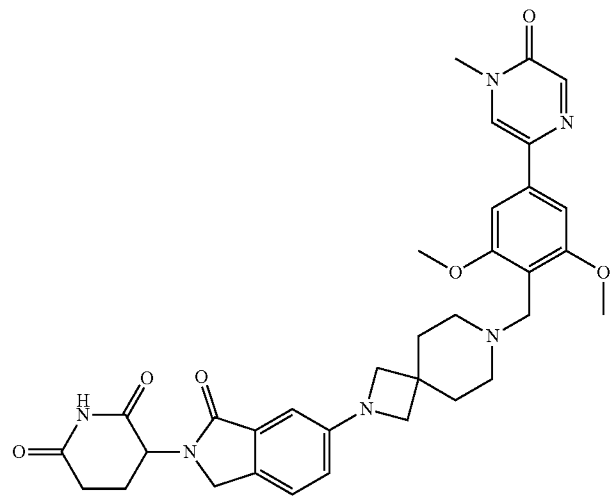 [SMILES: COc1cc(-c2cn(C)c(=O)cn2)cc(OC)c1CN1CCC2(CC1)CN(c1ccc3c(c1)C(=O)N(C1CCC(=O)NC1=O)C3)C2] |
| D430 | 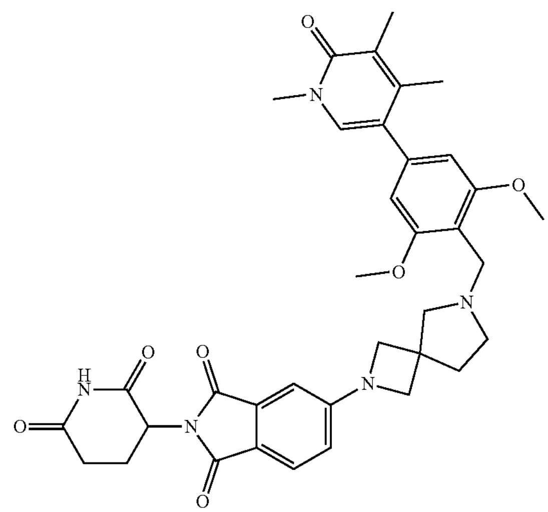 [SMILES: COc1cc(-c2cn(C)c(=O)c(C)c2C)cc(OC)c1CN1CCC2(C1)CN(c1ccc3c(c1)C(=O)N(C1CCC(=O)NC1=O)C3=O)C2] |
| D431 | 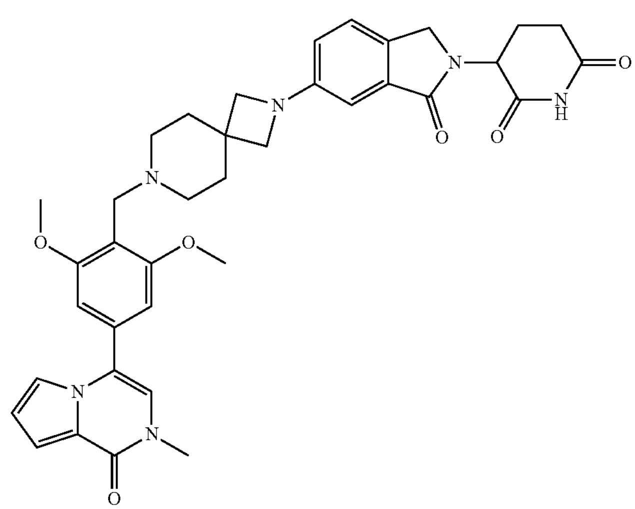 [SMILES: COc1cc(-c2cn(C)c(=O)c3cccn23)cc(OC)c1CN1CCC2(CC1)CN(c1ccc3c(c1)C(=O)N(C1CCC(=O)NC1=O)C3)C2] |

TABLE 1D-continued
Compounds D372-D477 of the disclosure
| Compound No. | Structure |
|---|---|
| D432 | 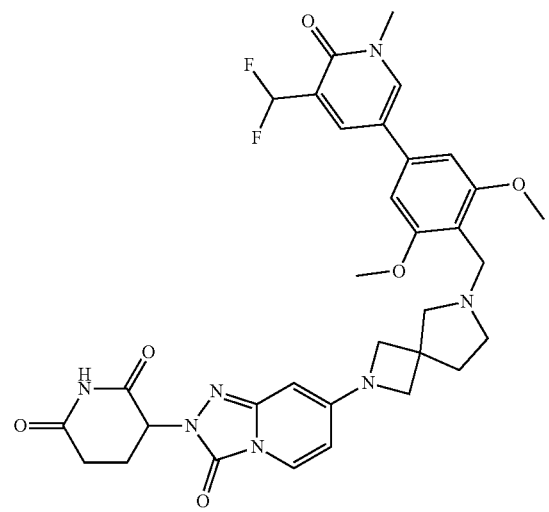 [SMILES: COc1cc(-c2cc(C(F)F)c(=O)n(C)c2)cc(OC)c1CN1CCC2(C1)CN(c1ccn3c(=O)n(C4CCC(=O)NC4=O)nc3c1)C2] |
| D433 | 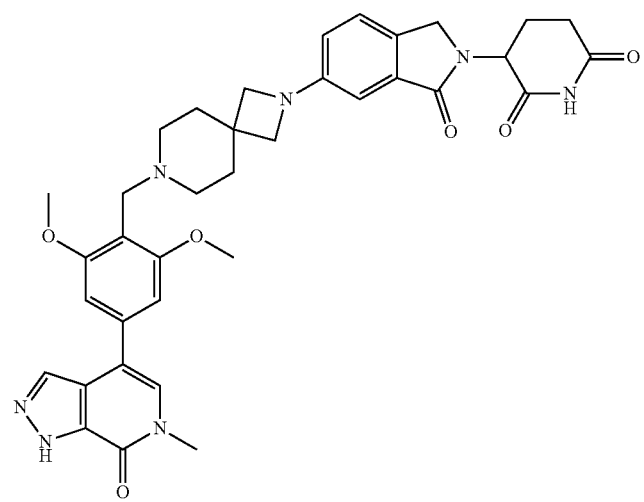 [SMILES: COc1cc(-c2cn(C)c(=O)c3[nH]ncc23)cc(OC)c1CN1CCC2(CC1)CN(c1ccc3c(c1)C(=O)N(C1CCC(=O)NC1=O)C3)C2] |
| D434 | 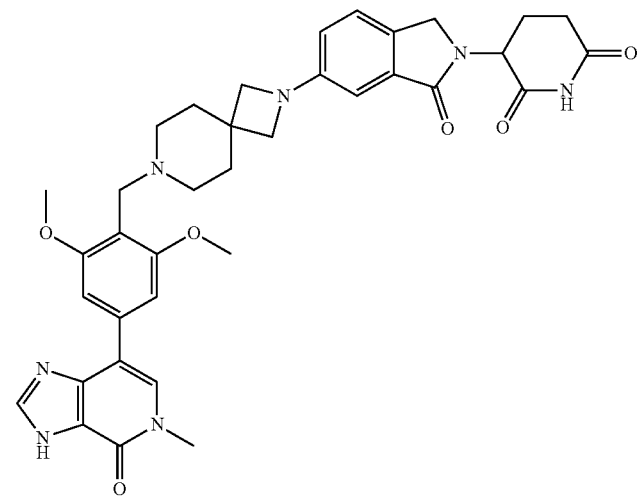 [SMILES: COc1cc(-c2cn(C)c(=O)c3[nH]cnc23)cc(OC)c1CN1CCC2(CC1)CN(c1ccc3c(c1)C(=O)N(C1CCC(=O)NC1=O)C3)C2] |

TABLE 1D-continued
Compounds D372-D477 of the disclosure
| Compound No. | Structure |
|---|---|
| D435 | 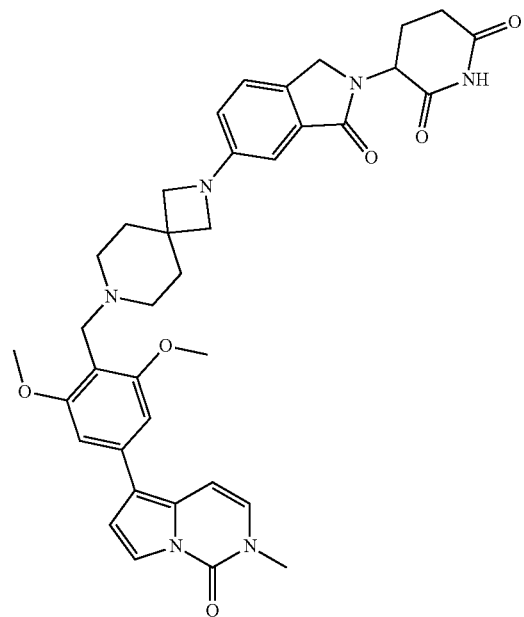 [SMILES: COc1cc(-c2ccn3c(=O)n(C)ccc23)cc(OC)c1CN1CCC2(CC1)CN(c1ccc3c(c1)C(=O)N(C1CCC(=O)NC1=O)C3)C2] |
| D436 | 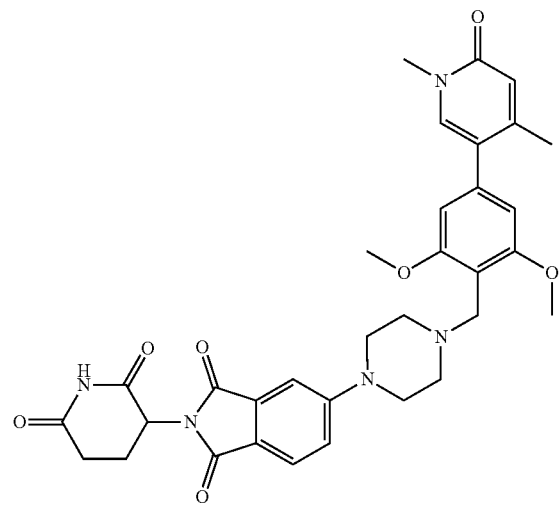 [SMILES: COc1cc(-c2cn(C)c(=O)cc2C)cc(OC)c1CN1CCN(c2ccc3c(c2)C(=O)N(C2CCC(=O)NC2=O)C3=O)CC1] |

TABLE 1D-continued
Compounds D372-D477 of the disclosure
| Compound No. | Structure |
|---|---|
| D437 | 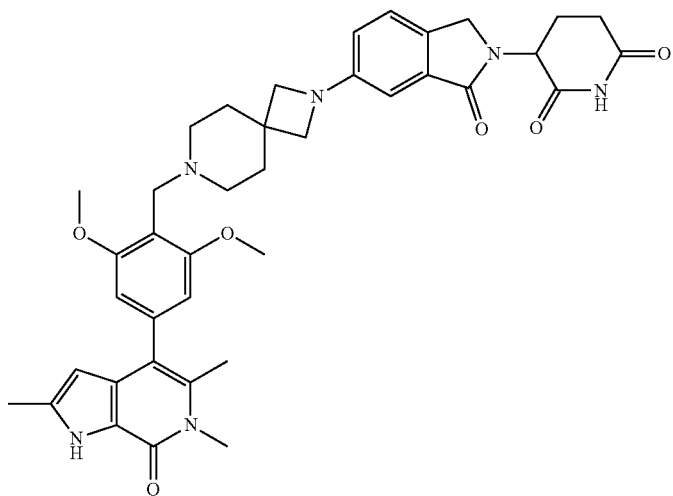 [SMILES: COc1cc(-c2c(C)n(C)c(=O)c3[nH]c(C)cc23)cc(OC)c1CN1CCC2(CC1)CN(c1ccc3c(c1)C(=O)N(C1CCC(=O)NC1=O)C3)C2] |
| D438 | 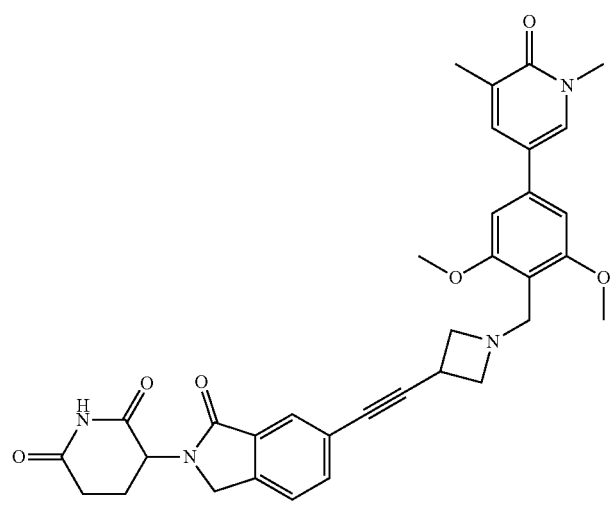 [SMILES: COc1cc(-c2cc(C)c(=O)n(C)c2)cc(OC)c1CN1CC(C#Cc2ccc3c(c2)C(=O)N(C2CCC(=O)NC2=O)C3)C1] |
| D439 | 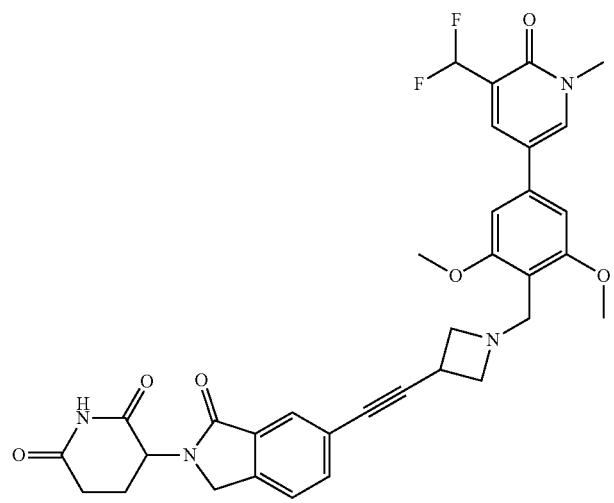 [SMILES: COc1cc(-c2cc(C(F)F)c(=O)n(C)c2)cc(OC)c1CN1CC(C#Cc2ccc3c(c2)C(=O)N(C2CCC(=O)NC2=O)C3)C1] |

TABLE 1D-continued
Compounds D372-D477 of the disclosure
| Compound No. | Structure |
|---|---|
| D440 | 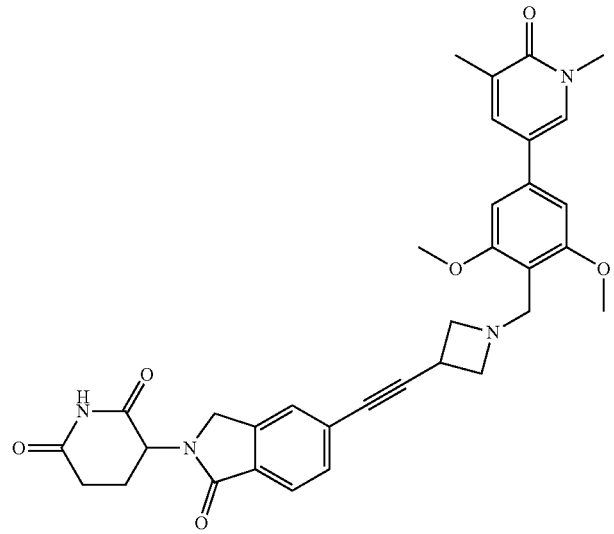 [SMILES: COc1cc(-c2cc(C)c(=O)n(C)c2)cc(OC)c1CN1CC(C#Cc2ccc3c(c2)CN(C2CCC(=O)NC2=O)C3=O)C1] |
| D441 | 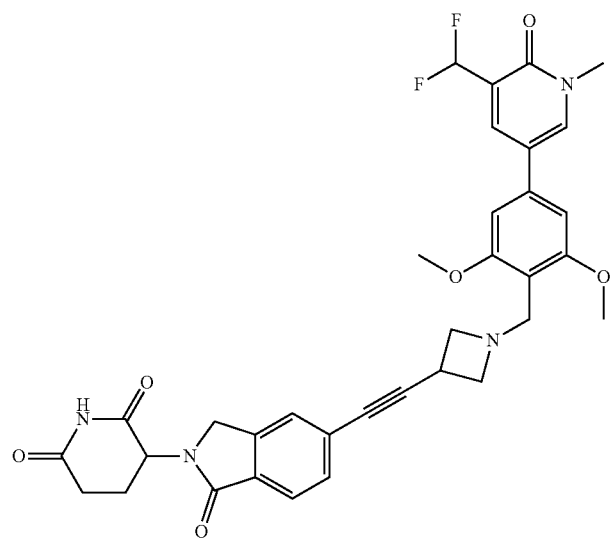 [SMILES: COc1cc(-c2cc(C(F)F)c(=O)n(C)c2)cc(OC)c1CN1CC(C#Cc2ccc3c(c2)CN(C2CCC(=O)NC2=O)C3=O)C1] |
| D442 | 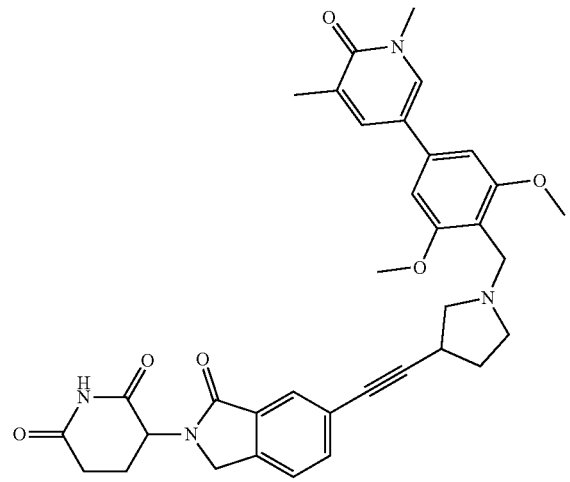 [SMILES: COc1cc(-c2cc(C)c(=O)n(C)c2)cc(OC)c1CN1CCC(C#Cc2ccc3c(c2)C(=O)N(C2CCC(=O)NC2=O)C3)C1] |

TABLE 1D-continued
Compounds D372-D477 of the disclosure
| Compound No. | Structure |
|---|---|
| D443 | 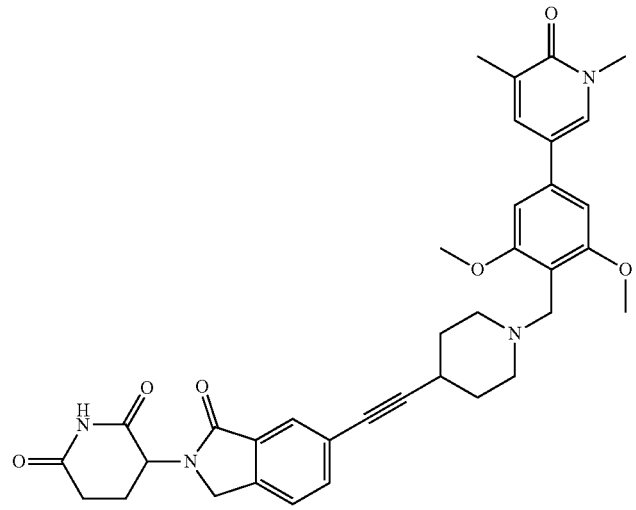 [SMILES: COc1cc(-c2cc(C)c(=O)n(C)c2)cc(OC)c1CN1CCC(C#Cc2ccc3c(c2)C(=O)N(C2CCC(=O)NC2=O)C3)CC1] |
| D444 | 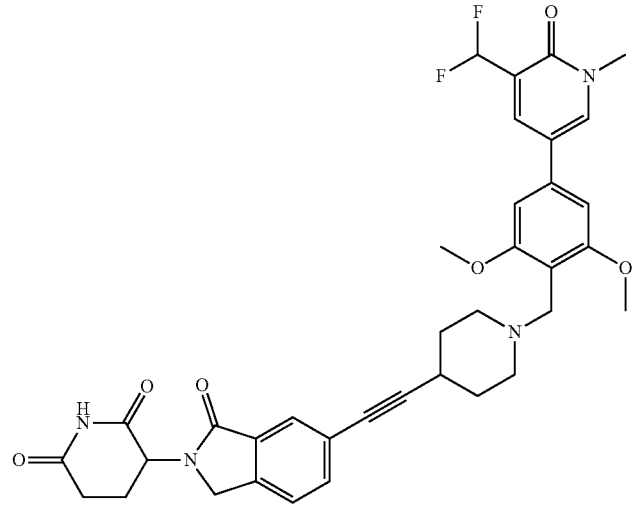 [SMILES: COc1cc(-c2cc(C(F)F)c(=O)n(C)c2)cc(OC)c1CN1CCC(C#Cc2ccc3c(c2)C(=O)N(C2CCC(=O)NC2=O)C3)CC1] |

TABLE 1D-continued

Compounds D372-D477 of the disclosure

| Compound No. | Structure |
|---|---|
| D445 | 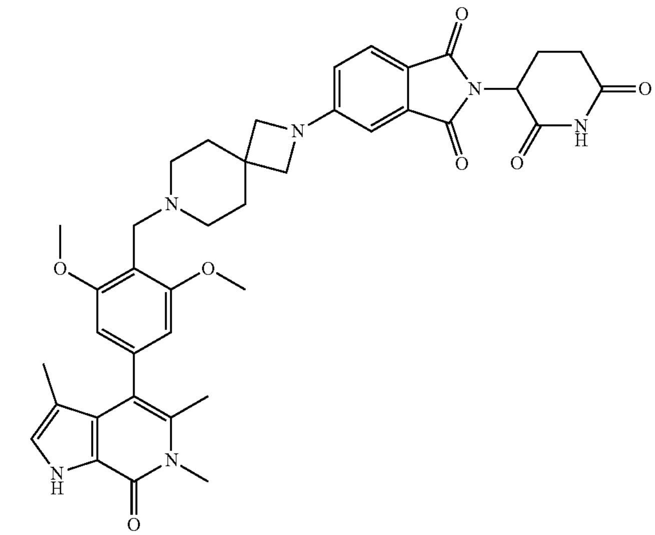 [SMILES: COc1cc(-c2c(C)n(C)c(=O)c3[nH]cc(C)c23)cc(OC)c1CN1CCC2(CC1)CN(c1ccc3c(c1)C(=O)N(C1CCC(=O)NC1=O)C3=O)C2] |
| D446 | 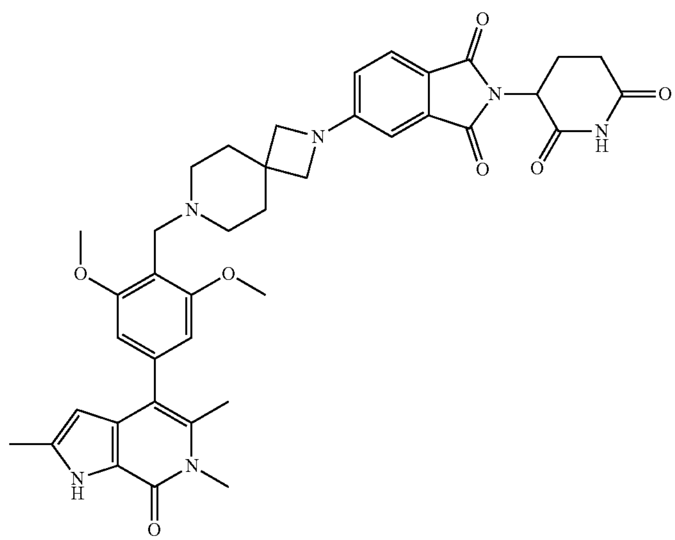 [SMILES: COc1cc(-c2c(C)n(C)c(=O)c3[nH]c(C)cc23)cc(OC)c1CN1CCC2(CC1)CN(c1ccc3c(c1)C(=O)N(C1CCC(=O)NC1=O)C3=O)C2] |
| D447 | 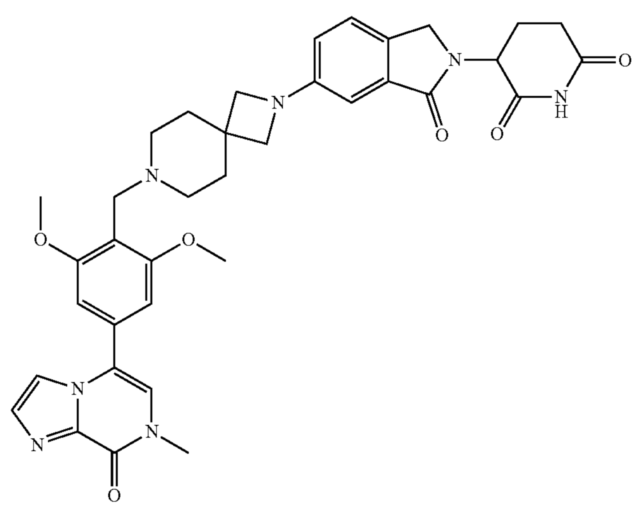 [SMILES: COc1cc(-c2cn(C)c(=O)c3nccn23)cc(OC)c1CN1CCC2(CC1)CN(c1ccc3c(c1)C(=O)N(C1CCC(=O)NC1=O)C3)C2] |

TABLE 1D-continued
Compounds D372-D477 of the disclosure
| Compound No. | Structure |
|---|---|
| D448 | 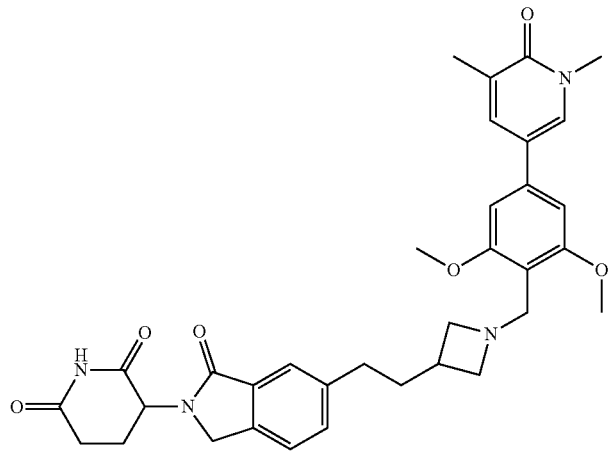 [SMILES: COc1cc(-c2cc(C)c(=O)n(C)c2)cc(OC)c1CN1CC(CCc2ccc3c(c2)C(=O)N(C2CCC(=O)NC2=O)C3)C1] |
| D449 | 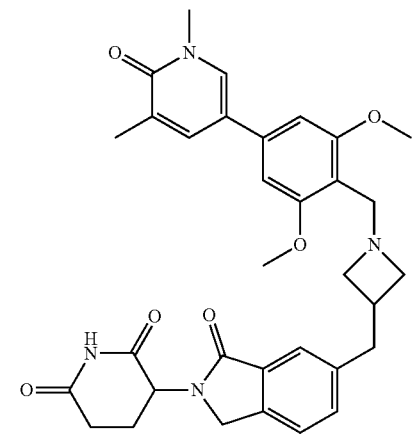 [SMILES: COc1cc(-c2cc(C)c(=O)n(C)c2)cc(OC)c1CN1CC(Cc2ccc3c(c2)C(=O)N(C2CCC(=O)NC2=O)C3)C1] |
| D450 | 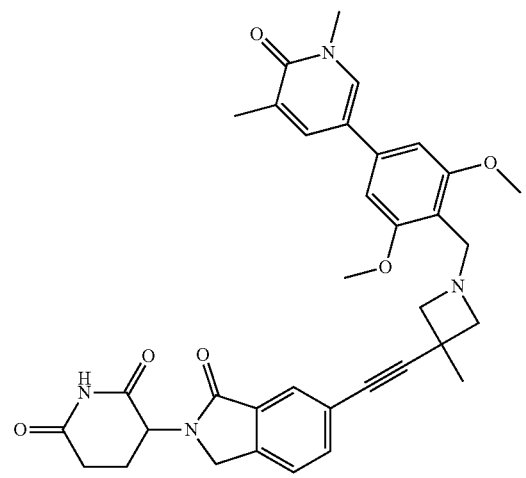 |

TABLE 1D-continued
Compounds D372-D477 of the disclosure
| Compound No. | Structure |
| --- | --- |
| D451 | 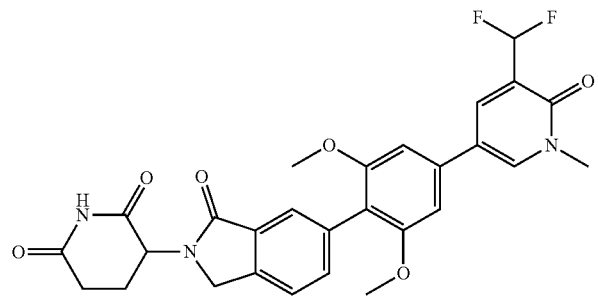 [SMILES: COc1cc(-c2cc(C(F)F)c(=O)n(C)c2)cc(OC)c1-c1ccc2c(c1)C(=O)N(C1CCC(=O)NC1=O)C2] |
| D452 | 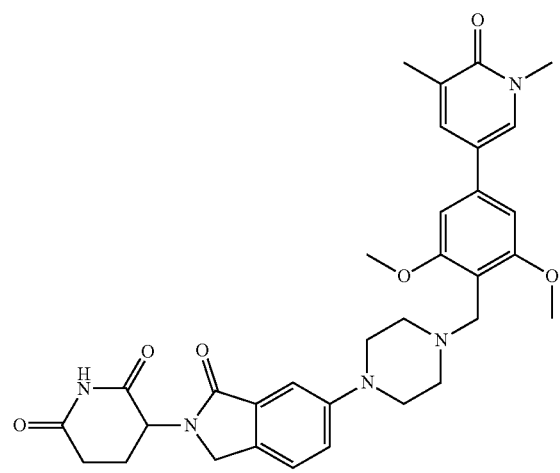 [SMILES: COc1cc(-c2cc(C)c(=O)n(C)c2)cc(OC)c1CN1CCN(c2ccc3c(c2)C(=O)N(C2CCC(=O)NC2=O)C3)CC1] |
| D453 | 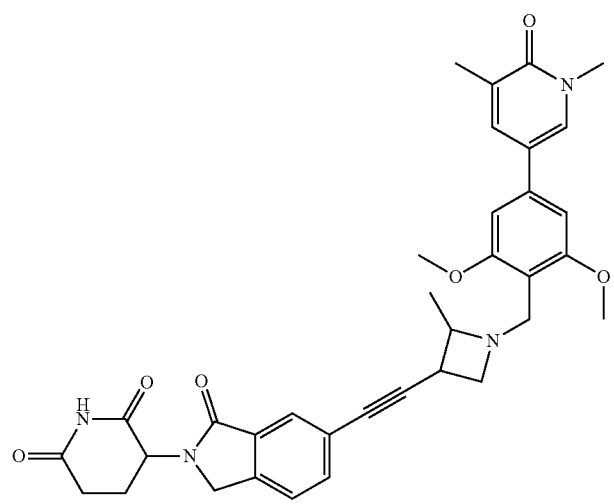 [SMILES: COc1cc(-c2cc(C)c(=O)n(C)c2)cc(OC)c1CN1CC(C#Cc2ccc3c(c2)C(=O)N(C2CCC(=O)NC2=O)C3)C1C] |

TABLE 1D-continued
Compounds D372-D477 of the disclosure
| Compound No. | Structure |
|---|---|
| D454 | 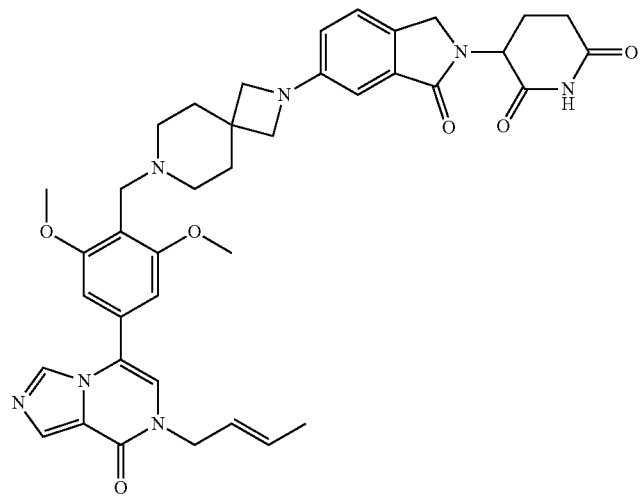 [SMILES: C/C=C/Cn1cc(-c2cc(OC)c(CN3CCC4(CC3)CN(c3ccc5c(c3)C(=O)N(C3CCC(=O)NC3=O)C5)C4)c(OC)c2)n2cncc2c1=O] |
| D455 | 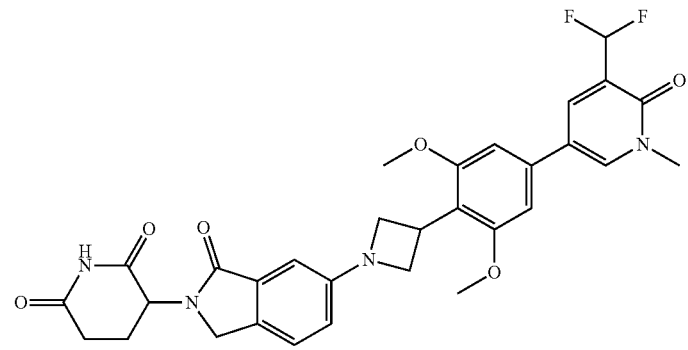 [SMILES: COc1cc(-c2cc(C(F)F)c(=O)n(C)c2)cc(OC)c1C1CN(c2ccc3c(c2)C(=O)N(C2CCC(=O)NC2=O)C3)C1] |
| D456 | 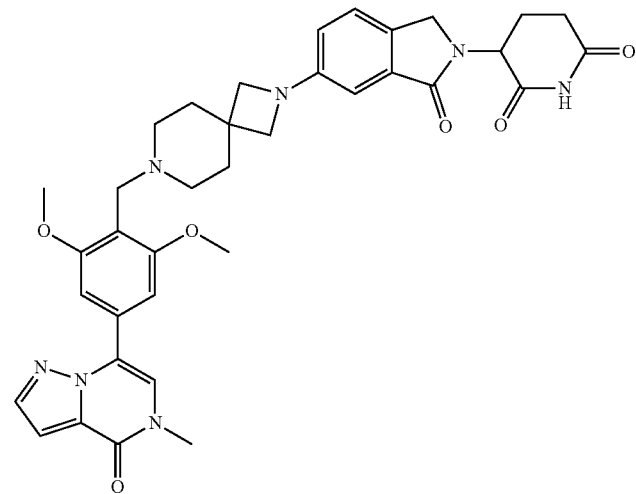 [SMILES: COc1cc(-c2cn(C)c(=O)c3ccnn23)cc(OC)c1CN1CCC2(CC1)CN(c1ccc3c(c1)C(=O)N(C1CCC(=O)NC1=O)C3)C2] |

TABLE 1D-continued
Compounds D372-D477 of the disclosure
| Compound No. | Structure |
|---|---|
| D457 | 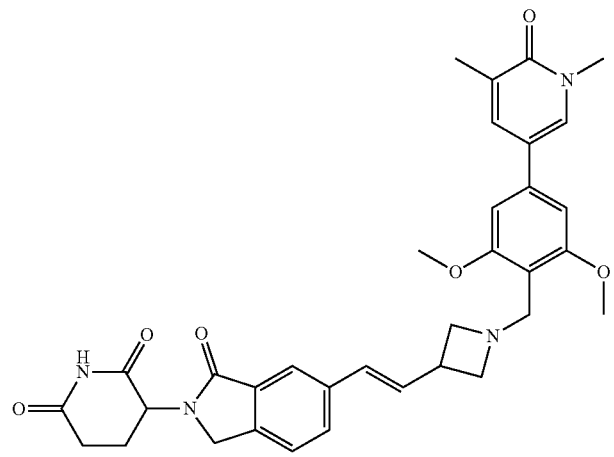 [SMILES: COc1cc(-c2cc(C)c(=O)n(C)c2)cc(OC)c1CN1CC(/C=C/c2ccc3c(c2)C(=O)N(C2CCC(=O)NC2=O)C3)C1] |
| D458 | 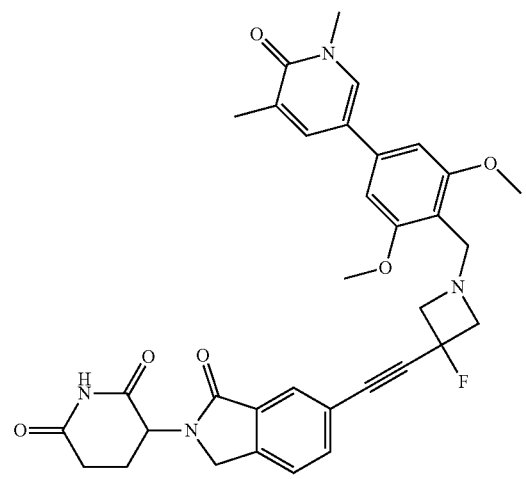 [SMILES: COc1cc(-c2cc(C)c(=O)n(C)c2)cc(OC)c1CN1CC(F)(C#Cc2ccc3c(c2)C(=O)N(C2CCC(=O)NC2=O)C3)C1] |
| D459 | 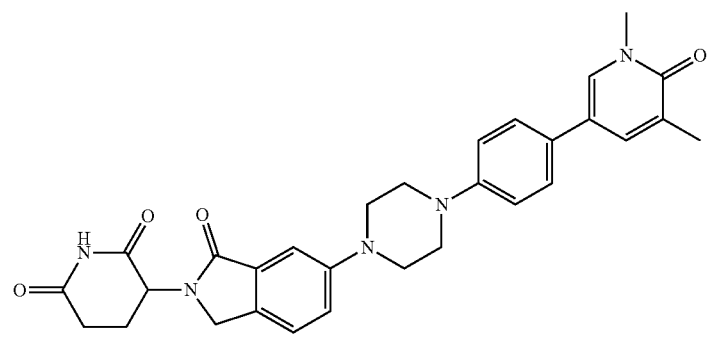 [SMILES: Cc1cc(-c2ccc(N3CCN(c4ccc5c(c4)C(=O)N(C4CCC(=O)NC4=O)C5)CC3)cc2)cn(C)c1=O] |

TABLE 1D-continued
Compounds D372-D477 of the disclosure
| Compound No. | Structure |
|---|---|
| D460 | 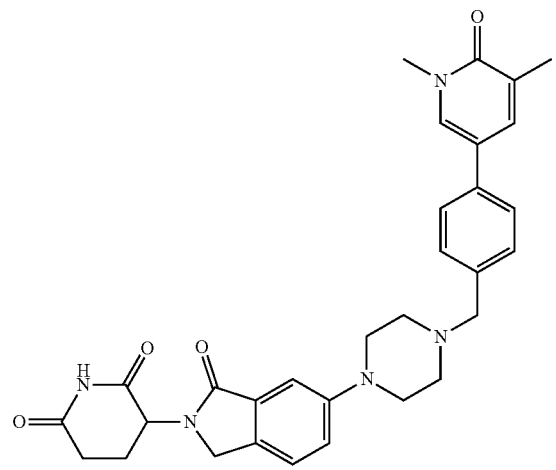 [SMILES: Cc1cc(-c2ccc(CN3CCN(c4ccc5c(c4)C(=O)N(C4CCC(=O)NC4=O)C5)CC3)cc2)cn(C)c1=O] |
| D461 | 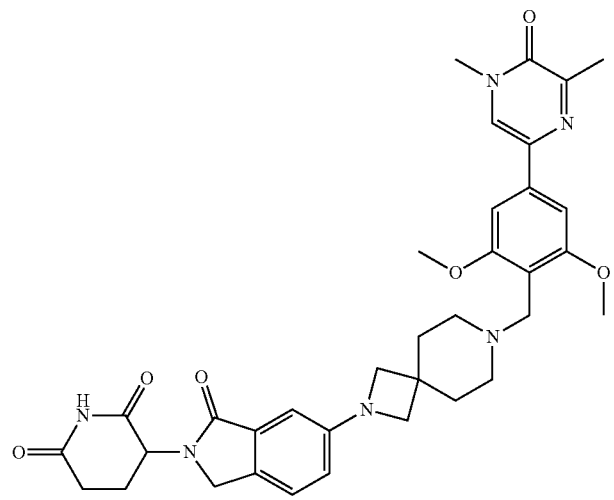 [SMILES: COc1cc(-c2cn(C)c(=O)c(C)n2)cc(OC)c1CN1CCC2(CC1)CN(c1ccc3c(c1)C(=O)N(C1CCC(=O)NC1=O)C3)C2] |
| D462 | 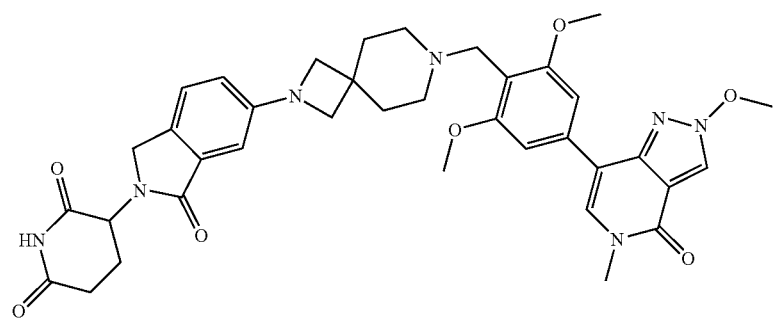 [SMILES: COc1cc(-c2cn(C)c(=O)c3cn(OC)nc23)cc(OC)c1CN1CCC2(CC1)CN(c1ccc3c(c1)C(=O)N(C1CCC(=O)NC1=O)C3)C2] |

TABLE 1D-continued
Compounds D372-D477 of the disclosure
| Compound No. | Structure |
| --- | --- |
| D463 | 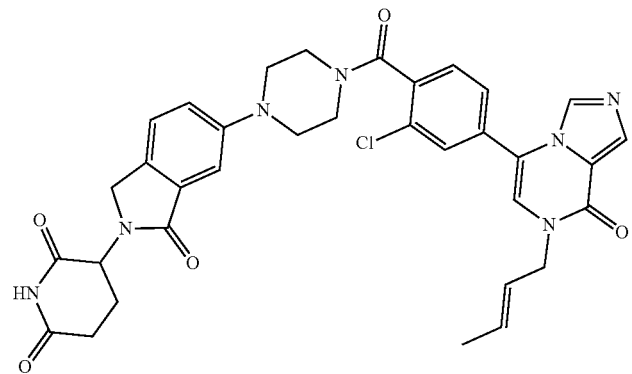 [SMILES: C/C=C/Cn1cc(-c2ccc(C(=O)N3CCN(c4ccc5c(c4)C(=O)N(C4CCC(=O)NC4=O)C5)CC3)c(Cl)c2)n2cncc2c1=O] |
| D464 | 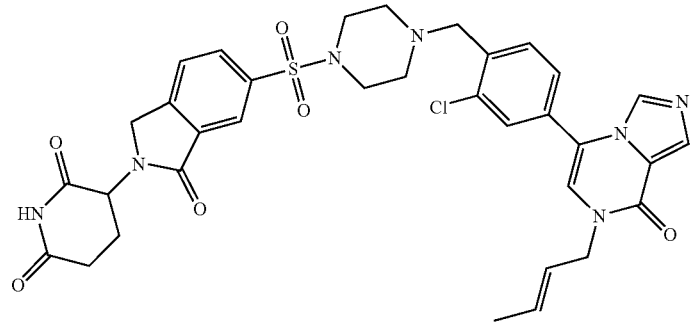 [SMILES: C/C=C/Cn1cc(-c2ccc(CN3CCN(S(=O)(=O)c4ccc5c(c4)C(=O)N(C4CCC(=O)NC4=O)C5)CC3)c(Cl)c2)n2cncc2c1=O] |
| D465 | 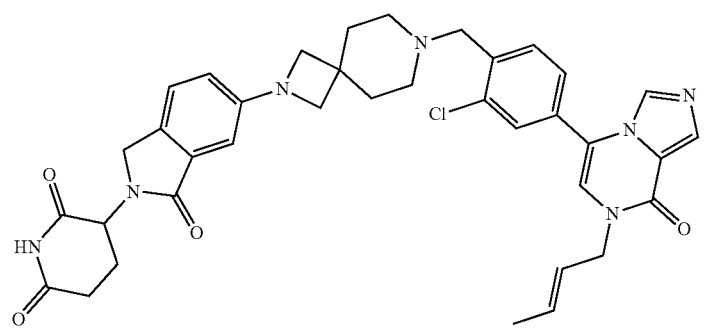 [SMILES: C/C=C/Cn1cc(-c2ccc(CN3CCC4(CC3)CN(c3ccc5c(c3)C(=O)N(C3CCC(=O)NC3=O)C5)C4)c(Cl)c2)n2cncc2c1=O] |
| D466 | 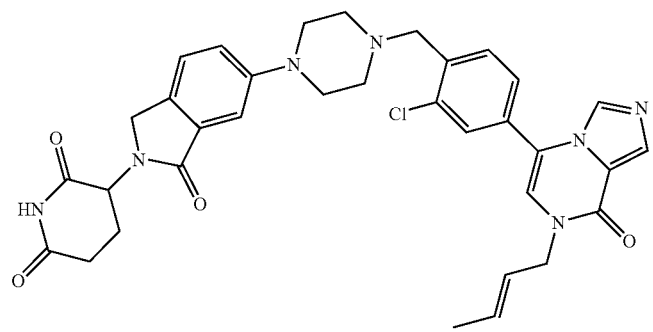 [SMILES: C/C=C/Cn1cc(-c2ccc(CN3CCN(c4ccc5c(c4)C(=O)N(C4CCC(=O)NC4=O)C5)CC3)c(Cl)c2)n2cncc2c1=O] |

TABLE 1D-continued
Compounds D372-D477 of the disclosure
| Compound No. | Structure |
|---|---|
| D467 | 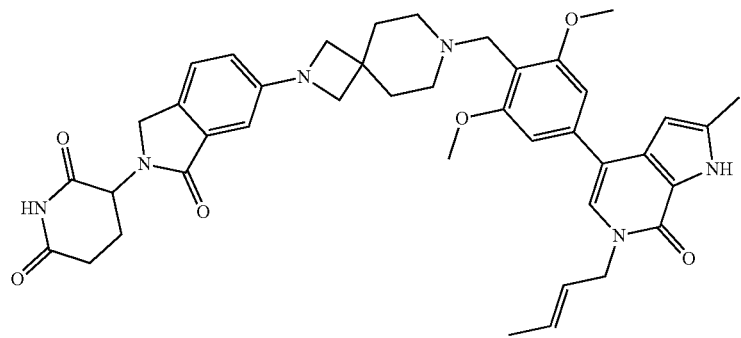 [SMILES: C/C=C/Cn1cc(-c2cc(OC)c(CN3CCC4(CC3)CN(c3ccc5c(c3)C(=O)N(C3CCC(=O)NC3=O)C5)C4)c(OC)c2)c2cc(C)[nH]c2c1=O] |
| D468 | 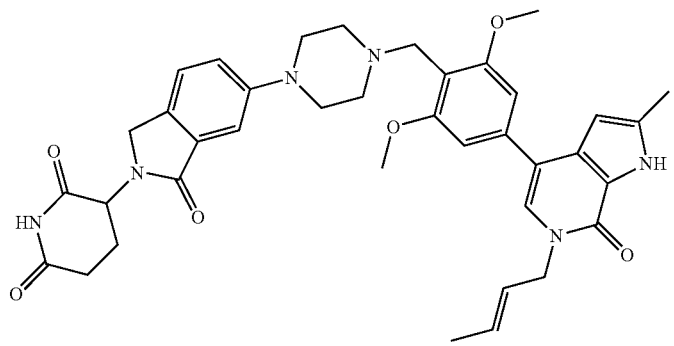 [SMILES: C/C=C/Cn1cc(-c2cc(OC)c(CN3CCN(c4ccc5c(c4)C(=O)N(C4CCC(=O)NC4=O)C5)CC3)c(OC)c2)c2cc(C)[nH]c2c1=O] |
| D469 | 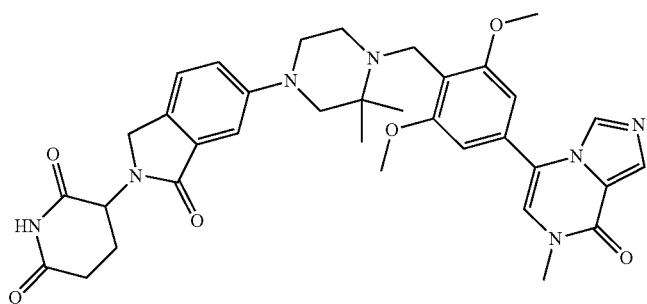 [SMILES: COc1cc(-c2cn(C)c(=O)c3cncn23)cc(OC)c1CN1CCN(c2ccc3c(c2)C(=O)N(C2CCC(=O)NC2=O)C3)CC1(C)C] |
| D470 | 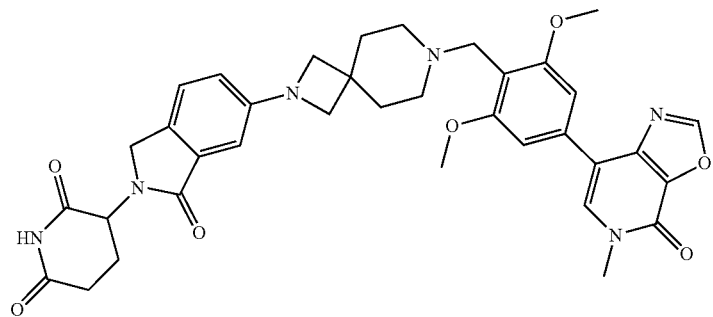 [SMILES: COc1cc(-c2cn(C)c(=O)c3ocnc23)cc(OC)c1CN1CCC2(CC1)CN(c1ccc3c(c1)C(=O)N(C1CCC(=O)NC1=O)C3)C2] |

TABLE 1D-continued
Compounds D372-D477 of the disclosure
| Compound No. | Structure |
|---|---|
| D471 | 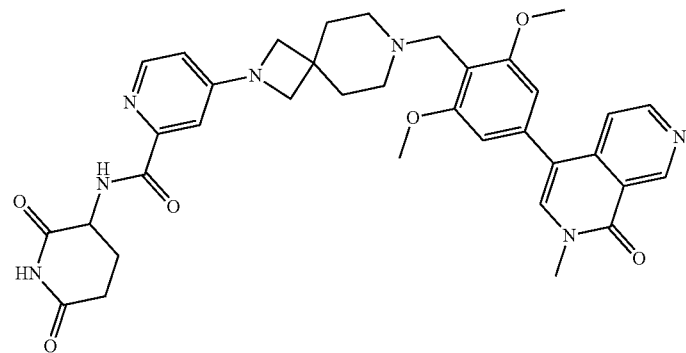 [SMILES: COc1cc(-c2cn(C)c(=O)c3cnccc23)cc(OC)c1CN1CCC2(CC1)CN(c1ccnc(C(=O)NC3CCC(=O)NC3=O)c1)C2] |
| D472 | 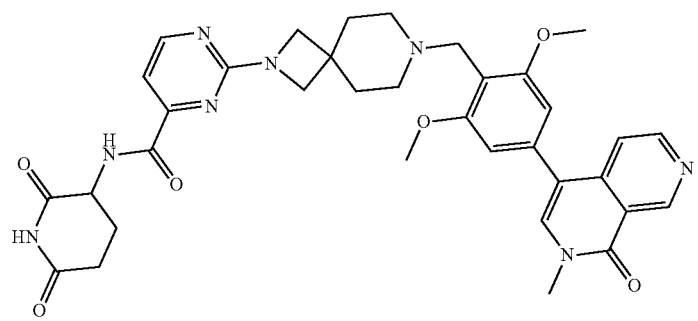 [SMILES: COc1cc(-c2cn(C)c(=O)c3cnccc23)cc(OC)c1CN1CCC2(CC1)CN(c1nccc(C(=O)NC3CCC(=O)NC3=O)n1)C2] |
| D473 | 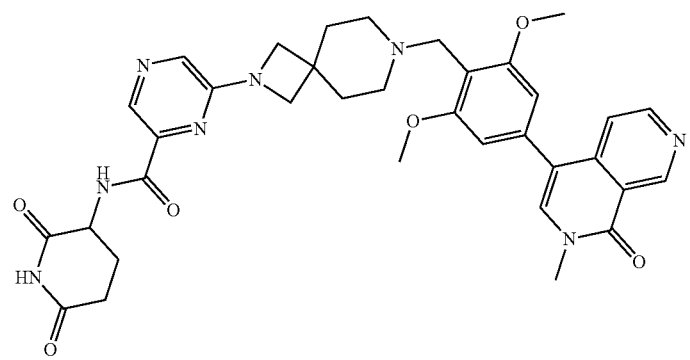 [SMILES: COc1cc(-c2cn(C)c(=O)c3cnccc23)cc(OC)c1CN1CCC2(CC1)CN(c1cncc(C(=O)NC3CCC(=O)NC3=O)n1)C2] |
| D474 | 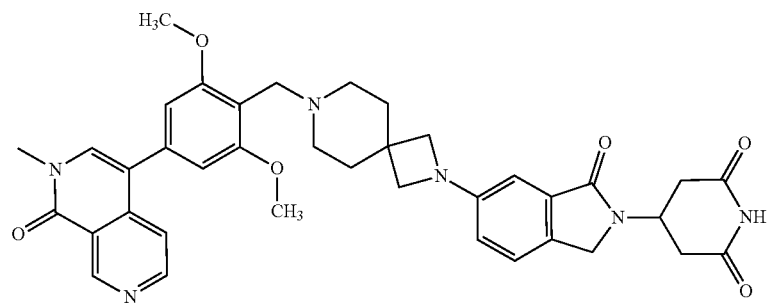 [SMILES: COc1cc(-c2cn(C)c(=O)c3cnccc23)cc(OC)c1CN1CCC2(CC1)CN(c1ccc3c(c1)C(=O)N(C1CC(=O)NC(=O)C1)C3)C2] |

TABLE 1E
Compounds DD11-DD16 of the disclosure
| Compound No. | Structure |
|---|---|
| DD11 | 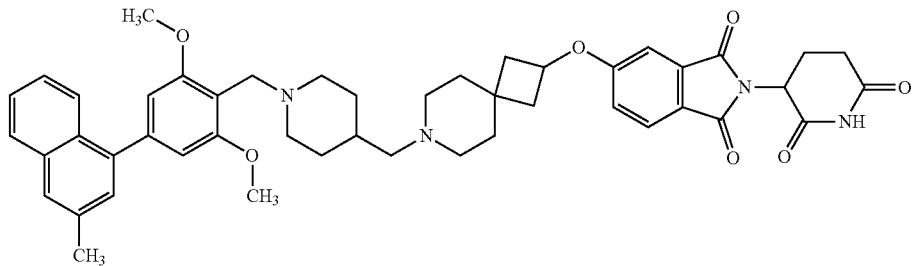 [SMILES: COc1cc(-c2cc(C)cc3ccccc23)cc(OC)c1CN1CCC(CN2CCC3(CC2)CC(Oc2ccc4c(c2)C(=O)N(C2CCC(=O)NC2=O)C4=O)C3)CC1] |
| DD12 | 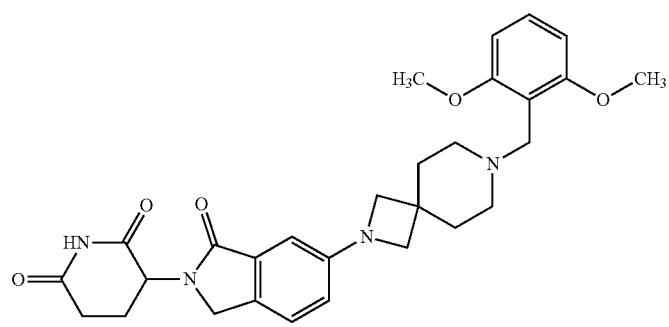 [SMILES: COc1cccc(OC)c1CN1CCC2(CC1)CN(c1ccc3c(c1)C(=O)N(C1CCC(=O)NC1=O)C3)C2] |
| DD13 | 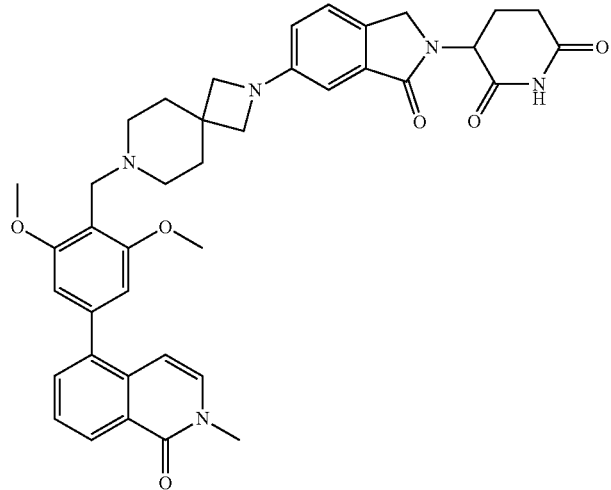 [SMILES: COc1cc(-c2cccc3c(=O)n(C)ccc23)cc(OC)c1CN1CCC2(CC1)CN(c1ccc3c(c1)C(=O)N(C1CCC(=O)NC1=O)C3)C2] |
| DD14 | 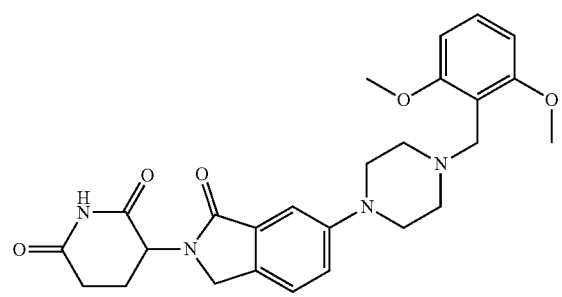 [SMILES: COc1cccc(OC)c1CN1CCN(c2ccc3c(c2)C(=O)N(C2CCC(=O)NC2=O)C3)CC1] |

TABLE 1E-continued

Compounds DD11-DD16 of the disclosure

| Compound No. | Structure |
|---|---|
| DD15 | *(chemical structure)* |
| DD16 | *(chemical structure)* |

In another aspect, the disclosure features a pharmaceutical composition including any of the foregoing compounds, or pharmaceutically acceptable salts thereof, and a pharmaceutically acceptable excipient.

In an aspect, the disclosure features a method of inhibiting the level and/or activity of BRD9 in a cell, the method involving contacting the cell with an effective amount of any of the foregoing compounds, or pharmaceutically acceptable salts thereof, or a pharmaceutical composition thereof.

In another aspect, the disclosure features a method of reducing the level and/or activity of BRD9 in a cell, the method involving contacting the cell with an effective amount of any of the foregoing compounds, or pharmaceutically acceptable salts thereof, or a pharmaceutical composition thereof.

In some embodiments, the cell is a cancer cell.

In some embodiments, the cancer is a malignant, rhabdoid tumor, a CD8+ T-cell lymphoma, endometrial carcinoma, ovarian carcinoma, bladder cancer, stomach cancer, pancreatic cancer, esophageal cancer, prostate cancer, renal cell carcinoma, melanoma, colorectal cancer, a sarcoma (e.g., a soft tissue sarcoma, synovial sarcoma, Ewing's sarcoma, osteosarcoma, rhabdomyosarcoma, adult fibrosarcoma, alveolar soft-part sarcoma, angiosarcoma, clear cell sarcoma, desmoplastic small round cell tumor, epithelioid sarcoma, fibromyxoid sarcoma, gastrointestinal stromal tumor, Kaposi sarcoma, liposarcoma, leiomyosarcoma, malignant mesenchymoma malignant peripheral nerve sheath tumors, myxofibrosarcoma, low-grade rhabdomyosarcoma), non-small cell lung cancer (e.g., squamous or adenocarcinoma), stomach cancer, or breast cancer. In some embodiments, the cancer is a malignant, rhabdoid tumor, a CD8+ T-cell lymphoma, endometrial carcinoma, ovarian carcinoma, bladder cancer, stomach cancer, pancreatic cancer, esophageal cancer, prostate cancer, renal cell carcinoma, melanoma, or colorectal cancer. In some embodiments, the cancer is a sarcoma (e.g., synovial sarcoma or Ewing's sarcoma), non-small cell lung cancer (e.g., squamous or adenocarcinoma), stomach cancer, or breast cancer. In some embodiments, the cancer is sarcoma (e.g., synovial sarcoma or Ewing's sarcoma). In some embodiments, the sarcoma is synovial sarcoma.

In an aspect, the disclosure features a method of treating a BAF complex-related disorder in a subject in need thereof, the method involving administering to the subject an effective amount of any of the foregoing compounds, or pharmaceutically acceptable salts thereof, or a pharmaceutical composition thereof. In some embodiments, the BAF complex-related disorder is cancer. In some embodiments, the BAF complex-related disorder is infection.

In another aspect, the disclosure features a method of treating an SS18-SSX fusion protein-related disorder in a subject in need thereof, the method involving administering to the subject an effective amount of any of the foregoing compounds, or pharmaceutically acceptable salts thereof, or a pharmaceutical composition thereof. In some embodiments, the SS18-SSX fusion protein-related disorder is cancer. In some embodiments, the SS18-SSX fusion protein-related disorder is infection. In some embodiments of any of the foregoing methods, the SS18-SSX fusion protein is a SS18-SSX1 fusion protein, a SS18-SSX2 fusion protein, or a SS18-SSX4 fusion protein.

In yet another aspect, the disclosure features a method of treating a BRD9-related disorder in a subject in need thereof, the method involving administering to the subject an effective amount of any of the foregoing compounds, or pharmaceutically acceptable salts thereof, or a pharmaceutical composition thereof. In some embodiments, the BRD9-related disorder is cancer. In some embodiments, the BRD9-related disorder is infection.

In some embodiments, the cancer is squamous cell carcinoma, basal cell carcinoma, adenocarcinoma, hepatocellular carcinomas, and renal cell carcinomas, cancer of the bladder, bowel, breast, cervix, colon, esophagus, head, kidney, liver, lung, neck, ovary, pancreas, prostate, and stomach; leukemias; benign and malignant lymphomas, particularly Burkitt's lymphoma and Non-Hodgkin's lymphoma; benign and malignant melanomas; myeloproliferative diseases; sarcomas, including Ewing's sarcoma, hemangiosarcoma, Kaposi's sarcoma, liposarcoma, myosarcomas, peripheral neuroepithelioma, synovial sarcoma, gliomas, astrocytomas, oligodendrogliomas, ependymomas, gliobastomas, neuroblastomas, ganglioneuromas, gangliogliomas, medulloblastomas, pineal cell tumors, meningiomas, meningeal sarcomas, neurofibromas, and Schwannomas; bowel cancer, breast cancer, prostate cancer, cervical cancer, uterine cancer, lung cancer, ovarian cancer, testicular cancer, thyroid cancer, astrocytoma, esophageal cancer, pancreatic cancer, stomach cancer, liver cancer, colon cancer, melanoma; carcinosarcoma, Hodgkin's disease, Wilms' tumor and teratocarcinomas. Additional cancers which may be treated using the disclosed compounds according to the present invention include, for example, acute granulocytic leukemia, acute lymphocytic leukemia (ALL), acute myelogenous leukemia (AML), adenocarcinoma, adenosarcoma, adrenal cancer, adrenocortical carcinoma, anal cancer, anaplastic astrocytoma, angiosarcoma, appendix cancer, astrocytoma, Basal cell carcinoma, B-Cell lymphoma, bile duct cancer, bladder cancer, bone cancer, bone marrow cancer, bowel cancer, brain cancer, brain stem glioma, breast cancer, triple (estrogen, progesterone and HER-2) negative breast cancer, double negative breast cancer (two of estrogen, progesterone and HER-2 are negative), single negative (one of estrogen, progesterone and HER-2 is negative), estrogen-receptor positive, HER2-negative breast cancer, estrogen receptor-negative breast cancer, estrogen receptor positive breast cancer, metastatic breast cancer, luminal A breast cancer, luminal B breast cancer, Her2-negative breast cancer, HER2-positive or negative breast cancer, progesterone receptor-negative breast cancer, progesterone receptor-positive breast cancer, recurrent breast cancer, carcinoid tumors, cervical cancer, cholangiocarcinoma, chondrosarcoma, chronic lymphocytic leukemia (CLL), chronic myelogenous leukemia (CML), colon cancer, colorectal cancer, craniopharyngioma, cutaneous lymphoma, cutaneous melanoma, diffuse astrocytoma, ductal carcinoma in situ (DCIS), endometrial cancer, ependymoma, epithelioid sarcoma, esophageal cancer, ewing sarcoma, extrahepatic bile duct cancer, eye cancer, fallopian tube cancer, fibrosarcoma, gallbladder cancer, gastric cancer, gastrointestinal cancer, gastrointestinal carcinoid cancer, gastrointestinal stromal tumors (GIST), germ cell tumor glioblastoma multiforme (GBM), glioma, hairy cell leukemia, head and neck cancer, hemangioendothelioma, Hodgkin lymphoma, hypopharyngeal cancer, infiltrating ductal carcinoma (IDC), infiltrating lobular carcinoma (ILC), inflammatory breast cancer (IBC), intestinal Cancer, intrahepatic bile duct cancer, invasive/infiltrating breast cancer, Islet cell cancer, jaw cancer, Kaposi sarcoma, kidney cancer, laryngeal cancer, leiomyosarcoma, leptomeningeal metastases, leukemia, lip cancer, liposarcoma, liver cancer, lobular carcinoma in situ, low-grade astrocytoma, lung cancer, lymph node cancer, lymphoma, male breast cancer, medullary carcinoma, medulloblastoma, melanoma, meningioma, Merkel cell carcinoma, mesenchymal chondrosarcoma, mesenchymous, mesothelioma metastatic breast cancer, metastatic melanoma metastatic squamous neck cancer, mixed gliomas, monodermal teratoma, mouth cancer mucinous carcinoma, mucosal melanoma, multiple myeloma, Mycosis Fungoides, myelodysplastic syndrome, nasal cavity cancer, nasopharyngeal cancer, neck cancer, neuroblastoma, neuroendocrine tumors (NETs), non-Hodgkin's lymphoma, non-small cell lung cancer (NSCLC), oat cell cancer, ocular cancer, ocular melanoma, oligodendroglioma, oral cancer, oral cavity cancer, oropharyngeal cancer, osteogenic sarcoma, osteosarcoma, ovarian cancer, ovarian epithelial cancer ovarian germ cell tumor, ovarian primary peritoneal carcinoma, ovarian sex cord stromal tumor, Paget's disease, pancreatic cancer, papillary carcinoma, paranasal sinus cancer, parathyroid cancer, pelvic cancer, penile cancer, peripheral nerve cancer, peritoneal cancer, pharyngeal cancer, pheochromocytoma, pilocytic astrocytoma, pineal region tumor, pineoblastoma, pituitary gland cancer, primary central nervous system (CNS) lymphoma, prostate cancer, rectal cancer, renal cell carcinoma, renal pelvis cancer, rhabdomyosarcoma, salivary gland cancer, soft tissue sarcoma, bone sarcoma, sarcoma, sinus cancer, skin cancer, small cell lung cancer (SCLC), small intestine cancer, spinal cancer, spinal column cancer, spinal cord cancer, squamous cell carcinoma, stomach cancer, synovial sarcoma, T-cell lymphoma, testicular cancer, throat cancer, thymoma/thymic carcinoma, thyroid cancer, tongue cancer, tonsil cancer, transitional cell cancer, tubal cancer, tubular carcinoma, undiagnosed cancer, ureteral cancer, urethral cancer, uterine adenocarcinoma, uterine cancer, uterine sarcoma, vaginal cancer, vulvar cancer, T-cell lineage acute lymphoblastic leukemia (T-ALL), T-cell lineage lymphoblastic lymphoma (T-LL), peripheral T-cell lymphoma, Adult T-cell leukemia, Pre-B ALL, Pre-B lymphomas, large B-cell lymphoma, Burkitts lymphoma, B-cell ALL, Philadelphia chromosome positive ALL, Philadelphia chromosome positive CML, juvenile myelomonocytic leukemia (JMML), acute promyelocytic leukemia (a subtype of AML), large granular lymphocytic leukemia, Adult T-cell chronic leukemia, diffuse large B cell lymphoma, follicular lymphoma; Mucosa-Associated Lymphatic Tissue lymphoma (MALT), small cell lymphocytic lymphoma, mediastinal large B cell lymphoma, nodal marginal zone B cell lymphoma (NMZL); splenic marginal zone lymphoma (SMZL); intravascular large B-cell lymphoma; primary effusion lymphoma; or lymphomatoid granulomatosis; B-cell prolymphocytic leukemia; splenic lymphoma/leukemia, unclassifiable, splenic diffuse red pulp small B-cell lymphoma; lymphoplasmacytic lymphoma; heavy chain diseases, for example, Alpha heavy chain disease, Gamma heavy chain disease, Mu heavy chain disease, plasma cell myeloma, solitary plasmacytoma of bone; extraosseous plasmacytoma; primary cutaneous follicle center lymphoma, T cell/histocyte rich large B-cell lymphoma, DLBCL associated with chronic inflammation; Epstein-Barr virus (EBV)+DLBCL of the elderly; primary mediastinal (thymic) large B-cell lymphoma, primary cutaneous DLBCL, leg type, ALK+ large B-cell lymphoma, plasmablastic lymphoma; large B-cell lymphoma arising in HHV8-associated multicentric, Castleman disease; B-cell lymphoma, unclassifiable, with features intermediate between diffuse large B-cell lymphoma, or B-cell lymphoma, unclassifiable, with features intermediate between diffuse large B-cell lymphoma and classical Hodgkin lymphoma.

In some embodiments, the cancer is a malignant, rhabdoid tumor, a CD8+ T-cell lymphoma, endometrial carcinoma, ovarian carcinoma, bladder cancer, stomach cancer, pancreatic cancer, esophageal cancer, prostate cancer, renal cell carcinoma, melanoma, colorectal cancer, a sarcoma (e.g., a soft tissue sarcoma, synovial sarcoma, Ewing's sarcoma, osteosarcoma, rhabdomyosarcoma, adult fibrosarcoma, alveolar soft-part sarcoma, angiosarcoma, clear cell sarcoma, desmoplastic small round cell tumor, epithelioid sarcoma, fibromyxoid sarcoma, gastrointestinal stromal tumor, Kaposi sarcoma, liposarcoma, leiomyosarcoma, malignant mesenchymoma malignant peripheral nerve sheath tumors, myxofibrosarcoma, low-grade rhabdomyosarcoma), non-small cell lung cancer (e.g., squamous or adenocarcinoma), stomach cancer, or breast cancer. In some embodiments, the cancer is a malignant, rhabdoid tumor, a CD8+ T-cell lymphoma, endometrial carcinoma, ovarian carcinoma, bladder cancer, stomach cancer, pancreatic cancer, esophageal cancer, prostate cancer, renal cell carcinoma, melanoma, or colorectal cancer. In some embodiments, the cancer is a sarcoma (e.g., synovial sarcoma or Ewing's sarcoma), non-small cell lung cancer (e.g., squamous or adenocarcinoma), stomach cancer, or breast cancer. In some embodiments, the cancer is sarcoma (e.g., synovial sarcoma or Ewing's sarcoma). In some embodiments, the sarcoma is synovial sarcoma.

In some embodiments, the infection is viral infection (e.g., an infection with a virus of the Retroviridae family such as the lentiviruses (e.g. Human immunodeficiency virus (HIV) and deltaretroviruses (e.g., human T cell leukemia virus I (HTLV-1), human T cell leukemia virus II (HTLV-II)); Hepadnaviridae family (e.g. hepatitis B virus (HBV)); Flaviviridae family (e.g. hepatitis C virus (HCV)); Adenoviridae family (e.g. Human Adenovirus); Herpesviridae family (e.g. Human cytomegalovirus (HCMV), Epstein-Barr virus, herpes simplex virus 1 (HSV-1), herpes simplex virus 2 (HSV-2), human herpesvirus 6 (HHV-6), Herpesvitus K*, CMV, varicella-zoster virus); Papillomaviridae family (e.g. Human Papillomavirus (HPV, HPV $E^1$)); Parvoviridae family (e.g. Parvovirus B19); Polyomaviridae family (e.g. JC virus and BK virus); Paramyxoviridae family (e.g. Measles virus); or Togaviridae family (e.g. Rubella virus)). In some embodiments, the disorder is Coffin Siris, Neurofibromatosis (e.g., NF-1, NF-2, or Schwannomatosis), or Multiple Meningioma. In an aspect, the disclosure features a method of treating a cancer in a subject in need thereof, the method including administering to the subject an effective amount of any of the foregoing compounds, or pharmaceutically acceptable salts thereof, or any of the foregoing pharmaceutical compositions.

In some embodiments, the cancer is squamous cell carcinoma, basal cell carcinoma, adenocarcinoma, hepatocellular carcinomas, and renal cell carcinomas, cancer of the bladder, bowel, breast, cervix, colon, esophagus, head, kidney, liver, lung, neck, ovary, pancreas, prostate, and stomach; leukemias; benign and malignant lymphomas, particularly Burkitt's lymphoma and Non-Hodgkin's lymphoma; benign and malignant melanomas; myeloproliferative diseases; sarcomas, including Ewing's sarcoma, hemangiosarcoma, Kaposi's sarcoma, liposarcoma, myosarcomas, peripheral neuroepithelioma, synovial sarcoma, gliomas, astrocytomas, oligodendrogliomas, ependymomas, glioblastomas, neuroblastomas, ganglioneuromas, gangliogliomas, medulloblastomas, pineal cell tumors, meningiomas, meningeal sarcomas, neurofibromas, and Schwannomas; bowel cancer, breast cancer, prostate cancer, cervical cancer, uterine cancer, lung cancer, ovarian cancer, testicular cancer, thyroid cancer, astrocytoma, esophageal cancer, pancreatic cancer, stomach cancer, liver cancer, colon cancer, melanoma; carcinosarcoma, Hodgkin's disease, Wilms' tumor and teratocarcinomas. Additional cancers which may be treated using the disclosed compounds according to the present invention include, for example, acute granulocytic leukemia, acute lymphocytic leukemia (ALL), acute myelogenous leukemia (AML), adenocarcinoma, adenosarcoma, adrenal cancer, adrenocortical carcinoma, anal cancer, anaplastic astrocytoma, angiosarcoma, appendix cancer, astrocytoma, Basal cell carcinoma, B-Cell lymphoma, bile duct cancer, bladder cancer, bone cancer, bone marrow cancer, bowel cancer, brain cancer, brain stem glioma, breast cancer, triple (estrogen, progesterone and HER-2) negative breast cancer, double negative breast cancer (two of estrogen, progesterone and HER-2 are negative), single negative (one of estrogen, progesterone and HER-2 is negative), estrogen-receptor positive, HER2-negative breast cancer, estrogen receptor-negative breast cancer, estrogen receptor positive breast cancer, metastatic breast cancer, luminal A breast cancer, luminal B breast cancer, Her2-negative breast cancer, HER2-positive or negative breast cancer, progesterone receptor-negative breast cancer, progesterone receptor-positive breast cancer, recurrent breast cancer, carcinoid tumors, cervical cancer, cholangiocarcinoma, chondrosarcoma, chronic lymphocytic leukemia (CLL), chronic myelogenous leukemia (CML), colon cancer, colorectal cancer, craniopharyngioma, cutaneous lymphoma, cutaneous melanoma, diffuse astrocytoma, ductal carcinoma in situ (DCIS), endometrial cancer, ependymoma, epithelioid sarcoma, esophageal cancer, ewing sarcoma, extrahepatic bile duct cancer, eye cancer, fallopian tube cancer, fibrosarcoma, gallbladder cancer, gastric cancer, gastrointestinal cancer, gastrointestinal carcinoid cancer, gastrointestinal stromal tumors (GIST), germ cell tumor glioblastoma multiforme (GBM), glioma, hairy cell leukemia, head and neck cancer, hemangioendothelioma, Hodgkin lymphoma, hypopharyngeal cancer, infiltrating ductal carcinoma (IDC), infiltrating lobular carcinoma (ILC), inflammatory breast cancer (IBC), intestinal Cancer, intrahepatic bile duct cancer, invasive/infiltrating breast cancer, Islet cell cancer, jaw cancer, Kaposi sarcoma, kidney cancer, laryngeal cancer, leiomyosarcoma, leptomeningeal metastases, leukemia, lip cancer, liposarcoma, liver cancer, lobular carcinoma in situ, low-grade astrocytoma, lung cancer, lymph node cancer, lymphoma, male breast cancer, medullary carcinoma, medulloblastoma, melanoma, meningioma, Merkel cell carcinoma, mesenchymal chondrosarcoma, mesenchymous, mesothelioma metastatic breast cancer, metastatic melanoma metastatic squamous neck cancer, mixed gliomas, monodermal teratoma, mouth cancer mucinous carcinoma, mucosal melanoma, multiple myeloma, Mycosis Fungoides, myelodysplastic syndrome, nasal cavity cancer, nasopharyngeal cancer, neck cancer, neuroblastoma, neuroendocrine tumors (NETs), non-Hodgkin's lymphoma, non-small cell lung cancer (NSCLC), oat cell cancer, ocular cancer, ocular melanoma, oligodendroglioma, oral cancer, oral cavity cancer, oropharyngeal cancer, osteogenic sarcoma, osteosarcoma, ovarian cancer, ovarian epithelial cancer ovarian germ cell tumor, ovarian primary peritoneal carcinoma, ovarian sex cord stromal tumor, Paget's disease, pancreatic cancer, papillary carcinoma, paranasal sinus cancer, parathyroid cancer, pelvic cancer, penile cancer, peripheral nerve cancer, peritoneal cancer, pharyngeal cancer, pheochromocytoma, pilocytic astrocytoma, pineal region tumor, pineoblastoma, pituitary gland cancer, primary central nervous system (CNS) lymphoma, prostate cancer, rectal cancer, renal cell carcinoma, renal pelvis cancer, rhabdomyosarcoma, salivary gland cancer, soft tissue sarcoma, bone sarcoma, sarcoma, sinus cancer, skin cancer, small cell lung cancer (SCLC), small intestine cancer, spinal cancer, spinal column cancer, spinal cord cancer, squamous cell carcinoma, stomach cancer, synovial sarcoma, T-cell lymphoma, testicular cancer, throat cancer, thymoma/thymic carcinoma, thyroid cancer, tongue cancer, tonsil cancer, transitional cell cancer, tubal cancer, tubular carcinoma, undiagnosed cancer, ureteral cancer, urethral cancer, uterine adenocarcinoma, uterine cancer, uterine sarcoma, vaginal cancer, vulvar cancer, T-cell lineage acute lymphoblastic leukemia (T-ALL), T-cell lineage lymphoblastic lymphoma (T-LL), peripheral . . . T-cell lymphoma, Adult T-cell leukemia, Pre-B ALL, Pre-B lymphomas, large B-cell lymphoma, Burkitts lymphoma, B-cell ALL, Philadelphia chromosome positive ALL, Philadelphia chromosome positive CML, juvenile myelomonocytic leukemia (JMML), acute promyelocytic leukemia (a subtype of AML), large granular lymphocytic leukemia, Adult T-cell chronic leukemia, diffuse large B cell lymphoma, follicular lymphoma; Mucosa-Associated Lymphatic Tissue lymphoma (MALT), small cell lymphocytic lymphoma, mediastinal large B cell lymphoma, nodal marginal zone B cell lymphoma (NMZL); splenic marginal zone lymphoma (SMZL); intravascular large B-cell lymphoma; primary effusion lymphoma; or lymphomatoid granulomatosis; B-cell prolymphocytic leukemia; splenic lymphoma/leukemia, unclassifiable, splenic diffuse red pulp small B-cell lymphoma; lymphoplasmacytic lymphoma; heavy chain diseases, for example, Alpha heavy chain disease, Gamma heavy chain disease, Mu heavy chain disease, plasma cell myeloma, solitary plasmacytoma of bone; extraosseous plasmacytoma; primary cutaneous follicle center lymphoma, T cell/histocyte rich large B-cell lymphoma, DLBCL associated with chronic inflammation; Epstein-Barr virus (EBV)+DLBCL of the elderly; primary mediastinal (thymic) large B-cell lymphoma, primary cutaneous DLBCL, leg type, ALK+ large B-cell lymphoma, plasmablastic lymphoma; large B-cell lymphoma arising in HHV8-associated multicentric, Castleman disease; B-cell lymphoma, unclassifiable, with features intermediate between diffuse large B-cell lymphoma, or B-cell lymphoma, unclassifiable, with features intermediate between diffuse large B-cell lymphoma and classical Hodgkin lymphoma.

In some embodiments, the cancer is a malignant, rhabdoid tumor, a CD8+ T-cell lymphoma, endometrial carcinoma, ovarian carcinoma, bladder cancer, stomach cancer, pancreatic cancer, esophageal cancer, prostate cancer, renal cell carcinoma, melanoma, colorectal cancer, a sarcoma (e.g., a soft tissue sarcoma, synovial sarcoma, Ewing's sarcoma, osteosarcoma, rhabdomyosarcoma, adult fibrosarcoma, alveolar soft-part sarcoma, angiosarcoma, clear cell sarcoma, desmoplastic small round cell tumor, epithelioid sarcoma, fibromyxoid sarcoma, gastrointestinal stromal tumor, Kaposi sarcoma, liposarcoma, leiomyosarcoma, malignant mesenchymoma malignant peripheral nerve sheath tumors, myxofibrosarcoma, low-grade rhabdomyosarcoma), non-small cell lung cancer (e.g., squamous or adenocarcinoma), stomach cancer, or breast cancer. In some embodiments, the cancer is a malignant, rhabdoid tumor, a CD8+ T-cell lymphoma, endometrial carcinoma, ovarian carcinoma, bladder cancer, stomach cancer, pancreatic cancer, esophageal cancer, prostate cancer, renal cell carcinoma, melanoma, or colorectal cancer. In some embodiments, the cancer is a sarcoma (e.g., synovial sarcoma or Ewing's sarcoma), non-small cell lung cancer (e.g., squamous or adenocarcinoma), stomach cancer, or breast cancer. In some embodiments, the cancer is sarcoma (e.g., synovial sarcoma or Ewing's sarcoma). In some embodiments, the sarcoma is synovial sarcoma.

In another aspect, the disclosure features a method for treating a viral infection in a subject in need thereof. This method includes administering to the subject an effective amount of any of the foregoing compounds, or pharmaceutically acceptable salts thereof, or any of the foregoing pharmaceutical compositions. In some embodiments, the viral infection is an infection with a virus of the. Retroviridae family such as the lentiviruses (e.g. Human immunodeficiency virus (HIV) and deltaretroviruses (e.g., human T cell leukemia virus I (HTLV-I), human T cell leukemia virus II (HTLV-II)); Hepadnaviridae family (e.g. hepatitis B virus (HBV)), Flaviviridae family (e.g. hepatitis C virus (HCV)), Adenoviridae family (e.g. Human Adenovirus), Herpesviridae family (e.g. Human cytomegalovirus (HCMV), Epstein-Barr virus, herpes simplex virus 1 (HSV-1), herpes simplex virus 2 (HSV-2), human herpesvirus 6 (HHV-6), Herpesvitus K*, CMV, varicella-zoster virus), Papillomaviridae family (e.g. Human Papillomavirus (HPV, HPV $E^1$)), Parvoviridae family (e.g. Parvovirus B19), Polyomaviridae family (e.g. JC virus and BK virus), Paramyxoviridae family (e.g. Measles virus), Togaviridae family (e.g. Rubella virus).

In another embodiment of any of the foregoing methods, the method further includes administering to the subject an additional anticancer therapy (e.g., chemotherapeutic or cytotoxic agent or radiotherapy).

In particular embodiments, the additional anticancer therapy is: a chemotherapeutic or cytotoxic agent (e.g., doxorubicin or ifosfamide), a differentiation-inducing agent (e.g., retinoic acid, vitamin D, cytokines), a hormonal agent, an immunological agent, or an anti-angiogenic agent. Chemotherapeutic and cytotoxic agents include, but are not limited to, alkylating agents, cytotoxic antibiotics, antimetabolites, *vinca* alkaloids, etoposides, and others (e.g., paclitaxel, taxol; docetaxel, taxotere, cis-platinum). A list of additional compounds having anticancer activity can be found in L. Brunton, B. Chabner and B. Knollman (eds). Goodman and Gilman's The Pharmacological Basis of Therapeutics, Twelfth Edition, 2011, McGraw Hill Companies, New York, NY.

In particular embodiments, the compound of the invention and the additional anticancer therapy and any of the foregoing compounds or pharmaceutical compositions are administered within 28 days of each other (e.g., within 21, 14, 10, 7, 5, 4, 3, 2, or 1 days) or within 24 hours (e.g., 12, 6, 3, 2, or 1 hours; or concomitantly) each in an amount that together are effective to treat the subject.

Chemical Terms

The terminology employed herein is for the purpose of describing particular embodiments and is not intended to be limiting.

For any of the following chemical definitions, a number following an atomic symbol indicates that total number of atoms of that element that are present in a particular chemical moiety. As will be understood, other atoms, such as hydrogen atoms, or substituent groups, as described herein, may be present, as necessary, to satisfy the valences of the atoms. For example, an unsubstituted $C_2$ alkyl group has the formula —$CH_2CH_3$. When used with the groups defined herein, a reference to the number of carbon atoms includes the divalent carbon in acetal and ketal groups but does not include the carbonyl carbon in acyl, ester, carbonate, or carbamate groups. A reference to the number of oxygen, nitrogen, or sulfur atoms in a heteroaryl group only includes those atoms that form a part of a heterocyclic ring.

Herein a phrase of the form "optionally substituted X" (e.g., optionally substituted alkyl) is intended to be equivalent to "X, wherein X is optionally substituted" (e.g., "alkyl, wherein said alkyl is optionally substituted"). It is not intended to mean that the feature "X" (e.g., alkyl) per se is optional. As described herein, certain compounds of interest may contain one or more "optionally substituted" moieties. In general, the term "substituted", whether preceded by the term "optionally" or not, means that one or more hydrogens of the designated moiety are replaced with a suitable substituent, e.g., any of the substituents or groups described herein. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by the present disclosure are preferably those that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

The term "aliphatic," as used herein, refers to a saturated or unsaturated, straight, branched, or cyclic hydrocarbon. "Aliphatic" is intended herein to include, but is not limited to, alkyl, alkenyl, alkynyl, cycloalkyl, cycloalkenyl, and cycloalkynyl moieties, and thus incorporates each of these definitions. In one embodiment, "aliphatic" is used to indicate those aliphatic groups having 1-20 carbon atoms. The aliphatic chain can be, for example, mono-unsaturated, di-unsaturated, tri-unsaturated, or polyunsaturated, or alkynyl. Unsaturated aliphatic groups can be in a cis or trans configuration. In one embodiment, the aliphatic group contains from 1 to about 12 carbon atoms, more generally from 1 to about 6 carbon atoms or from 1 to about 4 carbon atoms. In one embodiment, the aliphatic group contains from 1 to about 8 carbon atoms. In certain embodiments, the aliphatic group is $C_1$-$C_2$, $C_1$-$C_3$, $C_1$-$C_4$, $C_1$-$C_5$, or $C_1$-$C_6$. The specified ranges as used herein indicate an aliphatic group having each member of the range described as an independent species. For example, the term $C_1$-$C_6$ aliphatic as used herein indicates a straight or branched alkyl, alkenyl, or alkynyl group having from 1, 2, 3, 4, 5, or 6 carbon atoms and is intended to mean that each of these is described as an independent species. For example, the term $C_1$-$C_4$ aliphatic as used herein indicates a straight or branched alkyl, alkenyl, or alkynyl group having from 1, 2, 3, or 4 carbon atoms and is intended to mean that each of these is described as an independent species. In one embodiment, the aliphatic group is substituted with one or more functional groups that results in the formation of a stable moiety.

The term "heteroaliphatic," as used herein, refers to an aliphatic moiety that contains at least one heteroatom in the chain, for example, an amine, carbonyl, carboxy, oxo, thio, phosphate, phosphonate, nitrogen, phosphorus, silicon, or boron atoms in place of a carbon atom. In one embodiment, the only heteroatom is nitrogen. In one embodiment, the only heteroatom is oxygen. In one embodiment, the only heteroatom is sulfur. "Heteroaliphatic" is intended herein to include, but is not limited to, heteroalkyl, heteroalkenyl, heteroalkynyl, heterocycloalkyl, heterocycloalkenyl, and heterocycloalkynyl moieties. In one embodiment, "heteroaliphatic" is used to indicate a heteroaliphatic group (cyclic, acyclic, substituted, unsubstituted, branched or unbranched) having 1-20 carbon atoms. In one embodiment, the heteroaliphatic group is optionally substituted in a manner that results in the formation of a stable moiety. Nonlimiting examples of heteroaliphatic moieties are polyethylene glycol, polyalkylene glycol, amide, polyamide, polylactide, polyglycolide, thioether, ether, alkyl-heterocycle-alkyl, —O-alkyl-O-alkyl, and alkyl-O-haloalkyl.

The term "acyl," as used herein, represents a hydrogen or an alkyl group that is attached to a parent molecular group through a carbonyl group, as defined herein, and is exemplified by formyl (i.e., a carboxyaldehyde group), acetyl, trifluoroacetyl, propionyl, and butanoyl. Exemplary unsubstituted acyl groups include from 1 to 6, from 1 to 11, or from 1 to 21 carbons.

The term "alkyl," as used herein, refers to a branched or straight-chain monovalent saturated aliphatic hydrocarbon radical of 1 to 20 carbon atoms (e.g., 1 to 16 carbon atoms, 1 to 10 carbon atoms, 1 to 6 carbon atoms, or 1 to 3 carbon atoms). An "alkylene" is a divalent alkyl group.

The term "alkenyl," as used herein, alone or in combination with other groups, refers to a straight chain or branched hydrocarbon residue having a carbon-carbon double bond and having 2 to 20 carbon atoms (e.g., 2 to 16 carbon atoms, 2 to 10 carbon atoms, 2 to 6, or 2 carbon atoms). An "alkenylene" is a divalent alkenyl group.

The term "alkynyl," as used herein, alone or in combination with other groups, refers to a straight chain or branched hydrocarbon residue having a carbon-carbon triple bond and having 2 to 20 carbon atoms (e.g., 2 to 16 carbon atoms, 2 to 10 carbon atoms, 2 to 6, or 2 carbon atoms). An "alkynylene" is a divalent alkynyl group.

The term "amino," as used herein, represents -$N(R^N1)_2$, wherein each $R^N1$ is, independently, H, OH, $NO_2$, $N(R^N2)_2$, $SO_2OR^{N2}$, $SO_2R^{N2}$, $SOR^{N2}$, an N-protecting group, alkyl, alkoxy, aryl, arylalkyl, cycloalkyl, acyl (e.g., acetyl, trifluoroacetyl, or others described herein), wherein each of these recited $R^N1$ groups can be optionally substituted; or two $R^N1$ combine to form an alkylene or heteroalkylene, and wherein each $R^N2$ is, independently, H, alkyl, or aryl. The amino groups of the compounds described herein can be an unsubstituted amino (i.e., —$NH_2$) or a substituted amino (i.e., —$N(R^N1)_2$).

The term "aryl," as used herein, refers to an aromatic mono- or polycarbocyclic radical of, e.g., 6 to 12, carbon atoms having at least one aromatic ring. Examples of such groups include, but are not limited to, phenyl, naphthyl, 1,2,3,4-tetrahydronaphthyl, 1,2-dihydronaphthyl, indanyl, and 1H-indenyl.

The term "arylalkyl," as used herein, represents an alkyl group substituted with an aryl group. Exemplary unsubstituted arylalkyl groups are from 7 to 30 carbons (e.g., from 7 to 16 or from 7 to 20 carbons, such as $C_1$-$C_6$ alkyl $C_6$-$C_{10}$ aryl, $C_1$-$C_{10}$ alkyl $C_6$-$C_{10}$ aryl, or $C_1$-$C_{20}$ alkyl $C_6$-$C_{10}$ aryl), such as, benzyl and phenethyl. In some embodiments, the alkyl and the aryl each can be further substituted with 1, 2, 3, or 4 substituent groups as defined herein for the respective groups.

The term "azido," as used herein, represents a —$N_3$ group.

The term "bridged cyclyl," as used herein, refers to a bridged polycyclic group of 5 to 20 atoms, containing from 1 to 3 bridges. Bridged cyclyl includes bridged carbocyclyl (e.g., norbornyl) and bridged heterocyclyl (e.g., 1,4-diazabicyclo[2.2.2]octane).

The term "cyano," as used herein, represents a —CN group.

The term "carbocyclyl," as used herein, refers to a non-aromatic $C_3$-$C_{12}$, monocyclic or polycyclic (e.g., bicyclic or tricyclic) structure in which the rings are formed by carbon atoms. Carbocyclyl structures include cycloalkyl groups (e.g., cyclohexyl) and unsaturated carbocyclyl radicals (e.g., cyclohexenyl). Polycyclic carbocyclyl includes spirocyclic carbocyclyl, bridged carbocyclyl, and fused carbocyclyl. A "carbocyclylene" is a divalent carbocyclyl group.

The term "cycloalkyl," as used herein, refers to a saturated, non-aromatic, monovalent mono- or polycarbocyclic radical of 3 to 10, preferably 3 to 6 carbon atoms. This term is further exemplified by radicals such as cyclopropyl, cyclobutyl, cyclopentyl, cyclohexyl, cycloheptyl, norbornyl, and adamantyl.

The terms "halo" or "halogen," as used herein, mean a fluorine (fluoro), chlorine (chloro), bromine (bromo), or iodine (iodo) radical.

The term "heteroalkyl," as used herein, refers to an alkyl group, as defined herein, in which one or more of the constituent carbon atoms have been replaced by nitrogen, oxygen, or sulfur. In some embodiments, the heteroalkyl group can be further substituted with 1, 2, 3, or 4 substituent groups as described herein for alkyl groups. Examples of heteroalkyl groups are an "alkoxy" which, as used herein, refers to alkyl-O— (e.g., methoxy and ethoxy), and an "alkylamino" which, as used herein, refers to —N(alkyl)$R^{Na}$, where $R^{Na}$ is H or alkyl (e.g., methylamino). A "heteroalkylene" is a divalent heteroalkyl group.

The term "heteroalkenyl," as used herein, refers to an alkenyl group, as defined herein, in which one or more of the constituent carbon atoms have been replaced by nitrogen, oxygen, or sulfur. In some embodiments, the heteroalkenyl group can be further substituted with 1, 2, 3, or 4 substituent groups as described herein for alkenyl groups. Examples of heteroalkenyl groups are an "alkenoxy" which, as used herein, refers to alkenyl-O—. A "heteroalkenylene" is a divalent heteroalkenyl group.

The term "heteroalkynyl," as used herein, refers to an alkynyl group, as defined herein, in which one or more of the constituent carbon atoms have been replaced by nitrogen, oxygen, or sulfur. In some embodiments, the heteroalkynyl group can be further substituted with 1, 2, 3, or 4 substituent groups as described herein for alkynyl groups. Examples of heteroalkynyl groups are an "alkynoxy" which, as used herein, refers to alkynyl-O—. A "heteroalkynylene" is a divalent heteroalkynyl group.

The term "heteroaryl," as used herein, refers to an aromatic monocyclic or polycyclic structure of 5 to 12 atoms having at least one aromatic ring containing 1, 2, or 3 ring atoms selected from nitrogen, oxygen, and sulfur, with the remaining ring atoms being carbon. One or two ring carbon atoms of the heteroaryl group may be replaced with a carbonyl group. Examples of heteroaryl groups are pyridyl, pyrazoyl, benzooxazolyl, benzoimidazolyl, benzothiazolyl, imidazolyl, oxaxolyl, and thiazolyl. A "heteroarylene" is a divalent heteroaryl group.

The term "heteroarylalkyl," as used herein, represents an alkyl group substituted with a heteroaryl group. Exemplary unsubstituted heteroarylalkyl groups are from 7 to 30 carbons (e.g., from 7 to 16 or from 7 to 20 carbons, such as $C_1$-$C_6$ alkyl $C_2$-$C_9$ heteroaryl, $C_1$-$C_{10}$ alkyl $C_2$-$C_9$ heteroaryl, or $C_1$-$C_{20}$ alkyl $C_2$-$C_9$ heteroaryl). In some embodiments, the alkyl and the heteroaryl each can be further substituted with 1, 2, 3, or 4 substituent groups as defined herein for the respective groups.

The term "heterocyclyl," as used herein, refers a monocyclic or polycyclic radical (e.g., bicyclic or tricyclic) having 3 to 12 atoms having at least one non-aromatic ring containing 1, 2, 3, or 4 ring atoms selected from N, O, or S, and no aromatic ring containing any N, O, or S atoms. Polycyclic heterocyclyl includes spirocyclic heterocyclyl, bridged heterocyclyl, and fused heterocyclyl. Examples of heterocyclyl groups include, but are not limited to, morpholinyl, thiomorpholinyl, furyl, piperazinyl, piperidinyl, pyranyl, pyrrolidinyl, tetrahydropyranyl, tetrahydrofuranyl, and 1,3-dioxanyl. A "heterocyclylene" is a divalent heterocyclyl group.

The term "heterocyclylalkyl," as used herein, represents an alkyl group substituted with a heterocyclyl group. Exemplary unsubstituted heterocyclylalkyl groups are from 7 to 30 carbons (e.g., from 7 to 16 or from 7 to 20 carbons, such as $C_1$-$C_6$ alkyl $C_2$-$C_9$ heterocyclyl, $C_1$-$C_{10}$ alkyl $C_2$-$C_9$ heterocyclyl, or $C_1$-$C_{20}$ alkyl $C_2$-$C_9$ heterocyclyl). In some embodiments, the alkyl and the heterocyclyl each can be further substituted with 1, 2, 3, or 4 substituent groups as defined herein for the respective groups.

The term "hydroxyalkyl," as used herein, represents alkyl group substituted with an —OH group.

The term "hydroxyl," as used herein, represents an —OH group.

The term "imine," as used herein, represents =$NR^N$- group, where $R^N$ is, e.g., H or alkyl. The term "N-protecting group," as used herein, represents those groups intended to protect an amino group against undesirable reactions during synthetic procedures. Commonly used N-protecting groups are disclosed in Greene, "Protective Groups in Organic Synthesis," 3rd Edition (John Wiley & Sons, New York, 1999). N-protecting groups include, but are not limited to, acyl, aryloyl, or carbamyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, a-chlorobutyryl, benzoyl, 4-chlorobenzoyl, 4-bromobenzoyl, 4-nitrobenzoyl, and chiral auxiliaries such as protected or unprotected D, L, or D, L-amino acids such as alanine, leucine, and phenylalanine; sulfonyl-containing groups such as benzenesulfonyl, and p-toluenesulfonyl; carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-20 dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, a,a-dimethyl-3,5-dimethoxybenzyloxycarbonyl, benzhydryloxy carbonyl, t-butyloxycarbonyl, diisopropylmethoxycarbonyl, isopropyloxycarbonyl, ethoxycarbonyl, methoxycarbonyl, allyloxycarbonyl, 2,2,2,-trichloroethoxycarbonyl, phenoxycarbonyl, 4-nitrophenoxy carbonyl, fluorenyl-9-methoxycarbonyl, cyclopentyloxycarbonyl, adamantyloxycarbonyl, cyclohexyloxycarbonyl, and phenylthiocarbonyl, arylalkyl groups such as benzyl, triphenylmethyl, and benzyloxymethyl, and silyl groups, such as trimethylsilyl. Preferred N-protecting groups are alloc, formyl, acetyl, benzoyl, pivaloyl, t-butylacetyl, alanyl, phenylsulfonyl, benzyl, t-butyloxycarbonyl (Boc), and benzyloxycarbonyl (Cbz).

The term "nitro," as used herein, represents an —NO$_2$ group.

The term "oxo," as used herein, represents an =O group.

The term "thiol," as used herein, represents an —SH group.

The alkyl, alkenyl, alkynyl, heteroalkyl, heteroalkenyl, heteroalkynyl, carbocyclyl (e.g., cycloalkyl), aryl, heteroaryl, and heterocyclyl groups may be substituted or unsubstituted. When substituted, there will generally be 1 to 4 substituents present, unless otherwise specified. Substituents include, for example: alkyl (e.g., unsubstituted and substituted, where the substituents include any group described herein, e.g., aryl, halo, hydroxy), aryl (e.g., substituted and unsubstituted phenyl), carbocyclyl (e.g., substituted and unsubstituted cycloalkyl), halogen (e.g., fluoro), hydroxyl, heteroalkyl (e.g., substituted and unsubstituted methoxy, ethoxy, or thioalkoxy), heteroaryl, heterocyclyl, amino (e.g., NH$_2$ or mono- or dialkyl amino), azido, cyano, nitro, oxo, sulfonyl, or thiol. Aryl, carbocyclyl (e.g., cycloalkyl), heteroaryl, and heterocyclyl groups may also be substituted with alkyl(unsubstituted and substituted such as arylalkyl (e.g., substituted and unsubstituted benzyl)).

Compounds described herein (e.g., compounds of the invention) can have one or more asymmetric carbon atoms and can exist in the form of optically pure enantiomers, mixtures of enantiomers such as, for example, racemates, optically pure diastereoisomers, mixtures of diastereoisomers, diastereoisomeric racemates, or mixtures of diastereoisomeric racemates. The optically active forms can be obtained for example by resolution of the racemates, by asymmetric synthesis or asymmetric chromatography (chromatography with a chiral adsorbent or eluant). That is, certain of the disclosed compounds may exist in various stereoisomeric forms. Stereoisomers are compounds that differ only in their spatial arrangement. Enantiomers are pairs of stereoisomers whose mirror images are not superimposable, most commonly because they contain an asymmetrically substituted carbon atom that acts as a chiral center. "Enantiomer" means one of a pair of molecules that are mirror images of each other and are not superimposable. Diastereomers are stereoisomers that are not related as mirror images, most commonly because they contain two or more asymmetrically substituted carbon atoms and represent the configuration of substituents around one or more chiral carbon atoms. Enantiomers of a compound can be prepared, for example, by separating an enantiomer from a racemate using one or more well-known techniques and methods, such as, for example, chiral chromatography and separation methods based thereon. The appropriate technique and/or method for separating an enantiomer of a compound described herein from a racemic mixture can be readily determined by those of skill in the art. "Racemate" or "racemic mixture" means a compound containing two enantiomers, wherein such mixtures exhibit no optical activity; i.e., they do not rotate the plane of polarized light. "Geometric isomer" means isomers that differ in the orientation of substituent atoms in relationship to a carbon-carbon double bond, to a cycloalkyl ring, or to a bridged bicyclic system. Atoms (other than H) on each side of a carbon-carbon double bond may be in anE(substituents are on opposite sides of the carbon-carbon double bond) or Z (substituents are oriented on the same side) configuration. "R," "S," "S*," "R*," "E," "Z," "cis," and "trans," indicate configurations relative to the core molecule. Certain of the disclosed compounds may exist in atropisomeric forms. Atropisomers are stereoisomers resulting from hindered rotation about single bonds where the steric strain barrier to rotation is high enough to allow for the isolation of the conformers. The compounds described herein (e.g., the compounds of the invention) may be prepared as individual isomers by either isomer-specific synthesis or resolved from an isomeric mixture. Conventional resolution techniques include forming the salt of a free base of each isomer of an isomeric pair using an optically active acid (followed by fractional crystallization and regeneration of the free base), forming the salt of the acid form of each isomer of an isomeric pair using an optically active amine (followed by fractional crystallization and regeneration of the free acid), forming an ester or amide of each of the isomers of an isomeric pair using an optically pure acid, amine or alcohol (followed by chromatographic separation and removal of the chiral auxiliary), or resolving an isomeric mixture of either a starting material or a final product using various well known chromatographic methods. When the stereochemistry of a disclosed compound is named or depicted by structure, the named or depicted stereoisomer is at least 60%, 70%, 80%, 90%, 99%, or 99.9% by weight relative to the other stereoisomers. When a single enantiomer is named or depicted by structure, the depicted or named enantiomer is at least 60%, 70%, 80%, 90%, 99%, or 99.9% by weight optically pure. When a single diastereomer is named or depicted by structure, the depicted or named diastereomer is at least 60%, 70%, 80%, 90%, 99%, or 99.9% by weight pure. Percent optical purity is the ratio of the weight of the enantiomer or over the weight of the enantiomer plus the weight of its optical isomer. Diastereomeric purity by weight is the ratio of the weight of one diastereomer or over the weight of all the diastereomers. When the stereochemistry of a disclosed compound is named or depicted by structure, the named or depicted stereoisomer is at least 60%, 70%, 80%, 90%, 99%, or 99.9% by mole fraction pure relative to the other stereoisomers. When a single enantiomer is named or depicted by structure, the depicted or named enantiomer is at least 60%, 70%, 80%, 90%, 99%, or 99.9% by mole fraction pure. When a single diastereomer is named or depicted by structure, the depicted or named diastereomer is at least 60%, 70%, 80%, 90%, 99%, or 99.9% by mole fraction pure. Percent purity by mole fraction is the ratio of the moles of the enantiomer or over the moles of the enantiomer plus the moles of its optical isomer. Similarly, percent purity by moles fraction is the ratio of the moles of the diastereomer or over the moles of the diastereomer plus the moles of its isomer. When a disclosed compound is named or depicted by structure without indicating the stereochemistry, and the compound has at least one chiral center, it is to be understood that the name or structure encompasses either enantiomer of the compound free from the corresponding optical isomer, a racemic mixture of the compound, or mixtures enriched in one enantiomer relative to its corresponding optical isomer. When a disclosed compound is named or depicted by structure without indicating the stereochemistry and has two or more chiral centers, it is to be understood that the name or structure encompasses a diastereomer free of other diastereomers, a number of diastereomers free from other diastereomeric pairs, mixtures of diastereomers, mixtures of diastereomeric pairs, mixtures of diastereomers in which one diastereomer is enriched relative to the other diastereomer(s), or mixtures of diastereomers in which one or more diastereomer is enriched relative to the other diastereomers. The invention embraces all of these forms.

Compounds of the present disclosure also include all of the isotopes of the atoms occurring in the intermediate or final compounds. "Isotopes" refers to atoms having the same atomic number but different mass numbers resulting from a different number of neutrons in the nuclei. For example, isotopes of hydrogen include tritium and deuterium.

Unless otherwise stated, structures depicted herein are also meant to include compounds that differ only in the presence of one or more isotopically enriched atoms. Exemplary isotopes that can be incorporated into compounds of the present invention include isotopes of hydrogen, carbon, nitrogen, oxygen, phosphorus, sulfur, fluorine, chlorine, and iodine, such as $^2$H, $^3$H, $^{11}$C, $^{13}$C, $^{14}$C, $^{13}$N, $^{15}$N, $^{15}$O, $^{17}$O, $^{18}$O, $^{32}$P, $^{33}$P, $^{35}$S, $^{18}$F, $^{36}$Cl, $^{123}$I and $^{125}$I. Isotopically-labeled compounds (e.g., those labeled with 3H and $^{14}$C) can be useful in compound or substrate tissue distribution assays. Tritiated (i.e., $^3$H) and carbon-14 (i.e., $^{14}$C) isotopes can be useful for their ease of preparation and detectability. Further, substitution with heavier isotopes such as deuterium (i.e., $^2$H) may afford certain therapeutic advantages resulting from greater metabolic stability (e.g., increased in vivo half-life or reduced dosage requirements). In some embodiments, one or more hydrogen atoms are replaced by $^2$H or $^3$H, or one or more carbon atoms are replaced by $^{13}$C- or $^{14}$C-enriched carbon. Positron emitting isotopes such as $^{15}$O, $^{13}$N, $^{11}$C, and $^{18}$F are useful for positron emission tomography (PET) studies to examine substrate receptor occupancy. Preparations of isotopically labelled compounds are known to those of skill in the art. For example, isotopically labeled compounds can generally be prepared by following procedures analogous to those disclosed for compounds of the present invention described herein, by substituting an isotopically labeled reagent for a non-isotopically labeled reagent.

As is known in the art, many chemical entities can adopt a variety of different solid forms such as, for example, amorphous forms or crystalline forms (e.g., polymorphs, hydrates, solvate). In some embodiments, compounds of the present invention may be utilized in any such form, including in any solid form. In some embodiments, compounds described or depicted herein may be provided or utilized in hydrate or solvate form.

Unless otherwise defined, all technical and scientific terms used herein have the same meaning as commonly understood by one of ordinary skill in the art to which this invention belongs. Methods and materials are described herein for use in the present disclosure; other, suitable methods and materials. known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Definitions

In this application, unless otherwise clear from context, (i) the term "a" may be understood to mean "at least one"; (ii) the term "or" may be understood to mean "and/or"; and (iii) the terms "including" and "including" may be understood to encompass itemized components or steps whether presented by themselves or together with one or more additional components or steps.

As used herein, the terms "about" and "approximately" refer to a value that is within 10% above or below the value being described. For example, the term "about 5 nM" indicates a range of from 4.5 to 5.5 nM.

As used herein, the term "administration" refers to the administration of a composition (e.g., a compound or a preparation that includes a compound as described herein) to a subject or system. Administration to an animal subject (e.g., to a human) may be by any appropriate route. For example, in some embodiments, administration may be bronchial (including by bronchial instillation), buccal, enteral, interdermal, intra-arterial, intradermal, intragastric, intramedullary, intramuscular, intranasal, intraperitoneal, intrathecal, intratumoral, intravenous, intraventricular, mucosal, nasal, oral, rectal, subcutaneous, sublingual, topical, tracheal (including by intratracheal instillation), transdermal, vaginal, and vitreal.

As used herein, the term "adult soft tissue sarcoma" refers to a sarcoma that develops in the soft tissues of the body, typically in adolescent and adult subjects (e.g., subjects who are at least 10 years old, 11 years old, 12 years old, 13 years old, 14 years old, 15 years old, 16 years old, 17 years old, 18 years old, or 19 years old). Non-limiting examples of adult soft tissue sarcoma include, but are not limited to, synovial sarcoma, fibrosarcoma, malignant fibrous histiocytoma, dermatofibrosarcoma, liposarcoma, leiomyosarcoma, hemangiosarcoma, Kaposi's sarcoma, lymphangiosarcoma, malignant peripheral nerve sheath tumor/neurofibrosarcoma, extraskeletal chondrosarcoma, extraskeletal osteosarcoma, extraskeletal myxoid chondrosarcoma, and extraskeletal mesenchymal.

The term "antisense," as used herein, refers to a nucleic acid comprising a polynucleotide that is sufficiently complementary to all or a portion of a gene, primary transcript, or processed mRNA, so as to interfere with expression of the endogenous gene (e.g., BRD9). "Complementary" polynucleotides are those that are capable of base pairing according to the standard Watson-Crick complementarity rules. Specifically, purines will base pair with pyrimidines to form a combination of guanine paired with cytosine (G: C) and adenine paired with either thymine (A: T) in the case of DNA, or adenine paired with uracil (A: U) in the case of RNA. It is understood that two polynucleotides may hybridize to each other even if they are not completely complementary to each other, provided that each has at least one region that is substantially complementary to the other.

The term "antisense nucleic acid" includes single-stranded RNA as well as double-stranded DNA expression cassettes that can be transcribed to produce an antisense RNA. "Active" antisense nucleic acids are antisense RNA molecules that are capable of selectively hybridizing with a primary transcript or mRNA encoding a polypeptide having at least 80% sequence identity (e.g., 80%, 85%, 86%, 87%, 88%, 89%, 90%, 91%, 92%, 93%, 94%, 95%, 96%, 97%, 98%, 99%, 99.9% identity, or more) with the targeted polypeptide sequence (e.g., a BRD9 polypeptide sequence). The antisense nucleic acid can be complementary to an entire coding strand, or to only a portion thereof. In some embodiments, an antisense nucleic acid molecule is antisense to a "coding region" of the coding strand of a nucleotide sequence. The term "coding region" refers to the region of the nucleotide sequence comprising codons that are translated into amino acid residues. In some embodiments, the antisense nucleic acid molecule is antisense to a "noncoding region" of the coding strand of a nucleotide sequence. The term "noncoding region" refers to 5' and 3' sequences that flank the coding region that are not translated into amino acids (i.e., also referred to as 5' and 3' untranslated regions). The antisense nucleic acid molecule can be complementary to the entire coding region of mRNA, or can be antisense to only a portion of the coding or noncoding region of an mRNA. For example, the antisense oligonucleotide can be complementary to the region surrounding the translation start site. An antisense oligonucleotide can be, for example, about 5, 10, 15, 20, 25, 30, 35, 40, 45, or 50 nucleotides in length.

As used herein, the term "BAF complex" refers to the BRG1- or HRBM-associated factors complex in a human cell.

As used herein, the term "BAF complex-related disorder" refers to a disorder that is caused or affected by the level and/or activity of a BAF complex.

As used herein, the terms "GBAF complex" and "GBAF" refer to a SWI/SNF ATPase chromatin remodeling complex in a human cell. GBAF complex subunits may include, but are not limited to, ACTB, ACTL6A, ACTL6B, BICRA, BICRAL, BRD9, SMARCA2, SMARCA4, SMARCC1, SMARCD1, SMARCD2, SMARCD3, and SS18. The term "cancer" refers to a condition caused by the proliferation of malignant neoplastic cells, such as tumors, neoplasms, carcinomas, sarcomas, leukemias, and lymphomas.

As used herein, the term "BRD9" refers to bromodomain-containing protein 9, a component of the BAF (BRG1- or BRM-associated factors) complex, a SWI/SNF ATPase chromatin remodeling complex, and belongs to family IV of the bromodomain-containing proteins. BRD9 is encoded by the BRD9 gene, the nucleic acid sequence of which is set forth in SEQ ID NO: 1. The term "BRD9" also refers to natural variants of the wild-type BRD9 protein, such as proteins having at least 85% identity (e.g., 85%, 86%, 87%, 88%, 89%, 90%, 91%, 92%, 93%, 94%, 95%, 96%, 97%, 98%, 99%, 99.9% identity, or more) to the amino acid sequence of wild-type BRD9.

As used herein, the term "BRD9-related disorder" refers to a disorder that is caused or affected by the level and/or activity of BRD9. The term "cancer" refers to a condition caused by the proliferation of malignant neoplastic cells, such as tumors, neoplasms, carcinomas, sarcomas, leukemias, and lymphomas.

As used herein, a "combination therapy" or "administered in combination" means that two (or more) different agents or treatments are administered to a subject as part of a defined treatment regimen for a particular disease or condition. The treatment regimen defines the doses and periodicity of administration of each agent such that the effects of the separate agents on the subject overlap. In some embodiments, the delivery of the two or more agents is simultaneous or concurrent and the agents may be co-formulated. In some embodiments, the two or more agents are not co-formulated and are administered in a sequential manner as part of a prescribed regimen. In some embodiments, administration of two or more agents or treatments in combination is such that the reduction in a symptom, or other parameter related to the disorder is greater than what would be observed with one agent or treatment delivered alone or in the absence of the other. The effect of the two treatments can be partially additive, wholly additive, or greater than additive (e.g., synergistic). Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination may be administered by intravenous injection while a second therapeutic agent of the combination may be administered orally.

A "compound of the present invention" and similar terms as used herein, whether explicitly noted or not, refers to compounds useful for treating BAF-related disorders (e.g., cancer or infection) described herein, including, e.g., compounds of Formula I (e.g., compounds of Table 1A, Table 1B, and Table 1D) and compounds of Table 1C and 1E, as well as salts (e.g., pharmaceutically acceptable salts), solvates, hydrates, stereoisomers (including atropisomers), and tautomers thereof. Those skilled in the art will appreciate that certain compounds described herein can exist in one or more different isomeric (e.g., stereoisomers, geometric isomers, atropisomers, and tautomers) or isotopic (e.g., in which one or more atoms has been substituted with a different isotope of the atom, such as hydrogen substituted for deuterium) forms. Unless otherwise indicated or clear from context, a depicted structure can be understood to represent any such isomeric or isotopic form, individually or in combination. Compounds described herein can be asymmetric (e.g., having one or more stereocenters). All stereoisomers, such as enantiomers and diastereomers, are intended unless otherwise indicated. Compounds of the present disclosure that contain asymmetrically substituted carbon atoms can be isolated in optically active or racemic forms. Methods on how to prepare optically active forms from optically active starting materials are known in the art, such as by resolution of racemic mixtures or by stereoselective synthesis. Many geometric isomers of olefins, C=N double bonds, and the like can also be present in the compounds described herein, and all such stable isomers are contemplated in the present disclosure. Cis and trans geometric isomers of the compounds of the present disclosure are described and may be isolated as a mixture of isomers or as separated isomeric forms. In some embodiments, one or more compounds depicted herein may exist in different tautomeric forms. As will be clear from context, unless explicitly excluded, references to such compounds encompass all such tautomeric forms. In some embodiments, tautomeric forms result from the swapping of a single bond with an adjacent double bond and the concomitant migration of a proton. In certain embodiments, a tautomeric form may be a prototropic tautomer, which is an isomeric protonation states having the same empirical formula and total charge as a reference form. Examples of moieties with prototropic tautomeric forms are ketone-enol pairs, amide-imidic acid pairs, lactam-lactim pairs, amide-imidic acid pairs, enamine-imine pairs, and annular forms where a proton can occupy two or more positions of a heterocyclic system, such as, 1H- and 3H-imidazole, 1H-, 2H- and 4H-1,2,4-triazole, 1H- and 2H-isoindole, and 1H- and 2H-pyrazole. In some embodiments, tautomeric forms can be in equilibrium or sterically locked into one form by appropriate substitution. In certain embodiments, tautomeric forms result from acetal interconversion. As used herein, the term "degrader" refers to a small molecule compound including a degradation moiety, wherein the compound interacts with a protein (e.g., BRD9) in a way which results in degradation of the protein, e.g., binding of the compound results in at least 5% reduction of the level of the protein, e.g., in a cell or subject.

As used herein, the term "degradation moiety" refers to a moiety whose binding results in degradation of a protein, e.g., BRD9. In one example, the moiety binds to a protease or a ubiquitin ligase that metabolizes the protein, e.g., BRD9.

By "determining the level of a protein" is meant the detection of a protein, or an mRNA encoding the protein, by methods known in the art either directly or indirectly. "Directly determining" means performing a process (e.g., performing an assay or test on a sample or "analyzing a sample" as that term is defined herein) to obtain the physical entity or value. "Indirectly determining" refers to receiving the physical entity or value from another party or source (e.g., a third-party laboratory that directly acquired the physical entity or value). Methods to measure protein level generally include, but are not limited to, western blotting, immunoblotting, enzyme-linked immunosorbent assay (ELISA), radioimmunoassay (RIA), immunoprecipitation, immunofluorescence, surface plasmon resonance, chemiluminescence, fluorescent polarization, phosphorescence, immunohistochemical analysis, matrix-assisted laser desorption/ionization time-of-flight (MALDI-TOF) mass spectrometry, liquid chromatography (LC)-mass spectrometry, microcytometry, microscopy, fluorescence activated cell sorting (FACS), and flow cytometry, as well as assays based on a property of a protein including, but not limited to, enzymatic activity or interaction with other protein partners. Methods to measure mRNA levels are known in the art.

As used herein, the terms "effective amount," "therapeutically effective amount," and "a "sufficient amount" of an agent that reduces the level and/or activity of BRD9 (e.g., in a cell or a subject) described herein refer to a quantity sufficient to, when administered to the subject, including a human, effect beneficial or desired results, including clinical results, and, as such, an "effective amount" or synonym thereto depends on the context in which it is being applied. For example, in the context of treating cancer, it is an amount of the agent that reduces the level and/or activity of BRD9 sufficient to achieve a treatment response as compared to the response obtained without administration of the agent that reduces the level and/or activity of BRD9. The amount of a given agent that reduces the level and/or activity of BRD9 described herein that will correspond to such an amount will vary depending upon various factors, such as the given agent, the pharmaceutical formulation, the route of administration, the type of disease or disorder, the identity of the subject (e.g., age, sex, and/or weight) or host being treated, and the like, but can nevertheless be routinely determined by one of skill in the art. Also, as used herein, a "therapeutically effective amount" of an agent that reduces the level and/or activity of BRD9 of the present disclosure is an amount which results in a beneficial or desired result in a subject as compared to a control. As defined herein, a therapeutically effective amount of an agent that reduces the level and/or activity of BRD9 of the present disclosure may be readily determined by one of ordinary skill by routine methods known in the art. Dosage regimen may be adjusted to provide the optimum therapeutic response.

As used herein, the term "inhibitor" refers to any agent which reduces the level and/or activity of a protein (e.g., BRD9). Non-limiting examples of inhibitors include small molecule inhibitors, degraders, antibodies, enzymes, or polynucleotides (e.g., siRNA).

The term "inhibitory RNA agent" refers to an RNA, or analog thereof, having sufficient sequence complementarity to a target RNA to direct RNA interference. Examples also include a DNA that can be used to make the RNA. RNA interference (RNAi) refers to a sequence-specific or selective process by which a target molecule (e.g., a target gene, protein, or RNA) is down-regulated. Generally, an interfering RNA ("iRNA") is a double-stranded short-interfering RNA (siRNA), short hairpin RNA (shRNA), or single-stranded micro-RNA (miRNA) that results in catalytic degradation of specific mRNAs, and also can be used to lower or inhibit gene expression.

By "level" is meant a level of a protein, or mRNA encoding the protein, as compared to a reference. The reference can be any useful reference, as defined herein. By a "decreased level" or an "increased level" of a protein is meant a decrease or increase in protein level, as compared to a reference (e.g., a decrease or an increase by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 150%, about 200%, about 300%, about 400%, about 500%, or more; a decrease or an increase of more than about 10%, about 15%, about 20%, about 50%, about 75%, about 100%, or about 200%, as compared to a reference; a decrease or an increase by less than about 0.01-fold, about 0.02-fold, about 0.1-fold, about 0.3-fold, about 0.5-fold, about 0.8-fold, or less; or an increase by more than about 1.2-fold, about 1.4-fold, about 1.5-fold, about 1.8-fold, about 2.0-fold, about 3.0-fold, about 3.5-fold, about 4.5-fold, about 5.0-fold, about 10-fold, about 15-fold, about 20-fold, about 30-fold, about 40-fold, about 50-fold, about 100-fold, about 1000-fold, or more). A level of a protein may be expressed in mass/vol (e.g., g/dL, mg/ml, µg/mL, ng/ml) or percentage relative to total protein or mRNA in a sample.

The terms "miRNA" and "microRNA" refer to an RNA agent, preferably a single-stranded agent, of about 10-50 nucleotides in length, preferably between about 15-25 nucleotides in length, which is capable of directing or mediating RNA interference. Naturally-occurring miRNAs are generated from stem-loop precursor RNAs (i.e., pre-miRNAs) by Dicer. The term "Dicer" as used herein, includes Dicer as well as any Dicer ortholog or homolog capable of processing dsRNA structures into siRNAs, miRNAs, siRNA-like or miRNA-like molecules. The term microRNA ("miRNA") is used interchangeably with the term "small temporal RNA" ("stRNA") based on the fact that naturally-occurring miRNAs have been found to be expressed in a temporal fashion (e.g., during development).

By "modulating the activity of a BAF complex," is meant altering the level of an activity related to a BAF complex (e.g., GBAF), or a related downstream effect. The activity level of a BAF complex may be measured using any method known in the art, e.g., the methods described in Kadoch et al, Cell 153:71-85 (2013), the methods of which are herein incorporated by reference.

"Percent (%) sequence identity" with respect to a reference polynucleotide or polypeptide sequence is defined as the percentage of nucleic acids or amino acids in a candidate sequence that are identical to the nucleic acids or amino acids in the reference polynucleotide or polypeptide sequence, after aligning the sequences and introducing gaps, if necessary, to achieve the maximum percent sequence identity. Alignment for purposes of determining percent nucleic acid or amino acid sequence identity can be achieved in various ways that are within the capabilities of one of skill in the art, for example, using publicly available computer software such as BLAST, BLAST-2, or Megalign software. Those skilled in the art can determine appropriate parameters for aligning sequences, including any algorithms needed to achieve maximal alignment over the full length of the sequences being compared. For example, percent sequence identity values may be generated using the sequence comparison computer program BLAST. As an illustration, the percent sequence identity of a given nucleic acid or amino acid sequence, A, to, with, or against a given nucleic acid or amino acid sequence, B, (which can alternatively be phrased as a given nucleic acid or amino acid sequence, A that has a certain percent sequence identity to, with, or against a given nucleic acid or amino acid sequence, B) is calculated as follows:

100 multiplied by (the fraction X/Y)

where X is the number of nucleotides or amino acids scored as identical matches by a sequence alignment program (e.g., BLAST) in that program's alignment of A and B, and where Y is the total number of nucleic acids in B. It will be appreciated that where the length of nucleic acid or amino acid sequence A is not equal to the length of nucleic acid or amino acid sequence B, the percent sequence identity of A to B will not equal the percent sequence identity of B to A.

A "pharmaceutically acceptable excipient," as used herein, refers any ingredient other than the compounds described herein (for example, a vehicle capable of suspending or dissolving the active compound) and having the properties of being substantially nontoxic and non-inflammatory in a patient. Excipients may include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspending or dispersing agents, sweeteners, and waters of hydration. Exemplary excipients include, but are not limited to: butylated hydroxytoluene (BHT), calcium carbonate, calcium phosphate (dibasic), calcium stearate, croscarmellose, crosslinked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, sucrose, talc, titanium dioxide, vitamin A, vitamin E, vitamin C, and xylitol.

As used herein, the term "pharmaceutically acceptable salt" means any pharmaceutically acceptable salt of the compound of any of the compounds described herein. For example, pharmaceutically acceptable salts of any of the compounds described herein include those that are within the scope of sound medical judgment, suitable for use in contact with the tissues of humans and animals without undue toxicity, irritation, allergic response and are commensurate with a reasonable benefit/risk ratio. Pharmaceutically acceptable salts are well known in the art. For example, pharmaceutically acceptable salts are described in: Berge et al., J. Pharmaceutical Sciences 66:1-19, 1977 and in Pharmaceutical Salts: Properties, Selection, and Use, (Eds. P. H. Stahl and C. G. Wermuth), Wiley-VCH, 2008. The salts can be prepared in situ during the final isolation and purification of the compounds described herein or separately by reacting a free base group with a suitable organic acid.

The compounds described herein may have ionizable groups so as to be capable of preparation as pharmaceutically acceptable salts. These salts may be acid addition salts involving inorganic or organic acids or the salts may, in the case of acidic forms of the compounds described herein, be prepared from inorganic or organic bases. Frequently, the compounds are prepared or used as pharmaceutically acceptable salts prepared as addition products of pharmaceutically acceptable acids or bases. Suitable pharmaceutically acceptable acids and bases and methods for preparation of the appropriate salts are well-known in the art. Salts may be prepared from pharmaceutically acceptable non-toxic acids and bases including inorganic and organic acids and bases. Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, and valerate salts. Representative alkali or alkaline earth metal salts include sodium, lithium, potassium, calcium, and magnesium, as well as nontoxic ammonium, quaternary ammonium, and amine cations, including, but not limited to ammonium, tetramethylammonium, tetraethylammonium, methylamine, dimethylamine, trimethylamine, triethylamine, and ethylamine.

The term "pharmaceutical composition," as used herein, represents a composition containing a compound described herein formulated with a pharmaceutically acceptable excipient, and manufactured or sold with the approval of a governmental regulatory agency as part of a therapeutic regimen for the treatment of disease in a mammal. Pharmaceutical compositions can be formulated, for example, for oral administration in unit dosage form (e.g., a tablet, capsule, caplet, gelcap, or syrup); for topical administration (e.g., as a cream, gel, lotion, or ointment); for intravenous administration (e.g., as a sterile solution free of particulate emboli and in a solvent system suitable for intravenous use); or in any other pharmaceutically acceptable formulation.

By "reducing the activity of BRD9," is meant decreasing the level of an activity related to an BRD9, or a related downstream effect. A non-limiting example of inhibition of an activity of BRD9 is decreasing the level of a BAF complex (e.g., GBAF) in a cell. The activity level of BRD9 may be measured using any method known in the art. In some embodiments, an agent which reduces the activity of BRD9 is a small molecule BRD9 inhibitor. In some embodiments, an agent which reduces the activity of BRD9 is a small molecule BRD9 degrader.

By "reducing the level of BRD9," is meant decreasing the level of BRD9 in a cell or subject. The level of BRD9 may be measured using any method known in the art.

By a "reference" is meant any useful reference used to compare protein or mRNA levels. The reference can be any sample, standard, standard curve, or level that is used for comparison purposes. The reference can be a normal reference sample or a reference standard or level. A "reference sample" can be, for example, a control, e.g., a predetermined negative control value such as a "normal control" or a prior sample taken from the same subject; a sample from a normal healthy subject, such as a normal cell or normal tissue; a sample (e.g., a cell or tissue) from a subject not having a disease; a sample from a subject that is diagnosed with a disease, but not yet treated with a compound described herein; a sample from a subject that has been treated by a compound described herein; or a sample of a purified protein (e.g., any described herein) at a known normal concentration. By "reference standard or level" is meant a value or number derived from a reference sample. A "normal control value" is a predetermined value indicative of non-disease state, e.g., a value expected in a healthy control subject. Typically, a normal control value is expressed as a range ("between X and Y"), a high threshold ("no higher than X"), or a low threshold ("no lower than X"). A subject having a measured value within the normal control value for a particular biomarker is typically referred to as "within normal limits" for that biomarker. A normal reference standard or level can be a value or number derived from a normal subject not having a disease or disorder (e.g., cancer); a subject that has been treated with a compound described herein. In preferred embodiments, the reference sample, standard, or level is matched to the sample subject sample by at least one of the following criteria: age, weight, sex, disease stage, and overall health. A standard curve of levels of a purified protein, e.g., any described herein, within the normal reference range can also be used as a reference.

The terms "short interfering RNA" and "siRNA" (also known as "small interfering RNAs") refer to an RNA agent, preferably a double-stranded agent, of about 10-50 nucleotides in length, the strands optionally having overhanging ends comprising, for example 1, 2 or 3 overhanging nucleotides (or nucleotide analogs), which is capable of directing or mediating RNA interference. Naturally-occurring siRNAs are generated from longer dsRNA molecules (e.g., >25 nucleotides in length) by a cell's RNAi machinery (e.g., Dicer or a homolog thereof).

The term "shRNA", as used herein, refers to an RNA agent having a stem-loop structure, comprising a first and second region of complementary sequence, the degree of complementarity and orientation of the regions being sufficient such that base pairing occurs between the regions, the first and second regions being joined by a loop region, the loop resulting from a lack of base pairing between nucleotides (or nucleotide analogs) within the loop region.

As used herein, the term "subject" refers to any organism to which a composition in accordance with the invention may be administered, e.g., for experimental, diagnostic, prophylactic, and/or therapeutic purposes. Typical subjects include any animal (e.g., mammals such as mice, rats, rabbits, non-human primates, and humans). A subject may seek or be in need of treatment, require treatment, be receiving treatment, be receiving treatment in the future, or be a human or animal who is under care by a trained professional for a particular disease or condition.

As used herein, the term "SS18-SSX fusion protein-related disorder" refers to a disorder that is caused or affected by the level and/or activity of SS18-SSX fusion protein.

As used herein, the terms "treat," "treated," or "treating" mean both therapeutic treatment and prophylactic or preventative measures wherein the object is to prevent or slow down (lessen) an undesired physiological condition, disorder, or disease, or obtain beneficial or desired clinical results. Beneficial or desired clinical results include, but are not limited to, alleviation of symptoms; diminishment of the extent of a condition, disorder, or disease; stabilized (i.e., not worsening) state of condition, disorder, or disease; delay in onset or slowing of condition, disorder, or disease progression; amelioration of the condition, disorder, or disease state or remission (whether partial or total), whether detectable or undetectable; an amelioration of at least one measurable physical parameter, not necessarily discernible by the patient; or enhancement or improvement of condition, disorder, or disease. Treatment includes eliciting a clinically significant response without excessive levels of side effects. Treatment also includes prolonging survival as compared to expected survival if not receiving treatment.

As used herein, the terms "variant" and "derivative" are used interchangeably and refer to naturally-occurring, synthetic, and semi-synthetic analogues of a compound, peptide, protein, or other substance described herein. A variant or derivative of a compound, peptide, protein, or other substance described herein may retain or improve upon the biological activity of the original material.

The details of one or more embodiments of the invention are set forth in the description below. Other features, objects, and advantages of the invention will be apparent from the description and from the claims.

DETAILED DESCRIPTION

Figure 1:
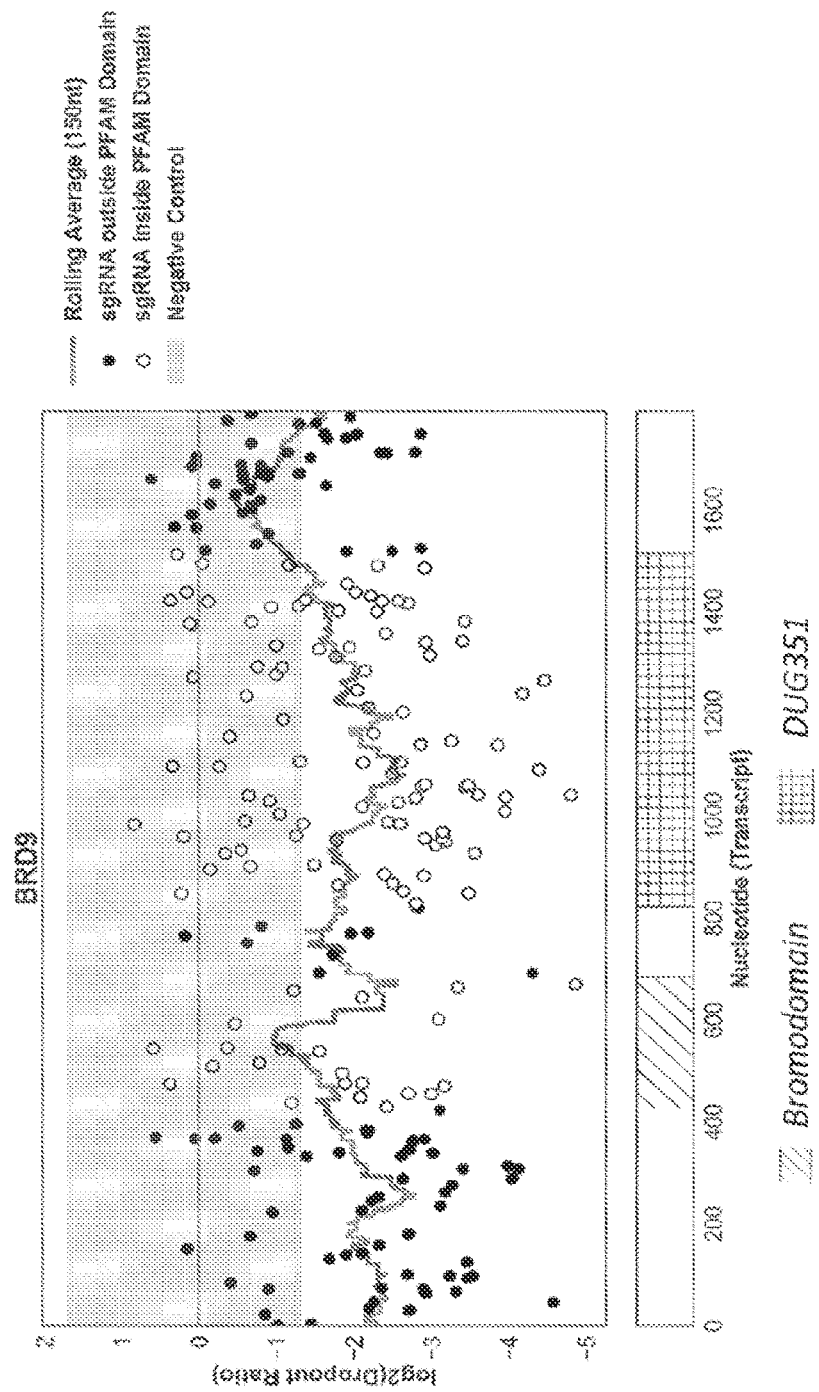
FIG. 1 is a series of graphs illustrating the effect of specific guide RNA (sgRNA) targeting of the BRD9 BAF complex subunit on synovial sarcoma cell growth. The Y-axis indicated the dropout ratio. The X-axis indicates the nucleotide position of the BRD9 gene. The grey box indicates the range of the negative control sgRNAs in the screen. The SYO1 cell line carries SS18-SSX2 fusion protein. The breakpoint joining the N-terminal region of SS18 to the C-terminal region of SSX2 are indicated by the black lines in their respective panel. The linear protein sequence is show with BRD9 PFAM domains annotated from the PFAM database.

The present disclosure features compositions and methods useful for the treatment of BAF-related disorders (e.g., cancer and infection). The disclosure further features compositions and methods useful for inhibition of the level and/or activity of BRD9, e.g., for the treatment of disorders such as cancer (e.g., sarcoma) and infection (e.g., viral infection), e.g., in a subject in need thereof.

Compounds Compounds described herein reduce the level of an activity related to BRD9, or a related downstream effect, or reduce the level of BRD9 in a cell or subject. Exemplary compounds described herein have the structure according to Formula I.

Formula I is

A-L-B

Formula I,
where
A is a BRD9 binding moiety;
B is a degradation moiety; and
L has the structure of Formula II:

$A^1\text{-}(E^1)\text{-}(F^1)\text{-}(C^3)_m\text{-}(E^3)_n\text{-}(F^2)_{o1}\text{-}(F^3)_{o2}\text{-}(E^2)_p\text{-}A^2$, Formula II wherein
$A^1$ is a bond between the linker and A;
$A^2$ is a bond between B and the linker;
each of m, n, o1, o2, and p is, independently, 0 or 1;
each of $E^1$ and $E^2$ is, independently, O, S, $NR^N$, optionally substituted $C_{1-10}$ alkyl, optionally substituted $C_{2-10}$ alkenyl, optionally substituted $C_{2-10}$ alkynyl, optionally substituted $C_2$-$C_{10}$ polyethylene glycol, or optionally substituted $C_{1-10}$ heteroalkyl;
$E^3$ is O, S, or $NR^N$;
each $R^N$ is, independently, H, optionally substituted $C_{1-4}$ alkyl, optionally substituted $C_{2-4}$ alkenyl, optionally substituted $C_{2-4}$ alkynyl, optionally substituted $C_{2-6}$ heterocyclyl, optionally substituted $C_{6-12}$ aryl, or optionally substituted $C_{1-7}$ heteroalkyl;
$C_3$ is carbonyl, thiocarbonyl, sulphonyl, or phosphoryl; and
each of $F^1$, $F^2$, and $F^3$ is, independently, optionally substituted $C_3$-$C_{10}$ carbocyclyl, optionally substituted $C_2$-$C_9$ heterocyclyl, optionally substituted $C_6$-$C_{10}$ aryl, or optionally substituted $C_2$-$C_9$ heteroaryl, or a pharmaceutically acceptable salt thereof.

Pharmaceutical Uses

The compounds described herein are useful in the methods of the invention and, while not bound by theory, are believed to exert their desirable effects through their ability to modulate the level, status, and/or activity of a BAF complex, e.g., by inhibiting the activity or level of the BRD9 protein in a cell within the BAF complex in a mammal.

An aspect of the present invention relates to methods of treating disorders related to BRD9 such as cancer in a subject in need thereof. In some embodiments, the compound is administered in an amount and for a time effective to result in one of (or more, e.g., two or more, three or more, four or more of): (a) reduced tumor size, (b) reduced rate of tumor growth, (c) increased tumor cell death (d) reduced tumor progression, (e) reduced number of metastases, (f) reduced rate of metastasis, (g) decreased tumor recurrence (h) increased survival of subject, and (i) increased progression free survival of a subject.

Treating cancer can result in a reduction in size or volume of a tumor. For example, after treatment, tumor size is reduced by 5% or greater (e.g., 10%, 20%, 30%, 40%, 50%, 60%, 70%, 80%, 90%, or greater) relative to its size prior to treatment. Size of a tumor may be measured by any reproducible means of measurement. For example, the size of a tumor may be measured as a diameter of the tumor.

Treating cancer may further result in a decrease in number of tumors. For example, after treatment, tumor number is reduced by 5% or greater (e.g., 10%, 20%, 30%, 40%, 50%, 60%, 70%, 80%, 90%, or greater) relative to number prior to treatment. Number of tumors may be measured by any reproducible means of measurement, e.g., the number of tumors may be measured by counting tumors visible to the naked eye or at a specified magnification (e.g., 2×, 3×, 4×, 5×, 10×, or 50×).

Treating cancer can result in a decrease in number of metastatic nodules in other tissues or organs distant from the primary tumor site. For example, after treatment, the number of metastatic nodules is reduced by 5% or greater (e.g., 10%, 20%, 30%, 40%, 50%, 60%, 70%, 80%, 90% or greater) relative to number prior to treatment. The number of metastatic nodules may be measured by any reproducible means of measurement. For example, the number of metastatic nodules may be measured by counting metastatic nodules visible to the naked eye or at a specified magnification (e.g., 2×, 10×, or 50×).

Treating cancer can result in an increase in average survival time of a population of subjects treated according to the present invention in comparison to a population of untreated subjects. For example, the average survival time is increased by more than 30 days (more than 60 days, 90 days, or 120 days). An increase in average survival time of a population may be measured by any reproducible means. An increase in average survival time of a population may be measured, for example, by calculating for a population the average length of survival following initiation of treatment with the compound described herein. An increase in average survival time of a population may also be measured, for example, by calculating for a population the average length of survival following completion of a first round of treatment with a pharmaceutically acceptable salt of a compound described herein.

Treating cancer can also result in a decrease in the mortality rate of a population of treated subjects in comparison to an untreated population. For example, the mortality rate is decreased by more than 2% (e.g., more than 5%, 10%, or 25%). A decrease in the mortality rate of a population of treated subjects may be measured by any reproducible means, for example, by calculating for a population the average number of disease-related deaths per unit time following initiation of treatment with a pharmaceutically acceptable salt of a compound described herein. A decrease in the mortality rate of a population may also be measured, for example, by calculating for a population the average number of disease-related deaths per unit time following completion of a first round of treatment with a pharmaceutically acceptable salt of a compound described herein.

Combination Therapies

A method of the invention can be used alone or in combination with an additional therapeutic agent, e.g., other agents that treat cancer or symptoms associated therewith, or in combination with other types of therapies to treat cancer. In combination treatments, the dosages of one or more of the therapeutic compounds may be reduced from standard dosages when administered alone. For example, doses may be determined empirically from drug combinations and permutations or may be deduced by isobolographic analysis (e.g., Black et al., *Neurology* 65: S3-S6 (2005)). In this case, dosages of the compounds when combined should provide a therapeutic effect.

In some embodiments, the second therapeutic agent is a chemotherapeutic agent (e.g., a cytotoxic agent or other chemical compound useful in the treatment of cancer). These include alkylating agents, antimetabolites, folic acid analogs, pyrimidine analogs, purine analogs and related inhibitors, *vinca* alkaloids, epipodopyyllotoxins, antibiotics, L-Asparaginase, topoisomerase inhibitors, interferons, platinum coordination complexes, anthracenedione substituted urea, methyl hydrazine derivatives, adrenocortical suppressant, adrenocorticosteroides, progestins, estrogens, antiestrogen, androgens, antiandrogen, and gonadotropin-releasing hormone analog. Also included is 5-fluorouracil (5-FU), leucovorin (LV), irenotecan, oxaliplatin, capecitabine, paclitaxel, and doxetaxel. Non-limiting examples of chemotherapeutic agents include alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammall and calicheamicin omegall (see, e.g., *Agnew, Chem. Intl. Ed Engl.* 33:183-186 (1994)); dynemicin, including dynemicin A; bisphosphonates, such as clodronate; an esperamicin; as well as neocarzinostatin chromophore and related chromoprotein enediyne antiobiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® (doxorubicin, including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfomithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, OR); razoxane; rhizoxin; sizofuran; spirogermanium; tenuazonic acid; triaziquone; 2,2',2''-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® (paclitaxel; Bristol-Myers Squibb Oncology, Princeton, NJ), ABRAXANE®, cremophor-free, albumin-engineered nanoparticle formulation of paclitaxel (American Pharmaceutical Partners, Schaumberg, IL), and TAXOTERE® doxetaxel (Rhone-Poulenc Rorer, Antony, France); chloranbucil; GEMZAR® gemcitabine; 6-thioguanine; mercaptopurine; methotrexate; platinum coordination complexes such as cisplatin, oxaliplatin and carboplatin; vinblastine; platinum; etoposide (VP-16); ifosfamide; mitoxantrone; vincristine; NAVELBINE® vinorelbine; novantrone; teniposide; edatrexate; daunomycin; aminopterin; xeloda; ibandronate; irinotecan (e.g., CPT-11); topoisomerase inhibitor RFS 2000; difluoromethylornithine (DMFO); retinoids such as retinoic acid; capecitabine; and pharmaceutically acceptable salts, acids or derivatives of any of the above. Two or more chemotherapeutic agents can be used in a cocktail to be administered in combination with the first therapeutic agent described herein. Suitable dosing regimens of combination chemotherapies are known in the art and described in, for example, Saltz et al., *Proc. Am. Soc. Clin. Oncol.* 18: 233a (1999), and Douillard et al., *Lancet* 355 (9209): 1041-1047 (2000).

In some embodiments, the second therapeutic agent is a therapeutic agent which is a biologic such a cytokine (e.g., interferon or an interleukin (e.g., IL-2)) used in cancer treatment. In some embodiments the biologic is an anti-angiogenic agent, such as an anti-VEGF agent, e.g., bevacizumab (AVASTIN®). In some embodiments the biologic is an immunoglobulin-based biologic, e.g., a monoclonal antibody (e.g., a humanized antibody, a fully human antibody, an Fc fusion protein or a functional fragment thereof) that agonizes a target to stimulate an anti-cancer response, or antagonizes an antigen important for cancer. Such agents include RITUXAN® (rituximab); ZENAPAX® (daclizumab); SIMULECT® (basiliximab); SYNAGIS® (palivizumab); REMICADE® (infliximab); HERCEPTIN® (trastuzumab); MYLOTARG® (gemtuzumab ozogamicin); CAMPATH® (alemtuzumab); ZEVALIN® (ibritumomab tiuxetan); HUMIRA® (adalimumab); XOLAIR® (omalizumab); BEXXAR® (tositumomab-I-131); RAPTIVA® (efalizumab); ERBITUX® (cetuximab); AVASTIN® (bevacizumab); TYSABRI® (natalizumab); ACTEMRA® (tocilizumab); VECTIBIX® (panitumumab); LUCENTIS® (ranibizumab); SOLIRIS® (eculizumab); CIMZIA® (certolizumab pegol); SIMPONI® (golimumab); ILARIS® (canakinumab); STELARA® (ustekinumab); ARZERRA® (ofatumumab); PROLIA® (denosumab); NUMAX® (motavizumab); ABTHRAX® (raxibacumab); BENLYSTA® (belimumab); YERVOY® (ipilimumab); ADCETRIS® (brentuximab vedotin); PERJETA® (pertuzumab); KADCYLA® (ado-trastuzumab emtansine); and GAZYVA® (obinutuzumab). Also included are antibody-drug conjugates.

The second agent may be a therapeutic agent which is a non-drug treatment. For example, the second therapeutic agent is radiation therapy, cryotherapy, hyperthermia, and/or surgical excision of tumor tissue.

The second agent may be a checkpoint inhibitor. In one embodiment, the inhibitor of checkpoint is an inhibitory antibody (e.g., a monospecific antibody such as a monoclonal antibody). The antibody may be, e.g., humanized or fully human. In some embodiments, the inhibitor of checkpoint is a fusion protein, e.g., an Fc-receptor fusion protein. In some embodiments, the inhibitor of checkpoint is an agent, such as an antibody, that interacts with a checkpoint protein. In some embodiments, the inhibitor of checkpoint is an agent, such as an antibody, that interacts with the ligand of a checkpoint protein. In some embodiments, the inhibitor of checkpoint is an inhibitor (e.g., an inhibitory antibody or small molecule inhibitor) of CTLA-4 (e.g., an anti-CTLA4 antibody or fusion a protein such as ipilimumab/YERVOY® or tremelimumab). In some embodiments, the inhibitor of checkpoint is an inhibitor (e.g., an inhibitory antibody or small molecule inhibitor) of PD-1 (e.g., nivolumab/OPDIVO®; pembrolizumab/KEYTRUDA®; pidilizumab/CT-011). In some embodiments, the inhibitor of checkpoint is an inhibitor (e.g., an inhibitory antibody or small molecule inhibitor) of PDL1 (e.g., MPDL3280A/RG7446; MEDI4736; MSB0010718C; BMS 936559). In some embodiments, the inhibitor of checkpoint is an inhibitor (e.g., an inhibitory antibody or Fc fusion or small molecule inhibitor) of PDL2 (e.g., a PDL2/Ig fusion protein such as AMP 224). In some embodiments, the inhibitor of checkpoint is an inhibitor (e.g., an inhibitory antibody or small molecule inhibitor) of B7-H3 (e.g., MGA271), B7-H4, BTLA, HVEM, TIM3, GAL9, LAG3, VISTA, KIR, 2B4, CD160, CGEN-15049, CHK 1, CHK2, A2aR, B-7 family ligands, or a combination thereof.

In some embodiments, the anti-cancer therapy is a T cell adoptive transfer (ACT) therapy. In some embodiments, the T cell is an activated T cell. The T cell may be modified to express a chimeric antigen receptor (CAR). CAR modified T (CAR-T) cells can be generated by any method known in the art. For example, the CAR-T cells can be generated by introducing a suitable expression vector encoding the CAR to a T cell. Prior to expansion and genetic modification of the T cells, a source of T cells is obtained from a subject. T cells can be obtained from a number of sources, including peripheral blood mononuclear cells, bone marrow, lymph node tissue, cord blood, thymus tissue, tissue from a site of infection, ascites, pleural effusion, spleen tissue, and tumors. In certain embodiments of the present invention, any number of T cell lines available in the art, may be used. In some embodiments, the T cell is an autologous T cell. Whether prior to or after genetic modification of the T cells to express a desirable protein (e.g., a CAR), the T cells can be activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005.

In any of the combination embodiments described herein, the first and second therapeutic agents are administered simultaneously or sequentially, in either order. The first therapeutic agent may be administered immediately, up to 1 hour, up to 2 hours, up to 3 hours, up to 4 hours, up to 5 hours, up to 6 hours, up to 7 hours, up to, 8 hours, up to 9 hours, up to 10 hours, up to 11 hours, up to 12 hours, up to 13 hours, 14 hours, up to hours 16, up to 17 hours, up 18 hours, up to 19 hours up to 20 hours, up to 21 hours, up to 22 hours, up to 23 hours up to 24 hours or up to 1-7, 1-14, 1-21 or 1-30 days before or after the second therapeutic agent.

Pharmaceutical Compositions

The pharmaceutical compositions described herein are preferably formulated into pharmaceutical compositions for administration to human subjects in a biologically compatible form suitable for administration in vivo.

The compounds described herein may be used in the form of the free base, in the form of salts, solvates, and as prodrugs. All forms are within the methods described herein. In accordance with the methods of the invention, the described compounds or salts, solvates, or prodrugs thereof may be administered to a patient in a variety of forms depending on the selected route of administration, as will be understood by those skilled in the art. The compounds described herein may be administered, for example, by oral, parenteral, buccal, sublingual, nasal, rectal, patch, pump, intratumoral, or transdermal administration and the pharmaceutical compositions formulated accordingly. Parenteral administration includes intravenous, intraperitoneal, subcutaneous, intramuscular, transepithelial, nasal, intrapulmonary, intrathecal, rectal, and topical modes of administration. Parenteral administration may be by continuous infusion over a selected period of time.

A compound described herein may be orally administered, for example, with an inert diluent or with an assimilable edible carrier, or it may be enclosed in hard or soft shell gelatin capsules, or it may be compressed into tablets, or it may be incorporated directly with the food of the diet. For oral therapeutic administration, a compound described herein may be incorporated with an excipient and used in the form of ingestible tablets, buccal tablets, troches, capsules, elixirs, suspensions, syrups, and wafers. A compound described herein may also be administered parenterally. Solutions of a compound described herein can be prepared in water suitably mixed with a surfactant, such as hydroxypropylcellulose. Dispersions can also be prepared in glycerol, liquid polyethylene glycols, DMSO, and mixtures thereof with or without alcohol, and in oils. Under ordinary conditions of storage and use, these preparations may contain a preservative to prevent the growth of microorganisms. Conventional procedures and ingredients for the selection and preparation of suitable formulations are described, for example, in Remington's Pharmaceutical Sciences (2012, 22nd ed.) and in The United States Pharmacopeia: The National Formulary (USP 41 NF36), published in 2018. The pharmaceutical forms suitable for injectable use include sterile aqueous solutions or dispersions and sterile powders for the extemporaneous preparation of sterile injectable solutions or dispersions. In all cases the form must be sterile and must be fluid to the extent that may be easily administered via syringe. Compositions for nasal administration may conveniently be formulated as aerosols, drops, gels, and powders. Aerosol formulations typically include a solution or fine suspension of the active substance in a physiologically acceptable aqueous or non-aqueous solvent and are usually presented in single or multidose quantities in sterile form in a sealed container, which can take the form of a cartridge or refill for use with an atomizing device. Alternatively, the sealed container may be a unitary dispensing device, such as a single dose nasal inhaler or an aerosol dispenser fitted with a metering valve which is intended for disposal after use. Where the dosage form includes an aerosol dispenser, it will contain a propellant, which can be a compressed gas, such as compressed air or an organic propellant, such as fluorochlorohydrocarbon. The aerosol dosage forms can also take the form of a pump-atomizer. Compositions suitable for buccal or sublingual administration include tablets, lozenges, and pastilles, where the active ingredient is formulated with a carrier, such as sugar, acacia, tragacanth, gelatin, and glycerine. Compositions for rectal administration are conveniently in the form of suppositories containing a conventional suppository base, such as cocoa butter. A compound described herein may be administered intratumorally, for example, as an intratumoral injection. Intratumoral injection is injection directly into the tumor vasculature and is specifically contemplated for discrete, solid, accessible tumors. Local, regional, or systemic administration also may be appropriate. A compound described herein may advantageously be contacted by administering an injection or multiple injections to the tumor, spaced for example, at approximately, 1 cm intervals. In the case of surgical intervention, the present invention may be used preoperatively, such as to render an inoperable tumor subject to resection. Continuous administration also may be applied where appropriate, for example, by implanting a catheter into a tumor or into tumor vasculature.

The compounds described herein may be administered to an animal, e.g., a human, alone or in combination with pharmaceutically acceptable carriers, as noted herein, the proportion of which is determined by the solubility and chemical nature of the compound, chosen route of administration, and standard pharmaceutical practice.

Dosages

The dosage of the compounds described herein, and/or compositions including a compound described herein, can vary depending on many factors, such as the pharmacodynamic properties of the compound; the mode of administration; the age, health, and weight of the recipient; the nature and extent of the symptoms; the frequency of the treatment, and the type of concurrent treatment, if any; and the clearance rate of the compound in the animal to be treated. One of skill in the art can determine the appropriate dosage based on the above factors. The compounds described herein may be administered initially in a suitable dosage that may be adjusted as required, depending on the clinical response. In general, satisfactory results may be obtained when the compounds described herein are administered to a human at a daily dosage of, for example, between 0.05 mg and 3000 mg (measured as the solid form). Dose ranges include, for example, between 10-1000 mg (e.g., 50-800 mg). In some embodiments, 50, 100, 150, 200, 250, 300, 350, 400, 450, 500, 550, 600, 650, 700, 750, 800, 850, 900, 950, or 1000 mg of the compound is administered.

Alternatively, the dosage amount can be calculated using the body weight of the patient. For example, the dose of a compound, or pharmaceutical composition thereof, administered to a patient may range from 0.1-100 mg/kg (e.g., 0.1-50 mg/kg (e.g., 0.25-25 mg/kg)). In exemplary, non-limiting embodiments, the dose may range from 0.5-5.0 mg/kg (e.g., 0.5, 1.0, 1.5, 2.0, 2.5, 3.0, 3.5, 4.0, 4.5, or 5.0 mg/kg) or from 5.0-20 mg/kg (e.g., 5.5, 6.0, 6.5, 7.0, 7.5, 8.0, 8.5, 9.0, 9.5, 10, 11, 12, 13, 14, 15, 16, 17, 18, 19, or 20 mg/kg).

Kits

The invention also features kits including (a) a pharmaceutical composition including an agent that reduces the level and/or activity of BRD9 in a cell or subject described herein, and (b) a package insert with instructions to perform any of the methods described herein. In some embodiments, the kit includes (a) a pharmaceutical composition including an agent that reduces the level and/or activity of BRD9 in a cell or subject described herein, (b) an additional therapeutic agent (e.g., an anti-cancer agent), and (c) a package insert with instructions to perform any of the methods described herein.

EXAMPLES

Example 1—High Density Tiling sgRNA Screen Against Human BAF Complex Subunits in Synovial Sarcoma Cell Line SYO1

The following example shows that BRD9 sgRNA inhibits cell growth in synovial sarcoma cells.

Procedure: To perform high density sgRNA tiling screen, an sgRNA library against BAF complex subunits was custom synthesized at Cellecta (Mountain View, CA). Sequences of DNA encoding the BRD9-targeting sgRNAs used in this screen are listed in Table 2. Negative and positive control sgRNA were included in the library. Negative controls consisted of 200 sgRNAs that do not target human genome. The positive controls are sgRNAs targeting essential genes (CDC16, GTF2B, HSPA5, HSPA9, PAFAH1B1, PCNA, POLR2L, RPL9, and SF3A$^3$). DNA sequences encoding all positive and negative control sgRNAs are listed in Table 3. Procedures for virus production, cell infection, and performing the sgRNA screen were previously described (Tsherniak et al, *Cell* 170:564-576 (2017); Munoz et al, *Cancer Discovery* 6:900-913 (2016)). For each sgRNA, 50 counts were added to the sequencing counts and for each time point the resulting counts were normalized to the total number of counts. The log 2 of the ratio between the counts (defined as dropout ratio) at day 24 and day 1 post-infection was calculated. For negative control sgRNAs, the 2.5 and 97.5 percentile of the log 2 dropout ratio of all non-targeting sgRNAs was calculated and considered as background (grey box in the graph). Protein domains were obtained from PFAM regions defined for the UNIPROT identifier: Q9H8M2.

Results: As shown in FIG. 1, targeted inhibition of the GBAF complex component BRD9 by sgRNA resulted in growth inhibition of the SYO1 synovial sarcoma cell line. sgRNAs against other components of the BAF complexes resulted in increased proliferation of cells, inhibition of cell growth, or had no effect on SYO1 cells. These data show that targeting various subunits of the GBAF complex represents a therapeutic strategy for the treatment of synovial sarcoma.

TABLE 2

BRD9 sgRNA Library

| SEQ ID NO | Nucleic Acid Sequence |
|---|---|
| 203 | CAAGAAGCACAAGAAGCACA |
| 204 | CTTGTGCTTCTTGCCCATGG |
| 205 | CTTCTTGTGCTTCTTGCCCA |
| 206 | ACAAGAAGCACAAGGCCGAG |
| 207 | CTCGTAGGACGAGCGCCACT |
| 208 | CGAGTGGCGCTCGTCCTACG |
| 209 | GAGTGGCGCTCGTCCTACGA |
| 210 | AGGCTTCTCCAGGGGCTTGT |
| 211 | AGATTATGCCGACAAGCCCC |
| 212 | ACCTTCAGGACTAGCTTTAG |
| 213 | AGCTTTAGAGGCTTCTCCAG |
| 214 | CTAGCTTTAGAGGCTTCTCC |
| 215 | TAGCTTTAGAGGCTTCTCCA |
| 216 | CTAAAGCTAGTCCTGAAGGT |
| 217 | GCCTCTAAAGCTAGTCCTGA |
| 218 | CTTCACTTCCTCCGACCTTC |
| 219 | AAGCTAGTCCTGAAGGTCGG |
| 220 | AGTGAAGTGACTGAACTCTC |
| 221 | GTGACTGAACTCTCAGGATC |
| 222 | ATAGTAACTGGAGTCGTGGC |
| 223 | CATCATAGTAACTGGAGTCG |
| 224 | TGACCTGTCATCATAGTAAC |
| 225 | ACTCCAGTTACTATGATGAC |
| 226 | CTTTGTGCCTCTCTCGCTCA |
| 227 | GGTCAGACCATGAGCGAGAG |
| 228 | GAAGAAGAAGAAGTCCGAGA |
| 229 | GTCCAGATGCTTCTCCTTCT |
| 230 | GTCCGAGAAGGAGAAGCATC |
| 231 | GGAGAAGCATCTGGACGATG |
| 232 | TGAGGAAAGAAGGAAGCGAA |
| 233 | ATCTGGACGATGAGGAAAGA |
| 234 | AGAAGAAGCGGAAGCGAGAG |
| 235 | GAAGAAGCGGAAGCGAGAGA |
| 236 | CCGCCCAGGAAGAGAAGAAG |
| 237 | AGAGAGGGAGCACTGTGACA |
| 238 | AGGGAGCACTGTGACACGGA |
| 239 | GAGGGAGCACTGTGACACGG |
| 240 | GCACTGTGACACGGAGGGAG |
| 241 | GAGGCTGACGACTTTGATCC |
| 242 | AGGCTGACGACTTTGATCCT |
| 243 | TCCACCTCCACCTTCTTCCC |
| 244 | CGACTTTGATCCTGGGAAGA |
| 245 | CTTTGATCCTGGGAAGAAGG |
| 246 | TGATCCTGGGAAGAAGGTGG |
| 247 | TCCTGGGAAGAAGGTGGAGG |
| 248 | CGGACTGGCCGATCTGGGGG |
| 249 | ACGCTCGGACTGGCCGATCT |
| 250 | AGGTGGAGCCGCCCCCAGAT |
| 251 | CGCTCGGACTGGCCGATCTG |
| 252 | GCTCGGACTGGCCGATCTGG |
| 253 | CACGCTCGGACTGGCCGATC |
| 254 | TGTGTCCGGCACGCTCGGAC |
| 255 | CTGGCTGTGTCCGGCACGCT |
| 256 | ATCGGCCAGTCCGAGCGTGC |
| 257 | CACCCTTGCCTGGCTGTGTC |
| 258 | CGAGCGTGCCGGACACAGCC |
| 259 | TGTTCCAGGAGTTGCTGAAT |
| 260 | CACACCTATTCAGCAACTCC |
| 261 | GCTGGCGGAGGAAGTGTTCC |
| 262 | TTTACCTCTGAAGCTGGCGG |
| 263 | CCCCGGTTTACCTCTGAAGC |
| 264 | ACTTCCTCCGCCAGCTTCAG |
| 265 | CAGGAAAAGCAAAAAATCCA |
| 266 | GCTTTCAGAAAAGATCCCCA |
| 267 | AGGAAAAGCAAAAAATCCAT |
| 268 | GGAAAAGCAAAAAATCCATG |
| 269 | GGAGCAATTGCATCCGTGAC |
| 270 | GTCACGGATGCAATTGCTCC |
| 271 | TTTATTATCATTGAATATCC |
| 272 | AATGATAATAAAACATCCCA |
| 273 | ATAAAACATCCCATGGATTT |
| 274 | TTCATGGTGCCAAAATCCAT |
| 275 | TTTCATGGTGCCAAAATCCA |
| 276 | TAATGAATACAAGTCAGTTA |
| 277 | CAAGTCAGTTACGGAATTTA |
| 278 | ATAATGCAATGACATACAAT |

TABLE 2-continued

BRD9 sgRNA Library

| SEQ ID NO | Nucleic Acid Sequence |
|---|---|
| 279 | AACTTGTAGTACACGGTATC |
| 280 | CTTCGCCAACTTGTAGTACA |
| 281 | AGATACCGTGTACTACAAGT |
| 282 | GCGAAGAAGATCCTTCACGC |
| 283 | TCATCTTAAAGCCTGCGTGA |
| 284 | TTCTCAGCAGGCAGCTCTTT |
| 285 | CAATGAAGATACAGCTGTTG |
| 286 | ACTGGTACAACTTCAGGGAC |
| 287 | CTTGTACTGGTACAACTTCA |
| 288 | ACTTGTACTGGTACAACTTC |
| 289 | TTGGCAGTTTCTACTTGTAC |
| 290 | TACCTGATAACTTCTCTACT |
| 291 | AGCCGAGTAGAGAAGTTATC |
| 292 | AGCTGCATGTTTGAGCCTGA |
| 293 | GCTGCATGTTTGAGCCTGAA |
| 294 | AAGCTGCAGGCATTCCCTTC |
| 295 | GGTACTGTCCGTCAAGCTGC |
| 296 | AGGGAATGCCTGCAGCTTGA |
| 297 | CTTGACGGACAGTACCGCAG |
| 298 | CGCCAGCACGTGCTCCTCTG |
| 299 | TACCGCAGAGGAGCACGTGC |
| 300 | AGAGGAGCACGTGCTGGCGC |
| 301 | GGAGCACGTGCTGGCGCTGG |
| 302 | AGCACGCAGCTGACGAAGCT |
| 303 | GCACGCAGCTGACGAAGCTC |
| 304 | CAGCTGACGAAGCTCGGGAC |
| 305 | AAGCTCGGGACAGGATCAAC |
| 306 | CCTTGCCGCCTGGGAGGAAC |
| 307 | AGGATCAACCGGTTCCTCCC |
| 308 | ATCAACCGGTTCCTCCCAGG |
| 309 | GCACTACCTTGCCGCCTGGG |
| 310 | AGAGCACTACCTTGCCGCCT |
| 311 | CCGGTTCCTCCCAGGCGGCA |
| 312 | TCCTCTTCAGATAGCCCATC |
| 313 | ATGGGCTATCTGAAGAGGAA |
| 314 | GGGCTATCTGAAGAGGAACG |
| 315 | TGGGCTATCTGAAGAGGAAC |
| 316 | TATCTGAAGAGGAACGGGGA |
| 317 | ATCTGAAGAGGAACGGGGAC |
| 318 | TGTTGACCACGCTGTAGAGC |
| 319 | GCTCTACAGCGTGGTCAACA |
| 320 | CGGGAGCCTGCTCTACAGCG |
| 321 | CGTGGTCAACACGGCCGAGC |
| 322 | CCCACCATCAGCGTCCGGCT |
| 323 | ACGGCCGAGCCGGACGCTGA |
| 324 | GGGCACCCACCATCAGCGTC |
| 325 | GCCGAGCCGGACGCTGATGG |
| 326 | CCATGTCCGTGTTGCAGAGG |
| 327 | CCGAGCCGGACGCTGATGGT |
| 328 | CGAGCTCAAGTCCACCGGGT |
| 329 | GCGAGCTCAAGTCCACCGGG |
| 330 | AGAGCGAGCTCAAGTCCACC |
| 331 | GAGAGCGAGCTCAAGTCCAC |
| 332 | GAAGCCTGGGAGTAGCTTAC |
| 333 | CTCTCCAGTAAGCTACTCCC |
| 334 | AGCCCAGCGTGGTGAAGCCT |
| 335 | AAGCCCAGCGTGGTGAAGCC |
| 336 | ACTCCCAGGCTTCACCACGC |
| 337 | CTCCCAGGCTTCACCACGCT |
| 338 | CTCGTCTTTGAAGCCCAGCG |
| 339 | CACTGGAGAGAAAGGTGACT |
| 340 | GCACTGGAGAGAAAGGTGAC |
| 341 | AGTAGTGGCACTGGAGAGAA |
| 342 | CGAAAGCGCAGTAGTGGCAC |
| 343 | CTGCATCGAAAGCGCAGTAG |
| 344 | ATGCAGAATAATTCAGTATT |
| 345 | AGTATTTGGCGACTTGAAGT |
| 346 | CGACTTGAAGTCGGACGAGA |
| 347 | GAGCTGCTCTACTCAGCCTA |
| 348 | CACGCCTGTCTCATCTCCGT |
| 349 | TCAGCCTACGGAGATGAGAC |
| 350 | CAGGCGTGCAGTGTGCGCTG |
| 351 | CCGCGGCCCCTCTAGCCTGC |
| 352 | CATCCTTCACAAACTCCTGC |
| 353 | TAGCCTGCAGGAGTTTGTGA |
| 354 | CAGGAGTTTGTGAAGGATGC |

TABLE 2-continued

BRD9 sgRNA Library

| SEQ ID NO | Nucleic Acid Sequence |
|---|---|
| 355 | AGGAGTTTGTGAAGGATGCT |
| 356 | TGGGAGCTACAGCAAGAAAG |
| 357 | GAGCTACAGCAAGAAAGTGG |
| 358 | GAAAGTGGTGGACGACCTCC |
| 359 | CGCCTGTGATCTGGTCCAGG |
| 360 | CTCCGCCTGTGATCTGGTCC |
| 361 | GACCTCCTGGACCAGATCAC |
| 362 | CTCCTGGACCAGATCACAGG |
| 363 | GCTGGAAGAGCGTCCTAGAG |
| 364 | TGCAGCCCACCTGCTTCAGC |
| 365 | GACGCTCTTCCAGCTGAAGC |
| 366 | CTCTTCCAGCTGAAGCAGGT |
| 367 | GCTCTTCCAGCTGAAGCAGG |
| 368 | CCTCCAGATGAAGCCAAGGT |
| 369 | GCTTCATCTGGAGGCTTCAT |
| 370 | GGCTTCATCTGGAGGCTTCA |
| 371 | CTTACCTTGGCTTCATCTGG |
| 372 | AAACTTACCTTGGCTTCATC |
| 373 | GAAGCCTCCAGATGAAGCCA |
| 374 | TCCTAGGGTGTCCCCAACCT |
| 375 | CCTAGGGTGTCCCCAACCTG |
| 376 | GTGTCTGTCTCCACAGGTTG |
| 377 | TGTGTCTGTCTCCACAGGTT |
| 378 | CCACAGGTTGGGGACACCCT |
| 379 | AGAGCTGCTGCTGTCTCCTA |
| 380 | CAGAGCTGCTGCTGTCTCCT |
| 381 | AGACAGCAGCAGCTCTGTTC |
| 382 | ATCCACAGAAACGTCGGGAT |
| 383 | GAGATATCCACAGAAACGTC |
| 384 | GGAGATATCCACAGAAACGT |
| 385 | GTCCTATCCCGACGTTTCTG |
| 386 | TCTCCATGCTCAGCTCTCTG |
| 387 | CTCACCCAGAGAGCTGAGCA |
| 388 | ATCTCCATGCTCAGCTCTCT |
| 389 | TATCTCCATGCTCAGCTCTC |
| 390 | ATGTCCTGTTTACACAGGGA |
| 391 | TTACACAGGGAAGGTGAAGA |
| 392 | AGTTCAAATGGCTGTCGTCA |
| 393 | TGACGACAGCCATTTGAACT |
| 394 | AAGTTCAAATGGCTGTCGTC |
| 395 | TCGTCTCATCCAAGTTCAAA |
| 396 | TGAGACGACGAAGCTCCTGC |
| 397 | GTGCTTCGTGCAGGTCCTGC |
| 398 | GCAGGACCTGCACGAAGCAC |
| 399 | GCTCCGCCTGTGCTTCGTGC |
| 400 | GGACCTGCACGAAGCACAGG |
| 401 | CACGAAGCACAGGCGGAGCG |
| 402 | AGGCGGAGCGCGGCGGCTCT |
| 403 | AGGGAGCTGAGGTTGGACGA |
| 404 | GTTGGACAGGGAGCTGAGGT |
| 405 | AGGCGTTGGACAGGGAGCTG |
| 406 | CCCTCTCGGAGGCGTTGGAC |
| 407 | CCTCTCGGAGGCGTTGGACA |
| 408 | CTGGTCCCTCTCGGAGGCGT |
| 409 | CCCTGTCCAACGCCTCCGAG |
| 410 | CCTGTCCAACGCCTCCGAGA |
| 411 | GTGGTGCTGGTCCCTCTCGG |
| 412 | CAGGTGGTGCTGGTCCCTCT |
| 413 | GCATCTCACCCAGGTGGTGC |
| 414 | CGAGAGGGACCAGCACCACC |
| 415 | GAGAGGGACCAGCACCACCT |
| 416 | GTGGGGCATCTCACCCAGG |
| 417 | CCCCGACACTCAGGCGAGAA |
| 418 | TCCCCGACACTCAGGCGAGA |
| 419 | AGCCCTTCTCGCCTGAGTGT |
| 420 | CTGGCTGCTCCCCGACACTC |
| 421 | CCCTTCTCGCCTGAGTGTCG |
| 422 | GCCCTTCTCGCCTGAGTGTC |
| 423 | TAGGGGTCGTGGGTGACGTC |
| 424 | AAGAAACTCATAGGGGTCGT |
| 425 | GAAGAAACTCATAGGGGTCG |
| 426 | GAGACTGAAGAAACTCATAG |
| 427 | GGAGACTGAAGAAACTCATA |
| 428 | TGGAGACTGAAGAAACTCAT |
| 429 | TCTTCAGTCTCCAGAGCCTG |

TABLE 2-continued

BRD9 sgRNA Library

| SEQ ID NO | Nucleic Acid Sequence |
|---|---|
| 430 | TTGGCAGAGGCCGCAGGCTC |
| 431 | TAGGTCTTGGCAGAGGCCGC |
| 432 | CTAGAGTTAGGTCTTGGCAG |
| 433 | GGTGGTCTAGAGTTAGGTCT |

TABLE 3

Control sgRNA Library

| SEQ ID NO. | gRNA Label | Gene | Nucleic Acid Sequence |
|---|---|---|---|
| 434 | 1\|sg_Non_Targeting_Human_0001\|Non_Targeting_Human | Non_Targeting_Human | GTAGCGAACGTGTCCGGCGT |
| 435 | 1\|sg_Non_Targeting_Human_0002\|Non_Targeting_Human | Non_Targeting_Human | GACCGGAACGATCTCGCGTA |
| 436 | 1\|sg_Non_Targeting_Human_0003\|Non_Targeting_Human | Non_Targeting_Human | GGCAGTCGTTCGGTTGATAT |
| 437 | 1\|sg_Non_Targeting_Human_0004\|Non_Targeting_Human | Non_Targeting_Human | GCTTGAGCACATACGCGAAT |
| 438 | 1\|sg_Non_Targeting_Human_0005\|Non_Targeting_Human | Non_Targeting_Human | GTGGTAGAATAACGTATTAC |
| 439 | 1\|sg_Non_Targeting_Human_0006\|Non_Targeting_Human | Non_Targeting_Human | GTCATACATGGATAAGGCTA |
| 440 | 1\|sg_Non_Targeting_Human_0007\|Non_Targeting_Human | Non_Targeting_Human | GATACACGAAGCATCACTAG |
| 441 | 1\|sg_Non_Targeting_Human_0008\|Non_Targeting_Human | Non_Targeting_Human | GAACGTTGGCACTACTTCAC |
| 442 | 1\|sg_Non_Targeting_Human_0009\|Non_Targeting_Human | Non_Targeting_Human | GATCCATGTAATGCGTTCGA |
| 443 | 1\|sg_Non_Targeting_Human_0010\|Non_Targeting_Human | Non_Targeting_Human | GTCGTGAAGTGCATTCGATC |
| 444 | 1\|sg_Non_Targeting_Human_0011\|Non_Targeting_Human | Non_Targeting_Human | GTTCGACTCGCGTGACCGTA |
| 445 | 1\|sg_Non_Targeting_Human_0012\|Non_Targeting_Human | Non_Targeting_Human | GAATCTACCGCAGCGGTTCG |
| 446 | 1\|sg_Non_Targeting_Human_0013\|Non_Targeting_Human | Non_Targeting_Human | GAAGTGACGTCGATTCGATA |
| 447 | 1\|sg_Non_Targeting_Human_0014\|Non_Targeting_Human | Non_Targeting_Human | GCGGTGTATGACAACCGCCG |
| 448 | 1\|sg_Non_Targeting_Human_0015\|Non_Targeting_Human | Non_Targeting_Human | GTACCGCGCCTGAAGTTCGC |
| 449 | 1\|sg_Non_Targeting_Human_0016\|Non_Targeting_Human | Non_Targeting_Human | GCAGCTCGTGTGTCGTACTC |
| 450 | 1\|sg_Non_Targeting_Human_0017\|Non_Targeting_Human | Non_Targeting_Human | GCGCCTTAAGAGTACTCATC |
| 451 | 1\|sg_Non_Targeting_Human_0018\|Non_Targeting_Human | Non_Targeting_Human | GAGTGTCGTCGTTGCTCCTA |
| 452 | 1\|sg_Non_Targeting_Human_0019\|Non_Targeting_Human | Non_Targeting_Human | GCAGCTCGACCTCAAGCCGT |
| 453 | 1\|sg_Non_Targeting_Human_0020\|Non_Targeting_Human | Non_Targeting_Human | GTATCCTGACCTACGCGCTG |

TABLE 3-continued

Control sgRNA Library

| SEQ ID NO. | gRNA Label | Gene | Nucleic Acid Sequence |
|---|---|---|---|
| 454 | 1\|sg_Non_Targeting_Human_0021\|Non_Targeting_Human | Non_Targeting_Human | GTGTATCTCAGCACGCTAAC |
| 455 | 1\|sg_Non_Targeting_Human_0022\|Non_Targeting_Human | Non_Targeting_Human | GTCGTCATACAACGGCAACG |
| 456 | 1\|sg_Non_Targeting_Human_0023\|Non_Targeting_Human | Non_Targeting_Human | GTCGTGCGCTTCCGGCGGTA |
| 457 | 1\|sg_Non_Targeting_Human_0024\|Non_Targeting_Human | Non_Targeting_Human | GCGGTCCTCAGTAAGCGCGT |
| 458 | 1\|sg_Non_Targeting_Human_0025\|Non_Targeting_Human | Non_Targeting_Human | GCTCTGCTGCGGAAGGATTC |
| 459 | 1\|sg_Non_Targeting_Human_0026\|Non_Targeting_Human | Non_Targeting_Human | GCATGGAGGAGCGTCGCAGA |
| 460 | 1\|sg_Non_Targeting_Human_0027\|Non_Targeting_Human | Non_Targeting_Human | GTAGCGCGCGTAGGAGTGGC |
| 461 | 1\|sg_Non_Targeting_Human_0028\|Non_Targeting_Human | Non_Targeting_Human | GATCACCTGCATTCGTACAC |
| 462 | 1\|sg_Non_Targeting_Human_0029\|Non_Targeting_Human | Non_Targeting_Human | GCACACCTAGATATCGAATG |
| 463 | 1\|sg_Non_Targeting_Human_0030\|Non_Targeting_Human | Non_Targeting_Human | GTTGATCAACGCGCTTCGCG |
| 464 | 1\|sg_Non_Targeting_Human_0031\|Non_Targeting_Human | Non_Targeting_Human | GCGTCTCACTCACTCCATCG |
| 465 | 1\|sg_Non_Targeting_Human_0032\|Non_Targeting_Human | Non_Targeting_Human | GCCGACCAACGTCAGCGGTA |
| 466 | 1\|sg_Non_Targeting_Human_0033\|Non_Targeting_Human | Non_Targeting_Human | GGATACGGTGCGTCAATCTA |
| 467 | 1\|sg_Non_Targeting_Human_0034\|Non_Targeting_Human | Non_Targeting_Human | GAATCCAGTGGCGGCGACAA |
| 468 | 1\|sg_Non_Targeting_Human_0035\|Non_Targeting_Human | Non_Targeting_Human | GCACTGTCAGTGCAACGATA |
| 469 | 1\|sg_Non_Targeting_Human_0036\|Non_Targeting_Human | Non_Targeting_Human | GCGATCCTCAAGTATGCTCA |
| 470 | 1\|sg_Non_Targeting_Human_0037\|Non_Targeting_Human | Non_Targeting_Human | GCTAATATCGACACGGCCGC |
| 471 | 1\|sg_Non_Targeting_Human_0038\|Non_Targeting_Human | Non_Targeting_Human | GGAGATGCATCGAAGTCGAT |
| 472 | 1\|sg_Non_Targeting_Human_0039\|Non_Targeting_Human | Non_Targeting_Human | GGATGCACTCCATCTCGTCT |
| 473 | 1\|sg_Non_Targeting_Human_0040\|Non_Targeting_Human | Non_Targeting_Human | GTGCCGAGTAATAACGCGAG |
| 474 | 1\|sg_Non_Targeting_Human_0041\|Non_Targeting_Human | Non_Targeting_Human | GAGATTCCGATGTAACGTAC |
| 475 | 1\|sg_Non_Targeting_Human_0042\|Non_Targeting_Human | Non_Targeting_Human | GTCGTCACGAGCAGGATTGC |
| 476 | 1\|sg_Non_Targeting_Human_0043\|Non_Targeting_Human | Non_Targeting_Human | GCGTTAGTCACTTAGCTCGA |
| 477 | 1\|sg_Non_Targeting_Human_0044\|Non_Targeting_Human | Non_Targeting_Human | GTTCACACGGTGTCGGATAG |
| 478 | 1\|sg_Non_Targeting_Human_0045\|Non_Targeting_Human | Non_Targeting_Human | GGATAGGTGACCTTAGTACG |

TABLE 3-continued

Control sgRNA Library

| SEQ ID NO. | gRNA Label | Gene | Nucleic Acid Sequence |
|---|---|---|---|
| 479 | 1\|sg_Non_Targeting_Human_0046\|Non_Targeting_Human | Non_Targeting_Human | GTATGAGTCAAGCTAATGCG |
| 480 | 1\|sg_Non_Targeting_Human_0047\|Non_Targeting_Human | Non_Targeting_Human | GCAACTATTGGAATACGTGA |
| 481 | 1\|sg_Non_Targeting_Human_0048\|Non_Targeting_Human | Non_Targeting_Human | GTTACCTTCGCTCGTCTATA |
| 482 | 1\|sg_Non_Targeting_Human_0049\|Non_Targeting_Human | Non_Targeting_Human | GTACCGAGCACCACAGGCCG |
| 483 | 1\|sg_Non_Targeting_Human_0050\|Non_Targeting_Human | Non_Targeting_Human | GTCAGCCATCGGATAGAGAT |
| 484 | 1\|sg_Non_Targeting_Human_0051\|Non_Targeting_Human | Non_Targeting_Human | GTACGGCACTCCTAGCCGCT |
| 485 | 1\|sg_Non_Targeting_Human_0052\|Non_Targeting_Human | Non_Targeting_Human | GGTCCTGTCGTATGCTTGCA |
| 486 | 1\|sg_Non_Targeting_Human_0053\|Non_Targeting_Human | Non_Targeting_Human | GCCGCAATATATGCGGTAAG |
| 487 | 1\|sg_Non_Targeting_Human_0054\|Non_Targeting_Human | Non_Targeting_Human | GCGCACGTATAATCCTGCGT |
| 488 | 1\|sg_Non_Targeting_Human_0055\|Non_Targeting_Human | Non_Targeting_Human | GTGCACAACACGATCCACGA |
| 489 | 1\|sg_Non_Targeting_Human_0056\|Non_Targeting_Human | Non_Targeting_Human | GCACAATGTTGACGTAAGTG |
| 490 | 1\|sg_Non_Targeting_Human_0057\|Non_Targeting_Human | Non_Targeting_Human | GTAAGATGCTGCTCACCGTG |
| 491 | 1\|sg_Non_Targeting_Human_0058\|Non_Targeting_Human | Non_Targeting_Human | GTCGGTGATCCAACGTATCG |
| 492 | 1\|sg_Non_Targeting_Human_0059\|Non_Targeting_Human | Non_Targeting_Human | GAGCTAGTAGGACGCAAGAC |
| 493 | 1\|sg_Non_Targeting_Human_0060\|Non_Targeting_Human | Non_Targeting_Human | GTACGTGGAAGCTTGTGGCC |
| 494 | 1\|sg_Non_Targeting_Human_0061\|Non_Targeting_Human | Non_Targeting_Human | GAGAACTGCCAGTTCTCGAT |
| 495 | 1\|sg_Non_Targeting_Human_0062\|Non_Targeting_Human | Non_Targeting_Human | GCCATTCGGCGCGGCACTTC |
| 496 | 1\|sg_Non_Targeting_Human_0063\|Non_Targeting_Human | Non_Targeting_Human | GCACACGACCAATCCGCTTC |
| 497 | 1\|sg_Non_Targeting_Human_0064\|Non_Targeting_Human | Non_Targeting_Human | GAGGTGATCGATTAAGTACA |
| 498 | 1\|sg_Non_Targeting_Human_0065\|Non_Targeting_Human | Non_Targeting_Human | GTCACTCGCAGACGCCTAAC |
| 499 | 1\|sg_Non_Targeting_Human_0066\|Non_Targeting_Human | Non_Targeting_Human | GCGCTACGGAATCATACGTT |
| 500 | 1\|sg_Non_Targeting_Human_0067\|Non_Targeting_Human | Non_Targeting_Human | GGTAGGACCTCACGGCGCGC |
| 501 | 1\|sg_Non_Targeting_Human_0068\|Non_Targeting_Human | Non_Targeting_Human | GAACTGCATCTTGTTGTAGT |
| 502 | 1\|sg_Non_Targeting_Human_0069\|Non_Targeting_Human | Non_Targeting_Human | GATCCTGATCCGGCGGCGCG |

TABLE 3-continued

Control sgRNA Library

| SEQ ID NO. | gRNA Label | Gene | Nucleic Acid Sequence |
|---|---|---|---|
| 503 | 1\|sg_Non_Targeting_Human_0070\|Non_Targeting_Human | Non_Targeting_Human | GGTATGCGCGATCCTGAGTT |
| 504 | 1\|sg_Non_Targeting_Human_0071\|Non_Targeting_Human | Non_Targeting_Human | GCGGAGCTAGAGAGCGGTCA |
| 505 | 1\|sg_Non_Targeting_Human_0072\|Non_Targeting_Human | Non_Targeting_Human | GAATGGCAATTACGGCTGAT |
| 506 | 1\|sg_Non_Targeting_Human_0073\|Non_Targeting_Human | Non_Targeting_Human | GTATGGTGAGTAGTCGCTTG |
| 507 | 1\|sg_Non_Targeting_Human_0074\|Non_Targeting_Human | Non_Targeting_Human | GTGTAATTGCGTCTAGTCGG |
| 508 | 1\|sg_Non_Targeting_Human_0075\|Non_Targeting_Human | Non_Targeting_Human | GGTCCTGGCGAGGAGCCTTG |
| 509 | 1\|sg_Non_Targeting_Human_0076\|Non_Targeting_Human | Non_Targeting_Human | GAAGATAAGTCGCTGTCTCG |
| 510 | 1\|sg_Non_Targeting_Human_0077\|Non_Targeting_Human | Non_Targeting_Human | GTCGGCGTTCTGTTGTGACT |
| 511 | 1\|sg_Non_Targeting_Human_0078\|Non_Targeting_Human | Non_Targeting_Human | GAGGCAAGCCGTTAGGTGTA |
| 512 | 1\|sg_Non_Targeting_Human_0079\|Non_Targeting_Human | Non_Targeting_Human | GCGGATCCAGATCTCATTCG |
| 513 | 1\|sg_Non_Targeting_Human_0080\|Non_Targeting_Human | Non_Targeting_Human | GGAACATAGGAGCACGTAGT |
| 514 | 1\|sg_Non_Targeting_Human_0081\|Non_Targeting_Human | Non_Targeting_Human | GTCATCATTATGGCGTAAGG |
| 515 | 1\|sg_Non_Targeting_Human_0082\|Non_Targeting_Human | Non_Targeting_Human | GCGACTAGCGCCATGAGCGG |
| 516 | 1\|sg_Non_Targeting_Human_0083\|Non_Targeting_Human | Non_Targeting_Human | GGCGAAGTTCGACATGACAC |
| 517 | 1\|sg_Non_Targeting_Human_0084\|Non_Targeting_Human | Non_Targeting_Human | GCTGTCGTGTGGAGGCTATG |
| 518 | 1\|sg_Non_Targeting_Human_0085\|Non_Targeting_Human | Non_Targeting_Human | GCGGAGAGCATTGACCTCAT |
| 519 | 1\|sg_Non_Targeting_Human_0086\|Non_Targeting_Human | Non_Targeting_Human | GACTAATGGACCAAGTCAGT |
| 520 | 1\|sg_Non_Targeting_Human_0087\|Non_Targeting_Human | Non_Targeting_Human | GCGGATTAGAGGTAATGCGG |
| 521 | 1\|sg_Non_Targeting_Human_0088\|Non_Targeting_Human | Non_Targeting_Human | GCCGACGGCAATCAGTACGC |
| 522 | 1\|sg_Non_Targeting_Human_0089\|Non_Targeting_Human | Non_Targeting_Human | GTAACCTCTCGAGCGATAGA |
| 523 | 1\|sg_Non_Targeting_Human_0090\|Non_Targeting_Human | Non_Targeting_Human | GACTTGTATGTGGCTTACGG |
| 524 | 1\|sg_Non_Targeting_Human_0091\|Non_Targeting_Human | Non_Targeting_Human | GTCACTGTGGTCGAACATGT |
| 525 | 1\|sg_Non_Targeting_Human_0092\|Non_Targeting_Human | Non_Targeting_Human | GTACTCCAATCCGCGATGAC |
| 526 | 1\|sg_Non_Targeting_Human_0093\|Non_Targeting_Human | Non_Targeting_Human | GCGTTGGCACGATGTTACGG |

TABLE 3-continued

Control sgRNA Library

| SEQ ID NO. | gRNA Label | Gene | Nucleic Acid Sequence |
|---|---|---|---|
| 527 | 1\|sg_Non_Targeting_Human_0094\|Non_Targeting_Human | Non_Targeting_Human | GAACCAGCCGGCTAGTATGA |
| 528 | 1\|sg_Non_Targeting_Human_0095\|Non_Targeting_Human | Non_Targeting_Human | GTATACTAGCTAACCACACG |
| 529 | 1\|sg_Non_Targeting_Human_0096\|Non_Targeting_Human | Non_Targeting_Human | GAATCGGAATAGTTGATTCG |
| 530 | 1\|sg_Non_Targeting_Human_0097\|Non_Targeting_Human | Non_Targeting_Human | GAGCACTTGCATGAGGCGGT |
| 531 | 1\|sg_Non_Targeting_Human_0098\|Non_Targeting_Human | Non_Targeting_Human | GAACGGCGATGAAGCCAGCC |
| 532 | 1\|sg_Non_Targeting_Human_0099\|Non_Targeting_Human | Non_Targeting_Human | GCAACCGAGATGAGAGGTTC |
| 533 | 1\|sg_Non_Targeting_Human_0100\|Non_Targeting_Human | Non_Targeting_Human | GCAAGATCAATATGCGTGAT |
| 534 | 1\|sg_Non_Targeting_Human_GA_0101\|Non_Targeting_Human | Non_Targeting_Human | ACGGAGGCTAAGCGTCGCAA |
| 535 | 1\|sg_Non_Targeting_Human_GA_0102\|Non_Targeting_Human | Non_Targeting_Human | CGCTTCCGCGGCCCGTTCAA |
| 536 | 1\|sg_Non_Targeting_Human_GA_0103\|Non_Targeting_Human | Non_Targeting_Human | ATCGTTTCCGCTTAACGGCG |
| 537 | 1\|sg_Non_Targeting_Human_GA_0104\|Non_Targeting_Human | Non_Targeting_Human | GTAGGCGCGCCGCTCTCTAC |
| 538 | 1\|sg_Non_Targeting_Human_GA_0105\|Non_Targeting_Human | Non_Targeting_Human | CCATATCGGGGCGAGACATG |
| 539 | 1\|sg_Non_Targeting_Human_GA_0106\|Non_Targeting_Human | Non_Targeting_Human | TACTAACGCCGCTCCTACAG |
| 540 | 1\|sg_Non_Targeting_Human_GA_0107\|Non_Targeting_Human | Non_Targeting_Human | TGAGGATCATGTCGAGCGCC |
| 541 | 1\|sg_Non_Targeting_Human_GA_0108\|Non_Targeting_Human | Non_Targeting_Human | GGGCCCGCATAGGATATCGC |
| 542 | 1\|sg_Non_Targeting_Human_GA_0109\|Non_Targeting_Human | Non_Targeting_Human | TAGACAACCGCGGAGAATGC |
| 543 | 1\|sg_Non_Targeting_Human_GA_0110\|Non_Targeting_Human | Non_Targeting_Human | ACGGGCGGCTATCGCTGACT |
| 544 | 1\|sg_Non_Targeting_Human_GA_0111\|Non_Targeting_Human | Non_Targeting_Human | CGCGGAAATTTTACCGACGA |
| 545 | 1\|sg_Non_Targeting_Human_GA_0112\|Non_Targeting_Human | Non_Targeting_Human | CTTACAATCGTCGGTCCAAT |
| 546 | 1\|sg_Non_Targeting_Human_GA_0113\|Non_Targeting_Human | Non_Targeting_Human | GCGTGCGTCCCGGGTTACCC |
| 547 | 1\|sg_Non_Targeting_Human_GA_0114\|Non_Targeting_Human | Non_Targeting_Human | CGGAGTAACAAGCGGACGGA |
| 548 | 1\|sg_Non_Targeting_Human_GA_0115\|Non_Targeting_Human | Non_Targeting_Human | CGAGTGTTATACGCACCGTT |
| 549 | 1\|sg_Non_Targeting_Human_GA_0116\|Non_Targeting_Human | Non_Targeting_Human | CGACTAACCGGAAACTTTTT |
| 550 | 1\|sg_Non_Targeting_Human_GA_0117\|Non_Targeting_Human | Non_Targeting_Human | CAACGGGTTCTCCCGGCTAC |

TABLE 3-continued

| Control sgRNA Library | | | |
|---|---|---|---|
| SEQ ID NO. | gRNA Label | Gene | Nucleic Acid Sequence |
| 551 | 1\|sg_Non_Targeting_Human_GA_0118\|Non_Targeting_Human | Non_Targeting_Human | CAGGAGTCGCCGATACGCGT |
| 552 | 1\|sg_Non_Targeting_Human_GA_0119\|Non_Targeting_Human | Non_Targeting_Human | TTCACGTCGTCTCGCGACCA |
| 553 | 1\|sg_Non_Targeting_Human_GA_0120\|Non_Targeting_Human | Non_Targeting_Human | GTGTCGGATTCCGCCGCTTA |
| 554 | 1\|sg_Non_Targeting_Human_GA_0121\|Non_Targeting_Human | Non_Targeting_Human | CACGAACTCACACCGCGCGA |
| 555 | 1\|sg_Non_Targeting_Human_GA_0122\|Non_Targeting_Human | Non_Targeting_Human | CGCTAGTACGCTCCTCTATA |
| 556 | 1\|sg_Non_Targeting_Human_GA_0123\|Non_Targeting_Human | Non_Targeting_Human | TCGCGCTTGGGTTATACGCT |
| 557 | 1\|sg_Non_Targeting_Human_GA_0124\|Non_Targeting_Human | Non_Targeting_Human | CTATCTCGAGTGGTAATGCG |
| 558 | 1\|sg_Non_Targeting_Human_GA_0125\|Non_Targeting_Human | Non_Targeting_Human | AATCGACTCGAACTTCGTGT |
| 559 | 1\|sg_Non_Targeting_Human_GA_0126\|Non_Targeting_Human | Non_Targeting_Human | CCCGATGGACTATACCGAAC |
| 560 | 1\|sg_Non_Targeting_Human_GA_0127\|Non_Targeting_Human | Non_Targeting_Human | ACGTTCGAGTACGACCAGCT |
| 561 | 1\|sg_Non_Targeting_Human_GA_0128\|Non_Targeting_Human | Non_Targeting_Human | CGCGACGACTCAACCTAGTC |
| 562 | 1\|sg_Non_Targeting_Human_GA_0129\|Non_Targeting_Human | Non_Targeting_Human | GGTCACCGATCGAGAGCTAG |
| 563 | 1\|sg_Non_Targeting_Human_GA_0130\|Non_Targeting_Human | Non_Targeting_Human | CTCAACCGACCGTATGGTCA |
| 564 | 1\|sg_Non_Targeting_Human_GA_0131\|Non_Targeting_Human | Non_Targeting_Human | CGTATTCGACTCTCAACGCG |
| 565 | 1\|sg_Non_Targeting_Human_GA_0132\|Non_Targeting_Human | Non_Targeting_Human | CTAGCCGCCCAGATCGAGCC |
| 566 | 1\|sg_Non_Targeting_Human_GA_0133\|Non_Targeting_Human | Non_Targeting_Human | GAATCGACCGACACTAATGT |
| 567 | 1\|sg_Non_Targeting_Human_GA_0134\|Non_Targeting_Human | Non_Targeting_Human | ACTTCAGTTCGGCGTAGTCA |
| 568 | 1\|sg_Non_Targeting_Human_GA_0135\|Non_Targeting_Human | Non_Targeting_Human | GTGCGATGTCGCTTCAACGT |
| 569 | 1\|sg_Non_Targeting_Human_GA_0136\|Non_Targeting_Human | Non_Targeting_Human | CGCCTAATTTCCGGATCAAT |
| 570 | 1\|sg_Non_Targeting_Human_GA_0137\|Non_Targeting_Human | Non_Targeting_Human | CGTGGCCGGAACCGTCATAG |
| 571 | 1\|sg_Non_Targeting_Human_GA_0138\|Non_Targeting_Human | Non_Targeting_Human | ACCCTCCGAATCGTAACGGA |
| 572 | 1\|sg_Non_Targeting_Human_GA_0139\|Non_Targeting_Human | Non_Targeting_Human | AAACGGTACGACAGCGTGTG |
| 573 | 1\|sg_Non_Targeting_Human_GA_0140\|Non_Targeting_Human | Non_Targeting_Human | ACATAGTCGACGGCTCGATT |

TABLE 3-continued

Control sgRNA Library

| SEQ ID NO. | gRNA Label | Gene | Nucleic Acid Sequence |
|---|---|---|---|
| 574 | 1\|sg_Non_Targeting_Human_GA_0141\|Non_Targeting_Human | Non_Targeting_Human | GATGGCGCTTCAGTCGTCGG |
| 575 | 1\|sg_Non_Targeting_Human_GA_0142\|Non_Targeting_Human | Non_Targeting_Human | ATAATCCGGAAACGCTCGAC |
| 576 | 1\|sg_Non_Targeting_Human_GA_0143\|Non_Targeting_Human | Non_Targeting_Human | CGCCGGGCTGACAATTAACG |
| 577 | 1\|sg_Non_Targeting_Human_GA_0144\|Non_Targeting_Human | Non_Targeting_Human | CGTCGCCATATGCCGGTGGC |
| 578 | 1\|sg_Non_Targeting_Human_GA_0145\|Non_Targeting_Human | Non_Targeting_Human | CGGGCCTATAACACCATCGA |
| 579 | 1\|sg_Non_Targeting_Human_GA_0146\|Non_Targeting_Human | Non_Targeting_Human | CGCCGTTCCGAGATACTTGA |
| 580 | 1\|sg_Non_Targeting_Human_GA_0147\|Non_Targeting_Human | Non_Targeting_Human | CGGGACGTCGCGAAAATGTA |
| 581 | 1\|sg_Non_Targeting_Human_GA_0148\|Non_Targeting_Human | Non_Targeting_Human | TCGGCATACGGGACACACGC |
| 582 | 1\|sg_Non_Targeting_Human_GA_0149\|Non_Targeting_Human | Non_Targeting_Human | AGCTCCATCGCCGCGATAAT |
| 583 | 1\|sg_Non_Targeting_Human_GA_0150\|Non_Targeting_Human | Non_Targeting_Human | ATCGTATCATCAGCTAGCGC |
| 584 | 1\|sg_Non_Targeting_Human_GA_0151\|Non_Targeting_Human | Non_Targeting_Human | TCGATCGAGGTTGCATTCGG |
| 585 | 1\|sg_Non_Targeting_Human_GA_0152\|Non_Targeting_Human | Non_Targeting_Human | CTCGACAGTTCGTCCCGAGC |
| 586 | 1\|sg_Non_Targeting_Human_GA_0153\|Non_Targeting_Human | Non_Targeting_Human | CGGTAGTATTAATCGCTGAC |
| 587 | 1\|sg_Non_Targeting_Human_GA_0154\|Non_Targeting_Human | Non_Targeting_Human | TGAACGCGTGTTTCCTTGCA |
| 588 | 1\|sg_Non_Targeting_Human_GA_0155\|Non_Targeting_Human | Non_Targeting_Human | CGACGCTAGGTAACGTAGAG |
| 589 | 1\|sg_Non_Targeting_Human_GA_0156\|Non_Targeting_Human | Non_Targeting_Human | CATTGTTGAGCGGGCGCGCT |
| 590 | 1\|sg_Non_Targeting_Human_GA_0157\|Non_Targeting_Human | Non_Targeting_Human | CCGCTATTGAAACCGCCCAC |
| 591 | 1\|sg_Non_Targeting_Human_GA_0158\|Non_Targeting_Human | Non_Targeting_Human | AGACACGTCACCGGTCAAAA |
| 592 | 1\|sg_Non_Targeting_Human_GA_0159\|Non_Targeting_Human | Non_Targeting_Human | TTTACGATCTAGCGGCGTAG |
| 593 | 1\|sg_Non_Targeting_Human_GA_0160\|Non_Targeting_Human | Non_Targeting_Human | TTCGCACGATTGCACCTTGG |
| 594 | 1\|sg_Non_Targeting_Human_GA_0161\|Non_Targeting_Human | Non_Targeting_Human | GGTTAGAGACTAGGCGCGCG |
| 595 | 1\|sg_Non_Targeting_Human_GA_0162\|Non_Targeting_Human | Non_Targeting_Human | CCTCCGTGCTAACGCGGACG |
| 596 | 1\|sg_Non_Targeting_Human_GA_0163\|Non_Targeting_Human | Non_Targeting_Human | TTATCGCGTAGTGCTGACGT |
| 597 | 1\|sg_Non_Targeting_Human_GA_0164\|Non_Targeting_Human | Non_Targeting_Human | TACGCTTGCGTTTAGCGTCC |

TABLE 3-continued

Control sgRNA Library

| SEQ ID NO. | gRNA Label | Gene | Nucleic Acid Sequence |
|---|---|---|---|
| 598 | 1\|sg_Non_Targeting_Human_GA_0165\|Non_Targeting_Human | Non_Targeting_Human | CGCGGCCCACGCGTCATCGC |
| 599 | 1\|sg_Non_Targeting_Human_GA_0166\|Non_Targeting_Human | Non_Targeting_Human | AGCTCGCCATGTCGGTTCTC |
| 600 | 1\|sg_Non_Targeting_Human_GA_0167\|Non_Targeting_Human | Non_Targeting_Human | AACTAGCCCGAGCAGCTTCG |
| 601 | 1\|sg_Non_Targeting_Human_GA_0168\|Non_Targeting_Human | Non_Targeting_Human | CGCAAGGTGTCGGTAACCCT |
| 602 | 1\|sg_Non_Targeting_Human_GA_0169\|Non_Targeting_Human | Non_Targeting_Human | CTTCGACGCCATCGTGCTCA |
| 603 | 1\|sg_Non_Targeting_Human_GA_0170\|Non_Targeting_Human | Non_Targeting_Human | TCCTGGATACCGCGTGGTTA |
| 604 | 1\|sg_Non_Targeting_Human_GA_0171\|Non_Targeting_Human | Non_Targeting_Human | ATAGCCGCCGCTCATTACTT |
| 605 | 1\|sg_Non_Targeting_Human_GA_0172\|Non_Targeting_Human | Non_Targeting_Human | GTCGTCCGGGATTACAAAAT |
| 606 | 1\|sg_Non_Targeting_Human_GA_0173\|Non_Targeting_Human | Non_Targeting_Human | TAATGCTGCACACGCCGAAT |
| 607 | 1\|sg_Non_Targeting_Human_GA_0174\|Non_Targeting_Human | Non_Targeting_Human | TATCGCTTCCGATTAGTCCG |
| 608 | 1\|sg_Non_Targeting_Human_GA_0175\|Non_Targeting_Human | Non_Targeting_Human | GTACCATACCGCGTACCCTT |
| 609 | 1\|sg_Non_Targeting_Human_GA_0176\|Non_Targeting_Human | Non_Targeting_Human | TAAGATCCGCGGGTGGCAAC |
| 610 | 1\|sg_Non_Targeting_Human_GA_0177\|Non_Targeting_Human | Non_Targeting_Human | GTAGACGTCGTGAGCTTCAC |
| 611 | 1\|sg_Non_Targeting_Human_GA_0178\|Non_Targeting_Human | Non_Targeting_Human | TCGCGGACATAGGGCTCTAA |
| 612 | 1\|sg_Non_Targeting_Human_GA_0179\|Non_Targeting_Human | Non_Targeting_Human | AGCGCAGATAGCGCGTATCA |
| 613 | 1\|sg_Non_Targeting_Human_GA_0180\|Non_Targeting_Human | Non_Targeting_Human | GTTCGCTTCGTAACGAGGAA |
| 614 | 1\|sg_Non_Targeting_Human_GA_0181\|Non_Targeting_Human | Non_Targeting_Human | GACCCCCGATAACTTTTGAC |
| 615 | 1\|sg_Non_Targeting_Human_GA_0182\|Non_Targeting_Human | Non_Targeting_Human | ACGTCCATACTGTCGGCTAC |
| 616 | 1\|sg_Non_Targeting_Human_GA_0183\|Non_Targeting_Human | Non_Targeting_Human | GTACCATTGCCGGCTCCCTA |
| 617 | 1\|sg_Non_Targeting_Human_GA_0184\|Non_Targeting_Human | Non_Targeting_Human | TGGTTCCGTAGGTCGGTATA |
| 618 | 1\|sg_Non_Targeting_Human_GA_0185\|Non_Targeting_Human | Non_Targeting_Human | TCTGGCTTGACACGACCGTT |
| 619 | 1\|sg_Non_Targeting_Human_GA_0186\|Non_Targeting_Human | Non_Targeting_Human | CGCTAGGTCCGGTAAGTGCG |
| 620 | 1\|sg_Non_Targeting_Human_GA_0187\|Non_Targeting_Human | Non_Targeting_Human | AGCACGTAATGTCCGTGGAT |
| 621 | 1\|sg_Non_Targeting_Human_GA_0188\|Non_Targeting_Human | Non_Targeting_Human | AAGGCGCGCGAATGTGGCAG |

TABLE 3-continued

Control sgRNA Library

| SEQ ID NO. | gRNA Label | Gene | Nucleic Acid Sequence |
|---|---|---|---|
| 622 | 1\|sg_Non_Targeting_Human_GA_0189\|Non_Targeting_Human | Non_Targeting_Human | ACTGCGGAGCGCCCAATATC |
| 623 | 1\|sg_Non_Targeting_Human_GA_0190\|Non_Targeting_Human | Non_Targeting_Human | CGTCGAGTGCTCGAACTCCA |
| 624 | 1\|sg_Non_Targeting_Human_GA_0191\|Non_Targeting_Human | Non_Targeting_Human | TCGCAGCGGCGTGGGATCGG |
| 625 | 1\|sg_Non_Targeting_Human_GA_0192\|Non_Targeting_Human | Non_Targeting_Human | ATCTGTCCTAATTCGGATCG |
| 626 | 1\|sg_Non_Targeting_Human_GA_0193\|Non_Targeting_Human | Non_Targeting_Human | TGCGGCGTAATGCTTGAAAG |
| 627 | 1\|sg_Non_Targeting_Human_GA_0194\|Non_Targeting_Human | Non_Targeting_Human | CGAACTTAATCCCGTGGCAA |
| 628 | 1\|sg_Non_Targeting_Human_GA_0195\|Non_Targeting_Human | Non_Targeting_Human | GCCGTGTTGCTGGATACGCC |
| 629 | 1\|sg_Non_Targeting_Human_GA_0196\|Non_Targeting_Human | Non_Targeting_Human | TACCCTCCGGATACGGACTG |
| 630 | 1\|sg_Non_Targeting_Human_GA_0197\|Non_Targeting_Human | Non_Targeting_Human | CCGTTGGACTATGGCGGGTC |
| 631 | 1\|sg_Non_Targeting_Human_GA_0198\|Non_Targeting_Human | Non_Targeting_Human | GTACGGGCGATCATCCACA |
| 632 | 1\|sg_Non_Targeting_Human_GA_0199\|Non_Targeting_Human | Non_Targeting_Human | AAGAGTAGTAGACGCCCGGG |
| 633 | 1\|sg_Non_Targeting_Human_GA_0200\|Non_Targeting_Human | Non_Targeting_Human | AAGAGCGAATCGATTTCGTG |
| 634 | 3\|sg_hCDC16_CC_1\|CDC16 | CDC16 | TCAACACCAGTGCCTGACGG |
| 635 | 3\|sg_hCDC16_CC_2\|CDC16 | CDC16 | AAAGTAGCTTCACTCTCTCG |
| 636 | 3\|sg_hCDC16_CC_3\|CDC16 | CDC16 | GAGCCAACCAATAGATGTCC |
| 637 | 3\|sg_hCDC16_CC_4\|CDC16 | CDC16 | GCGCCGCCATGAACCTAGAG |
| 638 | 3\|sg_hGTF2B_CC_1\|GTF2B | GTF2B | ACAAAGGTTGGAACAGAACC |
| 639 | 3\|sg_hGTF2B_CC_2\|GTF2B | GTF2B | GGTGACCGGGTTATTGATGT |
| 640 | 3\|sg_hGTF2B_CC_3\|GTF2B | GTF2B | TTAGTGGAGGACTACAGAGC |
| 641 | 3\|sg_hGTF2B_CC_4\|GTF2B | GTF2B | ACATATAGCCCGTAAAGCTG |
| 642 | 3\|sg_hHSPA5_CC_1\|HSPA5 | HSPA5 | CGTTGGCGATGATCTCCACG |
| 643 | 3\|sg_hHSPA5_CC_2\|HSPA5 | HSPA5 | TGGCCTTTTCTACCTCGCGC |
| 644 | 3\|sg_hHSPA5_CC_3\|HSPA5 | HSPA5 | AATGGAGATACTCATCTGGG |
| 645 | 3\|sg_hHSPA5_CC_4\|HSPA5 | HSPA5 | GAAGCCCGTCCAGAAAGTGT |
| 646 | 3\|sg_hHSPA9_CC_1\|HSPA9 | HSPA9 | CAATCTGAGGAACTCCACGA |
| 647 | 3\|sg_hHSPA9_CC_2\|HSPA9 | HSPA9 | AGGCTGCGGCGCCCACGAGA |
| 648 | 3\|sg_hHSPA9_CC_3\|HSPA9 | HSPA9 | ACTTTGACCAGGCCTTGCTA |

TABLE 3-continued

Control sgRNA Library

| SEQ ID NO. | gRNA Label | Gene | Nucleic Acid Sequence |
|---|---|---|---|
| 649 | 3\|sg_hHSPA9_CC_4\|HSPA9 | HSPA9 | ACCTTCCATAACTGCCACGC |
| 650 | 3\|sg_hPAFAH1B1_CC_1\|PAFAH1B1 | PAFAH1B1 | CGAGGCGTACATACCCAAGG |
| 651 | 3\|sg_hPAFAH1B1_CC_2\|PAFAH1B1 | PAFAH1B1 | ATGGTACGGCCAAATCAAGA |
| 652 | 3\|sg_hPAFAH1B1_CC_3\|PAFAH1B1 | PAFAH1B1 | TCTTGTAATCCCATACGCGT |
| 653 | 3\|sg_hPAFAH1B1_CC_4\|PAFAH1B1 | PAFAH1B1 | ATTCACAGGACACAGAGAAT |
| 654 | 3\|sg_hPCNA_CC_1\|PCNA | PCNA | CCAGGGCTCCATCCTCAAGA |
| 655 | 3\|sg_hPCNA_CC_2\|PCNA | PCNA | TGAGCTGCACCAAAGAGACG |
| 656 | 3\|sg_hPCNA_CC_3\|PCNA | PCNA | ATGTCTGCAGATGTACCCCT |
| 657 | 3\|sg_hPCNA_CC_4\|PCNA | PCNA | CGAAGATAACGCGGATACCT |
| 658 | 3\|sg_hPOLR2L_CC_1\|POLR2L | POLR2L | GCTGCAGGCCGAGTACACCG |
| 659 | 3\|sg_hPOLR2L_CC_2\|POLR2L | POLR2L | ACAAGTGGGAGGCTTACCTG |
| 660 | 3\|sg_hPOLR2L_CC_3\|POLR2L | POLR2L | GCAGCGTACAGGGATGATCA |
| 661 | 3\|sg_hPOLR2L_CC_4\|POLR2L | POLR2L | GCAGTAGCGCTTCAGGCCCA |
| 662 | 3\|sg_hRPL9_CC_1\|RPL9 | RPL9 | CAAATGGTGGGTAACAGAA |
| 663 | 3\|sg_hRPL9_CC_2\|RPL9 | RPL9 | GAAAGGAACTGGCTACCGTT |
| 664 | 3\|sg_hRPL9_CC_3\|RPL9 | RPL9 | AGGGCTTCCGTTACAAGATG |
| 665 | 3\|sg_hRPL9_CC_4\|RPL9 | RPL9 | GAACAAGCAACACCTAAAAG |
| 666 | 3\|sg_hSF3A3_CC_1\|SF3A3 | SF3A3 | TGAGGAGAAGGAACGGCTCA |
| 667 | 3\|sg_hSF3A3_CC_2\|SF3A3 | SF3A3 | GGAAGAATGCAGAGTATAAG |
| 668 | 3\|sg_hSF3A3_CC_3\|SF3A3 | SF3A3 | GGAATTTGAGGAACTCCTGA |
| 669 | 3\|sg_hSF3A3_CC_4\|SF3A3 | SF3A3 | GCTCACCGGCCATCCAGGAA |
| 670 | 3\|sg_hSF3B3_CC_1\|SF3B3 | SF3B3 | ACTGGCCAGGAACGATGCGA |
| 671 | 3\|sg_hSF3B3_CC_2\|SF3B3 | SF3B3 | GCAGCTCCAAGATCTTCCCA |
| 672 | 3\|sg_hSF3B3_CC_3\|SF3B3 | SF3B3 | GAATGAGTACACAGAACGGA |
| 673 | 3\|sg_hSF3B3_CC_4\|SF3B3 | SF3B3 | GGAGCAGGACAAGGTCGGGG |

Example 2—BRD9 Degrader Depletes BRD9 Protein

The following example demonstrates the depletion of the BRD9 protein in synovial sarcoma cells treated with a BRD9 degrader.

Procedure: Cells were treated with DMSO or the BRD9 degrader, Compound 1 (also known as dBRD9, see Remillard et al, *Angew. Chem. Int. Ed. Engl.* 56 (21): 5738-5743 (2017); see structure of Compound 1 below), for indicated doses and timepoints.

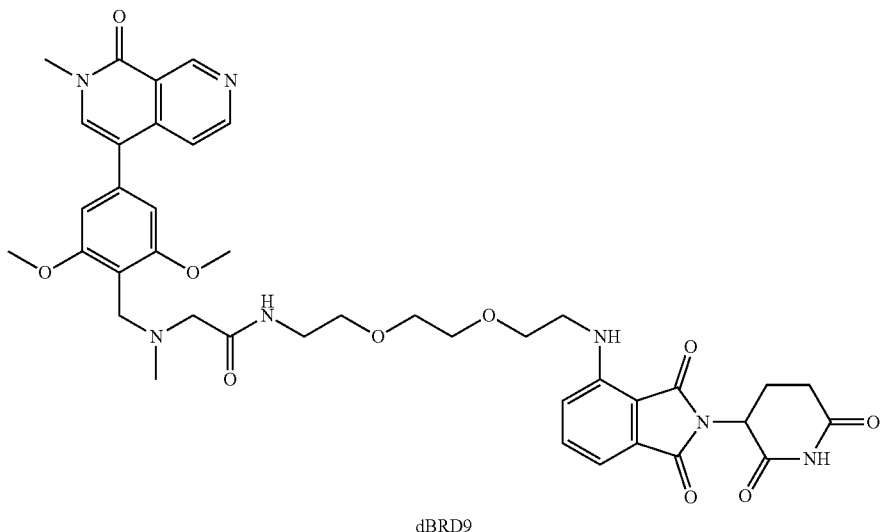

dBRD9

(Compound 1)

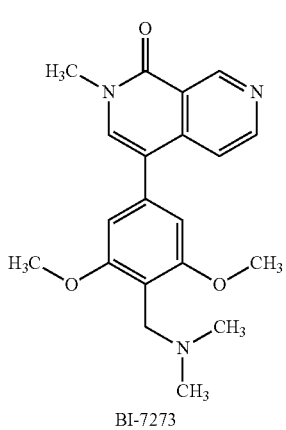

BI-7273

(Compound 2)

Figure 2:
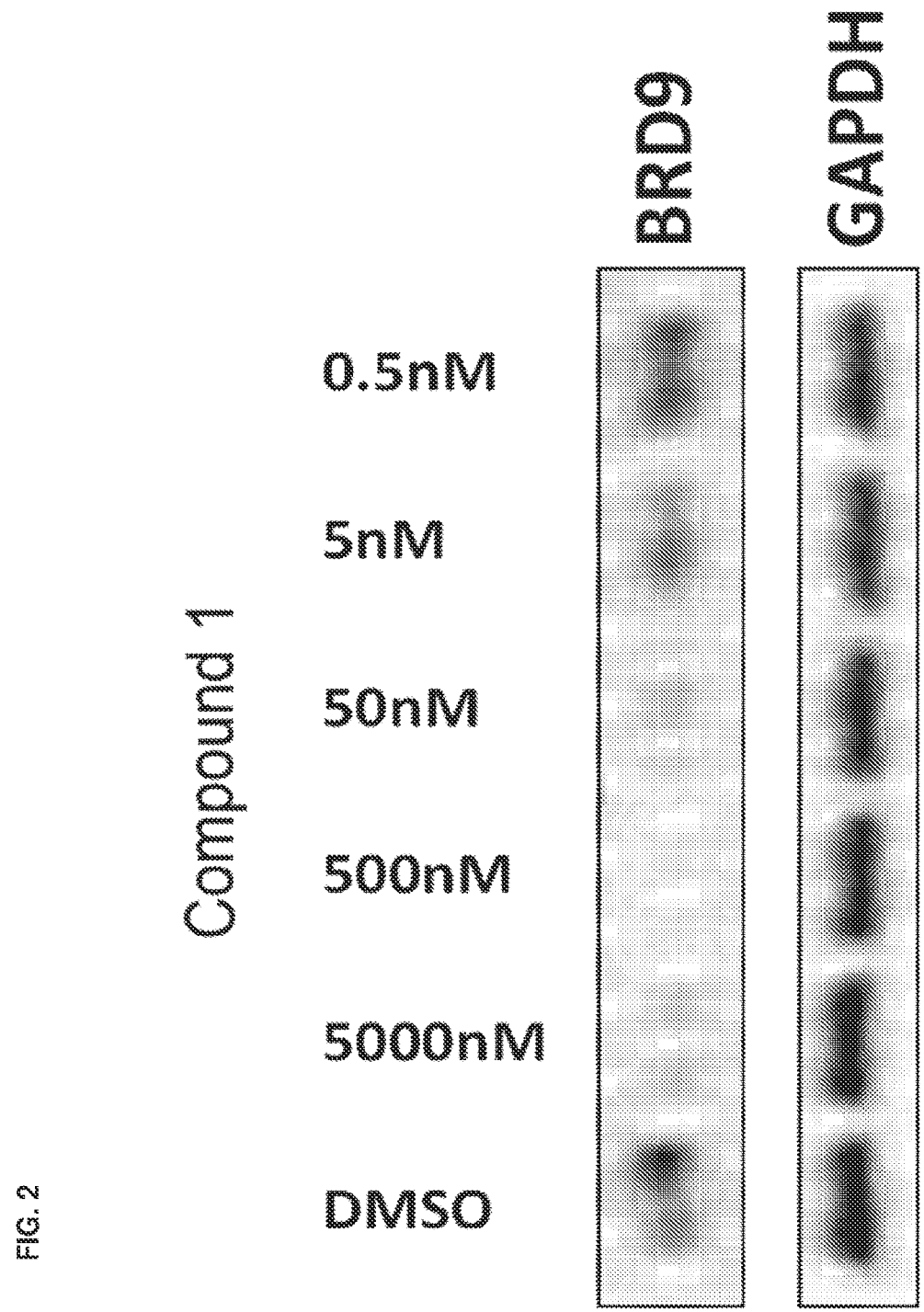
FIG. 2 is an image illustrating dose dependent depletion of BRD9 levels in a synovial sarcoma cell line (SYO1) in the presence of a BRD9 degrader.
Figure 3:
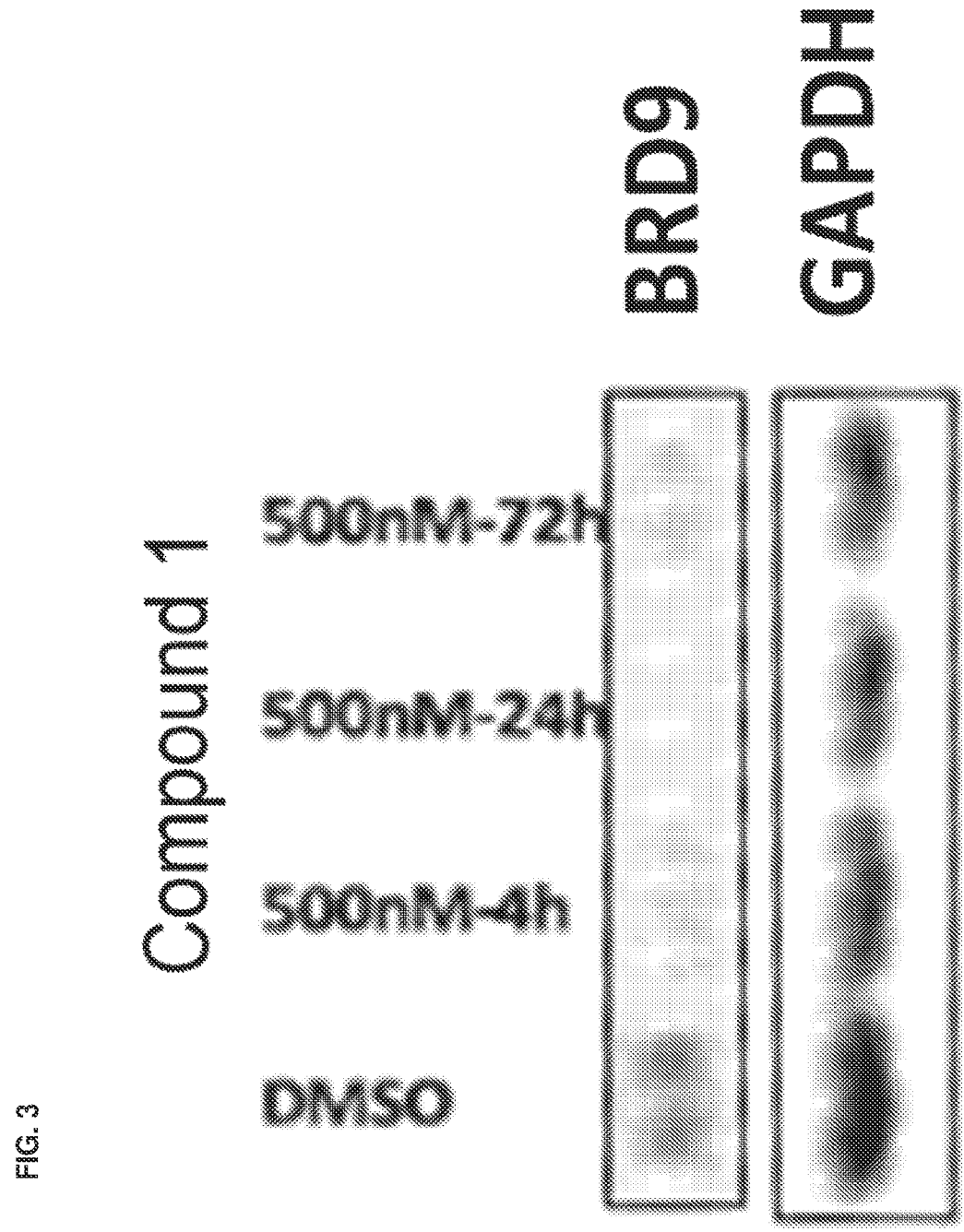
FIG. 3 is an image illustrating sustained suppression of BRD9 levels in a synovial sarcoma cell line (SYO1) in the presence of a BRD9 degrader over 72 hours.
Figure 4:
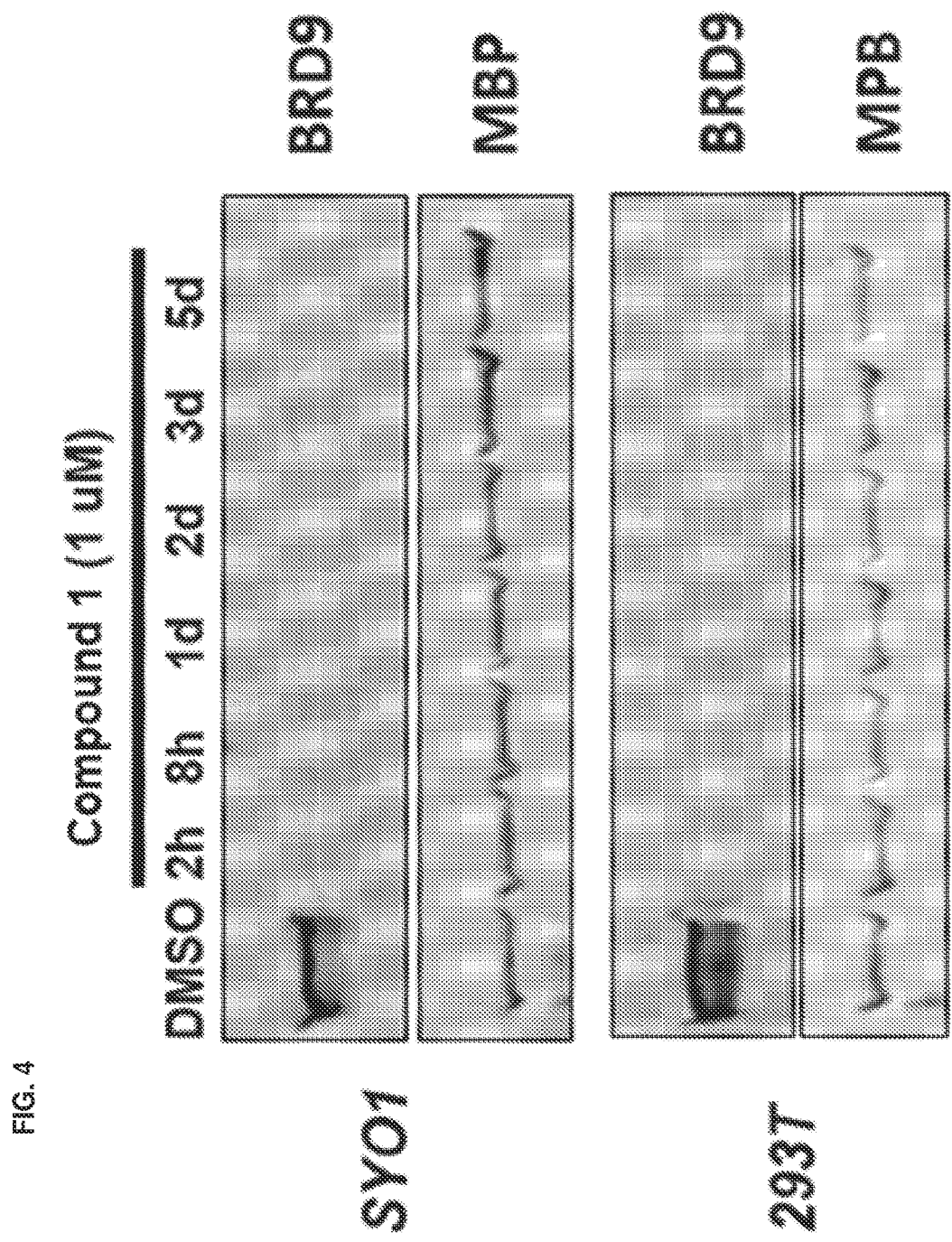
FIG. 4 is an image illustrating sustained suppression of BRD9 levels in two cell lines (293T and SYO1) in the presence of a BRD9 degrader over 5 days.

Whole cell extracts were fractionated by SDS-PAGE and transferred to a polyvinylidene difluoride membrane using a transfer apparatus according to the manufacturer's protocols (Bio-Rad). After incubation with 5% nonfat milk in TBST (10 mM Tris, pH 8.0, 150 mM NaCl, 0.5% Tween 20) for 60 minutes, the membrane was incubated with antibodies against BRD9 (1:1,000, Bethyl laboratory A303-781A), GAPDH (1:5,000, Cell Signaling Technology), and/or MBP (1:1,000, BioRad) overnight at 4° C. Membranes were washed three times for 10 min and incubated with anti-mouse or anti-rabbit antibodies conjugated with either horseradish peroxidase (HRP, FIGS. 2-3) or IRDye (FIG. 4, 1:20,000, LI-COR) for at least 1 h. Blots were washed with TBST three times and developed with either the ECL system according to the manufacturer's protocols (FIGS. 2-3) or scanned on an Odyssey CLx Imaging system (FIG. 4).

Results: Treatment of SYO1 synovial sarcoma cells with the BRD9 degrader Compound 1 results in dose dependent (FIG. 2) and time dependent (FIG. 3) depletion of BRD9 in the cells. Further, as shown in FIG. 4, the depletion of BRD9 by Compound 1 is replicated in a non-synovial sarcoma cell line (293T) and may be sustained for at least 5 days.

Example 3—Inhibition of Growth of Synovial Cell Lines by BRD9 Inhibitors and BRD9 Degraders The following example demonstrates that BRD9 degraders and inhibitors selectively inhibit growth of synovial sarcoma cells.

Figure 5:
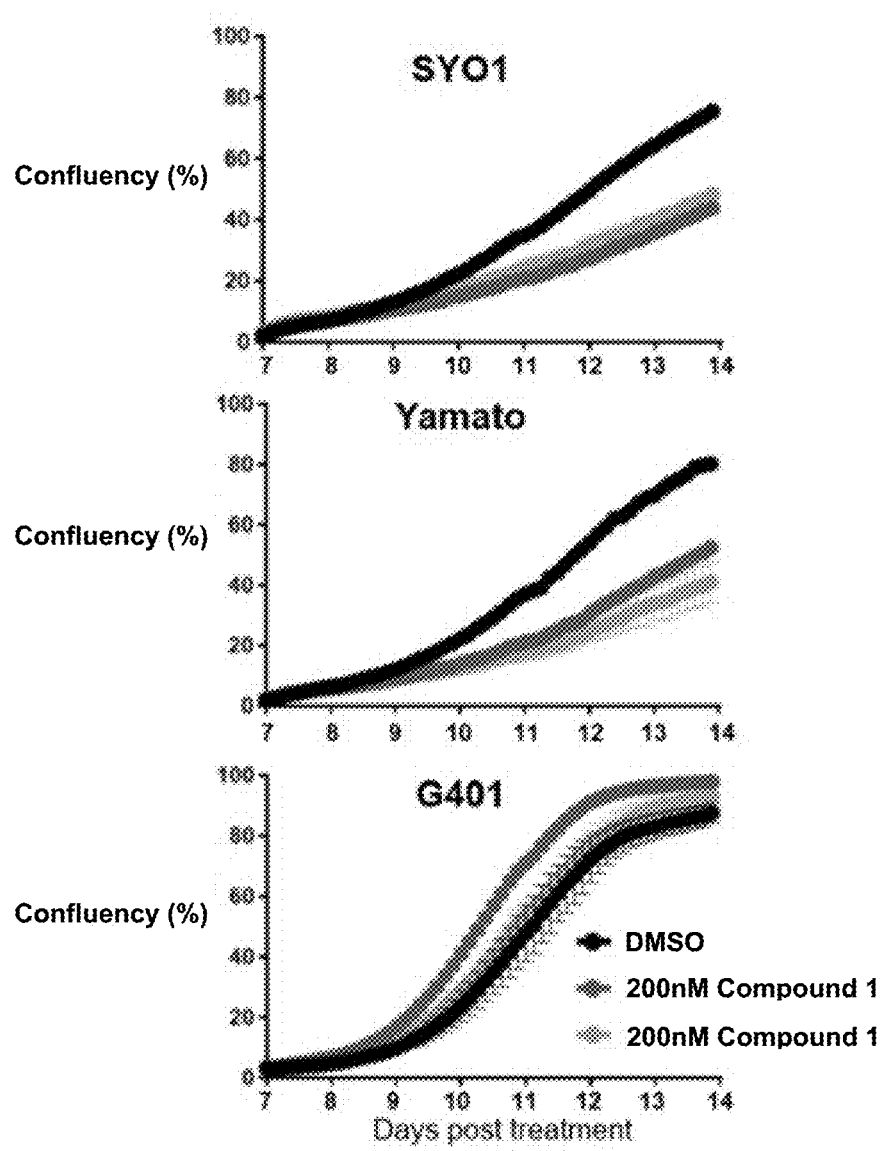
FIG. 5 is an image illustrating sustained suppression of BRD9 levels in synovial sarcoma cell lines (SYO1 and Yamato) in the presence of a BRD9 degrader over 7 days compared to the levels in cells treated with CRISPR reagents.

Procedures:

Cells were treated with DMSO or the BRD9 degrader, Compound 1, at indicated concentrations, and proliferation was monitored from day 7 to day 14 by measuring confluency over time using an IncuCyte live cell analysis system (FIG. 5). Growth medium and compounds were refreshed every 3-4 days.

Cells were seeded into 12-well plates and treated with DMSO, 1 μM BRD9 inhibitor, Compound 2 (also known as BI-7273, see Martin et al, *J Med Chem.* 59 (10): 4462-4475 (2016); see structure of Compound 2 below), or 1 μM BRD9 degrader, Compound 1.

Figure 6:
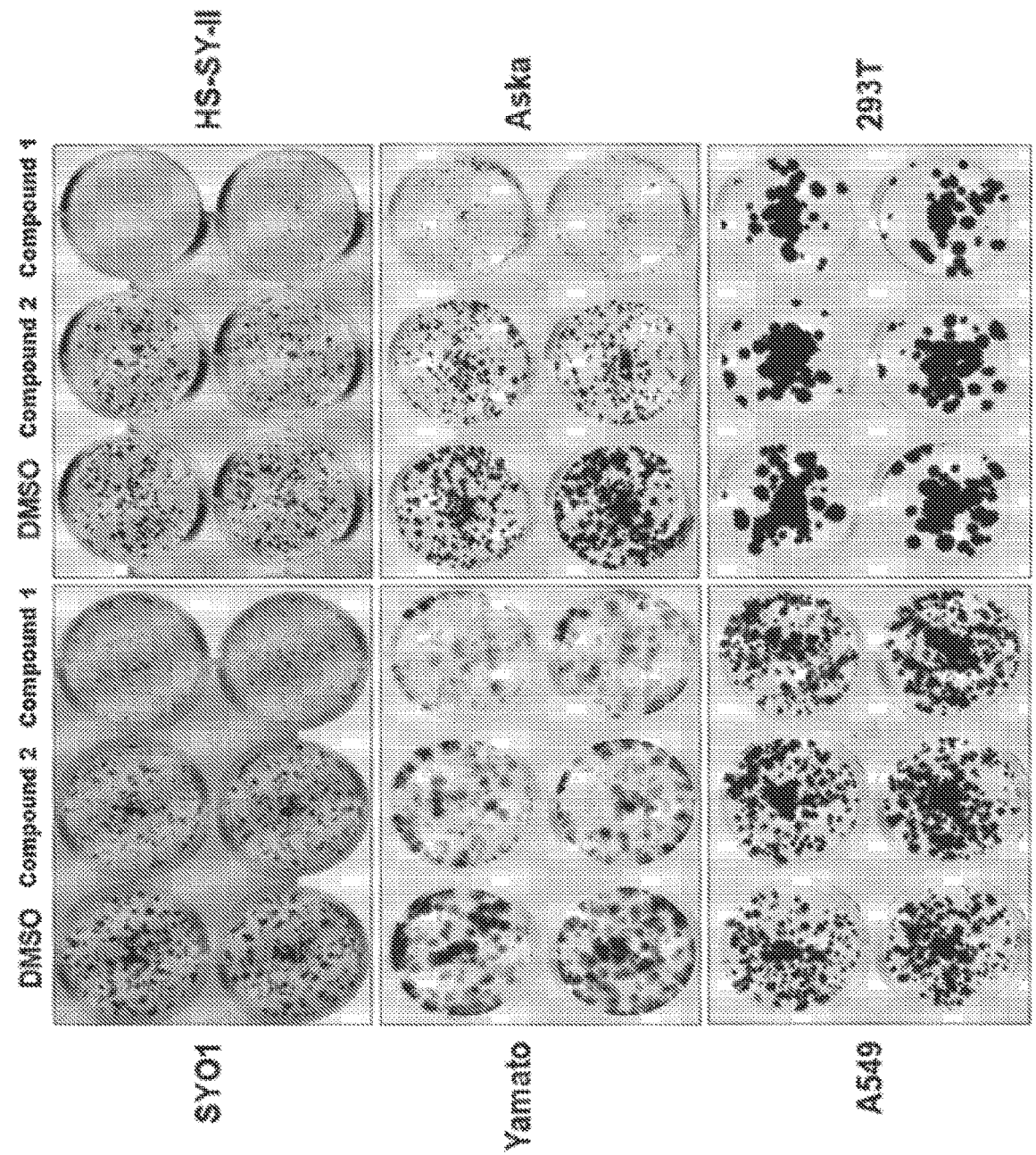
FIG. 6 is an image illustrating the effect on cell growth of six cell lines (SYO1, Yamato, A549, HS-SY-II, ASKA, and 293T) in the presence of a BRD9 degrader and a BRD9 inhibitor.

The number of cells was optimized for each cell line. Growth medium and compounds were refreshed every 3-5 days. SYO1, Yamato, A549, 293T and HS-SY-II cells were fixed and stained at day 11. ASKA cells were fixed and stained at day 23. Staining was done by incubation with crystal violet solution (0.5 g Crystal Violet, 27 ml 37% Formaldehyde, 100 mL 10×PBS, 10 mL Methanol, 863 dH20 to 1L) for 30 min followed by 3× washes with water and drying the plates for at least 24 h at room temperature. Subsequently plates were scanned on an Odyssey CLx Imaging system (FIG. 6).

Figure 7:
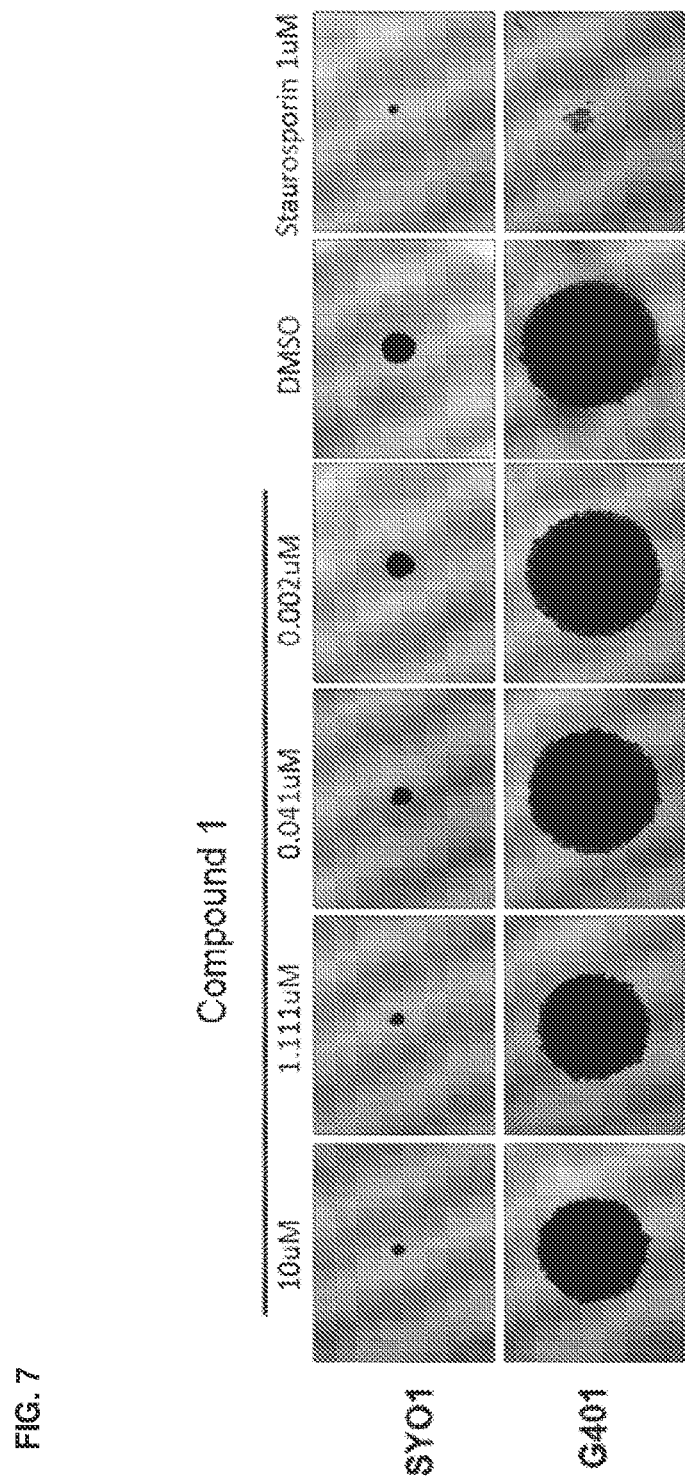
FIG. 7 is an image illustrating the effect on cell growth of two cell lines (SYO1 and G401) in the presence of a BRD9 degrader.

Cells were seeded into 96-well ultra low cluster plate (Costar, #7007) in 200 UL complete media and treated at day 2 with DMSO, Staurosporin, or BRD9 degarder, Compound 1, at indicated doses (FIG. 7). Media and compounds were changed every 5 d and cell colonies were imaged at day 14.

Results: As shown in FIGS. 5, 6, and 7, treatment of synovial sarcoma cell lines (SYO1, Yamato, HS-SY-II, and ASKA) with a BRD9 inhibitor, Compound 2, or a BRD9 degrader, Compound 1, results in inhibition of the growth of the cells, but does not result in inhibition of the growth of non-synovial control cancer cell lines (293T, $A^{549}$, G401).

Example 4—Selective Inhibition of Growth of Synovial Cell Lines by BRD9 Degraders and BRD9 Binders The following example demonstrates that BRD9 degraders and binders selectively inhibit growth of synovial sarcoma cells.

Procedure: Cells were seeded into 6-well or 12-well plates and were treated daily with a BRD9 degrader (Compound 1), a bromo-domain BRD9 binder (Compound 2), E3 ligase binder (lenalidomide), DMSO, or staurosporin (positive control for cell killing), at indicated concentrations. The number of cells was optimized for each cell line. Growth media was refreshed every 5 days. By day 14, medium was removed, cells were washed with PBS, and stained using 500 µL of 0.005% (w/v) crystal violet solution in 25% (v/v) methanol for at least 1 hour at room temperature. Subsequently plates were scanned on an Odyssey CLx Imaging system.

Figure 8:
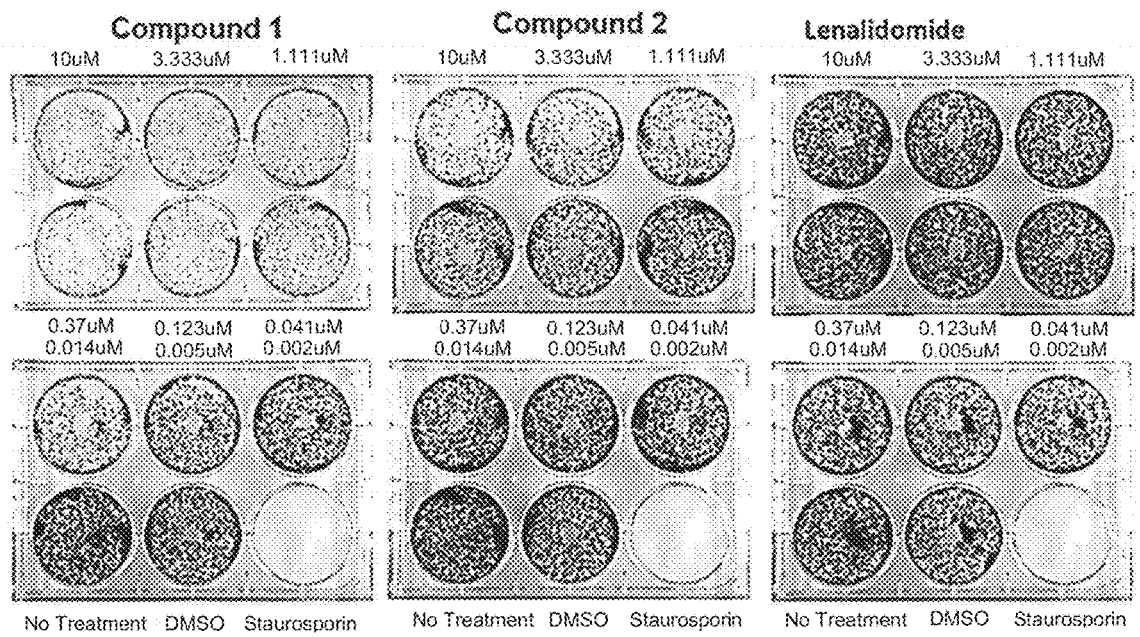
FIG. 8 is an image illustrating the effect on cell growth of three synovial sarcoma cell lines (SYO1, HS-SY-II, and ASKA) in the presence of a BRD9 degrader, BRD9 binder and $E^3$ ligase binder.
Figure 8:
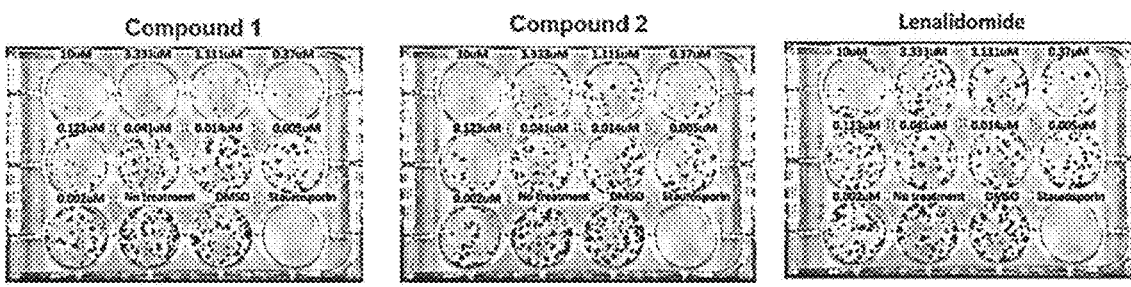
Figure 8:
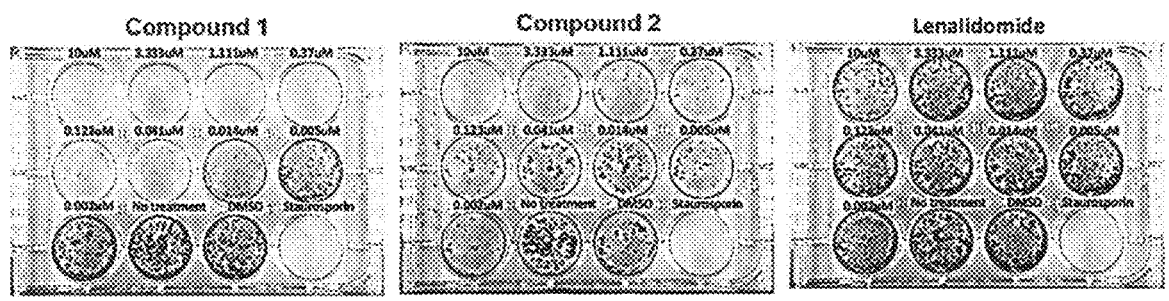
Figure 9:
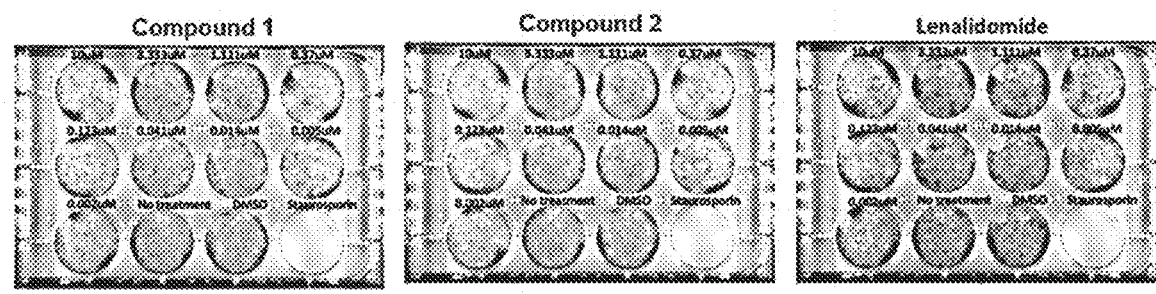
FIG. 9 is an image illustrating the effect on cell growth of three non-synovial sarcoma cell lines (RD, HCT116, and Calu6) in the presence of a BRD9 degrader, BRD9 binder and $E^3$ ligase binder.
Figure 9:
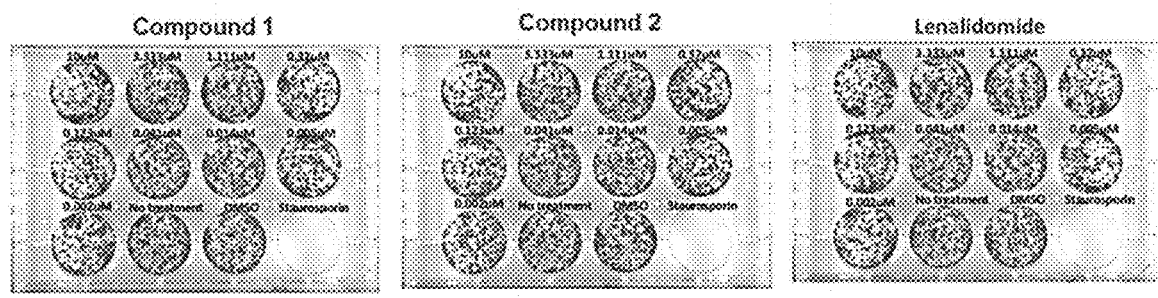
Figure 9:
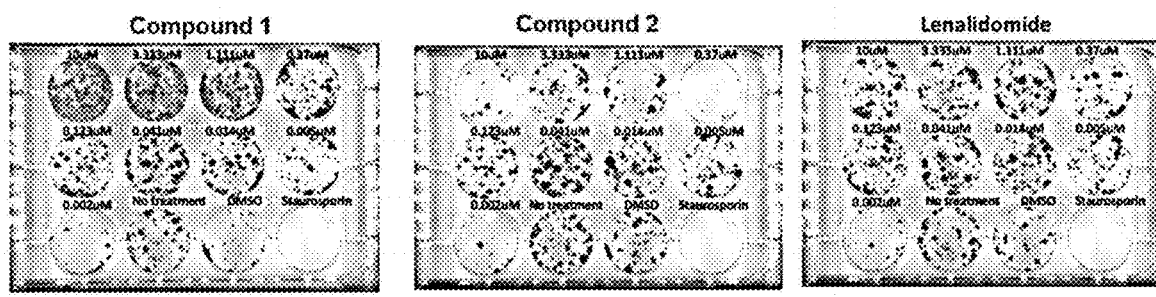
Figure 10:
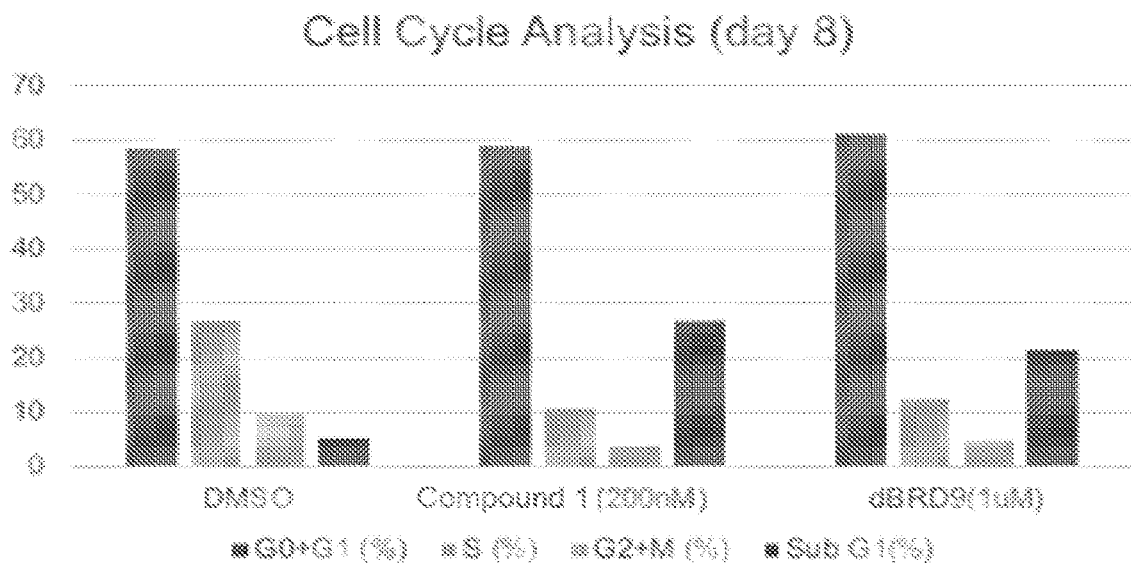
FIG. 10 is a graph illustrating the percentage of SYO1 in various cell cycle phases following treatment with DMSO, Compound 1 at 200 nM, or Compound 1 at 1 µM for 8 or 13 days.
Figure 10:
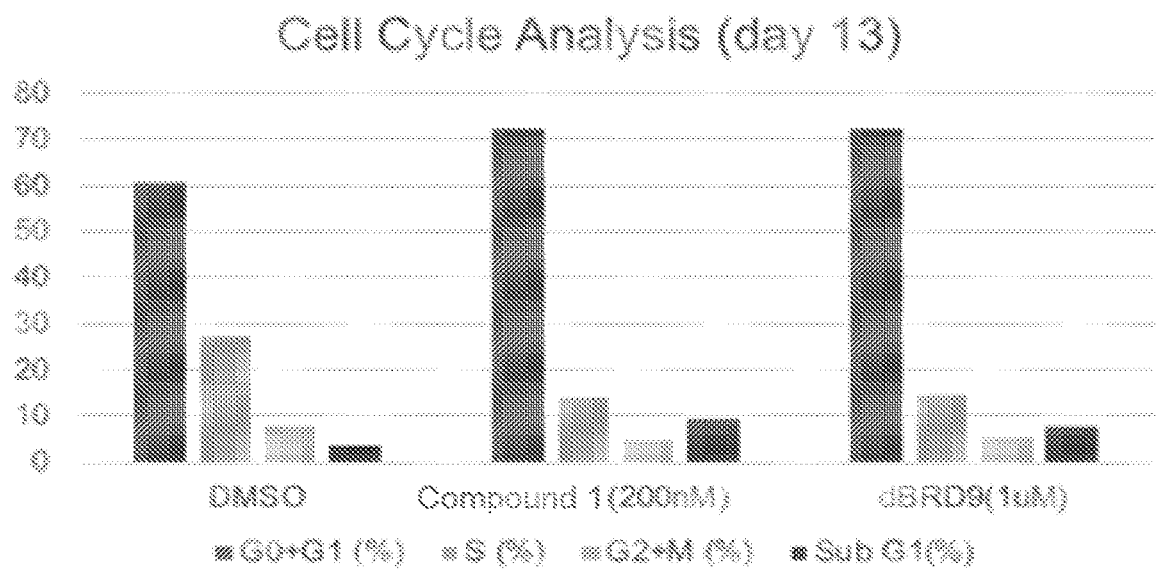
Figure 11:
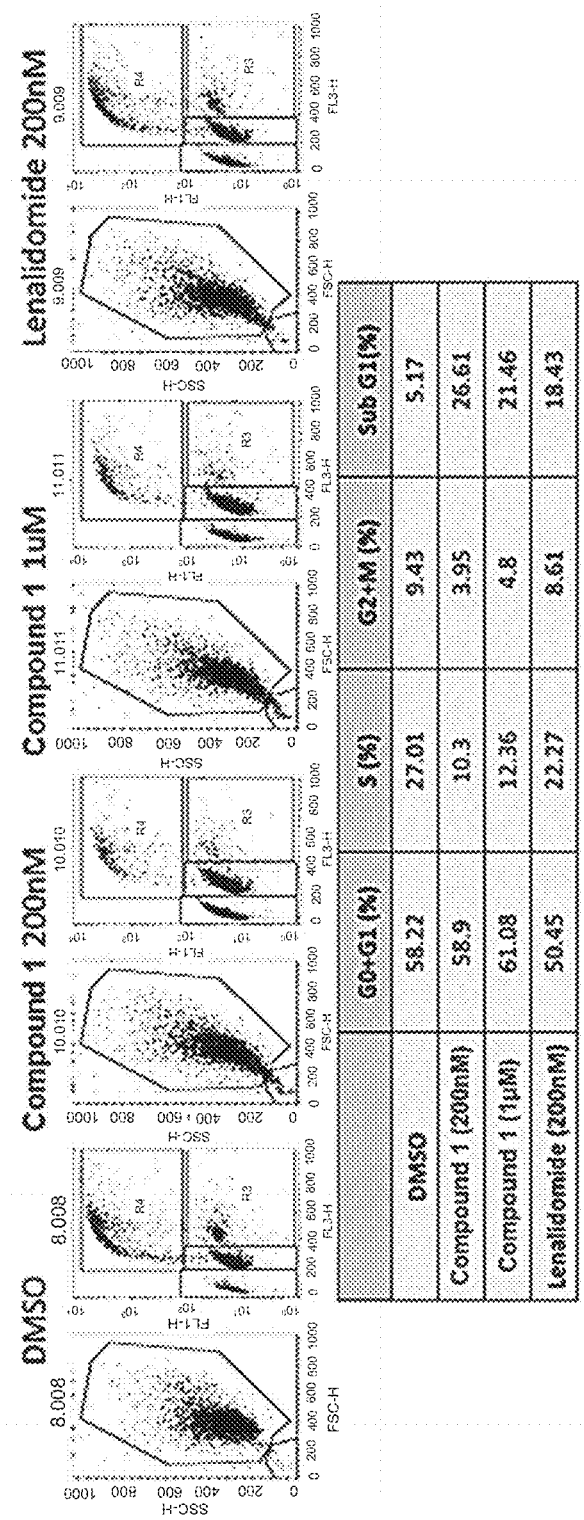
FIG. 11 is a series of contour plots illustrating the percentage of SYO1 cells in various cell cycle phases following treatment with DMSO, Compound 1 at 200 nM, Compound 1 at 1 UM, or lenalidomide at 200 nM for 8 days. Numerical values corresponding to each contour plot are found in the table below.
Figure 12:
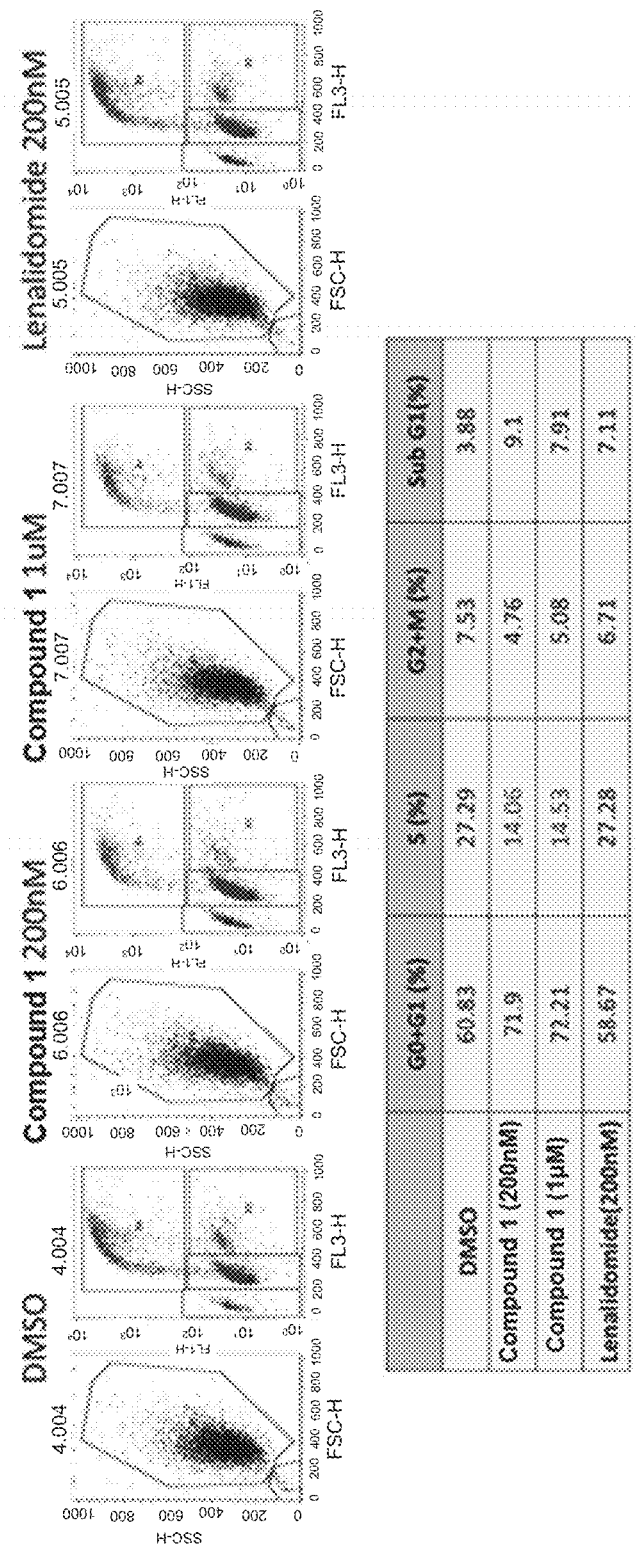
FIG. 12 is a series of contour plots illustrating the percentage of SYO1 cells in various cell cycle phases following treatment with DMSO, Compound 1 at 200 nM, Compound 1 at 1 UM, or lenalidomide at 200 nM for 13 days. Numerical values corresponding to each contour plot are found in the table below.
Figure 13:
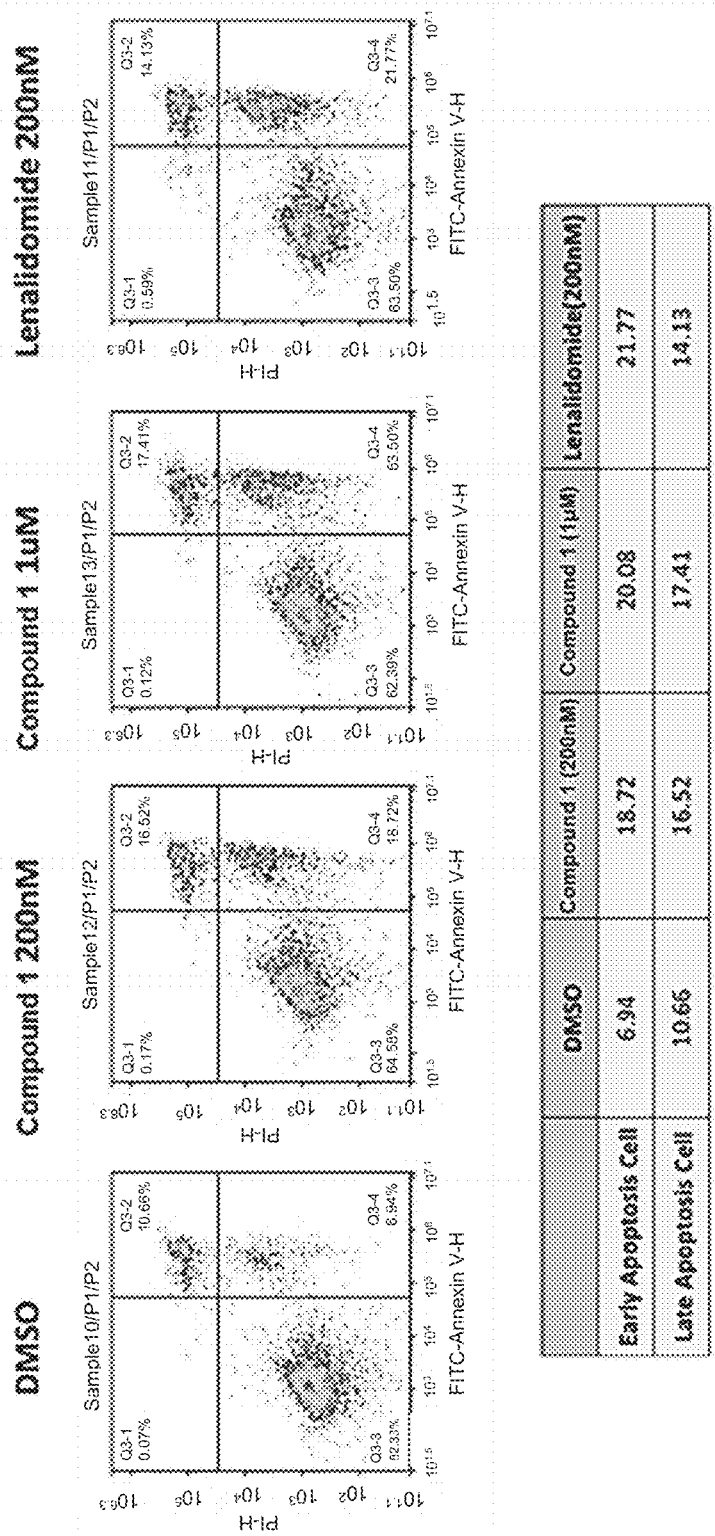
FIG. 13 is a series of contour plots illustrating the percentage of early- and late-apoptotic SYO1 cells following treatment with DMSO, Compound 1 at 200 nM, Compound 1 at 1 µM, or lenalidomide at 200 nM for 8 days. Numerical values corresponding to each contour plot are found in the table below.

Results: As shown in FIGS. 8 and 9, treatment of synovial sarcoma cell lines (SYO1, HS-SY-II, and ASKA) with Compound 1 or Compound 2 resulted in inhibition of the growth of the cells, but did not result in inhibition of the growth of non-synovial control cancer cell lines (RD, HCT116, and Calu6). Overall, Compound 1 showed most significant growth inhibition in all synovial cell lines.

Example 5—Inhibition of Cell Growth in Synovial Sarcoma Cells

The following example shows that BRD9 degraders inhibit cell growth and induce apoptosis in synovial sarcoma cells.

Procedure: SYO1 cells were treated for 8 or 13 days with DMSO, a BRD9 degrader (Compound 1) at 200 nM or 1 µM, or an E3 ligase binder (lenalidomide) at 200 nM. Compounds were refreshed every 5 days. Cell cycle analysis was performed using the Click-iT™ Plus EdU Flow Cytometry Assay (Invitrogen). The apoptosis assay was performed using the Annexin V-FITC Apoptosis Detection Kit (Sigma $A^{9210}$). Assays were performed according to the manufacturer's protocol.

Results: As shown in FIGS. 10-13, treatment with Compound 1 for 8 or 13 days resulted in reduced numbers of cells in the S-phase of the cell cycle as compared to DMSO and lenalidomide. Treatment with Compound 1 for 8 days also resulted in increased numbers of early- and late-apoptotic cells as compared to DMSO controls.

Example 6—Composition for SS18-SSX1-BAF

The following example shows the identification of BRD9 as a component of SS18-SSX containing BAF complexes.

Procedure: A stable 293T cell line expressing HA-SS18SSX1 was generated using lentiviral integration. SS18-SSX1 containing BAF complexes were subject to affinity purification and subsequent mass spectrometry analysis revealed SS18-SSX1 interacting proteins.

Figure 14:
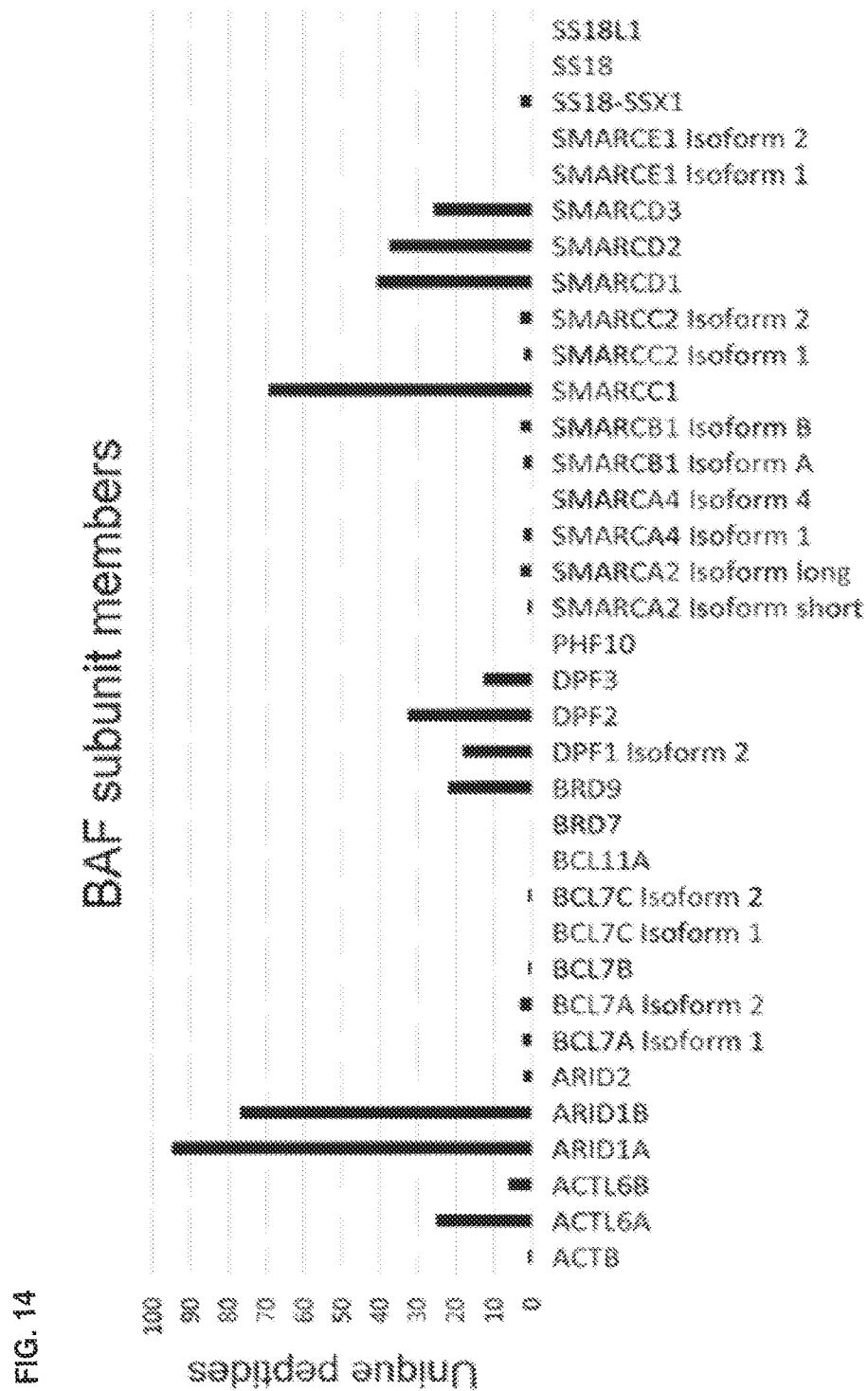
FIG. 14 is a graph illustrating the proteins present in BAF complexes including the SS18-SSX fusion protein.

Results: As shown in FIG. 14, BAF complexes including the SS18-SSX fusion protein also included BRD9. More than 5 unique peptides were identified for ARID1A (95 peptides), ARID1B (77 peptides), SMARCC1 (69 peptides), SMARCD1 (41 peptides), SMARCD2 (37 peptides), DPF2 (32 peptides), SMARCD3 (26 peptides), ACTL6A (25 peptides), BRD9 (22 peptides), DPF1 Isoform 2 (18 peptides), DPF3 (13 peptides), and ACTL6B (6 peptides).

Example 7-Preparation of 1-[2,6-Dimethoxy-4-(2-Methyl-1-Oxo-1,2-Dihydro-2,7-Naphthyridin-4-Yl) Phenyl]Methyl]-N-(8-[2-(2,6-Dioxopiperidin-3-Yl)-1,3-Dioxo-2,3-Dihydro-1H-Isoindol-4-Yl]Amino] Octyl) Azetidine-3-Carboxamide Formic Acid (Compound D1 Formic Acid)

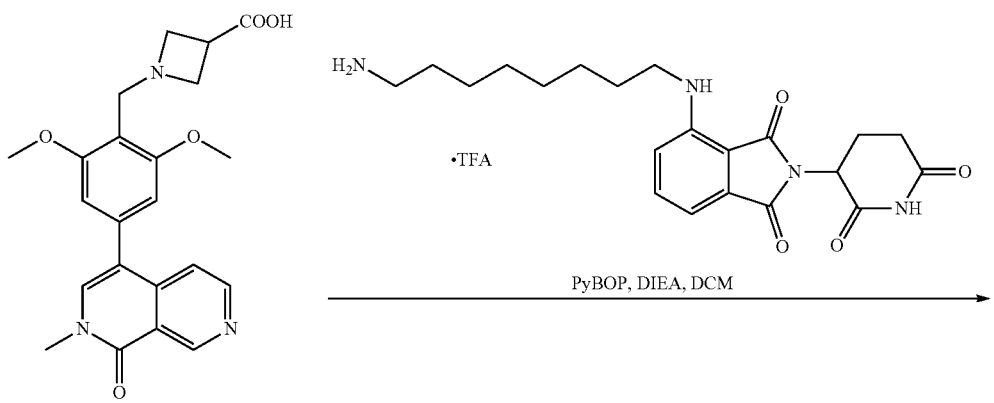

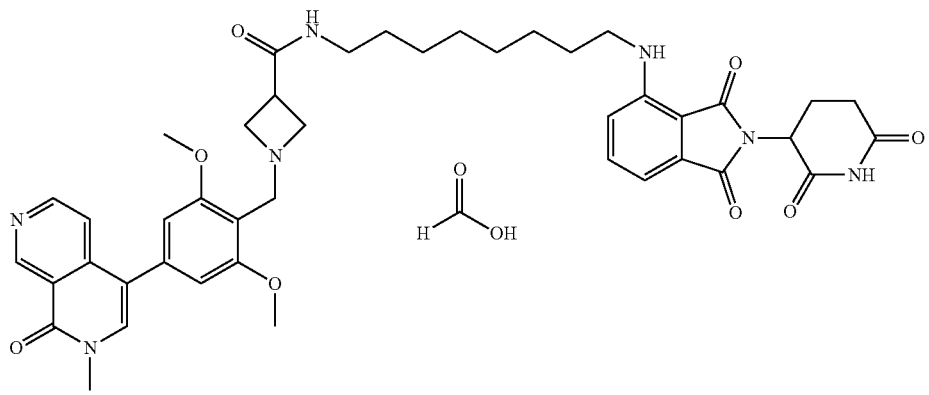

compound D1 formic acid

To a stirred mixture of 4-[(8-aminooctyl)amino]-2-(2,6-dioxopiperidin-3-yl)-2,3-dihydro-1H-isoindole-1,3-dione trifluoroacetic acid salt (50 mg, 0.097 mmol, 1 equiv) and 1-[2,6-dimethoxy-4-(2-methyl-1-oxo-1,2-dihydro-2,7-naphthyridin-4-yl)phenyl]methyl]azetidine-3-carboxylic acid trifluoroacetic acid salt (50.87 mg, 0.097 mmol, 1 equiv) in DCM (2 mL, 31.460 mmol, 323.73 equiv) was added DIEA (37.68 mg, 0.292 mmol, 3 equiv) and PyBOP (75.86 mg, 0.146 mmol, 1.5 equiv). The mixture was stirred for 2 hours at room temperature, and then it was concentrated under vacuum. The residue was purified by Prep-HPLC(conditions: X Select CSH Prep C18 OBD Column, 5 μm, 19*150 mm; mobile phase, Water (0.1% FA) and ACN (25% Phase B up to 45% in 8 minutes); Detector, UV). This resulted in 1-[2,6-dimethoxy-4-(2-methyl-1-oxo-1,2-dihydro-2,7-naphthyridin-4-yl)phenyl]methyl]-N-(8-[2-(2,6-dioxopiperidin-3-yl)-1,3-dioxo-2,3-dihydro-1H-isoindol-4-yl]amino]octyl) azetidine-3-carboxamide formic acid (4 mg, 4.81%) as a yellow solid. $^1$H NMR (400 MHZ, Methanol-d4)$_{\delta\ 9.54}$ (s, 1H), 8.69 (d, J=5.7 Hz, 1H), 8.54 (s, 1H), 7.76 (s, 1H), 7.62 (d, J=5.8 Hz, 1H), 7.60-7.51 (m, 1H), 7.04 (d, J=7.8 Hz, 2H), 6.83 (s, 2H), 5.07 (dd, J=12.5, 5.5 Hz, 1H), 4.31 (s, 2H), 4.05 (s, 4H), 3.94 (s, 6H), 3.71 (s, 3H), 3.52-3.45 (s, 2H), 3.22 (t, J=7.0 Hz, 2H), 2.91-2.66 (m, 4H), 2.14-2.11 (m, 1H), 1.67 (q, J=7.3 Hz, 2H), 1.54 (d, J=7.3 Hz, 2H), 1.45-1.38 (m, 8H). LCMS (ESI) m/z: [M+H]$^+$=792.36.

Example 8—Preparation of 4-(2-[1-[2-([[2,6-Dimethoxy-4-(2-Methyl-1-Oxo-1,2-Dihydro-2,7-Naphthyridin-4-Yl)Phenyl]Methyl](Methyl)Amino) Acetyl]-[4,4-Bipiperidin]-1-Yl]-2-Oxoethoxy)-2-(2,6-Dioxopiperidin-3-Yl)-2,3-Dihydro-1H-Isoindole-1,3-Dione (Compound D2)

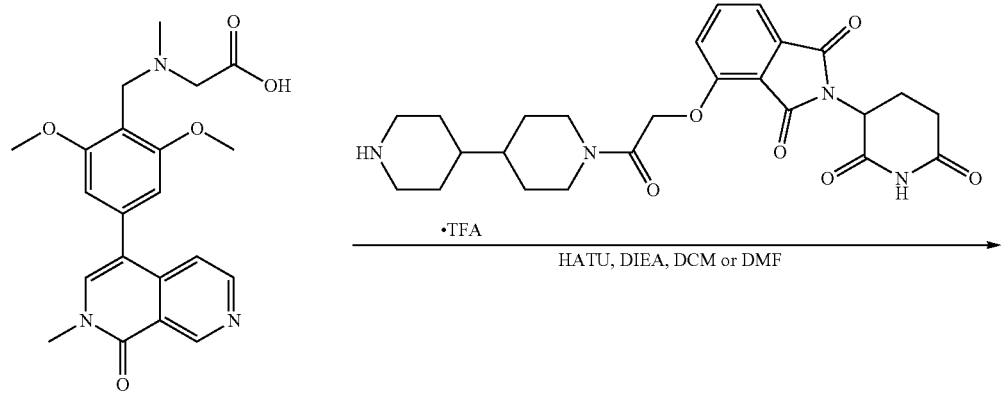

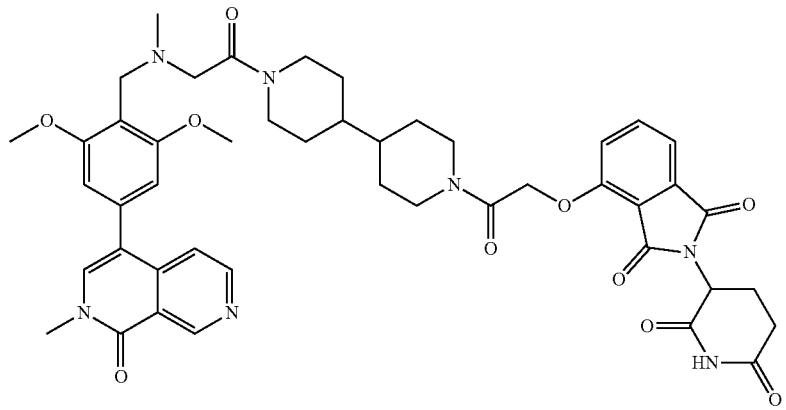

compound D2

To a stirred solution of 2-([2,6-dimethoxy-4-(2-methyl-1-oxo-1,2-dihydro-2,7-naphthyridin-4-yl)phenyl]methyl](methyl)amino) acetic acid (19.99 mg, 0.050 mmol, 1 equiv) and DIPEA (19.50 mg, 0.151 mmol, 3 equiv) in DMF (3 mL) was added PyBOP (28.68 mg, 0.075 mmol, 1.5 equiv) and 4-(2-[[4,4-bipiperidin]-1-yl]-2-oxoethoxy)-2-(2,6-dioxopiperidin-3-yl)-2,3-dihydro-1H-isoindole-1,3-dione trifluoroacetic acid salt (30 mg, 0.050 mmol, 1 equiv). The solution was stirred for 2 hours at room temperature. The resulting mixture was purified by Prep-HPLC(conditions: XSelect CSH Prep C18 OBD Column, 5 μm, 19*150 mm; Mobile Phase A: Water (0.1% FA), Mobile Phase B: ACN; Flow rate: 25 mL/minute; Gradient: 5% B to 30% B in 8 minutes; 254 nm; Rt: 7.56 minutes) to afford 4-(2-[1-[2-([2,6-dimethoxy-4-(2-methyl-1-oxo-1,2-dihydro-2,7-naphthyridin-4-yl)phenyl]methyl](methyl)amino) acetyl]-[4,4-bipiperidin]-1-yl]-2-oxoethoxy)-2-(2,6-dioxopiperidin-3-yl)-2,3-dihydro-1H-isoindole-1,3-dione (19 mg, 43.83%) as a white solid. $^1$H NMR (300 MHZ, Methanol-d4)δ 9.53 (d, J=0.8 Hz, 1H), 8.69 (d, J=5.8 Hz, 1H), 8.56 (s, 0.3H), 7.76 (s, 2H), 7.64 (d, J=5.7 Hz, 1H), 7.49 (d, J=7.3 Hz, 1H), 7.36 (d, J=8.2 Hz, 1H), 6.80 (s, 2H), 5.14 (t, J=15.7 Hz, 3H), 4.60-4.43 (m, 3H), 4.02 (d, J=13.6 Hz, 4H), 3.91 (s, 6H), 3.71 (s, 3H), 3.58 (s, 2H), 3.15-2.59 (m, 6H), 2.53 (s, 3H), 2.15 (s, 1H), 1.85-1.67 (m, 4H), 1.41-1.16 (m, 6H). LCMS (ESI) m/z: $[M+H]^+$=862.

Example 9—Preparation of 1-[2,6-Dimethoxy-4-(2-Methyl-1-Oxo-1,2-Dihydro-2,7-Naphthyridin-4-Yl) Phenyl]Methyl]-N-(5-[[2-(2,6-Dioxopiperidin-3-Yl)-1,3-Dioxo-2,3-Dihydro-1H-Isoindol-4-Yl]Amino] Pentyl) Azetidine-3-Carboxamide (Compound D3)

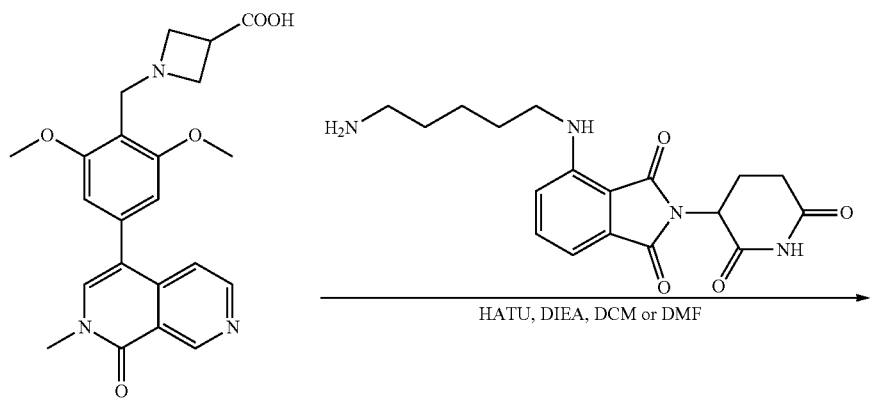

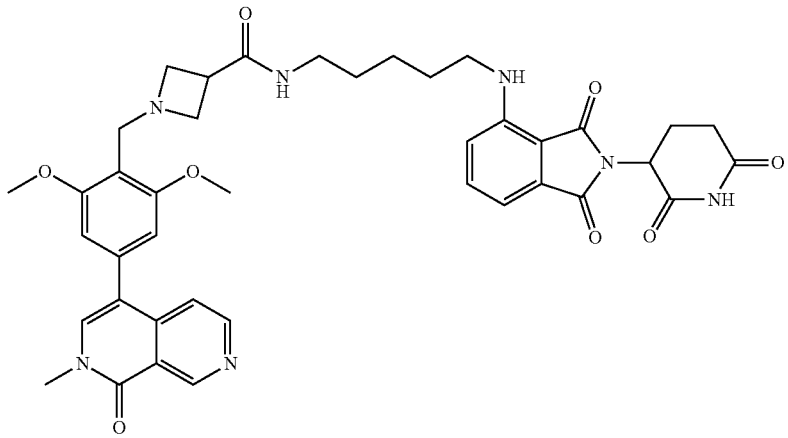

compound D3

To a stirred mixture of 1-[2,6-dimethoxy-4-(2-methyl-1-oxo-1,2-dihydro-2,7-naphthyridin-4-yl)phenyl]methyl]azetidine-3-carboxylic acid trifluoroacetic acid salt (55.40 mg, 0.106 mmol, 1 equiv) and 4-[(5-aminopentyl)amino]-2-(2,6-dioxopiperidin-3-yl)-2,3-dihydro-1H-isoindole-1,3-dione; trifluoroacetic acid salt (50 mg, 0.106 mmol, 1 equiv) in DCM (2 mL) was added DIEA (41.04 mg, 0.318 mmol, 3 equiv) and PyBOP (82.62 mg, 0.159 mmol, 1.5 equiv). The mixture was stirred for 2 hours at room temperature, and then it was concentrated under vacuum. The residue was purified by Prep-HPLC(conditions: X Select CSH Prep C18 OBD Column, 5 μm, 19*150 mm; mobile phase, Water (0.1% FA) and ACN (15% Phase B up to 35% in 8 minutes); Detector, UV). This resulted in 6 mg (6.98%) of 1-[2,6-dimethoxy-4-(2-methyl-1-oxo-1,2-dihydro-2,7-naphthyridin-4-yl)phenyl]methyl]-N-(5-[2-(2,6-dioxopiperidin-3-yl)-1,3-dioxo-2,3-dihydro-1H-isoindol-4-yl]amino]pentyl) azetidine-3-carboxamide formate as a yellow solid. $^1$H NMR (400 MHZ, Methanol-d4)δ 9.54 (s, 1H), 8.69 (d, J=5.8 Hz, 1H), 8.53 (s, 1H), 7.76 (s, 1H), 7.65-7.51 (m, 2H), 7.05 (dd, J=7.8, 6.0 Hz, 2H), 6.83 (s, 2H), 5.11-5.02 (m, 1H), 4.57 (s, 1H), 4.36 (s, 2H), 4.10 (s, 4H), 3.95 (s, 6H), 3.71 (s, 3H), 3.36-3.26 (m, 3H), 2.91-2.68 (m, 3H), 2.12 (d, J=10.0 Hz, 1H), 1.76-1.67 (m, 2H), 1.60 (q, J=7.3, 6.8 Hz, 2H), 1.49 (d, J=7.1 Hz, 2H). LCMS (ESI) m/z: [M+H]$^+$=750.32.

Example 10—Preparation of N-[8-[(1-[[2,6-Dimethoxy-4-(2-Methyl-1-Oxo-1,2-Dihydro-2,7-Naphthyridin-4-Yl)Phenyl]Methyl]Azetidin-3-Yl) Formamido]Octyl]-2-[[2-(2,6-Dioxopiperidin-3-Yl)-1,3-Dioxo-2,3-Dihydro-1H-Isoindol-4-Yl]Oxy] Acetamide Formic Acid (Compound D4 Formic Acid)

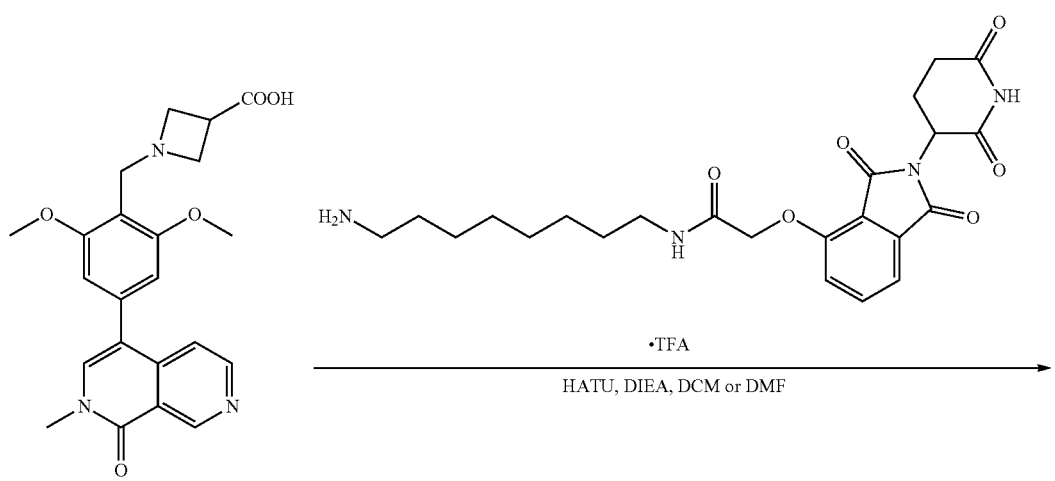

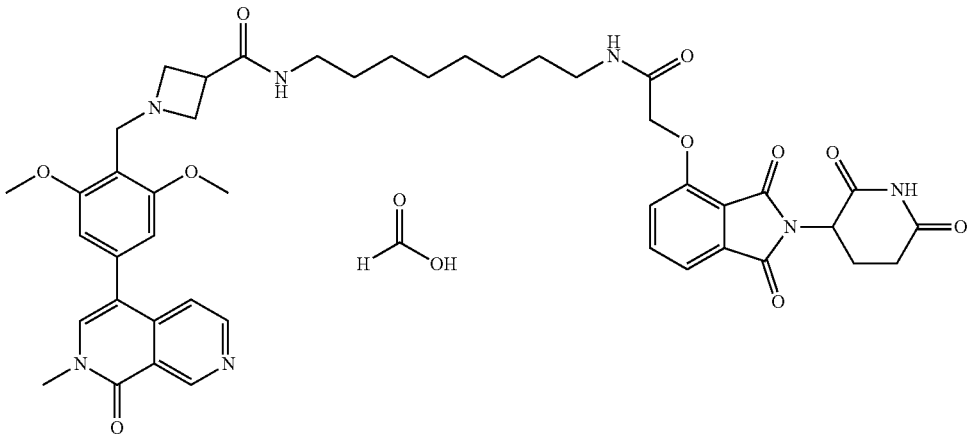

compound D3

To a stirred mixture of 1-[2,6-dimethoxy-4-(2-methyl-1-oxo-2,7-naphthyridin-4-yl)phenyl]methyl]azetidine-3-carboxylic acid; trifluoroacetic acid salt (68.57 mg, 0.131 mmol, 1.50 equiv) and N-(8-aminooctyl)-2-[2-(2,6-dioxopiperidin-3-yl)-1,3-dioxoisoindol-4-yl]oxy]acetamide trifluoroacetic acid salt (50.00 mg, 0.087 mmol, 1.00 equiv) in DCM (2.00 mL) was added DIEA (67.72 mg, 0.524 mmol, 6.00 equiv) and PyBOP (68.17 mg, 0.131 mmol, 1.50 equiv). The mixture was stirred for 2 hours at room temperature, and then it was concentrated under vacuum. The residue was purified by Prep-HPLC (conditions: X Bridge Shield RP18 OBD Column, 5 μm, 19*150 mm; mobile phase, Water (0.1% FA) and ACN (20% Phase B up to 32% in 7 minutes); Detector, UV). This resulted in N-[8-[(1-[[2,6-dimethoxy-4-(2-methyl-1-oxo-1,2-dihydro-2,7-naphthyridin-4-yl)phenyl]methyl]azetidin-3-yl) formamido]octyl]-2-[2-(2,6-dioxopiperidin-3-yl)-1,3-dioxo-2,3-dihydro-1H-isoindol-4-yl]oxy]acetamide formic acid (12 mg, 14.77%) as a white solid. $^1$H NMR (400 MHZ, Methanol-d4)δ 9.53 (s, 1H), 8.68 (d, J=5.8 Hz, 1H), 7.87-7.78 (m, 1H), 7.75 (s, 1H), 7.63 (d, J=5.8 Hz, 1H), 7.55 (d, J=7.4 Hz, 1H), 7.44 (d, J=8.4 Hz, 1H), 6.80 (s, 2H), 5.15 (dd, J=12.6, 5.3 Hz, 1H), 4.76 (s, 2H), 4.14 (s, 2H), 3.92 (s, 6H), 3.80 (s, 4H), 3.71 (s, 3H), 3.20 (t, J=7.0 Hz, 2H), 2.94-2.71 (m, 6H), 2.15 (s, 1H), 1.58 (d, J=7.9 Hz, 2H), 1.51 (s, 2H), 1.35 (s, 8H). LCMS (ESI) m/z: [M+H]$^+$=850.37.

Example 11—Preparation of N-(1-[[2,6-Dimethoxy-4-(2-Methyl-1-Oxo-1,2-Dihydro-2,7-Naphthyridin-4-Yl)Phenyl]Methyl]Azetidin-3-Yl)-6-[2-(2,6-Dioxopiperidin-3-Yl)-1,3-Dioxo-2,3-Dihydro-1H-Isoindol-4-Yl]Oxy]Hexanamide (Compound D5)

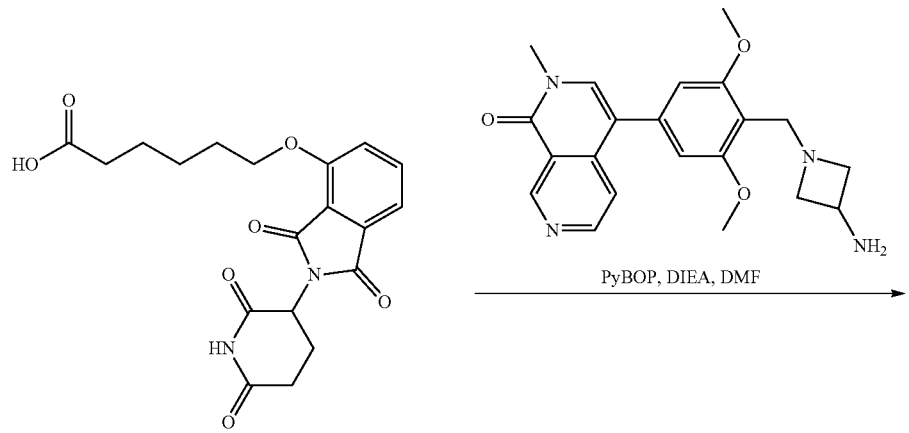

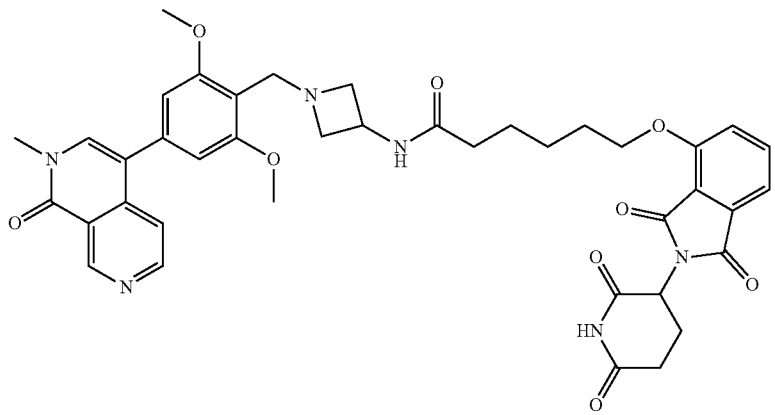

compound D5

To a solution of 6-[2-(2,6-dioxopiperidin-3-yl)-1,3-dioxo-2,3-dihydro-1H-isoindol-4-yl]oxy]hexanoic acid (50.00 mg, 0.129 mmol, 1.00 eq.) and DIEA (49.92 mg, 0.386 mmol, 3 eq.) in DCM (2.00 mL, 31.460 mmol, 244.37 eq.) was added PyBOP (100.49 mg, 0.193 mmol, 1.5 eq.) and 4-[4-[(3-aminoazetidin-1-yl)methyl]-3,5-dimethoxyphenyl]-2-methyl-1,2-dihydro-2,7-naphthyridin-1-one (48.98 mg, 0.129 mmol, 1 eq.). The resulting solution was stirred at room temperature for 1 hour. The crude product (50 mg) was purified by Prep-HPLC(conditions: XSelect CSH Prep C18 OBD Column, 5 μm, 19*150 mm; Mobile Phase A: Water (0.1% FA), Mobile Phase B: ACN; Flow rate: 25 mL/minute; Gradient: 10% B to 30% B in 8 minutes; 254 nm; Rt: 6.57 minutes) to afford N-(1-[[2,6-dimethoxy-4-(2-methyl-1-oxo-1,2-dihydro-2,7-naphthyridin-4-yl)phenyl]methyl]azetidin-3-yl)-6-[2-(2,6-dioxopiperidin-3-yl)-1,3-dioxo-2,3-dihydro-1H-isoindol-4-yl]oxy]hexanamide (14.8 mg, 15.31%) as a white solid. $^1$H NMR (400 MHZ, Methanol-d4) δ 9.54 (s, 1H), 8.69 (d, J=5.7 Hz, 1H), 7.82-7.73 (m, 2H), 7.65-7.58 (m, 1H), 7.44 (dd, J=7.9, 3.2 Hz, 2H), 6.83 (s, 2H), 5.10 (dd, J=12.4, 5.4 Hz, 1H), 4.60-4.47 (m, 1H), 4.34 (s, 2H), 4.25 (t, J=6.1 Hz, 2H), 4.18 (s, 2H), 3.94 (s, 8H), 3.71 (s, 3H), 2.87-2.64 (m, 3H), 2.30 (t, J=7.3 Hz, 2H), 2.17-2.09 (m, 1H), 1.90 (p, J=6.4 Hz, 2H), 1.75 (p, J=7.4 Hz, 2H), 1.61 (q, J=8.0 Hz, 2H). LCMS (ESI) m/z: [M+H]$^+$=751.25.

Example 12—Preparation of 4-[2-[1-(1-[[2,6-Dimethoxy-4-(2-Methyl-1-Oxo-1,2-Dihydro-2,7-Naphthyridin-4-Yl)Phenyl]Methyl]Azetidine-3-Carbonyl)-[4,4-Bipiperidin]-1-Yl]-2-Oxoethoxy]-2-(2,6-Dioxo Piperidin-3-Yl)-2,3-Dihydro-1H-Isoindole-1,3-Dione Formic Acid (Compound D6 Formic Acid)

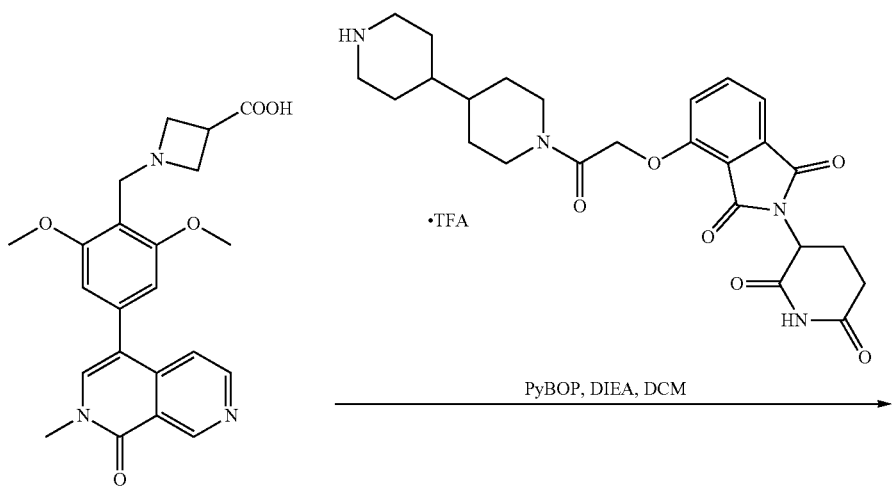

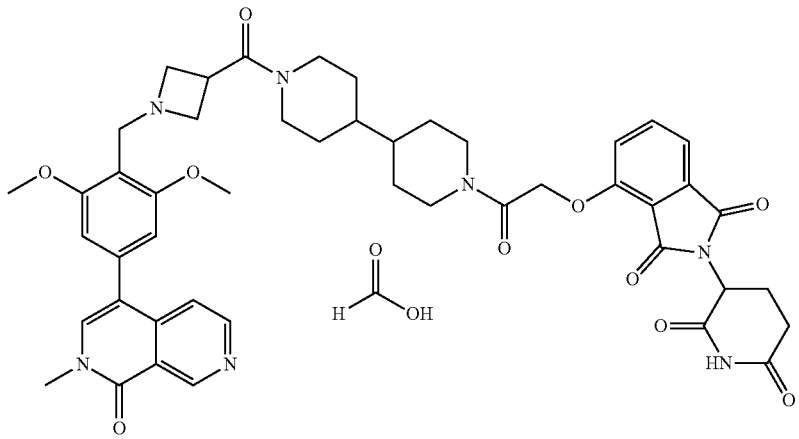

compound D6 formic acid

To a stirred mixture of 1-[[2,6-dimethoxy-4-(2-methyl-1-oxo-2,7-naphthyridin-4-yl)phenyl]methyl]azetidine-3-carboxylic acid trifluoroacetic acid salt (26.32 mg, 0.050 mmol, 1.50 equiv) and 4-(2-[4,4-bipiperidin]-1-yl)-2-oxoethoxy)-2-(2,6-dioxopiperidin-3-yl) isoindole-1,3-dione trifluoroacetic acid salt (20.00 mg, 0.034 mmol, 1.00 equiv) in DCM (2 mL) was added DIEA (26.00 mg, 0.201 mmol, 6.00 equiv) and PyBOP (26.17 mg, 0.050 mmol, 1.50 equiv). The mixture was stirred for 2 hours at room temperature, and then it was concentrated under vacuum. The residue was purified was purified by Prep-HPLC(conditions: X Select CSH Prep C18 OBD Column, 5 μm, 19*150 mm; mobile phase, Water (0.1% FA) and ACN (8% Phase B up to 22% in 8 minutes); Detector, UV). This resulted in 4-[2-[1-(1-[2,6-dimethoxy-4-(2-methyl-1-oxo-1,2-dihydro-2,7-naphthyridin-4-yl)phenyl]methyl]azetidine-3-carbonyl)-[4,4-bipiperidin]-1-yl]-2-oxoethoxy]-2-(2,6-dioxo piperidin-3-yl)-2,3-dihydro-1H-isoindole-1,3-dione formic acid (3.5 mg, 10.89%) as a white solid. $^1$H NMR (300 MHZ, Methanol-d4) δ 9.54 (d, J=0.8 Hz, 1H), 8.69 (d, J=5.7 Hz, 1H), 8.56 (s, 1H), 7.84-7.72 (m, 2H), 7.63 (d, J=5.8 Hz, 1H), 7.51 (d, J=7.3 Hz, 1H), 7.38 (d, J=8.6 Hz, 1H), 6.81 (s, 2H), 5.31-4.98 (m, 3H), 4.68-4.44 (m, 2H), 4.16 (s, 2H), 3.93 (s, 10H), 3.79-3.56 (m, 5H), 3.09-2.93 (m, 2H), 2.93-2.61 (m, 6H), 2.15 (d, J=10.4 Hz, 1H), 1.86-1.67 (m, 4H), 1.50-1.25 (m, 3H), 1.23-1.04 (m, 2H). LCMS (ESI) m/z: [M+H]$^+$=874.37.

Example 13—Preparation of 1-[[2,6-Dimethoxy-4-(2-Methyl-1-Oxo-1,2-Dihydro-2,7-Naphthyridin-4-Yl)Phenyl]Methyl]-N-[2-[2-(2-[[2-(2,6-Dioxopiperidin-3-Yl)-1,3-Dioxo-2,3-Dihydro-1H-Isoindol-4-Yl]Amino]Ethoxy) Ethoxy]Ethyl]Azetidine-3-Carboxamide Formic Acid (Compound D7 Formic Acid)

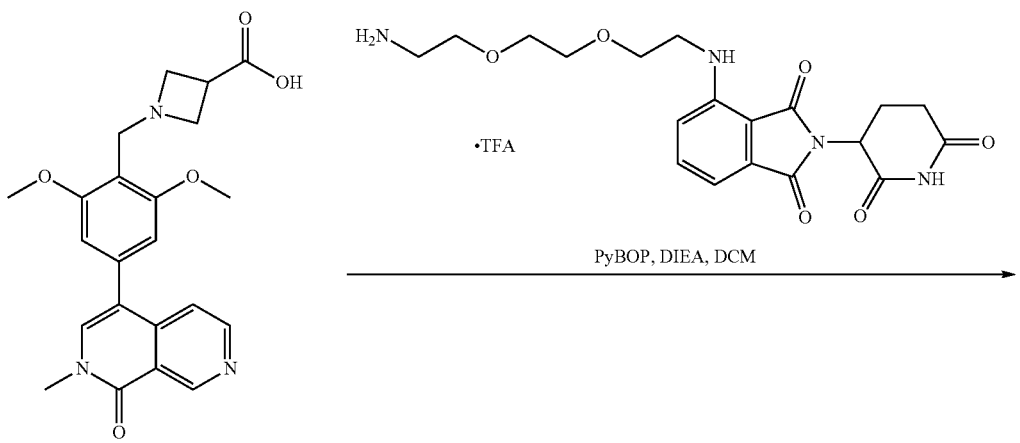

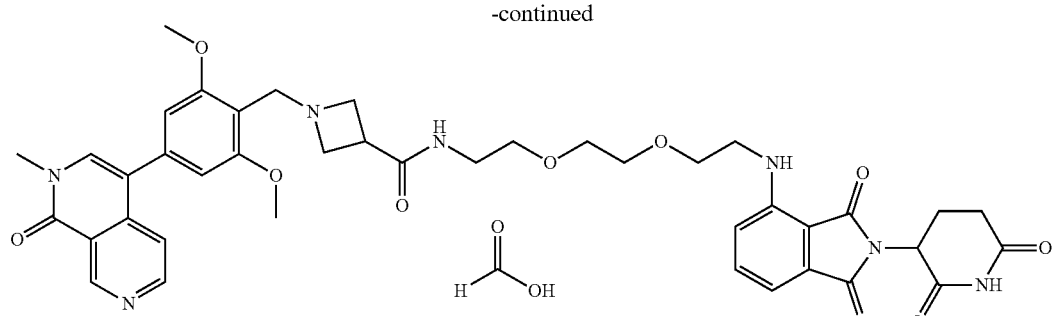

compound D7 formic acid

To a stirred mixture of 1-[[2,6-dimethoxy-4-(2-methyl-1-oxo-1,2-dihydro-2,7-naphthyridin-4-yl)phenylmethyl]azetidine-3-carboxylic acid trifluoroacetic acid salt (75.73 mg, 0.145 mmol, 1.5 equiv) and 4-([2-[2-(2-aminoethoxy)ethoxy]ethyl]amino)-2-(2,6-dioxopiperidin-3-yl)-2,3-dihydro-1H-isoindole-1,3-dione trifluoroacetic acid salt (50 mg, 0.096 mmol, 1 equiv) in DCM (2 mL) was added DIEA (74.79 mg, 0.579 mmol, 6 equiv) and PyBOP (75.28 mg, 0.145 mmol, 1.5 equiv). The mixture was stirred for 2 hours at room temperature, and then it was concentrated under vacuum. The residue was purified by Prep-HPLC(conditions: X Select CSH Prep C18 OBD Column, 5 μm, 19*150 mm; mobile phase, Water (0.1% FA) and ACN (10% Phase B up to 32% in 8 minutes); Detector, UV). This resulted in 1-[2,6-dimethoxy-4-(2-methyl-1-oxo-1,2-dihydro-2,7-naphthyridin-4-yl)phenyl]methyl]-N-[2-[2-(2-[2-(2,6-dioxopiperidin-3-yl)-1,3-dioxo-2,3-dihydro-1H-isoindol-4-yl]amino]ethoxy) ethoxy]ethyl]azetidine-3-carboxamide formic acid (13.2 mg, 15.77%) as a yellow solid. $^1$H NMR (400 MHZ, Methanol-d4)δ 9.53 (s, 1H), 8.68 (d, J=5.8 Hz, 1H), 8.56 (s, 1H), 7.75 (s, 1H), 7.62 (d, J=5.9 Hz, 1H), 7.55 (dd, J=8.6, 7.1 Hz, 1H), 7.07 (dd, J=11.7, 7.8 Hz, 2H), 6.80 (s, 2H), 5.07 (dd, J=12.4, 5.5 Hz, 1H), 4.20 (s, 2H), 3.92 (s, 10H), 3.78-3.57 (m, 9H), 3.61-3.43 (m, 4H), 3.41 (td, J=5.2, 1.6 Hz, 2H), 2.88 (ddd, J=19.0, 14.0, 5.0 Hz, 1H), 2.80-2.64 (m, 3H), 2.17-2.08 (m, 1H). LCMS (ESI) m/z: [M+H]$^+$=796.25.

Example 14—Preparation of 1-[[2,6-Dimethoxy-4-(2-Methyl-1-Oxo-1,2-Dihydro-2,7-Naphthyridin-4-Yl)Phenyl]Methyl]-N-(8-[[2-(1-Methyl-2,6-Dioxopiperidin-3-Yl)-1,3-Dioxo-2,3-Dihydro-1H-Isoindol-4-Yl]Amino]Octyl) Azetidine-3-Carboxamide Formic Acid (Compound D8 Formic Acid)

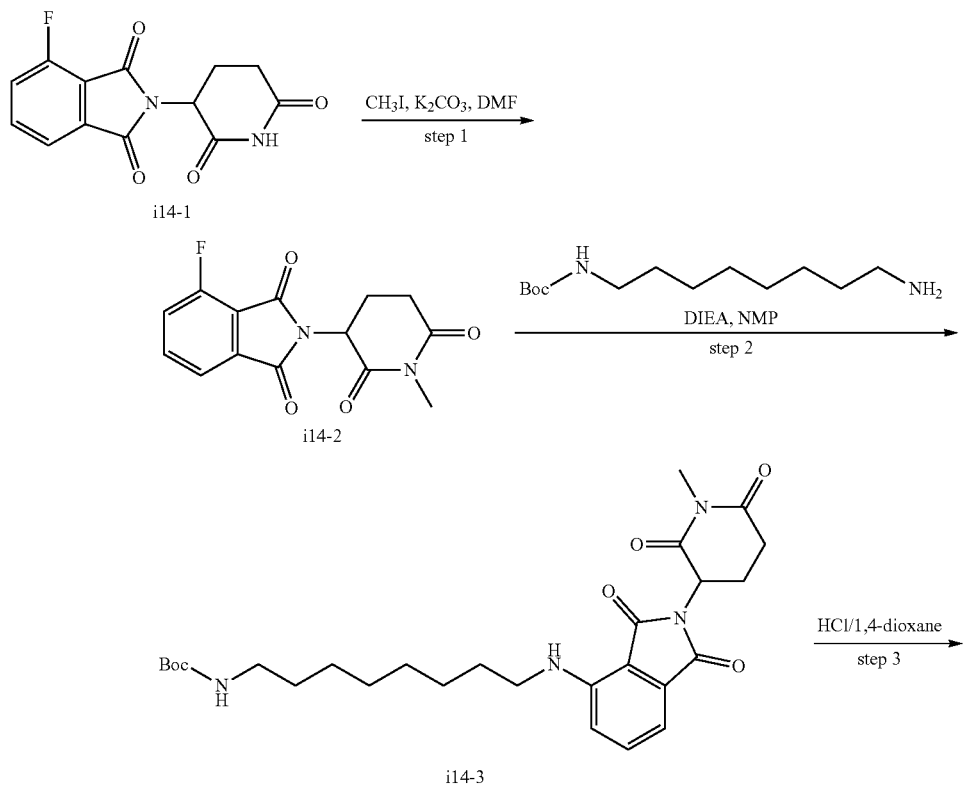

-continued

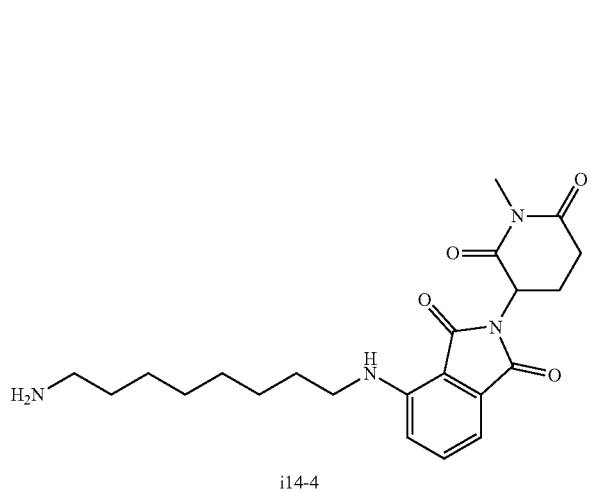

i14-4

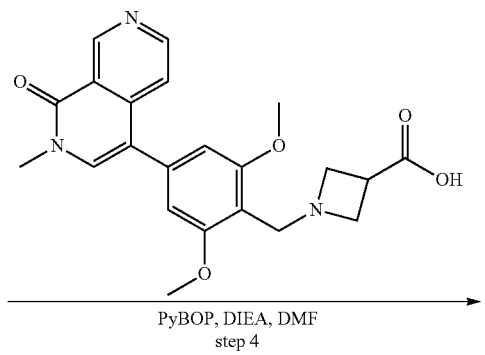

PyBOP, DIEA, DMF
step 4

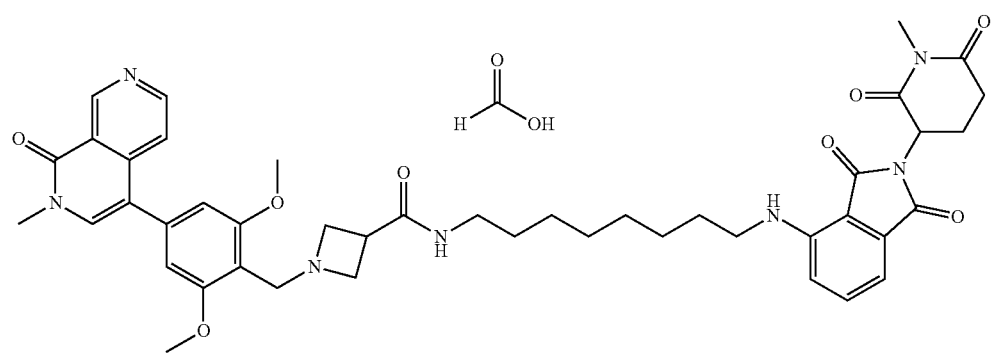

compound D8 formic acid

Step 1: Preparation of 4-Fluoro-2-(1-Methyl-2,6-Dioxopiperidin-3-Yl)-2,3-Dihydro-1H-Isoindole-1,3-Dione (i14-2)

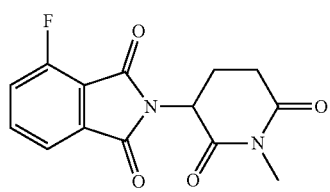

i14-2

To a solution of 2-(2,6-dioxopiperidin-3-yl)-4-fluoro-2,3-dihydro-1H-isoindole-1,3-dione (500 mg, 1.810 mmol, 1 equiv) in DMF (10 mL) was added $CH_3I$ (385.39 mg, 2.715 mmol, 1.5 equiv) and $K_2CO_3$ (750.51 mg, 5.430 mmol, 3 equiv). The resulting solution was stirred for overnight at 25° C. The solids were filtered out. The resulting mixture was concentrated. The residue was applied onto a silica gel column with ethyl acetate/petroleum ether (1:2). This resulted in 4-fluoro-2-(1-methyl-2,6-dioxopiperidin-3-yl)-2, 3-dihydro-1H-isoindole-1,3-dione (480 mg, 91.36%) as a white solid. LCMS (ESI) m/z: $[M-H]^+=291$.

Step 2: Preparation of Tert-Butyl N-(8-[[2-(1-Methyl-2,6-Dioxopiperidin-3-Yl)-1,3-Dioxo-2,3-Dihydro-1H-Isoindol-4-Yl]Amino]Octyl) Carbamate (i14-3)

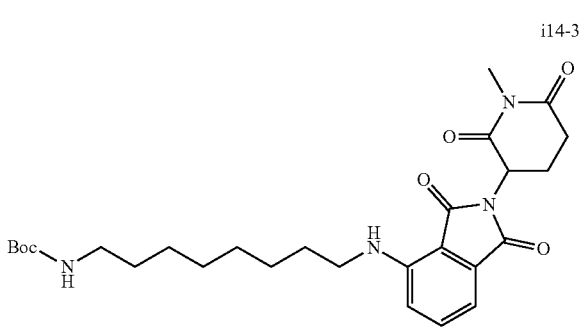 [SMILES: CN1C(=O)CCC(N2C(=O)c3cccc(NCCCCCCCCNC(=O)OC(C)(C)C)c3C2=O)C1=O]

i14-3

To a solution of 4-fluoro-2-(1-methyl-2,6-dioxopiperidin-3-yl)-2,3-dihydro-1H-isoindole-1,3-dione (480 mg, 1.654 mmol, 1 equiv) and tert-butyl N-(8-aminooctyl) carbamate (404.14 mg, 1.654 mmol, 1 equiv) in NMP (10 mL) was added DIEA (641.21 mg, 4.961 mmol, 3 equiv). The resulting solution was stirred for 6 hours at 90° C. The resulting solution was diluted with 20 ml of water and extracted with ethyl acetate (2×20 mL), and the organic layers were combined and dried over anhydrous sodium sulfate and concentrated. The residue was applied onto a silica gel column with ethyl acetate/petroleum ether (1:1). This resulted in tert-butyl N-(8-[2-(1-methyl-2,6-dioxopiperidin-3-yl)-1,3-dioxo-2,3-dihydro-1H-isoindol-4-yl]amino]octyl) carbamate (480 mg, 56.40%) as a green solid. LCMS (ESI) m/z: [M−H]$^+$=515.

Step 3: Preparation of 4-[(8-Aminooctyl)Amino]-2-(1-Methyl-2,6-Dioxopiperidin-3-Yl)-2,3-Dihydro-1H-Isoindole-1,3-Dione (i14-4)

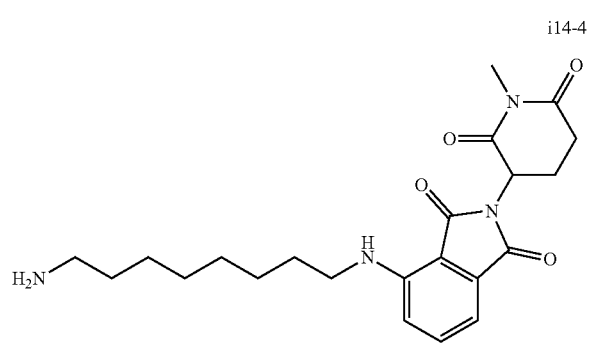 [SMILES: CN1C(=O)CCC(N2C(=O)c3cccc(NCCCCCCCCN)c3C2=O)C1=O]

i14-4

A mixture of tert-butyl N-(8-[[2-(1-methyl-2,6-dioxopiperidin-3-yl)-1,3-dioxo-2,3-dihydro-1H-isoindol-4-yl]amino]octyl) carbamate (150 mg, 0.291 mmol, 1 equiv) and 4 M HCl in 1,4-dioxane (5 mL) was stirred for 1 hour at 25° C. The resulting mixture was concentrated. This resulted in 4-[(8-aminooctyl)amino]-2-(1-methyl-2,6-dioxopiperidin-3-yl)-2,3-dihydro-1H-isoindole-1,3-dione (100 mg, 82.77%) as a white solid, that was used directly without further purification. LCMS (ESI) m/z: [M−H]$^+$=415.

Step 4: Preparation of 1-[[2,6-Dimethoxy-4-(2-Methyl-1-Oxo-1,2-Dihydro-2,7-Naphthyridin-4-Yl)Phenyl]Methyl]-N-(8-[2-(1-Methyl-2,6-Dioxopiperidin-3-Yl)-1,3-Dioxo-2,3-Dihydro-1H-Isoindol-4-Yl]Amino]Octyl) Azetidine-3-Carboxamide Formic Acid (Compound D8 Formic Acid)

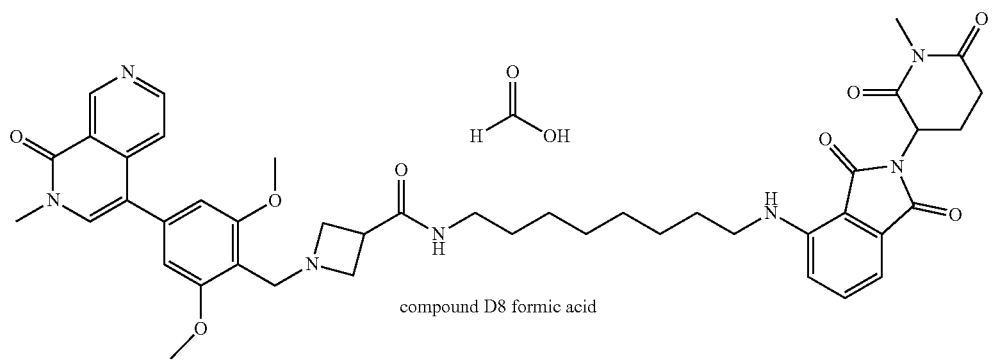 [SMILES: COc1cc(-c2cn(C)c(=O)c3cnccc23)cc(OC)c1CN1CC(C(=O)NCCCCCCCCNc2cccc3c2C(=O)N(C2CCC(=O)N(C)C2=O)C3=O)C1 ; O=CO]

compound D8 formic acid

To a solution of 4-[(8-aminooctyl)amino]-2-(1-methyl-2,6-dioxopiperidin-3-yl)-2,3-dihydro-1H-isoindole-1,3-dione (80 mg, 0.193 mmol, 1 equiv) and 1-[[2,6-dimethoxy-4-(2-methyl-1-oxo-1,2-dihydro-2,7-naphthyridin-4-yl)phenyl]methyl]azetidine-3-carboxylic acid (79.02 mg, 0.193 mmol, 1 equiv) in DMF (3 mL) was added HATU (110.08 mg, 0.290 mmol, 1.5 equiv) and DIEA (49.89 mg, 0.386 mmol, 2 equiv). The resulting solution was stirred for 2 hours at 25° C. The crude product was purified by Prep-HPLC (conditions: XBridge Prep C18 OBD Column, 5 μm, 19*150 mm; mobile phase, Water (0.1% FA) and ACN; Detector, UV 254 nm). This resulted in 1-[[2,6-dimethoxy-4-(2-methyl-1-oxo-1,2-dihydro-2,7-naphthyridin-4-yl)phenyl]methyl]-N-(8-[[2-(1-methyl-2,6-dioxopiperidin-3-yl)-1,3-dioxo-2,3-dihydro-1H-isoindol-4-yl]amino]octyl) azetidine-3-carboxamide (15 mg, 9.64%) as a yellow solid. $^1$H NMR (400 MHZ, Methanol-d4) δ 9.54 (d, J=0.8 Hz, 1H), 8.69 (d, J=5.8 Hz, 1H), 8.54 (s, 1.2H, FA), 7.77 (s, 1H), 7.65-7.52 (m, 2H), 7.10-7.01 (m, 2H), 6.84 (s, 2H), 5.10 (dd, J=12.9, 5.4 Hz, 1H), 4.39 (s, 2H), 4.14 (d, J=8.2 Hz, 3H), 3.95 (s, 6H), 3.71 (s, 3H), 3.54 (d, J=8.1 Hz, 1H), 3.22 (t, J=7.0 Hz, 2H), 3.17 (d, J=3.1 Hz, 1H), 3.15 (s, 3H), 2.99 (s, 1H), 2.96-2.86 (m, 2H), 2.69 (dt, J=12.7, 6.3 Hz, 2H), 2.15-2.05 (m, 1H), 1.68 (p, J=7.1 Hz, 2H), 1.52 (q, J=7.1 Hz, 2H), 1.38 (s, 8H). LCMS (ESI) m/z: [M−H]$^+$=806.40.

Example 15—Preparation of 2-(1-[[2,6-Dimethoxy-4-(2-Methyl-1-Oxo-1,2-Dihydro-2,7-Naphthyridin-4-Yl)Phenyl]Methyl]Azetidin-3-Yl)-N-(8-[[2-(2,6-Dioxopiperidin-3-Yl)-1,3-Dioxo-2,3-Dihydro-1H-Isoindol-4-Yl]Amino]Octyl) Acetamide Formic Acid (Compound D9 Formic Acid)

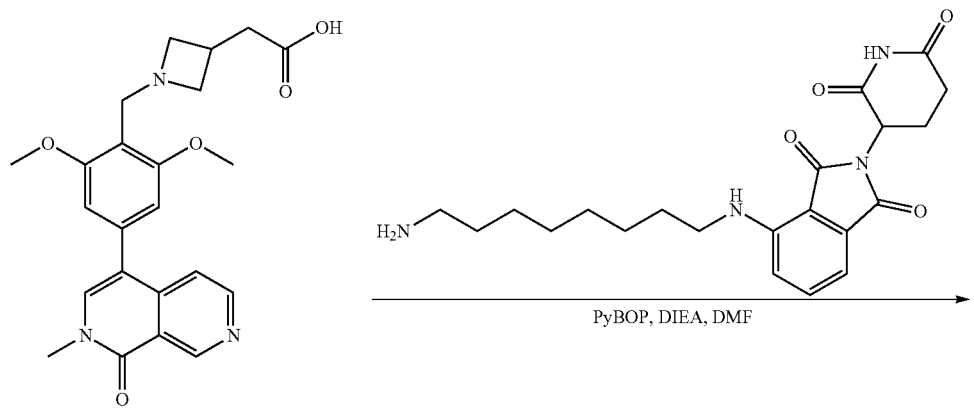

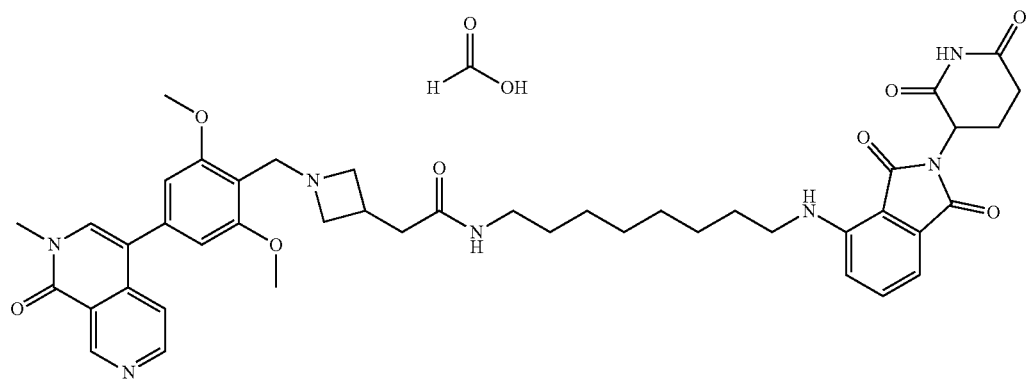

compound D9 formic acid

To a solution of 2-(1-[2,6-dimethoxy-4-(2-methyl-1-oxo-1,2-dihydro-2,7-naphthyridin-4-yl)phenyl]methyl]azetidin-3-yl) acetic acid (110 mg, 0.260 mmol, 1 equiv) in DMF (3 mL) was added 4-[(8-aminooctyl)amino]-2-(2,6-dioxopiperidin-3-yl)-2,3-dihydro-1H-isoindole-1,3-dione (104.03 mg, 0.260 mmol, 1.00 equiv), PyBOP (202.77 mg, 0.390 mmol, 1.50 equiv), and DIEA (167.86 mg, 1.299 mmol, 5.00 equiv). The resulting mixture was stirred at room temperature for 16 hours. Without workup, the crude product was purified by Prep-HPLC(conditions: SunFire C18 OBD Prep Column, 100 Å, 5 μm, 19 mm×250 mm; Mobile Phase A: Water (0.1% FA), Mobile Phase B: ACN; Flow rate: 25 mL/minute; Gradient: 27% B to 34% B in 8 minutes; 254 nm; Rt: 6.28 minutes) to afford 2-(1-[[2,6-dimethoxy-4-(2-methyl-1-oxo-1,2-dihydro-2,7-naphthyridin-4-yl)phenyl]methyl]azetidin-3-yl)-N-(8-[2-(2,6-dioxopiperidin-3-yl)-1,3-dioxo-2,3-dihydro-1H-isoindol-4-yl]amino]octyl) acetamide formic acid (26.7 mg) as a yellow solid. $^1$H NMR (300 MHZ, Methanol-d4)δ 9.52 (s, 1H), 8.69 (d, J=5.8 Hz, 1H), 8.56 (s, 0.8H, FA), 7.76 (s, 1H), 7.61 (d, J=5.7 Hz, 1H), 7.54 (dd, J=8.5, 7.1 Hz, 1H), 7.03 (dd, J=7.8, 3.5 Hz, 2H), 6.85 (s, 2H), 5.06 (dd, J=12.4, 5.4 Hz, 1H), 4.43 (s, 2H), 4.18 (t, J=9.5 Hz, 2H), 4.02-3.90 (m, 7H), 3.70 (s, 3H), 3.30 (d, J=6.8 Hz, 2H), 3.17 (t, J=7.1 Hz, 3H), 2.97-2.62 (m, 3H), 2.58 (d, J=7.4 Hz, 2H), 2.19-2.05 (m, 1H), 1.65 (q, J=7.0 Hz, 2H), 1.57-1.37 (m, 10H). LCMS (ESI) m/z: $[M+H]^+$=806.25.

Example 16—Preparation of 1-[2,6-Dimethoxy-4-(2-Methyl-1-Oxo-1,2-Dihydro-2,7-Naphthyridin-4-Yl)Phenyl]Methyl]-N-(8-[[2-(2,6-Dioxopiperidin-3-Yl)-1,3-Dioxo-2,3-Dihydro-1H-Isoindol-4-Yl]Amino]Octyl) Azetidine-3-Carboxamide (D10)

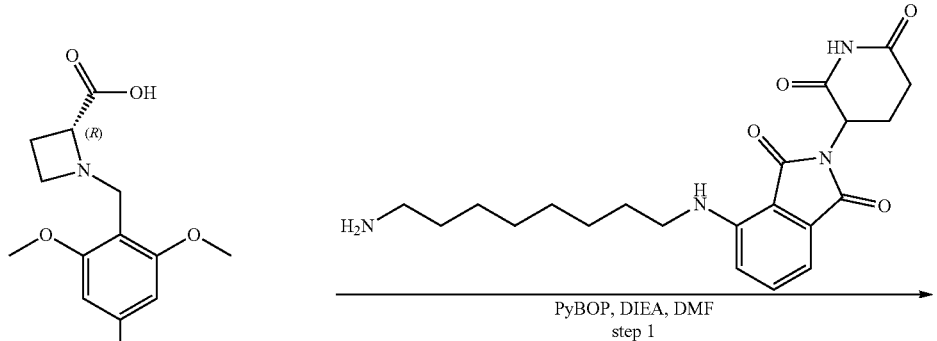

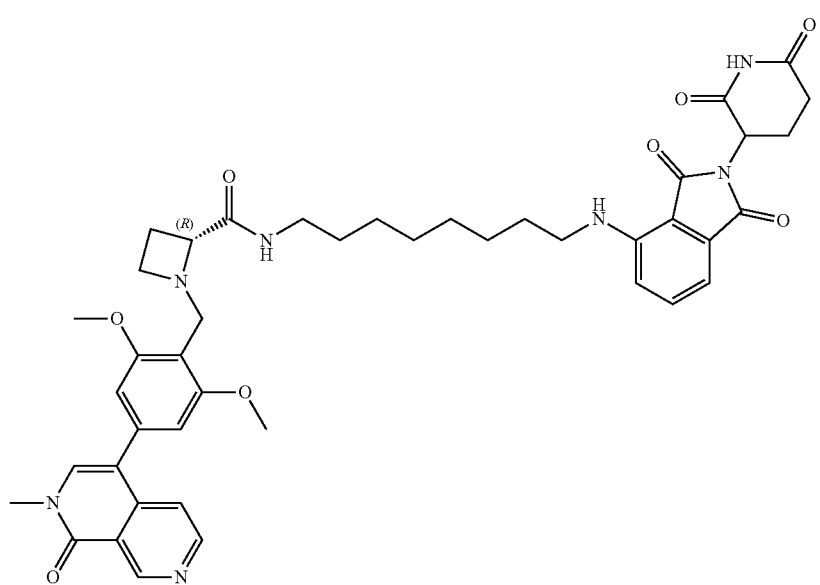

compound D10

To a stirred solution of (R)-1-[2,6-dimethoxy-4-(2-methyl-1-oxo-1,2-dihydro-2,7-naphthyridin-4-yl)phenyl]methyl]azetidine-3-carboxylic acid (40.9 mg, 0.100 mmol, 1 equiv), DIEA (64.55 mg, 0.499 mmol, 5 equiv), and PyBOP (155.95 mg, 0.300 mmol, 3 equiv) in DMF (1 mL) was added 4-[(8-aminooctyl)amino]-2-(2,6-dioxopiperidin-3-yl)-2,3-dihydro-1H-isoindole-1,3-dione hydrochloride (43.65 mg, 0.100 mmol, 1 equiv) at ambient atmosphere. The mixture was stirred for 1 hour at room (conditions: XBridge Shield RP18 OBD Column, 5 μm, 19*150 mm; Mobile Phase A: Water (0.1% FA), Mobile Phase B: ACN; Flow rate: 25 mL/minuteute; Gradient: 18% B to 35% B in 12 minutes; 254/220 nm; Rt: 11.74 minutes) to afford (R)-1-[[2,6-dimethoxy-4-(2-methyl-1-oxo-1,2-dihydro-2,7-naphthyridin-4-yl)phenyl]methyl]-N-(8-[2-(2,6-dioxopiperidin-3-yl)-1,3-dioxo-2,3-dihydro-1H-isoindol-4-yl]amino]octyl) azetidine-3-carboxamide (25 mg, 31.60%) as a yellow solid. $^1$H NMR (300 MHZ, Methanol-d4) δ 9.52 (s, 1H), 8.68 (d, J=5.8 Hz, 1H), 7.74 (s, 1H), 7.62 (d, J=5.8 Hz, 1H), 7.54 (dd, J=8.5, 7.1 Hz, 1H), 7.01 (t, J=7.8 Hz, 2H), 6.78 (s, 2H), 5.06 (dd, J=12.3, 5.5 Hz, 1H), 4.17 (s, 2H), 3.93 (s, 6H), 3.97-3.82 (m, 1H), 3.74 (s, 2H), 3.69 (s, 3H), 3.31-3.09 (m, 4H), 2.97-2.62 (m, 3H), 2.50 (d, J=9.2 Hz, 1H), 2.32-2.20 (m, 1H), 2.19-2.09 (m, 1H), 1.57 (q, J=6.9 Hz, 2H), 1.45-1.30 (m, 10H). LCMS (ESI) m/z: [M+H]$^+$=792.20.

Example 17—Preparation of (2S)-1-[[2,6-Dimethoxy-4-(2-Methyl-1-Oxo-2,7-Naphthyridin-4-Yl)Phenyl]Methyl]-N-(8-[[2-(2,6-Dioxopiperidin-3-Yl)-1,3-Dioxoisoindol-4-Yl]Amino]Octyl) Azetidine-2-Carboxamide (Compound D11)

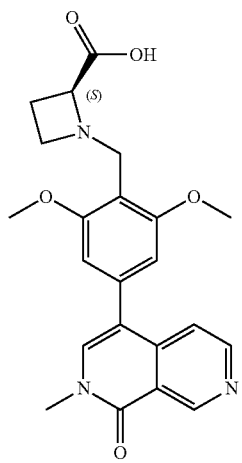
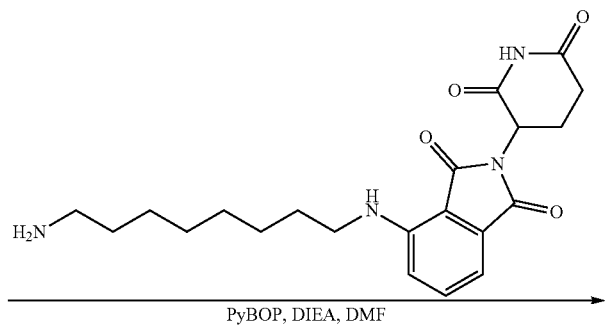
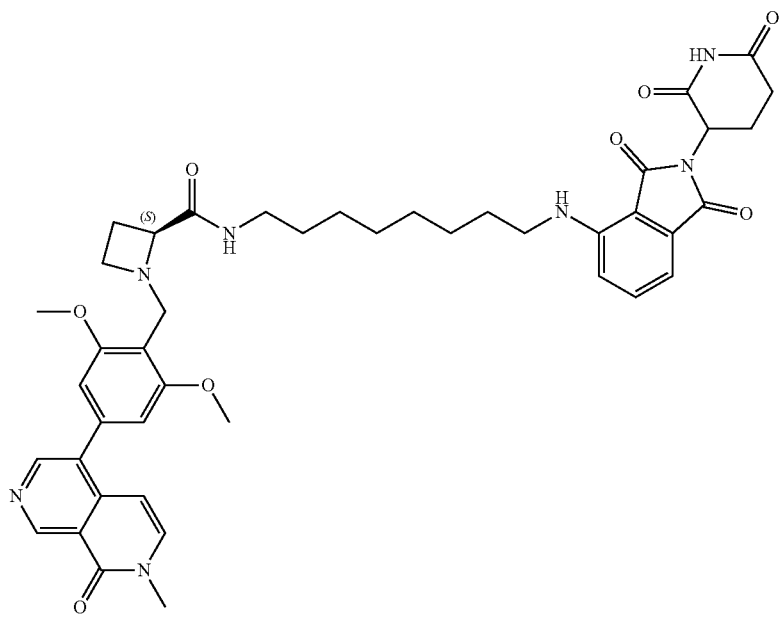

compound D11

To a solution of (2S)-1-[2,6-dimethoxy-4-(2-methyl-1-oxo-1,2-dihydro-2,7-naphthyridin-4-yl)phenyl]methyl]azetidine-2-carboxylic acid (50.00 mg, 0.122 mmol, 1.00 equiv) and 4-[(8-aminooctyl)amino]-2-(2,6-dioxopiperidin-3-yl)-2,3-dihydro-1H-isoindole-1,3-dione (48.91 mg, 0.122 mmol, 1.00 equiv) in DMF (2.00 mL) was added PyBOP (127.10 mg, 0.244 mmol, 2.00 equiv) and DIEA (47.35 mg, 0.366 mmol, 3.00 equiv). The resulting solution was stirred at 25° C. for 2 hours. The crude product was purified by preparative HPLC(condition: XSelect CSH Prep C18 OBD Column, 5 μm, 19*150 mm; Mobile Phase A: Water (0.1% FA), Mobile Phase B: ACN; Flow rate: 25 mL/minuteute; Gradient: 20% B to 55% B in 8 minutes; 254 nm; Rt: 7.12 minutes). Fractions containing the desired compound were evaporated to dryness to afford (2S)-1-[[2,6-dimethoxy-4-(2-methyl-1-oxo-2,7-naphthyridin-4-yl)phenyl]methyl]-N-(8-[2-(2,6-dioxopiperidin-3-yl)-1,3-dioxoisoindol-4-yl]amino]octyl) azetidine-2-carboxamide (35 mg, 35.47%) as a yellow solid. $^1$H NMR (400 MHZ, Methanol-d4)δ 9.51 (s, 1H), 8.68 (d, J=5.7 Hz, 1H), 7.72 (s, 1H), 7.62 (d, J=5.8 Hz, 1H), 7.53 (t, J=7.8 Hz, 1H), 7.00 (dd, J=10.6, 7.8 Hz, 2H), 6.75 (s, 2H), 5.05 (dd, J=12.4, 5.4 Hz, 1H), 3.89 (s, 9H), 3.69 (s, 3H), 3.30 (s, 2H), 3.25 (t, J=6.9 Hz, 2H), 3.15 (t, J=7.1 Hz, 2H), 2.94-2.64 (m, 3H), 2.35 (d, J=9.5 Hz, 1H), 2.16-2.00 (m, 1H), 1.58 (t, J=7.1 Hz, 2H), 1.40 (d, J=6.7 Hz, 2H), 1.30 (s, 8H). LCMS (ESI) m/z: [M+H]$^+$=792.60.

Example 18—Preparation of 1-[[2,6-Dimethoxy-4-(2-Methyl-1-Oxo-1,2-Dihydro-2,7-Naphthyridin-4-Yl)Phenyl]Methyl]-N-(8-[2-(2,6-Dioxopiperidin-3-Yl)-1,3-Dioxo-2,3-Dihydro-1H-Isoindol-4-Yl]Amino]Octyl) Azetidine-3-Sulfonamide (Compound D12)
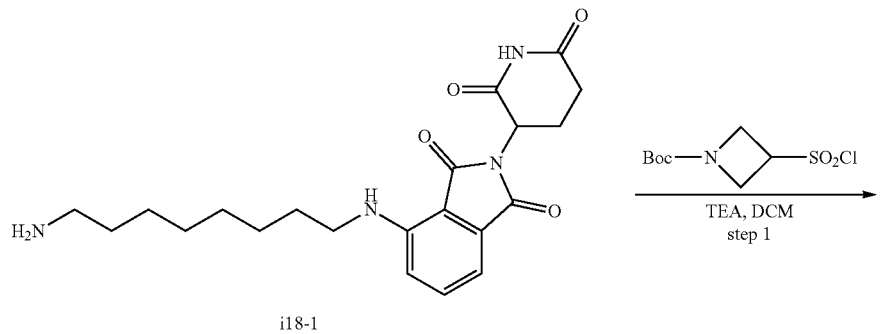
i18-1
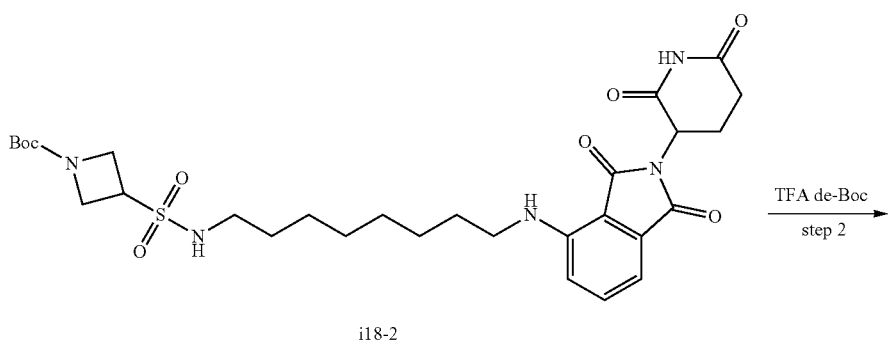
i18-2
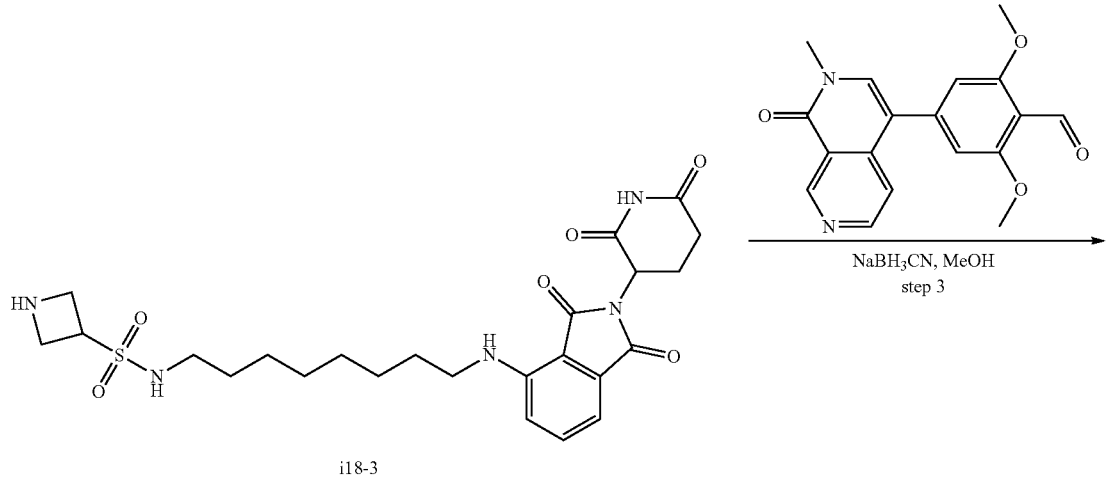
i18-3

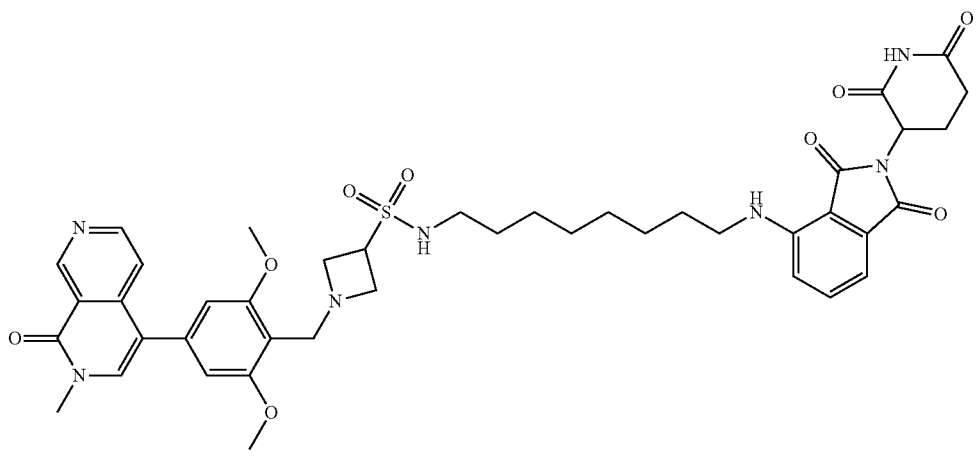

compound D12

Step 1: Preparation of Tert-Butyl 3-[(8-[2-(2,6-Dioxopiperidin-3-Yl)-1,3-Dioxo-2,3-Dihydro-1H-Isoindol-4-Yl]Amino]Octyl) Sulfamoyl]Azetidine-1-Carboxylate (i18-2)

Step 2: Preparation of N-(8-[[2-(2,6-Dioxopiperidin-3-Yl)-1,3-Dioxoisoindol-4-Yl]Amino]Octyl) Azetidine-3-Sulfonamide (i18-3)

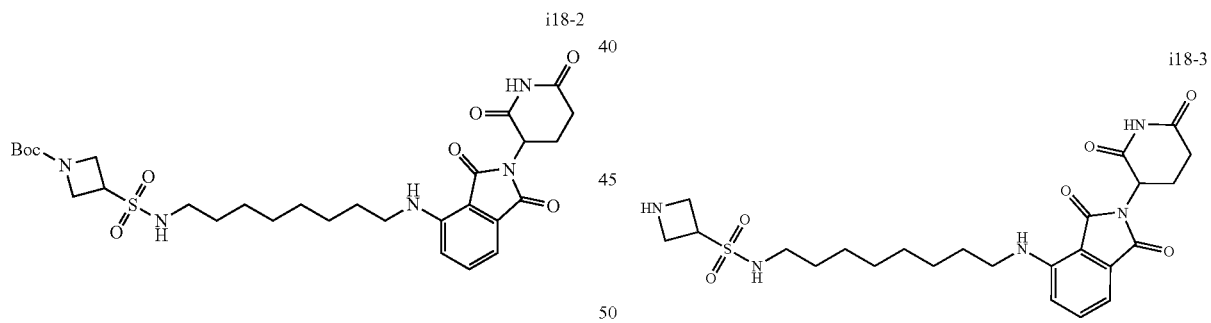

To a solution of 4-[(8-aminooctyl)amino]-2-(2,6-dioxopiperidin-3-yl)-2,3-dihydro-1H-isoindole-1,3-dione (100.00 mg, 0.250 mmol, 1.00 equiv) in DCM (2.00 mL) was added tert-butyl 3-(chlorosulfonyl) azetidine-1-carboxylate (95.78 mg, 0.375 mmol, 1.50 equiv) and TEA (50.53 mg, 0.499 mmol, 2.00 equiv) at 0° C. The resulting solution was stirred for 2 hours at 25° C. The reaction was then quenched by the addition of 5 mL of MeOH. The resulting mixture was concentrated. The residue was applied onto a silica gel column with ethyl DCM/MeOH (20:1). This resulted in 110 mg (71.08%) of tert-butyl 3-[(8-[2-(2,6-dioxopiperidin-3-yl)-1,3-dioxo-2,3-dihydro-1H-isoindol-4-yl]amino]octyl) sulfamoyl]azetidine-1-carboxylate as a yellow solid. LCMS (ESI) m/z: [M+H]$^+$=620.

A solution of tert-butyl 3-[(8-[[2-(2,6-dioxopiperidin-3-yl)-1,3-dioxoisoindol-4-yl]amino]octyl) sulfamoyl]azetidine-1-carboxylate (110.00 mg, 0.177 mmol, 1.00 equiv) in TFA (2.00 mL) and CH$_2$Cl2 (2.00 mL) was stirred at 0° C. for 1 hour. The resulting mixture was concentrated under reduced pressure to afford N-(8-[2-(2,6-dioxopiperidin-3-yl)-1,3-dioxoisoindol-4-yl]amino]octyl) azetidine-3-sulfonamide (85 mg, 92.16%) as a yellow solid, which was used directly without further purification. LCMS (ESI) m/z: [M+H]$^+$=520.

Step 3: Preparation of 1-[[2,6-Dimethoxy-4-(2-Methyl-1-Oxo-1,2-Dihydro-2,7-Naphthyridin-4-Yl)Phenyl]Methyl]-N-(8-[[2-(2,6-Dioxopiperidin-3-Yl)-1,3-Dioxo-2,3-Dihydro-1H-Isoindol-4-Yl]Amino]Octyl) Azetidine-3-Sulfonamide (Compound D12)

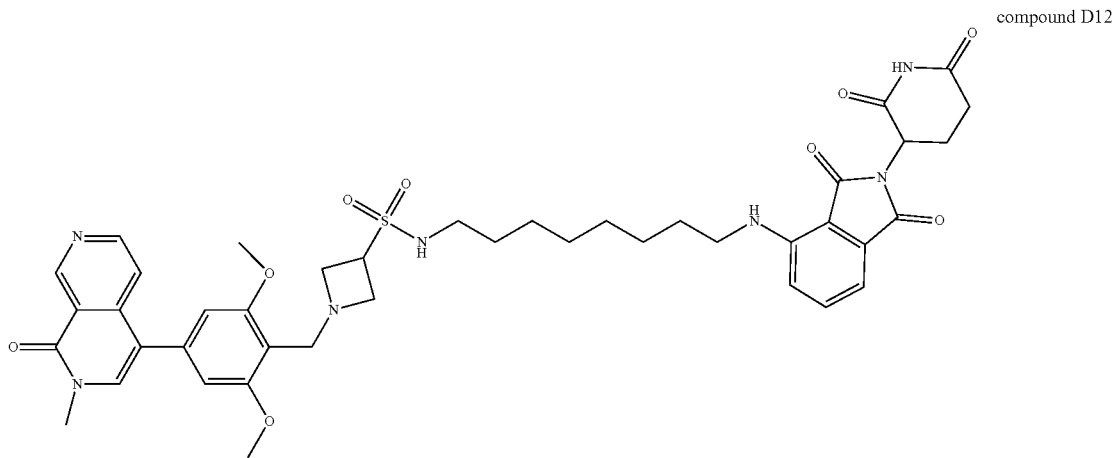 [SMILES: COc1cc(-c2cn(C)c(=O)c3cnccc23)cc(OC)c1CN1CC(S(=O)(=O)NCCCCCCCCNc2cccc3c2C(=O)N(C2CCC(=O)NC2=O)C3=O)C1]

compound D12

To a solution of N-(8-[2-(2,6-dioxopiperidin-3-yl)-1,3-dioxo-2,3-dihydro-1H-isoindol-4-yl]amino]octyl) azetidine-3-sulfonamide (85.00 mg, 0.164 mmol, 1.00 equiv) and 2,6-dimethoxy-4-(2-methyl-1-oxo-1,2-dihydro-2,7-naphthyridin-4-yl)benzaldehyde (53.06 mg, 0.164 mmol, 1.00 equiv) in MeOH (2.00 mL) was added NaBH$_3$CN (20.56 mg, 0.327 mmol, 2.00 equiv). The resulting solution was stirred at 25° C. for 2 hours. The crude product was purified by preparative HPLC Column (condition: XSelect CSH Prep C18 OBD Column, 5 μm, 19*150 mm; Mobile Phase A: Water (0.1% FA), Mobile Phase B: ACN; Flow rate: 25 mL/minuteutes; Gradient: 20% B to 55% B in 8 minutes; 254 nm; Rt: 7.12 minutes). Fractions containing the desired compound were evaporated to dryness to afford 1-[[2,6-dimethoxy-4-(2-methyl-1-oxo-1,2-dihydro-2,7-naphthyridin-4-yl)phenyl]methyl]-N-(8-[2-(2,6-dioxopiperidin-3-yl)-1,3-dioxo-2,3-dihydro-1H-isoindol-4-yl]amino]octyl) azetidine-3-sulfonamide (50 mg,36.92%) as a white solid. $^1$H NMR (400 MHZ, Methanol-d4)δ 9.52 (d, J=0.9 Hz, 1H), 8.68 (d, J=5.7 Hz, 1H), 8.53 (s, 0.47H, FA), 7.74 (s, 1H), 7.63 (dd, J=5.8, 0.9 Hz, 1H), 7.55 (dd, J=8.5, 7.1 Hz, 1H), 7.03 (dd, J=7.8, 4.8 Hz, 2H), 6.77 (s, 2H), 5.06 (dd, J=12.5, 5.5 Hz, 1H), 4.03 (p, J=8.2, 7.8 Hz, 1H), 3.91 (d, J=4.1 Hz, 2H), 3.89 (s, 6H), 3.78-3.68 (m, 8H), 3.30 (d, J=6.8 Hz, 1H), 3.03 (t, J=7.0 Hz, 2H), 2.94-2.80 (m, 1H), 2.80-2.66 (m, 2H), 2.17-2.08 (m, 1H), 1.70-1.62 (m, 2H), 1.51 (d, J=6.9 Hz, 2H), 1.44-1.37 (m, 8H). LCMS (ESI) m/z: [M+H]$^+$=828.35.

Example 19—Preparation of 1-(2,6-Dimethoxy-4-(2-Methyl-1-Oxo-1,2-Dihydro-2,7-Naphthyridin-4-Yl)Benzyl)-N-(8-((2-(2,6-Dioxopiperidin-3-Yl)-1,3-Dioxoisoindolin-4-Yl)Amino) Octyl)-3-Methylazetidine-3-Carboxamide (Compound D13)

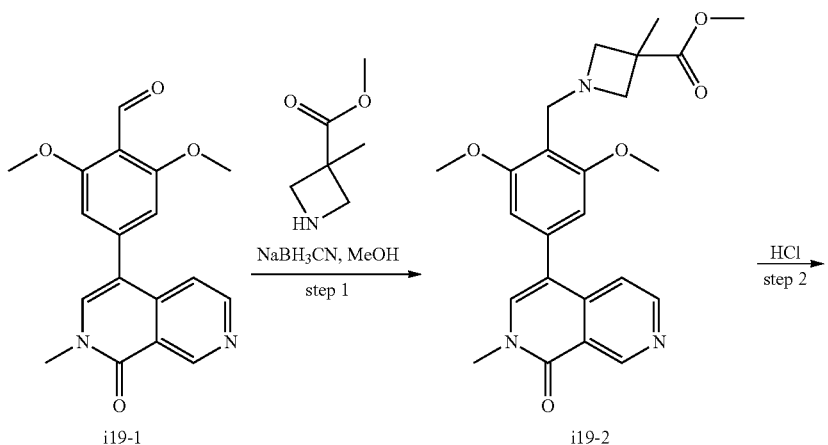

i19-1     i19-2

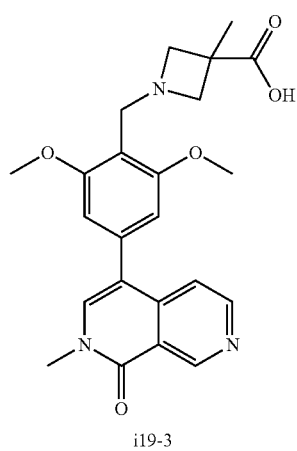

i19-3

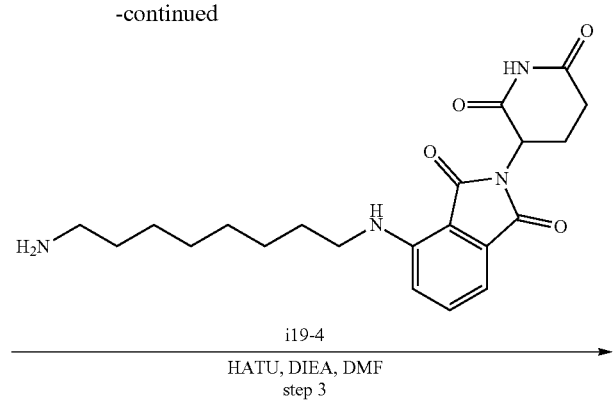

i19-4

HATU, DIEA, DMF
step 3

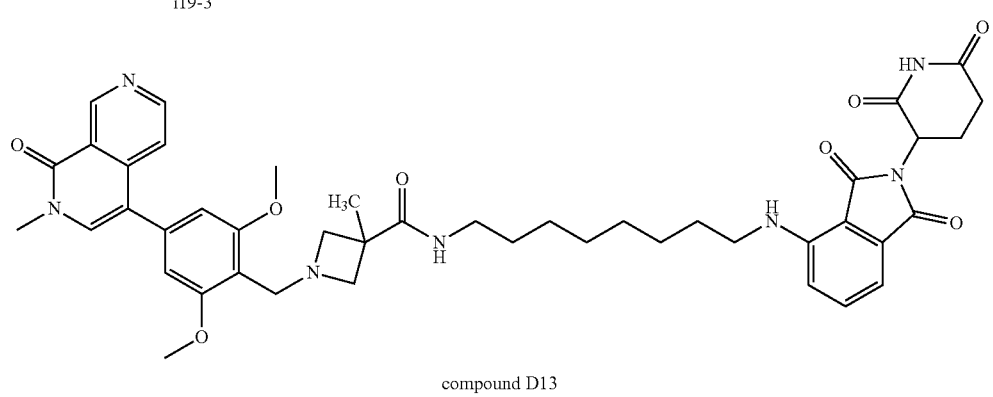

compound D13

Step 1: Preparation of Methyl 1-(2,6-Dimethoxy-4-(2-Methyl-1-Oxo-1,2-Dihydro-2,7-Naphthyridin-4-Yl)Benzyl)-3-Methylazetidine-3-Carboxylate (i19-2)

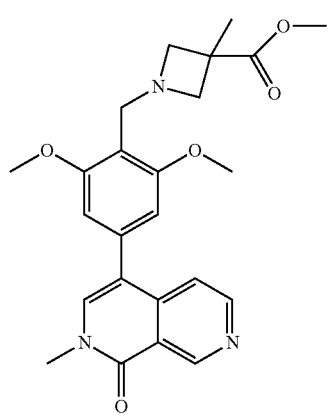

i19-2

To a solution of 2,6-dimethoxy-4-(2-methyl-1-oxo-1,2-dihydro-2,7-naphthyridin-4-yl)benzaldehyde (200 mg, 0.617 mmol, 1 equiv) and methyl 3-methylazetidine-3-carboxylate (79.65 mg, 0.617 mmol, 1.00 equiv) in MeOH (2 mL) was added NaBH₃CN (77.50 mg, 1.233 mmol, 2 equiv). The resulting solution was stirred at 25° C. for 1 hour. The residue was purified by silica gel column chromatography, eluted with DCM/MeOH (9:1) to afford methyl 1-[2,6-dimethoxy-4-(2-methyl-1-oxo-1,2-dihydro-2,7-naphthyridin-4-yl)phenyl]methyl]-3-methylazetidine-3-carboxylate (247 mg, 91.56%) as a yellow solid. LCMS (ESI) m/z: [M+H]⁺=438.

Step 2: Preparation of 1-(2,6-Dimethoxy-4-(2-Methyl-1-Oxo-1,2-Dihydro-2,7-Naphthyridin-4-Yl)Benzyl)-3-Methylazetidine-3-Carboxylic Acid (i19-3)

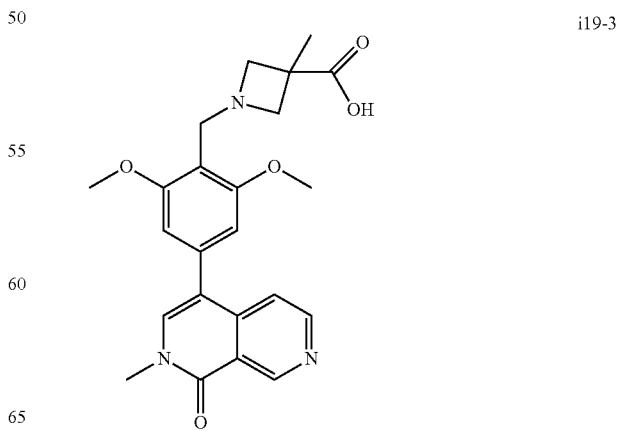

i19-3

A solution of methyl 1-[[2,6-dimethoxy-4-(2-methyl-1-oxo-1,2-dihydro-2,7-naphthyridin-4-yl)phenyl]methyl]-3-methylazetidine-3-carboxylate (235 mg, 0.537 mmol, 1 equiv) in HCl (12 M, 5 mL) was stirred at 25° C. for 40 minutes. The mixture was concentrated under reduced pressure afford 1-[2,6-dimethoxy-4-(2-methyl-1-oxo-1,2-dihydro-2,7-naphthyridin-4-yl)phenyl]methyl]-3-methylazetidine-3-carboxylic acid (185 mg, 81.33%) as a brown solid, that was used directly without further purification. LCMS (ESI) m/z: [M+H]$^+$=424.

Step 3: Preparation of 1-(2,6-Dimethoxy-4-(2-Methyl-1-Oxo-1,2-Dihydro-2,7-Naphthyridin-4-Yl)Benzyl)-N-(8-((2-(2,6-Dioxopiperidin-3-Yl)-1,3-Dioxoisoindolin-4-Yl)Amino) Octyl)-3-Methylazetidine-3-Carboxamide (Compound D13)

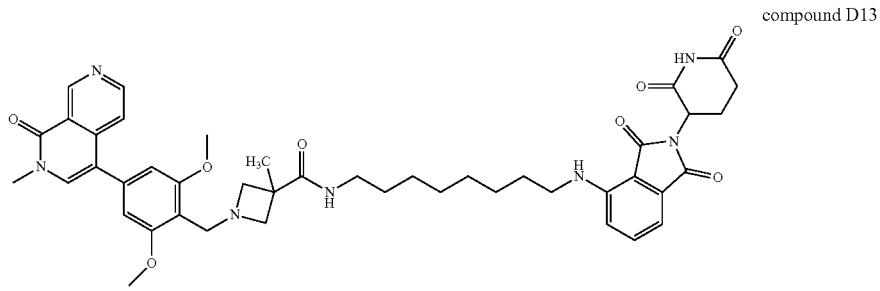 [SMILES: COc1cc(-c2cn(C)c(=O)c3cnccc23)cc(OC)c1CN1CC(C)(C(=O)NCCCCCCCCNc2cccc3c2C(=O)N(C2CCC(=O)NC2=O)C3=O)C1]

compound D13

To a solution of 1-[2,6-dimethoxy-4-(2-methyl-1-oxo-1,2-dihydro-2,7-naphthyridin-4-yl)phenyl]methyl]-3-methylazetidine-3-carboxylic acid (50 mg, 0.118 mmol, 1 equiv), 4-[(8-aminooctyl)amino]-2-(2,6-dioxopiperidin-3-yl)-2,3-dihydro-1H-isoindole-1,3-dione (94.57 mg, 0.236 mmol, 2 equiv) and Et$_3$N (119.48 mg, 1.181 mmol, 10.00 equiv) in DMF (3 mL), was added EDCI (27.16 mg, 0.142 mmol, 1.2 equiv) and HOBT (19.15 mg, 0.142 mmol, 1.2 equiv), the resulting solution was stirred at 25° C. for 24 hours. The crude product was purified by Prep-HPLC with the following conditions (condition: XBridge Prep C18 OBD Column, 5 μm, 19*150 mm; mobile phase, Water (0.1% FA) and ACN; Detector, UV) to give 1-[[2,6-dimethoxy-4-(2-methyl-1-oxo-1,2-dihydro-2,7-naphthyridin-4-yl)phenyl]methyl]-N-(8-[2-(2,6-dioxopiperidin-3-yl)-1,3-dioxo-2,3-dihydro-1H-isoindol-4-yl]amino]octyl)-3-methylazetidine-3-carboxamide (21.7 mg, 22.80%) as a yellow solid. $^1$H NMR (300 MHZ, Methanol-d4)δ 9.53 (s, 1H), 8.69 (d, J=5.7 Hz, 1H), 8.55 (s, 1H), 7.76 (s, 1H), 7.62 (d, J=5.7 Hz, 1H), 7.59-7.49 (m, 1H), 7.07-6.98 (m, 2H), 6.81 (s, 2H), 5.06 (dd, J=12.3, 5.4 Hz, 1H), 4.19 (s, 2H), 4.06 (s, 2H), 3.93 (s, 6H), 3.71 (s, 5H), 3.32-3.16 (m, 1H), 2.92-2.66 (m, 4H), 2.15-2.06 (m, 1H), 1.64 (d, J=7.4 Hz, 2H), 1.55 (s, 5H), 1.39-1.32 (m, 8H). LCMS (ESI) m/z: [M+H]$^+$=806.50.

Example 20—Preparation of 1,2-Dihydro-2,7-Naphthyridin-4-Yl)Phenyl]Methyl]-N-(8-[2-(2,6-Dioxopiperidin-3-Yl)-1,3-Dioxo-2,3-Dihydro-1H-Isoindol-4-Yl]Amino]Octyl)-N-Methylazetidine-3-Carboxamide (Compound D14)

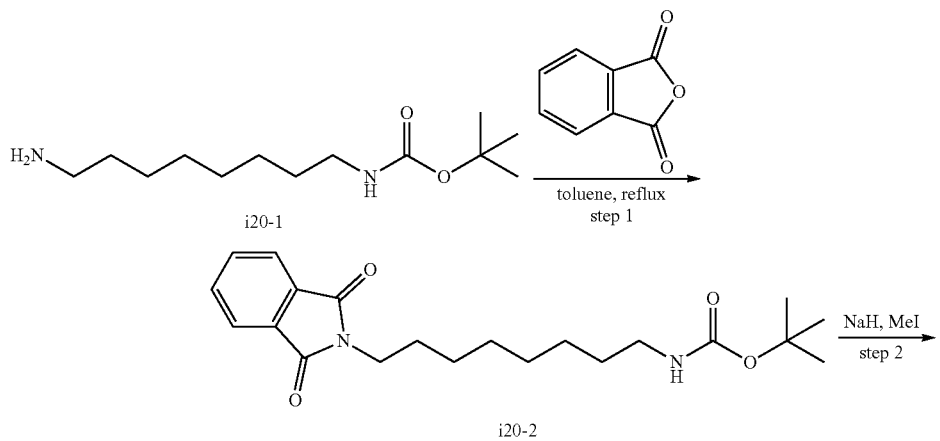

-continued
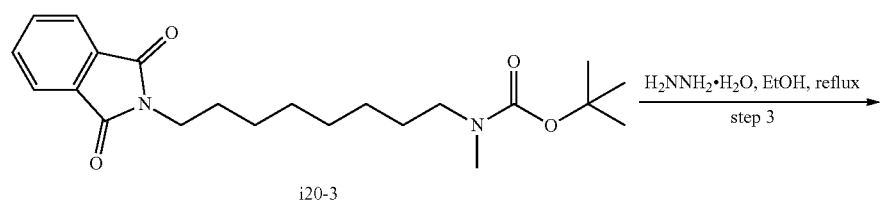
i20-3
H₂NNH₂·H₂O, EtOH, reflux
step 3
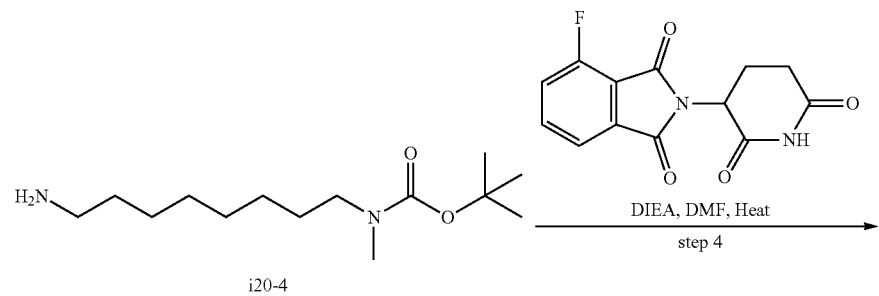
i20-4
DIEA, DMF, Heat
step 4
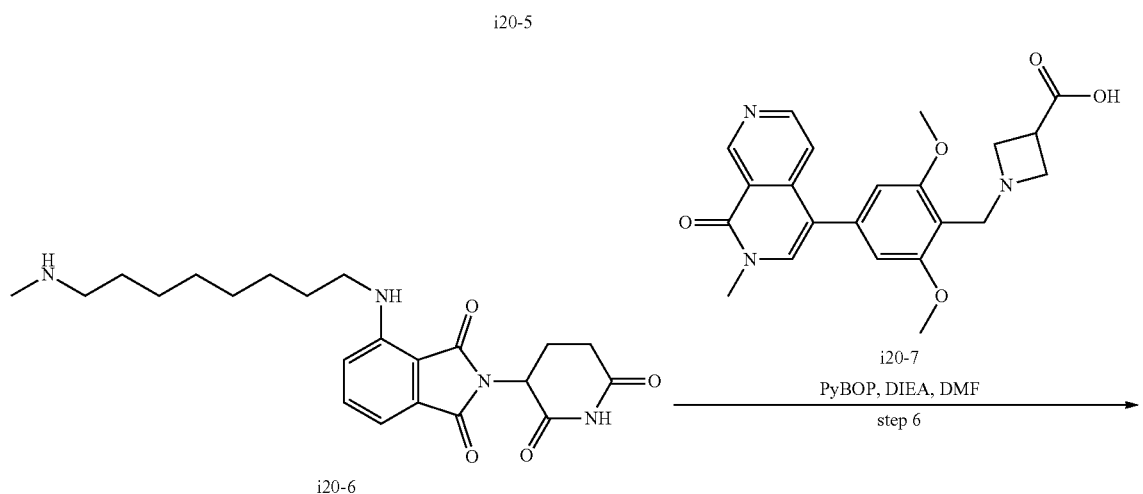
i20-5
TFA, DCM
step 5
i20-6
i20-7
PyBOP, DIEA, DMF
step 6
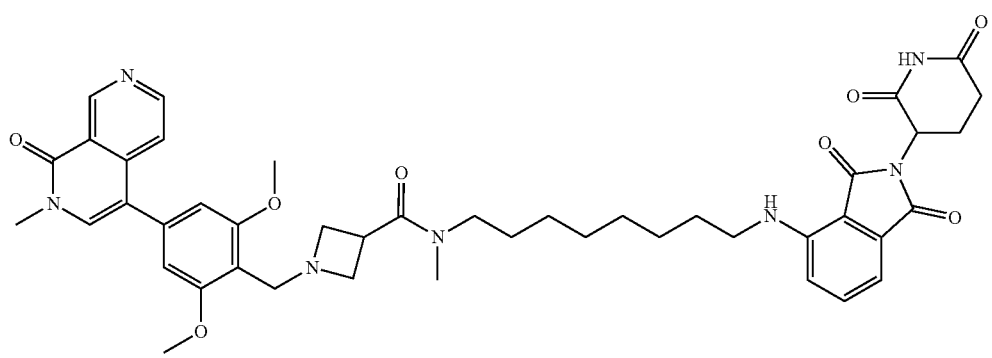
compound D14

Step 1: Preparation of Tert-Butyl N-[8-(1,3-Dioxoisoindol-2-Yl) Octyl]Carbamate (i20-2)

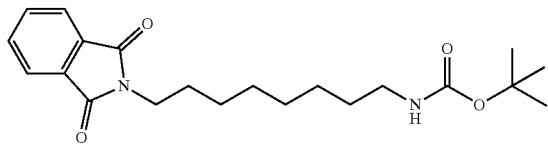

i20-2

A mixture of tert-butyl N-(8-aminooctyl) carbamate (1.00 g, 4.092 mmol, 1.00 equiv) and phthalic anhydride (606.10 mg, 4.092 mmol, 1.00 equiv) in toluene (20.00 mL) was stirred for 2 hours at 130° C. under nitrogen atmosphere. The mixture was allowed to cool down to room temperature and the solvent was evaporated. The resulting residue was purified by silica gel column chromatography, eluted with PE/EtOAc (10:1) to afford tert-butyl N-[8-(1,3-dioxoisoindol-2-yl) octyl]carbamate (1.7 g, 95.41%) as a white solid. LCMS (ESI) m/z: [M+H]$^+$=375.

Step 2: Preparation of Tert-Butyl N-[8-(1,3-Dioxoisoindol-2-Yl) Octyl]-N-Methylcarbamate (i20-3)

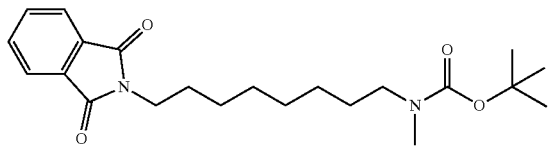

i20-3

To a stirred solution of tert-butyl N-[8-(1,3-dioxoisoindol-2-yl) octyl]carbamate (1.24 g, 3.311 mmol, 1.00 equiv) in DMF (1.00 mL) was added NaH (0.16 g, 6.622 mmol, 2 equiv) in portions at 0° C. under nitrogen atmosphere. Then CH$_3$I (1.88 g, 13.245 mmol, 4 equiv) was added. The resulting mixture was stirred for 1 hour at room temperature under nitrogen atmosphere. The residue was purified by silica gel column chromatography, eluted with PE/EtOAc (12:1) to afford tert-butyl N-[8-(1,3-dioxoisoindol-2-yl) octyl]-N-methylcarbamate (800 mg, 62.19%) as a colorless liquid. LCMS (ESI) m/z: [M+H]$^+$=389.

Step 3: Preparation of Tert-Butyl N-(8-Aminooctyl)-N-Methylcarbamate (i20-4)

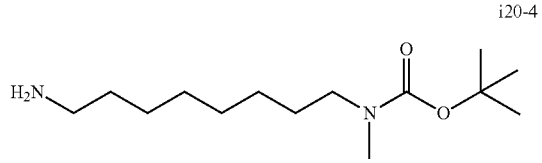 [SMILES: CN(CCCCCCCCN)C(=O)OC(C)(C)C]

i20-4

A solution of tert-butyl N-[8-(1,3-dioxoisoindol-2-yl) octyl]-N-methylcarbamate (700.00 mg, 1.802 mmol, 1.00 equiv) and NH$_2$NH$_2$ (259.84 mg, 3.604 mmol, 2 equiv) in EtOH (5.00 mL) was stirred for 1 hour at 90° C. under nitrogen atmosphere. The mixture was allowed to cool down to room temperature. After filtration, the filtrate was concentrated under reduced pressure. The resulting residue was purified by silica gel column chromatography, eluted with PE/EtOAc (12:1) to afford tert-butyl N-(8-aminooctyl)-N-methylcarbamate (580 mg, 94.68%) as a colorless liquid. LCMS (ESI) m/z: [M+H]$^+$=259.

Step 4: Preparation of Tert-Butyl N-(8-[[2-(2,6-Dioxopiperidin-3-Yl)-1,3-Dioxoisoindol-4-Yl]Amino]Octyl)-N-Methylcarbamate (i20-5)

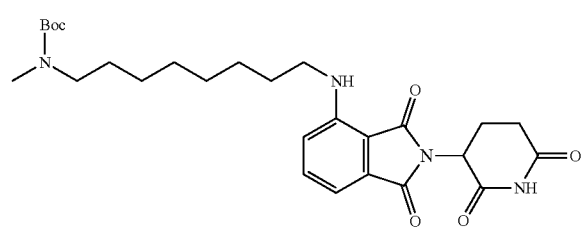

i20-5

To a stirred solution of 2-(2,6-dioxopiperidin-3-yl)-4-fluoroisoindole-1,3-dione (520.00 mg, 1.883 mmol, 1.00 equiv) and tert-butyl N-(8-aminooctyl)-N-methylcarbamate (486.46 mg, 1.883 mmol, 1 equiv) in DMF (5.00 mL) was added DIPEA (1216.53 mg, 9.413 mmol, 5 equiv). The solution was stirred for 1 hour at 90° C. under nitrogen atmosphere, then it was cooled down to room temperature. The resulting mixture was concentrated under reduced pressure. The residue was purified by silica gel column chromatography, eluted with CH$_2$Cl$_2$/MeOH (12:1) to afford tert-butyl N-(8-[2-(2,6-dioxopiperidin-3-yl)-1,3-dioxoisoindol-4-yl]amino]octyl)-N-methylcarbamate (260 mg, 26.84%) as a yellow solid. LCMS (ESI) m/z: [M+H]$^+$=515.

Step 5: Preparation of 2-(2,6-Dioxopiperidin-3-Yl)-4-[[8-(Methylamino) Octyl]Amino]Isoindole-1,3-Dione (i20-6)

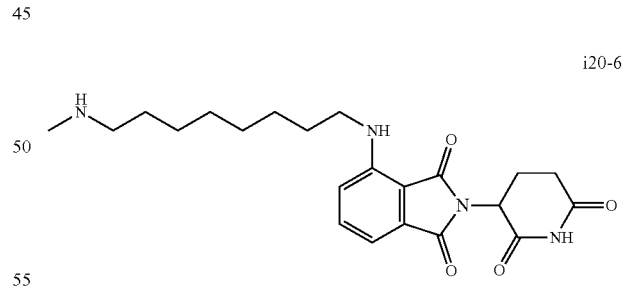

i20-6

A solution of tert-butyl N-(8-[[2-(2,6-dioxopiperidin-3-yl)-1,3-dioxoisoindol-4-yl]amino]octyl)-N-methylcarbamate (220.00 mg, 0.427 mmol, 1.00 equiv) in 4 M HCl in dioxane (6.00 mL) was stirred for 2 hours at room temperature. The solvent was evaporated and the residue was purified by reverse flash chromatography (condition: C18 silica gel column; mobile phase, MeOH in water, 10% to 50% gradient in 10 minutes; detector, UV 254 nm) to afford 2-(2,6-dioxopiperidin-3-yl)-4-[[8-(methylamino) octyl] amino]isoindole-1,3-dione (170 mg, 95.94%) as a dark yellow oil. LCMS (ESI) m/z: [M+H]$^+$=415.

Step 6: Preparation of 1,2-Dihydro-2,7-Naphthyridin-4-Yl)Phenyl]Methyl]-N-(8-[[2-(2,6-Dioxopiperidin-3-Yl)-1,3-Dioxo-2,3-Dihydro-1H-Isoindol-4-Yl]Amino]Octyl)-N-Methylazetidine-3-Carboxamide (Compound D14)

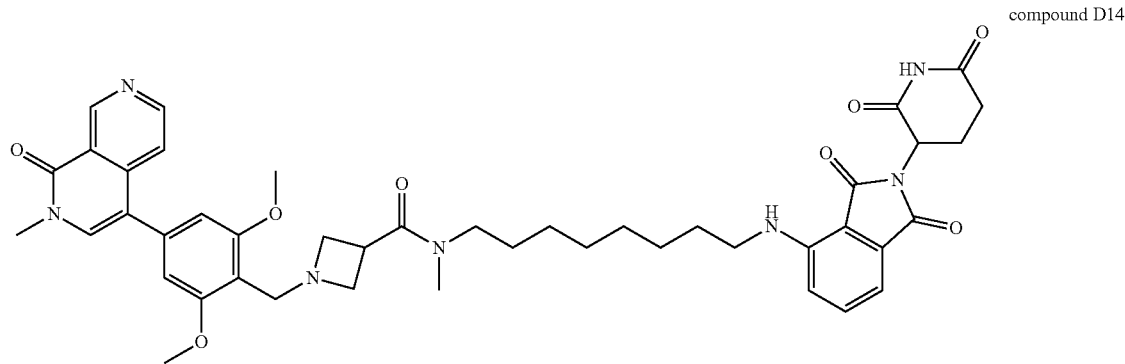 [SMILES: COc1cc(-c2cn(C)c(=O)c3cnccc23)cc(OC)c1CN1CC(C(=O)N(C)CCCCCCCCNc2cccc3c2C(=O)N(C2CCC(=O)NC2=O)C3=O)C1]

To a stirred solution of 1-[[2,6-dimethoxy-4-(2-methyl-1-oxo-1,2-dihydro-2,7-naphthyridin-4-yl)phenyl]methyl]azetidine-3-carboxylic acid (30 mg, 0.073 mmol, 1 equiv) in DMF (0.5 mL), was added DIPEA (47.35 mg, 0.366 mmol, 5 equiv), HATU (55.72 mg, 0.147 mmol, 2 equiv), and 2-(2,6-dioxopiperidin-3-yl)-4-[[8-(methylamino) octyl]amino]-2,3-dihydro-1H-isoindole-1,3-dione (30.37 mg, 0.073 mmol, 1 equiv). The reaction was stirred at ambient atmosphere for 1 hour. The mixture was purified directly by Prep-HPLC(condition: SunFire C18 OBD Prep Column, 100 Å, 5 μm, 19 mm×250 mm; Mobile Phase A: Water (0.1% FA), Mobile Phase B: ACN; Flow rate: 25 mL/minuteutes; Gradient: 24% B to 36% B in 8 minutes; 254 nm; Rt: 7.9 minutes) to afford 1-[2,6-dimethoxy-4-(2-methyl-1-oxo-1,2-dihydro-2,7-naphthyridin-4-yl)phenyl]methyl]-N-(8-[2-(2,6-dioxopiperidin-3-yl)-1,3-dioxo-2,3-dihydro-1H-isoindol-4-yl]amino]octyl)-N-methylazetidine-3-carboxamide formate (25 mg, 40.05%) as a yellow solid. $^1$H NMR (300 MHZ, Methanol-d4) δ 9.52 (dd, J=4.5, 0.9 Hz, 1H), 8.68 (dd, J=5.8, 2.5 Hz, 1H), 8.56 (s, 0.5H, FA), 7.75 (d, J=2.0 Hz, 1H), 7.67-7.58 (m, 1H), 7.53 (ddd, J=8.5, 7.1, 4.7 Hz, 1H), 7.07-6.95 (m, 2H), 6.81 (d, J=1.8 Hz, 2H), 5.06 (ddd, J=12.1, 5.4, 2.5 Hz, 1H), 4.21 (d, J=4.7 Hz, 2H), 4.00 (dd, J=17.1, 8.8 Hz, 4H), 3.93 (s, 6H), 3.80 (t, J=8.2 Hz, 1H), 3.70 (d, J=3.3 Hz, 3H), 3.45-3.19 (m, 2H), 2.94 (d, J=4.3 Hz, 3H), 2.91-2.68 (m, 3H), 2.12 (s, 1H), 1.67 (s, 2H), 1.57 (d, J=6.9 Hz, 2H), 1.41-1.33 (m, 8H). LCMS (ESI) m/z: [M+H]$^+$=806.35.

Example 21—Preparation of 1-[[2,6-Dimethoxy-4-(2-Methyl-1-Oxo-1,2-Dihydro-2,7-Naphthyridin-4-Yl)Phenyl]Methyl]-N-(5-[[2-(2,6-Dioxopiperidin-3-Yl)-1,3-Dioxo-2,3-Dihydro-1H-Isoindol-4-Yl]Amino]Pentyl)-N-Methylazetidine-3-Carboxamide Formic Acid (Compound D15 Formic Acid)

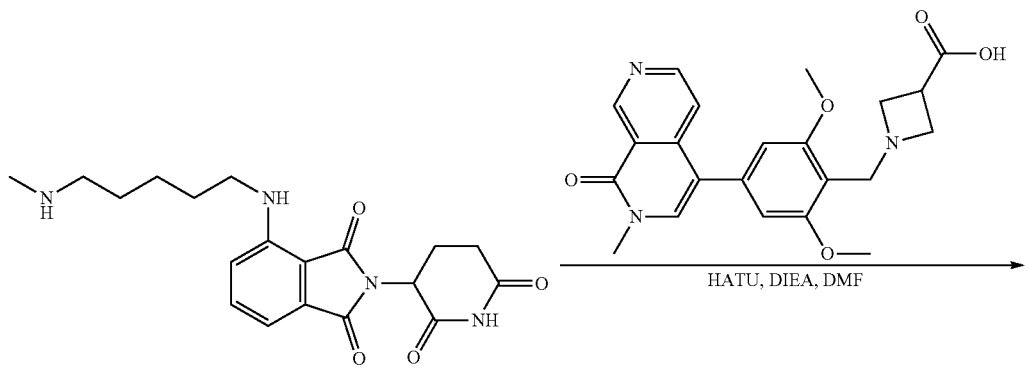

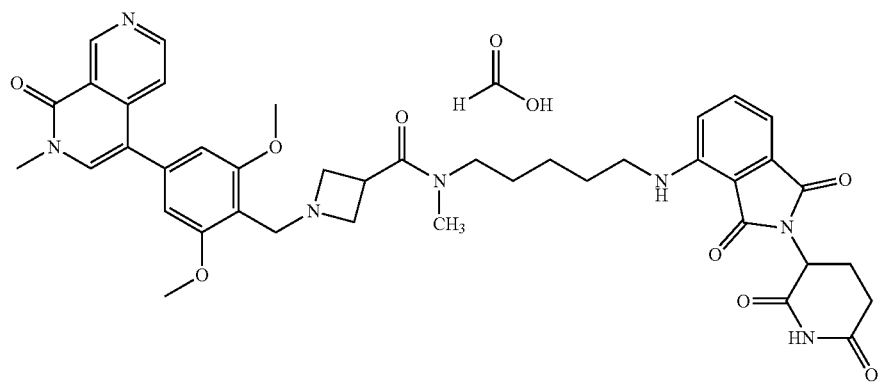

compound D15 formic acid

To a solution of 2-(2,6-dioxopiperidin-3-yl)-4-[[5-(methylamino) pentyl]amino]-2,3-dihydro-1H-isoindole-1,3-dione (60.00 mg, 0.161 mmol, 1.00 equiv), 1-[[2,6-dimethoxy-4-(2-methyl-1-oxo-1,2-dihydro-2,7-naphthyridin-4-yl)phenyl]methyl]azetidine-3-carboxylic acid (65.96 mg, 0.161 mmol, 1.00 equiv), and DIEA (41.64 mg, 0.322 mmol, 2.00 equiv) in DMF (2.00 mL, 25.844 mmol, 160.41 equiv) was added HATU (91.89 mg, 0.242 mmol, 1.50 equiv). The resulting mixture was stirred at room temperature for 16 hours. Without workup, the crude product was purified by Prep-HPLC(condition: XBridge Shield RP18 OBD Column 30*150 mm, 5 um; Mobile Phase A: Water (0.1% FA), Mobile Phase B: ACN; Flow rate: 40 mL/minuteute; Gradient: 18% B to 18% B in 2 minutes; 254/220 nm; Rt: 11.43 minutes) to afford 1-[2,6-dimethoxy-4-(2-methyl-1-oxo-1,2-dihydro-2,7-naphthyridin-4-yl)phenyl]methyl]-N-(5-[2-(2, 6-dioxopiperidin-3-yl)-1,3-dioxo-2,3-dihydro-1H-isoindol-4-yl]amino]pentyl)-N-methylazetidine-3-carboxamide;

formic acid (25.1 mg) as a yellow solid. $^1$H NMR (400 MHZ, Methanol-d4)δ 9.53 (dd, J=5.4, 0.9 Hz, 1H), 8.68 (dd, J=5.8, 1.2 Hz, 1H), 8.56 (s, 0.53H, FA), 7.79-7.73 (m, 1H), 7.67-7.50 (m, 2H), 7.09-6.99 (m, 2H), 6.80 (d, J=3.2 Hz, 2H), 5.06 (ddd, J=12.3, 5.4, 2.8 Hz, 1H), 4.17 (s, 2H), 3.92-3.90 (m, 10H), 3.78 (q, J=9.0, 8.5 Hz, 1H), 3.71 (d, J=2.2 Hz, 3H), 3.48-3.35 (m, 2H), 3.27 (t, J=7.5 Hz, 1H), 2.98-2.85 (m, 3H), 2.89-2.64 (m, 4H), 2.22-2.08 (m, 1H), 1.75-1.62 (m, 4H), 1.43 (s, 2H). LCMS (ESI) m/z: [M+H]$^+$=764.45.

Example 22—Preparation of 2-(2,6-dihydroxypiperidin-3-yl)-4-[(8-[hydroxy (1-[[4-(6-hydroxy-1,5-dimethyl-1,6-dihydropyridin-3-yl)-2,6-dimethoxyphenyl]methyl]azetidin-3-yl)methyl]amino]octyl) amino]-2,3-dihydro-1H-isoindole-1,3-diol formic acid (compound D16 formic acid)

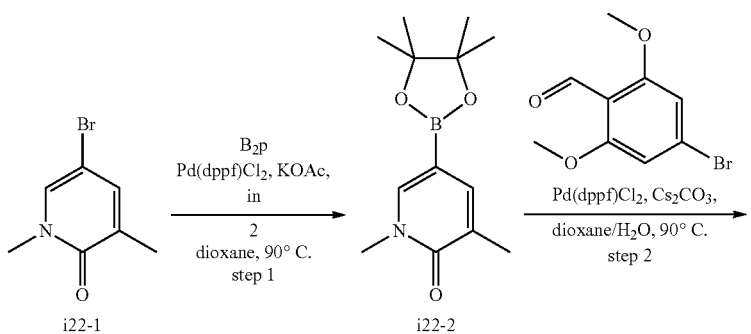

-continued
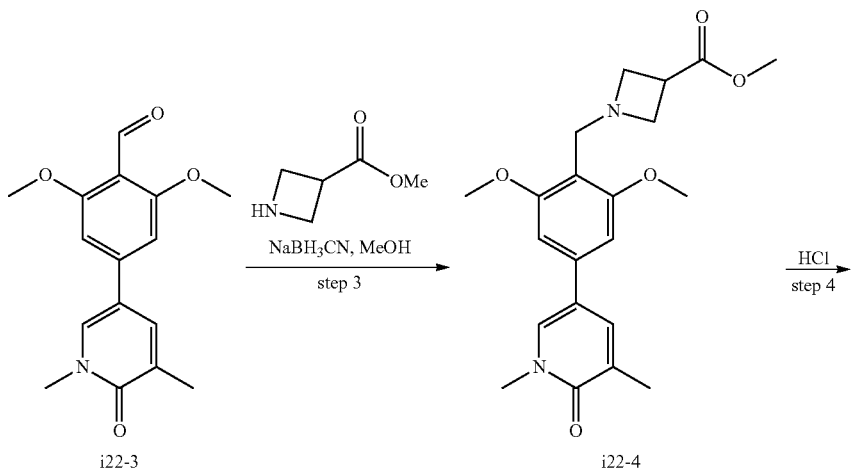
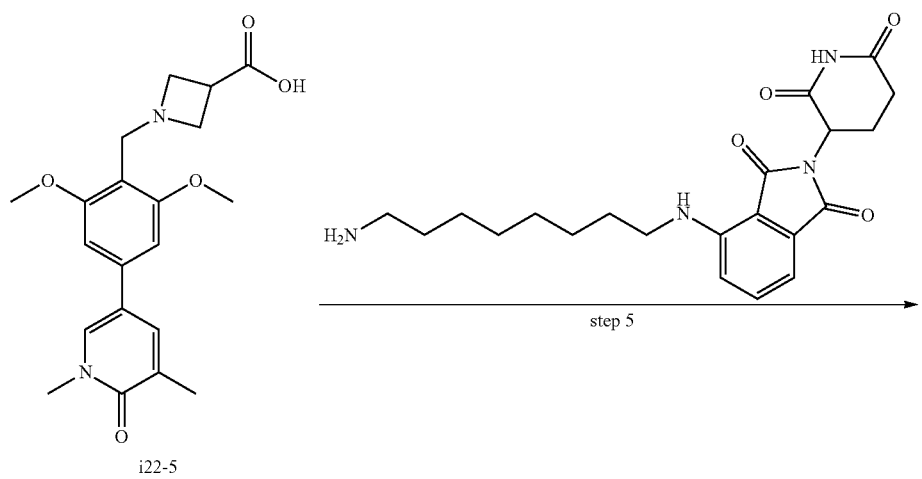
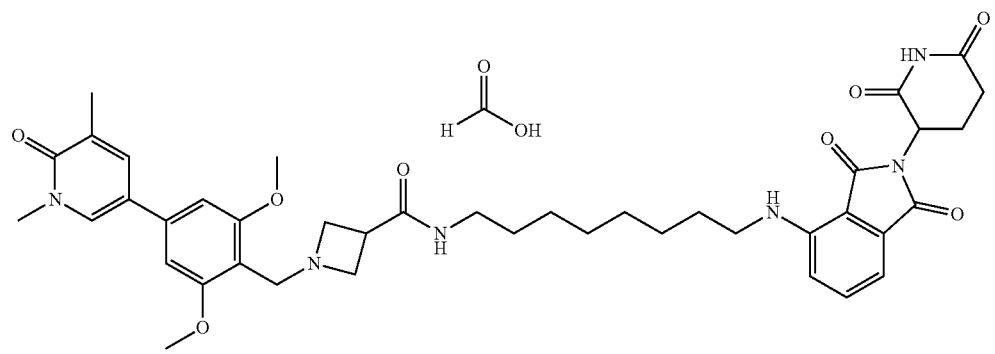
compound D16 formic acid

Step 1: Preparation of 1,3-Dimethyl-5-(4,4,5,5-Tetramethyl-1,3,2-Dioxaborolan-2-Yl) Pyridin-2 (1H)-One (i22-2)

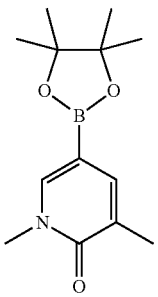

i22-2

To a solution of 5-bromo-1,3-dimethylpyridin-2-one (1.00 g, 4.949 mmol, 1.00 equiv) and bis(pinacolato)diboron (1508.17 mg, 5.939 mmol, 1.20 equiv) in dioxane (10.00 mL) was added KOAc (971.46 mg, 9.898 mmol, 2.00 equiv) and Pd (dppf) Cl$_2$·CH$_2$Cl$_2$ (404.18 mg, 0.495 mmol, 0.10 equiv). After stirring for 2 hours at 90° C. under a nitrogen atmosphere, the resulting mixture was concentrated under reduced pressure. The crude product was used in the next step directly without further purification. LCMS (ESI) m/z: [M+H]$^+$=250.

Step 2: Preparation of 4-(1,5-Dimethyl-6-Oxopyridin-3-Yl)-2,6-Dimethoxybenzaldehyde (i22-3)

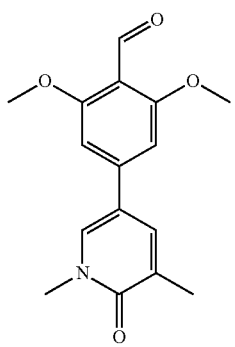

i22-3

To a solution of 1,3-dimethyl-5-(4,4,5,5-tetramethyl-1,3,2-dioxaborolan-2-yl) pyridin-2-one (1.20 g, 4.817 mmol, 1.00 equiv) and 4-bromo-2,6-dimethoxybenzaldehyde (1.18 g, 4.817 mmol, 1.00 equiv) in 1,4-dioxane (40.00 mL) and H$_2$O (4.00 mL) was added CS$_2$CO$_3$ (3.14 g, 9.634 mmol, 2.00 equiv) and Pd (dppf) Cl$_2$ (0.35 g, 0.482 mmol, 0.10 equiv). After stirring for 2 hours at 80° C. under a nitrogen atmosphere, the resulting mixture was concentrated under reduced pressure. The residue was purified by silica gel column chromatography, eluted with CH$_2$Cl$_2$/MeOH (18:1) to afford 4-(1,5-dimethyl-6-oxopyridin-3-yl)-2,6-dimethoxybenzaldehyde (1.43 g, 87.83%) as a brown syrup. LCMS (ESI) m/z: [M+H]$^+$=288.

Step 3: Preparation of Methyl 1-[4-(1,5-Dimethyl-6-Oxopyridin-3-Yl)-2,6-Dimethoxyphenyl]Methyl] Azetidine-3-Carboxylate (i22-4)

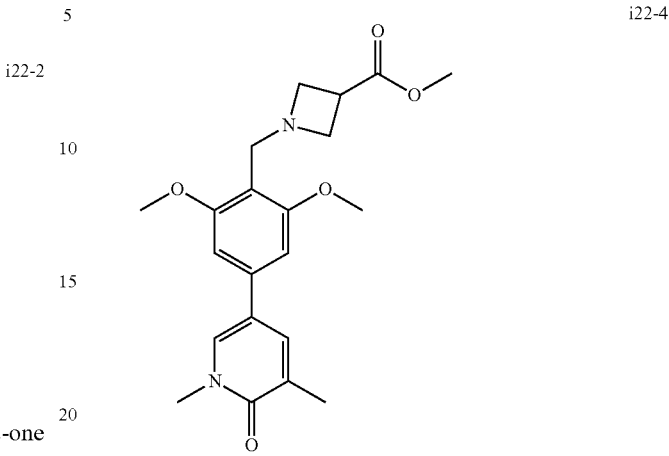

i22-4

To a solution of methyl azetidine-3-carboxylate hydrochloride (1.13 g, 7.466 mmol, 1.50 equiv) in MeOH (10.00 mL) was added Et$_3$N to pH 7-8. Then 4-(1,5-dimethyl-6-oxopyridin-3-yl)-2,6-dimethoxybenzaldehyde (1.43 g, 4.977 mmol, 1.00 equiv) was added. After stirring for 5-10 minutes, NaBH$_3$CN (0.63 g, 9.954 mmol, 2.00 equiv) was added in portions at ambient atmosphere. The resulting mixture was concentrated after stirring for 1 hour at room temperature. The residue was purified by silica gel column chromatography, eluted with CH$_2$Cl$_2$/MeOH (20:1) to afford methyl 1-[4-(1,5-dimethyl-6-oxopyridin-3-yl)-2,6-dimethoxyphenyl]methyl]azetidine-3-carboxylate (1.06 g, 52.36%) as a yellow solid. LCMS (ESI) m/z: [M+H]$^+$=387.

Step 4: Preparation of 1-[4-(1,5-Dimethyl-6-Oxopyridin-3-Yl)-2,6-Dimethoxyphenyl]Methyl] Azetidine-3-Carboxylic Acid (i22-5)

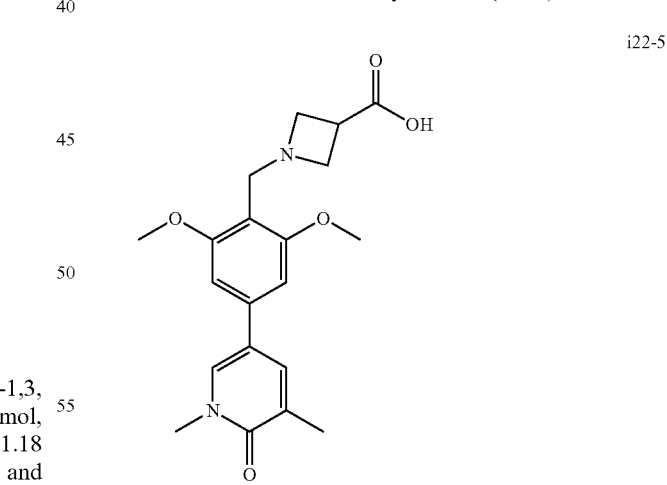

i22-5

A mixture of methyl 1-[[4-(1,5-dimethyl-6-oxopyridin-3-yl)-2,6-dimethoxyphenyl]methyl]azetidine-3-carboxylate (203.00 mg, 0.525 mmol, 1.00 equiv) in HCl (12 N, 2.00 mL) was stirred for 2 hours at 90° C. The resulting mixture was concentrated under reduced pressure to give 1-[4-(1,5-dimethyl-6-oxopyridin-3-yl)-2,6-dimethoxyphenyl]methyl] azetidine-3-carboxylic acid (150 mg, 71.31%) as a yellow solid. LCMS (ESI) m/z: [M+H]$^+$=373.

Step 4: Preparation of 2-(2,6-Dihydroxypiperidin-3-Yl)-4-[(8-[[Hydroxy (1-[[4-(6-Hydroxy-1,5-Dimethyl-1,6-Dihydropyridin-3-Yl)-2,6-Dimethoxyphenyl]Methyl]Azetidin-3-Yl)Methyl]Amino]Octyl) Amino]-2,3-Dihydro-1H-Isoindole-1,3-Diol Formic Acid (Compound D16 Formic Acid)

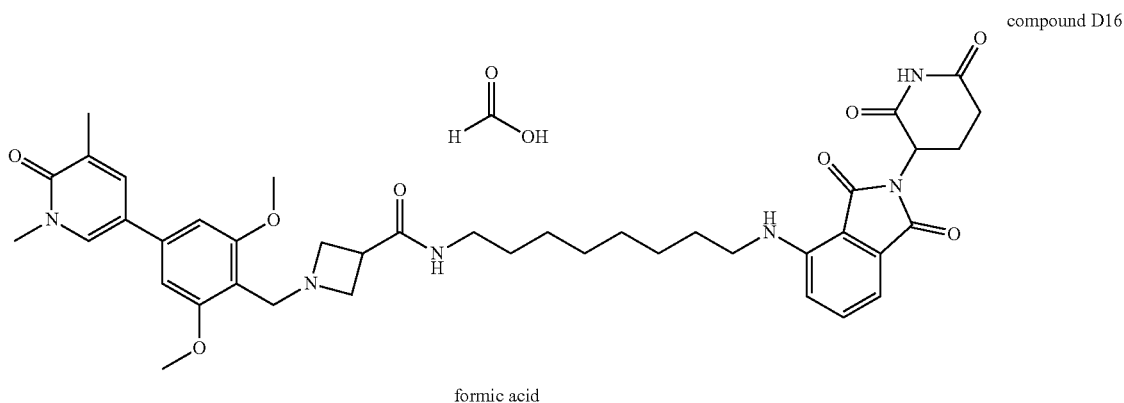 [SMILES: COc1cc(-c2cc(C)c(=O)n(C)c2)cc(OC)c1CN1CC(C(=O)NCCCCCCCCNc2cccc3c2C(=O)N(C2CCC(=O)NC2=O)C3=O)C1 ; O=CO]

To a stirred mixture of 1-[4-(1,5-dimethyl-6-oxo-1,6-dihydropyridin-3-yl)-2,6-dimethoxyphenyl]methyl]azetidine-3-carboxylic acid trifluoroacetic acid (50 mg, 0.103 mmol, 1 equiv) and 4-[(8-aminooctyl)amino]-2-(2,6-dioxopiperidin-3-yl)-2,3-dihydro-1H-isoindole-1,3-dione hydrochloride (44.91 mg, 0.103 mmol, 1 equiv) in DCM (2 mL) was added DIEA (53.57 mg, 0.415 mmol, 4 equiv). After stirring for 10 minutes, PyBOP (80.89 mg, 0.155 mmol, 1.5 equiv) was added. The resulting mixture was concentrated under reduced pressure, and then the residue was purified by Prep-HPLC(conditions: Sun Fire C18 OBD Prep Column, 19 mm×250 mm; mobile phase, Water (0.1% FA) and ACN (23% Phase B up to 33% in 8 min, hold 33% in 1 minutes); Detector, UV). This resulted in 2-(2,6-dihydroxypiperidin-3-yl)-4-[(8-[hydroxy (1-[4-(6-hydroxy-1,5-dimethyl-1,6-dihydropyridin-3-yl)-2,6-dimethoxyphenyl]methyl]azetidin-3-yl)methyl]amino]octyl)amino]-2,3-dihydro-1H-isoindole-1,3-diol formic acid (2.4 mg, 2.73%) as a yellow solid. $^1$H NMR (300 MHZ, Methanol-d4)δ 8.56 (s, 2H, FA), 7.96 (s, 1H), 7.83 (s, 1H), 7.61-7.50 (m, 1H), 7.04 (d, J=7.7 Hz, 2H), 6.88 (s, 2H), 4.62 (s, 1H), 4.32 (s, 2H), 4.09 (d, J=7.9 Hz, 4H), 3.98 (s, 6H), 3.68 (s, 3H), 3.55-3.44 (m, 2H), 3.21 (t, J=7.0 Hz, 2H), 2.91-2.68 (m, 4H), 2.22 (s, 3H), 2.12 (s, 1H), 1.68 (s, 2H), 1.64-1.39 (m, 10H). LCMS (ESI) m/z: [M+H]$^+$=373.17.

Example 23—Preparation of 3-Amino-1-[[2,6-Dimethoxy-4-(2-Methyl-1-Oxo-1,2-Dihydro-2,7-Naphthyridin-4-Yl)Phenyl]Methyl]-N-(8-[[2-(2,6-Dioxopiperidin-3-Yl)-1,3-Dioxo-2,3-Dihydro-1H-Isoindol-4-Yl]Amino]Octyl) Azetidine-3-Carboxamide (Compound D17)

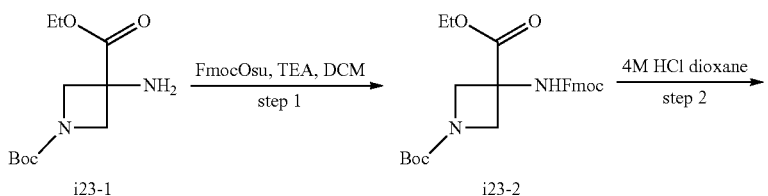

-continued
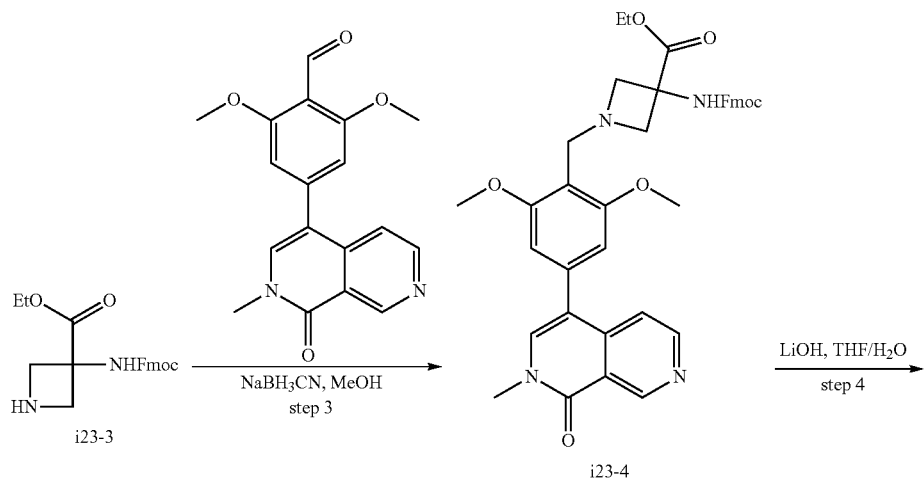
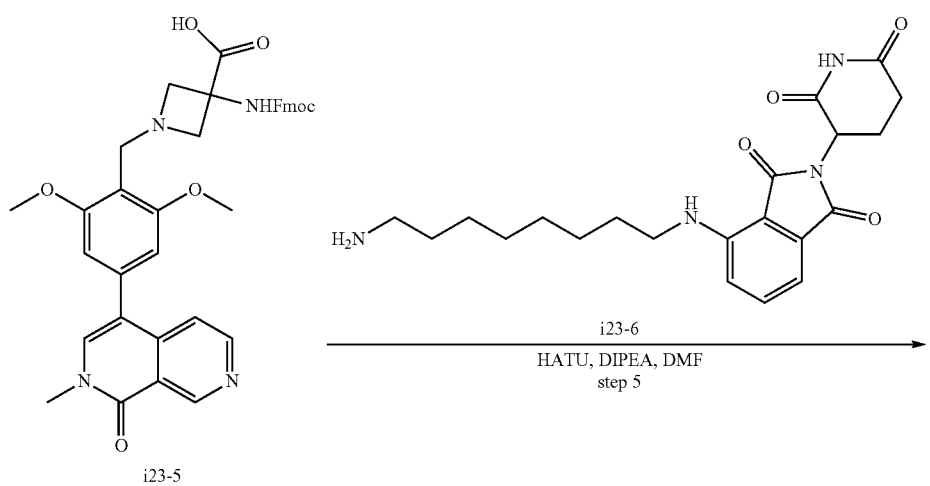
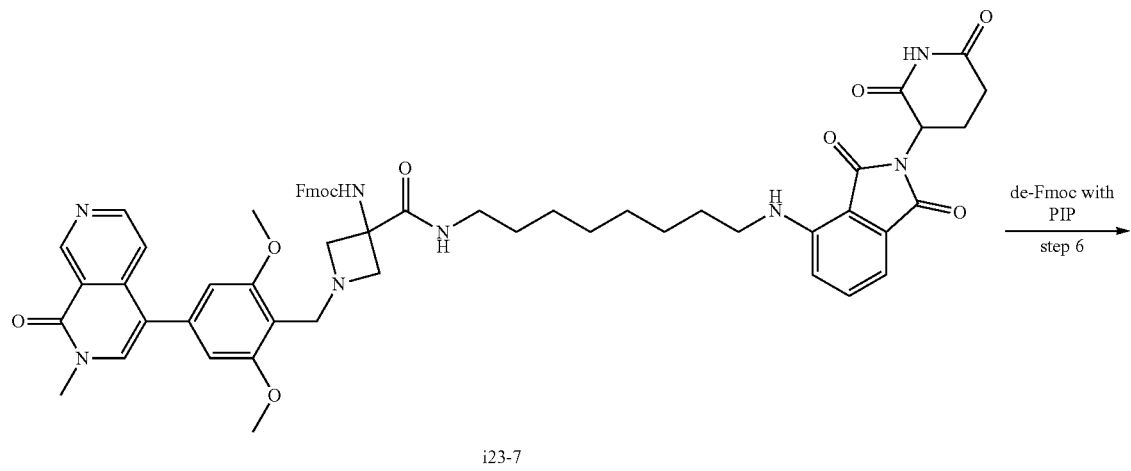

-continued

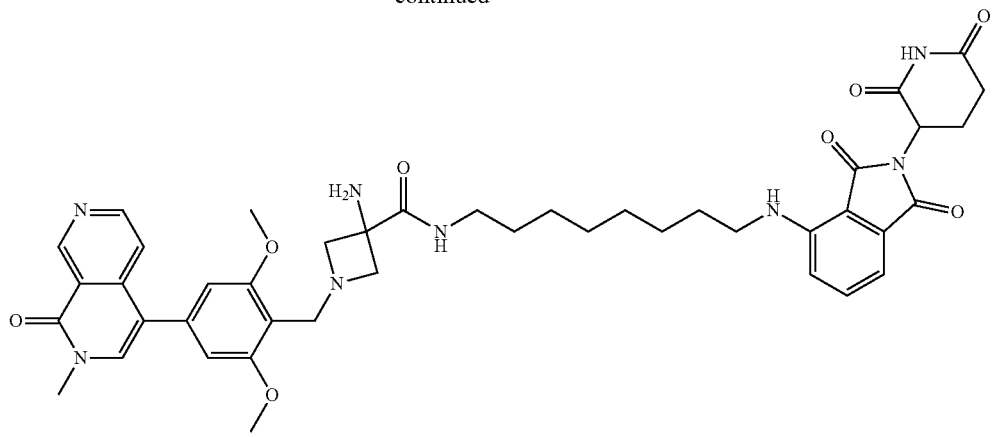

compound D17

Step 1: Preparation of 1-Tert-Butyl 3-Ethyl 3-([[(9H-Fluoren-9-Yl) Methoxy]Carbonyl]Amino) Azetidine-1,3-Dicarboxylate (i23-2)

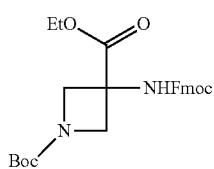

i23-2

To a solution of 1-tert-butyl 3-ethyl 3-aminoazetidine-1,3-dicarboxylate (120 mg, 0.491 mmol, 1 equiv) and 2,5-dioxopyrrolidin-1-yl(9H-fluoren-9-yl)methyl carbonate (182.3 mg, 0.540 mmol, 1.1 equiv) in DCM (1 mL) was added TEA (149.1 mg, 1.474 mmol, 3 equiv). The resulting solution was stirred at room temperature for 1 hour. The residue was purified by Prep-TLC(PE/EtOAc 1:1) to afford 1-tert-butyl 3-ethyl 3-([[(9H-fluoren-9-yl) methoxy]carbonyl]amino) azetidine-1,3-dicarboxylate (120 mg, 48%) as a white solid. LCMS (ESI) m/z: [M+H]$^+$=467.

Step 2: Preparation of Ethyl 3-([[(9H-Fluoren-9-Yl) Methoxy]Carbonyl]Amino) Azetidine-3-Carboxylate (i23-3)

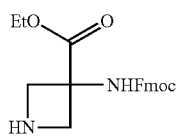

i23-3

A mixture of 1-tert-butyl 3-ethyl 3-([(9H-fluoren-9-yl) methoxy] carbonyl]amino) azetidine-1,3-dicarboxylate (120.00 mg, 0.257 mmol, 1.00 equiv) and 4 M HCl in 1,4-dioxane (2 mL) was stirred at room temperature for 1 hour. The reaction solution was concentrated under reduced pressure to afford ethyl 3-([[(9H-fluoren-9-yl) methoxy]carbonyl]amino) azetidine-3-carboxylate (120 mg, 89%) as a white solid that was used directly without further purification. LCMS (ESI) m/z: [M+H]$^+$=367.

Step 3: Preparation of Ethyl 1-[[2,6-Dimethoxy-4-(2-Methyl-1-Oxo-1,2-Dihydro-2,7-Naphthyridin-4-Yl)Phenyl]Methyl]-3-([[(9H-Fluoren-9-Yl) Methoxy]Carbonyl]Amino) Azetidine-3-Carboxylate (i23-4)

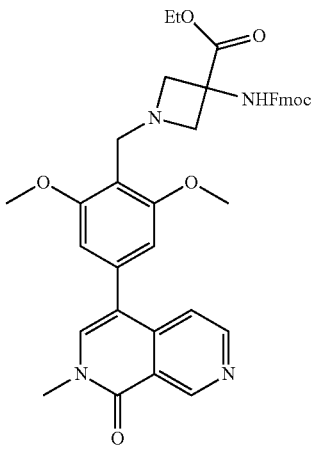

i23-4

To a solution of 2,6-dimethoxy-4-(2-methyl-1-oxo-1,2-dihydro-2,7-naphthyridin-4-yl)benzaldehyde (127.5 mg, 0.393 mmol, 1.20 equiv) and ethyl 3-([[(9H-fluoren-9-yl) methoxy]carbonyl]amino) azetidine-3-carboxylate (120 mg, 0.327 mmol, 1 equiv) in MeOH (1 mL) was added NaBH$_3$CN (41.2 mg, 0.655 mmol, 2 equiv). The resulting solution was stirred at room temperature for 1 hour. The mixture was then concentrated under reduced pressure and the residue was purified by Prep-TLC(CH$_2$Cl$_2$/MeOH 12:1) to afford ethyl 1-[2,6-dimethoxy-4-(2-methyl-1-oxo-1,2-dihydro-2,7-naphthyridin-4-yl)phenyl]methyl]-3-([[(9H-fluoren-9-yl) methoxy]carbonyl]amino) azetidine-3-carboxylate (100 mg, 45%) as a yellow solid. LCMS (ESI) m/z: [M+H]$^+$=675.

543

Step 4: Preparation of Ethyl 1-[2,6-Dimethoxy-4-(2-Methyl-1-Oxo-1,2-Dihydro-2,7-Naphthyridin-4-Yl)Phenyl]Methyl]-3-([(9H-Fluoren-9-Yl) Methoxy] Carbonyl]Amino) Azetidine-3-Carboxylic Acid (i23-5)

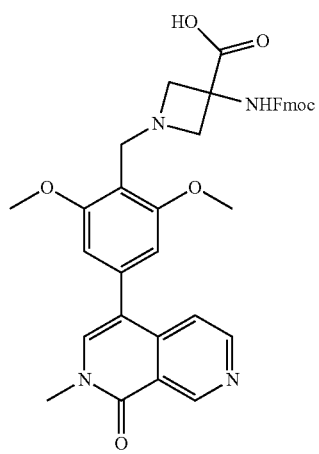

i23-5

A solution of ethyl 1-[2,6-dimethoxy-4-(2-methyl-1-oxo-1,2-dihydro-2,7-naphthyridin-4-yl)phenyl]methyl]-3-([(9H-fluoren-9-yl) methoxy]carbonyl]amino) azetidine-3-carboxylate (100 mg, 0.148 mmol, 1 equiv) in concentrated HCl (2 mL) was stirred at 90° C. for 1 hour. The resulting mixture was concentrated under reduced pressure to afford 1-[2,6-dimethoxy-4-(2-methyl-1-oxo-1,2-dihydro-2,7-naphthyridin-4-yl)phenyl]methyl]-3-([(9H-fluoren-9-yl) methoxy]carbonyl]amino) azetidine-3-carboxylic acid (100 mg, 94%) as a yellow solid that was used directly without further purification. LCMS (ESI) m/z: [M+H]$^+$=647.3

Step 5: Preparation of (9H-Fluoren-9-Yl)Methyl N-(1-[[2,6-Dimethoxy-4-(2-Methyl-1-Oxo-1,2-Dihydro-2,7-Naphthyridin-4-Yl)Phenyl]Methyl]-3-[(8-[[2-(2,6-Dioxopiperidin-3-Yl)-1,3-Dioxo-2,3-Dihydro-1H-Isoindol-4-Yl]Amino]Octyl) Carbamoyl] Azetidin-3-Yl) Carbamate (i23-7)

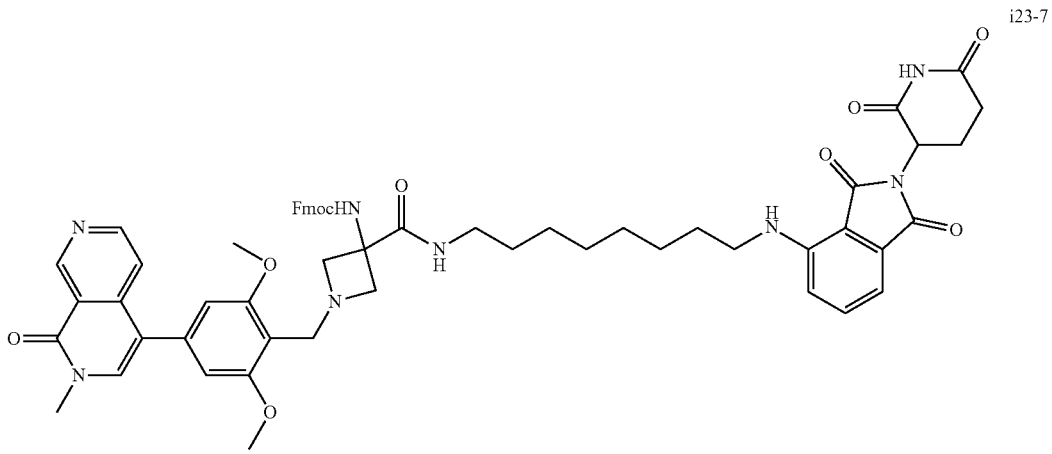

i23-7

To a solution of 1-[2,6-dimethoxy-4-(2-methyl-1-oxo-1,2-dihydro-2,7-naphthyridin-4-yl)phenyl]methyl]-3-([(9H-fluoren-9-yl) methoxy]carbonyl]amino) azetidine-3-carboxylic acid (100 mg, 0.155 mmol, 1 equiv) and 4-[(8-aminooctyl)amino]-2-(2,6-dioxopiperidin-3-yl)-2,3-dihydro-1H-isoindole-1,3-dione (74.3 mg, 0.186 mmol, 1.2 equiv) in DMF (1 mL) was added DIEA (60.0 mg, 0.464 mmol, 3 equiv) and HATU (88.2 mg, 0.232 mmol, 1.5 equiv). The resulting solution was stirred at room temperature for 1 hour. The mixture was then concentrated under reduced pressure and the residue was purified by Prep-TLC (CH$_2$Cl$_2$/MeOH 12:1) to afford (9H-fluoren-9-yl)methyl N-(1-[2,6-dimethoxy-4-(2-methyl-1-oxo-1,2-dihydro-2,7-naphthyridin-4-yl)phenyl]methyl]-3-[(8-[2-(2,6-dioxopiperidin-3-yl)-1,3-dioxo-2,3-dihydro-1H-isoindol-4-yl] amino]octyl) carbamoyl]azetidin-3-yl) carbamate (90 mg, 51%) as a yellow solid. LCMS (ESI) m/z: [M+H]$^+$=1029.

Step 6: Preparation of 3-Amino-1-[[2,6-Dimethoxy-4-(2-Methyl-1-Oxo-1,2-Dihydro-2,7-Naphthyridin-4-Yl)Phenyl]Methyl]-N-(8-[[2-(2,6-Dioxopiperidin-3-Yl)-1,3-Dioxo-2,3-Dihydro-1H-Isoindol-4-Yl]Amino]Octyl) Azetidine-3-Carboxamide (Compound D17)

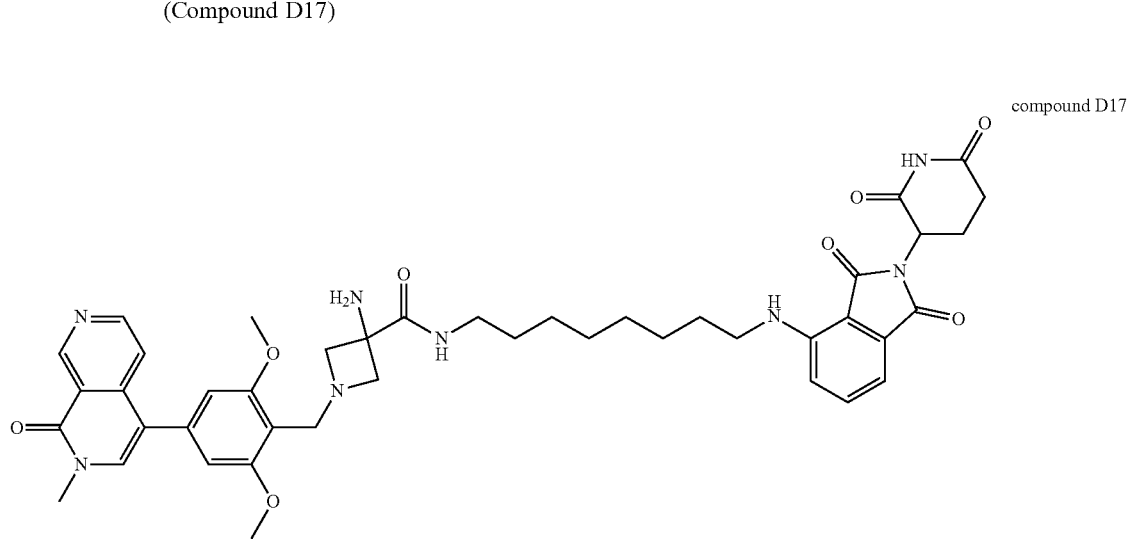

compound D17

A solution of (9H-fluoren-9-yl)methyl N-(1-[2,6-dimethoxy-4-(2-methyl-1-oxo-1,2-dihydro-2,7-naphthyridin-4-yl)phenyl]methyl]-3-[(8-[2-(2,6-dioxopiperidin-3-yl)-1,3-dioxo-2,3-dihydro-1H-isoindol-4-yl]amino]octyl) carbamoyl]azetidin-3-yl) carbamate (90 mg, 0.087 mmol, 1.00 equiv) in piperidine (1 mL) and DMF (4 mL) was stirred at room temperature for 1 hour. The crude solution was purified by Prep-HPLC(condition: SunFire C18 OBD Prep Column, 100 Å, 5 μm, 19 mm×250 mm; Mobile Phase A: Water (0.1% FA), Mobile Phase B: ACN; Flow rate: 25 mL/minuteute; Gradient: 28% B to 28% B in 2 minutes; 254 nm; Rt: 6.9 minutes) to afford 3-amino-1-[[2,6-dimethoxy-4-(2-methyl-1-oxo-1,2-dihydro-2,7-naphthyridin-4-yl)phenyl]methyl]-N-(8-[2-(2,6-dioxopiperidin-3-yl)-1,3-dioxo-2,3-dihydro-1H-isoindol-4-yl]amino]octyl) azetidine-3-carboxamide (3.8 mg, 5.2%) as a yellow solid. $^1$H NMR (300 MHZ, Acetonitrile-d3) δ 9.52 (s, 1H), 8.70 (d, J=5.7 Hz, 1H), 8.26 (s, 0.53H, FA), 7.78-7.42 (m, 4H), 7.02 (dd, J=7.8, 4.2 Hz, 2H), 6.75 (s, 2H), 6.30 (t, J=5.9 Hz, 1H), 4.95 (dd, J=12.4, 5.2 Hz, 1H), 4.10 (s, 2H), 3.95 (d, J=8.8 Hz, 2H), 3.87 (s, 6H), 3.50 (s, 3H), 3.24 (dq, J=23.4, 6.6 Hz, 4H), 2.83-2.59 (m, 3H), 1.63 (s, 2H), 1.49 (s, 2H), 1.32 (d, J=13.1 Hz, 10H). LCMS (ESI) m/z: [M+H]$^+$=807.40.

Example 24—Preparation of (2S)-1-[[2,6-Dimethoxy-4-(2-Methyl-1-Oxo-2,7-Naphthyridin-4-Yl)Phenyl]Methyl]-N-(8-[[2-(2,6-Dioxopiperidin-3-Yl)-1,3-Dioxoisoindol-4-Yl]Amino]Octyl) Azetidine-2-Carboxamide (Compound D18)

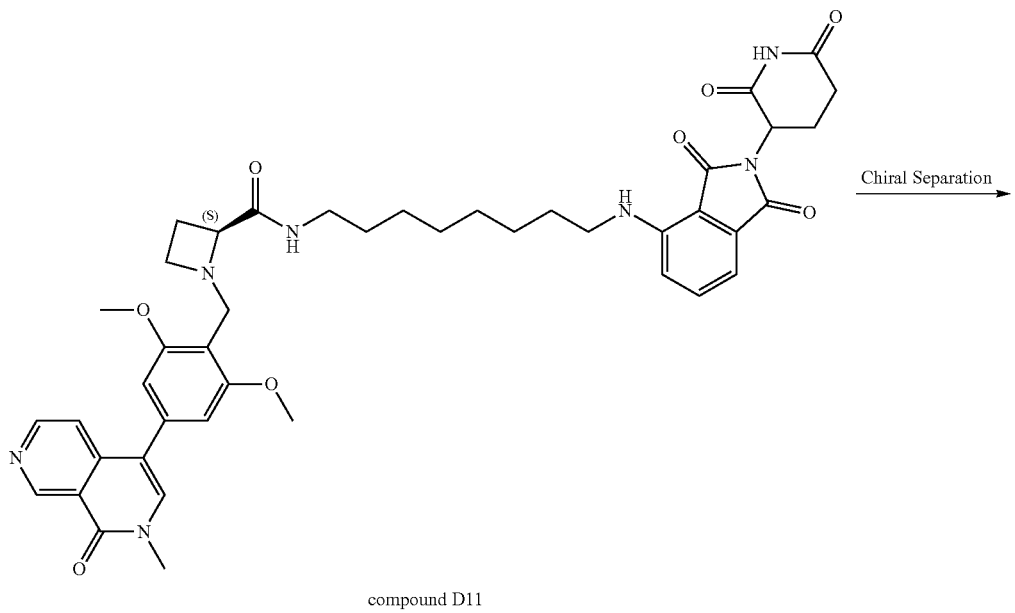

compound D11

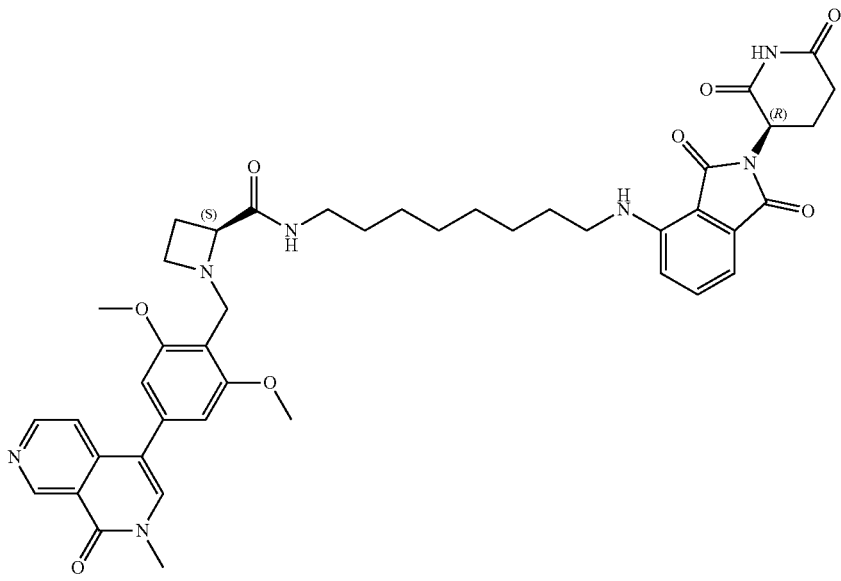

compound D18

Compound D11 was further separated by chiral HPLC to afford (2S)-1-((2,6-dimethoxy-4-(2-methyl-1-oxo-2,7-naphthyridin-4-yl)phenyl)methyl)-N-(8-((2-((R)-2,6-dioxopiperidin-3-yl)-1,3-dioxoisoindol-4-yl)amino) octyl) azetidine-2-carboxamide (10 mg, 10.34%) as a yellow solid. $^1$H NMR (400 MHZ, Methanol-d4) δ 9.51 (s, 1H), 8.68 (d, J=5.7 Hz, 1H), 7.72 (s, 1H), 7.62 (d, J=5.8 Hz, 1H), 7.53 (t, J=7.8 Hz, 1H), 7.00 (dd, J=10.6, 7.8 Hz, 2H), 6.75 (s, 2H), 5.05 (dd, J=12.4, 5.4 Hz, 1H), 3.89 (s, 9H), 3.69 (s, 3H), 3.30 (s, 2H), 3.25 (t, J=6.9 Hz, 2H), 3.15 (t, J=7.1 Hz, 2H), 2.94-2.64 (m, 3H), 2.35 (d, J=9.5 Hz, 1H), 2.16-2.00 (m, 1H), 1.58 (t, J=7.1 Hz, 2H), 1.40 (d, J=6.7 Hz, 2H), 1.30 (s, 8H). LCMS (ESI) m/z: [M+H]$^+$=792.60.

Example 25—Preparation of (2S)-1-[2,6-Dimethoxy-4-(2-Methyl-1-Oxo-2,7-Naphthyridin-4-Yl) Phenyl]Methyl]-N-(8-[2-(2,6-Dioxopiperidin-3-Yl)-1,3-Dioxoisoindol-4-Yl]Amino]Octyl) Azetidine-2-Carboxamide (Compound D19)

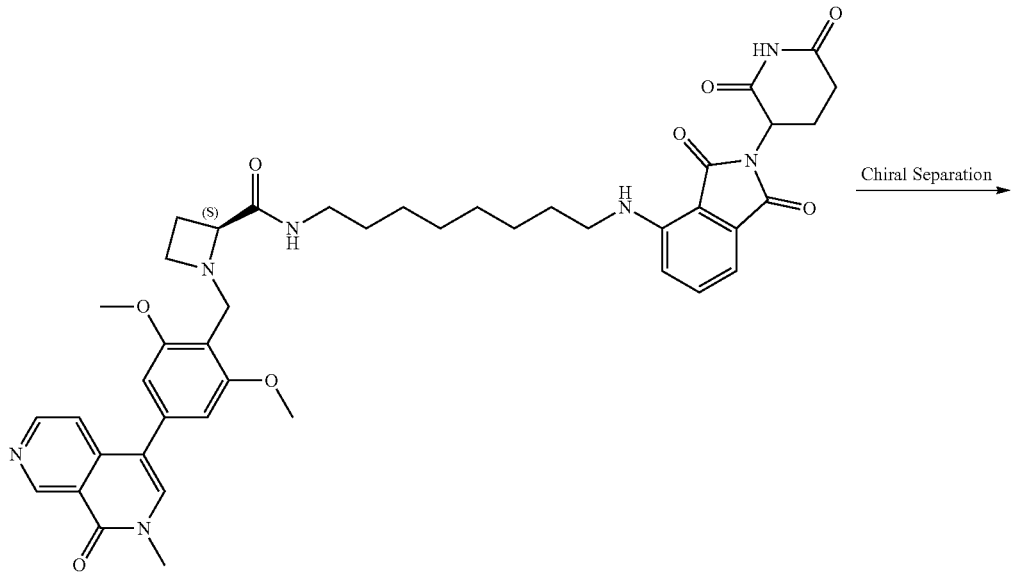

compound D11

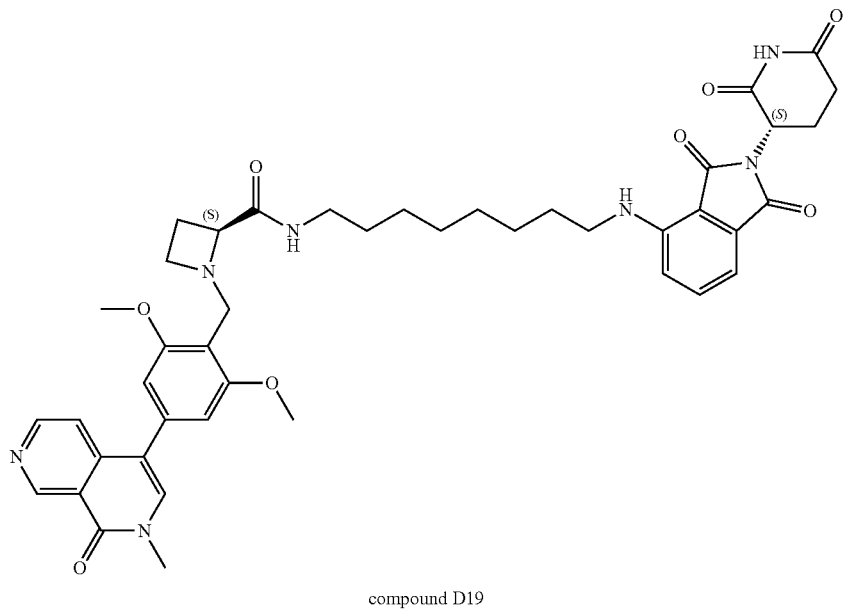

compound D19

Compound D11 was further separated by chiral HPLC to afford (2S)-1-((2,6-dimethoxy-4-(2-methyl-1-oxo-2,7-naphthyridin-4-yl)phenyl)methyl)-N-(8-((2-((S)-2,6-dioxopiperidin-3-yl)-1,3-dioxoisoindol-4-yl)amino) octyl) azetidine-2-carboxamide (10 mg, 10.34%) as a yellow solid. $^1$H NMR (400 MHZ, Methanol-d4) δ 9.51 (s, 1H), 8.68 (d, J=5.7 Hz, 1H), 7.72 (s, 1H), 7.62 (d, J=5.8 Hz, 1H), 7.53 (t, J=7.8 Hz, 1H), 7.00 (dd, J=10.6, 7.8 Hz, 2H), 6.75 (s, 2H), 5.05 (dd, J=12.4, 5.4 Hz, 1H), 3.89 (s, 9H), 3.69 (s, 3H), 3.30 (s, 2H), 3.25 (t, J=6.9 Hz, 2H), 3.15 (t, J=7.1 Hz, 2H), 2.94-2.64 (m, 3H), 2.35 (d, J=9.5 Hz, 1H), 2.16-2.00 (m, 1H), 1.58 (t, J=7.1 Hz, 2H), 1.40 (d, J=6.7 Hz, 2H), 1.30 (s, 8H). LCMS (ESI) m/z: [M+H]$^+$=792.60

Example 26—Preparation of 6-[[2,6-Dimethoxy-4-(2-Methyl-1-Oxo-1,2,4a,8a-Tetrahydro-2,7-Naphthyridin-4-Yl)Phenyl]Methyl]-N-(8-[[2-(2,6-Dioxopiperidin-3-Yl)-1,3-Dioxo-2,3-Dihydro-1H-Isoindol-4-Yl]Amino]Octyl)Spiro[3.3]Heptane-2-Carboxamide (Compound D20)

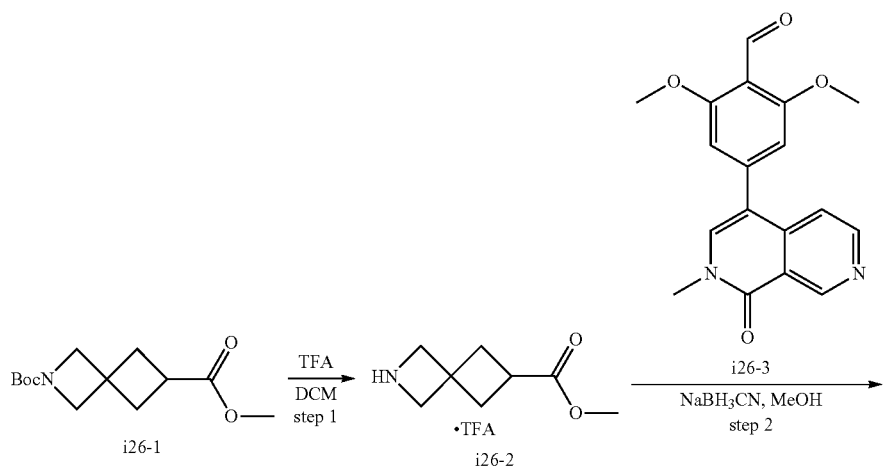

-continued
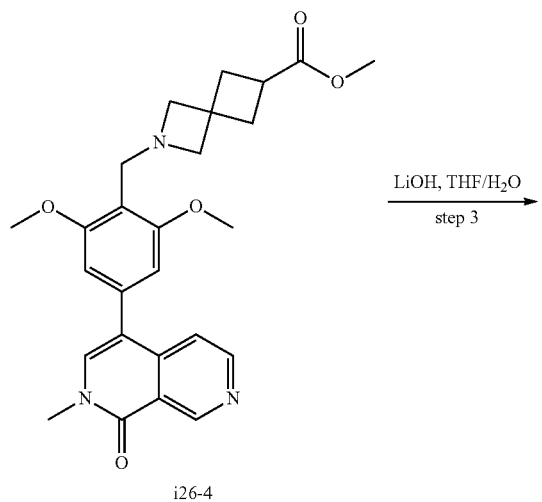
i26-4
LiOH, THF/H₂O
step 3
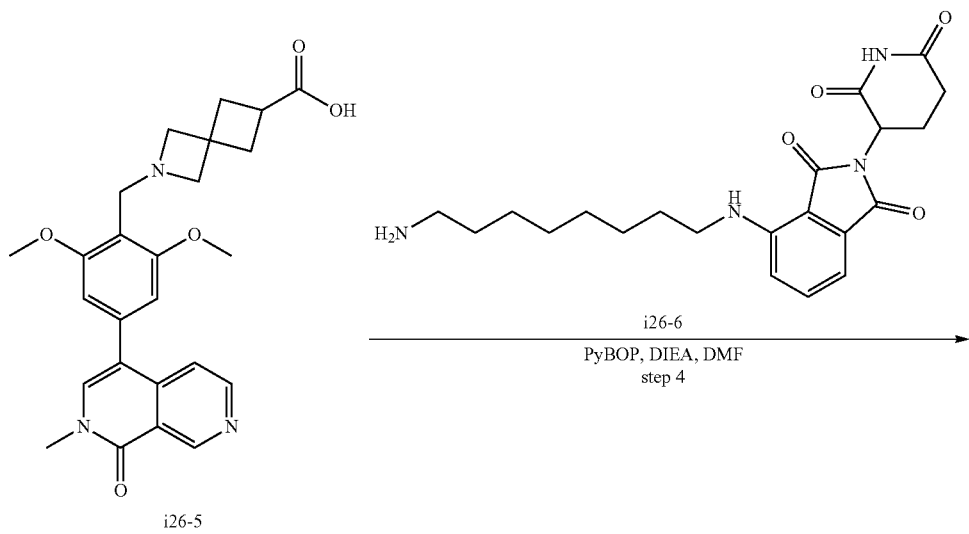
i26-5
i26-6
PyBOP, DIEA, DMF
step 4
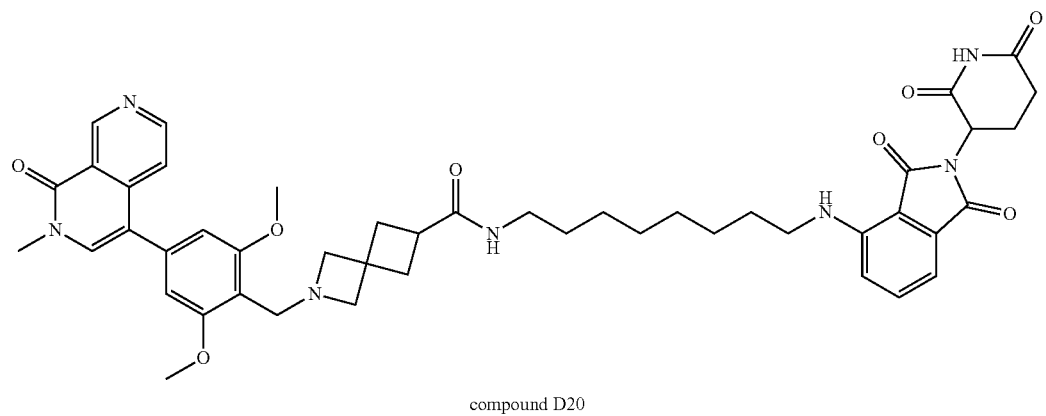 [SMILES: COc1cc(-c2cn(C)c(=O)c3cnccc23)cc(OC)c1CN1CC2(CC(C(=O)NCCCCCCCCNc3cccc4c3C(=O)N(C3CCC(=O)NC3=O)C4=O)C2)C1]
compound D20

Step 1: Preparation of Methyl 2-Azaspiro[3.3]Heptane-6-Carboxylate Trifluoroacetic Acid (i26-2)

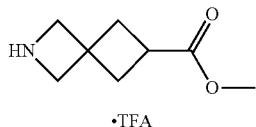

i26-2

·TFA

A mixture of 2-tert-butyl 6-methyl 2-azaspiro[3.3]heptane-2,6-dicarboxylate (127.60 mg, 0.500 mmol, 1.00 equiv) and TFA (1 mL) in DCM (3.00 mL) was stirred for 2 hours at room temperature. Then, the solvent was evaporated, and the resulting residue was used in the next step directly without further purification. LCMS (ESI) m/z: $[M+H]^+=156$.

Step 2: Preparation of Methyl 2-[[2,6-Dimethoxy-4-(2-Methyl-1-Oxo-2,7-Naphthyridin-4-Yl)Phenyl]Methyl]-2-Azaspiro[3.3]Heptane-6-Carboxylate (i26-4)

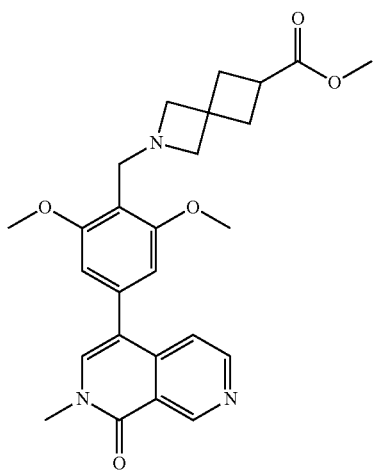

i26-4

To a stirred solution of methyl 2-azaspiro[3.3]heptane-6-carboxylate trifluoroacetic acid (77.60 mg, 0.288 mmol, 1.00 equiv), Et₃N (116.67 mg, 1.153 mmol, 4 equiv), and 2,6-dimethoxy-4-(2-methyl-1-oxo-2,7-naphthyridin-4-yl)benzaldehyde (93.49 mg, 0.288 mmol, 1 equiv) in MeOH (2.00 mL) was added NaBH₃CN (36.23 mg, 0.576 mmol, 2 equiv) in portions at room temperature. After the solvent was evaporated, the residue was purified by silica gel column chromatography, eluted with CH₂Cl₂/MeOH (12:1) to afford methyl 2-[2,6-dimethoxy-4-(2-methyl-1-oxo-2,7-naphthyridin-4-yl)phenyl]methyl]-2-azaspiro[3.3]heptane-6-carboxylate (156 mg, 96.91%) as a yellow solid. LCMS (ESI) m/z: $[M+H]^+=464$.

Step 3: Preparation of 2-[[2,6-Dimethoxy-4-(2-Methyl-1-Oxo-2,7-Naphthyridin-4-Yl)Phenyl]Methyl]-2-Azaspiro[3.3]Heptane-6-Carboxylic Acid (i26-5)

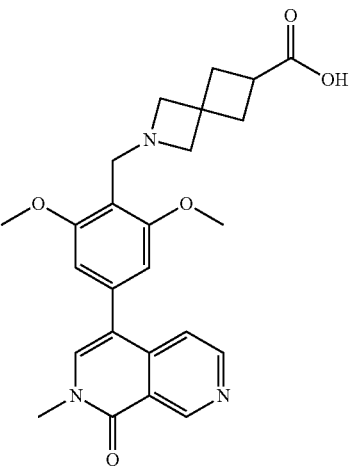

i26-5

A solution of methyl 2-[[2,6-dimethoxy-4-(2-methyl-1-oxo-2,7-naphthyridin-4-yl)phenyl]methyl]-2-azaspiro[3.3]heptane-6-carboxylate (156.00 mg, 0.347 mmol, 1.00 equiv) and LiOH (83.28 mg, 3.47 mmol, 10.0 equiv) in mixed THF (2.00 mL) and H₂O (1.00 mL) was stirred for 1 hour at room temperature. Then solvent was evaporated, and the resulting solution was purified by Prep-HPLC(0-100% ACN/water, with 0.1% TFA) to afford 2-[2,6-dimethoxy-4-(2-methyl-1-oxo-2,7-naphthyridin-4-yl)phenyl]methyl]-2-azaspiro[3.3]heptane-6-carboxylic acid (114.7 mg, 75.89%) as a dark yellow oil. LCMS (ESI) m/z: $[M+H]^+=450$.

Step 4: Preparation of 6-[[2,6-Dimethoxy-4-(2-Methyl-1-Oxo-1,2,4a,8a-Tetrahydro-2,7-Naphthyridin-4-Yl)Phenyl]Methyl]-N-(8-[[2-(2,6-Dioxopiperidin-3-Yl)-1,3-Dioxo-2,3-Dihydro-1H-Isoindol-4-Yl]Amino]Octyl)Spiro[3.3]Heptane-2-Carboxamide (Compound D20)

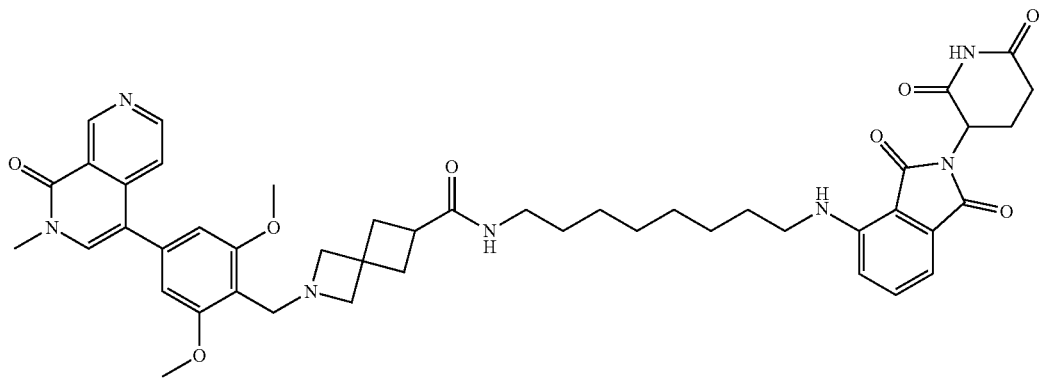

compound D20

To a stirred solution of 6-[2,6-dimethoxy-4-(2-methyl-1-oxo-1,2,4a,8a-tetrahydro-2,7-naphthyridin-4-yl)phenyl]methyl]spiro[3.3]heptane-2-carboxylic acid (45 mg, 0.100 mmol, 1 equiv) and 4-[(8-aminooctyl)amino]-2-(2,6-dioxopiperidin-3-yl)-2,3-dihydro-1H-isoindole-1,3-dione (40.00 mg, 0.100 mmol, 1 equiv) in DMF (0.5 mL), was added DIEA (64.54 mg, 0.499 mmol, 5 equiv) and PyBOP (103.95 mg, 0.200 mmol, 2 equiv) at room temperature. The mixture was stirred for 1 h and directly purified by Prep-HPLC with the following conditions (conditions: SunFire C18 OBD Prep Column, 19 mm×250 mm; Mobile Phase A: Water (0.1% FA), Mobile Phase B: ACN; Flow rate: 25 mL/minuteute; Gradient: 29% B to 32% B in 8 minutes; 254 nm; Rt: 6.55 minutes) to afford 6-[[2,6-dimethoxy-4-(2-methyl-1-oxo-1,2,4a,8a-tetrahydro-2,7-naphthyridin-4-yl)phenyl]methyl]-N-(8-[2-(2,6-dioxopiperidin-3-yl)-1,3-dioxo-2,3-dihydro-1H-isoindol-4-yl]amino]octyl)spiro[3.3]heptane-2-carboxamide (14.1 mg, 14.24%) as a yellow solid. 1H NMR (300 MHZ, Methanol-d4) δ 9.54 (d, J=0.9 Hz, 1H), 8.69 (d, J=5.8 Hz, 1H), 7.78 (s, 1H), 7.65-7.50 (m, 2H), 7.04 (d, J=7.9 Hz, 2H), 6.86 (s, 2H), 5.05 (dd, J=12.6, 5.7 Hz, 1H), 4.63 (s, 2H), 4.44 (s, 2H), 4.18 (s, 3H), 3.97 (s, 6H), 3.88 (s, 1H), 3.71 (s, 3H), 3.34-3.11 (m, 3H), 3.10-2.67 (m, 5H), 2.61-2.37 (m, 4H), 2.27-2.13 (m, 1H), 1.67 (q, J=7.0 Hz, 2H), 1.59-1.26 (m, 10H). LCMS (ESI) m/z: [M+H]⁺=832.5.

Example 27—Preparation of 6-[[2,6-Dimethoxy-4-(2-Methyl-1-Oxo-1,2,4a,8a-Tetrahydro-2,7-Naphthyridin-4-Yl)Phenyl]Methyl]-N-(6-[[2-(2,6-Dioxopiperidin-3-Yl)-1,3-Dioxo-2,3-Dihydro-1H-Isoindol-4-Yl]Amino]Hexyl)Spiro[3.3]Heptane-2-Carboxamide (Compound D21)

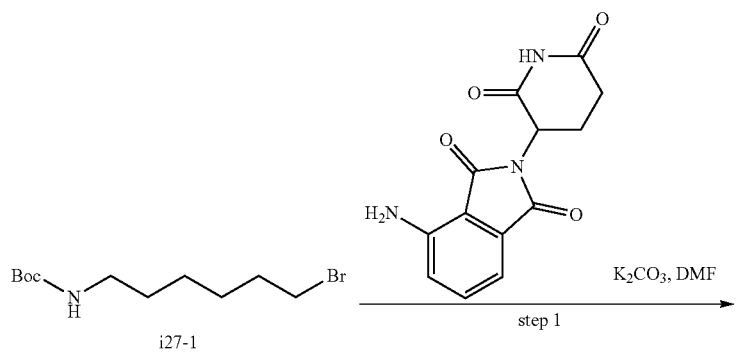

-continued
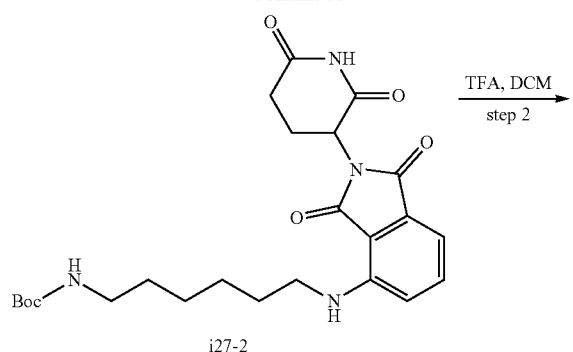
i27-2
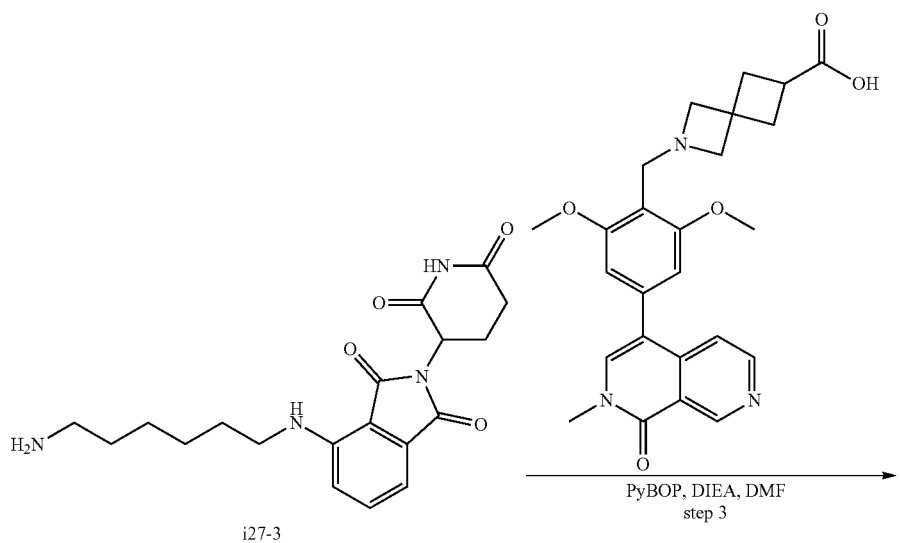
i27-3
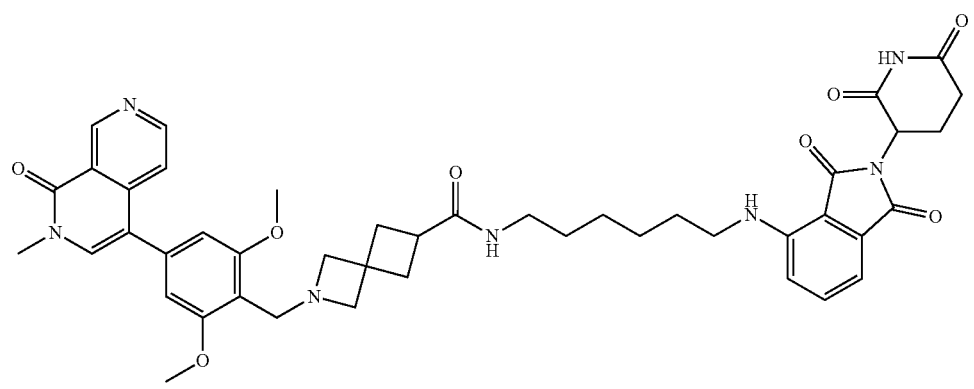
compound D21

Step 1: Preparation o Tert-Butyl N-(6-[[2-(2,6-Di-oxopiperidin-3-Yl)-1,3-Dioxoisoindol-4-Yl]Amino] Hexyl) Carbamate (i27-2)

Step 2: Preparation of 4-[(6-Aminohexyl)Amino]-2-(2,6-Dioxopiperidin-3-Yl) Isoindole-1,3-Dione Trifluoroacetic Acid (i27-3)

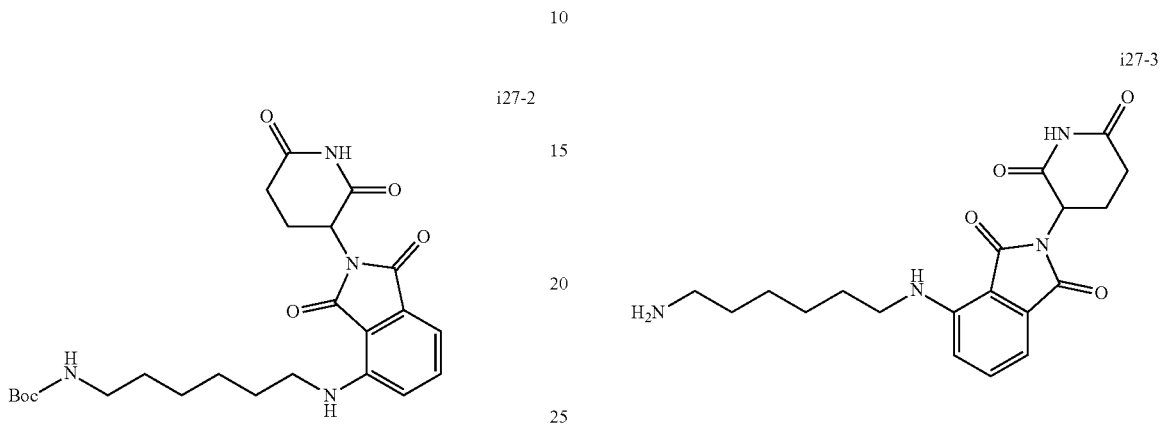

To a stirred solution of pomalidomide (150.30 mg, 0.550 mmol, 1.00 equiv) and tert-butyl N-(6-bromohexyl) carbamate (154.13 mg, 0.550 mmol, 1 equiv) in DMF (1.00 mL) was added $K_2CO_3$ (152.04 mg, 1.100 mmol, 2 equiv) at room temperature. The resulting mixture was stirred overnight at room temperature, and then it was concentrated and purified by silica gel column chromatography, elutinged with PE/EtOAc (10:1) to afford tert-butyl N-(6-[2-(2,6-dioxopiperidin-3-yl)-1,3-dioxoisoindol-4-yl]amino]hexyl) carbamate (293 mg, 95.82%) as a yellow oil. LCMS (ESI) m/z: [M+H]$^+$=473.

A solution of tert-butyl N-(6-[2-(2,6-dioxopiperidin-3-yl)-1,3-dioxoisoindol-4-yl]amino]hexyl) carbamate (293.00 mg, 0.620 mmol, 1.00 equiv) and TFA (2.0 mL) in DCM (5.00 mL) was stirred for 1 h at room temperature. The mixture was then concentrated to afford 4-[(6-aminohexyl)amino]-2-(2,6-dioxopiperidin-3-yl) isoindole-1,3-dione (243 mg, 80.56%) as a yellow semi-solid, that was used directly without further purification. LCMS (ESI) m/z: [M+H]$^+$=373.

Step 3: Preparation of 6-[[2,6-Dimethoxy-4-(2-Methyl-1-Oxo-1,2,4a,8a-Tetrahydro-2,7-Naphthyridin-4-Yl)Phenyl]Methyl]-N-(6-[[2-(2,6-Dioxopiperidin-3-Yl)-1,3-Dioxo-2,3-Dihydro-1H-Isoindol-4-Yl]Amino]Hexyl)Spiro[3.3]Heptane-2-Carboxamide (Compound D21)

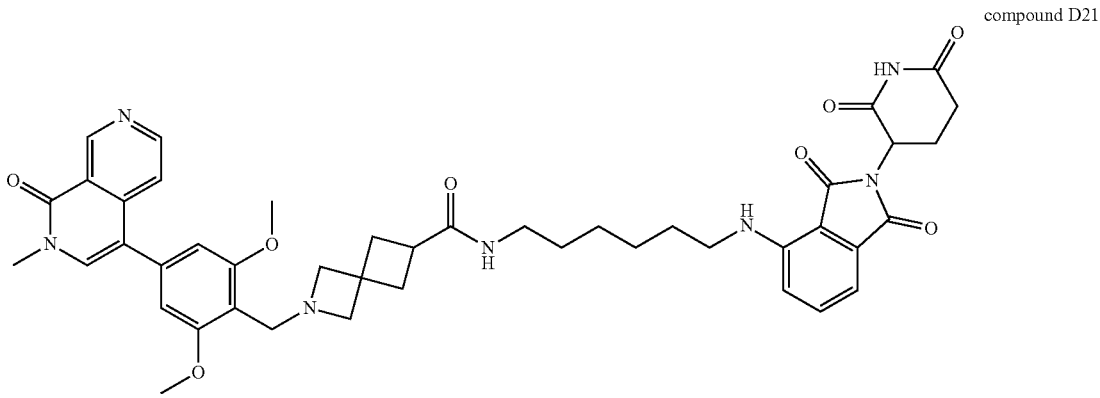 [SMILES: COc1cc(-c2cn(C)c(=O)c3cnccc23)cc(OC)c1CN1CC2(CC(C(=O)NCCCCCCNc3cccc4c3C(=O)N(C3CCC(=O)NC3=O)C4=O)C2)C1]

To a stirred solution of 6-[2,6-dimethoxy-4-(2-methyl-1-oxo-1,2,4a,8a-tetrahydro-2,7-naphthyridin-4-yl)phenyl]methyl]spiro[3.3]heptane-2-carboxylic acid (30 mg, 0.067 mmol, 1 equiv) in DMF (0.5 mL) was added DIEA (43.03 mg, 0.333 mmol, 5 equiv), PyBOP (69.30 mg, 0.133 mmol, 2 equiv), and 4-[(6-aminohexyl)amino]-2-(2,6-dioxopiperidin-3-yl)-2,3-dihydro-1H-isoindole-1,3-dione (24.80 mg, 0.067 mmol, 1 equiv). The reaction was stirred at ambient atmosphere for 1 hour. The mixture was purified directly by Prep-HPLC(condition: SunFire C18 OBD Prep Column, 100 Å, 5 μm, 19 mm×250 mm; Mobile Phase A: Water (0.1% FA), Mobile Phase B: ACN; Flow rate: 25 mL/minuteute; Gradient: 12% B to 38% B in 8 minutes; 254 nm; Rt: 7.58 minutes), to afford 6-[[2,6-dimethoxy-4-(2-methyl-1-oxo-1,2,4a,8a-tetrahydro-2,7-naphthyridin-4-yl)phenyl]methyl]-N-(6-[2-(2,6-dioxopiperidin-3-yl)-1,3-dioxo-2,3-dihydro-1H-isoindol-4-yl]amino]hexyl)spiro[3.3]heptane-2-carboxamide (11.2 mg,20.90%) as a yellow solid. $^1$H NMR (400 MHz, Methanol-d4) δ 9.52 (s, 1H), 8.69 (d, J=5.8 Hz, 1H), 7.77 (s, 1H), 7.61 (d, J=5.8 Hz, 1H), 7.50-7.39 (m, 1H), 7.01 (dd, J=17.7, 7.7 Hz, 2H), 6.85 (s, 2H), 5.09 (dd, J=12.9, 5.5 Hz, 1H), 4.42 (s, 2H), 4.16 (d, J=3.1 Hz, 4H), 3.96 (s, 6H), 3.78 (t, J=7.4 Hz, 2H), 3.71 (s, 3H), 3.50 (q, J=7.3 Hz, 1H), 3.20 (qd, J=7.3, 5.4 Hz, 9H), 2.99-2.87 (m, 2H), 2.91-2.83 (m, 1H), 2.75-2.61 (m, 1H), 2.53 (s, 2H), 2.53-2.47 (m, 1H), 2.47-2.37 (m, 2H), 2.22-2.09 (m, 2H), 1.94 (s, 2H), 1.93 (s, 6H), 1.61 (s, 1H), 1.51 (tt, J=15.1, 8.0 Hz, 4H), 1.46-1.26 (m, 23H), 1.12 (t, J=7.3 Hz, 10H), 0.91 (q, J=9.7, 7.9 Hz, 3H). LCMS (ESI) m/z: [M+H]$^+$=804.40.

Example 28—Preparation of 1-[[2,6-Dimethoxy-4-(2-Methyl-1-Oxo-1,2-Dihydro-2,7-Naphthyridin-4-Yl)Phenyl]Methyl]-N-(4-[2-(2,6-Dioxopiperidin-3-Yl)-1,3-Dioxo-2,3-Dihydro-1H-Isoindol-5-Yl]Amino]Butyl) Azetidine-3-Sulfonamide Formic Acid (Compound D22 Formic Acid)

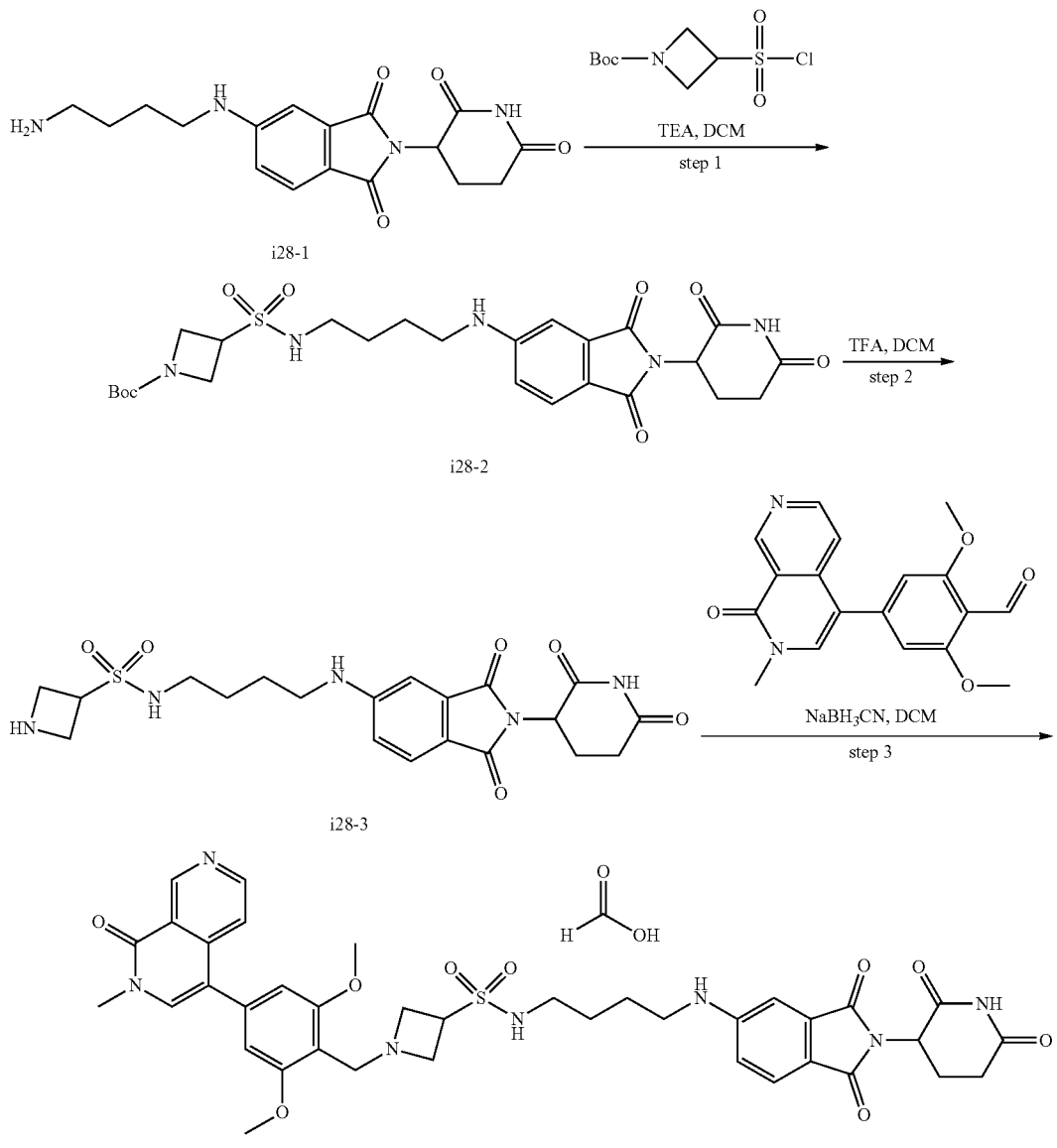

11Step 1: Preparation of Tert-Butyl-3-[(4-[[2-(2,6-Dioxopiperidin-3-Yl)-1,3-Dioxoisoindol-5-Yl]Amino]Butyl) Sulfa Moyl]Azetidine-1-Carboxylate (i28-2)

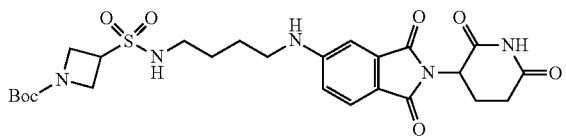

i28-2

To a stirred mixture of 5-[(4-aminobutyl)amino]-2-(2,6-dioxopiperidin-3-yl) isoindole-1,3-dione (60.00 mg, 0.174 mmol, 1.00 equiv) and tert-butyl 3-(chlorosulfonyl) azetidine-1-carboxylate (111.38 mg, 0.436 mmol, 2.50 equiv) in DCM (2.00 mL) was added TEA (52.89 mg, 0.523 mmol, 3.00 equiv). After stirring for 1.5 hours at room temperature, the resulting mixture was concentrated under reduced pressure. The residue was purified by Prep-TLC(CH$_2$Cl$_2$/EtOAc (1:2) to afford tert-butyl-3-[(4-[2-(2,6-dioxopiperidin-3-yl)-1,3-dioxoisoindol-5-yl]amino]butyl) sulfamoyl]azetidine-1-carboxylate (78 mg, 73.87%) as a yellow solid. LCMS (ESI) m/z: [M+H]$^+$=564.20.

Step 2: Preparation of N-(4-((2-(2,6-Dioxopiperidin-3-Yl)-1,3-Dioxoisoindolin-5-Yl)Amino) Butyl) Azetidine-3-Sulfonamide (i28-3)

i28-3

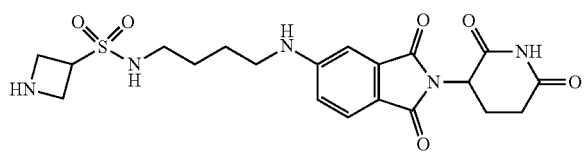

To a stirred mixture of tert-butyl-3-[(4-[2-(2,6-dioxopiperidin-3-yl)-1,3-dioxoisoindol-5-yl]amino]butyl) sulfamoyl]azetidine-1-carboxylate (78.00 mg, 0.138 mmol, 1.00 equiv) in DCM (2.00 mL, 0.012 mmol, 0.10 equiv) was added TFA (0.40 mL, 5.385 mmol, 38.91 equiv). After stirring for 1 hour at room temperature, the resulting mixture was concentrated under reduced pressure. The residue was used in the next step directly without further purification. LCMS (ESI) m/z: [M+H]$^+$=464.15.

Step 3: Preparation of 1-[[2,6-Dimethoxy-4-(2-Methyl-1-Oxo-1,2-Dihydro-2,7-Naphthyridin-4-Yl) Phenyl]Methyl]-N-(4-[[2-(2,6-Dioxopiperidin-3-Yl)-1,3-Dioxo-2,3-Dihydro-1H-Isoindol-5-Yl]Amino] Butyl) Azetidine-3-Sulfonamide Formic Acid (Compound D38 Formic Acid)

compound D22

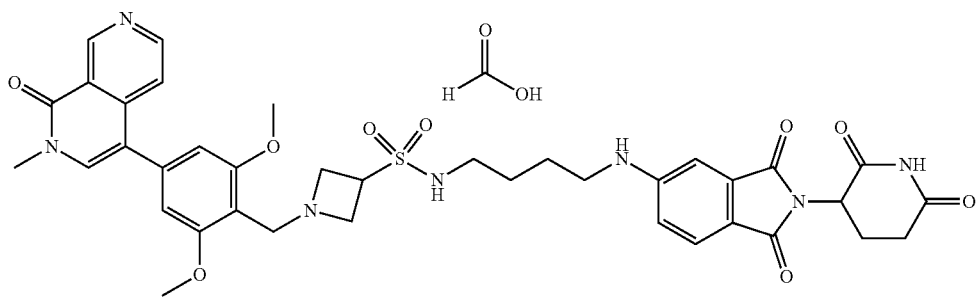

formic acid

A mixture of N-(4-[2-(2,6-dioxopiperidin-3-yl)-1,3-dioxo-2,3-dihydro-1H-isoindol-5-yl]amino]butyl) azetidine-3-sulfonamide (64.17 mg, 0.138 mmol, 1.00 equiv) and 2,6-dimethoxy-4-(2-methyl-1-oxo-1,2-dihydro-2,7-naphthyridin-4-yl)benzaldehyde (44.90 mg, 0.138 mmol, 1.00 equiv) in DMF (2 mL) was stirred at room temperature, then adjusted to pH 8~9 by addition of TEA. The above mixture was added NaBH$_3$CN (26.10 mg, 0.415 mmol, 3.00 equiv) in portions, the resulting mixture was stirred for 2 hours at room temperature. The resulting mixture was concentrated under reduced pressure, the residue was purified by Prep-HPLC(condition: X Select CSH Prep C18 OBD Column, 5 μm, 19*150 mm; mobile phase, Water (0.1% FA) and ACN (15% Phase B up to 30% in 14 minutes); Detector, UV). This resulted in 15 mg (12.59%) of 1-[2,6-dimethoxy-4-(2-methyl-1-oxo-1,2-dihydro-2,7-naphthyridin-4-yl)phenyl]methyl]-N-(4-[2-(2,6-dioxopiperidin-3-yl)-1,3-dioxo-2,3-dihydro-1H-isoindol-5-yl]amino]butyl) azetidine-3-sulfonamide formic acid as a yellow solid. $^1$H NMR (400 MHZ, DMSO-d6)δ 11.07 (s, 1H), 9.45 (s, 1H), 8.73 (d, J=5.7 Hz, 1H), 8.14 (s, 0.5 H, FA), 7.87 (s, 1H), 7.59-7.52 (m, 2H), 7.13 (s, 1H), 6.94 (s, 1H), 6.84 (d, J=8.6 Hz, 1H), 6.78 (s, 2H), 6.55 (s, 1H), 5.03 (dd, J=12.9, 5.4 Hz, 1H), 3.84 (s, 7H), 3.60 (s, 4H), 3.28-3.20 (m, 3H), 3.16 (d, J=6.3 Hz, 3H), 2.97 (d, J=6.5 Hz, 2H), 2.92-2.81 (m, 1H), 2.61-2.53 (m, 3H), 2.03-1.95 (m, 1H), 1.55 (s, 4H). LCMS (ESI) m/z: [M+H]$^+$=772.30.

Example 29—Preparation of 1-[[2,6-Dimethoxy-4-(2-Methyl-1-Oxo-1,2-Dihydro-2,7-Naphthyridin-4-Yl)Phenyl]Methyl]-N-(5-[[2-(2,6-Dioxopiperidin-3-Yl)-1,3-Dioxo-2,3-Dihydro-1H-Isoindol-5-Yl]Amino]Pentyl) Azetidine-3-Sulfonamide Formic Acid (Compound D23 Formic Acid)
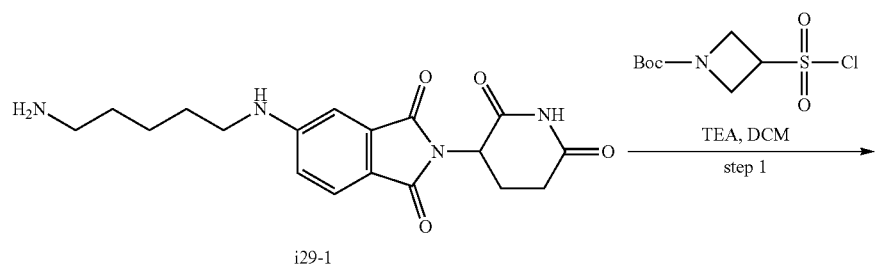
i29-1
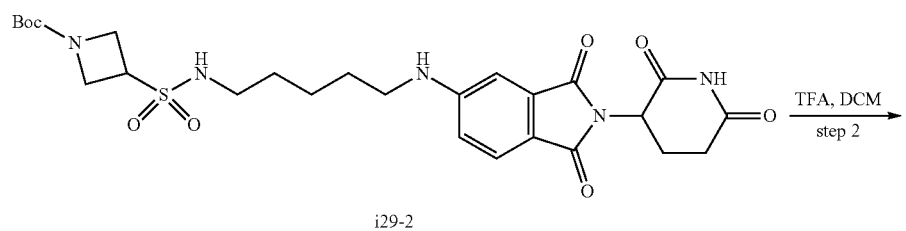
i29-2
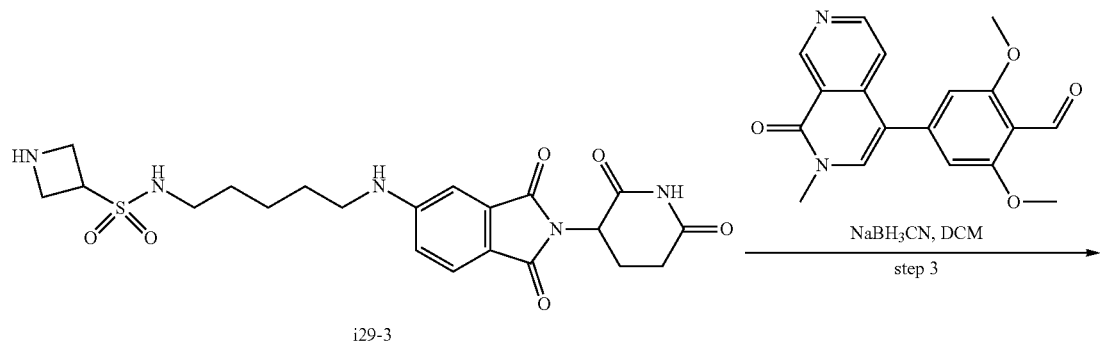
i29-3
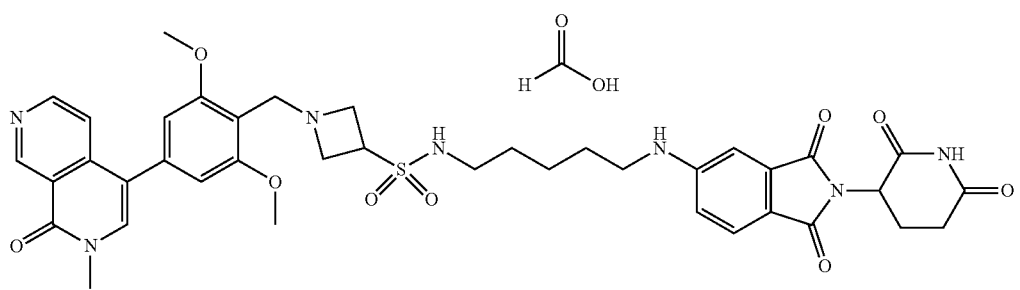
compound D22 formic acid

Step 1: Preparation of Tert-Butyl-3-[(5-[[2-(2,6-Dioxopiperidin-3-Yl)-1,3-Dioxoisoindol-5-Yl] Amino]Pentyl) Sulfamoyl]Azetidine-1-Carboxylate (i28-2)

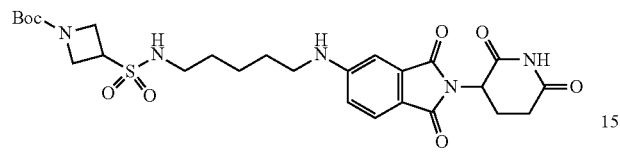

i29-2

To a stirred mixture of 5-[(5-aminopentyl)amino]-2-(2,6-dioxopiperidin-3-yl) isoindole-1,3-dione (100.00 mg, 0.279 mmol, 1.00 equiv) and tert-butyl 3-(chlorosulfonyl) azetidine-1-carboxylate (178.37 mg, 0.698 mmol, 2.50 equiv) in DCM (2.00 mL) was added TEA (84.70 mg, 0.837 mmol, 3.00 equiv). After stirring for 1.5 hours at room temperature, the resulting mixture was concentrated under reduced pressure. The residue was purified by Prep-TLC(CH$_2$Cl$_2$/EA (1:2) to afford tert-butyl-3-[(5-[[2-(2,6-dioxopiperidin-3-yl)-1,3-dioxoisoindol-5-yl]amino]pentyl) sulfamoyl]azetidine-1-carboxylate (58.7 mg,33.87%) as a yellow solid. LCMS (ESI) m/z: [M+H]$^+$=578.

Step 2: Preparation of N-(5-((2-(2,6-Dioxopiperidin-3-Yl)-1,3-Dioxoisoindolin-5-Yl)Amino) Pentyl) Azetidine-3-Sulfonamide (i28-3)

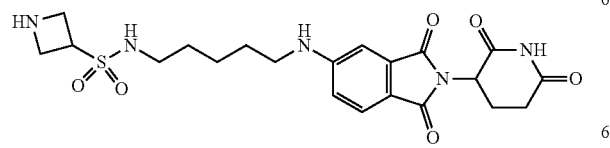

i29-3

To a stirred mixture of tert-butyl 3-[(5-[2-(2,6-dioxopiperidin-3-yl)-1,3-dioxoisoindol-5-yl]amino]pentyl) sulfamoyl]azetidine-1-carboxylate (58.70 mg, 0.102 mmol, 1.00 equiv) in DCM (2.00 mL) was added TFA (0.40 mL, 5.385 mmol, 52.99 equiv). After stirring for 1 hour at room temperature, the resulting mixture was concentrated under reduced pressure. The residue was used in the next step directly without further purification. LCMS (ESI) m/z: [M+H]$^+$=478.17.

Step 3: Preparation of 1-[[2,6-Dimethoxy-4-(2-Methyl-1-Oxo-1,2-Dihydro-2,7-Naphthyridin-4-Yl) Phenyl]Methyl]-N-(5-[2-(2,6-Dioxopiperidin-3-Yl)-1,3-Dioxo-2,3-Dihydro-1H-Isoindol-5-Yl]Amino] Pentyl) Azetidine-3-Sulfonamide Formic Acid (Compound D22 Formic Acid)

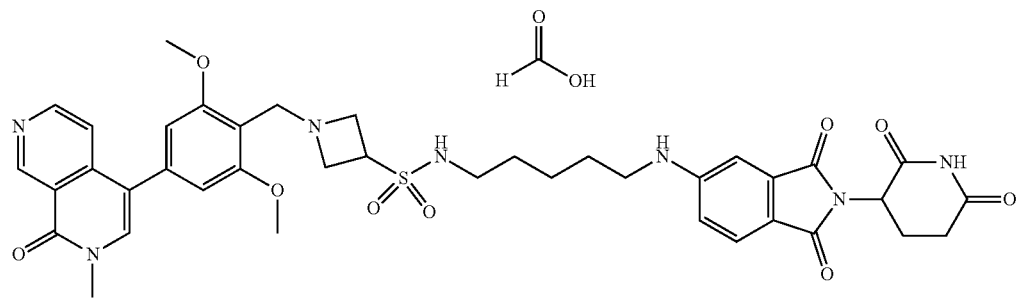

compound D22 formic acid

A mixture of N-(5-[2-(2,6-dioxopiperidin-3-yl)-1,3-dioxo-2,3-dihydro-1H-isoindol-5-yl]amino]pentyl) azetidine-3-sulfonamide (48.54 mg, 0.102 mmol, 1.00 equiv) and 2,6-dimethoxy-4-(2-methyl-1-oxo-1,2-dihydro-2,7-naphthyridin-4-yl)benzaldehyde (39.56 mg, 0.122 mmol, 1.20 equiv) in THF (2 mL) was stirred at room temperature, then adjusted to pH 8-9 with TEA. To the above mixture was added NaBH$_3$CN (12.78 mg, 0.203 mmol, 2.00 equiv) in portions, and the resulting mixture was stirred for 2 hours at room temperature. The resulting mixture was concentrated under reduced pressure, and the residue was purified by Prep-HPLC(conditions: Sun Fire C18 OBD Prep Column, 19 mm×250 mm; mobile phase, Water (0.1% FA) and ACN (hold 3% Phase B in 2 minutes, up to 15% in 8 minutes); Detector, UV). This resulted in 7.4 mg (8.31%) of 1-[2,6-dimethoxy-4-(2-methyl-1-oxo-1,2-dihydro-2,7-naphthyridin-4-yl)phenyl]methyl]-N-(5-[2-(2,6-dioxopiperidin-3-yl)-1,3-dioxo-2,3-dihydro-1H-isoindol-5-yl]amino]pentyl) azetidine-3-sulfonamide formic acid as a yellow solid. $^1$H NMR (400 MHZ, DMSO-d6) δ 11.07 (s, 1H), 9.44 (s, 1H), 8.72 (d, J=5.7 Hz, 1H), 7.86 (s, 1H), 7.59-7.52 (m, 2H), 7.21 (s, 1H), 7.11 (s, 1H), 6.93 (s, 1H), 6.83 (dd, J=8.3, 1.7 Hz, 1H), 6.76 (s, 2H), 6.55 (s, 1H), 5.03 (dd, J=13.0, 5.4 Hz, 1H), 4.02 (s, 1H), 3.83 (s, 6H), 3.60 (s, 4H), 3.29-3.20 (m, 2H), 3.19-3.08 (m, 3H), 3.01-2.78 (m, 4H), 2.61-2.51 (m, 3H), 2.06-1.93 (t, J=12.7 Hz, 1H), 1.60-1.51 (m, 2H), 1.50-1.42 (m, 2H), 1.42-1.32 (m, 2H). LCMS (ESI) m/z: [M+H]$^+$=786.28.

Example 30—Preparation of 1-[[2,6-Dimethoxy-4-(2-Methyl-1-Oxo-2,7-Naphthyridin-4-Yl)Phenyl]Methyl]-N-(2-[4-[2-(2,6-Dioxopiperidin-3-Yl)-1,3-Dioxoisoindol-5-Yl]Piperazin-1-Yl]Ethyl)Azetidine-3-Sulfonamide Formic Acid (Compound D24 Formic Acid)
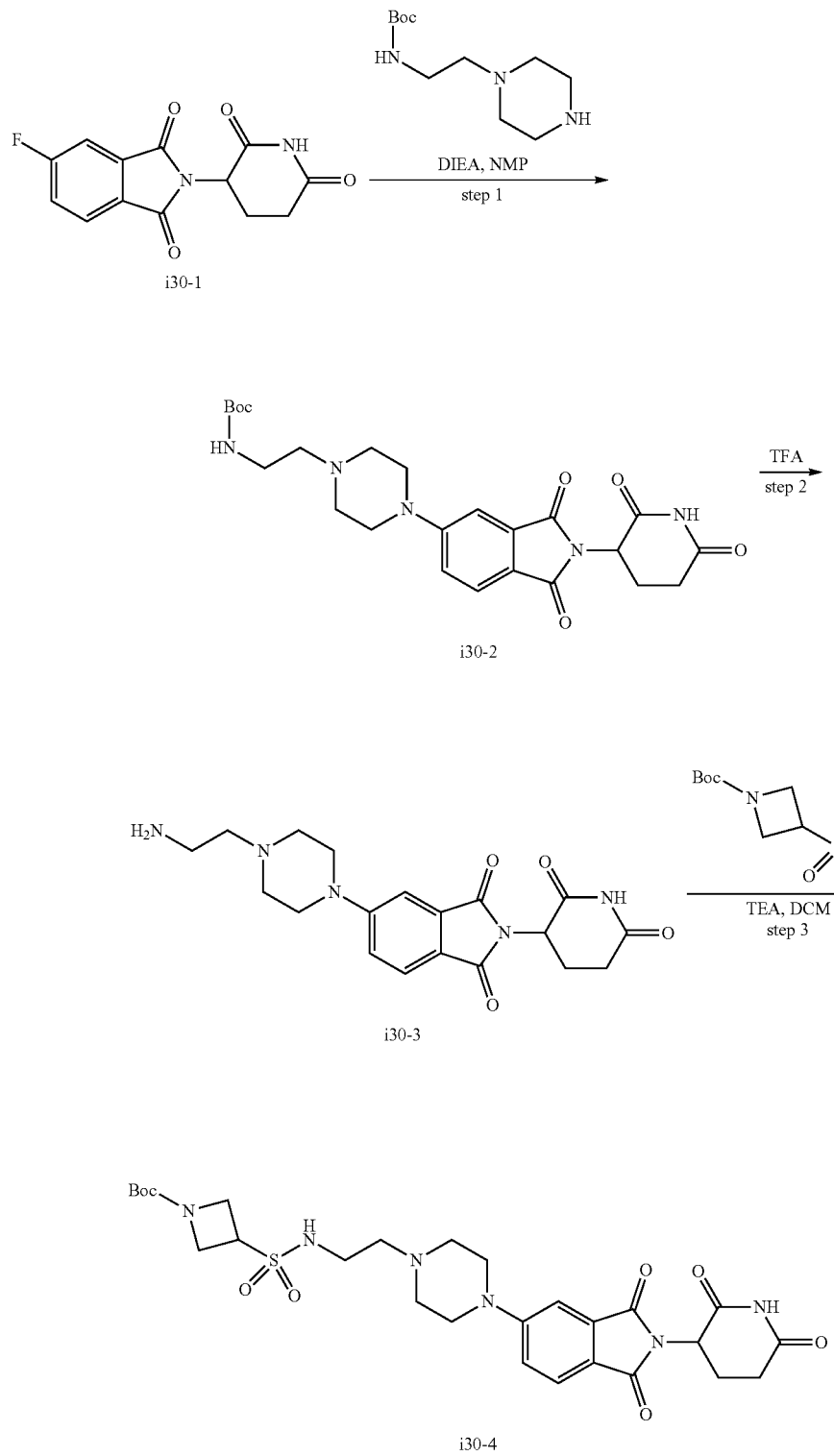

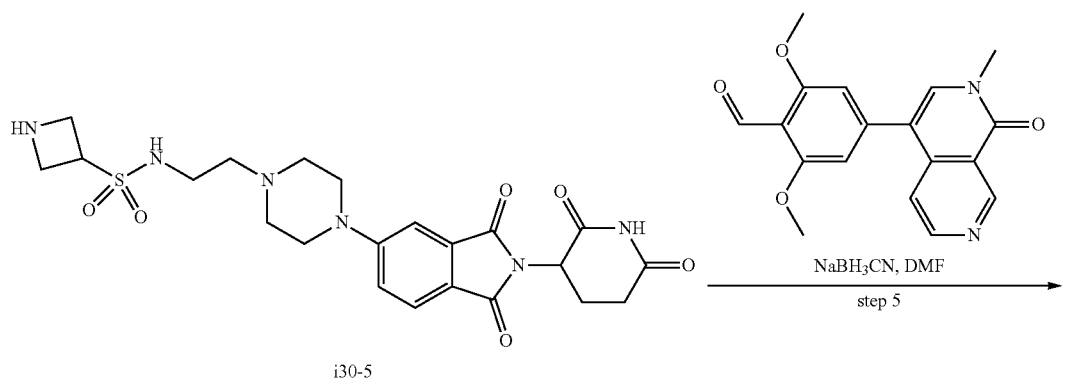

i30-5

NaBH₃CN, DMF
step 5

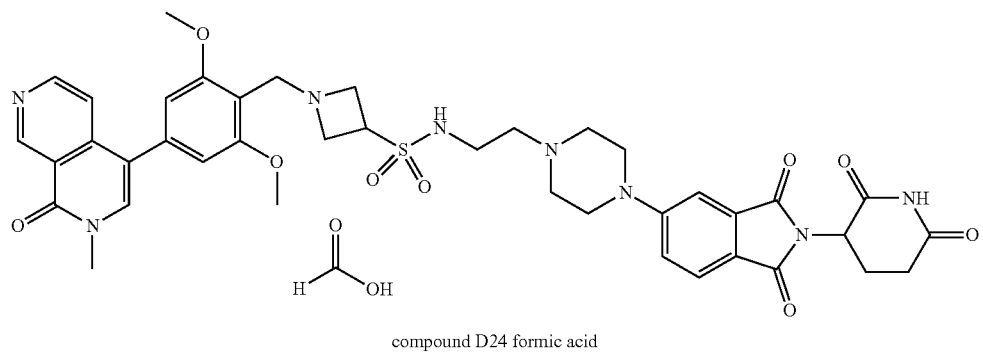

compound D24 formic acid

Step 1: Preparation of Tert-Butyl N-(2-[4-[2-(2,6-Dioxopiperidin-3-Yl)-1,3-Dioxoisoindol-5-Yl]Piperazin-1-Ylethyl) Carbamate (i30-2)

Step 2: Preparation of 5-[4-(2-Aminoethyl) Piperazin-1-Yl]-2-(2,6-Dioxopiperidin-3-Yl) Isoindole-1,3-Dione (i30-3)

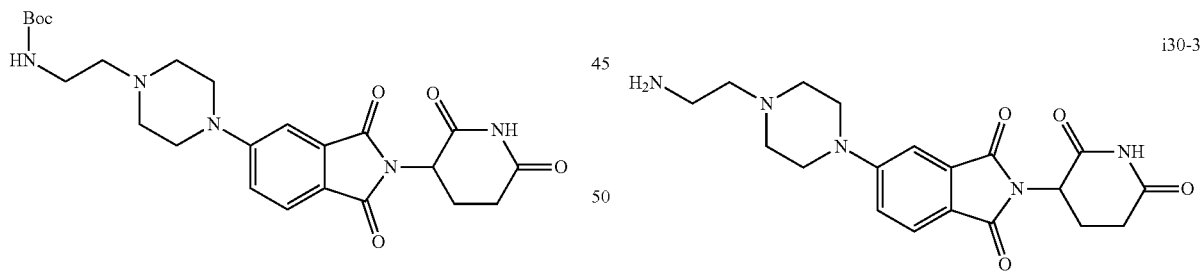

To a stirred solution of 2-(2,6-dioxopiperidin-3-yl)-5-fluoroisoindole-1,3-dione (1.50 g, 5.430 mmol, 1.00 equiv) and tert-butyl N-[2-(piperazin-1-yl)ethyl]carbamate (1.49 g, 6.516 mmol, 1.20 equiv) in NMP (10.00 mL) was added DIEA (1.40 g, 10.861 mmol, 2.00 equiv) dropwise at room temperature. The resulting mixture was stirred for 6 hours at 90° C. under nitrogen atmosphere. The residue was purified by reverse flash chromatography (conditions: column, C18 silica gel; mobile phase, ACN in water, 10% to 50% gradient in 20 minutes; detector, UV 254 nm). This resulted in tert-butyl N-(2-[4-[2-(2,6-dioxopiperidin-3-yl)-1,3-dioxoisoindol-5-yl]piperazin-1-yl]ethyl) carbamate (2 g, 75.85%) as a green oil. LCMS (ESI) m/z: [M+H]⁺=486.

A solution of tert-butyl N-(2-[4-[2-(2,6-dioxopiperidin-3-yl)-1,3-dioxoisoindol-5-yl]piperazin-1-ylethyl) carbamate (2.00 g, 4.119 mmol, 1.00 equiv) and TFA (2.00 mL, 26.926 mmol, 6.54 equiv) in DCM (5.00 mL, 78.650 mmol, 19.09 equiv) was stirred for 1 hours at room temperature. The resulting mixture was concentrated under vacuum. This resulted in 5-[4-(2-aminoethyl) piperazin-1-yl]-2-(2,6-dioxopiperidin-3-yl) isoindole-1,3-dione (1.5 g, 94.48%) as a green solid. LCMS (ESI) m/z: [M+H]⁺=386.

Step 3: Preparation of Tert-Butyl 3-[(2-[4-[2-(2,6-Dioxopiperidin-3-Yl)-1,3-Dioxoisoindol-5-Yl]Piperazin-1-Yl]Ethyl) Sulfamoyl]Azetidine-1-Carboxylate (i30-4)

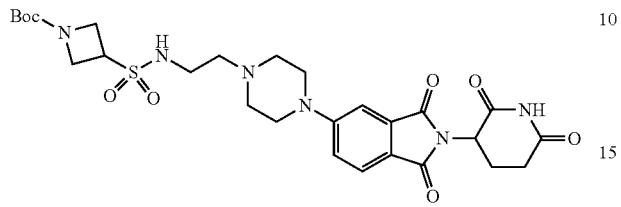

i30-4

To a stirred solution of 5-[4-(2-aminoethyl) piperazin-1-yl]-2-(2,6-dioxopiperidin-3-yl) isoindole-1,3-dione (400.00 mg, 1.038 mmol, 1.00 equiv) and tert-butyl 3-(chlorosulfonyl) azetidine-1-carboxylate (318.46 mg, 1.245 mmol, 1.20 equiv) in DCM (10.00 mL) was added TEA (210.03 mg, 2.076 mmol, 2.00 equiv) at room temperature. The resulting mixture was stirred for 2 hours at room temperature. The resulting mixture was concentrated under vacuum. The residue was purified by silica gel column chromatography, eluted with DCM/EtOAc (1:1) to afford tert-butyl 3-[(2-[4-[2-(2,6-dioxopiperidin-3-yl)-1,3-dioxoisoindol-5-yl]piperazin-1-yl]ethyl) sulfamoyl]azetidine-1-carboxylate (500 mg, 79.68%) as a green solid. LCMS (ESI) m/z: [M+H]$^+$=605.

Step 4: Preparation of N-(2-[4-[2-(2,6-Dioxopiperidin-3-Yl)-1,3-Dioxoisoindol-5-Yl]Piperazin-1-Yl]Ethyl) Azeti Dine-3-Sulfonamide (i30-5)

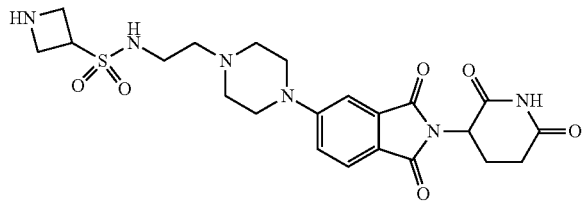

i30-5

A solution of tert-butyl 3-[(2-[4-[2-(2,6-dioxopiperidin-3-yl)-1,3-dioxoisoindol-5-yl]piperazin-1-ylethyl) sulfamoyl] azetidine-1-carboxylate (500.00 mg, 0.827 mmol, 1.00 equiv) and TFA (3.00 mL) in DCM (5.00 mL) was stirred for 1 hour at room temperature. The resulting mixture was concentrated under vacuum. This resulted in N-(2-[4-[2-(2, 6-dioxopiperidin-3-yl)-1,3-dioxoisoindol-5-yl]piperazin-1-yl]ethyl) azetidine-3-sulfonamide (400 mg, 95.87%) as a green solid. LCMS (ESI) m/z: [M+H]$^+$=505.

Step 5: Preparation of 1-[[2,6-Dimethoxy-4-(2-Methyl-1-Oxo-2,7-Naphthyridin-4-Yl)Phenyl]Methyl]-N-(2-[4-[2-(2,6-Dioxopiperidin-3-Yl)-1,3-Dioxoisoindol-5-Yl]Piperazin-1-Yl]Ethyl) Azetidine-3-Sulfonamide Formic Acid (Compound D24 Formic Acid)

compound D24

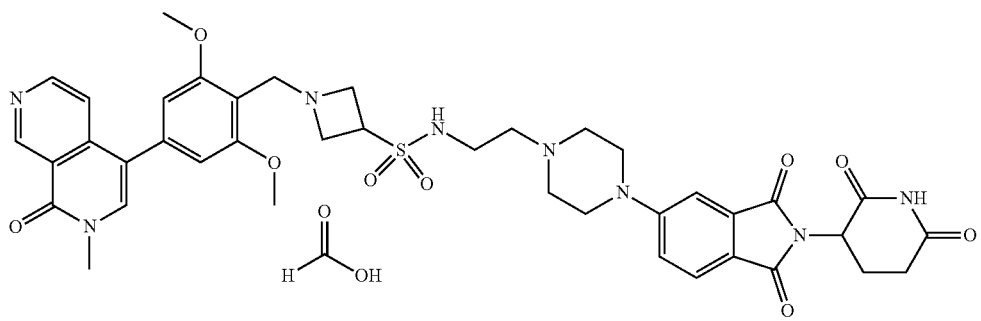

formic acid

A solution of N-(2-[4-[2-(2,6-dioxopiperidin-3-yl)-1,3-dioxoisoindol-5-yl]piperazin-1-ylethyl) azetidine-3-sulfonamide (60.00 mg, 0.119 mmol, 1.00 equiv) and 2,6-dimethoxy-4-(2-methyl-1-oxo-2,7-naphthyridin-4-yl) benzaldehyde (46.28 mg, 0.143 mmol, 1.20 equiv) in DMF (1.50 mL) was stirred for 20 minutes at room temperature. Then NaBH$_3$CN (14.95 mg, 0.238 mmol, 2.00 equiv) was added to the reaction mixture. The resulting mixture was stirred for 1 hour at room temperature. The residue was purified by reverse flash chromatography (conditions: column, C18 silica gel; mobile phase, ACN in water, 10% to 50% gradient in 20 minutes; detector, UV 254 nm). This resulted in 1-[2,6-dimethoxy-4-(2-methyl-1-oxo-2,7-naphthyridin-4-yl)phenyl]methyl]-N-(2-[4-[2-(2,6-dioxopiperidin-3-yl)-1,3-dioxoisoindol-5-yl]piperazin-1-ylethyl) azetidine-3-sulfonamide (9.4 mg, 9.72%) as a green solid. $^1$H NMR (400 MHZ, DMSO-d6) § 12.79 (brs, 0.8H, FA (COOH)), 11.08 (s, 1H), 9.44 (s, 1H), 8.71 (d, J=5.7 Hz, 1H), 8.14 (s, 0.8H, FA), 7.86 (s, 1H), 7.66 (d, J=8.5 Hz, 1H), 7.56 (d, J=5.8 Hz, 1H), 7.33 (d, J=2.3 Hz, 1H), 7.24 (dd, J=8.8, 2.3 Hz, 1H), 7.11 (s, 1H), 6.73 (s, 2H), 5.07 (dd, J=13.0, 5.4 Hz, 1H), 4.08-4.02 (m, 1H), 3.82 (s, 7H), 3.69-3.62 (m, 2H), 3.60 (s, 3H), 3.50-3.39 (m, 8H), 3.12-3.05 (m, 2H), 2.95-2.83 (m, 1H), 2.63-2.55 (m, 3H), 2.55 (s, 2H), 2.47-2.39 (m, 3H), 2.07-1.98 (m, 1H). LCMS (ESI) m/z: [M+H]$^+$=813.30.

Example 31—Preparation of (2S)-1-[2,6-Dimethoxy-4-(2-Methyl-1-Oxo-1,2-Dihydro-2,7-Naphthyridin-4-Yl)Phenyl]Methyl]-N-[2-[(2-[[2-(2,6-Dioxopiperidin-3-Yl)-1,3-Dioxo-2,3-Dihydro-1H-Isoindol-4-Yl]Amino]Ethyl)(Methyl)Amino]Ethyl]Azetidine-2-Carboxamide (Compound D25)

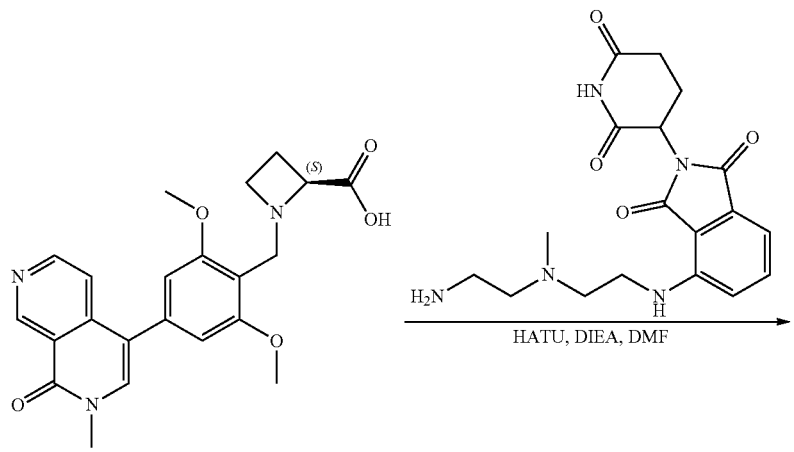

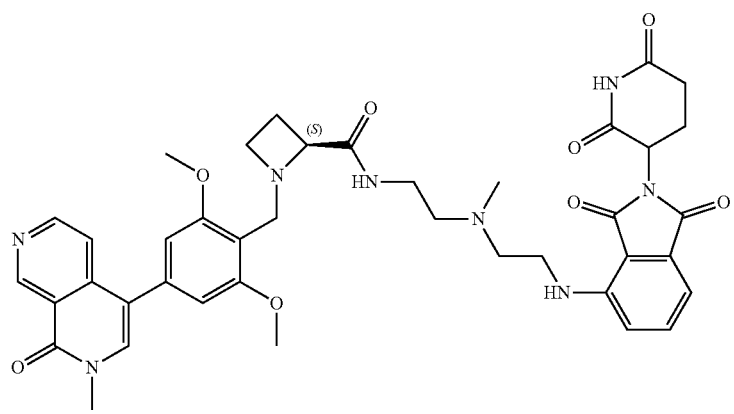

compound D25

To a solution of (2S)-1-[[2,6-dimethoxy-4-(2-methyl-1-oxo-1,2-dihydro-2,7-naphthyridin-4-yl)phenyl]methyl]azetidine-2-carboxylic acid (80 mg, 0.195 mmol, 1.00 equiv) and DIEA (75.8 mg, 0.586 mmol, 3.00 equiv) in DMF (1.50 mL) was added HATU (111.4 mg, 0.293 mmol, 1.50 equiv), and the resulting solution was stirred at room temperature for 1 hour. The crude mixture was directly purified by Prep-HPLC(conditions: SunFire C18 OBD Prep Column, 100 Å, 5 μm, 19 mm×250 mm; Mobile Phase A: Water (0.1% FA), Mobile Phase B: ACN; Flow rate: 25 mL/minuteute; Gradient: 7% B to 22% B in 8 minutes; 254 nm; Rt: 7.75 minutes) to afford (2S)-1-[[2,6-dimethoxy-4-(2-methyl-1-oxo-1,2-dihydro-2,7-naphthyridin-4-yl)phenyl]methyl]-N-[2-[(2-[2-(2,6-dioxopiperidin-3-yl)-1,3-dioxo-2,3-dihydro-1H-isoindol-4-yl]amino]ethyl)(methyl)amino]ethyl]azetidine-2-carboxamide (5.5 mg, 3.5%) as a yellow solid. $^1$H NMR (300 MHz, Methanol-d4) δ 9.45 (d, J=1.1 Hz, 1H), 8.67 (d, J=5.8 Hz, 1H), 7.72 (s, 1H), 7.63 (d, J=5.9 Hz, 1H), 7.54-7.42 (m, 1H), 6.99 (d, J=7.1 Hz, 1H), 6.91 (dd, J=8.5, 3.1 Hz, 1H), 6.71 (d, J=0.9 Hz, 2H), 5.13-5.02 (m, 1H), 3.86 (s, 8H), 3.66 (d, J=1.0 Hz, 5H), 3.28 (s, 5H), 2.76-2.66 (m, 6H), 2.53-2.42 (m, 2H), 2.34 (s, 3H), 2.30-2.19 (m, 1H), 2.15-1.94 (m, 2H). LCMS (ESI) m/z: [M+H]$^+$=765.30.

Example 32—Preparation of N-[2-[(2-[[(2S)-1-[[2,6-Dimethoxy-4-(2-Methyl-1-Oxo-1,2-Dihydro-2,7-Naphthyridin-4-Yl)Phenyl]Methyl]Azetidin-2-Yl]Formamido]Ethyl)(Methyl)Amino]Ethyl]-2-[[2-(2,6-Dioxopiperidin-3-Yl)-1,3-Dioxo-2,3-Dihydro-1H-Isoindol-5-Yl]Oxy]Acetamide (Compound D26)

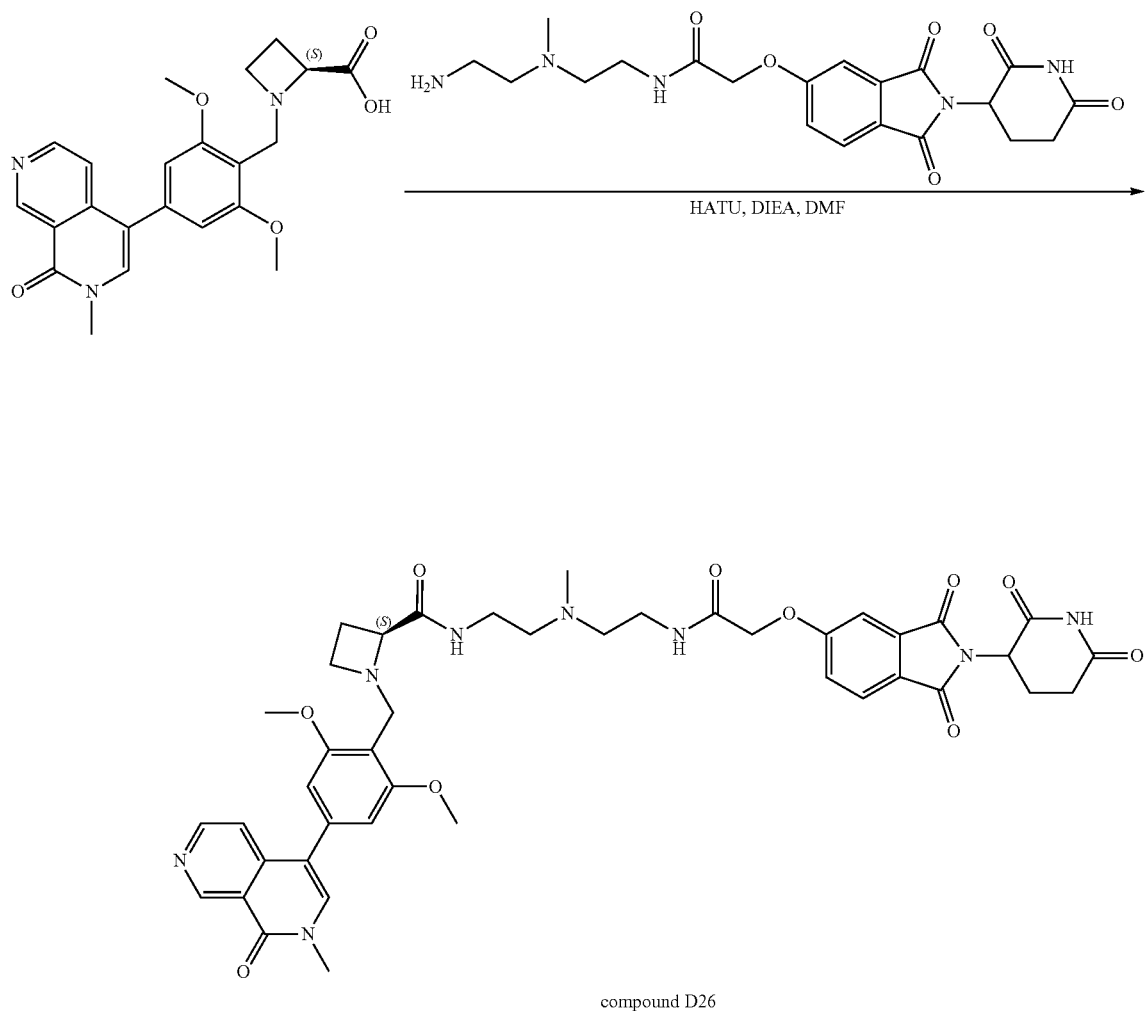

compound D26

To a solution of (2S)-1-[2,6-dimethoxy-4-(2-methyl-1-oxo-1,2-dihydro-2,7-naphthyridin-4-yl)phenyl]methyl]azetidine-2-carboxylic acid (30 mg, 0.073 mmol, 1.00 equiv) and DIEA (28.4 mg, 0.220 mmol, 3.00 equiv) in DMF (1.00 mL) was added HATU (41.8 mg, 0.110 mmol, 1.50 equiv) and N-[2-[(2-aminoethyl)(methyl)amino]ethyl]-2-[2-(2,6-dioxopiperidin-3-yl)-1,3-dioxo-2,3-dihydro-1H-isoindol-5-ylloxy]acetamide (31.61 mg, 0.073 mmol, 1.00 equiv). The resulting solution was stirred at room temperature for 1 hour. The crude mixture was directly purified by Prep-HPLC (condition: SunFire C18 OBD Prep Column, 100 Å, 5 μm, 19 mm×250 mm; Mobile Phase A: Water (0.1% FA), Mobile Phase B: ACN; Flow rate: 25 mL/minuteute; Gradient: 5% B to 5% B in 2 minutes; 254 nm; Rt: 9.88 minutes) to afford N-[2-[(2-[[(2S)-1-[2,6-dimethoxy-4-(2-methyl-1-oxo-1,2-dihydro-2,7-naphthyridin-4-yl)phenyl]methyl]azetidin-2-yl]formamido]ethyl)(methyl)amino]ethyl]-2-[2-(2,6-dioxopiperidin-3-yl)-1,3-dioxo-2,3-dihydro-1H-isoindol-5-yl]oxy]acetamide (4.8 mg, 7.5%) as a yellow solid. $^1$H NMR (300 MHZ, Acetonitrile-d3) δ 9.52 (s, 1H), 9.11 (s, 1H), 8.70 (d, J=5.7 Hz, 1H), 8.20-8.02 (m, 1H), 7.79 (t, J=6.5 Hz, 2H), 7.57 (d, J=5.0 Hz, 2H), 7.45-7.23 (m, 2H), 6.73 (s, 2H), 4.99 (dd, J=12.1, 5.3 Hz, 1H), 4.63 (s, 2H), 4.38 (s, 1H), 4.11 (s, 2H), 3.87 (s, 6H), 3.72-3.60 (m, 5H), 3.59-3.49 (m, 2H), 3.45 (d, J=5.6 Hz, 2H), 3.01 (dt, J=11.1, 5.7 Hz, 4H), 2.83-2.72 (m, 2H), 2.72-2.60 (m, 5H), 2.13 (ddd, J=10.6, 5.5, 3.1 Hz, 2H). LCMS (ESI) m/z: [M+H]$^+$=823.45.

Example 33—Preparation of 4-(((((S)-1-(2,6-Dimethoxy-4-(2-Methyl-1-Oxo-1,2-Dihydro-2,7-Naphthyridin-4-Yl)Benzyl) Azetidin-2-Yl)Methyl)(Methyl) Amino)Methyl)-2-(2,6-Dioxopiperidin-3-Yl) Isoindoline-1,3-Dione (Compound D27)
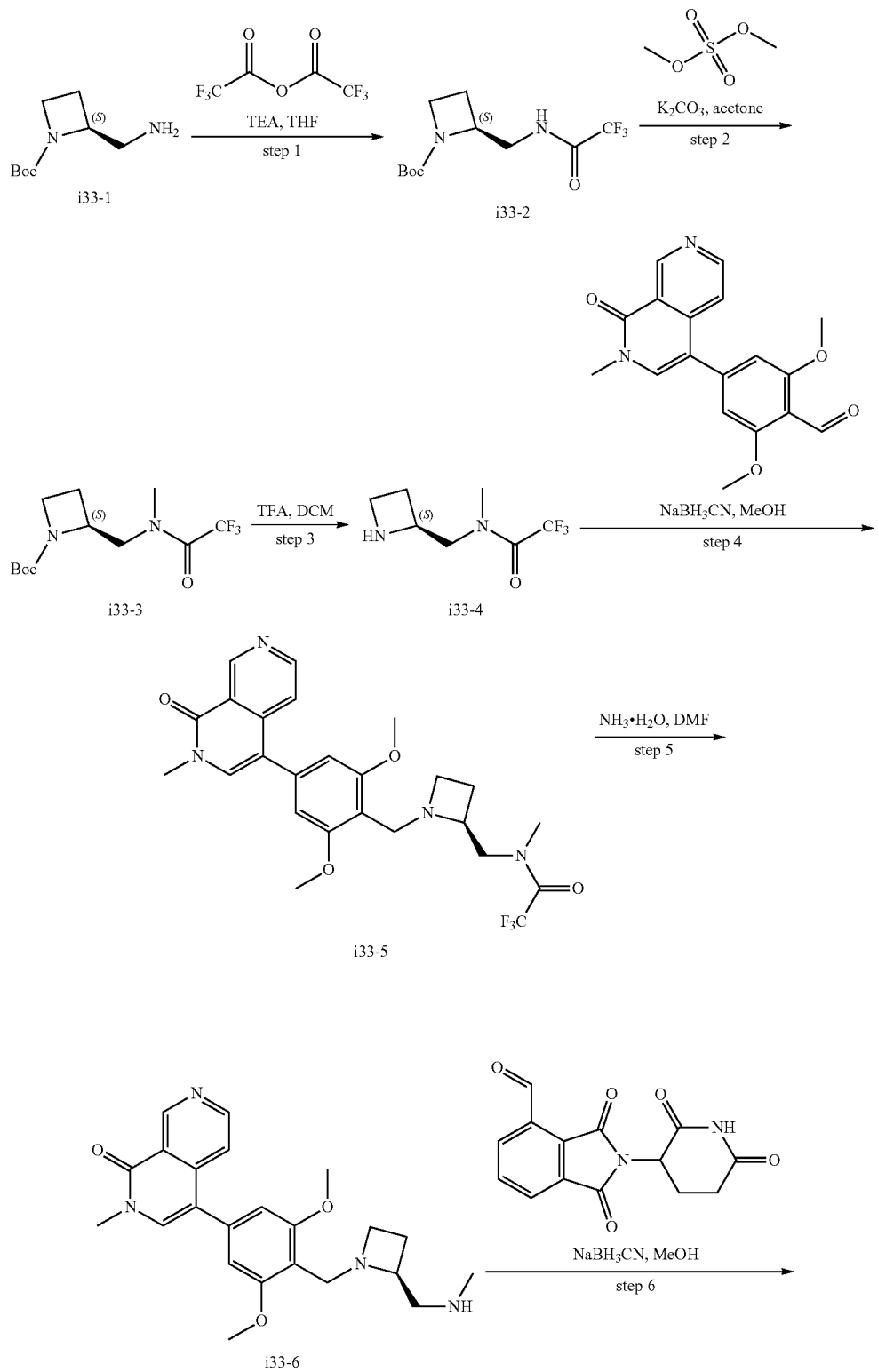

-continued

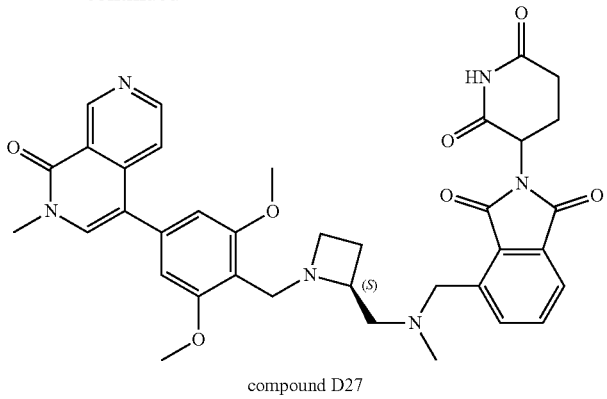

compound D27

Step 1: Preparation of Tert-Butyl(2S)-2-((2,2,2-Trifluoroacetamido)Methyl) Azetidine-1-Carboxylate (i33-2)

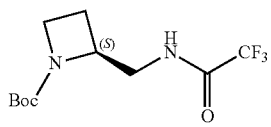

i33-2

To a solution of tert-butyl(2S)-2-(aminomethyl) azetidine-1-carboxylate (900.00 mg, 4.832 mmol, 1.00 equiv) and trifluoroacetic anhydride (1522.33 mg, 7.248 mmol, 1.5 equiv) in THF (9.00 mL) was added TEA (977.92 mg, 9.664 mmol, 2 equiv). The mixture was stirred at 25° C. for 12 hours. The resulting solution was diluted with EA. Then washed with water (3×50 mL). The residue was applied onto a silica gel column with ethyl EA/PE (15/85). The resulting mixture were evaporated to dryness to afford tert-butyl(2S)-2-[(2,2,2-trifluoroacetamido)methyl]azetidine-1-carboxylate (1270 mg, 93.11%) as a yellow oil. LCMS (ESI) m/z: [M+H]$^+$=283.

Step 2: Preparation of Tert-Butyl(2S)-2-[(2,2,2-Trifluoro-N-Methylacetamido)Methyl]Azetidine-1-Carboxylate (i33-3)

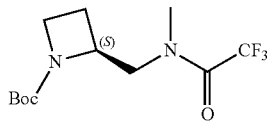

i33-3

To a solution of tert-butyl(2S)-2-[(2,2,2-trifluoroacetamido)methyl]azetidine-1-carboxylate (1270.00 mg, 4.499 mmol, 1.00 equiv) and dimethyl sulfate (681.00 mg, 5.399 mmol, 1.2 equiv) in acetone (15.00 mL) was added K$_2$CO$_3$ (621.83 mg, 4.499 mmol, 1 equiv). The mixture was stirred at 25° C. for 12 hours. The resulting mixture were evaporated to dryness to afford tert-butyl(2S)-2-[(2,2,2-trifluoro-N-methylacetamido)methyl]azetidine-1-carboxylate (1640 mg, 123.02%) as a yellow oil that was used directly without further purification. LCMS (ESI) m/z: [M+H]$^+$=297.

Step 3: Preparation of N-[(2S)-Azetidin-2-Ylmethyl]-2,2,2-Trifluoro-N-Methylacetamide (i33-4)

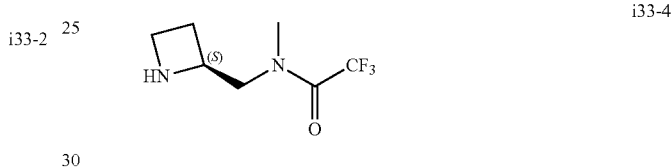

i33-4

A solution of tert-butyl(2S)-2-[(2,2,2-trifluoro-N-methylacetamido)methyl]azetidine-1-carboxylate (1.64 g, 5.535 mmol, 1.00 equiv) and TFA (3.50 mL, 47.121 mmol, 8.51 equiv) in DCM (16.00 mL) was stirred for 1 hour at 25° C. The mixture was concentrated to give N-[(2S)-azetidin-2-ylmethyl]-2,2,2-trifluoro-N-methylacetamide (2.08 g) as a brown oil that was used directly without further purification. LCMS (ESI) m/z: [M+H]$^+$=197.

Step 4: Preparation of N-[[(2S)-1-[[2,6-Dimethoxy-4-(2-Methyl-1-Oxo-2,7-Naphthyridin-4-Yl)Phenyl]Methyl]Azetidin-2-Yl]Methyl]-2,2,2-Trifluoro-N-Methylacetamide (i33-5)

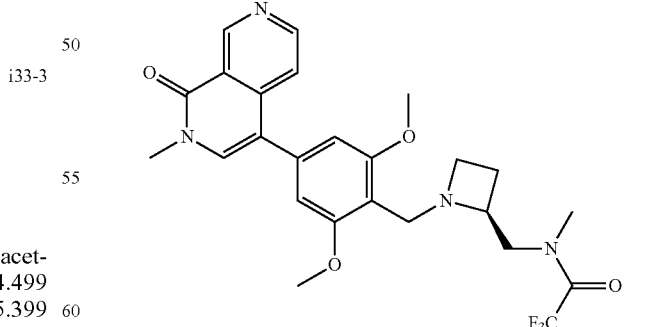

i33-5

To a solution of 2,6-dimethoxy-4-(2-methyl-1-oxo-2,7-naphthyridin-4-yl)benzaldehyde (552.00 mg, 1.702 mmol, 1.00 equiv) and N-[(2S)-azetidin-2-ylmethyl]-2,2,2-trifluoro-N-methylacetamide (500.81 mg, 2.553 mmol, 1.50 equiv) in DMF (6.00 mL) was added NaBH(OAc)$_3$ (721.42 mg, 3.404 mmol, 2.00 equiv). The resulting solution was stirred at 25° C. for 1 hour. The mixture was concentrated to give crude product that was purified by chromatography on silica gel eluted with MeOH/DCM (5:95) to give N-[[(2S)-1-[2,6-dimethoxy-4-(2-methyl-1-oxo-2,7-naphthyridin-4-yl)phenyl]methyl]azetidin-2-yl]methyl]-2,2,2-trifluoro-N-methylacetamide (275 mg, 32.03%) as an off-white solid. LCMS (ESI) m/z: [M+H]$^+$=505.

Step 5: Preparation of(S)-4-(3,5-Dimethoxy-4-((2-((Methylamino)Methyl) Azetidin-1-Yl)Methyl)Phenyl)-2-Methyl-2,7-Naphthyridin-1 (2H)-One (i33-6)

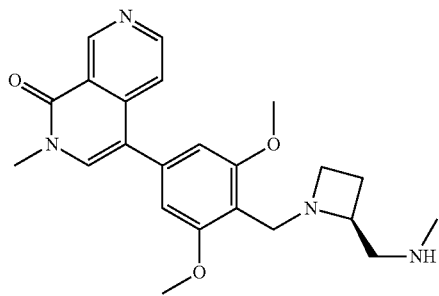

i33-6

A solution of N-[[(2R)-1-[2,6-dimethoxy-4-(2-methyl-1-oxo-2,7-naphthyridin-4-yl)phenyl]methyl]azetidin-2-yl] methyl]-2,2,2-trifluoro-N-methylacetamide (230 mg, 0.456 mmol, 1.00 equiv) and NH$_3$·H$_2$O (1 mL, 0.008 mmol, 0.05 equiv) in DMF (2.50 mL) was stirred at 25° C. for 1 hour. The resulting mixture were evaporated to dryness to afford 4-(3,5-dimethoxy-4-[[(2R)-2-[(methylamino)methyl]azetidin-1-yl]methyl]phenyl)-2-methyl-2,7-naphthyridin-1-one (219 mg) as a brown oil that was used directly without further purification. LCMS (ESI) m/z: [M+H]$^+$=409.

Step 6: Preparation of 4-(((((S)-1-(2,6-Dimethoxy-4-(2-Methyl-1-Oxo-1,2-Dihydro-2,7-Naphthyridin-4-Yl)Benzyl) Azetidin-2-Yl)Methyl)(Methyl) Amino)Methyl)-2-(2,6-Dioxopiperidin-3-Yl) Isoindoline-1,3-Dione (Compound D27)

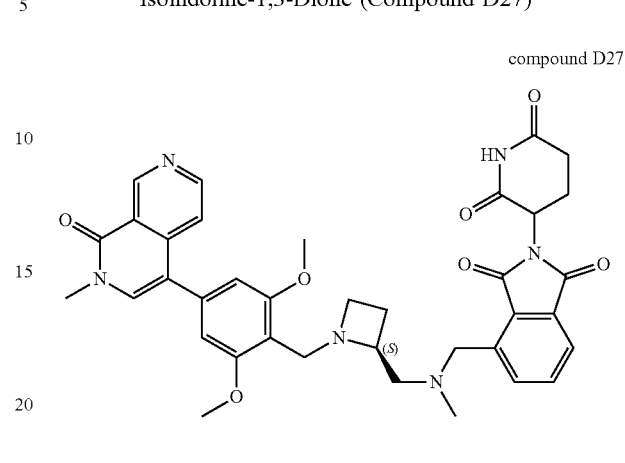

compound D27

To a stirred solution of 4-(3,5-dimethoxy-4-[[(2R)-2-[(methylamino)methyl]azetidin-1-yl]methyl]phenyl)-2-methyl-1,2-dihydro-2,7-naphthyridin-1-one (150.00 mg, 0.367 mmol, 1.00 equiv) and 2-(2,6-dioxopiperidin-3-yl)-1,3-dioxo-2,3-dihydro-1H-isoindole-4-carbaldehyde (105.11 mg, 0.367 mmol, 1.00 equiv) in MeOH (2.00 mL) was added NaBH$_3$CN (115.38 mg, 1.836 mmol, 5 equiv). The mixture was stirred at 25° C. for 1 hour. Without any additional work-up, the mixture was purified by prep-HPLC (conditions: SunFire C18 OBD Prep Column, 100 Å, 5 μm, 19 mm×250 mm; Mobile Phase A: Water (0.05% TFA), Mobile Phase B: ACN; Flow rate: 25 mL/minute; Gradient: 3% B to 3% B in 2 minutes; 254 nm; Rt: 14.55 minutes) to give 4-(((((S)-1-(2,6-dimethoxy-4-(2-methyl-1-oxo-1,2-dihydro-2,7-naphthyridin-4-yl)benzyl) azetidin-2-yl)methyl)(methyl)amino)methyl)-2-(2,6-dioxopiperidin-3-yl) isoindoline-1,3-dione (8.0 mg, 3.01%) as a yellow solid. $^1$H NMR (400 MHZ, Methanol-d4) δ 9.54 (s, 1H), 8.67 (d, J=5.7 Hz, 1H), 8.57 (s, 0.4H, FA), 7.91-7.86 (m, 1H), 7.84 (d, J=6.0 Hz, 2H), 7.74 (d, J=6.5 Hz, 1H), 7.57 (t, J=6.3 Hz, 1H), 6.84 (d, J=5.4 Hz, 2H), 5.20-5.08 (m, 1H), 4.72-4.31 (m, 3H), 4.15-3.98 (m, 3H), 3.92 (d, J=11.5 Hz, 6H), 3.71 (d, J=1.8 Hz, 3H), 2.99-2.80 (m, 3H), 2.80-2.49 (m, 4H), 2.38-1.98 (m, 5H). LCMS (ESI) m/z: [M+H]$^+$=679.30.

Example 34—Preparation of 4-(((1-(2,6-Dimethoxy-4-(2-Methyl-1-Oxo-1,2-Dihydro-2,7-Naphthyridin-4-Yl)Benzyl) Azetidin-3-Yl)(Methyl)Amino) Methyl)-2-(2,6-Dioxopiperidin-3-Yl) Isoindoline-1,3-Dione (Compound D28)

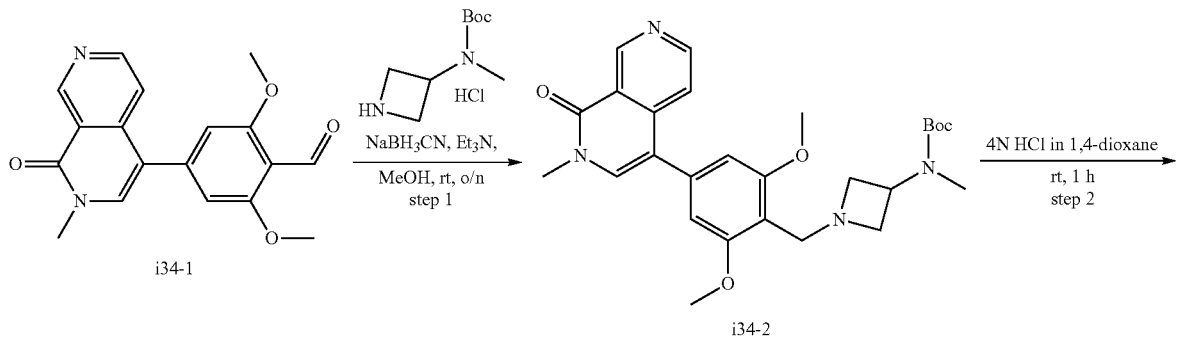

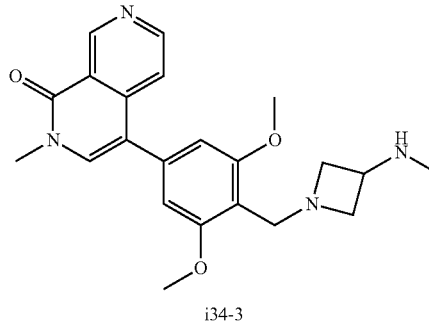

i34-3

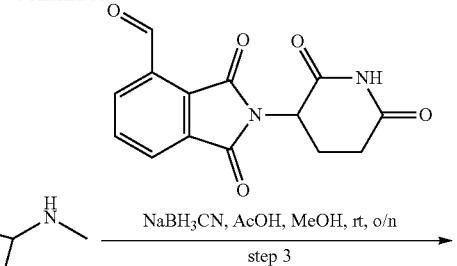

step 3
NaBH₃CN, AcOH, MeOH, rt, o/n

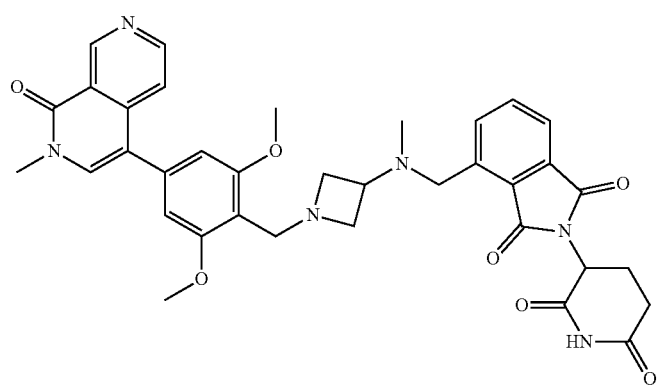

compound D28

Step 1: Preparation of Tert-Butyl(1-(2,6-Dimethoxy-4-(2-Methyl-1-Oxo-1,2-Dihydro-2,7-Naphthyridin-4-Yl)Benzyl) Azetidin-3-Yl)(Methyl) Carbamate (i34-2)

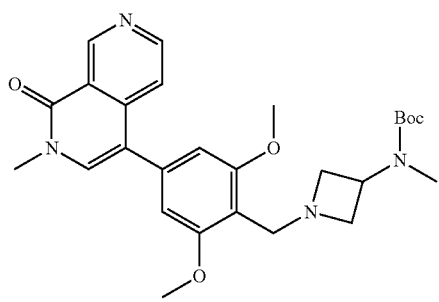

i34-2

To a solution of 2,6-dimethoxy-4-(2-methyl-1-oxo-1,2-dihydro-2,7-naphthyridin-4-yl)benzaldehyde (250.00 mg, 0.772 mmol, 1.00 equiv) and tert-butyl azetidin-3-yl (methyl) carbamate hydrochloride (171.38 mg, 0.772 mmol, 1.00 equiv), was added Et₃N (77.97 mg, 0.772 mmol, 1.00 equiv) and NaBH₃CN (97.27 mg, 1.544 mmol, 2.00 equiv). The resulting mixture was stirred overnight. The mixture was concentrated under vacuum. The residue was purified by silica gel column chromatography, eluted with EA in PE from 0% to 40% to afford tert-butyl(1-(2,6-dimethoxy-4-(2-methyl-1-oxo-1,2-dihydro-2,7-naphthyridin-4-yl)benzyl) azetidin-3-yl)(methyl) carbamate (170 mg, 0.344 mmol, 44.62%) as a white solid. LCMS (ESI) m/z: [M+H]⁺=495.

Step 2: Preparation of 4-(3,5-Dimethoxy-4-((3-(Methylamino) Azetidin-1-Yl)Methyl)Phenyl)-2-Methyl-2,7-Naphthyridin-1 (2H)-One (i34-3)

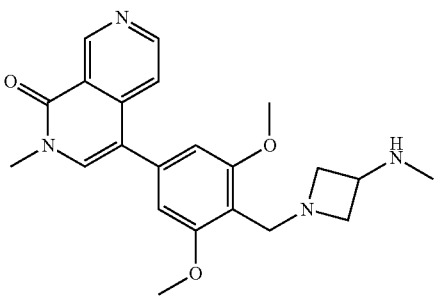

i34-3

Tert-butyl(1-(2,6-dimethoxy-4-(2-methyl-1-oxo-1,2-dihydro-2,7-naphthyridin-4-yl)benzyl) azetidin-. 3-yl) (methyl) carbamate (170 mg, 0.344 mmol, 1.00 equiv) was dissolved in 4 N HCl in 1,4-dioxane (5 mL, 20 mmol, 58.13 equiv). The resulting solution was stirred for one hour at room temperature. The resulting mixture was concentrated to afford 4-(3,5-dimethoxy-4-((3-(methylamino) azetidin-1-yl)methyl)phenyl)-2-methyl-2,7-naphthyridin-1 (2H)-one (180 mg, crude) as a white solid, that was used directly without further purification. LCMS (ESI) m/z: [M+H]⁺=395.

Step 3: Preparation of 4-(((1-(2,6-Dimethoxy-4-(2-Methyl-1-Oxo-1,2-Dihydro-2,7-Naphthyridin-4-Yl) Benzyl) Azetidin-3-Yl)(Methyl)Amino)Methyl)-2-(2,6-Dioxopiperidin-3-Yl) Isoindoline-1,3-Dione (Compound D28)

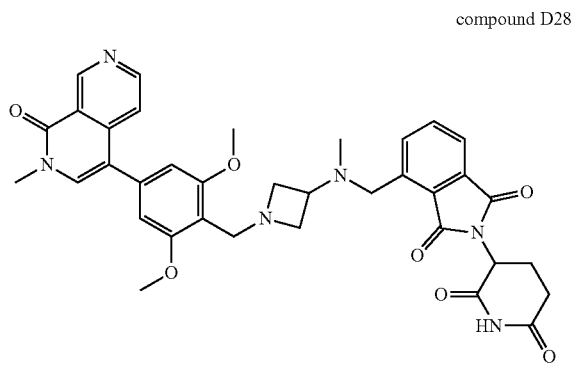 [SMILES: COc1cc(-c2cn(C)c(=O)c3cnccc23)cc(OC)c1CN1CC(N(C)Cc2cccc3c2C(=O)N(C2CCC(=O)NC2=O)C3=O)C1]

compound D28

To a mixture of 4-(3,5-dimethoxy-4-[3-(methylamino)azetidin-1-yl]methyl]phenyl)-2-methyl-1,2-dihydro-2,7-naphthyridin-1-one (30.00 mg, 0.076 mmol, 1.00 equiv) and 2-(2,6-dioxopiperidin-3-yl)-1,3-dioxo-2,3-dihydro-1H-isoindole-4-carbaldehyde (21.77 mg, 0.076 mmol, 1.00 equiv) in MeOH (2.00 mL) was added AcOH (0.05 mg, 0.001 mmol, 0.01 equiv). The mixture was stirred for 1 hour. NaBH₃CN (9.56 mg, 0.152 mmol, 2.00 equiv) was added. The resulting mixture was stirred for 1 hour. The crude product was purified by preparative HPLC(condition: SunFire C18 OBD Prep Column, 100 Å, 5 μm, 19 mm×250 mm; Mobile Phase A: Water (0.05% TFA), Mobile Phase B: ACN; Flow rate: 25 mL/minuteute; Gradient: 5% B to 5% B in 2 minutes; 254 nm; Rt: 12.63 minutes. This afforded 4-[(1-[2,6-dimethoxy-4-(2-methyl-1-oxo-1,2-dihydro-2,7-naphthyridin-4-yl)phenyl]methyl]azetidin-3-yl)(methyl)amino]methyl]-2-(2,6-dioxopiperidin-3-yl)-2,3-dihydro-1H-isoindole-1,3-dione (18.90 mg, 0.028 mmol, 36.53%) as a light yellow solid. $^1$H NMR (400 MHZ, Methanol-d4)δ 9.60 (s, 1H), 8.70 (d, J=6.3 Hz, 1H), 8.00 (s, 1H), 7.96-7.82 (m, 4H), 6.88 (s, 2H), 5.17 (dd, J=12.4, 5.4 Hz, 1H), 4.58 (s, 2H), 4.33 (t, J=7.2 Hz, 4H), 4.10 (d, J=13.2 Hz, 1H), 4.02 (d, J=13.2 Hz, 1H), 3.97 (s, 6H), 3.75 (s, 4H), 2.95-2.83 (m, 1H), 2.81-2.67 (m, 2H), 2.29 (s, 3H), 2.21-2.11 (m, 1H). LCMS (ESI) m/z: [M+H]⁺=665.30.

Example 35—Preparation of 1-(2,6-Dimethoxy-4-(2-Methyl-1-Oxo-1,2-Dihydro-2,7-Naphthyridin-4-Yl)Benzyl)-N-((2-(2,6-Dioxopiperidin-3-Yl)-1,3-Dioxoisoindolin-4-Yl)Methyl)-N-Methylazetidine-3-Carboxamide (Compound D29)

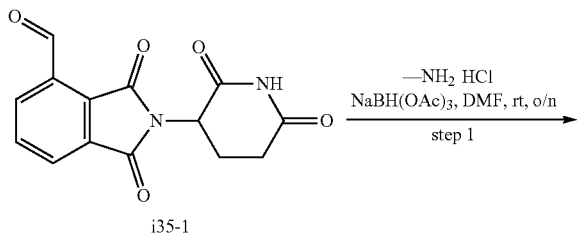

i35-1

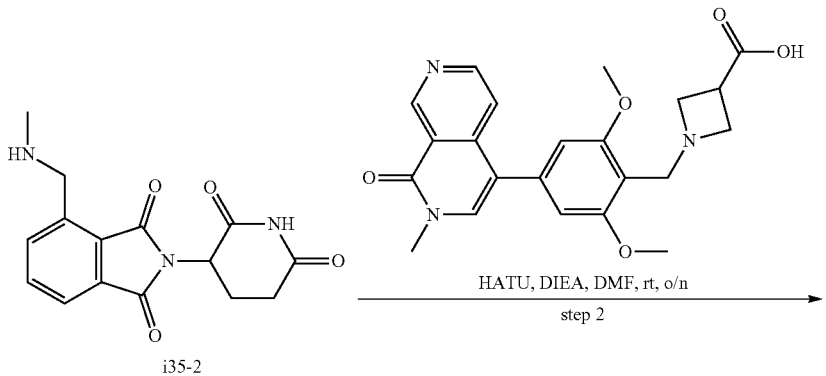

i35-2

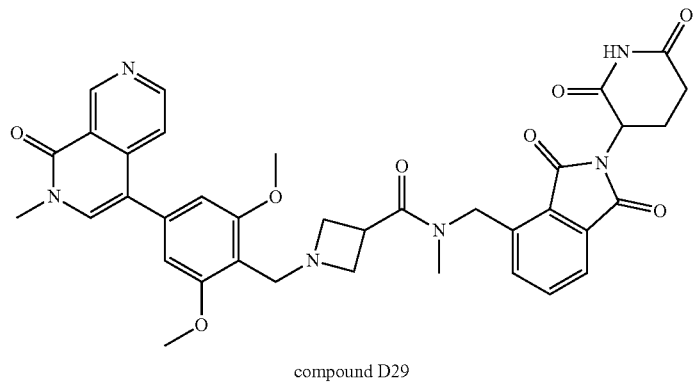

compound D29

Step 1: Preparation of 2-(2,6-Dioxopiperidin-3-Yl)-4-((Methylamino)Methyl) Isoindoline-1,3-Dione (i35-2)

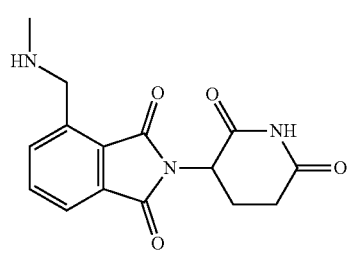

To a solution of 2-(2,6-dioxopiperidin-3-yl)-1,3-dioxoisoindoline-4-carbaldehyde (70.00 mg, 0.245 mmol, 1.00 equiv) in DMF (3.00 mL) was added methanamine hydrochloride (24.77 mg, 0.367 mmol, 1.50 equiv). The resulting mixture was stirred overnight at room temperature. Then NaBH(OAc)$_3$ (103.88 mg, 0.490 mmol, 2.00 equiv) was added. The resulting mixture was stirred for 1 hour at room temperature. The resulting mixture was purified by reverse phase column with ACN in water from (0% to 50%) to afford 2-(2,6-dioxopiperidin-3-yl)-4-((methylamino)methyl) isoindoline-1,3-dione (30 mg, 41.10%) as a white solid. LCMS (ESI) m/z: [M+H]$^+$=302.

Step 2: Preparation of 1-(2,6-Dimethoxy-4-(2-Methyl-1-Oxo-1,2-Dihydro-2,7-Naphthyridin-4-Yl) b Enzyl)-N-((2-(2,6-Dioxopiperidin-3-Yl)-1,3-Dioxoisoindolin-4-Yl)Methyl)-N-Methylazetidine-3-Carboxamide (Compound D29)

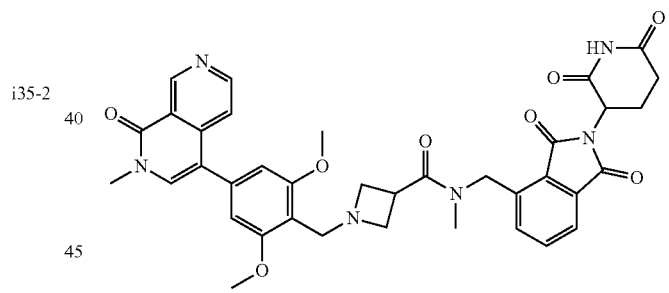

compound D29

To a mixture of 1-(2,6-dimethoxy-4-(2-methyl-1-oxo-1,2-dihydro-2,7-naphthyridin-4-yl)benzyl) azetidine-3-carboxylic acid (40.77 mg, 0.100 mmol, 1.00 equiv) in DMF (3.00 mL) was added HATU (94.65 mg, 0.250 mmol, 2.50 equiv) and DIEA (38.61 mg, 0.300 mmol, 3.00 equiv). The resulting mixture was stirred for 2 hours at room temperature. Then 2-(2,6-dioxopiperidin-3-yl)-4-((methylamino) methyl) isoindoline-1,3-dione (30.00 mg, 0.100 mmol, 1.00 equiv) was added. The resulting mixture was stirred for 1 hour. The crude product was purified by preparative HPLC (conditions: XSelect CSH Prep C18 OBD Column, 5 μm, 19*150 mm; Mobile Phase A: Water (0.1% FA), Mobile Phase B: ACN; Flow rate: 25 mL/minuteute; Gradient: 12% B to 12% B in 2 minutes; 254/220 nm; Rt: 13.57 min Fractions containing the desired compound were evaporated to dryness to afford 1-(2,6-dimethoxy-4-(2-methyl-1-oxo-1,2-dihydro-2,7-naphthyridin-4-yl)benzyl)-N-((2-(2,6-dioxopiperidin-3-yl)-1,3-dioxoisoindolin-4-yl)methyl)-N-methylazetidine-3-carboxamide (17.10 mg, 24.25%) as a light yellow solid. 1H-NMR (400 MHZ, Methanol-d4)δ 9.58 (s, 1H), 8.69 (t, J=7.8 Hz, 1H), 7.98-7.87 (m, 2H), 7.85-7.77 (m, 2H), 7.72-7.64 (m, 1H), 6.89 (d, J=8.2 Hz, 2H), 5.22-5.01 (m, 3H), 4.65-4.36 (m, 5H), 4.34-4.21 (m, 1H), 4.20-4.07 (m, 1H), 4.01-3.92 (m, 6H), 3.74 (s, 3H), 3.02 (s, 3H), 2.96-2.84 (m, 1H), 2.80-2.71 (m, 2H), 2.24-2.12 (m, 1H). LCMS (ESI) m/z: [M+H]$^+$=693.35.

Example 36—Preparation of 1-(2,6-Dimethoxy-4-(2-Methyl-1-Oxo-1,2-Dihydro-2,7-Naphthyridin-4-Yl)Benzyl)-N-(2-((2-((2-(2,6-Dioxopiperidin-3-Yl)-1,3-Dioxoisoindolin-4-Yl)Amino) Ethyl) Sulfonyl) Ethyl) Azetidine-3-Carboxamide (Compound D30)

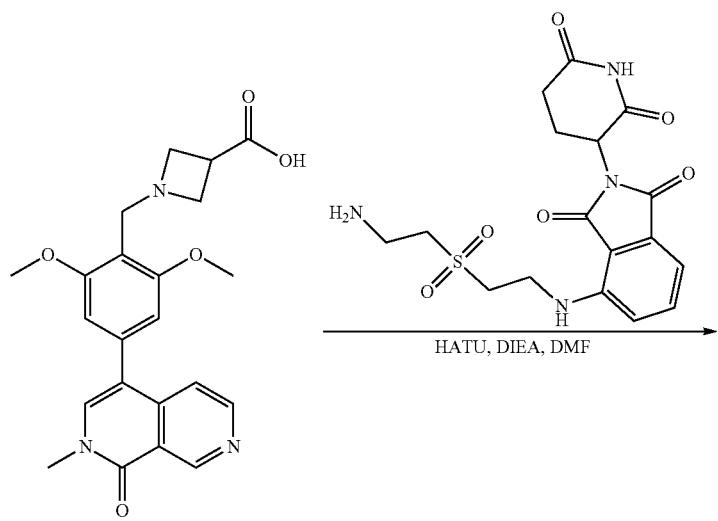

(HATU) (73.83 mg, 0.194 mmol, 1.50 equiv) at 0° C. After 10 minutes, to the above mixture was added 4-[2-(2-aminoethanesulfonyl)ethyl]amino]-2-(2,6-dioxopiperidin-3-yl) isoindole-1,3-dione (63.44 mg, 0.155 mmol, 1.20 equiv). Then the reaction was stirred at room temperature for 2 hours under N$_2$ atmosphere. The crude product was purified by Prep-HPLC (conditions: Sunfire C18 OBD Prep Column, 5 μm, 19 mm*250 mm; Mobile Phase A: Water (0.05% TFA, trifluoroacetic acid), Mobile Phase B: acetonitrile (MeCN or ACN); Flow rate: 25 mL/minuteute; Gradient: 3% B to 3% B in 2 minutes; 254 nm; Rt: 13.98 minutes). This resulted in 1-(2,6-dimethoxy-4-(2-methyl-1-oxo-1,2-dihydro-2,7-naphthyridin-4-yl)benzyl)-N-(2-((2-((2-(2,6-dioxopiperidin-3-yl)-1,3-dioxoisoindolin-4-yl)amino) ethyl) sulfonyl)

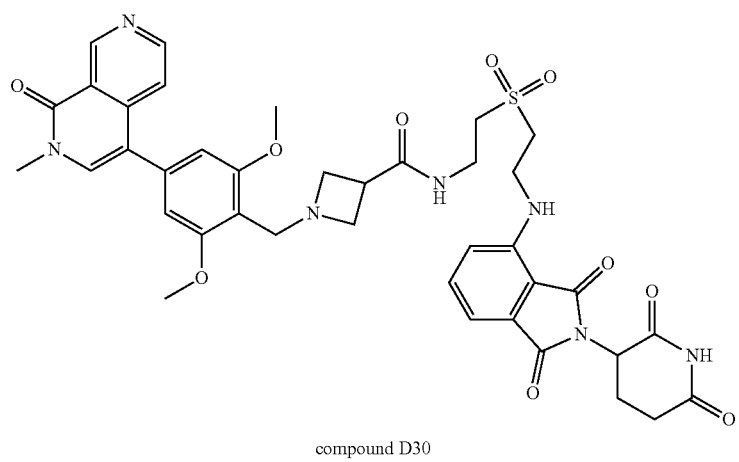

compound D30

Into a stirred mixture of 1-[2,6-dimethoxy-4-(2-methyl-1-oxo-2,7-naphthyridin-4-yl)phenyl]methyl]azetidine-3-carboxylic acid (53.00 mg, 0.129 mmol, 1.00 equiv) and DIEA (N,N-diisopropylamine) (50.19 mg, 0.388 mmol, 3.00 equiv) in DMF (dimethylformamide) (1.00 mL) was added 1-[Bis(dimethylamino)methylene]-1H-1,2,3-triazolo[4,5-b]pyridinium 3-oxid hexafluorophosphate, N-[(Dimethylamino)-1H-1,2,3-triazolo-[4,5-b]pyridin-1-ylmethylene]-N-methylmethanaminium hexafluorophosphate N-oxide ethyl) azetidine-3-carboxamide 18.4 mg (16.47%) as a yellow solid. $^1$H NMR (300 MHZ, Methanol-d4) δ 9.52 (d, J=0.8 Hz, 1H), 8.69 (d, J=5.8 Hz, 1H), 8.56 (br s, 0.5 H, FA), 7.77 (s, 1H), 7.67-7.55 (m, 2H), 7.13 (t, J=7.6 Hz, 2H), 6.83 (s, 2H), 5.06 (dd, J=12.3, 5.4 Hz, 1H), 4.37 (s, 2H), 4.23-4.06 (m, 4H), 3.95 (s, 6H), 3.89 (t, J=6.3 Hz, 2H), 3.77-3.69 (m, 2H), 3.71 (s, 3H), 3.52 (q, J=6.9, 6.3 Hz, 3H), 3.38 (t, J=6.3 Hz, 2H), 2.62-2.93 (m, 3H), 2.07-2.17 (m, 1H). LCMS (ESI) m/z: [M+H]$^+$=800.35.

Example 37—Preparation of 5-((1-(3-((2,6-Dimethoxy-4-(2-Methyl-1-Oxo-1,2-Dihydro-2,7-Naphthyridin-4-Yl)Benzyl)Amino) Propyl) Azetidin-3-Yl) Oxy)-2-(2,6-Dioxopiperidin-3-Yl) Isoindoline-1,3-Dione Formic Acid (Compound D31 Formic Acid)
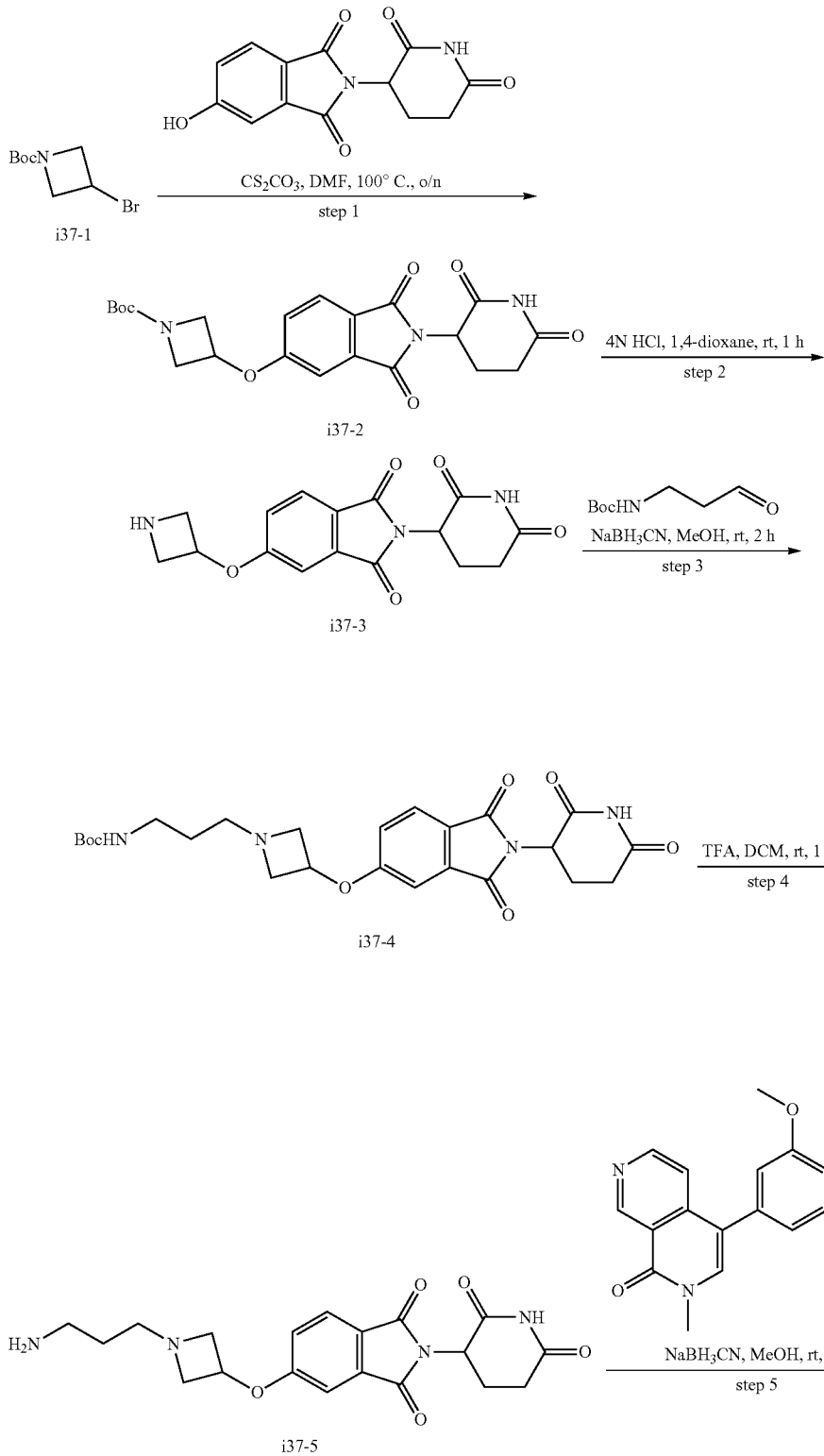

-continued

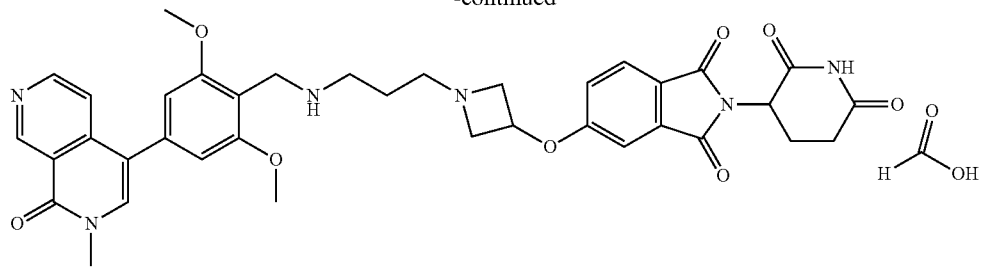

compound D31 formic acid

Step 1: Preparation of Tert-Butyl 3-((2-(2,6-Dioxopiperidin-3-Yl)-1,3-Dioxoisoindolin-5-Yl)Oxy) Aze Tidine-1-Carboxylate (i37-2)

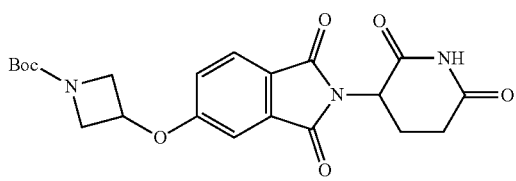

i37-2

To a mixture of tert-butyl 3-bromoazetidine-1-carboxylate (2.00 g, 8.511 mmol, 1.00 equiv) and 2-(2,6-dioxopiperidin-3-yl)-5-hydroxyisoindoline-1,3-dione (2.33 g, 8.511 mmol, 1.00 equiv) in DMF (30.00 mL) was added $Cs_2CO_3$ (5.53 g, 17.022 mmol, 2.00 equiv). The resulting mixture was stirred overnight at 90° C. The resulting mixture was concentrated under vacuum. The residue was purified by silica gel column chromatography, eluted with EA in PE from 0% to 50% to afford tert-butyl 3-((2-(2,6-dioxopiperidin-3-yl)-1,3-dioxoisoindolin-5-yl)oxy) azetidine-1-carboxylate (400 mg, 10.96%) as a light yellow solid. LCMS (ESI) m/z: $[M+H]^+$=430.

Step 2: Preparation of 5-(Azetidin-3-Yloxy)-2-(2,6-Dioxopiperidin-3-Yl) Isoindoline-1,3-Dione (i37-3)

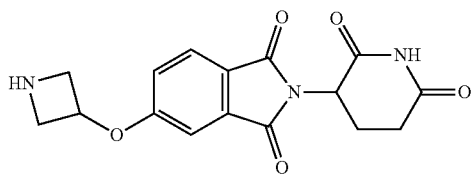

i37-3

To a solution of tert-butyl 3-((2-(2,6-dioxopiperidin-3-yl)-1,3-dioxoisoindolin-5-yl)oxy) azetidine-1-carboxylate (400.00 mg, 0.932 mmol, 1.00 equiv) in 1,4-dioxane (5 mL) was added HCl (4 N in 1,4-dioxane) (5 mL, 20.000 mmol, 21.46 equiv). The resulting solution was stirred for 1 hour at room temperature. The resulting mixture was concentrated under vacuum to afford 5-(azetidin-3-yloxy)-2-(2,6-dioxopiperidin-3-yl) isoindoline-1,3-dione (440.00 mg, crude) as a white solid. LCMS (ESI) m/z: $[M+H]^+$=330.

Step 3: Preparation of Tert-Butyl(3-(3-((2-(2,6-Dioxopiperidin-3-Yl)-1,3-Dioxoisoindolin-5-Yl)Oxy) Zetidin-1-Yl) Propyl) Carbamate (i37-4)

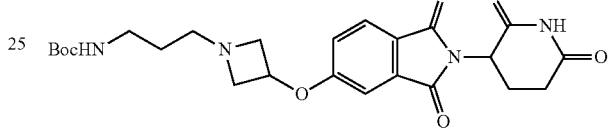

i37-4

A mixture of 5-(azetidin-3-yloxy)-2-(2,6-dioxopiperidin-3-yl) isoindoline-1,3-dione (200.00 mg, 0.608 mmol, 1.00 equiv) and tert-butyl(3-oxopropyl) carbamate (105.18 mg, 0.608 mmol, 1.00 equiv) in MeOH (5.00 mL) was stirred for 1.5 hours at room temperature. Then $NaBH_3CN$ (75.39 mg, 1.216 mmol, 2.00 equiv) was added. The resulting mixture was stirred for 1 hour at room temperature. The resulting mixture was concentrated under vacuum. The residue was purified by silica gel column chromatograpy, eluted with EA in PE from 0% to 50% to afford tert-butyl(3-(3-((2-(2,6-dioxopiperidin-3-yl)-1,3-dioxoisoindolin-5-yl)oxy) zetidin-1-yl) propyl) carbamate (100.00 mg, 33.89%) as a white solid. LCMS (ESI) m/z: $[M+H]^+$=487.

Step 4: Preparation of 5-((1-(3-Aminopropyl) Azetidin-3-Yl)Oxy)-2-(2,6-Dioxopiperidin-3-Yl) Isoindoline-1,3-Dione (i37-5)

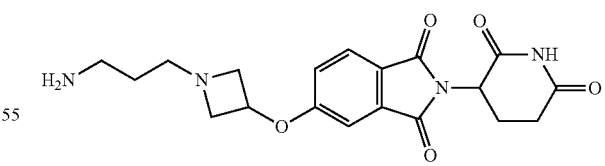

i37-5

To a solution of tert-butyl(3-(3-((2-(2,6-dioxopiperidin-3-yl)-1,3-dioxoisoindolin-5-yl)oxy) azetidin-1-yl) propyl) carbamate (100.00 mg, 0.206 mmol, 1.00 equiv) in DCM (4.00 mL) was added TFA (4.00 mL, 53.860 mmol, 261.46 equiv). The resulting mixture was stirred for one hour at room temperature. The resulting mixture was concentrated under vacuum to afford 5-((1-(3-aminopropyl) azetidin-3-yl)oxy)-2-(2,6-dioxopiperidin-3-yl) isoindoline-1,3-dione (120 mg, crude). LCMS (ESI) m/z: $[M+H]^+$=387.

Step 5: Preparation of 5-((1-(3-((2,6-Dimethoxy-4-(2-Methyl-1-Oxo-1,2-Dihydro-2,7-Naphthyridin-4-Yl)Benzyl)Amino) Propyl) Azetidin-3-Yl)Oxy)-2-(2,6-Dioxopiperidin-3-Yl) Isoindoline-1,3-Dione Formic Acid (Compound D31 Formic Acid)

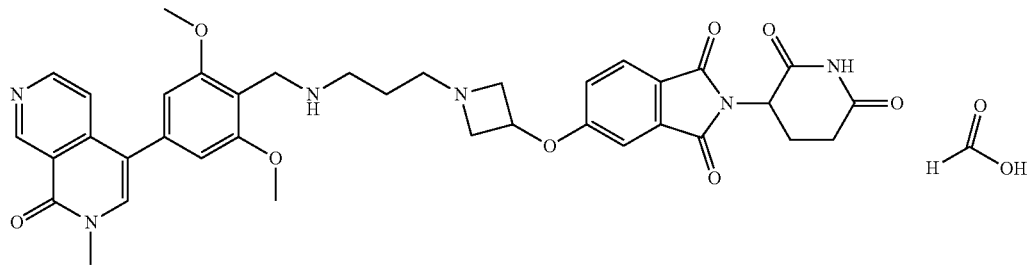

compound D31 formic acid

To a solution of 5-((1-(3-aminopropyl) azetidin-3-yl)oxy)-2-(2,6-dioxopiperidin-3-yl) isoindoline-1,3-dione (60.00 mg, 0.155 mmol, 1.00 equiv) in MeOH (5.00 mL, 123.495 mmol, 795.32 equiv) was added 2,6-dimethoxy-4-(2-methyl-1-oxo-2,7-naphthyridin-4-yl)benzaldehyde (50.36 mg, 0.155 mmol, 1 equiv). The resulting mixture was stirred for 1 hour. Then NaBH$_3$CN (19.52 mg, 0.311 mmol, 2 equiv) was added. The resulting mixture was stirred for 1 hour. The resulting mixture was filtered, and the filtrate was purified by prep-HPLC(conditions: SunFire C18 OBD Prep Column, 100 Å, 5 μm, 19 mm×250 mm; Mobile Phase A: Water (0.1% FA), Mobile Phase B: ACN; Flow rate: 25 mL/minute; Gradient: 5% B to 5% B in 2 minutes; 254 nm; Rt: 9.75 minutes) to afford 5-((1-(3-((2,6-dimethoxy-4-(2-methyl-1-oxo-1,2-dihydro-2,7-naphthyridin-4-yl)benzyl) amino) propyl) azetidin-3-yl)oxy)-2-(2,6-dioxopiperidin-3-yl) isoindoline-1,3-dione;formate (14.4 mg, 12.52%) as a yellow solid. $^1$H NMR (400 MHZ, Methanol-d4)δ 9.52 (s, 1H), 8.67 (d, J=5.7 Hz, 1H), 8.26 (br s, 0.65H, FA), 7.82-7.75 (m, 2H), 7.60 (dd, J=5.8, 0.9 Hz, 1H), 7.21 (dq, J=4.6, 2.3 Hz, 2H), 6.88 (s, 2H), 5.13-5.00 (m, 2H), 4.36 (s, 2H), 3.99 (s, 6H), 3.93-3.89 (m, 2H), 3.71 (s, 3H), 3.44 (d, J=8.2 Hz, 2H), 3.22 (t, J=6.7 Hz, 2H), 2.95-2.82 (m, 3H), 2.82-2.62 (m, 2H), 2.21-2.05 (m, 1H), 1.89-1.81 (m, 2H). LCMS (ESI) m/z: [M+H]$^+$=695.40.

Example 38—Preparation of 4-(4-(6-(2,6-Dimethoxy-4-(2-Methyl-1-Oxo-1,2-Dihydro-2,7-Naphthyridin-4-Yl)Benzyl)-2,6-Diazaspiro[3.3]Heptan-2-Yl)-4-Oxobutoxy)-2-(2,6-Dioxopiperidin-3-Yl) Isoindoline-1,3-Dione (Compound D32)

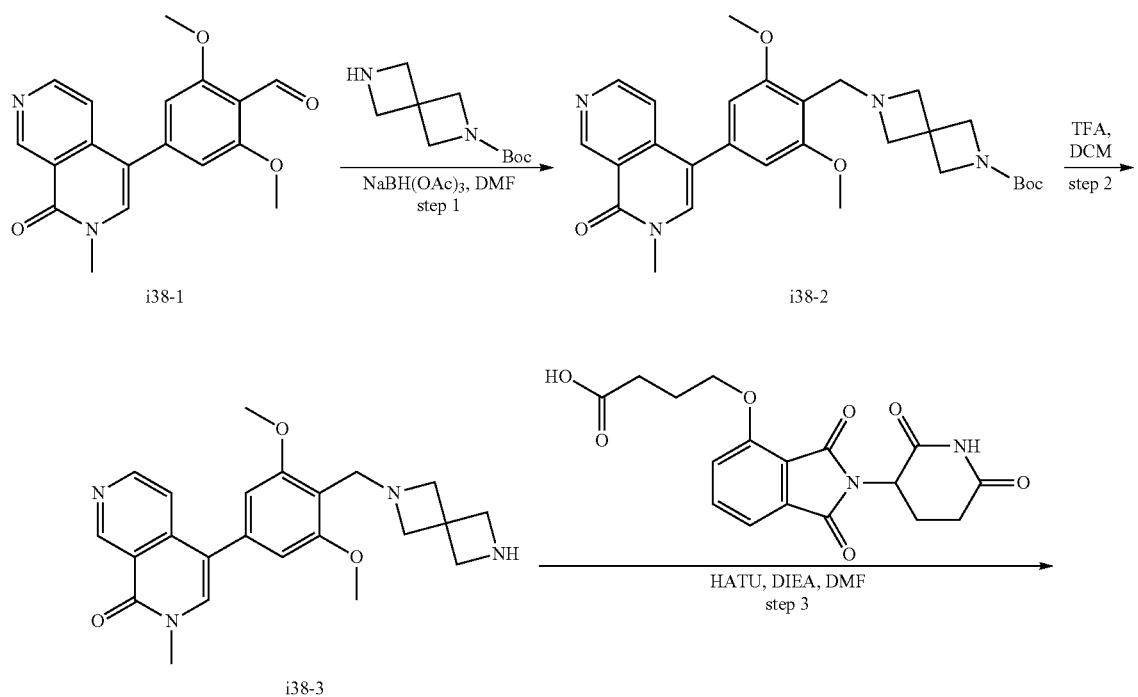

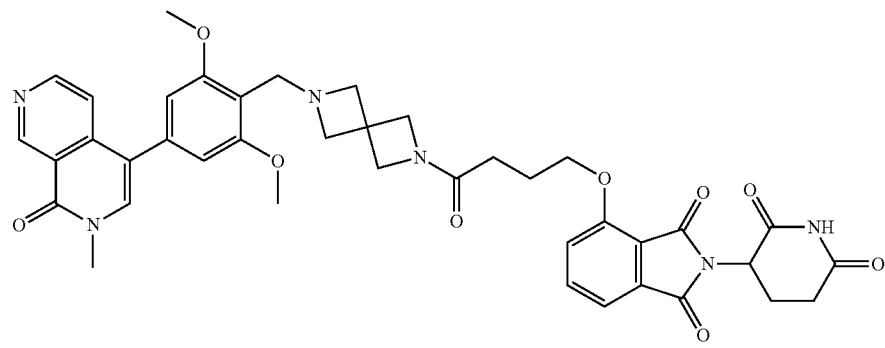

compound D32

Step 1: Preparation of Tert-Butyl 6-(2,6-Dimethoxy-4-(2-Methyl-1-Oxo-1,2-Dihydro-2,7-Naphthyridin-4-Yl)Benzyl)-2,6-Diazaspiro[3.3]Heptane-2-Carboxylate (i38-2)

Step 2: Preparation of 4-(4-((2,6-Diazaspiro[3.3]Heptan-2-Yl)Methyl)-3,5-Dimethoxyphenyl)-2-Methyl-2,7-Naphthyridin-1 (2H)-One (i38-3)

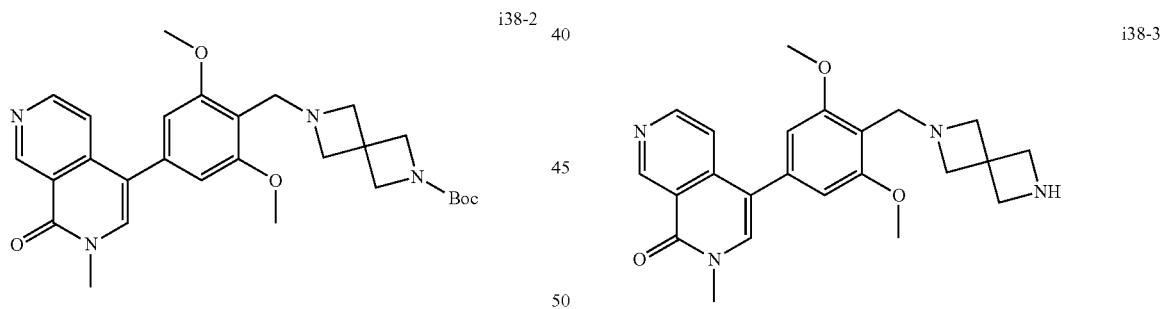

To a solution of 2,6-dimethoxy-4-(2-methyl-1-oxo-2,7-naphthyridin-4-yl)benzaldehyde (700.00 mg, 2.158 mmol, 1.00 equiv) and tert-butyl 2,6-diazaspiro[3.3]heptane-2-carboxylate (427.91 mg, 2.158 mmol, 1.00 equiv) in DMF (10.00 mL, 129.218 mmol, 59.87 equiv) was added NaBH(OAc)$_3$ (914.85 mg, 4.317 mmol, 2.00 equiv). The resulting solution was stirred at 25° C. for 1 hour. The mixture was concentrated to give crude product that was purified by chromatography on silica gel eluted with MeOH/DCM (6:94) to give tert-butyl6-[2,6-dimethoxy-4-(2-methyl-1-oxo-2,7-naphthyridin-4-yl)phenyl]methyl]-2,6-diazaspiro[3.3]heptane-2-carboxylate (808 mg,73.90%) as an off-white solid. LCMS (ESI) m/z: [M+H]$^+$=507.

A solution of tert-butyl 6-[2,6-dimethoxy-4-(2-methyl-1-oxo-2,7-naphthyridin-4-yl)phenyl]methyl]-2,6-diazaspiro[3.3]heptane-2-carboxylate (708.00 mg, 1.398 mmol, 1.00 equiv) and TFA (1.50 mL, 20.195 mmol, 14.45 equiv) in DCM (7.00 mL, 110.110 mmol, 78.79 equiv) was stirred at 25° C. for 1 hour. The mixture was concentrated to give crude product 4-(4-[2,6-diazaspiro[3.3]heptan-2-ylmethyl]-3,5-dimethoxyphenyl)-2-methyl-2,7-naphthyridin-1-one (696 mg) as a brown oil that was used directly without further purification. LCMS (ESI) m/z: [M+H]$^+$=407.

Step 3: Preparation of 4-(4-(6-(2,6-Dimethoxy-4-(2-Methyl-1-Oxo-1,2-Dihydro-2,7-Naphthyridin-4-Yl)Benzyl)-2,6-Diazaspiro[3.3]Heptan-2-Yl)-4-Oxobutoxy)-2-(2,6-Dioxopiperidin-3-Yl) Isoindoline-1,3-Dione (Compound D32)

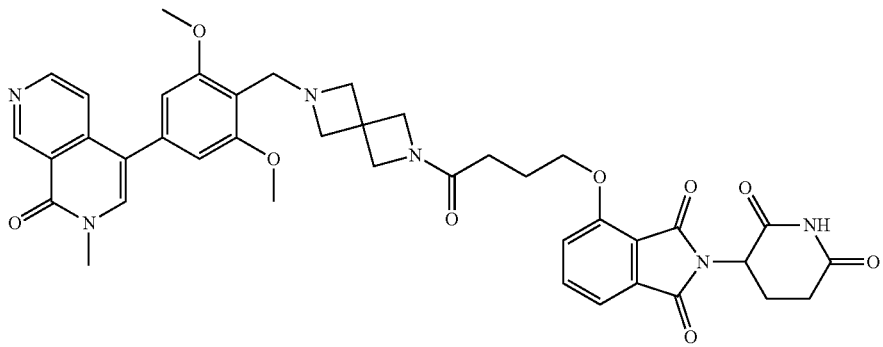

compound D32

To a solution of 4-(4-[2,6-diazaspiro[3.3]heptan-2-ylmethyl]-3,5-dimethoxyphenyl)-2-methyl-2,7-naphthyridin-1-one (40.00 mg, 0.098 mmol, 1.00 equiv) and 4-[[2-(2,6-dioxopiperidin-3-yl)-1,3-dioxoi soindol-4-yl]oxy]butanoic acid (35.46 mg, 0.098 mmol, 1.00 equiv) in DMF (1.0 mL) was added HATU (56.12 mg, 0.148 mmol, 1.5 equiv) and DIEA (31.80 mg, 0.246 mmol, 10 equiv). The mixture was stirred at 25° C. for 1 hour. The mixture was purified by prep-HPLC(conditions: Kinetex EVO C18 Column 21.2*150, 5 um; Mobile Phase A: Water (0.1% FA), Mobile Phase B: ACN; Flow rate: 25 mL/minute; Gradient: 16% B to 26% B in 8 minutes; 254/220 nm; Rt: 7.03 minutes) to afford 4-[4-(6-[2,6-dimethoxy-4-(2-methyl-1-oxo-2,7-naphthyridin-4-yl)phenyl]methyl]-2,6-diazaspiro[3.3]heptan-2-yl)-4-oxobutoxy]-2-(2,6-dioxopiperidin-3-yl) isoindole-1,3-dione (12 mg, 16.29%) as a white solid. $^1$H NMR (400 MHZ, Methanol-d4) δ 9.53 (s, 1H), 8.70 (d, J=5.8 Hz, 1H), 7.79 (dd, J=8.5, 7.4 Hz, 1H), 7.78 (s, 1H), 7.62 (d, J=5.8 Hz, 1H), 7.46 (dd, J=14.7, 7.9 Hz, 2H), 6.86 (s, 2H), 5.13 (dd, J=12.5, 5.4 Hz, 1H), 4.60 (s, 1H), 4.40 (d, J=13.7 Hz, 4H), 4.32-4.19 (m, 6H), 4.14 (s, 2H), 3.96 (s, 6H), 3.71 (s, 3H), 2.95-2.68 (m, 3H), 2.53-2.34 (m, 2H), 2.20-2.10 (m, 3H). LCMS (ESI) m/z: [M+H]$^+$=749.40.

Example 39—Preparation of 4-(4-(4-(2,6-Dimethoxy-4-(2-Methyl-1-Oxo-1,2-Dihydro-2,7-Naphthyridin-4-Yl)Benzyl) Piperazin-1-Yl)-4-Oxobutoxy)-2-(2,6-Dioxopiperidin-3-Yl) Isoindoline-1,3-Dione (Compound D33)

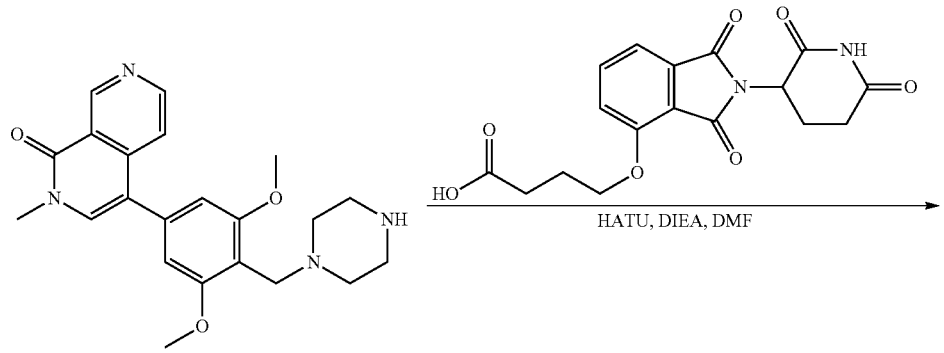

HATU, DIEA, DMF

-continued

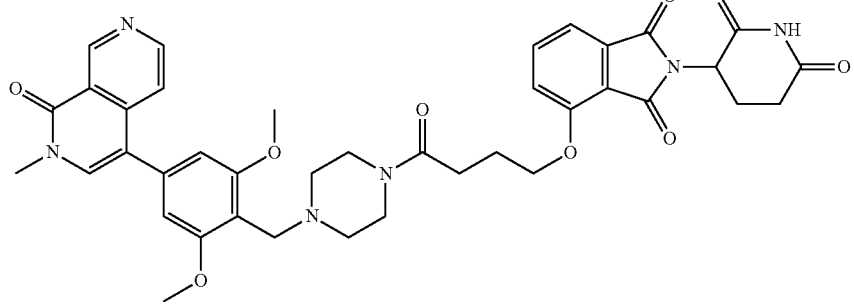

compound D33

To a stirred mixture of 4-[3,5-dimethoxy-4-(piperazin-1-ylmethyl)phenyl]-2-methyl-2,7-naphthyridin-1-one (50.00 mg, 0.127 mmol, 1.00 equiv) and 4-[[2-(2,6-dioxopiperidin-3-yl)-1,3-dioxoisoindol-4-yl]oxy]butanoic acid (45.67 mg, 0.127 mmol, 1.00 equiv) in DMF (2.00 mL) was added DIEA (163.82 mg, 1.268 mmol, 10.00 equiv) and HATU (96.39 mg, 0.254 mmol, 2.00 equiv) at 0° C. The above mixture was stirred for 3 hours at room temperature. Then the crude product was purified by preparative HPLC(conditions: XBridge Shield RP18 OBD Column, 5 µm, 19*250 mm; Mobile Phase A: Water (0.1% FA), Mobile Phase B: ACN; Flow rate: 25 mL/minute; Gradient: 12% B to 26% B in 8 minutes; 254 nm; Rt: 7.91 minutes). This resulted in 4-(4-(4-(2,6-dimethoxy-4-(2-methyl-1-oxo-1,2-dihydro-2,7-naphthyridin-4-yl)benzyl) piperazin-1-yl)-4-oxobutoxy)-2-(2,6-dioxopiperidin-3-yl) isoindoline-1,3-dione (5.60 mg, 5.54%) as a white solid. $^1$H NMR (300 MHz, Methanol-d4)δ 9.54 (s, 1H), 8.69 (d, J=5.8 Hz, 1H), 7.85-7.73 (m, 2H), 7.63 (d, J=5.7 Hz, 1H), 7.52-7.43 (m, 2H), 6.79 (s, 2H), 5.11 (dd, J=12.2, 5.4 Hz, 1H), 4.30 (t, J=5.8 Hz, 2H), 4.01 (s, 2H), 3.90 (s, 6H), 3.81-3.65 (m, 7H), 2.98-2.81 (m, 6H), 2.79-2.67 (m, 3H), 2.24-2.07 (m, 3H). vLCMS (ESI) m/z: [M+H]$^+$=737.40.

Example 40—Preparation of 4-((5-(6-(2,6-Dimethoxy-4-(2-Methyl-1-Oxo-1,2-Dihydro-2,7-Naphthyridin-4-Yl)Benzyl)-2,6-Diazaspiro[3.3]Heptan-2-Yl)-5-Oxopentyl)Oxy)-2-(2,6-Dioxopiperidin-3-Yl) Isoindoline-1,3-Dione (Compound D34)

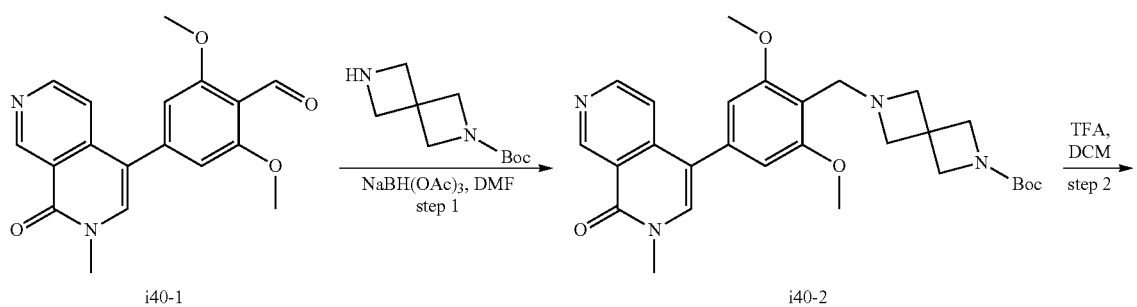

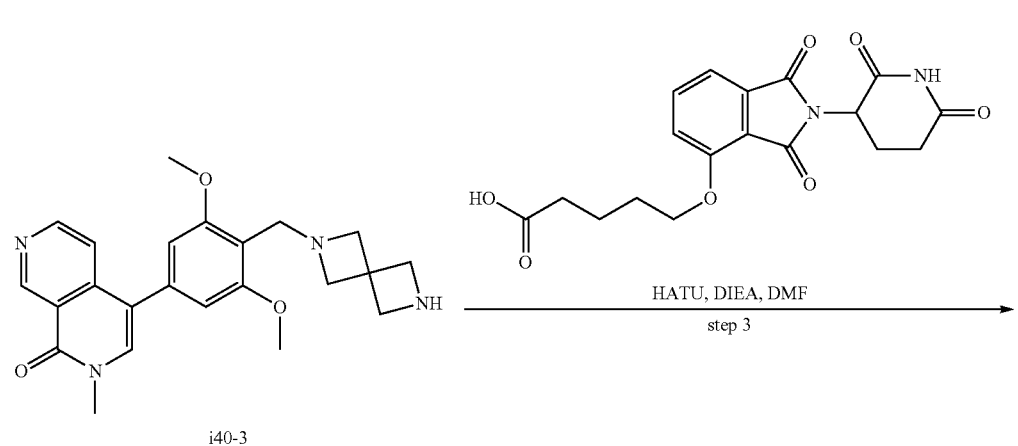

-continued

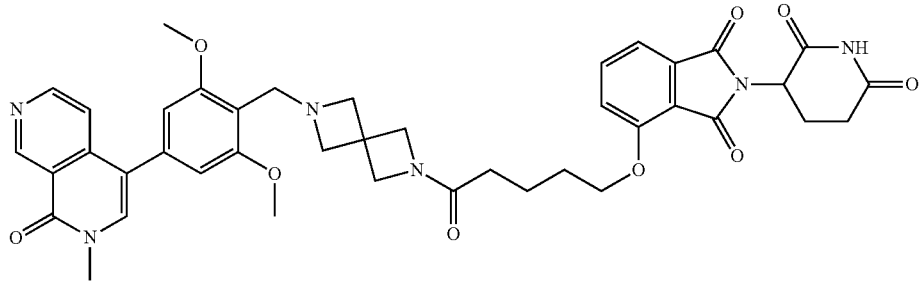

compound D34

Step 1: Preparation of Tert-Butyl 6-(2,6-Dimethoxy-4-(2-Methyl-1-Oxo-1,2-Dihydro-2,7-Naphthyridin-4-Yl)Benzyl)-2,6-Diazaspiro[3.3]Heptane-2-Carboxylate (i40-2)

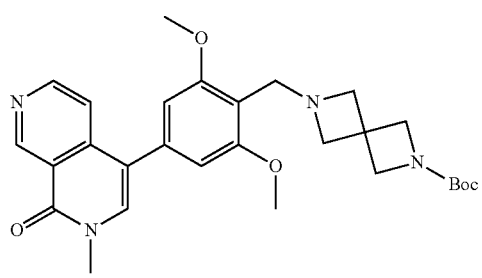

i40-2

To a solution of 2,6-dimethoxy-4-(2-methyl-1-oxo-2,7-naphthyridin-4-yl)benzaldehyde (700.00 mg, 2.158 mmol, 1.00 equiv) and tert-butyl 2,6-diazaspiro[3.3]heptane-2-carboxylate (427.91 mg, 2.158 mmol, 1.00 equiv) in DMF (10.00 mL, 129.218 mmol, 59.87 equiv) was added NaBH(OAc)$_3$ (914.85 mg, 4.317 mmol, 2.00 equiv). The resulting solution was stirred at 25° C. for 1 hour. The mixture was concentrated to give crude product that was purified by chromatography on silica gel eluted with MeOH]/DCM (6:94) to give tert-butyl 6-[2,6-dimethoxy-4-(2-methyl-1-oxo-2,7-naphthyridin-4-yl)phenyl]methyl]-2,6-diazaspiro[3.3]heptane-2-carboxylate (808 mg,73.90%) as an off-white solid. LCMS (ESI) m/z: [M+H]$^+$=507.

Step 2: Preparation of 4-(4-((2,6-Diazaspiro[3.3]Heptan-2-Yl)Methyl)-3,5-Dimethoxyphenyl)-2-Methyl-2,7-Naphthyridin-1 (2H)-One (i40-3)

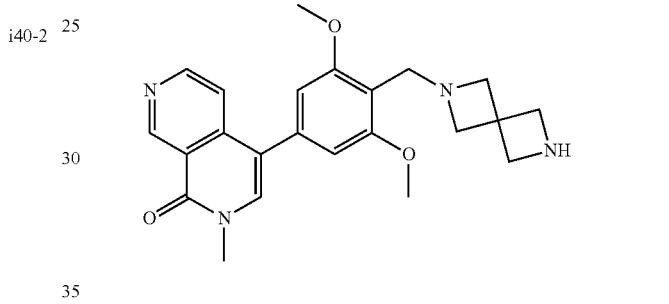

i40-3

A solution of tert-butyl 6-[[2,6-dimethoxy-4-(2-methyl-1-oxo-2,7-naphthyridin-4-yl)phenyl]methyl]-2,6-diazaspiro[3.3]heptane-2-carboxylate (708.00 mg, 1.398 mmol, 1.00 equiv) and TFA (1.50 mL, 20.195 mmol, 14.45 equiv) in DCM (7 mL) was stirred at 25° C. for 1 hour. The mixture was concentrated to give crude product 4-(4-[2,6-diazaspiro[3.3]heptan-2-ylmethyl]-3,5-dimethoxyphenyl)-2-methyl-2,7-naphthyridin-1-one (696 mg) as a brown oil that was used directly without further purification. LCMS (ESI) m/z: [M+H]$^+$=407.

Step 3: Preparation of 4-((5-(6-(2,6-Dimethoxy-4-(2-Methyl-1-Oxo-1,2-Dihydro-2,7-Naphthyridin-4-Yl)Benzyl)-2,6-Diazaspiro[3.3]Heptan-2-Yl)-5-Oxopentyl)Oxy)-2-(2,6-Dioxopiperidin-3-Yl)Isoindoline-1,3-Dione (Compound D34)

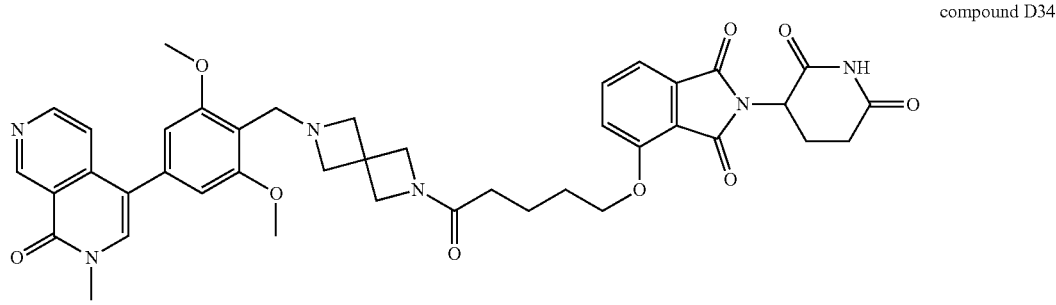 [SMILES: COc1cc(-c2cn(C)c(=O)c3cnccc23)cc(OC)c1CN1CC2(C1)CN(C(=O)CCCCOc1cccc3c1C(=O)N(C1CCC(=O)NC1=O)C3=O)C2]

compound D34

To a solution of 4-(4-[2,6-diazaspiro[3.3]heptan-2-ylmethyl]-3,5-dimethoxyphenyl)-2-methyl-2,7-naphthyridin-1-one (40.00 mg, 0.098 mmol, 1.00 equiv) and 5-[[2-(2,6-dioxopiperidin-3-yl)-1,3-dioxoisoindol-4-yl]oxy]pentanoic acid (36.84 mg, 0.098 mmol, 1 equiv) in DMF (1 mL) was added HATU (56.12 mg, 0.148 mmol, 1.5 equiv) and DIEA (31.80 mg, 0.246 mmol, 10 equiv). The mixture was stirred at 25° C. for 1 hour. The mixture was purified by prep-HPLC(conditions: XSelect CSH Prep C18 OBD Column, 5 μm, 19*150 mm; Mobile Phase A: Water (0.1% FA), Mobile Phase B: ACN; Flow rate: 25 mL/minute; Gradient: 12% B to 22% B in 12 minutes; 254/220 nm; Rt: 10.52 minutes) to afford 4-[[5-(6-[[2,6-dimethoxy-4-(2-methyl-1-oxo-2,7-naphthyridin-4-yl)phenyl]methyl]-2,6-diazaspiro[3.3]heptan-2-yl)-5-oxopentyl]oxy]-2-(2,6-dioxopiperidin-3-yl) isoindole-1,3-dione (10.1 mg, 13.46%) as a light yellow solid. $^1$H NMR (400 MHZ, Methanol-d4) δ 9.58 (s, 1H), 8.73-8.67 (m, 1H), 7.92 (d, J=6.9 Hz, 1H), 7.84-7.76 (m, 1H), 7.47 (t, J=8.1 Hz, 2H), 6.89 (d, J=3.5 Hz, 2H), 5.17-5.07 (m, 1H), 4.51 (d, J=3.0 Hz, 2H), 4.45-4.31 (m, 6H), 4.27 (t, J=5.5 Hz, 2H), 4.19 (s, 1H), 4.12 (s, 1H), 3.98 (d, J=3.4 Hz, 6H), 3.74 (d, J=1.7 Hz, 3H), 2.96-2.65 (m, 3H), 2.34-2.30 (m, 2H), 2.19-2.12 (m, 1H), 1.96-1.89 (m, 2H), 1.88-1.80 (m, 2H). LCMS (ESI) m/z: [M+H]$^+$=763.40.

Example 41—Preparation of 4-((5-(4-(2,6-Dimethoxy-4-(2-Methyl-1-Oxo-1,2-Dihydro-2,7-Naphthyridin-4-Yl)Benzyl) Piperazin-1-Yl)-5-Oxopentyl) Oxy)-2-(2,6-Dioxopiperidin-3-Yl) Isoindoline-1,3-Dione Formic Acid (Compound D35 Formic Acid)

To a stirred solution of 4-[3,5-dimethoxy-4-(piperazin-1-ylmethyl)phenyl]-2-methyl-2,7-naphthyridin-1-one (50.0 mg, 0.127 mmol, 1.00 equiv) and 5-[[2-(2,6-dioxopiperidin-3-yl)-1,3-dioxoisoindol-4-yl]oxy]pentanoic acid (47.5 mg, 0.127 mmol, 1.00 equiv) in DMF (1 mL) was added DIEA (163.8 mg, 1.268 mmol, 10.00 equiv) dropwise at room temperature. The resulting mixture was stirred for 10 min at room temperature. To the above mixture was added HATU (96.4 mg, 0.254 mmol, 2.00 equiv). The resulting mixture was stirred for additional 2 hours at room temperature. The residue was purified by reverse flash chromatography (conditions: SunFire C18 OBD Prep Column, 100 Å, 5 μm, 19 mm×250 mm; Mobile Phase A: Water (0.1% FA), Mobile Phase B: ACN; Flow rate: 25 mL/minute; Gradient: 9 B to 27 B in 10 minutes; 254 nm; RT: 10.12) to afford 4-[5-(4-[[2,6-dimethoxy-4-(2-methyl-1-oxo-2,7-naphthyridin-4-yl)phenyl]methyl]piperazin-1-yl)-5-oxopentyl]oxy]-2-(2,6-dioxopiperidin-3-yl) isoindole-1,3-dione (6.6 mg, 6.7%) as a white solid. $^1$H NMR (400 MHz, Methanol-d4)δ 9.53 (d, J=0.9 Hz, 1H), 8.69 (d, J=5.8 Hz, 1H), 8.45 (br s, 0.13H, FA), 7.81-7.73 (m, 2H), 7.64 (dd, J=5.8, 0.9 Hz, 1H), 7.45 (dd, J=7.9, 6.2 Hz, 2H), 6.79 (s, 2H), 5.11 (dd, J=12.5, 5.5 Hz, 1H), 4.28 (t, J=5.7 Hz, 2H), 3.97 (s, 2H), 3.90 (s, 6H), 3.74-3.62 (m, 7H), 2.95-2.81 (m, 3H), 2.80-2.65 (m, 4H), 2.60 (t, J=7.4 Hz, 2H), 2.17-2.07 (m, 1H), 1.99-1.83 (m, 4H). LCMS (ESI) m/z: [M+H]$^+$=751.40

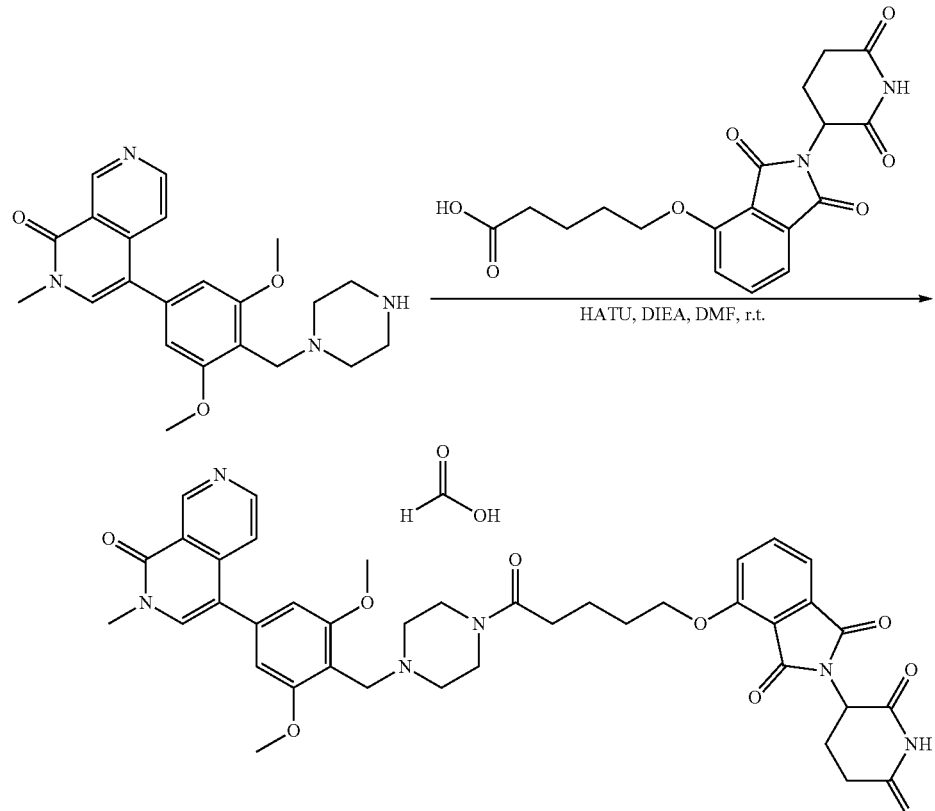

compound D35 formic acid

Example 42—Preparation of 4-(2-(6-(2,6-Dimethoxy-4-(2-Methyl-1-Oxo-1,2-Dihydro-2,7-Naphthyridin-4-Yl)Benzyl)-2,6-Diazaspiro[3.3]Heptan-2-Yl)-2-Oxoethoxy)-2-(2,6-Dioxopiperidin-3-Yl)Isoindoline-1,3-Dione (Compound D36 Formic Acid)
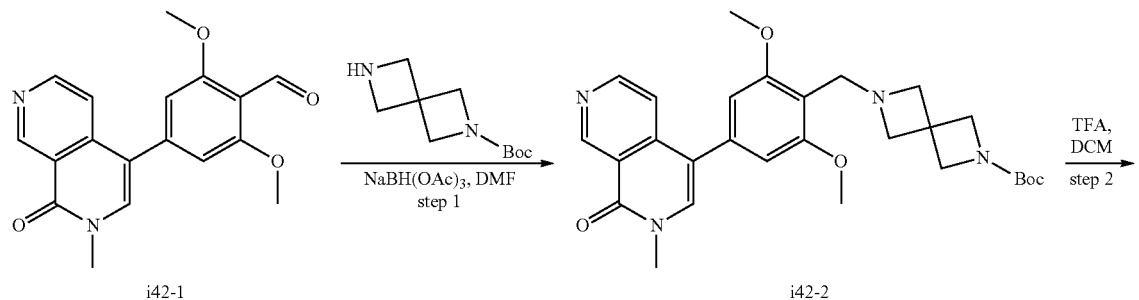
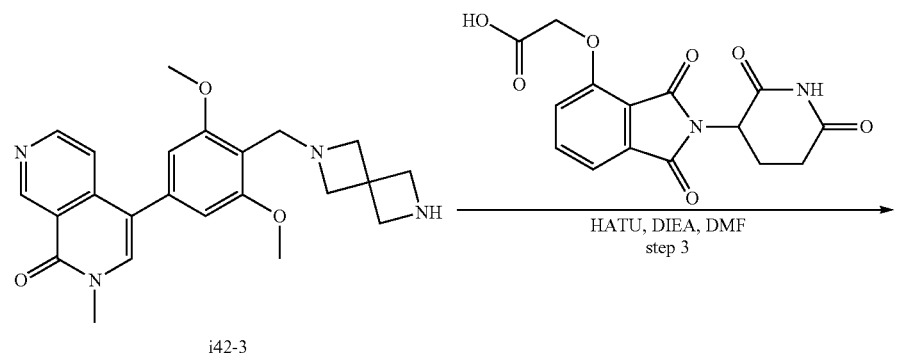
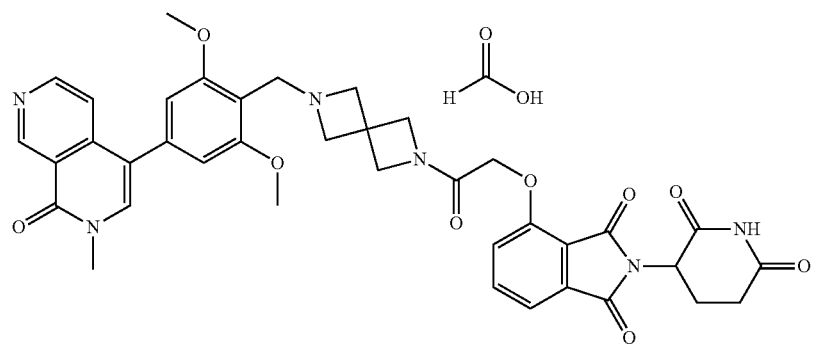
compound D36 formic acid

611

Step 1: Preparation of Tert-Butyl 6-(2,6-Dimethoxy-4-(2-Methyl-1-Oxo-1,2-Dihydro-2,7-Naphthyridin-4-Yl)Benzyl)-2,6-Diazaspiro[3.3]Heptane-2-Carboxylate (i42-2)

612

Step 2: Preparation of 4-(4-((2,6-Diazaspiro[3.3]Heptan-2-Yl)Methyl)-3,5-Dimethoxyphenyl)-2-Methyl-2,7-Naphthyridin-1 (2H)-One (i42-3)

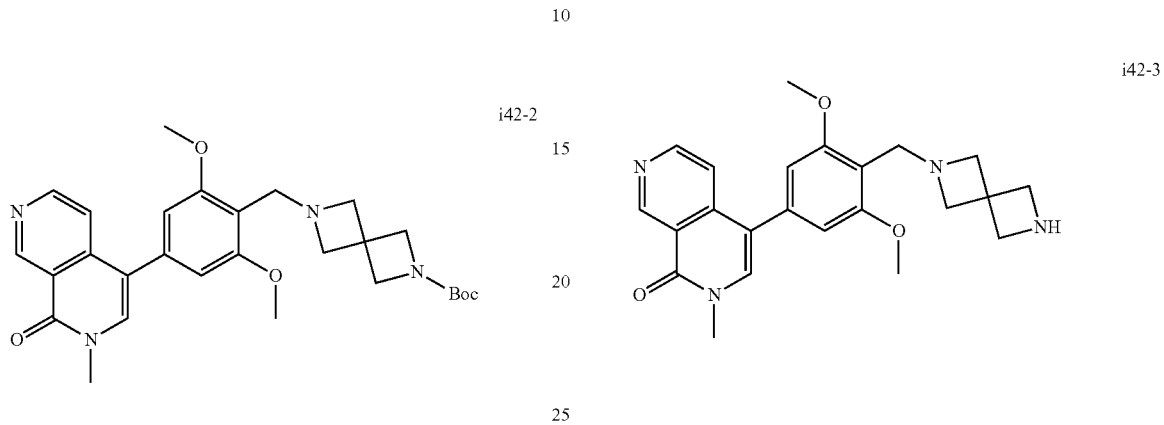

i42-2 i42-3

To a solution of 2,6-dimethoxy-4-(2-methyl-1-oxo-2,7-naphthyridin-4-yl)benzaldehyde (700.00 mg, 2.158 mmol, 1.00 equiv) and tert-butyl 2,6-diazaspiro[3.3]heptane-2-carboxylate (427.91 mg, 2.158 mmol, 1.00 equiv) in DMF (10 mL) was added NaBH (OAc)₃ (914.85 mg, 4.317 mmol, 2.00 equiv). The resulting solution was stirred at 25° C. for 1 hour. The mixture was concentrated to give crude product that was purified by chromatography on silica gel eluted with MeOHJ/DCM (6:94) to give tert-butyl 6-[2,6-dimethoxy-4-(2-methyl-1-oxo-2,7-naphthyridin-4-yl)phenyl]methyl]-2,6-diazaspiro[3.3]heptane-2-carboxylate (808 mg, 73.90%) as an off-white solid. LCMS (ESI) m/z: [M+H]⁺=507.

To a solution of tert-butyl 6-[2,6-dimethoxy-4-(2-methyl-1-oxo-2,7-naphthyridin-4-yl)phenyl]methyl]-2,6-diazaspiro[3.3]heptane-2-carboxylate (708.00 mg, 1.398 mmol, 1.00 equiv) and TFA (1.50 mL, 20.195 mmol, 14.45 equiv) in DCM (7 mL) was stirred at 25° C. for 1 hour. The mixture was concentrated to give crude product 4-(4-[2,6-diazaspiro[3.3]heptan-2-ylmethyl]-3,5-dimethoxyphenyl)-2-methyl-2,7-naphthyridin-1-one (696 mg) as a brown oil that was used directly without further purification. LCMS (ESI) m/z: [M+H]⁺=407.

Step 3: Preparation of 4-(2-(6-(2,6-Dimethoxy-4-(2-Methyl-1-Oxo-1,2-Dihydro-2,7-Naphthyridin-4-Yl) Benzyl)-2,6-Diazaspiro[3.3]Heptan-2-Yl)-2-Oxoethoxy)-2-(2,6-Dioxopiperidin-3-Yl) Isoindoline-1,3-Dione Formic Acid (Compound D35 Formic Acid)

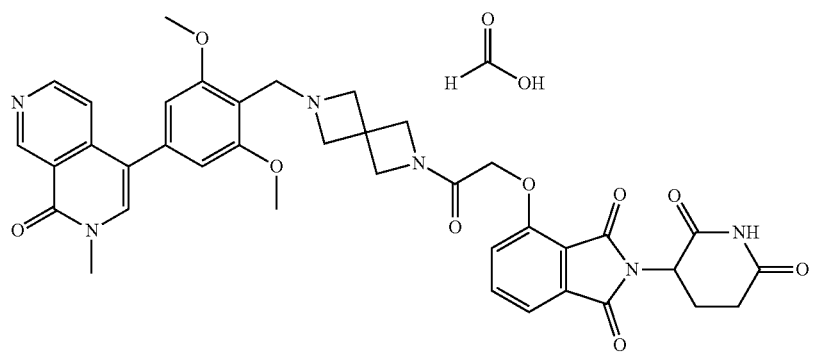

compound D36 formic acid

To a solution of 4-(4-[2,6-diazaspiro[3.3]heptan-2-ylmethyl]-3,5-dimethoxyphenyl)-2-methyl-2,7-naphthyridin-1-one (40.00 mg, 0.098 mmol, 1.00 equiv) and [[2-(2,6-dioxopiperidin-3-yl)-1,3-dioxoisoindol-4-yl]oxy]acetic acid (32.70 mg, 0.098 mmol, 1.00 equiv) in DMF (1 mL) was added HATU (56.12 mg, 0.148 mmol, 1.50 equiv) and DIEA (31.80 mg, 0.246 mmol, 10 equiv). The mixture was stirred at 25° C. for 1 hour. The mixture was purified by prep-HPLC(conditions: SunFire Prep C18 OBD Column 19×150 mm 5 μm 10 nm;Mobile Phase A: Water (0.1% FA), Mobile Phase B: ACN; Flow rate: 25 mL/minute; Gradient: 8% B to 21% B in 10 minutes; 254/220 nm; Rt: 8.20 minutes) to afford 4-[2-(6-[[2,6-dimethoxy-4-(2-methyl-1-oxo-2,7-naphthyridin-4-yl)phenyl]methyl]-2,6-diazaspiro[3.3]heptan-2-yl)-2-oxoethoxy]-2-(2,6-dioxopiperidin-3-yl) isoindole-1,3-dione (6.2 mg, 8.74%) as a white solid. $^1$H NMR (300 MHZ, Methanol-d4)δ 9.51 (s, 1H), 8.68 (d, J=5.8 Hz, 1H), 8.55 (br s, 0.46H, FA), 7.80 (s, 1H), 7.69 (t, J=8.1 Hz, 1H), 7.62 (d, J=5.7 Hz, 1H), 7.44 (dd, J=11.8, 7.2 Hz, 1H), 7.29 (d, J=8.5 Hz, 1H), 6.87 (s, 2H), 5.19-5.10 (m, 1H), 4.69-4.51 (m, 6H), 4.39 (s, 2H), 4.34-4.26 (m, 2H), 4.22 (s, 2H), 3.97 (s, 6H), 3.69 (s, 3H), 2.95-2.68 (m, 3H), 2.20-2.09 (m, 1H). LCMS (ESI) m/z: [M+H]$^+$=721.35.

Example 43—Preparation of 4-(2-(4-(2,6-Dimethoxy-4-(2-Methyl-1-Oxo-1,2-Dihydro-2,7-. Naphthyridin-4-Yl)Benzyl) Piperazin-1-Yl)-2-Oxoethoxy)-2-(2,6-Dioxopiperidin-3-Yl) Isoindoline-1,3-Dione Formic Acid (Compound D37 Formic Acid)

To a stirred solution of 4-[3,5-dimethoxy-4-(piperazin-1-ylmethyl)phenyl]-2-methyl-2,7-naphthyridin-1-one (50.0 mg, 0.127 mmol, 1.00 equiv) and [[2-(2,6-dioxopiperidin-3-yl)-1,3-dioxoisoindol-4-yl]oxy]acetic acid (42.1 mg, 0.127 mmol, 1.00 equiv) in DMF (1 mL) was added DIEA (163.8 mg, 1.268 mmol, 10.00 equiv) dropwise at room temperature. The resulting mixture was stirred for 10 minutes at room temperature. To the above mixture was added HATU (96.4 mg, 0.254 mmol, 2.00 equiv). The resulting mixture was stirred for additional 2 hours at room temperature. The residue was purified by reverse flash chromatography (conditions: SunFire C18 OBD Prep Column, 100 Å, 5 μm, 19 mm×250 mm; Mobile Phase A: Water (0.1% FA), Mobile Phase B: ACN; Flow rate: 25 mL/minute; Gradient: 9 B to 27 B in 10 minutes; 254 nm; RT: 10.12 minutes) to afford 4-[2-(4-[[2,6-dimethoxy-4-(2-methyl-1-oxo-2,7-naphthyridin-4-yl)phenyl]methyl]piperazin-1-yl)-2-oxoethoxy]-2-(2,6-dioxopiperidin-3-yl) isoindole-1,3-dione formic acid (12.2 mg, 13.6%) as a white solid. $^1$H NMR (400 MHZ, Methanol-d4)δ 9.54 (s, 1H), 8.69 (d, J=5.8 Hz, 1H), 8.34 (br s, 0.28H, FA), 7.83-7.73 (m, 2H), 7.67-7.61 (m, 1H), 7.52 (d, J=7.1 Hz, 1H), 7.40 (d, J=8.5 Hz, 1H), 6.81 (s, 2H), 5.15-5.09 (m, 3H), 4.08 (s, 2H), 3.92 (s, 6H), 3.83-3.73 (m, 4H), 3.72 (s, 3H), 3.05-2.96 (m, 2H), 2.96-2.80 (m, 3H), 2.77-2.69 (m, 2H), 2.17-2.11 (m, 1H). LCMS (ESI) m/z: [M+H]$^+$=709.35.

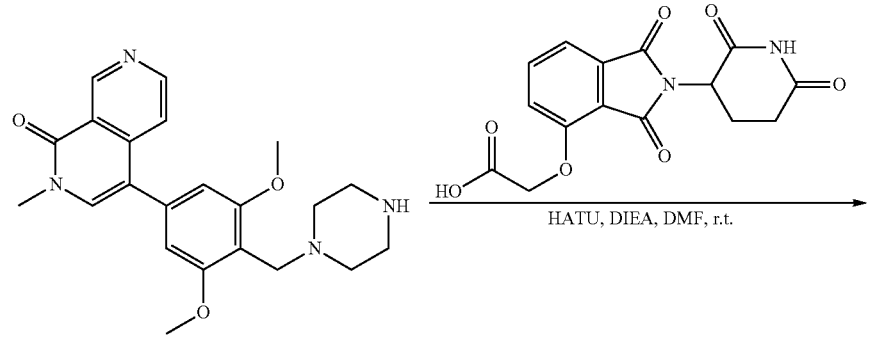

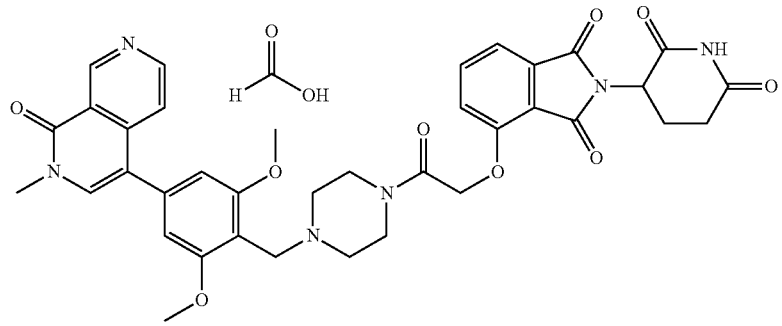

compound D37 formic acid

Example 44—Preparation of 1-[2,6-Dimethoxy-4-(2-Methyl-1-Oxo-2,7-Naphthyridin-4-Yl)Phenyl]Methyl]-N-[2-[2-(2-[[2-(2,6-Dioxopiperidin-3-Yl)-1,3-Dioxoisoindol-4-Ylamino]Ethoxy) Ethoxy]Ethyl] Azetidine-3-Sulfonamide Formic Acid (Compound D38 Formic Acid)
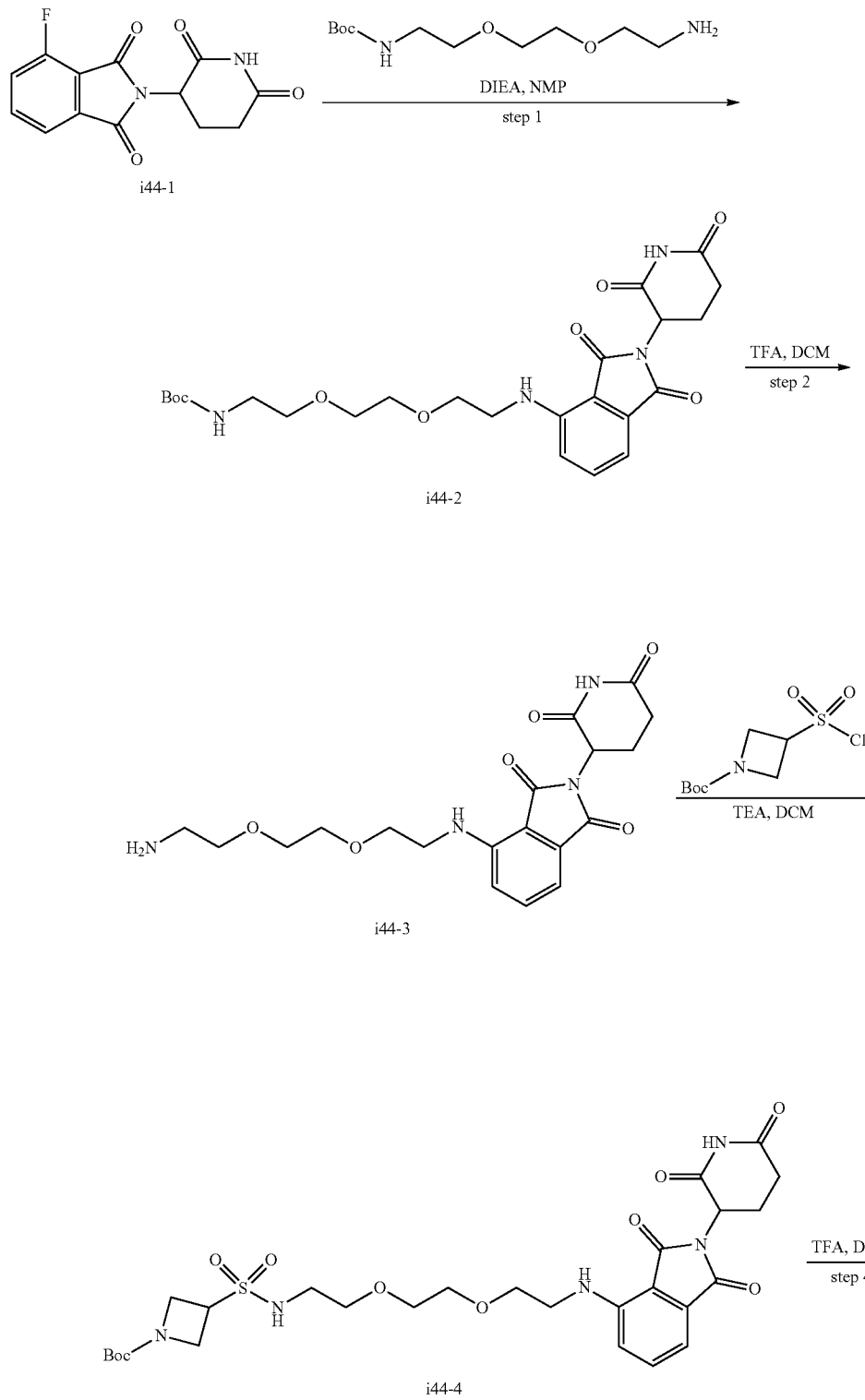

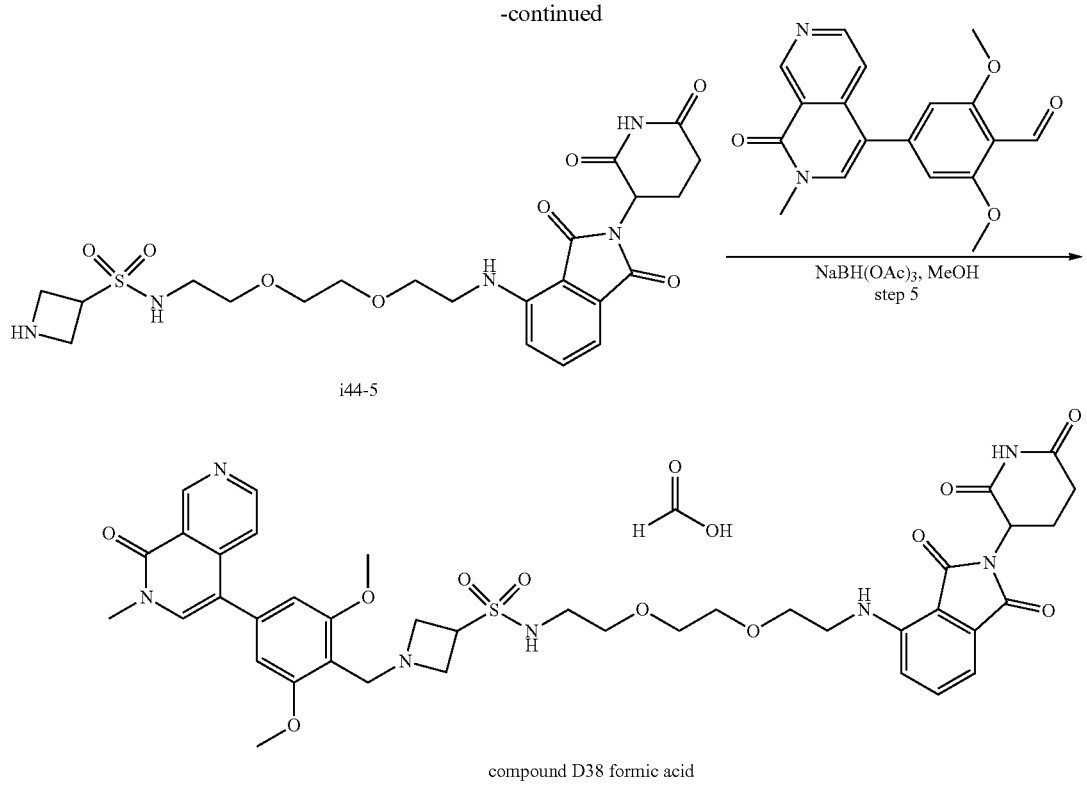

compound D38 formic acid

Step 1: Preparation of Tert-Butyl N-[2-[2-(2-[[2-(2, 6-Dioxopiperidin-3-Yl)-1,3-Dioxo-2,3-Dihydro-1H-Isoindol-4-Yl]Amino]Ethoxy) Ethoxy]Ethyl]Carbamate (i44-2)

Step 2: Preparation of 4-([2-[2-(2-Aminoethoxy) Ethoxy]Ethyl]Amino)-2-(2,6-Dioxopiperidin-3-Yl)-2,3-Dihydro-1H-Isoindole-1,3-Dione (i44-3)

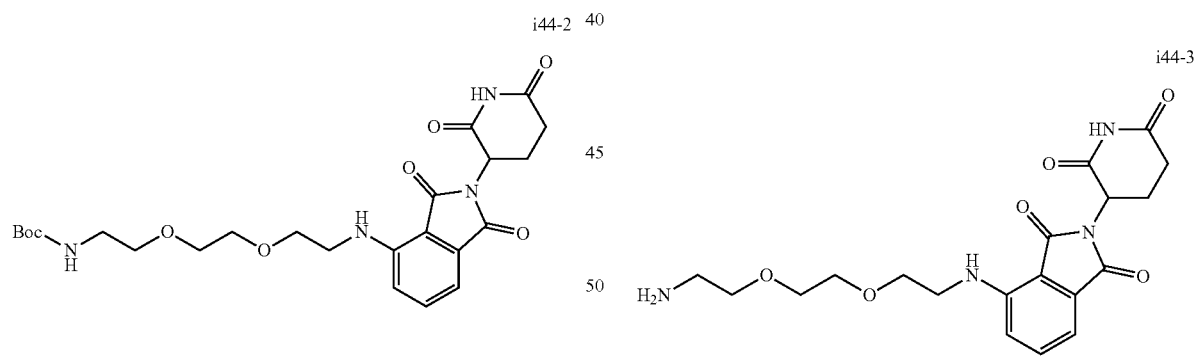

To a stirred solution of 2-(2,6-dioxopiperidin-3-yl)-4-fluoro-2,3-dihydro-1H-isoindole-1,3-dione (1.0 g, 3.620 mmol, 1.00 equiv) in NMP (15.00 mL) was added DIEA (940.47 mg, 7.277 mmol, 2.01 equiv) and tert-butyl N-[2-[2-(2-aminoethoxy) ethoxy]ethyl]carbamate (988.89 mg, 3.982 mmol, 1.10 equiv) in portions at room temperature. The resulting solution was stirred for 12 hours at 90° C. The resulting mixture was washed with water (3×100 mL). The resulting solution was extracted with ethyl acetate (3×200 mL). The organic layers combined and concentrated. This resulted in tert-butyl N-[2-[2-(2-[2-(2,6-dioxopiperidin-3-yl)-1,3-dioxo-2,3-dihydro-1H-isoindol-4-yl]amino]ethoxy) ethoxy]ethyl]carbamate (1.2 g, 20 65.70%) as light yellow oil. LCMS (ESI) m/z: [M+H]⁺=505.

To a stirred solution of tert-butyl N-[2-[2-(2-[2-(2,6-dioxopiperidin-3-yl)-1,3-dioxo-2,3-dihydro-1H-isoindol-4yl]amino]ethoxy) ethoxy]ethyl]carbamate (1.2 g, 2.378 mmol, 1.00 equiv) in DCM (40 mL) was added TFA (10 mL) in portions at room temperature. The resulting solution was stirred for 4 hours at room temperature. The resulting mixture was concentrated. This resulted in 4-([2-[2-(2-aminoethoxy) ethoxy]ethyl]amino)-2-(2,6-dioxopiperidin-3-yl)-2,3-dihydro-1H-isoindole-1,3-dione (0.8 g, 83.17%) as light yellow oil. LCMS (ESI) m/z: [M+H]⁺=405.

Step 3: Preparation of Tert-Butyl 3-([2-[2-(2-[[2-(2, 6-Dioxopiperidin-3-Yl)-1,3-Dioxoisoindol-4-Yl] Amino]Eth Oxy) Ethoxy]Ethyl]Sulfamoyl) Azetidine-1-Carboxylate (i44-4)

Step 4: Preparation of N-(2-(2-(2-((2-(2,6-Dioxopiperidin-3-Yl)-1,3-Dioxoisoindolin-4-Yl)Amino) Ethoxy) Ethoxy)Ethyl) Azetidine-3-Sulfonamide (i44-5)

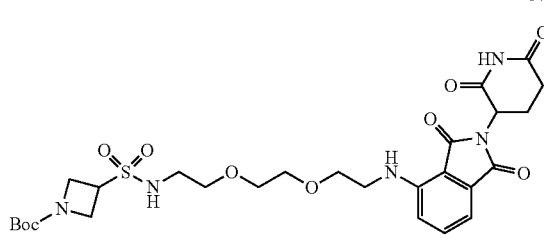

i44-4

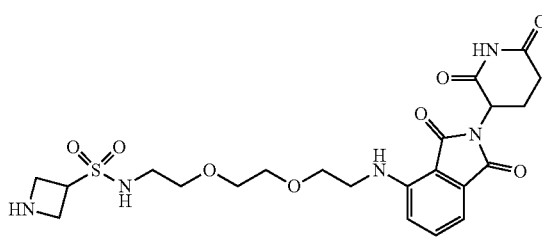

i44-5

To a stirred solution of 4-([2-[2-(2-aminoethoxy) ethoxy] ethyl]amino)-2-(2,6-dioxopiperidin-3-yl) isoindole-1,3-dione (238.00 mg, 0.588 mmol, 1.00 equiv) in DCM was added TEA (120.00 mg, 1.186 mmol, 2.02 equiv) in portions at room temperature. To the above mixture was added tert-butyl 3-(chlorosulfonyl) azetidine-1-carboxylate (150.00 mg, 0.587 mmol, 1.00 equiv) in portions. The resulting mixture was stirred for additional 2 hours at room temperature. The resulting mixture was concentrated under reduced pressure. The residue was purified by silica gel column chromatography, eluted with CH$_2$Cl$_2$/EtOAc (1:1) to afford tert-butyl 3-([2-[2-(2-[[2-(2,6-dioxopiperidin-3-yl)-1,3-dioxoisoindol-4-yl]amino]ethoxy) ethoxy]ethyl]sulfamoyl) azetidine-1-carboxylate (130 mg, 35.42%) as a light yellow oil. LCMS (ESI) m/z: [M+H]$^+$=624.

To a stirred solution/mixture of tert-butyl 3-([2-[2-(2-[2-(2,6-dioxopiperidin-3-yl)-1,3-dioxoisoindol-4-yl]amino] ethoxy) ethoxy]ethyl]sulfamoyl) azetidine-1-carboxylate (120.00 mg, 0.192 mmol, 1.00 equiv) in DCM (4 mL) was added TFA (1 mL) in portions at room temperature. The resulting mixture was stirred for 1 hour at room temperature. The resulting mixture was concentrated under reduced pressure. The crude product 130 mg was used in the next step directly without further purification. LCMS (ESI) m/z: [M+H]$^+$=524.

Step 5: Preparation of 1-[[2,6-Dimethoxy-4-(2-Methyl-1-Oxo-2,7-Naphthyridin-4-Yl)Phenyl] Methyl]-N-[2-[2-(2-[[2-(2,6-Dioxopiperidin-3-Yl)-1, 3-Dioxoisoindol-4-Yl]Amino]Ethoxy) Ethoxy] Ethyl]Azetidine-3-Sulfonamide Formic Acid (Compound D38 Formic Acid)

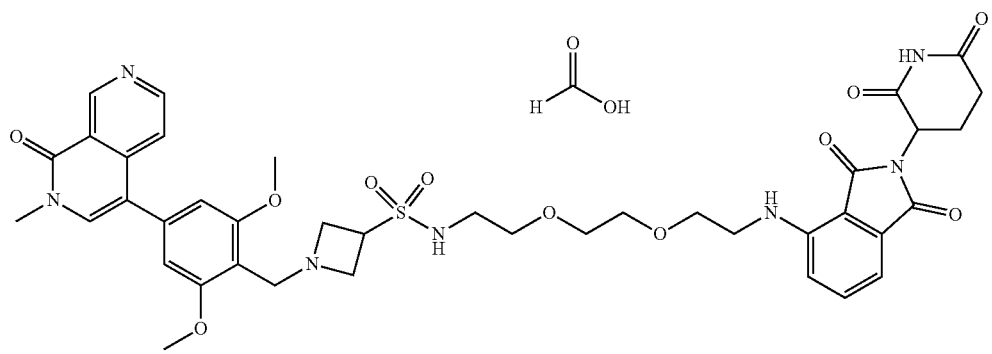

compound D38 formic acid

To a stirred solution of N-[2-[2-(2-[2-(2,6-dioxopiperidin-3-yl)-1,3-dioxoisoindol-4-yl]amino]ethoxy) ethoxy]ethyl] azetidine-3-sulfonamide (60.00 mg, 0.115 mmol, 1.00 equiv) and 2,6-dimethoxy-4-(2-methyl-1-oxo-2,7-naphthyridin-4-yl)benzaldehyde (74.34 mg, 0.229 mmol, 2.00 equiv) in MeOH was added NaBH(OAc)$_3$ (97.15 mg, 0.458 mmol, 4.00 equiv) in portions at room temperature. The resulting mixture was stirred for 12 hours at room temperature. The crude product was purified by Prep-HPLC(conditions: SunFire Prep C18 OBD Column, 19*150 mm 5 μm 10 nm; mobile phase, Water (0.1% FA) and ACN (10% Phase B up to 27% in 8 minutes); Detector, UV). This resulted in 1-[[2,6-dimethoxy-4-(2-methyl-1-oxo-2,7-naphthyridin-4-yl)phenyl]methyl]-N-[2-[2-(2 [2-(2,6-dioxopiperidin-3-yl)-1,3-dioxoisoindol-4-yl]amino]ethoxy) ethoxy]ethyl]azetidine-3-sulfonamide formic acid (8.1 mg, 8.05%) as a yellow solid. 1H NMR (300 MHZ, Methanol-d4) δ 9.49 (d, J=0.9 Hz, 1H), 8.66 (d, J=5.8 Hz, 1H), 8.45 (br s, 1H, FA), 7.74 (s, 1H), 7.62 (dd, J=5.8, 0.9 Hz, 1H), 7.50 (dd, J=8.5, 7.1 Hz, 1H), 7.02 (dd, J=7.8, 5.3 Hz, 2H), 6.79 (s, 2H), 5.07 (dd, J=12.4, 5.4 Hz, 1H), 4.61 (s, 1H), 4.36-4.23 (m, 1H), 4.20 (s, 2H), 4.13-3.99 (m, 4H), 3.92 (s, 6H), 3.73-3.64 (m, 9H), 3.55 (t, J=5.1 Hz, 2H), 3.50-3.41 (m, 2H), 3.28 (t, J=5.1 Hz, 2H), 2.96-2.61 (m, 3H), 2.18-2.04 (m, 1H). LCMS (ESI) m/z: [M+H]$^+$=832.45.

Example 45—Preparation of 4-[4-(9-[[2,6-Dimethoxy-4-(2-Methyl-1-Oxo-2,7-Naphthyridin-4-Yl)Phenyl]Methyl]-1-Oxa-4,9-Diazaspiro[5.5]Undecan-4-Yl)-4-Oxobutoxy]-2-(2,6-Dioxopiperidin-3-Yl) Isoindole-1,3-Dione. (Compound D39)

To a stirred solution of 4-(3,5-dimethoxy-4-[1-oxa-4,9-diazaspiro[5.5]undecan-9-ylmethyl]phenyl)-2-methyl-2,7naphthyridin-1-one (20.00 mg, 0.043 mmol, 1.00 equiv) and 4-[[2-(2,6-dioxopiperidin-3-yl)-1,3-dioxoisoindol-4-yl]oxy]butanoic acid (15.00 mg, 0.042 mmol, 0.97 equiv) in DMF was added HATU (25.00 mg, 0.066 mmol, 1.53 equiv) and DIEA (60.00 mg, 0.464 mmol, 10.78 equiv) in portions at room temperature. The resulting mixture was stirred for 2 hours at room temperature. The crude product was purified by Prep-HPLC(conditions: Gemini-NX C18 AXAI Packed, 21.2*150 mm 5 um; mobile phase, Water (0.1% FA) and ACN (14% Phase B up to 19% in 10 minutes); Detector, UV). This resulted in 4-[4-(9-[2,6-dimethoxy-4-(2-methyl-1-oxo-2,7-naphthyridin-4-yl)phenyl]methyl]-1-oxa-4,9diaza spiro[5.5]undecan-4-yl)-4-oxobutoxy]-2-(2,6-dioxopiperidin-3-yl) isoindole-1,3-dione (5.1 mg, 14.68%) as a white solid. $^1$H NMR (300 MHZ, Methanol-d4) δ 9.55 (s, 1H), 8.70 (d, J=5.6 Hz, 1H), 7.85-7.75 (m, 2H), 7.63 (d, J=5.8 Hz, 1H), 7.57-7.43 (m, 2H), 6.87 (d, J=5.2 Hz, 2H), 5.12 (d, J=11.8 Hz, 1H), 4.41 (s, 2H), 4.37-4.27 (m, 2H), 3.96 (d, J=8.2 Hz, 6H), 3.84-3.60 (m, 9H), 3.58-3.45 (m, 3H), 2.92-2.69 (m, 5H), 2.26-2.04 (m, 6H), 1.85-1.60 (m, 2H). LCMS (ESI) m/z: [M+H]$^+$=807.40.

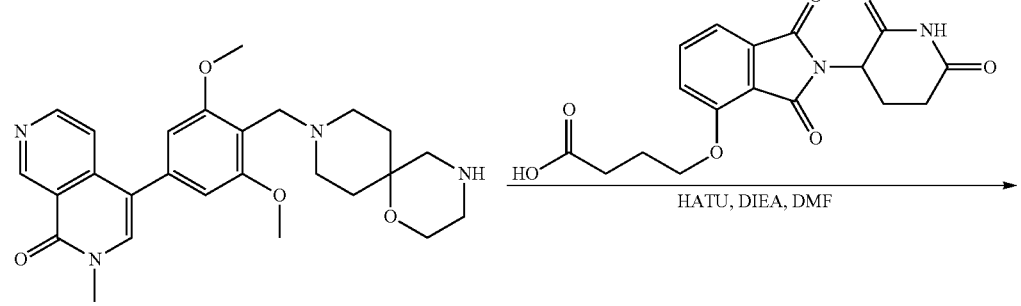

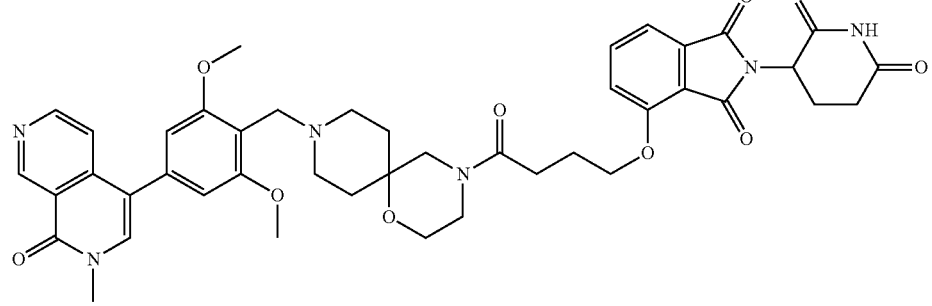

compound D39

Example 46—Preparation of 4-[5-(9-[2,6-Dimethoxy-4-(2-Methyl-1-Oxo-2,7-Naphthyridin-4-Yl)Phenyl]Methyl]-1-Oxa-4,9-Diazaspiro[5.5]Undecan-4-Yl)-5-Oxopentyl]Oxy]-2-(2,6-Dioxopiperidin-3-Yl) Isoindole-1,3-Dione Formic Acid (Compound D40 Formic Acid)

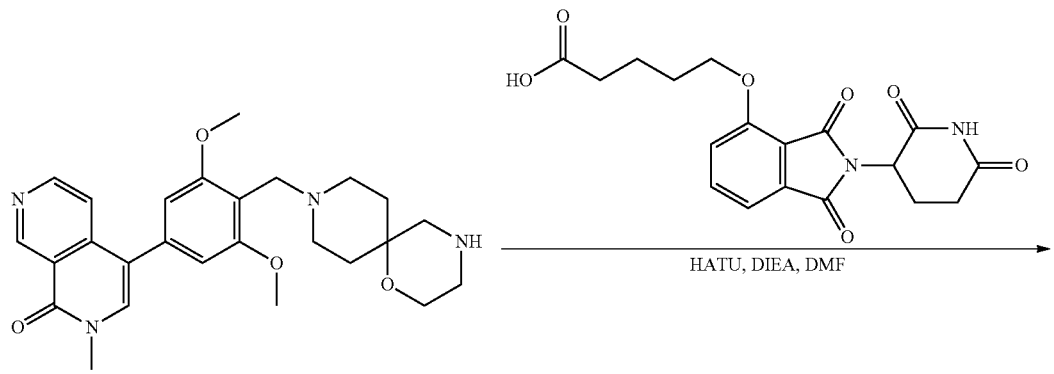

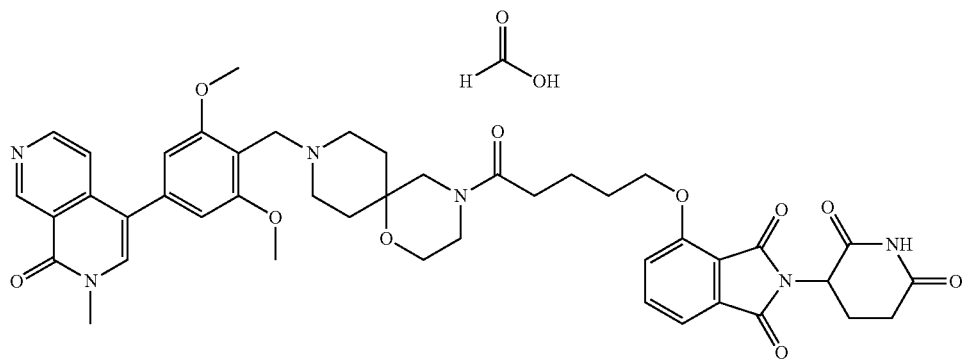

compound D40 formic acid

To a stirred solution of 4-(3,5-dimethoxy-4-[1-oxa-4,9-diazaspiro[5.5]undecan-9-ylmethyl]phenyl)-2-methyl-2,7-naphthyridin-1-one (30.00 mg, 0.065 mmol, 1.00 equiv) and 5-[2-(2,6-dioxopiperidin-3-yl)-1,3-dioxoisoindol-4-yl]oxy] pentanoic acid (24.17 mg, 0.065 mmol, 1 equiv) in DMF (1.00 mL) was added DIEA (83.46 mg, 0.646 mmol, 10.00 equiv) and HATU (36.83 mg, 0.097 mmol, 1.50 equiv). The resulting solution was stirred at room temperature for 1 hour. Without any additional work-up, the mixture was purified by prep-HPLC(conditions: SunFire C18 OBD Prep Column, 100 Å, 5 μm, 19 mm×250 mm; Mobile Phase A: Water (0.1% FA), Mobile Phase B: ACN; Flow rate: 25 mL/minute; Gradient: 9% B to 25% B in 10 minutes; 254 nm; Rt: 10.95 minutes) to give (4-[[5-(9-[[2,6-dimethoxy-4-(2-methyl-1-oxo-2,7-naphthyridin-4-yl)phenyl]methyl]-1-oxa-4,9-diazaspiro[5.5]undecan-4-yl)-5-oxopentyl]oxy]-2-(2,6-dioxopip eridin-3-yl) isoindole-1,3-dione formic acid (8.6 mg, 15.25%) as a white solid. $^1$H NMR (300 MHZ, Methanol-d4)δ 9.54 (s, 1H), 8.69 (d, J=5.8 Hz, 1H), 8.53 (br s, 1H, FA), 7.85-7.74 (m, 2H), 7.62 (dd, J=5.9, 0.9 Hz, 1H), 7.46 (dd, J=7.8, 2.3 Hz, 2H), 6.86 (d, J=5.7 Hz, 2H), 5.12 (dd, J=12.3, 5.4 Hz, 1H), 4.39 (s, 2H), 4.35-4.25 (m, 3H), 3.96 (s, 6H), 3.83-3.74 (m, 2H), 3.72 (s, 3H), 3.67-3.61 (m, 2H), 3.55-3.50 (m, 3H), 3.00-2.51 (m, 6H), 2.20-1.71 (m, 10H). LCMS (ESI) m/z: [M+H]$^+$=821.45.

Example 47—Preparation of 4-[2-(9-[[2,6-Dimethoxy-4-(2-Methyl-1-Oxo-2,7-Naphthyridin-4-Yl)Phenyl]Methyl]-1-Oxa-4,9-Diazaspiro[5.5]Undecan-4-Yl)-2-Oxoethoxy]-2-(2,6-Dioxopiperidin-3-Yl)Isoindole-1,3-Dione Formic Acid (Compound D41 Formic Acid)

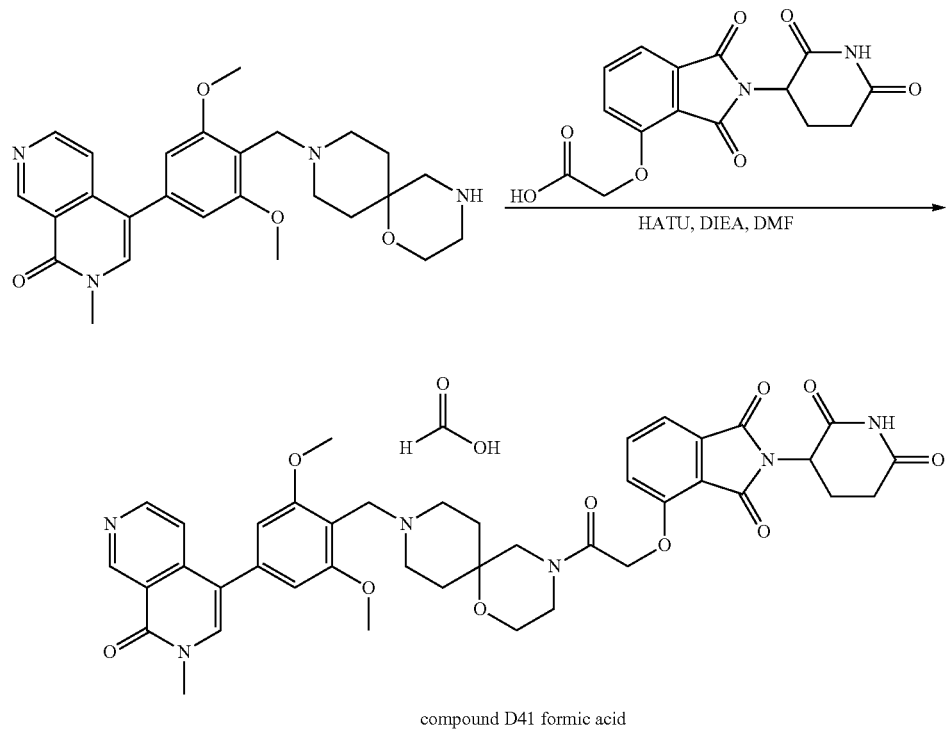

compound D41 formic acid

To a solution of 4-(3,5-dimethoxy-4-[1-oxa-4,9-diazaspiro[5.5]undecan-9-ylmethyl]phenyl)-2-methyl-2,7-naphthyridin-1-one (30.00 mg, 0.065 mmol, 1.00 equiv) and [[2-(2,6-dioxopiperidin-3-yl)-1,3-dioxoisoindol-4-yl]oxy] acetic acid (21.46 mg, 0.065 mmol, 1.00 equiv) in DMF (1.00 mL) was added DIEA (83.46 mg, 0.646 mmol, 10.00 equiv) and HATU (36.83 mg, 0.097 mmol, 1.50 equiv). The resulting solution was stirred at room temperature for 1 hour. Without any additional work-up, the mixture was purified by prep-HPLC(conditions: Phenomenex Gemini C6-Phenyl, 21.2*250 mm, 5 um; Mobile Phase A: Water (0.05% FA), Mobile Phase B: ACN; Flow rate: 25 mL/minute; Gradient: 7 B to 26 B in 15 minutes; 254 nm; RT: 14.62 minutes) to give 4-[2-(9-[[2,6-dimethoxy-4-(2-methyl-1-oxo-2,7-naphthyridin-4-yl)phenyl]methyl]-1-oxa-4,9-diazaspiro[5.5]undecan-4-yl)-2-oxoethoxy]-2-(2,6-dioxopiperidin-3-yl) isoindole-1,3-dione formic acid (3.7 mg, 6.80%) as a white solid. $^1$H NMR (300 MHz, Methanol-d4)δ 9.54 (d, J=0.8 Hz, 1H), 8.70 (d, J=5.8 Hz, 1H), 8.56 (br s, 1H, FA), 7.86-7.75 (m, 2H), 7.63 (dd, J=5.8, 0.9 Hz, 1H), 7.54 (d, J=7.2 Hz, 1H), 7.44 (d, J=8.5 Hz, 1H), 6.86 (s, 2H), 5.17-5.07 (m, 3H), 4.30 (s, 2H), 3.95 (s, 6H), 3.87-3.75 (m, 2H), 3.72 (s, 3H), 3.68-3.62 (m, 2H), 3.54 (s, 2H), 3.23-3.17 (m, 4H), 2.91-2.65 (m, 3H), 2.22-2.02 (m, 3H), 1.80 (s, 2H). LCMS (ESI) m/z: [M+H]$^+$=779.40.

Example 48—Preparation of 5-(4-(2-(1-(2,6-Dimethoxy-4-(2-Methyl-1-Oxo-1,2-Dihydro-2,7-Naphthyridin-4-Yl)Benzyl) Piperidin-4-Yl)Ethyl) Piperazin-1-Yl)-2-(2,6-Dioxopiperidin-3-Yl) Isoindoline-1,3-Dione Formic Acid (Compound D42 Formic Acid)

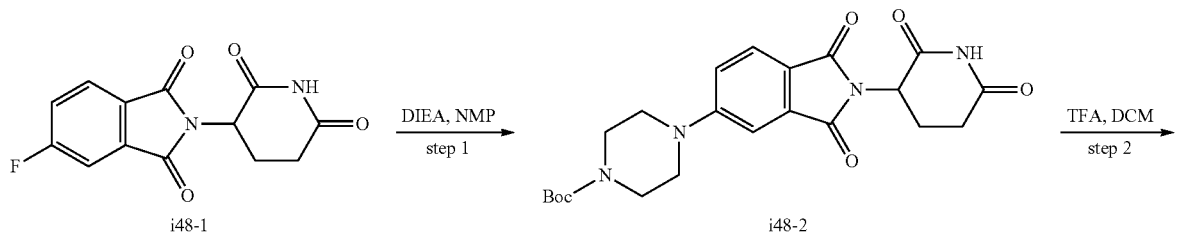

-continued
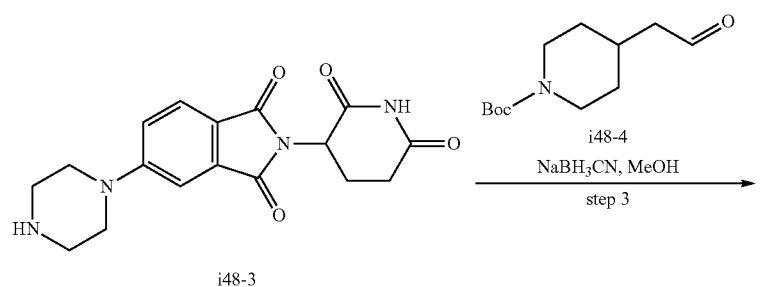
i48-3    i48-4
NaBH₃CN, MeOH
step 3
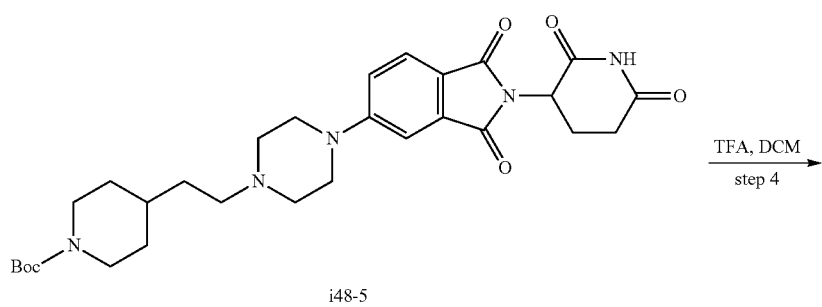
i48-5
TFA, DCM
step 4
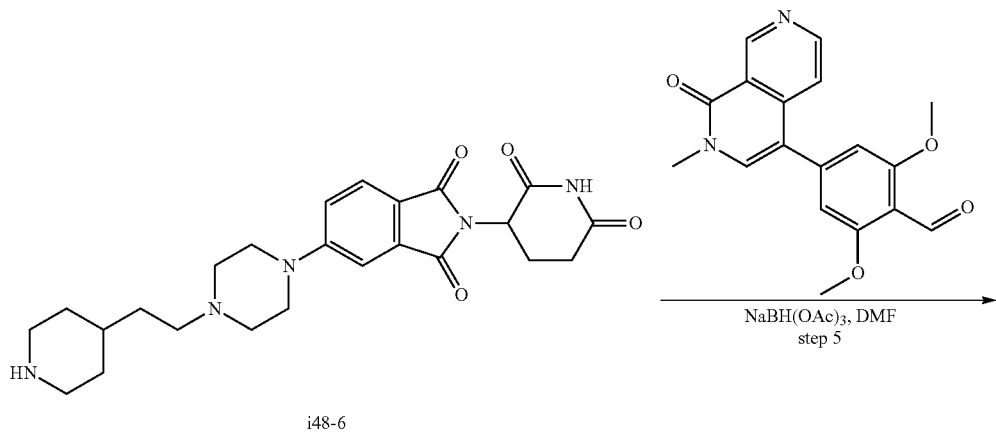
i48-6
NaBH(OAc)₃, DMF
step 5
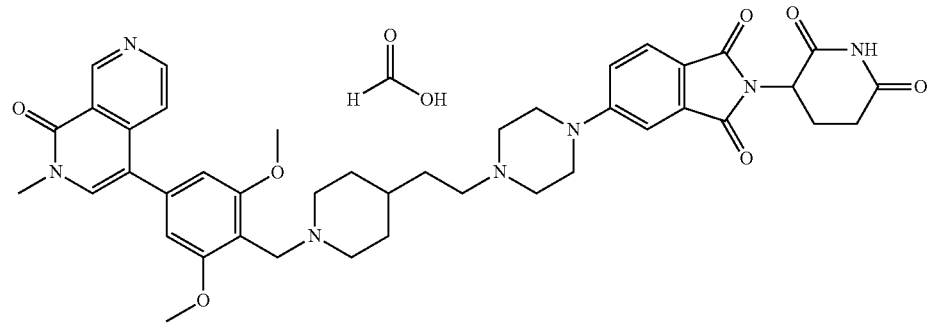
compound D42 formic acid

Step 1: Preparation of Tert-Butyl 4-(2-(2,6-Dioxopiperidin-3-Yl)-1,3-Dioxoisoindolin-5-Yl) Piperazine-1-Carboxylate (i42-2)

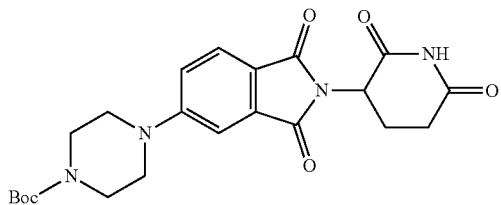

i48-2

To a solution of 2-(2,6-dioxopiperidin-3-yl)-5-fluoroisoindole-1,3-dione (1.38 g, 4.996 mmol, 1.00 equiv) and tert-butyl piperazine-1-carboxylate (930.52 mg, 4.996 mmol, 1.00 equiv) in NMP (20 mL) was added DIPEA (1937.08 mg, 14.988 mmol, 3 equiv). The mixture was stirred at 90° C. for 2 hours (under nitrogen atmosphere). The reaction was monitored by LC-MS. The resulting mixture was diluted with water (70 mL) and then extracted with EA (3×25 mL). The combined organic layers were washed with water (2×25 mL) and dried over anhydrous $Na_2SO_4$. After filtration, the filtrate was concentrated under reduced pressure. The resulting mixture was concentrated under vacuum. The residue was purified by reverse flash chromatography (conditions: column, C18 silica gel; mobile phase, 0.5% FA in water, 10% to 90% gradient in 25 minutes; detector, UV 220 nm). The fractions were concentrated under reduced pressure afford tert-butyl 4-(2-(2,6-dioxopiperidin-3-yl)-1,3-dioxoisoindolin-5-yl) piperazine-1-carboxylate (700 mg, 31.67%) as a yellow solid. LCMS (ESI) m/z: [M+H]$^+$=443.

Step 2: Preparation of 2-(2,6-Dioxopiperidin-3-Yl)-5-(Piperazin-1-Yl) Isoindoline-1,3-Dione (i42-3)

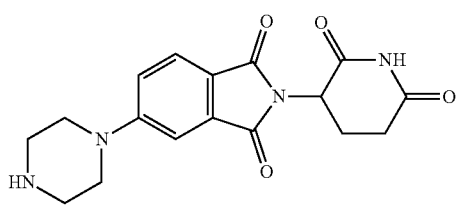

i48-3

A solution of tert-butyl 4-[2-(2,6-dioxopiperidin-3-yl)-1,3-dioxoisoindol-5-yl]piperazine-1-carboxylate (500.00 mg, 1.130 mmol, 1.00 equiv) and TFA (1.50 mL, 20.195 mmol, 17.87 equiv) in DCM (5.00 mL) was stirred at 25° C. for 1 hour. The resulting mixture were evaporated to dryness to afford 2-(2,6-dioxopiperidin-3-yl)-5-(piperazin-1-yl) isoindole-1,3-dione (350 mg, 90.47%) as a brown solid. LCMS (ESI) m/z: [M+H]$^+$=343

Step 3: Preparation of Tert-Butyl 4-(2-(4-(2-(2,6-Dioxopiperidin-3-Yl)-1,3-Dioxoisoindolin-5-Yl) Piperazin-1-Yl)Ethyl) Piperidine-1-Carboxylate (i42-5)

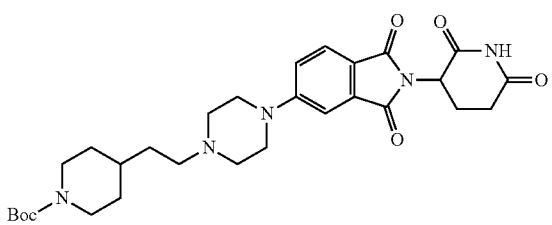

i48-5

To a solution of 2-(2,6-dioxopiperidin-3-yl)-5-(piperazin-1-yl) isoindole-1,3-dione (200.00 mg, 0.584 mmol, 1.00 equiv) and tert-butyl 4-(2-oxoethyl) piperidine-1-carboxylate (132.79 mg, 0.584 mmol, 1 equiv) in DMF (3.00 mL) was added NaBH (OAc)$_3$ (247.63 mg, 1.168 mmol, 2 equiv). The resulting solution was stirred at 25° C. for 1 hour. The residue was purified by reverse flash chromatography (conditions: column, C18 silica gel; mobile phase, ACN in water, 10% to 50% gradient in 10 minutes; detector, UV 254 nm) to give tert-butyl 4-(2-[4-[2-(2,6-dioxopiperidin-3-yl)-1,3-dioxoisoindol-5-yl]piperazin-1-yl]ethyl) piperidine-1-carboxylate (197.5 mg, 61.06%) as a yellow solid. LCMS (ESI) m/z: [M+H]$^+$=554.

Step 4: Preparation of 2-(2,6-Dioxopiperidin-3-Yl)-5-(4-(2-(Piperidin-4-Yl)Ethyl) Piperazin-1-Yl) Isoindoline-1,3-Dione (i42-6)

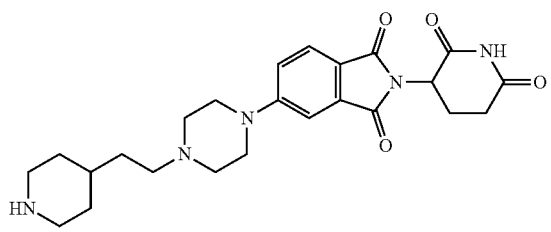

i48-6

To a solution of tert-butyl 4-(2-[4-[2-(2,6-dioxopiperidin-3-yl)-1,3-dioxoisoindol-5-yl]piperazin-1-ylethyl) piperidine-1-carboxylate (197.00 mg, 0.356 mmol, 1.00 equiv) and TFA (0.50 mL, 6.732 mmol, 18.92 equiv) in DCM (2.00 mL) was stirred at 25° C. for 1 hour. The mixture was concentrated to give crude product 2-(2,6-dioxopiperidin-3-yl)-5-[4-[2-(piperidin-4-yl)ethyl]piperazin-1-yl]isoindole-1,3-dione (320 mg) as a yellow oil, that was used directly without further purification. LCMS (ESI) m/z: [M+H]$^+$=454.

Step 5: Preparation of 5-(4-(2-(1-(2,6-Dimethoxy-4-(2-Methyl-1-Oxo-1,2-Dihydro-2,7-Naphthyridin-4-Yl)Benzyl) Piperidin-4-Yl)Ethyl) Piperazin-1-Yl)-2-(2,6-Dioxopiperidin-3-Yl) Isoindoline-1,3-Dione Formic Acid (Compound D42 Formic Acid)

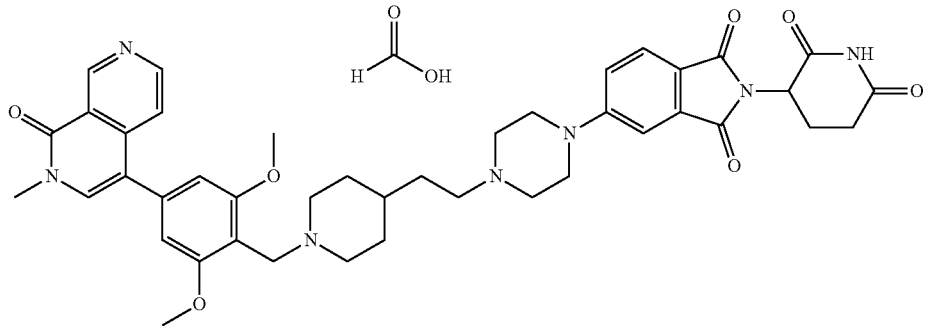

compound D42 formic acid

To a solution of 2-(2,6-dioxopiperidin-3-yl)-5-[4-[2-(piperidin-4-yl)ethyl]piperazin-1-yl]isoindole-1,3-dione (100.68 mg, 0.222 mmol, 1.20 equiv) and 2,6-dimethoxy-4-(2-methyl-1-oxo-2,7-naphthyridin-4-yl)benzaldehyde (60.00 mg, 0.185 mmol, 1.00 equiv) in DMF (1.5 mL) was added NaBH(OAc)$_3$ (78.42 mg, 0.370 mmol, 2 equiv). The mixture was stirred at 25° C. for 1 hour. The mixture was purified by prep-HPLC(conditions: SunFire C18 OBD Prep Column, 100 Å, 5 μm, 19 mm×250 mm; Mobile Phase A: Water (0.1% FA), Mobile Phase B: ACN; Flow rate: 25 mL/minute; Gradient: 10 B to 12 B in 10 minutes; 254 nm; RT: 8.7 minutes) to afford 5-[4-[2-(1-[[2,6-dimethoxy-4-(2-methyl-1-oxo-2,7-naphthyridin-4-yl)phenyl]methyl]piperidin-4-yl)ethyl]piperazin-1-yl]-2-(2,6-dioxopiperidin-3-yl)isoindole-1,3-dione (24 mg, 17.03%) as a yellow solid. $^1$H NMR (300 MHZ, Methanol-d4)δ 9.55 (d, J=0.9 Hz, 1H), 8.69 (d, J=5.8 Hz, 1H), 8.15 (br s, 0.2H, FA), 7.80-7.71 (m, 2H), 7.63 (d, J=5.8 Hz, 1H), 7.43 (s, 1H), 7.31 (d, J=9.2 Hz, 1H), 6.89 (s, 2H), 5.10 (dd, J=12.3, 5.4 Hz, 1H), 4.41 (s, 2H), 3.98 (s, 6H), 3.72 (s, 3H), 3.67-3.55 (m, 6H), 3.17 (d, J=12.9 Hz, 2H), 3.05-2.92 (m, 4H), 2.90-2.70 (m, 5H), 2.17-2.00 (m, 3H), 1.81-1.51 (m, 5H). LCMS (ESI) m/z: [M+H]$^+$=762.45.

Example 49—Preparation of 5-[2-(6-[[2,6-Dimethoxy-4-(2-Methyl-1-Oxo-2,7-Naphthyridin-4-Yl) Phenyl]Methyl]-2,6-Diazaspiro[3.3]Heptan-2-Yl) Ethoxy]-2-(2,6-Dioxopiperidin-3-Yl) Isoindole-1,3-Dione Formic Acid (Compound D43 Formic Acid)

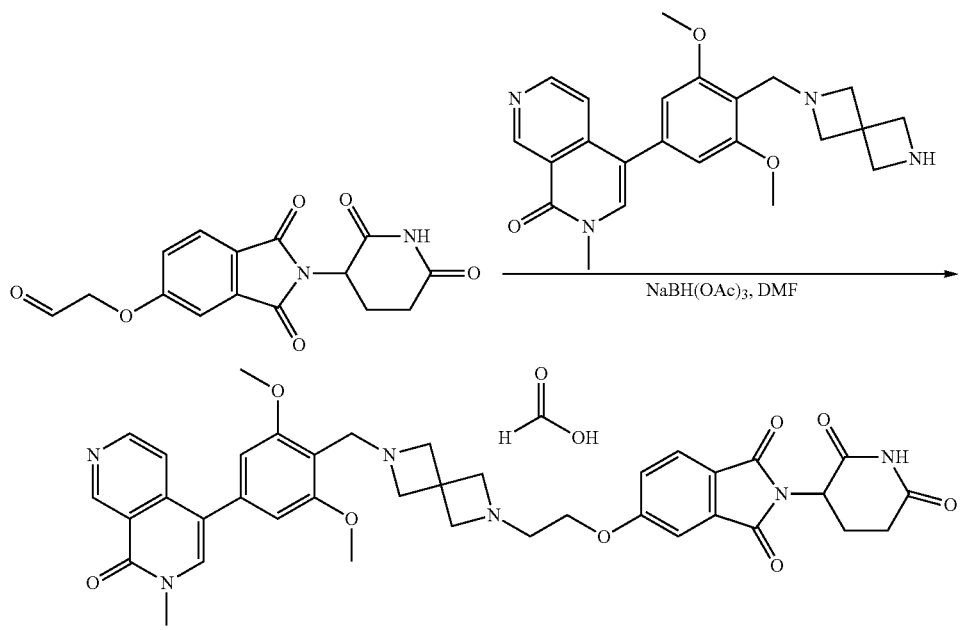

compound D43 formic acid

To a solution of 2-[[2-(2,6-dioxopiperidin-3-yl)-1,3-dioxoisoindol-5-yl]oxy]acetaldehyde (60.00 mg, 0.190 mmol, 1.00 equiv) and 4-(4-[2,6-diazaspiro[3.3]heptan-2-ylmethyl]-3,5-dimethoxyphenyl)-2-methyl-2,7-naphthyridin-1-one (77.12 mg, 0.190 mmol, 1 equiv) in DMF (1.00 mL) was added NaBH(OAc)$_3$ (80.42 mg, 0.379 mmol, 2 equiv). The resulting solution was stirred at room temperature for 1 hour. The crude product (60 mg) was purified by Prep-HPLC (conditions: SunFire Prep C18 OBD Column 19×150 mm 5 μm 10 nm; Mobile Phase A: Water (0.1% FA), Mobile Phase B: ACN; Flow rate: 25 mL/minute; Gradient: 7% B to 10% B in 12 minutes; 254/220 nm; Rt: 9.65 minutes) to afford 5-[2-(6-[[2,6-dimethoxy-4-(2-methyl-1-oxo-2,7-naphthyridin-4-yl)phenyl]methyl]-2,6-diazaspiro[3.3]heptan-2-yl)ethoxy]-2-(2,6-dioxopiperidin-3-yl) isoindole-1,3-dione formic acid (14.3 mg, 9.82%) as a light yellow solid. $^1$H NMR (300 MHz, Methanol-d4) δ 9.54 (s, 1H), 8.68 (d, J=5.8 Hz, 1H), 8.14 (br s, 0.2H, FA), 7.76 (s, 1H), 7.70 (d, J=8.2 Hz, 1H), 7.62-7.54 (m, 1H), 7.19 (d, J=2.2 Hz, 1H), 7.13 (dd, J=8.2, 2.2 Hz, 1H), 6.86 (s, 2H), 5.16 (dd, J=12.8, 5.4 Hz, 1H), 4.47 (s, 2H), 4.34 (s, 4H), 3.98 (s, 6H), 3.95-3.87 (m, 2H), 3.80 (s, 4H), 3.71 (s, 3H), 3.00-2.85 (m, 4H), 2.81-2.63 (m, 1H), 2.20-2.05 (m, 1H). LCMS (ESI) m/z: [M+H]$^+$=707.5.

Example 50—Preparation of 5-((5-(4-(2,6-Dimethoxy-4-(2-Methyl-1-Oxo-1,2-Dihydro-2,7-Naphthyridin-4-Yl)Benzyl) Piperazin-1-Yl) Pentyl)Oxy)-2-(2,6-Dioxopiperidin-3-Yl) Isoindoline-1,3-Dione Formic Acid (Compound D44 Formic Acid)

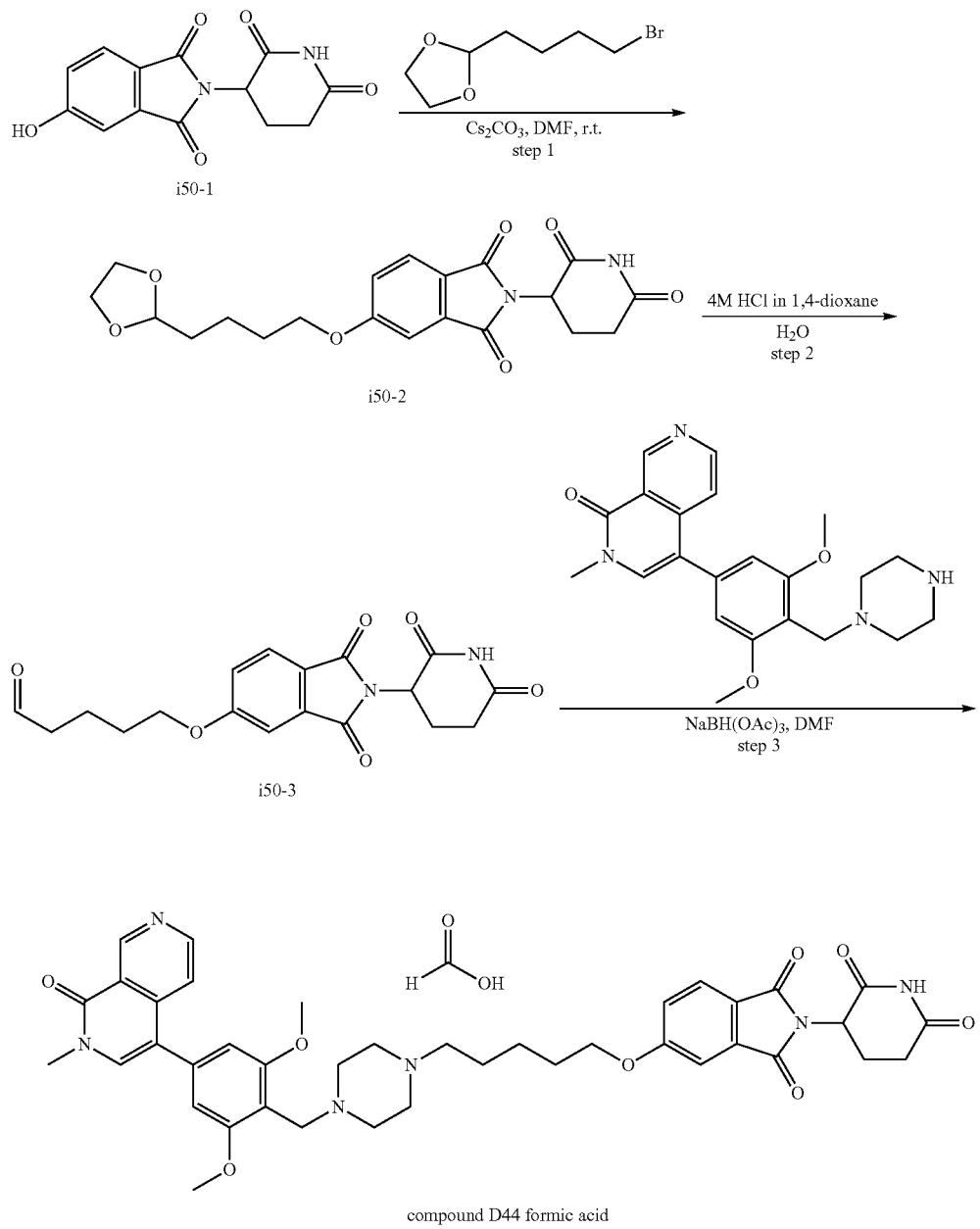

compound D44 formic acid

Step 1: 5-(4-(1,3-Dioxolan-2-Yl) Butoxy)-2-(2,6-Dioxopiperidin-3-Yl) Isoindoline-1,3-Dione (i50-2)

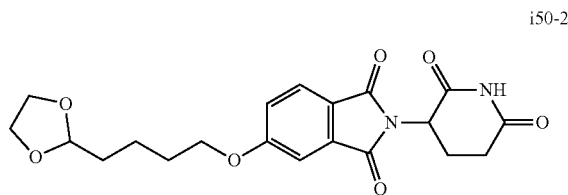 [SMILES: O=C1CCC(N2C(=O)c3ccc(OCCCCC4OCCO4)cc3C2=O)C(=O)N1]

To a stirred solution of 2-(2,6-dioxopiperidin-3-yl)-5-hydroxy-2,3-dihydro-1H-isoindole-1,3-dione (400.0 mg, 1.459 mmol, 1.00 equiv) and 2-(4-bromobutyl)-1,3-dioxolane (305.0 mg, 1.459 mmol, 1.00 equiv) in DMF was added cesium carbonate (475.3 mg, 1.459 mmol, 1.00 equiv) at room temperature. The resulting mixture was filtered, and the filter cake was washed with DCM (3×5 mL). The filtrate was concentrated under reduced pressure. The residue was purified by Prep-TLC(PE/EtOAc 1:1) to afford 5-[4-(1,3-dioxolan-2-yl) butoxy]-2-(2,6-dioxopiperidin-3-yl)-2,3-dihydro-1H-isoindole-1,3-dione (40 mg, 6.5%) as an off-white oil. LCMS (ESI) m/z: [M+H]$^+$=403.

Step 2: Preparation of 5-((2-(2,6-Dioxopiperidin-3-Yl)-1,3-Dioxoisoindolin-5-Yl)Oxy) Pentanal (i50-3)

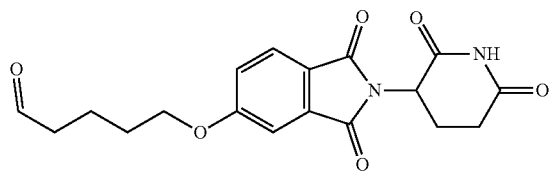

To a stirred mixture of 5-[4-(1,3-dioxolan-2-yl) butoxy]-2-(2,6-dioxopiperidin-3-yl) isoindole-1,3-dione (40.0 mg, 0.099 mmol, 1.00 equiv) in water (1.50 mL) was added HCl in 1,4-dioxane (4 M, 3.00 mL) at room temperature. The resulting mixture was stirred for 2 hours at room temperature. The resulting mixture was extracted with EtOAc (2×10 mL). The combined organic layers were washed with brine (8 mL), and dried over anhydrous Na$_2$SO$_4$. After filtration, the filtrate was concentrated under reduced pressure. The crude product was used in the next step directly without further purification. LCMS (ESI) m/z: [M+H]$^+$=359.

Step 3: Preparation of N-(6-[4-[(Dimethylamino) Methyl]-3,5-Dimethoxyphenyl]-3-Methyl-[1,2,4] Triazolo[4,3-a]Pyridin-8-Yl) Acetamide Formic Acid (Compound D44 Formic Acid)

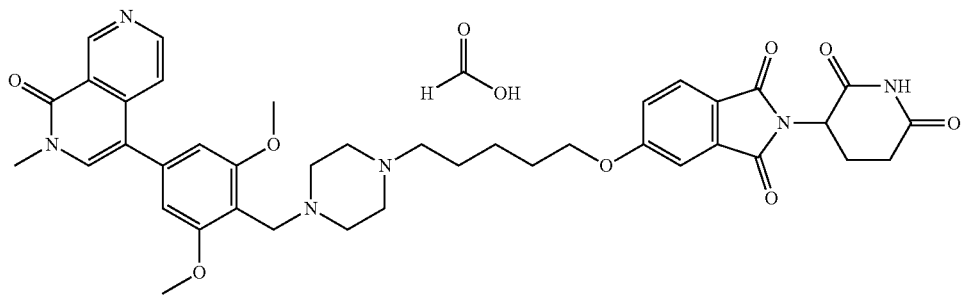

compound D44 formic acid

To a stirred solution/mixture of 5-[2-(2,6-dioxopiperidin-3-yl)-1,3-dioxoisoindol-5-yl]oxy]pentanal (20 mg, 0.056 mmol, 1.00 equiv) in DMF (1 mL) was added 4-[3,5-dimethoxy-4-(piperazin-1-ylmethyl)phenyl]-2-methyl-2,7-naphthyridin-1-one (22.0 mg, 0.056 mmol, 1 equiv) at room temperature. The resulting mixture was stirred for 30 minutes at room temperature. To the above mixture was added NaBH(OAc)$_3$ (23.7 mg, 0.112 mmol, 2.00 equiv) at room temperature. The resulting mixture was stirred for additional 2 hours at room temperature. The crude product was purified by Prep-HPLC(conditions: SunFire Prep C18 OBD Column, 19×150 mm 5 µm 10 nm; Mobile Phase A: Water (0.1% FA), Mobile Phase B: ACN; Flow rate: 25 mL/minute; Gradient: 10 B to 25 B in 8 minutes; 254/220 nm; RT: 6.53 minutes) to afford 5-[5-(4-[2,6-dimethoxy-4-(2-methyl-1-oxo-2,7-naphthyridin-4-yl)phenyl]methyl]piperazin-1-yl) pentyl] oxy]-2-(2,6-dioxopiperidin-3-yl) isoindole-1,3-dione; formic acid (5 mg, 10.9%) as a white solid. $^1$H NMR (400 MHZ, Methanol-d4) δ 9.54 (d, J=0.9 Hz, 1H), 8.69 (d, J=5.7 Hz, 1H), 8.52 (br s, 0.3H, FA), 7.82 (d, J=8.3 Hz, 1H), 7.75 (s, 1H), 7.62 (dd, J=5.8, 0.9 Hz, 1H), 7.41 (d, J=2.2 Hz, 1H), 7.33 (dd, J=8.3, 2.3 Hz, 1H), 6.82 (s, 2H), 5.12 (dd, J=12.5, 5.4 Hz, 1H), 4.20 (t, J=6.2 Hz, 2H), 4.10 (s, 2H), 3.93 (s, 6H), 3.72 (s, 3H), 3.12-2.59 (m, 13H), 2.19-2.10 (m, 1H), 1.97-1.86 (m, 2H), 1.72-1.54 (m, 4H). LCMS (ESI) m/z: [M+H]$^+$=737.40.

Example 51—Preparation of 1-[[2,6-Dimethoxy-4-(2-Methyl-1-Oxo-2,7-Naphthyridin-4-Yl)Phenyl]Methyl]-N-[2-(2-[[2-(2,6-Dioxopiperidin-3-Yl)-1,3-Dioxoisoindol-4-Yl]Amino]Ethoxy)Ethyl]Azetidine-3-Sulfonamide (Compound D45)
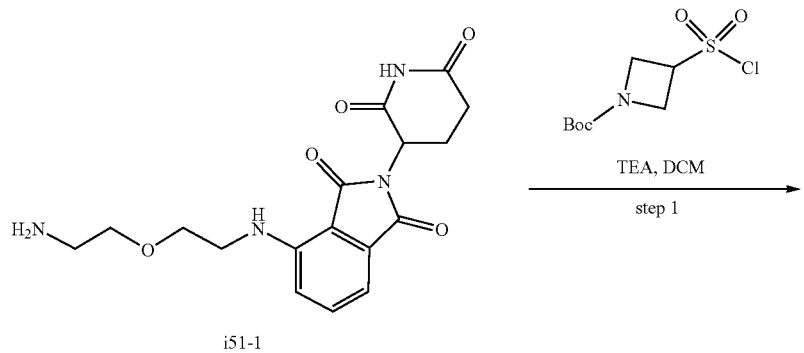
i51-1
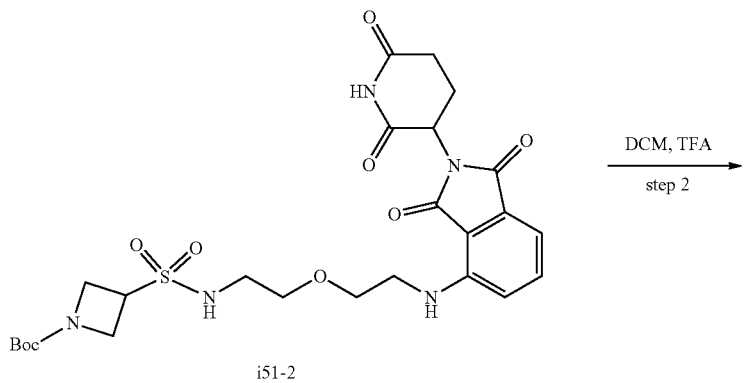
i51-2
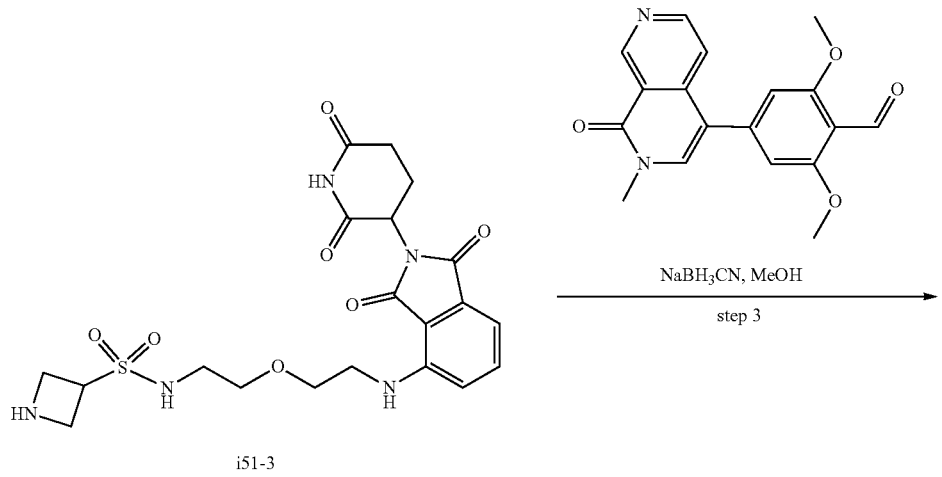
i51-3

-continued

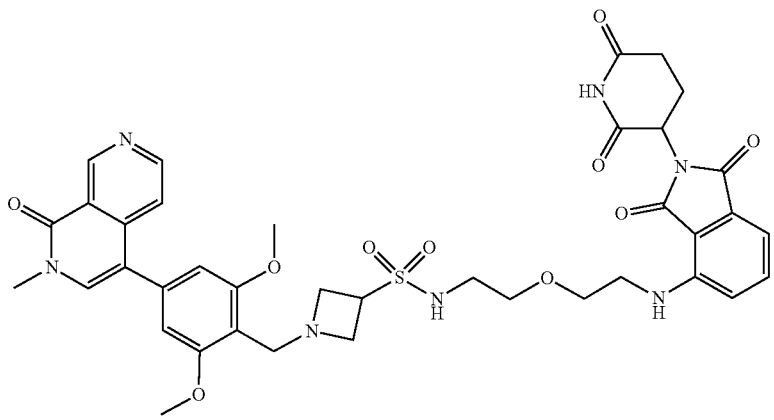

compound D45

Step 1: Preparation of Tert-Butyl 3-[[2-(2-[[2-(2,6-Dioxopiperidin-3-Yl)-1,3-Dioxoisoindol-4-Yl]Amino]Ethoxy)Ethyl]Sulfamoyl]Azetidine-1-Carboxylate (i51-2)

Step 2: Preparation of N-[2-(2-[[2-(2,6-Dioxopiperidin-3-Yl)-1,3-Dioxoisoindol-4-Yl]Amino]Ethoxy)ethyl]azeti Dine-3-Sulfonamide (i51-3)

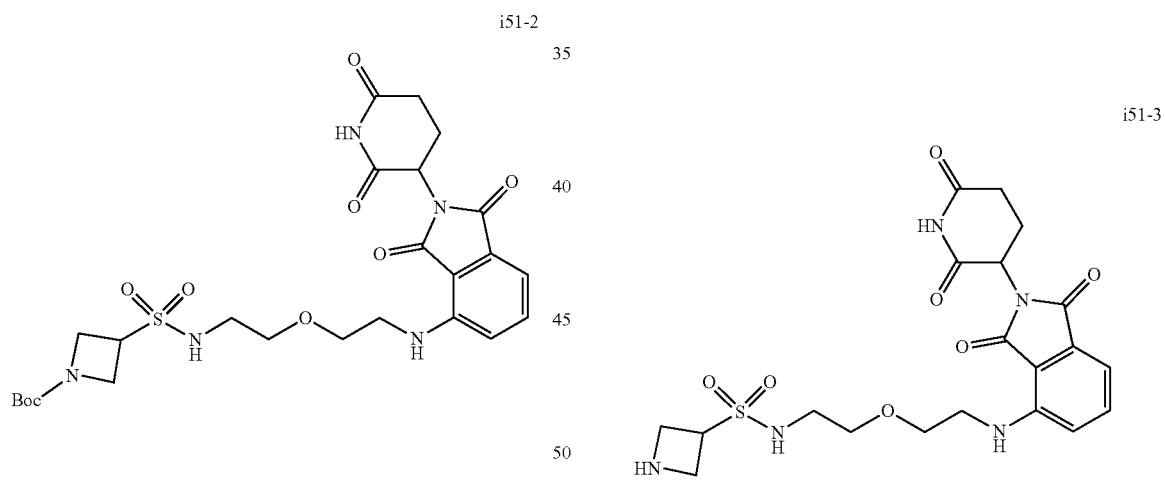

To a stirred solution of 4-[2-(2-aminoethoxy)ethyl]amino]-2-(2,6-dioxopiperidin-3-yl) isoindole-1,3-dione (200.00 mg, 0.555 mmol, 1.00 equiv) and TEA (168.48 mg, 1.665 mmol, 3.00 equiv) in DCM (2 mL) was added tert-butyl 3-(chlorosulfonyl) azetidine-1-carboxylate (170.30 mg, 0.666 mmol, 1.20 equiv) at room temperature. The resulting mixture was stirred for 2 hours at room temperature. The resulting mixture was concentrated under vacuum. The residue was purified by silica gel column chromatography, eluted with CH$_2$Cl$_2$/MeOH (7:1) to afford tert-butyl 3-[2-(2-[2-(2,6-dioxopiperidin-3-yl)-1,3-dioxoisoindol-4-yl]amino]ethoxy)ethyl]sulfamoyl]azetidine-1-carboxylate (150 mg, 46.63%) as a yellow solid. LCMS (ESI) m/z: [M−H]$^+$=580.20.

A solution of tert-butyl 3-[2-(2-[2-(2,6-dioxopiperidin-3-yl)-1,3-dioxoisoindol-4-yl]amino]ethoxy)ethyl]sulfamoyl] azetidine-1-carboxylate (100.00 mg, 0.173 mmol, 1.00 equiv) and TFA (1.00 mL) in DCM was stirred for 1 hour at room temperature. The resulting mixture was concentrated under vacuum. This resulted in N-[2-(2-[2-(2,6-dioxopiperidin-3-yl)-1,3-dioxoisoindol-4-yl]amino]ethoxy)ethyl]azetidine-3-sulfonamide (75 mg, 90.66%) as a red oil. LCMS (ESI) m/z: [M−H]$^+$=480.15.

Step 3: Preparation of 1-[[2,6-Dimethoxy-4-(2-Methyl-1-Oxo-2,7-Naphthyridin-4-Yl)Phenyl]Methyl]-N-[2-(2-[[2-(2,6-Dioxopiperidin-3-Yl)-1,3-Dioxoisoindol-4-Yl]Amino]Ethoxy)Ethyl]Azetidine-3-Sulfonamide (Compound D45)

compound D45

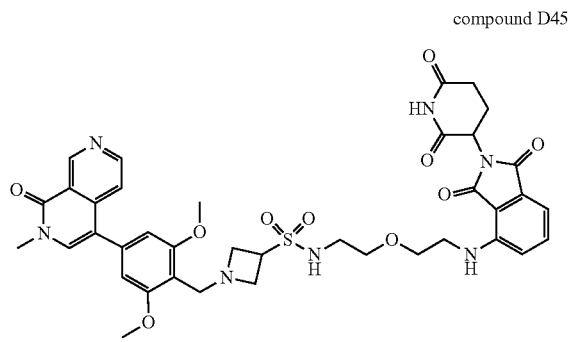 [SMILES: COc1cc(-c2cn(C)c(=O)c3cnccc23)cc(OC)c1CN1CC(S(=O)(=O)NCCOCCNc2cccc3c2C(=O)N(C2CCC(=O)NC2=O)C3=O)C1]

A solution of N-[2-(2-[2-(2,6-dioxopiperidin-3-yl)-1,3-dioxoisoindol-4-yl]amino]ethoxy)ethyl]azetidine-3-sulfonamide (30.00 mg, 0.063 mmol, 1.00 equiv) and 2,6-dimethoxy-4-(2-methyl-1-oxo-2,7-naphthyridin-4-yl)benzaldehyde (26.38 mg, 0.081 mmol, 1.30 equiv) in DMF (2.00 mL) was stirred for 20 minutes at room temperature. Then NaBH(OAc)$_3$ (39.78 mg, 0.188 mmol, 3.00 equiv) was added to the reaction mixture. The resulting mixture was stirred for 1 hour at room temperature. The crude product was purified by Prep-HPLC(conditions: SunFire C18 OBD Prep Column, 100 Å, 5 μm, 19 mm×250 mm; mobile phase, Water (0.1% FA) and ACN (11% PhaseB up to 18% in 20 min, hold 18% in 3 minutes); Detector, UV). This resulted in 1-[[2,6-dimethoxy-4-(2-methyl-1-oxo-2,7-naphthyridin-4-yl)phenyl]methyl]-N-[2-(2-[2-(2,6-dioxopiperidin-3-yl)-1,3-dioxoisoindol-4-yl]amino]ethoxy)ethyl]azetidine-3-sulfonamide (7.9 mg, 16.03%) as a green solid. $^1$H NMR (400 MHZ, Methanol-d4)δ 9.52 (s, 1H), 8.67 (d, J=5.8 Hz, 1H), 8.35 (br s, 0.3H, FA), 7.75 (s, 1H), 7.61 (dd, J=5.7, 0.9 Hz, 1H), 7.55 (dd, J=8.6, 7.1 Hz, 1H), 7.07 (dd, J=16.6, 7.8 Hz, 2H), 6.81 (s, 2H), 5.07 (d, J=12.3 Hz, 1H), 4.60 (s, 2H), 4.36 (s, 3H), 4.23 (d, J=7.7 Hz, 4H), 3.93 (s, 6H), 3.75 (t, J=5.2 Hz, 2H), 3.71 (s, 3H), 3.59 (t, J=5.2 Hz, 2H), 3.53 (t, J=5.2 Hz, 2H), 2.92-2.66 (m, 3H), 2.12 (ddd, J=12.7, 6.9, 3.9 Hz, 1H). LCMS (ESI) m/z: [M−H]+=788.26.

Example 52—Preparation of 5-(4-(2-(2-(((2,6-Dimethoxy-4-(2-Methyl-1-Oxo-1,2-Dihydro-2,7-Naphthyridin-4-Yl)Benzyl)(Methyl)Amino) Ethoxy)Ethyl) Piperazin-1-Yl)-2-(2,6-Dioxopiperidin-3-Yl) Isoindoline-1,3-Dione Formic Acid (Compound D46 Formic Acid)

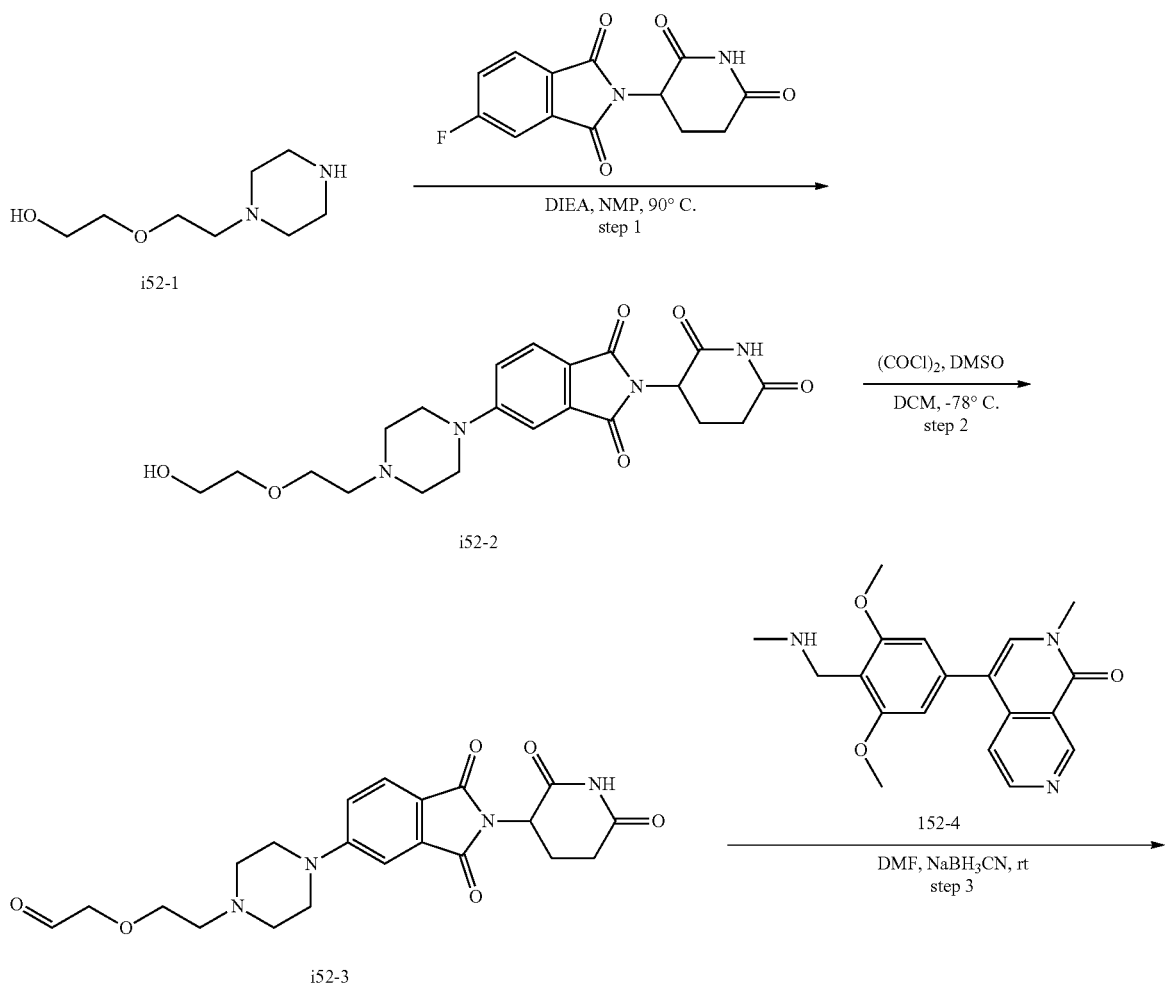

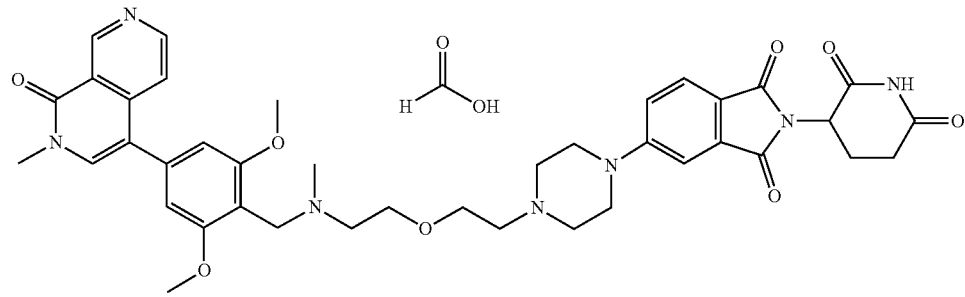

compound D46 formic acid

Step 1: Preparation of 2-(2,6-Dioxopiperidin-3-Y1)-5-(4-(2-(2-Hydroxyethoxy)Ethyl) Piperazin-1-Yl) Isoindoline-1,3-Dione (i52-2)

i52-2

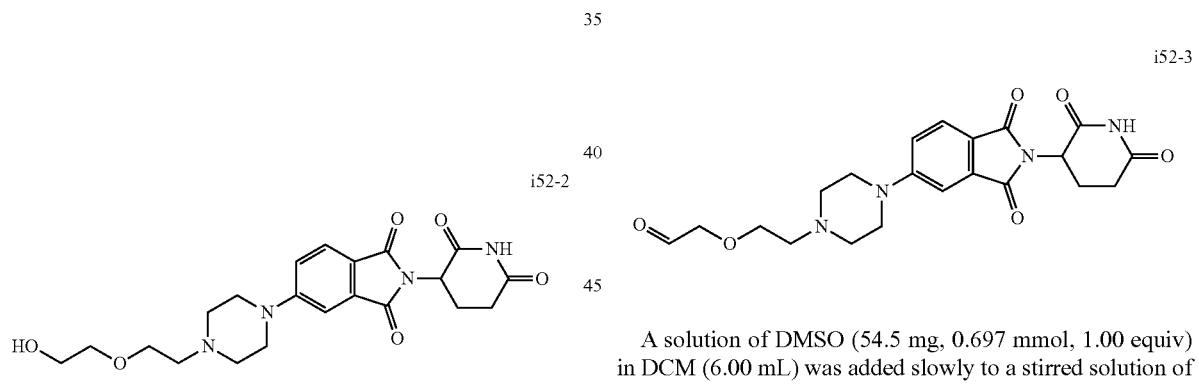

To a solution of 2-[2-(piperazin-1-yl) ethoxy]ethan-1-ol (315.4 mg, 1.810 mmol, 1.00 equiv) and 2-(2,6-dioxopiperidin-3-yl)-5-fluoro-2,3-dihydro-1H-isoindole-1,3-dione (500.0 mg, 1.810 mmol, 1.00 equiv) in NMP (5 mL) was added DIEA (467.9 mg, 3.620 mmol, 2.00 equiv). The resulting mixture was stirred for 3 hours at 90° C. Without any additional work-up, the mixture was purified by reverse phase column, elution gradient 0% to 50% ACN in water to afford 2-(2,6-dioxopiperidin-3-yl)-5-[4-[2-(2-hydroxyethoxy)ethyl]piperazin-1-yl]-2,3-dihydro-1H-isoindole-1,3-dione (700.0 mg, 89.8%) as a yellow solid. LCMS (ESI) m/z: [M+H]$^+$=431.

Step 2: Preparation of 2-(2-(4-(2-(2,6-Dioxopiperidin-3-Y1)-1,3-Dioxoisoindolin-5-Yl) Piperazin-1-Yl) Ethoxy) Acetaldehyde (i52-3)

i52-3

A solution of DMSO (54.5 mg, 0.697 mmol, 1.00 equiv) in DCM (6.00 mL) was added slowly to a stirred solution of oxalyl chloride (176.9 mg, 1.394 mmol, 2.00 equiv) in DCM (6.00 mL) at −78° C. under nitrogen atmosphere. After 30 minutes 2-(2,6-dioxopiperidin-3-yl)-5-[4-[2-(2-hydroxyethoxy)ethyl]piperazin-1-yl]isoindole-1,3-dione (300.0 mg, 0.697 mmol, 1.00 equiv) in DCM (6.00 mL) was added slowly. The resulting mixture was stirred for 2 hours at −78° C. and 1.5 hours at −55° C. EtsN (0.48 mL, 4.787 mmol, 5.00 equiv) was added slowly at −60° C. After stirring for an additional 10 minutes, the reaction was allowed to warm to room temperature. The resulting mixture was quenched with saturated ammonium chloride aqueous solution (50 mL) and extracted with DCM (100 mL×3). The combined organic layers were washed with brine (50 mL), dried over anhydrous sodium sulfate, filtered, and concentrated in vacuo. The residue was purified by prep-TLC(EtOAc/PE=1:1) to afford 2-(2-(4-(2-(2,6-dioxopiperidin-3-yl)-1,3-dioxoisoindolin-5-yl) piperazin-1-yl) ethoxy) acetaldehyde (30.0 mg, 5.7%) as a yellow solid. LCMS (ESI) m/z: [M+H]$^+$=429.

Step 3: Preparation of 5-(4-(2-(2-((2,6-Dimethoxy-4-(2-Methyl-1-Oxo-1,2-Dihydro-2,7-Naphthyri Din-4-Yl)Benzyl)(Methyl)Amino) Ethoxy)Ethyl) Piperazin-1-Yl)-2-(2,6-Dioxopiperidin-3-Yl) Isoindoline-1,3-Dione Formic Acid (Compound D46 Formic Acid)

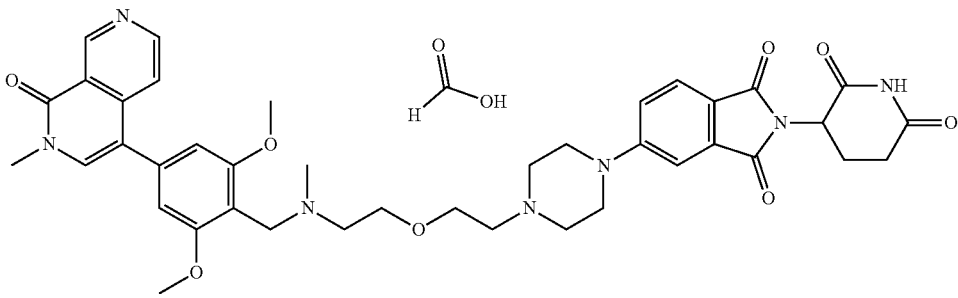

compound D46 formic acid

To a mixture of 2-(2-[4-[2-(2,6-dioxopiperidin-3-yl)-1,3-dioxoisoindol-5-yl]piperazin-1-yl]eth oxy) acetaldehyde (30.0 mg, 0.070 mmol, 1.00 equiv) in DMF (2.00 mL) was added 4-[3,5-dim ethoxy-4-[(methylamino)methyl]phenyl]-2-methyl-2,7-naphthyridin-1-one (23.7 mg, 0.070 mmol, 1.00 equiv). The resulting mixture was stirred for 1 hour at room temperature, STAB (29.6 mg, 0.140 mmol, 2.00 equiv) was added. The resulting mixture was stirred for 1 hour at room temperature. The resulting mixture, without any additional wok-up, was purified by prep-HPLC(conditions: SunFire C18 OBD Prep Column, 100 Å, 5 μm, 19 mm×250 mm; Mobile Phase A: Water (0.1% FA), Mobile Phase B: ACN; Flow rate: 25 mL/minute; Gradient: 5% B to 30% B in 10 minutes; 254 nm; RT: 8.82 minutes) to afford 5-(4-(2-(2-((2,6-dimethoxy-4-(2-methyl-1-oxo-1,2-dihydro-2,7-naphthyridin-4-yl)benzyl)(methyl)amino) ethoxy)ethyl) piperazin-1-yl)-2-(2,6-dioxopiperidin-3-yl) isoindoline-1,3-dione;formate (6.2 mg, 15.6%) as a light yellow solid. LCMS (ESI) m/z: [M+H]$^+$=752.15. $^1$H NMR (300 MHz, Methanol-d4)δ 9.47 (s, 1H), 8.64 (d, J=5.8 Hz, 1H), 8.57 (br s, 0.7H), 7.75 (s, 1H), 7.62 (dd, J=12.9, 7.1 Hz, 2H), 7.28 (d, J=2.3 Hz, 1H), 7.19 (d, J=9.0 Hz, 1H), 6.89 (s, 2H), 5.07 (dd, J=12.3, 5.4 Hz, 1H), 4.53 (s, 2H), 3.99 (s, 6H), 3.91 (t, J=4.7 Hz, 2H), 3.76 (t, J=5.1 Hz, 2H), 3.67 (s, 3H), 3.53-3.40 (m, 6H), 2.91 (s, 4H), 2.81-2.67 (m, 8H), 2.18-2.05 (m, 1H).

Example 53—Preparation of 5-[[5-(9-[[2,6-Dimethoxy-4-(2-Methyl-1-Oxo-2,7-Naphthyridin-4-Yl) Phenyl]Methyl]-1-Oxa-4,9-Diazaspiro[5.5]Undecan-4-Yl) Pentyl]Oxy]-2-(2,6-Dioxopiperidin-3-Yl) Isoindole-1,3-Dione Formic Acid (Compound D47 Formic Acid)

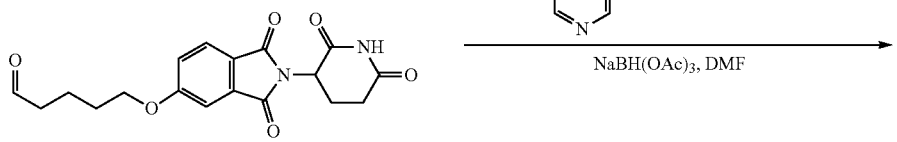

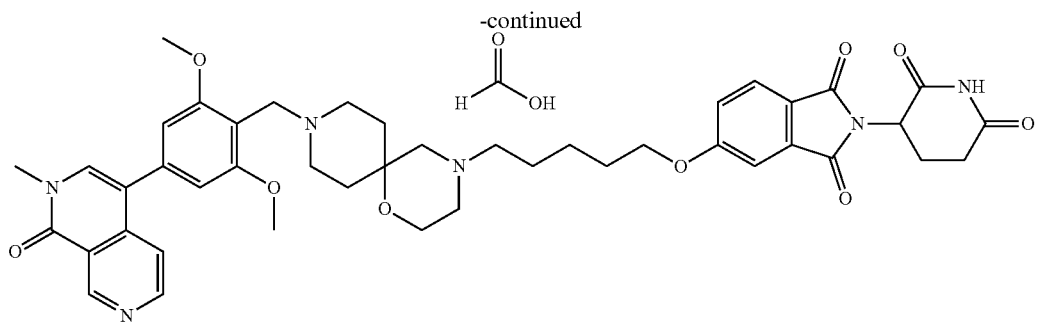

compound D47 formic acid

A solution of 5-[2-(2,6-dioxopiperidin-3-yl)-1,3-dioxoisoindol-5-yl]oxy]pentanal (25 mg, 0.070 mmol, 1.00 equiv) and 4-(3,5-dimethoxy-4-[1-oxa-4,9-diazaspiro[5.5]undecan-9-ylmethyl]phenyl)-2-methyl-2,7-naphthyridin-1-one (32.4 mg, 0.070 mmol, 1.00 equiv) in DMF (0.8 mL) was stirred for 30 minutes at room temperature. NaBH(OAc)$_3$ (29.57 mg, 0.140 mmol, 2.00 equiv) was then added and the resulting mixture was stirred for 1 hour at room temperature. Without any additional work-up, the mixture was purified by Prep-HPLC(conditions: SunFire C18 OBD Prep Column, 100 Å, 5 μm, 19 mm×250 mm;Mobile Phase A: Water (0.1% FA), Mobile Phase B: ACN; Flow rate: 25 mL/minute; Gradient: 7% B to 20% B in 12 minutes; 254 nm; Rt: 11.57 minutes) to afford 5-[[5-(9-[2,6-dimethoxy-4-(2-methyl-1-oxo-2,7-naphthyridin-4-yl)phenyl]methyl]-1-oxa-4,9-diazaspiro[5.5]undecan-4-yl) pentyl]oxy]-2-(2,6-dioxopiperidin-3-yl) isoindole-1,3-dione formic acid (7.9 mg, 13%) as a white solid. $^1$H NMR (300 MHZ, Methanol-d4) δ 9.55 (s, 1H), 8.69 (d, J=5.8 Hz, 1H), 8.50 (br s, 1H, FA), 7.86-7.75 (m, 2H), 7.63 (d, J=5.8 Hz, 1H), 7.40 (d, J=2.2 Hz, 1H), 7.32 (dd, J=8.3, 2.3 Hz, 1H), 6.88 (s, 2H), 5.11 (dd, J=12.3, 5.4 Hz, 1H), 4.42 (s, 2H), 4.19 (t, J=6.2 Hz, 2H), 3.98 (s, 6H), 3.76 (t, J=4.9 Hz, 2H), 3.72 (s, 3H), 3.44-3.35 (3H), 2.93-2.67 (m, 3H), 2.53-2.10 (m, 10H), 1.98-1.51 (m, 8H). LCMS (ESI) m/z: [M+H]$^+$=807.50.

Example 54—Preparation of N-(6-[4-[(Dimethylamino)Methyl]-3,5-Dimethoxyphenyl]-3-Methyl-[1,2,4]Triazolo[4,3-a]Pyridin-8-Yl) Acetamide Formic Acid (Compound D48 Formic Acid)

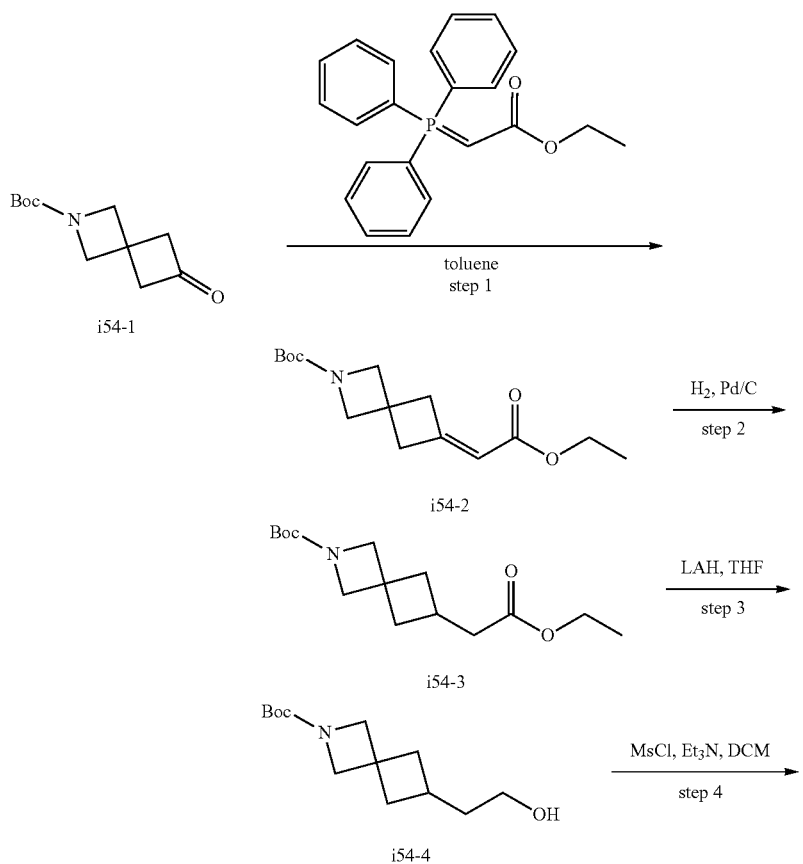

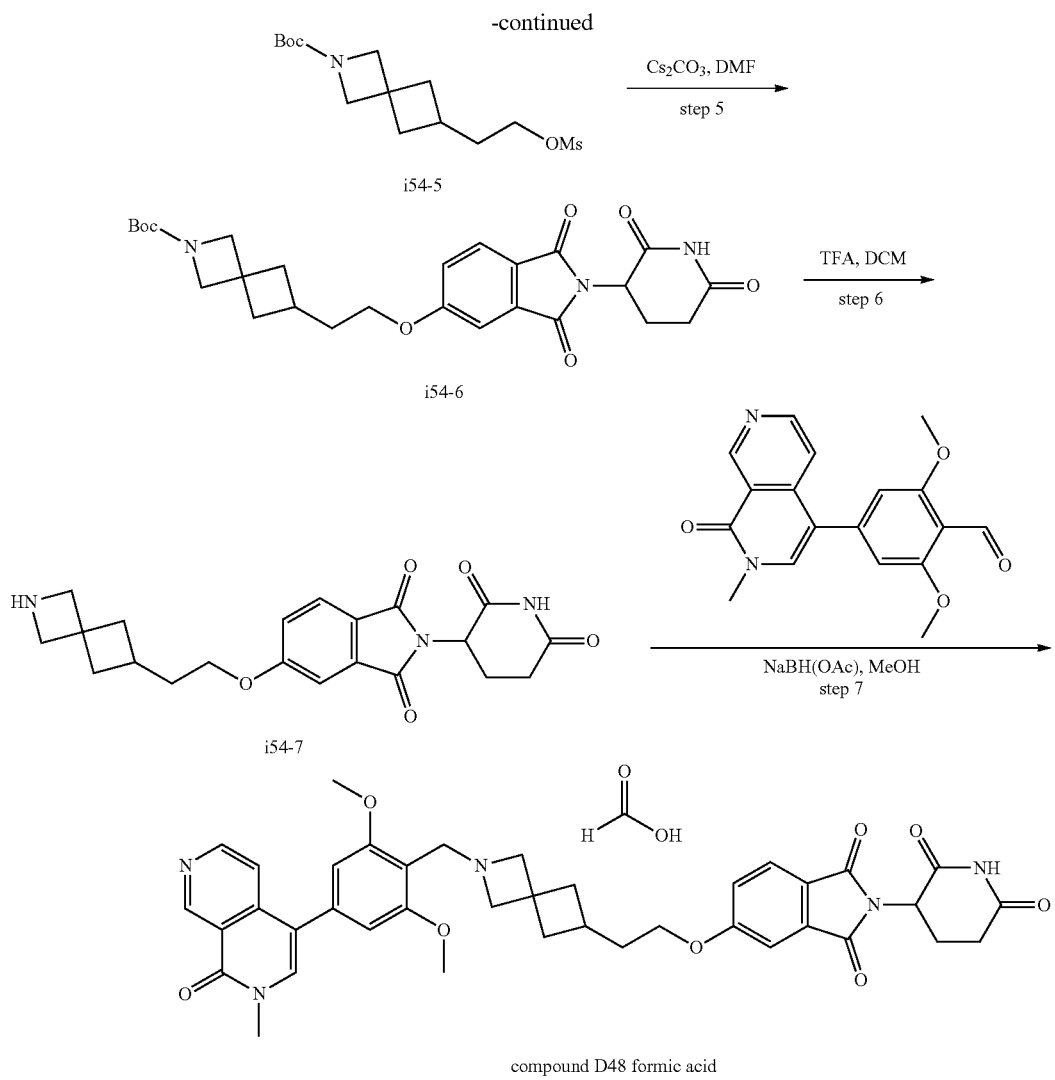

Step 1: Preparation of Tert-Butyl 6-(2-Ethoxy-2-Oxoethylidene)-2-Azaspiro[3.3]Heptane-2-Carboxylate (i54-2)

Step 2: Preparation of Tert-Butyl 6-(2-Ethoxy-2-Oxoethyl)-2-Azaspiro[3.3]Heptane-2-Carboxylate (i54-3)

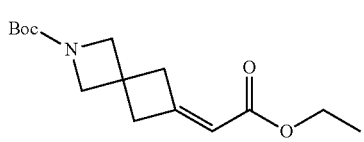

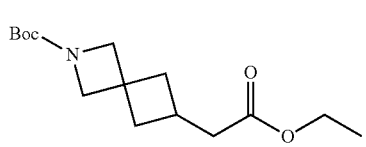

A solution of tert-butyl 6-oxo-2-azaspiro[3.3]heptane-2-carboxylate (2.0 g, 9.467 mmol, 1.00 equiv) and ethyl 2-(triphenyl-lambda5-phosphanylidene)acetate (3.63 g, 10.414 mmol, 1.10 equiv) in toluene was stirred for 4 hours at 80° C. under nitrogen atmosphere. The resulting mixture was washed with water (3×30 mL). The resulting mixture was concentrated under vacuum. The residue was purified by silica gel column chromatography, eluted with PE/EtOAc (1:1) to afford tert-butyl 6-(2-ethoxy-2-oxoethylidene)-2-azaspiro[3.3]heptane-2-carboxylate (2.51 g, 94.09%) as a light yellow oil. LCMS (ESI) m/z: [M+H]$^+$=282.

To a solution of tert-butyl 6-(2-ethoxy-2-oxoethylidene)-2-azaspiro[3.3]heptane-2-carboxylate (2506.00 mg, 8.907 mmol, 1.00 equiv) in MeOH (25 mL) was added Pd/C(10%, 1 g) under nitrogen atmosphere. The mixture was hydrogenated at room temperature for 1 day under hydrogen atmosphere using a hydrogen balloon, filtered through a Celite pad, and concentrated under reduced pressure afford tert-butyl 6-(2-ethoxy-2-oxoethyl)-2-azaspiro[3.3]heptane-2-carboxylate (2100.00 mg, 81.4%) as a light yellow oil. LCMS (ESI) m/z: [M+H]$^+$=284.

Step 3: Preparation of Tert-Butyl 6-(2-Hydroxy-ethyl)-2-Azaspiro[3.3]Heptane-2-Carboxylate (i54-4)

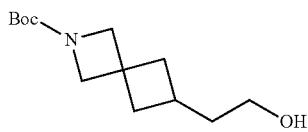

i-54-4

To a stirred solution of tert-butyl 6-(2-ethoxy-2-oxo-ethyl)-2-azaspiro[3.3]heptane-2-carboxylate (1.0 g, 3.529 mmol, 1.00 equiv) in THF (20 ml) was added LAH (267.88 mg, 7.058 mmol, 2 equiv) in portions at 0° C. under nitrogen atmosphere. The reaction was quenched with Na$_2$SO$_4$·10H$_2$O at room temperature. The resulting mixture was filtered. The filter cake was washed with MeOH (3×20 mL). The filtrate was concentrated under reduced pressure. The crude product (537.00 mg, 63.0%) was used in the next step directly without further purification. LCMS (ESI) m/z: [M+H]$^+$=242.

Step 4: Preparation of Tert-Butyl 6-(2-((Methyl-sulfonyl)Oxy)Ethyl)-2-Azaspiro[3.3]Heptane-2-Carboxylate (i54-5)

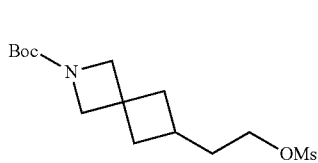

i54-5

A solution of tert-butyl 6-(2-hydroxyethyl)-2-azaspiro[3.3]heptane-2-carboxylate (537.00 mg, 2.225 mmol, 1.00 equiv), Et$_3$N (450.33 mg, 4.450 mmol, 2.00 equiv), and MsCl (280.38 mg, 2.448 mmol, 1.10 equiv) in DCM (5 mL) was stirred for 3 hours at room temperature under nitrogen atmosphere. The resulting mixture was extracted with EtOAc (1×20 mL). The combined organic layers were washed with water (3×10 mL), dried over anhydrous Na$_2$SO$_4$, and concentrated. The residue was purified by silica gel column chromatography, eluted with CH$_2$Cl$_2$/MeOH (0% to 18%) to afford tert-butyl 6-[2-(methanesulfonyloxy)ethyl]-2-azaspiro[3.3]heptane-2-carboxylate (593 mg, 83.43%) as a white solid. LCMS (ESI) m/z: [M+H]$^+$=320

Step 5: Preparation of Tert-Butyl 6-(2-((2-(2,6-Di-oxopiperidin-3-Yl)-1,3-Dioxoisoindolin-5-Yl)Oxy)Ethyl)-2-Azaspiro[3.3]Heptane-2-Carboxylate (i54-6)

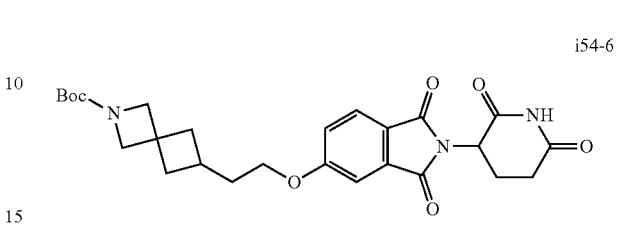

i54-6

A solution of tert-butyl 6-[2-(methanesulfonyloxy)ethyl]-2-azaspiro[3.3]heptane-2-carboxylate (320.00 mg, 1.002 mmol, 1.00 equiv), Cs$_2$CO$_3$ (652.82 mg, 2.004 mmol, 2.00 equiv), and 2-(2,6-dioxopiperidin-3-yl)-5-hydroxyisoindole-1,3-dione (274.73 mg, 1.002 mmol, 1.00 equiv) in DMF (3 mL) was stirred for 15 hours at room temperature under nitrogen atmosphere. The resulting mixture was extracted with EtOAc (1×100 mL). The combined organic layers was washed with water (3×100 mL), dried over anhydrous Na$_2$SO$_4$. After filtration, the filtrate was concentrated under reduced pressure to afford tert-butyl6-(2-[2-(2,6-dioxopiperidin-3-yl)-1,3-dioxoisoindol-5-yl]oxy]ethyl)-2-azaspiro[3.3]heptane-2-carboxylate (265.0 0 mg, 53.2%) as a yellow oil. LCMS (ESI) m/z: [M+H]$^+$=498.

Step 6: Preparation of 5-(2-(2-Azaspiro[3.3]Heptan-6-Yl) Ethoxy)-2-(2,6-Dioxopiperidin-3-Yl) Isoindo-line-1,3-Dione (i54-7)

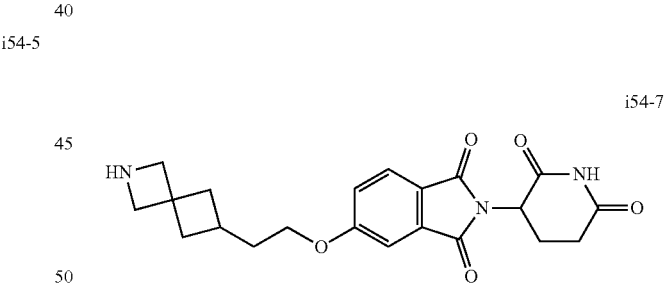

i54-7

A solution of tert-butyl 6-(2-[[2-(2,6-dioxopiperidin-3-yl)-1,3-dioxoisoindol-5-yl]oxy]ethyl)-2-azaspiro[3.3]hep-tane-2-carboxylate (265.00 mg, 0.533 mmol, 1.00 equiv) and TFA (2.5 mL) in DCM (5.0 mL) was stirred for 1.5 hours at room temperature under nitrogen atmosphere. The resulting mixture was concentrated under reduced pressure. The residue was purified by Prep-TLC(CH$_2$Cl$_2$/EtOAc 1:1) to afford 5-(2-[2-azaspiro[3.3]heptan-6-yl]ethoxy)-2-(2,6-di-oxopiperidin-3-yl) isoindole-1,3-dione (200 mg, 94.48%) as a yellow oil. LCMS (ESI) m/z: [M+H]$^+$=398.

Step 7: Preparation of 5-(2-(2-(2,6-Dimethoxy-4-(2-Methyl-1-Oxo-1,2-Dihydro-2,7-Naphthyridin-4-Yl)Benzyl)-2-Azaspiro[3.3]Heptan-6-Yl) Ethoxy)-2-(2,6-Dioxopiperidin-3-Yl) Isoindoline-1,3-Dione Formic Acid (Compound D48 Formic Acid)

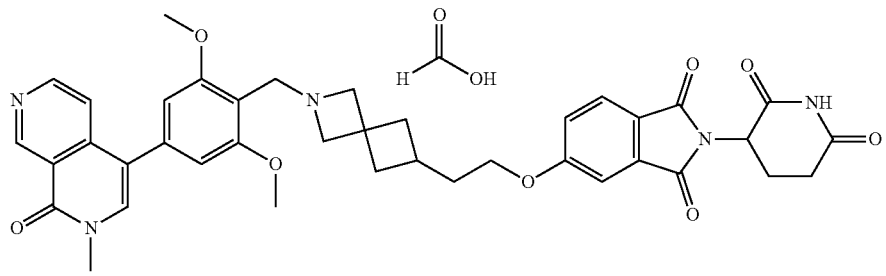

compound D48 formic acid

A solution of 5-(2-[2-azaspiro[3.3]heptan-6-yl]ethoxy)-2-(2,6-dioxopiperidin-3-yl) isoindole-1,3-dione (51.00 mg, 0.128 mmol, 1.00 equiv) in MeOH (1 mL) was treated with 2,6-dimethoxy-4-(2-methyl-1-oxo-2,7-naphthyridin-4-yl) benzaldehyde (41.62 mg, 0.128 mmol, 1.00 equiv) for 20 minutes at room temperature under nitrogen atmosphere followed by the addition of NaBH$_3$CN (16.13 mg, 0.257 mmol, 2.00 equiv) in portions at room temperature. The residue was purified by reverse flash chromatography (conditions: column, C18 silica gel; mobile phase, MeOH in water, 10% to 50% gradient in 10 minutes; detector, UV 254 nm). This resulted in 5-(2-(2-(2,6-dimethoxy-4-(2-methyl-1-oxo-1,2-dihydro-2,7-naphthyridin-4-yl)benzyl)-2-azaspiro[3.3]heptan-6-yl) ethoxy)-2-(2,6-dioxopiperidin-3-yl) iso indoline-1,3-dione formic acid (2.4 mg, 2.2%) as a yellow solid. $^1$H NMR (300 MHZ, Methanol-d4) δ 9.54 (s, 1H), 8.68 (d, J=5.7 Hz, 1H), 8.56 (brs, 1.1H, FA), 7.77 (s, 1H), 7.68-7.56 (m, 2H), 7.13 (d, J=2.2 Hz, 1H), 7.05 (dd, J=8.2, 2.2 Hz, 1H), 6.85 (s, 2H), 5.10 (dd, J=12.9, 5.5 Hz, 1H), 4.40 (s, 2H), 4.21-4.12 (m, 2H), 4.05 (s, 2H), 3.96 (s, 6H), 3.79-3.70 (m, 5H), 2.95-2.84 (m, 2H), 2.75-2.59 (m, 1H), 2.49-2.36 (m, 2H), 2.27-2.06 (m, 2H), 2.05-1.92 (m, 2H), 1.72-1.54 (m, 2H). LCMS (ESI) m/z: [M+H]$^+$=706.50.

Example 55—Preparation of 5-[2-(9-[[2,6-Dimethoxy-4-(2-Methyl-1-Oxo-2,7-Naphthyridin-4-Yl)Phenyl]Methyl]-1-Oxa-4,9-Diazaspiro[5.5]Undecan-4-Yl) Ethoxy]-2-(2,6-Dioxopiperidin-3-Yl) Isoindole-1,3-Dione (Compound D49)

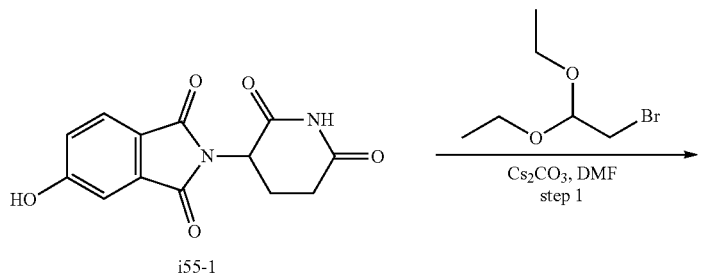

i55-1

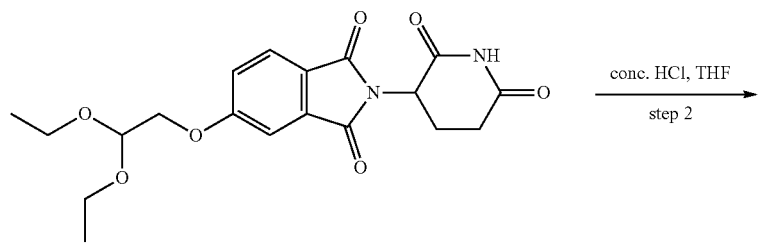

i55-2

-continued

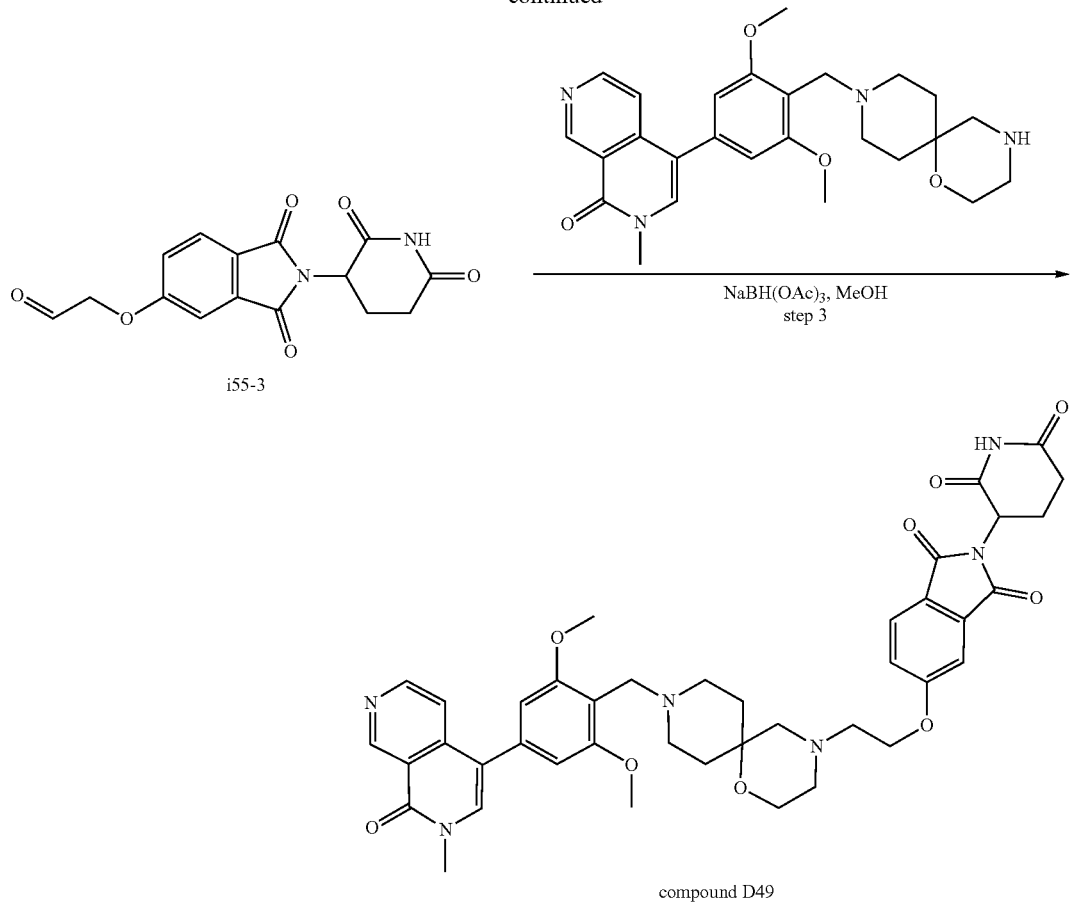

i55-3

NaBH(OAc)₃, MeOH
step 3 compound D49

Step 1: Preparation of 5-(2,2-Diethoxyethoxy)-2-(2, 6-Dioxopiperidin-3-Yl) Isoindole-1,3-Dione (i55-2)

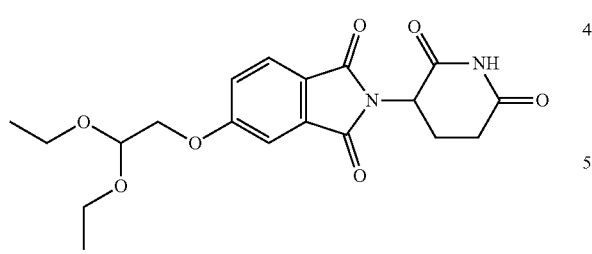

i55-2

To a stirred solution of 2-(2,6-dioxopiperidin-3-yl)-5-hydroxyisoindole-1,3-dione (500.00 mg, 1.823 mmol, 1.00 equiv) and Cs₂CO₃ (980.20 mg, 3.008 mmol, 3 equiv) in DMF (10.00 mL) was added 2-bromo-1,1-diethoxyethane (538.97 mg, 2.735 mmol, 1.5 equiv). The mixture was stirred at 80° C. for 16 hours. The mixture was acidified to pH 6 with HCl (aq.). The mixture was diluted with water (40 mL) and extracted with EtOAc/DCM (60 mL×3). The organic layers were combined and dried over anhydrous sodium sulfate, filtered, and concentrated to give a crude product. The residue was purified by Prep-TLC (PE/EtOAc 1:1) to afford 5-(2,2-diethoxyethoxy)-2-(2,6-dioxopiperidin-3-yl) isoindole-1,3-dione (110 mg, 15.45%) as a yellow solid. LCMS (ESI) m/z: [M+H]⁺=391.

Step 2: Preparation of 2-[[2-(2,6-Dioxopiperidin-3-Yl)-1,3-Dioxoisoindol-5-Yl]Oxy]Acetaldehyde (i55-3)

i55-3

To a stirred solution of 5-(2,2-diethoxyethoxy)-2-(2,6-dioxopiperidin-3-yl) isoindole-1,3-dione (100.00 mg, 0.256 mmol, 1.00 equiv) in THF (2.00 mL) was added HCl (4 M) (2.00 mL). The mixture was stirred at room temperature for 4 hours. The mixture was diluted with water (20 mL) and extracted with EtOAc/DCM (30 mL×3). The organic layers were combined and dried over anhydrous sodium sulfate, filtered, and concentrated to give a crude product. This resulted in 2-[2-(2,6-dioxopiperidin-3-yl)-1,3-dioxoisoindol-5-yl]oxy]aceta ldehyde (95 mg,crude) as a white solid. LCMS (ESI) m/z: [M+H]⁺=317.

Step 3: Preparation of 5-[2-(9-[[2,6-Dimethoxy-4-(2-Methyl-1-Oxo-2,7-Naphthyridin-4-Yl)Phenyl]Methyl]-1-Oxa-4,9-Diazaspiro[5.5]Undecan-4-Yl)Ethoxy]-2-(2,6-Dioxopiperidin-3-Yl) Isoindole-1,3-Dione (Compound D49)

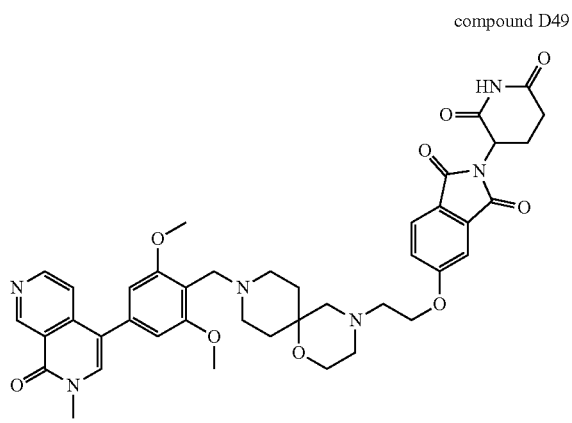 [SMILES: COc1cc(-c2cn(C)c(=O)c3cnccc23)cc(OC)c1CN1CCC2(CC1)CN(CCOc1ccc3c(c1)C(=O)N(C1CCC(=O)NC1=O)C3=O)CCO2]

compound D49

To a stirred solution of 2-[2-(2,6-dioxopiperidin-3-yl)-1,3-dioxoisoindol-5-yl]oxy]acetaldehyde (60.00 mg, 0.190 mmol, 1.00 equiv) and 4-(3,5-dimethoxy-4-[1-oxa-4,9-diazaspiro[5.5]undecan-9-ylmethyl]phenyl)-2-methyl-2,7-naphthyridin-1-one (88.13 mg, 0.190 mmol, 1.00 equiv) in DMF (1.50 mL) was added NaBH(OAc)$_3$ (80.42 mg, 0.379 mmol, 2.00 equiv). The mixture was stirred at room temperature for 2 hours. Without any additional work-up, the mixture was purified by prep-HPLC (conditions: Xcelect CSH F-pheny OBD Column, 19*250 mm, 5 um; Mobile Phase A: Water (0.05% TFA), Mobile Phase B: ACN; Flow rate: 25 mL/minute; Gradient: 11 B to 19 B in 12 minutes; 254/220 nm; RT: 10.70 minutes) to give 5-[2-(9-[[2,6-dimethoxy-4-(2-methyl-1-oxo-2,7-naphthyridin-4-yl)phenyl]methyl]-1-oxa-4,9-diazaspiro[5.5]undecan-4-yl) ethoxy]-2-(2,6-dioxopiperidin-3-yl) isoindole-1,3-dione (8.2 mg, 5.5 2%) as a yellow solid. $^1$H NMR (300 MHZ, Methanol-d4) δ 9.59 (s, 1H), 8.71 (s, 1H), 7.96 (d, J=7.2 Hz, 1H), 7.82 (d, J=11.3 Hz, 1H), 7.71 (t, J=8.8 Hz, 1H), 7.24-7.05 (m, 2H), 6.85 (d, J=18.8 Hz, 2H), 5.32-5.16 (m, 1H), 4.43 (s, 2H), 4.20 (s, 2H), 3.97 (s, 7H), 3.90 (s, 1H), 3.75 (s, 3H), 3.59-3.38 (m, 4H), 3.31-3.12 (m, 5H), 3.05-2.86 (m, 2H), 2.82-2.63 (m, 1H), 2.47-1.84 (m, 5H). LCMS (ESI) m/z: [M+H]$^+$=765.45.

Example 56—Preparation of 5-(4-(9-(2,6-Dimethoxy-4-(2-Methyl-1-Oxo-1,2-Dihydro-2,7-Naphthyridin-4-Yl)Benzyl)-1-Oxa-4,9-Diazaspiro[5.5]Undecan-4-Yl) Butoxy)-2-(2,6-Dioxopiperidin-3-Yl) Isoindoline-1,3-Dione (Compound D50)

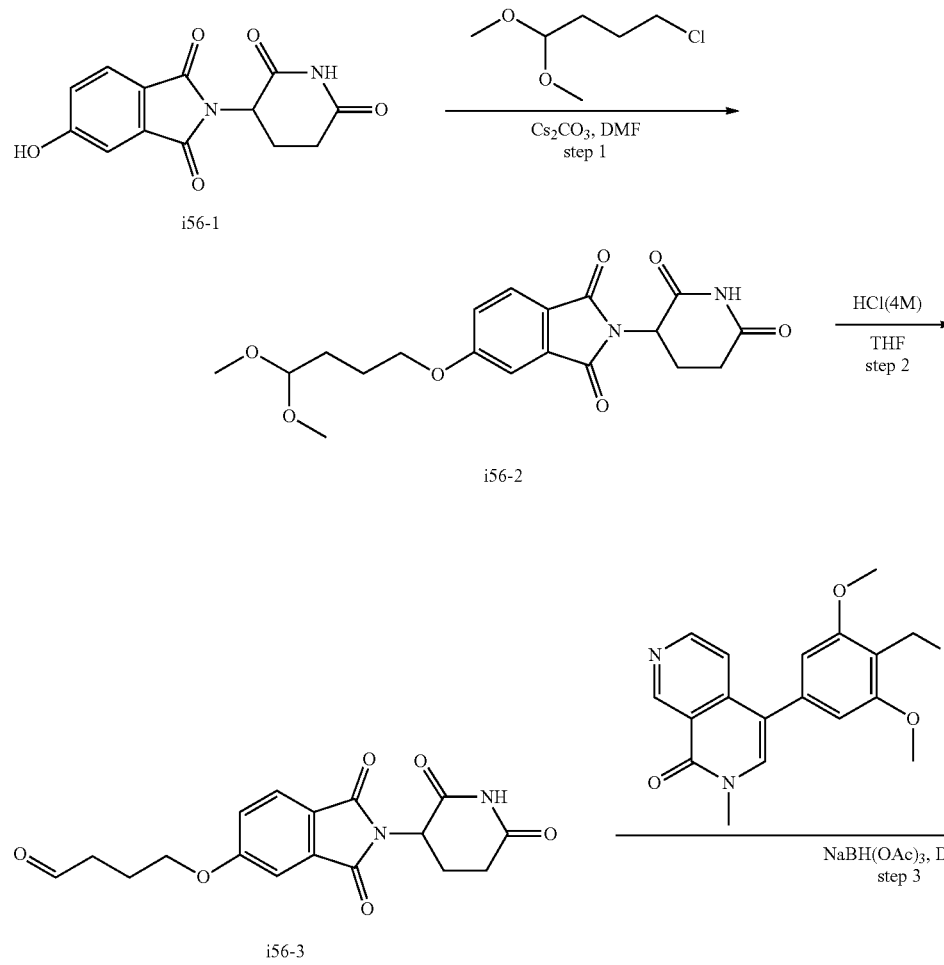

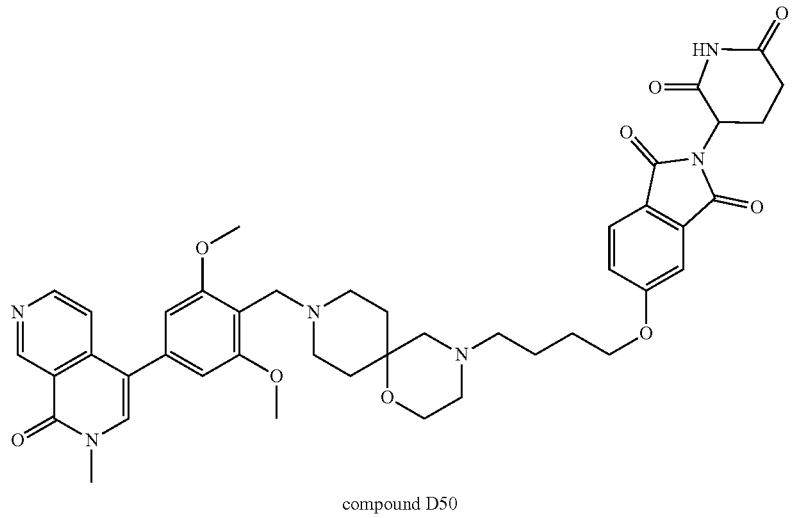

compound D50

Step 1: Preparation of 5-(4,4-Dimethoxybutoxy)-2-(2,6-Dioxopiperidin-3-Yl) Isoindoline-1,3-Dione (i56-2)

Step 2: Preparation of 4-((2-(2,6-Dioxopiperidin-3-Yl)-1,3-Dioxoisoindolin-5-Yl)Oxy) Butanal (i56-3)

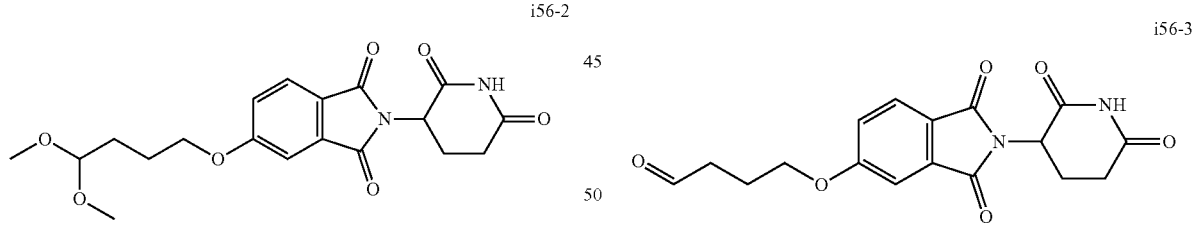

To a solution of 2-(2,6-dioxopiperidin-3-yl)-5-hydroxyisoindole-1,3-dione (500.00 mg, 1.823 mmol, 1.00 equiv) and 4-chloro-1,1-dimethoxybutane (278.27 mg, 1.823 mmol, 1 equiv) in DMF (7.00 mL) was added $K_2CO_3$ (755.96 mg, 5.470 mmol, 3 equiv). The resulting solution was stirred at 80° C. for 12 hours. The resulting mixture was extracted with EA (50 mL×2). The combined organic layers were washed with saturated NaCl (50 mL) and dried over anhydrous $Na_2SO_4$. After filtration, the filtrate was concentrated under reduced pressure. The residue was purified by silica gel column chromatography, eluted with EA/PE (100:0) to afford 5-(4,4-dimethoxybutoxy)-2-(2,6-dioxopiperidin-3-yl) isoindole-1,3-dione (43.6 mg, 6.13%) as an off-white solid. LCMS (ESI) m/z: [M+H]$^+$=391.

A solution of 5-(4,4-dimethoxybutoxy)-2-(2,6-dioxopiperidin-3-yl) isoindole-1,3-dione (43.60 mg, 0.112 mmol, 1.00 equiv) and HCl (1.00 mL, 4M) in THF (1.00 mL) was stirred at 25° C. for 1 hour. The resulting mixture was extracted with EA (50 mL×2). The combined organic layers were washed with saturated NaCl (50 mL) and dried over anhydrous $Na_2SO_4$. After filtration, the filtrate was concentrated under reduced pressure to afford 4-[2-(2,6-dioxopiperidin-3-yl)-1,3-dioxoisoindol-5-yl]oxy]butanal (34.6 mg, 89.98%) as an off-white solid. LCMS (ESI) m/z: [M+H]$^+$=345.

Step 3: Preparation of 5-(4-(9-(2,6-Dimethoxy-4-(2-Methyl-1-Oxo-1,2-Dihydro-2,7-Naphthyridin-4-Yl) Benzyl)-1-Oxa-4,9-Diazaspiro[5.5]Undecan-4-Yl) Butoxy)-2-(2,6-Dioxopiperidin-3-Yl) Isoindoline-1, 3-Dione (Compound D50)

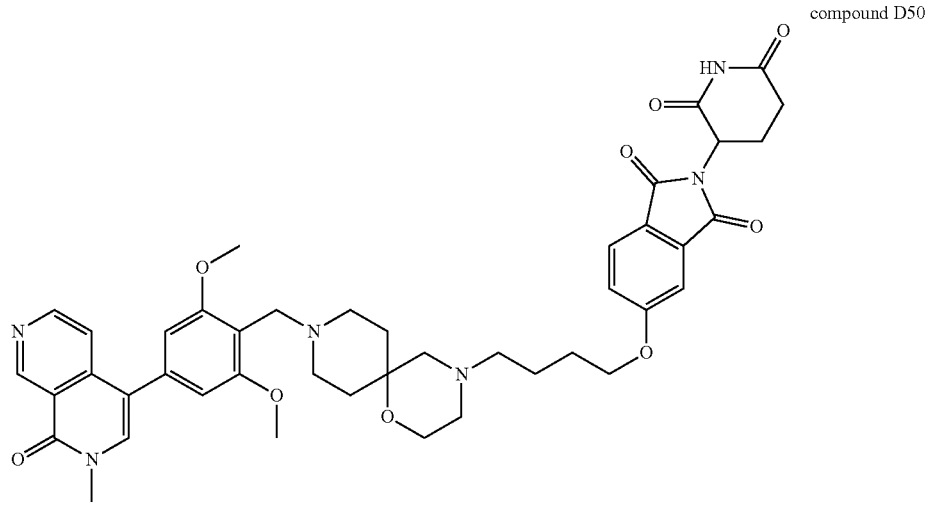 [SMILES: COc1cc(-c2cn(C)c(=O)c3cnccc23)cc(OC)c1CN1CCC2(CC1)CN(CCCCOc1ccc3c(c1)C(=O)N(C1CCC(=O)NC1=O)C3=O)CCO2]
compound D50

To a solution of 4-[2-(2,6-dioxopiperidin-3-yl)-1,3-dioxoisoindol-5-yl]oxy]butanal (34.00 mg, 0.099 mmol, 1.00 equiv) and 4-(3,5-dimethoxy-4-[1-oxa-4,9-diazaspiro[5.5] undecan-9-ylmethyl]phenyl)-2-methyl-2,7-naphthyridin-1-one (45.87 mg, 0.099 mmol, 1 equiv) in DMF (1.00 mL) was added NaBH (OAc)$_3$ (41.86 mg, 0.197 mmol, 2 equiv). The resulting solution was stirred at 25° C. for 1 hour. The mixture was purified by prep-HPLC(conditions: Xselect CSH F-Phenyl OBD Column 19*150 mm 5 um; Mobile Phase A: Water (0.05% TFA), Mobile Phase B: ACN; Flow rate: 25 mL/minute; Gradient: 10 B to 19 B in 15 minutes; 254/220 nm; RT: 14.53 minutes) to afford 5-[4-(9-[2,6-dimethoxy-4-(2-methyl-1-oxo-2,7-naphthyridin-4-yl)phenyl]methyl]-1-oxa-4,9-diazaspiro[5.5]undecan-4-yl) butoxy]-2-(2,6-dioxopiperidin-3-yl) isoindole-1,3-dione (14 mg, 17.88%) as an off-white solid. $^1$H NMR (300 MHZ, Methanol-d4) δ 9.57 (s, 1H), 8.70 (d, J=6.0 Hz, 1H), 7.87 (s, 1H), 7.74 (d, J=7.7 Hz, 2H), 7.27-7.14 (m, 2H), 6.89 (s, 2H), 5.16 (dd, J=12.8, 5.5 Hz, 1H), 4.45 (s, 2H), 4.09-4.01 (m, 2H), 3.98 (s, 6H), 3.89 (t, J=6.4 Hz, 2H), 3.73 (s, 3H), 3.57-3.48 (m, 2H), 3.28-3.17 (m, 4H), 2.98-2.87 (m, 2H), 2.85-2.59 (m, 2H), 2.41-2.25 (m, 1H), 2.23-2.07 (m, 2H), 2.05-1.90 (m, 2H), 1.89-1.59 (m, 5H). LCMS (ESI) m/z: [M+H]$^+$=793.3.

Example 57—Preparation of 5-[2-[4-([[2,6-Dimethoxy-4-(2-Methyl-1-Oxo-2,7-Naphthyridin-4-Yl) Phenyl]Methyl](Methyl)Amino) Piperidin-1-Yl] Ethoxy]-2-(2,6-Dioxopiperidin-3-Yl) Isoindole-1,3-Dione; Formic Acid (Compound D51 Formic Acid)

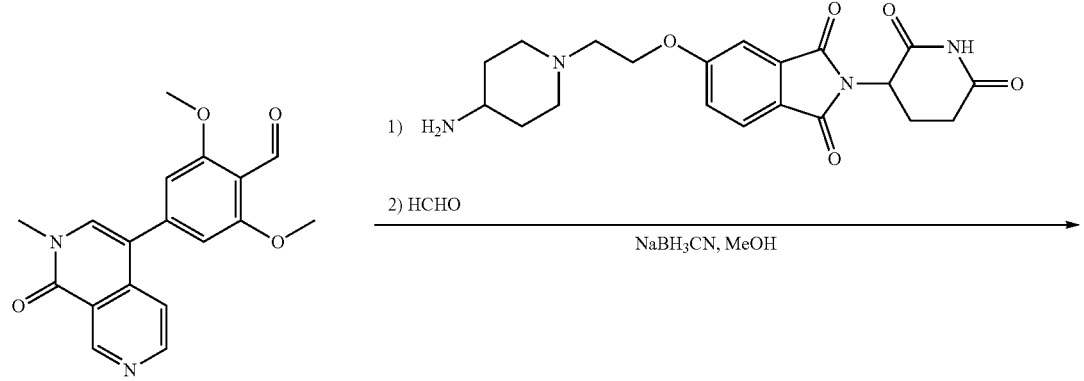

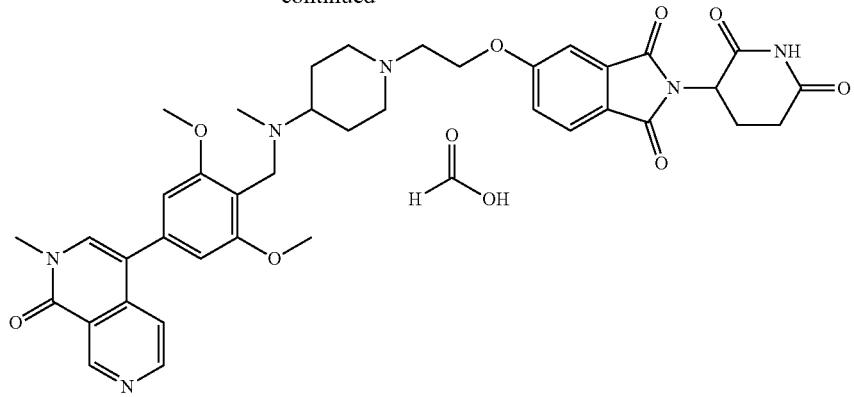

compound D51 formic acid

To a solution of 2,6-dimethoxy-4-(2-methyl-1-oxo-2,7-naphthyridin-4-yl)benzaldehyde (30.00 mg, 0.092 mmol, 1.00 equiv) and 5-[2-(4-aminopiperidin-1-yl) ethoxy]-2-(2,6-dioxopiperidin-3-yl) isoindole-1,3-dione (37.04 mg, 0.092 mmol, 1.00 equiv) in MeOH (1 mL) was stirred for 3 hours at room temperature under nitrogen atmosphere. To the above mixture was added NaBH$_3$CN (11.63 mg, 0.185 mmol, 2.00 equiv), and the reaction was stirred for additional 1 hour at room temperature. To the above mixture was added HCHO (27.77 mg, 0.925 mmol, 10.00 equiv), and the reaction was stirred for 1 hour at room temperature under nitrogen atmosphere. Then NaBH$_3$CN (11.63 mg, 0.185 mmol, 2.00 equiv) was added. The mixture was stirred for overnight at room temperature under nitrogen atmosphere. The crude product (40 mg) was purified by Prep-HPLC (conditions: Gemini-NX C18 AXAI Packed column, 21.2*150 mm 5 um; Mobile Phase A: Water (0.1% FA), Mobile Phase B: ACN; Flow rate: 25 mL/minute; Gradient: 5 B to 17 B in 9 minutes; 254-220 nm; RT: 8.30 minutes) to afford 5-[2-[4-([2,6-dimethoxy-4-(2-methyl-1-oxo-2,7-naphthyridin-4-yl)phenyl]methyl](methyl)amino) piperidin-1-yl]ethoxy]-2-(2,6-dioxopiperidin-3-yl) iso indole-1,3-dione formic acid (7.8 mg) as a white solid. $^1$H NMR (300 MHZ, DMSO-d6)δ 1.55 (2H, d), 1.77 (2H, d), 2.03 (3H, d), 2.16 (3H, s), 2.44 (3H, d), 2.73 (2H, s), 2.88-3.08 (3H, m), 3.61 (5H, s), 3.80 (6H, s), 4.30 (2H, s), 5.12 (1H, m), 6.72 (2H, s), 7.38 (1H, m), 7.48 (1H, d), 7.57 (1H, d), 7.80-7.90 (2H, m), 8.23 (1H, s), 8.72 (1H, d), 9.45 (1H, s), 11.12 (1H, s). LCMS (ESI) m/z: [M+H]$^+$=723.40.

Example 58—Preparation of 5-((1-(3-((2,6-Dimethoxy-4-(2-Methyl-1-Oxo-1,2-Dihydro-2,7-Naphthyridin-4-Yl)Benzyl)(Methyl)Amino) Propyl) Piperidin-4-Yl)Oxy)-2-(2,6-Dioxopiperidin-3-Yl) Isoindoline-1,3-Dione Formic Acid (Compound D52 Formic Acid)

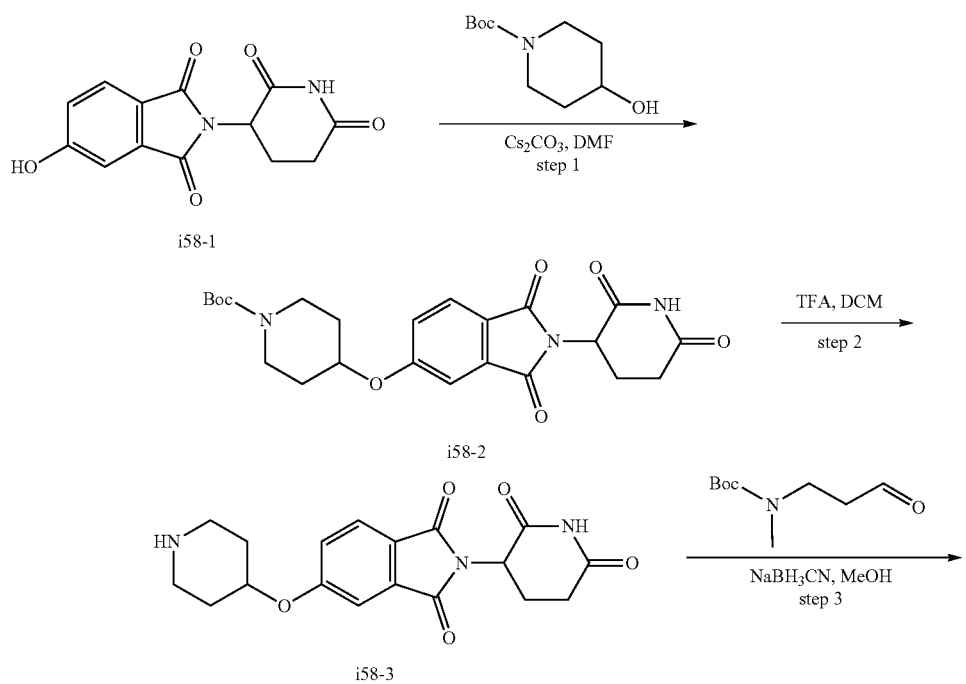

665

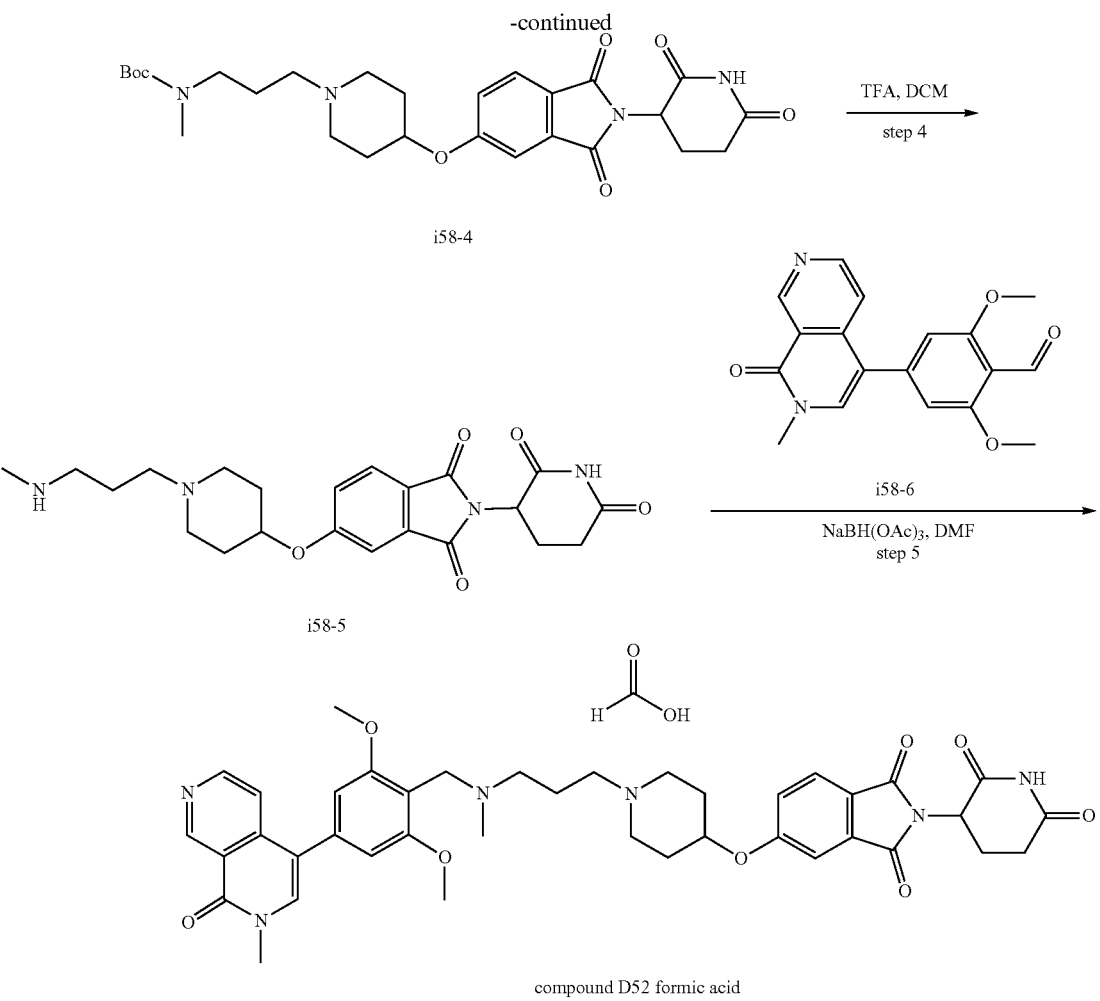

compound D52 formic acid

Step 1: Preparation of Tert-Butyl 4-((2-(2,6-Dioxopiperidin-3-Yl)-1,3-Dioxoisoindolin-5-Yl)Oxy) Piperidine-1-Carboxylate (i58-2)

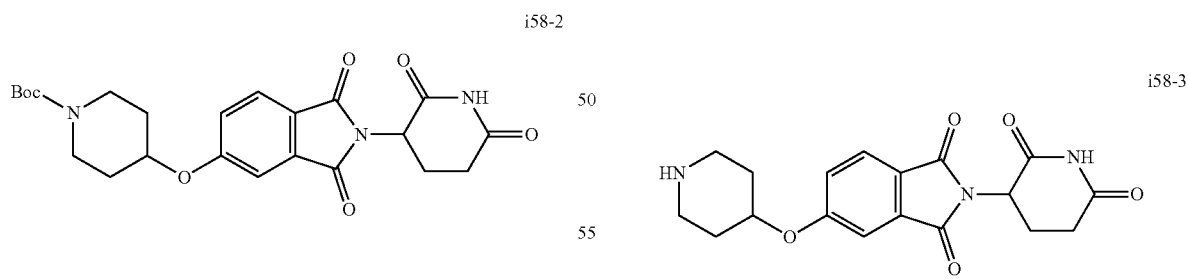

A mixture of 2-(2,6-dioxopiperidin-3-yl)-5-hydroxyisoindole-1,3-dione (1.00 g, 3.647 mmol, 1.00 equiv), tert-butyl 4-bromopiperidine-1-carboxylate (0.96 g, 3.634 mmol, 1.00 equiv) and Cs$_2$CO$_3$ (2.38 g, 7.293 mmol, 2.00 equiv) in DMF (20.00 mL) was stirred for overnight at 90° C. under air atmosphere. The resulting mixture was filtered, and the filter cake was washed with EtOAc (3×10 mL). The filtrate was concentrated under reduced pressure. The residue was purified by Prep-TLC(hexane/EtOAc 1:1) to afford tert-butyl4-[[2-(2,6-dioxopiperidin-3-yl)-1,3-dioxoisoindol-5-yl]oxy]piperidine-1-carboxylate (280 mg, 11.19%) as a yellow oil. LCMS (ESI) m/z: [M+H]$^+$=458.19.

Step 2: Preparation of 2-(2,6-dioxopiperidin-3-yl)-5-(piperidin-4-yloxy) isoindoline-1,3-dione (i58-3)

A solution of TFA (1.00 mL) and tert-butyl 4-[2-(2,6-dioxopiperidin-3-yl)-1,3-dioxoisoindol-5-yl]oxy]piperidine-1-carboxylate (200.00 mg, 0.437 mmol, 1.00 equiv) in DCM (4.00 mL) was stirred for 2 hours at room temperature under air atmosphere. The resulting mixture was concentrated under reduced pressure to afford 2-(2,6-dioxopiperidin-3-yl)-5-(piperidin-4-yloxy) isoindoline-1,3-dione (120 mg, 76.81%) as a brown solid. LCMS (ESI) m/z: [M+H]$^+$=358.14.

Step 3: Preparation of Tert-Butyl(3-(4-((2-(2,6-Dioxopiperidin-3-Yl)-1,3-Dioxoisoindolin-5-Yl)Oxy) Piperidin-1-Yl) Propyl)(Methyl) Carbamate (i58-4)

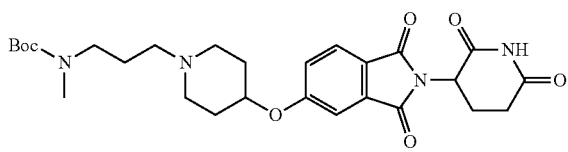

To a stirred solution of 2-(2,6-dioxopiperidin-3-yl)-5-(piperidin-4-yloxy) isoindole-1,3-dione (120.00 mg, 0.336 mmol, 1.00 equiv) and tert-butyl N-methyl-N-(3-oxopropyl) carbamate (62.87 mg, 0.336 mmol, 1.00 equiv) in MeOH (1.50 mL) was added NaBH$_3$CN (42.20 mg, 0.672 mmol, 2.00 equiv) in portions at room temperature under nitrogen atmosphere. The resulting mixture was stirred for 2 hours at room temperature under nitrogen atmosphere. The residue was purified by Prep-TLC(CH$_2$Cl$_2$/MeOH 10:1) to afford tert-butyl N-[3-(4-[2-(2,6-dioxopiperidin-3-yl)-1,3-dioxoisoindol-5-yl]oxy]piperidin-1-yl) propyl]-N-methylcarbamate (88.00 mg, 49.57%) as a yellow oil. LCMS (ESI) m/z: [M+H]$^+$=529.26.

Step 4: Preparation of 2-(2,6-Dioxopiperidin-3-Yl)-5-((1-(3-(Methylamino) Propyl) Piperidin-4-Yl) Oxy) Isoindo Line-1,3-Dione (i58-5)

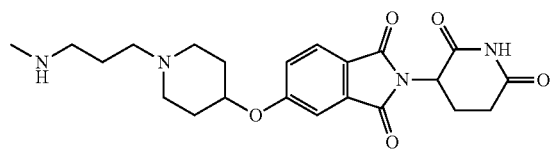

A solution of tert-butyl N-[3-(4-[2-(2,6-dioxopiperidin-3-yl)-1,3-dioxoisoindol-5-yl]oxy]piperidin-1-yl) propyl]-N-methyl carbamate (88.00 mg, 0.166 mmol, 1.00 equiv) and TFA (1.00 mL) in DCM (4.00 mL) was stirred for 1 hour at room temperature. The resulting mixture was concentrated under reduced pressure to afford 2-(2,6-dioxopiperidin-3-yl)-5-((1-(3-(methylamino) propyl) piperidin-4-yl)oxy) isoindoline-1,3-dione (70 mg, 98.50%) as a yellow solid. LCMS (ESI) m/z: [M+H]$^+$=429.21.

Step 5: Preparation of 5-((1-(3-((2,6-Dimethoxy-4-(2-Methyl-1-Oxo-1,2-Dihydro-2,7-Naphthyridin-4-Yl)Benz Yl)(Methyl)Amino) Propyl) Piperidin-4-Yl)Oxy)-2-(2,6-Dioxopiperidin-3-Yl) Isoindoline-1,3-Dione Formic Acid (Compound D52 Formic Acid)

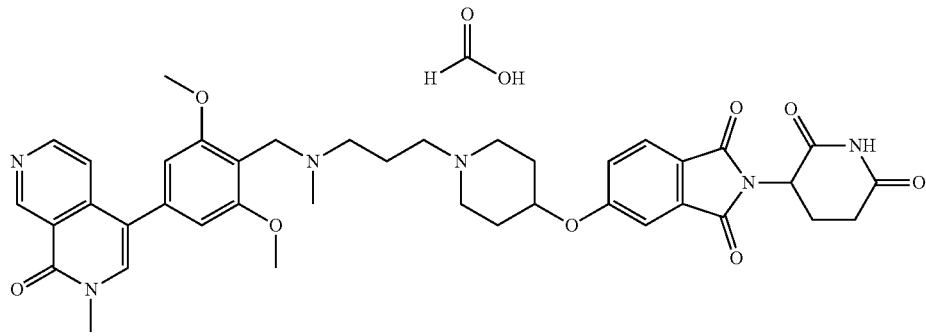

compound D52 formic acid

A solution of 2-(2,6-dioxopiperidin-3-yl)-5-([1-[3-(methylamino) propyl]piperidin-4-yl]oxy) isoindole-1,3-dione (70.00 mg, 0.163 mmol, 1.00 equiv) and 2,6-dimethoxy-4-(2-methyl-1-oxo-2,7-naphthyridin-4-yl)benzaldehyde (52.99 mg, 0.163 mmol, 1.00 equiv) in DMF (3.00 mL) was stirred for 30 minutes at room temperature. To the above mixture was added NaBH(AcO)$_3$ (69.25 mg, 0.327 mmol, 2.00 equiv) in portions at room temperature. The resulting mixture was stirred for additional 2 days at 50° C. The mixture was allowed to cool down to room temperature. The residue was purified by reverse flash chromatography (conditions: column, C18 silica gel; mobile phase, MeOH in water, 10% to 50% gradient in 10 minutes; detector, UV 254 nm). The crude product (75 mg) was purified by Prep-HPLC (conditions: SunFire C18 OBD Prep Column, 19 mm×250 mm; mobile phase, Water (0.1% FA) and ACN (hold 7% Phase B in 0 min, up to 12% in 10 minutes); Detector, UV 254/220 nm) to afford 5-([1-[3-([2,6-dimethoxy-4-(2-methyl-1-oxo-2,7-naphthyridin-4-yl)phenyl]methyl](methyl)amino) propyl]piperidin-4-yl]oxy)-2-(2,6-dioxopiperidin-3-yl) isoindole-1,3-dione (7.8 mg, 6.48%) as a white solid. $^1$H NMR (400 MHZ, Methanol-d4) δ 9.52 (s, 1H), 8.68 (d, J=5.7 Hz, 1H), 8.42 (brs, 1.4H, FA), 7.83-7.74 (m, 2H), 7.63 (d, J=5.6 Hz, 1H), 7.41 (d, J=2.1 Hz, 1H), 7.36-7.28 (m, 1H), 6.91 (s, 2H), 5.12 (dd, J=12.5, 5.4 Hz, 1H), 4.76 (s, 1H), 4.45 (s, 2H), 4.01 (s, 6H), 3.70 (s, 3H), 3.37 (s, 2H), 3.00 (s, 2H), 2.95-2.84 (m, 4H), 2.82-2.63 (m, 6H), 2.22-2.07 (m, 5H), 1.88 (s, 2H). LCMS (ESI) m/z: [M+H]$^+$=737.40.

Example 59—Preparation of 5-[3-(4-[2,6-Dimethoxy-4-(2-Methyl-1-Oxo-2,7-Naphthyridin-4-Yl) Phenyl]Methyl]Piperazin-1-Yl) Propoxy]-2-(2,6-Dioxopiperidin-3-Yl) Isoindole-1,3-Dione
(Compound D53)
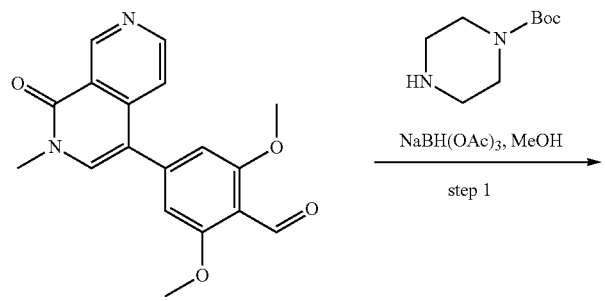
i59-1
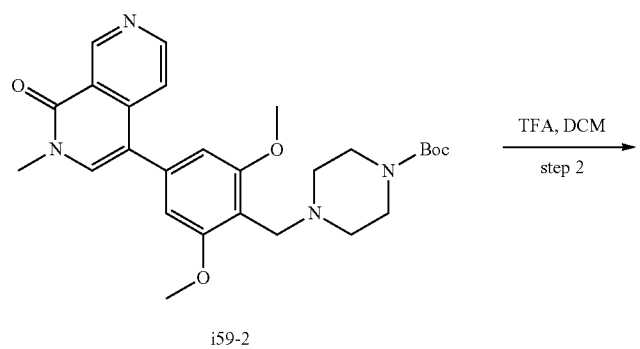
i59-2
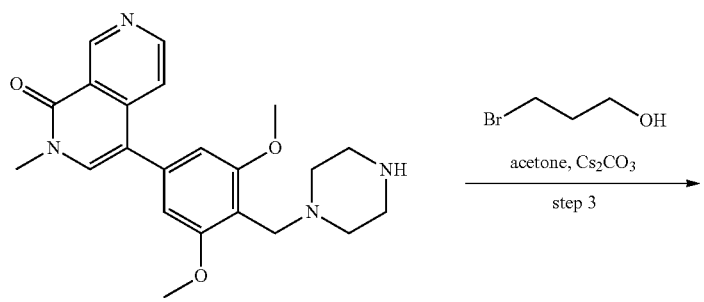
i59-3
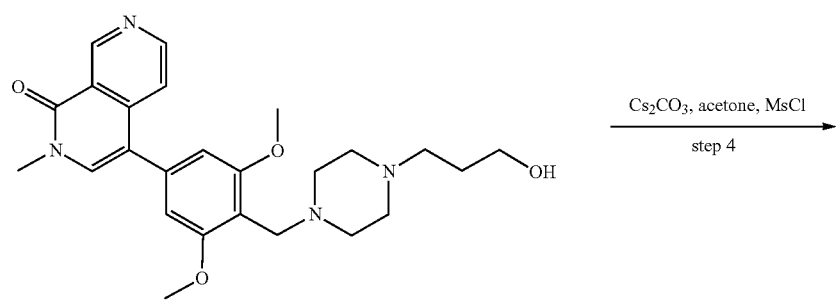
i59-4

-continued

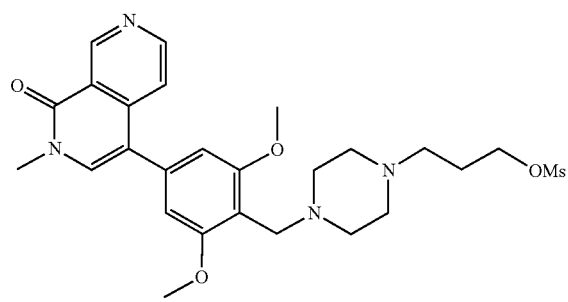

i59-5

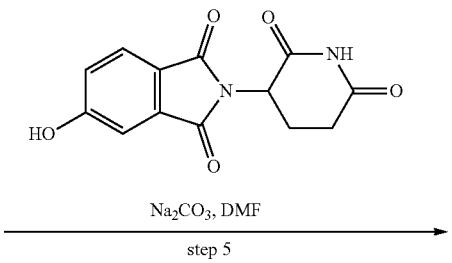

Na₂CO₃, DMF
―――――――→
step 5

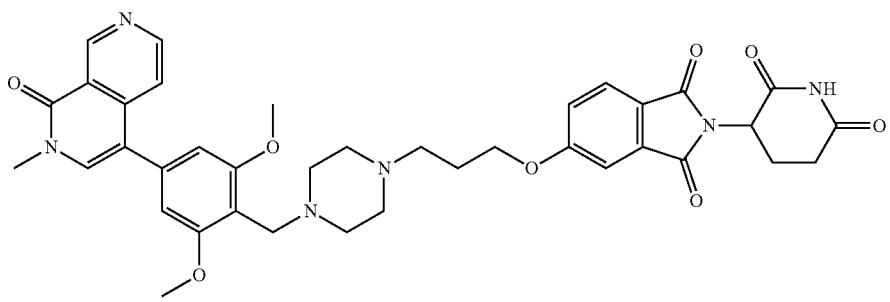

compound D53

Step 1: Preparation of Tert-Butyl 4-[[2,6-Dimethoxy-4-(2-Methyl-1-Oxo-2,7-Naphthyridin-4-Yl)Phenyl]Methyl]

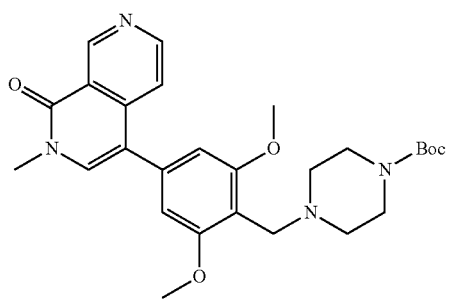

i59-2

To a stirred solution of 2,6-dimethoxy-4-(2-methyl-1-oxo-2,7-naphthyridin-4-yl)benzaldehyde (200.00 mg, 0.617 mmol, 1.00 equiv) and tert-butyl piperazine-1-carboxylate (173.00 mg, 0.929 mmol, 1.51 equiv) in MeOH was added NaBH(OAc)₃ (527.00 mg, 2.487 mmol, 4.03 equiv) in portions at room temperature. The resulting mixture was stirred for 3 hours at room temperature. The residue was purified by silica gel column chromatography, eluted with CH₂Cl₂/MeOH (10:1) to afford tert-butyl 4-[2,6-dimethoxy-4-(2-methyl-1-oxo-2,7-naphthyridin-4-yl)phenyl]methyl]piperazine-1-carboxylate (204 mg, 66.89%) as a light yellow oil. LCMS (ESI) m/z: [M+H]⁺=495.

Step 2: Preparation of 4-(3,5-Dimethoxy-4-(Piperazin-1-Ylmethyl)Phenyl)-2-Methyl-2,7-Naphthyridin-1(2H)-One (i59-3)

i59-3

To a stirred solution of tert-butyl 4-[2,6-dimethoxy-4-(2-methyl-1-oxo-2,7-naphthyridin-4-yl)phenyl]methyl]piperazine-1-carboxylate (204.00 mg, 0.412 mmol, 1.00 equiv) in DCM was added TFA (1.00 mL) dropwise at room temperature. The resulting mixture was stirred for 1 hour at room temperature. The resulting mixture was concentrated under vacuum. The 4-(3,5-dimethoxy-4-(piperazin-1-ylmethyl) phenyl)-2-methyl-2,7-naphthyridin-1 (2H)-one (210 mg crude) was used in the next step directly without further purification. LCMS (ESI) m/z: [M+H]$^+$=395.

Step 3: Preparation of 4-(4-((4-(3-Hydroxypropyl) Piperazin-1-Yl)Methyl)-3,5-Dimethoxyphenyl)-2-Methyl-2,7-Naphthyridin-1 (2H)-One (i59-4)

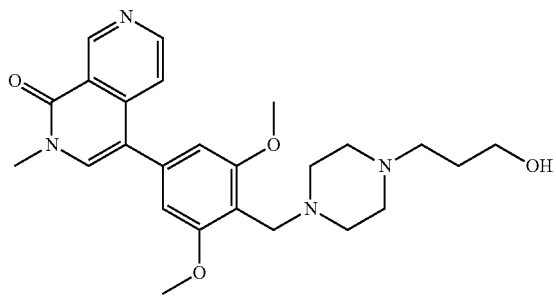

i59-4

To a stirred solution of 4-[3,5-dimethoxy-4-(piperazin-1-ylmethyl)phenyl]-2-methyl-2,7-naphthyridin-1-one (200.00 mg, 0.507 mmol, 1.00 equiv) and 3-bromopropanol (140.94 mg, 1.014 mmol, 2.00 equiv) in acetone was added Cs$_2$CO$_3$ (330.38 mg, 1.014 mmol, 2.00 equiv) in portions at room temperature. The resulting mixture was stirred for overnight at room temperature. Desired product could be detected by LCMS. The resulting mixture was used in the next step directly without further purification. LCMS (ESI) m/z: [M+H]$^+$=453.

Step 4: Preparation of 3-(4-[[2,6-Dimethoxy-4-(2-Methyl-1-Oxo-2,7-Naphthyridin-4-Yl)Phenyl] Methyl]Pipera-Zin-1-Yl) Propyl Methanesulfonate (i59-5)

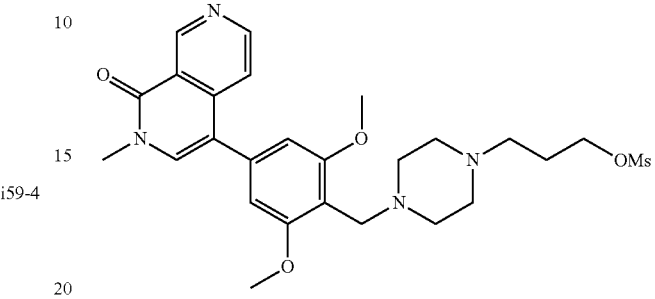

i59-5

To a stirred solution of 4-(4-[4-(3-hydroxypropyl) piperazin-1-yl]methyl]-3,5-dimethoxyphenyl)-2-methyl-2,7-naphthyridin-1-one (200.00 mg, 0.442 mmol, 1.00 equiv) and Cs$_2$CO$_3$ (287.98 mg, 0.884 mmol, 2.00 equiv) in acetone was added MsCl (101.25 mg, 0.884 mmol, 2.00 equiv) in portions at room temperature. The resulting mixture was stirred for overnight at room temperature. The resulting mixture was concentrated under vacuum. The residue was purified by silica gel column chromatography, eluted with CH$_2$Cl$_2$/MeOH (10:1) to afford 3-(4-[2,6-dimethoxy-4-(2-methyl-1-oxo-2,7-naphthyridin-4-yl)phenyl]methyl]piperazin-1-yl) propyl methanesulfonate (92 mg, 39.23%) as a light yellow oil. LCMS (ESI) m/z: [M+H]$^+$=531.

Step 5: Preparation of 5-[3-(4-[[2,6-Dimethoxy-4-(2-Methyl-1-Oxo-2,7-Naphthyridin-4-Yl)Phenyl] Methyl]Piper-Azin-1-Yl) Propoxy]-2-(2,6-Dioxopiperidin-3-Yl) Isoindole-1,3-Dione (Compound D53)

compound D53

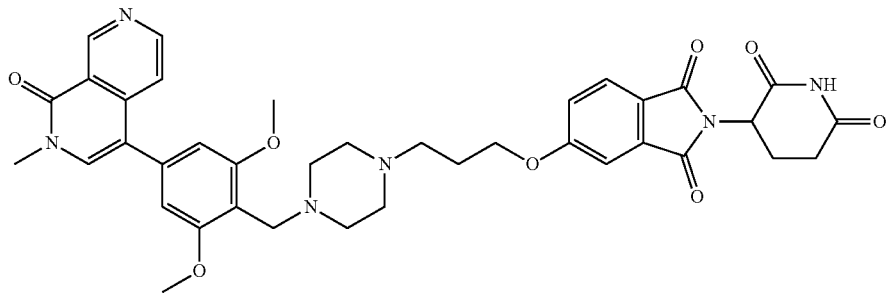

To a stirred solution of 3-(4-[2,6-dimethoxy-4-(2-methyl-1-oxo-2,7-naphthyridin-4-yl)phenyl]methyl]piperazin-1-yl) propyl methanesulfonate (90.00 mg, 0.170 mmol, 1.00 equiv) and 2-(2,6-dioxopiperidin-3-yl)-5-hydroxyisoindole-1,3-dione (47.00 mg, 0.171 mmol, 1.01 equiv) in DMF was added Na$_2$CO$_3$ (36.00 mg, 0.340 mmol, 2.00 equiv) in portions at room temperature. The resulting mixture was stirred for 2 hours at 80° C. The crude product was purified by Prep-HPLC(conditions: Xselect CSH F-Phenyl OBD column, 19*250, 5 um; mobile phase, Water (0.05% TFA) and ACN (hold 5% Phase B in 2 min, up to 22% in 13 minutes); Detector, UV). This resulted in 5-[3-(4-[[2,6-dimethoxy-4-(2-methyl-1-oxo-2,7-naphthyridin-4-yl)phenyl]methyl]piperazin-1-yl) propoxy]-2-(2,6-dioxopiperidin-3-yl) isoindole-1,3-dione (28.1 mg, 23.38%) as an off-white solid. $^1$H NMR (300 MHZ, Methanol-d4) δ 9.59 (s, 1H), 8.70 (d, J=6.0 Hz, 1H), 7.97 (s, 1H), 7.84 (t, J=7.6 Hz, 2H), 7.45 (d, J=2.1 Hz, 1H), 7.35 (dd, J=8.3, 2.2 Hz, 1H), 6.89 (s, 2H), 5.12 (dd, J=12.4, 5.4 Hz, 1H), 4.49 (s, 2H), 4.30 (t, J=5.7 Hz, 2H), 3.97 (s, 6H), 3.75 (s, 3H), 3.57 (s, 4H), 3.16 (s, 2H), 3.45-3.34 (m, 4H), 2.99-2.65 (m, 3H), 2.25 (s, 2H), 2.19-2.09 (m, 1H). LCMS (ESI) m/z: [M+H]$^+$=709.35.

Example 60—Preparation of 2-(2,6-Dioxopiperidin-3-Yl)-4-[4-(9-[4-(7-Hydroxy-2-Methyl-1-Oxoisoquinolin-4-Yl)-2,6-Dimethoxyphenyl]Methyl]-1-Oxa-4,9-Diazaspiro[5.5]Undecan-4-Yl)-4-Oxobutoxy]Isoindole-1,3-Dione Formic Acid (Compound D54 Formic Acid)
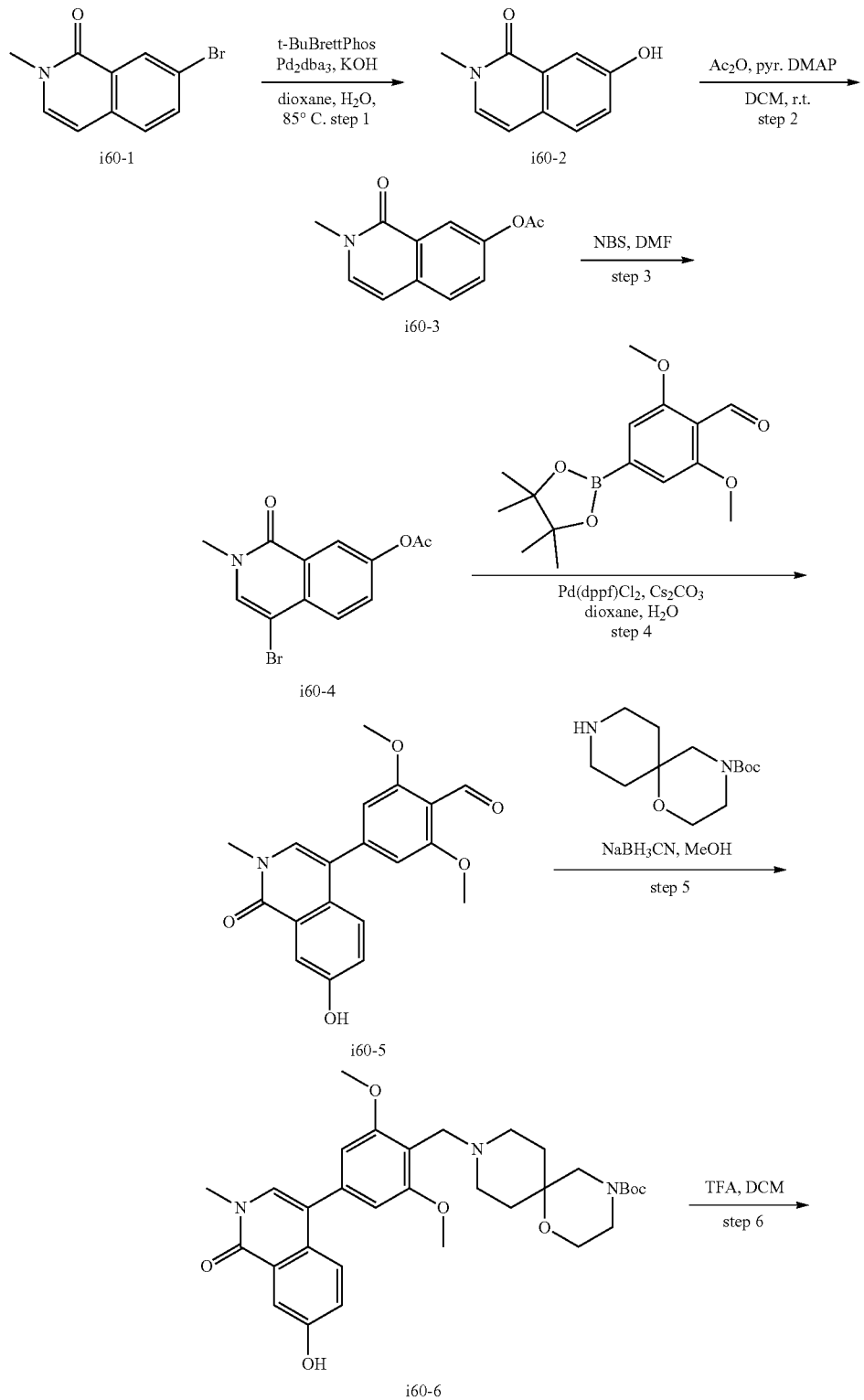

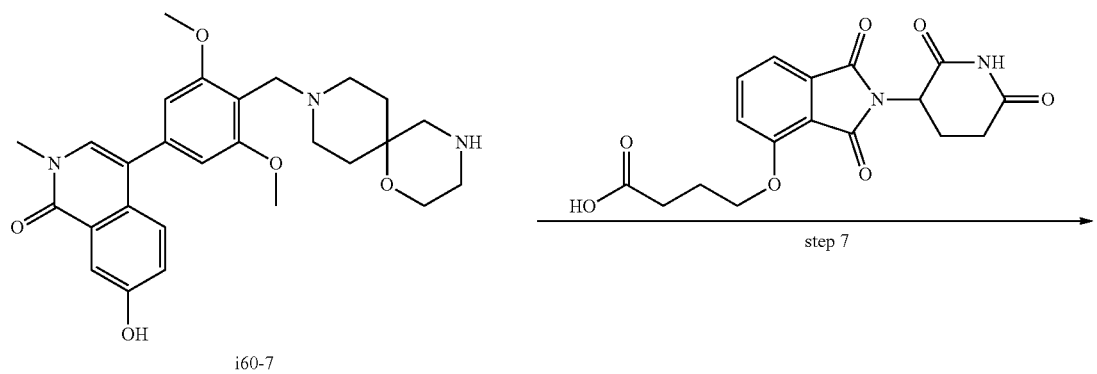

i60-7

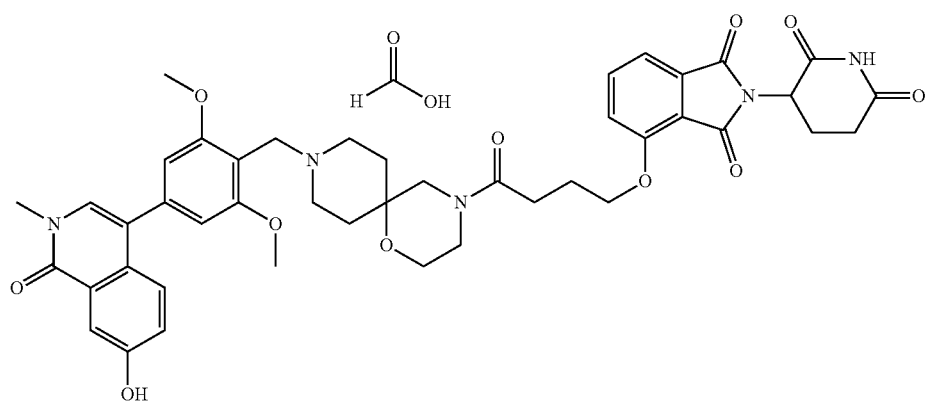

compound D54 formic acid

Step 1: Preparation of
7-Hydroxy-2-Methylisoquinolin-1-One (i60-2)

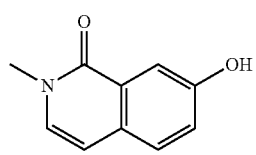

i60-2

To a mixture of 7-bromo-2-methylisoquinolin-1-one (500 mg, 2.100 mmol, 1.00 equiv), $Pd_2(dba)_3$ (96.2 mg, 0.105 mmol, 0.05 equiv), tert-BuBrettPhos (101.8 mg, 0.210 mmol, 0.10 equiv), and KOH (353.5 mg, 6.300 mmol, 3.00 equiv) was added dioxane (15 mL) and water (5 mL) at room temperature under nitrogen atmosphere. The resulting mixture was stirred overnight at 85° C. The mixture was acidified pH 4 with 1 M HCl (aq.) and extracted with EtOAc (3×30 mL). The combined organic layers were washed with brine (50 mL) and dried over anhydrous $Na_2SO_4$. After filtration, the filtrate was concentrated under reduced pressure. The residue was purified by silica gel column chromatography, eluted with PE/EtOAc (1:1 to 3:1) to afford 7-hydroxy-2-methylisoquinolin-1-one (312 mg, 85%) as a grey solid. LCMS (ESI) m/z: $[M+H]^+=176$.

Step 2: Preparation of
2-Methyl-1-Oxoisoquinolin-7-Yl Acetate (i60-3)

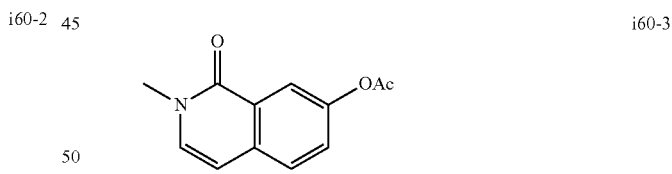

i60-3

To a stirred solution/mixture of 7-hydroxy-2-methylisoquinolin-1-one (272 mg, 1.553 mmol, 1.00 equiv) and pyridine (614 mg, 7.763 mmol, 5.00 equiv) in DCM (6 mL) was added DMAP (10 mg, 0.082 mmol, 0.05 equiv) and $Ac_2O$ (46.6 mg, 0.457 mmol, 2.00 equiv) at room temperature. The resulting mixture was stirred for 1 hour at room temperature. The resulting mixture was diluted with water (10 mL) and extracted with DCM (2×20 mL). The combined organic layers were washed with brine, dried over anhydrous $Na_2SO_4$. After filtration, the filtrate was concentrated under reduced pressure to afford 2-methyl-1-oxoisoquinolin-7-yl acetate (335 mg, 99%) as a light brown solid. LCMS (ESI) m/z: $[M+H]^+=218$.

Step 3: Preparation of 4-Bromo-2-Methyl-1-Oxoisoquinolin-7-Yl Acetate (i60-4)

To a stirred solution/mixture of 2-methyl-1-oxoisoquinolin-7-yl acetate (325 mg, 1.496 mmol, 1.00 equiv) in ACN (10 mL) was added NBS (292.9 mg, 1.646 mmol, 1.10 equiv) at room temperature. The resulting mixture was stirred for 0.5 h at room temperature. The resulting mixture was diluted with DCM (30 mL) and washed with 10 ml of water and 10 mL of brine. The organic layer was dried over anhydrous Na$_2$SO$_4$. After filtration, the filtrate was concentrated under reduced pressure. The residue was suspended in EtOAc (3 mL), then filtered and the light grey solid was collected as 4-bromo-2-methyl-1-oxoisoquinolin-7-yl acetate (297 mg, 67%). LCMS (ESI) m/z: [M+H]$^+$=296.

Step 4: Preparation of 4-(7-Hydroxy-2-Methyl-1-Oxoisoquinolin-4-Yl)-2,6-Dimethoxybenzaldehyde (i60-5)

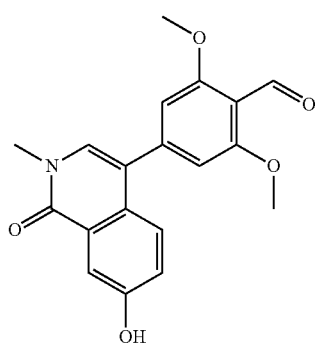

i60-5

To a mixture of 4-bromo-2-methyl-1-oxoisoquinolin-7-yl acetate (217 mg, 0.733 mmol, 1.00 equiv), 2,6-dimethoxy-4-(4,4,5,5-tetramethyl-1,3,2-dioxaborolan-2-yl)benzaldehyde (321.1 mg, 1.099 mmol, 1.50 equiv), Pd (dppf)Cl$_2$·CH$_2$Cl$_2$ (59.8 mg, 0.073 mmol, 0.10 equiv), and Cs$_2$CO$_3$ (716.3 mg, 2.198 mmol, 3.00 equiv) was added dioxane (4 mL) and water (1 mL) at room temperature under N$_2$ atmosphere. The resulting mixture was stirred overnight at 80° C. The resulting mixture was diluted with sat. NH$_4$Cl solution (10 mL) and extracted with DCM/i-PrOH (3/1) (5×20 mL). The combined organic layers were dried over anhydrous Na$_2$SO$_4$. After filtration, the filtrate was concentrated under reduced pressure. The residue was purified by silica gel column chromatography, eluted with DCM/MeOH (100:1 to 20:1) to afford 4-(7-hydroxy-2-methyl-1-oxoisoquinolin-4-yl)-2,6-dimethoxybenzaldehyde (248 mg, quant.) as a light brown solid. LCMS (ESI) m/z: [M+H]$^+$=340.

Step 5: Preparation of Tert-Butyl 9-[[4-(7-Hydroxy-2-Methyl-1-Oxoisoquinolin-4-Yl)-2,6-Dimethoxyphenyl]Methyl]-1-Oxa-4,9-Diazaspiro[5.5]Undecane-4-Carboxylate (i60-6)

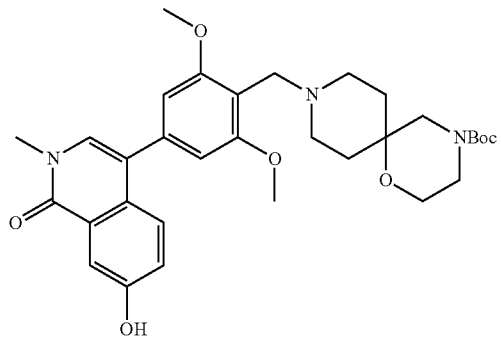

i60-6

A solution of 4-(7-hydroxy-2-methyl-1-oxoisoquinolin-4-yl)-2,6-dimethoxybenzaldehyde (100 mg, 0.295 mmol, 1.00 equiv) and tert-butyl 1-oxa-4,9-diazaspiro[5.5]undecane-4-carboxylate (83.1 mg, 0.324 mmol, 1.1 equiv) in MeOH (1.5 mL) was stirred for 30 minutes at room temperature. Then NaBH$_3$CN (125 mg, 1.989 mmol, 6.75 equiv) was added. The resulting mixture was stirred for 2 hours at room temperature. The reaction solution was purified by Prep-TLC(DCM/MeOH 20:1) to afford tert-butyl 9-[[4-(7-hydroxy-2-methyl-1-oxoisoquinolin-4-yl)-2,6-dimethoxyphenyl]methyl]-1-oxa-4,9-diazaspiro[5.5]undecane-4-carboxylate (134 mg, 78%) as a light brown foam. LCMS (ESI) m/z: [M+H]$^+$=580.

Step 6: Preparation of 4-(3,5-Dimethoxy-4-[1-Oxa-4,9-Diazaspiro[5.5]Undecan-9-Ylmethyl]Phenyl)-7-Hydro Xy-2-Methylisoquinolin-1-One (i60-7)

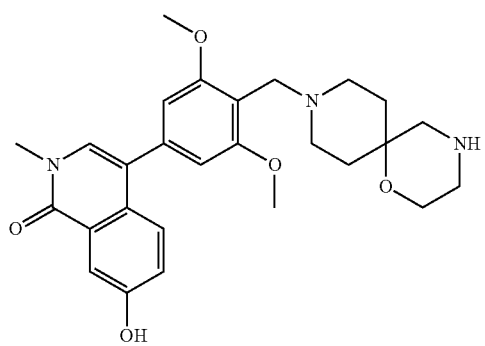

i60-7

To a stirred solution/mixture of tert-butyl 9-[4-(7-hydroxy-2-methyl-1-oxoisoquinolin-4-yl)-2,6-dimethoxy phenyl]methyl]-1-oxa-4,9-diazaspiro[5.5]undecane-4-carboxylate (134 mg, 0.231 mmol, 1.00 equiv) in DCM (3 mL) was added TFA (1 mL) at room temperature. The resulting mixture was stirred for 30 minutes at room temperature. The mixture was concentrated to dryness to give 4-(3,5-dimethoxy-4-[1-oxa-4,9-diazaspiro[5.5]undecan-9-ylmethyl]phenyl)-7-hydroxy-2-methylisoquinolin-1-one (135 mg, TFA salt, quant.) as a light brown solid. LCMS (ESI) m/z: [M+H]$^+$=480.

Step 7: Preparation of 2-(2,6-Dioxopiperidin-3-Y1)-4-[4-(9-[4-(7-Hydroxy-2-Methyl-1-Oxoisoquinolin-4-Y1)-2,6-Dimethoxyphenyl]Methyl]-1-Oxa-4,9-Diazaspiro[5.5]Undecan-4-Y1)-4-Oxobutoxy]Isoindole-1,3-Dione Formic Acid (Compound D54 Formic Acid)

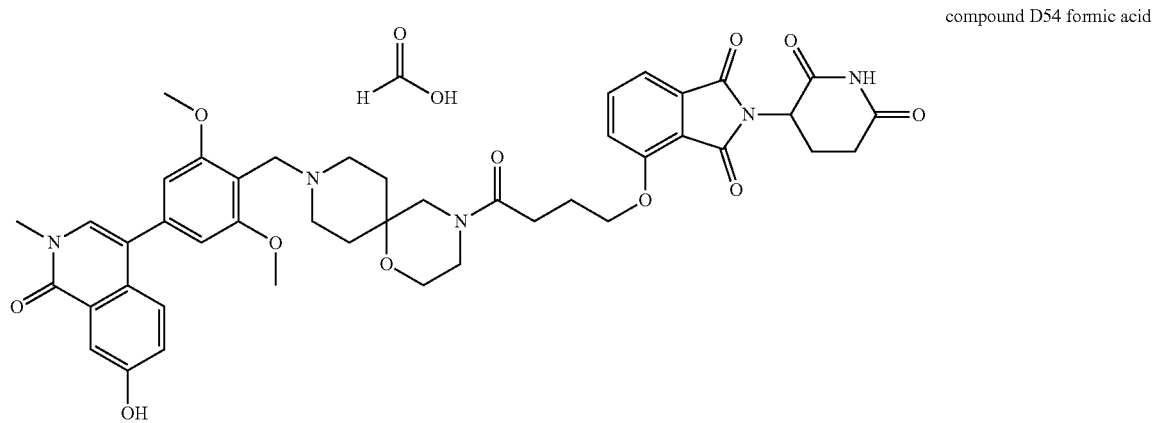 [SMILES: COc1cc(-c2cn(C)c(=O)c3cc(O)ccc23)cc(OC)c1CN1CCC2(CC1)CN(C(=O)CCCOc1cccc3c1C(=O)N(C1CCC(=O)NC1=O)C3=O)CCO2 ; O=CO]

compound D54 formic acid

To a stirred solution of 4-[2-(2,6-dioxopiperidin-3-yl)-1,3-dioxoisoindol-4-yl]oxy]butanoic acid (33.8 mg, 0.094 mmol, 0.90 equiv) in DMF (1 mL) was added EDCI (40.0 mg, 0.209 mmol, 2.00 equiv) and HOBt (28.2 mg, 0.209 mmol, 2.00 equiv) at room temperature. The resulting mixture was stirred at room temperature for 20 minutes followed by addition of 4-(3,5-dimethoxy-4-[1-oxa-4,9-diazaspiro[5.5]undecan-9-ylmethyl]phenyl)-7-hydroxy-2-methylisoquinolin-1-one (50.0 mg, 0.104 mmol, 1.00 equiv) and DIEA (67.4 mg, 0.521 mmol, 5.00 equiv). After stirring for 3 hours at room temperature, the reaction mixture was purified by Prep-HPLC(conditions: SunFire Prep C18 OBD Column, 19×150 mm 5 μm 10 nm; Mobile Phase A: Water (0.1% FA), Mobile Phase B: ACN; Flow rate: 25 mL/minute; Gradient: 15 B to 24 B in 12 minutes; 254/220 nm; RT: 11.28 minutes) to afford 2-(2,6-dioxopiperidin-3-yl)-4-[4-(9-[4-(7-hydroxy-2-methyl-1-oxoisoquinolin-4-yl)-2,6-dimethoxyphenyl]methyl]-1-oxa-4,9-diazaspiro[5.5]undecan-4-yl)-4-oxobutoxy]isoindole-1,3-dione formic acid (11.5 mg, 13%) as an off-white solid. $^1$H NMR (400 MHz, Methanol-d4)δ 8.55 (s, 0.5H, FA), 7.84-7.75 (m, 2H), 7.56 (dd, J=8.8, 3.3 Hz, 1H), 7.47 (dd, J=7.6, 2.7 Hz, 2H), 7.31-7.19 (m, 2H), 6.82 (d, J=8.8 Hz, 2H), 5.12 (dd, J=12.5, 5.6 Hz, 1H), 4.40-4.20 (m, 4H), 3.93 (d, J=12.4 Hz, 6H), 3.78-3.62 (m, 7H), 3.58-3.48 (m, 2H), 3.30-3.17 (m, 4H), 2.97-2.53 (m, 5H), 2.24-1.99 (m, 5H), 1.95-1.71 (s, 2H). LCMS (ESI) m/z: [M+H]$^+$=822.40.

Example 61—Preparation of 3-[([[2,6-Dimethoxy-4-(2-Methyl-1-Oxo-2,7-Naphthyridin-4-Yl)Phenyl]Methyl](Methyl)Amino)Methyl]-N-[2-[2-(2-[2-(2,6-Dioxopiperidin-3-Y1)-1,3-Dioxoisoindol-4-Yl]Amino]Ethoxy) Ethoxy]Ethyl]Bicyclo[1.1.1]Pentane-1-Carboxamide (Compound D55)

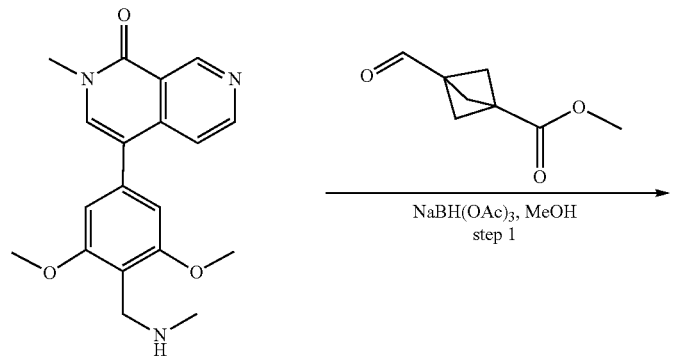

i61-1

-continued
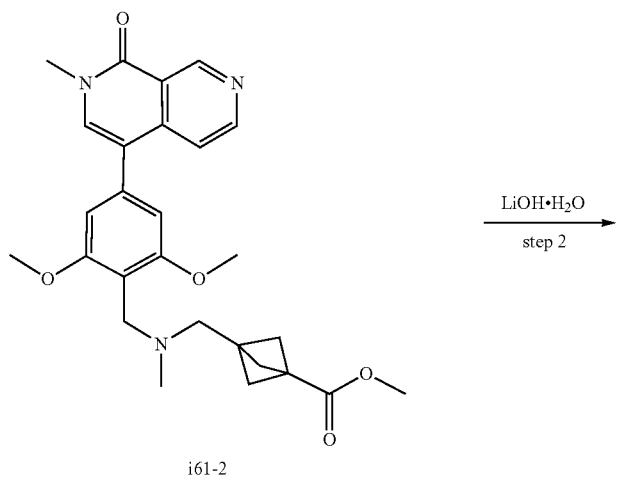
i61-2
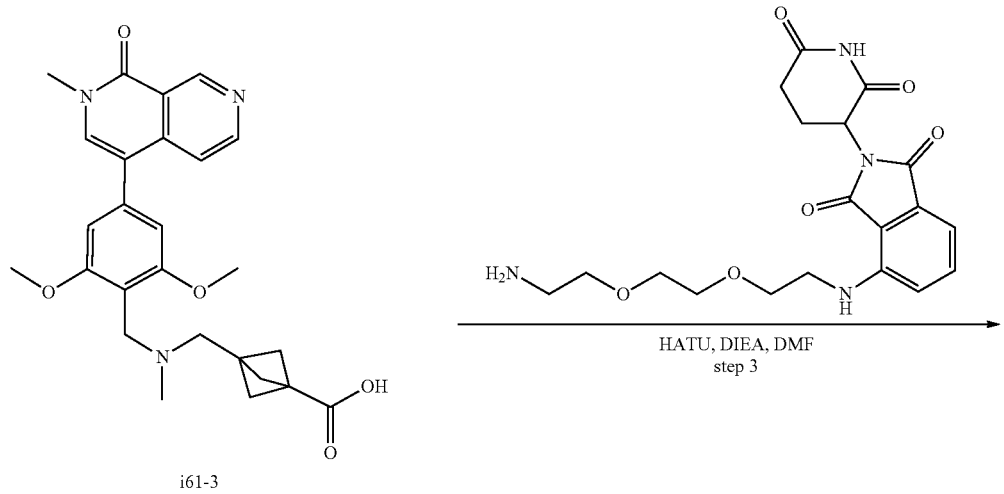
i61-3
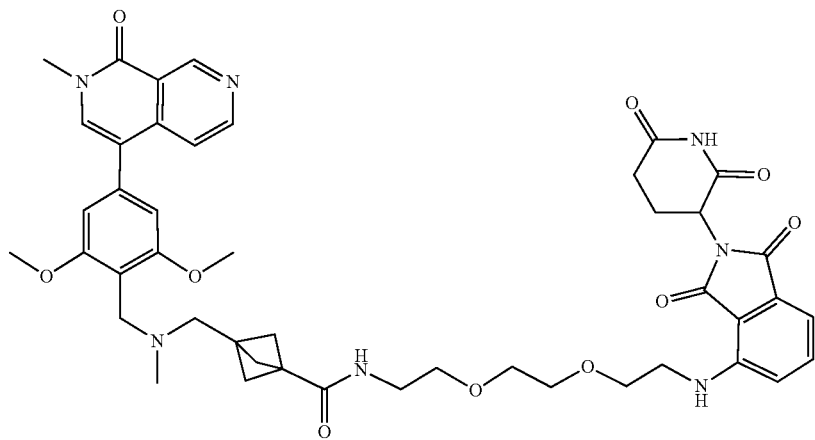
compound D55

Step 1: Preparation of Methyl 3-[([[2,6-Dimethoxy-4-(2-Methyl-1-Oxo-2,7-Naphthyridin-4-Yl)Phenyl]Methyl](Methyl)Amino)Methyl]Bicyclo[1.1.1]Pentane-1-Carboxylate (i61-2)

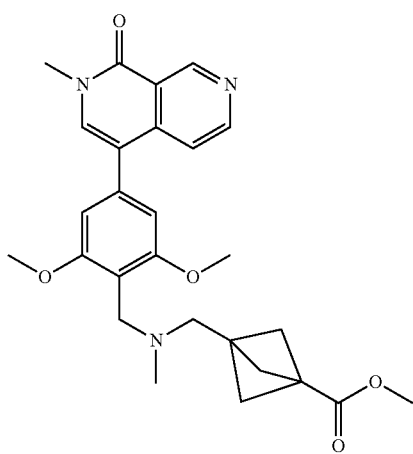

i61-2

Step 2: Preparation of 3-(((2,6-Dimethoxy-4-(2-Methyl-1-Oxo-1,2-Dihydro-2,7-Naphthyridin-4-Yl)Benzyl)(Methyl)Amino)Methyl) Bicyclo[1.1.1]Pentane-1-Carboxylic Acid (i61-3)

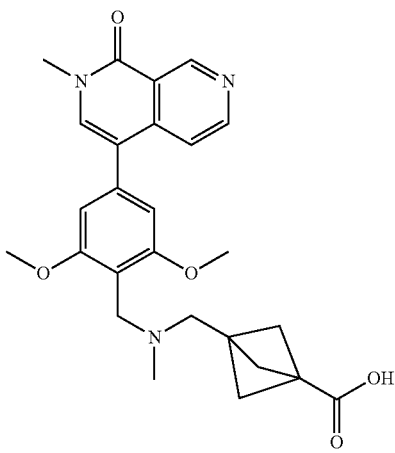

i61-3

To a stirred solution of 4-[3,5-dimethoxy-4-[(methylamino)methyl]phenyl]-2-methyl-2,7-naphthyridin-1-one (264.00 mg, 0.778 mmol, 1.20 equiv) and methyl 3-formylbicyclo[1.1.1]pentane-1-carboxylate (100.00 mg, 0.649 mmol, 1.00 equiv) in MeOH was added NaBH(OAc)$_3$ (549.91 mg, 2.595 mmol, 4.00 equiv) in portions at room temperature. The resulting solution was stirred for 4 hours at room temperature. Desired product could be detected by LCMS. The resulting mixture was concentrated under reduced pressure. The residue was purified by silica gel column chromatography, eluted with CH$_2$Cl$_2$/MeOH (8:1) to afford methyl3-[(([2,6-dimethoxy-4-(2-methyl-1-oxo-2,7-naphthyridin-4-yl)phenyl]methyl](methyl)amino)-methyl]bicyclo[1.1.1]pentane-1-carboxylate (220 mg, 71.02%) as a light yellow oil. LCMS (ESI) m/z: [M+H]$^+$=478.

To a stirred solution of methyl 3-[([[2,6-dimethoxy-4-(2-methyl-1-oxo-2,7-naphthyridin-4-yl)phenyl]methyl](methyl)amino)methyl]bicyclo[1.1.1]pentane-1-carboxylate (200.00 mg, 0.419 mmol, 1.00 equiv) and LiOH·H$_2$O (35.15 mg, 0.838 mmol, 2.00 equiv) in THF (6 mL) was added H$_2$O (2.00 mL) dropwise at room temperature. The resulting mixture was stirred for overnight at room temperature. The mixture was acidified to pH<7 with conc. HCl. The resulting mixture was concentrated under vacuum. The 3-(((2,6-dimethoxy-4-(2-methyl-1-oxo-1,2-dihydro-2,7-naphthyridin-4-yl)benzyl)(methyl)amino)methyl)-bicyclo[1.1.1]pentane-1-carboxylic acid (215 mg crude) was used in the next step directly without further purification. LCMS (ESI) m/z: [M+H]$^+$=464.

Step 3: Preparation of 3-[([[2,6-Dimethoxy-4-(2-Methyl-1-Oxo-2,7-Naphthyridin-4-Yl)Phenyl]Methyl](Methyl)-Amino)Methyl]-N-[2-[2-(2-[[2-(2,6-Dioxopiperidin-3-Yl)-1,3-Dioxoisoindol-4-Yl]Amino]Ethoxy) Ethoxy]Ethyl]Bic-Yclo[1.1.1]Pentane-1-Carboxamide (Compound D55)

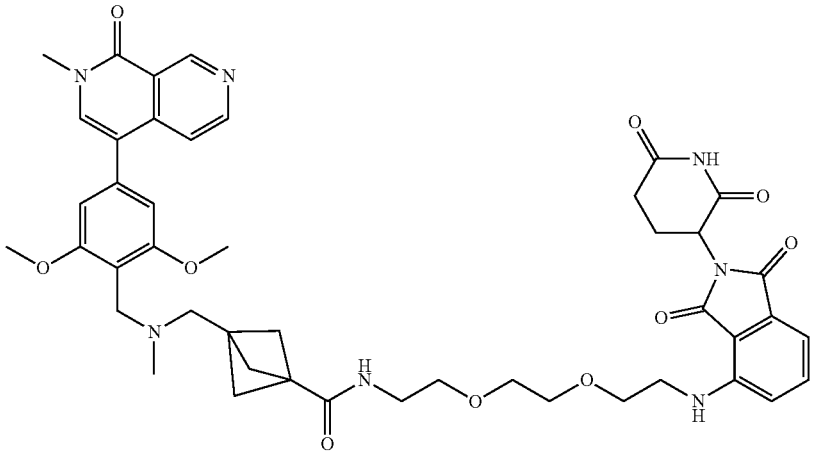

compound D55

To a stirred solution of 3-[([[2,6-dimethoxy-4-(2-methyl-1-oxo-2,7-naphthyridin-4-yl)phenyl]methyl](methyl)amino)methyl]bicyclo[1.1.1]pentane-1-carboxylic acid (50.00 mg, 0.108 mmol, 1.00 equiv) and 4-([2-[2-(2-aminoethoxy) ethoxy]ethyl]amino)-2-(2,6-dioxopiperidin-3-yl)isoindole-1,3-dione (65.44 mg, 0.162 mmol, 1.50 equiv) in DMF were added DIEA (55.76 mg, 0.431 mmol, 4.00 equiv) and HATU (61.52 mg, 0.162 mmol, 1.50 equiv) in portions at room temperature. The resulting mixture was stirred for 3 h at room temperature. The crude product was purified by Prep-HPLC with the following conditions (NB-Prep-HPLC-01): Column, XSelect CSH Prep C18 OBD Column, 5 μm, 19*150 mm; mobile phase, Water (0.05% TFA) and ACN (16% PhaseB up to 17% in 20 min, hold 17% in 8 minutes); Detector, uv. This resulted in 3-[([[2,6-dimethoxy-4-(2-methyl-1-oxo-2,7-naphthyridin-4-yl)phenyl]methyl](methyl) ami-no)methyl]-N-[2-[2-(2-[[2-(2,6-dioxopiperi-din-3-yl)-1,3-dioxoisoindol-4-yl]amino]ethoxy) ethoxy]ethyl]bicyc-lo[1.1.1]pentane-1-carboxamide; formic acid (4.1 mg, 4.24%) as a yellow solid. $^1$H NMR (300 MHZ, Methanol-d4)δ 9.55 (s, 1H), 8.70 (d, J=5.7 Hz, 1H), 8.55 (s, 1H), 7.78 (s, 1H), 7.65 (d, J=5.9 Hz, 1H), 7.52 (dd, J=8.6, 7.1 Hz, 1H), 7.09 (d, J=8.5 Hz, 1H), 6.99 (d, J=7.1 Hz, 1H), 6.84 (s, 2H), 5.07 (dd, J=12.4, 5.4 Hz, 1H), 4.22 (s, 2H), 3.95 (s, 6H), 3.77 (t, J=5.2 Hz, 2H), 3.73 (s, 3H), 3.71-3.65 (m, 4H), 3.59 (t, J=5.4 Hz, 2H), 3.52 (t, J=5.2 Hz, 2H), 3.44-3.38 (m, 2H), 3.28-3.24 (m, 1H), 2.91-2.81 (m, 1H), 2.80-2.77 (m, 1H), 2.75-2.69 (m, 1H), 2.66 (s, 3H), 2.20 (s, 6H), 2.17-2.05 (m, 2H). LCMS (ESI) m/z: [M+H]$^+$=850.45.

Example 62—Preparation of 3-[{[[2,6-Dimethoxy-4-(2-Methyl-1-Oxo-2,7-Naphthyridin-4-Yl)Phenyl]Methyl](Methyl)Amino)Methyl]-N-(5-[2-(2,6-Dioxopiperidin-3-Yl)-1,3-Dioxoisoindol-4-Yl]Amino] Pentyl) Bicyclo[1.1.1]Pentane-1-Carboxamide (Compound D56)

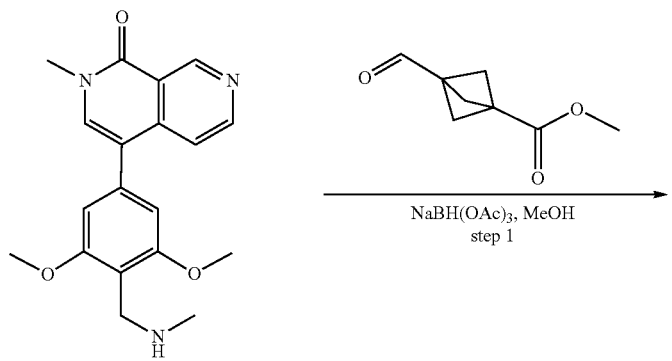

i62-1

-continued
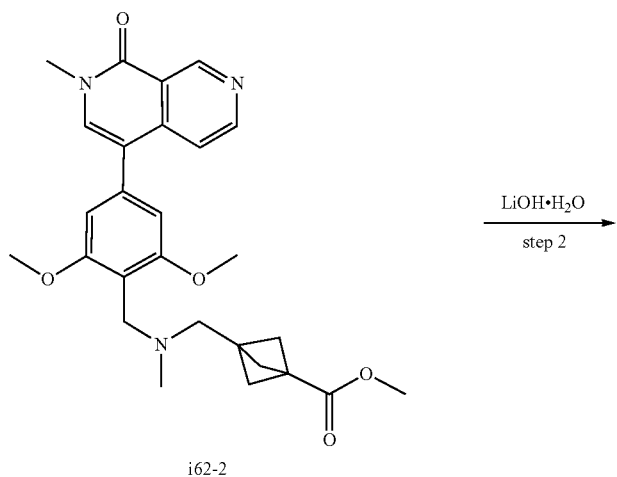
i62-2
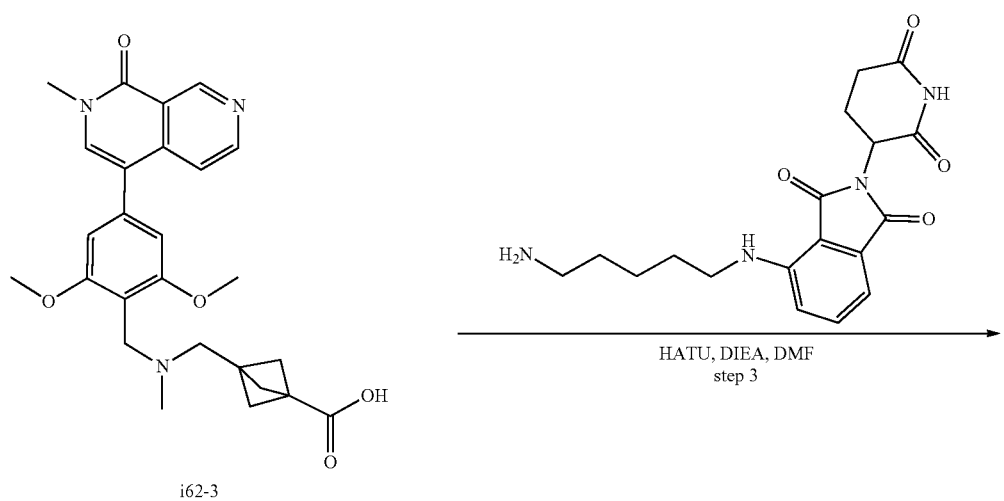
i62-3
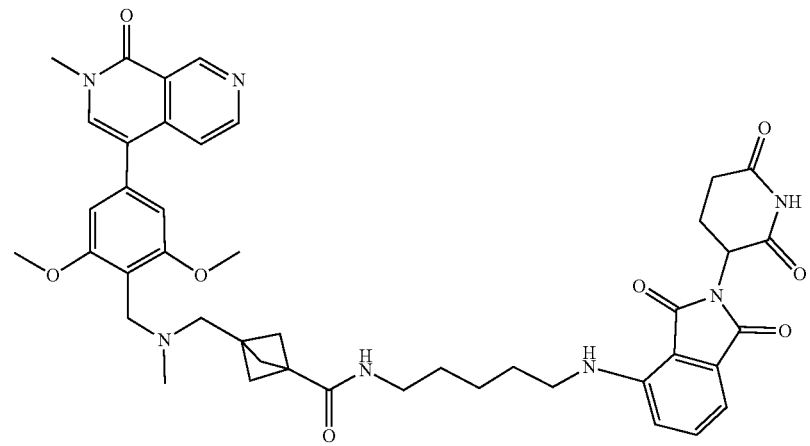
compound D56

Step 1: Preparation of Methyl 3-[([2,6-Dimethoxy-4-(2-Methyl-1-Oxo-2,7-Naphthyridin-4-Yl)Phenyl]Methyl](Methyl)Amino)Methyl]Bicyclo[1.1.1]Pentane-1-Carboxylate (i62-2)

Step 2: Preparation of 3-(((2,6-Dimethoxy-4-(2-Methyl-1-Oxo-1,2-Dihydro-2,7-Naphthyridin-4-Yl)Benzyl)(Methyl)Amino)Methyl) Bicyclo[1.1.1]Pentane-1-Carboxylic Acid (i62-3)

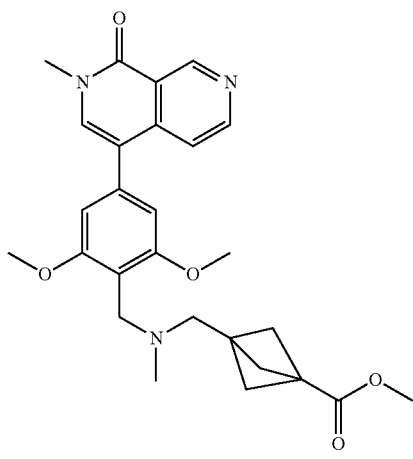

i62-2 i62-3

To a stirred solution of 4-[3,5-dimethoxy-4-[(methylamino)methyl]phenyl]-2-methyl-2,7-naphthyridin-1-one (264.18 mg, 0.778 mmol, 1.20 equiv) and methyl 3-formylbicyclo[1.1.1]pentane-1-carboxylate (100.00 mg, 0.649 mmol, 1.00 equiv) in MeOH was added NaBH(OAc)$_3$ (549.91 mg, 2.595 mmol, 4.00 equiv) in portions at room temperature. The resulting solution was stirred for 4 hours at room temperature. Desired product could be detected by LCMS. The resulting mixture was concentrated under reduced pressure. The residue was purified by silica gel column chromatography, eluted with CH$_2$Cl$_2$/MeOH (8:1) to afford methyl3-[([2,6-dimethoxy-4-(2-methyl-1-oxo-2,7-naphthyridin-4-yl)phenyl]methyl](methyl)amino)-methyl] bicyclo[1.1.1]pentane-1-carboxylate (220 mg, 71.02%) as a light yellow oil. LCMS (ESI) m/z: [M+H]$^+$=478.

To a stirred solution of methyl 3-[([[2,6-dimethoxy-4-(2-methyl-1-oxo-2,7-naphthyridin-4-yl)phenyl]methyl](methyl)amino)methyl]bicyclo[1.1.1]pentane-1-carboxylate (200.00 mg, 0.419 mmol, 1.00 equiv) and LiOH·H$_2$O (35.15 mg, 0.838 mmol, 2.00 equiv) in THF (6 mL) was added H$_2$O (2.00 mL) dropwise at room temperature. The resulting mixture was stirred for overnight at room temperature. The mixture was acidified to pH<7 with conc. HCl. The resulting mixture was concentrated under vacuum. The 3-(((2,6-dimethoxy-4-(2-methyl-1-oxo-1,2-dihydro-2,7-naphthyridin-4-yl)benzyl)(methyl)amino)methyl)-bicyclo[1.1.1]pentane-1-carboxylic acid (215 mg crude) was used in the next step directly without further purification. LCMS (ESI) m/z: [M+H]$^+$=464.

Step 3: Preparation of 3-[([[2,6-Dimethoxy-4-(2-Methyl-1-Oxo-2,7-Naphthyridin-4-Yl)Phenyl]Methyl](Methyl)Amino)Methyl]-N-(5-[[2-(2,6-Dioxopiperidin-3-Yl)-1,3-Dioxoisoindol-4-Yl]Amino]Pentyl) Bicyclo[1.1.1]Pentane-1-Carboxamide (Compound D56)

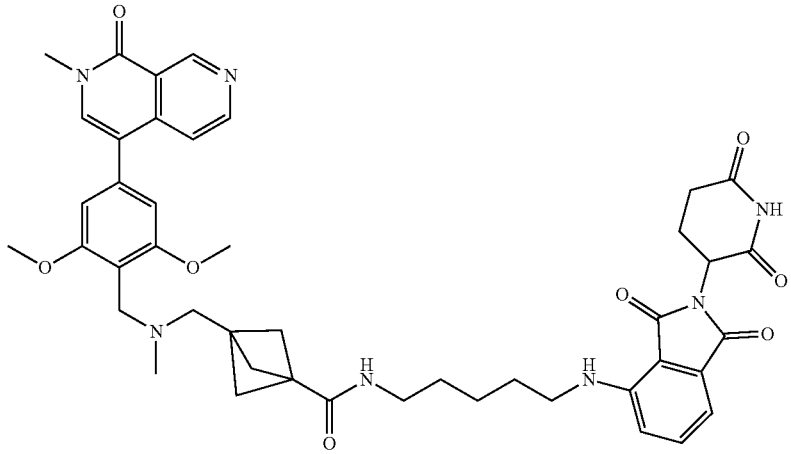

compound D56

To a stirred solution of 3-[(([2,6-dimethoxy-4-(2-methyl-1-oxo-2,7-naphthyridin-4-yl)phenyl]methyl](methyl)amino)methyl]bicyclo[1.1.1]pentane-1-carboxylic acid (50.00 mg, 0.108 mmol, 1.00 equiv) and 4-((5-aminopentyl)amino)-2-(2,6-dioxopiperidin-3-yl) isoindoline-1,3-dione (65.44 mg, 0.162 mmol, 1.50 equiv) in DMF was added DIEA (55.76 mg, 0.431 mmol, 4.00 equiv) and HATU (61.52 mg, 0.162 mmol, 1.50 equiv) in portions at room temperature. The resulting mixture was stirred for 3 hours at room temperature. The crude product was purified by Prep-HPLC(conditions: XSelect CSH Prep C18 OBD Column, 5 μm, 19*150 mm; mobile phase, Water (0.05% TFA) and ACN (16% Phase B up to 17% in 20 min, hold 17% in 8 minutes); Detector, UV). This resulted in 3-(((2,6-dimethoxy-4-(2-methyl-1-oxo-1,2-dihydro-2,7-naphthyridin-4-yl)benzyl)(methyl)amino)-methyl)-N-(5-((2-(2,6-dioxopiperidin-3-yl)-1,3-dioxoisoindolin-4-yl)amino) pentyl) bicyclo[1.1.1]pentane-1-carboxamide (12.3 mg, 13.42%) as a yellow solid. LCMS (ESI) m/z: [M+H]$^+$=804.45.

Example 63—Preparation of 3-([[2,6-Dimethoxy-4-(2-Methyl-1-Oxo-2,7-Naphthyridin-4-Yl)Phenyl]Methyl](Methyl)Amino)-N-(5-[2-(2,6-Dioxopiperidin-3-Yl)-1,3-Dioxoisoindol-4-Yl]Amino]Pentyl) Bicyclo[1.1.1]Pentane-1-Carboxamide; Formic Acid (Compound D57 Formic Acid)

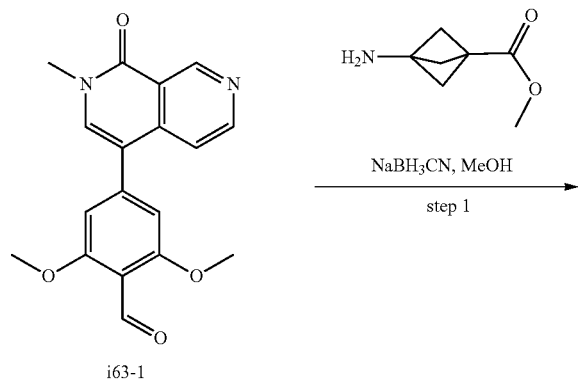

i63-1

-continued
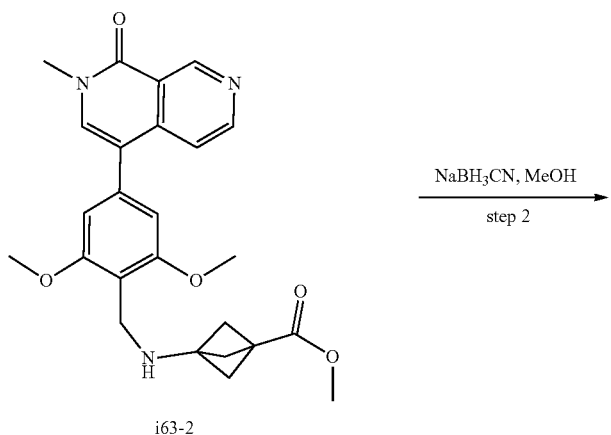
i63-2
NaBH₃CN, MeOH
step 2
i63-3
HCl
step 3
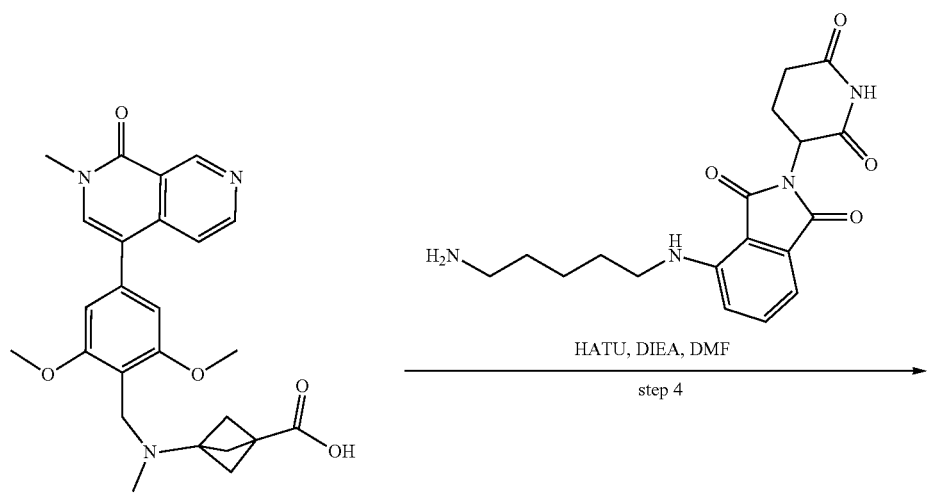
i63-4
HATU, DIEA, DMF
step 4

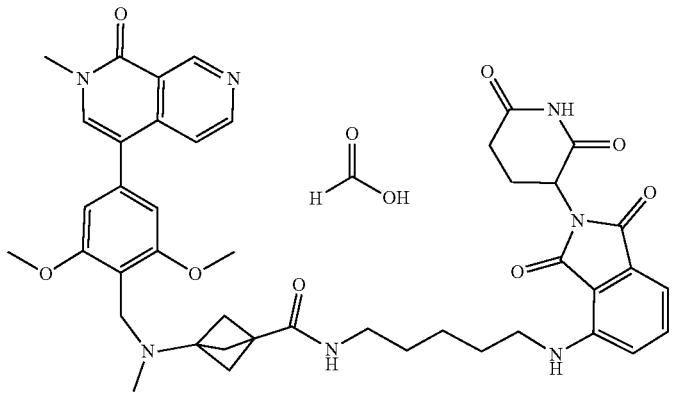

compound D57 formic acid

Step 1: Preparation of Methyl-3-((2,6-Dimethoxy-4-(2-Methyl-1-Oxo-1,2-Dihydro-2,7-Naphthyridin-4-Yl)Benzyl)Amino) Bicyclo[1.1.1]Pentane-1-Carboxylate (i63-2)

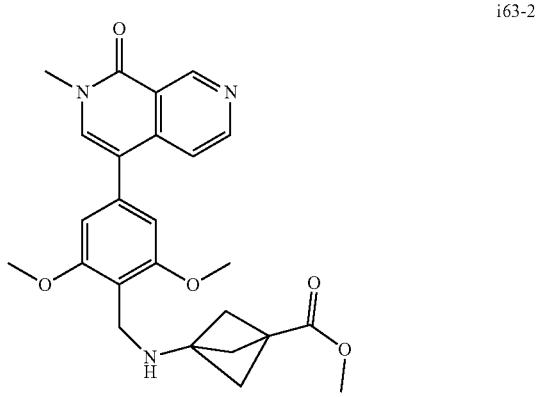 [SMILES: COC(=O)C12CC(NCc3c(OC)cc(-c4cn(C)c(=O)c5cnccc45)cc3OC)(C1)C2]

i63-2

To a solution of methyl 3-aminobicyclo[1.1.1]pentane-1-carboxylate hydrochloride (195.2 mg, 1.099 mmol, 1.10 equiv) in MeOH (5.00 mL) was added EtsN (111.0 mg, 1.099 mmol, 1.10 equiv), and then 2,6-dimethoxy-4-(2-methyl-1-oxo-2,7-naphthyridin-4-yl)benzaldehyde (324.0 mg, 0.999 mmol, 1.00 equiv) was added. After 10 minutes stirring, NaBH$_3$CN (125.6 mg, 1.998 mmol, 2.00 equiv) was added in portions at ambient atmosphere. The resulting mixture was concentrated after stirring for 1 hour at room temperature. The mixture was used in the next step directly without further purification. LCMS (ESI) m/z: [M+H]$^+$=450.

Step 2: Preparation of Methyl-3-([2,6-Dimethoxy-4-(2-Methyl-1-Oxo-2,7-Naphthyridin-4-Yl)Phenyl]Methyl](Methyl)Amino) Bicyclo[1.1.1]Pentane-1-Carboxylate (i63-3)

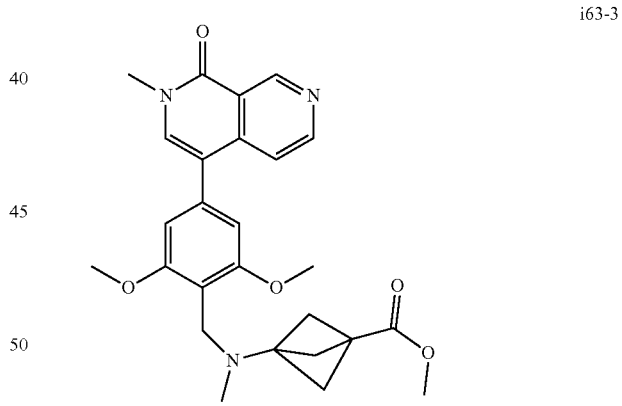

i63-3

To a solution of crude methyl-3-([[2,6-dimethoxy-4-(2-methyl-1-oxo-2,7-naphthyridin-4-yl)phenyl]methyl]amino) bicyclo[1.1.1]pentane-1-carboxylate obtained last step in MeOH (5.00 mL, 12.349 mmol) was added formaldehyde in water (226.0 μL). After 10 min stirring, NaBH$_3$CN (125.8 mg, 2.002 mmol, 2.00 equiv) was added in portions at ambient atmosphere. The resulting mixture was concentrated after stirring for 1 hour at room temperature. The mixture was purified by Prep-TLC(EtOAc) to afford methyl-3-([2,6-dimethoxy-4-(2-methyl-1-oxo-2,7-naphthyridin-4-yl)phenyl]methyl](methyl)amino) bicyclo[1.1.1]pentane-1-carboxylate (120 mg, 24.8%) as a light yellow solid. LCMS (ESI) m/z: [M+H]$^+$=464.

Step 3: Preparation of 3-((2,6-Dimethoxy-4-(2-Methyl-1-Oxo-1,2-Dihydro-2,7-Naphthyridin-4-Yl)Benzyl)(Methyl)Amino) Bicyclo[1.1.1]Pentane-1-Carboxylic Acid (i63-4)

Step 4: Preparation of 3-([[2,6-Dimethoxy-4-(2-Methyl-1-Oxo-2,7-Naphthyridin-4-Yl)Phenyl]Methyl](Methyl)Amino)-N-(5-[[2-(2,6-Dioxopiperidin-3-Yl)-1,3-Dioxoisoindol-4-Yl]Amino]Pentyl) Bicyclo[1.1.1]Pentane-1-Carboxamide Formic Acid (Compound D57 Formic Acid)

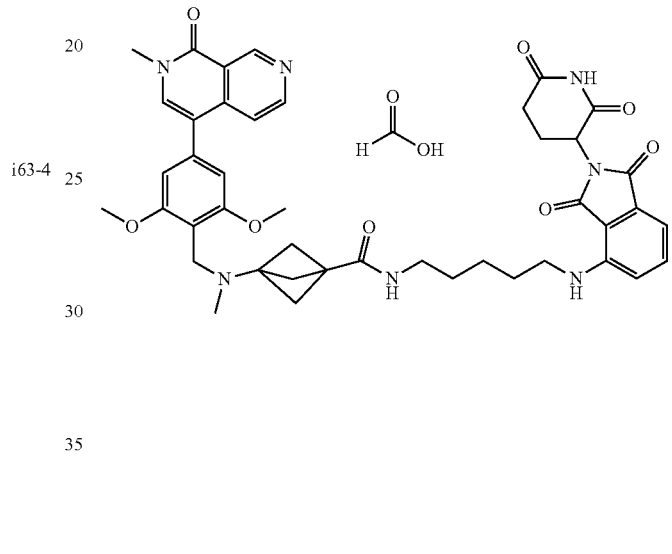

compound D57 formic acid

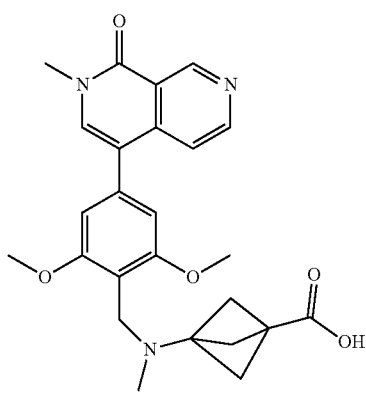

A mixture of methyl 3-([2,6-dimethoxy-4-(2-methyl-1-oxo-2,7-naphthyridin-4-yl)phenyl]methyl](methyl)amino) bicyclo[1.1.1]pentane-1-carboxylate (120.0 mg, 0.259 mmol, 1.00 equiv) in conc. HCl (2.00 mL) was stirred for 1 hour at 90° C. The resulting mixture was concentrated under vacuum. The crude product was used in the next step directly without further purification. LCMS (ESI) m/z: [M+H]$^+$=450.

To a stirred mixture of 3-([[2,6-dimethoxy-4-(2-methyl-1-oxo-2,7-naphthyridin-4-yl)phenyl]methyl](methyl) amino) bicyclo[1.1.1]pentane-1-carboxylic acid hydrochloride (50 mg, 0.103 mmol, 1.00 equiv) and 4-[(5-aminopentyl)amino]-2-(2,6-dioxopiperidin-3-yl) isoindole-1,3-dione; trifluoroacetic acid (53.5 mg, 0.113 mmol, 1.10 equiv) in DMF (2.00 mL) was added DIEA (39.9 mg, 0.309 mmol, 3.00 equiv). The mixture was stirred at room temperature for 5 minutes, and then HATU (78.2 mg, 0.206 mmol, 2.00 equiv) was added. After stirring at room temperature for 2 hours, the mixture was purified by Prep-HPLC (conditions: X-select CSH F-Phenyl OBD Column 19*150 mm 5 μm, mobile phase, Water (0.05% TFA) and ACN (10% Phase B up to 26% in 15 minutes)). This resulted in of 3-([2,6-dimethoxy-4-(2-methyl-1-oxo-2,7-naphthyridin-4-yl)phenyl]methyl](methyl)amino)-N-(5-[2-(2,6-dioxopiperidin-3-yl)-1,3-dioxoisoindol-4-yl]amino]pentyl) bicyclo [1.1.1]pentane-1-carboxamide formic acid (15.2 mg, 17.2%) as a yellow solid. $^1$H NMR (300 MHZ, Methanol-d4) δ 9.57 (s, 1H), 8.71 (d, J=5.9 Hz, 1H), 8.18 (brs, 0.4H, FA), 7.86 (s, 1H), 7.72 (s, 1H), 7.58 (dd, J=8.6, 7.1 Hz, 1H), 7.07 (dd, J=7.8, 5.2 Hz, 2H), 6.90 (s, 2H), 5.06 (dd, J=12.0, 5.4 Hz, 1H), 4.51 (s, 2H), 3.99 (s, 6H), 3.73 (s, 3H), 3.41-3.35 (m, 2H), 3.31-3.23 (m, 2H), 2.89-2.64 (m, 6H), 2.42 (s, 6H), 2.17-2.08 (m, 1H), 1.78-1.67 (m, 2H), 1.66-1.56 (m, 2H), 1.54-1.43 (m, 2H). LCMS (ESI) m/z: [M+H]$^+$=790.40.

Example 64—Preparation of 3-([[2,6-Dimethoxy-4-(2-Methyl-1-Oxo-2,7-Naphthyridin-4-Yl)Phenyl]Methyl](Methyl)Amino)-N-[2-[2-(2-[2-(2,6-Dioxopiperidin-3-Yl)-1,3-Dioxoisoindol-4-Yl]Amino]Ethoxy) Ethoxy]Ethyl]Bicyclo[1.1.1]Pentane-1-Carboxamide (Compound D58)

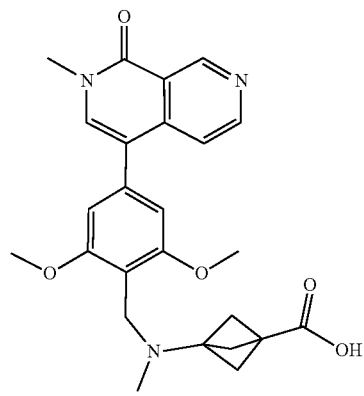
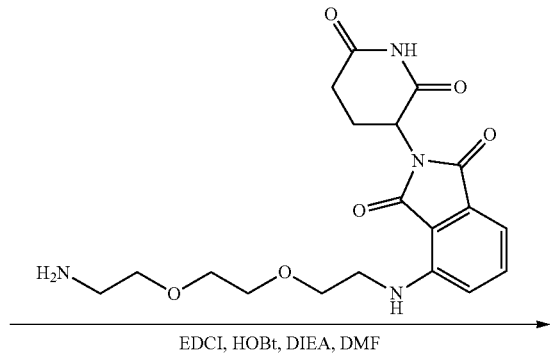

were added. After stirring at room temperature for 2 hours, without any additional work-up, the mixture was purified by Prep-HPLC(conditions: column, Phenomenex Gemini C6-Phenyl, 21.2*250 mm, 5 μm; mobile phase, Water (0.05% FA) and ACN (11% Phase B up to 21% in 28 minutes). This resulted in 3-([2,6-dimethoxy-4-(2-methyl-1-oxo-2,7-naphthyridin-4-yl)phenyl]methyl](methyl)

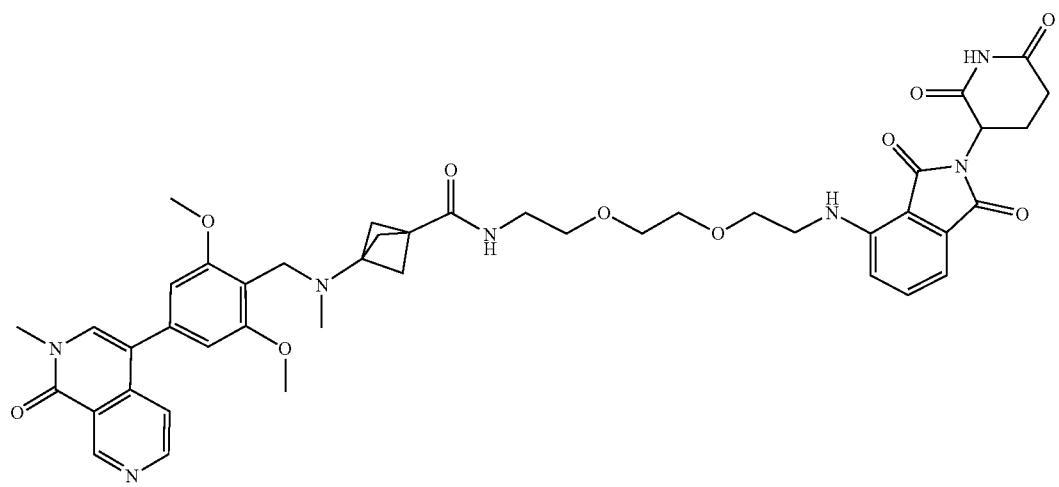

compound D58

To a stirred mixture of 3-([2,6-dimethoxy-4-(2-methyl-1-oxo-2,7-naphthyridin-4-yl)phenyl]methyl](methyl)amino) bicyclo[1.1.1]pentane-1-carboxylic acid (50.0 mg, 0.111 mmol, 1.00 equiv) in DMF (2.00 mL) was added EDCI (42.7 mg, 0.222 mmol, 2.00 equiv) and 4-([2-[2-(2-aminoethoxy) ethoxy]ethyl]amino)-2-(2,6-dioxopiperidin-3-yl) isoindole-1,3-dione (49.5 mg, 0.122 mmol, 1.10 equiv). The mixture was stirred at room temperature for 30 minutes, and then DIEA (71.9 mg, 0.556 mmol, 5.00 equiv) and 4-([2-[2-(2-aminoethoxy) ethoxy]ethyl]amino)-2-(2,6-dioxopiperidin-3-yl) isoindole-1,3-dione (9.9 mg, 0.024 mmol, 1.10 equiv) amino)-N-[2-[2-(2-[2-(2,6-dioxopiperidin-3-yl)-1,3-dioxoisoindol-4-yl]amino] ethoxy) ethoxy]ethyl] bicyclo[1.1.1]pentane-1-carboxamide (10.5 mg, 10.6%) as a yellow solid. $^1$H NMR (300 MHZ, Methanol-d4)δ 9.53 (s, 1H), 8.69 (d, J=5.7 Hz, 1H), 7.75 (s, 1H), 7.64 (d, J=5.7 Hz, 1H), 7.55 (dd, J=8.6, 7.1 Hz, 1H), 7.07 (dd, J=19.4, 7.8 Hz, 2H), 6.74 (s, 2H), 5.07 (dd, J=12.3, 5.4 Hz, 1H), 3.88 (s, 6H), 3.77 (t, J=5.2 Hz, 2H), 3.73-3.63 (m, 9H), 3.59 (t, J=5.5 Hz, 2H), 3.53 (t, J=5.2 Hz, 2H), 3.41 (t, J=5.5 Hz, 2H), 2.90-2.68 (m, 3H), 2.27 (s, 3H), 2.20-2.06 (m, 7H). LCMS (ESI) m/z: [M+H]$^+$=836.40.

Example 65—Preparation of N-[3-([[2,6-Dimethoxy-4-(2-Methyl-1-Oxo-2,7-Naphthyridin-4-Yl)Phenyl]Methyl](Methyl)Amino) Bicyclo[1.1.1]Pentan-1-Yl]-3-[2-(2-[2-(2,6-Dioxopiperidin-3-Yl)-1,3-Dioxoisoindol-4-Yl]Ami No]Ethoxy) Ethoxy] Propanamide Formic Acid (Compound D59 Formic Acid)
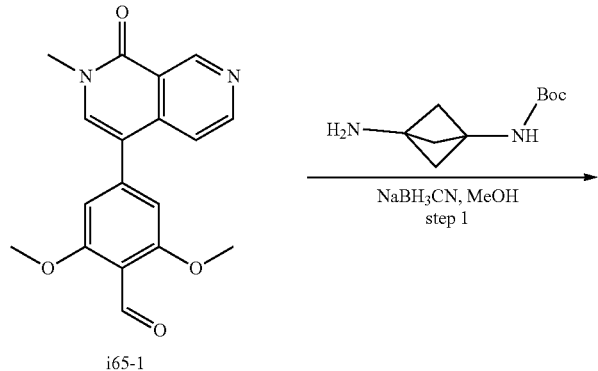
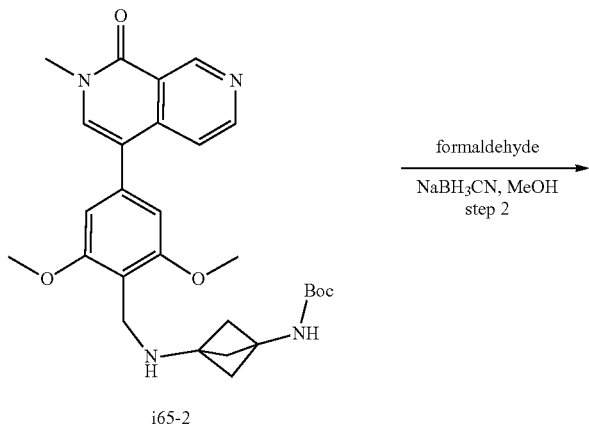
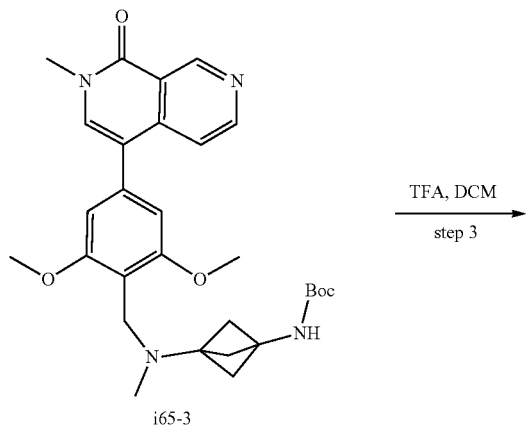

-continued

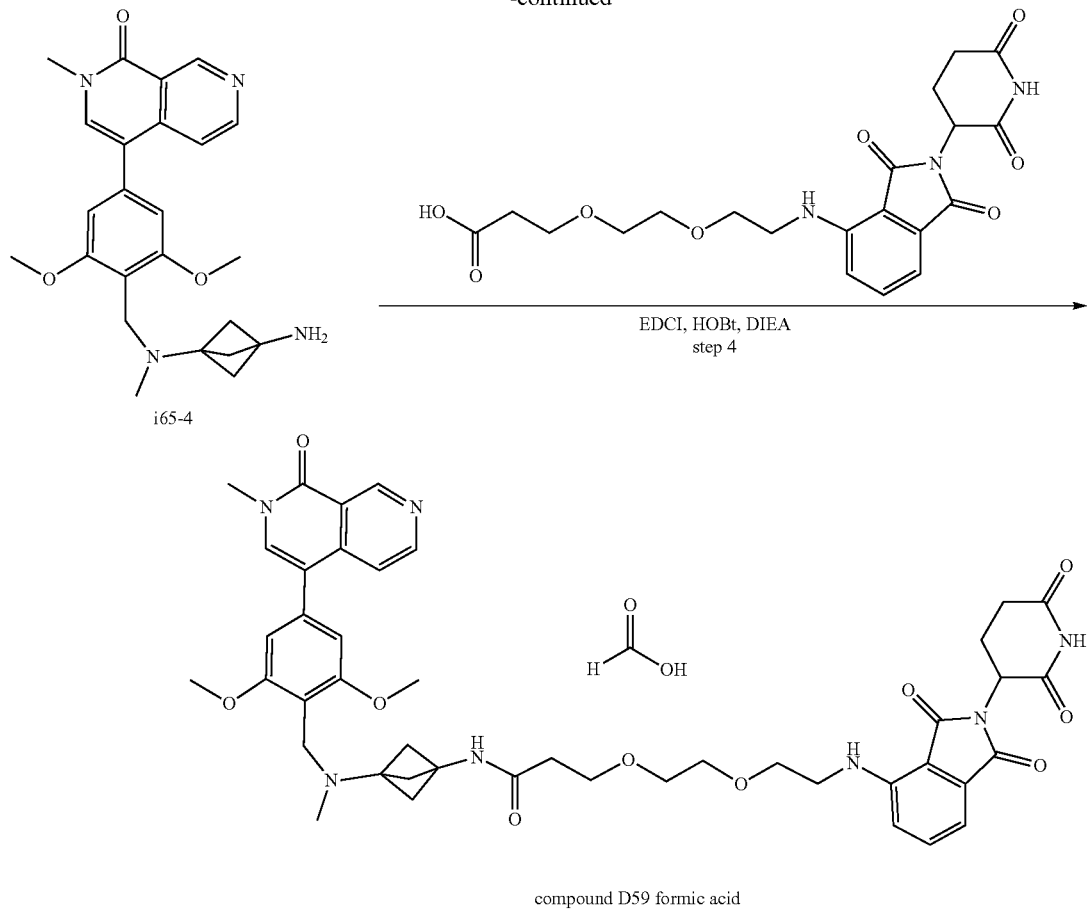

compound D59 formic acid

Step 1: Preparation of Tert-Butyl(3-((2,6-Dimethoxy-4-(2-Methyl-1-Oxo-1,2-Dihydro-2,7-Naphthyridin-4-Yl)Benzyl)Amino) Bicyclo[1.1.1]Pentan-1-Yl) Carbamate (i65-2)

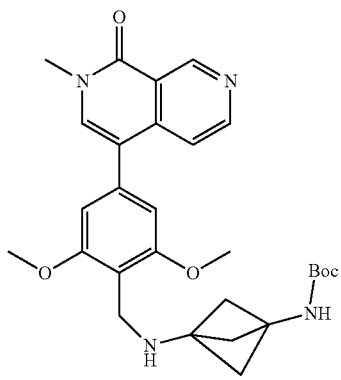

i65-2

To a stirred solution of tert-butyl N-[3-aminobicyclo[1.1.1]pentan-1-yl]carbamate (134.49 mg, 0.678 mmol, 1.10 equiv) and tert-butyl N-[3-aminobicyclo[1.1.1]pentan-1-yl] carbamate (134.49 mg, 0.678 mmol, 1.00 equiv) in MeOH (3 mL) was added NaBH$_3$CN (77.50 mg, 1.233 mmol, 2.00 equiv) in portions at room temperature. The resulting mixture was stirred for 2 hours at room temperature. The crude resulting mixture was used in the next step directly without further purification. LCMS (ESI) m/z: [M+H]$^+$=507.

Step 2: Preparation of Tert-Butyl N-[3-([[2,6-Dimethoxy-4-(2-Methyl-1-Oxo-2,7-Naphthyridin-4-Yl) Phenyl]Methyl](Methyl)Amino) Bicyclo[1.1.1]Pentan-1-Yl]Carbamate (i65-3)

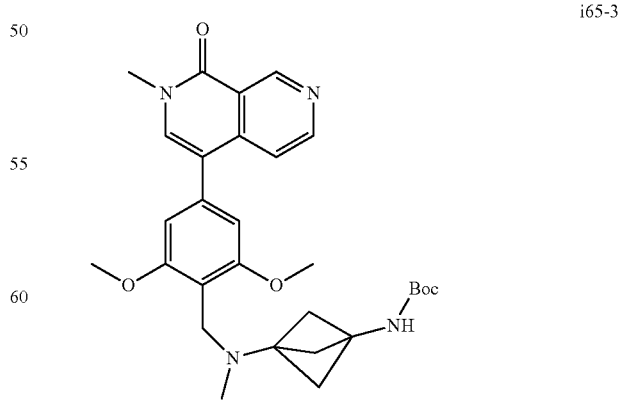

i65-3

To a stirred solution of the product from step 1 was added NaBH$_3$CN (49.62 mg, 0.790 mmol, 2.00 equiv) and formaldehyde (59.27 mg, 1.974 mmol, 5.00 equiv) in portions at room temperature. The resulting mixture was stirred for 2 hours at room temperature. Desired product could be detected by LCMS. The resulting mixture was concentrated under reduced pressure. The residue was purified by silica gel column chromatography, eluted with $CH_2Cl_2$/MeOH (8:1) to afford tert-butyl N-[3-([2,6-dimethoxy-4-(2-methyl-1-oxo-2,7-naphthyridin-4-yl)phenyl]methyl](methyl)amino) bicyclo[1.1.1]pentan-1-yl]carbamate (146 mg, 71.03%) as a light yellow oil. LCMS (ESI) m/z: $[M+H]^+$=521.

Step 3: Preparation of 4-(4-(((3-Aminobicyclo [1.1.1]Pentan-1-Yl)(Methyl)Amino)Methyl)-3,5-Dimethoxy Phenyl)-2-Methyl-2,7-Naphthyridin-1 (2H)-One (i65-4)

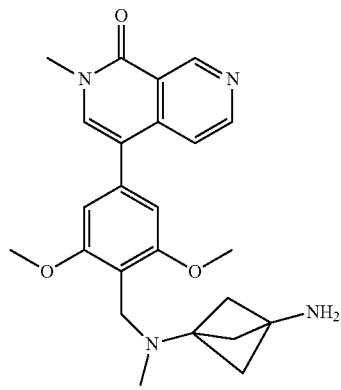

i65-4

To a stirred solution of tert-butyl N-[3-([2,6-dimethoxy-4-(2-methyl-1-oxo-2,7-naphthyridin-4-yl)phenyl]methyl] (methyl)amino) bicyclo[1.1.1]pentan-1-yl]carbamate (146.00 mg, 0.300 mmol, 1.00 equiv) in DCM was added TFA (1.00 mL) at room temperature. The resulting mixture was stirred for 2 hours at room temperature. The resulting mixture was concentrated under reduced pressure to afford 4-(4-(((3-aminobicyclo[1.1.1]pentan-1-yl)(methyl)amino) methyl)-3,5-dimethoxyphenyl)-2-methyl-2,7-naphthyridin-1 (2H)-one (210 mg crude), which was used in the next step directly without further purification. LCMS (ESI) m/z: $[M+H]^+$=421.

Step 4: Preparation of N-[3-([[2,6-Dimethoxy-4-(2-Methyl-1-Oxo-2,7-Naphthyridin-4-Yl)Phenyl] Methyl](Methyl)Amino) Bicyclo[1.1.1]Pentan-1-Yl]-3-[2-(2-[[2-(2,6-Dioxopiperidin-3-Yl)-1,3-Dioxoisoindol-4-Yl]Amino]Ethoxy) Ethoxy] Propanamide Formic Acid (Compound D59 Formic Acid)

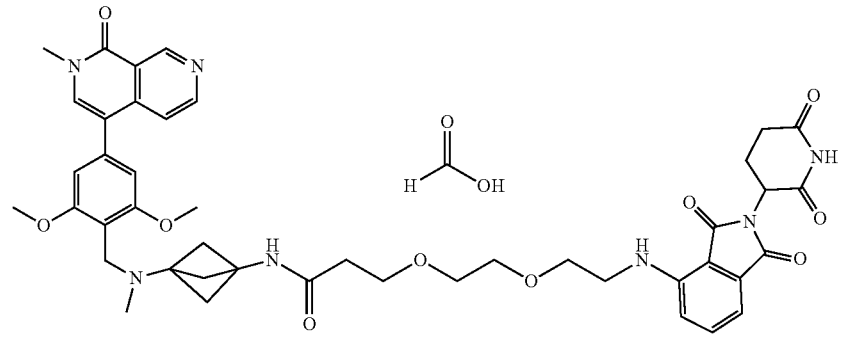

compound D59 formic acid

To a stirred solution of 4-[4-[([3-aminobicyclo[1.1.1]pentan-1-yl](methyl)amino)methyl]-3,5-dimethoxyphenyl]-2-methyl-2,7-naphthyridin-1-one (80.00 mg, 0.190 mmol, 1.00 equiv) and EDCI (72.94 mg, 0.380 mmol, 2.00 equiv) in DMF (1 mL) was added HOBT (51.41 mg, 0.380 mmol, 2.00 equiv) and DIEA (98.35 mg, 0.761 mmol, 4.00 equiv) in portions at room temperature. To the above mixture was added 3-[2-(2-[2-(2,6-dioxopiperidin-3-yl)-1,3-dioxoisoindol-4-yl]amino]ethoxy) ethoxy]propanoic acid (82.45 mg, 0.190 mmol, 1.00 equiv) at room temperature. The resulting mixture was stirred for additional overnight at room temperature. Desired product could be detected by LCMS. The crude product (78.2 mg) was purified by prep-HPLC(conditions: Xselect CSH F-Phenyl OBD column, 19*250, 5 µm; Mobile Phase A: Water (0.05% FA), Mobile Phase B: ACN; Flow rate: 25 mL/minute; Gradient: 15 B to 22 B in 17 minutes; 254/220 nm; RT: 15.32 minutes) to afford N-[3-([[2,6-dimethoxy-4-(2-methyl-1-oxo-2,7-naphthyridin-4-yl)phenyl]methyl](methyl)amino) bicyclo[1.1.1]pentan-1-yl]-3-[2-(2-[2-(2,6-dioxopiperidin-3-yl)-1,3-dioxoisoindol-4-yl]amino]ethoxy) ethoxy]propanamide formic acid (23.7 mg, 14.13%) as a yellow solid. $^1$H NMR (300 MHZ, Methanol-d4)δ 9.53 (s, 1H), 8.70 (d, J=5.8 Hz, 1H), 8.20 (brs, 0.3H, FA), 7.78 (s, 1H), 7.63 (d, J=5.7 Hz, 1H), 7.55 (dd, J=8.6, 7.1 Hz, 1H), 7.11 (d, J=8.6 Hz, 1H), 7.03 (d, J=7.1 Hz, 1H), 6.85 (s, 2H), 5.08 (dd, J=12.3, 5.4 Hz, 1H), 4.20 (s, 2H), 3.95 (s, 6H), 3.78-3.63 (m, 11H), 3.52 (t, J=5.3 Hz, 2H), 2.99-2.66 (m, 6H), 2.52-2.34 (m, 8H), 2.18-2.08 (m, 1H). LCMS (ESI) m/z: [M+H]$^+$=836.65.

Example 66—Preparation of N-[3-([2,6-Dimethoxy-4-(2-Methyl-1-Oxo-2,7-Naphthyridin-4-Yl)Phenyl]Methyl](Methyl)Amino) Bicyclo[1.1.1]Pentan-1-Yl]-6-[2-(2,6-Dioxopiperidin-3-Yl)-1,3-Dioxoisoindol-4-Yl]Oxy]Hexanamide Formic Acid (Compound D60 Formic Acid)

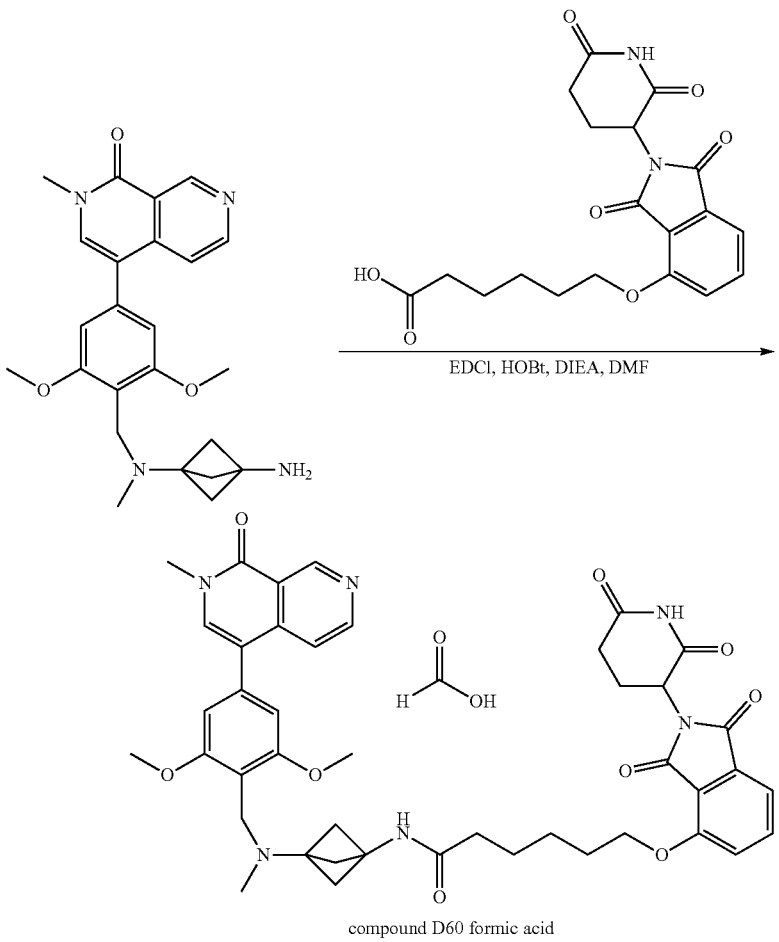

compound D60 formic acid

To a stirred solution of 4-[4-[([3-aminobicyclo[1.1.1]pentan-1-yl](methyl)amino)methyl]-3,5-dimethoxy phenyl]-2-methyl-2,7-naphthyridin-1-one (80.00 mg, 0.190 mmol, 1.00 equiv) and EDCI (72.94 mg, 0.380 mmol, 2.00 equiv) in DMF (1 mL) was added HOBt (51.41 mg, 0.380 mmol, 2.00 equiv) at room temperature. To the above mixture was added DIEA (98.35 mg, 0.761 mmol, 4.00 equiv). The resulting mixture was stirred for overnight at room temperature. Without any additional work-up, the mixture was purified by prep-HPLC(conditions: Xselect CSH F-Phenyl OBD column, 19*250, 5 µm; Mobile Phase A: Water (0.05% FA), Mobile Phase B: ACN; Flow rate: 25 mL/minute; Gradient: 5 B to 35 B in 13 minutes; 254/220 nm; RT: 12.05 minutes) to afford N-[3-([2,6-dimethoxy-4-(2-methyl-1-oxo-2,7-naphthyridin-4-yl)phenyl]methyl] (methyl)amino) bicycle[1.1.1]pentan-1-yl]-6-[2-(2,6-dioxopiperidin-3-yl)-1,3-dioxoisoindol-4-yl]oxy]hexanamide formic acid (14.9 mg, 9.36%) as a white solid. $^1$H NMR (300

MHZ, Methanol-d4) δ 9.53 (s, 1H), 8.69 (d, J=5.8 Hz, 1H), 8.44 (brs, 0.3H, FA), 7.84-7.74 (m, 2H), 7.64 (d, J=5.8 Hz, 1H), 7.46 (d, J=7.9 Hz, 2H), 6.78 (s, 2H), 5.10 (dd, J=12.0, 5.4 Hz, 1H), 4.25 (t, J=6.2 Hz, 2H), 3.91 (s, 8H), 3.72 (s, 3H), 2.91-2.67 (m, 3H), 2.39 (s, 3H), 2.29-2.20 (m, 8H), 2.18-2.08 (m, 1H), 1.91 (p, J=6.5 Hz, 2H), 1.73 (p, J=7.2 Hz, 2H), 1.60 (q, J=8.1 Hz, 2H). LCMS (ESI) m/z: $[M+H]^+$=791.40.
Example 67—Preparation of 5-(2-(4-(((1-(2,6-Dimethoxy-4-(2-Methyl-1-Oxo-1,2-Dihydro-2,7-Naphthyridin-4-Yl)Benzyl) Azetidin-3-Yl)Oxy)Methyl)-1H-1,2,3-Triazol-1-Yl) Ethoxy)-2-(2,6-Dioxopiperidin-3-Yl) Isoindoline-1,3-Dione (Compound D61)
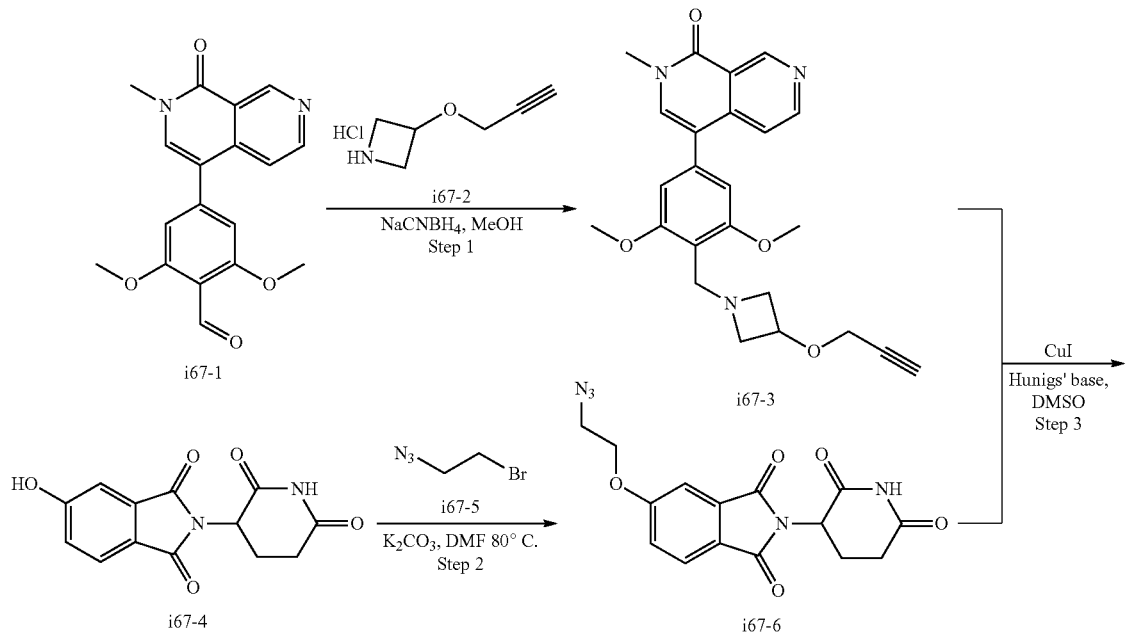
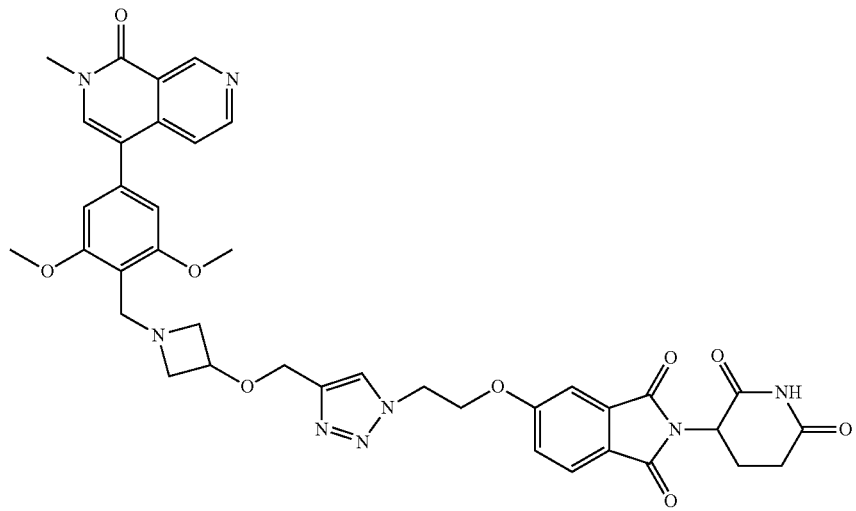
compound D61

Step 1: Preparation of 4-(3,5-Dimethoxy-4-((3-(Prop-2-Yn-1-Yloxy) Azetidin-1-Yl)Methyl)Phenyl)-2-Methyl-2,7-Naphthyridin-1 (2H)-One (i67-3)

Step 2: Preparation of 5-(2-Azidoethoxy)-2-(2,6-Dioxopiperidin-3-Yl) Isoindoline-1,3-Dione (i67-6)

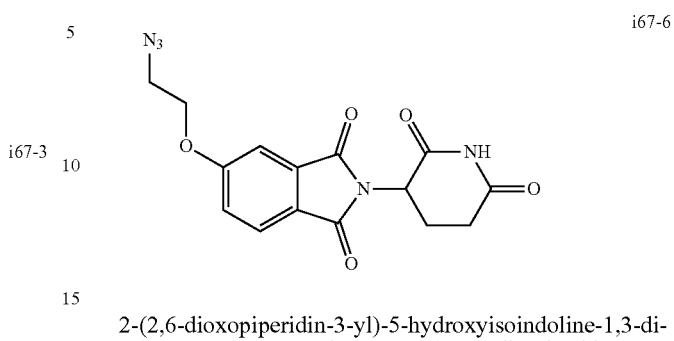

i67-6

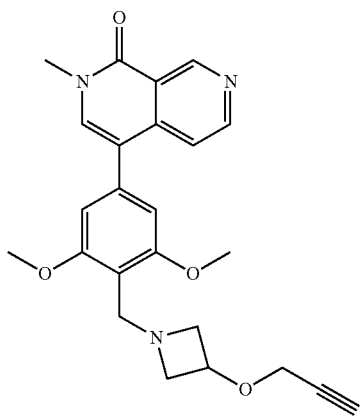

i67-3

2-(2,6-dioxopiperidin-3-yl)-5-hydroxyisoindoline-1,3-dione (500 mg, 1.82 mmol, 1.0 equiv) was dissolved in DMF (15 mL). Potassium carbonate was then added (753 mg, 545 mmol, 3 equiv) followed by potassium iodide (451 mg, 2.72 mmol, 1.5 equiv) and 1-azido-2-bromoethane (286 mg, 1.91 mmol, 1.05 equiv). The mixture was then heated to 80° C. and stirred for 2 hours. The solvent was then removed and Flash column chromatography with EtOAc/PE (0-100%), to afford 5-(2-azidoethoxy)-2-(2,6-dioxopiperidin-3-yl) isoindoline-1,3-dione (385 mg, 62%) as a solid. LCMS (ESI) m/z: [M+H]$^+$=344.4.

Step 3: Preparation of 5-(2-(4-(((1-(2,6-Dimethoxy-4-(2-Methyl-1-Oxo-1,2-Dihydro-2,7-Naphthyridin-4-Yl)Benzyl) Azetidin-3-Yl)Oxy)Methyl)-1H-1,2,3-Triazol-1-Yl) Ethoxy)-2-(2,6-Dioxopiperidin-3-Yl) Isoindoline-1,3-Dione (Compound D61)

To a stirred solution of 2,6-dimethoxy-4-(2-methyl-1-oxo-1,2-dihydro-2,7-naphthyridin-4-yl)benzaldehyde (500 mg, 1.54 mmol, 1.00 equiv) in MeOH (15 mL) was added NaBH$_3$CN (290 mg, 4.62 mmol, 3.00 equiv) and 3-(prop-2-yn-1-yloxy) azetidine hydrochloride (269 mg, 1.84 mmol, 1.20 equiv). The resulting mixture was stirred for 2 hours at room temperature. Solvent was removed and the residue was purified by Flash column chromatography with EtOAc/PE (0-100%) to afford 4-(3,5-dimethoxy-4-((3-(prop-2-yn-1-yloxy) azetidin-1-yl)methyl)phenyl)-2-methyl-2,7-naphthyridin-1 (2H)-one (451 mg, 70%) as a solid. LCMS (ESI) m/z: [M+H]$^+$=420.4.

compound D61

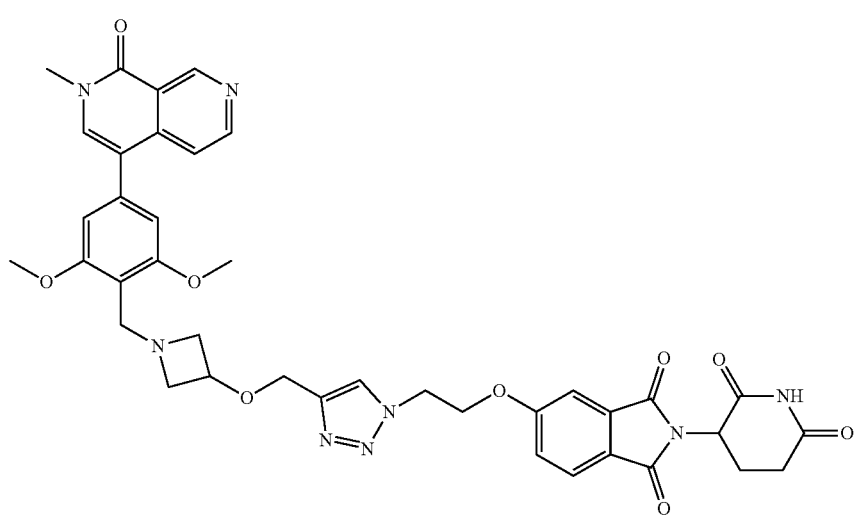

5-(2-azidoethoxy)-2-(2,6-dioxopiperidin-3-yl) isoindoline-1,3-dione (20 mg, 0.0595 mmol, 1.0 equiv) and 4-(3,5-dimethoxy-4-((3-(prop-2-yn-1-yloxy) azetidin-1-yl)methyl)phenyl)-2-methyl-2,7-naphthyridin-1 (2H)-one (25 mg, 0.0595 mmol, 1.0 equiv) were dissolved in DMSO (1 mL). Hünig's base (0.020 mL, 0.119 mmol, 2 equiv) was then added followed by CuI (5.69 mg, 0.0297 mmol, 0.5 equiv). The mixture was stirred for 1 hour at room temperature. The solution was submitted directly for HPLC purification to give 5-(2-(4-(((1-(2,6-dimethoxy-4-(2-methyl-1-oxo-1,2-dihydro-2,7-naphthyridin-4-yl)benzyl) azetidin-3-yl)oxy)methyl)-1H-1,2,3-triazol-1-yl) ethoxy)-2-(2,6- dioxopiperidin-3-yl) isoindoline-1,3-dione (14.8 mg, 33%) as a solid. $^1$H NMR (400 MHZ, DMSO-d6) δ 11.08 (s, 1H), 9.42 (s, 1H), 8.70 (s, 1H), 8.18 (s, 1H), 7.85 (s, 1H), 7.80 (d, J=8.3 Hz, 1H), 7.52 (d, J=5.8 Hz, 1H), 7.46 (d, J=2.3 Hz, 1H), 7.31 (dd, J=8.3, 2.3 Hz, 1H), 6.69 (s, 2H), 5.09 (dd, J=12.8, 5.4 Hz, 1H), 4.79 (t, J=4.9 Hz, 2H), 4.60 (t, J=5.0 Hz, 2H), 4.39 (s, 2H), 4.00 (t, J=6.1 Hz, 1H), 3.83-3.76 (m, 1H), 3.76 (s, 6H), 3.57 (d, J=4.2 Hz, 5H), 2.93-2.84 (m, 1H), 2.83 (s, 3H), 2.68-2.63 (m, 2H), 2.59 (s, 1H), 2.54 (s, 1H), 2.08-1.95 (m, 2H). LCMS (ESI) m/z: [M+H]$^+$=761.4.

Example 68—Preparation of 5-(4-(((2,6-Dimethoxy-4-(2-Methyl-1-Oxo-1,2-Dihydro-2,7-Naphthyridin-4-Yl)Benzyl)(Methyl)Amino)Methyl)-1H-1,2,3-Triazol-1-Yl)-2-(2,6-Dioxopiperidin-3-Yl) Isoindoline-1,3-Dione (Compound D62)

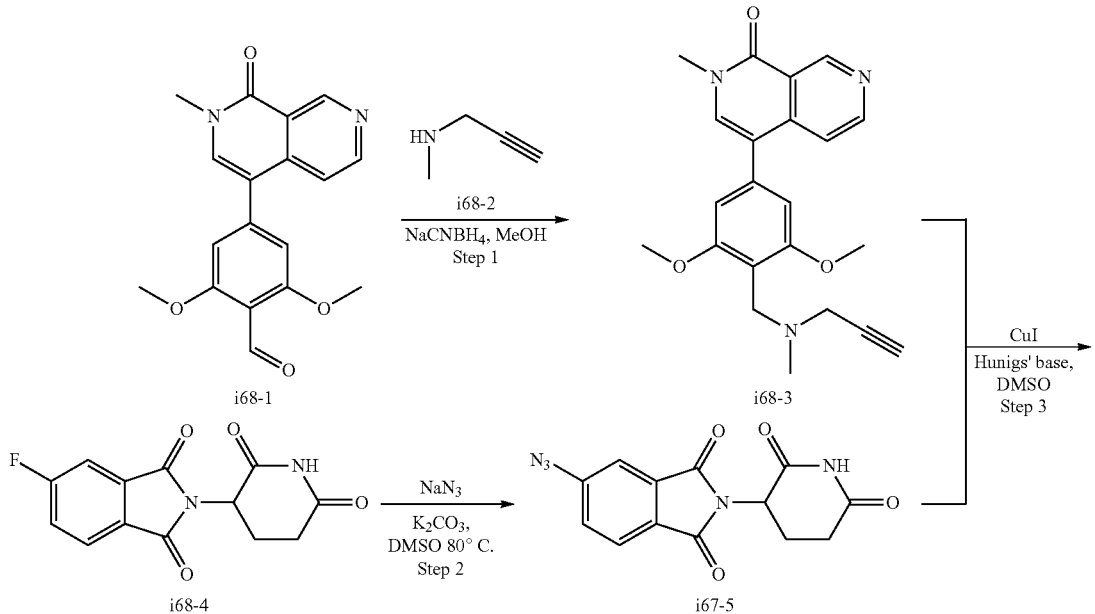

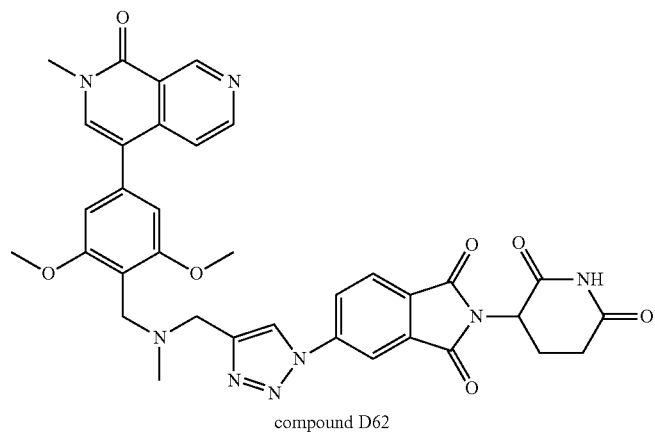

compound D62

Step 1: Preparation of 4-(3,5-Dimethoxy-4-((Methyl (Prop-2-Yn-1-Yl)Amino)Methyl)Phenyl)-2-Methyl-2,7-Naphthyridin-1 (2H)-One (i68-3)

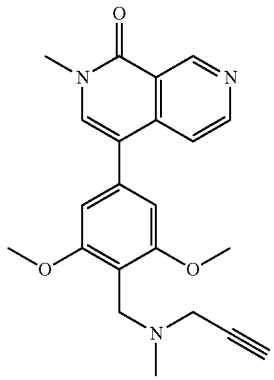

i68-3

To a stirred solution of 2,6-dimethoxy-4-(2-methyl-1-oxo-1,2-dihydro-2,7-naphthyridin-4-yl)benzaldehyde (500 mg, 1.54 mmol, 1.00 equiv) in MeOH (15 mL) was added NaBH$_3$CN (290 mg, 4.62 mmol, 3.00 equiv) and N-methylprop-2-yn-1-amine (127 mg, 1.84 mmol, 1.20 equiv). The resulting mixture was stirred for 2 hours at room temperature. Solvent was removed and the residue was purified by Flash column chromatography with EtOAc/PE (0-100%), to afford 4-(3,5-dimethoxy-4-((methyl(prop-2-yn-1-yl)amino) methyl)phenyl)-2-methyl-2,7-naphthyridin-1 (2H)-one (390 mg, 67%) as a solid. LCMS (ESI) m/z: [M+H]$^+$=378.7.

Step 2: Preparation of 5-Azido-2-(2,6-Dioxopiperidin-3-Yl) Isoindoline-1,3-Dione (i68-5)

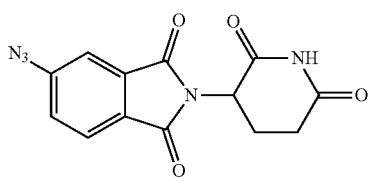

i68-5

2-(2,6-dioxopiperidin-3-yl)-5-fluoroisoindoline-1,3-dione (500 mg, 1.81 mmol, 1.0 equiv) was dissolved in DMSO (5 mL). Hünig's base was then added (0.944 mL, 5.43 mmol, 3 equiv) followed by sodium azide (176 mg, 2.71 mmol, 1.5 equiv) and 1-azido-2-bromoethane (286 mg, 1.91 mmol, 1.05 equiv). The mixture was then heated to 50° C. and stirred for 2 hours. The solution was then loaded directly onto silica gel and purified over silica gel with EtOAc/PE (0-100%) to afford 5-azido-2-(2,6-dioxopiperidin-3-yl) isoindoline-1,3-dione (480 mg, 89%) as a solid. LCMS (ESI) m/z: [M+H]$^+$=300.1.

Step 3: 5-(4-(((2,6-Dimethoxy-4-(2-Methyl-1-Oxo-1,2-Dihydro-2,7-Naphthyridin-4-Yl)Benzyl)(Methyl) Amino)Methyl)-1H-1,2,3-Triazol-1-Yl)-2-(2,6-Dioxopiperidin-3-Yl) Isoindoline-1,3-Dione (Compound D62)

compound D62

5-(2-azidoethoxy)-2-(2,6-dioxopiperidin-3-yl) isoindoline-1,3-dione (19.8 mg, 0.0662 mmol, 1.0 equiv) and 4-(3,5-dimethoxy-4-((3-(prop-2-yn-1-yloxy) azetidin-1-yl) methyl)phenyl)-2-methyl-2,7-naphthyridin-1 (2H)-one (25 mg, 0.0662 mmol, 1.0 equiv) were dissolved in DMSO (1 mL). Hünig's base (0.023 mL, 0.132 mmol, 2 equiv) was then added followed by CuI (6.3 mg, 0.0279 mmol, 0.5 equiv). The mixture was stirred for 1 hour at room temperature. The solution was submitted directly for HPLC purification to 5-(4-(((2,6-dimethoxy-4-(2-methyl-1-oxo-1,2-dihydro-2,7-naphthyridin-4-yl)benzyl)(methyl)amino) methyl)-1H-1,2,3-triazol-1-yl)-2-(2,6-dioxopiperidin-3-yl) isoindoline-1,3-dione (12.3 mg, 28%) as a solid. $^1$H NMR (400 MHz, DMSO-d6) δ 11.14 (s, 1H), 9.43 (s, 1H), 9.03 (s, 1H), 8.70 (d, J=5.7 Hz, 1H), 8.52-8.45 (m, 2H), 8.13 (d, J=14.2 Hz, 1H), 7.85 (s, 1H), 7.54 (d, J=5.7 Hz, 1H), 6.73 (s, 2H), 5.20 (dd, J=12.9, 5.3 Hz, 1H), 3.78 (s, 6H), 3.58 (s, 3H), 2.96-2.83 (m, 1H), 2.65-2.58 (m, 1H), 2.58-2.50 (m, 1H), 2.22 (s, 5H), 2.13-2.03 (m, 1H). LCMS (ESI) m/z: [M+H]$^+$=675.4.

Example 69—Preparation of 5-(4-(4-(((1-(2,6-Dimethoxy-4-(2-Methyl-1-Oxo-1,2-Dihydro-2,7-Naphthyridin-4-Yl)Benzyl) Piperidin-3-Yl)Oxy)Methyl)-1H-1,2,3-Triazol-1-Yl) Butoxy)-2-(2,6-Dioxopiperidin-3-Yl) Isoindoline-1,3-Dione (Compound D63)
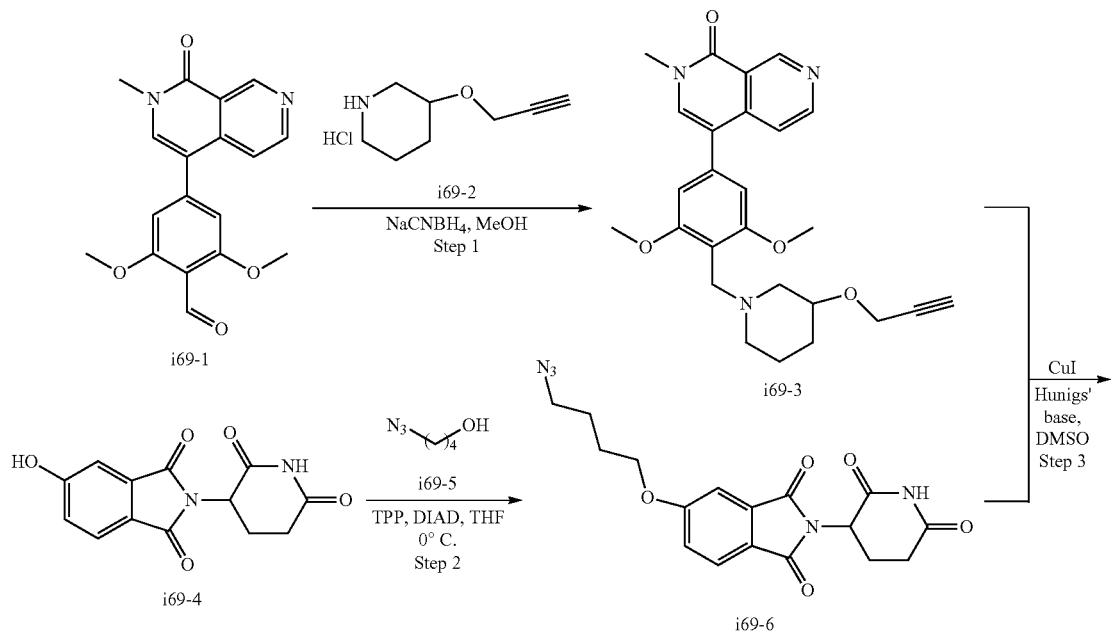
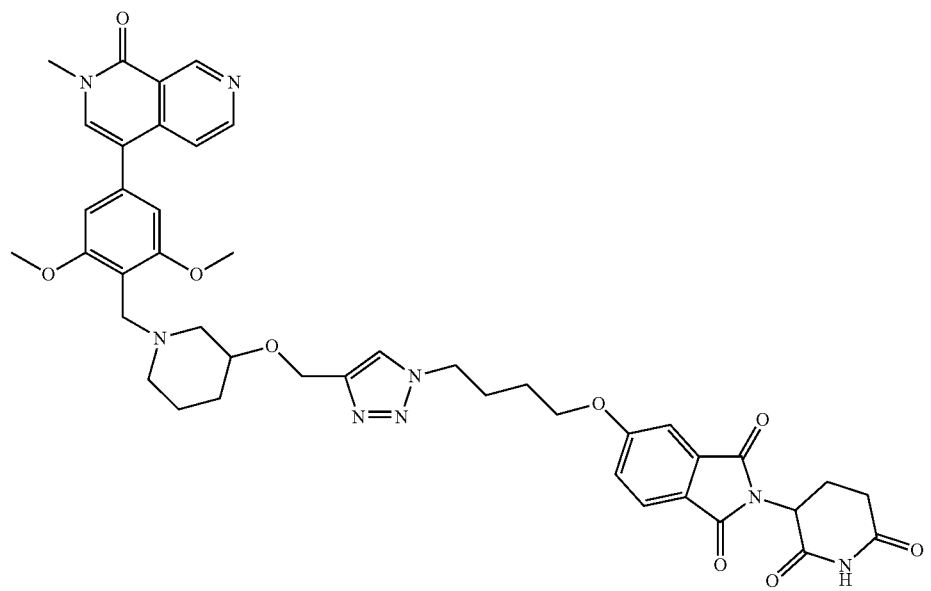
compound D63

Step 1: Preparation of 4-(3,5-Dimethoxy-4-((3-(Prop-2-Yn-1-Yloxy) Piperidin-1-Yl)Methyl)Phenyl)-2-Methyl-2,7-Naphthyridin-1 (2H)-One (i69-3)

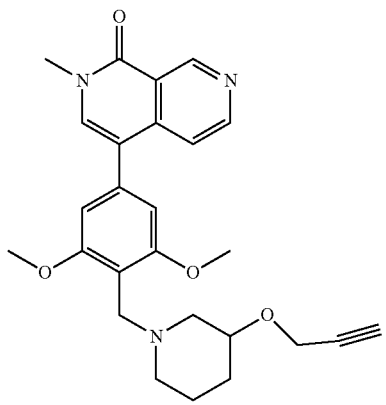

i70-3

To a stirred solution of 2,6-dimethoxy-4-(2-methyl-1-oxo-1,2-dihydro-2,7-naphthyridin-4-yl)benzaldehyde (500 mg, 1.54 mmol, 1.00 equiv) in MeOH (15 mL) was added NaBH$_3$CN (290 mg, 4.62 mmol, 3.00 equiv) and 3-(prop-2-yn-1-yloxy) piperidine hydrochloride (321 mg, 1.84 mmol, 1.20 equiv). The resulting mixture was stirred for 2 hours at room temperature. Solvent was removed and the residue was purified by Flash column chromatography with EtOAc/PE (0-100%) to afford 4-(3,5-dimethoxy-4-((3-(prop-2-yn-1-yloxy) piperidin-1-yl)methyl)phenyl)-2-methyl-2,7-naphthyridin-1 (2H)-one (323 mg, 47%) as a solid. LCMS (ESI) m/z: [M+H]$^+$=448.5.

Step 2: Preparation of 5-(4-Azidobutoxy)-2-(2,6-Dioxopiperidin-3-Yl) Isoindoline-1,3-Dione (i69-6)

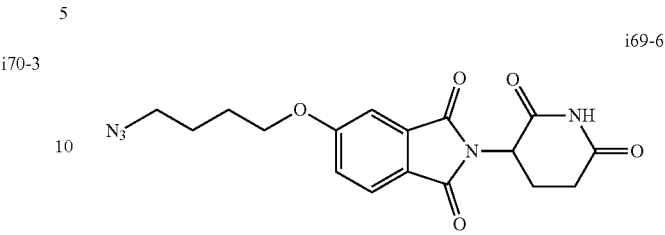

i69-6

2-(2,6-dioxopiperidin-3-yl)-5-hydroxyisoindoline-1,3-dione (500 mg, 1.82 mmol, 1.0 equiv) was dissolved in THF (18 mL). Triphenylphosphine was then added (571 mg, 2.18 mmol, 1.2 equiv) followed by 4-azidobutan-1-ol (246 mg, 2.91 mmol, 1.05 equiv). The solution was cooled to 0° C. and 1-diisopropyl azodicarboxylate (358 mL, 1.82 mmol, 1.0 equiv) was added. The mixture was then warmed to room temperature and stirred for 2 hours. Water was added and the reaction extracted 3 times with ethyl acetate. The organics were dried over MgSO$_4$, filtered, and evaporated. The resulting oil was columned over silica gel with EtOAc/PE (0-100%), to afford 5-(4-azidobutoxy)-2-(2,6-dioxopiperidin-3-yl) isoindoline-1,3-dione (391 mg, 56%) as a solid. LCMS (ESI) m/z: [M+H]$^+$=372.4.

Step 3:5-(4-(4-(((1-(2,6-Dimethoxy-4-(2-Methyl-1-Oxo-1,2-Dihydro-2,7-Naphthyridin-4-Yl)Benzyl) Piperidin-3-Yl)Oxy)Methyl)-1H-1,2,3-Triazol-1-Yl) Butoxy)-2-(2,6-Dioxopiperidin-3-Yl) Isoindoline-1, 3-Dione (Compound D63)

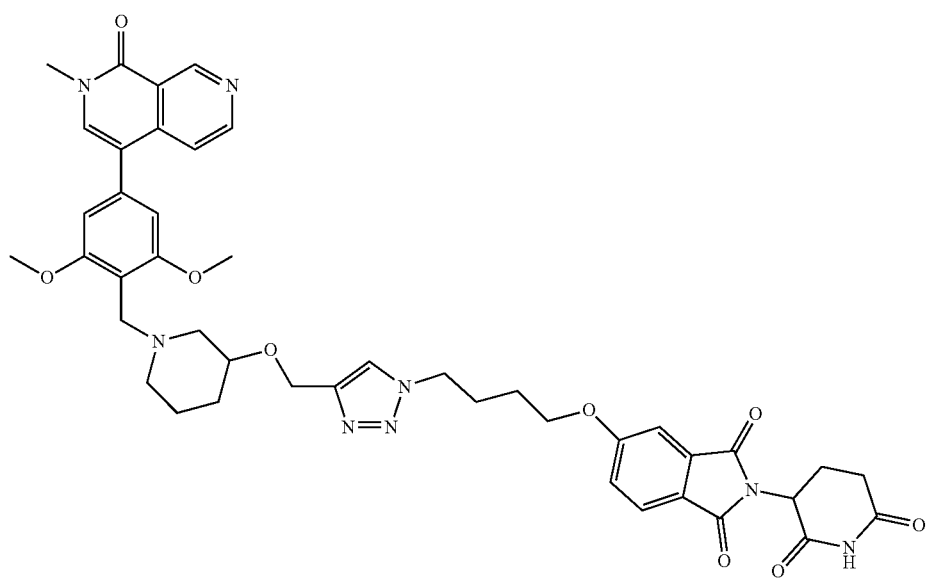

compound D63

5-(4-azidobutoxy)-2-(2,6-dioxopiperidin-3-yl) isoindoline-1,3-dione (21.5 mg, 0.0558 mmol, 1.0 equiv) and 4-(3,5-dimethoxy-4-((3-(prop-2-yn-1-yloxy) azetidin-1-yl)methyl)phenyl)-2-methyl-2,7-naphthyridin-1 (2H)-one (25 mg, 0.0558 mmol, 1.0 equiv) were dissolved in DMSO (1 mL). Hünig's base (0.0192 mL, 0.111 mmol, 2 equiv) was then added followed by CuI (5.31 mg, 0.0279 mmol, 0.5 equiv). The mixture was stirred for 1 hour at room temperature. The solution was submitted directly for HPLC purification to give 5-(4-(4-(((1-(2,6-dimethoxy-4-(2-methyl-1-oxo-1,2-dihydro-2,7-naphthyridin-4-yl)benzyl) piperidin-3-yl)oxy)methyl)-1H-1,2,3-triazol-1-yl) butoxy)-2-(2,6-dioxopiperidin-3-yl) isoindoline-1,3-dione (6.2 mg, 12%) as a solid. $^1$H NMR (400 MHZ, DMSO-d6) δ 11.08 (s, 1H), 8.09 (s, 1H), 7.87 (s, 1H), 7.80 (d, J=8.3 Hz, 1H), 7.77-7.56 (m, 1H), 7.39 (d, J=2.3 Hz, 1H), 7.31 (dd, J=8.3, 2.3 Hz, 1H), 6.73 (s, 2H), 6.58-6.39 (m, 1H), 5.09 (dd, J=12.9, 5.4 Hz, 1H), 4.59-4.47 (m, 2H), 4.42 (t, J=7.0 Hz, 2H), 4.17 (t, J=6.4 Hz, 2H), 3.80 (s, 6H), 3.70 (s, 2H), 3.58 (s, 2H), 3.00 (s, 1H), 2.87 (ddd, J=17.4, 14.1, 5.4 Hz, 1H), 2.74 (s, 1H), 2.68-2.63 (m, OH), 2.62-2.50 (m, 2H), 2.33-2.27 (m, 1H), 2.05 (s, 3H), 2.03-1.93 (m, 1H), 1.97-1.78 (m, OH), 1.71 (q, J=6.7 Hz, 3H), 1.40 (s, 1H). LCMS (ESI) m/z: [M+H]$^+$ =817.2.

Example 70—Preparation of 5-[2-(9-[2,6-Dimethoxy-4-(2-Methyl-1-Oxo-2,7-Naphthyridin-4-Yl)Phenyl]Methyl]-1-Oxa-4,9-Diazaspiro[5.5]Undecan-4-Yl)-2-Oxoethoxy]-2-(2,6-Dioxopiperidin-3-Yl) Isoindole-1,3-Dione Formic Acid (Compound D64 Formic Acid)

To a stirred solution of [[2-(2,6-dioxopiperidin-3-yl)-1,3-dioxoisoindol-5-yl]oxy]acetic acid (21.46 mg, 0.065 mmol, 1.00 equiv) and 4-(3,5-dimethoxy-4-[1-oxa-4,9-diazaspiro[5.5]undecan-9-ylmethyl]phenyl)-2-methyl-2,7-naphthyridin-1-one (30.00 mg, 0.065 mmol, 1.00 equiv) in DMF (1 mL) was added HATU (49.11 mg, 0.129 mmol, 2.00 equiv) and DIEA (33.38 mg, 0.258 mmol, 4.00 equiv) at room temperature. The mixture was stirred at room temperature for 16 hours. Without any additional work-up, the mixture was purified by prep-HPLC(conditions: SunFire Prep C18 OBD Column, 19×150 mm 5 μm 10 nm; Mobile Phase A: Water (0.1% FA), Mobile Phase B: ACN; Flow rate: 25 mL/minute; Gradient: 8 B to 33 B in 10 minutes; 254/220 nm; RT: 8.05 minutes) to afford 5-[2-(9-[[2,6-dimethoxy-4-(2-methyl-1-oxo-2,7-naphthyridin-4-yl)phenyl]methyl]-1-oxa-4,9-diazaspiro[5.5]undecan-4-yl)-2-oxoethoxy]-2-(2,6-diox opiperidin-3-yl) isoindole-1,3-dione formic acid as a white gum (6.8 mg, 12.77%). $^1$H NMR (400 MHZ, Methanol-d4)δ 9.54 (s, 1H), 8.69 (d, J=5.8 Hz, 1H), 8.56 (brs, 0.3H, FA), 7.84 (dd, J=8.4, 2.3 Hz, 1H), 7.76 (d, J=2.5 Hz, 1H), 7.67-7.62 (m, 1H), 7.45 (t, J=2.8 Hz, 1H), 7.40 (dd, J=8.3, 2.2 Hz, 1H), 6.81 (d, J=4.5 Hz, 2H), 5.16-5.00 (m, 3H), 4.18-3.98 (m, 2H), 3.92 (d, J=1.6 Hz, 6H), 3.85-3.75 (m, 2H), 3.72 (s, 3H), 3.67-3.59 (m, 2H), 3.56-3.45 (m, 2H), 3.11-2.91 (m, 3H), 2.90-2.64 (m, 4H), 2.18-2.09 (m, 1H), 2.08-1.91 (m, 2H), 1.85-1.69 (m, 2H). LCMS (ESI) m/z: [M+H]$^+$=779.55.

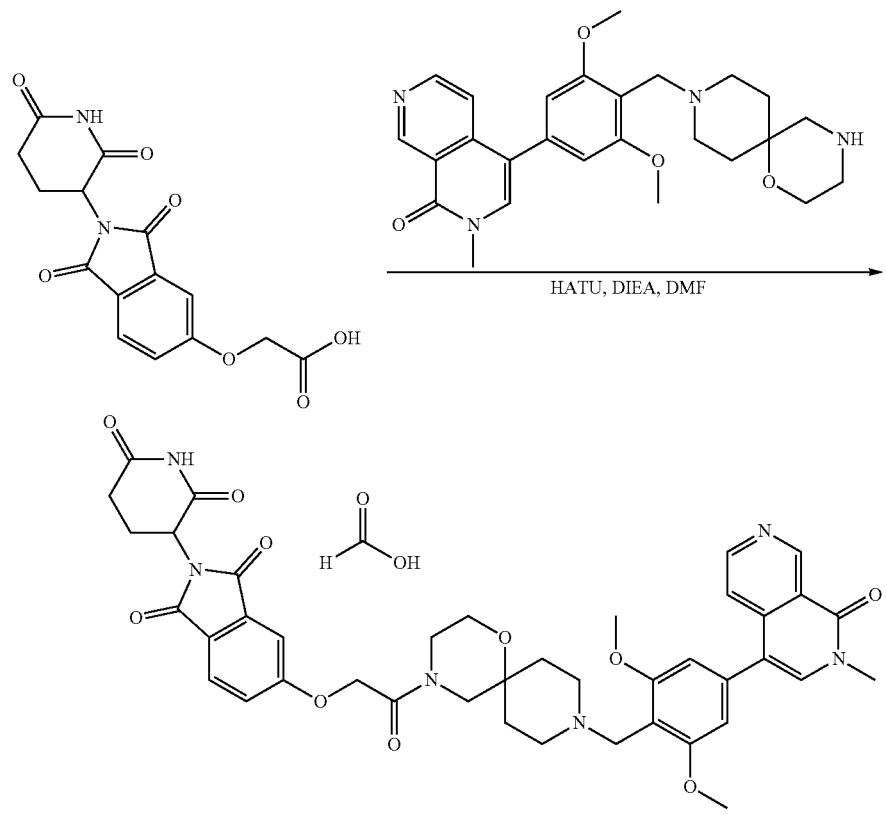

compound D64 formic acid

Example 71—Preparation of N-[[2-(4-[2,6-Dimethoxy-4-(2-Methyl-1-Oxo-2,7-Naphthyridin-4-Yl)Phenyl]Methyl]Piperazine-1-Carbonyl)Cyclopropyl]Methyl]-2-[[2-(2,6-Dioxopiperidin-3-Yl)-1,3-Dioxoisoindol-4-Yl]Oxy]Acetamide (Compound D65)

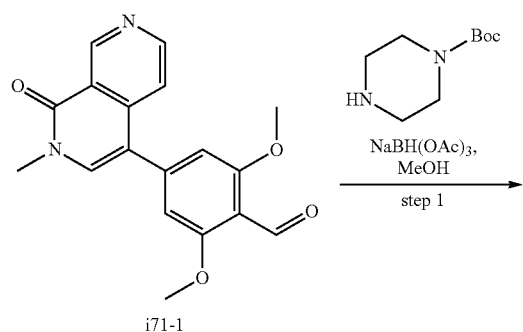

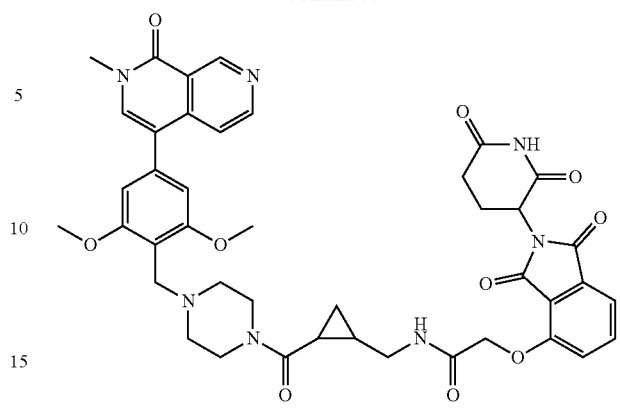

compound D65

Step 1: Preparation of Tert-Butyl 4-[[2,6-Dimethoxy-4-(2-Methyl-1-Oxo-2,7-Naphthyridin-4-Yl)Phenyl]Methyl]Piperazine-1-Carboxylate (i71-2)

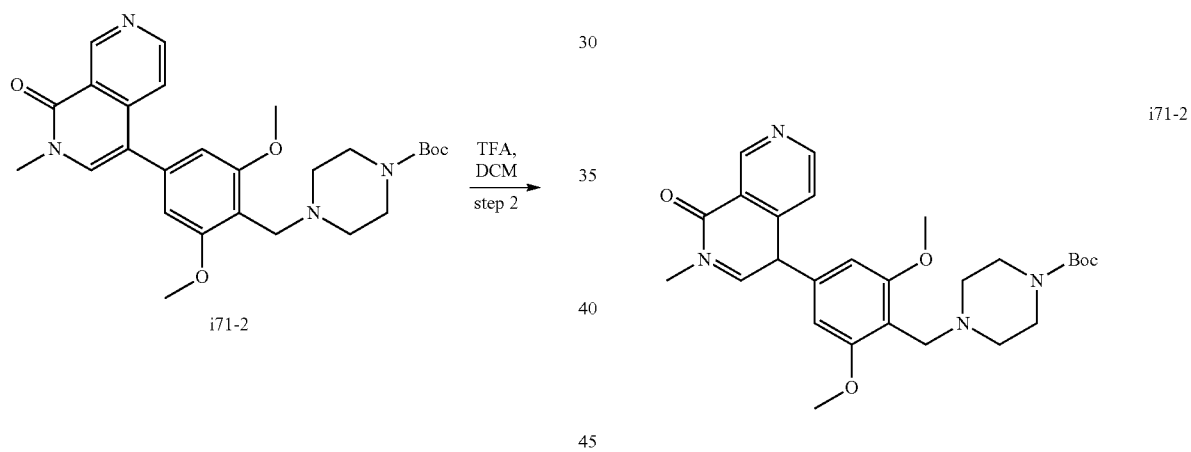

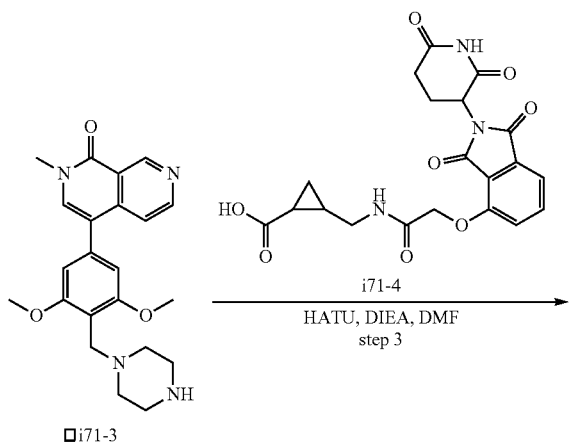

To a stirred solution of 2,6-dimethoxy-4-(2-methyl-1-oxo-2,7-naphthyridin-4-yl)benzaldehyde (100.00 mg, 0.308 mmol, 1.00 equiv) and tert-butyl piperazine-1-carboxylate (86.14 mg, 0.462 mmol, 1.50 equiv) in MeOH (1 mL) was added NaBH(OAc)$_3$ (261.38 mg, 1.233 mmol, 4.00 equiv) at room temperature. The resulting mixture was stirred for 2 hours at room temperature. The reaction mixture was filtered, and the filtrate was concentrated under reduced pressure. The crude product was purified by flash silica chromatography, elution gradient 0 to 60% EtOAc in petroleum ether. Pure fractions were evaporated to dryness to afford product tert-butyl 4-[2,6-dimethoxy-4-(2-methyl-1-oxo-2,7-naphthyridin-4-yl)phenyl]methyl]piperazine-1-carboxylate (115 mg, 75.4%) as a yellow gum. LCMS (ESI) m/z: [M+H]$^+$=495.

Step 2: Preparation of 4-[3,5-Dimethoxy-4-(Piperazin-1-Ylmethyl)Phenyl]-2-Methyl-2,7-Naphthyridin-1-One (i71-3)

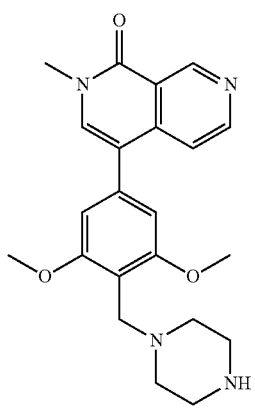

A solution of tert-butyl 4-[[2,6-dimethoxy-4-(2-methyl-1-oxo-2,7-naphthyridin-4-yl)phenyl]methyl]piperazine-1-carboxylate (115.00 mg) and TFA (1.00 mL) in DCM (1.00 mL) was stirred at room temperature for 2 hours. The reaction mixture was concentrated under reduced pressure to afford 4-[3,5-dimethoxy-4-(piperazin-1-ylmethyl)phenyl]-2-methyl-2,7-naphthyridin-1-one (305 mg, crude), which was used directly without further purification. LCMS (ESI) m/z: [M+H]$^+$=395.

Step 3: Preparation of N-[[2-(4-[[2,6-Dimethoxy-4-(2-Methyl-1-Oxo-2,7-Naphthyridin-4-Yl)Phenyl]Methyl]Piperazine-1-Carbonyl)Cyclopropyl]Methyl]-2-[[2-(2,6-Dioxopiperidin-3-Yl)-1,3-Dioxoisoindol-4-Yl]Oxy]Acet Amide (Compound D65)

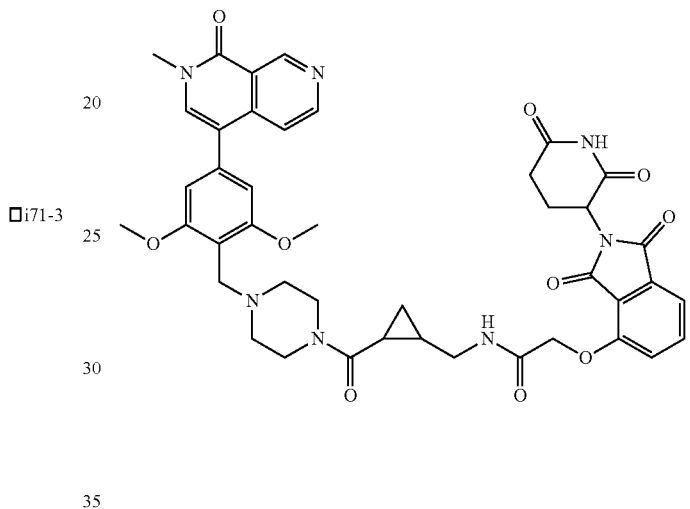

compound D65

To a stirred mixture of 4-[3,5-dimethoxy-4-(piperazin-1-ylmethyl)phenyl]-2-methyl-2,7-naphthyridin-1-one (22.05 mg, 0.056 mmol, 1.20 equiv) and 2-[(2-[2-(2,6-dioxopiperidin-3-yl)-1,3-dioxoisoindol-4-yl]oxy]acetamido)methyl]cyclopropane-1-carboxylic acid (20.00 mg, 0.047 mmol, 1.00 equiv) in DMF (1 mL) was added HATU (35.42 mg, 0.093 mmol, 2.00 equiv) and DIEA (12.04 mg, 0.093 mmol, 2.00 equiv) at room temperature. Without any additional work-up, the mixture was purified by prep-HPLC(conditions: XBridge Shield RP18 OBD Column, 30*150 mm, 5 μm; Mobile Phase A: Water (0.1% FA), Mobile Phase B: ACN; Flow rate: 25 mL/minute; Gradient: 13 B to 22 B in 12 minutes; 254/220 nm; RT: 9.45 minutes). Pure fractions were evaporated to dryness to afford N-[[2-(4-[[2,6-dimethoxy-4-(2-methyl-1-oxo-2,7-naphthyridin-4-yl)phenyl]methyl]piperazine-1-carbonyl)cyclopropyl]meth-yl]-2-[2-(2,6-dioxopiperidin-3-yl)-1,3-dioxoisoindol-4-yl]oxy]acetamide (12.4 mg, 33.04%) as a white solid. $^1$H NMR (400 MHZ, Methanol-d4)δ 9.52 (s, 1H), 8.68 (dd, J=5.8, 1.8 Hz, 1H), 8.43 (brs, 0.5H, FA), 7.81 (ddd, J=8.4, 7.3, 3.5 Hz, 1H), 7.75 (d, J=3.7 Hz, 1H), 7.65-7.61 (m, 1H), 7.54 (dd, J=6.9, 1.6 Hz, 1H), 7.45 (dd, J=8.3, 2.5 Hz, 1H), 6.76 (d, J=2.5 Hz, 2H), 5.19-5.11 (m, 1H), 4.80-4.68 (m, 2H), 3.93-3.81 (m, 9H), 3.78-3.68 (m, 5H), 3.51-3.35 (m, 2H), 3.29-3.16 (m, 1H), 2.93-2.67 (m, 7H), 2.21-2.06 (m, 2H), 1.72-1.60 (m, 1H), 1.21-1.12 (m, 1H), 1.09-0.99 (m, 1H). LCMS (ESI) m/z: [M+H]$^+$=806.70.

Example 72—Preparation of N-[[2-(4-[2,6-Dimethoxy-4-(2-Methyl-1-Oxo-2,7-Naphthyridin-4-Yl)Phenyl]Methyl]Piperazine-1-Carbonyl)Cyclopropyl]Methyl]-2-[2-(2,6-Dioxopiperidin-3-Yl)-1,3-Dioxoisoindol-5-Yl]Oxy]Acetamide Formic Acid (Compound D66 Formic Acid)

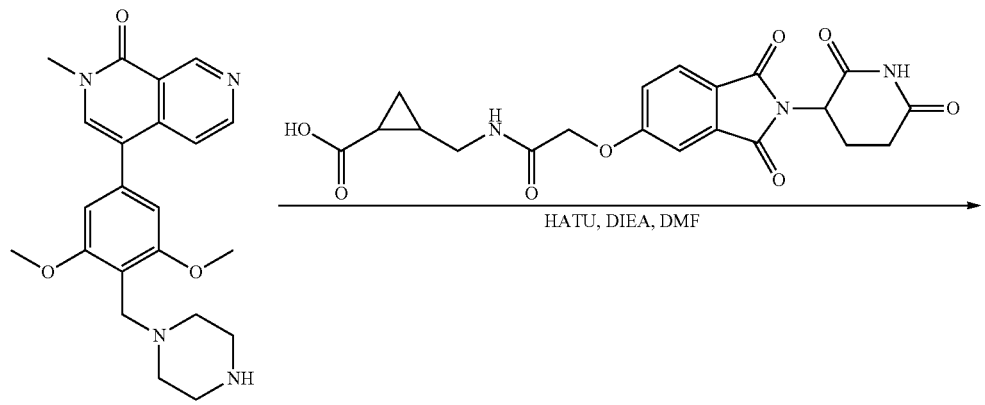

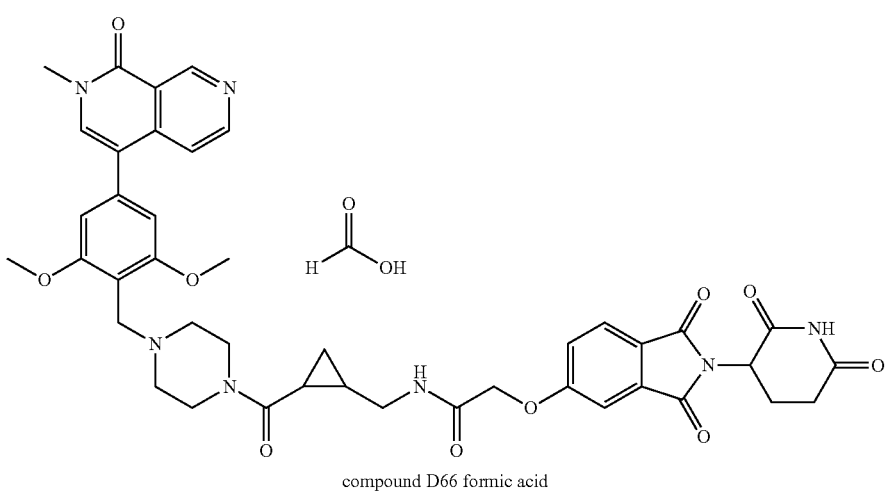

compound D66 formic acid

To a stirred mixture of 4-[3,5-dimethoxy-4-(piperazin-1-ylmethyl)phenyl]-2-methyl-2,7-naphthyridin-1-one (22.05 mg, 0.056 mmol, 1.20 equiv) and 2-[(2-[[2-(2,6-dioxopiperidin-3-yl)-1,3-dioxoisoindol-5-yl]oxy]acetamido)methyl]cyclopropane-1-carboxylic acid (20.00 mg, 0.047 mmol, 1.00 equiv) in DMF (1 mL) was added HATU (35.42 mg, 0.093 mmol, 2.00 equiv) and DIEA (12.04 mg, 0.093 mmol, 2.00 equiv) at room temperature. Without any additional work-up, the mixture was purified by prep-HPLC(conditions: XBridge Shield RP18 OBD Column, 19*250 mm, 10 µm; Mobile Phase A: Water (0.1% FA), Mobile Phase B: ACN; Flow rate: 25 mL/minute; Gradient: 13 B to 22 B in 12 minutes; 254/220 nm; RT: 10.22 minutes). Pure fractions were evaporated to dryness to afford N-[[2-(4-[2,6-dimethoxy-4-(2-methyl-1-oxo-2,7-naphthyridin-4-yl)phenyl]methyl]piperazine-1-carbonyl)cyclopropyl]methyl]-2-[2-(2,6-dioxopiperidin-3-yl)-1,3-dioxoisoindol-5-yl]oxy]acetamide (7.4 mg, 19.18%) as a white solid. $^1$H NMR (400 MHZ, Methanol-d4) δ 9.52 (s, 1H), 8.68 (d, J=5.8 Hz, 1H), 8.46 (brs, 1.0H, FA), 7.82 (d, J=8.3 Hz, 1H), 7.73 (s, 1H), 7.63 (d, J=5.8 Hz, 1H), 7.45 (d, J=2.3 Hz, 1H), 7.40 (dd, J=8.3, 2.3 Hz, 1H), 6.78 (s, 2H), 5.11 (dd, J=12.4, 5.4 Hz, 1H), 4.68 (s, 2H), 3.95 (s, 2H), 3.89 (s, 6H), 3.81 (s, 2H), 3.70 (s, 3H), 3.63 (s, 1H), 3.42-3.34 (m, 2H), 3.29-3.20 (m, 1H), 2.94-2.67 (m, 7H), 2.18-2.09 (m, 1H), 2.09-2.00 (m, 1H), 1.62 (q, J=7.5 Hz, 1H), 1.11 (q, J=5.5 Hz, 1H), 1.01 (td, J=8.1, 4.5 Hz, 1H). LCMS (ESI) m/z: [M+H]$^+$=806.40.

Example 73—Preparation of 1-[2,6-Dimethoxy-4-(2-Methyl-1-Oxo-1,2-Dihydro-2,7-Naphthyridin-4-Yl)Phenyl]Methyl]-N-(6-[[2-(2,6-Dioxopiperidin-3-Yl)-1,3-Dioxo-2,3-Dihydro-1H-Isoindol-5-Yl]Amino]Hexyl) Azetidine-3-Sulfonamide Formic Acid (Compound D67 Formic Acid)
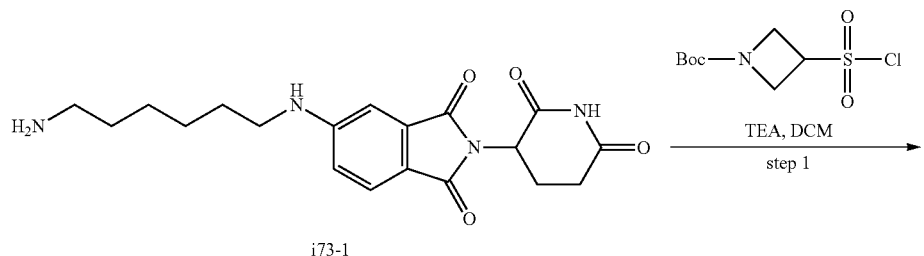
i73-1
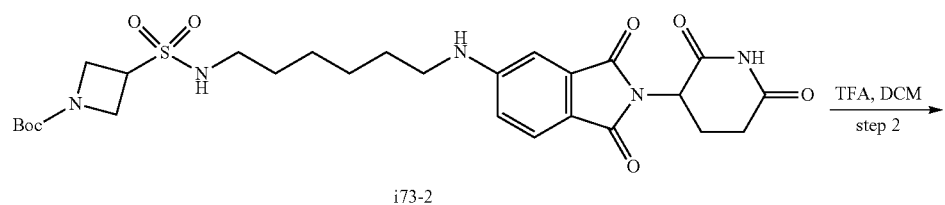
i73-2
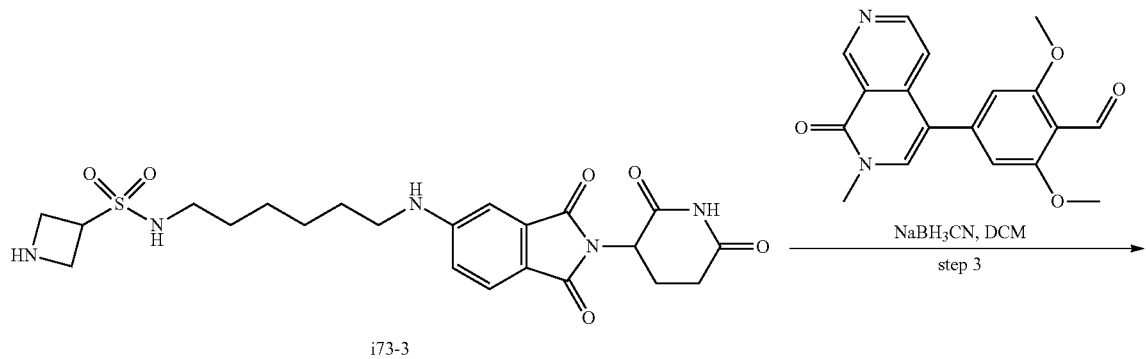
i73-3
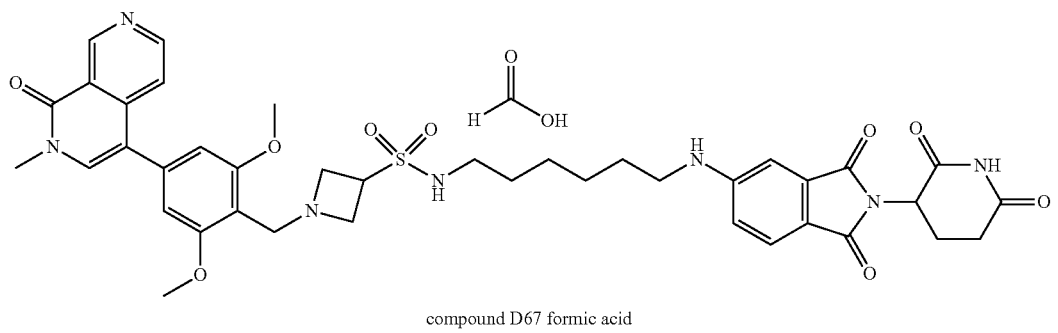
compound D67 formic acid Step 1: Preparation of Tert-Butyl-3-[(6-[[2-(2,6-Dioxopiperidin-3-Yl)-1,3-Dioxoisoindol-5-Yl]Amino]Hexyl) Sulfamoyl]Azetidine-1-Carboxylate (i73-2)

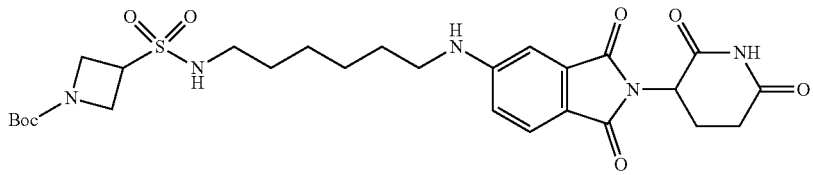

i73-2

To a stirred mixture of 5-[(6-aminohexyl)amino]-2-(2,6-dioxopiperidin-3-yl) isoindole-1,3-dione (60.00 mg, 0.161 mmol, 1.00 equiv) and tert-butyl 3-(chlorosulfonyl) azetidine-1-carboxylate (102.99 mg, 0.403 mmol, 2.50 equiv) in DCM (2.00 mL) was added TEA (48.91 mg, 0.483 mmol, 3.00 equiv). After stirring for 1.5 hours at room temperature, the resulting mixture was concentrated under reduced pressure. The residue was purified by Prep-TLC(CH$_2$Cl$_2$/EA=1:2) to afford tert-butyl-3-[(6-[2-(2,6-dioxopiperidin-3-yl)-1,3-dioxoisoindol-5-yl]amino]hexyl) sulfamoyl]azetidine-1-carboxylate (61.8 mg, 60.29%) as a light yellow solid. LCMS (ESI) m/z: [M+H]$^+$=592.

Step 2: Preparation of N-(6-((2-(2,6-Dioxopiperidin-3-Yl)-1,3-Dioxoisoindolin-5-Yl)Amino) Hexyl) Azetidine-3-Sulfonamide (i73-3)

i73-3

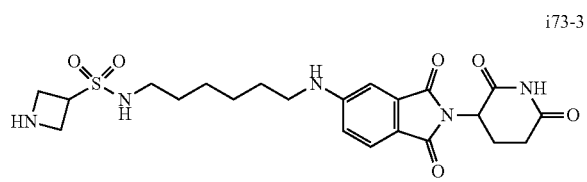

To a stirred mixture of tert-butyl 3-[(6-[2-(2,6-dioxopiperidin-3-yl)-1,3-dioxoisoindol-5-yl]amino]hexyl) sulfamoyl]azetidine-1-carboxylate (61.8 mg, 0.104 mmol, 1.00 equiv) in DCM (2.00 mL) was added TFA (0.40 mL, 5.385 mmol, 51.56 equiv). After stirring for 1 hour at room temperature, the resulting mixture was concentrated under reduced pressure. The residue was used in the next step directly without further purification. LCMS (ESI) m/z: [M+H]$^+$=492.

Step 3: Preparation of 1-[[2,6-Dimethoxy-4-(2-Methyl-1-Oxo-1,2-Dihydro-2,7-Naphthyridin-4-Yl) Phenyl]Methyl]-N-(6-[2-(2,6-Dioxopiperidin-3-Yl)-1,3-Dioxo-2,3-Dihydro-1H-Isoindol-5-Yl]Amino] Hexyl) Azetidine-3-Sulfonamide Formic Acid (Compound D67 Formic Acid)

compound D67 formic acid

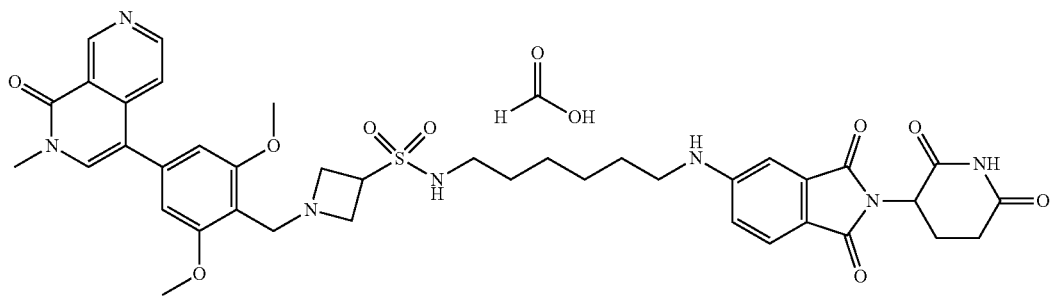

A mixture of N-(6-[[2-(2,6-dioxopiperidin-3-yl)-1,3-dioxo-2,3-dihydro-1H-isoindol-5-yl]amino]hexyl) azetidine-3-sulfonamide (51.36 mg, 0.104 mmol, 1.00 equiv) and 2,6-dimethoxy-4-(2-methyl-1-oxo-1,2-dihydro-2,7-naphthyridin-4-yl)benzaldehyde (33.89 mg, 0.104 mmol, 1.00 equiv) in DMF (2 mL) was stirred at room temperature. The reaction mixture was then adjusted to pH 8-9 with TEA. To the above mixture was added NaBH$_3$CN (19.70 mg, 0.313 mmol, 3.00 equiv) in portions, and the resulting mixture was stirred for 2 hours at room temperature. The resulting mixture was concentrated under reduced pressure, the residue was purified by Prep-HPLC(conditions: X Select CSH Prep C18 OBD Column, 5 μm, 19*150 mm; mobile phase, Water (0.1% FA) and ACN (15% Phase B up to 30% in 14 minutes); Detector, UV). This gave 1-[2,6-dimethoxy-4-(2-methyl-1-oxo-1,2-dihydro-2,7-naphthyridin-4-yl)phenyl] methyl]-N-(6-[2-(2,6-dioxopiperidin-3-yl)-1,3-dioxo-2,3-dihydro-1H-isoindol-5-yllamino]hexyl) azetidine-3-sulfonamide formic acid (13 mg, 14.12%) as a yellow solid.
$^1$H NMR (400 MHz, DMSO-d6) δ9.45 (s, 1H), 8.73 (d, J=5.7 Hz, 1H), 8.14 (s, 0.2H, FA), 7.87 (s, 1H), 7.56 (d, J=5.7 Hz, 1H), 7.51 (d, J=8.3 Hz, 1H), 7.27 (br s, 1H), 6.94 (d, J=2.0 Hz, 1H), 6.82 (dd, J=8.2, 2.0 Hz, 1H), 6.78 (s, 2H), 6.56 (d, J=8.2 Hz, 2H), 5.10 (dd, J=13.0, 5.4 Hz, 1H), 4.01 (br s, 2H), 3.84 (s, 7H), 3.60 (s, 6H), 3.47-3.35 (m, 2H), 3.05-2.83 (m, 3H), 2.77-2.65 (m, 1H), 2.49-2.41 (m, 2H), 2.03-1.96 (m, 1H), 1.39 (t, J=7.0 Hz, 4H), 1.24 (s, 4H). LCMS (ESI) m/z: [M+H]$^+$=800.25.

Example 74—Preparation of N-[3-[([[2,6-Dimethoxy-4-(2-Methyl-1-Oxo-2,7-Naphthyridin-4-Yl)Phenyl]Methyl](Meth-Yl)Amino)Methyl]Bicyclo[1.1.1]Pentan-1-Yl]-3-[2-(2-[[2-(2,6-Dioxopiperidin-3-Yl)-1,3-Dioxoisoindol-4-Yl]Amino]Ethoxy)Ethoxy]Propanamide Formic Acid (Compound D68 Formic Acid)
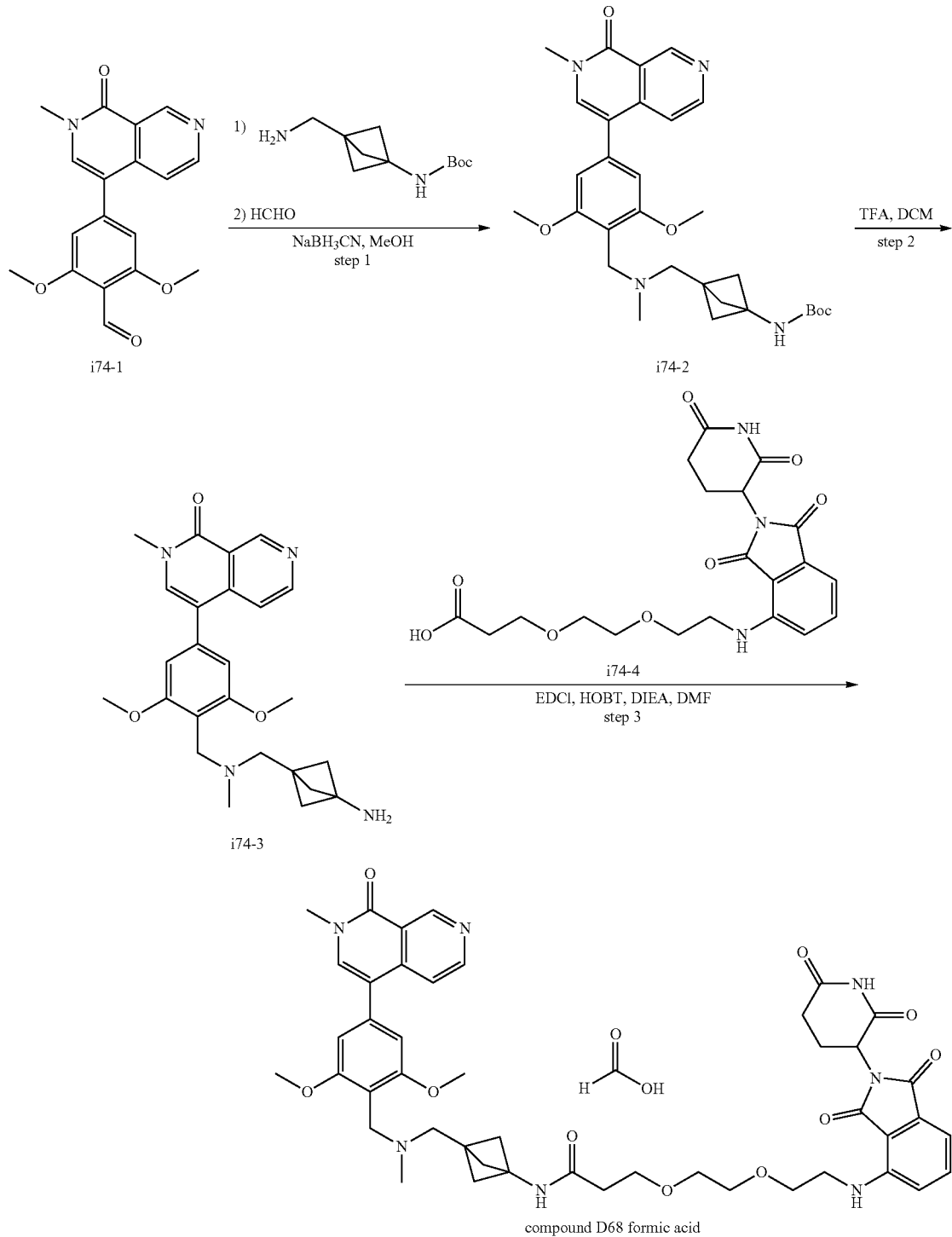

Step 1: Preparation of Tert-Butyl N-[3-[([[2,6-Dimethoxy-4-(2-Methyl-1-Oxo-2,7-Naphthyridin-4-Yl)Phenyl]Met Hyl]Amino)Methyl]Bicyclo[1.1.1]Pentan-1-Yl]Carbamate (i74-2)

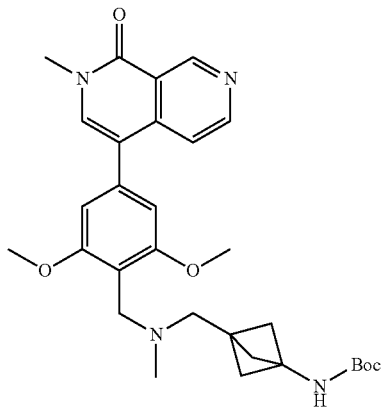

i74-2

Step 2: Preparation of 4-(4-[[([3-Aminobicyclo[1.1.1]Pentan-1-Yl]Methyl)(Methyl)Amino]Methyl]-3,5-Dimeth Oxyphenyl)-2-Methyl-2,7-Naphthyridin-1-One (i74-3)

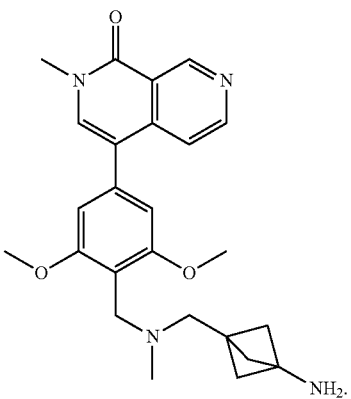

i74-3

To a stirred mixture of 2,6-dimethoxy-4-(2-methyl-1-oxo-2,7-naphthyridin-4-yl)benzaldehyde (200.00 mg, 0.617 mmol, 1.00 equiv) and tert-butyl N-[3-(aminomethyl) bicyclo[1.1.1]pentan-1-yl]carbamate (144.00 mg, 0.678 mmol, 1.10 equiv) in MeOH (1 mL) was added NaBH$_3$CN (77.50 mg, 1.233 mmol, 2.00 equiv) in portions at room temperature. The resulting mixture was stirred for 2 hours at room temperature. To the above mixture was added formaldehyde (0.50 mL). The resulting mixture was stirred for 1 hour at room temperature. The reaction mixture was filtered, and the filtrate was concentrated under reduced pressure. The crude product was purified by flash silica chromatography, elution gradient 0 to 30% EtOAc in petroleum ether. Pure fractions was concentrated under vacuum to afford tert-butyl N-[3-[([2,6-dimethoxy-4-(2-methyl-1-oxo-2,7-naphthyridin-4-yl)phenyl]methyl]amino)methyl]bicyclo[1.1.1]pentan-1-yl]carbamate (284.8 mg) as a yellow gum. LCMS (ESI) m/z: [M+H]$^+$=535.

A mixture of tert-butyl N-[3-[([2,6-dimethoxy-4-(2-methyl-1-oxo-2,7-naphthyridin-4-yl)phenyl]methyl](methyl)amino)methyl]bicyclo[1.1.1]pentan-1-yl]carbamate (284.80 mg) and TFA (1.00 mL) in DCM (1 mL) was stirred for overnight at room temperature. The reaction mixture was concentrated under vacuum to afford 4-(4-[[([3-aminobicyclo[1.1.1]pentan-1-yl]methyl)(methyl)amino]methyl]-3,5-dimethoxyphenyl)-2-methyl-2,7-naphthyridin-1-one (639.4 mg, crude) as a yellow gum. LCMS (ESI) m/z: [M+H]$^+$=435.

Step 3: Preparation of N-[3-[([2,6-Dimethoxy-4-(2-Methyl-1-Oxo-2,7-Naphthyridin-4-Yl)Phenyl]Methyl](Methyl)Amino)Methyl]Bicyclo[1.1.1]Pentan-1-Yl]-3-[2-(2-[[2-(2,6-Dioxopiperidin-3-Yl)-1,3-Dioxoisoindol-4-Yl]Ami-No]Ethoxy) Ethoxy] Propanamide Formic Acid (Compound D68 Formic Acid)

compound D68 formic acid

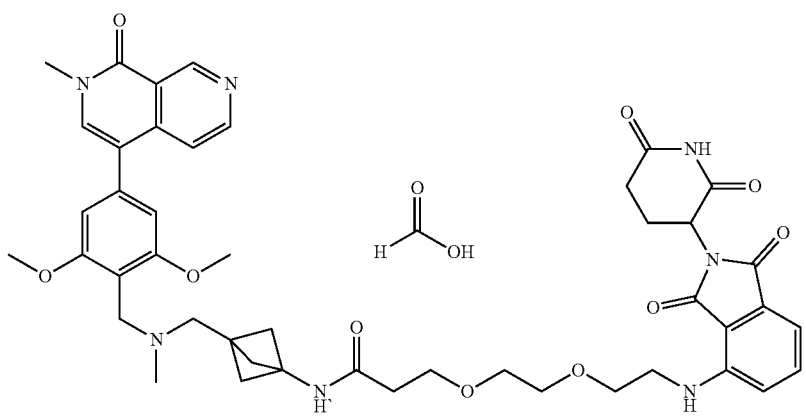

To a stirred solution of 4-(4-[([3-aminobicyclo[1.1.1]pentan-1-yl]methyl)(methyl)amino]methyl]-3,5-dimethoxyphenyl)-2-methyl-2,7-naphthyridin-1-one (20.05 mg, 0.046 mmol, 1 equiv) and 3-[2-(2-[2-(2,6-diox-opiperidin-3-yl)-1,3-dioxoisoindol-4-yl]amino]ethoxy) ethoxy]propanoic acid (20.00 mg, 0.046 mmol, 1.00 equiv) in DMF (1 mL) was added EDCI (17.69 mg, 0.092 mmol, 2.00 equiv), HOBT (12.47 mg, 0.092 mmol, 2.00 equiv), and DIEA (23.86 mg, 0.185 mmol, 4.00 equiv). The resulting mixture was stirred overnight at room temperature. Without any additional work-up, the mixture was purified by prep-HPLC (conditions: Column: Gemini-NX C18 AXAI Packed, 21.2*150 mm 5 μm; Mobile Phase A: Water (0.1% FA), Mobile Phase B: ACN; Flow rate: 25 mL/minute; Gradient: 8 B to 25 B in 12 minutes; 254/220 nm; RT: 11.04 minutes) to afford N-[3-[([[2,6-dimethoxy-4-(2-methyl-1-oxo-2,7-naphthyridin-4-yl)phenyl]methyl](methy-I)amino)methyl]bicycle[1.1.1]pentan-1-yl]-3-[2-(2-[2-(2,6-dioxopiperidin-3-yl)-1,3-dioxoisoindol-4-yl]amino]ethoxy) ethoxy] propanamide (3.4 mg, 8.67%) as a yellow solid. $^1$H NMR (300 MHz, DMSO-d6) δ11.09 (s, 1H), 9.45 (s, 1H), 8.72 (d, J=5.6 Hz, 1H), 8.29 (s, 1H), 8.23 (brs, 1.0H, FA), 7.87 (s, 1H), 7.58 (t, J=7.6 Hz, 2H), 7.14 (d, J=8.6 Hz, 1H), 7.03 (d, J=7.1 Hz, 1H), 6.72 (s, 2H), 6.61 (t, J=5.8 Hz, 1H), 5.06 (dd, J=12.7, 5.4 Hz, 1H), 3.81 (s, 6H), 3.58-3.54 (m, 5H), 3.54-3.49 (m, 6H), 3.48-3.42 (m, 4H), 2.96-2.81 (m, 1H), 2.64-2.58 (m, 1H), 2.55 (s, 3H), 2.26 (t, J=6.4 Hz, 2H), 2.12 (s, 3H), 2.08-1.98 (m, 1H), 1.92 (s, 6H). LCMS (ESI) m/z: [M+H]$^+$=850.50.

Example 75—Preparation of N-[3-[{[2,6-Dimethoxy-4-(2-Methyl-1-Oxo-2,7-Naphthyridin-4-Yl)Phenyl]Methyl](Meth-Yl)Amino)Methyl]Bicyclo[1.1.1]Pentan-1-Yl]-5-[[2-(2,6-Dioxopiperidin-3-Yl)-1,3-Dioxoisoindol-4-Yl]Ox-y]Pentanamide (Compound D69)

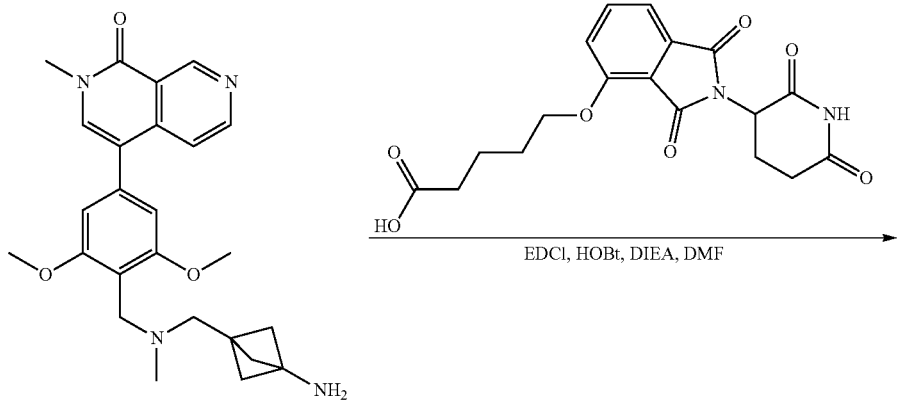

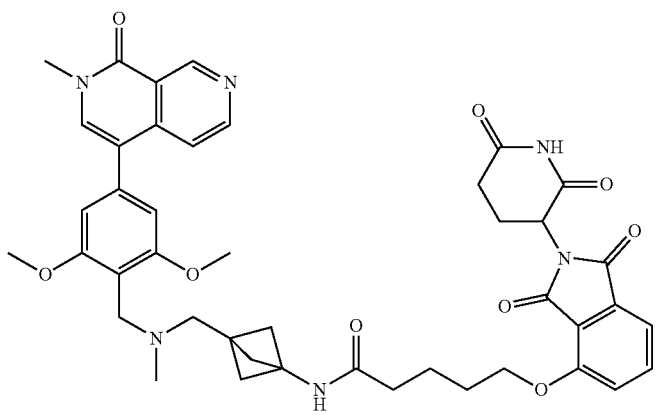

compound D69

To a stirred solution of 4-(4-[[([3-aminobicyclo[1.1.1]pentan-1-yl]methyl)(methyl)amino]methyl]-3,5-dimethoxyphenyl)-2-methyl-2,7-naphthyridin-1-one (23.22 mg, 0.053 mmol, 1.00 equiv) and 5-[2-(2,6-dioxopiperidin-3-yl)-1,3-dioxoisoindol-4-yl]oxy]pentanoic acid (20.00 mg, 0.053 mmol, 1.00 equiv) in DMF (1 mL) was added EDCI (20.48 mg, 0.107 mmol, 2.00 equiv) and HOBT (14.44 mg, 0.107 mmol, 2.00 equiv) at room temperature. To the above mixture was added DIEA (27.62 mg, 0.214 mmol, 4.00 equiv). The resulting mixture was stirred for overnight at room temperature. Without any additional work-up, the mixture was purified by prep-HPLC(conditions: SunFire Prep C18 OBD Column, 19×150 mm 5 μm 10 nm; Mobile Phase A: Water (0.1% FA), Mobile Phase B: ACN; Flow rate: 25 mL/minute; Gradient: 13 B to 22 B in 13 minutes; 254/220 nm; RT: 12.5 minutes) to afford N-[3-[{[[2,6-dimethoxy-4-(2-methyl-1-oxo-2,7-naphthyridin-4-yl)phenyl]methyl](methyl)amino) methy-I]bicyclo[1.1.1]pentan-1-yl]-5-[2-(2,6-dioxopiperidin-3-yl)-1,3-dioxoisoindol-4-yl]oxy]pentanamide (6.9 mg, 17.75%) as a white solid. $^1$H NMR (300 MHz, DMSO-d6) δ11.10 (s, 1H), 9.46 (d, J=0.8 Hz, 1H), 8.74 (d, J=5.7 Hz, 1H), 8.36 (s, 1H), 7.88 (s, 1H), 7.82 (dd, J=8.5, 7.2 Hz, 1H), 7.60-7.42 (m, 3H), 6.79 (s, 2H), 5.08 (dd, J=12.8, 5.4 Hz, 1H), 4.21 (t, J=6.0 Hz, 2H), 3.86 (s, 6H), 3.61 (s, 3H), 3.40 (s, 2H), 2.98-2.80 (m, 2H), 2.62 (s, 2H), 2.46-2.30 (m, 4H), 2.15-2.00 (m, 9H), 1.78-1.64 (m, 4H). LCMS (ESI) m/z: [M+H]$^+$=791.40.

Example 76—Preparation of 5-(4-[2-[3-([[2,6-Dimethoxy-4-(2-Methyl-1-Oxo-2,7-Naphthyridin-4-Yl)Phenyl]Methyl](Methyl)Amino) Propoxy]Ethyl] Piperazin-1-Yl)-2-(2,6-Dioxopiperidin-3-Yl) Isoindole-1,3-Dione Formic Acid (Compound D70 Formic Acid)

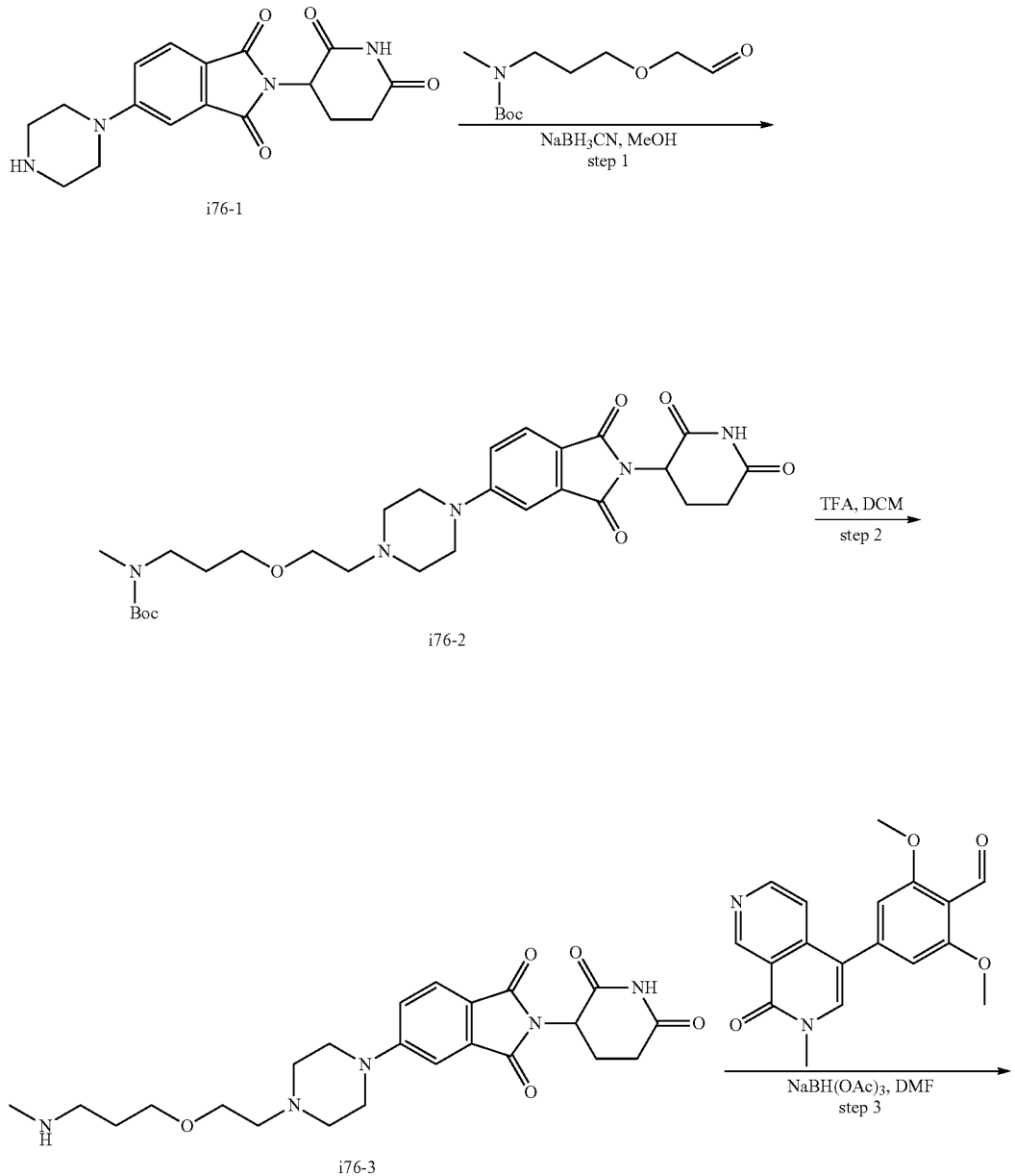

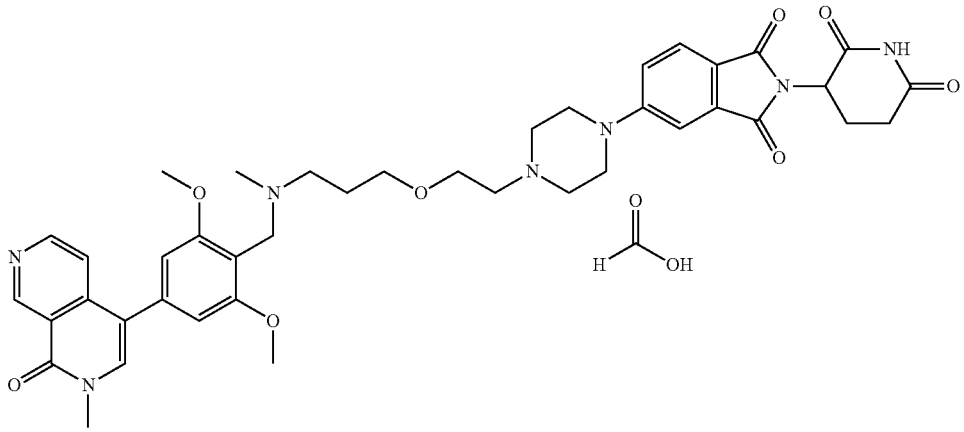

compound D70 formic acid

Step 1: Preparation of Tert-Butyl N-[3-(2-[4-[2-(2, 6-Dioxopiperidin-3-Yl)-1,3-Dioxoisoindol-5-Yl] Piperazin-1-Yl]Ethoxy) Propyl]-N-Methylcarbamate (i76-2)

Step 2: Preparation of 2-(2,6-Dioxopiperidin-3-Yl)-5-(4-[2-[3-(Methylamino) Propoxy]Ethyl]Piperazin-1-Yl) Isoindole-1,3-Dione (i76-3)

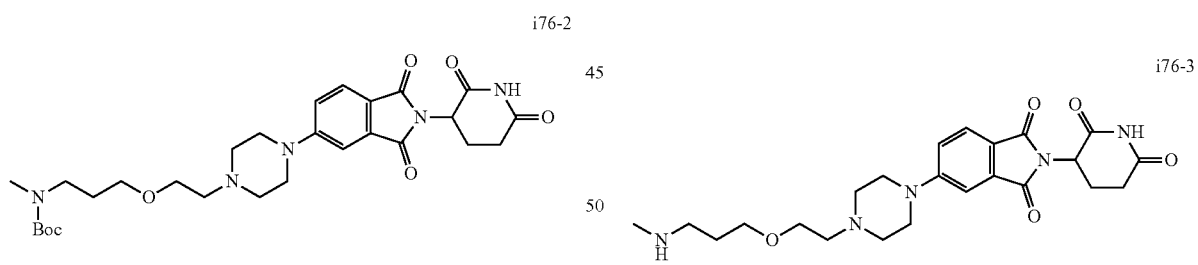

To a stirred solution of 2-(2,6-dioxopiperidin-3-yl)-5-(piperazin-1-yl) isoindole-1,3-dione (250.00 mg, 0.730 mmol, 1.00 equiv) and tert-butyl N-methyl-N-[3-(2-oxoethoxy) propyl]carbamate (168.90 mg, 0.730 mmol, 1 equiv) in MeOH (3.00 mL) was added NaBH$_3$CN (91.78 mg, 1.460 mmol, 2 equiv). The mixture was stirred at room temperature for 2 hours. The resulting mixture was concentrated under reduced pressure. The residue was purified by Prep-TLC(Petroleum ether/EtOAc 1:3) to afford tert-butyl N-[3-(2-[4-[2-(2,6-dioxopiperidin-3-yl)-1,3-dioxoisoindol-5-yl] piperazin-1-yl]ethoxy) propyl]-N-methylcarbamate (400 mg, crude) as a dark grey solid. LCMS (ESI) m/z: [M+H]$^+$=558.

To a stirred solution of tert-butyl N-[3-(2-[4-[2-(2,6-dioxopiperidin-3-yl)-1,3-dioxoisoindol-5-yl]piperazin-1-yl] ethoxy) propyl]-N-methylcarbamate (200.00 mg, 0.359 mmol, 1.00 equiv) in DCM (4.00 mL, 62.920 mmol) was added TFA (1.00 mg, 0.009 mmol). The mixture was stirred at room temperature for 2 hours. The resulting mixture was concentrated under reduced pressure to afford 2-(2,6-dioxopiperidin-3-yl)-5-(4-[2-[3-(methylamino) propoxy] ethyl]piperazin-1-yl) isoindole-1,3-dione (280 mg, crude) as a dark grey solid. LCMS (ESI) m/z: [M+H]$^+$=458.

Step 3: Preparation of 5-(4-[2-[3-([[2,6-Dimethoxy-4-(2-Methyl-1-Oxo-2,7-Naphthyridin-4-Yl)Phenyl] Methyl](Methyl)Amino) Propoxy]Ethyl]Piperazin-1-Yl)-2-(2,6-Dioxopiperidin-3-Yl) Isoindole-1,3-Dione Formic Acid (Compound D70 Formic Acid)

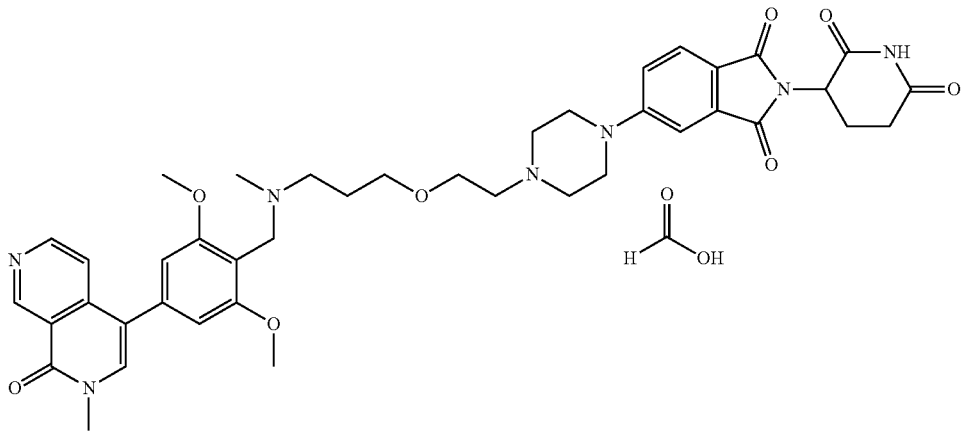

compound D70 formic acid

To a stirred solution of 2-(2,6-dioxopiperidin-3-yl)-5-(4-[2-[3-(methylamino) propoxy]ethyl]piperazin-1-yl) isoindole-1,3-dione (100.00 mg, 0.219 mmol, 1.00 equiv) and 2,6-dimethoxy-4-(2-methyl-1-oxo-2,7-naphthyridin-4-yl) benzaldehyde (70.89 mg, 0.219 mmol, 1 equiv) in DMF (1.50 mL) was added NaBH(OAc)₃ (92.65 mg, 0.437 mmol, 2 equiv). The mixture was stirred at room temperature for 2 hours. The crude product (100 mg) was purified by Prep-HPLC (conditions: SunFire C18 OBD Prep Column, 100 Å, 5 μm, 19 mm×250 mm; Mobile Phase A: Water (0.1% FA), Mobile Phase B: ACN; Flow rate: 25 mL/minute; Gradient: 5 B to 13 B in 15 minutes; 254 nm; RT: 12.23 minutes) to afford 5-(4-[2-[3-([2,6-dimethoxy-4-(2-methyl-1-oxo-2,7-naphthyridin-4-yl)phenyl]methyl](methyl)amino) propoxy] ethyl]piperazin-1-yl)-2-(2,6-dioxopiperidin-3-yl) isoindole-1,3-dione; formic acid (10 mg, 5.38%) as a yellow solid. ¹H NMR (300 MHZ, Methanol-d4) δ 9.51 (d, J=18.3 Hz, 1H), 8.68 (d, J=5.7 Hz, 1H), 8.53 (brs, 4.1H, FA), 7.76 (s, 1H), 7.64 (d, J=7.4 Hz, 2H), 7.25 (s, 1H), 7.17 (d, J=8.6 Hz, 1H), 6.90 (s, 2H), 5.11-5.04 (m, 2H), 4.69-4.53 (m, 2H), 4.47 (s, 2H), 4.00 (s, 6H), 3.74-3.62 (m, 7H), 3.40 (d, J=5.5 Hz, 4H), 2.91 (s, 3H), 2.87-2.73 (m, 3H), 2.69 (s, 6H), 2.23-2.08 (m, 3H). LCMS (ESI) m/z: [M+H]⁺=766.45.

Example 77—Preparation of 4-[2-([2,6-Dimethoxy-4-(2-Methyl-1-Oxo-2,7-Naphthyridin-4-Yl)Phenyl] Methyl](Meth Yl)Amino) Acetamido]-N-(3-[2-(2,6-Dioxopiperidin-3-Yl)-1,3-Dioxoisoindol-4-Yl] Amino]Bicycle[1.1.1]Pentan-1-Yl) Butanamide (Compound D71)

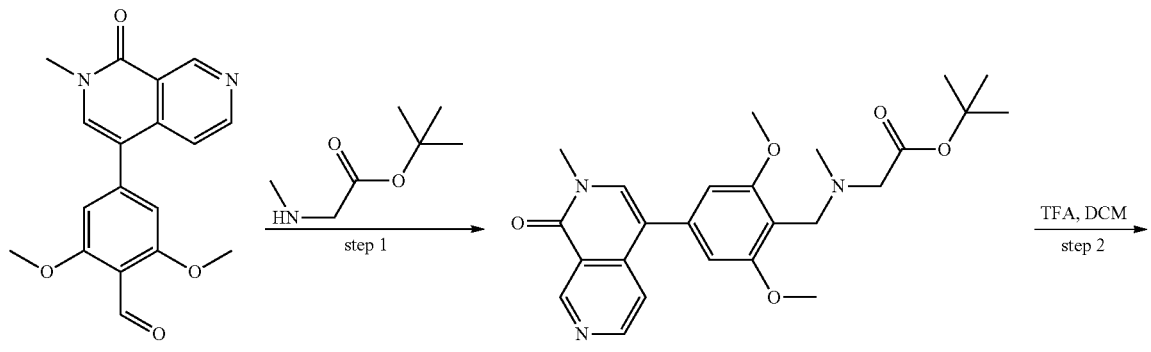

747
-continued
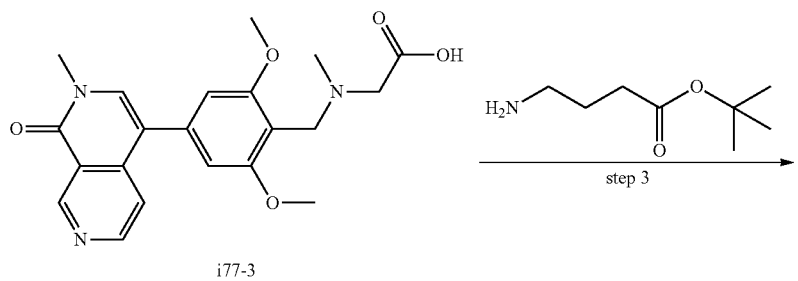
i77-3
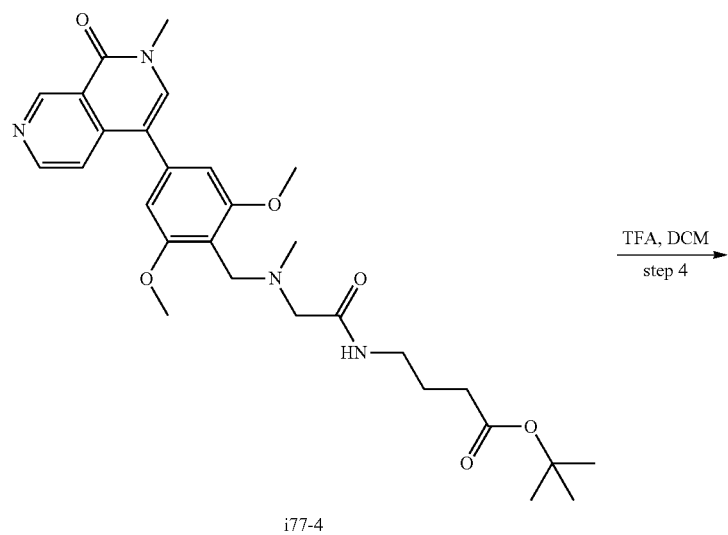
i77-4
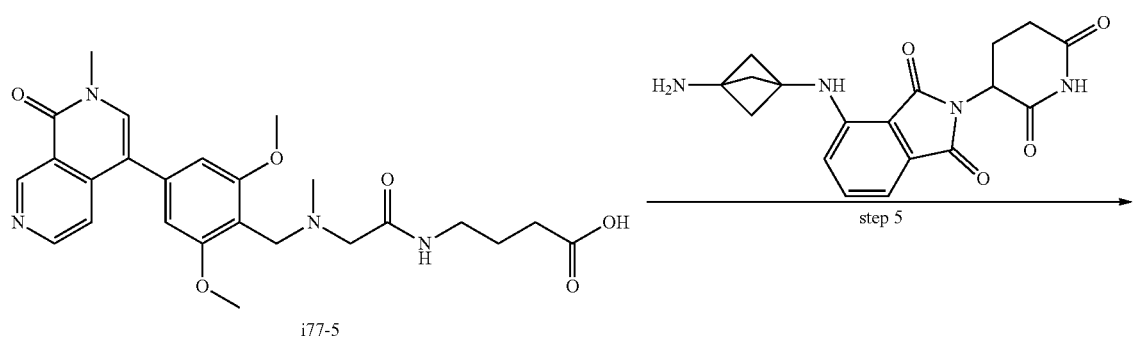
i77-5
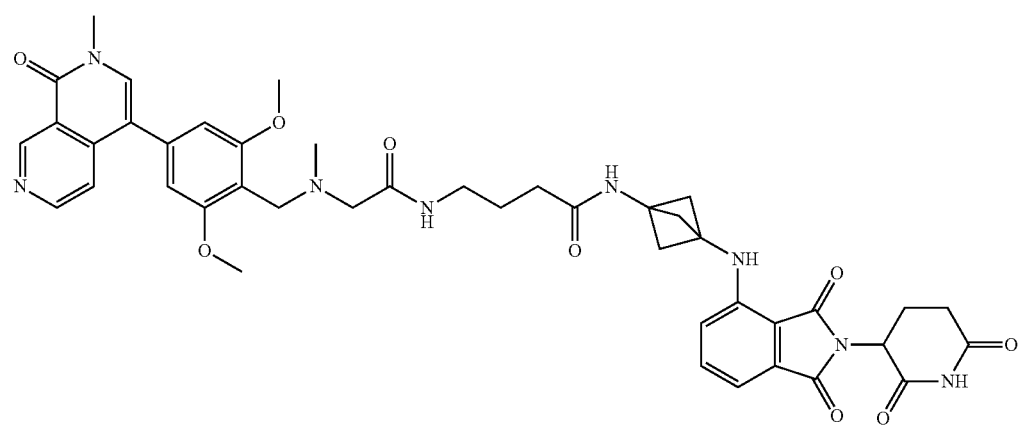
compound D71

Step 1: Preparation of Tert-Butyl N-(2,6-Dimethoxy-4-(2-Methyl-1-Oxo-1,2-Dihydro-2,7-Naphthyridin-4-Yl)Benzyl)-N-Methylglycinate (i77-2)

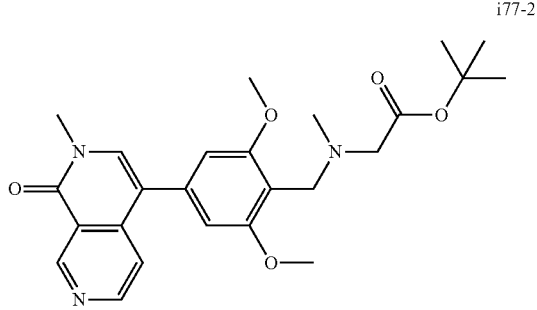 [SMILES: COc1cc(-c2cn(C)c(=O)c3cnccc23)cc(OC)c1CN(C)CC(=O)OC(C)(C)C]

i77-2

To a stirred solution of 2,6-dimethoxy-4-(2-methyl-1-oxo-2,7-naphthyridin-4-yl)benzaldehyde (250.00 mg, 0.771 mmol, 1.00 equiv) and tert-butyl 2-(methylamino)acetate (111.92 mg, 0.771 mmol, 1.00 equiv) in MeOH (10.00 mL) was added NaBH$_3$CN (96.88 mg, 1.542 mmol, 2.00 equiv) in portions at 50° C. under nitrogen atmosphere. The mixture was allowed to cool down to room temperature. The reaction was quenched with Water at room temperature. The aqueous layer was extracted with EtOAc (3×30 mL). The resulting solid was dried under vacuum. The residue was purified by reverse flash chromatography (conditions: column, C18 silica gel; mobile phase, MeOH in water, 10% to 50% gradient in 10 minutes; detector, UV 254 nm). This resulted in tert-butyl N-(2,6-dimethoxy-4-(2-methyl-1-oxo-1,2-dihydro-2,7-naphthyridin-4-yl)benzyl)-N-methylglycinate (101 mg, 28.92%) as a yellow oil. LCMS (ESI) m/z: [M+H]$^+$=454.

Step 2: Preparation of N-(2,6-dimethoxy-4-(2-methyl-1-oxo-1,2-dihydro-2,7-naphthyridin-4-yl)benzyl)-N-methylglycine (i77-3)

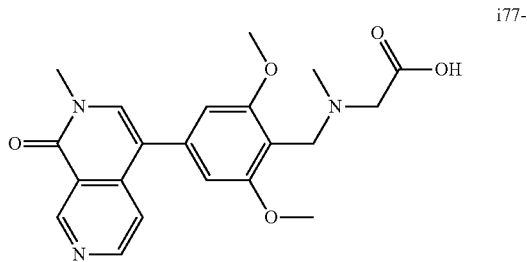 [SMILES: COc1cc(-c2cn(C)c(=O)c3cnccc23)cc(OC)c1CN(C)CC(=O)O]

i77-3

A solution of tert-butyl 2-([[2,6-dimethoxy-4-(2-methyl-1-oxo-2,7-naphthyridin-4-yl)phenyl]methyl](methyl)amino)acetate (101.00 mg, 0.223 mmol, 1.00 equiv) and TFA (7.21 mL, 63.270 mmol, 436.14 equiv) in DCM (29.00 mL) was stirred for 15 hours at room temperature under nitrogen atmosphere. The resulting mixture was concentrated under vacuum. The residue (108 mg, crude) was used in the next step directly without further purification. LCMS (ESI) m/z: [M+H]$^+$=398.

Step 3: Preparation of Tert-Butyl 4-(2-((2,6-Dimethoxy-4-(2-Methyl-1-Oxo-1,2-Dihydro-2,7-Naphthyridin-4-Yl)Benzyl)(Methyl)Amino) Acetamido) Butanoate (i77-4)

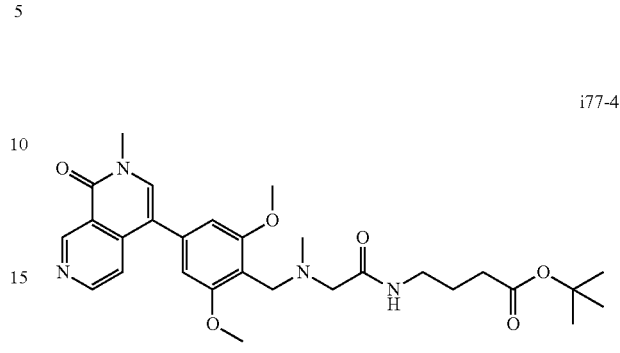

i77-4

A solution of ([2,6-dimethoxy-4-(2-methyl-1-oxo-2,7-naphthyridin-4-yl)phenyl]methyl](methyl)amino) acetic acid (108 mg (crude), 0.272 mmol, 1.00 equiv), DIEA (105.36 mg, 0.815 mmol, 3.00 equiv), and HATU (206.53 mg, 0.543 mmol, 2.00 equiv) in DMF (2.00 mL) was stirred for 30 minutes at room temperature under nitrogen atmosphere. To the above mixture was added tert-butyl 4-aminobutanoate (43.27 mg, 0.272 mmol, 1.00 equiv) at room temperature. The resulting mixture was stirred for additional 12 hours at room temperature. The residue was purified by reverse flash chromatography (conditions: column, C18 silica gel; mobile phase, MeOH in water, 10% to 50% gradient in 10 minutes; detector, UV 254 nm). This resulted in tert-butyl 4-(2-((2,6-dimethoxy-4-(2-methyl-1-oxo-1,2-dihydro-2,7-naphthyridin-4-yl)benzyl)(methyl)amino) acetamido) butanoate (75 mg, 62.33%) as a yellow oil. LCMS (ESI) m/z: [M+H]$^+$=539.

Step 4: Preparation of 4-(2-((2,6-Dimethoxy-4-(2-Methyl-1-Oxo-1,2-Dihydro-2,7-Naphthyridin-4-Yl) Benzyl)(Methyl)Amino) Acetamido) Butanoicacid (i77-5)

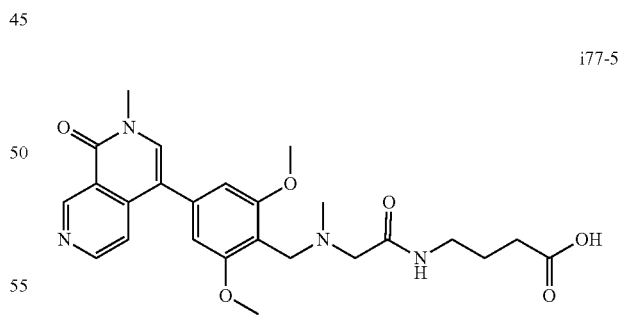

i77-5

A solution of tert-butyl 4-[2-([[2,6-dimethoxy-4-(2-methyl-1-oxo-2,7-naphthyridin-4-yl)phenyl]methyl](methyl)amino) acetamido]butanoate (75.00 mg, 0.139 mmol, 1.00 equiv) and TFA (1 mL) in DCM (4.00 mL) was stirred for 2 hours at room temperature under nitrogen atmosphere. The resulting mixture was concentrated under vacuum. The residue (73 mg, crude) was used in the next step directly without further purification. LCMS (ESI) m/z: [M+H]$^+$=483.

Step 5: Preparation of 4-(2-((2,6-Dimethoxy-4-(2-Methyl-1-Oxo-1,2-Dihydro-2,7-Naphthyridin-4-Yl) Benzyl)(Methyl)Amino) Acetamido)-N-(3-((2-(2,6-Dioxopiperidin-3-Yl)-1,3-Dioxoisoindolin-4-Yl) Amino) Bicycle[1.1.1]Pentan-1-Yl) Butanamide (Compound D71)

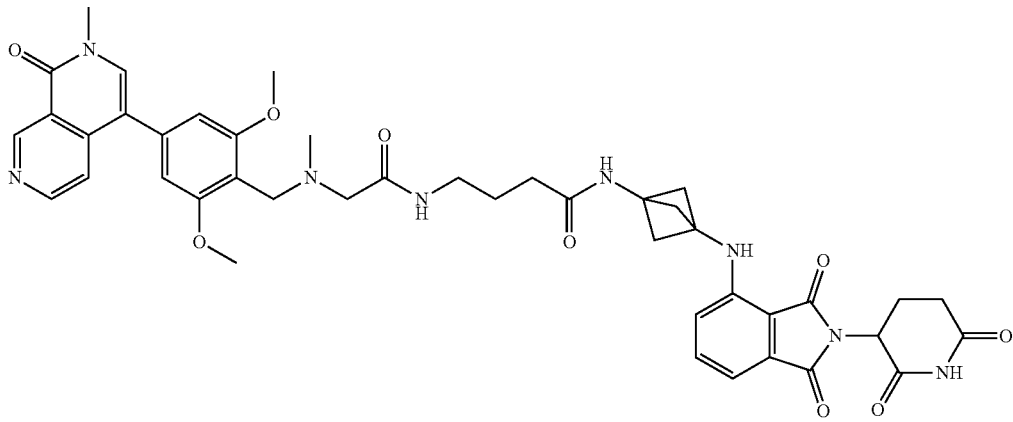

compound D71

To a stirred solution of 4-[2-([2,6-dimethoxy-4-(2-methyl-1-oxo-2,7-naphthyridin-4-yl)phenyl]methyl](methyl)amino) acetamido]butanoic acid (73.00 mg (crude), 0.151 mmol, 1.00 equiv), DIEA (58.66 mg, 0.454 mmol, 3.00 equiv), and EDCI (58.00 mg, 0.303 mmol, 2.00 equiv) in DMF (2.00 mL) was added HOBT (40.88 mg, 0.303 mmol, 2.00 equiv) in portions at room temperature under nitrogen atmosphere. The reaction mixture was irradiated with microwave radiation for 1 hour at room temperature. To the above mixture was added 4-([3-aminobicyclo[1.1.1]pentan-1-yl]amino)-2-(2,6-dioxopiperidin-3-yl) isoindole-1,3-dione (53.61 mg, 0.151 mmol, 1.00 equiv) at room temperature. The resulting mixture was stirred for additional 2 days at room temperature. The residue was purified by reverse flash chromatography (conditions: column, C18 silica gel; mobile phase, MeOH in water, 10% to 50% gradient in 10 minutes; detector, UV 254 nm). The crude product (70 mg) was purified by Prep-HPLC(conditions: Atlantis HILIC OBD Column 19*150 mm, 5 μm;Mobile Phase A: Water (0.1% FA), Mobile Phase B: ACN; Flow rate: 40 mL/minute; Gradient: 24% B to 24% B in 12 minutes; 254/220 nm; Rt: 11.43 minutes) to afford 4-[2-([[2,6-dimethoxy-4-(2-methyl-1-oxo-2,7-naphthyridin-4-yl)phenyl]methyl](methyl)amino) acetamido]-N-(3-[2-(2,6-dioxopiperidin-3-yl)-1,3-dioxoisoindol-4-yl]amino]bicyclo[1.1.1]pentan-1-yl) butanamide (10 mg, 8.07%) as a light yellow solid. $^1$H NMR (400 MHz, Methanol-d4) δ 9.56 (s, 1H), 8.70 (d, J=6.0 Hz, 1H), 7.88 (d, J=1.4 Hz, 1H), 7.75 (d, J=5.9 Hz, 1H), 7.58 (dd, J=9.5, 5.0 Hz, 1H), 7.27 (dd, J=8.6, 3.5 Hz, 1H), 7.14 (d, J=7.2 Hz, 1H), 6.89 (s, 2H), 5.08 (dd, J=12.4, 5.4 Hz, 1H), 4.56 (d, J=5.7 Hz, 2H), 4.01-3.97 (m, 7H), 3.93-3.87 (m, 1H), 3.73 (s, 3H), 3.29-3.23 (m, 2H), 2.97 (s, 3H), 2.90-2.83 (m, 1H), 2.80-2.68 (m, 2H), 2.43 (s, 6H), 2.22 (t, J=7.3 Hz, 2H), 2.16-2.10 (m, 1H), 1.80 (p, J=7.2 Hz, 2H). LCMS (ESI) m/z: [M+H]$^+$=819.35.

Example 78—Preparation of N-[[2,6-Dimethoxy-4-(2-Methyl-1-Oxo-2,7-Naphthyridin-4-Yl)Phenyl]Methyl]-5-[9-[2-(2,6-Dioxopiperidin-3-Yl)-1,3-Dioxoisoindol-5-Yl]-1-Oxa-4,9-Diazaspiro[5.5]Undecan-4-Yl]-N-Methyl Pentanamide Formic Acid (Compound D72 Formic Acid)

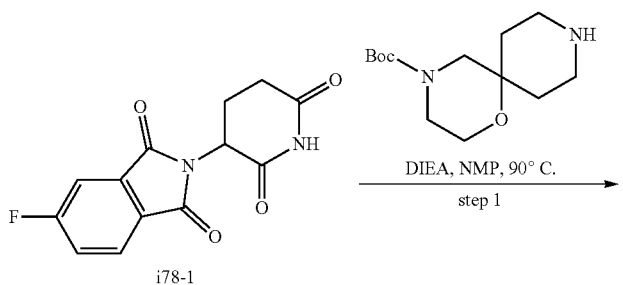

i78-1

-continued
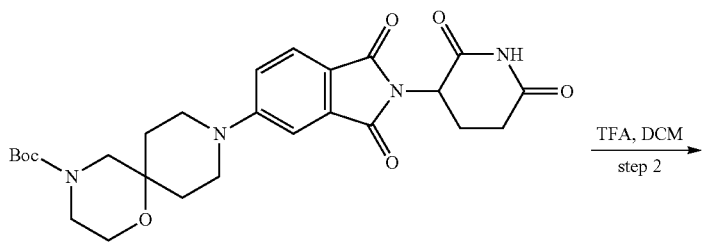
i78-2
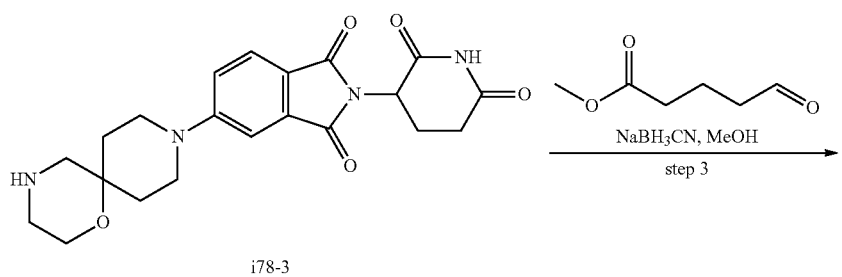
i78-3
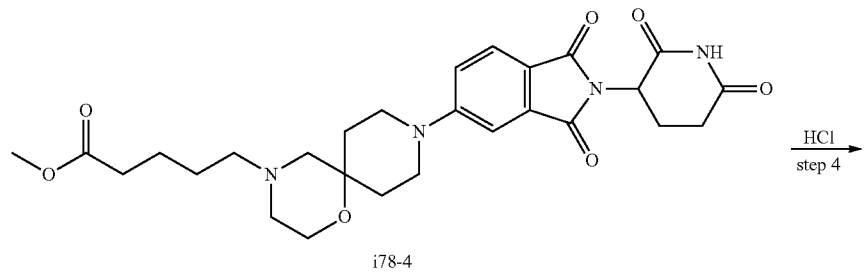
i78-4
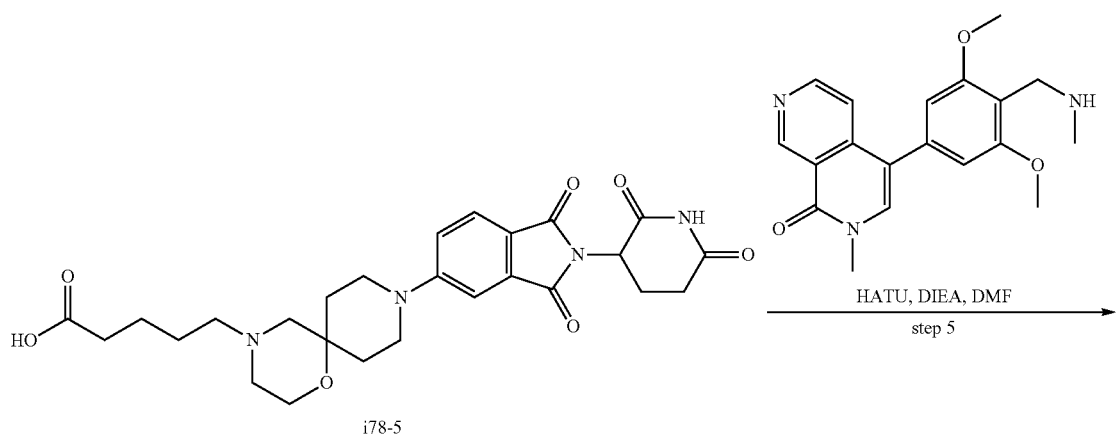
i78-5
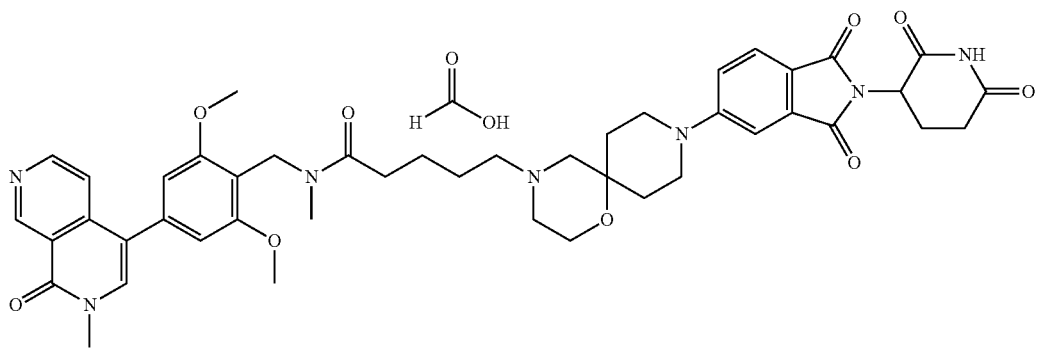
compound 72 formic acid

Step 1: Preparation of 2-(2,6-Dioxopiperidin-3-Yl)-5-[1-Oxa-4,9-Diazaspiro[5.5]Undecan-9-Yl]Isoindole-1,3-Dione (i78-2)

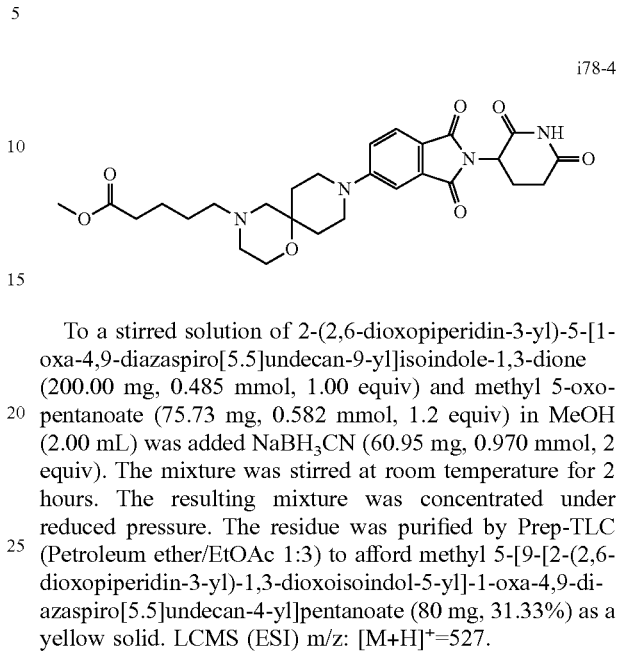

i78-2

To a stirred solution of 2-(2,6-dioxopiperidin-3-yl)-5-fluoroisoindole-1,3-dione (1.50 g, 5.430 mmol, 1.00 equiv) and tert-butyl 1-oxa-4,9-diazaspiro[5.5]undecane-4-carboxylate (1.67 g, 6.516 mmol, 1.20 equiv) in NMP (10.00 mL) was added DIEA (1.40 g, 10.861 mmol, 2.00 equiv) dropwise at room temperature. The resulting mixture was stirred for 6 hours at 90° C. under nitrogen atmosphere. The residue was purified by reverse flash chromatography (conditions: column, C18 silica gel; mobile phase, ACN in water, 10% to 50% gradient in 20 minutes; detector, UV 254 nm). This resulted in tert-butyl 9-(2-(2,6-dioxopiperidin-3-yl)-1,3-dioxoisoindolin-5-yl)-1-oxa-4,9-diazaspiro[5.5]undecane-4-carboxylate (2 g, 72%) as a green oil. LCMS (ESI) m/z: [M+H]$^+$=513.

Step 2: Preparation of 2-(2,6-Dioxopiperidin-3-Yl)-5-[1-Oxa-4,9-Diazaspiro[5.5]Undecan-9-Yl]Isoindole-1,3-Dione (i78-3)

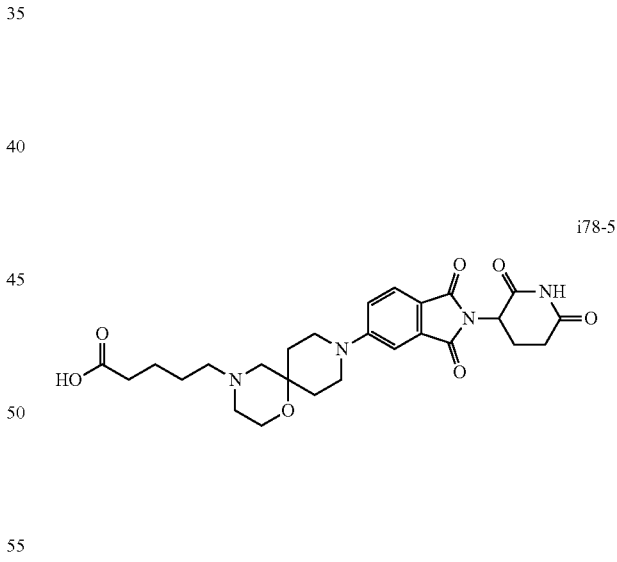

i78-3

To a stirred solution of tert-butyl 9-[2-(2,6-dioxopiperidin-3-yl)-1,3-dioxoisoindol-5-yl]-1-oxa-4,9-diazaspiro[5.5]undecane-4-carboxylate (430.00 mg, 0.839 mmol, 1.00 equiv) in DCM (3.50 mL) was added TFA (1.00 mL). The mixture was stirred at room temperature for 1 hour. The resulting mixture was concentrated under reduced pressure to afford 2-(2,6-dioxopiperidin-3-yl)-5-[1-oxa-4,9-diazaspiro[5.5]undecan-9-yl]isoindole-1,3-dione (670 mg, crude) as a yellow solid. LCMS (ESI) m/z: [M+H]$^+$=413

Step 3: Preparation of Methyl 5-[9-[2-(2,6-Dioxopiperidin-3-Yl)-1,3-Dioxoisoindol-5-Yl]-1-Oxa-4,9-Diazaspiro[5.5]Undecan-4-Yl]Pentanoate (i78-4)

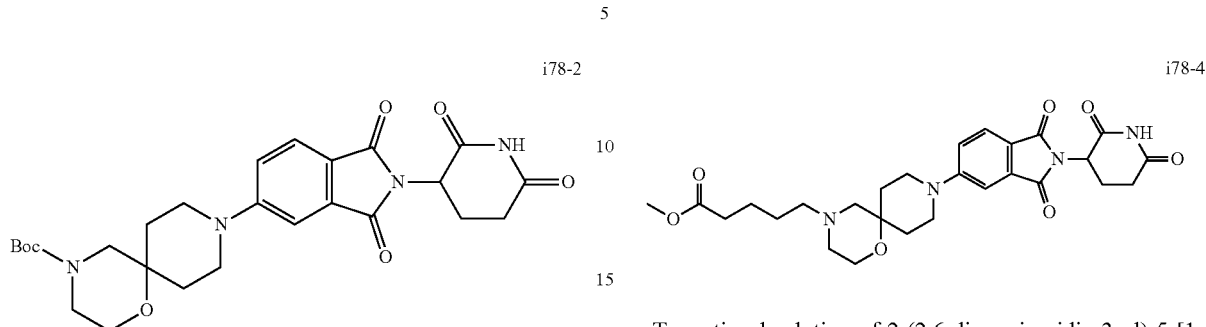

i78-4

To a stirred solution of 2-(2,6-dioxopiperidin-3-yl)-5-[1-oxa-4,9-diazaspiro[5.5]undecan-9-yl]isoindole-1,3-dione (200.00 mg, 0.485 mmol, 1.00 equiv) and methyl 5-oxopentanoate (75.73 mg, 0.582 mmol, 1.2 equiv) in MeOH (2.00 mL) was added NaBH$_3$CN (60.95 mg, 0.970 mmol, 2 equiv). The mixture was stirred at room temperature for 2 hours. The resulting mixture was concentrated under reduced pressure. The residue was purified by Prep-TLC (Petroleum ether/EtOAc 1:3) to afford methyl 5-[9-[2-(2,6-dioxopiperidin-3-yl)-1,3-dioxoisoindol-5-yl]-1-oxa-4,9-diazaspiro[5.5]undecan-4-yl]pentanoate (80 mg, 31.33%) as a yellow solid. LCMS (ESI) m/z: [M+H]$^+$=527.

Step 4: Preparation Of 5-[9-[2-(2,6-Dioxopiperidin-3-Yl)-1,3-Dioxoisoindol-5-Yl]-1-Oxa-4,9-Diazaspiro[5.5]Undecan-4-Yl]Pentanoic Acid (i78-5)

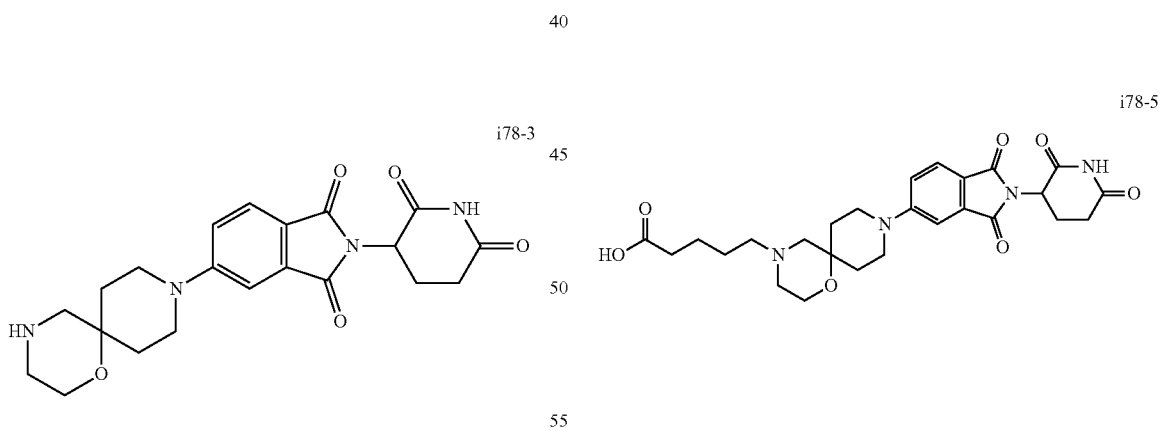

i78-5

Methyl 5-[9-[2-(2,6-dioxopiperidin-3-yl)-1,3-dioxoisoindol-5-yl]-1-oxa-4,9-diazaspiro[5.5]undecan-4-yl]pentanoate (70.00 mg, 0.133 mmol, 1.00 equiv) was stirred at room temperature with HCl (aq.) for 2 hours. The resulting mixture was concentrated under reduced pressure. This resulted in 5-[9-[2-(2,6-dioxopiperidin-3-yl)-1,3-dioxoisoindol-5-yl]-1-oxa-4,9-diazaspiro[5.5]undecan-4-yl]pentanoic acid (70 mg, crude) as a yellow solid. LCMS (ESI) m/z: [M+H]$^+$=513.

Step 5: Preparation of N-[[2,6-Dimethoxy-4-(2-Methyl-1-Oxo-2,7-Naphthyridin-4-Yl)Phenyl]Methyl]-5-[9-[2-(2,6-Dioxopiperidin-3-Yl)-1,3-Dioxoisoindol-5-Yl]-1-Oxa-4,9-Diazaspiro[5.5]Undecan-4-Yl]-N-Methylpentanamide Formic Acid (Compound D72 Formic Acid)

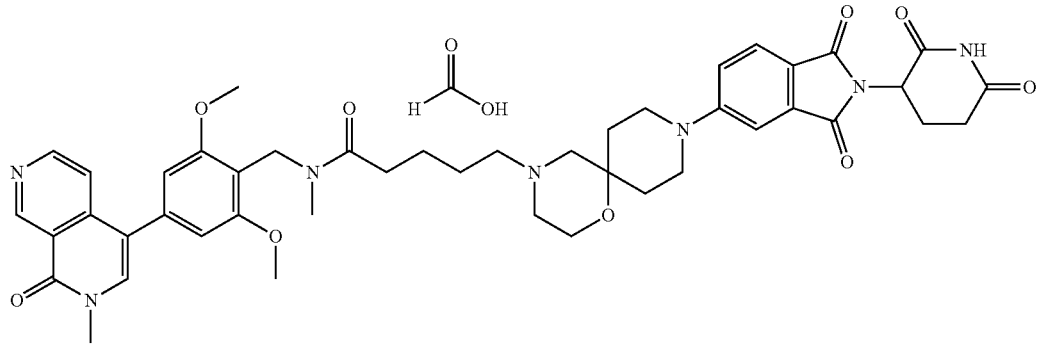

compound 72 formic acid

To a stirred solution of 5-[9-[2-(2,6-dioxopiperidin-3-yl)-1,3-dioxoisoindol-5-yl]-1-oxa-4,9-diazaspiro[5.5]undecan-4-yl]pentanoic acid (55.00 mg, 0.107 mmol, 1.00 equiv) and 4-[3,5-dimethoxy-4-[(methylamino)methyl]phenyl]-2-methyl-2,7-naphthyridin-1-one (36.42 mg, 0.107 mmol, 1.00 equiv) in DMF (1.00 mL) was added DIEA (69.34 mg, 0.537 mmol, 5.00 equiv) and HATU (61.20 mg, 0.161 mmol, 1.50 equiv). The mixture was stirred at room temperature for 1 hours. The crude product (55 mg) was purified by Prep-HPLC(conditions: SunFire C18 OBD Prep Column, 100 Å, 5 μm, 19 mm×250 mm; Mobile Phase A: Water (0.1% FA), Mobile Phase B: ACN; Flow rate: 25 mL/minute; Gradient: 9 B to 28 B in 13 minutes; 254 nm; RT: 14.08 minutes) to afford N-[[2,6-dimethoxy-4-(2-methyl-1-oxo-2,7-naphthyridin-4-yl)phenyl]methyl]-5-[9-[2-(2,6-dioxopiperidin-3-yl)-1,3-dioxoisoindol-5-yl]-1-oxa-4,9-diazaspiro[5.5]undecan-4-yl]-N-methylpentanamide formic acid (8.2 mg, 8.68%) as a yellow solid. 1H NMR (400 MHZ, Methanol-d4) δ 9.50 (d, J=3.4 Hz, 1H), 8.65 (dd, J=12.4, 5.8 Hz, 1H), 8.39 (brs, 0.6H, FA), 7.74 (d, J=4.5 Hz, 1H), 7.66-7.57 (m, 2H), 7.28 (dd, J=12.7, 2.3 Hz, 1H), 7.22-7.14 (m, 1H), 6.80 (d, J=20.6 Hz, 2H), 5.04 (dt, J=12.8, 5.8 Hz, 1H), 4.75 (d, J=16.1 Hz, 2H), 3.90 (d, J=16.5 Hz, 6H), 3.87-3.82 (m, 2H), 3.74-3.63 (m, 5H), 3.32-3.26 (m, 2H), 2.92-2.82 (m, 2H), 2.78 (d, J=6.8 Hz, 4H), 2.73-2.53 (m, 7H), 2.47 (t, J=6.7 Hz, 1H), 2.17-2.01 (m, 3H), 1.82-1.62 (m, 6H). LCMS (ESI) m/z: [M+H]$^+$=834.40.

Example 79—Preparation of 2-([2,6-Dimethoxy-4-(2-Methyl-1-Oxo-2,7-Naphthyridin-4-Yl)Phenyl]Methyl](Methyl)Amino)-N-(4-[9-[2-(2,6-Dioxopiperidin-3-Yl)-1,3-Dioxoisoindol-5-Yl]-1-Oxa-4,9-Diaza Spiro[5.5]Undecan-4-Yl]Butyl) Acetamide Formic Acid (Compound D73 Formic Acid)

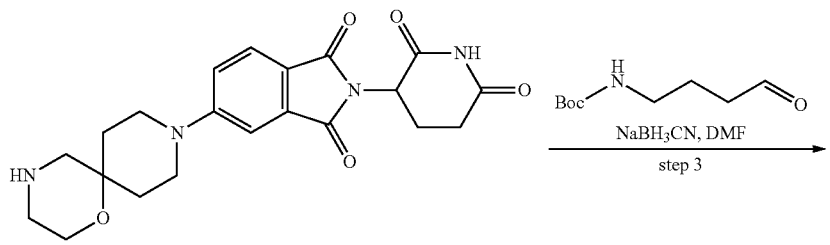

i79-1

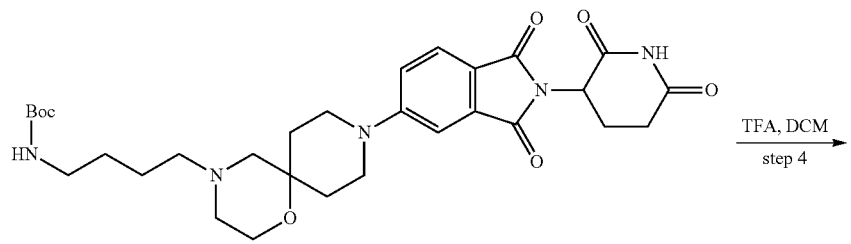

i79-2

-continued

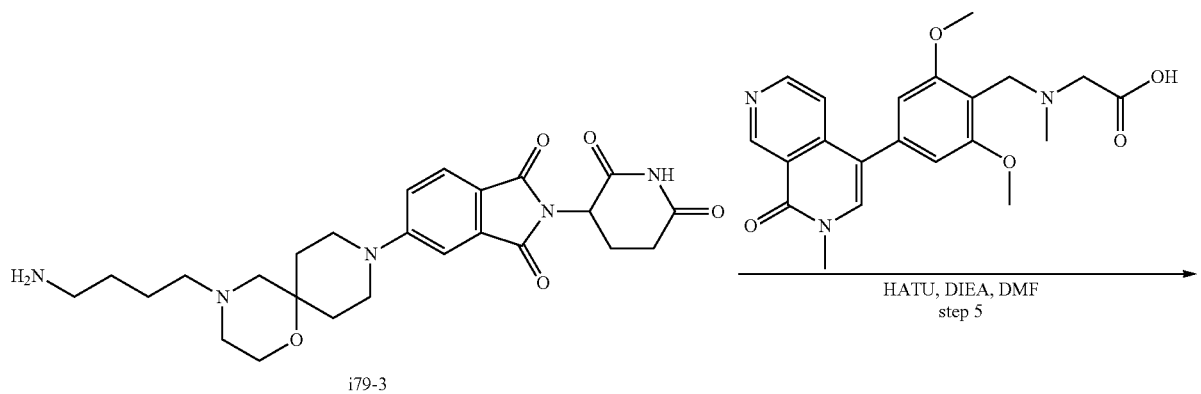

i79-3

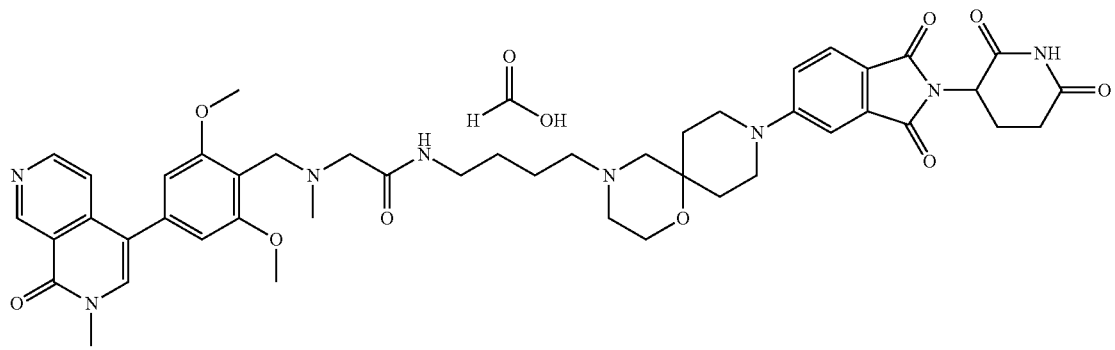

compound D73 formic acid

Step 1: Preparation of Tert-Butyl N-(4-[9-[2-(2,6-Dioxopiperidin-3-Yl)-1,3-Dioxoisoindol-5-Yl]-1-Oxa-4,9-Diazaspiro[5.5]Undecan-4-Yl]Butyl) Carbamate (i79-2)

Step 2: Preparation of 5-[4-(4-Aminobutyl)-1-Oxa-4,9-Diazaspiro[5.5]Undecan-9-Yl]-2-(2,6-Dioxopiperidin-3-Yl) Isoindole-1,3-Dione (i79-3)

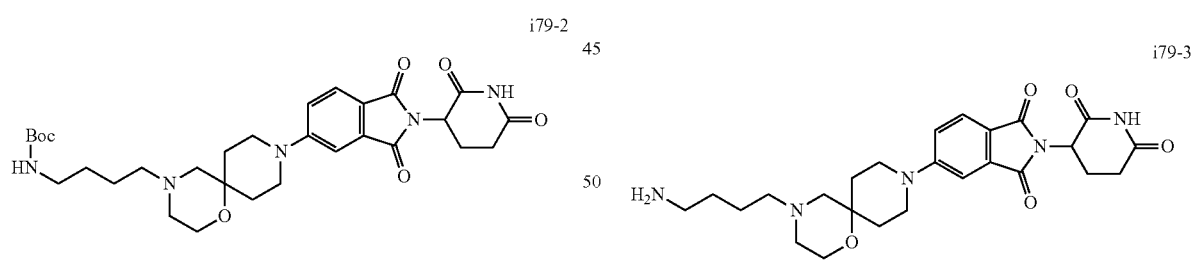

To a stirred solution of 2-(2,6-dioxopiperidin-3-yl)-5-[1-oxa-4,9-diazaspiro[5.5]undecan-9-yl]isoindole-1,3-dione (200.00 mg, 0.485 mmol, 1.00 equiv) and tert-butyl N-(4-oxobutyl) carbamate (907.94 mg, 4.849 mmol, 10.00 equiv) in DMF (1.50 mL) was added NaBH$_3$CN (60.95 mg, 0.970 mmol, 2.00 equiv). The mixture was stirred at room temperature for 5 hours. The resulting mixture was concentrated under vacuum. The residue was purified by Prep-TLC (Petroleum ether/EtOAc 1:3) to afford tert-butyl N-(4-[9-[2-(2,6-dioxopiperidin-3-yl)-1,3-dioxoisoindol-5-yl]-1-oxa-4,9-diazaspiro[5.5]undecan-4-yl]butyl) carbamate (200 mg,crude) as a yellow solid. LCMS (ESI) m/z: [M+H]$^+$=584.

To a stirred solution of tert-butyl N-(4-[9-[2-(2,6-dioxopiperidin-3-yl)-1,3-dioxoisoindol-5-yl]-1-oxa-4,9-diazaspiro [5.5]undecan-4-yl]butyl) carbamate (200.00 mg, 0.343 mmol, 1.00 equiv) in DCM (3.00 mL) was added TFA (1.00 mL). The mixture was stirred at room temperature for 2 hours. The residue was purified by Prep-TLC(CH$_2$Cl$_2$/MeOH 10:1) to afford 5-[4-(4-aminobutyl)-1-oxa-4,9-diazaspiro[5.5]undecan-9-yl]-2-(2,6-dioxopiperidin-3-yl) isoindole-1,3-dione (60 mg, 36.21%) as a yellow solid. LCMS (ESI) m/z: [M+H]$^+$=484.

Step 3: Preparation of 2-([[2,6-Dimethoxy-4-(2-Methyl-1-Oxo-2,7-Naphthyridin-4-Yl)Phenyl]Methyl](Methyl)Amino)-N-(4-[9-[2-(2,6-Dioxopiperidin-3-Yl)-1,3-Dioxoisoindol-5-Yl]-1-Oxa-4,9-Diazaspiro[5.5]Undecan-4-Yl]Butyl) Acetamide Formic Acid (Compound D73 Formic Acid)

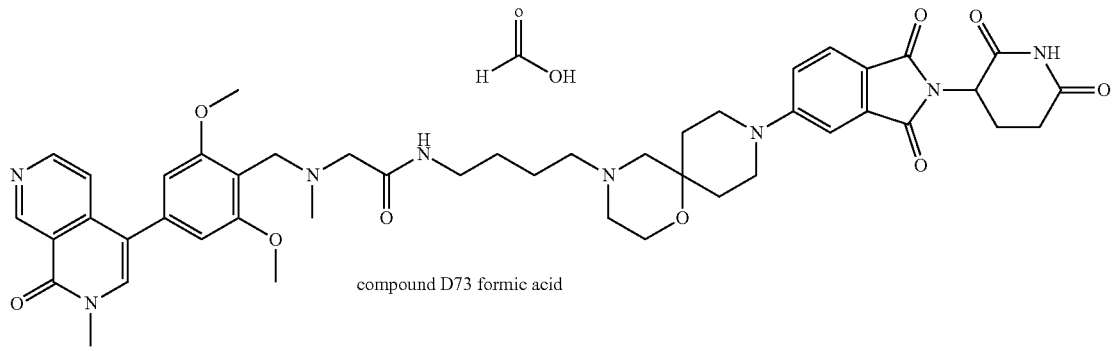

compound D73 formic acid

To a stirred solution of 5-[4-(4-aminobutyl)-1-oxa-4,9-diazaspiro[5.5]undecan-9-yl]-2-(2,6-dioxopiperidin-3-yl)isoindole-1,3-dione (60.00 mg, 0.124 mmol, 1.00 equiv) and ([[2,6-dimethoxy-4-(2-methyl-1-oxo-2,7-naphthyridin-4-yl)phenyl]methyl](methyl)amino) acetic acid (49.31 mg, 0.124 mmol, 1.00 equiv) in DMF (1.00 mg) was added DIEA (80.18 mg, 0.620 mmol, 5.00 equiv) and HATU (70.77 mg, 0.186 mmol, 1.50 equiv). The mixture was stirred at room temperature for 1 hour. The crude product (60 mg) was purified by Prep-HPLC(conditions: SunFire C18 OBD Prep Column, 100 Å, 5 μm, 19 mm×250 mm; Mobile Phase A: Water (0.1% FA), Mobile Phase B: ACN; Flow rate: 25 mL/minute; Gradient: 8 B to 17 B in 12 minutes; 254 nm; RT: 11.87 minutes) to afford 2-([[2,6-dimethoxy-4-(2-methyl-1-oxo-2,7-naphthyridin-4-yl)phenyl]methyl](methyl)amino)-N-(4-[9-[2-(2,6-dioxopiperidin-3-yl)-1,3-dioxoisoindol-5-yl]-1-oxa-4,9-diazaspiro[5.5]undecan-4-yl]butyl) acetamide formic acid (12.6 mg, 10.72%) as a yellow solid. $^1$H NMR (400 MHZ, Methanol-d4) δ 9.51 (s, 1H), 8.68 (d, J=5.8 Hz, 1H), 8.53 (brs, 0.9H, FA), 7.74 (s, 1H), 7.62 (dd, J=7.3, 6.3 Hz, 2H), 7.27 (d, J=2.3 Hz, 1H), 7.16 (dd, J=8.6, 2.4 Hz, 1H), 6.82 (s, 2H), 5.05 (dd, J=12.7, 5.5 Hz, 1H), 4.15 (s, 2H), 3.94 (s, 6H), 3.75 (t, J=4.8 Hz, 2H), 3.69 (s, 3H), 3.64 (d, J=13.0 Hz, 2H), 3.54 (s, 2H), 3.31-3.25 (m, 4H), 2.94-2.81 (m, 1H), 2.80-2.68 (m, 2H), 2.63 (s, 3H), 2.46 (s, 2H), 2.37 (t, J=6.6 Hz, 2H), 2.32 (s, 2H), 2.17-2.00 (m, 3H), 1.68-1.51 (m, 6H). LCMS (ESI) m/z: [M+H]$^+$=863.50.

Example 80—Preparation of 5-[(1-[2-[2-([2,6-Dimethoxy-4-(2-Methyl-1-Oxo-2,7-Naphthyridin-4-Yl)Phenyl]Methyl]Amino) Ethoxy]Acetyl]Azetidin-3-Yl) Methoxy]-2-(2,6-Dioxopiperidin-3-Yl) Isoindole-1,3-Dione Formic Acid (Compound D74 Formic Acid)

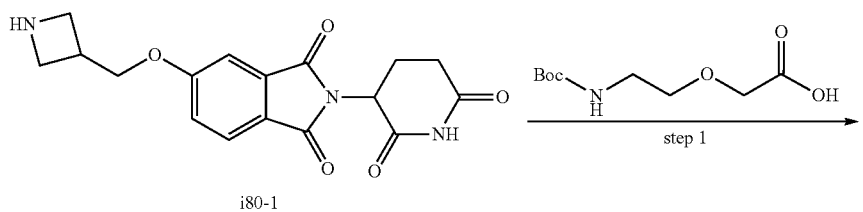

i80-1

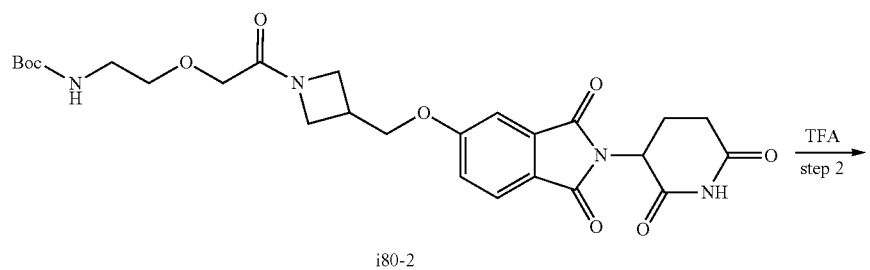

i80-2

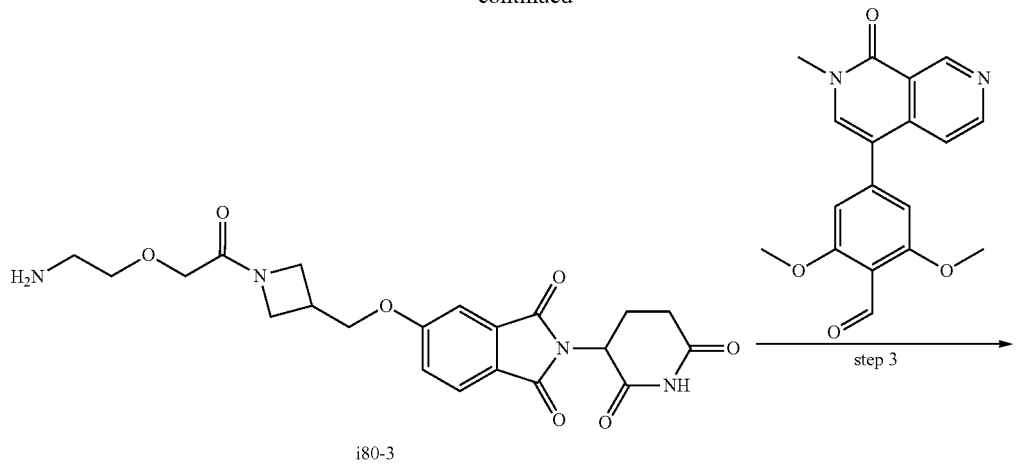

i80-3

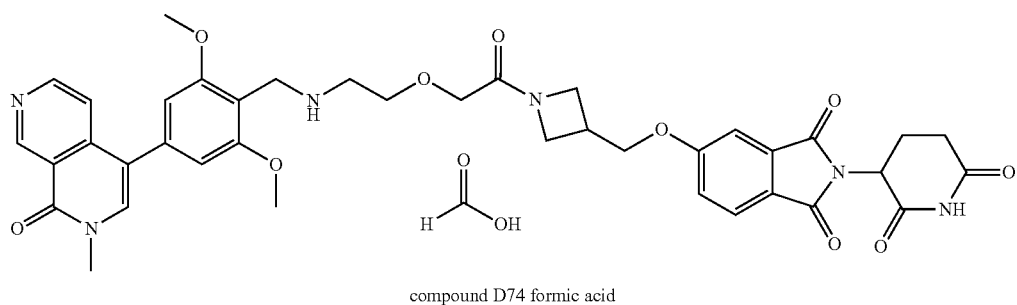

compound D74 formic acid

Step 1: Preparation of Tert-Butyl N-(2-[2-[3-([[2-(2, 6-Dioxopiperidin-3-Yl)-1,3-Dioxoisoindol-5-Yl] Oxy]Methyl) Azetidin-1-Yl]-2-Oxoethoxy]Ethyl) Carbamate (i80-2)

Step 2: Preparation of 5-([1-[2-(2-Aminoethoxy) Acetyl]Azetidin-3-Yl]Methoxy)-2-(2,6-Dioxopiperidin-3-Yl) Isoindole-1,3-Dione (i80-3)

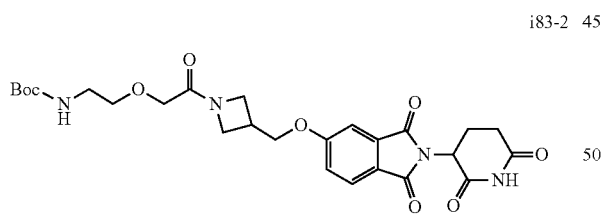

i83-2

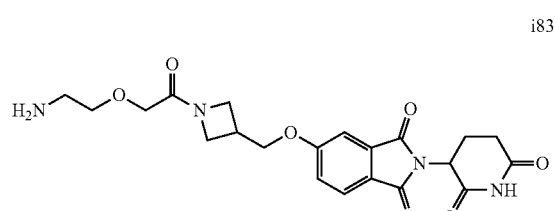

i83-3

To a solution of [2-[(tert-butoxycarbonyl)amino]ethoxy] acetic acid (30.65 mg, 0.140 mmol, 1.20 equiv) and HATU (88.60 mg, 0.233 mmol, 2.00 equiv) in DMF (1.00 mL) was added 5-(azetidin-3-ylmethoxy)-2-(2,6-dioxopiperidin-3-yl) isoindole-1,3-dione (40.00 mg, 0.117 mmol, 1.00 equiv) and DIEA (45.17 mg, 0.350 mmol, 3.00 equiv), and the resulting solution was stirred at 25° C. for 2 hours. The resulting mixture was concentrated. The residue was applied onto a silica gel column with $CH_2Cl_2$/MeOH (20:1). This resulted in (50 mg, 78.81%) of tert-butyl N-(2-[2-[3-([2-(2,6-dioxopiperidin-3-yl)-1,3-dioxoisoindol-5-yl]oxy]methyl) azetidin-1-yl]-2-oxoethoxy]ethyl) carbamate as a yellow solid. LCMS (ESI) m/z: $[M+H]^+$=545.30.

To a solution of tert-butyl N-(2-[2-[3-([2-(2,6-dioxopiperidin-3-yl)-1,3-dioxoisoindol-5-yl]oxy]methyl) azetidin-1-yl]-2-oxoethoxy]ethyl) carbamate (50.00 mg, 0.092 mmol, 1.00 equiv) in TFA (2.00 mL) and DCM (2.00 mL), and the resulting solution was stirred at 25° C. for 2 hours. The resulting mixture was concentrated and used directly without further purification. This resulted in (60 mg, crude) of 5-([1-[2-(2-aminoethoxy) acetyl]azetidin-3-yl]methoxy)-2-(2,6-dioxopiperidin-3-yl) isoindole-1,3-dione as a yellow solid. LCMS (ESI) m/z: $[M+H]^+$=445.50.

Step 3: Preparation of 5-[(1-[2-[2-([[2,6-Dimethoxy-4-(2-Methyl-1-Oxo-2,7-Naphthyridin-4-Yl) Phenyl]Methyl]Amino) Ethoxy]Acetyl]Azetidin-3-Yl) Methoxy]-2-(2,6-Dioxopiperidin-3-Yl) Isoindole-1,3-Dione Formic Acid (Compound D74 Formic Acid)

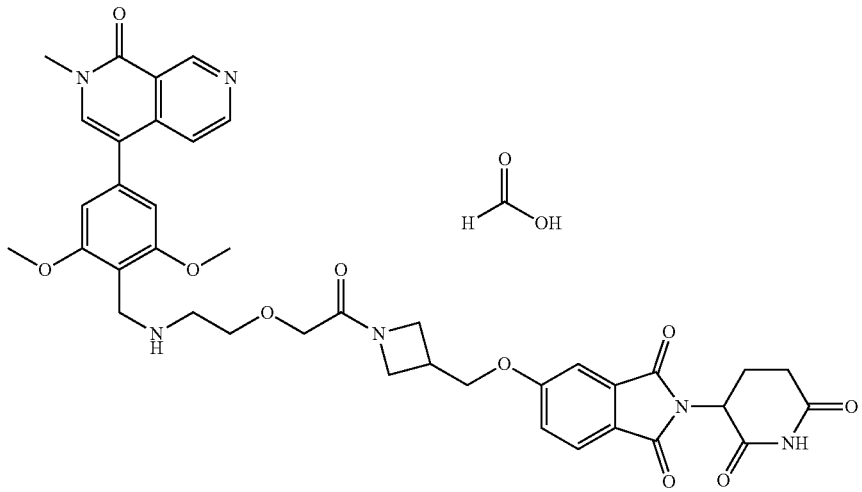

compound D76 formic acid

To a solution of 5-([1-[2-(2-aminoethoxy) acetyl]azetidin-3-yl]methoxy)-2-(2,6-dioxopiperidin-3-yl) isoindole-1,3-dione (20 mg, 0.045 mmol, 1.00 equiv) and 2,6-dimethoxy-4-(2-methyl-1-oxo-2,7-naphthyridin-4-yl)benzaldehyde (17.51 mg, 0.054 mmol, 1.20 equiv) in DMF (2.00 mL) was added NaBH$_3$CN (5.66 mg, 0.090 mmol, 2.00 equiv). The resulting solution was stirred at 25° C. for 2 hours. The resulting mixture was concentrated. The crude product was purified by preparative HPLC Column: XSelect CSH Prep C18 OBD Column, 5 μm, 19*150 mm;Mobile Phase A: Water (0.1% FA), Mobile Phase B: ACN; Flow rate: 25 mL/minute; Gradient: 20% B to 55% B in 8 minutes; 254 nm; Rt: 7.12 minutes). This resulted in (10 mg, 27.82%) of 5-[(1-[2-[2-([[2,6-dimethoxy-4-(2-methyl-1-oxo-2,7-naphthyridin-4-yl)phenyl]methyl]amino) ethoxy]acetyl]azetidin-3-yl) methoxy]-2-(2,6-dioxopiperidin-3-yl) isoindole-1,3-dione as an off-white solid. $^1$H NMR (400 MHZ, Methanol-d4)δ 9.53 (s, 1H), 8.68 (d, J=5.8 Hz, 1H), 8.57 (brs, 3.2H, FA), 7.82 (d, J=8.3 Hz, 1H), 7.76 (s, 1H), 7.61 (d, J=5.7 Hz, 1H), 7.43 (d, J=2.3 Hz, 1H), 7.35 (dd, J=8.1, 2.3 Hz, 1H), 6.84 (s, 2H), 5.12 (dd, J=12.6, 5.4 Hz, 1H), 4.40 (t, J=8.8 Hz, 1H), 4.35 (d, J=3.8 Hz, 4H), 4.27-4.13 (m, 4H), 4.02-3.93 (m, 7H), 3.83 (t, J=4.9 Hz, 2H), 3.71 (s, 3H), 3.27-3.21 (m, 3H), 2.94-2.83 (m, 1H), 2.82-2.67 (m, 2H), 2.20-2.10 (m, 1H). LCMS (ESI) m/z: [M+H]$^+$=753.40.

Example 81—Preparation of Compounds D75-D177

In analogy to the procedures described in the examples above, compounds D75-D177 were prepared using the appropriate starting materials.

| Compound No. | Analytical Data |
|---|---|
| D75 | LCMS: (ESI) m/z: [M + H]$^+$ = 835.70 |
| D76 | LCMS: (ESI) m/z: [M + H]$^+$ = 788.20 |
| D77 | LCMS: (ESI) m/z: [M + H]$^+$ = 774.10 |
| D78 | LCMS: 789.2; $^1$H NMR (400 MHz, DMSO-d6) δ 11.11 (s, 1H), 9.45 (s, 1H), 8.73 (d, J = 5.7 Hz, 1H), 8.21 (s, 0.7H, FA), 8.05 (d, J = 7.5 Hz, 1H), 7.87 (s, 1H), 7.82 (d, J = 8.2 Hz, 1H), 7.59-7.54 (m, 1H), 7.31-7.24 (m, 2H), 6.73 (s, 2H), 5.12 (dd, J = 12.8, 5.4 Hz, 1H), 4.87 (t, J = 6.8 Hz, 1H), 4.14-3.99 (m, 1H), 3.81 (s, 6H), 3.66 (s, 2H), 3.61 (s, 3H), 3.44-3.35 (m, 3H), 2.98 (s, 2H), 2.92-2.83 (m, 1H), 2.73-2.55 (m, 4H), 2.44-2.32 (m, 1H), 2.25 (dd, J = 18.0, 6.8 Hz, 3H), 2.15-2.00 (m, 3H), 1.95 (td, J = 11.2, 8.4 Hz, 2H). |
| D79 | LCMS: (ESI) m/z: [M + H]$^+$ = 789.20; $^1$H NMR (400 MHz, DMSO-d6) δ 11.11 (s, 1H), 9.45 (s, 1H), 8.73 (d, 5.7 Hz, 1H), 8.21 (s, 0.7H, FA), 8.05 (d, J = 7.5 Hz, 1H), 7.87 (s, 1H), 7.82 (d, J = 8.2 Hz, 1H), 7.59-7.54 (m, 1H), 7.31-7.24 (m, 2H), 6.73 (s, 2H), 5.12 (dd, J = 12.8, 5.4 Hz, 1H), 4.87 (t, J = 6.8 Hz, 1H), 4.14-3.99 (m, 1H), 3.81 (s, 6H), 3.66 (s, 2H), 3.61 (s, 3H), 3.44-3.35 (m, 3H), 2.98 (s, 2H), 2.92-2.83 (m, 1H), 2.73-2.55 (m, 4H), 2.44-2.32 (m, 1H), 2.25 (dd, J = 18.0, 6.8 Hz, 3H), 2.15-2.00 (m, 3H), 1.95 (td, J = 11.2, 8.4 Hz, 2H). |

| Compound No. | Analytical Data |
|---|---|
| D80 | LCMS: (ESI) m/z: [M + H]⁺ = 803.15; ¹H NMR (400 MHz, DMSO-d6) δ 11.12 (s, 1H), 9.45 (s, 1H), 8.73 (d, J = 5.6 Hz, 1H), 8.21 (s, 0.6H, FA), 7.97-7.77 (m, 2H), 7.56 (d, J = 5.7 Hz, 1H), 7.37-7.20 (m, 2H), 6.74 (s, 2H), 5.12 (dd, J = 12.8, 5.4 Hz, 1H), 5.10-4.97 (m, 1H), 3.82 (d, J = 2.0 Hz, 6H), 3.70 (s, 2H), 3.61 (s, 3H), 3.36 (s, 5H), 3.09-2.95 (m, 2H), 2.88 (d, J = 13.9 Hz, 1H), 2.58 (d, J = 10.3 Hz, 8H), 2.16-1.99 (m, 1H), 1.87 (d, J = 9.8 Hz, 2H), 1.63 (s, 1H), 1.55 (s, 2H), 1.47 (s, 1H). |
| D81 | LCMS: (ESI) m/z: [M + H]⁺ = 715.20 |
| D82 | LCMS: (ESI) m/z: [M + H]⁺ = 821.25; ¹H NMR (300 MHz, Methanol-d4) δ 9.54 (d, J = 0.9 Hz, 1H), 8.69 (d, J = 5.8 Hz, 1H), 8.54 (s, 0.4H, FA), 7.86-7.75 (m, 2H), 7.63 (dd, J = 5.8, 0.9 Hz, 1H), 7.50 (dd, J = 7.8, 5.7 Hz, 2H), 6.87 (s, 2H), 5.14 (dd, J = 12.3, 5.4 Hz, 1H), 4.44-4.32 (m, 4H), 4.24 (p, J = 8.3 Hz, 1H), 3.97 (s, 6H), 3.93-3.83 (m, 4H), 3.72 (s, 3H), 3.22-3.02 (m, 2H), 2.99-2.65 (m, 4H), 2.46 (t, J = 5.9 Hz, 2H), 2.27 (s, 2H), 2.22-2.09 (m, 2H), 1.91 (s, 2H), 1.76 (s, 4H). |
| D83 | LCMS: (ESI) m/z: [M + H]⁺ = 781.55; ¹H NMR (300 MHz, Methanol-d4) δ 9.53 (s, 1H), 8.69 (d, J = 6.0 Hz, 1H), 7.85 (s, 1H), 7.82-7.66 (m, 2H), 7.50-7.36 (m, 2H), 6.85 (d, J = 1.2 Hz, 2H), 5.12 (dd, J = 12.5, 5.4 Hz, 1H), 4.50 (s, 1H), 4.42 (s, 1H), 4.35-4.11 (m, 4H), 4.02 (dd, J = 11.0, 6.7 Hz, 1H), 3.94 (d, J = 2.7 Hz, 6H), 3.91-3.76 (m, 5H), 3.71 (d, J = 1.5 Hz, 3H), 3.22 (t, J = 6.5 Hz, 2H), 3.08-2.59 (m, 4H), 2.46 (t, J = 5.8 Hz, 2H), 2.21-2.07 (m, 1H), 1.84 (p, J = 7.2, 6.7 Hz, 2H). |
| D84 | LCMS: (ESI) m/z: [M + H]⁺ = 793.55 |
| D85 | LCMS: (ESI) m/z: [M + H]⁺ = 807.25 |
| D86 | LCMS: (ESI) m/z: [M + H]⁺ = 779.20 |
| D87 | LCMS: (ESI) m/z: [M + H]⁺ = 793.45 |
| D88 | LCMS: (ESI) m/z: [M + H]⁺ = 807.90; ¹H NMR (400 MHz, Methanol-d4) δ 9.55 (d, J = 0.8 Hz, 1H), 8.69 (d, J = 5.7 Hz, 1H), 8.56 (s, 0.5H, FA), 7.86-7.73 (m, 2H), 7.63 (d, J = 5.8 Hz, 1H), 7.48 (dd, J = 7.9, 6.2 Hz, 2H), 6.85 (s, 2H), 5.24-5.02 (m, 1H), 4.38 (t, J = 4.3 Hz, 2H), 4.33 (s, 2H), 3.95 (s, 6H), 3.93-3.81 (m, 4H), 3.72 (s, 4H), 3.71-3.40 (m, 4H), 3.25-3.01 (m, 3H), 2.98-2.82 (m, 2H), 2.82-2.61 (m, 3H), 2.21-2.07 (m, 1H), 1.91 (s, 2H), 1.63 (d, J = 17.7 Hz, 4H). |
| D89 | LCMS: (ESI) m/z: [M + H]⁺ = 821.30 |
| D90 | LCMS: (ESI) m/z: [M + H]⁺ = 793.45 |
| D91 | LCMS: (ESI) m/z: [M + H]⁺ = 807.50 |
| D92 | LCMS: (ESI) m/z: [M + H]⁺ = 793.60; ¹H NMR (300 MHz, Methanol-d4) δ 9.53 (s, 1H), 8.68 (dd, J = 5.8, 2.4 Hz, 1H), 8.52 (s, 0.5H, FA), 7.90-7.73 (m, 2H), 7.62 (s, 1H), 7.47 (dd, J = 9.3, 3.5 Hz, 2H), 6.89-6.74 (m, 2H), 5.24-5.04 (m, 1H), 4.31 (d, J = 33.1 Hz, 5H), 3.90 (dd, J = 6.6, 4.5 Hz, 12H), 3.78-3.58 (m, 7H), 3.00-2.48 (m, 6H), 2.26-1.78 (m, 3H). |
| D93 | LCMS: (ESI) m/z: [M + H]⁺ = 793.50 |
| D94 | LCMS: (ESI) m/z: [M + H]⁺ = 865.55 |
| D95 | LCMS: (ESI) m/z: [M + H]⁺ = 793.65 |
| D96 | LCMS: (ESI) m/z: [M + H]⁺ = 835.45 |
| D97 | LCMS: (ESI) m/z: [M + H]⁺ = 865.50; ¹H NMR (300 MHz, Methanol-d4) δ 9.54 (d, J = 0.8 Hz, 1H), 8.69 (d, J = 5.8 Hz, 1H), 8.55 (s, 0.6H, FA), 7.90-7.71 (m, 2H), 7.64 (d, J = 5.8 Hz, 1H), 7.48 (dd, J = 7.9, 3.5 Hz, 2H), 6.87 (s, 2H), 5.12 (dd, J = 12.3, 5.4 Hz, 1H), 4.50-4.23 (m, 4H), 3.97 (s, 6H), 3.95-3.79 (m, 5H), 3.72 (s, 5H), 3.66 (dd, J = 5.8, 1.9 Hz, 1H), 3.59-3.32 (m, 3H), 3.30-2.98 (m, 2H), 2.98-2.59 (m, 6H), 2.25-1.70 (m, 7H), 1.49 (s, 2H). |
| D98 | LCMS: (ESI) m/z: [M + H]⁺ = 779.40; ¹H NMR (400 MHz, Methanol-d4) δ 9.51 (d, J = 1.5 Hz, 1H), 8.67 (d, J = 5.7 Hz, 1H), 7.69 (d, J = 1.8 Hz, 1H), 7.63-7.49 (m, 2H), 7.27 (dd, J = 5.8, 2.3 Hz, 1H), 7.16 (ddd, J = 11.0, 8.4, 2.3 Hz, 1H), 6.65 (d, J = 2.1 Hz, 2H), 5.04 (td, J = 12.4, 5.5 Hz, 1H), 4.80 (d, J = 10.2 Hz, 1H), 4.33 (d, J = 10.5 Hz, 2H), 4.25 (d, J = 16.3 Hz, 2H), 4.03 (d, J = 11.4 Hz, 1H), 3.95-3.74 (m, 12H), 3.74 (d, J = 1.3 Hz, 4H), 3.39-3.30 (m, 1H), 2.80 (dt, J = 13.9, 4.7 Hz, 1H), 2.76-2.54 (m, 3H), 2.46-2.22 (m, 3H), 2.03 (td, J = 7.3, 6.8, 3.3 Hz, 1H). |
| D99 | LCMS: (ESI) m/z: [M + H]⁺ = 793.45 |
| D100 | LCMS: (ESI) m/z: [M + H]⁺ = 793.35 |
| D101 | LCMS: (ESI) m/z: [M + H]⁺ = 793.45; ¹H NMR (300 MHz, Methanol-d4) δ 9.53 (d, J = 0.8 Hz, 1H), 8.69 (d, J = 5.8 Hz, 1H), 8.56 (s, 0.7H, FA), 7.86-7.73 (m, 2H), 7.64-7.56 (m, 1H), 7.43 (d, J = 2.3 Hz, 1H), 7.34 (dd, J = 8.3, 2.3 Hz, 1H), 6.84 (s, 2H), 5.12 (dd, J = 12.4, 5.4 Hz, 1H), 4.36-4.20 (m, 4H), 4.20-4.05 (m, 3H), 3.96 (d, J = 8.5 Hz, 8H), 3.90-3.75 (m, 4H), 3.71 (s, 3H), 2.97-2.55 (m, 5H), 2.43 (t, J = 5.9 Hz, 2H), 2.25-2.08 (m, 3H). |
| D102 | LCMS: (ESI) m/z: [M + H]⁺ = 761.2 |
| D103 | LCMS: (ESI) m/z: [M + H]⁺ = 747.3 |
| D104 | LCMS: (ESI) m/z: [M + H]⁺ = 747.3 |
| D105 | LCMS: (ESI) m/z: [M + H]⁺ = 719.3 |
| D106 | LCMS: (ESI) m/z: [M + H]⁺ = 733.4 |
| D107 | LCMS: (ESI) m/z: [M + H]⁺ = 733.3 |
| D108 | LCMS: (ESI) m/z: [M + H]⁺ = 807.45 |
| D109 | LCMS: (ESI) m/z: [M + H]⁺ = 865.35 |
| D110 | LCMS: (ESI) m/z: [M + H]⁺ = 835.75 |
| D111 | LCMS: (ESI) m/z: [M + H]⁺ = 793.50 |

-continued

| Compound No. | Analytical Data |
|---|---|
| D112 | LCMS: (ESI) m/z: [M + H]⁺ = 793.50 |
| D113 | LCMS: (ESI) m/z: [M + H]⁺ = 779.35 |
| D114 | LCMS: (ESI) m/z: [M + H]⁺ = 851.25 |
| D115 | LCMS: (ESI) m/z: [M + H]⁺ = 793.45 |
| D116 | LCMS: (ESI) m/z: [M + H]⁺ = 821.30 |
| D117 | LCMS: (ESI) m/z: [M + H]⁺ = 781.60; $^1$H NMR (300 MHz, Methanol-d4) δ 9.51 (s, 1H), 8.68 (d, J = 5.8 Hz, 1H), 8.56 (s, 0.7H, FA), 7.76 (d, J = 8.6 Hz, 2H), 7.60 (d, J = 5.8 Hz, 1H), 7.39 (d, J = 2.2 Hz, 1H), 7.30 (dd, J = 8.3, 2.3 Hz, 1H), 6.84 (s, 2H), 5.10 (dd, J = 12.5, 5.4 Hz, 1H), 4.37 (s, 2H), 4.33-4.24 (m, 2H), 4.22-4.08 (m, 2H), 3.95 (s, 6H), 3.85 (dq, J = 7.2, 5.7 Hz, 6H), 3.70 (s, 3H), 3.20 (t, J = 6.5 Hz, 2H), 3.02-2.62 (m, 4H), 2.47 (t, J = 5.8 Hz, 2H), 2.23-2.05 (m, 1H), 1.84 (q, J = 6.9 Hz, 2H). |
| D118 | LCMS: (ESI) m/z: [M + H]⁺ = 807.60; $^1$H NMR (300 MHz, Methanol-d4) δ 9.53 (d, J = 0.8 Hz, 1H), 8.69 (d, J = 5.8 Hz, 1H), 8.55 (s, 0.7H, FA), 7.89-7.75 (m, 2H), 7.61 (dd, J = 5.8, 0.8 Hz, 1H), 7.44 (d, J = 2.2 Hz, 1H), 7.37-7.30 (m, 1H), 6.85 (s, 2H), 5.10 (dd, J = 12.4, 5.4 Hz, 1H), 4.41 (s, 2H), 4.35-4.25 (m, 2H), 3.95 (s, 6H), 3.91-3.77 (m, 8H), 3.72 (s, 3H), 3.54 (q, J = 5.6 Hz, 4H), 2.96-2.63 (m, 5H), 2.12 (dtd, J = 12.8, 4.8, 2.1 Hz, 1H), 1.83 (dt, J = 16.1, 5.8 Hz, 4H). |
| D119 | LCMS: (ESI) m/z: [M + H]⁺ = 807.45 |
| D120 | LCMS: (ESI) m/z: [M + H]⁺ = 821.45 |
| D121 | LCMS: (ESI) m/z: [M + H]⁺ = 807.40; $^1$H NMR (400 MHz, Methanol-d4) δ 9.53 (d, J = 1.0 Hz, 1H), 8.69 (d, J = 5.7 Hz, 1H), 8.54 (s, 0.5H, FA), 7.88-7.73 (m, 2H), 7.66-7.59 (m, 1H), 7.41 (dd, J = 4.4, 2.3 Hz, 1H), 7.32 (ddd, J = 8.1, 6.0, 2.1 Hz, 1H), 6.84 (d, J = 7.6 Hz, 2H), 5.10 (dd, J = 6.9, 5.4 Hz, 1H), 4.38 (s, 1H), 4.30 (d, J = 4.9 Hz, 3H), 3.95 (d, J = 8.8 Hz, 6H), 3.87 (t, J = 4.6 Hz, 4H), 3.71 (d, J = 1.2 Hz, 3H), 3.71-3.56 (m, 2H), 3.55-3.37 (m, 3H), 3.33-3.26 (m, 3H), 2.97-2.52 (m, 5H), 2.21-1.92 (m, 5H). |
| D122 | LCMS: (ESI) m/z: [M + H]⁺ = 793.35; $^1$H NMR (400 MHz, Methanol-d4) δ 9.53 (d, J = 2.5 Hz, 1H), 8.68 (dd, J = 5.7, 1.6 Hz, 1H), 8.54 (s, 0.6H, FA), 7.85-7.70 (m, 2H), 7.60 (dd, J = 6.0, 3.1 Hz, 1H), 7.42 (dd, J = 3.5, 2.2 Hz, 1H), 7.37-7.29 (m, 1H), 6.84 (d, J = 9.2 Hz, 2H), 5.11 (dd, J = 12.5, 5.4 Hz, 1H), 4.40 (s, 1H), 4.31 (dt, J = 6.1, 3.1 Hz, 3H), 4.08-4.00 (m, 2H), 3.99-3.91 (m, 8H), 3.90-3.82 (m, 4H), 3.81 (s, 1H), 3.71 (d, J = 1.2 Hz, 3H), 3.68-3.58 (m, 2H), 3.47 (t, J = 7.1 Hz, 1H), 2.96-2.81 (m, 1H), 2.74 (dtt, J = 12.1, 6.1, 3.4 Hz, 2H), 2.62 (dt, J = 11.5, 5.9 Hz, 2H), 2.25 (t, J = 7.0 Hz, 1H), 2.22-2.05 (m, 2H). |
| D123 | LCMS: (ESI) m/z: [M + H]⁺ = 807.30 |
| D124 | LCMS: (ESI) m/z: [M + H]⁺ = 865.90 |
| D125 | LCMS: (ESI) m/z: [M + H]⁺ = 793.20 |
| D126 | LCMS: (ESI) m/z: [M + H]⁺ = 793.20 |
| D127 | LCMS: (ESI) m/z: [M + H]⁺ = 793.55 |
| D128 | LCMS: (ESI) m/z: [M + H]⁺ = 779.40 |
| D129 | LCMS: (ESI) m/z: [M + H]⁺ = 835.70 |
| D130 | LCMS: (ESI) m/z: [M + H]⁺ = 851.40 |
| D131 | LCMS: (ESI) m/z: [M + H]⁺ = 865.35 |
| D132 | LCMS: (ESI) m/z: [M + H]⁺ = 775.3 |
| D133 | LCMS: (ESI) m/z: [M + H]⁺ = 777.5 |
| D134 | LCMS: (ESI) m/z: [M + H]⁺ = 761.4 |
| D135 | LCMS: (ESI) m/z: [M + H]⁺ = 763.4 |
| D136 | LCMS: (ESI) m/z: [M + H]⁺ = 775.2 |
| D137 | LCMS: (ESI) m/z: [M + H]⁺ = 789.3 |
| D138 | LCMS: (ESI) m/z: [M + H]⁺ = 803.5 |
| D139 | LCMS: (ESI) m/z: [M + H]⁺ = 805.4 |
| D140 | LCMS: (ESI) m/z: [M + H]⁺ = 775.2 |
| D141 | LCMS: (ESI) m/z: [M + H]⁺ = 789.3 |
| D142 | LCMS: (ESI) m/z: [M + H]⁺ = 803.5 |
| D143 | LCMS: (ESI) m/z: [M + H]⁺ = 817.5 |
| D144 | LCMS: (ESI) m/z: [M + H]⁺ = 819.3 |
| D145 | LCMS: (ESI) m/z: [M + H]⁺ = 689.3 |
| D146 | LCMS: (ESI) m/z: [M + H]⁺ = 717.3 |
| D147 | LCMS: (ESI) m/z: [M + H]⁺ = 731.4 |
| D148 | LCMS: (ESI) m/z: [M + H]⁺ = 745.2 |
| D149 | LCMS: (ESI) m/z: [M + H]⁺ = 745.3 |
| D150 | LCMS: (ESI) m/z: [M + H]⁺ = 789.5 |
| D151 | LCMS: (ESI) m/z: [M + H]⁺ = 805.9 |
| D152 | LCMS: (ESI) m/z: [M + H]⁺ = 831.4 |
| D153 | LCMS: (ESI) m/z: [M + H]⁺ = 833.3 |
| D154 | LCMS: (ESI) m/z: [M + H]⁺ = 789.3 |
| D155 | LCMS: (ESI) m/z: [M + H]⁺ = 803.2 |
| D156 | LCMS: (ESI) m/z: [M + H]⁺ = 817.6 |
| D157 | LCMS: (ESI) m/z: [M + H]⁺ = 831.6 |
| D158 | LCMS: (ESI) m/z: [M + H]⁺ = 833.5 |
| D159 | LCMS: (ESI) m/z: [M + H]⁺ = 851.25 |
| D160 | LCMS: (ESI) m/z: [M + H]⁺ = 821.45 |
| D161 | LCMS: (ESI) m/z: [M + H]⁺ = 821.35 |
| D162 | LCMS: (ESI) m/z: [M + H]⁺ = 807.35 |

-continued

| Compound No. | Analytical Data |
|---|---|
| D163 | LCMS: (ESI) m/z: [M + H]⁺ = 835.50 |
| D164 | LCMS: (ESI) m/z: [M + H]⁺ = 821.60 |
| D165 | LCMS: (ESI) m/z: [M + H]⁺ = 849.60; $^1$H NMR (300 MHz, Methanol-d4) δ 9.60-9.41 (m, 1H), 8.69 (dd, J = 5.6, 3.0 Hz, 1H), 8.53 (s, 0.6H, FA), 7.79-7.50 (m, 3H), 7.44-7.15 (m, 2H), 6.81-6.47 (m, 2H), 5.11 (dt, J = 11.6, 4.5 Hz, 1H), 4.57-4.07 (m, 5H), 4.05-3.76 (m, 13H), 3.74-3.66 (m, 3H), 3.64-3.44 (m, 1H), 3.05-2.65 (m, 5H), 2.64-2.02 (m, 6H). |
| D166 | LCMS: (ESI) m/z: [M + H]⁺ = 835.65 |
| D167 | LCMS: (ESI) m/z: [M + H]⁺ = 851.25 |
| D168 | LCMS: (ESI) m/z: [M + H]⁺ = 851.25 |
| D169 | LCMS: (ESI) m/z: [M + H]⁺ = 821.35 |
| D170 | LCMS: (ESI) m/z: [M + H]⁺ = 821.35 |
| D171 | LCMS: (ESI) m/z: [M + H]⁺ = 807.35 |
| D172 | LCMS: (ESI) m/z: [M + H]⁺ = 835.35 |
| D173 | LCMS: (ESI) m/z: [M + H]⁺ = 835.60 |
| D174 | LCMS: (ESI) m/z: [M + H]⁺ = 821.65 |
| D175 | LCMS: (ESI) m/z: [M + H]⁺ = 849.80 |
| D176 | LCMS: (ESI) m/z: [M + H]⁺ = 835.70 |
| D177 | LCMS: (ESI) m/z: [M + H]⁺ = 835.65 |

Example 82—Preparation of Compounds D178-D37

In analogy to the procedures described in the examples above, compounds D178-D371 were prepared using the appropriate starting materials.

| Compound No. | LCMS | $^1$H NMR |
|---|---|---|
| D178 | 723.4 | $^1$H NMR (300 MHz, DMSO-d6) δ 1.55 (2H, d), 1.77 (2H, d), 2.03 (3H, d), 2.16 (3H, s), 2.44 (3H, d), 2.73 (2H, s), 2.88-3.08 (3H, m), 3.61 (5H, s), 3.80 (6H, s), 4.30 (2H, s), 5.12 (1H, m), 6.72 (2H, s), 7.38 (1H, m), 7.48 (1H, d), 7.57 (1H, d), 7.80-7.90 (2H, m), 8.23 (1H, s), 8.72 (1H, d), 9.45 (1H, s), 11.12 (1H, s). |
| D179 | 813.3 | $^1$H NMR(400 MHz, D .79 (brs, 0.8H, FA(COOH), 11.08 (s, 1H), 9.44 (s, 1H), 8.71 (d, J = 5.7 Hz, 1H), 8.14 (s, 0.8H, FA), 7.86 (s, 1H), 7.66 (d, J = 8.5 Hz, 1H), 7.56 (d, J = 5.8 Hz, 1H), 7.33 (d, J = 2.3 Hz, 1H), 7.24 (dd, J = 8.8, 2.3 Hz, 1H), 7.11 (s, 1H), 6.73 (s, 2H), 5.07 (dd, J = 13.0, 5.4 Hz, 1H), 4.08-4.02 (m, 1H), 3.82 (s, 7H), 3.69-3.62 (m, 2H), 3.60 (s, 3H), 3.50-3.39 (m, 8H), 3.12-3.05 (m, 2H), 2.95-2.83 (m, 1H), 2.63-2.55 (m, 3H), 2.55 (s, 2H), 2.47-2.39 (m, 3H), 2.07-1.98 (m, 1H). |
| D180 | 788.2 | |
| D181 | 774.7 | |
| D182 | 789.2 | $^1$H NMR (400 MHz, DMSO-d6) δ 11.11 (s, 1H), 9.45 (s, 1H), 8.73 (d, J = 5.7 Hz, 1H), 8.21 (s, 0.7H, FA), 8.05 (d, J = 7.5 Hz, 1H), 7.87 (s, 1H), 7.82 (d, J = 8.2 Hz, 1H), 7.59-7.54 (m, 1H), 7.31-7.24 (m, 2H), 6.73 (s, 2H), 5.12 (dd, J = 12.8, 5.4 Hz, 1H), 4.87 (t, J = 6.8 Hz, 1H), 4.14-3.99 (m, 1H), 3.81 (s, 6H), 3.66 (s, 2H), 3.61 (s, 3H), 3.44-3.35 (m, 3H), 2.98 (s, 2H), 2.92-2.83 (m, 1H), 2.73-2.55 (m, 4H), 2.44-2.32 (m, 1H), 2.25 (dd, J = 18.0, 6.8 Hz, 3H), 2.15-2.00 (m, 3H), 1.95 (td, J = 11.2, 8.4 Hz, 2H). |
| D183 | 789.5 | |
| D184 | 803.15 | |
| D185 | 715.2 | |
| D186 | 804.65 | $^1$H NMR (400 MHz, DMSO-d6) δ 11.08 (s, 1H), 9.45 (d, J = 4.3 Hz, 1H), 8.73 (d, J = 5.7 Hz, 1H), 8.16 (s, 0.6H, FA), 7.90 (d, J = 6.4 Hz, 1H), 7.64 (dd, J = 8.3, 2.2 Hz, 1H), 7.58 (d, J = 5.7 Hz, 1H), 6.90-6.72 (m, 3H), 6.65 (dd, J = 8.5, 2.3 Hz, 1H), 5.06 (dd, J = 12.9, 5.4 Hz, 1H), 4.57 (d, J = 23.1 Hz, 2H), 3.83 (d, J = 18.2 Hz, 6H), 3.74 (s, 4H), 3.60 (d, J = 3.3 Hz, 3H), 2.88 (ddd, J = 17.7, 14.0, 5.4 Hz, 1H), 2.72 (s, 1H), 2.65 (s, 2H), 2.62-2.53 (m, 4H), 2.44-2.26 (m, 6H), 2.08-1.94 (m, 1H), 1.77 (d, J = 6.5 Hz, 4H), 1.53 (s, 4H). |
| D187 | 790.5 | |
| D188 | 804.6 | |
| D189 | 802.65 | |
| D190 | 788.6 | |
| D191 | 802.55 | |

-continued

| Compound No. | LCMS | ¹H NMR |
|---|---|---|
| D192 | 788.8 | |
| D193 | 774.55 | |
| D194 | 774.75 | ¹H NMR (400 MHz, DMSO-d6) δ 11.08 (s, 1H), 9.45 (s, 1H), 8.73 (d, J = 5.7 Hz, 1H), 8.22 (s, 1H, FA), 8.12 (d, J = 7.4 Hz, 1H), 7.88 (s, 1H), 7.64 (d, J = 8.2 Hz, 1H), 7.57 (d, J = 5.7 Hz, 1H), 6.74 (d, J = 6.3 Hz, 3H), 6.67-6.56 (m, 1H), 5.06 (dd, J = 12.8, 5.4 Hz, 1H), 4.08 (d, J = 10.2 Hz, 3H), 3.97 (s, 2H), 3.82 (s, 6H), 3.67 (s, 2H), 3.61 (s, 3H), 3.51 (s, 2H), 3.01 (d, J = 7.1 Hz, 2H), 2.95-2.80 (m, 1H), 2.65-2.53 (m, 5H), 2.29 (d, J = 7.6 Hz, 2H), 2.12 (t, J = 10.3 Hz, 2H), 2.07-1.93 (m, 1H). |
| D195 | 760.5 | ¹H NMR (400 MHz, DMSO-d6) δ 11.08 (s, 1H), 9.45 (s, 1H), 8.74 (d, J = 5.6 Hz, 1H), 7.89 (s, 1H), 7.67 (d, J = 8.3 Hz, 1H), 7.56 (d, J = 5.6 Hz, 1H), 6.82 (d, J = 2.4 Hz, 3H), 6.68 (dd, J = 8.4, 2.1 Hz, 1H), 5.07 (dd, J = 12.9, 5.4 Hz, 1H), 4.32 (s, 2H), 4.20 (s, 6H), 4.06 (s, 3H), 3.88 (s, 8H), 3.61 (s, 4H), 2.98-2.74 (m, 2H), 2.59 (d, J = 16.5 Hz, 2H), 2.44 (d, J = 7.2 Hz, 2H), 2.11-1.95 (m, 1H). |
| D196 | 757.5 | |
| D197 | 743.35 | |
| D198 | 743.25 | |
| D199 | 731.35 | ¹H NMR (400 MHz, DMSO-d6) δ 11.15 (s, 1H), 9.52 (s, 1H), 8.77 (d, J = 6.0 Hz, 1H), 8.06 (s, 1H), 7.91 (d, J = 8.1 Hz, 1H), 7.85 (dd, J = 5.5, 1.6 Hz, 2H), 7.75 (d, J = 6.0 Hz, 1H), 6.87 (s, 2H), 5.16 (dd, J = 12.8, 5.4 Hz, 1H), 4.43 (d, J = 13.9 Hz, 1H), 4.29 (s, 2H), 4.14-4.03 (m, 1H), 3.91 (s, 6H), 3.64 (s, 4H), 3.40 (t, J = 8.2 Hz, 2H), 3.18 (m, 2H), 3.23-3.13 (m, 2H), 3.02-2.72 (m, 4H), 2.68-2.56 (m, 2H), 2.12-1.99 (m, 1H). |
| D200 | 743.15 | |
| D201 | 804.7 | ¹H NMR (300 MHz, DMSO-d6) δ 11.09 (s, 1H), 9.45 (t, J = 1.4 Hz, 1H), 8.72 (d, J = 5.7 Hz, 1H), 8.23 (s, 0.8H, FA), 7.90 (d, J = 6.0 Hz, 1H), 7.76-7.56 (m, 2H), 7.40-7.16 (m, 2H), 6.77 (d, J = 10.7 Hz, 2H), 5.17-4.99 (m, 1H), 4.56 (d, J = 19.2 Hz, 2H), 3.83 (d, J = 13.5 Hz, 6H), 3.60 (d, J = 2.3 Hz, 3H), 3.43 (s, 6H), 3.01 (d, J = 5.0 Hz, 4H), 2.98-2.78 (m, 1H), 2.72 (d, J = 5.9 Hz, 1H), 2.65 (s, 2H), 2.63-2.55 (m, 1H), 2.47 (s, 2H), 2.27 (dd, J = 4.3, 2.4 Hz, 1H), 2.10-1.91 (m, 1H), 1.73 (d, J = 6.4 Hz, 4H), 1.62-1.47 (m, 2H), 1.44-1.26 (m, 2H). |
| D202 | 818.4 | |
| D203 | 790.6 | |
| D204 | 790.8 | |
| D205 | 776.35 | |
| D206 | 776.6 | |
| D207 | 805.65 | |
| D208 | 819.55 | ¹H NMR (300 MHz, DMSO-d6) δ 11.12 (s, 1H), 9.45 (s, 1H), 8.72 (dd, J = 5.7, 2.2 Hz, 1H), 8.20 (s, 0.6H, FA), 7.90 (d, J = 3.6 Hz, 1H), 7.83 (d, J = 8.2 Hz, 1H), 7.58 (dt, J = 5.7, 1.2 Hz, 1H), 7.37-7.22 (m, 2H), 6.77 (d, J = 9.7 Hz, 2H), 5.12 (dd, J = 12.9, 5.4 Hz, 1H), 5.04-4.92 (m, 1H), 4.56 (d, J = 17.5 Hz, 2H), 3.82 (d, J = 13.3 Hz, 6H), 3.60 (s, 3H), 2.90 (ddd, J = 17.3, 13.9, 5.4 Hz, 1H), 2.71 (s, 1H), 2.61 (d, J = 20.0 Hz, 5H), 2.47-2.22 (m, 9H), 2.06 (d, J = 5.9 Hz, 1H), 1.80 (dd, J = 12.2, 6.3 Hz, 2H), 1.70-1.43 (m, 8H). |
| D209 | 774.6 | |
| D210 | 760.7 | |
| D211 | 743.35 | ¹H NMR (400 MHz, DMSO-d6) δ 11.15 (s, 1H), 9.44 (s, 1H), 8.72 (d, J = 5.7 Hz, 1H), 8.21 (s, 1H), 7.94-7.79 (m, 4H), 7.56 (d, J = 5.7 Hz, 1H), 6.75 (s, 2H), 5.16 (dd, J = 12.8, 5.4 Hz, 1H), 3.82 (d, J = 9.2 Hz, 8H), 3.60 (s, 4H), 3.46-3.40 (m, 6H), 2.90 (ddd, J = 16.9, 13.8, 5.4 Hz, 1H), 2.70 (s, 2H), 2.66-2.53 (m, 5H), 2.07 (ddd, J = 13.3, 5.6, 3.2 Hz, 1H), 1.94 (t, J = 7.0 Hz, 2H), 1.74 (p, J = 7.1 Hz, 2H). |
| D212 | 757.35 | |
| D213 | 771.2 | |
| D214 | 717.35 | ¹H NMR (400 MHz, DMSO-d6) δ 11.15 (s, 1H), 9.45 (s, 1H), 8.73 (d, J = 5.7 Hz, 1H), 8.19 (s, 1H FA), 7.87 (d, J = 9.1 Hz, 4H), 7.58 (d, J = 5.6 Hz, 1H), 6.74 (s, 2H), 5.16 (dd, J = 12.8, 5.4 Hz, 1H), 3.81 (s, 6H), 3.60 (s, 6H), 3.47 (s, 5H), 2.94-2.85 (m, 1H), 2.68-2.58 (m, 2H), 2.44 (t, J = 7.2 Hz, 6H), 2.12-2.01 (m, 1H), 1.73 (p, J = 7.1 Hz, 2H). |
| D215 | 729.35 | |
| D216 | 703.15 | |
| D217 | 771.15 | ¹H NMR (300 MHz, DMSO-d6) δ 11.15 (s, 1H), 9.47 (s, 1H), 8.75 (d, J = 5.7 Hz, 1H), 7.97-7.79 (m, 4H), 7.58 (d, J = 5.6 Hz, 1H), 6.87 (s, 2H), 5.16 (dd, J = 12.9, 5.3 Hz, 1H), 4.27 (d, J = 4.0 Hz, 2H), 4.02 (s, 1H), 3.90 (s, 7H), 3.75 (s, 1H), 3.62 (s, 4H), 3.11 (s, 2H), 3.08 (s, 2H), 2.96-2.84 (m, 1H), 2.69 (dd, J = 7.2, 3.6 Hz, 2H), 2.66-2.54 (m, 2H), 2.47-2.39 (m, 2H), 2.13-2.00 (m, 3H), 1.92 (t, J = 12.4 Hz, 2H). |

-continued

| Compound No. | LCMS | ¹H NMR |
|---|---|---|
| D218 | 757.35 | |
| D219 | 771.35 | ¹H NMR (300 MHz, DMSO-d6) δ 11.15 (s, 1H), 9.45 (s, 1H), 8.73 (d, J = 5.7 Hz, 1H), 8.20 (s, 1H FA), 7.97-7.77 (m, 4H), 7.57 (d, J = 5.7 Hz, 1H), 6.74 (s, 2H), 5.24-5.08 (m, 1H), 3.82 (s, 6H), 3.71 (s, 3H), 3.61 (s, 4H), 3.11 (s, 4H), 2.98-2.80 (m, 2H), 2.76-2.62 (m, 6H), 2.15-2.01 (m, 1H), 1.61 (d, J = 27.8 Hz, 5H). |
| D220 | 785.15 | ¹H NMR (400 MHz, DMSO-d6) δ 11.15 (s, 1H), 9.45 (d, J = 2.0 Hz, 1H), 8.73 (dd, J = 5.6, 2.2 Hz, 1H), 7.94-7.87 (m, 2H), 7.84 (q, J = 2.9 Hz, 2H), 7.58 (dd, J = 5.7, 2.6 Hz, 1H), 6.74 (s, 2H), 5.16 (dd, J = 12.8, 5.4 Hz, 1H), 3.82 (s, 6H), 3.60 (d, J = 1.4 Hz, 5H), 3.52 (t, J = 7.0 Hz, 1H), 3.17 (s, 2H), 2.89 (ddd, J = 16.6, 13.6, 5.4 Hz, 1H), 2.70 (t, J = 7.0 Hz, 2H), 2.66-2.56 (m, 7H), 2.41 (s, 2H), 2.12-2.00 (m, 1H), 1.76 (t, J = 7.1 Hz, 1H), 1.67 (t, J = 7.2 Hz, 1H), 1.49 (s, 4H). |
| D221 | 817.35 | ¹H NMR (300 MHz, DMSO-d6) δ 11.13 (s, 1H), 9.45 (s, 1H), 8.73 (d, J = 5.7 Hz, 1H), 8.20 (s, 1H, FA), 7.92-7.80 (m, 2H), 7.60 (d, J = 5.7 Hz, 1H), 7.38-7.21 (m, 2H), 6.74 (s, 2H), 5.12 (dd, J = 12.9, 5.4 Hz, 1H), 5.03 (t, J = 6.9 Hz, 1H), 3.81 (s, 6H), 3.61 (s, 3H), 3.58 (s, 2H), 3.44 (s, 4H), 2.96-2.82 (m, 3H), 2.66-2.54 (m, 5H), 2.21-1.98 (m, 3H), 1.93-1.81 (m, 2H), 1.66-1.43 (m, 8H). |
| D222 | 776.4 | |
| D223 | 776.35 | |
| D224 | 790.4 | |
| D225 | 776.35 | |
| D226 | 762.8 | |
| D227 | 748.3 | ¹H NMR (300 MHz, DMSO-d6) δ 11.07 (s, 1H), 9.44 (s, 1H), 8.72 (d, J = 5.7 Hz, 1H), 8.17 (s, 0.6H, FA), 7.88 (s, 1H), 7.59 (dd, J = 9.7, 7.0 Hz, 2H), 6.76 (d, J = 7.3 Hz, 3H), 6.61 (d, J = 8.4 Hz, 1H), 5.05 (dd, J = 12.8, 5.4 Hz, 1H), 4.87 (t, J = 5.4 Hz, 1H), 4.15-3.95 (m, 2H), 3.84 (s, 6H), 3.67 (d, J = 15.2 Hz, 3H), 3.60 (s, 3H), 3.11-2.71 (m, 2H), 2.66-2.55 (m, 5H), 2.27 (s, 3H), 2.12-1.88 (m, 4H), 1.75 (d, J = 10.1 Hz, 1H), 1.64-1.36 (m, 4H). |
| D228 | 791.55 | |
| D229 | 751.2 | |
| D230 | 791.4 | ¹H NMR (300 MHz, DMSO-d6) δ 11.12 (s, 1H), 9.45 (t, J = 1.2 Hz, 1H), 8.73 (dd, J = 5.7, 1.0 Hz, 1H), 8.19 (s, 0.3H, FA), 7.99-7.73 (m, 2H), 7.66-7.50 (m, 1H), 7.39-7.22 (m, 2H), 6.77 (d, J = 9.5 Hz, 2H), 5.12 (dd, J = 12.9, 5.4 Hz, 1H), 4.87 (t, J = 6.8 Hz, 1H), 4.56 (d, J = 19.1 Hz, 2H), 3.82 (d, J = 13.1 Hz, 6H), 3.60 (d, J = 1.5 Hz, 3H), 3.26 (s, 2H), 3.17 (s, 2H), 2.89 (s, 1H), 2.78-2.61 (m, 6H), 2.61-2.52 (m, 2H), 2.48-2.33 (m, 2H), 2.28 (dd, J = 3.8, 1.9 Hz, 1H), 2.19 (dd, J = 11.7, 8.0 Hz, 2H), 2.04 (d, J = 11.6 Hz, 1H), 1.53 (d, J = 7.9 Hz, 2H), 1.42-1.19 (m, 2H). |
| D231 | 774.2 | |
| D232 | 774.4 | |
| D233 | 735.2 | ¹H NMR (300 MHz, DMSO-d6) δ 11.13 (s, 1H), 9.45 (d, J = 0.8 Hz, 1H), 8.72 (d, J = 5.7 Hz, 1H), 8.18 (s, 0.5H, FA), 7.93-7.79 (m, 2H), 7.56 (dd, J = 5.7, 0.9 Hz, 1H), 7.31 (d, J = 7.8 Hz, 2H), 6.74 (s, 2H), 5.27 (s, 1H), 5.14 (dd, J = 12.9, 5.3 Hz, 1H), 4.63 (t, J = 8.1 Hz, 1H), 4.34 (dd, J = 10.5, 6.5 Hz, 1H), 4.13 (d, J = 8.3 Hz, 1H), 3.82 (s, 7H), 3.73 (s, 2H), 3.60 (s, 3H), 3.50 (d, J = 9.7 Hz, 2H), 3.07 (s, 2H), 2.98-2.80 (m, 1H), 2.71-2.53 (m, 3H), 2.38 (d, J = 7.5 Hz, 2H), 2.17-1.97 (m, 1H). |
| D234 | 775.35 | ¹H NMR (300 MHz, DMSO-d6) δ 11.12 (s, 1H), 9.45 (s, 1H), 8.73 (dd, J = 5.7, 1.2 Hz, 1H), 8.20 (s, 1H, FA), 7.96-7.76 (m, 2H), 7.69-7.54 (m, 1H), 7.42-7.19 (m, 2H), 6.75 (d, J = 1.7 Hz, 2H), 5.12 (dd, J = 12.9, 5.3 Hz, 1H), 4.90 (t, J = 6.7 Hz, 1H), 4.14 (d, J = 27.9 Hz, 2H), 3.92 (s, 1H), 3.83 (d, J = 2.2 Hz, 7H), 3.75 (s, 2H), 3.61 (s, 3H), 3.49 (t, J = 6.8 Hz, 3H), 3.08 (s, 2H), 2.99-2.70 (m, 4H), 2.68-2.55 (m, 3H), 2.40-2.19 (m, 4H), 2.15-1.94 (m, 1H). |
| D235 | 729.3 | |
| D236 | 715.15 | |
| D237 | 689.2 | |
| D238 | 743.4 | |
| D239 | 729.35 | |
| D240 | 757.35 | |
| D241 | 729.15 | |
| D242 | 729.2 | |
| D243 | 757.35 | |
| D244 | 791.23 | |
| D245 | 762.4 | |
| D246 | 791.4 | |
| D247 | 790.4 | |
| D248 | 762.3 | |
| D249 | 723.3 | |
| D250 | 762.4 | |

| Compound No. | LCMS | ¹H NMR |
|---|---|---|
| D251 | 763.6 | ¹H NMR (400 MHz, DMSO-d6) δ 11.12 (s, 1H), 9.45 (s, 1H), 8.73 (d, J = 5.7 Hz, 1H), 8.21 (s, 1.4H, FA), 7.88 (s, 1H), 7.82 (d, J = 8.2 Hz, 1H), 7.57 (d, J = 5.6 Hz, 1H), 7.28 (d, J = 2.2 Hz, 1H), 7.24 (dd, J = 8.3, 2.3 Hz, 1H), 6.75 (s, 2H), 5.12 (dd, J = 12.8, 5.4 Hz, 1H), 4.90-4.80 (m, 1H), 3.82 (s, 6H), 3.61 (d, J = 3.2 Hz, 5H), 3.36 (s, 2H), 3.27 (s, 2H), 2.89 (ddd, J = 16.7, 13.7, 5.3 Hz, 1H), 2.75-2.56 (m, 4H), 2.45 (q, J = 7.1, 6.7 Hz, 4H), 2.26-2.13 (m, 5H), 2.11-1.98 (m, 1H), 1.50 (t, J = 7.2 Hz, 2H), 1.32 (t, J = 7.2 Hz, 2H). |
| D252 | 762.4 | |
| D253 | 777.35 | |
| D254 | 748.4 | |
| D255 | 790.25 | |
| D256 | 818.2 | |
| D257 | 777.7 | |
| D258 | 790.4 | |
| D259 | 777.2 | |
| D260 | 805.35 | |
| D261 | 819.2 | |
| D262 | 819.25 | |
| D263 | 805.35 | |
| D264 | 803.2 | |
| D265 | 803.15 | |
| D266 | 789.3 | |
| D267 | 789.3 | |
| D268 | 715.3 | |
| D269 | 757.35 | |
| D270 | 719.35 | |
| D271 | 719.28 | ¹H NMR (400 MHz, DMSO-d6) δ 11.03 (s, 1H), 9.42 (s, 1H), 8.68 (d, J = 5.6 Hz, 1H), 7.91 (s, 1H), 7.85 (s, 1H), 7.61 (d, J = 8.3 Hz, 1H), 7.55 (d, J = 5.7 Hz, 1H), 6.80 (s, 2H), 6.75 (d, J = 2.1 Hz, 1H), 6.62 (dd, J = 8.4, 2.1 Hz, 1H), 5.53 (s, 2H), 5.02 (dd, J = 12.8, 5.4 Hz, 1H), 4.57 (td, J = 6.3, 3.2 Hz, 1H), 4.53 (s, 2H), 4.24-4.15 (m, 2H), 3.86 (s, 6H), 3.79 (dd, J = 9.7, 3.9 Hz, 2H), 3.56 (s, 3H), 3.15 (d, J = 5.3 Hz, 1H), 2.85 (ddd, J = 16.8, 13.8, 5.3 Hz, 1H), 2.60-2.50 (m, 2H), 2.05 (s, 1H), 2.03-1.94 (m, 1H). |
| D272 | 747.28 | |
| D273 | 720.03 | |
| D274 | 735.52 | |
| D275 | 765.06 | |
| D276 | 776.47 | |
| D277 | 776.33 | |
| D278 | 804.19 | |
| D279 | 761.28 | ¹H NMR (400 MHz, DMSO-d₆) δ 11.08 (s, 1H), 9.43 (s, 1H), 8.71 (d, J = 5.6 Hz, 1H), 8.05 (s, 1H), 7.86 (s, 1H), 7.82 (d, J = 8.3 Hz, 1H), 7.56 (d, J = 5.7 Hz, 1H), 7.45 (d, J = 2.3 Hz, 1H), 7.35 (dd, J = 8.4, 2.3 Hz, 1H), 6.76 (s, 2H), 5.09 (dd, J = 12.9, 5.4 Hz, 1H), 4.41 (t, J = 6.6 Hz, 2H), 3.83 (s, 5H), 3.59 (s, 2H), 3.15 (d, J = 5.1 Hz, 1H), 3.11 (d, J = 6.4 Hz, 1H), 2.87 (ddd, J = 17.2, 13.9, 5.3 Hz, 1H), 2.70-2.51 (m, 2H), 2.03 (d, J = 15.9 Hz, 5H). |
| D280 | 802.16 | |
| D281 | 830.16 | |
| D282 | 735.45 | ¹H NMR (400 MHz, DMSO-d6) δ 11.08 (s, 1H), 7.97 (s, 1H), 7.86 (s, 1H), 7.75 (d, J = 8.2 Hz, 1H), 7.47 (d, J = 2.1 Hz, 1H), 7.32 (dd, J = 8.3, 2.2 Hz, 1H), 6.71 (s, 2H), 5.26 (s, 2H), 4.40 (s, 1H), 3.78 (s, 5H), 3.55 (s, 3H), 2.88 (ddd, J = 18.2, 13.8, 5.4 Hz, 1H), 2.71-2.53 (m, 2H), 2.38-2.24 (m, 2H), 2.09 (d, J = 28.1 Hz, 4H). |
| D283 | 749.31 | |
| D284 | 779.27 | |
| D285 | 790.33 | |
| D286 | 790.4 | ¹H NMR (400 MHz, DMSO-d6) δ 11.03 (s, 1H), 8.08 (s, 1H), 7.85 (s, 1H), 7.60 (d, J = 8.3 Hz, 1H), 6.72 (s, 2H), 5.03 (dd, J = 12.9, 5.4 Hz, 1H), 4.55 (s, 2H), 4.20 (dd, J = 9.2, 6.3 Hz, 2H), 3.80 (s, 6H), 3.58 (s, 2H), 2.97-2.72 (m, 0H), 2.18 (s, 1H), 2.05 (s, 1H), 2.02-1.94 (m, 1H). |
| D287 | 818.26 | |
| D288 | 765.27 | |
| D289 | 747.35 | |
| D290 | 791.24 | |
| D291 | 802.37 | |
| D292 | 779.2 | |
| D293 | 809.16 | |
| D294 | 820.29 | |
| D295 | 820.08 | |
| D296 | 847.22 | |
| D297 | 719.28 | |
| D298 | 733.49 | |

-continued

| Compound No. | LCMS | ¹H NMR |
|---|---|---|
| D299 | 763.31 | |
| D300 | 774.44 | |
| D301 | 774.02 | |
| D302 | 802.58 | |
| D303 | 708.22 | |
| D304 | 803.4 | ¹H NMR (400 MHz, Methanol-d4) δ 9.58 (s, 1H), 8.70 (d, J = 6.0 Hz, 1H), 7.91 (d, J = 2.2 Hz, 1H), 7.82 (d, J = 8.3 Hz, 1H), 7.78 (d, J = 6.1 Hz, 1H), 7.31 (d, J = 2.3 Hz, 1H), 7.26 (dd, J = 8.3, 2.3 Hz, 1H), 6.89 (s, 2H), 5.13 (dd, J = 12.6, 5.4 Hz, 1H), 4.98 (t, J = 6.5 Hz, 1H), 4.43 (s, 2H), 3.98 (d, J = 4.3 Hz, 6H), 3.74 (s, 3H), 3.70-3.50 (m, 4H), 3.33-2.94 (m, 6H), 2.93-2.66 (m, 4H), 2.56 (s, 1H), 2.27 (s, 1H), 2.17-1.95 (m, 10H), 1.67 (q, J = 12.6 Hz, 1H). |
| D305 | 789.7 | ¹H NMR (400 MHz, Methanol-d4) δ 9.54 (s, 1H), 8.69 (d, J = 5.8 Hz, 1H), 8.50 (s, 2H, FA), 7.83 (d, J = 8.3 Hz, 1H), 7.75 (s, 1H), 7.62 (d, J = 5.7 Hz, 1H), 7.31 (d, J = 2.2 Hz, 1H), 7.26 (dd, J = 8.3, 2.2 Hz, 1H), 6.82 (s, 2H), 5.13 (dd, J = 12.5, 5.4 Hz, 1H), 5.01-4.97 (m, 1H), 4.17 (s, 2H), 3.95 (s, 6H), 3.77-3.65 (m, 5H), 3.56-3.40 (m, 5H), 3.28 (s, 1H), 3.07-2.92 (m, 3H), 2.91-2.84 (m, 1H), 2.81-2.65 (m, 4H), 2.50-2.40 (m, 1H), 2.18-2.07 (m, 6H), 2.05-1.96 (m, 2H). |
| D306 | 715.3 | ¹H NMR (400 MHz, DMSO-d6) δ 11.15 (s, 1H), 9.45 (s, 1H), 8.72 (d, J = 5.6 Hz, 1H), 8.18 (s, 1H FA), 7.89 (d, J = 17.4 Hz, 4H), 7.56 (d, J = 5.6 Hz, 1H), 6.74 (s, 2H), 5.17 (dd, J = 12.8, 5.4 Hz, 1H), 3.82 (s, 6H), 3.74 (s, 2H), 3.63 (d, J = 19.3 Hz, 6H), 3.27 (s, 3H), 2.90 (ddd, J = 16.8, 13.7, 5.3 Hz, 1H), 2.78 (s, 2H), 2.66-2.57 (m, 3H), 2.55 (s, 1H), 2.11-2.02 (m, 1H), 1.96 (t, J = 6.9 Hz, 2H). |
| D307 | 729.3 | ¹H NMR (400 MHz, DMSO-d6) δ 11.15 (s, 1H), 9.45 (s, 1H), 8.72 (d, J = 5.7 Hz, 1H), 7.99-7.80 (m, 4H), 7.56 (d, J = 5.7 Hz, 1H), 6.73 (s, 2H), 5.16 (dd, J = 12.7, 5.4 Hz, 1H), 3.82 (s, 6H), 3.71 (s, 2H), 3.60 (s, 3H), 3.53 (s, 2H), 3.10 (s, 4H), 2.90 (ddd, J = 16.7, 13.6, 5.4 Hz, 1H), 2.65-2.54 (m, 1H), 2.44 (s, 5H), 2.12-2.01 (m, 1H), 1.67 (t, J = 5.5 Hz, 4H). |
| D308 | 743.35 | |
| D309 | 701.3 | |
| D310 | 743.55 | |
| D311 | 743.3 | |
| D312 | 757.3 | |
| D313 | 771.45 | |
| D314 | 743.3 | |
| D315 | 743.3 | |
| D316 | 717.3 | |
| D317 | 729.3 | |
| D318 | 757.3 | |
| D319 | 761.35 | |
| D320 | 761.28 | |
| D321 | 763.24 | |
| D322 | 747.42 | |
| D323 | 746.83 | |
| D324 | 746.55 | |
| D325 | 747.33 | |
| D326 | 747.45 | |
| D327 | 706.67 | |
| D328 | 779.84 | ¹H NMR (400 MHz, DMSO-d6) δ 11.04 (s, 1H), 8.48 (d, J = 2.7 Hz, 1H), 8.25 (d, J = 2.7 Hz, 1H), 8.19 (s, 2H), 7.65 (d, J = 8.5 Hz, 1H), 7.30 (d, J = 2.3 Hz, 1H), 7.22 (dd, J = 8.6, 2.3 Hz, 1H), 6.85 (d, J = 5.6 Hz, 2H), 5.04 (dd, J = 12.9, 5.4 Hz, 1H), 3.83 (d, J = 2.7 Hz, 7H), 3.59 (s, 3H), 3.48 (d, J = 5.0 Hz, 2H), 3.39 (t, J = 5.0 Hz, 4H), 2.81 (dd, J = 25.4, 11.4 Hz, 3H), 2.63-2.51 (m, 2H), 2.32-2.22 (m, 2H), 2.06-1.90 (m, 1H), 1.56 (s, 1H), 1.34 (d, J = 7.5 Hz, 2H), 1.09 (s, 1H) |
| D329 | 725.87 | ¹H NMR (400 MHz, DMSO-d6) δ 11.04 (s, 1H), 8.24-8.12 (m, 2H), 8.03 (d, J = 2.6 Hz, 1H), 7.88-7.72 (m, 1H), 7.65 (d, J = 8.5 Hz, 1H), 7.30 (d, J = 2.2 Hz, 1H), 7.22 (dd, J = 8.6, 2.3 Hz, 1H), 6.79 (s, 2H), 3.83 (s, 6H), 3.57 (s, 2H), 3.51 (s, 3H), 3.40 (t, J = 5.1 Hz, 4H), 2.91-2.78 (m, 3H), 2.66-2.50 (m, 2H), 2.36-2.24 (m, 2H), 2.14 (t, J = 11.6 Hz, 2H), 2.08 (s, 3H), 1.99 (ddd, J = 11.5, 6.0, 3.7 Hz, 1H), 1.61 (d, J = 12.4 Hz, 2H), 1.35 (q, J = 7.0 Hz, 2H), 1.26 (s, 2H), 1.13 (q, J = 11.2, 10.7 Hz, 2H). |
| D330 | 614.68 | ¹H NMR (400 MHz, DMSO-d6) δ 11.04 (s, 1H), 8.15 (s, 1H), 8.02 (d, J = 2.7 Hz, 1H), 7.79 (dd, J = 2.8, 1.3 Hz, 1H), 7.63 (d, J = 8.5 Hz, 1H), 7.27 (d, J = 2.3 Hz, 1H), 7.20 (dd, J = 8.7, 2.3 Hz, 1H), 6.80 (s, 2H), 5.04 (dd, J = 12.9, 5.4 Hz, 1H), 3.84 (s, 6H), 3.55 (s, 2H), 3.37 (t, J = 5.1 Hz, 4H), 2.66-2.53 (m, 2H), 2.08 (s, 3H). |
| D331 | 654.74 | ¹H NMR (400 MHz, DMSO-d6) δ 11.03 (s, 1H), 8.12 (s, 1H), 8.04 (d, J = 2.6 Hz, 1H), 7.80 (dd, J = 2.7, 1.3 Hz, 1H), 7.61 (d, J = 8.3 Hz, 1H), 6.82 (s, 2H), 6.75 (d, J = 2.1 Hz, 1H), 5.02 (dd, J = 12.9, |

| Compound No. | LCMS | ¹H NMR |
|---|---|---|
| | | 5.4 Hz, 1H), 3.85 (s, 6H), 3.72 (s, 5H), 3.52 (s, 3H), 2.93-2.74 (m, 1H), 2.08 (s, 3H), 1.98 (dd, J = 9.2, 4.2 Hz, 1H), 1.76 (s, 5H). |
| D332 | 669.75 | |
| D333 | 724.79 | |
| D334 | 594.73 | ¹H NMR (400 MHz, DMSO-d6) δ 10.81 (s, 1H), 8.13 (s, 1H), 8.05 (d, J = 2.7 Hz, 1H), 7.80 (dd, J = 2.8, 1.3 Hz, 1H), 6.82 (s, 2H), 5.73 (s, 1H), 3.85 (s, 6H), 3.71 (s, 2H), 3.52 (s, 3H), 3.08-2.85 (m, 4H), 2.79-2.53 (m, 3H), 2.38-2.28 (m, 3H), 2.08 (s, 3H), 1.86-1.74 (m, 1H), 1.65 (d, J = 12.7 Hz, 2H), 1.33 (s, 3H), 1.27-1.12 (m, 3H). |
| D335 | 609.66 | |
| D336 | 654.74 | |
| D337 | 640.72 | |
| D338 | 640.72 | |
| D339 | 626.69 | |
| D340 | 679.75 | ¹H NMR (400 MHz, DMSO-d6) δ 12.12 (s, 1H), 11.03 (s, 1H), 8.14 (d, J = 1.1 Hz, 1H), 7.60 (d, J = 8.3 Hz, 1H), 7.45 (s, 1H), 7.34 (t, J = 2.8 Hz, 1H), 6.82 (s, 2H), 6.75 (d, J = 2.1 Hz, 1H), 6.62 (dd, J = 8.4, 2.2 Hz, 1H), 6.54 (t, J = 2.4 Hz, 1H), 5.73 (s, 1H), 5.02 (dd, J = 12.9, 5.4 Hz, 1H), 3.83 (s, 6H), 3.71 (s, 4H), 3.58 (s, 3H), 3.53 (s, 2H), 2.86 (ddd, J = 17.3, 13.9, 5.4 Hz, 1H), 2.64-2.50 (m, 1H), 1.98 (dd, J = 9.2, 4.0 Hz, 1H), 1.72 (d, J = 5.8 Hz, 4H). |
| D341 | 690.72 | ¹H NMR (400 MHz, DMSO-d6) δ 8.13 (dd, J = 9.6, 2.7 Hz, 2H), 6.83 (d, J = 0.9 Hz, 2H), 11.03 (s, 1H), 8.37 (d, J = 2.6 Hz, 1H), 7.60 (d, J = 8.3 Hz, 1H), 6.78-6.71 (m, 1H), 6.62 (dd, J = 8.4, 2.1 Hz, 1H), 5.02 (dd, J = 12.9, 5.4 Hz, 1H), 3.84 (d, J = 0.8 Hz, 6H), 3.69 (s, 4H), 3.57 (s, 3H), 3.50 (d, J = 4.1 Hz, 2H), 2.86 (ddd, J = 17.3, 13.9, 5.4 Hz, 1H), 2.38 (s, 5H), 1.69 (s, 4H). |
| D342 | 712.15 | ¹H NMR (400 MHz, DMSO-d6) δ 11.07 (s, 1H), 9.04 (d, J = 3.3 Hz, 1H), 8.66 (d, J = 3.4 Hz, 1H), 8.20 (s, 1H, FA), 7.64 (d, J = 8.5 Hz, 1H), 7.29 (s, 1H), 7.22 (d, J = 8.8 Hz, 1H), 6.88 (s, 2H), 5.06 (dd, J = 13.0, 5.3 Hz, 1H), 4.02 (d, J = 12.8 Hz, 2H), 3.84 (s, 6H), 3.57-3.47 (m, 5H), 2.91 (dt, J = 22.4, 13.1 Hz, 3H), 2.71-2.55 (m, 2H), 2.42-2.23 (m, 10H), 2.09-1.93 (m, 1H), 1.82-1.68 (m, 2H), 1.64-1.50 (m, 1H), 1.39-1.30 (m, 2H), 1.22-1.09 (m, 2H). |
| D343 | 628.5 | ¹H NMR (300 MHz, DMSO-d6) δ 11.10 (s, 1H), 9.47 (s, 1H, TFA), 7.77 (d, J = 8.5 Hz, 1H), 7.47 (d, J = 2.2 Hz, 1H), 7.38-7.23 (m, 2H), 6.69 (s, 2H), 5.10 (dd, J = 12.8, 5.4 Hz, 1H), 4.33 (s, 2H), 4.18 (d, J = 12.1 Hz, 2H), 3.89 (s, 6H), 3.55 (s, 4H), 3.53-3.45 (m, 5H), 2.99-2.81 (m, 1H), 2.60 (d, J = 18.3 Hz, 2H), 2.35 (s, 3H), 2.05 (s, 4H). |
| D344 | 600.2 | ¹H NMR (400 MHz, DMSO-d6) δ 11.07 (s, 1H), 8.21 (d, J = 2.8 Hz, 1H), 8.14 (s, 1H FA), 7.97-7.88 (m, 1H), 7.67 (d, J = 8.5 Hz, 1H), 7.32 (d, J = 2.3 Hz, 1H), 7.26-7.21 (m, 1H), 6.85 (s, 2H), 6.50 (d, J = 9.4 Hz, 1H), 5.10-5.00 (m, 1H), 3.87 (s, 6H), 3.67 (s, 2H), 3.53 (s, 3H), 3.44 (s, 5H). 2.97-2.78 (m, 1H), 2.67-2.60 (m, 5H), 2.58-2.52 (m, 1H), 2.09-1.92 (m, 1H). |
| D345 | 737.3 | ¹H NMR (300 MHz, Methanol-d4) δ 8.31 (s, 1H FA), 7.65 (d, J = 8.3 Hz, 1H), 7.48 (s, 1H), 6.84 (d, J = 2.1 Hz, 1H), 6.72-6.63 (m, 3H), 5.07 (dd, J = 12.4, 5.4 Hz, 1H), 4.48 (s, 2H), 4.25 (s, 2H), 4.06-3.90 (m, 8H), 3.82 (s, 4H), 3.58 (d, J = 20.8 Hz, 4H), 2.97-2.66 (m, 5H), 2.63 (s, 3H), 2.27-2.03 (m, 8H), 1.95 (s, 4H). |
| D346 | 737.7 | ¹H NMR (300 MHz, DMSO-d6) δ 11.07 (s, 1H), 8.16(s, 1H, FA), 7.64 (d, J = 8.3 Hz, 1H), 7.28 (d, J = 1.2 Hz, 1H), 6.77 (d, J = 2.1 Hz, 1H), 6.69-6.53 (m, 3H), 5.05 (dd, J = 12.7, 5.4 Hz, 1H), 3.92-3.85 (m, 2H), 3.82 (s, 6H), 3.74 (s, 4H), 3.71-3.61 (m, 2H), 3.54 (s, 4H), 2.98-2.78 (m, 2H), 2.71-2.54 (m, 2H), 2.54-2.50 (m, 2H), 2.48-2.42 (m, 3H), 2.37-2.20 (m, 4H), 2.11-1.93 (m, 4H), 1.82-1.65 (m, 4H), 1.20 (d, J = 26.6 Hz, 1H). |
| D347 | 709.2 | ¹H NMR (400 MHz, DMSO-d6) δ 11.08 (s, 1H), 8.23 (s, 1H), 8.17 (s, 1H, FA), 7.94 (d, J = 9.6 Hz, 1H), 7.64 (d, J = 8.3 Hz, 1H), 6.86 (d, J = 4.5 Hz, 2H), 6.77 (d, J = 2.1 Hz, 1H), 6.64 (dd, J = 8.4, 2.2 Hz, 1H), 6.50 (d, J = 9.4 Hz, 1H), 5.05 (dd, J = 12.9, 5.3 Hz, 1H), 3.88 (t, J = 2.1 Hz, 7H), 3.79 (s, 2H), 3.73 (s, 5H), 3.54 (s, 6H), 3.19 (d, J = 29.3 Hz, 1H), 2.99-2.81 (m, 1H), 2.58 (d, J = 16.2 Hz, 2H), 2.44 (s, 2H), 2.28 (s, 3H), 2.01 (d, J = 12.4 Hz, 1H), 1.73 (s, 4H). |
| D348 | 749.25 | ¹H NMR (300 MHz, DMSO-d6) δ 8.04 (d, J = 2.6 Hz, 1H), 7.88 (t, J = 1.8 Hz, 1H), 7.67 (d, J = 8.2 Hz, 1H), 6.90 (d, J = 2.1 Hz, 2H), 6.77 (d, J = 2.2 Hz, 1H), 6.66 (m, J = 8.3, 2.0 Hz, 1H), 6.09-5.91 (m, 1H), , 5.19 (m, J = 10.3, 1.5 Hz, 1H), 5.14-4.98 (m, 2H), 4.62 (d, J = 5.4 Hz, 2H), 4.34 (d, J = 16.5 Hz, 2H), 4.18 (d, J = 5.4 Hz, 2H), 3.99 (d, J = 10.2 Hz, 2H), 3.92 (s, 6H), 3.87 (s, 2H), 3.81 (s, 2H), 3.41 (d, J = 6.6 Hz, 4H), 3.17 (d, J = 8.1 Hz, 1H), 2.94 (s, 3H), 2.89-2.78 (m, 1H), 2.65-2.54 (m, 1H), 2.40-2.23 (m, 1H), 2.11 (s, 4H), 2.06-1.83 (m, 3H). |
| D349 | 723.2 | ¹H NMR (400 MHz, DMSO-d6) δ 11.08 (s, 1H), 9.78 (s, 2H, TFA), 7.69 (d, J = 8.2 Hz, 1H), 7.65 (s, 1H), 6.75 (dd, J = 21.5, 3.2 Hz, |

| Compound No. | LCMS | ¹H NMR |
|---|---|---|
| | | 3H), 6.66 (dd, J = 8.3, 2.4 Hz, 1H), 6.38 (s, 1H), 5.06 (dd, J = 12.9, 5.4 Hz, 1H), 4.39 (s, 1H), 4.34 (d, J = 5.5 Hz, 1H), 4.22 (s, 2H), 4.01 (d, J = 8.8 Hz, 2H), 3.89 (s, 8H), 3.82 (s, 2H), 3.46 (s, 5H), 3.25-3.08 (m, 2H), 3.03-2.82 (m, 3H), 2.64-2.59 (m, 2H), 2.21-2.09 (m, 5H), 2.09-1.77 (m, 4H). |
| D350 | 795.4 | ¹H NMR (300 MHz, MeOD) δ 8.04 (d, 1H), 7.82 (d, 1H), 7.67 (d, 1H), 6.95-6.84 (m, 3H), 6.71 (dd, 1H), 5.08 (dd, 1H), 4.58-4.45 (m, 2H), 4.34 (t, 2H), 4.24 (s, 2H), 4.17-4.09 (m, 2H), 4.01 (s, 6H), 3.94-3.86 (m, 4H), 3.69 (s, 3H), 3.55-3.49 (m, 5H), 3.20-3.03 (m, 2H), 2.91-2.77 (m, 2H), 2.72 (s, 4H), 2.35-2.00 (m, 5H). |
| D351 | 748.7 | ¹H NMR (400 MHz, DMSO-d6) δ 11.08 (s, 1H), 9.94 (br s, 2H, TFA salt), 8.07 (s, 1H), 7.69 (d, J = 8.2 Hz, 1H), 6.77 (d, J = 3.7 Hz, 3H), 6.66 (dd, J = 8.4, 2.3 Hz, 1H), 5.06 (dd, J = 12.8, 5.4 Hz, 1H), 4.40 (s, 1H), 4.35 (d, J = 5.6 Hz, 1H), 4.27-4.16 (m, 2H), 4.03 (q, J = 8.7, 7.5 Hz, 2H), 3.88 (s, 8H), 3.82 (s, 2H), 3.55 (s, 3H), 3.39 (s, 5H), 3.18 (s, 1H), 3.04-2.82 (m, 3H), 2.64-2.54 (m, 2H), 2.36 (s, 3H), 2.15 (d, J = 14.0 Hz, 2H), 2.02 (dd, J = 9.7, 4.6 Hz, 1H), 1.97-1.84 (m, 2H). |
| D352 | 734.45 | ¹H NMR (400 MHz, DMSO-d6) δ 11.07 (s, 1H), 8.77 (s, 1H), 8.69 (s, 1H), 8.14 (s, 0.4H, FA), 7.67 (d, J = 8.3 Hz, 1H), 7.02 (s, 2H), 6.77 (s, 1H), 6.65 (d, J = 8.4 Hz, 1H), 5.05 (dd, J = 12.6, 5.4 Hz, 1H), 4.30 (s, 2H), 4.14 (s, 3H), 3.95 (s, 7H), 3.91-3.78 (m, 6H), 3.63 (s, 4H), 2.96-2.80 (m, 2H), 2.97-2.79 (m, 5H), 2.05-1.79 (m, 5H). |
| D353 | 723.5 | ¹H NMR (400 MHz, DMSO-d6) δ 11.08 (s, 1H), 8.16 (s, 1H FA), 7.72 (d, J = 2.5 Hz, 1H), 7.64 (d, J = 8.3 Hz, 1H), 7.52 (dd, J = 2.7, 1.2 Hz, 1H), 6.99 (s, 1H), 6.88 (s, 2H), 6.78 (d, J = 2.1 Hz, 2H), 6.65 (dd, J = 8.5, 2.1 Hz, 1H), 5.05 (dd, J = 12.9, 5.4 Hz, 1H), 3.78 (s, 3H), 3.74 (d, J = 2.8 Hz, 7H), 3.60 (s, 2H), 3.49 (s, 6H), 2.90 (s, 3H), 2.73-2.58 (m, 5H), 2.39-2.19 (m, 3H), 2.05 (s, 3H), 2.02 (d, J = 7.1 Hz, 1H), 1.74 (s, 4H). |
| D354 | 737.45 | ¹H NMR (400 MHz, Methanol-d4) δ 8.30 (s, 2H FA), 7.64 (d, J = 8.3 Hz, 1H), 7.35 (s, 1H), 7.15 (s, 1H), 6.95 (s, 1H), 6.83 (d, J = 2.0 Hz, 1H), 6.67 (dd, J = 8.3, 2.0 Hz, 1H), 5.07 (dd, J = 12.4, 5.5 Hz, 1H), 4.43 (s, 2H), 4.26 (s, 2H), 4.03 (s, 2H), 3.91 (s, 3H), 3.83 (s, 4H), 3.79 (s, 3H), 3.60 (s, 3H), 3.29 (s, 1H), 3.03 (s, 2H), 2.95-2.64 (m, 7H), 2.16 (s, 3H), 2.15-2.07 (m, 1H), 2.07-1.87 (m, 7H). |
| D355 | 809.5 | ¹H NMR (300 MHz, MeOD) δ 8.07 (d, 1H), 7.74-7.63 (m, 2H), 6.88 (d, 3H), 6.71 (dd, 1H), 5.08 (dd, 1H), 4.58-4.45 (m, 2H), 4.41-4.28 (m, 4H), 4.19-4.07 (m, 2H), 4.01 (s, 6H), 3.98-3.82 (m, 4H), 3.70 (s, 3H), 3.58-3.41 (m, 5H), 3.18-3.02 (m, 2H), 2.98 (s, 3H), 2.93-2.79 (m, 2H), 2.76 (s, 3H), 2.77-2.66 (m, 1H), 2.40-2.01 (m, 5H). |
| D356 | 745.5 | ¹H NMR (300 MHz, DMSO-d6) δ 10.98 (s, 1H), 9.93 (br s, 2H, TFA salt), 8.36 (d, J = 8.0 Hz, 1H), 7.78-7.53 (m, 4H), 7.41 (d, J = 8.5 Hz, 1H), 6.85 (s, 2H), 6.70 (s, 2H), 5.07 (dd, J = 13.2, 4.9 Hz, 1H), 4.50-3.96 (m, 8H), 3.90 (s, 6H), 3.78-3.55 (m, 8H), 3.53-3.49 (m, 1H), 3.28-3.12 (m, 2H), 3.09-2.82 (m, 3H), 2.75-2.56 (m, 1H), 2.43-2.24 (m, 2H), 2.19-1.83 (m, 5H) |
| D357 | 641.748028 | |
| D358 | 641.748028 | |
| D359 | 737.4 | ¹H NMR (300 MHz, DMSO-d6) δ 11.10 (s, 1H), 10.32-9.43 (m, 2H), 7.69 (d, J = 8.3 Hz, 1H), 7.22-7.05 (m, 2H), 6.92 (s, 1H), 6.83-6.74 (m, 1H), 6.66 (dd, J = 8.2, 2.1 Hz, 1H), 5.17-4.99 (m, 1H), 4.57-4.33 (m, 2H), 4.34-4.15 (m, 2H), 4.15-3.94 (m, 2H), 3.90 (s, 2H), 3.82 (s, 6H), 3.73 (m, 3H), 3.52 (s, 4H), 3.25-3.10 (m, 2H), 3.08-2.79 (m, 4H), 2.62 (m, 2H), 2.59-2.54 (m, 1H), 2.54-2.41 (m, 1H), 2.23-2.06 (m, 3H), 2.02 (s, 4H), 2.00-1.83 (m, 2H). |
| D360 | 745.6 | ¹H NMR (300 MHz, DMSO-d6) δ 10.95 (s, 1H), 9.83 (br s, 2H, TFA salt), 8.36 (d, J = 7.9 Hz, 1H), 7.73 (t, J = 7.8 Hz, 1H), 7.66-7.48 (m, 4H), 6.85 (s, 2H), 6.55-6.44 (m, 2H), 5.04 (dd, J = 13.2, 4.8 Hz, 1H), 4.40 (t, J = 13.8 Hz, 2H), 4.32-4.13 (m, 4H), 4.05 (s, 2H), 3.90 (s, 6H), 3.81-3.65 (m, 5H), 3.60 (s, 4H), 3.55-3.50 (m, 2H), 3.20 (s, 1H), 3.10-2.80 (m, 3H), 2.62 (m, 2H), 2.41-2.24 (m, 1H), 2.19-2.05 (m, 2H), 2.02-1.82 (m, 3H). |
| D361 | 735.4 | ¹H NMR (400 MHz, DMSO-d6) δ 8.33 (s, 1H), 8.14 (s, FA, 1H), 7.91 (s, 1H), 7.40 (d, J = 8.9 Hz, 1H), 7.13 (s, 1H), 7.03 (s, 2H), 6.73-6.67 (m, 2H), 5.06 (dd, J = 13.2, 5.1 Hz, 1H), 4.34 (s, J = 16.7 Hz, 3H), 4.30 (d, J = 16.7 Hz, 1H), 4.19 (d, J = 16.7 Hz, 1H), 4.14 (m, 2H), 3.92 (s, 6H), 3.90-3.80 (m, 2H), 3.63 (s, 4H), 3.06 (s, 2H), 2.96-2.82 (m, 3H), 2.74-2.56 (m, 3H), 2.45-2.32 (m, 2H), 2.01-1.92 (m, 2H), 1.87 (s, 5H). |
| D362 | 725.3 | ¹H NMR (400 MHz, DMSO-d6) δ 10.95 (s, 1H), 8.17 (s, 1H, FA), 7.55-7.46 (m, 2H), 7.04 (s, 2H), 6.54 (s, 2H), 5.04 (dd, J = 13.3, 5.1 Hz, 1H), 4.36-4.12 (m, 2H), 3.85 (d, J = 12.7 Hz, 2H), 3.77 (s, |

| Compound No. | LCMS | ¹H NMR |
|---|---|---|
| | | 6H), 3.53 (s, 2H), 3.46 (s, 3H), 2.97-2.74 (m, 3H), 2.61 (s, 1H), 2.47-2.28 (m, 11H), 2.06 (d, J = 2.7 Hz, 6H), 1.97 (s, 1H), 1.73 (d, J = 12.6 Hz, 2H), 1.50 (s, 1H), 1.36 (d, J = 7.5 Hz, 2H), 1.26-1.13 (m, 2H). |
| D363 | 735.6 | ¹H NMR (400 MHz, DMSO-d6) δ 10.94 (s, 1H), 8.33 (s, 1H), 8.22 (s, FA, 1H), 7.89 (s, 1H), 7.48 (d, J = 8.3 Hz, 1H), 7.11 (s, 1H), 6.92 (s, 2H), 6.53-6.43 (t, 2H), 5.03 (dd, J = 13.3, 5.1 Hz, 1H), 4.30 (d, J = 16.9 Hz, 1H), 4.17 (d, J = 16.9 Hz, 1H), 3.85 (s, 6H), 3.67 (s, 2H), 3.61 (s, J = 6.9 Hz, 6H), 3.47 (s, J = 6.9 Hz, 4H), 2.98 (m, J = 6.9 Hz, 4H), 2.60 (s, 1H), 2.46-2.34 (m, 3H), 2.28 (s, 3H), 1.99-1.89 (m, 1H), 1.72 (t, J = 5.2 Hz, 4H). |
| D364 | 781.2 | ¹H NMR (300 MHz, MeOD) δ 8.05 (d, J = 2.5 Hz, 1H), 7.83 (s, 1H), 7.41 (d, J = 8.2 Hz, 1H), 6.95-6.84 (m, 3H), 6.79 (d, J = 8.2 Hz, 1H), 5.14 (dd, J = 13.2, 5.1 Hz, 1H), 4.51-1.45 (m, 2H), 4.44-4.30 (m, 4H), 4.25 (s, 2H), 4.14 (s, 2H), 4.01 (s, 6H), 3.79-3.73 (m, 4H), 3.69 (s, 3H), 3.55-3.48 (m, 4H), 3.18-3.04 (m, 2H), 3.00-2.78 (m, 2H), 2.72 (s, 3H), 2.60-2.41 (m, 1H), 2.28-2.12 (m, 5H), 1.38-1.28 (m, 2H). |
| D365 | 735.45 | ¹H NMR (400 MHz, MeOD) δ 8.48 (s, FA, 1H), 7.93 (d, J = 1.6 Hz, 1H), 7.77 (s, 1H), 7.49 (d, J = 1.6 Hz, 1H), 7.39 (d, J = 8.2 Hz, 1H), 7.25 (s, 2H), 6.85 (d, J = 2.2 Hz, 1H), 6.77 (dd, J = 8.3, 2.2 Hz, 1H), 5.14 (dd, J = 13.3, 5.2 Hz, 1H), 4.48 (s, 2H), 4.45-4.33 (m, 2H), 4.23 (s, 735.452H), 4.02 (s, 6H), 3.97 (s, 2H), 3.72 (s, 3H), 3.67 (s, 4H), 3.43-3.35 (m, 1H), 3.22-3.01 (m, 1H), 2.96-2.85 (m, 1H), 2.84-2.75 (m, 1H), 2.74 (s, 2H), 2.64-2.42 (m, 5H), 2.23-2.13 (m, 1H), 1.91 (s, 4H). |
| D366 | 790.2 | ¹H NMR (400 MHz, DMSO-d6) δ 10.98 (s, 1H), 9.56 (d, J = 5.4 Hz, 1H), 9.29 (s, 2H, TFA), 8.39 (d, J = 5.4 Hz, 1H), 8.08 (s, 1H), 7.64 (dd, J = 8.4, 3.2 Hz, 1H), 7.17-7.04 (m, 3H), 7.02-6.95 (m, 1H), 5.08 (dd, J = 13.3, 5.1 Hz, 1H), 4.88 (p, J = 6.7 Hz, 1H), 4.43-4.14 (m, 4H), 3.90 (s, 6H), 3.65 (s, 3H), 3.47-3.15 (m, 4H), 3.09-2.78 (m, 7H), 2.60 (d, J = 16.2 Hz, 2H), 2.46-2.34 (m, 2H), 2.17-2.08 (m, 1H), 1.98-1.87 (m, 6H), 1.86-1.82 (m, 3H), 1.49 (q, J = 12.7 Hz, 2H). |
| D367 | 790.5 | ¹H NMR (400 MHz, DMSO-d6) δ 10.98 (s, 1H), 9.56 (d, J = 5.4 Hz, 1H), 9.29 (s, 2H, TFA), 8.39 (d, J = 5.4 Hz, 1H), 8.08 (s, 1H), 7.64 (dd, J = 8.4, 3.2 Hz, 1H), 7.17-7.04 (m, 3H), 7.02-6.95 (m, 1H), 5.08 (dd, J = 13.3, 5.1 Hz, 1H), 4.88 (p, J = 6.7 Hz, 1H), 4.43-4.14 (m, 4H), 3.90 (s, 6H), 3.65 (s, 3H), 3.47-3.15 (m, 4H), 3.09-2.78 (m, 7H), 2.60 (d, J = 16.2 Hz, 2H), 2.46-2.34 (m, 2H), 2.17-2.08 (m, 1H), 1.98-1.87 (m, 6H), 1.86-1.82 (m, 3H), 1.49 (q, J = 12.7 Hz, 2H). |
| D368 | 790.65 | ¹H NMR (400 MHz, DMSO-d6) δ 11.00 (s, 1H), 9.75 (s, 1H), 9.55 (s, 1H), 9.32 (br s, 1H, TFA salt), 8.20 (s, 1H), 7.52 (dd, J = 8.4, 2.7 Hz, 1H), 7.19-7.09 (m, 2H), 6.97 (s, 2H), 5.11 (dd, J = 13.3, 5.1 Hz, 1H), 4.93-4.85 (m, 1H), 4.38 (d, J = 16.9 Hz, 2H), 4.26 (d, J = 16.9 Hz, 2H), 3.92 (s, 6H), 3.68 (s, 3H), 3.54-3.38 (m, 4H), 3.25-3.21 (m, 1H), 3.06-2.82 (m, 6H), 2.67-2.56 (m, 2H), 2.44-2.38 (m, 2H), 2.18-1.73 (m, 10H), 1.54-1.46 (m, 2H). |
| D369 | 749.25 | ¹H NMR (400 MHz, DMSO-d6) δ 10.95 (s, 1H), 10.05-9.61 (m, 2H, TFA salt), 8.15 (s, 1H), 7.56-7.46 (m, 2H), 6.90 (d, J = 4.6 Hz, 2H), 6.54-6.45 (m, 2H), 5.05 (dd, J = 13.2, 5.1 Hz, 1H), 4.40-4.28 (m, 2H), 4.27-4.15 (m, 4H), 4.12-3.98 (m, 2H), 3.90 (s, 6H), 3.78 (s, 2H), 3.70 (s, 2H), 3.60 (d, J = 2.0 Hz, 3H), 3.52 (s, 3H), 3.41 (s, 3H), 3.17 (s, 1H), 2.99-2.90 (m, 3H), 2.68-2.52 (m, 2H), 2.47-2.28 (m, 1H), 2.13 (d, J = 13.9 Hz, 2H), 2.00-1.88 (m, 3H). |
| D370 | 749.4 | ¹H NMR (400 MHz, DMSO-d6) δ 10.95 (s, 1H), 9.99-9.58 (m, 1H, TFA salt), 8.63 (s, 1H), 7.92 (s, 1H), 7.52 (d, J = 8.2 Hz, 1H), 7.41 (s, 2H), 6.54-6.45 (m, 2H), 5.05 (dd, J = 13.2, 5.1 Hz, 1H), 4.42-4.27 (m, 2H), 4.25-4.14 (m, 4H), 4.08 (s, 3H), 4.05-3.95 (m, 2H), 3.94 (s, 6H), 3.77 (s, 2H), 3.69 (s, 2H), 3.54 (s, 3H), 3.38 (s, 3H), 3.17 (d, J = 6.7 Hz, 1H), 2.96 (s, 3H), 2.65-2.51 (m, 2H), 2.43-2.36 (m, 1H), 2.12 (d, J = 14.3 Hz, 2H), 2.00-1.88 (m, 3H). |
| D371 | 805.45 | 1H NMR (400 MHz, Methanol-d4) δ 7.86 (d, J = 9.7 Hz, 1H), 7.72 (d, J = 8.4 Hz, 1H), 7.46 (s, 1H), 7.06-6.97 (m, 2H), 6.90-6.79 (m, 3H), 5.14 (dd, J = 13.3, 5.1 Hz, 1H), 4.55-4.39 (m, 4H), 4.01-3.86 (m, 6H), 3.74 (s, 3H), 3.69-3.52 (m, 3H), 3.41-3.36 (m, 1H), 3.28-3.16 (m, 2H), 3.13-2.98 (m, 4H), 2.96-2.86 (m, 2H), 2.85-2.75 (m, 1H), 2.74-2.65 (m, 1H), 2.60-2.43 (m, 2H), 2.27 (s, 1H), 2.22-2.15 (m, 1H), 2.14-1.92 (m, 8H), 1.73-1.59 (m, 2H). |

Example 83—Preparation of Compounds DD1-DD10

In analogy to the procedures described in the examples above, compounds DD1-DD10 were prepared using the appropriate starting materials.

| Compound No. | LCMS | ¹H NMR |
|---|---|---|
| DD1 | 942.5 | ¹H NMR (300 MHz, DMSO-d6) δ 9.45 (s, 1H), 8.98 (s, 1H), 8.72 (d, J = 5.7 Hz, 1H), 8.60 (t, J = 6.0 Hz, 1H), 8.19 (s, 1.0H, FA), 7.87 (s, 1H), 7.56 (d, J = 5.6 Hz, 1H), 7.47-7.35 (m, 5H), 6.72 (s, 2H), 4.57 (d, J = 9.5 Hz, 1H), 4.47-4.33 (m, 3H), 4.30-4.21 (m, 1H), 3.97 (s, 2H), 3.80 (s, 6H), 3.68-3.50 (m, 18H), 2.58 (t, J = 6.1 Hz, 2H), 2.44 (s, 3H), 2.18 (s, 3H), 2.11-2.00 (m, 1H), 1.97-1.85 (m, 1H), 0.95 (s, 9H). |
| DD2 | 754.2 | ¹H NMR (400 MHz, DMSO-d6) δ 11.12 (s, 1H), 9.43 (s, 1H), 8.71 (d, J = 5.8 Hz, 1H), 8.22 (s, 1, 5H, FA), 8.11 (s, 1H), 7.88-7.81 (m, 2H), 7.54 (d, J = 5.6 Hz, 1H), 7.40 (s, 1H), 7.35 (d, J = 8.6 Hz, 1H), 6.72 (s, 2H), 5.16-5.07 (m, 1H), 4.68 (s, 2H), 3.80 (s, 6H), 3.62-3.58 (m, 5H), 3.31-3.10 (m, 7H), 2.93-2.83 (m, 1H), 2.46 (s, 2H), 2.21 (s, 3H), 2.17 (s, 3H), 2.16-1.94 (m, 2H). |
| DD3 | 740.45 | ¹H NMR (300 MHz, Methanol-d4) δ 9.53 (s, 1H), 8.70 (d, J = 5.8 Hz, 1H), 8.55 (s, 1H, FA), 7.74 (s, 1H), 7.62 (d, J = 5.7 Hz, 1H), 7.38 (t, J = 8.1 Hz, 1H), 6.77 (s, 2H), 6.63 (d, J = 7.8 Hz, 1H), 6.44 (d, J = 8.4 Hz, 1H), 5.21 (dd, J = 10.9, 5.7 Hz, 1H), 4.52-4.25 (m, 2H), 4.12-4.00 (m, 1H), 3.90 (s, 8H), 3.85-3.75 (m, 6H), 3.71 (s, 3H), 3.53-3.42 (m, 2H), 2.93-2.70 (m, 7H), 2.64 (s, 3H), 2.26-2.17 (m, 1H). |
| DD4 | 709.4 | ¹H NMR (300 MHz, DMSO-d6) δ 11.02 (s, 1H), 9.48 (s, 1H), 8.75 (d, J = 5.7 Hz, 2H), 7.92 (s, 1H), 7.58 (d, J = 5.6 Hz, 1H), 7.29 (t, J = 7.7 Hz, 1H), 6.93 (d, J = 7.4 Hz, 1H), 6.87 (s, 2H), 6.74 (d, J = 8.0 Hz, 1H), 5.13 (dd, J = 13.2, 5.1 Hz, 1H), 4.37-4.26 (m, 2H), 4.22-4.13 (m, 2H), 3.89 (s, 7H), 3.62 (s, 3H), 3.21-3.03 (m, 4H), 2.98-2.84 (m, 1H), 2.77-2.63 (m, 3H), 2.30-2.23 (m, 1H), 2.10-1.98 (m, 1H), 1.84-1.66 (m, 2H), 1.66-1.53 (m, 2H), 1.44-1.29 (m, 8H). |
| DD5 | 736.45 | ¹H NMR (400 MHz, Methanol-d4) δ 9.51 (s, 1H), 8.69 (d, J = 5.7 Hz, 1H), 8.56 (s, 1H, FA), 7.76 (s, 1H), 7.61 (dd, J = 5.8, 0.9 Hz, 1H), 7.47 (t, J = 8.1 Hz, 1H), 6.87 (s, 2H), 6.67 (d, J = 7.8 Hz, 1H), 6.46 (d, J = 8.4 Hz, 1H), 5.19 (dd, J = 11.0, 5.7 Hz, 1H), 4.29 (s, 2H), 3.96 (s, 6H), 3.68 (s, 3H), 3.37-3.36 (m, 1H), 3.14-3.02 (m, 3H), 2.91-2.70 (m, 6H), 2.63 (s, 3H), 2.24-2.17 (m, 1H), 1.87-1.76 (m, 2H), 1.74-1.64 (m, 2H), 1.54-1.36 (m, 8H). |
| DD6 | 722.54 | ¹H NMR (400 MHz, DMSO-d6) δ 11.11 (s, 1H), 9.45 (s, 1H), 8.72 (d, J = 5.7 Hz, 1H), 7.91 (d, J = 44.8 Hz, 2H), 7.55 (d, J = 5.7 Hz, 1H), 6.84 (s, 2H), 5.22-5.02 (m, 0H), 4.98 (s, 1H), 4.71 (s, 1H), 4.35 (s, 2H), 3.94-3.78 (m, 6H), 3.59 (s, 3H), 3.13-2.80 (m, 2H), 2.73 (s, 2H), 2.67-2.53 (m, 1H), 2.05 (s, 2H). |
| DD7 | 800.3 | 1H NMR (400 MHz, DMSO-d6) δ 11.11 (s, 1H), 9.40 (s, 1H), 8.68 (d, J = 5.6 Hz, 1H), 8.14-8.04 (m, 3H), 7.92 (d, J = 8.3 Hz, 1H), 7.83 (s, 1H), 7.72 (d, J = 8.8 Hz, 2H), 7.53 (d, J = 5.6 Hz, 1H), 7.00 (d, J = 8.7 Hz, 2H), 6.74 (s, 2H), 5.15 (dd, J = 12.9, 5.4 Hz, 1H), 4.06 (q, J = 5.2 Hz, 1H), 4.02 (t, J = 6.4 Hz, 2H), 3.82 (s, 6H), 3.64 (s, 2H), 3.56 (s, 3H), 3.29-3.12 (m, 5H), 3.00 (s, 3H), 2.95-2.82 (m, 1H), 2.64-2.50 (m, 2H), 2.22 (s, 3H), 2.06 (d, J = 11.5 Hz, 1H), 1.71 (d, J = 15.0 Hz, 0H), 1.71 (s, 2H), 1.59 (q, J = 7.3 Hz, 2H). |
| DD8 | 814.3 | 1H NMR (400 MHz, DMSO-d6) δ 11.11 (s, 1H), 9.40 (s, 1H), 8.68 (d, J = 5.6 Hz, 1H), 8.23 (s, 1H), 8.10-8.01 (m, 2H), 7.90 (d, J = 8.3 Hz, 1H), 7.83 (s, 1H), 7.76-7.64 (m, 3H), 7.52 (d, J = 6.2 Hz, 1H), 7.00 (d, J = 8.8 Hz, 2H), 6.72 (s, 2H), 5.15 (dd, J = 12.9, 5.4 Hz, 1H), 4.00 (t, J = 6.3 Hz, 2H), 3.81 (s, 6H), 3.58 (d, J = 14.7 Hz, 5H), 3.18 (d, J = 6.3 Hz, 1H), 3.15 (s, 5H), 2.94 (s, 2H), 2.92-2.82 (m, 1H), 2.62 (s, 1H), 2.59-2.50 (m, 1H), 2.16 (s, 3H), 2.07 (d, J = 11.7 Hz, 1H), 1.73 (t, J = 7.0 Hz, 2H), 1.49 (d, J = 5.5 Hz, 2H), 1.42 (d, J = 7.9 Hz, 3H). |
| DD9 | 571.61 | ¹H NMR (400 MHz, DMSO-d6) δ 8.32 (s, 1H), 8.09-8.02 (m, 1H), 7.82-7.77 (m, 1H), 7.73 (s, 1H), 7.63 (s, 0H), 6.87 (d, J = 8.0 Hz, 1H), 6.82 (s, 2H), 5.09 (dt, J = 11.9, 5.8 Hz, 1H), 3.92 (d, J = 3.9 Hz, 5H), 3.86 (d, J = 3.7 Hz, 6H), 3.51 (d, J = 2.0 Hz, 4H), 3.15 (s, 1H), 2.08 (d, J = 2.6 Hz, 4H). |
| DD10 | 803.2 | 1H NMR (300 MHz, DMSO) δ 11.13 (s, 1H), 8.20 (s, FA, 1H), 8.09 (d, J = 8.3 Hz, 1H), 7.90 (d, J = 8.4 Hz, 1H), 7.83 (d, J = 8.1 Hz, 1H), 7.69-7.59 (m, 1H), 7.58-7.49 (m, 1H), 7.43 (d, J = 7.5 Hz, 1H), 7.34-7.23 (m, 2H), 6.73 (s, 2H), 5.12 (dd, J = 12.9, 5.4 Hz, 1H), 5.05-4.94 (m, 1H), 3.81 (s, 6H), 3.73-3.67 (m, 1H), 3.03-2.89 (m, 2H), 2.88-2.81 (m, 1H), 2.66-2.53 (m, 2H), 2.49-2.39 (m, 6H), 2.36-2.21 (m, 6H), 2.14-1.99 (m, 3H), 1.89-1.75 (m, 2H), 1.72-1.45 (m, 7H), 1.26-1.06 (m, 2H). |

Example 84—Preparation of Compounds D372-D476

In analogy to the procedures described in the examples above, compounds D372-D476 were prepared using the appropriate starting materials.

| Compound No. | LCMS | ¹H NMR |
|---|---|---|
| D372 | 638.25 | ¹H NMR (400 MHz, DMSO-d6) δ 11.13 (s, 1H), 9.45 (s, 1H), 8.73 (d, J = 5.7 Hz, 1H), 7.88 (d, J = 14.1 Hz, 2H), 7.57 (d, J = 5.6 Hz, 1H), 7.36-7.28 (m, 2H), 6.79 (s, 2H), 5.18-5.01 (m, 2H), 4.25-3.92 (m, 3H), 3.84 (s, 7H), 3.61 (s, 4H), 2.96-2.81 (m, 1H), 2.70-2.53 (m, 3H), 2.10-2.01 (m, 1H). |
| D373 | 691.30 | ¹H NMR (400 MHz, DMSO-d6) δ 11.08 (s, 1H), 9.45 (d, J = 0.8 Hz, 1H), 8.73 (d, J = 5.7 Hz, 1H), 8.18 (s, FA, 1H), 7.89 (s, 1H), 7.67-7.57 (m, 2H), 6.81-6.72 (m, 3H), 6.66 (dd, J = 8.4, 2.1 Hz, 1H), 5.06 (dd, J = 12.9, 5.4 Hz, 1H), 3.82 (s, 6H), 3.74 (s, 4H), 3.58 (d, J = 20.8 Hz, 6H), 2.95-2.82 (m, 1H), 2.63-2.52 (m, 2H), 2.46-2.41 (m, 3H), 2.04-1.97 (m, 1H), 1.77-1.70 (m, 4H). |
| D374 | 677.30 | ¹H NMR (400 MHz, MeOD) δ 9.59 (s, 1H), 8.71 (d, J = 6.1 Hz, 1H), 7.94 (s, 1H), 7.81 (d, J = 6.0 Hz, 1H), 7.67-7.60 (m, 1H), 6.91 (s, 2H), 6.59 (d, J = 7.8 Hz, 2H), 5.11 (dd, J = 13.3, 5.1 Hz, 1H), 4.47 (s, 2H), 4.40 (d, J = 7.0 Hz, 2H), 4.00 (s, 6H), 3.92 (s, 2H), 3.80 (s, 2H), 3.75 (s, 3H), 3.62-3.55 (m, 3H), 3.31-3.21 (m, 1H), 2.98-2.85 (m, 1H), 2.85-2.74 (m, 1H), 2.55-2.39 (m, 1H), 2.33-2.24 (m, 2H), 2.21-2.06 (m, 3H). |
| D375 | 624.25 | ¹H NMR (300 MHz, Methanol-d4) δ 9.57 (s, 1H), 8.70 (d, J = 6.0 Hz, 1H), 7.90 (s, 1H), 7.77 (dd, J = 14.9, 7.1 Hz, 2H), 7.09 (d, J = 10.5 Hz, 2H), 6.89 (s, 2H), 5.41-5.20 (m, 1H), 5.15 (dd, J = 13.3, 5.2 Hz, 1H), 4.86-4.60 (m, 4H), 4.49 (d, J = 4.5 Hz, 2H), 4.44-4.27 (m, 2H), 3.97 (d, J = 14.5 Hz, 6H), 3.73 (s, 3H), 3.01-2.74 (m, 2H), 2.60-2.41 (m, 1H), 2.25-2.13 (m, 1H). |
| D376 | 652.30 | ¹H NMR (400 MHz, DMSO-d6) δ 11.14 (s, 1H), 9.81 (s, TFA, 1H), 9.48 (d, J = 0.8 Hz, 1H), 8.75 (d, J = 5.7 Hz, 1H), 7.96-7.89 (m, 2H), 7.57 (d, J = 5.7 Hz, 1H), 7.44-7.34 (m, 2H), 6.88 (s, 2H), 5.15 (dd, J = 12.8, 5.4 Hz, 2H), 4.74-4.57 (m, 2H), 4.55-4.42 (m, 2H), 4.09 (s, 1H), 3.92 (s, 6H), 3.63 (s, 3H), 2.97-2.84 (m, 1H), 2.66-2.52 (m, 2H), 2.10-2.03 (m, 1H), 1.53 (d, J = 6.8 Hz, 3H). |
| D377 | 677.35 | ¹H NMR (400 MHz, DMSO-d6) δ 10.98 (s, 1H), 9.16 (s, 1H), 7.73 (s, 1H), 7.41 (d, J = 8.5 Hz, 1H), 7.25 (dd, J = 8.5, 2.4 Hz, 1H), 7.14 (d, J = 2.3 Hz, 1H), 6.74 (d, J = 20.0 Hz, 3H), 5.10 (dd, J = 13.3, 5.1 Hz, 1H), 4.38-4.15 (m, 2H), 3.93 (s, 3H), 3.79 (s, 6H), 3.73 (d, J = 12.3 Hz, 3H), 3.57-3.52 (m, 5H), 2.97-2.84 (m, 1H), 2.75-2.64 (m, 2H), 2.64-2.55 (m, 1H), 2.48-2.38 (m, 4H), 2.38-2.20 (m, 6H), 2.03-1.94 (m, 1H), 1.74 (d, J = 12.4 Hz, 2H), 1.52-1.42 (m, 1H), 1.41-1.32 (m, 2H), 1.31-1.17 (m, 2H). |
| D378 | 624.30 | ¹H NMR (300 MHz, Methanol-d4) δ 9.56 (s, 1H), 8.69 (d, J = 5.9 Hz, 1H), 7.84 (s, 1H), 7.68 (s, 1H), 7.60 (d, J = 8.3 Hz, 1H), 7.33-7.16 (m, 2H), 6.89 (s, 2H), 5.40-5.07 (m, 2H), 4.84-4.61 (m, 4H), 4.59-4.44 (m, 2H), 4.44-4.28 (m, 2H), 4.07-3.85 (m, 6H), 3.73 (s, 3H), 3.01-2.86 (m, 1H), 2.86-2.75 (m, 1H), 2.61-2.43 (m, 1H), 2.25-2.14 (m, 1H). |
| D379 | 810.35 | ¹H NMR (400 MHz, Methanol-d4) δ 9.55 (s, 1H), 8.70 (d, J = 5.8 Hz, 1H), 8.56 (s, 1H, FA), 7.78 (s, 1H), 7.69-7.56 (m, 2H), 6.88 (s, 2H), 6.65-6.53 (m, 2H), 5.11 (dd, J = 13.3, 5.2 Hz, 1H), 4.53-4.24 (m, 4H), 4.06 (d, 2H), 3.98 (s, 6H), 3.76 (d, J = 8.0 Hz, 2H), 3.72 (s, 3H), 3.56-3.48 (m, 2H), 3.16-3.01 (m, 2H), 2.99-2.85 (m, 1H), 2.84-2.64 (m, 3H), 2.60-2.40 (m, 3H), 2.36 (s, 2H), 2.21-2.11 (m, 3H), 2.05 (d, J = 13.9 Hz, 2H), 1.92 (s, 1H), 1.59-1.38 (m, 2H). |
| D380 | 661.35 | 1H), 9.49 (s, 1H), 8.75 (d, J = 5.9 Hz, 1H), 7.99 (s, 1H), 7.56 (d, J = 5.9 Hz, 1H), 7.39 (d, J = 8.5 Hz, 1H), 7.12 (t, J = 2.0 Hz, 1H), 7.04 (d, J = 2.0 Hz, 2H), 6.74-6.67 (m, 2H), 5.08 (dd, J = 13.3, 5.1 Hz, 1H), 4.32 (d, J = 16.6 Hz, 1H), 4.19 (d, J = 16.6 Hz, 1H), 3.86 (s, 3H), 3.67 (s, 6H), 3.61 (s, 3H), 3.39 (s, 2H), 2.98-2.84 (m, 1H), 2.63-2.59 (m, 1H), 2.42-2.33 (m, 1H), 2.02-1.95 (m, 1H), 1.90-1.72 (m, 4H). |
| D381 | 767.40 | ¹H NMR (400 MHz, DMSO-d6) δ 10.86-10.81 (m, HCl, 1H), 9.52 (s, 1H), 8.80-8.73 (m, 1H), 8.52 (s, 3H), 8.07 (s, 1H), 7.93 (d, J = 8.2 Hz, 1H), 7.72 (s, 1H), 7.44-7.34 (m, 2H), 6.88 (d, J = 6.1 Hz, 2H), 5.93-5.84 (m, 1H), 5.75-5.67 (m, 1H), 5.53-5.21 (m, 2H), 4.81-4.73 (m, 1H), 4.67-4.53 (m, 1H), 4.52-4.44 (m, 2H), 4.33-4.29 (m, 1H), 4.17-4.12 (m, 1H), 3.92 (s, 3H), 3.87 (s, 4H), 3.64 (s, 3H), 3.13-3.05 (m, 1H), 2.93-2.84 (m, 1H), 2.70-2.56 (m, 1H), 2.18-2.11 (m, 2H), 0.98-0.90 (m, 6H). |

| Compound No. | LCMS | ¹H NMR |
|---|---|---|
| D382 | 663.35 | ¹H NMR (300 MHz, DMSO-d6) δ 11.51 (s, 1H), 9.47 (s, 1H), 8.92 (s, 1H, FA), 8.76 (d, J = 5.7 Hz, 1H), 7.90 (s, 1H), 7.59 (d, J = 5.7 Hz, 1H), 7.40 (d, J = 8.2 Hz, 1H), 6.87 (s, 2H), 6.75-6.52 (m, 2H), 5.19 (dd, J = 9.1, 6.3 Hz, 1H), 4.49 (d, J = 16.8 Hz, 1H), 4.38-4.15 (m, 3H), 3.91 (s, 7H), 3.76 (s, 2H), 3.62 (s, 6H), 3.21-3.04 (m, 2H), 3.04-2.79 (m, 2H), 2.21-1.90 (m, 4H). |
| D383 | 667.30 | ¹H NMR (400 MHz, DMSO-d6 with a drop of D₂O) δ 9.46 (s, 1H), 8.75 (d, J = 5.7 Hz, 1H), 7.88 (s, 1H), 7.67 (d, J = 8.2 Hz, 1H), 7.60 (d, J = 5.6 Hz, 1H), 6.86 (s, 2H), 6.78 (d, J = 2.0 Hz, 1H), 6.67 (dd, J = 8.4, 2.1 Hz, 1H), 5.21 (dd, J = 9.6, 5.6 Hz, 1H), 4.29 (s, 2H), 3.91 (d, J = 8.4 Hz, 8H), 3.81 (s, 2H), 3.61 (s, 3H), 3.38 (d, J = 12.6 Hz, 2H), 3.13 (t, J = 12.0 Hz, 2H), 3.05-2.95 (m, 1H), 2.82 (dd, J = 17.9, 5.5 Hz, 1H), 2.15 (d, J = 14.1 Hz, 2H), 2.01 (t, J = 12.8 Hz, 2H). |
| D384 | 753.40 | ¹H NMR (400 MHz, DMSO-d6) δ 10.71 (s, 1H, HCl salt), 9.49 (s, 1H), 8.79-8.72 (m, 1H), 8.51 (br s, 3H), 7.99 (s, 1H), 7.71 (d, J = 8.4 Hz, 1H), 7.67-7.59 (m, 1H), 7.39-7.01 (m, 3H), 6.87 (d, J = 5.1 Hz, 2H), 5.86-5.78 (m, 1H), 5.76-5.68 (m, 1H), 5.35-5.02 (m, 2H), 4.80-4.67 (m, 1H), 4.60-4.54 (m, 1H), 4.52-4.41 (m, 3H), 4.34-4.22 (m, 2H), 4.16-4.10 (m, 1H), 3.94-3.82 (m, 7H), 3.63 (s, 3H), 3.20-3.06 (m, 1H), 2.91-2.82 (m, 1H), 2.46-2.36 (m, 1H), 2.21-2.06 (m, 2H), 0.97-0.90 (m, 6H). |
| D385 | 636.35 | ¹H NMR (300 MHz, DMSO-d6) δ 11.12 (s, 1H), 9.45 (s, 1H), 8.73 (d, J = 5.7 Hz, 1H), 8.13 (s, 0.1 H, FA salt), 7.90-7.81 (m, 2H), 7.51 (d, J = 5.7 Hz, 1H), 7.37-7.27 (m, 2H), 6.94 (s, 2H), 5.18-4.99 (m, 2H), 3.84 (s, 6H), 3.60 (s, 4H), 3.28-3.25 (m, 2H), 2.99-2.72 (m, 3H), 2.61-2.53 (m, 2H), 2.11-1.99 (m, 1H), 1.21 (t, J = 7.5 Hz, 3H). |
| D386 | 650.30 | ¹H NMR (300 MHz, DMSO-d6) δ 11.12 (s, 1H), 9.45 (s, 1H), 8.73 (dd, J = 5.7, 2.3 Hz, 1H), 8.13 (s, 0.1 H, FA salt), 7.89-7.80 (m, 2H), 7.49 (dd, J = 6.0, 2.1 Hz, 1H), 7.37-7.28 (m, 2H), 6.92 (s, 2H), 5.12 (dd, J = 12.9, 5.3 Hz, 1H), 4.63 (s, 1H), 3.90-3.68 (m, 6H), 3.60 (s, 4H), 3.44-3.37 (m, 1H), 2.99-2.72 (m, 3H), 2.62-2.52 (m, 2H), 2.11-1.95 (m, 1H), 1.29-1.12 (m, 6H). |
| D387 | 647.25 | ¹H NMR (300 MHz, DMSO-d6) δ 10.97 (s, 1H), 9.45 (s, 1H), 8.73 (d, J = 5.7 Hz, 1H), 7.85 (s, 1H), 7.48-7.36 (m, 2H), 7.01-6.89 (m, 3H), 6.73-6.65 (m, 2H), 5.11-5.04 (m, 1H), 4.31-4.18 (m, 2H), 3.82 (s, 3H), 3.60 (s, 7H), 3.52 (s, 2H), 2.94-2.87 (m, 1H), 2.67-2.61 (m, 1H), 2.46-2.34 (m, 4H), 2.04-1.92 (m, 2H), 1.83-1.73 (m, 4H). |
| D388 | 705.45 | ¹H NMR (300 MHz, DMSO-d6) δ 10.78 (s, 1H), 9.48 (s, 1H), 9.07 (br s, 1H), 8.76 (d, J = 5.7 Hz, 1H), 7.92 (s, 1H), 7.68 (d, J = 8.2 Hz, 1H), 7.61 (d, J = 5.8 Hz, 1H), 6.88 (s, 2H), 6.78 (d, J = 2.1 Hz, 1H), 6.67 (dd, J = 8.3, 2.2 Hz, 1H), 5.14 (dd, 1H), 4.38-4.24 (m, 2H), 3.97-3.88 (m, 8H), 3.83 (s, 2H), 3.63 (s, 3H), 3.46-3.35 (m, 3H), 3.18-3.06 (m, 3H), 2.76-2.66 (m, 1H), 2.22-2.13 (m, 2H), 2.11-1.80 (m, 5H). |
| D389 | 663.30 | ¹H NMR (300 MHz, DMSO-d6) δ 9.45 (s, 1H), 8.74 (d, J = 5.7 Hz, 1H), 7.89 (s, 1H), 7.73 (s, 1H), 7.58 (d, J = 5.6 Hz, 1H), 7.36 (d, J = 8.7 Hz, 1H), 6.80 (s, 2H), 6.70-6.64 (m, 2H), 4.64 (dd, J = 10.8, 6.8 Hz, 1H), 4.38-4.25 (m, 1H), 4.21-4.07 (m, 1H), 3.96-3.80 (m, 8H), 3.66-3.59 (m, 7H), 3.23-3.11 (m, 3H), 2.94-2.74 (m, 3H), 2.09-1.80 (m, 8H). |
| D390 | 663.50 | ¹H NMR (300 MHz, DMSO-d6) δ 9.48 (s, 1H), 8.99 (s, 1 H, TFA), 8.76 (d, J = 5.7 Hz, 1H), 7.91 (s, 1H), 7.60 (d, J = 5.7 Hz, 1H), 7.54 (d, J = 2.5 Hz, 1H), 7.40 (d, J = 8.5 Hz, 1H), 6.88 (s, 2H), 6.73-6.64 (m, 2H), 4.41-4.27 (m, 5H), 3.92 (s, 6H), 3.76 (s, 3H), 3.64 (s, 4H), 3.45-3.34 (m, 2H), 3.34-3.06 (m, 4H), 2.44-2.29 (m, 2H), 2.19-1.85 (m, 6H). |
| D391 | 667.45 | ¹H NMR (300 MHz, DMSO-d6) δ 10.95 (s, 1H), 9.54 (s, 1H), 9.10 (s, 1H), 8.97 (d, J = 8.2 Hz, 1H), 8.82 (d, J = 5.7 Hz, 1H), 8.37 (d, J = 5.9 Hz, 1H), 7.96 (s, 1H), 7.65 (d, J = 5.7 Hz, 1H), 6.94 (s, 2H), 6.60 (d, J = 6.0 Hz, 1H), 4.85-4.71 (m, 1H), 4.42-4.32 (m, 2H), 4.12-3.89 (m, 11H), 3.69 (s, 3H), 3.27-3.15 (m, 3H), 2.98-2.78 (m, 1H), 2.71-2.60 (m, 1H), 2.32-1.99 (m, 6H). |
| D392 | 665.25 | ¹H NMR (300 MHz, Methanol-d4) δ 9.63 (s, 1H), 8.72 (d, J = 6.4 Hz, 1H), 8.08 (s, 1H), 7.95 (d, J = 6.3 Hz, 1H), 7.32 (t, J = 7.8 Hz, 1H), 7.23 (dt, J = 7.9, 1.2 Hz, 1H), 7.02 (t, J = 2.0 Hz, 1H), 6.91 (s, 2H), 6.71 (ddd, J = 8.0, 2.5, 1.1 Hz, 1H), 4.86-4.85 (m, 1H), 4.46 (s, 2H), 4.00 (s, 6H), 3.85 (s, 2H), 3.75 (d, J = 9.0 Hz, 5H), 3.58 (d, J = 12.9 Hz, 2H), 3.25 (t, J = 11.8 Hz, 2H), 2.95-2.65 (m, 2H), 2.34-2.05 (m, 6H). |
| D393 | 571.25 | ¹H NMR (300 MHz, DMSO-d6) δ 11.00 (s, 1H), 9.45 (d, J = 0.8 Hz, 1H), 8.73 (d, J = 5.7 Hz, 1H), 8.19 (.1.0 FA, s, 1H), 7.89 (s, 1H), 7.63-7.50 (m, 2H), 7.36 (s, 1H), 6.74 (s, 2H), 5.27 (dd, J = 11.5, 5.1 Hz, 1H), 3.83 (s, 6H), 3.60 (d, J = 4.2 Hz, 5H), 2.92 (d, J = 11.3 Hz, 2H), 2.84-2.68 (m, 1H), 2.68-2.53 (m, 1H), 2.49-2.35 (m, 2H), 2.24-2.09 (m, 3H), 1.80 (d, J = 12.8 Hz, 2H), 1.58-1.38 (m, 2H). |

-continued

| Compound No. | LCMS | ¹H NMR |
|---|---|---|
| D394 | 613.25 | ¹H NMR (300 MHz, Methanol-d4) δ 9.60 (s, 1H), 8.71 (d, 1H), 7.97 (s, 1H), 7.85 (d, 1H), 6.91 (s, 2H), 6.70 (s, 1H), 6.12 (dd, 1H), 4.48 (s, 2H), 4.00 (s, 6H), 3.75 (s, 4H), 3.71 (s, 1H), 3.58-3.42 (m, 1H), 3.27 (s, 1H), 3.06-2.95 (m, 1H), 2.90-2.76 (m, 2H), 2.60 (d, 3H), 2.40-2.27 (m, 2H), 2.12 (dd, 4H). |
| D395 | 667.45 | ¹H NMR (300 MHz, DMSO-d6) δ 10.87 (s, 1H), 9.45 (s, 1H), 9.00 (d, J = 8.4 Hz, 1H), 8.73 (d, J = 5.6 Hz, 1H), 8.54 (d, J = 1.2 Hz, 1H), 8.17 (s, 1H, FA), 7.88 (s, 1H), 7.63-7.55 (m, 1H), 6.89 (d, J = 1.2 Hz, 1H), 6.74 (s, 2H), 4.76 (ddd, J = 12.9, 8.4, 5.3 Hz, 1H), 3.82 (d, J = 4.1 Hz, 10H), 3.61 (s, 3H), 3.58 (s, 2H), 2.84-2.74 (m, 1H), 2.55 (s, 2H), 2.48-2.40 (m, 3H), 2.25-2.13 (m, 1H), 2.05-1.93 (m, 1H), 1.75 (s, 4H). |
| D396 | 640.31 | ¹H NMR (400 MHz, DMSO-d6) δ 10.97 (s, 1H), 8.19 (s, FA, 1H), 7.41-7.26 (m, 2H), 6.72-6.66 (m, 2H), 6.53 (s, 2H), 5.09 (dd, J = 13.2, 5.0 Hz, 1H), 4.31 (d, J = 16.6 Hz, 1H), 4.18 (d, J = 16.6 Hz, 1H), 3.79 (s, 6H), 3.77 (d, J = 7.1 Hz, 2H), 3.74-3.66 (m, 4H), 3.54 (s, 3H), 2.97-2.84 (m, 1H), 2.77 (s, 2H), 2.64-2.59 (m, 2H), 2.40-2.28 (m, 5H), 2.04 (s, 3H), 2.01-1.95 (m, 3H). |
| D397 | 751.4 | ¹H NMR (400 MHz, DMSO-d6) δ 10.98 (s, 1H), 9.19 (br s, TFA salt, 2H), 7.45-7.38 (m, 1H), 7.28 (s, 1H), 6.74-6.66 (m, 4H), 5.07 (dd, J = 13.3, 5.1 Hz, 1H), 4.37-4.16 (m, 4H), 3.87 (s, 6H), 3.74 (d, J = 8.5 Hz, 2H), 3.67 (d, J = 6.9 Hz, 2H), 3.65 (s, 5H), 3.53-3.50 (m, 2H), 3.21 (s, 1H), 3.07-2.85 (m, 6H), 2.65-2.55 (m, 1H), 2.43-2.31 (m, 4H), 2.20-2.07 (m, 3H), 2.05 (s, 3H), 2.02-1.87 (m, 5H), 1.58-1.39 (m, 2H). |
| D398 | 761.2 | 1H), 8.40 (d, J = 2.6 Hz, 1H), 8.17 (s, 1H, FA), 8.15 (d, J = 2.5 Hz, 1H), 7.65 (d, J = 8.5 Hz, 1H), 7.30 (d, J = 2.2 Hz, 1H), 7.22 (dd, J = 8.7, 2.3 Hz, 1H), 7.14-6.71 (m, 3H), 5.06 (dd, J = 12.8, 5.3 Hz, 1H), 4.03 (d, J = 13.0 Hz, 2H), 3.85 (s, 6H), 3.59 (s, 3H), 3.54 (s, 2H), 3.00-2.80 (m, 3H), 2.65-2.52 (m, 2H), 2.48-2.24 (m, 10H), 2.06-1.96 (m, 1H), 1.73 (d, J = 12.6 Hz, 2H), 1.60-1.54 (m, 1H), 1.37 (t, J = 7.3 Hz, 2H), 1.16 (q, J = 11.6 Hz, 2H). |
| D399 | 747.3 | ¹H NMR (300 MHz, DMSO-d6) δ 10.99 (s, 1H), 8.40 (d, J = 2.6 Hz, 1H), 8.19 (s, 1H, FA), 8.15 (d, J = 2.6 Hz, 1H), 7.40 (d, J = 8.5 Hz, 1H), 7.24 (dd, J = 8.6, 2.3 Hz, 1H), 7.14 (d, J = 2.3 Hz, 1H), 7.12-6.72 (m, 3H), 5.10 (dd, J = 13.2, 5.1 Hz, 1H), 4.33 (d, J = 16.7 Hz, 1H), 4.19 (d, J = 16.7 Hz, 1H), 3.85 (s, 6H), 3.72 (d, J = 12.1 Hz, 2H), 3.59 (s, 3H), 3.53 (s, 2H), 3.01-2.82 (m, 1H), 2.78-2.51 (m, 4H), 2.46-2.20 (m, 10H), 1.98 (d, J = 13.3 Hz, 1H), 1.73 (d, J = 12.4 Hz, 2H), 1.47-1.36 (m, 3H), 1.24 (q, J = 11.2 Hz, 2H). |
| D400 | 751.5 | ¹H NMR (400 MHz, DMSO-d6) δ 10.98 (s, 1H), 8.63 (s, 1H), 7.91 (s, 1H), 7.47-7.39 (m, 3H), 7.29 (dd, J = 8.5, 2.4 Hz, 1H), 7.20 (d, J = 2.3 Hz, 1H), 5.09 (dd, J = 13.3, 5.1 Hz, 1H), 4.40-4.14 (m, 4H), 4.08 (s, 3H), 3.92 (s, 6H), 3.78-3.74 (m, 8H), 3.54 (s, 3H), 3.14 (s, 4H), 2.91 (ddd, J = 17.2, 13.6, 5.4 Hz, 2H), 2.75 (t, J = 11.8 Hz, 2H), 2.65-2.56 (m, 1H), 2.43-2.34 (m, 1H), 2.04-1.95 (m, 1H), 1.78 (d, J = 12.4 Hz, 2H), 1.64-1.46 (m, 3H), 1.38-1.23 (m, 2H). |
| D401 | 690.3 | ¹H NMR (300 MHz, DMSO-d6) δ 10.98 (s, 1H), 8.37 (s, 1H), 8.24 (s, 1H), 8.15 (s, 1H, FA), 7.41-7.32 (m, 1H), 7.20-6.73 (m, 3H), 6.68 (dd, J = 5.1, 2.5 Hz, 2H), 5.09 (dd, J = 13.3, 5.0 Hz, 1H), 4.45-4.10 (m, 2H), 4.00 (t, J = 7.5 Hz, 2H), 3.87 (s, 6H), 3.81-3.66 (m, 6H), 2.94-2.83 (m, 1H), 2.75 (s, 2H), 2.64-2.52 (m, 2H), 2.42-2.25 (m, 2H), 1.98 (t, J = 7.0 Hz, 3H), 1.75 (q, J = 7.5 Hz, 2H), 0.91 (t, J = 7.3 Hz, 3H). |
| D402 | 749.35 | ¹H NMR (400 MHz, DMSO-d6) δ 10.98 (s, 1H), 9.95-9.63 (m, 2H, TFA salt), 8.63 (s, 1H), 7.92 (s, 1H), 7.45-7.38 (m, 3H), 6.73-6.66 (m, 2H), 5.07 (dd, J = 13.3, 5.1 Hz, 1H), 4.43-4.28 (m, 3H), 4.24-4.15 (m, 3H), 4.08 (s, 3H), 4.03-3.98 (m, 2H), 3.94 (s, 6H), 3.76-3.62 (m, 4H), 3.54 (s, 3H), 3.22-3.12 (m, 2H), 2.97-2.88 (m, 4H), 2.70-2.56 (m, 2H), 2.44-2.30 (m, 2H), 2.12 (d, J = 14.1 Hz, 2H), 2.02-1.89 (m, 3H). |
| D403 | 662.15 | ¹H NMR (400 MHz, DMSO-d6) δ 10.97 (s, 1H), 8.41 (s, J = 2.6 Hz, 1H), 8.16 (s, 1H, FA), 7.37 (d, J = 8.8 Hz, 1H), 6.86-7.08 (m, 3H), 6.72-6.65 (m, 2H), 5.08 (dd, J = 13.3, 5.1 Hz, 1H), 4.31 (d, J = 16.6 Hz, 1H), 4.18 (d, J = 16.6 Hz, 1H), 3.87 (s, 6H), 3.79-3.67 (m, 6H), 3.60 (s, 3H), 2.97-2.84 (m, 2H), 2.76 (s, 2H), 2.63-2.55 (m, 3H), 2.31-2.42 (m, 2H), 2.02-1.94 (m, 3H). |
| D404 | 688.15 | ¹H NMR (300 MHz, DMSO-d6) δ 10.98 (s, 1H), 8.34 (d, J = 2.6 Hz, 1H), 8.22 (s, 1H), 8.18 (s, 1 H, FA), 7.37 (d, J = 8.8 Hz, 1H), 7.16-6.73 (m, 3H), 6.68 (dq, J = 4.0, 2.3 Hz, 2H), 6.03 (ddd, J = 17.2, 10.5, 5.3 Hz, 1H), 5.33-5.00 (m, 3H), 4.68 (d, J = 5.5 Hz, 2H), 4.31 (d, J = 16.7 Hz, 1H), 4.18 (d, J = 16.6 Hz, 1H), 3.90-3.79 (m, 7H), 3.77-3.71 (m, 2H), 3.72-3.63 (m, 3H), 3.00-2.82 (m, 1H), 2.76 (s, 2H), 2.59 (d, J = 17.1 Hz, 3H), 2.43-2.28 (m, 1H), 1.98 (t, J = 6.9 Hz, 3H). |
| D405 | 777.4 | ¹H NMR (400 MHz, DMSO-d6) δ 10.98 (s, 1H), 8.61 (s, 1H), 8.19-8.14 (m, 1H, FA), 7.89-7.82 (m, 1H), 7.37 (d, J = 8.0 Hz, 1H), 7.36- |

| Compound No. | LCMS | ¹H NMR |
|---|---|---|
| | | 7.29 (m, 2H), 6.72-6.65 (m, 2H), 5.08 (dd, J = 13.3, 5.1 Hz, 1H), 4.31 (d, J = 16.6 Hz, 1H), 4.18 (d, J = 16.6 Hz, 1H), 4.08 (s, 3H), 3.87 (s, 6H), 3.79 (s, 2H), 3.58 (s, 4H), 3.53 (s, 3H), 3.08-3.01 (m, 2H), 2.98-2.84 (m, 1H), 2.68-2.55 (m, 2H), 2.43-2.30 (m, 6H), 2.11 (d, J = 7.0 Hz, 2H), 2.02-1.93 (m, 1H), 1.77-1.67 (m, 6H), 1.59 (s, 1H), 1.21-1.17 (m, 2H). |
| D406 | 676.3 | ¹H NMR (300 MHz, DMSO-d6) δ 11.08 (s, 1H), 8.41 (d, J = 2.6 Hz, 1H), 8.19 (s, 1H, FA), 8.15 (d, J = 2.5 Hz, 1H), 7.63 (d, J = 8.3 Hz, 1H), 7.15-6.74 (m, 4H), 6.64 (dd, J = 8.3, 2.1 Hz, 1H), 5.06 (dd, J = 12.8, 5.4 Hz, 1H), 3.99-3.85 (m, 4H), 3.87 (s, 6H), 3.70 (s, 2H), 3.59 (s, 3H), 2.97-2.80 (m, 1H), 2.77 (s, 2H), 2.63-2.53 (m, 4H), 2.02 (t, J = 7.0 Hz, 3H). |
| D407 | 773.89 | ¹H NMR (400 MHz, DMSO-d6) δ 10.98 (s, 1H), 9.42 (s, 1H, TFA), 9.25 (s, 1H, TFA), 8.50 (d, J = 2.7 Hz, 1H), 8.21 (d, J = 2.5 Hz, 1H), 7.44-7.38 (m, 1H), 7.11-6.79 (m, 3H), 6.70 (dd, J = 5.8, 2.4 Hz, 2H), 5.07 (dd, J = 13.3, 5.1 Hz, 1H), 4.38-4.14 (m, 4H), 3.95 (s, 6H), 3.66 (d, J = 7.8 Hz, 2H), 3.61 (s, 3H), 3.54-3.39 (m, 4H), 3.21-3.14 (m, 1H), 3.02-2.82 (m, 7H), 2.64-2.56 (m, 1H), 2.43-2.35 (m, 1H), 2.15-2.07 (m, 3H), 2.02-1.88 (m, 5H), 1.48 (q, J = 12.8 Hz, 2H), 1.26 (q, J = 7.2, 6.7 Hz, 1H). |
| D408 | 662.3 | ¹H NMR (300 MHz, DMSO-d6) δ 10.95 (s, 1H), 8.41 (d, J = 2.6 Hz, 1H), 8.21 (s, 1H, FA), 8.17-8.10 (m, 1H), 7.48 (d, J = 8.2 Hz, 1H), 7.18-6.73 (m, 3H), 6.54-6.42 (m, 2H), 5.03 (dd, J = 13.3, 5.1 Hz, 1H), 4.30 (d, J = 16.9 Hz, 1H), 4.16 (d, J = 16.9 Hz, 1H), 3.87 (s, 6H), 3.79 (q, J = 7.9 Hz, 4H), 3.70 (s, 2H), 3.59 (s, 3H), 2.99-2.81 (m, 1H), 2.80-2.74 (m, 2H), 2.63-2.52 (m, 2H), 2.41-2.29 (m, 2H), 2.05-1.89 (m, 3H). |
| D409 | 676.25 | ¹H NMR (300 MHz, Methanol-d4) δ 8.55 (s, 1H, FA), 7.68 (s, 1H), 7.42 (d, J = 8.2 Hz, 1H), 7.03-6.77 (m, 3H), 6.71 (s, 2H), 5.14 (dd, J = 13.3, 5.1 Hz, 1H), 4.48-4.33 (m, 4H), 4.03-3.89 (m, 10H), 3.71 (s, 3H), 3.64-3.54 (m, 2H), 3.47-3.37 (m, 2H), 3.00-2.85 (m, 1H), 2.85-2.74 (m, 1H), 2.58-2.41 (m, 6H), 2.23-2.13 (m, 1H). |
| D410 | 787.25 | ¹H NMR (300 MHz, DMSO-d6) δ 10.98 (s, 1H), 8.17 (s, 1H, FA), 7.61 (s, 1H), 7.37 (d, J = 8.1 Hz, 1H), 6.91 (t, J = 55.2 Hz, 1H), 6.74-6.65 (m, 2H), 6.61 (s, 2H), 5.08 (dd, J = 13.3, 5.1 Hz, 1H), 4.32 (d, J = 16.6 Hz, 1H), 4.18 (d, J = 16.6 Hz, 1H), 3.81 (s, 6H), 3.69 (s, 2H), 3.63-3.58 (m, 6H), 3.01-2.88 (m, 4H), 2.65-2.59 (m, 1H), 2.41 (s, 4H), 2.37-2.26 (m, 6H), 2.11 (d, J = 6.9 Hz, 2H), 2.02-1.95 (m, 1H), 1.79-1.64 (m, 6H), 1.54 (s, 1H), 1.21-1.08 (m, 2H). |
| D411 | 680.35 | ¹H NMR (400 MHz, DMSO-d6) δ 10.96 (s, 1H), 9.06 (s, 1H, TFA salt), 8.15 (s, 1H), 7.56-7.48 (m, 2H), 6.91 (s, 2H), 6.55-6.46 (m, 2H), 5.05 (dd, J = 13.3, 5.1 Hz, 1H), 4.37-4.25 (m, 3H), 4.19 (d, J = 16.9 Hz, 1H), 3.92 (s, 6H), 3.81 (s, 2H), 3.70 (s, 2H), 3.63 (s, 3H), 3.52 (s, 3H), 3.13 (q, J = 11.1 Hz, 2H), 2.91 (ddd, J = 17.1, 13.6, 5.3 Hz, 1H), 2.64-2.55 (m, 3H), 2.44-2.28 (m, 1H), 2.14 (d, J = 13.9 Hz, 2H), 2.05-1.92 (m, 3H).19F NMR (377 MHz, DMSO-d6) δ −73.65. |
| D412 | 680.35 | ¹H NMR (400 MHz, DMSO-d6) δ 10.95 (s, 1H), 8.90 (s, 1H, TFA salt), 8.63 (s, 1H), 7.93 (s, 1H), 7.52 (d, J = 8.3 Hz, 1H), 7.43 (s, 2H), 6.55-6.46 (m, 2H), 5.05 (dd, J = 13.3, 5.1 Hz, 1H), 4.36-4.15 (m, 4H), 4.09 (s, 3H), 3.95 (s, 6H), 3.80 (s, 2H), 3.69 (s, 2H), 3.55 (s, 3H), 3.14-3.07 (m, 2H), 2.97-2.84 (m, 1H), 2.71-2.57 (m, 3H), 2.39-2.31 (m, 1H), 2.17-2.09 (m, 2H), 2.04-1.93 (m, 3H).19F NMR (377 MHz, DMSO-d6) δ −73.66. |
| D413 | 694.45 | ¹H NMR (400 MHz, DMSO-d6) δ 11.08 (s, 1H), 8.19-8.14 (m, 1H, FA), 8.12 (s, 1H), 7.64 (d, J = 8.3 Hz, 1H), 7.52 (s, 1H), 6.81-6.74 (m, 3H), 6.69-6.62 (m, 1H), 5.06 (dd, J = 12.9, 5.4 Hz, 1H), 3.82 (s, 6H), 3.74 (s, 4H), 3.61-3.54 (m, 5H), 3.51 (s, 3H), 2.95-2.82 (m, 1H), 2.63-2.52 (m, 2H), 2.46-2.39 (m, 4H), 2.06-1.97 (m, 1H), 1.78-1.69 (m, 4H). |
| D414 | 680.4 | ¹H NMR (400 MHz, DMSO-d6) δ 10.96 (s, 1H), 8.16 (s, 1H, FA), 8.12 (s, 1H), 7.51 (s, 1H), 7.37 (d, J = 8.0 Hz, 1H), 6.76 (s, 2H), 6.72-6.65 (m, 2H), 5.08 (dd, J = 13.3, 5.2 Hz, 1H), 4.36-4.12 (m, 2H), 3.82 (s, 6H), 3.61-3.55 (m, 9H), 3.51 (s, 3H), 2.94-2.85 (m, 1H), 2.66-2.54 (m, 2H), 2.46-2.40 (m, 4H), 2.02-1.95 (m, 1H), 1.76-1.69 (m, 4H). |
| D415 | 694.3 | ¹H NMR (400 MHz, DMSO-d6) δ 11.08 (s, 1H), 8.60 (s, 1H), 8.17 (s, 1H, FA), 7.80 (s, 1H), 7.62 (d, J = 8.3 Hz, 1H), 7.27 (s, 2H), 6.78 (d, J = 2.1 Hz, 1H), 6.68-6.61 (m, 1H), 5.05 (dd, J = 12.9, 5.3 Hz, 1H), 4.08 (s, 3H), 3.84 (s, 6H), 3.73 (s, 4H), 3.56 (s, 2H), 3.53 (s, 3H), 2.91-2.81 (m, 1H), 2.62-2.52 (m, 2H), 2.46-2.41 (m, 4H), 2.04-1.96 (m, 1H), 1.77-1.70 (m, 4H). |
| D416 | 680.4 | ¹H NMR (400 MHz, DMSO-d6) δ 10.96 (s, 1H), 8.59 (s, 1H), 8.18 (s, 1H, FA), 7.80 (s, 1H), 7.36 (d, J = 8.1 Hz, 1H), 7.27 (s, 2H), 6.72-6.65 (m, 2H), 5.08 (dd, J = 13.3, 5.1 Hz, 1H), 4.35-4.13 (m, 2H), 4.08 (s, 3H), 3.85 (s, 6H), 3.59-3.50 (m, 9H), 2.96-2.84 (m, 1H), 2.64-2.53 (m, 2H), 2.48-2.36 (m, 4H), 2.02-1.94 (m, 1H), 1.76-1.69 (m, 4H). |

| Compound No. | LCMS | ¹H NMR |
| --- | --- | --- |
| D417 | 694.25 | ¹H NMR (400 MHz, DMSO-d6) δ 10.97 (s, 1H), 8.65 (s, 1H), 8.20 (s, 1H FA), 7.83 (s, 1H), 7.36 (d, J = 8.1 Hz, 1H), 7.32 (s, 2H), 6.72-6.64 (m, 2H), 5.08 (dd, J = 13.3, 5.1 Hz, 1H), 4.38 (q, J = 7.3 Hz, 2H), 4.31 (d, J = 16.6 Hz, 1H), 4.18 (d, J = 16.7 Hz, 1H), 3.85 (s, 6H), 3.57 (d, J = 4.1 Hz, 6H), 3.53 (s, 3H), 2.98-2.84 (m, 1H), 2.70-2.52 (m, 2H), 2.49-2.42 (m, 3H), 2.37 (dd, J = 13.2, 4.6 Hz, 1H), 2.03-1.94 (m, 1H), 1.74 (t, J = 5.5 Hz, 4H), 1.50 (t, J = 7.3 Hz, 3H). |
| D418 | 693.45 | ¹H NMR (400 MHz, DMSO-d6) δ 11.85 (d, J = 2.7 Hz, 1H), 11.09 (s, 1H), 7.66 (d, J = 8.3 Hz, 1H), 7.17-7.10 (m, 2H), 6.78 (d, J = 2.1 Hz, 1H), 6.70 (s, 2H), 6.65 (dd, J = 8.4, 2.1 Hz, 1H), 5.06 (dd, J = 12.9, 5.4 Hz, 1H), 3.82 (d, J = 22.7 Hz, 12H), 3.55 (s, 3H), 2.95-2.83 (m, 2H), 2.82-2.66 (m, 2H), 2.64-2.53 (m, 4H), 2.01 (dd, J = 9.4, 4.3 Hz, 1H), 1.87 (s, 6H). |
| D419 | 665.25 | ¹H NMR (300 MHz, DMSO-d6) δ 12.17 (s, 1H), 10.98 (s, 1H), 8.15 (s, 1H, FA), 7.48 (s, 1H), 7.38-7.36 (m, 2H), 6.85 (s, 2H), 6.71-6.68 (m, 2H), 6.58-6.55 (m, 1H), 5.11-5.05 (m, 1H), 4.34-4.15 (m, 2H), 3.85 (s, 6H), 3.60 (s, 3H), 3.58 (s, 6H), 2.97-2.89 (m , 1H), 2.74-2.72 (m, 3H), 2.40-2.34 (m, 2H), 2.00-1.97 (m, 1H), 1.73 (s, 4H), 1.35-1.24 (m, 1H). |
| D420 | 666.35 | ¹H NMR (400 MHz, DMSO-d6) δ 13.50 (s, 1H), 10.97 (s, 1H), 8.15 (s, 1H), 7.77 (s, 1H), 7.38 (d, J = 8.0 Hz, 1H), 6.88 (s, 2H), 6.73-6.65 (m, 2H), 5.08 (dd, J = 13.3, 5.1 Hz, 1H), 4.31 (d, J = 16.6 Hz, 1H), 4.18 (d, J = 16.5 Hz, 1H), 3.89 (s, 6H), 3.69 (s, 2H), 3.60 (s, 4H), 3.55 (s, 3H), 2.96-2.84 (m, 1H), 2.64-2.55 (m, 4H), 2.42-2.22 (m, 2H), 1.98 (d, J = 12.9 Hz, 1H), 1.79 (s, 4H). |
| D421 | 680.45 | ¹H NMR (400 MHz, DMSO-d6) δ 10.97 (s, 1H), 8.45 (s, 1H), 8.18 (s, 1H, FA), 7.47 (s, 1H), 7.37 (d, J = 8.0 Hz, 1H), 6.83 (s, 2H), 6.72-6.64 (m, 2H), 5.08 (dd, J = 13.2, 5.1 Hz, 1H), 4.31 (d, J = 16.6 Hz, 1H), 4.18 (d, J = 16.6 Hz, 1H), 4.12 (s, 3H), 3.87 (s, 6H), 3.57 (s, 3H), 3.56-3.53 (m, 6H), 2.95-2.86 (m, 1H), 2.63-2.56 (m, 1H), 2.49-2.34 (m, 5H), 2.04-1.94 (m, 1H), 1.79-1.62 (m, 4H). |
| D422 | 679.25 | ¹H NMR (300 MHz, DMSO-d6) δ 11.99 (s, 1H), 10.99 (s, 1H), 9.05-8.75 (m, 1 H, TFA), 7.51 (s, 1H), 7.41 (d, J = 8.8 Hz, 1H), 6.94 (s, 2H), 6.71 (d, J = 5.7 Hz, 2H), 6.30 (s, 1H), 5.08 (dd, J = 13.2, 5.1 Hz, 1H), 4.36-4.15 (m, 4H), 3.95 (s, 6H), 3.76 (s, 2H), 3.65-3.63 (m, 2H), 3.62-3.60 (m, 3H), 3.38-3.33 (m, 2H), 3.18-3.05 (m, 2H), 3.00-2.84 (m, 1H), 2.67-2.59 (m, 1H), 2.44-2.39 (m, 1H), 2.36 (s, 3H), 2.13 (d, J = 13.3 Hz, 2H), 2.01 (d, J = 11.3 Hz, 3H). |
| D423 | 614.35 | ¹H NMR (400 MHz, DMSO-d6) δ 7.53 (d, J = 8.5 Hz, 1H), 7.31 (d, J = 1.2 Hz, 1H), 7.05 (d, J = 8.3 Hz, 2H), 6.56 (s, 2H), 5.00 (dd, J = 13.3, 5.1 Hz, 1H), 4.39-4.15 (m, 2H), 3.77 (d, J = 18.2 Hz, 8H), 3.53 (s, 3H), 3.32 (t, J = 4.8 Hz, 4H), 2.94-2.81 (m, 1H), 2.79-2.67 (m, 4H), 2.65-2.55 (m, 1H), 2.43-2.28 (m, 4H), 2.03 (s, 3H), 2.01-1.92 (m, 1H). |
| D424 | 671.4 | ¹H NMR (300 MHz, DMSO-d6) δ 8.56 (s, 1H), 8.24 (s, 1 H, FA), 7.77 (s, 1H), 7.43 (d, J = 8.4 Hz, 1H), 7.25 (s, 2H), 7.21 (d, J = 6.0 Hz, 1H), 7.15 (d, 1H), 5.05 (dd, J = 13.2, 5.0 Hz, 1H), 4.34-4.20 (m, 2H), 4.07 (s, 3H), 4.00 (d, J = 12.7 Hz, 1H), 3.86 (s, 6H), 3.83-3.77 (m, 1H), 3.28-3.14 (m, 4H), 3.06-2.96 (m, 2H), 2.91-2.79 (m, 1H), 2.66-2.55 (m, 1H), 2.43-2.20 (m, 1H), 2.00 (s, 1H), 1.26 (d, J = 6.1 Hz, 6H). |
| D425 | 676.35 | ¹H NMR (400 MHz, DMSO-d6) δ 10.97 (s, 1H), 8.41 (d, J = 2.6 Hz, 1H), 8.19 (d, J = 6.8 Hz, 1H), 8.16 (d, J = 2.6 Hz, 1 H, FA), 7.36 (d, J = 8.0 Hz, 1H), 6.90 (d, J = 33.7 Hz, 3H), 6.72-6.64 (m, 2H), 5.13-5.04 (m, 1H), 4.31 (d, J = 16.5 Hz, 1H), 4.18 (d, J = 16.6 Hz, 1H), 3.87 (s, 6H), 3.60 (s, 3H), 3.54 (d, J = 15.6 Hz, 7H), 2.97-2.84 (m, 1H), 2.63-2.54 (m, 1H), 2.45-2.31 (m, 4H), 1.98 (d, J = 12.6 Hz, 1H), 1.71 (s, 4H). |
| D426 | 679.5 | ¹H NMR (300 MHz, DMSO-d6) δ 11.82 (s, 1H), 10.98 (s, 1H), 8.24 FA (s, 1H), 7.37 (d, J = 8.0 Hz, 1H), 7.20-7.06 (m, 2H), 6.76-6.54 (m, 4H), 5.09 (dd, J = 13.3, 5.0 Hz, 1H), 4.40-4.10 (m, 2H), 3.80 (s, 6H), 3.60-3.54 (m, 9H), 3.00-2.83 (m, 2H), 2.62 (s, 1H), 2.40 (s, 3H), 1.99 (s, 2H), 1.85 (s, 3H), 1.78-1.64 (m, 4H). |
| D427 | 614.35 | ¹H NMR (400 MHz, DMSO-d6) δ 10.97 (s, 1H), 7.42 (d, J = 8.4 Hz, 1H), 7.31 (d, J = 1.2 Hz, 1H), 7.25 (dd, J = 8.5, 2.4 Hz, 1H), 7.14 (d, J = 2.3 Hz, 1H), 6.59-6.52 (m, 2H), 5.09 (dd, J = 13.3, 5.1 Hz, 1H), 4.39-4.16 (m, 2H), 3.81 (s, 6H), 3.62 (s, 2H), 3.54 (s, 3H), 3.22-3.11 (m, 4H), 2.98-2.84 (m, 1H), 2.72-2.56 (m, 5H), 2.46-2.36 (m, 1H), 2.33 (s, 3H), 2.04 (s, 3H), 2.02-1.94 (m, 1H). |
| D428 | 666.35 | ¹H NMR (300 MHz, DMSO-d6) δ 10.97 (s, 1H), 8.36 (s, 1H), 8.15 (d, J = 0.9 Hz, 1H, FA), 7.89 (s, 1H), 7.37 (d, J = 8.1 Hz, 1H), 7.12 (s, 1H), 6.93 (s, 2H), 6.69 (d, J = 7.7 Hz, 2H), 5.08 (dd, J = 13.2, 5.1 Hz, 1H), 4.43-4.14 (m, 2H), 3.86 (s, 6H), 3.64-3.57 (m, 6H), 3.44 (s, 5H), 2.99-2.84 (m, 2H), 2.68-2.60 (m, 1H), 2.45-2.32 (m, 2H), 2.05-1.91 (m, 1H), 1.81-1.68 (m, 4H). |
| D429 | 627.35 | ¹H NMR (400 MHz, DMSO-d6) δ 10.97 (s, 1H), 8.50 (d, J = 1.2 Hz, 1H), 8.14 (d, J = 1.1 Hz, 1H), 7.38 (d, J = 8.0 Hz, 1H), 7.18 (s, 2H), |

| Compound No. | LCMS | ¹H NMR |
|---|---|---|
| | | 6.68 (d, J = 7.7 Hz, 2H), 5.08 (dd, J = 13.3, 5.1 Hz, 1H), 4.42-4.14 (m, 2H), 3.88 (s, 6H), 3.77 (s, 2H), 3.60 (s, 4H), 3.56 (s, 4H), 2.97-2.84 (m, 1H), 2.69 (s, 3H), 2.64-2.55 (m, 2H), 2.39 (td, J = 13.1, 4.4 Hz, 1H), 2.02-1.93 (m, 1H), 1.82 (s, 4H). |
| D430 | 654.3 | ¹H NMR (300 MHz, DMSO-d6) δ 11.09 (s, 1H), 7.66 (d, J = 8.2 Hz, 1H), 7.53 (s, 1H), 6.82 (d, J = 2.1 Hz, 1H), 6.73-6.54 (m, 3H), 5.06 (dd, J = 12.8, 5.3 Hz, 1H), 4.14-3.94 (m, 5H), 3.85 (s, 6H), 3.49-3.46 (m, 5H), 3.14-2.97 (m, 2H), 2.96-2.70 (m, 2H), 2.68-2.58 (m, 1H), 2.36-2.17 (m, 2H), 2.14-1.95 (m, 7H). |
| D431 | 665.35 | ¹H NMR (300 MHz, DMSO-d6) δ 10.99 (s, 1H), 8.94 (s, 1H, TFA), 7.50 (d, J = 6.0 Hz, 1H), 7.41 (d, J = 8.9 Hz, 1H), 7.04 (d, J = 4.0 Hz, 1H), 6.92 (s, 2H), 6.87 (d, J = 10.2, 5.1 Hz, 2H), 6.75-6.66 (m, 2H), 5.08 (dd, J = 13.3, 5.1 Hz, 1H), 4.39-4.12 (m, 4H), 3.95 (s, 6H), 3.76 (s, 2H), 3.70 (s, 2H), 3.43-3.31 (m, 5H), 3.17-3.11 (m, 2H), 3.00-2.82 (m, 1H), 2.63 (s, 1H), 2.44-2.30 (m, 1H), 2.19-2.08 (m, 2H), 2.06-1.96 (m, 3H). |
| D432 | 664.3 | ¹H NMR (300 MHz, Methanol-d4) δ 8.30 (d, J = 2.6 Hz, 1H), 8.20-8.13 (m, 1H), 7.72 (d, J = 7.7 Hz, 1H), 7.10-6.61 (m, 3H), 6.26 (dd, J = 7.6, 2.0 Hz, 1H), 5.67 (d, J = 1.8 Hz, 1H), 5.25 (dd, J = 12.5, 5.3 Hz, 1H), 4.43 (s, 2H), 4.17-3.96 (m, 10H), 3.72 (s, 3H), 3.67 (s, 2H), 3.51-3.45 (m, 2H), 2.99-2.76 (m, 2H), 2.73-2.49 (m, 1H), 2.52-2.46 (m, 2H), 2.36-2.23 (m, 1H). |
| D433 | 666.25 | ¹H NMR (300 MHz, DMSO-d6) δ 14.27 (s, 1H), 10.98 (s, 1H), 8.24 (s, 1H, FA), 8.15 (s, 1H), 7.61 (s, 1H), 7.38 (d, J = 8.3 Hz, 1H), 6.90 (s, 2H), 6.74-6.64 (m, 2H), 5.08 (dd, J = 13.2, 5.1 Hz, 1H), 4.25 (dd, 2H), 3.90 (s, 6H), 3.74 (s, 2H), 3.61 (d, J = 6.9 Hz, 7H), 2.98-2.84 (m, 1H), 2.79-2.54 (m, 5H), 2.42-2.32 (m, 1H), 2.03-1.93 (m, 1H), 1.81 (s, 4H). |
| D434 | 666.25 | ¹H NMR (300 MHz, MeOD) δ 8.85-8.49 (m, 1H), 7.85 (d, J = 1.9 Hz, 1H), 7.42 (d, J = 8.2 Hz, 1H), 7.17-7.09 (m, 2H), 6.89 (d, J = 2.2 Hz, 1H), 6.81 (dd, J = 8.2, 2.3 Hz, 1H), 5.14 (dd, J = 13.2, 5.1 Hz, 1H), 4.49-4.31 (m, 4H), 4.04 (s, 6H), 3.85 (s, 3H), 3.73 (s, 2H), 3.56 (d, J = 12.7 Hz, 2H), 3.24 (t, J = 11.9, 11.9 Hz, 2H), 3.02-2.86 (m, 1H), 2.85-2.72 (m, 1H), 2.59-2.41 (m, 1H), 2.34-2.22 (m, 2H), 2.21-2.04 (m, 3H). |
| D435 | 665.35 | ¹H NMR (400 MHz, DMSO-d6) δ 10.96 (s, 1H), 8.23 (s, 1H, FA), 7.61 (d, J = 3.2 Hz, 1H), 7.36 (d, J = 8.0 Hz, 1H), 7.05 (d, J = 7.7 Hz, 1H), 7.03 (d, J = 3.2 Hz, 1H), 6.88 (d, J = 7.7 Hz, 1H), 6.77 (s, 2H), 6.70-6.67 (m, 2H), 5.08 (dd, J = 13.3, 5.1 Hz, 1H), 4.34-4.14 (m, 2H), 3.85 (s, 6H), 3.56 (s, 3H), 3.51-3.50 (m, 6H), 2.98-2.83 (m, 1H), 2.68-2.57 (m, 1H), 2.48-2.22 (m, 5H), 2.06-1.91 (m, 1H), 1.72-1.70 (m, 4H). |
| D436 | 614.3 | ¹H NMR (300 MHz, Methanol-d4) δ 7.71 (d, J = 8.5 Hz, 1H), 7.60 (s, 1H), 7.39 (d, J = 2.2 Hz, 1H), 7.27 (dd, J = 8.6, 2.3 Hz, 1H), 6.65 (s, 2H), 6.52 (s, 1H), 5.09 (dd, J = 12.3, 5.4 Hz, 1H), 3.91 (d, 8H), 3.58 (d, J = 18.3 Hz, 7H), 2.99-2.89 (m, 4H), 2.87-2.66 (m, 3H), 2.21 (s, 3H), 2.18-2.07 (m, 1H). |
| D437 | 693.4 | ¹H NMR (300 MHz, Methanol-d4) 7.41 (d, J = 8.2 Hz, 1H), 6.99-6.78 (m, 2H), 6.70 (m, 1H), 5.86 (s, 1H), 5.29-5.05 (m, 1H), 4.52-4.29 (m, 2H), 4.22-3.98 (m, 5H), 3.91 (s, 6H), 3.74 (s, 4H), 3.21-2.72 (m, 6H), 2.66-2.40 (m, 1H), 2.35 (s, 3H), 2.27-2.15 (m, 4H), 2.15-1.94 (m, 4H). |
| D438 | 595.3 | ¹H NMR (400 MHz, DMSO-d6 with a drop of D₂O) δ 8.15 (s, 1H, FA), 8.05 (d, J = 2.7 Hz, 1H), 7.82 (dd, J = 2.7, 1.3 Hz, 1H), 7.70-7.59 (m, 3H), 6.82 (s, 2H), 5.10 (dd, J = 13.3, 5.1 Hz, 1H), 4.42 (dd, 2H), 3.86 (s, 6H), 3.66 (s, 2H), 3.65-3.56 (m, 2H), 3.53 (s, 3H), 3.34 (s, 1H), 3.28 (d, J = 7.7 Hz, 2H), 2.97-2.84 (m, 1H), 2.66-2.56 (m, 1H), 2.44-2.35 (m, 1H), 2.10 (s, 3H), 2.07-1.95 (m, 1H). |
| D439 | 631.3 | ¹H NMR (300 MHz, Methanol-d4) δ 8.25 (s, 1H), 8.11 (s, 1H), 7.79 (d, J = 1.2 Hz, 1H), 7.67 (dd, J = 7.9, 1.5 Hz, 1H), 7.57 (d, J = 7.9 Hz, 1H), 7.09-6.61 (m, 3H), 5.17 (dd, J = 13.3, 5.2 Hz, 1H), 4.61-4.42 (m, 2H), 4.23 (s, 2H), 4.16 (t, J = 8.8 Hz, 2H), 4.00 (s, 6H), 3.97-3.85 (m, 2H), 3.77-3.63 (m, 4H), 3.03-2.75 (m, 2H), 2.61-2.40 (m, 1H), 2.29-2.13 (m, 1H). |
| D440 | 595.3 | ¹H NMR (400 MHz, Methanol-d4) δ 7.99-7.90 (m, 1H), 7.84-7.74 (m, 2H), 7.72-7.49 (m, 2H), 6.91 (d, J = 2.6 Hz, 2H), 5.20-5.11 (m, 1H), 4.55-4.37 (m, 6H), 4.34-4.22 (m, 2H), 4.00 (s, 6H), 3.95-3.84 (m, 1H), 3.66 (d, J = 6.7 Hz, 3H), 2.98-2.85 (m, 1H), 2.81 (s, 1H), 2.54-2.40 (m, 1H), 2.20 (d, J = 5.0 Hz, 4H). |
| D441 | 631.5 | ¹H NMR (400 MHz, Methanol-d4) δ 8.32-8.07 (m, 2H), 7.77 (d, J = 7.8 Hz, 1H), 7.70-7.53 (m, 2H), 7.07-6.67 (m, 3H), 5.15 (dd, J = 13.3, 5.1 Hz, 1H), 4.62-4.39 (m, 6H), 4.35-4.23 (m, 2H), 4.17-3.83 (m, 7H), 3.68 (s, 3H), 2.98-2.84 (m, 1H), 2.78 (d, J = 17.4 Hz, 1H), 2.48 (qd, J = 13.1, 4.7 Hz, 1H), 2.22-2.14 (m, 1H). |
| D442 | 609.5 | ¹H NMR (300 MHz, Methanol-d4) δ 8.56 (s, FA, 1H), 7.96 (d, 1H), 7.85-7.79 (m, 2H), 7.71-7.63 (m, 1H), 7.58 (d, 1H), 6.90 (s, 2H), 5.23-5.11 (m, 1H), 4.52 (d, 2H), 4.41 (s, 2H), 4.00 (s, 6H), 3.69 (s, |

-continued

| Compound No. | LCMS | ¹H NMR |
|---|---|---|
| | | 3H), 3.63-3.50 (m, 2H), 3.48-3.36 (m, 3H), 3.00-2.73 (m, 2H), 2.61-2.39 (m, 2H), 2.31-2.11 (m, 5H). |
| D443 | 623.35 | ¹H NMR (300 MHz, DMSO-d6) δ 11.01 (s, 1H), 8.06 (d, J = 2.7 Hz, 1H), 7.89-7.75 (m, 1H), 7.69-7.54 (m, 3H), 6.82 (s, 2H), 5.11 (dd, J = 13.2, 5.1 Hz, 1H), 4.61-4.25 (m, 2H), 3.86 (s, 6H), 3.58 (s, 2H), 3.54 (s, 3H), 3.02-2.84 (m, 1H), 2.84-2.70 (m, 2H), 2.67-2.53 (m, 2H), 2.48-2.35 (m, 1H), 2.33-2.21 (m, 2H), 2.10 (s, 3H), 2.06-1.95 (m, 1H), 1.92-1.79 (m, 2H), 1.69-1.53 (m, 2H). |
| D444 | 659.3 | ¹H NMR (300 MHz, DMSO-d6) δ 11.01 (s, 1H), 8.40 (.1.0 FA, d, J = 2.6 Hz, 1H), 8.26-8.05 (m, 2H), 7.75-7.51 (m, 3H), 7.20-6.69 (m, 3H), 5.11 (dd, J = 13.2, 5.1 Hz, 1H), 4.61-4.21 (m, 2H), 3.87 (s, 6H), 3.60 (s, 3H), 3.56 (s, 2H), 3.00-2.83 (m, 1H), 2.82-2.69 (m, 2H), 2.68-2.53 (m, 2H), 2.48-2.32 (m, 1H), 2.32-2.18 (m, 2H), 2.08-1.93 (m, 1H), 1.84 (d, 2H), 1.70-1.49 (m, 2H). |
| D445 | 707.4 | ¹H NMR (300 MHz, DMSO-d6) δ 11.58 (s, 1H), 11.08 (s, 1H), 8.28-8.13 (m, 1H, FA), 7.64 (d, J = 8.3 Hz, 1H), 6.99 (d, J = 2.6 Hz, 1H), 6.77 (d, J = 2.1 Hz, 1H), 6.64 (dd, J = 8.4, 2.2 Hz, 1H), 6.51 (s, 2H), 5.06 (dd, J = 12.7, 5.2 Hz, 1H), 3.74 (d, J = 8.4 Hz, 10H), 3.58 (d, J = 3.6 Hz, 5H), 2.94-2.83 (m, 1H), 2.65-2.55 (m, 3H), 2.47-2.38 (m, 3H), 2.17 (s, 3H), 2.07-1.97 (m, 1H), 1.79-1.67 (m, 4H), 1.51 (s, 3H). |
| D446 | 707.4 | ¹H NMR (300 MHz, DMSO-d6) δ 11.08 (s, 1H), 10.85 (s, 1H), 7.65 (d, J = 8.3 Hz, 1H), 6.79 (d, J = 2.1 Hz, 1H), 6.70-6.62 (m, 1H), 6.59 (s, 2H), 5.83 (s, 1H), 5.06 (dd, J = 12.7, 5.3 Hz, 1H), 4.00 (s, 3H), 3.89-3.72 (m, 10H), 3.68 (s, 2H), 3.00-2.78 (m, 1H), 2.70-2.53 (m, 6H), 2.27 (s, 3H), 2.14(s, 3H), 2.09-1.96 (m, 1H), 1.81 (s, 4H). |
| D447 | 666.4 | ¹H NMR (300 MHz, Methanol-d4) δ 8.52 (br s, 0.2H, FA), 7.84 (d, J = 1.2 Hz, 1H), 7.64 (s, 1H), 7.48 (d, J = 8.2 Hz, 1H), 7.30 (s, 1H), 7.10 (s, 2H), 6.95 (d, J = 2.2 Hz, 1H), 6.87 (dd, J = 8.2, 2.2 Hz, 1H), 5.20 (dd, 1H), 4.47 (d, J = 5.4 Hz, 2H), 4.07 (s, 6H), 3.86-3.71 (m, 8H), 3.38-3.28 (m, 3H) 3.18-2.80 (m, 2H), 2.62-2.54 (m, 1H), 2.36-2.10 (m, 5H). |
| D448 | 599.35 | ¹H NMR (400 MHz, DMSO-d6) δ 10.99 (s, 1H), 8.19 (s, 1H, FA), 8.06 (d, J = 2.6 Hz, 1H), 7.81 (d, J = 2.3 Hz, 1H), 7.54 (s, 1H), 7.51 (d, J = 7.8 Hz, 1H), 7.44 (dd, J = 7.8, 1.6 Hz, 1H), 6.81 (s, 2H), 5.10 (dd, J = 13.3, 5.2 Hz, 1H), 4.46-4.23 (m, 2H), 3.84 (s, 6H), 3.72 (d, J = 4.9 Hz, 2H), 3.53 (s, 3H), 3.46 (s, 2H), 3.07 (s, 2H), 2.96-2.85 (m, 1H), 2.64-2.56 (m, 4H), 2.39 (dd, J = 13.3, 4.7 Hz, 1H), 2.10 (s, 3H), 2.03-1.96 (m, 1H), 1.79 (q, J = 7.5 Hz, 2H). |
| D449 | 585.35 | ¹H NMR (400 MHz, DMSO-d6) δ 10.99 (s, 1H), 8.19 (s, 1H, FA), 8.06 (d, J = 2.6 Hz, 1H), 7.81 (d, J = 2.3 Hz, 1H), 7.54 (s, 1H), 7.51 (d, J = 7.8 Hz, 1H), 7.44 (dd, J = 7.8, 1.6 Hz, 1H), 6.81 (s, 2H), 5.10 (dd, J = 13.3, 5.2 Hz, 1H), 4.46-4.23 (m, 2H), 3.84 (s, 6H), 3.72 (d, J = 4.9 Hz, 2H), 3.53 (s, 3H), 3.46 (s, 2H), 3.07 (s, 2H), 2.96-2.85 (m, 1H), 2.64-2.56 (m, 4H), 2.39 (dd, J = 13.3, 4.7 Hz, 1H), 2.10 (s, 3H), 2.03-1.96 (m, 1H), 1.79 (q, J = 7.5 Hz, 2H). |
| D450 | 609.30 | ¹H NMR (400 MHz, DMSO-d6) δ 8.22 (s, 1 H, FA), 8.04 (d, J = 2.7 Hz, 1H), 7.86-7.80 (m, 1H), 7.70-7.57 (m, 3H), 6.82 (s, 2H), 5.09 (dd, J = 13.3, 5.1 Hz, 1H), 4.55-4.31 (m, 2H), 3.86 (s, 6H), 3.66 (s, 2H), 3.54 (s, 3H), 3.43 (d, J = 6.8 Hz, 2H), 3.27 (d, J = 6.8 Hz, 2H), 2.99-2.81 (m, 1H), 2.74-2.58 (m, 1H), 2.46-2.32 (m, 1H), 2.10 (s, 3H), 2.07-1.97 (m, 1H), 1.51 (s, 3H). |
| D451 | 538.25 | ¹H NMR (300 MHz, DMSO-d6) δ 11.02 (s, 1H), 8.48 (d, J = 2.4 Hz, 1H), 8.22 (s, 1H), 7.61 (d, J = 7.9 Hz, 1H), 7.54-7.45 (m, 2H), 7.18-6.74 (m, 3H), 5.14 (dd, J = 13.2, 5.0 Hz, 1H), 4.43 (dd, 2H), 3.79 (s, 6H), 3.62 (s, 3H), 3.04-2.91 (m, 1H), 2.67-2.59 (m, 1H), 2.47-2.34 (m, 1H), 2.07-1.97 (m, 1H). |
| D452 | 600.25 | ¹H NMR (400 MHz, DMSO-d6) δ 10.98 (s, 1H), 9.39 (s, 1H), 8.16 (d, J = 2.7 Hz, 1H, FA), 7.88 (dd, J = 2.7, 1.3 Hz, 1H), 7.49 (d, J = 8.4 Hz, 1H), 7.31 (dd, J = 8.4, 2.4 Hz, 1H), 7.26 (d, J = 2.3 Hz, 1H), 6.96 (s, 2H), 5.10 (dd, J = 13.3, 5.1 Hz, 1H), 4.36 (d, J = 16.9 Hz, 1H), 4.31 (d, J = 4.2 Hz, 2H), 4.23 (d, J = 16.9 Hz, 1H), 3.96 (s, 6H), 3.88 (d, J = 13.1 Hz, 2H), 3.55 (s, 3H), 3.47 (d, J = 12.0 Hz, 2H), 3.33-3.20 (m, 2H), 3.12 (t, J = 12.4 Hz, 2H), 2.98-2.84 (m, 1H), 2.60 (d, J = 17.7 Hz, 1H), 2.43-2.32 (m, 1H), 2.11 (s, 3H), 2.04-1.94 (m, 1H). |
| D453 | 609.50 | ¹H NMR (400 MHz, DMSO-d6) δ 11.00 (s, 1H), 8.25 (s, 1H, FA salt), 8.05 (d, J = 2.7 Hz, 1H), 7.82 (d, J = 2.6 Hz, 1H), 7.63-7.56 (m, 3H), 6.82 (s, 2H), 5.10 (dd, J = 13.3, 5.2 Hz, 1H), 4.37 (dd, 2H), 3.86 (s, 6H), 3.62-3.58 (m, 2H), 3.53 (s, 3H), 3.15-3.13 (m, 1H), 2.96-2.89 (m, 2H), 2.86-2.83 (m, 2H), 2.62-2.58 (m, 1H), 2.41-2.35 (m, 1H), 2.09 (s, 3H), 2.03-1.98 (m, 1H), 1.11 (d, J = 5.9 Hz, 3H). |

| Compound No. | LCMS | ¹H NMR |
|---|---|---|
| D454 | 706.4 | ¹H NMR (400 MHz, DMSO-d6) δ 10.89 (s, 1H), 8.28 (s, 1H), 7.82 (s, 1H), 7.30 (d, J = 8.0 Hz, 1H), 6.96 (s, 1H), 6.85 (s, 2H), 6.62 (d, J = 8.2 Hz, 2H), 5.73-5.62 (m, 1H), 5.59-5.48 (m, 1H), 5.00 (dd, J = 13.2, 5.1 Hz, 1H), 4.36 (d, J = 6.0 Hz, 2H), 4.28-4.07 (m, 2H), 3.79 (s, 6H), 3.61-3.49 (m, 8H), 2.91-2.77 (m, 1H), 2.54 (d, J = 3.7 Hz, 3H), 2.37-2.23 (m, 1H), 1.96-1.86 (m, 1H), 1.68 (t, J = 6.6 Hz, 4H), 1.60 (d, J = 6.3 Hz, 3H). |
| D455 | 593.25 | ¹H NMR (400 MHz, Methanol-d4) δ 8.16 (d, J = 2.6 Hz, 1H), 8.11-8.05 (m, 1H), 7.38 (d, J = 8.3 Hz, 1H), 6.99-6.78 (m, 3H), 6.76 (s, 2H), 5.12 (dd, J = 13.3, 5.1 Hz, 1H), 4.45-4.31 (m, 5H), 3.99 (q, J = 5.5, 4.1 Hz, 2H), 3.82 (s, 6H), 3.67 (s, 3H), 2.97-2.83 (m, 1H), 2.83-2.72 (m, 1H), 2.56-2.40 (m, 1H), 2.21-2.11 (m, 1H). |
| D456 | 666.5 | ¹H NMR (400 MHz, Methanol-d4) δ 8.52 (s, 0.67H, FA), 7.93 (d, J = 2.2 Hz, 1H), 7.39 (d, J = 8.2 Hz, 1H), 7.28 (s, 1H), 7.22-7.15 (m, 3H), 6.86 (d, J = 2.2 Hz, 1H), 6.81-6.74 (m, 1H), 5.16-5.07 (m, 1H), 4.45-4.30 (m, 4H), 3.97 (s, 6H), 3.75 (s, 4H), 3.63 (s, 3H), 3.39-3.36 (m, 2H), 3.28-3.21 (m, 2H), 2.96-2.83 (m, 1H), 2.82-2.72 (m, 1H), 2.56-2.40 (m, 1H), 2.19-2.02 (m, 5H). |
| D457 | 597.35 | ¹H NMR (400 MHz, DMSO-d6) δ 10.99 (s, 1H), 9.67-9.52 (m, 1H, TFA salt), 8.17-8.10 (m, 1H), 7.88-7.78 (m, 2H), 7.71-7.64 (m, 1H), 7.62-7.56 (m, 1H), 6.98-6.91 (m, 2H), 6.71-6.62 (m, 5.7 Hz, 2H), 5.17-5.06 (m, 1H), 4.49-4.41 (m, 1H), 4.41-4.27 (m, 3H), 4.27-4.22 (m, 2H), 4.16-4.15 (m, 2H), 3.95 (s, 6H), 3.54 (s, 3H), 2.97-2.85 (m, 1H), 2.61 (d, J = 17.1 Hz, 1H), 2.43-2.35 (m, 2H), 2.10 (s, 3H), 2.04-1.97 (m, 2H). |
| D458 | 613.35 | ¹H NMR (400 MHz, DMSO-d6) δ 8.08 (s, 1H), 7.89 (s, 1H), 7.79 (d, J = 8.0 Hz, 2H), 7.71 (d, J = 7.9 Hz, 1H), 6.92 (s, 2H), 5.09 (dd, J = 13.3, 5.1 Hz, 1H), 4.86-4.57 (m, 4H), 4.57-4.45 (m, 3H), 4.40 (d, J = 18.1 Hz, 1H), 3.94 (s, 6H), 3.54 (s, 3H), 2.97-2.83 (m, 1H), 2.71-2.59 (m, 1H), 2.47-2.33 (m, 1H), 2.16-2.01 (s, 4H). |
| D459 | 526.2 | ¹H NMR (400 MHz, DMSO-d6) δ 10.97 (s, 1H), 7.87 (d, J = 2.7 Hz, 1H), 7.69 (dd, J = 2.7, 1.3 Hz, 1H), 7.46 (t, J = 8.7 Hz, 3H), 7.35 (dd, J = 8.4, 2.4 Hz, 1H), 7.25 (d, J = 2.4 Hz, 1H), 7.05 (d, J = 8.8 Hz, 2H), 5.11 (dd, J = 13.3, 5.1 Hz, 1H), 4.46-4.19 (m, 2H), 3.50 (s, 3H), 3.35 (s, 8H), 2.98-2.85 (m, 1H), 2.60 (d, J = 17.0 Hz, 1H), 2.43-2.32 (m, 1H), 2.07 (s, 3H), 2.04-1.95 (m, 1H). |
| D460 | 540.25 | ¹H NMR (400 MHz, DMSO-d6) δ 7.99 (d, J = 2.7 Hz, 1H), 7.75 (d, J = 2.6 Hz, 1H), 7.57 (d, J = 7.7 Hz, 2H), 7.43 (dd, J = 11.4, 7.8 Hz, 3H), 7.27 (dd, J = 8.5, 2.4 Hz, 1H), 7.18 (s, 1H), 5.09 (dd, J = 13.3, 5.1 Hz, 1H), 4.44-4.17 (m, 2H), 3.66 (s, 3H), 3.52 (s, 3H), 3.24 (s, 3H), 2.97-2.84 (m, 1H), 2.77-2.64 (m, 1H), 2.67 (s, 4H), 2.45-2.33 (m, 1H), 2.09 (s, 3H), 2.04-1.95 (m, 1H). |
| D461 | 641.25 | ¹H NMR (300 MHz, DMSO-d6) δ 11.02 (s, 1H), 9.00 (s, 1H, TFA), 8.49 (s, 1H), 7.47 (d, J = 8.8 Hz, 1H), 7.32 (s, 2H), 6.77 (dt, J = 4.0, 2.0 Hz, 2H), 5.14 (dd, J = 13.2, 5.1 Hz, 1H), 4.46-4.21 (m, 4H), 4.02 (s, 6H), 3.81 (s, 2H), 3.71 (s, 2H), 3.62 (s, 3H), 3.43 (d, J = 12.6 Hz, 2H), 3.18 (t, J = 11.4 Hz, 2H), 3.07-2.89 (m, 1H), 2.67 (d, J = 17.2 Hz, 1H), 2.56-2.31 (m, 4H), 2.19 (d, J = 14.0 Hz, 2H), 2.12-1.98 (m, 3H), 0.08 (s, 1H). |
| D462 | 696.5 | ¹H NMR (400 MHz, DMSO-d6 with a drop of D2O) δ 8.75 (s, 1H), 8.26 (s, 1H, FA), 7.89 (s, 1H), 7.39 (d, J = 8.1 Hz, 1H), 7.24 (s, 2H), 6.74-6.67 (m, 2H), 5.05 (dd, J = 13.3, 5.1 Hz, 1H), 4.37-4.15 (m, 5H), 3.88 (s, 6H), 3.80 (s, 2H), 3.61 (s, 4H), 3.55 (s, 3H), 2.95-2.82 (m, 1H), 2.81-2.57 (m, 5H), 2.45-2.31 (m, 1H), 2.06-1.95 (m, 1H), 1.85 (t, J = 5.5 Hz, 4H). |
| D463 | 654.35 | ¹H NMR (400 MHz, Methanol-d4) δ 8.90 (s, 1H), 8.28 (d, J = 1.1 Hz, 1H), 7.87 (d, J = 1.7 Hz, 1H), 7.73 (dd, J = 7.9, 1.7 Hz, 1H), 7.61 (d, J = 7.9 Hz, 1H), 7.48 (d, J = 8.5 Hz, 1H), 7.39-7.31 (m, 2H), 7.15 (s, 1H), 5.95-5.80 (m, 1H), 5.71-5.54 (m, 1H), 5.13 (dd, J = 13.3, 5.1 Hz, 1H), 4.52 (d, J = 6.4 Hz, 2H), 4.48-4.34 (m, 2H), 4.01 (t, J = 5.3 Hz, 2H), 3.59-3.52 (m, 2H), 3.42-3.38 (m, 2H), 3.36-3.32 (m, 1H), 3.28-3.20 (m, 1H), 2.95-2.83 (m, 1H), 2.82-2.73 (m, 1H), 2.56-2.42 (m, 1H), 2.23-2.13 (m, 1H), 1.73 (dd, J = 6.5, 1.6 Hz, 3H). |
| D464 | 704.1 | ¹H NMR (300 MHz, DMSO-d6) δ 11.04 (s, 1H), 8.22 (s, 1H), 8.08-7.95 (m, 3H), 7.92 (s, 1H), 7.79 (s, 1H), 7.67 (s, 2H), 7.05 (s, 1H), 5.82-5.66 (m, 1H), 5.66-5.51 (m, 1H), 5.18 (dd, J = 13.2, 5.1 Hz, 1H), 4.68-4.46 (m, 3H), 4.41 (d, J = 6.0 Hz, 2H), 3.51 (s, 2H), 3.02-2.84 (m, 8H), 2.62 (d, J = 17.0 Hz, 1H), 2.49-2.34 (m, 1H), 2.05 (dd, J = 12.7, 6.4 Hz, 1H), 1.65 (dd, J = 6.3, 1.4 Hz, 3H). |
| D465 | 680.4 | ¹H NMR (400 MHz, Methanol-d4) δ 8.06 (s, 1H), 7.86 (s, 1H), 7.68-7.60 (m, 2H), 7.52 (dd, J = 7.9, 1.8 Hz, 1H), 7.27 (d, J = 8.2 Hz, 1H), 6.79-6.73 (m, 2H), 6.67 (dd, J = 8.2, 2.3 Hz, 1H), 5.82-5.68 (m, 1H), 5.61-5.47 (m, 1H), 5.02 (dd, J = 13.3, 5.2 Hz, 1H), 4.39 (d, J = 6.3 Hz, 2H), 4.34-4.20 (m, 2H), 3.71 (s, 2H), 3.59 (s, 4H), 2.87-2.74 (m, 1H), 2.72-2.65 (m, 1H), 2.62-2.51 (m, 4H), 2.45-2.31 (m, 1H), 2.10-2.03 (m, 1H), 1.87-1.81 (m, 4H), 1.63 (dd, J = 6.5, 1.5 Hz, 3H). |

| Compound No. | LCMS | ¹H NMR |
|---|---|---|
| D466 | 640.4 | ¹H NMR (300 MHz, DMSO-d6) δ 11.05 (s, 1H), 8.32 (s, 1H), 8.02-7.76 (m, 4H), 7.61-7.49 (m, 1H), 7.43-7.27 (m, 2H), 7.16 (s, 1H), 5.90-5.76 (m, 1H), 5.74-5.60 (m, 1H), 5.18 (dd, J = 13.2, 5.1 Hz, 1H), 4.88-4.57 (m, 1H), 4.54-4.38 (m, 3H), 4.36-4.24 (m, 1H), 4.10-3.56 (m, 3H), 3.32-3.14 (m, 3H), 3.07-2.90 (m, 2H), 2.75-2.62 (m, 3H), 2.52-2.38 (m, 1H), 2.14-2.04 (m, 1H), 1.78-1.70 (m, 3H). |
| D467 | 719.45 | ¹H NMR (400 MHz, DMSO-d6) δ 11.18 (d, J = 6.1 Hz, 1H), 10.96 (s, 1H), 8.94 (s, 1H, TFA), 7.40 (d, J = 8.9 Hz, 1H), 7.11 (s, 1H), 6.89 (s, 2H), 6.70 (h, J = 2.3 Hz, 2H), 6.35 (s, 1H), 5.67-5.55 (m, 1H), 5.45-5.29 (m, 1H), 5.15 (d, J = 5.5 Hz, 2H), 5.07 (dd, J = 13.2, 5.1 Hz, 1H), 4.32 (d, J = 16.7 Hz, 1H), 4.25 (d, J = 4.6 Hz, 2H), 4.19 (d, J = 16.6 Hz, 1H), 3.93 (s, 6H), 3.75 (s, 2H), 3.64 (s, 2H), 3.41-3.33 (m, 2H), 3.11 (q, J = 11.1 Hz, 2H), 2.90 (ddd, J = 17.5, 13.4, 5.4 Hz, 1H), 2.70-2.52 (m, 1H), 2.39 (dd, J = 13.2, 8.5 Hz, 1H), 2.34 (s, 3H), 2.12 (d, J = 13.9 Hz, 2H), 2.04-1.94 (m, 3H), 1.62 (dd, J = 6.6, 1.6 Hz, 3H). |
| D468 | 679.5 | ¹H NMR (400 MHz, DMSO-d6) δ 11.19 (d, J = 6.2 Hz, 1H), 10.98 (s, 1H), 9.42 (s, 1H, TFA), 7.50 (d, J = 8.4 Hz, 1H), 7.32 (dd, J = 8.4, 2.4 Hz, 1H), 7.29-7.20 (m, 1H), 7.12 (d, J = 6.0 Hz, 1H), 6.90 (s, 2H), 6.36 (s, 1H), 5.66-5.54 (m, 1H), 5.45-5.29 (m, 1H), 5.15 (d, J = 5.6 Hz, 1H), 5.10 (dd, J = 13.3, 5.1 Hz, 1H), 4.36 (d, J = 16.8 Hz, 3H), 4.23 (d, J = 16.9 Hz, 1H), 3.94 (s, 6H), 3.89 (d, J = 12.9 Hz, 2H), 3.74 (d, J = 7.0 Hz, 1H), 3.54-3.46 (m, 2H), 3.29 (d, J = 11.7 Hz, 2H), 3.14 (t, J = 12.1 Hz, 2H), 2.91 (ddd, J = 17.6, 13.6, 5.4 Hz, 1H), 2.60 (d, J = 17.0 Hz, 1H), 2.46-2.33 (m, 1H), 2.34 (s, 3H), 2.03-1.95 (m, 1H), 1.81-1.59 (m, 3H). |
| D469 | 654.25 | ¹H NMR (400 MHz, DMSO-d6) δ 10.96 (s, 1H), 8.35 (s, 1H), 7.88 (s, 1H), 7.41 (d, J = 8.4 Hz, 1H), 7.29-7.20 (m, 1H), 7.20-7.06 (m, 2H), 6.92 (s, 2H), 5.09 (dd, J = 13.3, 5.1 Hz, 1H), 4.37-4.15 (m, 2H), 3.86 (s, 6H), 3.66-3.51 (m, 2H), 3.43 (s, 3H), 3.11-2.85 (m, 5H), 2.70-2.55 (m, 3H), 2.43-2.31 (m, 1H), 2.05-1.93 (m, 1H), 1.39-1.14 (m, 6H). |
| D470 | 666.735 | |
| D471 | 666.45 | ¹H NMR (300 MHz, Methanol-d4) δ 9.62 (s, 1H), 8.72 (d, J = 6.3 Hz, 1H), 8.15 (d, J = 7.0 Hz, 1H), 8.05 (d, J = 6.3 Hz, 1H), 7.93 (d, J = 6.3 Hz, 1H), 7.36 (d, J = 2.4 Hz, 1H), 6.90 (s, 2H), 6.79 (dd, J = 7.1, 2.4 Hz, 1H), 4.96 (d, J = 9.1 Hz, 1H), 4.47 (s, 2H), 4.27 (s, 2H), 4.15 (s, 2H), 3.99 (s, 6H), 3.76 (s, 3H), 3.63 (d, J = 13.1 Hz, 2H), 3.25 (t, J = 12.2 Hz, 2H), 2.94-2.70 (m, 2H), 2.27 (dt, J = 28.7, 13.5 Hz, 6H). |
| D472 | 667.20 | ¹H NMR (300 MHz, Methanol-d4) δ 9.55 (d, J = 0.8 Hz, 1H), 8.70 (d, J = 5.8 Hz, 1H), 8.56 (d, J = 5.0 Hz, 1H), 7.77 (s, 1H), 7.64 (d, J = 5.8, 0.9 Hz, 1H), 7.28 (d, J = 4.9 Hz, 1H), 6.85 (s, 2H), 4.82 (dd, J = 12.6, 5.4 Hz, 1H), 4.20 (s, 2H), 4.06-3.91 (m, 10H), 3.72 (s, 3H), 3.06 (d, J = 27.6 Hz, 4H), 2.95-2.65 (m, 2H), 2.43-2.27 (m, 1H), 2.20 (s, 1H), 2.14-1.99 (m, 4H). |
| D473 | 667.20 | ¹H NMR (400 MHz, DMSO-d6) δ 10.93 (s, 1H), 9.48 (s, 1H), 9.02 (d, J = 15.8 Hz, 1H), 8.73 (dd, J = 16.7, 7.0 Hz, 2H), 8.40 (s, 1H), 8.10 (s, 1H), 7.91 (s, 1H), 7.60 (d, J = 5.7 Hz, 1H), 6.88 (s, 2H), 4.84-4.73 (m, 1H), 4.30 (d, J = 4.6 Hz, 2H), 4.02 (s, 2H), 3.91 (s, 8H), 3.62 (s, 3H), 3.40 (d, J = 12.2 Hz, 2H), 3.21-3.02 (m, 2H), 2.82 (s, 1H), 2.55 (d, J = 3.7 Hz, 1H), 2.25-2.11 (m, 3H), 2.08-1.91 (m, 3H). |
| D474 | 677.45 | ¹H NMR (300 MHz, DMSO-d6) δ 10.98 (s, 1H), 9.45 (s, 1H), 8.74 (d, J = 5.7 Hz, 1H), 7.89 (s, 1H), 7.59 (d, J = 5.6 Hz, 1H), 7.38 (d, J = 8.1 Hz, 1H), 6.76 (s, 2H), 6.70-6.61 (m, 2H), 4.80-4.67 (m, 1H), 4.33 (s, 2H), 3.83 (s, 6H), 3.67-3.53 (m, 9H), 3.03-2.88 (m, 2H), 2.78-2.64 (m, 2H), 2.60-2.53 (m, 4H), 1.82-1.69 (m, 4H). |
| D475 | 748.35 | ¹H NMR (400 MHz, Methanol-d4) δ 7.42 (d, J = 8.2 Hz, 1H), 7.21 (s, 1H), 7.03 (d, J = 3.2 Hz, 1H), 6.90-6.85 (m, 3H), 6.82-6.78 (m, 2H), 5.14 (dd, J = 13.2, 5.1 Hz, 1H), 4.64-4.49 (m, 2H), 4.45-4.34 (m, 4H), 4.25-4.13 (m, 2H), 3.97 (s, 6H), 3.87-3.71 (m, 4H), 3.66 (s, 3H), 3.62-3.46 (m, 5H), 3.44-3.38 (m, 4H), 3.16-3.05 (m, 1H), 2.98-2.86 (m, 1H), 2.85-2.75 (m, 1H), 2.56-2.42 (m, 1H), 2.32-2.06 (m, 5H). |
| D476 | 693.2 | ¹H NMR (400 MHz, DMSO-d6) δ 11.90 (s, 1H), 11.08 (s, 1H), 8.25 (s, 1H, FA), 7.63 (d, J = 8.3 Hz, 1H), 7.43 (s, 1H), 6.84-6.75 (m, 3H), 6.65 (dd, J = 8.5, 2.2 Hz, 1H), 6.29 (s, 1H), 5.05 (dd, J = 12.9, 5.4 Hz, 1H), 3.84 (s, 6H), 3.73 (s, 4H), 3.58 (s, 3H), 3.52 (s, 2H), 2.94-2.85 (m, 1H), 2.62-2.55 (m, 2H), 2.44-2.37 (m, 3H), 2.37-2.31 (m, 4H), 2.06-1.96 (m, 1H), 1.73 (t, J = 5.2 Hz, 4H). |

Example 85—Preparation of Compounds DD11-DD16

In analogy to the procedures described in the examples above, compounds DD11-DD16 were prepared using the appropriate starting materials.

| Compound No. | LCMS | $^1$H NMR |
|---|---|---|
| DD11 | 785.35 | $^1$H NMR (300 MHz, DMSO) δ 11.13 (s, 1H), 8.20 (s, FA, 1H), 8.09 (d, J = 8.3 Hz, 1H), 7.88-7.80 (m, 2H), 7.74 (s, 1H), 7.56-7.48 (m, 1H), 7.47-7.39 (m, 1H), 7.39-7.35 (m, 1H), 7.34-7.23 (m, 2H), 6.73 (s, 2H), 5.12 (dd, J = 12.9, 5.4 Hz, 1H), 5.06-4.91 (m, 1H), 3.81 (s, 6H), 3.70 (s, 2H), 3.58-3.50 (m, 1H), 3.00-2.81 (m, 4H), 2.66-2.53 (m, 1H), 2.49-2.38 (m, 4H), 2.35-2.18 (m, 6H), 2.14-1.99 (m, 3H), 1.86-1.75 (m, 2H), 1.72-1.61 (m, 4H), 1.60-1.49 (m, 3H), 1.27-1.07 (m, 2H). |
| DD12 | 519.45 | $^1$H NMR (400 MHz, DMSO-d6) δ 10.97 (s, 1H), 7.37 (d, J = 8.0 Hz, 1H), 7.28 (t, J = 8.3 Hz, 1H), 6.72-6.64 (m, 4H), 5.08 (dd, J = 13.3, 5.1 Hz, 1H), 4.35-4.12 (m, 2H), 3.79 (s, 6H), 3.64 (s, 2H), 3.57 (s, 4H), 2.98-2.84 (m, 1H), 2.64-2.55 (m, 5H), 2.45-2.33 (m, 1H), 2.02-1.94 (m, 1H), 1.79-1.72 (m, 4H). |
| DD13 | 676.35 | $^1$H NMR (400 MHz, DMSO-d6) δ 10.98 (s, 1H), 8.30 (dd, J = 8.2, 1.4 Hz, 1H), 7.71 (dd, J = 7.4, 1.4 Hz, 1H), 7.58 (t, J = 7.7 Hz, 1H), 7.45 (d, J = 7.7 Hz, 1H), 7.38 (d, J = 8.0 Hz, 1H), 6.69 (d, J = 4.3 Hz, 4H), 6.56 (d, J = 7.6 Hz, 1H), 5.09 (dd, J = 13.3, 5.1 Hz, 1H), 4.36-4.13 (m, 2H), 3.82 (s, 7H), 3.60 (d, J = 4.4 Hz, 7H), 3.53 (s, 3H), 2.98-2.84 (m, 1H), 2.64-2.55 (m, 2H), 2.38 (dd, J = 13.2, 4.6 Hz, 2H), 2.03-1.94 (m, 1H), 1.75 (t, J = 5.4 Hz, 4H). |
| DD14 | 479.30 | $^1$H NMR (300 MHz, Methanol-d4) δ 8.52 (s, 0.48H, FA), 7.53-7.40 (m, 2H), 7.40-7.32 (m, 2H), 6.78 (d, J = 8.4 Hz, 2H) 5.15 (dd, J = 13.3, 5.1 Hz, 1H), 4.52-4.35 (m, 2H), 4.27 (s, 2H), 3.93 (s, 6H), 3.62-3.39 (m, 4H), 3.30-3.18 (m, 4H), 3.12-2.73 (m, 2H), 2.62-2.41 (m, 1H), 2.26-2.12 (m, 1H). |
| DD15 | 652.30 | $^1$H NMR (300 MHz, DMSO-d6) δ 12.70 (s, 1H), 10.97 (s, 1H), 8.22-8.13 (m, 3H), 7.36 (d, J = 8.0 Hz, 1H), 6.74-6.34 (m, 4H), 5.07 (dd, J = 13.6, 5.2 Hz, 1H), 4.34-4.14 (m, 2H), 3.88 (s, 6H), 3.65-3.57 (m, 6H), 2.94-2.86 (m, 1H), 2.67-2.59 (m, 1H), 2.47-2.26 (m, 5H), 2.04-1.93 (m, 1H), 1.84-1.59 (m, 4H). |
| DD16 | 518.15 | $^1$H NMR (300 MHz, DMSO-d6) δ 10.98 (s, 1H), 8.47 (d, J = 7.9 Hz, 1H), 7.78 (d, J = 7.5 Hz, 1H), 7.66-7.53 (m, 1H), 7.45 (m, J = 8.4 Hz, 1H), 7.37-7.08 (m, 2H), 6.74 (m, J = 7.5, 0.9 Hz, 1H), 5.11 (dd, J = 13.2, 5.1 Hz, 1H), 4.44-4.13 (m, 2H), 4.00 (s, 1H), 3.89-3.67 (m, 2H), 3.52 (s, 3H), 3.00-2.91 (m, 3H), 2.63 (m, 1H), 2.45-2.23 (m, 1H), 2.11-1.94(m, 1H), 1.95-1.81 (m, 2H), 1.71-1.61 (m, 2H). |

Example 86—BRD9 Bromodomain TR-FRET Competition Binding Assay

This example demonstrates the ability of the compounds of the disclosure to biochemically inhibit BRD9 bromodomain in a competition binding assay.

Procedure: His-Flag-BRD9 (P133-K239; Swiss Prot Q9H8M2; SEQ ID NO:1 mgsshhhhhhenlyfq/gdykddddkgslevlfqg/PAENEST-PIQQLLEHFLRQLQRKDPHGFFAFPVTDAIAPGYSMII KHPMDFGTMKDKIVANEYKSVTEFKADFKLMCD-NAMTYNRPDTVYYKLAKKILHAGFKMMSK) was cloned, expressed, purified, and then treated with TEV protease. Cleaved His tag was removed by purification. The binding of a biotinylated small molecule ligand of BRD9 was assessed via the LANCE® TR-FRET platform (PerkinElmer), and the compounds were assayed for inhibitory activity against this interaction.

A mixture of biotinylated-ligand and SureLight™ Allophycocyanin-Streptavidin (APC-SA, PerkinElmer AD0201) in 50 mM HEPES (pH 7.4), 50 mM NaCl, 1 mM TCEP (pH 7), 0.01% (v/v) Tween-20, 0.01% (w/v) bovine serum albumin was added to a white 384-well PerkinElmer Proxiplate Plus plate. DMSO or 3-fold serially diluted compounds were then added to the Proxiplate followed by addition of Flag-BRD9. After a 10-minute incubation at room temperature, Eu-W1024 anti-FLAG (PerkinElmer, AD0273) was added. The final reaction mixture that contained 3.75 nM biotinylated ligand, 3 nM Flag-BRD9, 7.5 nM SureLight™ Allophycocyanin-Streptavidin, and 0.2 nM Eu-W1024 anti-FLAG was incubated at room temperature for 90 minutes.

Results: The plates were then read on a PerkinElmer Envision plate reader to determine the ratio of emission at 665 nm over 615 nm. Data was normalized to a DMSO control (100%) and a no protein control (0%) and then fit to a four parameter, non-linear curve fit to calculate $IC_{50}$ (UM) values as shown in Table 4. As shown by the results in Table 4, a number of compounds of the present disclosure exhibit an $IC_{50}$ value of <1 UM for BRD9 binding, indicating their affinity for targeting BRD9.

TABLE 4

Bromodomain 9 (BRD9) TR-FRET Binding of Compounds of the Disclosure

| Compound No. | Bromodomain TR-FRET BRD9 $IC_{50}$ (nM) |
|---|---|
| D1 | +++ |
| D2 | ++++ |
| D3 | ++++ |
| D4 | ++++ |
| D5 | ++++ |
| D6 | ++++ |
| D7 | ++++ |
| D8 | ++++ |
| D9 | ++++ |
| D10 | +++ |

TABLE 4-continued

Bromodomain 9 (BRD9) TR-FRET Binding of Compounds of the Disclosure

| Compound No. | Bromodomain TR-FRET BRD9 IC$_{50}$ (nM) |
|---|---|
| D11 | +++ |
| D12 | ++++ |
| D13 | ++++ |
| D14 | ++++ |
| D15 | ++++ |
| D16 | NT |
| D17 | NT |
| D18 | NT |
| D19 | NT |
| D20 | NT |
| D21 | NT |
| D22 | ++++ |
| D23 | ++++ |
| D24 | NT |
| D25 | ++++ |
| D26 | +++ |
| D27 | ++++ |
| D28 | NT |
| D29 | NT |
| D30 | ++++ |
| D31 | ++++ |
| D32 | ++++ |
| D33 | ++++ |
| D34 | ++++ |
| D35 | ++++ |
| D36 | ++++ |
| D37 | ++++ |
| D38 | ++++ |
| D39 | ++++ |
| D40 | ++++ |
| D41 | ++++ |
| D42 | NT |
| D43 | NT |
| D44 | NT |
| D45 | NT |
| D46 | NT |
| D47 | NT |
| D48 | NT |
| D49 | NT |
| D50 | NT |
| D51 | NT |
| D52 | ++++ |
| D53 | ++++ |
| D54 | +++ |
| D55 | +++ |
| D56 | ++++ |
| D57 | +++ |
| D58 | ++++ |
| D59 | ++++ |
| D60 | ++++ |
| D61 | ++++ |
| D62 | +++ |
| D63 | +++ |
| D64 | +++ |
| D65 | +++ |
| D66 | +++ |
| D67 | ++++ |
| D68 | ++++ |
| D69 | ++++ |
| D70 | +++ |
| D71 | ++++ |
| D72 | ++++ |
| D73 | +++ |
| D74 | ++++ |
| D75 | NT |
| D76 | NT |
| D77 | NT |
| D78 | NT |
| D79 | NT |
| D80 | NT |
| D81 | NT |
| D82 | NT |
| D83 | NT |
| D84 | +++ |
| D85 | +++ |
| D86 | +++ |
| D87 | ++++ |
| D88 | ++++ |
| D89 | ++++ |
| D90 | ++++ |
| D91 | +++ |
| D92 | ++++ |
| D93 | ++++ |
| D94 | +++ |
| D95 | +++ |
| D96 | ++++ |
| D97 | ++++ |
| D98 | ++ |
| D99 | +++ |
| D100 | ++++ |
| D101 | ++++ |
| D102 | ++++ |
| D103 | +++ |
| D104 | +++ |
| D105 | +++ |
| D106 | +++ |
| D107 | +++ |
| D108 | ++++ |
| D109 | ++++ |
| D110 | +++ |
| D111 | ++++ |
| D112 | ++++ |
| D113 | ++++ |
| D114 | ++++ |
| D115 | +++ |
| D116 | ++++ |
| D117 | ++++ |
| D118 | ++++ |
| D119 | ++++ |
| D120 | +++ |
| D121 | +++ |
| D122 | ++++ |
| D123 | ++++ |
| D124 | ++++ |
| D125 | ++++ |
| D126 | +++ |
| D127 | ++++ |
| D128 | +++ |
| D129 | ++++ |
| D130 | ++++ |
| D131 | ++++ |
| D132 | ++++ |
| D133 | ++++ |
| D134 | +++ |
| D135 | +++ |
| D136 | ++++ |
| D137 | ++++ |
| D138 | ++++ |
| D139 | ++++ |
| D140 | ++++ |
| D141 | +++ |
| D142 | +++ |
| D143 | ++++ |
| D144 | +++ |
| D145 | +++ |
| D146 | ++++ |
| D147 | +++ |
| D148 | +++ |
| D149 | ++++ |
| D150 | ++++ |
| D151 | ++++ |
| D152 | ++++ |
| D153 | +++ |
| D154 | ++++ |
| D155 | ++++ |
| D156 | ++++ |

TABLE 4-continued

Bromodomain 9 (BRD9) TR-FRET Binding of Compounds of the Disclosure

| Compound No. | Bromodomain TR-FRET BRD9 IC$_{50}$ (nM) |
|---|---|
| D157 | +++ |
| D158 | ++++ |
| D159 | ++++ |
| D160 | ++++ |
| D161 | ++++ |
| D162 | +++ |
| D163 | ++++ |
| D164 | ++++ |
| D165 | +++ |
| D166 | ++++ |
| D167 | ++++ |
| D168 | ++++ |
| D169 | ++++ |
| D170 | +++ |
| D171 | +++ |
| D172 | ++++ |
| D173 | +++ |
| D174 | +++ |
| D175 | +++ |
| D176 | ++++ |
| D177 | ++++ |

"+" indicates inhibitory effect of ≥1000 nM;
"++" indicates inhibitory effect of ≥100 nM;
"+++" indicates inhibitory effect of ≥10 nM;
"++++" indicates inhibitory effect of <10 nM;
"NT" indicates not tested

Example 87—SYO1 BRD9 NanoLuc Degradation Assay

This example demonstrates the ability of the compounds of the disclosure to degrade a Nanoluciferase-BRD9 fusion protein in a cell-based degradation assay.

Procedure: A stable SYO-1 cell line expressing 3×FLAG-NLuc-BRD9 was generated. On day 0 cells were seeded in 30 UL media into each well of 384-well cell culture plates. The seeding density was 8000 cells/well. On day 1, cells were treated with 30 nL DMSO or 30 nL of 3-fold serially DMSO-diluted compounds (10 points in duplicates with 1 µM as final top dose). Subsequently plates were incubated for 6 hours in a standard tissue culture incubator and equilibrated at room temperature for 15 minutes. Nanoluciferase activity was measured by adding 15 µL of freshly prepared Nano-Glo Luciferase Assay Reagent (Promega N1130), shaking the plates for 10 minutes and reading the bioluminescence using an EnVision reader.

Results: The Inhibition % was calculated using the following formula: % Inhibition=100×(Lum$_{Hc}$−Lum$_{sample}$)/(Lum$_{Hc}$−Lum$_{Lc}$). DMSO treated cells are employed as High Control (HC) and 1 UM of a known BRD9 degrader standard treated cells are employed as Low Control (LC). The data was fit to a four parameter, non-linear curve fit to calculate IC$_{50}$ (UM) values as shown in Table 5A, Table 5B, and Table 5C. As shown by the results in Table 5A, Table 5B, and Table 5C, a number of compounds of the present disclosure exhibit an IC$_{50}$ value of <1 UM for the degradation of BRD9, indicating their use as compounds for reducing the levels and/or activity of BRD9 and their potential for treating BRD9-related disorders.

TABLE 5A

SYO1 Bromodomain 9-NanoLuc Degradation by Compounds of the Disclosure

| Compound No. | SYO1 BRD9-NanoLuc degradation IC$_{50}$ (nM) |
|---|---|
| D1 | ++++ |
| D2 | +++ |
| D3 | ++++ |
| D4 | +++ |
| D5 | +++ |
| D6 | ++++ |
| D7 | +++ |
| D8 | + |
| D9 | ++++ |
| D10 | ++++ |
| D11 | ++++ |
| D12 | ++++ |
| D13 | ++++ |
| D14 | ++++ |
| D15 | ++++ |
| D16 | ++++ |
| D17 | ++++ |
| D18 | ++++ |
| D19 | ++++ |
| D20 | ++++ |
| D21 | + |
| D22 | +++ |
| D23 | ++++ |
| D24 | +++ |
| D25 | ++ |
| D26 | + |
| D27 | +++ |
| D28 | ++ |
| D29 | +++ |
| D30 | +++ |
| D31 | +++ |
| D32 | +++ |
| D33 | ++++ |
| D34 | ++++ |
| D35 | ++++ |
| D36 | ++ |
| D37 | ++++ |
| D38 | ++++ |
| D39 | ++++ |
| D40 | ++++ |
| D41 | +++ |
| D42 | ++++ |
| D43 | ++ |
| D44 | ++++ |
| D45 | ++++ |
| D46 | ++++ |
| D47 | ++++ |
| D48 | +++ |
| D49 | + |
| D50 | ++++ |
| D51 | ++++ |
| D52 | ++++ |
| D53 | ++++ |
| D54 | +++ |
| D55 | ++ |
| D56 | ++++ |
| D57 | ++++ |
| D58 | ++++ |
| D59 | ++++ |
| D60 | ++++ |
| D61 | +++ |
| D62 | ++ |
| D63 | +++ |
| D64 | ++ |
| D65 | ++ |
| D66 | ++ |
| D67 | ++++ |
| D68 | ++ |
| D69 | ++++ |
| D70 | +++ |
| D71 | ++++ |
| D72 | ++++ |
| D73 | ++++ |
| D74 | ++ |

TABLE 5A-continued

SYO1 Bromodomain 9-NanoLuc Degradation by Compounds of the Disclosure

| Compound No. | SYO1 BRD9-NanoLuc degradation IC$_{50}$ (nM) |
|---|---|
| D75 | ++++ |
| D76 | ++++ |
| D77 | ++ |
| D78 | +++ |
| D79 | ++ |
| D80 | ++++ |
| D81 | ++++ |
| D82 | +++ |
| D83 | ++ |
| D84 | + |
| D85 | ++ |
| D86 | ++ |
| D87 | +++ |
| D88 | +++ |
| D89 | ++++ |
| D90 | +++ |
| D91 | +++ |
| D92 | ++++ |
| D93 | +++ |
| D94 | +++ |
| D95 | ++ |
| D96 | +++ |
| D97 | +++ |
| D98 | ++ |
| D99 | +++ |
| D100 | ++++ |
| D101 | ++ |
| D102 | +++ |
| D103 | +++ |
| D104 | ++ |
| D105 | ++ |
| D106 | ++ |
| D107 | +++ |
| D108 | ++++ |
| D109 | +++ |
| D110 | +++ |
| D111 | +++ |
| D112 | ++ |
| D113 | ++++ |
| D114 | +++ |
| D115 | ++ |
| D116 | +++ |
| D117 | ++ |
| D118 | +++ |
| D119 | +++ |
| D120 | +++ |
| D121 | +++ |
| D122 | ++++ |
| D123 | ++++ |
| D124 | ++++ |
| D125 | +++ |
| D126 | ++ |
| D127 | ++ |
| D128 | ++++ |
| D129 | ++++ |
| D130 | ++++ |
| D131 | ++++ |
| D132 | ++++ |
| D133 | +++ |
| D134 | +++ |
| D135 | ++ |
| D136 | ++ |
| D137 | +++ |
| D138 | +++ |
| D139 | ++ |
| D140 | +++ |
| D141 | ++ |
| D142 | +++ |
| D143 | ++++ |
| D144 | +++ |
| D145 | +++ |
| D146 | +++ |
| D147 | +++ |
| D148 | ++ |
| D149 | +++ |
| D150 | +++ |
| D151 | +++ |
| D152 | ++++ |
| D153 | +++ |
| D154 | +++ |
| D155 | +++ |
| D156 | +++ |
| D157 | ++++ |
| D158 | +++ |
| D159 | +++ |
| D160 | +++ |
| D161 | +++ |
| D162 | +++ |
| D163 | +++ |
| D164 | +++ |
| D165 | +++ |
| D166 | +++ |
| D167 | ++++ |
| D168 | ++++ |
| D169 | +++ |
| D170 | ++++ |
| D171 | ++++ |
| D172 | +++ |
| D173 | ++++ |
| D174 | ++ |
| D175 | +++ |
| D176 | ++++ |
| D177 | +++ |

"+" indicates inhibitory effect of ≥1000 nM;
"++" indicates inhibitory effect of ≥100 nM;
"+++" indicates inhibitory effect of ≥10 nM;
"++++" indicates inhibitory effect of <10 nM;
"NT" indicates not tested

TABLE 5B

SYO1 Bromodomain 9-NanoLuc Degradation by Compounds of the Disclosure

| Compound No. | SYO1 BRD9-NanoLuc degradation IC$_{50}$ (nM) |
|---|---|
| D178 | ++++ |
| D179 | +++ |
| D180 | ++++ |
| D181 | ++ |
| D182 | +++ |
| D183 | ++ |
| D184 | ++++ |
| D185 | ++++ |
| D186 | ++++ |
| D187 | ++++ |
| D188 | ++++ |
| D189 | ++++ |
| D190 | +++ |
| D191 | ++++ |
| D192 | ++ |
| D193 | ++ |
| D194 | ++++ |
| D195 | +++ |
| D196 | +++ |
| D197 | ++++ |
| D198 | ++++ |
| D199 | ++++ |
| D200 | +++ |
| D201 | ++++ |
| D202 | ++++ |
| D203 | ++++ |
| D204 | ++++ |
| D205 | ++++ |

TABLE 5B-continued

SYO1 Bromodomain 9-NanoLuc Degradation by Compounds of the Disclosure

| Compound No. | SYO1 BRD9-NanoLuc degradation IC$_{50}$ (nM) |
|---|---|
| D206 | ++++ |
| D207 | ++++ |
| D208 | ++++ |
| D209 | ++ |
| D210 | +++ |
| D211 | ++++ |
| D212 | +++ |
| D213 | ++++ |
| D214 | ++++ |
| D215 | ++++ |
| D216 | ++++ |
| D217 | ++++ |
| D218 | ++++ |
| D219 | ++++ |
| D220 | ++++ |
| D221 | ++++ |
| D222 | ++++ |
| D223 | ++++ |
| D224 | ++++ |
| D225 | ++++ |
| D226 | ++++ |
| D227 | ++++ |
| D228 | ++++ |
| D229 | ++++ |
| D230 | ++++ |
| D231 | ++ |
| D232 | +++ |
| D233 | ++ |
| D234 | +++ |
| D235 | ++++ |
| D236 | ++++ |
| D237 | ++++ |
| D238 | ++++ |
| D239 | ++++ |
| D240 | ++++ |
| D241 | ++++ |
| D242 | ++++ |
| D243 | ++++ |
| D244 | ++++ |
| D245 | +++ |
| D246 | ++++ |
| D247 | ++++ |
| D248 | +++ |
| D249 | +++ |
| D250 | ++++ |
| D251 | ++++ |
| D252 | ++++ |
| D253 | ++++ |
| D254 | ++++ |
| D255 | ++++ |
| D256 | ++++ |
| D257 | ++++ |
| D258 | ++++ |
| D259 | ++++ |
| D260 | ++++ |
| D261 | ++++ |
| D262 | ++++ |
| D263 | ++++ |
| D264 | +++ |
| D265 | ++ |
| D266 | +++ |
| D267 | +++ |
| D268 | ++++ |
| D269 | ++++ |
| D270 | +++ |
| D271 | ++++ |
| D272 | ++++ |
| D273 | ++++ |
| D274 | ++++ |
| D275 | ++++ |
| D276 | +++ |
| D277 | ++++ |
| D278 | +++ |
| D279 | ++++ |
| D280 | ++++ |
| D281 | +++ |
| D282 | ++ |
| D283 | ++ |
| D284 | +++ |
| D285 | ++ |
| D286 | +++ |
| D287 | ++++ |
| D288 | ++++ |
| D289 | ++++ |
| D290 | ++++ |
| D291 | ++++ |
| D292 | ++ |
| D293 | +++ |
| D294 | ++ |
| D295 | ++ |
| D296 | ++ |
| D297 | ++++ |
| D298 | ++++ |
| D299 | ++++ |
| D300 | ++++ |
| D301 | ++++ |
| D302 | ++++ |
| D303 | +++ |
| D304 | ++++ |
| D305 | ++ |
| D306 | ++++ |
| D307 | ++++ |
| D308 | ++++ |
| D309 | +++ |
| D310 | ++++ |
| D311 | +++ |
| D312 | ++++ |
| D313 | ++++ |
| D314 | +++ |
| D315 | ++++ |
| D316 | ++++ |
| D317 | +++ |
| D318 | ++++ |
| D319 | ++++ |
| D320 | ++++ |
| D321 | ++++ |
| D322 | ++++ |
| D323 | ++++ |
| D324 | ++++ |
| D325 | ++++ |
| D326 | ++++ |
| D327 | ++++ |
| D328 | ++++ |
| D329 | ++++ |
| D330 | ++++ |
| D331 | ++++ |
| D332 | ++++ |
| D333 | ++++ |
| D334 | + |
| D335 | ++++ |
| D336 | ++++ |
| D337 | ++++ |
| D338 | ++++ |
| D339 | ++++ |
| D340 | ++++ |
| D341 | ++++ |
| D342 | + |
| D343 | ++++ |
| D344 | ++++ |
| D345 | ++++ |
| D346 | ++++ |
| D347 | ++++ |
| D348 | ++++ |
| D349 | ++++ |
| D350 | ++ |
| D351 | + |
| D352 | + |
| D353 | ++++ |

TABLE 5B-continued

SYO1 Bromodomain 9-NanoLuc Degradation by Compounds of the Disclosure

| Compound No. | SYO1 BRD9-NanoLuc degradation IC$_{50}$ (nM) |
| --- | --- |
| D354 | ++++ |
| D355 | + |
| D356 | ++++ |
| D357 | ++++ |
| D358 | ++++ |
| D359 | ++++ |
| D360 | ++++ |
| D361 | ++++ |
| D362 | ++++ |
| D363 | ++++ |
| D364 | ++ |
| D365 | +++ |
| D366 | ++++ |
| D367 | ++++ |
| D368 | ++++ |
| D369 | ++++ |
| D370 | ++++ |
| D371 | ++++ |
| DD1 | + |
| DD2 | ++ |
| DD3 | + |
| DD4 | ++++ |
| DD5 | +++ |
| DD6 | +++ |
| DD7 | ++++ |
| DD8 | ++++ |
| DD9 | ++++ |
| DD10 | ++ |

"+" indicates inhibitory effect of ≥1000 nM;
"++" indicates inhibitory effect of ≥100 nM;
"+++" indicates inhibitory effect of ≥10 nM;
"++++" indicates inhibitory effect of <10 nM;
"NT" indicates not tested

TABLE 5C

SYO1 Bromodomain 9-NanoLuc Degradation by Compounds of the Disclosure

| Compound No. | SYO1 BRD9-NanoLuc degradation IC$_{50}$ (nM) |
| --- | --- |
| D372 | ++++ |
| D373 | ++++ |
| D374 | ++++ |
| D375 | ++++ |
| D376 | ++++ |
| D377 | ++++ |
| D378 | ++++ |
| D379 | ++++ |
| D380 | +++ |
| D381 | ++++ |
| D382 | ++++ |
| D383 | + |
| D384 | ++++ |
| D385 | ++++ |
| D386 | ++++ |
| D387 | ++++ |
| D388 | ++++ |
| D389 | + |
| D390 | + |
| D391 | ++ |
| D392 | +++ |
| D393 | +++ |
| D394 | + |
| D395 | ++++ |
| D396 | ++++ |
| D397 | ++++ |
| D398 | ++++ |
| D399 | ++++ |
| D400 | ++++ |
| D401 | ++++ |
| D402 | ++++ |
| D403 | ++++ |
| D404 | ++++ |
| D405 | ++++ |
| D406 | ++++ |
| D407 | ++++ |
| D408 | ++++ |
| D409 | ++++ |
| D410 | ++++ |
| D411 | ++++ |
| D412 | ++++ |
| D413 | ++++ |
| D414 | ++++ |
| D415 | ++++ |
| D416 | ++++ |
| D417 | ++++ |
| D418 | ++++ |
| D419 | ++++ |
| D420 | ++++ |
| D421 | ++++ |
| D422 | ++++ |
| D423 | ++++ |
| D424 | ++++ |
| D425 | ++++ |
| D426 | ++++ |
| D427 | ++++ |
| D428 | ++++ |
| D429 | + |
| D430 | ++++ |
| D431 | ++++ |
| D432 | +++ |
| D433 | ++++ |
| D434 | ++++ |
| D435 | + |
| D436 | ++++ |
| D437 | + |
| D438 | ++++ |
| D439 | ++++ |
| D440 | ++++ |
| D441 | ++++ |
| D442 | ++++ |
| D443 | ++++ |
| D444 | ++++ |
| D445 | + |
| D446 | + |
| D447 | ++ |
| D448 | ++++ |
| D449 | +++ |
| D450 | ++++ |
| D451 | +++ |
| D452 | ++++ |
| D453 | ++++ |
| D454 | ++++ |
| D455 | ++++ |
| D456 | ++++ |
| D457 | ++++ |
| D458 | ++++ |
| D459 | ++++ |
| D460 | ++++ |
| D461 | +++ |
| D462 | ++++ |
| D463 | ++++ |
| D464 | + |
| D465 | ++++ |
| D466 | ++++ |
| D467 | + |
| D468 | + |
| D469 | NT |
| D470 | NT |
| D471 | ++++ |
| D472 | + |
| D473 | + |
| D474 | + |

TABLE 5C-continued

SYO1 Bromodomain 9-NanoLuc Degradation
by Compounds of the Disclosure

| Compound No. | SYO1 BRD9-NanoLuc degradation IC$_{50}$ (nM) |
|---|---|
| D475 | +++ |
| D476 | ++++ |
| DD11 | + |
| DD12 | + |
| DD13 | +++ |
| DD14 | + |
| DD15 | +++ |
| DD16 | +++ |

"+" indicates inhibitory effect of ≥1000 nM;
"++" indicates inhibitory effect of ≥100 nM;
"+++" indicates inhibitory effect of ≥10 nM;
"++++" indicates inhibitory effect of <10 nM;
"NT" indicates not tested

Other Embodiments

All publications, patents, and patent applications mentioned in this specification are incorporated herein by reference in their entirety to the same extent as if each individual publication, patent, or patent application was specifically and individually indicated to be incorporated by reference in its entirety. Where a term in the present application is found to be defined differently in a document incorporated herein by reference, the definition provided herein is to serve as the definition for the term.

While the invention has been described in connection with specific embodiments thereof, it will be understood that invention is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth, and follows in the scope of the claims.

Other embodiments are in the claims.

The invention claimed is:

1. A compound of Formula I:

A-L-B              Formula I or a pharmaceutically acceptable salt thereof, wherein:

A has the structure of Formula IIIc:

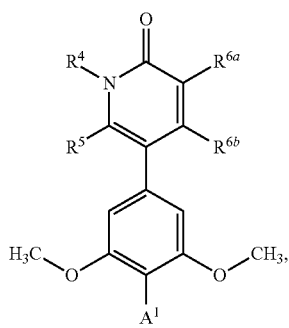

Formula IIIc wherein:

$A^1$ is a bond between L and A;

$R^4$ is -$CH_3$;

$R^5$ is H;

$R^{6a}$ is H, halogen, cyano, or optionally substituted $C_1$-$C_6$ alkyl;

$R^{6b}$ is H or —$CH_3$;

B has the structure of Formula AA0:

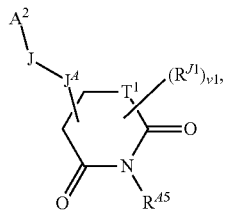

Formula AA0 wherein:

$A^2$ is a bond between B and L;

v1 is 0, 1, 2, 3, 4, or 5;

$R^{A5}$ is H;

$J^A$ is absent, O, optionally substituted amino, optionally substituted $C_1$-$C_6$ alkyl, or optionally substituted $C_1$-$C_6$ heteroalkyl;

J is absent, optionally substituted $C_3$-$C_{10}$ carbocyclylene, optionally substituted $C_6$-$C_{10}$ arylene, optionally substituted $C_2$-$C_9$ heterocyclylene, or optionally substituted $C_2$-$C_9$ heteroarylene;

L has the structure of Formula IIg:

$A^1$-$(E^1)$-$(F^1)$-$(E^3)_n$-$(F^2)_{o1}$-$A^2$      Formula IIg wherein:
each of n and o1 is, independently, 0 or 1;
E¹ is O, S, NR$^N$, optionally substituted $C_{1-10}$ alkylene, optionally substituted $C_{2-10}$ alkenylene, optionally substituted $C_{2-10}$ alkynylene, optionally substituted $C_2$-$C_{10}$ polyethylene glycol, or optionally substituted $C_{1-10}$ heteroalkylene;
E³ is optionally substituted $C_1$-$C_6$ alkylene, optionally substituted $C_1$-$C_6$ heteroalkylene, O, S, or NR$^N$;
each R$^N$ is, independently, H or methyl; and
each of F¹ and F² is, independently, optionally substituted $C_{2-9}$ heterocyclylene.

2. The compound of claim 1, wherein v1 is 0.
3. The compound of claim 2, wherein J$^A$ is absent.
4. The compound of claim 2, wherein J$^A$ is O or optionally substituted amino.
5. The compound of claim 2, wherein J is optionally substituted $C_2$-$C_9$ heterocyclylene or optionally substituted $C_2$-$C_9$ heteroarylene.
6. The compound of claim 5, wherein J is optionally substituted $C_2$-$C_9$ heterocyclylene.
7. The compound of claim 2, wherein J is optionally substituted $C_3$-$C_{10}$ carbocyclylene or optionally substituted $C_6$-$C_{10}$ arylene.
8. The compound of claim 7, wherein J is optionally substituted $C_6$-$C_{10}$ arylene.
9. The compound of claim 1, wherein B is

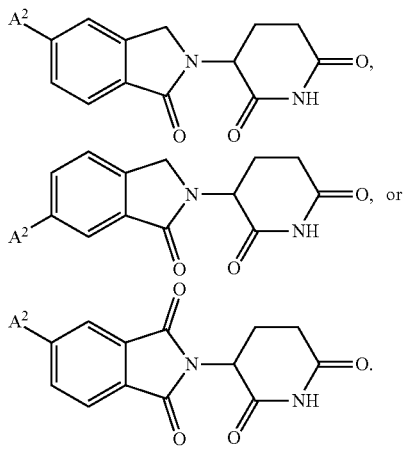

10. The compound of claim 1, wherein E³ is optionally substituted $C_{1-6}$ alkylene, O, S, or NR$^N$.
11. The compound of claim 10, wherein E³ is optionally substituted $C_{1-3}$ alkylene.
12. The compound of claim 1, wherein E¹ is NR$^N$, optionally substituted $C_{1-10}$ alkylene, optionally substituted $C_2$-$C_{10}$ polyethylene glycol, or optionally substituted $C_{1-10}$ heteroalkylene.
13. The compound of claim 12, wherein E¹ is

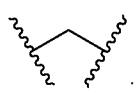

14. The compound of claim 1, wherein the $C_2$-$C_9$ heterocyclylene of F¹ and F² is monocyclic.

15. The compound of claim 14, wherein the $C_2$-$C_9$ heterocyclylene of F¹ and F² is

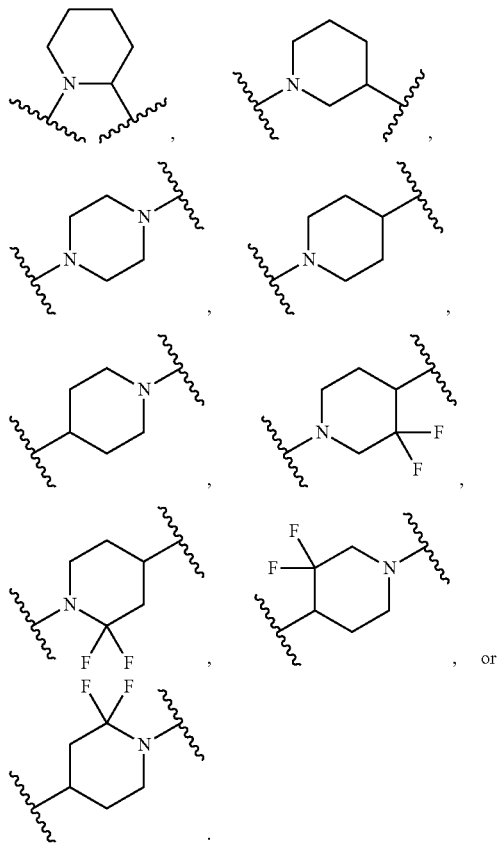

16. The compound of claim 1, wherein the $C_2$-$C_9$ heterocyclylene of F¹ and F² is spirocyclic.
17. The compound of claim 16, wherein the $C_2$-$C_9$ heterocyclylene of F¹ and F² is

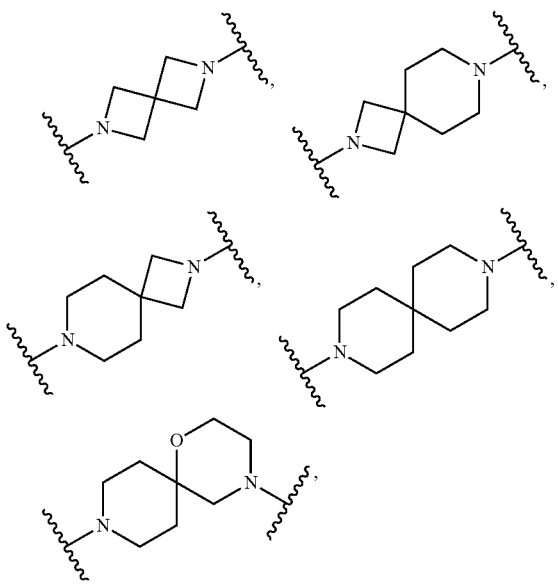

939
-continued
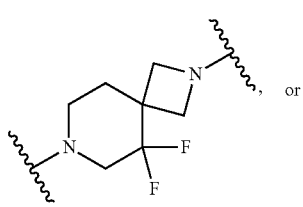, or
940
-continued
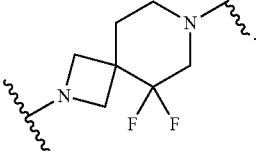.
18. The compound of claim 1, wherein the compound is selected from
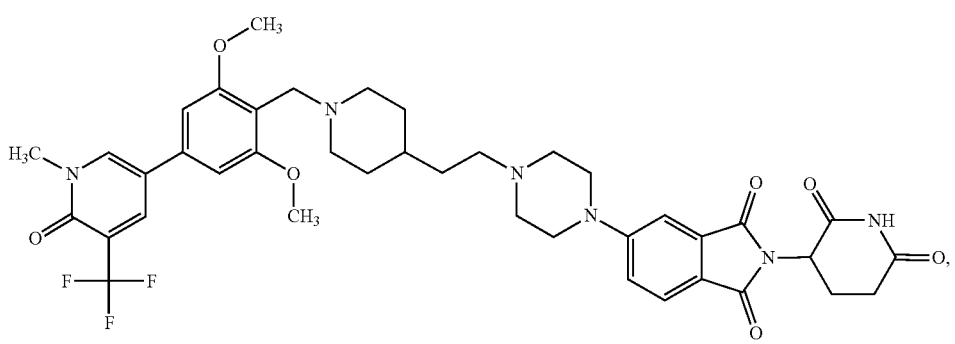
(D328)
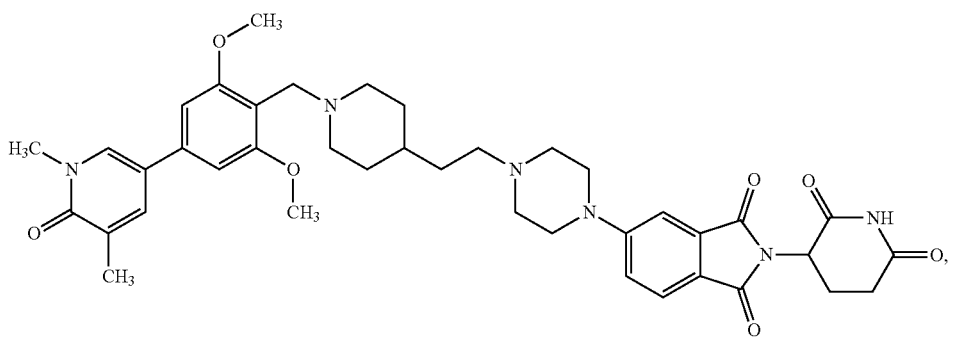
(D329)
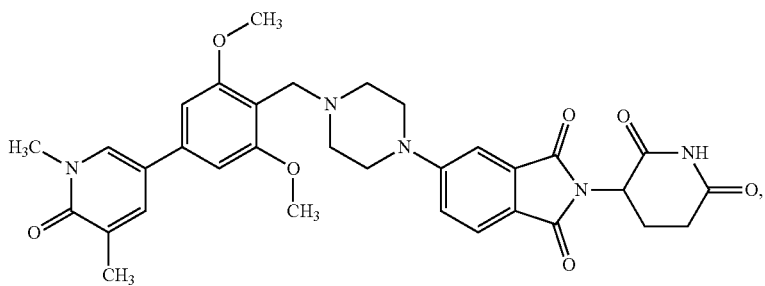
(D330)

-continued
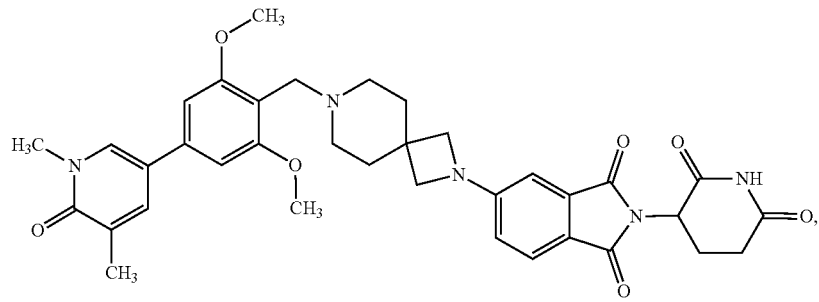
(D331)
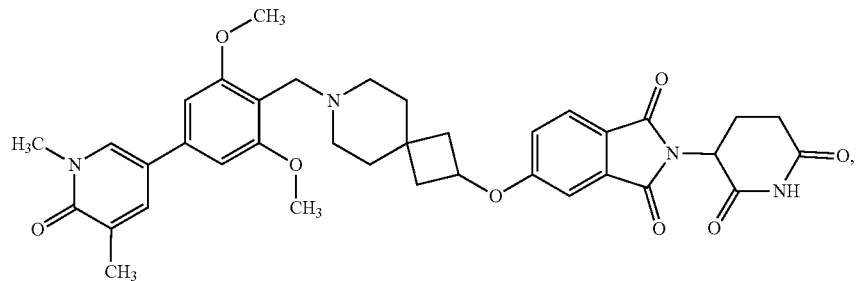
(D332)
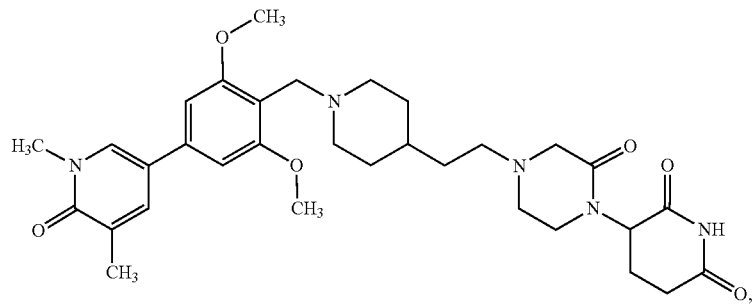
(D334)
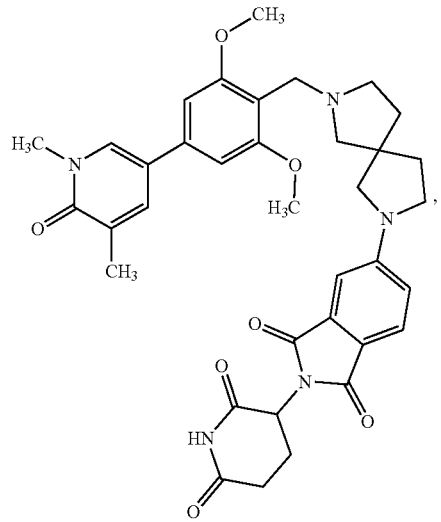
(D336)

(D337)
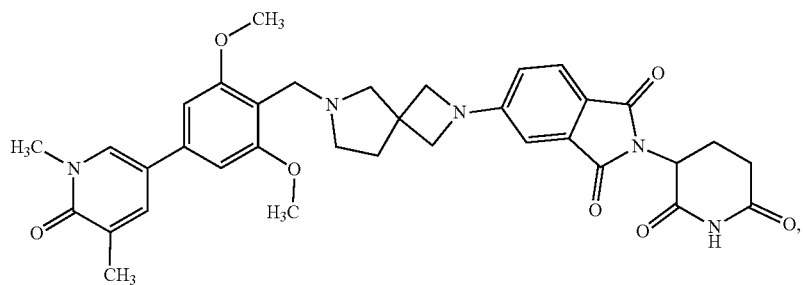
(D338)
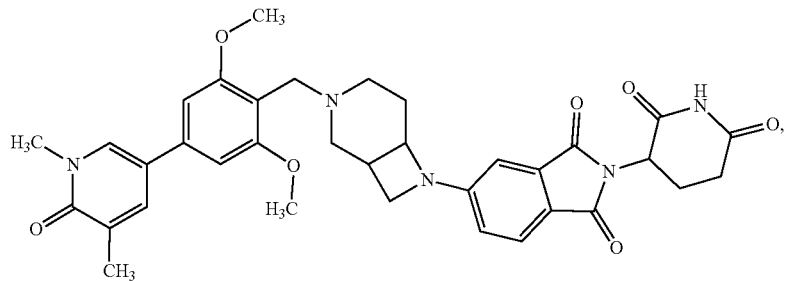
(D339)
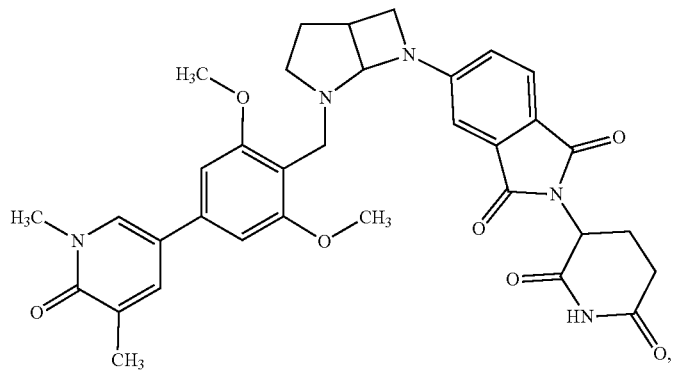
(D341)
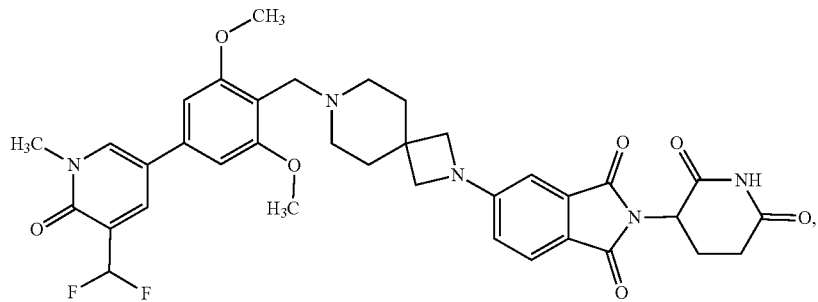
(D343)
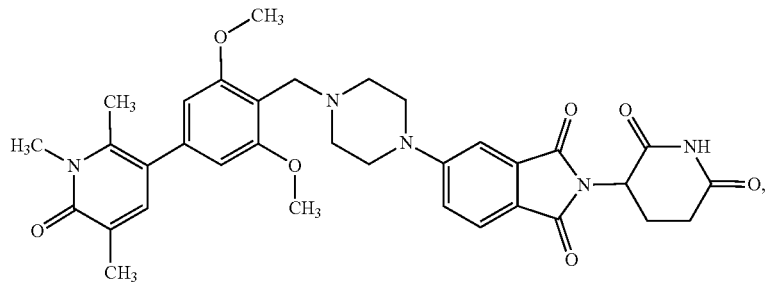

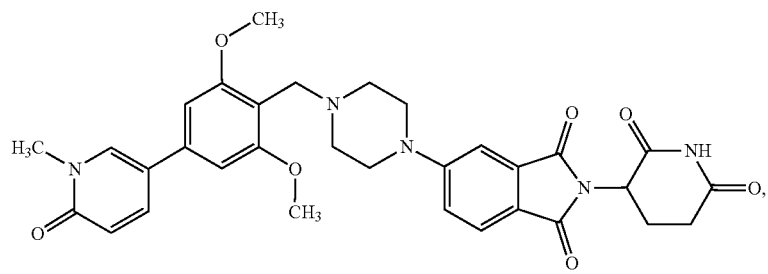
(D344)
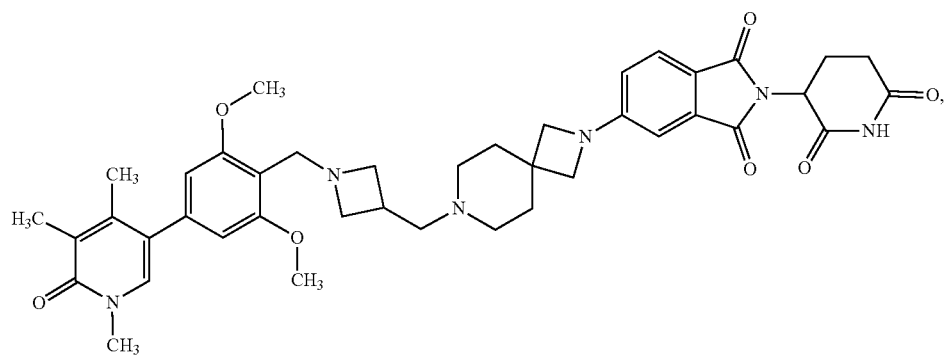
(D345)
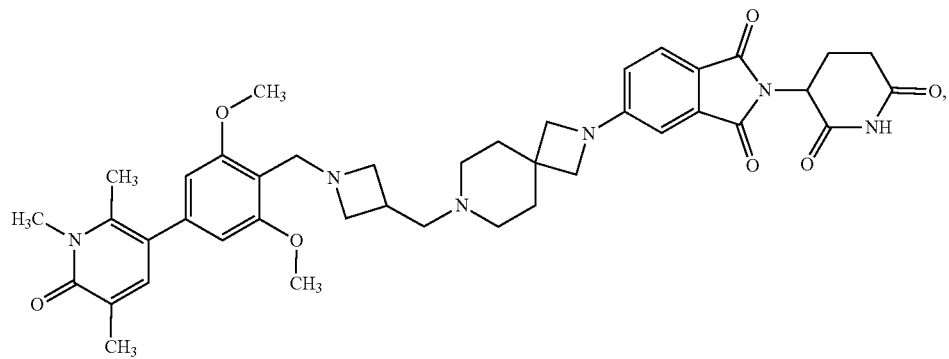
(D346)
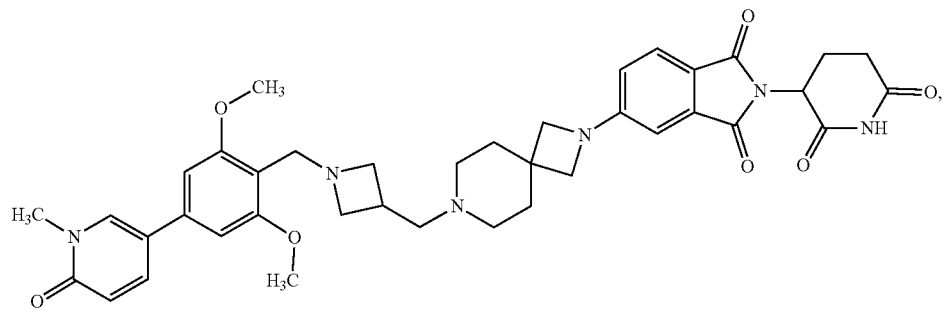
(D347)

-continued
(D349)
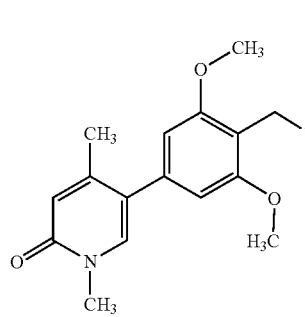
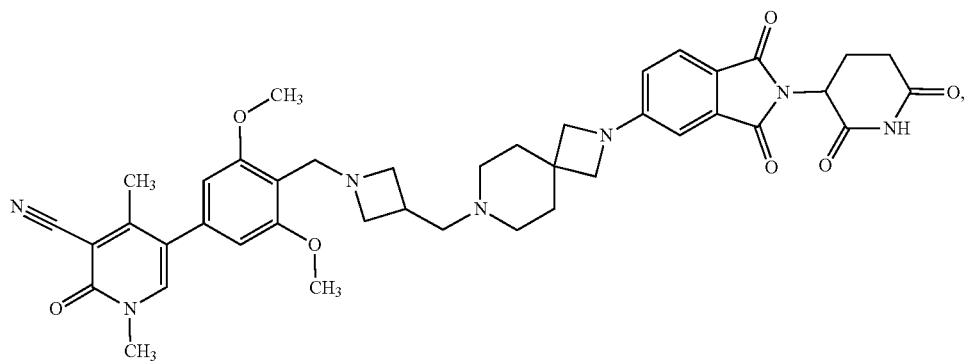
(D351)
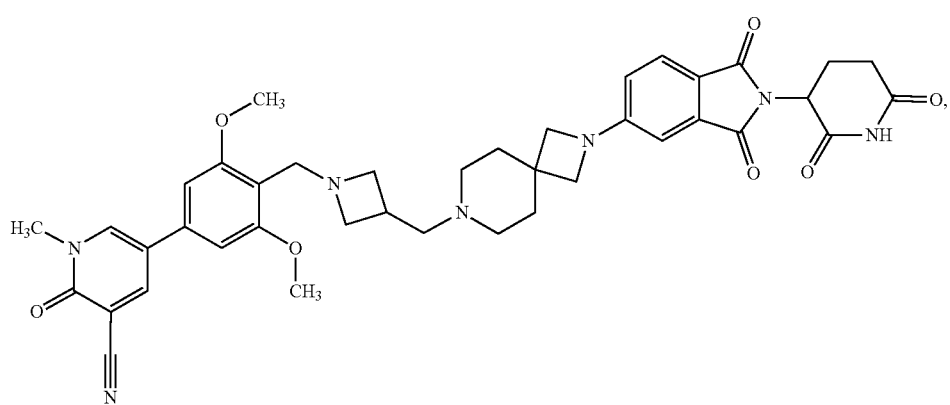
(D352)
(D362)
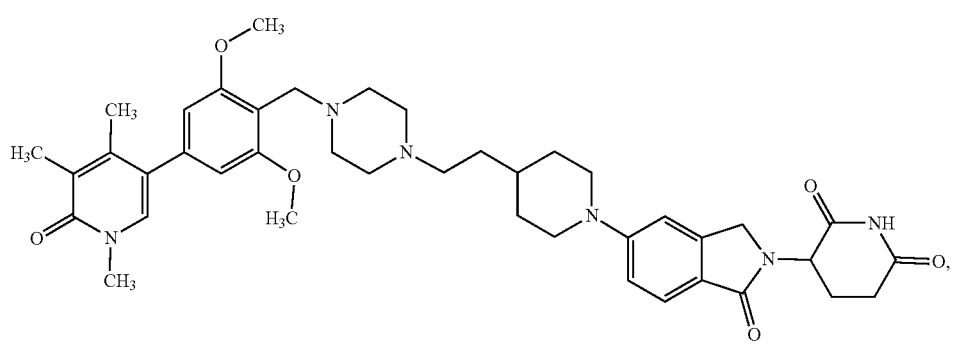

-continued
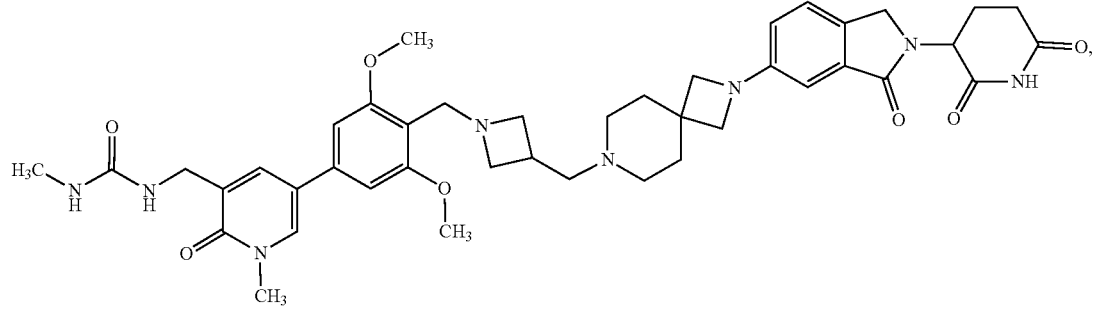
(D364)
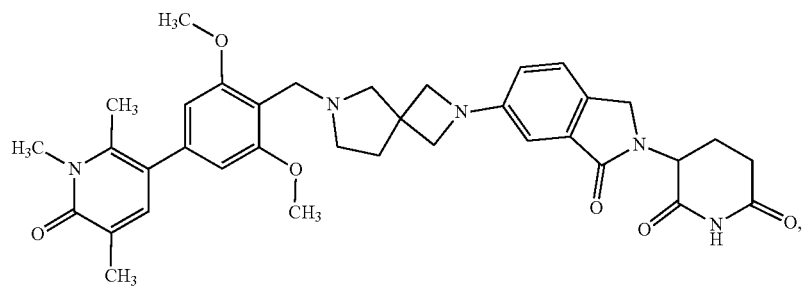
(D396)
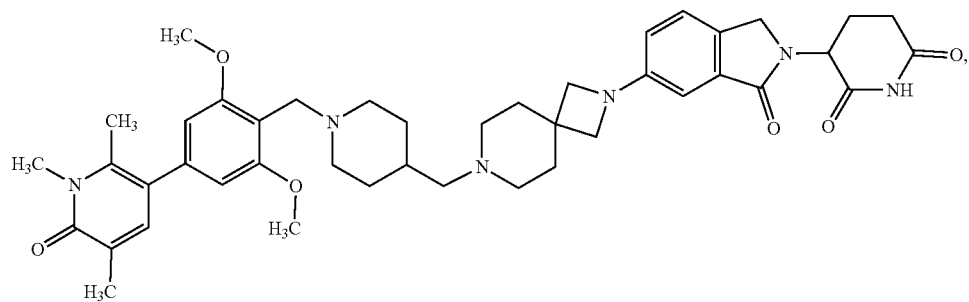
(D397)
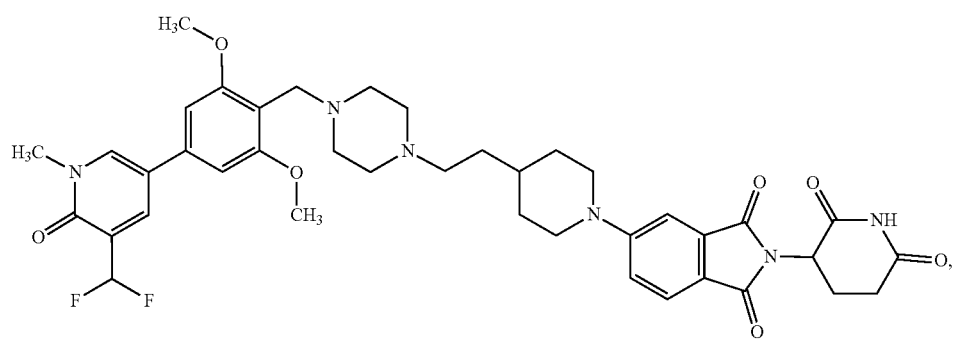
(D398)

| 951 | 952 |
|---|---|
| 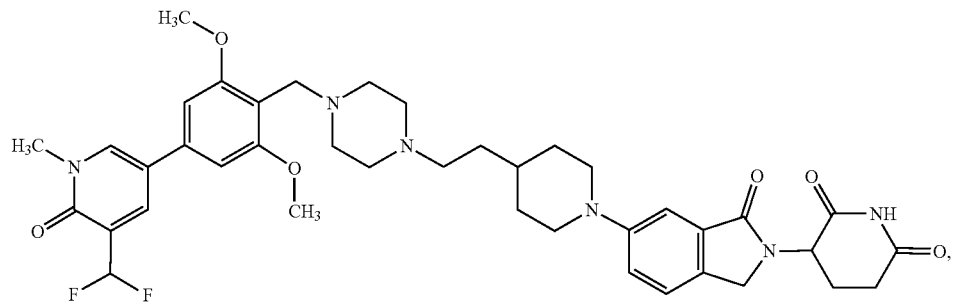 | (D339) |
| 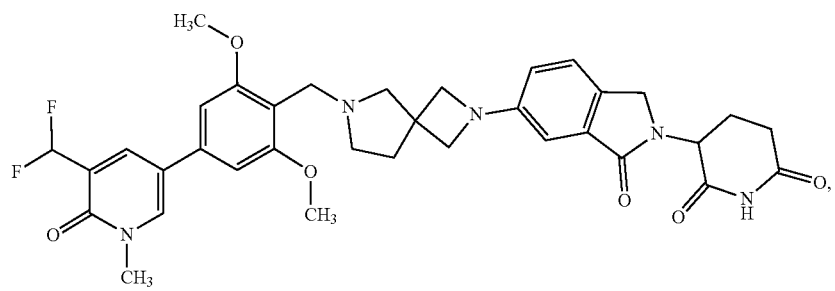 | (D403) |
| 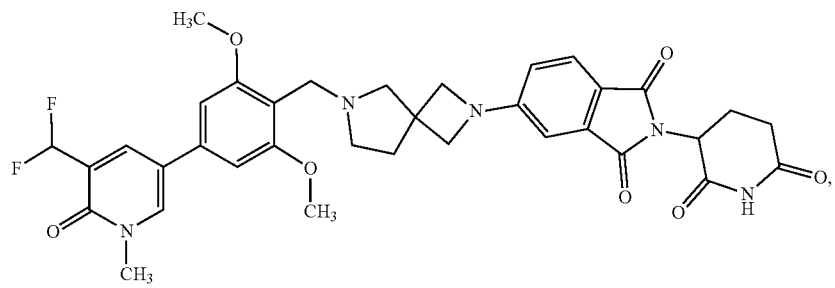 | (D406) |
| 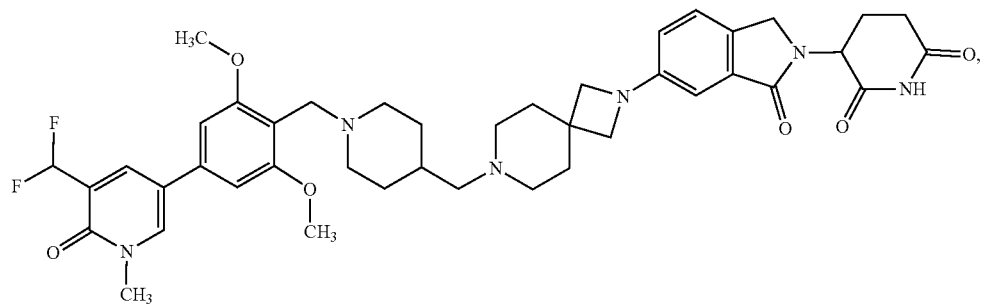 | (D407) |
| 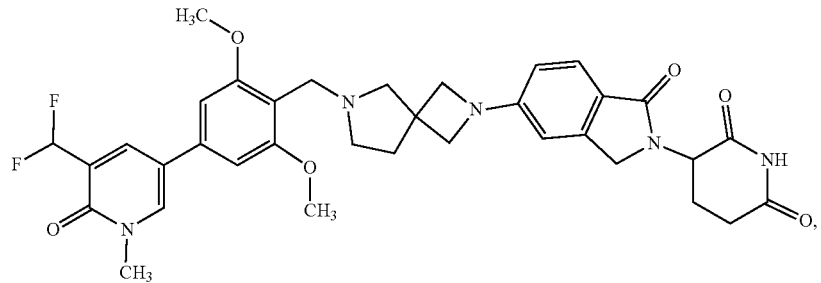 | (D408) |

953 954
-continued
(D425)
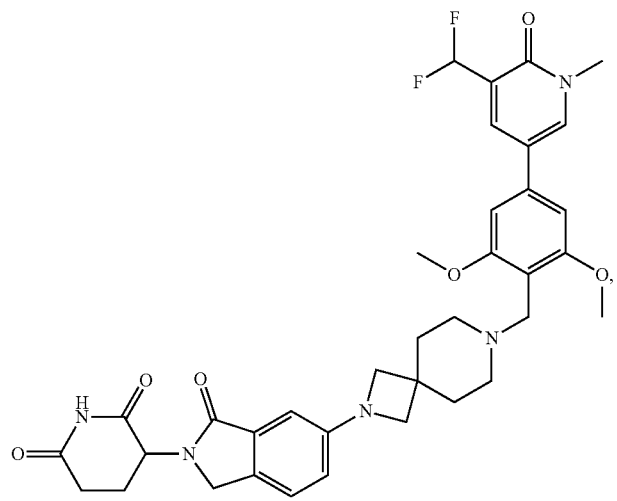
(D430)
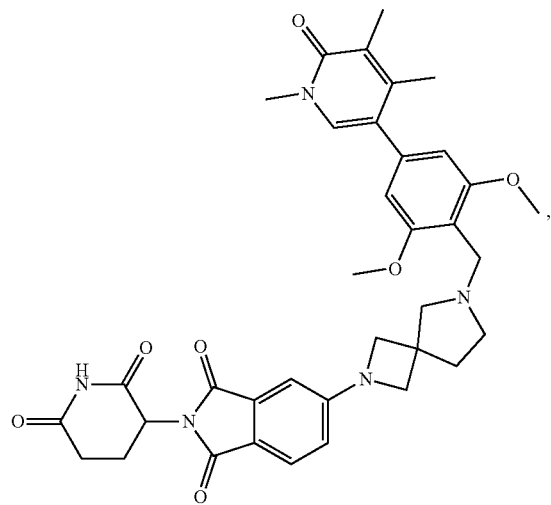
(D432)
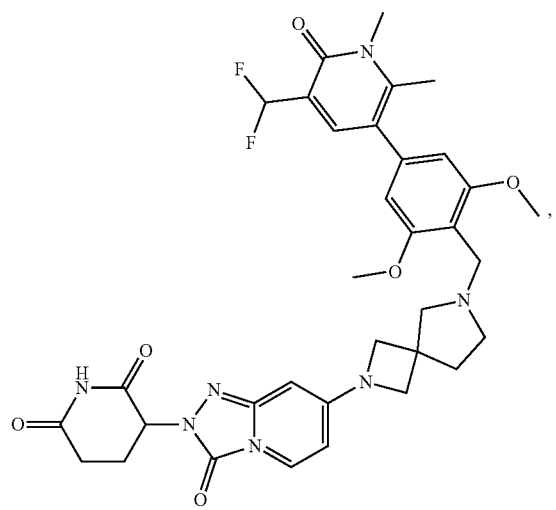
(D436)
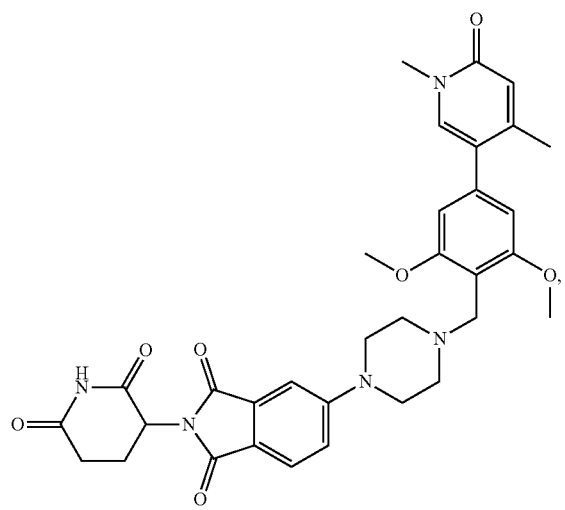

-continued
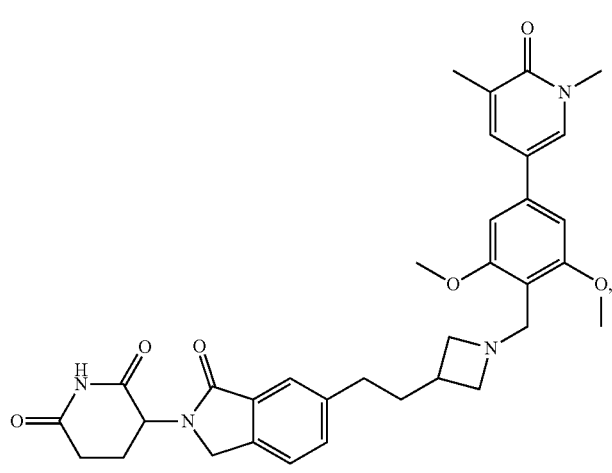
(D448)
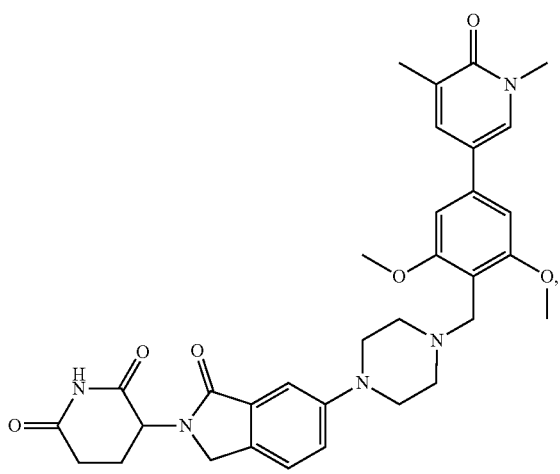
(D452)
(D449)
, and
or a pharmaceutically acceptable salt thereof.
* * * * *

SEQUENCE LISTING

```
Sequence total quantity: 673
SEQ ID NO: 1            moltype = AA  length = 141
FEATURE                 Location/Qualifiers
source                  1..141
                        mol_type = protein
                        organism = synthetic construct
SEQUENCE: 1
MGSSHHHHHH ENLYFQGDYK DDDDKGSLEV LFQGPAENES TPIQQLLEHF LRQLQRKDPH   60
GFFAFPVTDA IAPGYSMIIK HPMDFGTMKD KIVANEYKSV TEFKADFKLM CDNAMTYNRP  120
DTVYYKLAKK ILHAGFKMMS K                                            141

SEQ ID NO: 2            moltype =   length =
SEQUENCE: 2
000

SEQ ID NO: 3            moltype =   length =
SEQUENCE: 3
000

SEQ ID NO: 4            moltype =   length =
SEQUENCE: 4
000

SEQ ID NO: 5            moltype =   length =
SEQUENCE: 5
000

SEQ ID NO: 6            moltype =   length =
SEQUENCE: 6
000

SEQ ID NO: 7            moltype =   length =
SEQUENCE: 7
000

SEQ ID NO: 8            moltype =   length =
SEQUENCE: 8
000

SEQ ID NO: 9            moltype =   length =
SEQUENCE: 9
000

SEQ ID NO: 10           moltype =   length =
SEQUENCE: 10
000

SEQ ID NO: 11           moltype =   length =
SEQUENCE: 11
000
```

| | | |
|---|---|---|
| SEQ ID NO: 12 SEQUENCE: 12 | moltype = | length = 000 |
| SEQ ID NO: 13 SEQUENCE: 13 | moltype = | length = 000 |
| SEQ ID NO: 14 SEQUENCE: 14 | moltype = | length = 000 |
| SEQ ID NO: 15 SEQUENCE: 15 | moltype = | length = 000 |
| SEQ ID NO: 16 SEQUENCE: 16 | moltype = | length = 000 |
| SEQ ID NO: 17 SEQUENCE: 17 | moltype = | length = 000 |
| SEQ ID NO: 18 SEQUENCE: 18 | moltype = | length = 000 |
| SEQ ID NO: 19 SEQUENCE: 19 | moltype = | length = 000 |
| SEQ ID NO: 20 SEQUENCE: 20 | moltype = | length = 000 |
| SEQ ID NO: 21 SEQUENCE: 21 | moltype = | length = 000 |
| SEQ ID NO: 22 SEQUENCE: 22 | moltype = | length = 000 |
| SEQ ID NO: 23 SEQUENCE: 23 | moltype = | length = 000 |
| SEQ ID NO: 24 SEQUENCE: 24 | moltype = | length = 000 |
| SEQ ID NO: 25 SEQUENCE: 25 | moltype = | length = 000 |
| SEQ ID NO: 26 SEQUENCE: 26 | moltype = | length = 000 |
| SEQ ID NO: 27 SEQUENCE: 27 | moltype = | length = 000 |
| SEQ ID NO: 28 SEQUENCE: 28 | moltype = | length = 000 |
| SEQ ID NO: 29 SEQUENCE: 29 | moltype = | length = 000 |
| SEQ ID NO: 30 SEQUENCE: 30 | moltype = | length = 000 |
| SEQ ID NO: 31 SEQUENCE: 31 | moltype = | length = 000 |

SEQ ID NO: 32          moltype =    length =
SEQUENCE: 32
000

SEQ ID NO: 33          moltype =    length =
SEQUENCE: 33
000

SEQ ID NO: 34          moltype =    length =
SEQUENCE: 34
000

SEQ ID NO: 35          moltype =    length =
SEQUENCE: 35
000

SEQ ID NO: 36          moltype =    length =
SEQUENCE: 36
000

SEQ ID NO: 37          moltype =    length =
SEQUENCE: 37
000

SEQ ID NO: 38          moltype =    length =
SEQUENCE: 38
000

SEQ ID NO: 39          moltype =    length =
SEQUENCE: 39
000

SEQ ID NO: 40          moltype =    length =
SEQUENCE: 40
000

SEQ ID NO: 41          moltype =    length =
SEQUENCE: 41
000

SEQ ID NO: 42          moltype =    length =
SEQUENCE: 42
000

SEQ ID NO: 43          moltype =    length =
SEQUENCE: 43
000

SEQ ID NO: 44          moltype =    length =
SEQUENCE: 44
000

SEQ ID NO: 45          moltype =    length =
SEQUENCE: 45
000

SEQ ID NO: 46          moltype =    length =
SEQUENCE: 46
000

SEQ ID NO: 47          moltype =    length =
SEQUENCE: 47
000

SEQ ID NO: 48          moltype =    length =
SEQUENCE: 48
000

SEQ ID NO: 49          moltype =    length =
SEQUENCE: 49
000

SEQ ID NO: 50          moltype =    length =
SEQUENCE: 50
000

SEQ ID NO: 51          moltype =    length =
SEQUENCE: 51

000

SEQ ID NO: 52         moltype =    length =
SEQUENCE: 52
000

SEQ ID NO: 53         moltype =    length =
SEQUENCE: 53
000

SEQ ID NO: 54         moltype =    length =
SEQUENCE: 54
000

SEQ ID NO: 55         moltype =    length =
SEQUENCE: 55
000

SEQ ID NO: 56         moltype =    length =
SEQUENCE: 56
000

SEQ ID NO: 57         moltype =    length =
SEQUENCE: 57
000

SEQ ID NO: 58         moltype =    length =
SEQUENCE: 58
000

SEQ ID NO: 59         moltype =    length =
SEQUENCE: 59
000

SEQ ID NO: 60         moltype =    length =
SEQUENCE: 60
000

SEQ ID NO: 61         moltype =    length =
SEQUENCE: 61
000

SEQ ID NO: 62         moltype =    length =
SEQUENCE: 62
000

SEQ ID NO: 63         moltype =    length =
SEQUENCE: 63
000

SEQ ID NO: 64         moltype =    length =
SEQUENCE: 64
000

SEQ ID NO: 65         moltype =    length =
SEQUENCE: 65
000

SEQ ID NO: 66         moltype =    length =
SEQUENCE: 66
000

SEQ ID NO: 67         moltype =    length =
SEQUENCE: 67
000

SEQ ID NO: 68         moltype =    length =
SEQUENCE: 68
000

SEQ ID NO: 69         moltype =    length =
SEQUENCE: 69
000

SEQ ID NO: 70         moltype =    length =
SEQUENCE: 70
000

SEQ ID NO: 71         moltype =    length =

| | | |
|---|---|---|
| SEQUENCE: 71 000 | | |
| SEQ ID NO: 72 SEQUENCE: 72 000 | moltype = | length = |
| SEQ ID NO: 73 SEQUENCE: 73 000 | moltype = | length = |
| SEQ ID NO: 74 SEQUENCE: 74 000 | moltype = | length = |
| SEQ ID NO: 75 SEQUENCE: 75 000 | moltype = | length = |
| SEQ ID NO: 76 SEQUENCE: 76 000 | moltype = | length = |
| SEQ ID NO: 77 SEQUENCE: 77 000 | moltype = | length = |
| SEQ ID NO: 78 SEQUENCE: 78 000 | moltype = | length = |
| SEQ ID NO: 79 SEQUENCE: 79 000 | moltype = | length = |
| SEQ ID NO: 80 SEQUENCE: 80 000 | moltype = | length = |
| SEQ ID NO: 81 SEQUENCE: 81 000 | moltype = | length = |
| SEQ ID NO: 82 SEQUENCE: 82 000 | moltype = | length = |
| SEQ ID NO: 83 SEQUENCE: 83 000 | moltype = | length = |
| SEQ ID NO: 84 SEQUENCE: 84 000 | moltype = | length = |
| SEQ ID NO: 85 SEQUENCE: 85 000 | moltype = | length = |
| SEQ ID NO: 86 SEQUENCE: 86 000 | moltype = | length = |
| SEQ ID NO: 87 SEQUENCE: 87 000 | moltype = | length = |
| SEQ ID NO: 88 SEQUENCE: 88 000 | moltype = | length = |
| SEQ ID NO: 89 SEQUENCE: 89 000 | moltype = | length = |
| SEQ ID NO: 90 SEQUENCE: 90 000 | moltype = | length = |

| | | |
|---|---|---|
| SEQ ID NO: 91<br>SEQUENCE: 91<br>000 | moltype = | length = |
| SEQ ID NO: 92<br>SEQUENCE: 92<br>000 | moltype = | length = |
| SEQ ID NO: 93<br>SEQUENCE: 93<br>000 | moltype = | length = |
| SEQ ID NO: 94<br>SEQUENCE: 94<br>000 | moltype = | length = |
| SEQ ID NO: 95<br>SEQUENCE: 95<br>000 | moltype = | length = |
| SEQ ID NO: 96<br>SEQUENCE: 96<br>000 | moltype = | length = |
| SEQ ID NO: 97<br>SEQUENCE: 97<br>000 | moltype = | length = |
| SEQ ID NO: 98<br>SEQUENCE: 98<br>000 | moltype = | length = |
| SEQ ID NO: 99<br>SEQUENCE: 99<br>000 | moltype = | length = |
| SEQ ID NO: 100<br>SEQUENCE: 100<br>000 | moltype = | length = |
| SEQ ID NO: 101<br>SEQUENCE: 101<br>000 | moltype = | length = |
| SEQ ID NO: 102<br>SEQUENCE: 102<br>000 | moltype = | length = |
| SEQ ID NO: 103<br>SEQUENCE: 103<br>000 | moltype = | length = |
| SEQ ID NO: 104<br>SEQUENCE: 104<br>000 | moltype = | length = |
| SEQ ID NO: 105<br>SEQUENCE: 105<br>000 | moltype = | length = |
| SEQ ID NO: 106<br>SEQUENCE: 106<br>000 | moltype = | length = |
| SEQ ID NO: 107<br>SEQUENCE: 107<br>000 | moltype = | length = |
| SEQ ID NO: 108<br>SEQUENCE: 108<br>000 | moltype = | length = |
| SEQ ID NO: 109<br>SEQUENCE: 109<br>000 | moltype = | length = |
| SEQ ID NO: 110<br>SEQUENCE: 110<br>000 | moltype = | length = |

SEQ ID NO: 111    moltype =    length =
SEQUENCE: 111
000

SEQ ID NO: 112    moltype =    length =
SEQUENCE: 112
000

SEQ ID NO: 113    moltype =    length =
SEQUENCE: 113
000

SEQ ID NO: 114    moltype =    length =
SEQUENCE: 114
000

SEQ ID NO: 115    moltype =    length =
SEQUENCE: 115
000

SEQ ID NO: 116    moltype =    length =
SEQUENCE: 116
000

SEQ ID NO: 117    moltype =    length =
SEQUENCE: 117
000

SEQ ID NO: 118    moltype =    length =
SEQUENCE: 118
000

SEQ ID NO: 119    moltype =    length =
SEQUENCE: 119
000

SEQ ID NO: 120    moltype =    length =
SEQUENCE: 120
000

SEQ ID NO: 121    moltype =    length =
SEQUENCE: 121
000

SEQ ID NO: 122    moltype =    length =
SEQUENCE: 122
000

SEQ ID NO: 123    moltype =    length =
SEQUENCE: 123
000

SEQ ID NO: 124    moltype =    length =
SEQUENCE: 124
000

SEQ ID NO: 125    moltype =    length =
SEQUENCE: 125
000

SEQ ID NO: 126    moltype =    length =
SEQUENCE: 126
000

SEQ ID NO: 127    moltype =    length =
SEQUENCE: 127
000

SEQ ID NO: 128    moltype =    length =
SEQUENCE: 128
000

SEQ ID NO: 129    moltype =    length =
SEQUENCE: 129
000

SEQ ID NO: 130    moltype =    length =
SEQUENCE: 130

000

SEQ ID NO: 131        moltype =    length =
SEQUENCE: 131
000

SEQ ID NO: 132        moltype =    length =
SEQUENCE: 132
000

SEQ ID NO: 133        moltype =    length =
SEQUENCE: 133
000

SEQ ID NO: 134        moltype =    length =
SEQUENCE: 134
000

SEQ ID NO: 135        moltype =    length =
SEQUENCE: 135
000

SEQ ID NO: 136        moltype =    length =
SEQUENCE: 136
000

SEQ ID NO: 137        moltype =    length =
SEQUENCE: 137
000

SEQ ID NO: 138        moltype =    length =
SEQUENCE: 138
000

SEQ ID NO: 139        moltype =    length =
SEQUENCE: 139
000

SEQ ID NO: 140        moltype =    length =
SEQUENCE: 140
000

SEQ ID NO: 141        moltype =    length =
SEQUENCE: 141
000

SEQ ID NO: 142        moltype =    length =
SEQUENCE: 142
000

SEQ ID NO: 143        moltype =    length =
SEQUENCE: 143
000

SEQ ID NO: 144        moltype =    length =
SEQUENCE: 144
000

SEQ ID NO: 145        moltype =    length =
SEQUENCE: 145
000

SEQ ID NO: 146        moltype =    length =
SEQUENCE: 146
000

SEQ ID NO: 147        moltype =    length =
SEQUENCE: 147
000

SEQ ID NO: 148        moltype =    length =
SEQUENCE: 148
000

SEQ ID NO: 149        moltype =    length =
SEQUENCE: 149
000

SEQ ID NO: 150        moltype =    length =

| | | |
|---|---|---|
| SEQUENCE: 150 000 | | |
| SEQ ID NO: 151 SEQUENCE: 151 000 | moltype = | length = |
| SEQ ID NO: 152 SEQUENCE: 152 000 | moltype = | length = |
| SEQ ID NO: 153 SEQUENCE: 153 000 | moltype = | length = |
| SEQ ID NO: 154 SEQUENCE: 154 000 | moltype = | length = |
| SEQ ID NO: 155 SEQUENCE: 155 000 | moltype = | length = |
| SEQ ID NO: 156 SEQUENCE: 156 000 | moltype = | length = |
| SEQ ID NO: 157 SEQUENCE: 157 000 | moltype = | length = |
| SEQ ID NO: 158 SEQUENCE: 158 000 | moltype = | length = |
| SEQ ID NO: 159 SEQUENCE: 159 000 | moltype = | length = |
| SEQ ID NO: 160 SEQUENCE: 160 000 | moltype = | length = |
| SEQ ID NO: 161 SEQUENCE: 161 000 | moltype = | length = |
| SEQ ID NO: 162 SEQUENCE: 162 000 | moltype = | length = |
| SEQ ID NO: 163 SEQUENCE: 163 000 | moltype = | length = |
| SEQ ID NO: 164 SEQUENCE: 164 000 | moltype = | length = |
| SEQ ID NO: 165 SEQUENCE: 165 000 | moltype = | length = |
| SEQ ID NO: 166 SEQUENCE: 166 000 | moltype = | length = |
| SEQ ID NO: 167 SEQUENCE: 167 000 | moltype = | length = |
| SEQ ID NO: 168 SEQUENCE: 168 000 | moltype = | length = |
| SEQ ID NO: 169 SEQUENCE: 169 000 | moltype = | length = |

| | | |
|---|---|---|
| SEQ ID NO: 170<br>SEQUENCE: 170<br>000 | moltype = | length = |
| SEQ ID NO: 171<br>SEQUENCE: 171<br>000 | moltype = | length = |
| SEQ ID NO: 172<br>SEQUENCE: 172<br>000 | moltype = | length = |
| SEQ ID NO: 173<br>SEQUENCE: 173<br>000 | moltype = | length = |
| SEQ ID NO: 174<br>SEQUENCE: 174<br>000 | moltype = | length = |
| SEQ ID NO: 175<br>SEQUENCE: 175<br>000 | moltype = | length = |
| SEQ ID NO: 176<br>SEQUENCE: 176<br>000 | moltype = | length = |
| SEQ ID NO: 177<br>SEQUENCE: 177<br>000 | moltype = | length = |
| SEQ ID NO: 178<br>SEQUENCE: 178<br>000 | moltype = | length = |
| SEQ ID NO: 179<br>SEQUENCE: 179<br>000 | moltype = | length = |
| SEQ ID NO: 180<br>SEQUENCE: 180<br>000 | moltype = | length = |
| SEQ ID NO: 181<br>SEQUENCE: 181<br>000 | moltype = | length = |
| SEQ ID NO: 182<br>SEQUENCE: 182<br>000 | moltype = | length = |
| SEQ ID NO: 183<br>SEQUENCE: 183<br>000 | moltype = | length = |
| SEQ ID NO: 184<br>SEQUENCE: 184<br>000 | moltype = | length = |
| SEQ ID NO: 185<br>SEQUENCE: 185<br>000 | moltype = | length = |
| SEQ ID NO: 186<br>SEQUENCE: 186<br>000 | moltype = | length = |
| SEQ ID NO: 187<br>SEQUENCE: 187<br>000 | moltype = | length = |
| SEQ ID NO: 188<br>SEQUENCE: 188<br>000 | moltype = | length = |
| SEQ ID NO: 189<br>SEQUENCE: 189<br>000 | moltype = | length = |

| | | |
|---|---|---|
| SEQ ID NO: 190<br>SEQUENCE: 190<br>000 | moltype = | length = |
| SEQ ID NO: 191<br>SEQUENCE: 191<br>000 | moltype = | length = |
| SEQ ID NO: 192<br>SEQUENCE: 192<br>000 | moltype = | length = |
| SEQ ID NO: 193<br>SEQUENCE: 193<br>000 | moltype = | length = |
| SEQ ID NO: 194<br>SEQUENCE: 194<br>000 | moltype = | length = |
| SEQ ID NO: 195<br>SEQUENCE: 195<br>000 | moltype = | length = |
| SEQ ID NO: 196<br>SEQUENCE: 196<br>000 | moltype = | length = |
| SEQ ID NO: 197<br>SEQUENCE: 197<br>000 | moltype = | length = |
| SEQ ID NO: 198<br>SEQUENCE: 198<br>000 | moltype = | length = |
| SEQ ID NO: 199<br>SEQUENCE: 199<br>000 | moltype = | length = |
| SEQ ID NO: 200<br>SEQUENCE: 200<br>000 | moltype = | length = |
| SEQ ID NO: 201<br>SEQUENCE: 201<br>000 | moltype = | length = |
| SEQ ID NO: 202<br>SEQUENCE: 202<br>000 | moltype = | length = |
| SEQ ID NO: 203<br>FEATURE<br>source | moltype = DNA  length = 20<br>Location/Qualifiers<br>1..20<br>mol_type = other DNA<br>organism = synthetic construct | |
| SEQUENCE: 203<br>caagaagcac aagaagcaca | | 20 |
| SEQ ID NO: 204<br>FEATURE<br>source | moltype = DNA  length = 20<br>Location/Qualifiers<br>1..20<br>mol_type = other DNA<br>organism = synthetic construct | |
| SEQUENCE: 204<br>cttgtgcttc ttgcccatgg | | 20 |
| SEQ ID NO: 205<br>FEATURE<br>source | moltype = DNA  length = 20<br>Location/Qualifiers<br>1..20<br>mol_type = other DNA<br>organism = synthetic construct | |
| SEQUENCE: 205<br>cttcttgtgc ttcttgccca | | 20 |
| SEQ ID NO: 206<br>FEATURE | moltype = DNA  length = 20<br>Location/Qualifiers | |

```
source                   1..20
                         mol_type = other DNA
                         organism = synthetic construct
SEQUENCE: 206
acaagaagca caaggccgag                                                  20

SEQ ID NO: 207           moltype = DNA   length = 20
FEATURE                  Location/Qualifiers
source                   1..20
                         mol_type = other DNA
                         organism = synthetic construct
SEQUENCE: 207
ctcgtaggac gagcgccact                                                  20

SEQ ID NO: 208           moltype = DNA   length = 20
FEATURE                  Location/Qualifiers
source                   1..20
                         mol_type = other DNA
                         organism = synthetic construct
SEQUENCE: 208
cgagtggcgc tcgtcctacg                                                  20

SEQ ID NO: 209           moltype = DNA   length = 20
FEATURE                  Location/Qualifiers
source                   1..20
                         mol_type = other DNA
                         organism = synthetic construct
SEQUENCE: 209
gagtggcgct cgtcctacga                                                  20

SEQ ID NO: 210           moltype = DNA   length = 20
FEATURE                  Location/Qualifiers
source                   1..20
                         mol_type = other DNA
                         organism = synthetic construct
SEQUENCE: 210
aggcttctcc aggggcttgt                                                  20

SEQ ID NO: 211           moltype = DNA   length = 20
FEATURE                  Location/Qualifiers
source                   1..20
                         mol_type = other DNA
                         organism = synthetic construct
SEQUENCE: 211
agattatgcc gacaagcccc                                                  20

SEQ ID NO: 212           moltype = DNA   length = 20
FEATURE                  Location/Qualifiers
source                   1..20
                         mol_type = other DNA
                         organism = synthetic construct
SEQUENCE: 212
accttcagga ctagctttag                                                  20

SEQ ID NO: 213           moltype = DNA   length = 20
FEATURE                  Location/Qualifiers
source                   1..20
                         mol_type = other DNA
                         organism = synthetic construct
SEQUENCE: 213
agctttagag gcttctccag                                                  20

SEQ ID NO: 214           moltype = DNA   length = 20
FEATURE                  Location/Qualifiers
source                   1..20
                         mol_type = other DNA
                         organism = synthetic construct
SEQUENCE: 214
ctagctttag aggcttctcc                                                  20

SEQ ID NO: 215           moltype = DNA   length = 20
FEATURE                  Location/Qualifiers
source                   1..20
                         mol_type = other DNA
                         organism = synthetic construct
SEQUENCE: 215
tagctttaga ggcttctcca                                                  20

SEQ ID NO: 216           moltype = DNA   length = 20
```

```
FEATURE           Location/Qualifiers
source            1..20
                  mol_type = other DNA
                  organism = synthetic construct
SEQUENCE: 216
ctaaagctag tcctgaaggt                                                    20

SEQ ID NO: 217    moltype = DNA   length = 20
FEATURE           Location/Qualifiers
source            1..20
                  mol_type = other DNA
                  organism = synthetic construct
SEQUENCE: 217
gcctctaaag ctagtcctga                                                    20

SEQ ID NO: 218    moltype = DNA   length = 20
FEATURE           Location/Qualifiers
source            1..20
                  mol_type = other DNA
                  organism = synthetic construct
SEQUENCE: 218
cttcacttcc tccgaccttc                                                    20

SEQ ID NO: 219    moltype = DNA   length = 20
FEATURE           Location/Qualifiers
source            1..20
                  mol_type = other DNA
                  organism = synthetic construct
SEQUENCE: 219
aagctagtcc tgaaggtcgg                                                    20

SEQ ID NO: 220    moltype = DNA   length = 20
FEATURE           Location/Qualifiers
source            1..20
                  mol_type = other DNA
                  organism = synthetic construct
SEQUENCE: 220
agtgaagtga ctgaactctc                                                    20

SEQ ID NO: 221    moltype = DNA   length = 20
FEATURE           Location/Qualifiers
source            1..20
                  mol_type = other DNA
                  organism = synthetic construct
SEQUENCE: 221
gtgactgaac tctcaggatc                                                    20

SEQ ID NO: 222    moltype = DNA   length = 20
FEATURE           Location/Qualifiers
source            1..20
                  mol_type = other DNA
                  organism = synthetic construct
SEQUENCE: 222
atagtaactg gagtcgtggc                                                    20

SEQ ID NO: 223    moltype = DNA   length = 20
FEATURE           Location/Qualifiers
source            1..20
                  mol_type = other DNA
                  organism = synthetic construct
SEQUENCE: 223
catcatagta actggagtcg                                                    20

SEQ ID NO: 224    moltype = DNA   length = 20
FEATURE           Location/Qualifiers
source            1..20
                  mol_type = other DNA
                  organism = synthetic construct
SEQUENCE: 224
tgacctgtca tcatagtaac                                                    20

SEQ ID NO: 225    moltype = DNA   length = 20
FEATURE           Location/Qualifiers
source            1..20
                  mol_type = other DNA
                  organism = synthetic construct
SEQUENCE: 225
actccagtta ctatgatgac                                                    20
```

| | | |
|---|---|---|
| SEQ ID NO: 226<br>FEATURE<br>source | moltype = DNA   length = 20<br>Location/Qualifiers<br>1..20<br>mol_type = other DNA<br>organism = synthetic construct | |
| SEQUENCE: 226<br>ctttgtgcct ctctcgctca | | 20 |
| SEQ ID NO: 227<br>FEATURE<br>source | moltype = DNA   length = 20<br>Location/Qualifiers<br>1..20<br>mol_type = other DNA<br>organism = synthetic construct | |
| SEQUENCE: 227<br>ggtcagacca tgagcgagag | | 20 |
| SEQ ID NO: 228<br>FEATURE<br>source | moltype = DNA   length = 20<br>Location/Qualifiers<br>1..20<br>mol_type = other DNA<br>organism = synthetic construct | |
| SEQUENCE: 228<br>gaagaagaag aagtccgaga | | 20 |
| SEQ ID NO: 229<br>FEATURE<br>source | moltype = DNA   length = 20<br>Location/Qualifiers<br>1..20<br>mol_type = other DNA<br>organism = synthetic construct | |
| SEQUENCE: 229<br>gtccagatgc ttctccttct | | 20 |
| SEQ ID NO: 230<br>FEATURE<br>source | moltype = DNA   length = 20<br>Location/Qualifiers<br>1..20<br>mol_type = other DNA<br>organism = synthetic construct | |
| SEQUENCE: 230<br>gtccgagaag gagaagcatc | | 20 |
| SEQ ID NO: 231<br>FEATURE<br>source | moltype = DNA   length = 20<br>Location/Qualifiers<br>1..20<br>mol_type = other DNA<br>organism = synthetic construct | |
| SEQUENCE: 231<br>ggagaagcat ctggacgatg | | 20 |
| SEQ ID NO: 232<br>FEATURE<br>source | moltype = DNA   length = 20<br>Location/Qualifiers<br>1..20<br>mol_type = other DNA<br>organism = synthetic construct | |
| SEQUENCE: 232<br>tgaggaaaga aggaagcgaa | | 20 |
| SEQ ID NO: 233<br>FEATURE<br>source | moltype = DNA   length = 20<br>Location/Qualifiers<br>1..20<br>mol_type = other DNA<br>organism = synthetic construct | |
| SEQUENCE: 233<br>atctggacga tgaggaaaga | | 20 |
| SEQ ID NO: 234<br>FEATURE<br>source | moltype = DNA   length = 20<br>Location/Qualifiers<br>1..20<br>mol_type = other DNA<br>organism = synthetic construct | |
| SEQUENCE: 234<br>agaagaagcg gaagcgagag | | 20 |
| SEQ ID NO: 235<br>FEATURE<br>source | moltype = DNA   length = 20<br>Location/Qualifiers<br>1..20<br>mol_type = other DNA<br>organism = synthetic construct | |
| SEQUENCE: 235<br>gaagaagcgg aagcgagaga | | 20 |

| | | |
|---|---|---|
| SEQ ID NO: 236<br>FEATURE<br>source | moltype = DNA length = 20<br>Location/Qualifiers<br>1..20<br>mol_type = other DNA<br>organism = synthetic construct | |
| SEQUENCE: 236<br>ccgcccagga agagaagaag | | 20 |
| SEQ ID NO: 237<br>FEATURE<br>source | moltype = DNA length = 20<br>Location/Qualifiers<br>1..20<br>mol_type = other DNA<br>organism = synthetic construct | |
| SEQUENCE: 237<br>agagagggag cactgtgaca | | 20 |
| SEQ ID NO: 238<br>FEATURE<br>source | moltype = DNA length = 20<br>Location/Qualifiers<br>1..20<br>mol_type = other DNA<br>organism = synthetic construct | |
| SEQUENCE: 238<br>agggagcact gtgacacgga | | 20 |
| SEQ ID NO: 239<br>FEATURE<br>source | moltype = DNA length = 20<br>Location/Qualifiers<br>1..20<br>mol_type = other DNA<br>organism = synthetic construct | |
| SEQUENCE: 239<br>gagggagcac tgtgacacgg | | 20 |
| SEQ ID NO: 240<br>FEATURE<br>source | moltype = DNA length = 20<br>Location/Qualifiers<br>1..20<br>mol_type = other DNA<br>organism = synthetic construct | |
| SEQUENCE: 240<br>gcactgtgac acggagggag | | 20 |
| SEQ ID NO: 241<br>FEATURE<br>source | moltype = DNA length = 20<br>Location/Qualifiers<br>1..20<br>mol_type = other DNA<br>organism = synthetic construct | |
| SEQUENCE: 241<br>gaggctgacg actttgatcc | | 20 |
| SEQ ID NO: 242<br>FEATURE<br>source | moltype = DNA length = 20<br>Location/Qualifiers<br>1..20<br>mol_type = other DNA<br>organism = synthetic construct | |
| SEQUENCE: 242<br>aggctgacga ctttgatcct | | 20 |
| SEQ ID NO: 243<br>FEATURE<br>source | moltype = DNA length = 20<br>Location/Qualifiers<br>1..20<br>mol_type = other DNA<br>organism = synthetic construct | |
| SEQUENCE: 243<br>tccacctcca ccttcttccc | | 20 |
| SEQ ID NO: 244<br>FEATURE<br>source | moltype = DNA length = 20<br>Location/Qualifiers<br>1..20<br>mol_type = other DNA<br>organism = synthetic construct | |
| SEQUENCE: 244<br>cgactttgat cctgggaaga | | 20 |
| SEQ ID NO: 245<br>FEATURE<br>source | moltype = DNA length = 20<br>Location/Qualifiers<br>1..20<br>mol_type = other DNA<br>organism = synthetic construct | |
| SEQUENCE: 245 | | | ctttgatcct gggaagaagg                                                   20

SEQ ID NO: 246          moltype = DNA   length = 20
FEATURE                 Location/Qualifiers
source                  1..20
                        mol_type = other DNA
                        organism = synthetic construct SEQUENCE: 246
tgatcctggg aagaaggtgg                                                   20

SEQ ID NO: 247          moltype = DNA   length = 20
FEATURE                 Location/Qualifiers
source                  1..20
                        mol_type = other DNA
                        organism = synthetic construct SEQUENCE: 247
tcctgggaag aaggtggagg                                                   20

SEQ ID NO: 248          moltype = DNA   length = 20
FEATURE                 Location/Qualifiers
source                  1..20
                        mol_type = other DNA
                        organism = synthetic construct SEQUENCE: 248
cggactggcc gatctggggg                                                   20

SEQ ID NO: 249          moltype = DNA   length = 20
FEATURE                 Location/Qualifiers
source                  1..20
                        mol_type = other DNA
                        organism = synthetic construct SEQUENCE: 249
acgctcggac tggccgatct                                                   20

SEQ ID NO: 250          moltype = DNA   length = 20
FEATURE                 Location/Qualifiers
source                  1..20
                        mol_type = other DNA
                        organism = synthetic construct SEQUENCE: 250
aggtggagcc gcccccagat                                                   20

SEQ ID NO: 251          moltype = DNA   length = 20
FEATURE                 Location/Qualifiers
source                  1..20
                        mol_type = other DNA
                        organism = synthetic construct SEQUENCE: 251
cgctcggact ggccgatctg                                                   20

SEQ ID NO: 252          moltype = DNA   length = 20
FEATURE                 Location/Qualifiers
source                  1..20
                        mol_type = other DNA
                        organism = synthetic construct SEQUENCE: 252
gctcggactg gccgatctgg                                                   20

SEQ ID NO: 253          moltype = DNA   length = 20
FEATURE                 Location/Qualifiers
source                  1..20
                        mol_type = other DNA
                        organism = synthetic construct SEQUENCE: 253
cacgctcgga ctggccgatc                                                   20

SEQ ID NO: 254          moltype = DNA   length = 20
FEATURE                 Location/Qualifiers
source                  1..20
                        mol_type = other DNA
                        organism = synthetic construct SEQUENCE: 254
tgtgtccggc acgctcggac                                                   20

SEQ ID NO: 255          moltype = DNA   length = 20
FEATURE                 Location/Qualifiers
source                  1..20
                        mol_type = other DNA
                        organism = synthetic construct

```
SEQUENCE: 255
ctggctgtgt ccggcacgct                                                    20

SEQ ID NO: 256          moltype = DNA  length = 20
FEATURE                 Location/Qualifiers
source                  1..20
                        mol_type = other DNA
                        organism = synthetic construct
SEQUENCE: 256
atcggccagt ccgagcgtgc                                                    20

SEQ ID NO: 257          moltype = DNA  length = 20
FEATURE                 Location/Qualifiers
source                  1..20
                        mol_type = other DNA
                        organism = synthetic construct
SEQUENCE: 257
cacccttgcc tggctgtgtc                                                    20

SEQ ID NO: 258          moltype = DNA  length = 20
FEATURE                 Location/Qualifiers
source                  1..20
                        mol_type = other DNA
                        organism = synthetic construct
SEQUENCE: 258
cgagcgtgcc ggacacagcc                                                    20

SEQ ID NO: 259          moltype = DNA  length = 20
FEATURE                 Location/Qualifiers
source                  1..20
                        mol_type = other DNA
                        organism = synthetic construct
SEQUENCE: 259
tgttccagga gttgctgaat                                                    20

SEQ ID NO: 260          moltype = DNA  length = 20
FEATURE                 Location/Qualifiers
source                  1..20
                        mol_type = other DNA
                        organism = synthetic construct
SEQUENCE: 260
cacacctatt cagcaactcc                                                    20

SEQ ID NO: 261          moltype = DNA  length = 20
FEATURE                 Location/Qualifiers
source                  1..20
                        mol_type = other DNA
                        organism = synthetic construct
SEQUENCE: 261
gctggcggag gaagtgttcc                                                    20

SEQ ID NO: 262          moltype = DNA  length = 20
FEATURE                 Location/Qualifiers
source                  1..20
                        mol_type = other DNA
                        organism = synthetic construct
SEQUENCE: 262
tttacctctg aagctggcgg                                                    20

SEQ ID NO: 263          moltype = DNA  length = 20
FEATURE                 Location/Qualifiers
source                  1..20
                        mol_type = other DNA
                        organism = synthetic construct
SEQUENCE: 263
ccccggttta cctctgaagc                                                    20

SEQ ID NO: 264          moltype = DNA  length = 20
FEATURE                 Location/Qualifiers
source                  1..20
                        mol_type = other DNA
                        organism = synthetic construct
SEQUENCE: 264
acttcctccg ccagcttcag                                                    20

SEQ ID NO: 265          moltype = DNA  length = 20
FEATURE                 Location/Qualifiers
source                  1..20
                        mol_type = other DNA
```

```
                        organism = synthetic construct
SEQUENCE: 265
caggaaaagc aaaaaatcca                                                    20

SEQ ID NO: 266          moltype = DNA  length = 20
FEATURE                 Location/Qualifiers
source                  1..20
                        mol_type = other DNA
                        organism = synthetic construct
SEQUENCE: 266
gctttcagaa aagatcccca                                                    20

SEQ ID NO: 267          moltype = DNA  length = 20
FEATURE                 Location/Qualifiers
source                  1..20
                        mol_type = other DNA
                        organism = synthetic construct
SEQUENCE: 267
aggaaaagca aaaatccat                                                     20

SEQ ID NO: 268          moltype = DNA  length = 20
FEATURE                 Location/Qualifiers
source                  1..20
                        mol_type = other DNA
                        organism = synthetic construct
SEQUENCE: 268
ggaaaagcaa aaatccatg                                                     20

SEQ ID NO: 269          moltype = DNA  length = 20
FEATURE                 Location/Qualifiers
source                  1..20
                        mol_type = other DNA
                        organism = synthetic construct
SEQUENCE: 269
ggagcaattg catccgtgac                                                    20

SEQ ID NO: 270          moltype = DNA  length = 20
FEATURE                 Location/Qualifiers
source                  1..20
                        mol_type = other DNA
                        organism = synthetic construct
SEQUENCE: 270
gtcacggatg caattgctcc                                                    20

SEQ ID NO: 271          moltype = DNA  length = 20
FEATURE                 Location/Qualifiers
source                  1..20
                        mol_type = other DNA
                        organism = synthetic construct
SEQUENCE: 271
tttattatca ttgaatatcc                                                    20

SEQ ID NO: 272          moltype = DNA  length = 20
FEATURE                 Location/Qualifiers
source                  1..20
                        mol_type = other DNA
                        organism = synthetic construct
SEQUENCE: 272
aatgataata aacatccca                                                     20

SEQ ID NO: 273          moltype = DNA  length = 20
FEATURE                 Location/Qualifiers
source                  1..20
                        mol_type = other DNA
                        organism = synthetic construct
SEQUENCE: 273
ataaacatc ccatggattt                                                     20

SEQ ID NO: 274          moltype = DNA  length = 20
FEATURE                 Location/Qualifiers
source                  1..20
                        mol_type = other DNA
                        organism = synthetic construct
SEQUENCE: 274
ttcatggtgc caaaatccat                                                    20

SEQ ID NO: 275          moltype = DNA  length = 20
FEATURE                 Location/Qualifiers
source                  1..20
```

```
                              mol_type = other DNA
                              organism = synthetic construct
SEQUENCE: 275
tttcatggtg ccaaaatcca                                               20

SEQ ID NO: 276                moltype = DNA   length = 20
FEATURE                       Location/Qualifiers
source                        1..20
                              mol_type = other DNA
                              organism = synthetic construct
SEQUENCE: 276
taatgaatac aagtcagtta                                               20

SEQ ID NO: 277                moltype = DNA   length = 20
FEATURE                       Location/Qualifiers
source                        1..20
                              mol_type = other DNA
                              organism = synthetic construct
SEQUENCE: 277
caagtcagtt acggaattta                                               20

SEQ ID NO: 278                moltype = DNA   length = 20
FEATURE                       Location/Qualifiers
source                        1..20
                              mol_type = other DNA
                              organism = synthetic construct
SEQUENCE: 278
ataatgcaat gacatacaat                                               20

SEQ ID NO: 279                moltype = DNA   length = 20
FEATURE                       Location/Qualifiers
source                        1..20
                              mol_type = other DNA
                              organism = synthetic construct
SEQUENCE: 279
aacttgtagt acacggtatc                                               20

SEQ ID NO: 280                moltype = DNA   length = 20
FEATURE                       Location/Qualifiers
source                        1..20
                              mol_type = other DNA
                              organism = synthetic construct
SEQUENCE: 280
cttcgccaac ttgtagtaca                                               20

SEQ ID NO: 281                moltype = DNA   length = 20
FEATURE                       Location/Qualifiers
source                        1..20
                              mol_type = other DNA
                              organism = synthetic construct
SEQUENCE: 281
agataccgtg tactacaagt                                               20

SEQ ID NO: 282                moltype = DNA   length = 20
FEATURE                       Location/Qualifiers
source                        1..20
                              mol_type = other DNA
                              organism = synthetic construct
SEQUENCE: 282
gcgaagaaga tccttcacgc                                               20

SEQ ID NO: 283                moltype = DNA   length = 20
FEATURE                       Location/Qualifiers
source                        1..20
                              mol_type = other DNA
                              organism = synthetic construct
SEQUENCE: 283
tcatcttaaa gcctgcgtga                                               20

SEQ ID NO: 284                moltype = DNA   length = 20
FEATURE                       Location/Qualifiers
source                        1..20
                              mol_type = other DNA
                              organism = synthetic construct
SEQUENCE: 284
ttctcagcag gcagctcttt                                               20

SEQ ID NO: 285                moltype = DNA   length = 20
FEATURE                       Location/Qualifiers
```

```
source                     1..20
                           mol_type = other DNA
                           organism = synthetic construct
SEQUENCE: 285
caatgaagat acagctgttg                                                    20

SEQ ID NO: 286             moltype = DNA  length = 20
FEATURE                    Location/Qualifiers
source                     1..20
                           mol_type = other DNA
                           organism = synthetic construct
SEQUENCE: 286
actggtacaa cttcagggac                                                    20

SEQ ID NO: 287             moltype = DNA  length = 20
FEATURE                    Location/Qualifiers
source                     1..20
                           mol_type = other DNA
                           organism = synthetic construct
SEQUENCE: 287
cttgtactgg tacaacttca                                                    20

SEQ ID NO: 288             moltype = DNA  length = 20
FEATURE                    Location/Qualifiers
source                     1..20
                           mol_type = other DNA
                           organism = synthetic construct
SEQUENCE: 288
acttgtactg gtacaacttc                                                    20

SEQ ID NO: 289             moltype = DNA  length = 20
FEATURE                    Location/Qualifiers
source                     1..20
                           mol_type = other DNA
                           organism = synthetic construct
SEQUENCE: 289
ttggcagttt ctacttgtac                                                    20

SEQ ID NO: 290             moltype = DNA  length = 20
FEATURE                    Location/Qualifiers
source                     1..20
                           mol_type = other DNA
                           organism = synthetic construct
SEQUENCE: 290
tacctgataa cttctctact                                                    20

SEQ ID NO: 291             moltype = DNA  length = 20
FEATURE                    Location/Qualifiers
source                     1..20
                           mol_type = other DNA
                           organism = synthetic construct
SEQUENCE: 291
agccgagtag agaagttatc                                                    20

SEQ ID NO: 292             moltype = DNA  length = 20
FEATURE                    Location/Qualifiers
source                     1..20
                           mol_type = other DNA
                           organism = synthetic construct
SEQUENCE: 292
agctgcatgt ttgagcctga                                                    20

SEQ ID NO: 293             moltype = DNA  length = 20
FEATURE                    Location/Qualifiers
source                     1..20
                           mol_type = other DNA
                           organism = synthetic construct
SEQUENCE: 293
gctgcatgtt tgagcctgaa                                                    20

SEQ ID NO: 294             moltype = DNA  length = 20
FEATURE                    Location/Qualifiers
source                     1..20
                           mol_type = other DNA
                           organism = synthetic construct
SEQUENCE: 294
aagctgcagg cattcccttc                                                    20

SEQ ID NO: 295             moltype = DNA  length = 20
```

```
FEATURE                 Location/Qualifiers
source                  1..20
                        mol_type = other DNA
                        organism = synthetic construct
SEQUENCE: 295
ggtactgtcc gtcaagctgc                                              20

SEQ ID NO: 296          moltype = DNA  length = 20
FEATURE                 Location/Qualifiers
source                  1..20
                        mol_type = other DNA
                        organism = synthetic construct
SEQUENCE: 296
agggaatgcc tgcagcttga                                              20

SEQ ID NO: 297          moltype = DNA  length = 20
FEATURE                 Location/Qualifiers
source                  1..20
                        mol_type = other DNA
                        organism = synthetic construct
SEQUENCE: 297
cttgacggac agtaccgcag                                              20

SEQ ID NO: 298          moltype = DNA  length = 20
FEATURE                 Location/Qualifiers
source                  1..20
                        mol_type = other DNA
                        organism = synthetic construct
SEQUENCE: 298
cgccagcacg tgctcctctg                                              20

SEQ ID NO: 299          moltype = DNA  length = 20
FEATURE                 Location/Qualifiers
source                  1..20
                        mol_type = other DNA
                        organism = synthetic construct
SEQUENCE: 299
taccgcagag gagcacgtgc                                              20

SEQ ID NO: 300          moltype = DNA  length = 20
FEATURE                 Location/Qualifiers
source                  1..20
                        mol_type = other DNA
                        organism = synthetic construct
SEQUENCE: 300
agaggagcac gtgctggcgc                                              20

SEQ ID NO: 301          moltype = DNA  length = 20
FEATURE                 Location/Qualifiers
source                  1..20
                        mol_type = other DNA
                        organism = synthetic construct
SEQUENCE: 301
ggagcacgtg ctggcgctgg                                              20

SEQ ID NO: 302          moltype = DNA  length = 20
FEATURE                 Location/Qualifiers
source                  1..20
                        mol_type = other DNA
                        organism = synthetic construct
SEQUENCE: 302
agcacgcagc tgacgaagct                                              20

SEQ ID NO: 303          moltype = DNA  length = 20
FEATURE                 Location/Qualifiers
source                  1..20
                        mol_type = other DNA
                        organism = synthetic construct
SEQUENCE: 303
gcacgcagct gacgaagctc                                              20

SEQ ID NO: 304          moltype = DNA  length = 20
FEATURE                 Location/Qualifiers
source                  1..20
                        mol_type = other DNA
                        organism = synthetic construct
SEQUENCE: 304
cagctgacga agctcgggac                                              20
```

| | | |
|---|---|---|
| SEQ ID NO: 305<br>FEATURE<br>source | moltype = DNA   length = 20<br>Location/Qualifiers<br>1..20<br>mol_type = other DNA<br>organism = synthetic construct | |
| SEQUENCE: 305<br>aagctcggga caggatcaac | | 20 |
| SEQ ID NO: 306<br>FEATURE<br>source | moltype = DNA   length = 20<br>Location/Qualifiers<br>1..20<br>mol_type = other DNA<br>organism = synthetic construct | |
| SEQUENCE: 306<br>ccttgccgcc tgggaggaac | | 20 |
| SEQ ID NO: 307<br>FEATURE<br>source | moltype = DNA   length = 20<br>Location/Qualifiers<br>1..20<br>mol_type = other DNA<br>organism = synthetic construct | |
| SEQUENCE: 307<br>aggatcaacc ggttcctccc | | 20 |
| SEQ ID NO: 308<br>FEATURE<br>source | moltype = DNA   length = 20<br>Location/Qualifiers<br>1..20<br>mol_type = other DNA<br>organism = synthetic construct | |
| SEQUENCE: 308<br>atcaaccggt tcctcccagg | | 20 |
| SEQ ID NO: 309<br>FEATURE<br>source | moltype = DNA   length = 20<br>Location/Qualifiers<br>1..20<br>mol_type = other DNA<br>organism = synthetic construct | |
| SEQUENCE: 309<br>gcactacctt gccgcctggg | | 20 |
| SEQ ID NO: 310<br>FEATURE<br>source | moltype = DNA   length = 20<br>Location/Qualifiers<br>1..20<br>mol_type = other DNA<br>organism = synthetic construct | |
| SEQUENCE: 310<br>agagcactac cttgccgcct | | 20 |
| SEQ ID NO: 311<br>FEATURE<br>source | moltype = DNA   length = 20<br>Location/Qualifiers<br>1..20<br>mol_type = other DNA<br>organism = synthetic construct | |
| SEQUENCE: 311<br>ccggttcctc ccaggcggca | | 20 |
| SEQ ID NO: 312<br>FEATURE<br>source | moltype = DNA   length = 20<br>Location/Qualifiers<br>1..20<br>mol_type = other DNA<br>organism = synthetic construct | |
| SEQUENCE: 312<br>tcctcttcag atagcccatc | | 20 |
| SEQ ID NO: 313<br>FEATURE<br>source | moltype = DNA   length = 20<br>Location/Qualifiers<br>1..20<br>mol_type = other DNA<br>organism = synthetic construct | |
| SEQUENCE: 313<br>atgggctatc tgaagaggaa | | 20 |
| SEQ ID NO: 314<br>FEATURE<br>source | moltype = DNA   length = 20<br>Location/Qualifiers<br>1..20<br>mol_type = other DNA<br>organism = synthetic construct | |
| SEQUENCE: 314<br>gggctatctg aagaggaacg | | 20 |

```
SEQ ID NO: 315              moltype = DNA   length = 20
FEATURE                     Location/Qualifiers
source                      1..20
                            mol_type = other DNA
                            organism = synthetic construct
SEQUENCE: 315
tgggctatct gaagaggaac                                                   20

SEQ ID NO: 316              moltype = DNA   length = 20
FEATURE                     Location/Qualifiers
source                      1..20
                            mol_type = other DNA
                            organism = synthetic construct
SEQUENCE: 316
tatctgaaga ggaacgggga                                                   20

SEQ ID NO: 317              moltype = DNA   length = 20
FEATURE                     Location/Qualifiers
source                      1..20
                            mol_type = other DNA
                            organism = synthetic construct
SEQUENCE: 317
atctgaagag gaacggggac                                                   20

SEQ ID NO: 318              moltype = DNA   length = 20
FEATURE                     Location/Qualifiers
source                      1..20
                            mol_type = other DNA
                            organism = synthetic construct
SEQUENCE: 318
tgttgaccac gctgtagagc                                                   20

SEQ ID NO: 319              moltype = DNA   length = 20
FEATURE                     Location/Qualifiers
source                      1..20
                            mol_type = other DNA
                            organism = synthetic construct
SEQUENCE: 319
gctctacagc gtggtcaaca                                                   20

SEQ ID NO: 320              moltype = DNA   length = 20
FEATURE                     Location/Qualifiers
source                      1..20
                            mol_type = other DNA
                            organism = synthetic construct
SEQUENCE: 320
cgggagcctg ctctacagcg                                                   20

SEQ ID NO: 321              moltype = DNA   length = 20
FEATURE                     Location/Qualifiers
source                      1..20
                            mol_type = other DNA
                            organism = synthetic construct
SEQUENCE: 321
cgtggtcaac acggccgagc                                                   20

SEQ ID NO: 322              moltype = DNA   length = 20
FEATURE                     Location/Qualifiers
source                      1..20
                            mol_type = other DNA
                            organism = synthetic construct
SEQUENCE: 322
cccaccatca gcgtccggct                                                   20

SEQ ID NO: 323              moltype = DNA   length = 20
FEATURE                     Location/Qualifiers
source                      1..20
                            mol_type = other DNA
                            organism = synthetic construct
SEQUENCE: 323
acggccgagc cggacgctga                                                   20

SEQ ID NO: 324              moltype = DNA   length = 20
FEATURE                     Location/Qualifiers
source                      1..20
                            mol_type = other DNA
                            organism = synthetic construct
SEQUENCE: 324
```

```
gggcacccac catcagcgtc                                               20

SEQ ID NO: 325         moltype = DNA   length = 20
FEATURE                Location/Qualifiers
source                 1..20
                       mol_type = other DNA
                       organism = synthetic construct SEQUENCE: 325
gccgagccgg acgctgatgg                                               20

SEQ ID NO: 326         moltype = DNA   length = 20
FEATURE                Location/Qualifiers
source                 1..20
                       mol_type = other DNA
                       organism = synthetic construct SEQUENCE: 326
ccatgtccgt gttgcagagg                                               20

SEQ ID NO: 327         moltype = DNA   length = 20
FEATURE                Location/Qualifiers
source                 1..20
                       mol_type = other DNA
                       organism = synthetic construct SEQUENCE: 327
ccgagccgga cgctgatggt                                               20

SEQ ID NO: 328         moltype = DNA   length = 20
FEATURE                Location/Qualifiers
source                 1..20
                       mol_type = other DNA
                       organism = synthetic construct SEQUENCE: 328
cgagctcaag tccaccgggt                                               20

SEQ ID NO: 329         moltype = DNA   length = 20
FEATURE                Location/Qualifiers
source                 1..20
                       mol_type = other DNA
                       organism = synthetic construct SEQUENCE: 329
gcgagctcaa gtccaccggg                                               20

SEQ ID NO: 330         moltype = DNA   length = 20
FEATURE                Location/Qualifiers
source                 1..20
                       mol_type = other DNA
                       organism = synthetic construct SEQUENCE: 330
agagcgagct caagtccacc                                               20

SEQ ID NO: 331         moltype = DNA   length = 20
FEATURE                Location/Qualifiers
source                 1..20
                       mol_type = other DNA
                       organism = synthetic construct SEQUENCE: 331
gagagcgagc tcaagtccac                                               20

SEQ ID NO: 332         moltype = DNA   length = 20
FEATURE                Location/Qualifiers
source                 1..20
                       mol_type = other DNA
                       organism = synthetic construct SEQUENCE: 332
gaagcctggg agtagcttac                                               20

SEQ ID NO: 333         moltype = DNA   length = 20
FEATURE                Location/Qualifiers
source                 1..20
                       mol_type = other DNA
                       organism = synthetic construct SEQUENCE: 333
ctctccagta agctactccc                                               20

SEQ ID NO: 334         moltype = DNA   length = 20
FEATURE                Location/Qualifiers
source                 1..20
                       mol_type = other DNA
                       organism = synthetic construct
```

```
SEQUENCE: 334
agcccagcgt ggtgaagcct                                                    20

SEQ ID NO: 335          moltype = DNA  length = 20
FEATURE                 Location/Qualifiers
source                  1..20
                        mol_type = other DNA
                        organism = synthetic construct
SEQUENCE: 335
aagcccagcg tggtgaagcc                                                    20

SEQ ID NO: 336          moltype = DNA  length = 20
FEATURE                 Location/Qualifiers
source                  1..20
                        mol_type = other DNA
                        organism = synthetic construct
SEQUENCE: 336
actcccaggc ttcaccacgc                                                    20

SEQ ID NO: 337          moltype = DNA  length = 20
FEATURE                 Location/Qualifiers
source                  1..20
                        mol_type = other DNA
                        organism = synthetic construct
SEQUENCE: 337
ctcccaggct tcaccacgct                                                    20

SEQ ID NO: 338          moltype = DNA  length = 20
FEATURE                 Location/Qualifiers
source                  1..20
                        mol_type = other DNA
                        organism = synthetic construct
SEQUENCE: 338
ctcgtctttg aagcccagcg                                                    20

SEQ ID NO: 339          moltype = DNA  length = 20
FEATURE                 Location/Qualifiers
source                  1..20
                        mol_type = other DNA
                        organism = synthetic construct
SEQUENCE: 339
cactggagag aaaggtgact                                                    20

SEQ ID NO: 340          moltype = DNA  length = 20
FEATURE                 Location/Qualifiers
source                  1..20
                        mol_type = other DNA
                        organism = synthetic construct
SEQUENCE: 340
gcactggaga gaaaggtgac                                                    20

SEQ ID NO: 341          moltype = DNA  length = 20
FEATURE                 Location/Qualifiers
source                  1..20
                        mol_type = other DNA
                        organism = synthetic construct
SEQUENCE: 341
agtagtggca ctggagagaa                                                    20

SEQ ID NO: 342          moltype = DNA  length = 20
FEATURE                 Location/Qualifiers
source                  1..20
                        mol_type = other DNA
                        organism = synthetic construct
SEQUENCE: 342
cgaaagcgca gtagtggcac                                                    20

SEQ ID NO: 343          moltype = DNA  length = 20
FEATURE                 Location/Qualifiers
source                  1..20
                        mol_type = other DNA
                        organism = synthetic construct
SEQUENCE: 343
ctgcatcgaa agcgcagtag                                                    20

SEQ ID NO: 344          moltype = DNA  length = 20
FEATURE                 Location/Qualifiers
source                  1..20
                        mol_type = other DNA
```

```
                                 organism = synthetic construct
SEQUENCE: 344
atgcagaata attcagtatt                                                           20

SEQ ID NO: 345         moltype = DNA   length = 20
FEATURE                Location/Qualifiers
source                 1..20
                       mol_type = other DNA
                       organism = synthetic construct
SEQUENCE: 345
agtatttggc gacttgaagt                                                           20

SEQ ID NO: 346         moltype = DNA   length = 20
FEATURE                Location/Qualifiers
source                 1..20
                       mol_type = other DNA
                       organism = synthetic construct
SEQUENCE: 346
cgacttgaag tcggacgaga                                                           20

SEQ ID NO: 347         moltype = DNA   length = 20
FEATURE                Location/Qualifiers
source                 1..20
                       mol_type = other DNA
                       organism = synthetic construct
SEQUENCE: 347
gagctgctct actcagccta                                                           20

SEQ ID NO: 348         moltype = DNA   length = 20
FEATURE                Location/Qualifiers
source                 1..20
                       mol_type = other DNA
                       organism = synthetic construct
SEQUENCE: 348
cacgcctgtc tcatctccgt                                                           20

SEQ ID NO: 349         moltype = DNA   length = 20
FEATURE                Location/Qualifiers
source                 1..20
                       mol_type = other DNA
                       organism = synthetic construct
SEQUENCE: 349
tcagcctacg gagatgagac                                                           20

SEQ ID NO: 350         moltype = DNA   length = 20
FEATURE                Location/Qualifiers
source                 1..20
                       mol_type = other DNA
                       organism = synthetic construct
SEQUENCE: 350
caggcgtgca gtgtgcgctg                                                           20

SEQ ID NO: 351         moltype = DNA   length = 20
FEATURE                Location/Qualifiers
source                 1..20
                       mol_type = other DNA
                       organism = synthetic construct
SEQUENCE: 351
ccgcggcccc tctagcctgc                                                           20

SEQ ID NO: 352         moltype = DNA   length = 20
FEATURE                Location/Qualifiers
source                 1..20
                       mol_type = other DNA
                       organism = synthetic construct
SEQUENCE: 352
catccttcac aaactcctgc                                                           20

SEQ ID NO: 353         moltype = DNA   length = 20
FEATURE                Location/Qualifiers
source                 1..20
                       mol_type = other DNA
                       organism = synthetic construct
SEQUENCE: 353
tagcctgcag gagtttgtga                                                           20

SEQ ID NO: 354         moltype = DNA   length = 20
FEATURE                Location/Qualifiers
source                 1..20
```

-continued

```
                    mol_type = other DNA
                    organism = synthetic construct
SEQUENCE: 354
caggagtttg tgaaggatgc                                                     20

SEQ ID NO: 355      moltype = DNA  length = 20
FEATURE             Location/Qualifiers
source              1..20
                    mol_type = other DNA
                    organism = synthetic construct
SEQUENCE: 355
aggagtttgt gaaggatgct                                                     20

SEQ ID NO: 356      moltype = DNA  length = 20
FEATURE             Location/Qualifiers
source              1..20
                    mol_type = other DNA
                    organism = synthetic construct
SEQUENCE: 356
tgggagctac agcaagaaag                                                     20

SEQ ID NO: 357      moltype = DNA  length = 20
FEATURE             Location/Qualifiers
source              1..20
                    mol_type = other DNA
                    organism = synthetic construct
SEQUENCE: 357
gagctacagc aagaaagtgg                                                     20

SEQ ID NO: 358      moltype = DNA  length = 20
FEATURE             Location/Qualifiers
source              1..20
                    mol_type = other DNA
                    organism = synthetic construct
SEQUENCE: 358
gaaagtggtg gacgacctcc                                                     20

SEQ ID NO: 359      moltype = DNA  length = 20
FEATURE             Location/Qualifiers
source              1..20
                    mol_type = other DNA
                    organism = synthetic construct
SEQUENCE: 359
cgcctgtgat ctggtccagg                                                     20

SEQ ID NO: 360      moltype = DNA  length = 20
FEATURE             Location/Qualifiers
source              1..20
                    mol_type = other DNA
                    organism = synthetic construct
SEQUENCE: 360
ctccgcctgt gatctggtcc                                                     20

SEQ ID NO: 361      moltype = DNA  length = 20
FEATURE             Location/Qualifiers
source              1..20
                    mol_type = other DNA
                    organism = synthetic construct
SEQUENCE: 361
gacctcctgg accagatcac                                                     20

SEQ ID NO: 362      moltype = DNA  length = 20
FEATURE             Location/Qualifiers
source              1..20
                    mol_type = other DNA
                    organism = synthetic construct
SEQUENCE: 362
ctcctggacc agatcacagg                                                     20

SEQ ID NO: 363      moltype = DNA  length = 20
FEATURE             Location/Qualifiers
source              1..20
                    mol_type = other DNA
                    organism = synthetic construct
SEQUENCE: 363
gctggaagag cgtcctagag                                                     20

SEQ ID NO: 364      moltype = DNA  length = 20
FEATURE             Location/Qualifiers
```

```
source                  1..20
                        mol_type = other DNA
                        organism = synthetic construct
SEQUENCE: 364
tgcagcccac ctgcttcagc                                                    20

SEQ ID NO: 365          moltype = DNA   length = 20
FEATURE                 Location/Qualifiers
source                  1..20
                        mol_type = other DNA
                        organism = synthetic construct
SEQUENCE: 365
gacgctcttc cagctgaagc                                                    20

SEQ ID NO: 366          moltype = DNA   length = 20
FEATURE                 Location/Qualifiers
source                  1..20
                        mol_type = other DNA
                        organism = synthetic construct
SEQUENCE: 366
ctcttccagc tgaagcaggt                                                    20

SEQ ID NO: 367          moltype = DNA   length = 20
FEATURE                 Location/Qualifiers
source                  1..20
                        mol_type = other DNA
                        organism = synthetic construct
SEQUENCE: 367
gctcttccag ctgaagcagg                                                    20

SEQ ID NO: 368          moltype = DNA   length = 20
FEATURE                 Location/Qualifiers
source                  1..20
                        mol_type = other DNA
                        organism = synthetic construct
SEQUENCE: 368
cctccagatg aagccaaggt                                                    20

SEQ ID NO: 369          moltype = DNA   length = 20
FEATURE                 Location/Qualifiers
source                  1..20
                        mol_type = other DNA
                        organism = synthetic construct
SEQUENCE: 369
gcttcatctg gaggcttcat                                                    20

SEQ ID NO: 370          moltype = DNA   length = 20
FEATURE                 Location/Qualifiers
source                  1..20
                        mol_type = other DNA
                        organism = synthetic construct
SEQUENCE: 370
ggcttcatct ggaggcttca                                                    20

SEQ ID NO: 371          moltype = DNA   length = 20
FEATURE                 Location/Qualifiers
source                  1..20
                        mol_type = other DNA
                        organism = synthetic construct
SEQUENCE: 371
cttaccttgg cttcatctgg                                                    20

SEQ ID NO: 372          moltype = DNA   length = 20
FEATURE                 Location/Qualifiers
source                  1..20
                        mol_type = other DNA
                        organism = synthetic construct
SEQUENCE: 372
aaacttacct tggcttcatc                                                    20

SEQ ID NO: 373          moltype = DNA   length = 20
FEATURE                 Location/Qualifiers
source                  1..20
                        mol_type = other DNA
                        organism = synthetic construct
SEQUENCE: 373
gaagcctcca gatgaagcca                                                    20

SEQ ID NO: 374          moltype = DNA   length = 20
```

```
FEATURE          Location/Qualifiers
source           1..20
                 mol_type = other DNA
                 organism = synthetic construct
SEQUENCE: 374
tcctagggtg tccccaacct                                              20

SEQ ID NO: 375   moltype = DNA   length = 20
FEATURE          Location/Qualifiers
source           1..20
                 mol_type = other DNA
                 organism = synthetic construct
SEQUENCE: 375
cctagggtgt ccccaacctg                                              20

SEQ ID NO: 376   moltype = DNA   length = 20
FEATURE          Location/Qualifiers
source           1..20
                 mol_type = other DNA
                 organism = synthetic construct
SEQUENCE: 376
gtgtctgtct ccacaggttg                                              20

SEQ ID NO: 377   moltype = DNA   length = 20
FEATURE          Location/Qualifiers
source           1..20
                 mol_type = other DNA
                 organism = synthetic construct
SEQUENCE: 377
tgtgtctgtc tccacaggtt                                              20

SEQ ID NO: 378   moltype = DNA   length = 20
FEATURE          Location/Qualifiers
source           1..20
                 mol_type = other DNA
                 organism = synthetic construct
SEQUENCE: 378
ccacaggttg gggacaccct                                              20

SEQ ID NO: 379   moltype = DNA   length = 20
FEATURE          Location/Qualifiers
source           1..20
                 mol_type = other DNA
                 organism = synthetic construct
SEQUENCE: 379
agagctgctg ctgtctccta                                              20

SEQ ID NO: 380   moltype = DNA   length = 20
FEATURE          Location/Qualifiers
source           1..20
                 mol_type = other DNA
                 organism = synthetic construct
SEQUENCE: 380
cagagctgct gctgtctcct                                              20

SEQ ID NO: 381   moltype = DNA   length = 20
FEATURE          Location/Qualifiers
source           1..20
                 mol_type = other DNA
                 organism = synthetic construct
SEQUENCE: 381
agacagcagc agctctgttc                                              20

SEQ ID NO: 382   moltype = DNA   length = 20
FEATURE          Location/Qualifiers
source           1..20
                 mol_type = other DNA
                 organism = synthetic construct
SEQUENCE: 382
atccacagaa acgtcgggat                                              20

SEQ ID NO: 383   moltype = DNA   length = 20
FEATURE          Location/Qualifiers
source           1..20
                 mol_type = other DNA
                 organism = synthetic construct
SEQUENCE: 383
gagatatcca cagaaacgtc                                              20
```

```
SEQ ID NO: 384            moltype = DNA   length = 20
FEATURE                   Location/Qualifiers
source                    1..20
                          mol_type = other DNA
                          organism = synthetic construct
SEQUENCE: 384
ggagatatcc acagaaacgt                                                     20

SEQ ID NO: 385            moltype = DNA   length = 20
FEATURE                   Location/Qualifiers
source                    1..20
                          mol_type = other DNA
                          organism = synthetic construct
SEQUENCE: 385
gtcctatccc gacgtttctg                                                     20

SEQ ID NO: 386            moltype = DNA   length = 20
FEATURE                   Location/Qualifiers
source                    1..20
                          mol_type = other DNA
                          organism = synthetic construct
SEQUENCE: 386
tctccatgct cagctctctg                                                     20

SEQ ID NO: 387            moltype = DNA   length = 20
FEATURE                   Location/Qualifiers
source                    1..20
                          mol_type = other DNA
                          organism = synthetic construct
SEQUENCE: 387
ctcacccaga gagctgagca                                                     20

SEQ ID NO: 388            moltype = DNA   length = 20
FEATURE                   Location/Qualifiers
source                    1..20
                          mol_type = other DNA
                          organism = synthetic construct
SEQUENCE: 388
atctccatgc tcagctctct                                                     20

SEQ ID NO: 389            moltype = DNA   length = 20
FEATURE                   Location/Qualifiers
source                    1..20
                          mol_type = other DNA
                          organism = synthetic construct
SEQUENCE: 389
tatctccatg ctcagctctc                                                     20

SEQ ID NO: 390            moltype = DNA   length = 20
FEATURE                   Location/Qualifiers
source                    1..20
                          mol_type = other DNA
                          organism = synthetic construct
SEQUENCE: 390
atgtcctgtt tacacaggga                                                     20

SEQ ID NO: 391            moltype = DNA   length = 20
FEATURE                   Location/Qualifiers
source                    1..20
                          mol_type = other DNA
                          organism = synthetic construct
SEQUENCE: 391
ttacacaggg aaggtgaaga                                                     20

SEQ ID NO: 392            moltype = DNA   length = 20
FEATURE                   Location/Qualifiers
source                    1..20
                          mol_type = other DNA
                          organism = synthetic construct
SEQUENCE: 392
agttcaaatg gctgtcgtca                                                     20

SEQ ID NO: 393            moltype = DNA   length = 20
FEATURE                   Location/Qualifiers
source                    1..20
                          mol_type = other DNA
                          organism = synthetic construct
SEQUENCE: 393
tgacgacagc catttgaact                                                     20
```

```
SEQ ID NO: 394           moltype = DNA  length = 20
FEATURE                  Location/Qualifiers
source                   1..20
                         mol_type = other DNA
                         organism = synthetic construct
SEQUENCE: 394
aagttcaaat ggctgtcgtc                                                      20

SEQ ID NO: 395           moltype = DNA  length = 20
FEATURE                  Location/Qualifiers
source                   1..20
                         mol_type = other DNA
                         organism = synthetic construct
SEQUENCE: 395
tcgtctcatc caagttcaaa                                                      20

SEQ ID NO: 396           moltype = DNA  length = 20
FEATURE                  Location/Qualifiers
source                   1..20
                         mol_type = other DNA
                         organism = synthetic construct
SEQUENCE: 396
tgagacgacg aagctcctgc                                                      20

SEQ ID NO: 397           moltype = DNA  length = 20
FEATURE                  Location/Qualifiers
source                   1..20
                         mol_type = other DNA
                         organism = synthetic construct
SEQUENCE: 397
gtgcttcgtg caggtcctgc                                                      20

SEQ ID NO: 398           moltype = DNA  length = 20
FEATURE                  Location/Qualifiers
source                   1..20
                         mol_type = other DNA
                         organism = synthetic construct
SEQUENCE: 398
gcaggacctg cacgaagcac                                                      20

SEQ ID NO: 399           moltype = DNA  length = 20
FEATURE                  Location/Qualifiers
source                   1..20
                         mol_type = other DNA
                         organism = synthetic construct
SEQUENCE: 399
gctccgcctg tgcttcgtgc                                                      20

SEQ ID NO: 400           moltype = DNA  length = 20
FEATURE                  Location/Qualifiers
source                   1..20
                         mol_type = other DNA
                         organism = synthetic construct
SEQUENCE: 400
ggacctgcac gaagcacagg                                                      20

SEQ ID NO: 401           moltype = DNA  length = 20
FEATURE                  Location/Qualifiers
source                   1..20
                         mol_type = other DNA
                         organism = synthetic construct
SEQUENCE: 401
cacgaagcac aggcggagcg                                                      20

SEQ ID NO: 402           moltype = DNA  length = 20
FEATURE                  Location/Qualifiers
source                   1..20
                         mol_type = other DNA
                         organism = synthetic construct
SEQUENCE: 402
aggcggagcg cggcggctct                                                      20

SEQ ID NO: 403           moltype = DNA  length = 20
FEATURE                  Location/Qualifiers
source                   1..20
                         mol_type = other DNA
                         organism = synthetic construct
SEQUENCE: 403
```

```
agggagctga ggttggacga                                               20

SEQ ID NO: 404         moltype = DNA   length = 20
FEATURE                Location/Qualifiers
source                 1..20
                       mol_type = other DNA
                       organism = synthetic construct
SEQUENCE: 404
gttggacagg gagctgaggt                                               20

SEQ ID NO: 405         moltype = DNA   length = 20
FEATURE                Location/Qualifiers
source                 1..20
                       mol_type = other DNA
                       organism = synthetic construct
SEQUENCE: 405
aggcgttgga cagggagctg                                               20

SEQ ID NO: 406         moltype = DNA   length = 20
FEATURE                Location/Qualifiers
source                 1..20
                       mol_type = other DNA
                       organism = synthetic construct
SEQUENCE: 406
ccctctcgga ggcgttggac                                               20

SEQ ID NO: 407         moltype = DNA   length = 20
FEATURE                Location/Qualifiers
source                 1..20
                       mol_type = other DNA
                       organism = synthetic construct
SEQUENCE: 407
cctctcggag gcgttggaca                                               20

SEQ ID NO: 408         moltype = DNA   length = 20
FEATURE                Location/Qualifiers
source                 1..20
                       mol_type = other DNA
                       organism = synthetic construct
SEQUENCE: 408
ctggtccctc tcggaggcgt                                               20

SEQ ID NO: 409         moltype = DNA   length = 20
FEATURE                Location/Qualifiers
source                 1..20
                       mol_type = other DNA
                       organism = synthetic construct
SEQUENCE: 409
ccctgtccaa cgcctccgag                                               20

SEQ ID NO: 410         moltype = DNA   length = 20
FEATURE                Location/Qualifiers
source                 1..20
                       mol_type = other DNA
                       organism = synthetic construct
SEQUENCE: 410
cctgtccaac gcctccgaga                                               20

SEQ ID NO: 411         moltype = DNA   length = 20
FEATURE                Location/Qualifiers
source                 1..20
                       mol_type = other DNA
                       organism = synthetic construct
SEQUENCE: 411
gtggtgctgg tccctctcgg                                               20

SEQ ID NO: 412         moltype = DNA   length = 20
FEATURE                Location/Qualifiers
source                 1..20
                       mol_type = other DNA
                       organism = synthetic construct
SEQUENCE: 412
caggtggtgc tggtccctct                                               20

SEQ ID NO: 413         moltype = DNA   length = 20
FEATURE                Location/Qualifiers
source                 1..20
                       mol_type = other DNA
                       organism = synthetic construct
```

```
SEQUENCE: 413
gcatctcacc caggtggtgc                                                    20

SEQ ID NO: 414          moltype = DNA  length = 20
FEATURE                 Location/Qualifiers
source                  1..20
                        mol_type = other DNA
                        organism = synthetic construct
SEQUENCE: 414
cgagagggac cagcaccacc                                                    20

SEQ ID NO: 415          moltype = DNA  length = 20
FEATURE                 Location/Qualifiers
source                  1..20
                        mol_type = other DNA
                        organism = synthetic construct
SEQUENCE: 415
gagagggacc agcaccacct                                                    20

SEQ ID NO: 416          moltype = DNA  length = 20
FEATURE                 Location/Qualifiers
source                  1..20
                        mol_type = other DNA
                        organism = synthetic construct
SEQUENCE: 416
gtgggggcat ctcacccagg                                                    20

SEQ ID NO: 417          moltype = DNA  length = 20
FEATURE                 Location/Qualifiers
source                  1..20
                        mol_type = other DNA
                        organism = synthetic construct
SEQUENCE: 417
ccccgacact caggcgagaa                                                    20

SEQ ID NO: 418          moltype = DNA  length = 20
FEATURE                 Location/Qualifiers
source                  1..20
                        mol_type = other DNA
                        organism = synthetic construct
SEQUENCE: 418
tccccgacac tcaggcgaga                                                    20

SEQ ID NO: 419          moltype = DNA  length = 20
FEATURE                 Location/Qualifiers
source                  1..20
                        mol_type = other DNA
                        organism = synthetic construct
SEQUENCE: 419
agcccttctc gcctgagtgt                                                    20

SEQ ID NO: 420          moltype = DNA  length = 20
FEATURE                 Location/Qualifiers
source                  1..20
                        mol_type = other DNA
                        organism = synthetic construct
SEQUENCE: 420
ctggctgctc cccgacactc                                                    20

SEQ ID NO: 421          moltype = DNA  length = 20
FEATURE                 Location/Qualifiers
source                  1..20
                        mol_type = other DNA
                        organism = synthetic construct
SEQUENCE: 421
cccttctcgc ctgagtgtcg                                                    20

SEQ ID NO: 422          moltype = DNA  length = 20
FEATURE                 Location/Qualifiers
source                  1..20
                        mol_type = other DNA
                        organism = synthetic construct
SEQUENCE: 422
gcccttctcg cctgagtgtc                                                    20

SEQ ID NO: 423          moltype = DNA  length = 20
FEATURE                 Location/Qualifiers
source                  1..20
                        mol_type = other DNA
```

```
                        organism = synthetic construct
SEQUENCE: 423
tagggdtcgt gggtgacgtc                                               20

SEQ ID NO: 424          moltype = DNA  length = 20
FEATURE                 Location/Qualifiers
source                  1..20
                        mol_type = other DNA
                        organism = synthetic construct
SEQUENCE: 424
aagaaactca tagggdtcgt                                               20

SEQ ID NO: 425          moltype = DNA  length = 20
FEATURE                 Location/Qualifiers
source                  1..20
                        mol_type = other DNA
                        organism = synthetic construct
SEQUENCE: 425
gaagaaactc atagggdtcg                                               20

SEQ ID NO: 426          moltype = DNA  length = 20
FEATURE                 Location/Qualifiers
source                  1..20
                        mol_type = other DNA
                        organism = synthetic construct
SEQUENCE: 426
gagactgaag aaactcatag                                               20

SEQ ID NO: 427          moltype = DNA  length = 20
FEATURE                 Location/Qualifiers
source                  1..20
                        mol_type = other DNA
                        organism = synthetic construct
SEQUENCE: 427
ggagactgaa gaaactcata                                               20

SEQ ID NO: 428          moltype = DNA  length = 20
FEATURE                 Location/Qualifiers
source                  1..20
                        mol_type = other DNA
                        organism = synthetic construct
SEQUENCE: 428
tggagactga agaaactcat                                               20

SEQ ID NO: 429          moltype = DNA  length = 20
FEATURE                 Location/Qualifiers
source                  1..20
                        mol_type = other DNA
                        organism = synthetic construct
SEQUENCE: 429
tcttcagtct ccagagcctg                                               20

SEQ ID NO: 430          moltype = DNA  length = 20
FEATURE                 Location/Qualifiers
source                  1..20
                        mol_type = other DNA
                        organism = synthetic construct
SEQUENCE: 430
ttggcagagg ccgcaggctc                                               20

SEQ ID NO: 431          moltype = DNA  length = 20
FEATURE                 Location/Qualifiers
source                  1..20
                        mol_type = other DNA
                        organism = synthetic construct
SEQUENCE: 431
taggtcttgg cagaggccgc                                               20

SEQ ID NO: 432          moltype = DNA  length = 20
FEATURE                 Location/Qualifiers
source                  1..20
                        mol_type = other DNA
                        organism = synthetic construct
SEQUENCE: 432
ctagagttag gtcttggcag                                               20

SEQ ID NO: 433          moltype = DNA  length = 20
FEATURE                 Location/Qualifiers
source                  1..20
```

```
                        mol_type = other DNA
                        organism = synthetic construct
SEQUENCE: 433
ggtggtctag agttaggtct                                                 20

SEQ ID NO: 434          moltype = DNA   length = 20
FEATURE                 Location/Qualifiers
source                  1..20
                        mol_type = other DNA
                        organism = synthetic construct
SEQUENCE: 434
gtagcgaacg tgtccggcgt                                                 20

SEQ ID NO: 435          moltype = DNA   length = 20
FEATURE                 Location/Qualifiers
source                  1..20
                        mol_type = other DNA
                        organism = synthetic construct
SEQUENCE: 435
gaccggaacg atctcgcgta                                                 20

SEQ ID NO: 436          moltype = DNA   length = 20
FEATURE                 Location/Qualifiers
source                  1..20
                        mol_type = other DNA
                        organism = synthetic construct
SEQUENCE: 436
ggcagtcgtt cggttgatat                                                 20

SEQ ID NO: 437          moltype = DNA   length = 20
FEATURE                 Location/Qualifiers
source                  1..20
                        mol_type = other DNA
                        organism = synthetic construct
SEQUENCE: 437
gcttgagcac atacgcgaat                                                 20

SEQ ID NO: 438          moltype = DNA   length = 20
FEATURE                 Location/Qualifiers
source                  1..20
                        mol_type = other DNA
                        organism = synthetic construct
SEQUENCE: 438
gtggtagaat aacgtattac                                                 20

SEQ ID NO: 439          moltype = DNA   length = 20
FEATURE                 Location/Qualifiers
source                  1..20
                        mol_type = other DNA
                        organism = synthetic construct
SEQUENCE: 439
gtcatacatg gataaggcta                                                 20

SEQ ID NO: 440          moltype = DNA   length = 20
FEATURE                 Location/Qualifiers
source                  1..20
                        mol_type = other DNA
                        organism = synthetic construct
SEQUENCE: 440
gatacacgaa gcatcactag                                                 20

SEQ ID NO: 441          moltype = DNA   length = 20
FEATURE                 Location/Qualifiers
source                  1..20
                        mol_type = other DNA
                        organism = synthetic construct
SEQUENCE: 441
gaacgttggc actacttcac                                                 20

SEQ ID NO: 442          moltype = DNA   length = 20
FEATURE                 Location/Qualifiers
source                  1..20
                        mol_type = other DNA
                        organism = synthetic construct
SEQUENCE: 442
gatccatgta atgcgttcga                                                 20

SEQ ID NO: 443          moltype = DNA   length = 20
FEATURE                 Location/Qualifiers
```

```
source                        1..20
                              mol_type = other DNA
                              organism = synthetic construct
SEQUENCE: 443
gtcgtgaagt gcattcgatc                                                       20

SEQ ID NO: 444                moltype = DNA   length = 20
FEATURE                       Location/Qualifiers
source                        1..20
                              mol_type = other DNA
                              organism = synthetic construct
SEQUENCE: 444
gttcgactcg cgtgaccgta                                                       20

SEQ ID NO: 445                moltype = DNA   length = 20
FEATURE                       Location/Qualifiers
source                        1..20
                              mol_type = other DNA
                              organism = synthetic construct
SEQUENCE: 445
gaatctaccg cagcggttcg                                                       20

SEQ ID NO: 446                moltype = DNA   length = 20
FEATURE                       Location/Qualifiers
source                        1..20
                              mol_type = other DNA
                              organism = synthetic construct
SEQUENCE: 446
gaagtgacgt cgattcgata                                                       20

SEQ ID NO: 447                moltype = DNA   length = 20
FEATURE                       Location/Qualifiers
source                        1..20
                              mol_type = other DNA
                              organism = synthetic construct
SEQUENCE: 447
gcggtgtatg acaaccgccg                                                       20

SEQ ID NO: 448                moltype = DNA   length = 20
FEATURE                       Location/Qualifiers
source                        1..20
                              mol_type = other DNA
                              organism = synthetic construct
SEQUENCE: 448
gtaccgcgcc tgaagttcgc                                                       20

SEQ ID NO: 449                moltype = DNA   length = 20
FEATURE                       Location/Qualifiers
source                        1..20
                              mol_type = other DNA
                              organism = synthetic construct
SEQUENCE: 449
gcagctcgtg tgtcgtactc                                                       20

SEQ ID NO: 450                moltype = DNA   length = 20
FEATURE                       Location/Qualifiers
source                        1..20
                              mol_type = other DNA
                              organism = synthetic construct
SEQUENCE: 450
gcgccttaag agtactcatc                                                       20

SEQ ID NO: 451                moltype = DNA   length = 20
FEATURE                       Location/Qualifiers
source                        1..20
                              mol_type = other DNA
                              organism = synthetic construct
SEQUENCE: 451
gagtgtcgtc gttgctccta                                                       20

SEQ ID NO: 452                moltype = DNA   length = 20
FEATURE                       Location/Qualifiers
source                        1..20
                              mol_type = other DNA
                              organism = synthetic construct
SEQUENCE: 452
gcagctcgac ctcaagccgt                                                       20

SEQ ID NO: 453                moltype = DNA   length = 20
```

```
FEATURE                 Location/Qualifiers
source                  1..20
                        mol_type = other DNA
                        organism = synthetic construct
SEQUENCE: 453
gtatcctgac ctacgcgctg                                                    20

SEQ ID NO: 454          moltype = DNA  length = 20
FEATURE                 Location/Qualifiers
source                  1..20
                        mol_type = other DNA
                        organism = synthetic construct
SEQUENCE: 454
gtgtatctca gcacgctaac                                                    20

SEQ ID NO: 455          moltype = DNA  length = 20
FEATURE                 Location/Qualifiers
source                  1..20
                        mol_type = other DNA
                        organism = synthetic construct
SEQUENCE: 455
gtcgtcatac aacggcaacg                                                    20

SEQ ID NO: 456          moltype = DNA  length = 20
FEATURE                 Location/Qualifiers
source                  1..20
                        mol_type = other DNA
                        organism = synthetic construct
SEQUENCE: 456
gtcgtgcgct tccggcggta                                                    20

SEQ ID NO: 457          moltype = DNA  length = 20
FEATURE                 Location/Qualifiers
source                  1..20
                        mol_type = other DNA
                        organism = synthetic construct
SEQUENCE: 457
gcggtcctca gtaagcgcgt                                                    20

SEQ ID NO: 458          moltype = DNA  length = 20
FEATURE                 Location/Qualifiers
source                  1..20
                        mol_type = other DNA
                        organism = synthetic construct
SEQUENCE: 458
gctctgctgc ggaaggattc                                                    20

SEQ ID NO: 459          moltype = DNA  length = 20
FEATURE                 Location/Qualifiers
source                  1..20
                        mol_type = other DNA
                        organism = synthetic construct
SEQUENCE: 459
gcatggagga gcgtcgcaga                                                    20

SEQ ID NO: 460          moltype = DNA  length = 20
FEATURE                 Location/Qualifiers
source                  1..20
                        mol_type = other DNA
                        organism = synthetic construct
SEQUENCE: 460
gtagcgcgcg taggagtggc                                                    20

SEQ ID NO: 461          moltype = DNA  length = 20
FEATURE                 Location/Qualifiers
source                  1..20
                        mol_type = other DNA
                        organism = synthetic construct
SEQUENCE: 461
gatcacctgc attcgtacac                                                    20

SEQ ID NO: 462          moltype = DNA  length = 20
FEATURE                 Location/Qualifiers
source                  1..20
                        mol_type = other DNA
                        organism = synthetic construct
SEQUENCE: 462
gcacacctag atatcgaatg                                                    20
```

-continued

| | | |
|---|---|---|
| SEQ ID NO: 463<br>FEATURE<br>source | moltype = DNA   length = 20<br>Location/Qualifiers<br>1..20<br>mol_type = other DNA<br>organism = synthetic construct | |
| SEQUENCE: 463<br>gttgatcaac gcgcttcgcg | | 20 |
| SEQ ID NO: 464<br>FEATURE<br>source | moltype = DNA   length = 20<br>Location/Qualifiers<br>1..20<br>mol_type = other DNA<br>organism = synthetic construct | |
| SEQUENCE: 464<br>gcgtctcact cactccatcg | | 20 |
| SEQ ID NO: 465<br>FEATURE<br>source | moltype = DNA   length = 20<br>Location/Qualifiers<br>1..20<br>mol_type = other DNA<br>organism = synthetic construct | |
| SEQUENCE: 465<br>gccgaccaac gtcagcggta | | 20 |
| SEQ ID NO: 466<br>FEATURE<br>source | moltype = DNA   length = 20<br>Location/Qualifiers<br>1..20<br>mol_type = other DNA<br>organism = synthetic construct | |
| SEQUENCE: 466<br>ggatacggtg cgtcaatcta | | 20 |
| SEQ ID NO: 467<br>FEATURE<br>source | moltype = DNA   length = 20<br>Location/Qualifiers<br>1..20<br>mol_type = other DNA<br>organism = synthetic construct | |
| SEQUENCE: 467<br>gaatccagtg gcggcgacaa | | 20 |
| SEQ ID NO: 468<br>FEATURE<br>source | moltype = DNA   length = 20<br>Location/Qualifiers<br>1..20<br>mol_type = other DNA<br>organism = synthetic construct | |
| SEQUENCE: 468<br>gcactgtcag tgcaacgata | | 20 |
| SEQ ID NO: 469<br>FEATURE<br>source | moltype = DNA   length = 20<br>Location/Qualifiers<br>1..20<br>mol_type = other DNA<br>organism = synthetic construct | |
| SEQUENCE: 469<br>gcgatcctca agtatgctca | | 20 |
| SEQ ID NO: 470<br>FEATURE<br>source | moltype = DNA   length = 20<br>Location/Qualifiers<br>1..20<br>mol_type = other DNA<br>organism = synthetic construct | |
| SEQUENCE: 470<br>gctaatatcg acacggccgc | | 20 |
| SEQ ID NO: 471<br>FEATURE<br>source | moltype = DNA   length = 20<br>Location/Qualifiers<br>1..20<br>mol_type = other DNA<br>organism = synthetic construct | |
| SEQUENCE: 471<br>ggagatgcat cgaagtcgat | | 20 |
| SEQ ID NO: 472<br>FEATURE<br>source | moltype = DNA   length = 20<br>Location/Qualifiers<br>1..20<br>mol_type = other DNA<br>organism = synthetic construct | |
| SEQUENCE: 472<br>ggatgcactc catctcgtct | | 20 |

```
SEQ ID NO: 473             moltype = DNA  length = 20
FEATURE                    Location/Qualifiers
source                     1..20
                           mol_type = other DNA
                           organism = synthetic construct
SEQUENCE: 473
gtgccgagta ataacgcgag                                                     20

SEQ ID NO: 474             moltype = DNA  length = 20
FEATURE                    Location/Qualifiers
source                     1..20
                           mol_type = other DNA
                           organism = synthetic construct
SEQUENCE: 474
gagattccga tgtaacgtac                                                     20

SEQ ID NO: 475             moltype = DNA  length = 20
FEATURE                    Location/Qualifiers
source                     1..20
                           mol_type = other DNA
                           organism = synthetic construct
SEQUENCE: 475
gtcgtcacga gcaggattgc                                                     20

SEQ ID NO: 476             moltype = DNA  length = 20
FEATURE                    Location/Qualifiers
source                     1..20
                           mol_type = other DNA
                           organism = synthetic construct
SEQUENCE: 476
gcgttagtca cttagctcga                                                     20

SEQ ID NO: 477             moltype = DNA  length = 20
FEATURE                    Location/Qualifiers
source                     1..20
                           mol_type = other DNA
                           organism = synthetic construct
SEQUENCE: 477
gttcacacgg tgtcggatag                                                     20

SEQ ID NO: 478             moltype = DNA  length = 20
FEATURE                    Location/Qualifiers
source                     1..20
                           mol_type = other DNA
                           organism = synthetic construct
SEQUENCE: 478
ggataggtga ccttagtacg                                                     20

SEQ ID NO: 479             moltype = DNA  length = 20
FEATURE                    Location/Qualifiers
source                     1..20
                           mol_type = other DNA
                           organism = synthetic construct
SEQUENCE: 479
gtatgagtca agctaatgcg                                                     20

SEQ ID NO: 480             moltype = DNA  length = 20
FEATURE                    Location/Qualifiers
source                     1..20
                           mol_type = other DNA
                           organism = synthetic construct
SEQUENCE: 480
gcaactattg gaatacgtga                                                     20

SEQ ID NO: 481             moltype = DNA  length = 20
FEATURE                    Location/Qualifiers
source                     1..20
                           mol_type = other DNA
                           organism = synthetic construct
SEQUENCE: 481
gttaccttcg ctcgtctata                                                     20

SEQ ID NO: 482             moltype = DNA  length = 20
FEATURE                    Location/Qualifiers
source                     1..20
                           mol_type = other DNA
                           organism = synthetic construct
SEQUENCE: 482
```

```
gtaccgagca ccacaggccg                                              20

SEQ ID NO: 483         moltype = DNA   length = 20
FEATURE                Location/Qualifiers
source                 1..20
                       mol_type = other DNA
                       organism = synthetic construct SEQUENCE: 483
gtcagccatc ggatagagat                                              20

SEQ ID NO: 484         moltype = DNA   length = 20
FEATURE                Location/Qualifiers
source                 1..20
                       mol_type = other DNA
                       organism = synthetic construct SEQUENCE: 484
gtacggcact cctagccgct                                              20

SEQ ID NO: 485         moltype = DNA   length = 20
FEATURE                Location/Qualifiers
source                 1..20
                       mol_type = other DNA
                       organism = synthetic construct SEQUENCE: 485
ggtcctgtcg tatgcttgca                                              20

SEQ ID NO: 486         moltype = DNA   length = 20
FEATURE                Location/Qualifiers
source                 1..20
                       mol_type = other DNA
                       organism = synthetic construct SEQUENCE: 486
gccgcaatat atgcggtaag                                              20

SEQ ID NO: 487         moltype = DNA   length = 20
FEATURE                Location/Qualifiers
source                 1..20
                       mol_type = other DNA
                       organism = synthetic construct SEQUENCE: 487
gcgcacgtat aatcctgcgt                                              20

SEQ ID NO: 488         moltype = DNA   length = 20
FEATURE                Location/Qualifiers
source                 1..20
                       mol_type = other DNA
                       organism = synthetic construct SEQUENCE: 488
gtgcacaaca cgatccacga                                              20

SEQ ID NO: 489         moltype = DNA   length = 20
FEATURE                Location/Qualifiers
source                 1..20
                       mol_type = other DNA
                       organism = synthetic construct SEQUENCE: 489
gcacaatgtt gacgtaagtg                                              20

SEQ ID NO: 490         moltype = DNA   length = 20
FEATURE                Location/Qualifiers
source                 1..20
                       mol_type = other DNA
                       organism = synthetic construct SEQUENCE: 490
gtaagatgct gctcaccgtg                                              20

SEQ ID NO: 491         moltype = DNA   length = 20
FEATURE                Location/Qualifiers
source                 1..20
                       mol_type = other DNA
                       organism = synthetic construct SEQUENCE: 491
gtcggtgatc caacgtatcg                                              20

SEQ ID NO: 492         moltype = DNA   length = 20
FEATURE                Location/Qualifiers
source                 1..20
                       mol_type = other DNA
                       organism = synthetic construct
```

```
SEQUENCE: 492
gagctagtag gacgcaagac                                                    20

SEQ ID NO: 493         moltype = DNA   length = 20
FEATURE                Location/Qualifiers
source                 1..20
                       mol_type = other DNA
                       organism = synthetic construct
SEQUENCE: 493
gtacgtggaa gcttgtggcc                                                    20

SEQ ID NO: 494         moltype = DNA   length = 20
FEATURE                Location/Qualifiers
source                 1..20
                       mol_type = other DNA
                       organism = synthetic construct
SEQUENCE: 494
gagaactgcc agttctcgat                                                    20

SEQ ID NO: 495         moltype = DNA   length = 20
FEATURE                Location/Qualifiers
source                 1..20
                       mol_type = other DNA
                       organism = synthetic construct
SEQUENCE: 495
gccattcggc gcggcacttc                                                    20

SEQ ID NO: 496         moltype = DNA   length = 20
FEATURE                Location/Qualifiers
source                 1..20
                       mol_type = other DNA
                       organism = synthetic construct
SEQUENCE: 496
gcacacgacc aatccgcttc                                                    20

SEQ ID NO: 497         moltype = DNA   length = 20
FEATURE                Location/Qualifiers
source                 1..20
                       mol_type = other DNA
                       organism = synthetic construct
SEQUENCE: 497
gaggtgatcg attaagtaca                                                    20

SEQ ID NO: 498         moltype = DNA   length = 20
FEATURE                Location/Qualifiers
source                 1..20
                       mol_type = other DNA
                       organism = synthetic construct
SEQUENCE: 498
gtcactcgca gacgcctaac                                                    20

SEQ ID NO: 499         moltype = DNA   length = 20
FEATURE                Location/Qualifiers
source                 1..20
                       mol_type = other DNA
                       organism = synthetic construct
SEQUENCE: 499
gcgctacgga atcatacgtt                                                    20

SEQ ID NO: 500         moltype = DNA   length = 20
FEATURE                Location/Qualifiers
source                 1..20
                       mol_type = other DNA
                       organism = synthetic construct
SEQUENCE: 500
ggtaggacct cacggcgcgc                                                    20

SEQ ID NO: 501         moltype = DNA   length = 20
FEATURE                Location/Qualifiers
source                 1..20
                       mol_type = other DNA
                       organism = synthetic construct
SEQUENCE: 501
gaactgcatc ttgttgtagt                                                    20

SEQ ID NO: 502         moltype = DNA   length = 20
FEATURE                Location/Qualifiers
source                 1..20
                       mol_type = other DNA
```

-continued

| | | |
|---|---|---|
| SEQUENCE: 502<br>gatcctgatc cggcggcgcg | | 20 |
| SEQ ID NO: 503<br>FEATURE<br>source | moltype = DNA  length = 20<br>Location/Qualifiers<br>1..20<br>mol_type = other DNA<br>organism = synthetic construct | |
| SEQUENCE: 503<br>ggtatgcgcg atcctgagtt | | 20 |
| SEQ ID NO: 504<br>FEATURE<br>source | moltype = DNA  length = 20<br>Location/Qualifiers<br>1..20<br>mol_type = other DNA<br>organism = synthetic construct | |
| SEQUENCE: 504<br>gcggagctag agagcggtca | | 20 |
| SEQ ID NO: 505<br>FEATURE<br>source | moltype = DNA  length = 20<br>Location/Qualifiers<br>1..20<br>mol_type = other DNA<br>organism = synthetic construct | |
| SEQUENCE: 505<br>gaatggcaat tacggctgat | | 20 |
| SEQ ID NO: 506<br>FEATURE<br>source | moltype = DNA  length = 20<br>Location/Qualifiers<br>1..20<br>mol_type = other DNA<br>organism = synthetic construct | |
| SEQUENCE: 506<br>gtatggtgag tagtcgcttg | | 20 |
| SEQ ID NO: 507<br>FEATURE<br>source | moltype = DNA  length = 20<br>Location/Qualifiers<br>1..20<br>mol_type = other DNA<br>organism = synthetic construct | |
| SEQUENCE: 507<br>gtgtaattgc gtctagtcgg | | 20 |
| SEQ ID NO: 508<br>FEATURE<br>source | moltype = DNA  length = 20<br>Location/Qualifiers<br>1..20<br>mol_type = other DNA<br>organism = synthetic construct | |
| SEQUENCE: 508<br>ggtcctggcg aggagccttg | | 20 |
| SEQ ID NO: 509<br>FEATURE<br>source | moltype = DNA  length = 20<br>Location/Qualifiers<br>1..20<br>mol_type = other DNA<br>organism = synthetic construct | |
| SEQUENCE: 509<br>gaagataagt cgctgtctcg | | 20 |
| SEQ ID NO: 510<br>FEATURE<br>source | moltype = DNA  length = 20<br>Location/Qualifiers<br>1..20<br>mol_type = other DNA<br>organism = synthetic construct | |
| SEQUENCE: 510<br>gtcggcgttc tgttgtgact | | 20 |
| SEQ ID NO: 511<br>FEATURE<br>source | moltype = DNA  length = 20<br>Location/Qualifiers<br>1..20<br>mol_type = other DNA<br>organism = synthetic construct | |
| SEQUENCE: 511<br>gaggcaagcc gttaggtgta | | 20 |
| SEQ ID NO: 512<br>FEATURE<br>source | moltype = DNA  length = 20<br>Location/Qualifiers<br>1..20 | |

```
                        mol_type = other DNA
                        organism = synthetic construct
SEQUENCE: 512
gcggatccag atctcattcg                                              20

SEQ ID NO: 513          moltype = DNA  length = 20
FEATURE                 Location/Qualifiers
source                  1..20
                        mol_type = other DNA
                        organism = synthetic construct
SEQUENCE: 513
ggaacatagg agcacgtagt                                              20

SEQ ID NO: 514          moltype = DNA  length = 20
FEATURE                 Location/Qualifiers
source                  1..20
                        mol_type = other DNA
                        organism = synthetic construct
SEQUENCE: 514
gtcatcatta tggcgtaagg                                              20

SEQ ID NO: 515          moltype = DNA  length = 20
FEATURE                 Location/Qualifiers
source                  1..20
                        mol_type = other DNA
                        organism = synthetic construct
SEQUENCE: 515
gcgactagcg ccatgagcgg                                              20

SEQ ID NO: 516          moltype = DNA  length = 20
FEATURE                 Location/Qualifiers
source                  1..20
                        mol_type = other DNA
                        organism = synthetic construct
SEQUENCE: 516
ggcgaagttc gacatgacac                                              20

SEQ ID NO: 517          moltype = DNA  length = 20
FEATURE                 Location/Qualifiers
source                  1..20
                        mol_type = other DNA
                        organism = synthetic construct
SEQUENCE: 517
gctgtcgtgt ggaggctatg                                              20

SEQ ID NO: 518          moltype = DNA  length = 20
FEATURE                 Location/Qualifiers
source                  1..20
                        mol_type = other DNA
                        organism = synthetic construct
SEQUENCE: 518
gcggagagca ttgacctcat                                              20

SEQ ID NO: 519          moltype = DNA  length = 20
FEATURE                 Location/Qualifiers
source                  1..20
                        mol_type = other DNA
                        organism = synthetic construct
SEQUENCE: 519
gactaatgga ccaagtcagt                                              20

SEQ ID NO: 520          moltype = DNA  length = 20
FEATURE                 Location/Qualifiers
source                  1..20
                        mol_type = other DNA
                        organism = synthetic construct
SEQUENCE: 520
gcggattaga ggtaatgcgg                                              20

SEQ ID NO: 521          moltype = DNA  length = 20
FEATURE                 Location/Qualifiers
source                  1..20
                        mol_type = other DNA
                        organism = synthetic construct
SEQUENCE: 521
gccgacggca atcagtacgc                                              20

SEQ ID NO: 522          moltype = DNA  length = 20
FEATURE                 Location/Qualifiers
```

```
source                  1..20
                        mol_type = other DNA
                        organism = synthetic construct
SEQUENCE: 522
gtaacctctc gagcgataga                                                     20

SEQ ID NO: 523          moltype = DNA   length = 20
FEATURE                 Location/Qualifiers
source                  1..20
                        mol_type = other DNA
                        organism = synthetic construct
SEQUENCE: 523
gacttgtatg tggcttacgg                                                     20

SEQ ID NO: 524          moltype = DNA   length = 20
FEATURE                 Location/Qualifiers
source                  1..20
                        mol_type = other DNA
                        organism = synthetic construct
SEQUENCE: 524
gtcactgtgg tcgaacatgt                                                     20

SEQ ID NO: 525          moltype = DNA   length = 20
FEATURE                 Location/Qualifiers
source                  1..20
                        mol_type = other DNA
                        organism = synthetic construct
SEQUENCE: 525
gtactccaat ccgcgatgac                                                     20

SEQ ID NO: 526          moltype = DNA   length = 20
FEATURE                 Location/Qualifiers
source                  1..20
                        mol_type = other DNA
                        organism = synthetic construct
SEQUENCE: 526
gcgttggcac gatgttacgg                                                     20

SEQ ID NO: 527          moltype = DNA   length = 20
FEATURE                 Location/Qualifiers
source                  1..20
                        mol_type = other DNA
                        organism = synthetic construct
SEQUENCE: 527
gaaccagccg gctagtatga                                                     20

SEQ ID NO: 528          moltype = DNA   length = 20
FEATURE                 Location/Qualifiers
source                  1..20
                        mol_type = other DNA
                        organism = synthetic construct
SEQUENCE: 528
gtatactagc taaccacacg                                                     20

SEQ ID NO: 529          moltype = DNA   length = 20
FEATURE                 Location/Qualifiers
source                  1..20
                        mol_type = other DNA
                        organism = synthetic construct
SEQUENCE: 529
gaatcggaat agttgattcg                                                     20

SEQ ID NO: 530          moltype = DNA   length = 20
FEATURE                 Location/Qualifiers
source                  1..20
                        mol_type = other DNA
                        organism = synthetic construct
SEQUENCE: 530
gagcacttgc atgaggcggt                                                     20

SEQ ID NO: 531          moltype = DNA   length = 20
FEATURE                 Location/Qualifiers
source                  1..20
                        mol_type = other DNA
                        organism = synthetic construct
SEQUENCE: 531
gaacggcgat gaagccagcc                                                     20

SEQ ID NO: 532          moltype = DNA   length = 20
```

```
FEATURE            Location/Qualifiers
source             1..20
                   mol_type = other DNA
                   organism = synthetic construct
SEQUENCE: 532
gcaaccgaga tgagaggttc                                              20

SEQ ID NO: 533     moltype = DNA   length = 20
FEATURE            Location/Qualifiers
source             1..20
                   mol_type = other DNA
                   organism = synthetic construct
SEQUENCE: 533
gcaagatcaa tatgcgtgat                                              20

SEQ ID NO: 534     moltype = DNA   length = 20
FEATURE            Location/Qualifiers
source             1..20
                   mol_type = other DNA
                   organism = synthetic construct
SEQUENCE: 534
acggaggcta agcgtcgcaa                                              20

SEQ ID NO: 535     moltype = DNA   length = 20
FEATURE            Location/Qualifiers
source             1..20
                   mol_type = other DNA
                   organism = synthetic construct
SEQUENCE: 535
cgcttccgcg gcccgttcaa                                              20

SEQ ID NO: 536     moltype = DNA   length = 20
FEATURE            Location/Qualifiers
source             1..20
                   mol_type = other DNA
                   organism = synthetic construct
SEQUENCE: 536
atcgtttccg cttaacggcg                                              20

SEQ ID NO: 537     moltype = DNA   length = 20
FEATURE            Location/Qualifiers
source             1..20
                   mol_type = other DNA
                   organism = synthetic construct
SEQUENCE: 537
gtaggcgcgc cgctctctac                                              20

SEQ ID NO: 538     moltype = DNA   length = 20
FEATURE            Location/Qualifiers
source             1..20
                   mol_type = other DNA
                   organism = synthetic construct
SEQUENCE: 538
ccatatcggg gcgagacatg                                              20

SEQ ID NO: 539     moltype = DNA   length = 20
FEATURE            Location/Qualifiers
source             1..20
                   mol_type = other DNA
                   organism = synthetic construct
SEQUENCE: 539
tactaacgcc gctcctacag                                              20

SEQ ID NO: 540     moltype = DNA   length = 20
FEATURE            Location/Qualifiers
source             1..20
                   mol_type = other DNA
                   organism = synthetic construct
SEQUENCE: 540
tgaggatcat gtcgagcgcc                                              20

SEQ ID NO: 541     moltype = DNA   length = 20
FEATURE            Location/Qualifiers
source             1..20
                   mol_type = other DNA
                   organism = synthetic construct
SEQUENCE: 541
gggcccgcat aggatatcgc                                              20
```

```
-continued

SEQ ID NO: 542            moltype = DNA   length = 20
FEATURE                   Location/Qualifiers
source                    1..20
                          mol_type = other DNA
                          organism = synthetic construct
SEQUENCE: 542
tagacaaccg cggagaatgc                                              20

SEQ ID NO: 543            moltype = DNA   length = 20
FEATURE                   Location/Qualifiers
source                    1..20
                          mol_type = other DNA
                          organism = synthetic construct
SEQUENCE: 543
acgggcggct atcgctgact                                              20

SEQ ID NO: 544            moltype = DNA   length = 20
FEATURE                   Location/Qualifiers
source                    1..20
                          mol_type = other DNA
                          organism = synthetic construct
SEQUENCE: 544
cgcggaaatt ttaccgacga                                              20

SEQ ID NO: 545            moltype = DNA   length = 20
FEATURE                   Location/Qualifiers
source                    1..20
                          mol_type = other DNA
                          organism = synthetic construct
SEQUENCE: 545
cttacaatcg tcggtccaat                                              20

SEQ ID NO: 546            moltype = DNA   length = 20
FEATURE                   Location/Qualifiers
source                    1..20
                          mol_type = other DNA
                          organism = synthetic construct
SEQUENCE: 546
gcgtgcgtcc cgggttaccc                                              20

SEQ ID NO: 547            moltype = DNA   length = 20
FEATURE                   Location/Qualifiers
source                    1..20
                          mol_type = other DNA
                          organism = synthetic construct
SEQUENCE: 547
cggagtaaca agcggacgga                                              20

SEQ ID NO: 548            moltype = DNA   length = 20
FEATURE                   Location/Qualifiers
source                    1..20
                          mol_type = other DNA
                          organism = synthetic construct
SEQUENCE: 548
cgagtgttat acgcaccgtt                                              20

SEQ ID NO: 549            moltype = DNA   length = 20
FEATURE                   Location/Qualifiers
source                    1..20
                          mol_type = other DNA
                          organism = synthetic construct
SEQUENCE: 549
cgactaaccg gaaactttt                                               20

SEQ ID NO: 550            moltype = DNA   length = 20
FEATURE                   Location/Qualifiers
source                    1..20
                          mol_type = other DNA
                          organism = synthetic construct
SEQUENCE: 550
caacgggttc tcccggctac                                              20

SEQ ID NO: 551            moltype = DNA   length = 20
FEATURE                   Location/Qualifiers
source                    1..20
                          mol_type = other DNA
                          organism = synthetic construct
SEQUENCE: 551
caggagtcgc cgatacgcgt                                              20
```

```
SEQ ID NO: 552           moltype = DNA  length = 20
FEATURE                  Location/Qualifiers
source                   1..20
                         mol_type = other DNA
                         organism = synthetic construct
SEQUENCE: 552
ttcacgtcgt ctcgcgacca                                                     20

SEQ ID NO: 553           moltype = DNA  length = 20
FEATURE                  Location/Qualifiers
source                   1..20
                         mol_type = other DNA
                         organism = synthetic construct
SEQUENCE: 553
gtgtcggatt ccgccgctta                                                     20

SEQ ID NO: 554           moltype = DNA  length = 20
FEATURE                  Location/Qualifiers
source                   1..20
                         mol_type = other DNA
                         organism = synthetic construct
SEQUENCE: 554
cacgaactca caccgcgcga                                                     20

SEQ ID NO: 555           moltype = DNA  length = 20
FEATURE                  Location/Qualifiers
source                   1..20
                         mol_type = other DNA
                         organism = synthetic construct
SEQUENCE: 555
cgctagtacg ctcctctata                                                     20

SEQ ID NO: 556           moltype = DNA  length = 20
FEATURE                  Location/Qualifiers
source                   1..20
                         mol_type = other DNA
                         organism = synthetic construct
SEQUENCE: 556
tcgcgcttgg gttatacgct                                                     20

SEQ ID NO: 557           moltype = DNA  length = 20
FEATURE                  Location/Qualifiers
source                   1..20
                         mol_type = other DNA
                         organism = synthetic construct
SEQUENCE: 557
ctatctcgag tggtaatgcg                                                     20

SEQ ID NO: 558           moltype = DNA  length = 20
FEATURE                  Location/Qualifiers
source                   1..20
                         mol_type = other DNA
                         organism = synthetic construct
SEQUENCE: 558
aatcgactcg aacttcgtgt                                                     20

SEQ ID NO: 559           moltype = DNA  length = 20
FEATURE                  Location/Qualifiers
source                   1..20
                         mol_type = other DNA
                         organism = synthetic construct
SEQUENCE: 559
cccgatggac tataccgaac                                                     20

SEQ ID NO: 560           moltype = DNA  length = 20
FEATURE                  Location/Qualifiers
source                   1..20
                         mol_type = other DNA
                         organism = synthetic construct
SEQUENCE: 560
acgttcgagt acgaccagct                                                     20

SEQ ID NO: 561           moltype = DNA  length = 20
FEATURE                  Location/Qualifiers
source                   1..20
                         mol_type = other DNA
                         organism = synthetic construct
SEQUENCE: 561
```

```
cgcgacgact caacctagtc                                            20

SEQ ID NO: 562          moltype = DNA   length = 20
FEATURE                 Location/Qualifiers
source                  1..20
                        mol_type = other DNA
                        organism = synthetic construct
SEQUENCE: 562
ggtcaccgat cgagagctag                                            20

SEQ ID NO: 563          moltype = DNA   length = 20
FEATURE                 Location/Qualifiers
source                  1..20
                        mol_type = other DNA
                        organism = synthetic construct
SEQUENCE: 563
ctcaaccgac cgtatggtca                                            20

SEQ ID NO: 564          moltype = DNA   length = 20
FEATURE                 Location/Qualifiers
source                  1..20
                        mol_type = other DNA
                        organism = synthetic construct
SEQUENCE: 564
cgtattcgac tctcaacgcg                                            20

SEQ ID NO: 565          moltype = DNA   length = 20
FEATURE                 Location/Qualifiers
source                  1..20
                        mol_type = other DNA
                        organism = synthetic construct
SEQUENCE: 565
ctagccgccc agatcgagcc                                            20

SEQ ID NO: 566          moltype = DNA   length = 20
FEATURE                 Location/Qualifiers
source                  1..20
                        mol_type = other DNA
                        organism = synthetic construct
SEQUENCE: 566
gaatcgaccg acactaatgt                                            20

SEQ ID NO: 567          moltype = DNA   length = 20
FEATURE                 Location/Qualifiers
source                  1..20
                        mol_type = other DNA
                        organism = synthetic construct
SEQUENCE: 567
acttcagttc ggcgtagtca                                            20

SEQ ID NO: 568          moltype = DNA   length = 20
FEATURE                 Location/Qualifiers
source                  1..20
                        mol_type = other DNA
                        organism = synthetic construct
SEQUENCE: 568
gtgcgatgtc gcttcaacgt                                            20

SEQ ID NO: 569          moltype = DNA   length = 20
FEATURE                 Location/Qualifiers
source                  1..20
                        mol_type = other DNA
                        organism = synthetic construct
SEQUENCE: 569
cgcctaattt ccggatcaat                                            20

SEQ ID NO: 570          moltype = DNA   length = 20
FEATURE                 Location/Qualifiers
source                  1..20
                        mol_type = other DNA
                        organism = synthetic construct
SEQUENCE: 570
cgtggccgga accgtcatag                                            20

SEQ ID NO: 571          moltype = DNA   length = 20
FEATURE                 Location/Qualifiers
source                  1..20
                        mol_type = other DNA
                        organism = synthetic construct
```

```
SEQUENCE: 571
accctccgaa tcgtaacgga                                               20

SEQ ID NO: 572         moltype = DNA  length = 20
FEATURE                Location/Qualifiers
source                 1..20
                       mol_type = other DNA
                       organism = synthetic construct
SEQUENCE: 572
aaacggtacg acagcgtgtg                                               20

SEQ ID NO: 573         moltype = DNA  length = 20
FEATURE                Location/Qualifiers
source                 1..20
                       mol_type = other DNA
                       organism = synthetic construct
SEQUENCE: 573
acatagtcga cggctcgatt                                               20

SEQ ID NO: 574         moltype = DNA  length = 20
FEATURE                Location/Qualifiers
source                 1..20
                       mol_type = other DNA
                       organism = synthetic construct
SEQUENCE: 574
gatggcgctt cagtcgtcgg                                               20

SEQ ID NO: 575         moltype = DNA  length = 20
FEATURE                Location/Qualifiers
source                 1..20
                       mol_type = other DNA
                       organism = synthetic construct
SEQUENCE: 575
ataatccgga aacgctcgac                                               20

SEQ ID NO: 576         moltype = DNA  length = 20
FEATURE                Location/Qualifiers
source                 1..20
                       mol_type = other DNA
                       organism = synthetic construct
SEQUENCE: 576
cgccgggctg acaattaacg                                               20

SEQ ID NO: 577         moltype = DNA  length = 20
FEATURE                Location/Qualifiers
source                 1..20
                       mol_type = other DNA
                       organism = synthetic construct
SEQUENCE: 577
cgtcgccata tgccggtggc                                               20

SEQ ID NO: 578         moltype = DNA  length = 20
FEATURE                Location/Qualifiers
source                 1..20
                       mol_type = other DNA
                       organism = synthetic construct
SEQUENCE: 578
cgggcctata acaccatcga                                               20

SEQ ID NO: 579         moltype = DNA  length = 20
FEATURE                Location/Qualifiers
source                 1..20
                       mol_type = other DNA
                       organism = synthetic construct
SEQUENCE: 579
cgccgttccg agatacttga                                               20

SEQ ID NO: 580         moltype = DNA  length = 20
FEATURE                Location/Qualifiers
source                 1..20
                       mol_type = other DNA
                       organism = synthetic construct
SEQUENCE: 580
cgggacgtcg cgaaaatgta                                               20

SEQ ID NO: 581         moltype = DNA  length = 20
FEATURE                Location/Qualifiers
source                 1..20
                       mol_type = other DNA
```

```
                         organism = synthetic construct
SEQUENCE: 581
tcggcatacg ggacacacgc                                                        20

SEQ ID NO: 582           moltype = DNA  length = 20
FEATURE                  Location/Qualifiers
source                   1..20
                         mol_type = other DNA
                         organism = synthetic construct
SEQUENCE: 582
agctccatcg ccgcgataat                                                        20

SEQ ID NO: 583           moltype = DNA  length = 20
FEATURE                  Location/Qualifiers
source                   1..20
                         mol_type = other DNA
                         organism = synthetic construct
SEQUENCE: 583
atcgtatcat cagctagcgc                                                        20

SEQ ID NO: 584           moltype = DNA  length = 20
FEATURE                  Location/Qualifiers
source                   1..20
                         mol_type = other DNA
                         organism = synthetic construct
SEQUENCE: 584
tcgatcgagg ttgcattcgg                                                        20

SEQ ID NO: 585           moltype = DNA  length = 20
FEATURE                  Location/Qualifiers
source                   1..20
                         mol_type = other DNA
                         organism = synthetic construct
SEQUENCE: 585
ctcgacagtt cgtcccgagc                                                        20

SEQ ID NO: 586           moltype = DNA  length = 20
FEATURE                  Location/Qualifiers
source                   1..20
                         mol_type = other DNA
                         organism = synthetic construct
SEQUENCE: 586
cggtagtatt aatcgctgac                                                        20

SEQ ID NO: 587           moltype = DNA  length = 20
FEATURE                  Location/Qualifiers
source                   1..20
                         mol_type = other DNA
                         organism = synthetic construct
SEQUENCE: 587
tgaacgcgtg tttccttgca                                                        20

SEQ ID NO: 588           moltype = DNA  length = 20
FEATURE                  Location/Qualifiers
source                   1..20
                         mol_type = other DNA
                         organism = synthetic construct
SEQUENCE: 588
cgacgctagg taacgtagag                                                        20

SEQ ID NO: 589           moltype = DNA  length = 20
FEATURE                  Location/Qualifiers
source                   1..20
                         mol_type = other DNA
                         organism = synthetic construct
SEQUENCE: 589
cattgttgag cgggcgcgct                                                        20

SEQ ID NO: 590           moltype = DNA  length = 20
FEATURE                  Location/Qualifiers
source                   1..20
                         mol_type = other DNA
                         organism = synthetic construct
SEQUENCE: 590
ccgctattga aaccgcccac                                                        20

SEQ ID NO: 591           moltype = DNA  length = 20
FEATURE                  Location/Qualifiers
source                   1..20
```

```
                        mol_type = other DNA
                        organism = synthetic construct
SEQUENCE: 591
agacacgtca ccggtcaaaa                                                   20

SEQ ID NO: 592          moltype = DNA   length = 20
FEATURE                 Location/Qualifiers
source                  1..20
                        mol_type = other DNA
                        organism = synthetic construct
SEQUENCE: 592
tttacgatct agcggcgtag                                                   20

SEQ ID NO: 593          moltype = DNA   length = 20
FEATURE                 Location/Qualifiers
source                  1..20
                        mol_type = other DNA
                        organism = synthetic construct
SEQUENCE: 593
ttcgcacgat tgcaccttgg                                                   20

SEQ ID NO: 594          moltype = DNA   length = 20
FEATURE                 Location/Qualifiers
source                  1..20
                        mol_type = other DNA
                        organism = synthetic construct
SEQUENCE: 594
ggttagagac taggcgcgcg                                                   20

SEQ ID NO: 595          moltype = DNA   length = 20
FEATURE                 Location/Qualifiers
source                  1..20
                        mol_type = other DNA
                        organism = synthetic construct
SEQUENCE: 595
cctccgtgct aacgcggacg                                                   20

SEQ ID NO: 596          moltype = DNA   length = 20
FEATURE                 Location/Qualifiers
source                  1..20
                        mol_type = other DNA
                        organism = synthetic construct
SEQUENCE: 596
ttatcgcgta gtgctgacgt                                                   20

SEQ ID NO: 597          moltype = DNA   length = 20
FEATURE                 Location/Qualifiers
source                  1..20
                        mol_type = other DNA
                        organism = synthetic construct
SEQUENCE: 597
tacgcttgcg tttagcgtcc                                                   20

SEQ ID NO: 598          moltype = DNA   length = 20
FEATURE                 Location/Qualifiers
source                  1..20
                        mol_type = other DNA
                        organism = synthetic construct
SEQUENCE: 598
cgcggcccac gcgtcatcgc                                                   20

SEQ ID NO: 599          moltype = DNA   length = 20
FEATURE                 Location/Qualifiers
source                  1..20
                        mol_type = other DNA
                        organism = synthetic construct
SEQUENCE: 599
agctcgccat gtcggttctc                                                   20

SEQ ID NO: 600          moltype = DNA   length = 20
FEATURE                 Location/Qualifiers
source                  1..20
                        mol_type = other DNA
                        organism = synthetic construct
SEQUENCE: 600
aactagcccg agcagcttcg                                                   20

SEQ ID NO: 601          moltype = DNA   length = 20
FEATURE                 Location/Qualifiers
```

-continued

```
source                  1..20
                        mol_type = other DNA
                        organism = synthetic construct
SEQUENCE: 601
cgcaaggtgt cggtaaccct                                               20

SEQ ID NO: 602          moltype = DNA   length = 20
FEATURE                 Location/Qualifiers
source                  1..20
                        mol_type = other DNA
                        organism = synthetic construct
SEQUENCE: 602
cttcgacgcc atcgtgctca                                               20

SEQ ID NO: 603          moltype = DNA   length = 20
FEATURE                 Location/Qualifiers
source                  1..20
                        mol_type = other DNA
                        organism = synthetic construct
SEQUENCE: 603
tcctggatac cgcgtggtta                                               20

SEQ ID NO: 604          moltype = DNA   length = 20
FEATURE                 Location/Qualifiers
source                  1..20
                        mol_type = other DNA
                        organism = synthetic construct
SEQUENCE: 604
atagccgccg ctcattactt                                               20

SEQ ID NO: 605          moltype = DNA   length = 20
FEATURE                 Location/Qualifiers
source                  1..20
                        mol_type = other DNA
                        organism = synthetic construct
SEQUENCE: 605
gtcgtccggg attacaaaat                                               20

SEQ ID NO: 606          moltype = DNA   length = 20
FEATURE                 Location/Qualifiers
source                  1..20
                        mol_type = other DNA
                        organism = synthetic construct
SEQUENCE: 606
taatgctgca cacgccgaat                                               20

SEQ ID NO: 607          moltype = DNA   length = 20
FEATURE                 Location/Qualifiers
source                  1..20
                        mol_type = other DNA
                        organism = synthetic construct
SEQUENCE: 607
tatcgcttcc gattagtccg                                               20

SEQ ID NO: 608          moltype = DNA   length = 20
FEATURE                 Location/Qualifiers
source                  1..20
                        mol_type = other DNA
                        organism = synthetic construct
SEQUENCE: 608
gtaccatacc gcgtaccctt                                               20

SEQ ID NO: 609          moltype = DNA   length = 20
FEATURE                 Location/Qualifiers
source                  1..20
                        mol_type = other DNA
                        organism = synthetic construct
SEQUENCE: 609
taagatccgc gggtggcaac                                               20

SEQ ID NO: 610          moltype = DNA   length = 20
FEATURE                 Location/Qualifiers
source                  1..20
                        mol_type = other DNA
                        organism = synthetic construct
SEQUENCE: 610
gtagacgtcg tgagcttcac                                               20

SEQ ID NO: 611          moltype = DNA   length = 20
```

```
FEATURE            Location/Qualifiers
source             1..20
                   mol_type = other DNA
                   organism = synthetic construct
SEQUENCE: 611
tcgcggacat agggctctaa                                                      20

SEQ ID NO: 612     moltype = DNA  length = 20
FEATURE            Location/Qualifiers
source             1..20
                   mol_type = other DNA
                   organism = synthetic construct
SEQUENCE: 612
agcgcagata gcgcgtatca                                                      20

SEQ ID NO: 613     moltype = DNA  length = 20
FEATURE            Location/Qualifiers
source             1..20
                   mol_type = other DNA
                   organism = synthetic construct
SEQUENCE: 613
gttcgcttcg taacgaggaa                                                      20

SEQ ID NO: 614     moltype = DNA  length = 20
FEATURE            Location/Qualifiers
source             1..20
                   mol_type = other DNA
                   organism = synthetic construct
SEQUENCE: 614
gacccccgat aactttgac                                                       20

SEQ ID NO: 615     moltype = DNA  length = 20
FEATURE            Location/Qualifiers
source             1..20
                   mol_type = other DNA
                   organism = synthetic construct
SEQUENCE: 615
acgtccatac tgtcggctac                                                      20

SEQ ID NO: 616     moltype = DNA  length = 20
FEATURE            Location/Qualifiers
source             1..20
                   mol_type = other DNA
                   organism = synthetic construct
SEQUENCE: 616
gtaccattgc cggctcccta                                                      20

SEQ ID NO: 617     moltype = DNA  length = 20
FEATURE            Location/Qualifiers
source             1..20
                   mol_type = other DNA
                   organism = synthetic construct
SEQUENCE: 617
tggttccgta ggtcggtata                                                      20

SEQ ID NO: 618     moltype = DNA  length = 20
FEATURE            Location/Qualifiers
source             1..20
                   mol_type = other DNA
                   organism = synthetic construct
SEQUENCE: 618
tctggcttga cacgaccgtt                                                      20

SEQ ID NO: 619     moltype = DNA  length = 20
FEATURE            Location/Qualifiers
source             1..20
                   mol_type = other DNA
                   organism = synthetic construct
SEQUENCE: 619
cgctaggtcc ggtaagtgcg                                                      20

SEQ ID NO: 620     moltype = DNA  length = 20
FEATURE            Location/Qualifiers
source             1..20
                   mol_type = other DNA
                   organism = synthetic construct
SEQUENCE: 620
agcacgtaat gtccgtggat                                                      20
```

| | | |
|---|---|---|
| SEQ ID NO: 621<br>FEATURE<br>source | moltype = DNA   length = 20<br>Location/Qualifiers<br>1..20<br>mol_type = other DNA<br>organism = synthetic construct | |
| SEQUENCE: 621<br>aaggcgcgcg aatgtggcag | | 20 |
| SEQ ID NO: 622<br>FEATURE<br>source | moltype = DNA   length = 20<br>Location/Qualifiers<br>1..20<br>mol_type = other DNA<br>organism = synthetic construct | |
| SEQUENCE: 622<br>actgcggagc gcccaatatc | | 20 |
| SEQ ID NO: 623<br>FEATURE<br>source | moltype = DNA   length = 20<br>Location/Qualifiers<br>1..20<br>mol_type = other DNA<br>organism = synthetic construct | |
| SEQUENCE: 623<br>cgtcgagtgc tcgaactcca | | 20 |
| SEQ ID NO: 624<br>FEATURE<br>source | moltype = DNA   length = 20<br>Location/Qualifiers<br>1..20<br>mol_type = other DNA<br>organism = synthetic construct | |
| SEQUENCE: 624<br>tcgcagcggc gtgggatcgg | | 20 |
| SEQ ID NO: 625<br>FEATURE<br>source | moltype = DNA   length = 20<br>Location/Qualifiers<br>1..20<br>mol_type = other DNA<br>organism = synthetic construct | |
| SEQUENCE: 625<br>atctgtccta attcggatcg | | 20 |
| SEQ ID NO: 626<br>FEATURE<br>source | moltype = DNA   length = 20<br>Location/Qualifiers<br>1..20<br>mol_type = other DNA<br>organism = synthetic construct | |
| SEQUENCE: 626<br>tgcggcgtaa tgcttgaaag | | 20 |
| SEQ ID NO: 627<br>FEATURE<br>source | moltype = DNA   length = 20<br>Location/Qualifiers<br>1..20<br>mol_type = other DNA<br>organism = synthetic construct | |
| SEQUENCE: 627<br>cgaacttaat cccgtggcaa | | 20 |
| SEQ ID NO: 628<br>FEATURE<br>source | moltype = DNA   length = 20<br>Location/Qualifiers<br>1..20<br>mol_type = other DNA<br>organism = synthetic construct | |
| SEQUENCE: 628<br>gccgtgttgc tggatacgcc | | 20 |
| SEQ ID NO: 629<br>FEATURE<br>source | moltype = DNA   length = 20<br>Location/Qualifiers<br>1..20<br>mol_type = other DNA<br>organism = synthetic construct | |
| SEQUENCE: 629<br>taccctccgg atacggactg | | 20 |
| SEQ ID NO: 630<br>FEATURE<br>source | moltype = DNA   length = 20<br>Location/Qualifiers<br>1..20<br>mol_type = other DNA<br>organism = synthetic construct | |
| SEQUENCE: 630<br>ccgttggact atggcgggtc | | 20 |

```
SEQ ID NO: 631           moltype = DNA   length = 20
FEATURE                  Location/Qualifiers
source                   1..20
                         mol_type = other DNA
                         organism = synthetic construct
SEQUENCE: 631
gtacggggcg atcatccaca                                                  20

SEQ ID NO: 632           moltype = DNA   length = 20
FEATURE                  Location/Qualifiers
source                   1..20
                         mol_type = other DNA
                         organism = synthetic construct
SEQUENCE: 632
aagagtagta gacgcccggg                                                  20

SEQ ID NO: 633           moltype = DNA   length = 20
FEATURE                  Location/Qualifiers
source                   1..20
                         mol_type = other DNA
                         organism = synthetic construct
SEQUENCE: 633
aagagcgaat cgatttcgtg                                                  20

SEQ ID NO: 634           moltype = DNA   length = 20
FEATURE                  Location/Qualifiers
source                   1..20
                         mol_type = other DNA
                         organism = synthetic construct
SEQUENCE: 634
tcaacaccag tgcctgacgg                                                  20

SEQ ID NO: 635           moltype = DNA   length = 20
FEATURE                  Location/Qualifiers
source                   1..20
                         mol_type = other DNA
                         organism = synthetic construct
SEQUENCE: 635
aaagtagctt cactctctcg                                                  20

SEQ ID NO: 636           moltype = DNA   length = 20
FEATURE                  Location/Qualifiers
source                   1..20
                         mol_type = other DNA
                         organism = synthetic construct
SEQUENCE: 636
gagccaacca atagatgtcc                                                  20

SEQ ID NO: 637           moltype = DNA   length = 20
FEATURE                  Location/Qualifiers
source                   1..20
                         mol_type = other DNA
                         organism = synthetic construct
SEQUENCE: 637
gcgccgccat gaacctagag                                                  20

SEQ ID NO: 638           moltype = DNA   length = 20
FEATURE                  Location/Qualifiers
source                   1..20
                         mol_type = other DNA
                         organism = synthetic construct
SEQUENCE: 638
acaaaggttg gaacagaacc                                                  20

SEQ ID NO: 639           moltype = DNA   length = 20
FEATURE                  Location/Qualifiers
source                   1..20
                         mol_type = other DNA
                         organism = synthetic construct
SEQUENCE: 639
ggtgaccggg ttattgatgt                                                  20

SEQ ID NO: 640           moltype = DNA   length = 20
FEATURE                  Location/Qualifiers
source                   1..20
                         mol_type = other DNA
                         organism = synthetic construct
SEQUENCE: 640
```
ttagtggagg actacagagc                                               20

SEQ ID NO: 641          moltype = DNA   length = 20
FEATURE                 Location/Qualifiers
source                  1..20
                        mol_type = other DNA
                        organism = synthetic construct
SEQUENCE: 641
acatatagcc cgtaaagctg                                               20

SEQ ID NO: 642          moltype = DNA   length = 20
FEATURE                 Location/Qualifiers
source                  1..20
                        mol_type = other DNA
                        organism = synthetic construct
SEQUENCE: 642
cgttggcgat gatctccacg                                               20

SEQ ID NO: 643          moltype = DNA   length = 20
FEATURE                 Location/Qualifiers
source                  1..20
                        mol_type = other DNA
                        organism = synthetic construct
SEQUENCE: 643
tggccttttc tacctcgcgc                                               20

SEQ ID NO: 644          moltype = DNA   length = 20
FEATURE                 Location/Qualifiers
source                  1..20
                        mol_type = other DNA
                        organism = synthetic construct
SEQUENCE: 644
aatggagata ctcatctggg                                               20

SEQ ID NO: 645          moltype = DNA   length = 20
FEATURE                 Location/Qualifiers
source                  1..20
                        mol_type = other DNA
                        organism = synthetic construct
SEQUENCE: 645
gaagcccgtc cagaaagtgt                                               20

SEQ ID NO: 646          moltype = DNA   length = 20
FEATURE                 Location/Qualifiers
source                  1..20
                        mol_type = other DNA
                        organism = synthetic construct
SEQUENCE: 646
caatctgagg aactccacga                                               20

SEQ ID NO: 647          moltype = DNA   length = 20
FEATURE                 Location/Qualifiers
source                  1..20
                        mol_type = other DNA
                        organism = synthetic construct
SEQUENCE: 647
aggctgcggc gcccacgaga                                               20

SEQ ID NO: 648          moltype = DNA   length = 20
FEATURE                 Location/Qualifiers
source                  1..20
                        mol_type = other DNA
                        organism = synthetic construct
SEQUENCE: 648
actttgacca ggccttgcta                                               20

SEQ ID NO: 649          moltype = DNA   length = 20
FEATURE                 Location/Qualifiers
source                  1..20
                        mol_type = other DNA
                        organism = synthetic construct
SEQUENCE: 649
accttccata actgccacgc                                               20

SEQ ID NO: 650          moltype = DNA   length = 20
FEATURE                 Location/Qualifiers
source                  1..20
                        mol_type = other DNA
                        organism = synthetic construct -continued

```
SEQUENCE: 650
cgaggcgtac atacccaagg                                              20

SEQ ID NO: 651          moltype = DNA  length = 20
FEATURE                 Location/Qualifiers
source                  1..20
                        mol_type = other DNA
                        organism = synthetic construct
SEQUENCE: 651
atggtacggc caaatcaaga                                              20

SEQ ID NO: 652          moltype = DNA  length = 20
FEATURE                 Location/Qualifiers
source                  1..20
                        mol_type = other DNA
                        organism = synthetic construct
SEQUENCE: 652
tcttgtaatc ccatacgcgt                                              20

SEQ ID NO: 653          moltype = DNA  length = 20
FEATURE                 Location/Qualifiers
source                  1..20
                        mol_type = other DNA
                        organism = synthetic construct
SEQUENCE: 653
attcacagga cacagagaat                                              20

SEQ ID NO: 654          moltype = DNA  length = 20
FEATURE                 Location/Qualifiers
source                  1..20
                        mol_type = other DNA
                        organism = synthetic construct
SEQUENCE: 654
ccagggctcc atcctcaaga                                              20

SEQ ID NO: 655          moltype = DNA  length = 20
FEATURE                 Location/Qualifiers
source                  1..20
                        mol_type = other DNA
                        organism = synthetic construct
SEQUENCE: 655
tgagctgcac caaagagacg                                              20

SEQ ID NO: 656          moltype = DNA  length = 20
FEATURE                 Location/Qualifiers
source                  1..20
                        mol_type = other DNA
                        organism = synthetic construct
SEQUENCE: 656
atgtctgcag atgtacccct                                              20

SEQ ID NO: 657          moltype = DNA  length = 20
FEATURE                 Location/Qualifiers
source                  1..20
                        mol_type = other DNA
                        organism = synthetic construct
SEQUENCE: 657
cgaagataac gcggatacct                                              20

SEQ ID NO: 658          moltype = DNA  length = 20
FEATURE                 Location/Qualifiers
source                  1..20
                        mol_type = other DNA
                        organism = synthetic construct
SEQUENCE: 658
gctgcaggcc gagtacaccg                                              20

SEQ ID NO: 659          moltype = DNA  length = 20
FEATURE                 Location/Qualifiers
source                  1..20
                        mol_type = other DNA
                        organism = synthetic construct
SEQUENCE: 659
acaagtggga ggcttacctg                                              20

SEQ ID NO: 660          moltype = DNA  length = 20
FEATURE                 Location/Qualifiers
source                  1..20
                        mol_type = other DNA
```

```
                    organism = synthetic construct
SEQUENCE: 660
gcagcgtaca gggatgatca                                           20

SEQ ID NO: 661      moltype = DNA  length = 20
FEATURE             Location/Qualifiers
source              1..20
                    mol_type = other DNA
                    organism = synthetic construct
SEQUENCE: 661
gcagtagcgc ttcaggccca                                           20

SEQ ID NO: 662      moltype = DNA  length = 20
FEATURE             Location/Qualifiers
source              1..20
                    mol_type = other DNA
                    organism = synthetic construct
SEQUENCE: 662
caaatggtgg ggtaacagaa                                           20

SEQ ID NO: 663      moltype = DNA  length = 20
FEATURE             Location/Qualifiers
source              1..20
                    mol_type = other DNA
                    organism = synthetic construct
SEQUENCE: 663
gaaaggaact ggctaccgtt                                           20

SEQ ID NO: 664      moltype = DNA  length = 20
FEATURE             Location/Qualifiers
source              1..20
                    mol_type = other DNA
                    organism = synthetic construct
SEQUENCE: 664
agggcttccg ttacaagatg                                           20

SEQ ID NO: 665      moltype = DNA  length = 20
FEATURE             Location/Qualifiers
source              1..20
                    mol_type = other DNA
                    organism = synthetic construct
SEQUENCE: 665
gaacaagcaa cacctaaaag                                           20

SEQ ID NO: 666      moltype = DNA  length = 20
FEATURE             Location/Qualifiers
source              1..20
                    mol_type = other DNA
                    organism = synthetic construct
SEQUENCE: 666
tgaggagaag gaacggctca                                           20

SEQ ID NO: 667      moltype = DNA  length = 20
FEATURE             Location/Qualifiers
source              1..20
                    mol_type = other DNA
                    organism = synthetic construct
SEQUENCE: 667
ggaagaatgc agagtataag                                           20

SEQ ID NO: 668      moltype = DNA  length = 20
FEATURE             Location/Qualifiers
source              1..20
                    mol_type = other DNA
                    organism = synthetic construct
```

```
SEQUENCE: 668
ggaatttgag gaactcctga                                                                                        20

SEQ ID NO: 669          moltype = DNA  length = 20
FEATURE                 Location/Qualifiers
source                  1..20
                        mol_type = other DNA
                        organism = synthetic construct
SEQUENCE: 669
gctcaccggc catccaggaa                                                                                        20

SEQ ID NO: 670          moltype = DNA  length = 20
FEATURE                 Location/Qualifiers
source                  1..20
                        mol_type = other DNA
                        organism = synthetic construct
SEQUENCE: 670
actggccagg aacgatgcga                                                                                        20

SEQ ID NO: 671          moltype = DNA  length = 20
FEATURE                 Location/Qualifiers
source                  1..20
                        mol_type = other DNA
                        organism = synthetic construct
SEQUENCE: 671
gcagctccaa gatcttccca                                                                                        20

SEQ ID NO: 672          moltype = DNA  length = 20
FEATURE                 Location/Qualifiers
source                  1..20
                        mol_type = other DNA
                        organism = synthetic construct
SEQUENCE: 672
gaatgagtac acagaacgga                                                                                        20

SEQ ID NO: 673          moltype = DNA  length = 20
FEATURE                 Location/Qualifiers
source                  1..20
                        mol_type = other DNA
                        organism = synthetic construct
SEQUENCE: 673
ggagcaggac aaggtcgggg                                                                                        20
```